(12) United States Patent
Steward et al.

(10) Patent No.: US 7,811,584 B2
(45) Date of Patent: Oct. 12, 2010

(54) MULTIVALENT CLOSTRIDIAL TOXINS

(75) Inventors: Lance E. Steward, Irvine, CA (US);
Ester Fernandez-Salas, Fullerton, CA (US); Joseph Francis, Aliso Viejo, CA (US); Shengwen Li, Irvine, CA (US); Marcella A. Gilmore, Santa Ana, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 4 days.

(21) Appl. No.: 12/210,770

(22) Filed: Sep. 15, 2008

(65) Prior Publication Data

US 2009/0048431 A1   Feb. 19, 2009

Related U.S. Application Data

(63) Continuation-in-part of application No. 11/376,696, filed as application No. PCT/US2005/020578 on Jun. 9, 2005, now Pat. No. 7,514,088.

(60) Provisional application No. 60/584,378, filed on Jun. 30, 2004, provisional application No. 60/599,132, filed on Aug. 4, 2004.

(51) Int. Cl.
*A61K 39/08* (2006.01)
*A61K 39/38* (2006.01)
*A61K 39/02* (2006.01)

(52) U.S. Cl. .............. 424/239.1; 424/184.1; 424/185.1; 424/192.1; 424/234.1; 424/247.1

(58) Field of Classification Search .............. 424/184.1, 424/185.1, 192.1, 234.1, 239.1, 247.1
See application file for complete search history.

(56) References Cited

U.S. PATENT DOCUMENTS

| | | | |
|---|---|---|---|
| 5,437,291 A | 8/1995 | Pasricha et al. |
| 5,670,484 A | 9/1997 | Binder |
| 5,714,468 A | 2/1998 | Binder |
| 5,989,545 A | 11/1999 | Foster et al. |
| 6,063,768 A | 5/2000 | First |
| 6,113,915 A | 9/2000 | Aoki et al. |
| 6,139,845 A | 10/2000 | Donovan |
| 6,143,306 A | 11/2000 | Donovan |
| 6,203,794 B1 | 3/2001 | Dolly et al. |
| 6,261,572 B1 | 7/2001 | Donovan |
| 6,265,379 B1 | 7/2001 | Donovan |
| 6,299,893 B1 | 10/2001 | Schwartz et al. |
| 6,306,403 B1 | 10/2001 | Donovan |
| 6,319,505 B1 | 11/2001 | Aoki et al. |
| 6,337,075 B1 | 1/2002 | Donovan |
| 6,358,917 B1 | 3/2002 | Carruthers et al. |
| 6,358,926 B2 | 3/2002 | Donovan |
| 6,368,605 B1 | 4/2002 | Donovan |
| 6,395,513 B1 | 5/2002 | Foster et al. |
| 6,416,765 B1 | 7/2002 | Donovan |
| 6,423,319 B1 | 7/2002 | Brooks et al. |
| 6,458,365 B1 | 10/2002 | Aoki |
| 6,464,986 B1 | 10/2002 | Aoki et al. |
| 6,500,436 B2 | 12/2002 | Donovan |
| 6,565,870 B1 | 5/2003 | Donovan |
| 6,620,415 B2 | 9/2003 | Donovan |
| 6,623,742 B2 | 9/2003 | Voet |
| 6,632,440 B1 | 10/2003 | Quinn et al. |
| 6,641,820 B1 | 11/2003 | Donovan |
| 6,683,049 B1 | 1/2004 | Aoki et al. |
| 6,740,321 B1 | 5/2004 | Donovan |
| 6,767,544 B2 | 7/2004 | Brooks et al. |
| 6,776,990 B2 | 8/2004 | Sachs et al. |
| 6,776,992 B2 | 8/2004 | Aoki et al. |
| 6,827,931 B1 | 12/2004 | Donovan |
| 6,831,059 B2 | 12/2004 | Donovan |
| 6,838,434 B2 | 1/2005 | Voet |
| 6,843,998 B1 | 1/2005 | Steward et al. |
| 6,869,610 B2 | 3/2005 | Aoki et al. |
| 6,872,397 B2 | 3/2005 | Aoki et al. |
| 6,989,545 B1 | 1/2006 | Rathmell et al. |
| 7,052,702 B1 | 5/2006 | Duggan et al. |
| 7,056,729 B2 | 6/2006 | Donovan |
| 7,132,259 B1 | 11/2006 | Dolly et al. |
| 7,138,127 B1 | 11/2006 | Donovan |
| 7,192,596 B2 | 3/2007 | Shone et al. |
| 7,244,436 B2 | 7/2007 | Donovan |
| 7,244,437 B2 | 7/2007 | Donovan |
| 7,262,291 B2 | 8/2007 | Donovan |
| 7,276,473 B2 | 10/2007 | Sachs et al. |
| 7,413,742 B2 | 8/2008 | Donovan |
| 7,419,676 B2 | 9/2008 | Dolly et al. |
| 7,422,877 B2 | 9/2008 | Dolly et al. |
| 7,425,338 B2 | 9/2008 | Donovan |
| 7,514,088 B2 | 4/2009 | Steward et al. |

(Continued)

FOREIGN PATENT DOCUMENTS

WO    WO 94/21300    9/1994

(Continued)

OTHER PUBLICATIONS

Johnson et al., "Clostridial botulinum and its Neurotoxins: A Metabolic and Cellular Perspective", *39 Toxicon*, 1703-1722 (2001).

(Continued)

*Primary Examiner*—Rodney P. Swartz
(74) *Attorney, Agent, or Firm*—Kenton Abel; Joel German; Debra Condino

(57) ABSTRACT

The present invention is directed to multivalent Clostridial toxin comprising more than one binding domain directed to a cell surface molecule of a target cell. Such modified toxins are useful as therapeutic compositions to prevent exocytosis and secretion by the target cell. Conditions in which such compositions man be useful include, without limitation, disorders of the sensory or motor nervous system, acute or chronic pain, cancer, pancreatitis, hyperhydrosis, glandular disorders, viral infections, cystic fibrosis and the like. The invention is also directed to methods of using and administering such a composition, and methods of treating a given condition using such a composition.

12 Claims, 9 Drawing Sheets

U.S. PATENT DOCUMENTS

| | | |
|---|---|---|
| 2002/0010138 A1 | 1/2002 | Aoki et al. |
| 2002/0169942 A1 | 11/2002 | Sugimoto |
| 2003/0166238 A1 | 9/2003 | Shone et al. |
| 2003/0180289 A1 | 9/2003 | Foster et al. |
| 2003/0211121 A1 | 11/2003 | Donovan |
| 2004/0013692 A1 | 1/2004 | Aoki et al. |
| 2004/0037852 A1 | 2/2004 | Aoki et al. |
| 2004/0062776 A1 | 4/2004 | Voet |
| 2004/0071736 A1 | 4/2004 | Quinn et al. |
| 2004/0086531 A1 | 5/2004 | Barron |
| 2004/0115139 A1 | 6/2004 | Katz et al. |
| 2004/0126396 A1 | 7/2004 | Aoki et al. |
| 2004/0126397 A1 | 7/2004 | Aoki et al. |
| 2004/0151740 A1 | 8/2004 | Aoki et al. |
| 2004/0175399 A1 | 9/2004 | Schiffman |
| 2004/0176299 A1 | 9/2004 | Sachs et al. |
| 2004/0180061 A1 | 9/2004 | Donovan |
| 2004/0234532 A1 | 11/2004 | First |
| 2004/0253274 A1 | 12/2004 | Voet |
| 2005/0031648 A1 | 2/2005 | Brin et al. |
| 2006/0024331 A1 | 2/2006 | Fernandez-Salas |
| 2006/0211619 A1 | 9/2006 | Steward et al. |
| 2008/0032930 A1 | 2/2008 | Steward et al. |
| 2008/0032931 A1 | 2/2008 | Steward et al. |
| 2008/0081355 A1 | 4/2008 | Dolly et al. |
| 2008/0095872 A1 | 4/2008 | Donovan |
| 2008/0096248 A1 | 4/2008 | Steward et al. |
| 2008/0161226 A1 | 7/2008 | Steward et al. |
| 2008/0161543 A1 | 7/2008 | Steward et al. |
| 2008/0187960 A1 | 8/2008 | Foster et al. |
| 2008/0213311 A1 | 9/2008 | Donovan |
| 2008/0213830 A1 | 9/2008 | Steward et al. |
| 2008/0221012 A1 | 9/2008 | Steward et al. |
| 2008/0241881 A1 | 10/2008 | Steward et al. |
| 2008/0311622 A1 | 12/2008 | Dolly et al. |
| 2008/0317782 A1 | 12/2008 | Donovan |
| 2008/0317783 A1 | 12/2008 | Donovan |
| 2009/0004224 A1 | 1/2009 | Steward et al. |
| 2009/0004225 A1 | 1/2009 | Fernandez-Salas et al. |
| 2009/0005313 A1 | 1/2009 | Steward et al. |
| 2009/0010967 A1 | 1/2009 | Donovan |
| 2009/0017071 A1 | 1/2009 | Donovan |
| 2009/0018081 A1 | 1/2009 | Steward et al. |
| 2009/0023901 A1 | 1/2009 | Steward et al. |
| 2009/0028908 A1 | 1/2009 | Donovan |
| 2009/0030182 A1 | 1/2009 | Dolly et al. |
| 2009/0030188 A1 | 1/2009 | Dolly et al. |
| 2009/0035822 A1 | 2/2009 | Foster et al. |
| 2009/0042270 A1 | 2/2009 | Dolly et al. |
| 2009/0042799 A1 | 2/2009 | Donovan |
| 2009/0069238 A1 | 3/2009 | Steward et al. |
| 2009/0081730 A1 | 3/2009 | Dolly et al. |
| 2009/0087458 A1 | 4/2009 | Dolly et al. |
| 2009/0104234 A1 | 4/2009 | Francis et al. |
| 2009/0117157 A1 | 5/2009 | Brin et al. |

FOREIGN PATENT DOCUMENTS

| | | |
|---|---|---|
| WO | WO 95/32738 | 12/1995 |
| WO | WO 96/33273 | 10/1996 |
| WO | WO 98/07864 | 2/1998 |
| WO | WO 99/17806 | 4/1999 |
| WO | WO 99/29721 | 6/1999 |
| WO | WO 99/55359 | 11/1999 |
| WO | WO 01/14570 | 3/2001 |
| WO | WO 02/40506 | 5/2002 |
| WO | WO 02/44199 | 6/2002 |
| WO | WO 2004/024909 | 3/2004 |
| WO | WO 2005/023309 | 3/2005 |
| WO | WO 2005/035730 | 4/2005 |
| WO | WO 2005/068494 | 7/2005 |
| WO | WO 2005/077416 | 8/2005 |
| WO | WO 2006/011966 | 2/2006 |
| WO | WO 2006/017749 | 2/2006 |
| WO | WO 2006/026780 | 3/2006 |
| WO | WO 2006/027207 | 3/2006 |
| WO | WO 2006/059093 | 6/2006 |
| WO | WO 2006/059105 | 6/2006 |
| WO | WO2006/059113 | 6/2006 |
| WO | WO2006/099590 | 9/2006 |
| WO | WO 2006/101809 | 9/2006 |

OTHER PUBLICATIONS

Raffestin et al., "Organization and Regulation of the Neurotoxin Genes in Clostridium botulinum and Clostridium tetani", *10 Anaerobe*, 93-100 (2004).

Inoue et al., "Structural Analysis by X-Ray Crystallography and Calorimetry of Haemagglutinin Component (HA1) of the Progenitor Toxin from Clostridium botulinum", *149 Microbiol.*, 3361-3370 (2003).

Arndt et al., "The Structure of the Neurotoxin-Associated Protein HA33/A from Clostridial botulinum Suggests a Reoccurring β-trefoil Fold in the Progenitor Toxin Complex", *346 J. Mol. Biol.*, 1083-1093 (2005).

Zhou et al., "Haemagglutinin-33 of Type Q Botulinum Neurotoxin Complex Binds with Synaptotagmin II", *272 Febs Lett.*, 2717-2726 (2005).

Bonifacino et al., *J. Cell Biol.* 145: 923 (1999).

Drapkin et al., *J. Clin. Invest.* 105: 589-596 (2000).

Duman & Forte, *Am. J. Physiol. Cell Physiol.* 285: C237-C249 (2003).

Morris M.C., et al., *Nature Biotechnology*, 19:1173-1176 (2001).

Embury et al., *Diabetes*, 50:1706-1713 (2001).

Schwartz, J.J. et al., "Peptide-mediated cellular delivery", *Curr. Opin. Mol. Therapeutics*, 2:162-7 (2000).

Prochiantz, A., "Messenger proteins:homeoproteins, TAT and others", *Curr. Opin. Cell. Biol.*, 12:400-6 (2000).

Ho, A. et al., "Synthetic PTDs: enhanced transduction potential in vitro and in vivo", *Cancer Res.*, 61, 474-7 (2001).

Wender, P.A. et al., "The Design, Synthesis, And Evaluation of Molecules That Enable or Enhance Cellular Uptake: Peptoid Molecular Transporters", *Proc. Natl. Acad. Sci.*, 97:13003-13008 (2000).

Arndt et al, "The Structure of the Neurotoxin-associated Protein HA33/A from Clostridium botulinum Suggests a Reoccurring beta-Trefoil Fold in the Progenitor Toxin Complex", Journal of Molecular Biology, vol. 346, No. 4, 1083-1093, Mar. 4, 2005.

Herreros et al, "C-Terminal Half of Tetanus Toxin Fragment C is Sufficient for Neuronal Binding and Interaction with a Putative Protein Receptor", Biochemical Journal, vol. 347, No. Part I, pp. 199-204, Apr. 1, 2001.

Rummel et al., "The Hcc-domain of botulinum neurotoxins A and B exhibits a singular ganglioside binding site displaying serotype specifiic carbohydrate interation", Molecular Microbiology pp. 631-643, Dec. 15, 2003.

Halpern et al, "Characterization of the receptor-binding domain of tetanus toxin", Journal of Biological Chemistry, pp. 11188-11192, May 25, 1993.

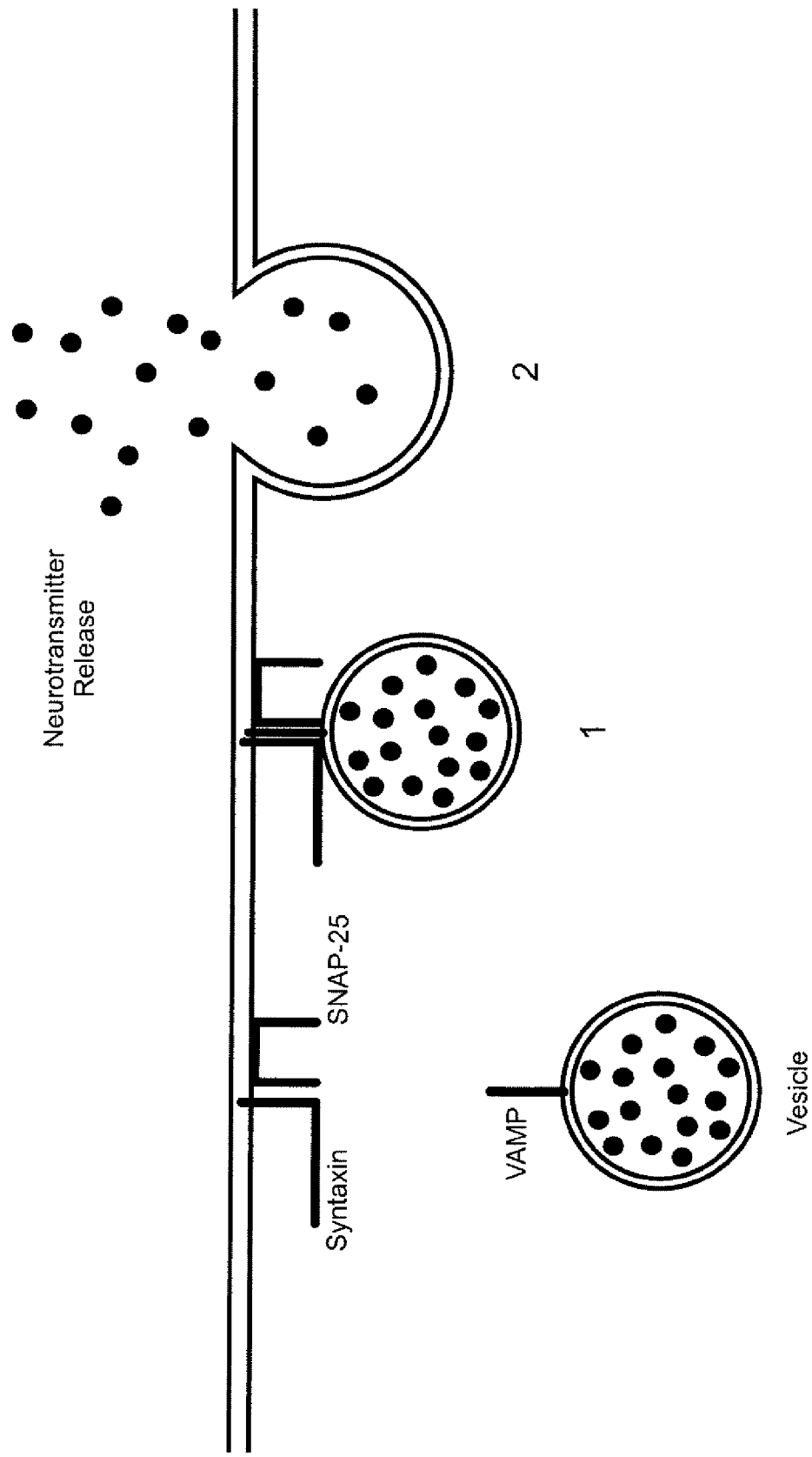

FIG. 3.

MULTIVALENT CLOSTRIDIAL TOXINS

This is a continuation in part and claims priority pursuant to 35 U.S.C. §120 to U.S. patent application Ser. No. 11/376,696, filed Mar. 15, 2006, now U.S. Pat. No. 7,514,088, a national stage application under 35 U.S.C. §371 of PCT application PCT/US 2005/020578, filed 9 June, 2005 which claims priority pursuant to 35 U.S.C. §119(e) to provisional patent application Ser. No. 60/584,378 filed Jun. 30, 2004 and provisional patent application Ser. No. 60/599,132 filed Aug. 4, 2004, which are all hereby incorporated by reference in their entirety.

The ability of Clostridial toxins to inhibit neuronal transmission are being exploited in a wide variety of therapeutic and cosmetic applications, see e.g., William J. Lipham, *Cosmetic and Clinical Applications of Botulinum Toxin* (Slack, Inc., 2004). Clostridial toxins commercially available as pharmaceutical compositions include, BoNT/A preparations, such as, e.g., BOTOX® (Allergan, Inc., Irvine, Calif.), Dysport®/Reloxin®, (Beaufour Ipsen, Porton Down, England), Linurase® (Prollenium, Inc., Ontario, Canada), Neuronox® (Medy-Tox, Inc., Ochang-myeon, South Korea) BTX-A (Lanzhou Institute Biological Products, China) and Xeomin® (Merz Pharmaceuticals, GmbH, Frankfurt, Germany); and BoNT/B preparations, such as, e.g., MyoBloc™/NeuroBloc™ (Elan Pharmaceuticals, San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

Clostridial toxin therapies are successfully used for many indications. Generally, administration of a Clostridial toxin treatment is well tolerated. However, toxin administration in some applications can be challenging because of the larger doses required to achieve a beneficial effect. First, larger doses can increase the likelihood that the toxin may move through the interstitial fluids and the circulatory systems, such as, e.g., the cardiovascular system and the lymphatic system, of the body, resulting in the undesirable dispersal of the toxin to areas not targeted for toxin treatment. Such dispersal can lead to undesirable side effects, such as, e.g., inhibition of neurotransmitter release in neurons not targeted for treatment or paralysis of a muscle not targeted for treatment. For example, a patient administered a therapeutically effective amount of a BoNT/A treatment into the neck muscles for torticollis may develop dysphagia because of dispersal of the toxin into the oropharynx. Thus, there remains a need for improved Clostridial toxins that are effective at the site of treatment, but have negligible to minimal effects in areas not targeted for a toxin treatment.

Second, larger doses of a Clostridial toxin treatment may elicit an antibody response against the toxin. While a potent and effective treatment, the inhibition of neurotransmitter release and the resulting neuromuscular paralysis elicited by Clostridial toxin therapies is not permanent. The reversible nature of these paralytic effects requires periodic treatments in order to maintain the therapeutic benefits from this toxin. As a consequence of this repeated exposure, an immune response against a Clostridial toxin can occur in some patients which reduce or completely prevent the individual's responsiveness to further treatments, see, e.g., Joseph Jankovic, *Botulinum toxin: Clinical Implications of Antigenicity and Immunoresistance*, (SCIENTIFIC AND THERAPEUTIC ASPECTS OF BOTULINUM TOXIN, 409-415, Mitchell F. Brin et al., eds., Lippincott Williams & Wilkins, 2002); Dirk Dressler, *Clinical Presentation and Management of Antibody-induced Failure of Botulinum Toxin Therapy*, 19(Suppl. 8) MOV. DISORD. S92-S100 (2004); M. Zouhair Atassi, *Basic Immunological Aspects of Botulinum Toxin Therapy*, 19(Suppl. 8) MOV. DISORD. S68-S84, (2004). Thus, there remains a need for improved Clostridial toxins that maintain effective therapeutic benefits, but have reduced ability to evoke an immunogenic response against itself.

Moreover, a Clostridial toxin treatment inhibits neurotransmitter release by disrupting the exocytotic process used to secret the neurotransmitter into the synaptic cleft. However, it is believed that current Clostridial toxin therapies may by expanded to treat new indications beyond those diseases or disorders whose underlying pathophysiology is aberrant cholinergic motor neuron activity.

Thus, the growing clinical, therapeutic and cosmetic use of Clostridial toxins in therapies requiring larger doses necessitates the pharmaceutical industry to develop modified Clostridial toxins that are effective at the target site of the application, but reduce or prevent the undesirable side-effects associated with the dispersal of the toxins to unwanted locations and reduce or prevent an unwanted immunogenic response. Additionally, there is a great desire by the pharmaceutical industry to expand the use of Clostridial toxin therapies beyond its current myo-relaxant applications to treat sensory-based ailment, such as, e.g., various kinds of chronic pain, as well as non-neuronal based disorders, such as, e.g., pancreatitis. The present invention provides novel multivalent Clostridial toxins that greatly extended the number of therapeutic applications that can exploit the advantages offered by current Clostridial toxin therapies. These and related advantages are useful for various clinical, therapeutic and cosmetic applications, such as, e.g., the treatment of neuropathic disorders, eye disorders, pain, muscle injuries, headache, cardiovascular diseases, neuropsychiatric disorders, endocrine disorders, cancers, otic disorders, as well as, other disorders where administration of a multivalent Clostridial toxin to an individual can produce a beneficial effect.

BRIEF DESCRIPTION OF THE DRAWINGS

FIG. 1 shows a schematic of the current paradigm of neurotransmitter release and Clostridial toxin intoxication in a central and peripheral neuron. FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed.

FIG. 3 shows a ribbon diagram of BoNT/A illustrating the modular three-dimensional structure of the light chain (LC) comprising the enzymatic domain, the heavy chain $H_N$ domain comprising the translocation domain, and the heavy chain $H_c$ domain, including the heavy chain $H_{CN}$ domain and the heavy chain $H_{CC}$ domain, that comprises the binding domain.

FIG. 4 shows examples of domain arrangements of multivalent Clostridial toxins.

FIG. 5 shows examples of domain arrangements of multivalent Clostridial toxins.

FIG. 6 shows examples of domain arrangements of multivalent Clostridial toxins.

DETAILED DESCRIPTION

Figure 1B:
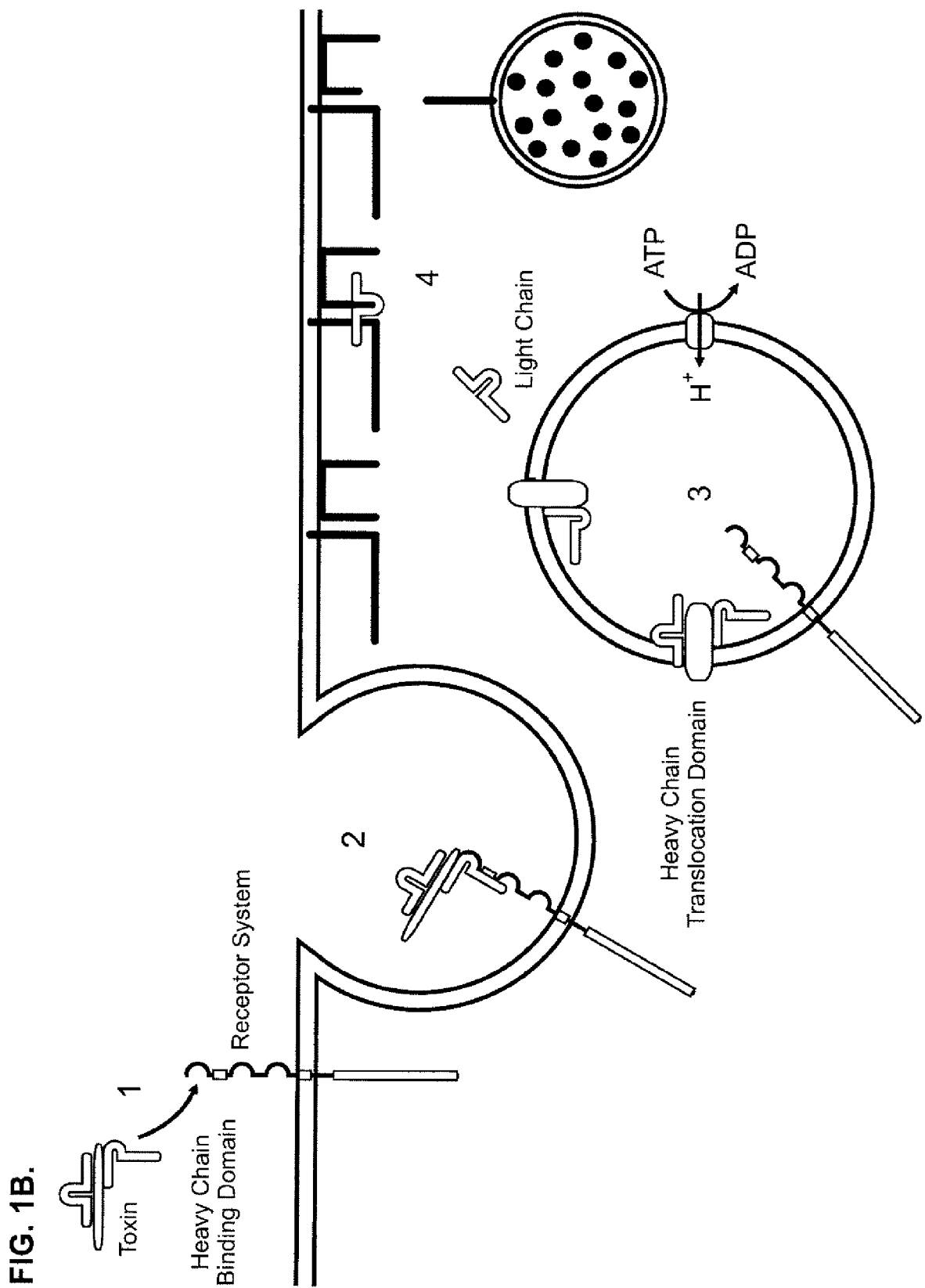
FIG. 1B shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor and initiates the intoxication process; 2) complex internalization, where after toxin binding, a vesicle containing the toxin/receptor complex is endocytosed into the cell; 3) light chain translocation, where multiple events result in the release of the active light chain into the cytoplasm; and 4) enzymatic target modification, where the active light chain of Clostridial toxin proteolytically cleaves its target SNARE substrate, such as, e.g., SNAP-25, VAMP or Syntaxin, thereby preventing vesicle docking and neurotransmitter release.

The present invention provides novel Clostridial toxins that greatly extended the number of therapeutic applications that can exploit the advantages offered by current Clostridial toxin therapies. These multivalent Clostridial toxins comprise, in part, multiple binding domains. Each binding domain can be capable of binding 1) the cognate Clostridial toxin receptor present on the surface of a naturally-occurring Clostridial toxin target cell; 2) a different receptor present on the surface of a naturally occurring Clostridial toxin target cell; or 3) a different receptor present on the surface of the non-Clostridial toxin target cell. As such, a multivalent Clostridial toxin comprising multiple binding domains can exhibit increased specificity, efficacy and efficiency by which such multivalent Clostridial toxins can interact with a particular target cell and enzymatically modify its target SNARE substrate. Additionally, a multivalent Clostridial toxin comprising multiple binding domains can exhibit increased the versatility and therapeutic scope of current Clostridial toxin therapeutic applications by simultaneously targeting multiple cell types responsible for different aspects of a diseased state, such as, e.g., a nerve spasticity symptom and a pain symptom, or an aberrant enzyme release symptom and a pain symptom.

Aspects of the present invention a composition comprising a multivalent Clostridial toxin comprising a Clostridial toxin enzymatic domain, a Clostridial toxin translocation domain, a first binding domain and a second binding domain, wherein each of the binding domains is independently capable of binding a cell surface receptor of a target cell. It is envisioned that the first binding domain and second binding domain may be identical to each other or different.

Other aspects of the present invention provide polynucleotide molecules encoding a multivalent Clostridial toxin comprising a Clostridial toxin enzymatic domain, a Clostridial toxin translocation domain, a first binding domain and a second binding domain.

Other aspects of the present invention provide methods of producing a multivalent Clostridial toxin disclosed in the present specification, the method comprising the step of expressing in a cell a polynucleotide molecule encoding a multivalent Clostridial toxin comprising a Clostridial toxin enzymatic domain, a Clostridial toxin translocation domain, a first binding domain and a second binding domain. Other aspects of the present invention provide methods of producing a multivalent Clostridial toxin disclosed in the present specification, the method comprising the steps of introducing in a cell an expression construct comprising a polynucleotide molecule encoding a multivalent Clostridial toxin comprising a Clostridial toxin enzymatic domain, a Clostridial toxin translocation domain, a first binding domain and a second binding domain and expressing the expression construct in the cell.

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. It is recognized by those of skill in the art that within each type of Clostridial toxin there can be subtypes that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific subtypes showing approximately 89% amino acid identity when compared to another BoNT/A subtype. While all seven BoNT serotypes have similar structure and pharmacological properties, each also displays heterogeneous bacteriological characteristics. In contrast, tetanus toxin (TeNT) is produced by a uniform group of *C. tetani*. Two other species of Clostridia, *C. baratii* and *C. butyricum*, also produce toxins, BaNT and BuNT respectively, which are similar to BoNT/F and BoNT/E, respectively.

Figure 2:
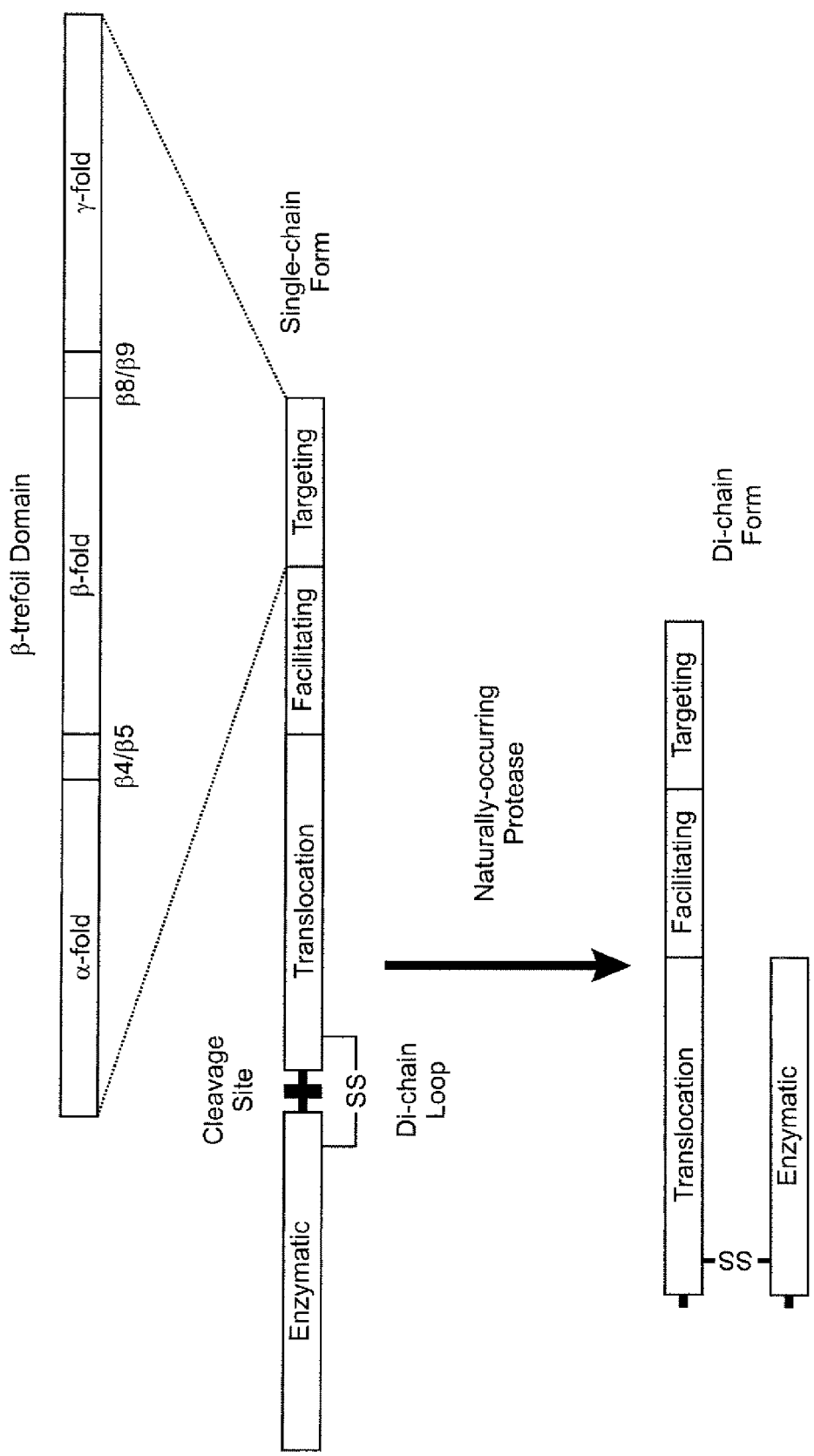
FIG. 2 shows the domain organization of naturally-occurring Clostridial toxins. The single chain form depicts the amino to carboxyl linear organization comprising an enzymatic domain, a translocation domain, a $H_{CN}$ translocation facilitating domain and a $H_{CC}$ targeting domain. The di-chain loop region located between the translocation and enzymatic domains is depicted by the double SS bracket. This region comprises an endogenous di-chain loop protease cleavage site that upon proteolytic cleavage with a naturally-occurring protease, such as, e.g., an endogenous Clostridial toxin protease or a naturally-occurring protease produced in the environment, converts the single chain form of the toxin into the di-chain form. As depicted above the single-chain form, the $H_{CC}$ targeting domain comprises the β-trefoil domain which comprises in an amino to carboxyl linear organization of an α-fold, a β4/β5 hairpin turn, a β-fold, a β8/β9 hairpin turn and a γ-fold.
Figure 4A:
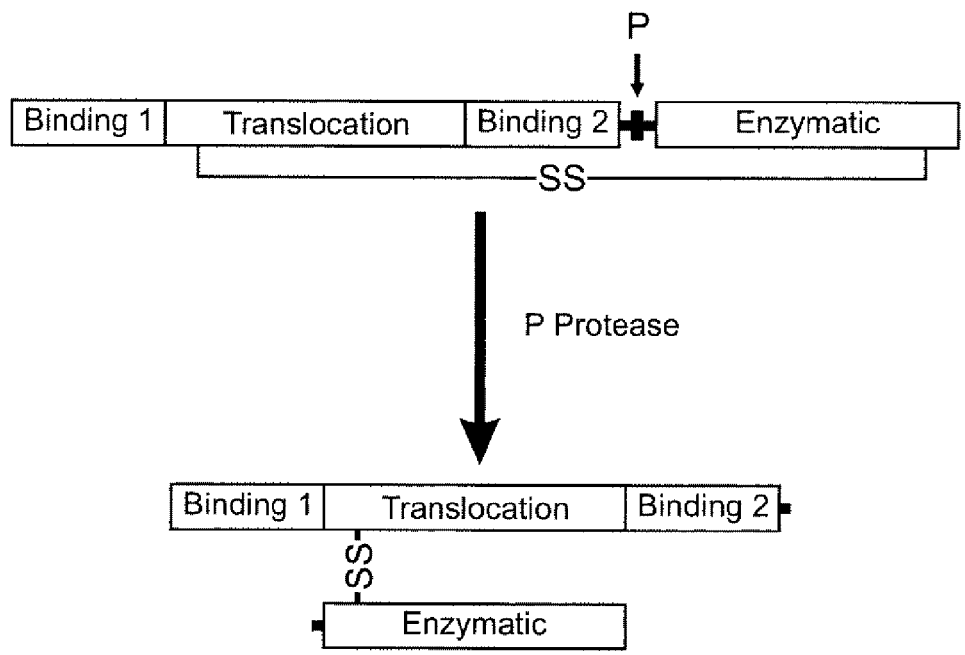
FIG. 4A depicts the single polypeptide form of a multivalent Clostridial toxin with an amino to carboxyl linear organization comprising a binding domain 1, a translocation domain, a binding domain 2 and an enzymatic domain, with the di-chain loop region depicted by the double SS bracket. A proteolytic cleavage site (P) within a di-chain loop region is located between the binding domain 2 and enzymatic domain. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the binding domain 1 and translocation domain, the translocation domain and binding domain 2, binding domain 2 and enzymatic domain, or any combination thereof.
Figure 4B:
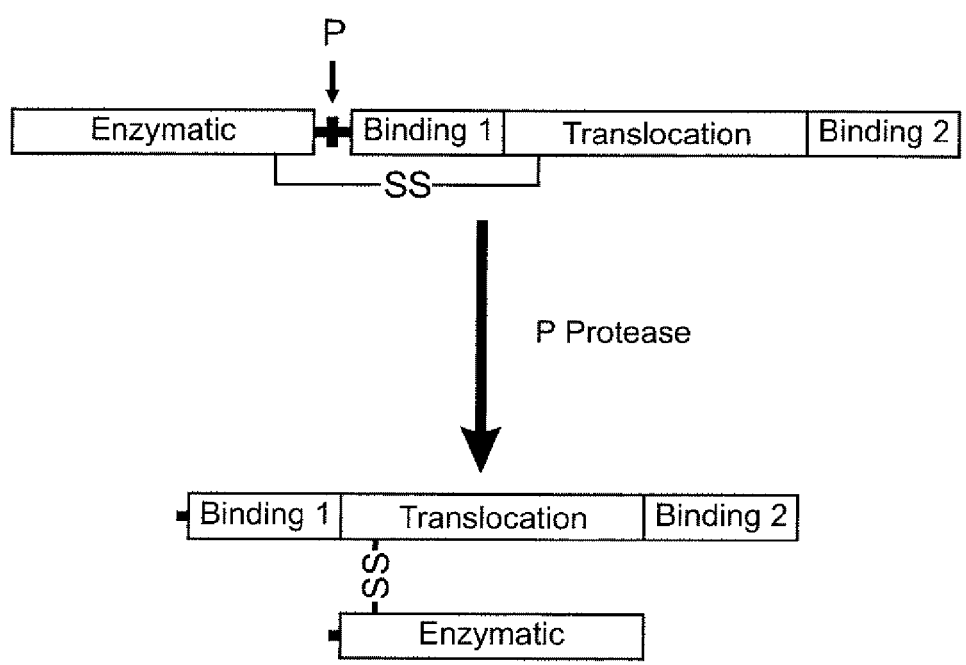
FIG. 4B depicts the single polypeptide form of a multivalent Clostridial toxin with an amino to carboxyl linear organization comprising an enzymatic domain, a binding domain 1, a translocation domain and a binding domain 2, with the di-chain loop region depicted by the double SS bracket. A proteolytic cleavage site (P) within a di-chain loop region is located between the enzymatic domain and binding domain 1. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the enzymatic domain and binding domain 1, the binding domain 1 and translocation domain, the translocation and binding domain 2, or any combination thereof.
Figure 4C:
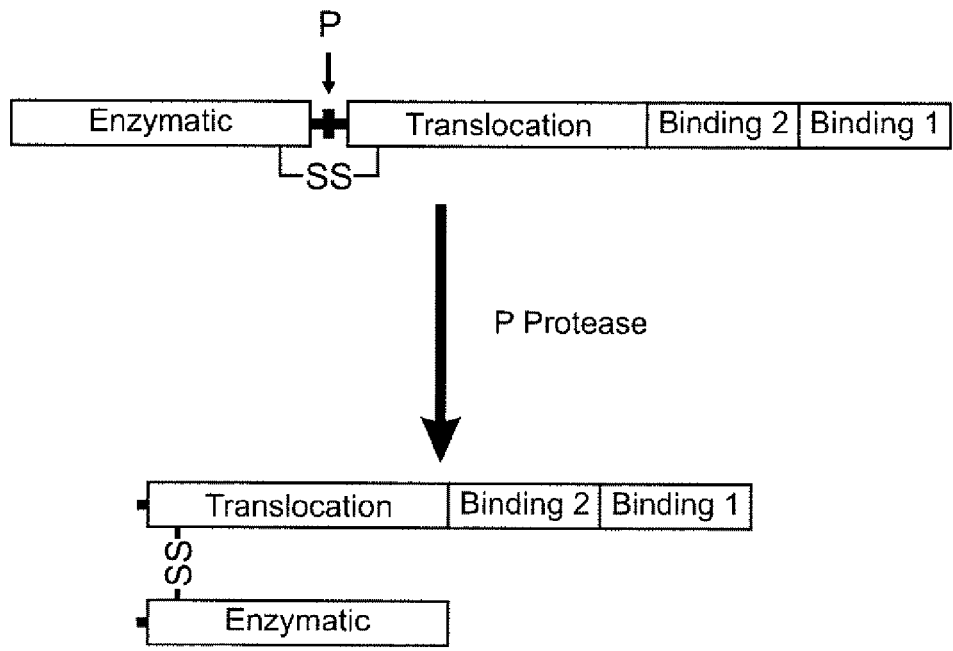
FIG. 4C depicts the single polypeptide form of a multivalent Clostridial toxin with an amino to carboxyl linear organization comprising an enzymatic domain, a translocation domain, a binding domain 1 and a binding domain 2, with the di-chain loop region depicted by the double SS bracket. A proteolytic cleavage site (P) within a di-chain loop region is located between the enzymatic domain and translocation domain. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the enzymatic domain and translocation domain, the translocation domain and binding domain 1, the binding domain 1 and a binding domain 2, or any combination thereof.
Figure 4D:
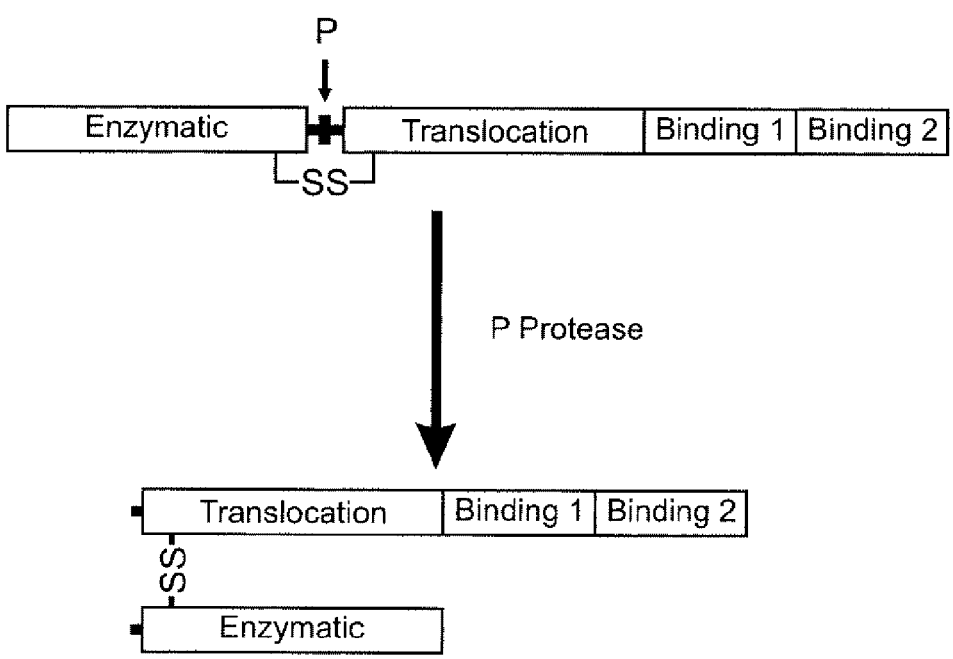
FIG. 4D depicts the single polypeptide form of a multivalent Clostridial toxin with an amino to carboxyl linear organization comprising an enzymatic domain, a translocation domain, a binding domain 2 and a binding domain 1, with the di-chain loop region depicted by the double SS bracket. A proteolytic cleavage site (P) within a di-chain loop region is located between the enzymatic domain and translocation domain. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the enzymatic domain and translocation domain, the translocation domain and binding domain 2, the binding domain 2 and a binding domain 1, or any combination thereof.
Figure 5A:
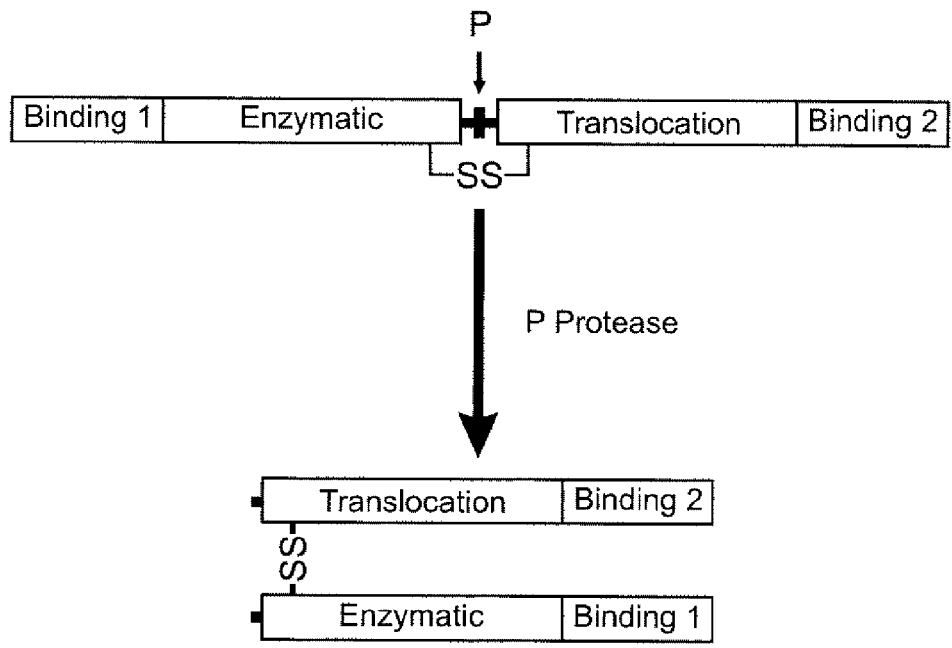
FIG. 5A depicts the single polypeptide form of a multivalent Clostridial toxin with an amino to carboxyl linear organization comprising a binding domain 1, an enzymatic domain, a translocation domain and a binding domain 2, with the di-chain loop region depicted by the double SS bracket. A proteolytic cleavage site (P) within a di-chain loop region is located between the enzymatic domain and translocation domain. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the binding domain 1 and the enzymatic domain, the enzymatic domain and translocation domain, the translocation domain and binding domain 2, or any combination thereof.
Figure 5B:
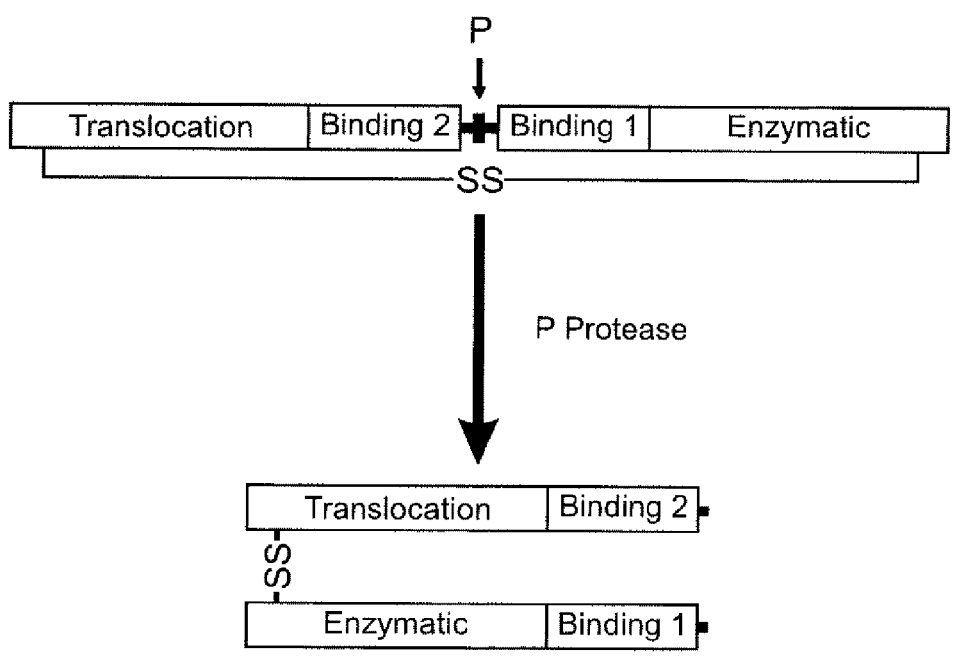
FIG. 5B depicts the single polypeptide form of a multivalent Clostridial toxin with an amino to carboxyl linear organization comprising a translocation domain, a binding domain 2, a binding domain 1 and an enzymatic domain, with the di-chain loop region depicted by the double SS bracket. A proteolytic cleavage site (P) within a di-chain loop region is located between the binding domain 2 and binding domain 1. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the translocation domain and binding domain 2, the binding domain 2 and binding domain 1, the binding domain 1 and enzymatic domain, or any combination thereof.
Figure 5C:
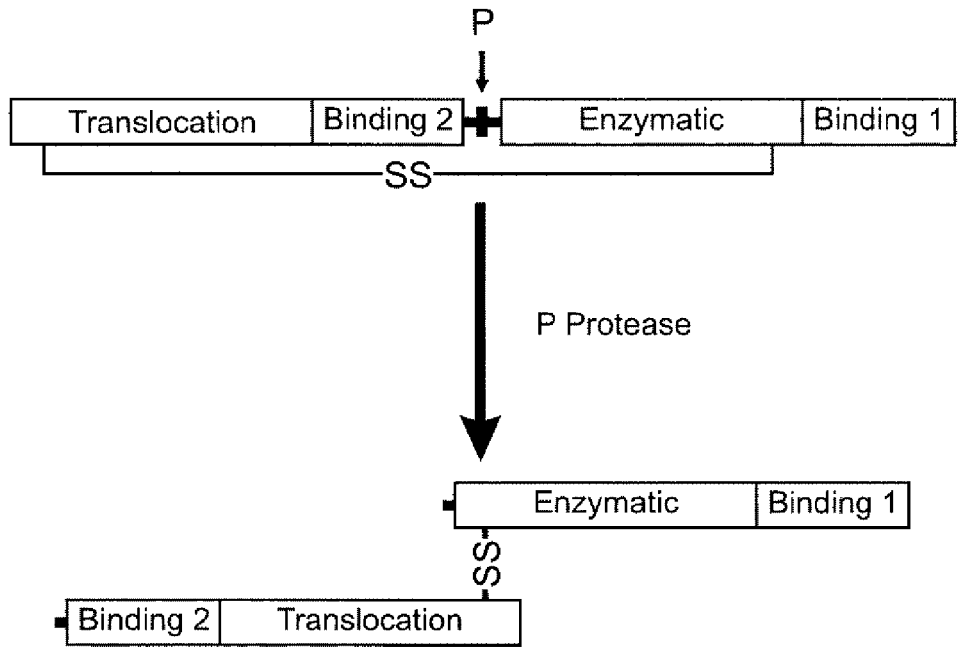
FIG. 5C depicts the single polypeptide form of a multivalent Clostridial toxin with an amino to carboxyl linear organization comprising a translocation domain, a binding domain 2, an enzymatic domain and a binding domain 1, with the di-chain loop region depicted by the double SS bracket. A proteolytic cleavage site (P) within a di-chain loop region is located between the binding domain 2 and enzymatic domain. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the translocation domain and binding domain 2, the binding domain 2 and enzymatic domain, the enzymatic domain and binding domain 1, or any combination thereof.
Figure 5D:
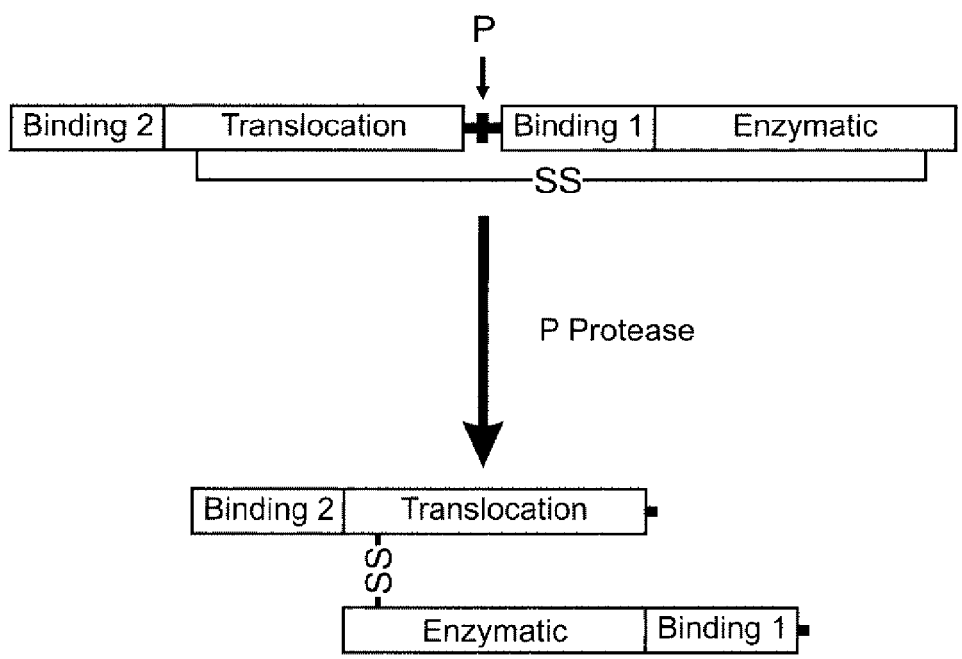
FIG. 5D depicts the single polypeptide form of a multivalent Clostridial toxin with an amino to carboxyl linear organization comprising a binding domain 2, a translocation domain, a binding domain 1 and an enzymatic domain, with the di-chain loop region depicted by the double SS bracket. A proteolytic cleavage site (P) within a di-chain loop region is located between the translocation domain and binding domain 1. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the binding domain 2 and translocation domain, the translocation domain and binding domain 1, the binding domain 1 and enzymatic domain, or any combination thereof.

Clostridial toxins are each translated as a single chain polypeptide of approximately 150 kDa that is subsequently cleaved by proteolytic scission within a disulfide loop by a naturally-occurring protease (FIG. 2). This cleavage occurs within the discrete di-chain loop region created between two cysteine residues that form a disulfide bridge. This posttranslational processing yields a di-chain molecule comprising an approximately 50 kDa light chain (LC) and an approximately 100 kDa heavy chain (HC) held together by the single disulfide bond and non-covalent interactions between the two chains. The naturally-occurring protease used to convert the single chain molecule into the di-chain is currently not known. In some serotypes, such as, e.g., BoNT/A, the naturally-occurring protease is produced endogenously by the bacteria serotype and cleavage occurs within the cell before the toxin is release into the environment. However, in other serotypes, such as, e.g., BoNT/E, the bacterial strain appears not to produce an endogenous protease capable of converting the single chain form of the toxin into the di-chain form. In these situations, the toxin is released from the cell as a single-chain toxin which is subsequently converted into the di-chain form by a naturally-occurring protease found in the environment.

overall cellular intoxication mechanism whereby Clostridial toxins enter a neuron and inhibit neurotransmitter release is similar, regardless of type. Although the applicants have no wish to be limited by the following description, the intoxication mechanism can be described as comprising at least four steps: 1) receptor binding, 2) complex internalization, 3) light chain translocation, and 4) enzymatic target modification (see FIG. 1). The process is initiated when the $H_C$ domain of a Clostridial toxin binds to a toxin-specific receptor complex located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain

TABLE 1

Clostridial Toxin Reference Sequences and Regions

| Toxin | SEQ ID NO: | LC | $H_N$ | $H_C$ | |
|---|---|---|---|---|---|
| | | | | $H_{CN}$ | $H_{CC}$ |
| BoNT/A | 1 | M1-K448 | A449-I873 | I874-P1110 | Y1111-L1296 |
| BoNT/B | 2 | M1-K441 | A442-I860 | L861-E1097 | Y1098-E1291 |
| BoNT/C1 | 3 | M1-K449 | T450-I868 | N869-E1111 | Y1112-E1291 |
| BoNT/D | 4 | M1-K445 | D446-I864 | N865-E1098 | Y1099-E1276 |
| BoNT/E | 5 | M1-R422 | K423-I847 | K848-E1085 | Y1086-K1252 |
| BoNT/F | 6 | M1-K439 | A440-I866 | K867-K1105 | Y1106-E1274 |
| BoNT/G | 7 | M1-K446 | S447-I865 | S866-Q1105 | Y1106-E1297 |
| TeNT | 8 | M1-A457 | S458-L881 | K882-E1127 | Y1128-D1315 |
| BaNT | 9 | M1-K431 | N432-I857 | I858-K1094 | Y1095-E1268 |
| BuNT | 10 | M1-R422 | K423-I847 | K848-E1085 | Y1086-K1251 |

Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC($H_N$) that facilitates release of the LC from intracellular vesicles into the cytoplasm of the target cell; and 3) a binding domain found within the carboxyl-terminal half of the HC ($H_C$) that determines the binding activity and binding specificity of the toxin to the receptor complex located at the surface of the target cell. The $H_C$ domain comprises two distinct structural features of roughly equal size that indicate function and are designated the $H_{CN}$ and $H_{CC}$ subdomains. Table 1 gives approximate boundary regions for each domain and subdomain found in exemplary Clostridial toxins. When discussing the three general neurotoxin domains of each clostridial neurotoxin subtype (binding, translocation and endopeptidase) it will be understood that clostridial neurotoxin research is a well-developed field, and the correlation of the amino acid sequences comprising each of these domains with their functions is well known. Additionally, the nucleotide and amino acid sequences of each of these domains are known and have been disclosed in this specification.

The binding, translocation and enzymatic activity of these three functional domains are all necessary for toxicity. While all details of this process are not yet precisely known, the overall cellular intoxication mechanism whereby Clostridial endopeptidase of the toxin is released from the intracellular vesicle into the cytosol where it specifically targets one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem.

Sci. 552-558. (2002); Giovanna Lalli et al., *The Journey of Tetanus and Botulinum Neurotoxins in Neurons*, 11(9) Trends Microbiol. 431-437, (2003).

The three-dimensional crystal structures of BoNT/A, BoNT/B and the $H_C$ domain of TeNT indicate that the three functional domains of Clostridial neurotoxins are structurally distinct domains that are shared by all Clostridial toxins. The HEXXH consensus motif of the light chain forms the tetrahedral zinc binding pocket of the catalytic site located in a deep cleft on the protein surface that is accessible by a channel. The structure of the $H_N$ and $H_C$ domains consists primarily of β-sheet topologies that are linked by a single α-helix. The cylindrical-shaped $H_N$ domain comprises two long amphipathic α-helices that resemble the coiled-coil motif found in some viral proteins. The $H_N$ domain also forms a long unstructured loop called the 'translocation belt,' which wraps around a large negatively charged cleft of the light chain that blocks access of the zinc atom to the catalytic-binding pocket of active site. The $H_C$ domain comprises two distinct structural features of roughly equal size that indicate function. The first, designated the $H_{CN}$ domain, is located in the amino half of the $H_C$ domain. The $H_{CN}$ domain forms a β-barrel, jelly-roll fold. The $H_{CC}$ domain is the second domain that comprises the $H_C$ domain. This carboxyl-terminal domain comprises a modified β-trefoil domain which forms three distinct carbohydrate binding regions that resembles the carbohydrate binding moiety found in many sugar-binding proteins, such as, e.g., serum amyloid P, sialidase, cryia, insecticidal ∂-endotoxin and lectins. Biochemical studies indicate that the β-trefoil domain structure of the $H_{CC}$ domain appears to mediate the binding to specific carbohydrate containing components of the Clostridial toxin receptor on the cell surface, see, e.g., Krzysztof Ginalski et al., *Structure-based Sequence Alignment for the Beta-Trefoil Subdomain of the Clostridial Neurotoxin Family Provides Residue Level Information About the Putative Ganglioside Binding Site*, 482(1-2) FEBS Lett. 119-124 (2000). The $H_C$ domain tilts away from the $H_N$ domain exposing the surface loops and making them accessible for binding. No contacts occur between the light chain and the $H_C$ domain.

Aspects of the present invention provide, in part, a Clostridial toxin. As used herein, the term "Clostridial toxin" means any neurotoxin produced by a Clostridial toxin strain that can execute the overall cellular mechanism whereby a Clostridial toxin intoxicates a cell and encompasses the binding of a Clostridial toxin to a low or high affinity receptor complex, the internalization of the toxin/receptor complex, the translocation of the Clostridial toxin light chain into the cytoplasm and the enzymatic modification of a Clostridial toxin substrate. Exemplary Clostridial toxins include those produced by a *Clostridium botulinum*, a *Clostridium tetani*, a *Clostridium baratii* and a *Clostridium butyricum*.

A Clostridial toxin includes, without limitation, naturally occurring Clostridial toxin variants, such as, e.g., Clostridial toxin isoforms and Clostridial toxin subtypes; non-naturally occurring Clostridial toxin variants, such as, e.g., conservative Clostridial toxin variants, non-conservative Clostridial toxin variants, Clostridial toxin chimeric variants and active Clostridial toxin fragments thereof, or any combination thereof. As used herein, the term "Clostridial toxin variant," whether naturally-occurring or non-naturally-occurring, means a Clostridial toxin that has at least one amino acid change from the corresponding region of the disclosed reference sequences (see Table 1) and can be described in percent identity to the corresponding region of that reference sequence. As non-limiting examples, a BoNT/A variant comprising amino acids 1-1296 of SEQ ID NO: 1 will have at least one amino acid difference, such as, e.g., an amino acid substitution, deletion or addition, as compared to the amino acid region 1-1296 of SEQ ID NO: 1; a BoNT/B variant comprising amino acids 1-1291 of SEQ ID NO: 2 will have at least one amino acid difference, such as, e.g., an amino acid substitution, deletion or addition, as compared to the amino acid region 1-1291 of SEQ ID NO: 2; a BoNT/C1 variant comprising amino acids 1-1291 of SEQ ID NO: 3 will have at least one amino acid difference, such as, e.g., an amino acid substitution, deletion or addition, as compared to the amino acid region 1-1291 of SEQ ID NO: 3; a BoNT/D variant comprising amino acids 1-1276 of SEQ ID NO: 4 will have at least one amino acid difference, such as, e.g., an amino acid substitution, deletion or addition, as compared to the amino acid region 1-1276 of SEQ ID NO: 4; a BoNT/E variant comprising amino acids 1-1252 of SEQ ID NO: 5 will have at least one amino acid difference, such as, e.g., an amino acid substitution, deletion or addition, as compared to the amino acid region 1-1252 of SEQ ID NO: 5; a BoNT/F variant comprising amino acids 1-1274 of SEQ ID NO: 6 will have at least one amino acid difference, such as, e.g., an amino acid substitution, deletion or addition, as compared to the amino acid region 1-1274 of SEQ ID NO: 6; a BoNT/G variant comprising amino acids 1-1297 of SEQ ID NO: 7 will have at least one amino acid difference, such as, e.g., an amino acid substitution, deletion or addition, as compared to the amino acid region 1-1297 of SEQ ID NO: 7; a TeNT variant comprising amino acids 1-1315 of SEQ ID NO: 8 will have at least one amino acid difference, such as, e.g., an amino acid substitution, deletion or addition, as compared to the amino acid region 1-1315 of SEQ ID NO: 8; a BaNT variant comprising amino acids 1-1268 of SEQ ID NO: 9 will have at least one amino acid difference, such as, e.g., an amino acid substitution, deletion or addition, as compared to the amino acid region 1-1268 of SEQ ID NO: 9; and a BuNT variant comprising amino acids 1-1251 of SEQ ID NO: 10 will have at least one amino acid difference, such as, e.g., an amino acid substitution, deletion or addition, as compared to the amino acid region 1-1251 of SEQ ID NO: 10.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align- M, see, e.g., Ivo Van Walle et al., *Align-M—A New Algorithm for Multiple Alignment of Highly Divergent Sequences*, 20(9) Bioinformatics:1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

As used herein, the term "naturally occurring Clostridial toxin variant" means any Clostridial toxin produced without the aid of any human manipulation, including, without limitation, Clostridial toxin isoforms produced from alternatively-spliced transcripts, Clostridial toxin isoforms produced by spontaneous mutation and Clostridial toxin subtypes. Non-limiting examples of a Clostridial toxin isoform include, e.g., BoNT/A isoforms, BoNT/B isoforms, BoNT/C1 isoforms, BoNT/D isoforms, BoNT/E isoforms, BoNT/F isoforms, BoNT/G isoforms, TeNT isoforms, BaNT isoforms and BuNT isoforms. Non-limiting examples of a Clostridial toxin subtype include, e.g., BoNT/A subtypes BoNT/A1, BoNT/A2, BoNT/A3 and BoNT/A4; BoNT/B subtypes BoNT/B1, BoNT/B2, BoNT/B bivalent and BoNT/B nonproteolytic; BoNT/C1 subtypes BoNT/C1-1 and BoNT/C1-2; BoNT/E subtypes BoNT/E1, BoNT/E2 and BoNT/E3; and BoNT/F subtypes BoNT/F1, BoNT/F2, BoNT/F3 and BoNT/F4.

As used herein, the term "non-naturally occurring Clostridial toxin variant" means any Clostridial toxin produced with the aid of human manipulation, including, without limitation, Clostridial toxins produced by genetic engineering using random mutagenesis or rational design and Clostridial toxins produced by chemical synthesis. Non-limiting examples of non-naturally occurring Clostridial toxin variants include, e.g., conservative Clostridial toxin variants, non-conservative Clostridial toxin variants, Clostridial toxin chimeric variants and active Clostridial toxin fragments.

As used herein, the term "conservative Clostridial toxin variant" means a Clostridial toxin that has at least one amino acid substituted by another amino acid or an amino acid analog that has at least one property similar to that of the original amino acid from the reference Clostridial toxin sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin variant can function in substantially the same manner as the reference Clostridial toxin on which the conservative Clostridial toxin variant is based, and can be substituted for the reference Clostridial toxin in any aspect of the present invention. A conservative Clostridial toxin variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin on which the conservative Clostridial toxin variant is based. A conservative Clostridial toxin variant can also substitute at least 10 contiguous amino acids, at least 15 contiguous amino acids, at least 20 contiguous amino acids, or at least 25 contiguous amino acids from the reference Clostridial toxin on which the conservative Clostridial toxin variant is based, that possess at least 50% amino acid identity, 65% amino acid identity, 75% amino acid identity, 85% amino acid identity or 95% amino acid identity to the reference Clostridial toxin on which the conservative Clostridial toxin variant is based. Non-limiting examples of a conservative Clostridial toxin variant include, e.g., conservative BoNT/A variants, conservative BoNT/B variants, conservative BoNT/C1 variants, conservative BoNT/D variants, conservative BoNT/E variants, conservative BoNT/F variants, conservative BoNT/G variants, conservative TeNT variants, conservative BaNT variants and conservative BuNT variants.

As used herein, the term "non-conservative Clostridial toxin variant" means a Clostridial toxin in which 1) at least one amino acid is deleted from the reference Clostridial toxin on which the non-conservative Clostridial toxin variant is based; 2) at least one amino acid added to the reference Clostridial toxin on which the non-conservative Clostridial toxin is based; or 3) at least one amino acid is substituted by another amino acid or an amino acid analog that does not share any property similar to t h at of the original amino acid from the reference Clostridial toxin sequence (Table 1). A non-conservative Clostridial toxin variant can function in substantially the same manner as the reference Clostridial toxin on which the non-conservative Clostridial toxin variant is based, and can be substituted for the reference Clostridial toxin in any aspect of the present invention. A non-conservative Clostridial toxin variant can delete one or more amino acids, two or more amino acids, three or more amino acids, four or more amino acids, five or more amino acids, and ten or more amino acids from the reference Clostridial toxin on which the non-conservative Clostridial toxin variant is based. A non-conservative Clostridial toxin variant can add one or more amino acids, two or more amino acids, three or more amino acids, four or more amino acids, five or more amino acids, and ten or more amino acids to the reference Clostridial toxin on which the non-conservative Clostridial toxin variant is based. A non-conservative Clostridial toxin variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin on which the non-conservative Clostridial toxin variant is based. A non-conservative Clostridial toxin variant can also substitute at least 10 contiguous amino acids, at least 15 contiguous amino acids, at least 20 contiguous amino acids, or at least 25 contiguous amino acids from the reference Clostridial toxin on which the non-conservative Clostridial toxin variant is based, that possess at least 50% amino acid identity, 65% amino acid identity, 75% amino acid identity, 85% amino acid identity or 95% amino acid identity to the reference Clostridial toxin on which the non-conservative Clostridial toxin variant is based. Non-limiting examples of a non-conservative Clostridial toxin variant include, e.g., non-conservative BoNT/A variants, non-conservative BoNT/B variants, non-conservative BoNT/C1 variants, non-conservative BoNT/D variants, non-conservative BoNT/E variants, non-conservative BoNT/F variants, non-conservative BoNT/G variants, non-conservative TeNT variants, non-conservative BaNT variants and non-conservative BuNT variants.

As used herein, the term "Clostridial toxin chimeric variant" means a molecule comprising at least a portion of a Clostridial toxin and at least a portion of at least one other protein to form a toxin with at least one property different from the reference Clostridial toxins of Table 1. One class of Clostridial toxin chimeric variant comprises a modified Clostridial toxin were the endogenous cell binding domain of a naturally-occurring Clostridial toxin is either modified or replaced with a cell binding domain of another molecule. Such modified Clostridial toxin possesses an altered cell binding activity because the modified toxin can, e.g., use the same receptor present on the surface of a naturally occurring Clostridial toxin target cell, referred to as an enhanced cell binding activity for a naturally-occurring Clostridial toxin target cell; use a different receptor present on the surface of a naturally occurring Clostridial toxin target cell, referred to as an altered cell binding activity for a naturally-occurring Clostridial toxin target cell, or use a different receptor present on the surface of the non-Clostridial toxin target cell, referred to as an altered cell binding activity for a non-naturally-occurring Clostridial toxin target cell.

A Clostridial toxin chimeric variant can be a modified Clostridial toxin with an enhanced cell binding activity capable of intoxicating a naturally occurring Clostridial toxin target cell, e.g., a motor neuron. One way this enhanced binding activity is achieved by modifying the endogenous targeting domain of a naturally-occurring Clostridial toxin in order to enhance a cell binding activity of the toxin for its naturally-occurring receptor. Such modifications to a targeting domain result in, e.g., a enhanced cell binding activity that increases binding affinity for an endogenous Clostridial toxin receptor present on a naturally-occurring Clostridial toxin target cell; an enhanced cell binding activity that increases binding specificity for a subgroup of endogenous Clostridial toxin receptors present on a naturally-occurring Clostridial toxin target cell; or an enhanced cell binding activity that increases both binding affinity and binding specificity. Non-limiting examples of modified Clostridial toxins an enhanced cell binding activity for a naturally-occurring Clostridial toxin receptor are described in, e.g., Lance E. Steward, et al., *Modified Clostridial Toxins with Enhanced Targeting Capabilities For Endogenous Clostridial Toxin Receptors*, International Patent Publication No. 2006/008956 (Mar. 14, 2006), Lance E. Steward, *Modified Clostridial Toxins with Enhanced Translocation Capability, and Enhanced Targeting Activity*, U.S. Provisional Patent Application No. 60/807,063 (Jul. 11, 2006); the content of which are all hereby incorporated by reference in their entirety.

A Clostridial toxin chimeric variant can be a modified Clostridial toxin with an altered cell binding activity capable of intoxicating a naturally occurring Clostridial toxin target cell, e.g., a motor neuron. One way this altered capability is achieved by replacing the endogenous targeting domain of a naturally-occurring Clostridial toxin with a targeting domain of another molecule that selectively binds to a different receptor present on the surface of a naturally occurring Clostridial toxin target cell. Such a modification to a targeting domain results in a modified toxin that is able to selectively bind to a non-Clostridial toxin receptor (target receptor) present on a Clostridial toxin target cell. This enhanced binding activity for a naturally occurring Clostridial toxin target cell allows for lower effective doses of a modified Clostridial toxin to be administered to an individual because more toxin will be delivered to the target cell. Thus, modified Clostridial toxins with an enhanced binding activity will reduce the undesirable dispersal of the toxin to areas not targeted for treatment, thereby reducing or preventing the undesirable side-effects associated with diffusion of a Clostridial toxin to an unwanted location. Non-limiting examples of modified Clostridial toxins with an altered cell binding capability for a Clostridial toxin target cell are described in, e.g., Lance E. Steward et al., Modified Clostridial Toxins with Altered Targeting Capabilities For Clostridial Toxin Target Cells, International Patent Publication No. 2006/009831 (Mar. 14, 2005); Lance E. Steward et al., *Multivalent Clostridial Toxin Derivatives and Methods of Their Use*, U.S. patent application Ser. No. 11/376,696 (Mar. 15, 2006); and Lance E. Steward, *Modified Clostridial Toxins with Enhanced Translocation Capabilities and Altered Targeting Activity for Clostridial Toxin Target Cells*, U.S. Provisional Patent Application No. 60/807,062, (Jul. 11, 2006); the contents of all of which are hereby incorporated by reference in their entirety.

A Clostridial toxin chimeric variant can be a modified Clostridial toxin with an altered cell binding activity capable of intoxicating a cell other than a naturally occurring Clostridial toxin target cell, e.g., a cell other than a motor neuron. These modified toxins achieve this intoxication by using a target receptor present on non-Clostridial toxin target cell. This re-targeted capability is achieved by replacing a naturally-occurring targeting domain of a Clostridial toxin with a targeting domain showing a selective binding activity for a non-Clostridial toxin receptor present in a non-Clostridial toxin target cell. Such modifications to a targeting domain result in a modified toxin that is able to selectively bind to a non-Clostridial toxin receptor (target receptor) present on a non-Clostridial toxin target cell (re-targeted). A modified Clostridial toxin with an altered targeting activity for a non-Clostridial toxin target cell can bind to a target receptor, translocate into the cytoplasm, and exert its proteolytic effect on the SNARE complex of the non-Clostridial toxin target cell. Non-limiting examples of modified Clostridial toxins with an altered targeting activity for a non-Clostridial toxin target cell are described in, e.g., Keith A. Foster et al., Clostridial Toxin Derivatives Able To Modify Peripheral Sensory Afferent Functions, U.S. Pat. No. 5,989, 545 (Nov. 23, 1999); Clifford C. Shone et al., Recombinant Toxin Fragments, U.S. Pat. No. 6,461,617 (Oct. 8, 2002); Conrad P. Quinn et al., Methods and Compounds for the Treatment of Mucus Hypersecretion, U.S. Pat. No. 6,632,440 (Oct. 14, 2003); Lance E. Steward et al., Methods And Compositions For The Treatment Of Pancreatitis, U.S. Pat. No. 6,843,998 (Jan. 18, 2005); Stephan Donovan, Clostridial Toxin Derivatives and Methods For Treating Pain, U.S. Patent Publication 2002/0037833 (Mar. 28, 2002); Keith A. Foster et al., Inhibition of Secretion from Non-neural Cells, U.S. Patent Publication 2003/0180289 (Sep. 25, 2003); J. Oliver Dolly et al., Activatable Recombinant Neurotoxins, International Patent Publication WO 2001/014570 (Mar. 1, 2001); Keith A. Foster et al., Re-targeted Toxin Conjugates, International Patent Publication WO 2005/023309 (Mar. 17, 2005); Lance E. Steward et al., Multivalent Clostridial Toxin Derivatives and Methods of Their Use, U.S. patent application Ser. No. 11/376,696 (Mar. 15, 2006); Keith A. Foster, Fusion Proteins, International Patent Publication WO 2006/059093 (Jun. 8, 2005); Keith A. Foster, Non-Cytotoxic Protein Conjugates, International Patent Publication WO 2006/059105 (Jun. 8, 2005); and Lance E. Steward, Modified Clostridial Toxins with Enhanced Translocation Capabilities and Altered Targeting Capabilities for Non-Clostridial Toxin Target Cells, U.S. Provisional Patent Application No. 60/807,059, (Jul. 11, 2006); the contents of all of which are hereby incorporated by reference in their entirety. The ability to re-target the therapeutic effects associated with Clostridial toxins has greatly extended the number of medicinal applications able to use a Clostridial toxin therapy. As a non-limiting example, modified Clostridial toxins retargeted to sensory neurons are useful in treating various kinds of chronic pain, such as, e.g., hyperalgesia and allodynia, neuropathic pain and inflammatory pain, see, e.g., Foster, supra, (1999); and Donovan, supra, (2002); and Stephan Donovan, Method For Treating Neurogenic Inflammation Pain with Botulinum Toxin and Substance P Components, U.S. Pat. No. 7,022,329 (Apr. 4, 2006). As another non-limiting example, modified Clostridial toxins retargeted to pancreatic cells are useful in treating pancreatitis, see, e.g., Steward, supra, (2005).

Thus, in an embodiment, a Clostridial toxin chimeric variant can comprise a modified Clostridial toxin disclosed in the present specification where the binding domain comprises an enhanced cell binding activity capable of intoxicating a naturally occurring Clostridial toxin target cell. In another embodiment, a Clostridial toxin chimeric variant can comprise a modified Clostridial toxin disclosed in the present specification where the binding domain comprises an altered cell binding activity capable of intoxicating a naturally occurring Clostridial toxin target cell. In still another embodiment, a Clostridial toxin chimeric variant can comprise a modified Clostridial toxin disclosed in the present specification where the binding domain comprises an altered cell binding activity capable of intoxicating a non-naturally occurring Clostridial toxin target cell.

It is also envisioned that any of a variety of Clostridial toxin fragments can be useful in aspects of the present invention with the proviso that these active fragments can execute the overall cellular mechanism whereby a Clostridial toxin proteolytically cleaves a substrate. Thus, aspects of this embodiment can include Clostridial toxin fragments having a length of, e.g., at least 300 amino acids, at least 400 amino acids, at least 500 amino acids, at least 600 amino acids, at least 700 amino acids, at least 800 amino acids, at least 900 amino acids, at least 1000 amino acids, at least 1100 amino acids and at least 1200 amino acids. Other aspects of this embodiment, can include Clostridial toxin fragments having a length of, e.g., at most 300 amino acids, at most 400 amino acids, at most 500 amino acids, at most 600 amino acids, at most 700 amino acids, at most 800 amino acids, at most 900 amino acids, at most 1000 amino acids, at most 1100 amino acids and at most 1200 amino acids.

It is also envisioned that any of a variety of Clostridial toxin fragments comprising the light chain can be useful in aspects of the present invention with the proviso that these light chain fragments can specifically target the core components of the neurotransmitter release apparatus and thus participate in executing the overall cellular mechanism whereby a Clostridial toxin proteolytically cleaves a substrate. The light chains of Clostridial toxins are approximately 420-460 amino acids in length and comprise an enzymatic domain (Table 1). Research has shown that the entire length of a Clostridial toxin light chain is not necessary for the enzymatic activity of the enzymatic domain. As a non-limiting example, the first eight amino acids of the BoNT/A light chain (residues 1-8 of SEQ ID NO: 1) are not required for enzymatic activity. As another non-limiting example, the first eight amino acids of the TeNT light chain (residues 1-8 of SEQ ID NO: 8) are not required for enzymatic activity. Likewise, the carboxyl-terminus of the light chain is not necessary for activity. As a non-limiting example, the last 32 amino acids of the BoNT/A light chain (residues 417-448 of SEQ ID NO: 1) are not required for enzymatic activity. As another non-limiting example, the last 31 amino acids of the TeNT light chain (residues 427-457 of SEQ ID NO: 8) are not required for enzymatic activity. Thus, aspects of this embodiment can include Clostridial toxin light chains comprising an enzymatic domain having a length of, e.g., at least 350 amino acids, at least 375 amino acids, at least 400 amino acids, at least 425 amino acids and at least 450 amino acids. Other aspects of this embodiment can include Clostridial toxin light chains comprising an enzymatic domain having a length of, e.g., at most 350 amino acids, at most 375 amino acids, at most 400 amino acids, at most 425 amino acids and at most 450 amino acids.

It is also envisioned that any of a variety of Clostridial toxin $H_N$ regions comprising a translocation domain can be useful in aspects of the present invention with the proviso that these active fragments can facilitate the release of the LC from intracellular vesicles into the cytoplasm of the target cell and thus participate in executing the overall cellular mechanism whereby a Clostridial toxin proteolytically cleaves a substrate. The $H_N$ regions from the heavy chains of Clostridial toxins are approximately 410-430 amino acids in length and comprise a translocation domain (Table 1). Research has shown that the entire length of a $H_N$ region from a Clostridial toxin heavy chain is not necessary for the translocating activity of the translocation domain. Thus, aspects of this embodiment can include Clostridial toxin $H_N$ regions comprising a translocation domain having a length of, e.g., at least 350 amino acids, at least 375 amino acids, at least 400 amino acids and at least 425 amino acids. Other aspects of this embodiment can include Clostridial toxin $H_N$ regions comprising translocation domain having a length of, e.g., at most 350 amino acids, at most 375 amino acids, at most 400 amino acids and at most 425 amino acids.

It is also envisioned that any of a variety of Clostridial toxin $H_C$ regions comprising a binding domain can be useful in aspects of the present invention with the proviso that these active fragments can determine the binding activity and binding specificity of the toxin to the receptor complex located at the surface of the target cell execute the overall cellular mechanism whereby a Clostridial toxin proteolytically cleaves a substrate. The $H_C$ regions from the heavy chains of Clostridial toxins are approximately 400-440 amino acids in length and comprise a binding domain (Table 1). Research has shown that the entire length of a $H_C$ region from a Clostridial toxin heavy chain is not necessary for the binding activity of the binding domain. Thus, aspects of this embodiment can include Clostridial toxin $H_C$ regions comprising a binding domain having a length of, e.g., at least 350 amino acids, at least 375 amino acids, at least 400 amino acids and at least 425 amino acids. Other aspects of this embodiment can include Clostridial toxin $H_C$ regions comprising a binding domain having a length of, e.g., at most 350 amino acids, at most 375 amino acids, at most 400 amino acids and at most 425 amino acids.

Thus, in an embodiment, a Clostridial toxin comprises a Clostridial toxin enzymatic domain, a Clostridial toxin translocation domain and a Clostridial toxin binding domain. In an aspect of this embodiment, a Clostridial toxin comprises a naturally occurring Clostridial toxin variant, such as, e.g., a Clostridial toxin isoform or a Clostridial toxin subtype. In another aspect of this embodiment, a Clostridial toxin comprises a non-naturally occurring Clostridial toxin variant, such as, e.g., a conservative Clostridial toxin variant, a non-conservative Clostridial toxin variant or an active Clostridial toxin fragment, or any combination thereof. In another aspect of this embodiment, a Clostridial toxin comprises a Clostridial toxin enzymatic domain or an active fragment thereof, a Clostridial toxin translocation domain or an active fragment thereof, a Clostridial toxin binding domain or an active fragment thereof, or any combination thereof. In other aspects of this embodiment, a Clostridial toxin can comprise a BoNT/A, a BoNT/B, a BoNT/C1, a BoNT/D, a BoNT/E, a BoNT/F, a BoNT/G, a TeNT, a BaNT or a BuNT.

In another embodiment, a Clostridial toxin comprises a BoNT/A. In an aspect of this embodiment, a BoNT/A comprises a BoNT/A enzymatic domain, a BoNT/A translocation domain and a BoNT/A binding domain. In another aspect of this embodiment, a BoNT/A comprises SEQ ID NO: 1. In another aspect of this embodiment, a BoNT/A comprises a naturally occurring BoNT/A variant, such as, e.g., a BoNT/A isoform or a BoNT/A subtype. In another aspect of this embodiment, a BoNT/A comprises a naturally occurring BoNT/A variant of SEQ ID NO: 1, such as, e.g., a BoNT/A isoform of SEQ ID NO: 1 or a BoNT/A subtype of SEQ ID NO: 1. In still another aspect of this embodiment, a BoNT/A comprises a non-naturally occurring BoNT/A variant, such as, e.g., a conservative BoNT/A variant, a non-conservative BoNT/A variant or an active BoNT/A fragment, or any combination thereof. In still another aspect of this embodiment, a BoNT/A comprises a non-naturally occurring BoNT/A variant of SEQ ID NO: 1, such as, e.g., a conservative BoNT/A variant of SEQ ID NO: 1, a non-conservative BoNT/A variant of SEQ ID NO: 1 or an active BoNT/A fragment of SEQ ID NO: 1, or any combination thereof. In yet another aspect of this embodiment, a BoNT/A comprises a BoNT/A enzymatic domain or an active fragment thereof, a BoNT/A translocation domain or an active fragment thereof, a BoNT/A binding domain or an active fragment thereof, or any combination thereof. In yet another aspect of this embodiment, a BoNT/A comprising a BoNT/A enzymatic domain of amino acids 1-448 from SEQ ID NO: 1 or an active fragment thereof, a BoNT/A translocation domain of amino acids 449-871 from SEQ ID NO: 1 or an active fragment thereof, a BoNT/A binding domain of amino acids 872-1296 from SEQ ID NO: 1 or an active fragment thereof, and any combination thereof.

In other aspects of this embodiment, a BoNT/A comprises a polypeptide having, e.g., at least 70% amino acid identity with SEQ ID NO: 1, at least 75% amino acid identity with the SEQ ID NO: 1, at least 80% amino acid identity with SEQ ID NO: 1, at least 85% amino acid identity with SEQ ID NO: 1, at least 90% amino acid identity with SEQ ID NO: 1 or at least 95% amino acid identity with SEQ ID NO: 1. In yet other aspects of this embodiment, a BoNT/A comprises a polypeptide having, e.g., at most 70% amino acid identity with SEQ ID NO: 1, at most 75% amino acid identity with the SEQ ID NO: 1, at most 80% amino acid identity with SEQ ID NO: 1, at most 85% amino acid identity with SEQ ID NO: 1, at most 90% amino acid identity with SEQ ID NO: 1 or at most 95% amino acid identity with SEQ ID NO: 1.

In other aspects of this embodiment, a BoNT/A comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 1. In yet other aspects of this embodiment, a BoNT/A comprises a polypeptide having, e.g., at most one, two, three, four, five, six, seven, eight, nine, 10, 20, 30, 40, 50, 100, 200 or 500 non-contiguous amino acid deletions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 non-contiguous amino acid deletions relative to SEQ ID NO: 1. In still other aspects of this embodiment, a BoNT/A comprises a polypeptide having, e.g., at most one, two, three, four, five, six, seven, eight, nine, 10, 20, 30, 40, 50, 100, 200 or 500 non-contiguous amino acid additions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 non-contiguous amino acid additions relative to SEQ ID NO: 1.

In other aspects of this embodiment, a BoNT/A comprises a polypeptide having, e.g., at most one, two, three, four, five, six, seven, eight, nine, 10, 20, 30, 40, 50, 100, 200 or 500 contiguous amino acid substitutions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 contiguous amino acid substitutions relative to SEQ ID NO: 1. In yet other aspects of this embodiment, a BoNT/A comprises a polypeptide having, e.g., at most one, two, three, four, five, six, seven, eight, nine, 10, 20, 30, 40, 50, 100, 200 or 500 contiguous amino acid deletions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 contiguous amino acid deletions relative to SEQ ID NO: 1. In still other aspects of this embodiment, a BoNT/A comprises a polypeptide having, e.g., at most one, two, three, four, five, six, seven, eight, nine, 10, 20, 30, 40, 50, 100, 200 or 500 contiguous amino acid additions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 contiguous amino acid additions relative to SEQ ID NO: 1.

In another embodiment, a Clostridial toxin comprises a BoNT/B. In an aspect of this embodiment, a BoNT/B comprises a BoNT/B enzymatic domain, a BoNT/B translocation domain and a BoNT/B binding domain. In another aspect of this embodiment, a BoNT/B comprises SEQ ID NO: 2. In another aspect of this embodiment, a BoNT/B comprises a naturally occurring BoNT/B variant, such as, e.g., a BoNT/B isoform or a BoNT/B subtype. In another aspect of this embodiment, a BoNT/B comprises a naturally occurring BoNT/B variant of SEQ ID NO: 2, such as, e.g., a BoNT/B isoform of SEQ ID NO: 2 or a BoNT/B subtype of SEQ ID NO: 2. In still another aspect of this embodiment, a BoNT/B comprises a non-naturally occurring BoNT/B variant, such as, e.g., a conservative BoNT/B variant, a non-conservative BoNT/B variant or an active BoNT/B fragment, or any combination thereof. In still another aspect of this embodiment, a BoNT/B comprises a non-naturally occurring BoNT/B variant of SEQ ID NO: 2, such as, e.g., a conservative BoNT/B variant of SEQ ID NO: 2, a non-conservative BoNT/B variant of SEQ ID NO: 2 or an active BoNT/B fragment of SEQ ID NO: 2, or any combination thereof. In yet another aspect of this embodiment, a BoNT/B comprising a BoNT/B enzymatic domain or an active fragment thereof, a BoNT/B translocation domain or active fragment thereof, a BoNT/B binding domain or active fragment thereof, and any combination thereof. In yet another aspect of this embodiment, a BoNT/B comprising a BoNT/B enzymatic domain of amino acids 1-441 from SEQ ID NO: 2 or active fragment thereof, a BoNT/B translocation domain of amino acids 442-858 from SEQ ID NO: 2 or active fragment thereof, a BoNT/B binding domain of amino acids 859-1291 from SEQ ID NO: 2 or active fragment thereof, and any combination thereof.

In other aspects of this embodiment, a BoNT/B comprises a polypeptide having, e.g., at least 70% amino acid identity with SEQ ID NO: 2, at least 75% amino acid identity with the SEQ ID NO: 2, at least 80% amino acid identity with SEQ ID NO: 2, at least 85% amino acid identity with SEQ ID NO: 2, at least 90% amino acid identity with SEQ ID NO: 2 or at least 95% amino acid identity with SEQ ID NO: 2. In yet other aspects of this embodiment, a BoNT/B comprises a polypeptide having, e.g., at most 70% amino acid identity with SEQ ID NO: 2, at most 75% amino acid identity with the SEQ ID NO: 2, at most 80% amino acid identity with SEQ ID NO: 2, at most 85% amino acid identity with SEQ ID NO: 2, at most 90% amino acid identity with SEQ ID NO: 2 or at most 95% amino acid identity with SEQ ID NO: 2.

In other aspects of this embodiment, a BoNT/B comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 2. In yet other aspects of this embodiment, a BoNT/B comprises a polypeptide having, e.g., at most one, two, three, four, five, six, seven, eight, nine, 10, 20, 30, 40, 50, 100, 200 or 500 non-contiguous amino acid deletions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 non-contiguous amino acid deletions relative to SEQ ID NO: 2. In still other aspects of this embodiment, a BoNT/B comprises a polypeptide having, e.g., at most one, two, three, four, five, six, seven, eight, nine, 10, 20, 30, 40, 50, 100, 200 or 500 non-contiguous amino acid additions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 non-contiguous amino acid additions relative to SEQ ID NO: 2.

In other aspects of this embodiment, a BoNT/B comprises a polypeptide having, e.g., at most one, two, three, four, five, six, seven, eight, nine, 10, 20, 30, 40, 50, 100, 200 or 500 contiguous amino acid substitutions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 contiguous amino acid substitutions relative to SEQ ID NO: 2. In yet other aspects of this embodiment, a BoNT/B comprises a polypeptide having, e.g., at most one, two, three, four, five, six, seven, eight, nine, 10, 20, 30, 40, 50, 100, 200 or 500 contiguous amino acid deletions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 contiguous amino acid deletions relative to SEQ ID NO: 2. In still other aspects of this embodiment, a BoNT/B comprises a polypeptide having, e.g., at most one, two, three, four, five, six, seven, eight, nine, 10, 20, 30, 40, 50, 100, 200 or 500 contiguous amino acid additions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 contiguous amino acid additions relative to SEQ ID NO: 2.

In another embodiment, a Clostridial toxin comprises a BoNT/C1. In an aspect of this embodiment, a BoNT/C1 comprises a BoNT/C1 enzymatic domain, a BoNT/C1 translocation domain and a BoNT/C1 binding domain. In another aspect of this embodiment, a BoNT/C1 comprises SEQ ID NO: 3. In another aspect of this embodiment, a BoNT/C1 comprises a naturally occurring BoNT/C1 variant, such as, e.g., a BoNT/C1 isoform or a BoNT/C1 subtype. In another aspect of this embodiment, a BoNT/C1 comprises a naturally occurring BoNT/C1 variant of SEQ ID NO: 3, such as, e.g., a BoNT/C1 isoform of SEQ ID NO: 3 or a BoNT/C1 subtype of SEQ ID NO: 3. In still another aspect of this embodiment, a BoNT/C1 comprises a non-naturally occurring BoNT/C1 variant, such as, e.g., a conservative BoNT/C1 variant, a non-conservative BoNT/C1 variant or an active BoNT/C1 fragment, or any combination thereof. In still another aspect of this embodiment, a BoNT/C1 comprises a non-naturally occurring BoNT/C1 variant of SEQ ID NO: 3, such as, e.g., a conservative BoNT/C1 variant of SEQ ID NO: 3, a non-conservative BoNT/C1 variant of SEQ ID NO: 3 or an active BoNT/C1 fragment of SEQ ID NO: 3, or any combination thereof. In yet another aspect of this embodiment, a BoNT/C1 comprises a BoNT/C1 enzymatic domain or active fragment thereof, a BoNT/C1 translocation domain or active fragment thereof, a BoNT/C1 binding domain or active fragment thereof, and any combination thereof. In yet another aspect of this embodiment, a BoNT/C1 comprises a BoNT/C1 enzymatic domain of amino acid 1-449 from SEQ ID NO: 3 or active fragment thereof, a BoNT/C1 translocation domain of amino acids 450-866 from SEQ ID NO: 3 or active fragment thereof, a BoNT/C1 binding domain of amino acids 867-1291 from SEQ ID NO: 3 or active fragment thereof, and any combination thereof.

In other aspects of this embodiment, a BoNT/C1 comprises a polypeptide having, e.g., at least 70% amino acid identity with SEQ ID NO: 3, at least 75% amino acid identity with the SEQ ID NO: 3, at least 80% amino acid identity with SEQ ID NO: 3, at least 85% amino acid identity with SEQ ID NO: 3, at least 90% amino acid identity with SEQ ID NO: 3 or at least 95% amino acid identity with SEQ ID NO: 3. In yet other aspects of this embodiment, a BoNT/C1 comprises a polypeptide having, e.g., at most 70% amino acid identity with SEQ ID NO: 3, at most 75% amino acid identity with the SEQ ID NO: 3, at most 80% amino acid identity with SEQ ID NO: 3, at most 85% amino acid identity with SEQ ID NO: 3, at most 90% amino acid identity with SEQ ID NO: 3 or at most 95% amino acid identity with SEQ ID NO: 3.

In other aspects of this embodiment, a BoNT/C1 comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 3. In yet other aspects of this embodiment, a BoNT/C1 comprises a polypeptide having, e.g., at most one, two, three, four, five, six, seven, eight, nine, 10, 20, 30, 40, 50, 100, 200 or 500 non-contiguous amino acid deletions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 non-contiguous amino acid deletions relative to SEQ ID NO: 3. In still other aspects of this embodiment, a BoNT/C1 comprises a polypeptide having, e.g., at most one, two, three, four, five, six, seven, eight, nine, 10, 20, 30, 40, 50, 100, 200 or 500 non-contiguous amino acid additions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 non-contiguous amino acid additions relative to SEQ ID NO: 3.

In other aspects of this embodiment, a BoNT/C1 comprises a polypeptide having, e.g., at most one, two, three, four, five, six, seven, eight, nine, 10, 20, 30, 40, 50, 100, 200 or 500 contiguous amino acid substitutions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 contiguous amino acid substitutions relative to SEQ ID NO: 3. In yet other aspects of this embodiment, a BoNT/C1 comprises a polypeptide having, e.g., at most one, two, three, four, five, six, seven, eight, nine, 10, 20, 30, 40, 50, 100, 200 or 500 contiguous amino acid deletions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 contiguous amino acid deletions relative to SEQ ID NO: 3. In still other aspects of this embodiment, a BoNT/C1 comprises a polypeptide having, e.g., at most one, two, three, four, five, six, seven, eight, nine, 10, 20, 30, 40, 50, 100, 200 or 500 contiguous amino acid additions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 contiguous amino acid additions relative to SEQ ID NO: 3.

In another embodiment, a Clostridial toxin comprises a BoNT/D. In an aspect of this embodiment, a BoNT/D comprises a BoNT/D enzymatic domain, a BoNT/D translocation domain and a BoNT/D binding domain. In another aspect of this embodiment, a BoNT/D comprises SEQ ID NO: 4. In another aspect of this embodiment, a BoNT/D comprises a naturally occurring BoNT/D variant, such as, e.g., a BoNT/D isoform or a BoNT/D subtype. In another aspect of this embodiment, a BoNT/D comprises a naturally occurring BoNT/D variant of SEQ ID NO: 4, such as, e.g., a BoNT/D isoform of SEQ ID NO: 4 or a BoNT/D subtype of SEQ ID NO: 4. In still another aspect of this embodiment, a BoNT/D comprises a non-naturally occurring BoNT/D variant, such as, e.g., a conservative BoNT/D variant, a non-conservative BoNT/D variant or an active BoNT/D fragment, or any combination thereof. In still another aspect of this embodiment, a BoNT/D comprises a non-naturally occurring BoNT/D variant of SEQ ID NO: 4, such as, e.g., a conservative BoNT/D variant of SEQ ID NO: 4, a non-conservative BoNT/D variant of SEQ ID NO: 4 or an active BoNT/D fragment of SEQ ID NO: 4, or any combination thereof. In yet another aspect of this embodiment, a BoNT/D comprises a BoNT/D enzymatic domain or an active fragment thereof, a BoNT/D translocation domain or an active fragment thereof, a BoNT/D binding domain or an active fragment thereof, or any combination thereof. In yet another aspect of this embodiment, a BoNT/D comprising a BoNT/D enzymatic domain of amino acids 1-445 from SEQ ID NO: 4 or an active fragment thereof, a BoNT/D translocation domain of amino acids 446-862 from SEQ ID NO: 4 or an active fragment thereof, a BoNT/D binding domain of amino acids 863-1276 from SEQ ID NO: 4 or an active fragment thereof, and any combination thereof.

In other aspects of this embodiment, a BoNT/D comprises a polypeptide having, e.g., at least 70% amino acid identity with SEQ ID NO: 4, at least 75% amino acid identity with the SEQ ID NO: 4, at least 80% amino acid identity with SEQ ID NO: 4, at least 85% amino acid identity with SEQ ID NO: 4, at least 90% amino acid identity with SEQ ID NO: 4 or at least 95% amino acid identity with SEQ ID NO: 4. In yet other aspects of this embodiment, a BoNT/D comprises a polypeptide having, e.g., at most 70% amino acid identity with SEQ ID NO: 4, at most 75% amino acid identity with the SEQ ID NO: 4, at most 80% amino acid identity with SEQ ID NO: 4, at most 85% amino acid identity with SEQ ID NO: 4, at most 90% amino acid identity with SEQ ID NO: 4 or at most 95% amino acid identity with SEQ ID NO: 4.

In other aspects of this embodiment, a BoNT/D comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 4. In yet other aspects of this embodiment, a BoNT/D comprises a polypeptide having, e.g., at most one, two, three, four, five, six, seven, eight, nine, 10, 20, 30, 40, 50, 100, 200 or 500 non-contiguous amino acid deletions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 non-contiguous amino acid deletions relative to SEQ ID NO: 4. In still other aspects of this embodiment, a BoNT/D comprises a polypeptide having, e.g., at most one, two, three, four, five, six, seven, eight, nine, 10, 20, 30, 40, 50, 100, 200 or 500 non-contiguous amino acid additions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 non-contiguous amino acid additions relative to SEQ ID NO: 4.

In other aspects of this embodiment, a BoNT/D comprises a polypeptide having, e.g., at most one, two, three, four, five, six, seven, eight, nine, 10, 20, 30, 40, 50, 100, 200 or 500 contiguous amino acid substitutions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 contiguous amino acid substitutions relative to SEQ ID NO: 4. In yet other aspects of this embodiment, a BoNT/D comprises a polypeptide having, e.g., at most one, two, three, four, five, six, seven, eight, nine, 10, 20, 30, 40, 50, 100, 200 or 500 contiguous amino acid deletions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 contiguous amino acid deletions relative to SEQ ID NO: 4. In still other aspects of this embodiment, a BoNT/D comprises a polypeptide having, e.g., at most one, two, three, four, five, six, seven, eight, nine, 10, 20, 30, 40, 50, 100, 200 or 500 contiguous amino acid additions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 contiguous amino acid additions relative to SEQ ID NO: 4.

In another embodiment, a Clostridial toxin comprises a BoNT/E. In an aspect of this embodiment, a BoNT/E comprises a BoNT/E enzymatic domain, a BoNT/E translocation domain and a BoNT/E binding domain. In another aspect of this embodiment, a BoNT/E comprises SEQ ID NO: 5. In another aspect of this embodiment, a BoNT/E comprises a naturally occurring BoNT/E variant, such as, e.g., a BoNT/E isoform or a BoNT/E subtype. In another aspect of this embodiment, a BoNT/E comprises a naturally occurring BoNT/E variant of SEQ ID NO: 5, such as, e.g., a BoNT/E isoform of SEQ ID NO: 5 or a BoNT/E subtype of SEQ ID NO: 5. In still another aspect of this embodiment, a BoNT/E comprises a non-naturally occurring BoNT/E variant, such as, e.g., a conservative BoNT/E variant, a non-conservative BoNT/E variant or an active BoNT/E fragment, or any combination thereof. In still another aspect of this embodiment, a BoNT/E comprises a non-naturally occurring BoNT/E variant of SEQ ID NO: 5, such as, e.g., a conservative BoNT/E variant of SEQ ID NO: 5, a non-conservative BoNT/E variant of SEQ ID NO: 5 or an active BoNT/E fragment of SEQ ID NO: 5, or any combination thereof. In yet another aspect of this embodiment, a BoNT/E comprising a BoNT/E enzymatic domain or an active fragment thereof, a BoNT/E translocation domain or active fragment thereof, a BoNT/E binding domain or active fragment thereof, and any combination thereof. In yet another aspect of this embodiment, a BoNT/E comprising a BoNT/E enzymatic domain of amino acids 1-422 from SEQ ID NO: 5 or active fragment thereof, a BoNT/E translocation domain of amino acids 423-845 from SEQ ID NO: 5 or active fragment thereof, a BoNT/E binding domain of amino acids 846-1252 from SEQ ID NO: 5 or active fragment thereof, and any combination thereof.

In other aspects of this embodiment, a BoNT/E comprises a polypeptide having, e.g., at least 70% amino acid identity with SEQ ID NO: 5, at least 75% amino acid identity with the SEQ ID NO: 5, at least 80% amino acid identity with SEQ ID NO: 5, at least 85% amino acid identity with SEQ ID NO: 5, at least 90% amino acid identity with SEQ ID NO: 5 or at least 95% amino acid identity with SEQ ID NO: 5. In yet other aspects of this embodiment, a BoNT/E comprises a polypeptide having, e.g., at most 70% amino acid identity with SEQ ID NO: 5, at most 75% amino acid identity with the SEQ ID NO: 5, at most 80% amino acid identity with SEQ ID NO: 5, at most 85% amino acid identity with SEQ ID NO: 5, at most 90% amino acid identity with SEQ ID NO: 5 or at most 95% amino acid identity with SEQ ID NO: 5.

In other aspects of this embodiment, a BoNT/E comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 5. In yet other aspects of this embodiment, a BoNT/E comprises a polypeptide having, e.g., at most one, two, three, four, five, six, seven, eight, nine, 10, 20, 30, 40, 50, 100, 200 or 500 non-contiguous amino acid deletions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 non-contiguous amino acid deletions relative to SEQ ID NO: 5. In still other aspects of this embodiment, a BoNT/E comprises a polypeptide having, e.g., at most one, two, three, four, five, six, seven, eight, nine, 10, 20, 30, 40, 50, 100, 200 or 500 non-contiguous amino acid additions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 non-contiguous amino acid additions relative to SEQ ID NO: 5.

In other aspects of this embodiment, a BoNT/E comprises a polypeptide having, e.g., at most one, two, three, four, five, six, seven, eight, nine, 10, 20, 30, 40, 50, 100, 200 or 500 contiguous amino acid substitutions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 contiguous amino acid substitutions relative to SEQ ID NO: 5. In yet other aspects of this embodiment, a BoNT/E comprises a polypeptide having, e.g., at most one, two, three, four, five, six, seven, eight, nine, 10, 20, 30, 40, 50, 100, 200 or 500 contiguous amino acid deletions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 contiguous amino acid deletions relative to SEQ ID NO: 5. In still other aspects of this embodiment, a BoNT/E comprises a polypeptide having, e.g., at most one, two, three, four, five, six, seven, eight, nine, 10, 20, 30, 40, 50, 100, 200 or 500 contiguous amino acid additions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 contiguous amino acid additions relative to SEQ ID NO: 5.

In another embodiment, a Clostridial toxin comprises a BoNT/F. In an aspect of this embodiment, a BoNT/F comprises a BoNT/F enzymatic domain, a BoNT/F translocation domain and a BoNT/F binding domain. In another aspect of this embodiment, a BoNT/F comprises SEQ ID NO: 6. In another aspect of this embodiment, a BoNT/F comprises a naturally occurring BoNT/F variant, such as, e.g., a BoNT/F isoform or a BoNT/F subtype. In another aspect of this embodiment, a BoNT/F comprises a naturally occurring BoNT/F variant of SEQ ID NO: 6, such as, e.g., a BoNT/F isoform of SEQ ID NO: 6 or a BoNT/F subtype of SEQ ID NO: 6. In still another aspect of this embodiment, a BoNT/F comprises a non-naturally occurring BoNT/F variant, such as, e.g., a conservative BoNT/F variant, a non-conservative BoNT/F variant or an active BoNT/F fragment, or any combination thereof. In still another aspect of this embodiment, a BoNT/F comprises a non-naturally occurring BoNT/F variant of SEQ ID NO: 6, such as, e.g., a conservative BoNT/F variant of SEQ ID NO: 6, a non-conservative BoNT/F variant of SEQ ID NO: 6 or an active BoNT/F fragment of SEQ ID NO: 6, or any combination thereof. In yet another aspect of this embodiment, a BoNT/F comprises a BoNT/F enzymatic domain or active fragment thereof, a BoNT/F translocation domain or active fragment thereof, a BoNT/F binding domain or active fragment thereof, and any combination thereof. In yet another aspect of this embodiment, a BoNT/F comprises a BoNT/F enzymatic domain of amino acid 1-439 from SEQ ID NO: 6 or active fragment thereof, a BoNT/F translocation domain of amino acids 440-864 from SEQ ID NO: 6 or active fragment thereof, a BoNT/F binding domain of amino acids 865-1274 from SEQ ID NO: 6 or active fragment thereof, and any combination thereof.

In other aspects of this embodiment, a BoNT/F comprises a polypeptide having, e.g., at least 70% amino acid identity with SEQ ID NO: 6, at least 75% amino acid identity with the SEQ ID NO: 6, at least 80% amino acid identity with SEQ ID NO: 6, at least 85% amino acid identity with SEQ ID NO: 6, at least 90% amino acid identity with SEQ ID NO: 6 or at least 95% amino acid identity with SEQ ID NO: 6. In yet other aspects of this embodiment, a BoNT/F comprises a polypeptide having, e.g., at most 70% amino acid identity with SEQ ID NO: 6, at most 75% amino acid identity with the SEQ ID NO: 6, at most 80% amino acid identity with SEQ ID NO: 6, at most 85% amino acid identity with SEQ ID NO: 6, at most 90% amino acid identity with SEQ ID NO: 6 or at most 95% amino acid identity with SEQ ID NO: 6.

In other aspects of this embodiment, a BoNT/F comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 6. In yet other aspects of this embodiment, a BoNT/F comprises a polypeptide having, e.g., at most one, two, three, four, five, six, seven, eight, nine, 10, 20, 30, 40, 50, 100, 200 or 500 non-contiguous amino acid deletions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 non-contiguous amino acid deletions relative to SEQ ID NO: 6. In still other aspects of this embodiment, a BoNT/F comprises a polypeptide having, e.g., at most one, two, three, four, five, six, seven, eight, nine, 10, 20, 30, 40, 50, 100, 200 or 500 non-contiguous amino acid additions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 non-contiguous amino acid additions relative to SEQ ID NO: 6.

In other aspects of this embodiment, a BoNT/F comprises a polypeptide having, e.g., at most one, two, three, four, five, six, seven, eight, nine, 10, 20, 30, 40, 50, 100, 200 or 500 contiguous amino acid substitutions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 contiguous amino acid substitutions relative to SEQ ID NO: 6. In yet other aspects of this embodiment, a BoNT/F comprises a polypeptide having, e.g., at most one, two, three, four, five, six, seven, eight, nine, 10, 20, 30, 40, 50, 100, 200 or 500 contiguous amino acid deletions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 contiguous amino acid deletions relative to SEQ ID NO: 6. In still other aspects of this embodiment, a BoNT/F comprises a polypeptide having, e.g., at most one, two, three, four, five, six, seven, eight, nine, 10, 20, 30, 40, 50, 100, 200 or 500 contiguous amino acid additions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 contiguous amino acid additions relative to SEQ ID NO: 6.

In another embodiment, a Clostridial toxin comprises a BoNT/G. In an aspect of this embodiment, a BoNT/G comprises a BoNT/G enzymatic domain, a BoNT/G translocation domain and a BoNT/G binding domain. In another aspect of this embodiment, a BoNT/G comprises SEQ ID NO: 7. In another aspect of this embodiment, a BoNT/G comprises a naturally occurring BoNT/G variant, such as, e.g., a BoNT/G isoform or a BoNT/G subtype. In another aspect of this embodiment, a BoNT/G comprises a naturally occurring BoNT/G variant of SEQ ID NO: 7, such as, e.g., a BoNT/G isoform of SEQ ID NO: 7 or a BoNT/G subtype of SEQ ID NO: 7. In still another aspect of this embodiment, a BoNT/G comprises a non-naturally occurring BoNT/G variant, such as, e.g., a conservative BoNT/G variant, a non-conservative BoNT/G variant or an active BoNT/G fragment, or any combination thereof. In still another aspect of this embodiment, a BoNT/D comprises a non-naturally occurring BoNT/G variant of SEQ ID NO: 7, such as, e.g., a conservative BoNT/G variant of SEQ ID NO: 7, a non-conservative BoNT/G variant of SEQ ID NO: 7 or an active BoNT/G fragment of SEQ ID NO: 7, or any combination thereof. In yet another aspect of this embodiment, a BoNT/G comprises a BoNT/G enzymatic domain or an active fragment thereof, a BoNT/G transloca- tion domain or an active fragment thereof, a BoNT/G binding domain or an active fragment thereof, or any combination thereof. In yet another aspect of this embodiment, a BoNT/G comprising a BoNT/G enzymatic domain of amino acids 1-446 from SEQ ID NO: 7 or an active fragment thereof, a BoNT/G translocation domain of amino acids 447-863 from SEQ ID NO: 7 or an active fragment thereof, a BoNT/G binding domain of amino acids 864-1297 from SEQ ID NO: 7 or an active BoNT/G fragment thereof, and any combination thereof.

In other aspects of this embodiment, a BoNT/G comprises a polypeptide having, e.g., at least 70% amino acid identity with SEQ ID NO: 7, at least 75% amino acid identity with the SEQ ID NO: 7, at least 80% amino acid identity with SEQ ID NO: 7, at least 85% amino acid identity with SEQ ID NO: 7, at least 90% amino acid identity with SEQ ID NO: 7 or at least 95% amino acid identity with SEQ ID NO: 7. In yet other aspects of this embodiment, a BoNT/G comprises a polypeptide having, e.g., at most 70% amino acid identity with SEQ ID NO: 7, at most 75% amino acid identity with the SEQ ID NO: 7, at most 80% amino acid identity with SEQ ID NO: 7, at most 85% amino acid identity with SEQ ID NO: 7, at most 90% amino acid identity with SEQ ID NO: 7 or at most 95% amino acid identity with SEQ ID NO: 7.

In other aspects of this embodiment, a BoNT/G comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 7. In other aspects of this embodiment, a BoNT/G com- prises a polypeptide having, e.g., at least one, two, three, four, five, six, seven, eight, nine, 10, 20, 30, 40, 50, 100, 200 or 500 non-contiguous amino acid substitutions relative to SEQ ID NO: 7. In yet other aspects of this embodiment, a BoNT/G comprises a polypeptide having, e.g., at most one, two, three, four, five, six, seven, eight, nine, 10, 20, 30, 40, 50, 100, 200 or 500 non-contiguous amino acid deletions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 non-contiguous amino acid deletions relative to SEQ ID NO: 7. In still other aspects of this embodiment, a BoNT/G comprises a polypeptide having, e.g., at most one, two, three, four, five, six, seven, eight, nine, 10, 20, 30, 40, 50, 100, 200 or 500 non-contiguous amino acid additions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 non-contiguous amino acid additions relative to SEQ ID NO: 7.

In other aspects of this embodiment, a BoNT/G comprises a polypeptide having, e.g., at most one, two, three, four, five, six, seven, eight, nine, 10, 20, 30, 40, 50, 100, 200 or 500 contiguous amino acid substitutions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 contiguous amino acid substitutions relative to SEQ ID NO: 7. In yet other aspects of this embodiment, a BoNT/G com- prises a polypeptide having, e.g., at most one, two, three, four, five, six, seven, eight, nine, 10, 20, 30, 40, 50, 100, 200 or 500 contiguous amino acid deletions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 contiguous amino acid deletions relative to SEQ ID NO: 7. In still other aspects of this embodiment, a BoNT/G comprises a polypeptide having, e.g., at most one, two, three, four, five, six, seven, eight, nine, 10, 20, 30, 40, 50, 100, 200 or 500 contiguous amino acid additions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 contiguous amino acid additions relative to SEQ ID NO: 7.

In another embodiment, a Clostridial toxin comprises a TeNT. In an aspect of this embodiment, a TeNT comprises a TeNT enzymatic domain, a TeNT translocation domain and a TeNT binding domain. In an aspect of this embodiment, a TeNT comprises SEQ ID NO: 8. In another aspect of this embodiment, a TeNT comprises a naturally occurring TeNT variant, such as, e.g., a TeNT isoform or a TeNT subtype. In another aspect of this embodiment, a TeNT comprises a naturally occurring TeNT variant of SEQ ID NO: 8, such as, e.g., a TeNT isoform of SEQ ID NO: 8 or a TeNT subtype of SEQ ID NO: 8. In still another aspect of this embodiment, a TeNT comprises a non-naturally occurring TeNT variant, such as, e.g., a conservative TeNT variant, a non-conservative TeNT variant or an active TeNT fragment, or any combination thereof. In still another aspect of this embodiment, a TeNT comprises a non-naturally occurring TeNT variant of SEQ ID NO: 8, such as, e.g., a conservative TeNT variant of SEQ ID NO: 8, a non-conservative TeNT variant of SEQ ID NO: 8 or an active TeNT fragment of SEQ ID NO: 8, or any combination thereof. In yet another aspect of this embodiment, a TeNT comprising a TeNT enzymatic domain or an active fragment thereof, a TeNT translocation domain or active fragment thereof, a TeNT binding domain or active fragment thereof, and any combination thereof. In yet another aspect of this embodiment, a TeNT comprising a TeNT enzymatic domain of amino acids 1-457 from SEQ ID NO: 8 or active fragment thereof, a TeNT translocation domain of amino acids 458-879 from SEQ ID NO: 8 or active fragment thereof, a TeNT binding domain of amino acids 880-1315 from SEQ ID NO: 8 or active fragment thereof, and any combination thereof.

In other aspects of this embodiment, a TeNT comprises a polypeptide having, e.g., at least 70% amino acid identity with SEQ ID NO: 8, at least 75% amino acid identity with the SEQ ID NO: 8, at least 80% amino acid identity with SEQ ID NO: 8, at least 85% amino acid identity with SEQ ID NO: 8, at least 90% amino acid identity with SEQ ID NO: 8 or at least 95% amino acid identity with SEQ ID NO: 8. In yet other aspects of this embodiment, a TeNT comprises a polypeptide having, e.g., at most 70% amino acid identity with SEQ ID NO: 8, at most 75% amino acid identity with the SEQ ID NO: 8, at most 80% amino acid identity with SEQ ID NO: 8, at most 85% amino acid identity with SEQ ID NO: 8, at most 90% amino acid identity with SEQ ID NO: 8 or at most 95% amino acid identity with SEQ ID NO: 8.

In other aspects of this embodiment, a TeNT comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 8. In yet other aspects of this embodiment, a TeNT comprises a polypeptide having, e.g., at most one, two, three, four, five, six, seven, eight, nine, 10, 20, 30, 40, 50, 100, 200 or 500 non-contiguous amino acid deletions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 non-contiguous amino acid deletions relative to SEQ ID NO: 8. In still other aspects of this embodiment, a TeNT comprises a polypeptide having, e.g., at most one, two, three, four, five, six, seven, eight, nine, 10, 20, 30, 40, 50, 100, 200 or 500 non-contiguous amino acid additions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 non-contiguous amino acid additions relative to SEQ ID NO: 8.

In other aspects of this embodiment, a TeNT comprises a polypeptide having, e.g., at most one, two, three, four, five, six, seven, eight, nine, 10, 20, 30, 40, 50, 100, 200 or 500 contiguous amino acid substitutions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 contiguous amino acid substitutions relative to SEQ ID NO: 8. In yet other aspects of this embodiment, a TeNT comprises a polypeptide having, e.g., at most one, two, three, four, five, six, seven, eight, nine, 10, 20, 30, 40, 50, 100, 200 or 500 contiguous amino acid deletions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 contiguous amino acid deletions relative to SEQ ID NO: 8. In still other aspects of this embodiment, a TeNT comprises a polypeptide having, e.g., at most one, two, three, four, five, six, seven, eight, nine, 10, 20, 30, 40, 50, 100, 200 or 500 contiguous amino acid additions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 contiguous amino acid additions relative to SEQ ID NO: 8.

In another embodiment, a Clostridial toxin comprises a BaNT. In an aspect of this embodiment, a BaNT comprises a BaNT enzymatic domain, a BaNT translocation domain and a BaNT binding domain. In another aspect of this embodiment, a BaNT comprises SEQ ID NO: 9. In another aspect of this embodiment, a BaNT comprises a naturally occurring BaNT variant, such as, e.g., a BaNT isoform or a BaNT subtype. In another aspect of this embodiment, a BaNT comprises a naturally occurring BaNT variant of SEQ ID NO: 9, such as, e.g., a BaNT isoform of SEQ ID NO: 9 or a BaNT subtype of SEQ ID NO: 9. In still another aspect of this embodiment, a BaNT comprises a non-naturally occurring BaNT variant, such as, e.g., a conservative BaNT variant, a non-conservative BaNT variant or an active BaNT fragment, or any combination thereof. In still another aspect of this embodiment, a BaNT comprises a non-naturally occurring BaNT variant of SEQ ID NO: 9, such as, e.g., a conservative BaNT variant of SEQ ID NO: 9, a non-conservative BaNT variant of SEQ ID NO: 9 or an active BaNT fragment of SEQ ID NO: 9, or any combination thereof. In yet another aspect of this embodiment, a BaNT comprises a BaNT enzymatic domain or an active fragment thereof, a BaNT translocation domain or an active fragment thereof, a BaNT binding domain or an active fragment thereof, or any combination thereof. In yet another aspect of this embodiment, a BaNT comprising a BaNT enzymatic domain of amino acids 1-448 from SEQ ID NO: 9 or an active fragment thereof, a BaNT translocation domain of amino acids 449-871 from SEQ ID NO: 9 or an active fragment thereof, a BaNT binding domain of amino acids 872-1296 from SEQ ID NO: 9 or an active fragment thereof, and any combination thereof.

In other aspects of this embodiment, a BaNT comprises a polypeptide having, e.g., at least 70% amino acid identity with SEQ ID NO: 9, at least 75% amino acid identity with the SEQ ID NO: 9, at least 80% amino acid identity with SEQ ID NO: 9, at least 85% amino acid identity with SEQ ID NO: 9, at least 90% amino acid identity with SEQ ID NO: 9 or at least 95% amino acid identity with SEQ ID NO: 9. In yet other aspects of this embodiment, a BaNT comprises a polypeptide having, e.g., at most 70% amino acid identity with SEQ ID NO: 9, at most 75% amino acid identity with the SEQ ID NO: 9, at most 80% amino acid identity with SEQ ID NO: 9, at most 85% amino acid identity with SEQ ID NO: 9, at most 90% amino acid identity with SEQ ID NO: 9 or at most 95% amino acid identity with SEQ ID NO: 9.

In other aspects of this embodiment, a BaNT comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 9. In yet other aspects of this embodiment, a BaNT comprises a polypeptide having, e.g., at most one, two, three, four, five, six, seven, eight, nine, 10, 20, 30, 40, 50, 100, 200 or 500 non-contiguous amino acid deletions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 non-contiguous amino acid deletions relative to SEQ ID NO: 9. In still other aspects of this embodiment, a BaNT comprises a polypeptide having, e.g., at most one, two, three, four, five, six, seven, eight, nine, 10, 20, 30, 40, 50, 100, 200 or 500 non-contiguous amino acid additions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 non-contiguous amino acid additions relative to SEQ ID NO: 9.

In other aspects of this embodiment, a BaNT comprises a polypeptide having, e.g., at most one, two, three, four, five, six, seven, eight, nine, 10, 20, 30, 40, 50, 100, 200 or 500 contiguous amino acid substitutions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 contiguous amino acid substitutions relative to SEQ ID NO: 9. In yet other aspects of this embodiment, a BaNT comprises a polypeptide having, e.g., at most one, two, three, four, five, six, seven, eight, nine, 10, 20, 30, 40, 50, 100, 200 or 500 contiguous amino acid deletions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 contiguous amino acid deletions relative to SEQ ID NO: 9. In still other aspects of this embodiment, a BaNT comprises a polypeptide having, e.g., at most one, two, three, four, five, six, seven, eight, nine, 10, 20, 30, 40, 50, 100, 200 or 500 contiguous amino acid additions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 contiguous amino acid additions relative to SEQ ID NO: 9.

In another embodiment, a Clostridial toxin comprises a BuNT. In an aspect of this embodiment, a BuNT comprises a BuNT enzymatic domain, a BuNT translocation domain and a BuNT binding domain. In another aspect of this embodiment, a BuNT comprises SEQ ID NO: 10. In another aspect of this embodiment, a BuNT comprises a naturally occurring BuNT variant, such as, e.g., a BuNT isoform or a BuNT subtype. In another aspect of this embodiment, a BuNT comprises a naturally occurring BuNT variant of SEQ ID NO: 10, such as, e.g., a BuNT isoform of SEQ ID NO: 10 or a BuNT subtype of SEQ ID NO: 10. In still another aspect of this embodiment, a BuNT comprises a non-naturally occurring BuNT variant, such as, e.g., a conservative BuNT variant, a non-conservative BuNT variant or an active BuNT fragment, or any combination thereof. In still another aspect of this embodiment, a BuNT comprises a non-naturally occurring BuNT variant of SEQ ID NO: 10, such as, e.g., a conservative BuNT variant of SEQ ID NO: 10, a non-conservative BuNT variant of SEQ ID NO: 10 or an active BuNT fragment of SEQ ID NO: 10, or any combination thereof. In yet another aspect of this embodiment, a BuNT comprises a BuNT enzymatic domain or an active fragment thereof, a BuNT translocation domain or an active fragment thereof, a BuNT binding domain or an active fragment thereof, or any combination thereof. In yet another aspect of this embodiment, a BuNT comprising a BuNT enzymatic domain of amino acids 1-448 from SEQ ID NO: 10 or an active fragment thereof, a BuNT translocation domain of amino acids 449-871 from SEQ ID NO: 10 or an active fragment thereof, a BuNT binding domain of amino acids 872-1296 from SEQ ID NO: 10 or an active fragment thereof, and any combination thereof.

In other aspects of this embodiment, a BuNT comprises a polypeptide having, e.g., at least 70% amino acid identity with SEQ ID NO: 10, at least 75% amino acid identity with the SEQ ID NO: 10, at least 80% amino acid identity with SEQ ID NO: 10, at least 85% amino acid identity with SEQ ID NO: 10, at least 90% amino acid identity with SEQ ID NO: 10 or at least 95% amino acid identity with SEQ ID NO: 10. In yet other aspects of this embodiment, a BuNT comprises a polypeptide having, e.g., at most 70% amino acid identity with SEQ ID NO: 10, at most 75% amino acid identity with the SEQ ID NO: 10, at most 80% amino acid identity with SEQ ID NO: 10, at most 85% amino acid identity with SEQ ID NO: 10, at most 90% amino acid identity with SEQ ID NO: 10 or at most 95% amino acid identity with SEQ ID NO: 10.

In other aspects of this embodiment, a BuNT comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 10. In yet other aspects of this embodiment, a BuNT comprises a polypeptide having, e.g., at most one, two, three, four, five, six, seven, eight, nine, 10, 20, 30, 40, 50, 100, 200 or 500 non-contiguous amino acid deletions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 non-contiguous amino acid deletions relative to SEQ ID NO: 10. In still other aspects of this embodiment, a BuNT comprises a polypeptide having, e.g., at most one, two, three, four, five, six, seven, eight, nine, 10, 20, 30, 40, 50, 100, 200 or 500 non-contiguous amino acid additions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 non-contiguous amino acid additions relative to SEQ ID NO: 10.

In other aspects of this embodiment, a BuNT comprises a polypeptide having, e.g., at most one, two, three, four, five, six, seven, eight, nine, 10, 20, 30, 40, 50, 100, 200 or 500 contiguous amino acid substitutions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 contiguous amino acid substitutions relative to SEQ ID NO: 10. In yet other aspects of this embodiment, a BuNT comprises a polypeptide having, e.g., at most one, two, three, four, five, six, seven, eight, nine, 10, 20, 30, 40, 50, 100, 200 or 500 contiguous amino acid deletions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 contiguous amino acid deletions relative to SEQ ID NO: 10. In still other aspects of this embodiment, a BuNT comprises a polypeptide having, e.g., at most one, two, three, four, five, six, seven, eight, nine, 10, 20, 30, 40, 50, 100, 200 or 500 contiguous amino acid additions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 contiguous amino acid additions relative to SEQ ID NO: 10.

Using this information it is possible to construct an expressible open nucleic acid reading frame for insertion into an expression vector and subsequent expression within a chosen host cell. Indeed, International Patent publication WO 01/14570 discloses methods of making single-chain, cleavable recombinant modified or unmodified Clostridial neurotoxin derivatives and chimeric and hybrid forms thereof using such methods. Additional publications disclosing methods of making expressible recombinant neurotoxins and derivatives thereof include U.S. Pat. Nos. 5,989,545; 6,203,794; 6,395,513; U.S. Publication Numbers U.S. 2003/0166238; U.S. 2002/169942; U.S. 2004/176299; U.S. 2004/126397; U.S. 2005/035730; U.S. 2005/068494; U.S. 2006/011966; International Patent Applications W095/32738; WO 99/55359; W096/33273; W098/07864; W099/17806; WO98/07864; WO02/44199; WO02/40506. All these publications are incorporated by reference herein in their entirety.

The use of recombinant DNA techniques permits the construction of modified clostridial neurotoxins having different functional properties from the naturally occurring toxin subtypes and strains thereof. For example, altering the naturally occurring amino acid sequence of the native neurotoxin light chain and/or adding a different therapeutic moiety permits the construction of transport proteins designed to carry a therapeutic agent within a neuron. See U.S. Pat. No. 6,203,794 (incorporated by reference herein). Altering the targeting (binding) domain permits the toxin to be transported within pancreatic cells, such as acinar cells, thereby preventing secretion of activated digestive enzymes by such cells, See U.S. Pat. No. 6,843,998 (hereby incorporated by reference herein), or sensory afferent neurons, thereby preventing neurotransmitter release and thus providing relief from pain; see U.S. Pat. No. 6,395,513 (hereby incorporated by reference herein.)

In addition, the creation of chimeric neurotoxin derivatives comprising, for example, the binding domain and the translocation domain (or modified versions thereof) of one neurotoxin subtype for example, BoNT/A, and the light chain region of another neurotoxin subtype, for example, BoNT/E. It will be seen that given the general structural homology between the neurotoxin subtypes, any combination of the three basic clostridial neurotoxin domains, may be made in a single amino acid chain (or cleaved di-chain molecule). Thus, a binding region from any of neurotoxin BoNT/A, BoNT/B, BoNT/C1, BoNT/D, BoNT/E, BoNT/F, BoNT/G, TeNT, BaNT or BuNT may be independently combined with a translocation domain from BoNT/A, BoNT/B, BoNT/C1, BoNT/D, BoNT/E, BoNT/F, BoNT/G, TeNT, BaNT or BuNT, and further independently combined with a endopeptidase domain from BoNT/A, BoNT/B, BoNT/C1, BoNT/D, BoNT/E, BoNT/F, BoNT/G, TeNT, BaNT or BuNT.

The therapeutic utility of a Clostridial toxin may be enhanced or altered by the inclusion of at least two cell binding domains. All such modified Clostridial toxins are referred to herein as "multivalent Clostridial toxin." Each binding domain of a multivalent Clostridial toxin may comprise any binding domain capable of binding under physiological conditions to a cell surface receptor capable of selectively binding to the ligand. Furthermore, each binding domain is capable of selectively binding to a receptor present on the surface of a target cell, or facilitating the entry of the multivalent Clostridial toxin into a target cell. In addition, at least one of said binding domains will bind selectively to the target cell and at least one of the binding domains will bind to a cell surface receptor capable of mediating the internalization of the multivalent Clostridial toxin within the target cell. By adding, for example, multiple binding domains the binding constant (Kd) (which equals [toxin][target cell]/[toxin:target cell complex]) of the multivalent Clostridial toxin will be increased over that of an unmodified toxin or monovalent toxin.

Aspects of the present invention provide, in part, a binding domain. As used herein, the term "binding domain" is synonymous with "ligand" and means any molecule that can selectively interact with another molecule present on the surface of a cell and initiate the overall internalization mechanism whereby the multivalent Clostridial toxin disclosed in the present specification intoxicates a target cell. Each of the two or more binding domains in a multivalent Clostridial neurotoxin may be, for example, a binding domain that facilitates stability, solubility and/or cell penetration. At least one such binding domain is selective for a cell surface molecule of a target cell. In addition, at least one cell surface molecule to which a binding domain of a multivalent Clostridial neurotoxin binds is capable of being internalized by the target cell after binding. Preferably, at least one cell surface molecule to which a binding domain of a multivalent Clostridial neurotoxin selectively binds is capable of being internalized by the target cell after binding. As used herein, the term "selectively" means having a highly preferred activity or effect. As used herein, the term "selectively bind" or "selective binding" means a molecule is able to bind its target receptor under physiological conditions, or in vitro conditions substantially approximating physiological conditions, to a statistically significantly greater degree relative to other, non-target receptors. Thus, with reference to a binding domain or ligand of the present specification, there is a discriminatory binding of the binding domain to a cell surface receptor present on a cell. Thus, in an embodiment, a binding domain or ligand can selectively bind a cell surface receptor with a dissociation constant (Kd) of the ligand for target receptor by at least four fold, at least 10 fold, at least 50 fold, at least 100 fold, at least 1000, at least 100,000 fold the value of Kd of the ligand for other cell surface receptors.

A binding domain disclosed in the present specification may facilitate the binding activity of a multivalent Clostridial toxin to a molecule located at the surface of a cell. As used herein, the term "binding activity" means that one molecule is directly or indirectly contacting another molecule via at least one intermolecular or intramolecular force, including, without limitation, a covalent bond, an ionic bond, a metallic bond, a hydrogen bond, a hydrophobic interaction, a van der Waals interaction, and the like, or any combination thereof. "Bound" and "bind" are considered terms for binding.

As used herein, the term "binding affinity" means how strong a binding domain's activity is for a particular cell surface molecule. In general, high binding affinity results from greater intermolecular force between a binding domain and its cell surface molecule while low binding affinity involves less intermolecular force between the ligand and its cell surface molecule. High binding affinity involves a longer residence time for the binding domain at its cell surface molecule binding site than is the case for low binding affinity. As such, a binding domain with a high binding affinity means a lower concentration of that binding domain is required to maximally occupy the binding sites of a cell surface molecule and trigger a physiological response. Conversely, low binding affinity means a relatively high concentration of a binding domain is required before the binding sites of a cell surface molecule is maximally occupied and the maximum physiological response is achieved. Thus, multivalent Clostridial toxins with increased binding activity due to high binding affinity will allow administration of reduced doses of the toxin, thereby reducing or preventing unwanted side-effects associated with toxin dispersal into non-targeted areas.

As used herein, the term "binding specificity" means how specific a binding domain's activity is one particular cell surface molecule. In general, high binding specificity results in a more exclusive interaction with one particular cell surface molecule or subgroup of cell surface molecules while low binding specificity results in a more promiscuous interaction with a larger group of cell surface molecules. As such, a binding domain with a high binding specificity means that binding domain will occupy the binding sites of a particular cell surface molecule and trigger a physiological response. Conversely, low binding specificity means a binding domain will occupy the binding sites of many cell surface molecules and trigger a multitude of physiological responses. Thus, multivalent Clostridial toxins with increased binding activity due to high binding specificity will only target cell surface molecules present on a subgroup of target cells, thereby reducing the side effects associated with the targeting of all target cells.

As used herein, the term "cell surface molecule" means both a traditional receptor capable of binding a ligand and thereby causing a ligand-selective response (at e.g., the cell surface, the cytoplasm, or both), and a cell surface feature such as caveolae, membrane "patches", or lipid rafts, which appear to serve at least in part to gather together and locally concentrate at the cell surface specific receptors and bound ligand types for later processing such as endocytosis, often mediated by a cell surface receptor.

Thus, in an embodiment, a multivalent Clostridial toxin can comprises a plurality of binding domains. In aspects of this embodiment, a multiivalent Clostridal toxion can comprise, e.g., at least two binding domains, at least three binding domains, at least four binding domains or at least five binding domains. In other aspects of this embodiment, a multiivalent Clostridal toxion can comprise, e.g., at most two binding domains, at most three binding domains, at most four binding domains or at most five binding domains. In other aspects of this embodiment, a multiivalent Clostridal toxion comprises, e.g., two binding domains, three binding domains, four binding domains or five binding domains.

It is envisioned that any and all binding domains capable of binding a Clostridial toxin receptor present on a naturally-occurring Clostridial toxin target cell can be used to practice aspects of the present invention, including, without limitation, a Clostridial toxin binding domain, such as, e.g., a BoNT/A binding domain, a BoNT/B binding domain, a BoNT/C1 binding domain, a BoNT/D binding domain, a BoNT/E binding domain, a BoNT/F binding domain, a BoNT/G binding domain, a TeNT binding domain, a BaNT binding domain, and a BuNT binding domain; a Clostridial non-toxin associated protein, such as, e.g., a BoNT/A HA-33, a BoNT/B HA-33, a BoNT/C1 HA-33, a BoNT/D HA-33, a BoNT/A HA-17, a BoNT/B HA-17, a BoNT/C1 HA-17, a BoNT/D HA-17, a BoNT/A NTNH, a BoNT/B NTNH, a BoNT/C1 NTNH, a BoNT/D NTNH, a BoNT/E NTNH, a BoNT/F NTNH and a BoNT/G NTNH; and a FGF, such as, e.g., a FGF-1, a FGF-2, a FGF-4, a FGF-8, a FGF-9, a FGF-17 and a FGF-18.

It is envisioned that any and all binding domains capable of binding a non-Clostridial toxin receptor present on a naturally-occurring Clostridial toxin target cell can be used to practice aspects of the present invention, including, without limitation, polypeptides that selectively bind to a receptor present on a presynaptic membrane and polypeptides that selectively bind to a receptor present on a postsynaptic membrane. Polypeptides that appear to bind to a receptor present on a presynaptic membrane, include, without limitation, Glucagon like hormones, such as, e.g., secretin, Ghrelin (GHS), glucagon-like peptide-1 (GLP-1), glucagon-like peptide-2 (GLP-2), pituitary adenylate cyclase activating peptide (PACAP), glicentin, glicentin-related polypeptide (GRPP), oxyntomodulin (OXY), vasoactive intestinal peptide-1 (VIP-1), vasoactive intestinal peptide-2 (VIP-2), gastric inhibitory polypeptide (GIP), a galanin (Gal) or a calcitonin-related peptidesvisceral gut peptide; neurohormones, such as, e.g., corticotropin-releasing hormone (CCRH) and parathyroid hormone (PTH); neuroregulatory cytokines, such as, e.g., ciliary neurotrophic factor (CNTF), glycophorin-A (GPA), leukemia inhibitory factor (LIF), an interleukin (IL), onostatin M (OSM), cardiotrophin-1 (CT-1), cardiotrophin-like cytokine (CLC), neuroleukin (NL), VEGF, insulin-like growth factor-1 (IGF-1), insulin-like growth factor-2 (IGF-2) and epidermal growth factor (EGF); neurotrophins, such as, e.g., nerve growth factors (NGFs), brain-derived growth factors (BDNFs), neurotrophin-3s (NT-3s) and neurotrophin-4/5s (NT-4/5s); growth factors, such as, e.g., glial cell derived neurotrophic factor (GDNF), neurturin (NRTN), persephrin (PSPN), artemin (ARTN); transformation growth factor betas (TGFβs), bone morphogenetic proteins (BMPs), growth and differentiation factors (GDFs), activins; axon guidance signaling molecules, such as, e.g., netrins, semaphrorings and ephrins; sugar binding proteins, such as, e.g., serum amyloid P, β-glucanase, sialidase, lectin, cryia, insecticidal delta-endotoxin, agglutinin, abrin and ricin; ligands that selectively bind neurexins, such as, e.g., ligands for neurexin-1α and neurexin-1β; ligands for neurexin-2α and neurexin-2β; and ligands for neurexin-3α and neurexin-3β; and WNTs. Ligands that appear to bind to a receptor present on a postsynaptic membrane, include, without limitation, Ng-CAM (L1), NCAM, N-cadherin, Agrin-MUSK, basement membrane polypeptides, such as, e.g., laminin β-2.

It is envisioned that any and all binding domains capable of binding a non-Clostridial toxin receptor present on a non-Clostridial toxin target cell can be used to practice aspects of the present invention, including, without limitation, polypeptides that selectively bind to a receptor present on a sensory neuron, an autonomic neuron or a non-neuronal cell. Such binding domains include, without limitation, an opioid peptide, such as, e.g., an enkephalin, a bovine adrenomedullary-22 (BAM22) peptide, an endomorphin, an endorphin, a dynorphin, a nociceptin or a hemorphin; a melanocortin peptide, such as, e.g., an α-melanocyte stimulating hormones (α-MSH), a β-melanocyte stimulating hormones (β-MSH), a γ-melanocyte stimulating hormones (γ-MSH), an adrenocorticotropin (ACTH), a Corticotropin-like intermediary peptide (CLIP), a β-lipotropin (β-LPH) and a γ-lipotropin (γ-LPH); a galanin, such as, e.g., a galanin and a galanin message-associated peptide (GMAP); a granin, such as, e.g., a chromogranin A peptide like a β-granin, a vasostatin, a chromostatin, a pancreastatin, a WE-14, a catestatin, a parastatin and a GE-25, a chromogranin B (secretogranin I) peptide like a GAWK peptide, an adrenomedullary peptide and a secretolytin and a chromogranin C (secretogranin II) peptide like secretoneurin, EM66 and manserin; a tachykinin peptide, such as, e.g., Substance P, neuropeptide K (NPK), neuropeptide gamma (NP gamma), neurokinin A (NKA; Substance K, neurokinin alpha, neuromedin L), neurokinin B (NKB), a hemokinin and a endokinin; a cholecystokinin peptide, such as, e.g., a cholecystokinin 58, a cholecystokinin 39, a cholecystokinin 33, a cholecystokinin 12 and a cholecystokinin 8; a Neuropeptide Y related peptide, such as, e.g., a Neuropeptide Y (NPY), a Peptide YY (PYY), Pancreatic peptide (PP) and a Pancreatic icosapeptide (PIP); a kinin peptide, such as, e.g., a bradykinin, a kallidan, a desArg$^9$ bradykinin and a desArg$^{10}$ bradykinin; a protease activated receptor (PAR) peptide, such as, e.g., a PAR1 peptide, a PAR2 peptide, a PAR3 peptide and a PAR4 peptide; a corticotropin-releasing hormone; a thyrotropin-releasing hormone; a somatostatin; a leukemia inhibitor factor (LIF); and an interleukin-1 (IL1).

It is envisioned that any and all binding domains capable of facilitating the transport of the multivalent Clostridial toxin across a cell membrane of a target cell can be used to practice aspects of the present invention, including, without limitation, a translocator like a protein translocation domain (PTD), such as, e.g., a herpes simplex virus type 1 VP22 protein translocating sequence, a SV-40 virus large T translocating sequence, a TAT translocating sequence, an adenovirus translocating sequence, a synthetic integrin binding domain translocating sequence, a Kaposi fibroblast growth factor membrane translocating sequence, a nuclear localization signal, a Transportan translocating sequence, a ciliary neurotrophic factor translocating sequence, a caveolin, an interleukin 1-β translocating sequence, a thioredoxin translocating sequence, a fibroblast growth factor-1 translocating sequence, a fibroblast growth factor-2 translocating sequence, an integrin β1 translocating sequence, an integrin β3 translocating sequence, a lactoferrin translocating sequence, a homeodomain translocating sequence, like, a penetratin translocating sequence, an Engrailed-1 translocating sequence, an Engrailed-2 translocating sequence, a Hoxa-5 translocating sequence, a Hoxb-4 translocating sequence, a Hoxc-8 translocating sequence It is envisioned that any and all binding domains capable of binding to a cell surface molecule capable of facilitating the transport of a multivalent Clostridial toxin across a cell membrane of a target cell can be used to practice aspects of the present invention, including, without limitation, an antibody to a coated pit protein, such as, e.g., a clatherin antibody and an Adaptor Protein-2 (adaptin) antibody; an antibody to a caveolae-associated protein, such as, e.g., a caveolin-1 antibody and a GPI-linked receptor protein antibody.

Figure 3:
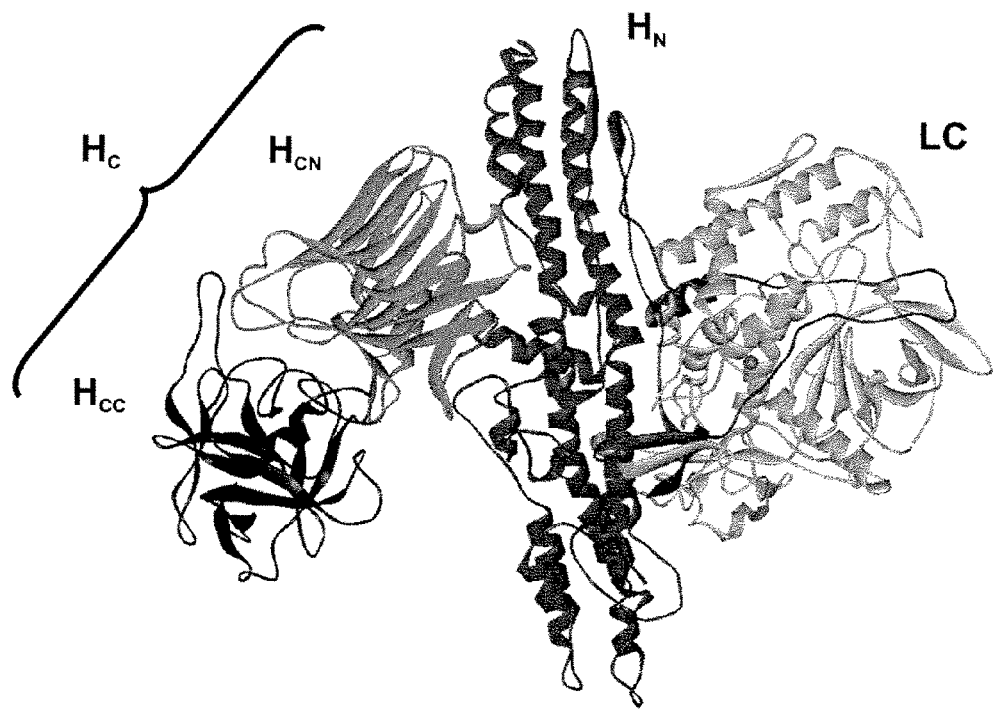

An example of a binding domain, includes, without limitation, a Clostridial toxin binding domain such, as, e.g., a BoNT/A binding domain, a BoNT/B binding domain, a BoNT/C1 binding domain, a BoNT/D binding domain, a BoNT/E binding domain, a BoNT/F binding domain, a BoNT/G binding domain, a TeNT binding domain, a BaNT binding domain and a BuNT binding domain The three-dimensional crystal structures of BoNT/A, BoNT/B and the H$_C$ domain of TeNT indicate that the carboxyl-terminal H$_{CC}$ domain comprises a modified β-trefoil domain which forms three distinct carbohydrate binding regions domains that resembles the carbohydrate binding moiety found in many sugar-binding proteins, such as, e.g., serum amyloid P, sialidase, cryia, insecticidal ∂-endotoxin and lectins (FIG. 3). Biochemical studies indicate that the β-trefoil domain structure of the H$_{CC}$ domain appears to mediate the binding to specific carbohydrate containing components of the Clostridial toxin receptor on the cell surface, see, e.g., Krzysztof Ginalski et al., *Structure-based Sequence Alignment for the Beta-Trefoil Subdomain of the Clostridial Neurotoxin Family Provides Residue Level Information About the Putative Ganglioside Binding Site*, 482(1-2) FEBS Lett. 119-124 (2000).

Proteins containing the structural β-trefoil domain represents a diverse group of proteins, see, e.g., C. A. Orengo et al., *Protein Superfamilies and Domain Superfolds*, 372 Nature 631-634 (1994). The β-trefoil domain comprises a six-stranded β-barrel closed off at one end by three β-hairpin structures that exhibits a characteristic pseudo-threefold axis symmetry. The monomeric structural unit of this three-fold symmetry is referred to as the β-trefoil fold that contains four β-sheets organized as a pair of antiparallel β-sheets. Dividing each of these β-trefoil folds is a β-hairpin turn. Therefore, in a linear fashion, a β-trefoil domain comprises four β-sheets of the first β-trefoil fold (α-fold), a β-hairpin turn, four β-sheets of the second β-trefoil fold (β-fold), a second β-hairpin turn four β-sheets of the third β-trefoil fold (γ-fold) (see FIG. 2). Because the first hairpin turn is located between the fourth and fifth β-sheets of the β-trefoil domain, it is designated the β4/β5 β-hairpin turn. Likewise, since the second hairpin turn is located between the eight and ninth β-sheets of the β-trefoil domain, it is designated the β8/β9 β-hairpin turn.

TABLE 2

β-trefoil Domains of Clostridial Toxins

| | | Amino Acid Sequence Region of Carbohydrate Binding Moieties | | | | |
|---|---|---|---|---|---|---|
| Protein | SEQ ID NO: | α-fold | β4/β5 β-hairpin turn | β-fold | β8/β9 β-hairpin turn | γ-fold |
| BoNT/A | 1 | 1111-1162 | 1163-1178 | 1179-1223 | 1224-1236 | 1237-1296 |
| BoNT/B | 2 | 1098-1147 | 1148-1165 | 1166-1210 | 1211-1222 | 1223-1291 |
| BoNT/C1 | 3 | 1112-1150 | 1151-1166 | 1167-1218 | 1219-1229 | 1230-1291 |
| BoNT/D | 4 | 1099-1137 | 1138-1153 | 1154-1207 | 1208-1218 | 1219-1276 |
| BoNT/E | 5 | 1086-1129 | 1130-1146 | 1147-1190 | 1191-1198 | 1199-1252 |
| BoNT/F | 6 | 1106-1152 | 1153-1171 | 1172-1213 | 1214-1221 | 1222-1274 |
| BoNT/G | 7 | 1106-1153 | 1154-1172 | 1173-1218 | 1219-1230 | 1231-1297 |
| TeNT | 8 | 1128-1177 | 1178-1194 | 1195-1240 | 1241-1254 | 1255-1315 |
| BaNT | 9 | 1095-1142 | 1143-1161 | 1162-1207 | 1208-1215 | 1216-1268 |
| BuNT | 10 | 1086-1129 | 1130-1146 | 1147-1190 | 1191-1197 | 1198-1251 |

Continuing research has elucidated that β4/β5 and β8/β9 β-hairpin turns are important in conferring the proper pseudo-threefold axis symmetry observed in the β-trefoil domain. Additionally, this work has demonstrated that amino acid changes in these two β-hairpin turns can increase the stability of the β-trefoil domain, which in turn results in increased binding activity, see, e.g., Stephen R. Brych et al., *Structure and Stability Effects of Mutations Designed to Increase the Primary Sequence Symmetry Within the Core Region of a β-trefoil*, 10 Protein Sci. 2587-2599 (2001); Jaewon Kim et al., *Alternative Type I and I' Turn Conformations in the β8/β9 β-hairpin of Human Acidic Fibroblast Growth Factor*, 11 Protein Sci. 459-466 (2002); Jaewon Kim et al., *Sequence swapping Does Not Result in Conformation Swapping for the β4/β5 and β8/β9 β-hairpin Turns in Human Acidic Fibroblast Growth Factor*, 14 Protein Sci. 351-359 (2005). As a non-limiting example, replacement of an amino acid comprising either the β4/β5 hairpin turn or β8/β9 β-hairpin turn with a glycine results in increased stabilization of the β-trefoil domain. Therefore, replacement of amino acids located in the β4/β5 and β8/β9 β-hairpin turns of the β-trefoil domains present in the binding domain of Clostridial toxins will increase binding activity of such a modified Clostridial toxin by increasing the structural stability of the β-trefoil domain. The amino acid sequences comprising the β-trefoil domains found in various Clostridial toxins are shown in Table 2.

As is typical for proteins containing a β-trefoil fold, the overall amino acid sequence identity of the $H_{CC}$ domain between Clostridial toxins is low. However, key residues essential for binding activity have been identified by structural analysis and mutagenesis experiments, see, e.g., Krzysztof Ginalski et al., *Structure-based Sequence Alignment for the Beta-Trefoil Subdomain of the Clostridial Neurotoxin Family Provides Residue Level Information About the Putative Ganglioside Binding Site*, 482(1-2) FEBS Lett. 119-124 (2000). For example, analysis of the $H_{CC}$ domain structure by crystallography identified five highly conserved residues critical for forming a shallow surface pocket of a carbohydrate binding moiety. These polar residues make hydrogen bonds with the carbohydrate ring. In BoNT/A these five polar residues are Glu 1203, Phe 1252, Ser 1264, Tyr 1267 and Gly 1279, while in TeNT, these residues are Asp 1222, Thr 1270, Ser 1287, Tyr 1290 and Gly 1300. Additionally, tyrosine residues forming the hydrophilic wall of this pocket were also important (Trp 1266 of BoNT/A and Trp 1289 of TeNT) and tryptophan fluorescence quenching experiments indicated that Trp 1266 of BoNT/A bound carbohydrate molecules. In another studies, photoaffinity labeling experiments revealed that Gln 1270 of BoNT/A and His 1293 of TeNT were also involved in binding carbohydrate molecules. Mutagenesis experiments designed to assay loss-of-function binding activity mutations confirmed the importance of many of the residues described above for BoNT/A and TeNT and extended this analysis to BoNT/B (Glu 1190, His 1241, Typ 1262, Tyr 1263), see, e.g., Andreas Rummel et al., *The $H_{CC}$-Domain of Botulinum Neurotoxins A and B Exhibits a Singular Ganglioside Binding Site Displaying Serotype Specific Carbohydrate Interaction*, 51(3) Mol. Microbiol. 631-643 (2004).

As used herein, the term "Clostridial toxin binding domain" means any Clostridial toxin polypeptide that can execute the cell binding step of the intoxication process, including, e.g., the selective binding of the Clostridial toxin to a toxin-specific receptor located on the plasma membrane surface of a target cell. Non-limiting examples of a Clostridial toxin binding domain include, e.g., a Clostridial toxin $H_C$ binding domain, such as, e.g., a BoNT/A $H_C$ binding domain, a BoNT/B $H_C$ binding domain, a BoNT/C1 $H_C$ binding domain, a BoNT/D $H_C$ binding domain, a BoNT/E $H_C$ binding domain, a BoNT/F $H_C$ binding domain, a BoNT/G $H_C$ binding domain, a TeNT $H_C$ binding domain, a BaNT $H_C$ binding domain and a BuNT $H_C$ binding domain. Other non-limiting examples of a Clostridial toxin $H_{CC}$ binding domain, include a BoNT/A $H_{CC}$ binding domain, a BoNT/B $H_{CC}$ binding domain, a modified BoNT/C1 $H_{CC}$ binding domain, a BoNT/D $H_{CC}$ binding domain, a BoNT/E $H_{CC}$ binding domain, a BoNT/F $H_{CC}$ binding domain, a BoNT/G $H_{CC}$ binding domain, a TeNT $H_{CC}$ binding domain, a BaNT $H_{CC}$ binding domain and a BuNT $H_{CC}$ binding domain.

A Clostridial toxin binding domain includes, without limitation, naturally occurring Clostridial toxin binding domain variants, such as, e.g., Clostridial toxin binding domain isoforms and Clostridial toxin binding domain subtypes; non-naturally occurring Clostridial toxin binding domain variants, such as, e.g., conservative Clostridial toxin binding domain variants, non-conservative Clostridial toxin binding domain variants, Clostridial toxin binding domain chimerics, active Clostridial toxin binding domain fragments thereof, or any combination thereof.

As used herein, the term "Clostridial toxin binding domain variant," whether naturally-occurring or non-naturally-occurring, means a Clostridial toxin binding domain that has at least one amino acid change from the corresponding region of the disclosed reference sequences (see Table 1) and can be described in percent identity to the corresponding region of that reference sequence. Unless expressly indicated, all Clostridial toxin binding domain variants disclosed in the present specification are capable of executing the cell binding step of the intoxication process, including, e.g., the selective binding of the Clostridial toxin to a toxin-specific receptor located on the plasma membrane surface of a target cell.

As a non-limiting example, a BoNT/A $H_C$ binding domain variant comprising amino acids 874-1296 of SEQ ID NO: 1 will have at least one amino acid difference, such as, e.g., an amino acid substitution, deletion or addition, as compared to the amino acid region 874-1296 of SEQ ID NO: 1; a BoNT/B $H_C$ binding domain variant comprising amino acids 861-1291 of SEQ ID NO: 2 will have at least one amino acid difference, such as, e.g., an amino acid substitution, deletion or addition, as compared to the amino acid region 861-1291 of SEQ ID NO: 2; a BoNT/C1 $H_C$ binding domain variant comprising amino acids 869-1291 of SEQ ID NO: 3 will have at least one amino acid difference, such as, e.g., an amino acid substitution, deletion or addition, as compared to the amino acid region 869-1291 of SEQ ID NO: 3; a BoNT/D $H_C$ binding domain variant comprising amino acids 865-1276 of SEQ ID NO: 4 will have at least one amino acid difference, such as, e.g., an amino acid substitution, deletion or addition, as compared to the amino acid region 865-1276 of SEQ ID NO: 4; a BoNT/E $H_C$ binding domain variant comprising amino acids 848-1252 of SEQ ID NO: 5 will have at least one amino acid difference, such as, e.g., an amino acid substitution, deletion or addition, as compared to the amino acid region 848-1252 of SEQ ID NO: 5; a BoNT/F $H_C$ binding domain variant comprising amino acids 867-1274 of SEQ ID NO: 6 will have at least one amino acid difference, such as, e.g., an amino acid substitution, deletion or addition, as compared to the amino acid region 867-1274 of SEQ ID NO: 6; a BoNT/G $H_C$ binding domain variant comprising amino acids 866-1297 of SEQ ID NO: 7 will have at least one amino acid difference, such as, e.g., an amino acid substitution, deletion or addition, as compared to the amino acid region 866-1297 of SEQ ID NO: 7; a TeNT $H_C$ binding domain variant comprising amino acids 882-1315 of SEQ ID NO: 8 will have at least one amino acid difference, such as, e.g., an amino acid substitution, deletion or addition, as compared to the amino acid region 882-1315 of SEQ ID NO: 8, a BaNT $H_C$ binding domain variant comprising amino acids 858-1269 of SEQ ID NO: 9 will have at least one amino acid difference, such as, e.g., an amino acid substitution, deletion or addition, as compared to the amino acid region 858-1268 of SEQ ID NO: 9, and a BuNT $H_C$ binding domain variant comprising amino acids 848-1251 of SEQ ID NO: 10 will have at least one amino acid difference, such as, e.g., an amino acid substitution, deletion or addition, as compared to the amino acid region 848-1251 of SEQ ID NO: 10.

As another non-limiting example, a BoNT/A $H_{CC}$ binding domain comprising amino acids 1092-1296 of SEQ ID NO: 1 will have at least one amino acid difference, such as, e.g., an amino acid substitution, deletion or addition, as compared to the amino acid region 1092-1296 of SEQ ID NO: 1; a modified BoNT/B $H_{CC}$ binding domain comprising amino acids 1079-1291 of SEQ ID NO: 2 will have at least one amino acid difference, such as, e.g., an amino acid substitution, deletion or addition, as compared to the amino acid region 1079-1291 of SEQ ID NO: 2; a modified BoNT/C1 $H_{CC}$ binding domain comprising amino acids 1093-1291 of SEQ ID NO: 3 will have at least one amino acid difference, such as, e.g., an amino acid substitution, deletion or addition, as compared to the amino acid region 1093-1291 of SEQ ID NO: 3; a modified BoNT/D $H_{CC}$ binding domain comprising amino acids 1080-1276 of SEQ ID NO: 4 will have at least one amino acid difference, such as, e.g., an amino acid substitution, deletion or addition, as compared to the amino acid region 1080-1276 of SEQ ID NO: 4; a modified BoNT/E $H_{CC}$ binding domain comprising amino acids 1067-1252 of SEQ ID NO: 5 will have at least one amino acid difference, such as, e.g., an amino acid substitution, deletion or addition, as compared to the amino acid region 1067-1252 of SEQ ID NO: 5; a modified BoNT/F $H_{CC}$ binding domain comprising amino acids 1087-1274 of SEQ ID NO: 6 will have at least one amino acid difference, such as, e.g., an amino acid substitution, deletion or addition, as compared to the amino acid region 1087-1274 of SEQ ID NO: 6; a modified BoNT/G $H_{CC}$ binding domain comprising amino acids 1087-1297 of SEQ ID NO: 7 will have at least one amino acid difference, such as, e.g., an amino acid substitution, deletion or addition, as compared to the amino acid region 1087-1297 of SEQ ID NO: 7; a modified TeNT $H_{CC}$ binding domain comprising amino acids 1109-1315 of SEQ ID NO: 8 will have at least one amino acid difference, such as, e.g., an amino acid substitution, deletion or addition, as compared to the amino acid region 1109-1315 of SEQ ID NO: 8, a modified BaNT $H_{CC}$ binding domain comprising amino acids 1095-1269 of SEQ ID NO: 9 will have at least one amino acid difference, such as, e.g., an amino acid substitution, deletion or addition, as compared to the amino acid region 1095-1268 of SEQ ID NO: 9, and a modified BuNT $H_{CC}$ binding domain comprising amino acids 1086-1251 of SEQ ID NO: 10 will have at least one amino acid difference, such as, e.g., an amino acid substitution, deletion or addition, as compared to the amino acid region 1086-1251 of SEQ ID NO: 10.

It is recognized by those of skill in the art that within each serotype of Clostridial toxin there can be naturally occurring Clostridial toxin binding domain variants that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific binding domain subtypes showing approximately 87% amino acid identity when compared to another BoNT/A binding domain subtype. As used herein, the term "naturally occurring Clostridial toxin binding domain variant" means any Clostridial toxin binding domain produced by a naturally-occurring process, including, without limitation, Clostridial toxin binding domain isoforms produced from alternatively-spliced transcripts, Clostridial toxin binding domain isoforms produced by spontaneous mutation and Clostridial toxin binding domain subtypes. A naturally occurring Clostridial toxin binding domain variant can function in substantially the same manner as the reference Clostridial toxin binding domain on which the naturally occurring Clostridial toxin binding domain variant is based, and can be substituted for the reference Clostridial toxin binding domain in any aspect of the present invention. A naturally occurring Clostridial toxin binding domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial toxin binding domain on which the naturally occurring Clostridial toxin binding domain variant is based. A naturally occurring Clostridial toxin binding domain variant can also substitute at least 10 contiguous amino acids, at least 15 contiguous amino acids, at least 20 contiguous amino acids, or at least 25 contiguous amino acids from the reference Clostridial toxin binding domain on which the naturally occurring Clostridial toxin binding domain variant is based, that possess at least 50% amino acid identity, 65% amino acid identity, 75% amino acid identity, 85% amino acid identity or 95% amino acid identity to the reference Clostridial toxin binding domain on which the naturally occurring Clostridial toxin binding domain variant is based.

A non-limiting examples of a naturally occurring Clostridial toxin binding domain variant is a Clostridial toxin binding domain isoform such as, e.g., a BoNT/A binding domain isoform, a BoNT/B binding domain isoform, a BoNT/C1 binding domain isoform, a BoNT/D binding domain isoform, a BoNT/E binding domain isoform, a BoNT/F binding domain isoform, a BoNT/G binding domain isoform, a TeNT binding domain isoform, a BaNT binding domain isoform, and a BuNT binding domain isoform. A Clostridial toxin binding domain isoform can function in substantially the same manner as the reference Clostridial toxin binding domain on which the Clostridial toxin binding domain isoform is based, and can be substituted for the reference Clostridial toxin binding domain in any aspect of the present invention.

Another non-limiting examples of a naturally occurring Clostridial toxin binding domain variant is a Clostridial toxin binding domain subtype such as, e.g., a binding domain from subtype BoNT/A1, BoNT/A2, BoNT/A3 and BoNT/A4; a binding domain from subtype BoNT/B1, BoNT/B2, BoNT/B bivalent and BoNT/B nonproteolytic; a binding domain from subtype BoNT/C1-1 and BoNT/C1-2; a binding domain from subtype BoNT/E1, BoNT/E2 and BoNT/E3; and a binding domain from subtype BoNT/F1, BoNT/F2, BoNT/F3 and BoNT/F4. A Clostridial toxin binding domain subtype can function in substantially the same manner as the reference Clostridial toxin binding domain on which the Clostridial toxin binding domain subtype is based, and can be substituted for the reference Clostridial toxin binding domain in any aspect of the present invention.

As used herein, the term "non-naturally occurring Clostridial toxin binding domain variant" means any Clostridial toxin binding domain produced with the aid of human manipulation, including, without limitation, Clostridial toxin binding domains produced by genetic engineering using random mutagenesis or rational design and Clostridial toxin binding domains produced by chemical synthesis. Non-limiting examples of non-naturally occurring Clostridial toxin binding domain variants include, e.g., conservative Clostridial toxin binding domain variants, non-conservative Clostridial toxin binding domain variants, Clostridial toxin binding domain chimeric variants and active Clostridial toxin binding domain fragments.

As used herein, the term "conservative Clostridial toxin binding domain variant" means a Clostridial toxin binding domain that has at least one amino acid substituted by another amino acid or an amino acid analog that has at least one property similar to that of the original amino acid from the reference Clostridial toxin binding domain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin binding domain variant can function in substantially the same manner as the reference Clostridial toxin binding domain on which the conservative Clostridial toxin binding domain variant is based, and can be substituted for the reference Clostridial toxin binding domain in any aspect of the present invention. A conservative Clostridial toxin binding domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin binding domain on which the conservative Clostridial toxin binding domain variant is based. A conservative Clostridial toxin binding domain variant can also substitute at least 10 contiguous amino acids, at least 15 contiguous amino acids, at least 20 contiguous amino acids, or at least 25 contiguous amino acids from the reference Clostridial toxin binding domain on which the conservative Clostridial toxin binding domain variant is based, that possess at least 50% amino acid identity, 65% amino acid identity, 75% amino acid identity, 85% amino acid identity or 95% amino acid identity to the reference Clostridial toxin binding domain on which the conservative Clostridial toxin binding domain variant is based. Non-limiting examples of a conservative Clostridial toxin binding domain variant include, e.g., conservative BoNT/A binding domain variants, conservative BoNT/B binding domain variants, conservative BoNT/C1 binding domain variants, conservative BoNT/D binding domain variants, conservative BoNT/E binding domain variants, conservative BoNT/F binding domain variants, conservative BoNT/G binding domain variants, conservative TeNT binding domain variants, conservative BaNT binding domain variants and conservative BuNT binding domain variants.

As used herein, the term "non-conservative Clostridial toxin binding domain variant" means a Clostridial toxin binding domain in which 1) at least one amino acid is deleted from the reference Clostridial toxin binding domain on which the non-conservative Clostridial toxin binding domain variant is based; 2) at least one amino acid added to the reference Clostridial toxin binding domain on which the non-conservative Clostridial toxin binding domain is based; or 3) at least one amino acid is substituted by another amino acid or an amino acid analog that does not share any property similar to that of the original amino acid from the reference Clostridial toxin binding domain sequence (Table 1). A non-conservative Clostridial toxin binding domain variant can function in substantially the same manner as the reference Clostridial toxin binding domain on which the non-conservative Clostridial toxin binding domain variant is based, and can be substituted for the reference Clostridial toxin binding domain in any aspect of the present invention. A non-conservative Clostridial toxin binding domain variant can delete one or more amino acids, two or more amino acids, three or more amino acids, four or more amino acids, five or more amino acids, and ten or more amino acids from the reference Clostridial toxin binding domain on which the non-conservative Clostridial toxin binding domain variant is based. A non-conservative Clostridial toxin binding domain variant can add one or more amino acids, two or more amino acids, three or more amino acids, four or more amino acids, five or more amino acids, and ten or more amino acids to the reference Clostridial toxin binding domain on which the non-conservative Clostridial toxin binding domain variant is based. A non-conservative Clostridial toxin binding domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin binding domain on which the non-conservative Clostridial toxin binding domain variant is based. A non-conservative Clostridial toxin binding domain variant can also substitute at least 10 contiguous amino acids, at least 15 contiguous amino acids, at least 20 contiguous amino acids, or at least 25 contiguous amino acids from the reference Clostridial toxin binding domain on which the non-conservative Clostridial toxin binding domain variant is based, that possess at least 50% amino acid identity, 65% amino acid identity, 75% amino acid identity, 85% amino acid identity or 95% amino acid identity to the reference Clostridial toxin binding domain on which the non-conservative Clostridial toxin binding domain variant is based. Non-limiting examples of a non-conservative Clostridial toxin binding domain variant include, e.g., non-conservative BoNT/A binding domain variants, non-conservative BoNT/B binding domain variants, non-conservative BoNT/C1 binding domain variants, non-conservative BoNT/D binding domain variants, non-conservative BoNT/E binding domain variants, non-conservative BoNT/F binding domain variants, non-conservative BoNT/G binding domain variants, non-conservative TeNT binding domain variants, non-conservative BaNT binding domain variants and non-conservative BuNT binding domain variants.

As used herein, the term "Clostridial toxin binding domain chimeric" means a polypeptide comprising at least a portion of a Clostridial toxin binding domain and at least a portion of at least one other polypeptide to form a toxin binding domain with at least one property different from the reference Clostridial toxin binding domains of Table 1, with the proviso that this Clostridial toxin binding domain chimeric is still capable of executing the cell binding step of the intoxication process, including, e.g., the selective binding of the Clostridial toxin to a toxin-specific receptor located on the plasma membrane surface of a target cell.

As used herein, the term "active Clostridial toxin binding domain fragment" means any of a variety of Clostridial toxin fragments comprising the binding domain can be useful in aspects of the present invention with the proviso that these active fragments can execute the cell binding step of the intoxication process, including, e.g., the selective binding of the Clostridial toxin to a toxin-specific receptor located on the plasma membrane surface of a target cell. For example, the H$_C$ binding domains from the heavy chains of Clostridial toxins are approximately 400-435 amino acids in length and comprise a translocation domain (Table 1). Research has shown that the entire length of a binding domain from a Clostridial toxin heavy chain is not necessary for the translocating activity of the translocation domain. Thus, aspects of this embodiment can include Clostridial toxin binding domains comprising a translocation domain having a length of, e.g., at least 350 amino acids, at least 375 amino acids, at least 400 amino acids and at least 425 amino acids. Other aspects of this embodiment can include Clostridial toxin binding domains comprising translocation domain having a length of, e.g., at most 350 amino acids, at most 375 amino acids, at most 400 amino acids and at most 425 amino acids. As another example, the H$_{CC}$ binding domain from the heavy chains of Clostridial toxins are approximately 165-195 amino acids in length and comprise a binding domain (Table 1). Research has shown that the entire length of a H$_{CC}$ binding domain from a Clostridial toxin heavy chain is not necessary for the binding activity of the binding domain. Thus, aspects of this embodiment can include a Clostridial toxin H$_{CC}$ binding domain comprising a binding domain having a length of, e.g., at least 150 amino acids, at least 175 amino acids, at least 200 amino acids and at least 225 amino acids. Other aspects of this embodiment can include a Clostridial toxin H$_{CC}$ binding domain comprising a binding domain having a length of, e.g., at most 150 amino acids, at most 175 amino acids, at most 200 amino acids and at most 225 amino acids.

Any of a variety of sequence alignment methods can be used to determine percent identity of naturally-occurring Clostridial toxin binding domain variants and non-naturally-occurring Clostridial toxin binding domain variants, including, without limitation, global methods, local methods and hybrid methods, such as, e.g., segment approach methods. Protocols to determine percent identity are routine procedures within the scope of one skilled in the art and from the teaching herein.

Thus, in an embodiment, a multivalent Clostridial toxin disclosed in the present specification comprises a Clostridial toxin binding domain. In an aspect of this embodiment, a Clostridial toxin binding domain comprises a naturally occurring Clostridial toxin binding domain variant, such as, e.g., a Clostridial toxin binding domain isoform or a Clostridial toxin binding domain subtype. In another aspect of this embodiment, a Clostridial toxin binding domain comprises a non-naturally occurring Clostridial toxin binding domain variant, such as, e.g., a conservative Clostridial toxin binding domain variant, a non-conservative Clostridial toxin binding domain variant, a Clostridial toxin chimeric binding domain, an active Clostridial toxin binding domain fragment, or any combination thereof.

In an embodiment, a binding domain comprises a BoNT/A binding domain. In an aspect of this embodiment, a BoNT/A binding domain comprises a BoNT/A H$_C$ binding domain. In aspects of this embodiment, a BoNT/A binding domain comprising BoNT/A H$_C$ binding domain comprises a polypeptide having, e.g., at least 70% amino acid identity with amino acids 874-1296 of SEQ ID NO: 1, at least 75% amino acid identity with amino acids 874-1296 of SEQ ID NO: 1, at least 80% amino acid identity with amino acids 874-1296 of SEQ ID NO: 1, at least 85% amino acid identity with amino acids 874-1296 of SEQ ID NO: 1, at least 90% amino acid identity with amino acids 874-1296 of SEQ ID NO: 1 or at least 95% amino acid identity with amino acids 874-1296 of SEQ ID NO: 1. In yet other aspects of this embodiment, a BoNT/A binding domain comprising a BoNT/A H$_C$ binding domain comprises a polypeptide having, e.g., at most 70% amino acid identity with amino acids 874-1296 of SEQ ID NO: 1, at most 75% amino acid identity with amino acids 874-1296 of SEQ ID NO: 1, at most 80% amino acid identity with amino acids 874-1296 of SEQ ID NO: 1, at most 85% amino acid identity with amino acids 874-1296 of SEQ ID NO: 1, at most 90% amino acid identity with amino acids 874-1296 of SEQ ID NO: 1 or at most 95% amino acid identity with amino acids 874-1296 of SEQ ID NO: 1.

In other aspects of this embodiment, a BoNT/A binding domain comprising a BoNT/A H$_C$ binding domain comprises a polypeptide having, e.g., at most one, two, three, four, five, six, seven, eight, nine, 10, 20, 30, 40, 50, 100, or 200 non-contiguous amino acid substitutions relative to amino acids 874-1296 of SEQ ID NO: 1. In other aspects of this embodiment, a BoNT/A binding domain comprising a BoNT/A H$_C$ binding domain comprises a polypeptide having, e.g., at least one, two, three, four, five, six, seven, eight, nine, 10, 20, 30, 40, 50, 100 or 200 non-contiguous amino acid substitutions relative to amino acids 874-1296 of SEQ ID NO: 1. In yet other aspects of this embodiment, a BoNT/A binding domain comprising a BoNT/A H$_C$ binding domain comprises a polypeptide having, e.g., at most one, two, three, four, five, six, seven, eight, nine, 10, 20, 30, 40, 50, 100 or 200 non-contiguous amino acid deletions relative to amino acids 874-1296 of SEQ ID NO: 1. In other aspects of this embodiment, a BoNT/A binding domain comprising a BoNT/A H$_C$ binding domain comprises a polypeptide having, e.g., at least one, two, three, four, five, six, seven, eight, nine, 10, 20, 30, 40, 50, 100 or 200 non-contiguous amino acid deletions relative to amino acids 874-1296 of SEQ ID NO: 1. In still other aspects of this embodiment, a BoNT/A binding domain comprising a BoNT/A H$_C$ binding domain comprises a polypeptide having, e.g., at most one, two, three, four, five, six, seven, eight, nine, 10, 20, 30, 40, 50, 100 or 200 non-contiguous amino acid additions relative to amino acids 874-1296 of SEQ ID NO: 1. In other aspects of this embodiment, a BoNT/A binding domain comprising a BoNT/A H$_C$ binding domain comprises a polypeptide having, e.g., at least one, two, three, four, five, six, seven, eight, nine, 10, 20, 30, 40, 50, 100 or 200 non-contiguous amino acid additions relative to amino acids 874-1296 of SEQ ID NO: 1.

In other aspects of this embodiment, a BoNT/A binding domain comprising a BoNT/A H$_C$ binding domain comprises a polypeptide having, e.g., at most one, two, three, four, five, six, seven, eight, nine, 10, 20, 30, 40, 50, 100 or 200 contiguous amino acid substitutions relative to amino acids 874-1296 of SEQ ID NO: 1. In other aspects of this embodiment, a BoNT/A binding domain comprising a BoNT/A H$_C$ binding domain comprises a polypeptide having, e.g., at least one, two, three, four, five, six, seven, eight, nine, 10, 20, 30, 40, 50, 100 or 200 contiguous amino acid substitutions relative to amino acids 874-1296 of SEQ ID NO: 1. In yet other aspects of this embodiment, a BoNT/A binding domain comprising a BoNT/A H$_C$ binding domain comprises a polypeptide having, e.g., at most one, two, three, four, five, six, seven, eight, nine, 10, 20, 30, 40, 50, 100 or 200 contiguous amino acid deletions relative to amino acids 874-1296 of SEQ ID NO: 1. In other aspects of this embodiment, a BoNT/A binding domain comprising a BoNT/A H$_C$ binding domain comprises a polypeptide having, e.g., at least one, two, three, four, five, six, seven, eight, nine, 10, 20, 30, 40, 50, 100 or 200 contiguous amino acid deletions relative to amino acids 874-1296 of SEQ ID NO: 1. In still other aspects of this embodiment, a BoNT/A binding domain comprising a BoNT/A H$_C$ binding domain comprises a polypeptide having, e.g., at most one, two, three, four, five, six, seven, eight, nine, 10, 20, 30, 40, 50, 100 or 200 contiguous amino acid additions relative to amino acids 874-

1296 of SEQ ID NO: 1. In other aspects of this embodiment, a BoNT/A binding domain comprising a BoNT/A $H_C$ binding domain comprises a polypeptide having, e.g., at least one, two, three, four, five, six, seven, eight, nine, 10, 20, 30, 40, 50, 100 or 200 contiguous amino acid additions relative to amino acids 874-1296 of SEQ ID NO: 1.

In another aspect of this embodiment, a BoNT/A binding domain comprises a BoNT/A $H_{CC}$ binding domain. In aspects of this embodiment, a BoNT/A binding domain comprising a BoNT/A $H_{CC}$ binding domain comprises a modification of amino acids 1111-1296 of SEQ ID NO: 1. In another aspect of this embodiment, a BoNT/A binding domain comprising a BoNT/A $H_{CC}$ binding domain comprises a α-fold motif of a β-trefoil domain of a BoNT/A $H_{CC}$ binding domain, a β-fold motif of a β-trefoil domain of a BoNT/A $H_{CC}$ binding domain, or a γ-fold motif of a β-trefoil domain of a BoNT/A $H_{CC}$ binding domain. In another aspect of this embodiment, a BoNT/A binding domain comprising a BoNT/A $H_{CC}$ binding domain comprises a modification to amino acids 1111-1162, amino acids 1179-1223, or amino acids 1237-1296 of SEQ ID NO: 1.

In other aspects of this embodiment, a BoNT/A $H_{CC}$ binding domain comprising a β-trefoil fold domain comprises a polypeptide having, e.g., at least 70% amino acid identity with amino acids 1111-1162, amino acids 1179-1223, or amino acids 1237-1296 of SEQ ID NO: 1, at least 75% amino acid identity with amino acids 1111-1162, amino acids 1179-1223, or amino acids 1237-1296 of SEQ ID NO: 1, at least 80% amino acid identity with amino acids 1111-1162, amino acids 1179-1223, or amino acids 1237-1296 of SEQ ID NO: 1, at least 85% amino acid identity with amino acids 1111-1162, amino acids 1179-1223, or amino acids 1237-1296 of SEQ ID NO: 1, at least 90% amino acid identity with amino acids 1111-1162, amino acids 1179-1223, or amino acids 1237-1296 of SEQ ID NO: 1 or at least 95% amino acid identity with amino acids 1111-1162, amino acids 1179-1223, or amino acids 1237-1296 of SEQ ID NO: 1. In yet other aspects of this embodiment, a BoNT/A $H_{CC}$ binding domain comprising a β-trefoil fold domain comprises a polypeptide having, e.g., at most 70% amino acid identity with amino acids 1111-1162, amino acids 1179-1223, or amino acids 1237-1296 of SEQ ID NO: 1, at most 75% amino acid identity with amino acids 1111-1162, amino acids 1179-1223, or amino acids 1237-1296 of SEQ ID NO: 1, at most 80% amino acid identity with amino acids 1111-1162, amino acids 1179-1223, or amino acids 1237-1296 of SEQ ID NO: 1, at most 85% amino acid identity with amino acids 1111-1162, amino acids 1179-1223, or amino acids 1237-1296 of SEQ ID NO: 1, at most 90% amino acid identity with amino acids 1111-1162, amino acids 1179-1223, or amino acids 1237-1296 of SEQ ID NO: 1 or at most 95% amino acid identity with amino acids 1111-1162, amino acids 1179-1223, or amino acids 1237-1296 of SEQ ID NO: 1.

In other aspects of this embodiment, a BoNT/A $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1111-1162, amino acids 1179-1223, or amino acids 1237-1296 of SEQ ID NO: 1. In other aspects of this embodiment, a BoNT/A $H_{CC}$ binding domain comprises a polypeptide having, e.g., at least one, two, three, four, five, six, seven, eight, nine, 10 or 20 non-contiguous amino acid substitutions relative to amino acids 1111-1162, amino acids 1179-1223, or amino acids 1237-1296 of SEQ ID NO: 1. In yet other aspects of this embodiment, a BoNT/A $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1111-1162, amino acids 1179-1223, or amino acids 1237-1296 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1111-1162, amino acids 1179-1223, or amino acids 1237-1296 of SEQ ID NO: 1. In still other aspects of this embodiment, a BoNT/A $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1111-1162, amino acids 1179-1223, or amino acids 1237-1296 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1111-1162, amino acids 1179-1223, or amino acids 1237-1296 of SEQ ID NO: 1.

In other aspects of this embodiment, a BoNT/A $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1111-1162, amino acids 1179-1223, or amino acids 1237-1296 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1111-1162, amino acids 1179-1223, or amino acids 1237-1296 of SEQ ID NO: 1. In yet other aspects of this embodiment, a BoNT/A $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1111-1162, amino acids 1179-1223, or amino acids 1237-1296 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1111-1162, amino acids 1179-1223, or amino acids 1237-1296 of SEQ ID NO: 1. In still other aspects of this embodiment, a BoNT/A $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1111-1162, amino acids 1179-1223, or amino acids 1237-1296 of SEQ ID NO: 1. In other aspects of this embodiment, a BoNT/A $H_{CC}$ binding domain comprises a polypeptide having, e.g., at least one, two, three, four, five, six, seven, eight, nine, 10 or 20 contiguous amino acid additions relative to amino acids 1111-1162, amino acids 1179-1223, or amino acids 1237-1296 of SEQ ID NO: 1.

In another embodiment, a BoNT/A binding domain comprising a BoNT/A $H_{CC}$ binding domain comprises a β4/β5 hairpin turn of a β-trefoil domain of a BoNT/A $H_{CC}$ binding domain or a β8/β9 hairpin turn of a β-trefoil domain of a BoNT/A $H_{CC}$ binding domain. In another aspect of this embodiment, a BoNT/A binding domain comprising a BoNT/A $H_{CC}$ binding domain comprises a modification of amino acids 1163-1178 or amino acids 1224-1236 of SEQ ID NO: 1.

In other aspects of this embodiment, a BoNT/A $H_{CC}$ binding domain comprising a β-trefoil fold domain comprises a polypeptide having, e.g., at least 70% amino acid identity with amino acids 1163-1178 or amino acids 1224-1236 of SEQ ID NO: 1, at least 75% amino acid identity with amino acids 1163-1178 or amino acids 1224-1236 of SEQ ID NO: 1, at least 80% amino acid identity with amino acids 1163-1178 or amino acids 1224-1236 of SEQ ID NO: 1, at least 85% amino acid identity with amino acids 1163-1178 or amino acids 1224-1236 of SEQ ID NO: 1, at least 90% amino acid identity with amino acids 1163-1178 or amino acids 1224-1236 of SEQ ID NO: 1 or at least 95% amino acid identity with amino acids 1163-1178 or amino acids 1224-1236 of SEQ ID NO: 1. In yet other aspects of this embodiment, a BoNT/A $H_{CC}$ binding domain comprising a β-trefoil fold domain comprises a polypeptide having, e.g., at most 70% amino acid identity with amino acids 1163-1178 or amino acids 1224-1236 of SEQ ID NO: 1, at most 75% amino acid identity with amino acids 1163-1178 or amino acids 1224-1236 of SEQ ID NO: 1, at most 80% amino acid identity with amino acids 1163-1178 or amino acids 1224-1236 of SEQ ID NO: 1, at most 85% amino acid identity with amino acids 1163-1178 or amino acids 1224-1236 of SEQ ID NO: 1, at most 90% amino acid identity with amino acids 1163-1178 or amino acids 1224-1236 of SEQ ID NO: 1 or at most 95% amino acid identity with amino acids 1163-1178 or amino acids 1224-1236 of SEQ ID NO: 1.

In other aspects of this embodiment, a BoNT/A $H_{CC}$ binding domain comprising a β-trefoil fold domain comprises a polypeptide having, e.g., at most one, two, three, four, five, six, seven, eight, nine or 10 non-contiguous amino acid substitutions relative to amino acids 1163-1178 or amino acids 1224-1236 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine or 10 non-contiguous amino acid substitutions relative to amino acids 1163-1178 or amino acids 1224-1236 of SEQ ID NO: 1. In other aspects of this embodiment, a non-contiguous amino acid substitution of any amino acid from amino acids 1163-1178 or amino acids 1224-1236 of SEQ ID NO: 1 can be replaced with glycine. In other aspects of this embodiment, a non-contiguous amino acid substitution of any hydrophobic amino acid from amino acids 1163-1178 or amino acids 1224-1236 of SEQ ID NO: 1 can be replaced with phenylalanine. In yet other aspects of this embodiment, a BoNT/A $H_{CC}$ binding domain comprising a β-trefoil fold domain comprises a polypeptide having, e.g., at most one, two, three, four, five, six, seven, eight, nine or 10 non-contiguous amino acid deletions relative to amino acids 1163-1178 or amino acids 1224-1236 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine or 10 non-contiguous amino acid deletions relative to amino acids 1163-1178 or amino acids 1224-1236 of SEQ ID NO: 1. In still other aspects of this embodiment, a BoNT/A $H_{CC}$ binding domain comprising a β-trefoil fold domain comprises a polypeptide having, e.g., at most one, two, three, four, five, six, seven, eight, nine or 10 non-contiguous amino acid additions relative to amino acids 1163-1178 or amino acids 1224-1236 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine or 10 non-contiguous amino acid additions relative to amino acids 1163-1178 or amino acids 1224-1236 of SEQ ID NO: 1.

In other aspects of this embodiment, a BoNT/A $H_{CC}$ binding domain comprising a β-trefoil fold domain comprises a polypeptide having, e.g., at most one, two, three, four, five, six, seven, eight, nine or 10 contiguous amino acid substitutions relative to amino acids 1163-1178 or amino acids 1224-1236 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine or 10 contiguous amino acid substitutions relative to amino acids 1163-1178 or amino acids 1224-1236 of SEQ ID NO: 1. In other aspects of this embodiment, contiguous amino acid substitutions of amino acids from amino acids 1163-1178 or amino acids 1224-1236 of SEQ ID NO: 1 can be replaced with glycine. In other aspects of this embodiment, contiguous amino acid substitutions of hydrophobic amino acids from amino acids 1163-1178 or amino acids 1224-1236 of SEQ ID NO: 1 can be replaced with phenylalanine. In yet other aspects of this embodiment, a BoNT/A $H_{CC}$ binding domain comprising a β-trefoil fold domain comprises a polypeptide having, e.g., at most one, two, three, four, five, six, seven, eight, nine or 10 contiguous amino acid deletions relative to amino acids 1163-1178 or amino acids 1224-1236 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine or 10 contiguous amino acid deletions relative to amino acids 1163-1178 or amino acids 1224-1236 of SEQ ID NO: 1. In still other aspects of this embodiment, a BoNT/A $H_{CC}$ binding domain comprising a β-trefoil fold domain comprises a polypeptide having, e.g., at most one, two, three, four, five, six, seven, eight, nine or 10 contiguous amino acid additions relative to amino acids 1163-1178 or amino acids 1224-1236 of SEQ ID NO: 1. In other aspects of this embodiment, a BoNT/A $H_{CC}$ binding domain comprising a β-trefoil fold domain comprises a polypeptide having, e.g., at least one, two, three, four, five, six, seven, eight, nine or 10 contiguous amino acid additions relative to amino acids 1163-1178 or amino acids 1224-1236 of SEQ ID NO: 1.

In other aspects of this embodiment, a BoNT/A $H_{CC}$ binding domain comprises a substitution of amino acid Trp 1101, Gly 1102, Leu 1105, Tyr 1111, Tyr 1112, Gly 1158, Ile 1163, Asp 1179, Glu 1203, Phe 1252, Ser 1264, Trp 1266, Tyr 1267, Gln 1270, Gly 1279 or Trp 1282, or any combination thereof, the substitution enhancing the binding activity of the BoNT/A $H_{CC}$ binding domain. In other aspects of this embodiment, a BoNT/A $H_{CC}$ binding domain comprises a deletion of amino acid Trp 1101, Gly 1102, Leu 1105, Tyr 1111, Tyr 1112, Gly 1158, Ile 1163, Asp 1179, Glu 1203, Phe 1252, Ser 1264, Trp 1266, Tyr 1267, Gln 1270, Gly 1279 or Trp 1282, or any combination thereof, the deletion enhancing the binding activity of the BoNT/A $H_{CC}$ binding domain.

In another embodiment, a binding domain comprises a BoNT/B binding domain. In an aspect of this embodiment, a BoNT/B binding domain comprises a BoNT/B $H_C$ binding domain. In other aspects of this embodiment, a BoNT/B binding domain comprising a BoNT/B $H_C$ binding domain comprises a polypeptide, e.g., at least 70% amino acid identity with amino acids 861-1291 of SEQ ID NO: 2, at least 75% amino acid identity with amino acids 861-1291 of SEQ ID NO: 2, at least 80% amino acid identity with amino acids 861-1291 of SEQ ID NO: 2, at least 85% amino acid identity with amino acids 861-1291 of SEQ ID NO: 2, at least 90% amino acid identity with amino acids 861-1291 of SEQ ID NO: 2 or at least 95% amino acid identity with amino acids 861-1291 of SEQ ID NO: 2. In yet other aspects of this embodiment, a BoNT/B binding domain comprising a BoNT/B $H_C$ binding domain comprises a polypeptide having, e.g., at most 70% amino acid identity with amino acids 861-1291 of SEQ ID NO: 2, at most 75% amino acid identity with amino acids 861-1291 of SEQ ID NO: 2, at most 80% amino acid identity with amino acids 861-1291 of SEQ ID NO: 2, at most 85% amino acid identity with amino acids 861-1291 of SEQ ID NO: 2, at most 90% amino acid identity with amino acids 861-1291 of SEQ ID NO: 2 or at most 95% amino acid identity with amino acids 861-1291 of SEQ ID NO: 2.

In other aspects of this embodiment, a BoNT/B binding domain comprising a BoNT/B $H_C$ binding domain comprises a polypeptide having, e.g., at most one, two, three, four, five, six, seven, eight, nine, 10, 20, 30, 40, 50, 100, or 200 non-contiguous amino acid substitutions relative to amino acids 861-1291 of SEQ ID NO: 2. In other aspects of this embodiment, a BoNT/B binding domain comprising a BoNT/B $H_C$ binding domain comprises a polypeptide having, e.g., at least one, two, three, four, five, six, seven, eight, nine, 10, 20, 30, 40, 50, 100 or 200 non-contiguous amino acid substitutions relative to amino acids 861-1291 of SEQ ID NO: 2. In yet other aspects of this embodiment, a BoNT/B binding domain comprising a BoNT/B $H_C$ binding domain comprises a polypeptide having, e.g., at most one, two, three, four, five, six, seven, eight, nine, 10, 20, 30, 40, 50, 100 or 200 non-contiguous amino acid deletions relative to amino acids 861-1291 of SEQ ID NO: 2. In other aspects of this embodiment, a BoNT/B binding domain comprising a BoNT/B $H_C$ binding domain comprises a polypeptide having, e.g., at least one, two, three, four, five, six, seven, eight, nine, 10, 20, 30, 40, 50, 100 or 200 non-contiguous amino acid deletions relative to amino acids 861-1291 of SEQ ID NO: 2. In still other aspects of this embodiment, a BoNT/B binding domain comprising a BoNT/B $H_C$ binding domain comprises a polypeptide having, e.g., at most one, two, three, four, five, six, seven, eight, nine, 10, 20, 30, 40, 50, 100 or 200 non-contiguous amino acid additions relative to amino acids 861-1291 of SEQ ID NO: 2. In other aspects of this embodiment, a BoNT/B $H_C$ binding domain comprises a polypeptide having, e.g., at least one, two, three, four, five, six, seven, eight, nine, 10, 20, 30, 40, 50, 100 or 200 non-contiguous amino acid additions relative to amino acids 861-1291 of SEQ ID NO: 2.

In other aspects of this embodiment, a BoNT/B binding domain comprising a BoNT/B $H_C$ binding domain comprises a polypeptide having, e.g., at most one, two, three, four, five, six, seven, eight, nine, 10, 20, 30, 40, 50, 100 or 200 contiguous amino acid substitutions relative to amino acids 861-1291 of SEQ ID NO: 2. In other aspects of this embodiment, a BoNT/B binding domain comprising a BoNT/B $H_C$ binding domain comprises a polypeptide having, e.g., at least one, two, three, four, five, six, seven, eight, nine, 10, 20, 30, 40, 50, 100 or 200 contiguous amino acid substitutions relative to amino acids 861-1291 of SEQ ID NO: 2. In yet other aspects of this embodiment, a BoNT/B binding domain comprising a BoNT/B $H_C$ binding domain comprises a polypeptide having, e.g., at most one, two, three, four, five, six, seven, eight, nine, 10, 20, 30, 40, 50, 100 or 200 contiguous amino acid deletions relative to amino acids 861-1291 of SEQ ID NO: 2. In other aspects of this embodiment, a BoNT/B binding domain comprising a BoNT/B $H_C$ binding domain comprises a polypeptide having, e.g., at least one, two, three, four, five, six, seven, eight, nine, 10, 20, 30, 40, 50, 100 or 200 contiguous amino acid deletions relative to amino acids 861-1291 of SEQ ID NO: 2. In still other aspects of this embodiment, a BoNT/B binding domain comprising a BoNT/B $H_C$ binding domain comprises a polypeptide having, e.g., at most one, two, three, four, five, six, seven, eight, nine, 10, 20, 30, 40, 50, 100 or 200 contiguous amino acid additions relative to amino acids 861-1291 of SEQ ID NO: 2. In other aspects of this embodiment, a BoNT/B binding domain comprising a BoNT/B $H_C$ binding domain comprises a polypeptide having, e.g., at least one, two, three, four, five, six, seven, eight, nine, 10, 20, 30, 40, 50, 100 or 200 contiguous amino acid additions relative to amino acids 861-1291 of SEQ ID NO: 2.

In another aspect of this embodiment, a BoNT/B binding domain comprises a BoNT/B $H_{CC}$ binding domain. In another aspect of this embodiment, a BoNT/B binding domain comprising a BoNT/B $H_{CC}$ binding domain comprises an α-fold motif of a β-trefoil domain of a BoNT/B $H_{CC}$ binding domain, a β-fold motif of a β-trefoil domain of a BoNT/B $H_{CC}$ binding domain, or a γ-fold motif of a β-trefoil domain of a BoNT/B $H_{CC}$ binding domain. In another aspect of this embodiment, a BoNT/B binding domain comprising a BoNT/B $H_{CC}$ binding domain comprises a modification to amino acids 1098-1147, amino acids 1166-1210, or amino acids 1223-1291 of SEQ ID NO: 2.

In other aspects of this embodiment, a BoNT/B $H_{CC}$ binding domain comprising a β-trefoil fold domain comprises a polypeptide having, e.g., at least 70% amino acid identity with amino acids 1098-1147, amino acids 1166-1210, or amino acids 1223-1291 of SEQ ID NO: 2, at least 75% amino acid identity with amino acids 1098-1147, amino acids 1166-1210, or amino acids 1223-1291 of SEQ ID NO: 2, at least 80% amino acid identity with amino acids 1098-1147, amino acids 1166-1210, or amino acids 1223-1291 of SEQ ID NO: 2, at least 85% amino acid identity with amino acids 1098-1147, amino acids 1166-1210, or amino acids 1223-1291 of SEQ ID NO: 2, at least 90% amino acid identity with amino acids 1098-1147, amino acids 1166-1210, or amino acids 1223-1291 of SEQ ID NO: 2 or at least 95% amino acid identity with amino acids 1098-1147, amino acids 1166-1210, or amino acids 1223-1291 of SEQ ID NO: 2. In yet other aspects of this embodiment, a BoNT/B $H_{CC}$ binding domain comprising a β-trefoil fold domain comprises a polypeptide having, e.g., at most 70% amino acid identity with amino acids 1098-1147, amino acids 1166-1210, or amino acids 1223-1291 of SEQ ID NO: 2, at most 75% amino acid identity with amino acids 1098-1147, amino acids 1166-1210, or amino acids 1223-1291 of SEQ ID NO: 2, at most 80% amino acid identity with amino acids 1098-1147, amino acids 1166-1210, or amino acids 1223-1291 of SEQ ID NO: 2, at most 85% amino acid identity with amino acids 1098-1147, amino acids 1166-1210, or amino acids 1223-1291 of SEQ ID NO: 2, at most 90% amino acid identity with amino acids 1098-1147, amino acids 1166-1210, or amino acids 1223-1291 of SEQ ID NO: 2 or at most 95% amino acid identity with amino acids 1098-1147, amino acids 1166-1210, or amino acids 1223-1291 of SEQ ID NO: 2.

In other aspects of this embodiment, a BoNT/B $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1098-1147, amino acids 1166-1210, or amino acids 1223-1291 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine, 10 or 20 non-contiguous amino acid substitutions relative to amino acids 1098-1147, amino acids 1166-1210, or amino acids 1223-1291 of SEQ ID NO: 2. In yet other aspects of this embodiment, a BoNT/B $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1098-1147, amino acids 1166-1210, or amino acids 1223-1291 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1098-1147, amino acids 1166-1210, or amino acids 1223-1291 of SEQ ID NO: 2. In still other aspects of this embodiment, a BoNT/B $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1098-1147, amino acids 1166-1210, or amino acids 1223-1291 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1098-1147, amino acids 1166-1210, or amino acids 1223-1291 of SEQ ID NO: 2.

In other aspects of this embodiment, a BoNT/B $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1098-1147, amino acids 1166-1210, or amino acids 1223-1291 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1098-1147, amino acids 1166-1210, or amino acids 1223-1291 of SEQ ID NO: 2. In yet other aspects of this embodiment, a BoNT/B $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1098-1147, amino acids 1166-1210, or amino acids 1223-1291 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1098-1147, amino acids 1166-1210, or amino acids 1223-1291 of SEQ ID NO: 2. In still other aspects of this embodiment, a BoNT/B $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1098-1147, amino acids 1166-1210, or amino acids 1223-1291 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine, 10 or 20 contiguous amino acid additions relative to amino acids 1098-1147, amino acids 1166-1210, or amino acids 1223-1291 of SEQ ID NO: 2.

In another embodiment, a binding domain comprising a BoNT/B H binding domain comprises a β4/β5 hairpin turn of a β-trefoil domain of a BoNT/B $H_{CC}$ binding domain or a β8/β9 hairpin turn of a β-trefoil domain of a BoNT/B $H_{CC}$ binding domain. In another aspect of this embodiment, a binding domain comprising a BoNT/B $H_{CC}$ binding domain comprises a modification of amino acids 1148-1165 or amino acids 1211-1222 of SEQ ID NO: 2.

In other aspects of this embodiment, a BoNT/B $H_{CC}$ binding domain comprising a β-trefoil fold domain comprises a polypeptide having, e.g., at least 70% amino acid identity with amino acids 1148-1165 or amino acids 1211-1222 of SEQ ID NO: 2, at least 75% amino acid identity with amino acids 1148-1165 or amino acids 1211-1222 of SEQ ID NO: 2, at least 80% amino acid identity with amino acids 1148-1165 or amino acids 1211-1222 of SEQ ID NO: 2, at least 85% amino acid identity with amino acids 1148-1165 or amino acids 1211-1222 of SEQ ID NO: 2, at least 90% amino acid identity with amino acids 1148-1165 or amino acids 1211-1222 of SEQ ID NO: 2 or at least 95% amino acid identity with amino acids 1148-1165 or amino acids 1211-1222 of SEQ ID NO: 2. In yet other aspects of this embodiment, a BoNT/B $H_{CC}$ binding domain comprising a β-trefoil fold domain comprises a polypeptide having, e.g., at most 70% amino acid identity with amino acids 1148-1165 or amino acids 1211-1222 of SEQ ID NO: 2, at most 75% amino acid identity with amino acids 1148-1165 or amino acids 1211-1222 of SEQ ID NO: 2, at most 80% amino acid identity with amino acids 1148-1165 or amino acids 1211-1222 of SEQ ID NO: 2, at most 85% amino acid identity with amino acids 1148-1165 or amino acids 1211-1222 of SEQ ID NO: 2, at most 90% amino acid identity with amino acids 1148-1165 or amino acids 1211-1222 of SEQ ID NO: 2 or at most 95% amino acid identity with amino acids 1148-1165 or amino acids 1211-1222 of SEQ ID NO: 2.

In other aspects of this embodiment, a BoNT/B $H_{CC}$ binding domain comprising a β-trefoil fold domain comprises a polypeptide having, e.g., at most one, two, three, four, five, six, seven, eight, nine or 10 non-contiguous amino acid substitutions relative to amino acids 1148-1165 or amino acids 1211-1222 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine or 10 non-contiguous amino acid substitutions relative to amino acids 1148-1165 or amino acids 1211-1222 of SEQ ID NO: 2. In other aspects of this embodiment, a non-contiguous amino acid substitution of any amino acid from amino acids 1148-1165 or amino acids 1211-1222 of SEQ ID NO: 2 can be replaced with glycine. In other aspects of this embodiment, a non-contiguous amino acid substitution of any hydrophobic amino acid from amino acids 1148-1165 or amino acids 1211-1222 of SEQ ID NO: 2 can be replaced with phenylalanine. In yet other aspects of this embodiment, a BoNT/B $H_{CC}$ binding domain comprising a β-trefoil fold domain comprises a polypeptide having, e.g., at most one, two, three, four, five, six, seven, eight, nine or 10 non-contiguous amino acid deletions relative to amino acids 1148-1165 or amino acids 1211-1222 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine or 10 non-contiguous amino acid deletions relative to amino acids 1148-1165 or amino acids 1211-1222 of SEQ ID NO: 2. In still other aspects of this embodiment, a BoNT/B $H_{CC}$ binding domain comprising a β-trefoil fold domain comprises a polypeptide having, e.g., at most one, two, three, four, five, six, seven, eight, nine or 10 non-contiguous amino acid additions relative to amino acids 1148-1165 or amino acids 1211-1222 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine or 10 non-contiguous amino acid additions relative to amino acids 1148-1165 or amino acids 1211-1222 of SEQ ID NO: 2.

In other aspects of this embodiment, a BoNT/B $H_{CC}$ binding domain comprising a β-trefoil fold domain comprises a polypeptide having, e.g., at most one, two, three, four, five, six, seven, eight, nine or 10 contiguous amino acid substitutions relative to amino acids 1148-1165 or amino acids 1211-1222 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine or 10 contiguous amino acid substitutions relative to amino acids 1148-1165 or amino acids 1211-1222 of SEQ ID NO: 2. In other aspects of this embodiment, contiguous amino acid substitutions of amino acids from amino acids 1148-1165 or amino acids 1211-1222 of SEQ ID NO: 2 can be replaced with glycine. In other aspects of this embodiment, contiguous amino acid substitutions of hydrophobic amino acids from amino acids 1148-1165 or amino acids 1211-1222 of SEQ ID NO: 2 can be replaced with phenylalanine. In yet other aspects of this embodiment, a BoNT/B $H_{CC}$ binding domain comprising a β-trefoil fold domain comprises a polypeptide having, e.g., at most one, two, three, four, five, six, seven, eight, nine or 10 contiguous amino acid deletions relative to amino acids 1148-1165 or amino acids 1211-1222 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine or 10 contiguous amino acid deletions relative to amino acids 1148-1165 or amino acids 1211-1222 of SEQ ID NO: 2. In still other aspects of this embodiment, a BoNT/B $H_{CC}$ binding domain comprising a β-trefoil fold domain comprises a polypeptide having, e.g., at most one, two, three, four, five, six, seven, eight, nine or 10 contiguous amino acid additions relative to amino acids 1148-1165 or amino acids 1211-1222 of SEQ ID NO: 2. In other aspects of this embodiment, a BoNT/B $H_{CC}$ binding domain comprising a β-trefoil fold domain comprises a polypeptide having, e.g., at least one, two, three, four, five, six, seven, eight, nine or 10 contiguous amino acid additions relative to amino acids 1148-1165 or amino acids 1211-1222 of SEQ ID NO: 2.

In other aspects of this embodiment, a BoNT/B $H_{CC}$ binding domain comprises a substitution of amino acid Trp 1088, Gly 1089, Leu 1092, Tyr 1098, Tyr 1099, Gly 1142, Ile 1147, Asp 1165, Glu 1191, Ile 1240, Ser 1260, Trp 1262, Tyr 1263, Glu 1266, Gly 1277 or Trp 1280, or any combination thereof, the substitution enhancing the binding capability of the BoNT/B $H_{CC}$ binding domain. In other aspects of this embodiment, a BoNT/B $H_{CC}$ binding domain comprises a deletion of amino acid Trp 1088, Gly 1089, Leu 1092, Tyr 1098, Tyr 1099, Gly 1142, Ile 1147, Asp 1165, Glu 1191, Ile 1240, Ser 1260, Trp 1262, Tyr 1263, Glu 1266, Gly 1277 or Trp 1280, or any combination thereof, the deletion enhancing the binding capability of the BoNT/B $H_{CC}$ binding domain.

In another embodiment, a binding domain comprises a BoNT/C1 binding domain. In an aspect of this embodiment, a BoNT/C1 binding domain comprises a BoNT/C1 $H_C$ binding domain. In other aspects of this embodiment, a BoNT/C1 binding domain comprising a BoNT/C1 $H_C$ binding domain comprises a polypeptide having, e.g., at least 70% amino acid identity with amino acids 869-1291 of SEQ ID NO: 3, at least 75% amino acid identity with amino acids 869-1291 of SEQ ID NO: 3, at least 80% amino acid identity with amino acids 869-1291 of SEQ ID NO: 3, at least 85% amino acid identity with amino acids 869-1291 of SEQ ID NO: 3, at least 90% amino acid identity with amino acids 869-1291 of SEQ ID NO: 3 or at least 95% amino acid identity with amino acids 869-1291 of SEQ ID NO: 3. In yet other aspects of this embodiment, a BoNT/C1 binding domain comprising a BoNT/C1 $H_C$ binding domain comprises a polypeptide having, e.g., at most 70% amino acid identity with amino acids 869-1291 of SEQ ID NO: 3, at most 75% amino acid identity with amino acids 869-1291 of SEQ ID NO: 3, at most 80% amino acid identity with amino acids 869-1291 of SEQ ID NO: 3, at most 85% amino acid identity with amino acids 869-1291 of SEQ ID NO: 3, at most 90% amino acid identity with amino acids 869-1291 of SEQ ID NO: 3 or at most 95% amino acid identity with amino acids 869-1291 of SEQ ID NO: 3.

In other aspects of this embodiment, a BoNT/C1 binding domain comprising a BoNT/C1 $H_C$ binding domain comprises a polypeptide having, e.g., at most one, two, three, four, five, six, seven, eight, nine, 10, 20, 30, 40, 50, 100, or 200 non-contiguous amino acid substitutions relative to amino acids 869-1291 of SEQ ID NO: 3. In other aspects of this embodiment, a BoNT/C1 binding domain comprising a BoNT/C1 $H_C$ binding domain comprises a polypeptide having, e.g., at least one, two, three, four, five, six, seven, eight, nine, 10, 20, 30, 40, 50, 100 or 200 non-contiguous amino acid substitutions relative to amino acids 869-1291 of SEQ ID NO: 3. In yet other aspects of this embodiment, a BoNT/C1 binding domain comprising a BoNT/C1 $H_C$ binding domain comprises a polypeptide having, e.g., at most one, two, three, four, five, six, seven, eight, nine, 10, 20, 30, 40, 50, 100 or 200 non-contiguous amino acid deletions relative to amino acids 869-1291 of SEQ ID NO: 3. In other aspects of this embodiment, a BoNT/C1 binding domain comprising a BoNT/C1 $H_C$ binding domain comprises a polypeptide having, e.g., at least one, two, three, four, five, six, seven, eight, nine, 10, 20, 30, 40, 50, 100 or 200 non-contiguous amino acid deletions relative to amino acids 869-1291 of SEQ ID NO: 3. In still other aspects of this embodiment, a BoNT/C1 binding domain comprising a BoNT/C1 $H_C$ binding domain comprises a polypeptide having, e.g., at most one, two, three, four, five, six, seven, eight, nine, 10, 20, 30, 40, 50, 100 or 200 non-contiguous amino acid additions relative to amino acids 869-1291 of SEQ ID NO: 3. In other aspects of this embodiment, a BoNT/C1 binding domain comprising a BoNT/C1 $H_C$ binding domain comprises a polypeptide having, e.g., at least one, two, three, four, five, six, seven, eight, nine, 10, 20, 30, 40, 50, 100 or 200 non-contiguous amino acid additions relative to amino acids 869-1291 of SEQ ID NO: 3.

In other aspects of this embodiment, a BoNT/C1 binding domain comprising a BoNT/C1 $H_C$ binding domain comprises a polypeptide having, e.g., at most one, two, three, four, five, six, seven, eight, nine, 10, 20, 30, 40, 50, 100 or 200 contiguous amino acid substitutions relative to amino acids 869-1291 of SEQ ID NO: 3. In other aspects of this embodiment, a BoNT/C1 binding domain comprising a BoNT/C1 $H_C$ binding domain comprises a polypeptide having, e.g., at least one, two, three, four, five, six, seven, eight, nine, 10, 20, 30, 40, 50, 100 or 200 contiguous amino acid substitutions relative to amino acids 869-1291 of SEQ ID NO: 3. In yet other aspects of this embodiment, a BoNT/C1 binding domain comprising a BoNT/C1 $H_C$ binding domain comprises a polypeptide having, e.g., at most one, two, three, four, five, six, seven, eight, nine, 10, 20, 30, 40, 50, 100 or 200 contiguous amino acid deletions relative to amino acids 869-1291 of SEQ ID NO: 3. In other aspects of this embodiment, a BoNT/C1 binding domain comprising a BoNT/C1 $H_C$ binding domain comprises a polypeptide having, e.g., at least one, two, three, four, five, six, seven, eight, nine, 10, 20, 30, 40, 50, 100 or 200 contiguous amino acid deletions relative to amino acids 869-1291 of SEQ ID NO: 3. In still other aspects of this embodiment, a BoNT/C1 binding domain comprising a BoNT/C1 $H_C$ binding domain comprises a polypeptide having, e.g., at most one, two, three, four, five, six, seven, eight, nine, 10, 20, 30, 40, 50, 100 or 200 contiguous amino acid additions relative to amino acids 869-1291 of SEQ ID NO: 3. In other aspects of this embodiment, a BoNT/C1 binding domain comprising a BoNT/C1 $H_C$ binding domain comprises a polypeptide having, e.g., at least one, two, three, four, five, six, seven, eight, nine, 10, 20, 30, 40, 50, 100 or 200 contiguous amino acid additions relative to amino acids 869-1291 of SEQ ID NO: 3.

In another aspect of this embodiment, a BoNT/C1 binding domain comprises a BoNT/C1 $H_{CC}$ binding domain. In an aspect of this embodiment, a BoNT/C1 binding domain comprising a BoNT/C1 $H_{CC}$ binding domain comprises a modification of amino acids 1112-1291 of SEQ ID NO: 3. In another aspect of this embodiment, a BoNT/C1 binding domain comprising a BoNT/C1 $H_{CC}$ binding domain comprises a α-fold motif of a β-trefoil domain of a BoNT/C1 $H_{CC}$ binding domain, a β-fold motif of a β-trefoil domain of a BoNT/C1 $H_{CC}$ binding domain, or a γ-fold motif of a β-trefoil domain of a BoNT/C1 $H_{CC}$ binding domain. In another aspect of this embodiment, a BoNT/C1 binding domain comprising a BoNT/C1 $H_{CC}$ binding domain comprises a modification to amino acids 1112-1150, amino acids 1167-1218, or amino acids 1230-1291 of SEQ ID NO: 3.

In other aspects of this embodiment, a BoNT/C1 $H_{CC}$ binding domain comprising a β-trefoil fold domain comprises a polypeptide having, e.g., at least 70% amino acid identity with amino acids 1112-1150, amino acids 1167-1218, or amino acids 1230-1291 of SEQ ID NO: 3, at least 75% amino acid identity with amino acids 1112-1150, amino acids 1167-1218, or amino acids 1230-1291 of SEQ ID NO: 3, at least 80% amino acid identity with amino acids 1112-1150, amino acids 1167-1218, or amino acids 1230-1291 of SEQ ID NO: 3, at least 85% amino acid identity with amino acids 1112-1150, amino acids 1167-1218, or amino acids 1230-1291 of SEQ ID NO: 3, at least 90% amino acid identity with amino acids 1112-1150, amino acids 1167-1218, or amino acids 1230-1291 of SEQ ID NO: 3 or at least 95% amino acid identity with amino acids 1112-1150, amino acids 1167-1218, or amino acids 1230-1291 of SEQ ID NO: 3. In yet other aspects of this embodiment, a BoNT/C1 $H_{CC}$ binding domain comprising a β-trefoil fold domain comprises a polypeptide having, e.g., at most 70% amino acid identity with amino acids 1112-1150, amino acids 1167-1218, or amino acids 1230-1291 of SEQ ID NO: 3, at most 75% amino acid identity with amino acids 1112-1150, amino acids 1167-1218, or amino acids 1230-1291 of SEQ ID NO: 3, at most 80% amino acid identity with amino acids 1112-1150, amino acids 1167-1218, or amino acids 1230-1291 of SEQ ID NO: 3, at most 85% amino acid identity with amino acids 1112-1150, amino acids 1167-1218, or amino acids 1230-1291 of SEQ ID NO: 3, at most 90% amino acid identity with amino acids 1112-1150, amino acids 1167-1218, or amino acids 1230-1291 of SEQ ID NO: 3 or at most 95% amino acid identity with amino acids 1112-1150, amino acids 1167-1218, or amino acids 1230-1291 of SEQ ID NO: 3.

In other aspects of this embodiment, a BoNT/C1 $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1112-1150, amino acids 1167-1218, or amino acids 1230-1291 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine, 10 or 20 non-contiguous amino acid substitutions relative to amino acids 1112-1150, amino acids 1167-1218, or amino acids 1230-1291 of SEQ ID NO: 3. In yet other aspects of this embodiment, a BoNT/C1 $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1112-1150, amino acids 1167-1218, or amino acids 1230-1291 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1112-1150, amino acids 1167-1218, or amino acids 1230-1291 of SEQ ID NO: 3. In still other aspects of this embodiment, a BoNT/C1 $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1112-1150, amino acids 1167-1218, or amino acids 1230-1291 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1112-1150, amino acids 1167-1218, or amino acids 1230-1291 of SEQ ID NO: 3.

In other aspects of this embodiment, a BoNT/C1 $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1112-1150, amino acids 1167-1218, or amino acids 1230-1291 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1112-1150, amino acids 1167-1218, or amino acids 1230-1291 of SEQ ID NO: 3. In yet other aspects of this embodiment, a BoNT/C1 $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1112-1150, amino acids 1167-1218, or amino acids 1230-1291 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1112-1150, amino acids 1167-1218, or amino acids 1230-1291 of SEQ ID NO: 3. In still other aspects of this embodiment, a BoNT/C1 $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1112-1150, amino acids 1167-1218, or amino acids 1230-1291 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine, 10 or 20 contiguous amino acid additions relative to amino acids 1112-1150, amino acids 1167-1218, or amino acids 1230-1291 of SEQ ID NO: 3.

In another embodiment, a BoNT/C1 binding domain comprising a BoNT/C1 $H_{CC}$ binding domain comprises a β4/β5 hairpin turn of a β-trefoil domain of a BoNT/C1 $H_{CC}$ binding domain or a β8/β9 hairpin turn of a β-trefoil domain of a BoNT/C1 $H_{CC}$ binding domain. In another aspect of this embodiment, a BoNT/C1 binding domain comprising a BoNT/C1 $H_{CC}$ binding domain comprises a modification of amino acids 1151-1166 or amino acids 1219-1229 of SEQ ID NO: 3.

In other aspects of this embodiment, a BoNT/C1 $H_{CC}$ binding domain comprising a β-trefoil fold domain comprises a polypeptide having, e.g., at least 70% amino acid identity with amino acids 1151-1166 or amino acids 1219-1229 of SEQ ID NO: 3, at least 75% amino acid identity with amino acids 1151-1166 or amino acids 1219-1229 of SEQ ID NO: 3, at least 80% amino acid identity with amino acids 1151-1166 or amino acids 1219-1229 of SEQ ID NO: 3, at least 85% amino acid identity with amino acids 1151-1166 or amino acids 1219-1229 of SEQ ID NO: 3, at least 90% amino acid identity with amino acids 1151-1166 or amino acids 1219-1229 of SEQ ID NO: 3 or at least 95% amino acid identity with amino acids 1151-1166 or amino acids 1219-1229 of SEQ ID NO: 3. In yet other aspects of this embodiment, a BoNT/C1 $H_{CC}$ binding domain comprising a β-trefoil fold domain comprises a polypeptide having, e.g., at most 70% amino acid identity with amino acids 1151-1166 or amino acids 1219-1229 of SEQ ID NO: 3, at most 75% amino acid identity with amino acids 1151-1166 or amino acids 1219-1229 of SEQ ID NO: 3, at most 80% amino acid identity with amino acids 1151-1166 or amino acids 1219-1229 of SEQ ID NO: 3, at most 85% amino acid identity with amino acids 1151-1166 or amino acids 1219-1229 of SEQ ID NO: 3, at most 90% amino acid identity with amino acids 1151-1166 or amino acids 1219-1229 of SEQ ID NO: 3 or at most 95% amino acid identity with amino acids 1151-1166 or amino acids 1219-1229 of SEQ ID NO: 3.

In other aspects of this embodiment, a BoNT/C1 $H_{CC}$ binding domain comprising a β-trefoil fold domain comprises a polypeptide having, e.g., at most one, two, three, four, five, six, seven, eight, nine or 10 non-contiguous amino acid substitutions relative to amino acids 1151-1166 or amino acids 1219-1229 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine or 10 non-contiguous amino acid substitutions relative to amino acids 1151-1166 or amino acids 1219-1229 of SEQ ID NO: 3. In other aspects of this embodiment, a non-contiguous amino acid substitution of any amino acid from amino acids 1151-1166 or amino acids 1219-1229 of SEQ ID NO: 3 can be replaced with glycine. In other aspects of this embodiment, a non-contiguous amino acid substitution of any hydrophobic amino acid from amino acids 1151-1166 or amino acids 1219-1229 of SEQ ID NO: 3 can be replaced with phenylalanine. In yet other aspects of this embodiment, a BoNT/C1 $H_{CC}$ binding domain comprising a β-trefoil fold domain comprises a polypeptide having, e.g., at most one, two, three, four, five, six, seven, eight, nine or 10 non-contiguous amino acid deletions relative to amino acids 1151-1166 or amino acids 1219-1229 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine or 10 non-contiguous amino acid deletions relative to amino acids 1151-1166 or amino acids 1219-1229 of SEQ ID NO: 3. In still other aspects of this embodiment, a BoNT/C1 $H_{CC}$ binding domain comprising a β-trefoil fold domain comprises a polypeptide having, e.g., at most one, two, three, four, five, six, seven, eight, nine or 10 non-contiguous amino acid additions relative to amino acids 1151-1166 or amino acids 1219-1229 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine or 10 non-contiguous amino acid additions relative to amino acids 1151-1166 or amino acids 1219-1229 of SEQ ID NO: 3.

In other aspects of this embodiment, a BoNT/C1 $H_{CC}$ binding domain comprising a β-trefoil fold domain comprises a polypeptide having, e.g., at most one, two, three, four, five, six, seven, eight, nine or 10 contiguous amino acid substitutions relative to amino acids 1151-1166 or amino acids 1219-1229 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine or 10 contiguous amino acid substitutions relative to amino acids 1151-1166 or amino acids 1219-1229 of SEQ ID NO: 3. In other aspects of this embodiment, contiguous amino acid substitutions of amino acids from amino acids 1151-1166 or amino acids 1219-1229 of SEQ ID NO: 3 can be replaced with glycine. In other aspects of this embodiment, contiguous amino acid substitutions of hydrophobic amino acids from amino acids 1151-1166 or amino acids 1219-1229 of SEQ ID NO: 3 can be replaced with phenylalanine. In yet other aspects of this embodiment, a BoNT/C1 $H_{CC}$ binding domain comprising a β-trefoil fold domain comprises a polypeptide having, e.g., at most one, two, three, four, five, six, seven, eight, nine or 10 contiguous amino acid deletions relative to amino acids 1151-1166 or amino acids 1219-1229 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine or 10 contiguous amino acid deletions relative to amino acids 1151-1166 or amino acids 1219-1229 of SEQ ID NO: 3. In still other aspects of this embodiment, a BoNT/C1 $H_{CC}$ binding domain comprising a β-trefoil fold domain comprises a polypeptide having, e.g., at most one, two, three, four, five, six, seven, eight, nine or 10 contiguous amino acid additions relative to amino acids 1151-1166 or amino acids 1219-1229 of SEQ ID NO: 3. In other aspects of this embodiment, a BoNT/C1 $H_{CC}$ binding domain comprising a β-trefoil fold domain comprises a polypeptide having, e.g., at least one, two, three, four, five, six, seven, eight, nine or 10 contiguous amino acid additions relative to amino acids 1151-1166 or amino acids 1219-1229 of SEQ ID NO: 3.

In other aspects of this embodiment, a BoNT/C1 $H_{CC}$ binding domain comprises a substitution of amino acid Trp 1102, Gly 1103, Leu 1106, Tyr 1112, Tyr 1113, Gly 1145, Ile 1150, Asp 1166, Glu 1196, Ile 1247, Gly 1256, Trp 1258, Tyr 1259, His 1261, Gly 1281 or Trp 1284, or any combination thereof, the substitution enhancing the binding activity of the BoNT/C1 $H_{CC}$ binding domain. In other aspects of this embodiment, a BoNT/C1 $H_{CC}$ binding domain comprises a deletion of amino acid Trp 1102, Gly 1103, Leu 1106, Tyr 1112, Tyr 1113, Gly 1145, Ile 1150, Asp 1166, Glu 1196, Ile 1247, Gly 1256, Trp 1258, Tyr 1259, His 1261, Gly 1281 or Trp 1284, or any combination thereof, the deletion enhancing the binding activity of the BoNT/C1 $H_{CC}$ binding domain.

In another embodiment, a binding domain comprises a BoNT/D binding domain. In an aspect of this embodiment, a BoNT/D binding domain comprises a BoNT/D $H_C$ binding domain. In other aspects of this embodiment, a BoNT/D binding domain comprising a BoNT/D $H_C$ binding domain comprises a polypeptide having, e.g., at least 70% amino acid identity with amino acids 865-1276 of SEQ ID NO: 4, at least 75% amino acid identity with amino acids 865-1276 of SEQ ID NO: 4, at least 80% amino acid identity with amino acids 865-1276 of SEQ ID NO: 4, at least 85% amino acid identity with amino acids 865-1276 of SEQ ID NO: 4, at least 90% amino acid identity with amino acids 865-1276 of SEQ ID NO: 4 or at least 95% amino acid identity with amino acids 865-1276 of SEQ ID NO: 4. In yet other aspects of this embodiment, a BoNT/D binding domain comprising a BoNT/D $H_C$ binding domain comprises a polypeptide having, e.g., at most 70% amino acid identity with amino acids 865-1276 of SEQ ID NO: 4, at most 75% amino acid identity with amino acids 865-1276 of SEQ ID NO: 4, at most 80% amino acid identity with amino acids 865-1276 of SEQ ID NO: 4, at most 85% amino acid identity with amino acids 865-1276 of SEQ ID NO: 4, at most 90% amino acid identity with amino acids 865-1276 of SEQ ID NO: 4 or at most 95% amino acid identity with amino acids 865-1276 of SEQ ID NO: 4.

In other aspects of this embodiment, a BoNT/D binding domain comprising a BoNT/D $H_C$ binding domain comprises a polypeptide having, e.g., at most one, two, three, four, five, six, seven, eight, nine, 10, 20, 30, 40, 50, 100, or 200 non-contiguous amino acid substitutions relative to amino acids 865-1276 of SEQ ID NO: 4. In other aspects of this embodiment, a BoNT/D binding domain comprising a BoNT/D $H_C$ binding domain comprises a polypeptide having, e.g., at least one, two, three, four, five, six, seven, eight, nine, 10, 20, 30, 40, 50, 100 or 200 non-contiguous amino acid substitutions relative to amino acids 865-1276 of SEQ ID NO: 4. In yet other aspects of this embodiment, a BoNT/D binding domain comprising a BoNT/D $H_C$ binding domain comprises a polypeptide having, e.g., at most one, two, three, four, five, six, seven, eight, nine, 10, 20, 30, 40, 50, 100 or 200 non-contiguous amino acid deletions relative to amino acids 865-1276 of SEQ ID NO: 4. In other aspects of this embodiment, a BoNT/D binding domain comprising a BoNT/D $H_C$ binding domain comprises a polypeptide having, e.g., at least one, two, three, four, five, six, seven, eight, nine, 10, 20, 30, 40, 50, 100 or 200 non-contiguous amino acid deletions relative to amino acids 865-1276 of SEQ ID NO: 4. In still other aspects of this embodiment, a BoNT/D binding domain comprising a BoNT/D $H_C$ binding domain comprises a polypeptide having, e.g., at most one, two, three, four, five, six, seven, eight, nine, 10, 20, 30, 40, 50, 100 or 200 non-contiguous amino acid additions relative to amino acids 865-1276 of SEQ ID NO: 4. In other aspects of this embodiment, a BoNT/D binding domain comprising a BoNT/D $H_C$ binding domain comprises a polypeptide having, e.g., at least one, two, three, four, five, six, seven, eight, nine, 10, 20, 30, 40, 50, 100 or 200 non-contiguous amino acid additions relative to amino acids 865-1276 of SEQ ID NO: 4.

In other aspects of this embodiment, a BoNT/D binding domain comprising a BoNT/D $H_C$ binding domain comprises a polypeptide having, e.g., at most one, two, three, four, five, six, seven, eight, nine, 10, 20, 30, 40, 50, 100 or 200 contiguous amino acid substitutions relative to amino acids 865-1276 of SEQ ID NO: 4. In other aspects of this embodiment, a BoNT/D binding domain comprising a BoNT/D $H_C$ binding domain comprises a polypeptide having, e.g., at least one, two, three, four, five, six, seven, eight, nine, 10, 20, 30, 40, 50, 100 or 200 contiguous amino acid substitutions relative to amino acids 865-1276 of SEQ ID NO: 4. In yet other aspects of this embodiment, a BoNT/D binding domain comprising a BoNT/D $H_C$ binding domain comprises a polypeptide having, e.g., at most one, two, three, four, five, six, seven, eight, nine, 10, 20, 30, 40, 50, 100 or 200 contiguous amino acid deletions relative to amino acids 865-1276 of SEQ ID NO: 4. In other aspects of this embodiment, a BoNT/D binding domain comprising a BoNT/D $H_C$ binding domain comprises a polypeptide having, e.g., at least one, two, three, four, five, six, seven, eight, nine, 10, 20, 30, 40, 50, 100 or 200 contiguous amino acid deletions relative to amino acids 865-1276 of SEQ ID NO: 4. In still other aspects of this embodiment, a BoNT/D binding domain comprising a BoNT/D $H_C$ binding domain comprises a polypeptide having, e.g., at most one, two, three, four, five, six, seven, eight, nine, 10, 20, 30, 40, 50, 100 or 200 contiguous amino acid additions relative to amino acids 865-1276 of SEQ ID NO: 4. In other aspects of this embodiment, a BoNT/D binding domain comprising a BoNT/D $H_C$ binding domain comprises a polypeptide having, e.g., at least one, two, three, four, five, six, seven, eight, nine, 10, 20, 30, 40, 50, 100 or 200 contiguous amino acid additions relative to amino acids 865-1276 of SEQ ID NO: 4.

In another aspect of this embodiment, a BoNT/D binding domain comprises a BoNT/D $H_{CC}$ binding domain. In an aspect of this embodiment, a BoNT/D binding domain comprising a BoNT/D $H_{CC}$ binding domain comprises a modification of amino acids 1099-1276 of SEQ ID NO: 4. In another aspect of this embodiment, a BoNT/D binding domain comprising a BoNT/D $H_{CC}$ binding domain comprises a α-fold motif of a β-trefoil domain of a BoNT/D $H_{CC}$ binding domain, a β-fold motif of a β-trefoil domain of a BoNT/D $H_{CC}$ binding domain, or a γ-fold motif of a β-trefoil domain of a BoNT/D $H_{CC}$ binding domain. In another aspect of this embodiment, a BoNT/D binding domain comprising a BoNT/D $H_{CC}$ binding domain comprises a modification to amino acids 1099-1137, amino acids 1154-1207, or amino acids 1219-1276 of SEQ ID NO: 4.

In other aspects of this embodiment, a BoNT/D $H_{CC}$ binding domain comprising a β-trefoil fold domain comprises a polypeptide having, e.g., at least 70% amino acid identity with amino acids 1099-1137, amino acids 1154-1207, or amino acids 1219-1276 of SEQ ID NO: 4, at least 75% amino acid identity with amino acids 1099-1137, amino acids 1154-1207, or amino acids 1219-1276 of SEQ ID NO: 4, at least 80% amino acid identity with amino acids 1099-1137, amino acids 1154-1207, or amino acids 1219-1276 of SEQ ID NO: 4, at least 85% amino acid identity with amino acids 1099-1137, amino acids 1154-1207, or amino acids 1219-1276 of SEQ ID NO: 4, at least 90% amino acid identity with amino acids 1099-1137, amino acids 1154-1207, or amino acids 1219-1276 of SEQ ID NO: 4 or at least 95% amino acid identity with amino acids 1099-1137, amino acids 1154-1207, or amino acids 1219-1276 of SEQ ID NO: 4. In yet other aspects of this embodiment, a BoNT/D $H_{CC}$ binding domain comprising a β-trefoil fold domain comprises a polypeptide having, e.g., at most 70% amino acid identity with amino acids 1099-1137, amino acids 1154-1207, or amino acids 1219-1276 of SEQ ID NO: 4, at most 75% amino acid identity with amino acids 1099-1137, amino acids 1154-1207, or amino acids 1219-1276 of SEQ ID NO: 4, at most 80% amino acid identity with amino acids 1099-1137, amino acids 1154-1207, or amino acids 1219-1276 of SEQ ID NO: 4, at most 85% amino acid identity with amino acids 1099-1137, amino acids 1154-1207, or amino acids 1219-1276 of SEQ ID NO: 4, at most 90% amino acid identity with amino acids 1099-1137, amino acids 1154-1207, or amino acids 1219-1276 of SEQ ID NO: 4 or at most 95% amino acid identity with amino acids 1099-1137, amino acids 1154-1207, or amino acids 1219-1276 of SEQ ID NO: 4.

In other aspects of this embodiment, a BoNT/D $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1099-1137, amino acids 1154-1207, or amino acids 1219-1276 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine, 10 or 20 non-contiguous amino acid substitutions relative to amino acids 1099-1137, amino acids 1154-1207, or amino acids 1219-1276 of SEQ ID NO: 4. In yet other aspects of this embodiment, a BoNT/D $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1099-1137, amino acids 1154-1207, or amino acids 1219-1276 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1099-1137, amino acids 1154-1207, or amino acids 1219-1276 of SEQ ID NO: 4. In still other aspects of this embodiment, a BoNT/D $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1099-1137, amino acids 1154-1207, or amino acids 1219-1276 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1099-1137, amino acids 1154-1207, or amino acids 1219-1276 of SEQ ID NO: 4.

In other aspects of this embodiment, a BoNT/D $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1099-1137, amino acids 1154-1207, or amino acids 1219-1276 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1099-1137, amino acids 1154-1207, or amino acids 1219-1276 of SEQ ID NO: 4. In yet other aspects of this embodiment, a BoNT/D $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1099-1137, amino acids 1154-1207, or amino acids 1219-1276 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1099-1137, amino acids 1154-1207, or amino acids 1219-1276 of SEQ ID NO: 4. In still other aspects of this embodiment, a BoNT/D $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1099-1137, amino acids 1154-1207, or amino acids 1219-1276 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine, 10 or 20 contiguous amino acid additions relative to amino acids 1099-1137, amino acids 1154-1207, or amino acids 1219-1276 of SEQ ID NO: 4.

In another embodiment, a BoNT/D binding domain comprising a BoNT/D $H_{CC}$ binding domain comprises a β4/β5 hairpin turn of a β-trefoil fold domain of a BoNT/D $H_{CC}$ binding domain or a β8/β9 hairpin turn of a β-trefoil fold domain of a BoNT/D $H_{CC}$ binding domain. In another aspect of this embodiment, a BoNT/D binding domain comprising a BoNT/D $H_{CC}$ binding domain comprises a modification of amino acids 1138-1153 or amino acids 1208-1218 of SEQ ID NO: 4.

In other aspects of this embodiment, a BoNT/D $H_{CC}$ binding domain comprising a β-trefoil fold domain comprises a polypeptide having, e.g., at least 70% amino acid identity with amino acids 1138-1153 or amino acids 1208-1218 of SEQ ID NO: 4, at least 75% amino acid identity with amino acids 1138-1153 or amino acids 1208-1218 of SEQ ID NO: 4, at least 80% amino acid identity with amino acids 1138-1153 or amino acids 1208-1218 of SEQ ID NO: 4, at least 85% amino acid identity with amino acids 1138-1153 or amino acids 1208-1218 of SEQ ID NO: 4, at least 90% amino acid identity with amino acids 1138-1153 or amino acids 1208-1218 of SEQ ID NO: 4 or at least 95% amino acid identity with amino acids 1138-1153 or amino acids 1208-1218 of SEQ ID NO: 4. In yet other aspects of this embodiment, a BoNT/D $H_{CC}$ binding domain comprising a β-trefoil fold domain comprises a polypeptide having, e.g., at most 70% amino acid identity with amino acids 1138-1153 or amino acids 1208-1218 of SEQ ID NO: 4, at most 75% amino acid identity with amino acids 1138-1153 or amino acids 1208-1218 of SEQ ID NO: 4, at most 80% amino acid identity with amino acids 1138-1153 or amino acids 1208-1218 of SEQ ID NO: 4, at most 85% amino acid identity with amino acids 1138-1153 or amino acids 1208-1218 of SEQ ID NO: 4, at most 90% amino acid identity with amino acids 1138-1153 or amino acids 1208-1218 of SEQ ID NO: 4 or at most 95% amino acid identity with amino acids 1138-1153 or amino acids 1208-1218 of SEQ ID NO: 4.

In other aspects of this embodiment, a BoNT/D $H_{CC}$ binding domain comprising a β-trefoil fold domain comprises a polypeptide having, e.g., at most one, two, three, four, five, six, seven, eight, nine or 10 non-contiguous amino acid substitutions relative to amino acids 1138-1153 or amino acids 1208-1218 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine or 10 non-contiguous amino acid substitutions relative to amino acids 1138-1153 or amino acids 1208-1218 of SEQ ID NO: 4. In other aspects of this embodiment, a non-contiguous amino acid substitution of any amino acid from amino acids 1138-1153 or amino acids 1208-1218 of SEQ ID NO: 4 can be replaced with glycine. In other aspects of this embodiment, a non-contiguous amino acid substitution of any hydrophobic amino acid from amino acids 1138-1153 or amino acids 1208-1218 of SEQ ID NO: 4 can be replaced with phenylalanine. In yet other aspects of this embodiment, a BoNT/D $H_{CC}$ binding domain comprising a β-trefoil fold domain comprises a polypeptide having, e.g., at most one, two, three, four, five, six, seven, eight, nine or 10 non-contiguous amino acid deletions relative to amino acids 1138-1153 or amino acids 1208-1218 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine or 10 non-contiguous amino acid deletions relative to amino acids 1138-1153 or amino acids 1208-1218 of SEQ ID NO: 4. In still other aspects of this embodiment, a BoNT/D $H_{CC}$ binding domain comprising a β-trefoil fold domain comprises a polypeptide having, e.g., at most one, two, three, four, five, six, seven, eight, nine or 10 non-contiguous amino acid additions relative to amino acids 1138-1153 or amino acids 1208-1218 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine or 10 non-contiguous amino acid additions relative to amino acids 1138-1153 or amino acids 1208-1218 of SEQ ID NO: 4.

In other aspects of this embodiment, a BoNT/D $H_{CC}$ binding domain comprising a β-trefoil fold domain comprises a polypeptide having, e.g., at most one, two, three, four, five, six, seven, eight, nine or 10 contiguous amino acid substitutions relative to amino acids 1138-1153 or amino acids 1208-1218 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine or 10 contiguous amino acid substitutions relative to amino acids 1138-1153 or amino acids 1208-1218 of SEQ ID NO: 4. In other aspects of this embodiment, contiguous amino acid substitutions of amino acids from amino acids 1138-1153 or amino acids 1208-1218 of SEQ ID NO: 4 can be replaced with glycine. In other aspects of this embodiment, contiguous amino acid substitutions of hydrophobic amino acids from amino acids 1138-1153 or amino acids 1208-1218 of SEQ ID NO: 4 can be replaced with phenylalanine. In yet other aspects of this embodiment, a BoNT/D $H_{CC}$ binding domain comprising a β-trefoil fold domain comprises a polypeptide having, e.g., at most one, two, three, four, five, six, seven, eight, nine or 10 contiguous amino acid deletions relative to amino acids 1138-1153 or amino acids 1208-1218 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine or 10 contiguous amino acid deletions relative to amino acids 1138-1153 or amino acids 1208-1218 of SEQ ID NO: 4. In still other aspects of this embodiment, a BoNT/D $H_{CC}$ binding domain comprising a β-trefoil fold domain comprises a polypeptide having, e.g., at most one, two, three, four, five, six, seven, eight, nine or 10 contiguous amino acid additions relative to amino acids 1138-1153 or amino acids 1208-1218 of SEQ ID NO: 4. In other aspects of this embodiment, a BoNT/D $H_{CC}$ binding domain comprising a β-trefoil fold domain comprises a polypeptide having, e.g., at least one, two, three, four, five, six, seven, eight, nine or 10 contiguous amino acid additions relative to amino acids 1138-1153 or amino acids 1208-1218 of SEQ ID NO: 4.

In other aspects of this embodiment, a BoNT/D $H_{CC}$ binding domain comprises a substitution of amino acid Trp 1089, Gly 1090, Leu 1093, Tyr 1099, Tyr 1100, Gly 1132, Ile 1137, Asp 1153, Asn 1186, Lys 1236, Trp 1238, Arg 1239, Phe 1242, Ser 1262 or Trp 1265, or any combination thereof, the substitution enhancing the binding activity of the BoNT/D $H_{CC}$ binding domain. In other aspects of this embodiment, a BoNT/D $H_{CC}$ binding domain comprises a deletion of amino acid Trp 1089, Gly 1090, Leu 1093, Tyr 1099, Tyr 1100, Gly 1132, Ile 1137, Asp 1153, Asn 1186, Lys 1236, Trp 1238, Arg 1239, Phe 1242, Ser 1262 or Trp 1265, or any combination thereof, the deletion enhancing the binding activity of the BoNT/D $H_{CC}$ binding domain.

In another embodiment, a binding domain comprises a BoNT/E binding domain. In an aspect of this embodiment, a BoNT/E binding domain comprises a BoNT/E $H_C$ binding domain. In other aspects of this embodiment, a BoNT/E binding domain comprising a BoNT/E $H_C$ comprises a polypeptide having, e.g., at least 70% amino acid identity with amino acids 848-1252 of SEQ ID NO: 5, at least 75% amino acid identity with amino acids 848-1252 of SEQ ID NO: 5, at least 80% amino acid identity with amino acids 848-1252 of SEQ ID NO: 5, at least 85% amino acid identity with amino acids 848-1252 of SEQ ID NO: 5, at least 90% amino acid identity with amino acids 848-1252 of SEQ ID NO: 5 or at least 95% amino acid identity with amino acids 848-1252 of SEQ ID NO: 5. In yet other aspects of this embodiment, a BoNT/E binding domain comprising a BoNT/E $H_C$ comprises a polypeptide having, e.g., at most 70% amino acid identity with amino acids 848-1252 of SEQ ID NO: 5, at most 75% amino acid identity with amino acids 848-1252 of SEQ ID NO: 5, at most 80% amino acid identity with amino acids 848-1252 of SEQ ID NO: 5, at most 85% amino acid identity with amino acids 848-1252 of SEQ ID NO: 5, at most 90% amino acid identity with amino acids 848-1252 of SEQ ID NO: 5 or at most 95% amino acid identity with amino acids 848-1252 of SEQ ID NO: 5.

In other aspects of this embodiment, a BoNT/E binding domain comprising a BoNT/E $H_C$ comprises a polypeptide having, e.g., at most one, two, three, four, five, six, seven, eight, nine, 10, 20, 30, 40, 50, 100, or 200 non-contiguous amino acid substitutions relative to amino acids 848-1252 of SEQ ID NO: 5. In other aspects of this embodiment, a BoNT/E binding domain comprising a BoNT/E $H_C$ comprises a polypeptide having, e.g., at least one, two, three, four, five, six, seven, eight, nine, 10, 20, 30, 40, 50, 100 or 200 non-contiguous amino acid substitutions relative to amino acids 848-1252 of SEQ ID NO: 5. In yet other aspects of this embodiment, a BoNT/E binding domain comprising a BoNT/E $H_C$ comprises a polypeptide having, e.g., at most one, two, three, four, five, six, seven, eight, nine, 10, 20, 30, 40, 50, 100 or 200 non-contiguous amino acid deletions relative to amino acids 848-1252 of SEQ ID NO: 5. In other aspects of this embodiment, a BoNT/E binding domain comprising a BoNT/E $H_C$ comprises a polypeptide having, e.g., at least one, two, three, four, five, six, seven, eight, nine, 10, 20, 30, 40, 50, 100 or 200 non-contiguous amino acid deletions relative to amino acids 848-1252 of SEQ ID NO: 5. In still other aspects of this embodiment, a BoNT/E binding domain comprising a BoNT/E $H_C$ comprises a polypeptide having, e.g., at most one, two, three, four, five, six, seven, eight, nine, 10, 20, 30, 40, 50, 100 or 200 non-contiguous amino acid additions relative to amino acids 848-1252 of SEQ ID NO: 5. In other aspects of this embodiment, a BoNT/E binding domain comprising a BoNT/E $H_C$ comprises a polypeptide having, e.g., at least one, two, three, four, five, six, seven, eight, nine, 10, 20, 30, 40, 50, 100 or 200 non-contiguous amino acid additions relative to amino acids 848-1252 of SEQ ID NO: 5.

In other aspects of this embodiment, a BoNT/E binding domain comprising a BoNT/E $H_C$ comprises a polypeptide having, e.g., at most one, two, three, four, five, six, seven, eight, nine, 10, 20, 30, 40, 50, 100 or 200 contiguous amino acid substitutions relative to amino acids 848-1252 of SEQ ID NO: 5. In other aspects of this embodiment, a BoNT/E binding domain comprising a BoNT/E $H_C$ comprises a polypeptide having, e.g., at least one, two, three, four, five, six, seven, eight, nine, 10, 20, 30, 40, 50, 100 or 200 contiguous amino acid substitutions relative to amino acids 848-1252 of SEQ ID NO: 5. In yet other aspects of this embodiment, a BoNT/E binding domain comprising a BoNT/E $H_C$ comprises a polypeptide having, e.g., at most one, two, three, four, five, six, seven, eight, nine, 10, 20, 30, 40, 50, 100 or 200 contiguous amino acid deletions relative to amino acids 848-1252 of SEQ ID NO: 5. In other aspects of this embodiment, a BoNT/E binding domain comprising a BoNT/E $H_C$ comprises a polypeptide having, e.g., at least one, two, three, four, five, six, seven, eight, nine, 10, 20, 30, 40, 50, 100 or 200 contiguous amino acid deletions relative to amino acids 848-1252 of SEQ ID NO: 5. In still other aspects of this embodiment, a BoNT/E binding domain comprising a BoNT/E $H_C$ comprises a polypeptide having, e.g., at most one, two, three, four, five, six, seven, eight, nine, 10, 20, 30, 40, 50, 100 or 200 contiguous amino acid additions relative to amino acids 848-1252 of SEQ ID NO: 5. In other aspects of this embodiment, a BoNT/E binding domain comprising a BoNT/E $H_C$ comprises a polypeptide having, e.g., at least one, two, three, four, five, six, seven, eight, nine, 10, 20, 30, 40, 50, 100 or 200 contiguous amino acid additions relative to amino acids 848-1252 of SEQ ID NO: 5.

In another aspect of this embodiment, a BoNT/E binding domain comprises a BoNT/E $H_{CC}$ binding domain. In an aspect of this embodiment, a BoNT/E binding domain comprising a BoNT/E $H_{CC}$ binding domain comprises a modification of amino acids 1086-1252 of SEQ ID NO: 5. In another aspect of this embodiment, a BoNT/E binding domain comprising a BoNT/E $H_{CC}$ binding domain comprises a α-fold motif of a β-trefoil domain of a BoNT/E $H_{CC}$ binding domain, a β-fold motif of a β-trefoil domain of a BoNT/E $H_{CC}$ binding domain, or a γ-fold motif of a β-trefoil domain of a BoNT/E $H_{CC}$ binding domain. In another aspect of this embodiment, a BoNT/E binding domain comprising a BoNT/E $H_{CC}$ binding domain comprises a modification to amino acids 1086-1129, amino acids 1147-1190, or amino acids 1199-1252 of SEQ ID NO: 5.

In other aspects of this embodiment, a BoNT/E $H_{CC}$ binding domain comprising a β-trefoil fold domain comprises a polypeptide having, e.g., at least 70% amino acid identity with amino acids 1086-1129, amino acids 1147-1190, or amino acids 1199-1252 of SEQ ID NO: 5, at least 75% amino acid identity with amino acids 1086-1129, amino acids 1147-1190, or amino acids 1199-1252 of SEQ ID NO: 5, at least 80% amino acid identity with amino acids 1086-1129, amino acids 1147-1190, or amino acids 1199-1252 of SEQ ID NO: 5, at least 85% amino acid identity with amino acids 1086-1129, amino acids 1147-1190, or amino acids 1199-1252 of SEQ ID NO: 5, at least 90% amino acid identity with amino acids 1086-1129, amino acids 1147-1190, or amino acids 1199-1252 of SEQ ID NO: 5 or at least 95% amino acid identity with amino acids 1086-1129, amino acids 1147-1190, or amino acids 1199-1252 of SEQ ID NO: 5. In yet other aspects of this embodiment, a BoNT/E $H_{CC}$ binding domain comprising a β-trefoil fold domain comprises a polypeptide having, e.g., at most 70% amino acid identity with amino acids 1086-1129, amino acids 1147-1190, or amino acids 1199-1252 of SEQ ID NO: 5, at most 75% amino acid identity with amino acids 1086-1129, amino acids 1147-1190, or amino acids 1199-1252 of SEQ ID NO: 5, at most 80% amino acid identity with amino acids 1086-1129, amino acids 1147-1190, or amino acids 1199-1252 of SEQ ID NO: 5, at most 85% amino acid identity with amino acids 1086-1129, amino acids 1147-1190, or amino acids 1199-1252 of SEQ ID NO: 5, at most 90% amino acid identity with amino acids 1086-1129, amino acids 1147-1190, or amino acids 1199-1252 of SEQ ID NO: 5 or at most 95% amino acid identity with amino acids 1086-1129, amino acids 1147-1190, or amino acids 1199-1252 of SEQ ID NO: 5.

In other aspects of this embodiment, a BoNT/E $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1086-1129, amino acids 1147-1190, or amino acids 1199-1252 of SEQ ID NO: 5. In other aspects of this embodiment, a BoNT/E $H_{CC}$ binding domain comprising a β-trefoil fold domain comprises a polypeptide having, e.g., at least one, two, three, four, five, six, seven, eight, nine, 10 or 20 non-contiguous amino acid substitutions relative to amino acids 1086-1129, amino acids 1147-1190, or amino acids 1199-1252 of SEQ ID NO: 5. In yet other aspects of this embodiment, a BoNT/E $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1086-1129, amino acids 1147-1190, or amino acids 1199-1252 of SEQ ID NO: 5. In other aspects of this embodiment, a BoNT/E $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1086-1129, amino acids 1147-1190, or amino acids 1199-1252 of SEQ ID NO: 5. In still other aspects of this embodiment, a BoNT/E $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1086-1129, amino acids 1147-1190, or amino acids 1199-1252 of SEQ ID NO: 5. In other aspects of this embodiment, a BoNT/E $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1086-1129, amino acids 1147-1190, or amino acids 1199-1252 of SEQ ID NO: 5.

In other aspects of this embodiment, a BoNT/E $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1086-1129, amino acids 1147-1190, or amino acids 1199-1252 of SEQ ID NO: 5. In other aspects of this embodiment, a BoNT/E $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1086-1129, amino acids 1147-1190, or amino acids 1199-1252 of SEQ ID NO: 5. In yet other aspects of this embodiment, a BoNT/E $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1086-1129, amino acids 1147-1190, or amino acids 1199-1252 of SEQ ID NO: 5. In other aspects of this embodiment, a BoNT/E $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1086-1129, amino acids 1147-1190, or amino acids 1199-1252 of SEQ ID NO: 5. In still other aspects of this embodiment, a BoNT/E $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1086-1129, amino acids 1147-1190, or amino acids 1199-1252 of SEQ ID NO: 5. In other aspects of this embodiment, a BoNT/E $H_{CC}$ binding domain comprising a β-trefoil fold domain comprises a polypeptide having, e.g., at least one, two, three, four, five, six, seven, eight, nine, 10 or 20 contiguous amino acid additions relative to amino acids 1086-1129, amino acids 1147-1190, or amino acids 1199-1252 of SEQ ID NO: 5.

In another embodiment, a BoNT/E binding domain comprising a BoNT/E $H_{CC}$ binding domain comprises a β4/β5 hairpin turn of a β-trefoil domain of a BoNT/E $H_{CC}$ binding domain or a β8/β9 hairpin turn of a β-trefoil domain of a BoNT/E $H_{CC}$ binding domain. In another aspect of this embodiment, a BoNT/E binding domain comprising a BoNT/E H$_{CC}$ binding domain comprises a modification of amino acids 1130-1146 or amino acids 1191-1198 of SEQ ID NO: 5.

In other aspects of this embodiment, a BoNT/E H$_{CC}$ binding domain comprising a β-trefoil fold domain comprises a polypeptide having, e.g., at least 70% amino acid identity with amino acids 1130-1146 or amino acids 1191-1198 of SEQ ID NO: 5, at least 75% amino acid identity with amino acids 1130-1146 or amino acids 1191-1198 of SEQ ID NO: 5, at least 80% amino acid identity with amino acids 1130-1146 or amino acids 1191-1198 of SEQ ID NO: 5, at least 85% amino acid identity with amino acids 1130-1146 or amino acids 1191-1198 of SEQ ID NO: 5, at least 90% amino acid identity with amino acids 1130-1146 or amino acids 1191-1198 of SEQ ID NO: 5 or at least 95% amino acid identity with amino acids 1130-1146 or amino acids 1191-1198 of SEQ ID NO: 5. In yet other aspects of this embodiment, a BoNT/E H$_{CC}$ binding domain comprising a β-trefoil fold domain comprises a polypeptide having, e.g., at most 70% amino acid identity with amino acids 1130-1146 or amino acids 1191-1198 of SEQ ID NO: 5, at most 75% amino acid identity with amino acids 1130-1146 or amino acids 1191-1198 of SEQ ID NO: 5, at most 80% amino acid identity with amino acids 1130-1146 or amino acids 1191-1198 of SEQ ID NO: 5, at most 85% amino acid identity with amino acids 1130-1146 or amino acids 1191-1198 of SEQ ID NO: 5, at most 90% amino acid identity with amino acids 1130-1146 or amino acids 1191-1198 of SEQ ID NO: 5 or at most 95% amino acid identity with amino acids 1130-1146 or amino acids 1191-1198 of SEQ ID NO: 5.

In other aspects of this embodiment, a BoNT/E H$_{CC}$ binding domain comprising a β-trefoil fold domain comprises a polypeptide having, e.g., at most one, two, three, four, five, six, seven, eight, nine or 10 non-contiguous amino acid substitutions relative to amino acids 1130-1146 or amino acids 1191-1198 of SEQ ID NO: 5. In other aspects of this embodiment, a BoNT/E H$_{CC}$ binding domain comprising a β-trefoil fold domain comprises a polypeptide having, e.g., at least one, two, three, four, five, six, seven, eight, nine or 10 non-contiguous amino acid substitutions relative to amino acids 1130-1146 or amino acids 1191-1198 of SEQ ID NO: 5. In other aspects of this embodiment, a non-contiguous amino acid substitution of any amino acid from amino acids 1130-1146 or amino acids 1191-1198 of SEQ ID NO: 5 can be replaced with glycine. In other aspects of this embodiment, a non-contiguous amino acid substitution of any hydrophobic amino acid from amino acids 1130-1146 or amino acids 1191-1198 of SEQ ID NO: 5 can be replaced with phenylalanine. In yet other aspects of this embodiment, a BoNT/E H$_{CC}$ binding domain comprising a β-trefoil fold domain comprises a polypeptide having, e.g., at most one, two, three, four, five, six, seven, eight, nine or 10 non-contiguous amino acid deletions relative to amino acids 1130-1146 or amino acids 1191-1198 of SEQ ID NO: 5. In other aspects of this embodiment, a BoNT/E H$_{CC}$ binding domain comprising a β-trefoil fold domain comprises a polypeptide having, e.g., at least one, two, three, four, five, six, seven, eight, nine or 10 non-contiguous amino acid deletions relative to amino acids 1130-1146 or amino acids 1191-1198 of SEQ ID NO: 5. In still other aspects of this embodiment, a BoNT/E H$_{CC}$ binding domain comprising a β-trefoil fold domain comprises a polypeptide having, e.g., at most one, two, three, four, five, six, seven, eight, nine or 10 non-contiguous amino acid additions relative to amino acids 1130-1146 or amino acids 1191-1198 of SEQ ID NO: 5. In other aspects of this embodiment, a BoNT/E H$_{CC}$ binding domain comprising a β-trefoil fold domain comprises a polypeptide having, e.g., at least one, two, three, four, five, six, seven, eight, nine or 10 non-contiguous amino acid additions relative to amino acids 1130-1146 or amino acids 1191-1198 of SEQ ID NO: 5.

In other aspects of this embodiment, a BoNT/E H$_{CC}$ binding domain comprising a β-trefoil fold domain comprises a polypeptide having, e.g., at most one, two, three, four, five, six, seven, eight, nine or 10 contiguous amino acid substitutions relative to amino acids 1130-1146 or amino acids 1191-1198 of SEQ ID NO: 5. In other aspects of this embodiment, a BoNT/E H$_{CC}$ binding domain comprising a β-trefoil fold domain comprises a polypeptide having, e.g., at least one, two, three, four, five, six, seven, eight, nine or 10 contiguous amino acid substitutions relative to amino acids 1130-1146 or amino acids 1191-1198 of SEQ ID NO: 5. In other aspects of this embodiment, contiguous amino acid substitutions of amino acids from amino acids 1130-1146 or amino acids 1191-1198 of SEQ ID NO: 5 can be replaced with glycine. In other aspects of this embodiment, contiguous amino acid substitutions of hydrophobic amino acids from amino acids 1130-1146 or amino acids 1191-1198 of SEQ ID NO: 5 can be replaced with phenylalanine. In yet other aspects of this embodiment, a BoNT/E H$_{CC}$ binding domain comprising a β-trefoil fold domain comprises a polypeptide having, e.g., at most one, two, three, four, five, six, seven, eight, nine or 10 contiguous amino acid deletions relative to amino acids 1130-1146 or amino acids 1191-1198 of SEQ ID NO: 5. In other aspects of this embodiment, a BoNT/E H binding domain comprising a β-trefoil fold domain comprises a polypeptide having, e.g., at least one, two, three, four, five, six, seven, eight, nine or 10 contiguous amino acid deletions relative to amino acids 1130-1146 or amino acids 1191-1198 of SEQ ID NO: 5. In still other aspects of this embodiment, a BoNT/E H$_{CC}$ binding domain comprising a β-trefoil fold domain comprises a polypeptide having, e.g., at most one, two, three, four, five, six, seven, eight, nine or 10 contiguous amino acid additions relative to amino acids 1130-1146 or amino acids 1191-1198 of SEQ ID NO: 5. In other aspects of this embodiment, a BoNT/E H$_{CC}$ binding domain comprising a β-trefoil fold domain comprises a polypeptide having, e.g., at least one, two, three, four, five, six, seven, eight, nine or 10 contiguous amino acid additions relative to amino acids 1130-1146 or amino acids 1191-1198 of SEQ ID NO: 5.

In other aspects of this embodiment, a BoNT/E H$_{CC}$ binding domain comprises a substitution of amino acid Trp 1076, Gly 1077, Leu 1080, Tyr 1086, Tyr 1087, Gly 1124, Ile 1129, Asp 1146, Glu 1172, Phe 1213, Ser 1221, Trp 1223, Tyr 1224, His 1227, Gly 1236 or Trp 1239, or any combination thereof, the substitution enhancing the binding activity of the BoNT/E H$_{CC}$ binding domain. In other aspects of this embodiment, a BoNT/E H$_{CC}$ binding domain comprises a deletion of amino acid Trp 1076, Gly 1077, Leu 1080, Tyr 1086, Tyr 1087, Gly 1124, Ile 1129, Asp 1146, Glu 1172, Phe 1213, Ser 1221, Trp 1223, Tyr 1224, His 1227, Gly 1236 or Trp 1239, or any combination thereof, the deletion enhancing the binding activity of the BoNT/E H$_{CC}$ binding domain.

In another embodiment, a binding domain comprises a BoNT/F binding domain. In an aspect of this embodiment, a BoNT/F binding domain comprises a BoNT/F H$_C$ binding domain. In other aspects of this embodiment, a BoNT/F binding domain comprising a BoNT/F H$_C$ binding domain comprises a polypeptide having, e.g., at least 70% amino acid identity with amino acids 867-1274 of SEQ ID NO: 6, at least 75% amino acid identity with amino acids 867-1274 of SEQ ID NO: 6, at least 80% amino acid identity with amino acids 867-1274 of SEQ ID NO: 6, at least 85% amino acid identity with amino acids 867-1274 of SEQ ID NO: 6, at least 90% amino acid identity with amino acids 867-1274 of SEQ ID NO: 6 or at least 95% amino acid identity with amino acids 867-1274 of SEQ ID NO: 6. In yet other aspects of this embodiment, a BoNT/F binding domain comprising a BoNT/F $H_C$ binding domain comprises a polypeptide having, e.g., at most 70% amino acid identity with amino acids 867-1274 of SEQ ID NO: 6, at most 75% amino acid identity with amino acids 867-1274 of SEQ ID NO: 6, at most 80% amino acid identity with amino acids 867-1274 of SEQ ID NO: 6, at most 85% amino acid identity with amino acids 867-1274 of SEQ ID NO: 6, at most 90% amino acid identity with amino acids 867-1274 of SEQ ID NO: 6 or at most 95% amino acid identity with amino acids 867-1274 of SEQ ID NO: 6.

In other aspects of this embodiment, a BoNT/F binding domain comprising a BoNT/F $H_C$ binding domain comprises a polypeptide having, e.g., at most one, two, three, four, five, six, seven, eight, nine, 10, 20, 30, 40, 50, 100, or 200 non-contiguous amino acid substitutions relative to amino acids 867-1274 of SEQ ID NO: 6. In other aspects of this embodiment, a BoNT/F binding domain comprising a BoNT/F $H_C$ binding domain comprises a polypeptide having, e.g., at least one, two, three, four, five, six, seven, eight, nine, 10, 20, 30, 40, 50, 100 or 200 non-contiguous amino acid substitutions relative to amino acids 867-1274 of SEQ ID NO: 6. In yet other aspects of this embodiment, a BoNT/F binding domain comprising a BoNT/F $H_C$ binding domain comprises a polypeptide having, e.g., at most one, two, three, four, five, six, seven, eight, nine, 10, 20, 30, 40, 50, 100 or 200 non-contiguous amino acid deletions relative to amino acids 867-1274 of SEQ ID NO: 6. In other aspects of this embodiment, a BoNT/F binding domain comprising a BoNT/F $H_C$ binding domain comprises a polypeptide having, e.g., at least one, two, three, four, five, six, seven, eight, nine, 10, 20, 30, 40, 50, 100 or 200 non-contiguous amino acid deletions relative to amino acids 867-1274 of SEQ ID NO: 6. In still other aspects of this embodiment, a BoNT/F binding domain comprising a BoNT/F $H_C$ binding domain comprises a polypeptide having, e.g., at most one, two, three, four, five, six, seven, eight, nine, 10, 20, 30, 40, 50, 100 or 200 non-contiguous amino acid additions relative to amino acids 867-1274 of SEQ ID NO: 6. In other aspects of this embodiment, a BoNT/F binding domain comprising a BoNT/F $H_C$ binding domain comprises a polypeptide having, e.g., at least one, two, three, four, five, six, seven, eight, nine, 10, 20, 30, 40, 50, 100 or 200 non-contiguous amino acid additions relative to amino acids 867-1274 of SEQ ID NO: 6.

In other aspects of this embodiment, a BoNT/F binding domain comprising a BoNT/F $H_C$ binding domain comprises a polypeptide having, e.g., at most one, two, three, four, five, six, seven, eight, nine, 10, 20, 30, 40, 50, 100 or 200 contiguous amino acid substitutions relative to amino acids 867-1274 of SEQ ID NO: 6. In other aspects of this embodiment, a BoNT/F binding domain comprising a BoNT/F $H_C$ binding domain comprises a polypeptide having, e.g., at least one, two, three, four, five, six, seven, eight, nine, 10, 20, 30, 40, 50, 100 or 200 contiguous amino acid substitutions relative to amino acids 867-1274 of SEQ ID NO: 6. In yet other aspects of this embodiment, a BoNT/F binding domain comprising a BoNT/F $H_C$ binding domain comprises a polypeptide having, e.g., at most one, two, three, four, five, six, seven, eight, nine, 10, 20, 30, 40, 50, 100 or 200 contiguous amino acid deletions relative to amino acids 867-1274 of SEQ ID NO: 6. In other aspects of this embodiment, a BoNT/F binding domain comprising a BoNT/F $H_C$ binding domain comprises a polypeptide having, e.g., at least one, two, three, four, five, six, seven, eight, nine, 10, 20, 30, 40, 50, 100 or 200 contiguous amino acid deletions relative to amino acids 867-1274 of SEQ ID NO: 6. In still other aspects of this embodiment, a BoNT/F binding domain comprising a BoNT/F $H_C$ binding domain comprises a polypeptide having, e.g., at most one, two, three, four, five, six, seven, eight, nine, 10, 20, 30, 40, 50, 100 or 200 contiguous amino acid additions relative to amino acids 867-1274 of SEQ ID NO: 6. In other aspects of this embodiment, a BoNT/F binding domain comprising a BoNT/F $H_C$ binding domain comprises a polypeptide having, e.g., at least one, two, three, four, five, six, seven, eight, nine, 10, 20, 30, 40, 50, 100 or 200 contiguous amino acid additions relative to amino acids 867-1274 of SEQ ID NO: 6.

In another aspect of this embodiment, a BoNT/F binding domain comprises a BoNT/F $H_{CC}$ binding domain. In an aspect of this embodiment, a BoNT/F binding domain comprising a BoNT/F $H_{CC}$ binding domain comprises a modification of amino acids 1106-1274 of SEQ ID NO: 6. In another aspect of this embodiment, a BoNT/F binding domain comprising a BoNT/F $H_{CC}$ binding domain comprises a α-fold motif of a β-trefoil domain of a BoNT/F $H_{CC}$ binding domain, a β-fold motif of a β-trefoil domain of a BoNT/F $H_{CC}$ binding domain, or a γ-fold motif of a β-trefoil domain of a BoNT/F $H_{CC}$ binding domain. In another aspect of this embodiment, a BoNT/F binding domain comprising a BoNT/F $H_{CC}$ binding domain comprises a modification to amino acids 1106-1152, amino acids 1172-1213, or amino acids 1222-1274 of SEQ ID NO: 6.

In other aspects of this embodiment, a BoNT/F $H_{CC}$ binding domain comprising a β-trefoil fold domain comprises a polypeptide having, e.g., at least 70% amino acid identity with amino acids 1106-1152, amino acids 1172-1213, or amino acids 1222-1274 of SEQ ID NO: 6, at least 75% amino acid identity with amino acids 1106-1152, amino acids 1172-1213, or amino acids 1222-1274 of SEQ ID NO: 6, at least 80% amino acid identity with amino acids 1106-1152, amino acids 1172-1213, or amino acids 1222-1274 of SEQ ID NO: 6, at least 85% amino acid identity with amino acids 1106-1152, amino acids 1172-1213, or amino acids 1222-1274 of SEQ ID NO: 6, at least 90% amino acid identity with amino acids 1106-1152, amino acids 1172-1213, or amino acids 1222-1274 of SEQ ID NO: 6 or at least 95% amino acid identity with amino acids 1106-1152, amino acids 1172-1213, or amino acids 1222-1274 of SEQ ID NO: 6. In yet other aspects of this embodiment, a BoNT/F $H_{CC}$ binding domain comprising a β-trefoil fold domain comprises a polypeptide having, e.g., at most 70% amino acid identity with amino acids 1106-1152, amino acids 1172-1213, or amino acids 1222-1274 of SEQ ID NO: 6, at most 75% amino acid identity with amino acids 1106-1152, amino acids 1172-1213, or amino acids 1222-1274 of SEQ ID NO: 6, at most 80% amino acid identity with amino acids 1106-1152, amino acids 1172-1213, or amino acids 1222-1274 of SEQ ID NO: 6, at most 85% amino acid identity with amino acids 1106-1152, amino acids 1172-1213, or amino acids 1222-1274 of SEQ ID NO: 6, at most 90% amino acid identity with amino acids 1106-1152, amino acids 1172-1213, or amino acids 1222-1274 of SEQ ID NO: 6 or at most 95% amino acid identity with amino acids 1106-1152, amino acids 1172-1213, or amino acids 1222-1274 of SEQ ID NO: 6.

In other aspects of this embodiment, a BoNT/F $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1106-1152, amino acids 1172-1213, or amino acids 1222-1274 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine, 10 or 20 non-contiguous amino acid substitutions relative to amino acids 1106-1152, amino acids 1172-1213, or amino acids 1222-1274 of SEQ ID NO: 6. In yet other aspects of this embodiment, a BoNT/F $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1106-1152, amino acids 1172-1213, or amino acids 1222-1274 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1106-1152, amino acids 1172-1213, or amino acids 1222-1274 of SEQ ID NO: 6. In still other aspects of this embodiment, a BoNT/F $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1106-1152, amino acids 1172-1213, or amino acids 1222-1274 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1106-1152, amino acids 1172-1213, or amino acids 1222-1274 of SEQ ID NO: 6.

In other aspects of this embodiment, a BoNT/F $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1106-1152, amino acids 1172-1213, or amino acids 1222-1274 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1106-1152, amino acids 1172-1213, or amino acids 1222-1274 of SEQ ID NO: 6. In yet other aspects of this embodiment, a BoNT/F $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1106-1152, amino acids 1172-1213, or amino acids 1222-1274 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1106-1152, amino acids 1172-1213, or amino acids 1222-1274 of SEQ ID NO: 6. In still other aspects of this embodiment, a BoNT/F $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1106-1152, amino acids 1172-1213, or amino acids 1222-1274 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine, 10 or 20 contiguous amino acid additions relative to amino acids 1106-1152, amino acids 1172-1213, or amino acids 1222-1274 of SEQ ID NO: 6.

In another embodiment, a BoNT/F binding domain comprises a BoNT/F $H_{CC}$ binding domain of comprises a β4/β5 hairpin turn of a β-trefoil domain of a BoNT/F $H_{CC}$ binding domain or a β8/β9 hairpin turn of a β-trefoil domain of a BoNT/F $H_{CC}$ binding domain. In another aspect of this embodiment, a BoNT/F binding domain comprising a BoNT/F $H_{CC}$ binding domain comprises a modification of amino acids 1153-1171 or amino acids 1214-1221 of SEQ ID NO: 6.

In other aspects of this embodiment, a BoNT/F $H_{CC}$ binding domain comprising a β-trefoil fold domain comprises a polypeptide having, e.g., at least 70% amino acid identity with amino acids 1153-1171 or amino acids 1214-1221 of SEQ ID NO: 6, at least 75% amino acid identity with amino acids 1153-1171 or amino acids 1214-1221 of SEQ ID NO: 6, at least 80% amino acid identity with amino acids 1153-1171 or amino acids 1214-1221 of SEQ ID NO: 6, at least 85% amino acid identity with amino acids 1153-1171 or amino acids 1214-1221 of SEQ ID NO: 6, at least 90% amino acid identity with amino acids 1153-1171 or amino acids 1214-1221 of SEQ ID NO: 6 or at least 95% amino acid identity with amino acids 1153-1171 or amino acids 1214-1221 of SEQ ID NO: 6. In yet other aspects of this embodiment, a BoNT/F $H_{CC}$ binding domain comprising a β-trefoil fold domain comprises a polypeptide having, e.g., at most 70% amino acid identity with amino acids 1153-1171 or amino acids 1214-1221 of SEQ ID NO: 6, at most 75% amino acid identity with amino acids 1153-1171 or amino acids 1214-1221 of SEQ ID NO: 6, at most 80% amino acid identity with amino acids 1153-1171 or amino acids 1214-1221 of SEQ ID NO: 6, at most 85% amino acid identity with amino acids 1153-1171 or amino acids 1214-1221 of SEQ ID NO: 6, at most 90% amino acid identity with amino acids 1153-1171 or amino acids 1214-1221 of SEQ ID NO: 6 or at most 95% amino acid identity with amino acids 1153-1171 or amino acids 1214-1221 of SEQ ID NO: 6.

In other aspects of this embodiment, a BoNT/F $H_{CC}$ binding domain comprising a β-trefoil fold domain comprises a polypeptide having, e.g., at most one, two, three, four, five, six, seven, eight, nine or 10 non-contiguous amino acid substitutions relative to amino acids 1153-1171 or amino acids 1214-1221 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine or 10 non-contiguous amino acid substitutions relative to amino acids 1153-1171 or amino acids 1214-1221 of SEQ ID NO: 6. In other aspects of this embodiment, a non-contiguous amino acid substitution of any amino acid from amino acids 1153-1171 or amino acids 1214-1221 of SEQ ID NO: 6 can be replaced with glycine. In other aspects of this embodiment, a non-contiguous amino acid substitution of any hydrophobic amino acid from amino acids 1153-1171 or amino acids 1214-1221 of SEQ ID NO: 6 can be replaced with phenylalanine. In yet other aspects of this embodiment, a BoNT/F $H_{CC}$ binding domain comprising a β-trefoil fold domain comprises a polypeptide having, e.g., at most one, two, three, four, five, six, seven, eight, nine or 10 non-contiguous amino acid deletions relative to amino acids 1153-1171 or amino acids 1214-1221 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine or 10 non-contiguous amino acid deletions relative to amino acids 1153-1171 or amino acids 1214-1221 of SEQ ID NO: 6. In still other aspects of this embodiment, a BoNT/F $H_{CC}$ binding domain comprising a β-trefoil fold domain comprises a polypeptide having, e.g., at most one, two, three, four, five, six, seven, eight, nine or 10 non-contiguous amino acid additions relative to amino acids 1153-1171 or amino acids 1214-1221 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine or 10 non-contiguous amino acid additions relative to amino acids 1153-1171 or amino acids 1214-1221 of SEQ ID NO: 6.

In other aspects of this embodiment, a BoNT/F $H_{CC}$ binding domain comprising a β-trefoil fold domain comprises a polypeptide having, e.g., at most one, two, three, four, five, six, seven, eight, nine or 10 contiguous amino acid substitutions relative to amino acids 1153-1171 or amino acids 1214-1221 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine or 10 contiguous amino acid substitutions relative to amino acids 1153-1171 or amino acids 1214-1221 of SEQ ID NO: 6. In other aspects of this embodiment, contiguous amino acid substitutions of amino acids from amino acids 1153-1171 or amino acids 1214-1221 of SEQ ID NO: 6 can be replaced with glycine. In other aspects of this embodiment, contiguous amino acid substitutions of hydrophobic amino acids from amino acids 1153-1171 or amino acids 1214-1221 of SEQ ID NO: 6 can be replaced with phenylalanine. In yet other aspects of this embodiment, a BoNT/F $H_{CC}$ binding domain comprising a β-trefoil fold domain comprises a polypeptide having, e.g., at most one, two, three, four, five, six, seven, eight, nine or 10 contiguous amino acid deletions relative to amino acids 1153-1171 or amino acids 1214-1221 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine or 10 contiguous amino acid deletions relative to amino acids 1153-1171 or amino acids 1214-1221 of SEQ ID NO: 6. In still other aspects of this embodiment, a BoNT/F $H_{CC}$ binding domain comprising a β-trefoil fold domain comprises a polypeptide having, e.g., at most one, two, three, four, five, six, seven, eight, nine or 10 contiguous amino acid additions relative to amino acids 1153-1171 or amino acids 1214-1221 of SEQ ID NO: 6. In other aspects of this embodiment, a BoNT/F $H_{CC}$ binding domain comprising a β-trefoil fold domain comprises a polypeptide having, e.g., at least one, two, three, four, five, six, seven, eight, nine or 10 contiguous amino acid additions relative to amino acids 1153-1171 or amino acids 1214-1221 of SEQ ID NO: 6.

In other aspects of this embodiment, a BoNT/F $H_{CC}$ binding domain comprises a substitution of amino acid Trp 1096, Gly 1097, Leu 1100, Tyr 1106, Tyr 1107, Gly 1147, Ile 1152, Asp 1171, Glu 1195, Phe 1237, Ser 1245, Trp 1247, Tyr 1248, Asn 1251, Gly 1260 or Trp 1263, or any combination thereof, the substitution enhancing the binding activity of the BoNT/F $H_{CC}$ binding domain. In other aspects of this embodiment, a BoNT/F $H_{CC}$ binding domain comprises a deletion of amino acid Trp 1096, Gly 1097, Leu 1100, Tyr 1106, Tyr 1107, Gly 1147, Ile 1152, Asp 1171, Glu 1195, Phe 1237, Ser 1245, Trp 1247, Tyr 1248, Asn 1251, Gly 1260 or Trp 1263, or any combination thereof, the deletion enhancing the binding activity of the BoNT/F $H_{CC}$ binding domain.

In another embodiment, a binding domain comprises a BoNT/G binding domain. In an aspect of this embodiment, a BoNT/G binding domain comprises a BoNT/G $H_C$ binding domain. In other aspects of this embodiment, a BoNT/G binding domain comprising a BoNT/G $H_C$ binding domain comprises a polypeptide having, e.g., at least 70% amino acid identity with amino acids 866-1297 of SEQ ID NO: 7, at least 75% amino acid identity with amino acids 866-1297 of SEQ ID NO: 7, at least 80% amino acid identity with amino acids 866-1297 of SEQ ID NO: 7, at least 85% amino acid identity with amino acids 866-1297 of SEQ ID NO: 7, at least 90% amino acid identity with amino acids 866-1297 of SEQ ID NO: 7 or at least 95% amino acid identity with amino acids 866-1297 of SEQ ID NO: 7. In yet other aspects of this embodiment, a BoNT/G binding domain comprising a BoNT/G $H_C$ binding domain comprises a polypeptide having, e.g., at most 70% amino acid identity with amino acids 866-1297 of SEQ ID NO: 7, at most 75% amino acid identity with amino acids 866-1297 of SEQ ID NO: 7, at most 80% amino acid identity with amino acids 866-1297 of SEQ ID NO: 7, at most 85% amino acid identity with amino acids 866-1297 of SEQ ID NO: 7, at most 90% amino acid identity with amino acids 866-1297 of SEQ ID NO: 7 or at most 95% amino acid identity with amino acids 866-1297 of SEQ ID NO: 7.

In other aspects of this embodiment, a BoNT/G binding domain comprising a BoNT/G $H_C$ binding domain comprises a polypeptide having, e.g., at most one, two, three, four, five, six, seven, eight, nine, 10, 20, 30, 40, 50, 100, or 200 non-contiguous amino acid substitutions relative to amino acids 866-1297 of SEQ ID NO: 7. In other aspects of this embodiment, a BoNT/G binding domain comprising a BoNT/G $H_C$ binding domain comprises a polypeptide having, e.g., at least one, two, three, four, five, six, seven, eight, nine, 10, 20, 30, 40, 50, 100 or 200 non-contiguous amino acid substitutions relative to amino acids 866-1297 of SEQ ID NO: 7. In yet other aspects of this embodiment, a BoNT/G binding domain comprising a BoNT/G $H_C$ binding domain comprises a polypeptide having, e.g., at most one, two, three, four, five, six, seven, eight, nine, 10, 20, 30, 40, 50, 100 or 200 non-contiguous amino acid deletions relative to amino acids 866-1297 of SEQ ID NO: 7. In other aspects of this embodiment, a BoNT/G binding domain comprising a BoNT/G $H_C$ binding domain comprises a polypeptide having, e.g., at least one, two, three, four, five, six, seven, eight, nine, 10, 20, 30, 40, 50, 100 or 200 non-contiguous amino acid deletions relative to amino acids 866-1297 of SEQ ID NO: 7. In still other aspects of this embodiment, a BoNT/G binding domain comprising a BoNT/G $H_C$ binding domain comprises a polypeptide having, e.g., at most one, two, three, four, five, six, seven, eight, nine, 10, 20, 30, 40, 50, 100 or 200 non-contiguous amino acid additions relative to amino acids 866-1297 of SEQ ID NO: 7. In other aspects of this embodiment, a BoNT/G binding domain comprising a BoNT/G $H_C$ binding domain comprises a polypeptide having, e.g., at least one, two, three, four, five, six, seven, eight, nine, 10, 20, 30, 40, 50, 100 or 200 non-contiguous amino acid additions relative to amino acids 866-1297 of SEQ ID NO: 7.

In other aspects of this embodiment, a BoNT/G binding domain comprising a BoNT/G $H_C$ binding domain comprises a polypeptide having, e.g., at most one, two, three, four, five, six, seven, eight, nine, 10, 20, 30, 40, 50, 100 or 200 contiguous amino acid substitutions relative to amino acids 866-1297 of SEQ ID NO: 7. In other aspects of this embodiment, a BoNT/G binding domain comprising a BoNT/G $H_C$ binding domain comprises a polypeptide having, e.g., at least one, two, three, four, five, six, seven, eight, nine, 10, 20, 30, 40, 50, 100 or 200 contiguous amino acid substitutions relative to amino acids 866-1297 of SEQ ID NO: 7. In yet other aspects of this embodiment, a BoNT/G binding domain comprising a BoNT/G $H_C$ binding domain comprises a polypeptide having, e.g., at most one, two, three, four, five, six, seven, eight, nine, 10, 20, 30, 40, 50, 100 or 200 contiguous amino acid deletions relative to amino acids 866-1297 of SEQ ID NO: 7. In other aspects of this embodiment, a BoNT/G binding domain comprising a BoNT/G $H_C$ binding domain comprises a polypeptide having, e.g., at least one, two, three, four, five, six, seven, eight, nine, 10, 20, 30, 40, 50, 100 or 200 contiguous amino acid deletions relative to amino acids 866-1297 of SEQ ID NO: 7. In still other aspects of this embodiment, a BoNT/G binding domain comprising a BoNT/G $H_C$ binding domain comprises a polypeptide having, e.g., at most one, two, three, four, five, six, seven, eight, nine, 10, 20, 30, 40, 50, 100 or 200 contiguous amino acid additions relative to amino acids 866-1297 of SEQ ID NO: 7. In other aspects of this embodiment, a BoNT/G binding domain comprising a BoNT/G $H_C$ binding domain comprises a polypeptide having, e.g., at least one, two, three, four, five, six, seven, eight, nine, 10, 20, 30, 40, 50, 100 or 200 contiguous amino acid additions relative to amino acids 866-1297 of SEQ ID NO: 7.

In another aspect of this embodiment, a BoNT/G binding domain comprises a BoNT/G $H_{CC}$ binding domain. In an aspect of this embodiment, a BoNT/G binding domain comprising a BoNT/G $H_{CC}$ binding domain comprises a modification of amino acids 1106-1297 of SEQ ID NO: 7. In another aspect of this embodiment, a BoNT/G binding domain comprising a BoNT/G $H_{CC}$ binding domain comprises a α-fold motif of a β-trefoil domain of a BoNT/G $H_{CC}$ binding domain, a β-fold motif of a β-trefoil domain of a BoNT/G $H_{CC}$ binding domain, or a γ-fold motif of a β-trefoil domain of a BoNT/G $H_{CC}$ binding domain. In another aspect of this embodiment, a BoNT/G binding domain comprising a BoNT/G $H_{CC}$ binding domain comprises a modification to amino acids 1106-1153, amino acids 1173-1218, or amino acids 1231-1297 of SEQ ID NO: 7.

In other aspects of this embodiment, a BoNT/G $H_{CC}$ binding domain comprising a β-trefoil fold domain comprises a polypeptide having, e.g., at least 70% amino acid identity with amino acids 1106-1153, amino acids 1173-1218, or amino acids 1231-1297 of SEQ ID NO: 7, at least 75% amino acid identity with amino acids 1106-1153, amino acids 1173-1218, or amino acids 1231-1297 of SEQ ID NO: 7, at least 80% amino acid identity with amino acids 1106-1153, amino acids 1173-1218, or amino acids 1231-1297 of SEQ ID NO: 7, at least 85% amino acid identity with amino acids 1106-1153, amino acids 1173-1218, or amino acids 1231-1297 of SEQ ID NO: 7, at least 90% amino acid identity with amino acids 1106-1153, amino acids 1173-1218, or amino acids 1231-1297 of SEQ ID NO: 7 or at least 95% amino acid identity with amino acids 1106-1153, amino acids 1173-1218, or amino acids 1231-1297 of SEQ ID NO: 7. In yet other aspects of this embodiment, a BoNT/G $H_{CC}$ binding domain comprising a β-trefoil fold domain comprises a polypeptide having, e.g., at most 70% amino acid identity with amino acids 1106-1153, amino acids 1173-1218, or amino acids 1231-1297 of SEQ ID NO: 7, at most 75% amino acid identity with amino acids 1106-1153, amino acids 1173-1218, or amino acids 1231-1297 of SEQ ID NO: 7, at most 80% amino acid identity with amino acids 1106-1153, amino acids 1173-1218, or amino acids 1231-1297 of SEQ ID NO: 7, at most 85% amino acid identity with amino acids 1106-1153, amino acids 1173-1218, or amino acids 1231-1297 of SEQ ID NO: 7, at most 90% amino acid identity with amino acids 1106-1153, amino acids 1173-1218, or amino acids 1231-1297 of SEQ ID NO: 7 or at most 95% amino acid identity with amino acids 1106-1153, amino acids 1173-1218, or amino acids 1231-1297 of SEQ ID NO: 7.

In other aspects of this embodiment, a BoNT/G $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1106-1153, amino acids 1173-1218, or amino acids 1231-1297 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine, 10 or 20 non-contiguous amino acid substitutions relative to amino acids 1106-1153, amino acids 1173-1218, or amino acids 1231-1297 of SEQ ID NO: 7. In yet other aspects of this embodiment, a BoNT/G $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1106-1153, amino acids 1173-1218, or amino acids 1231-1297 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1106-1153, amino acids 1173-1218, or amino acids 1231-1297 of SEQ ID NO: 7. In still other aspects of this embodiment, a BoNT/G $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1106-1153, amino acids 1173-1218, or amino acids 1231-1297 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1106-1153, amino acids 1173-1218, or amino acids 1231-1297 of SEQ ID NO: 7.

In other aspects of this embodiment, a BoNT/G $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1106-1153, amino acids 1173-1218, or amino acids 1231-1297 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1106-1153, amino acids 1173-1218, or amino acids 1231-1297 of SEQ ID NO: 7. In yet other aspects of this embodiment, a BoNT/G $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1106-1153, amino acids 1173-1218, or amino acids 1231-1297 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1106-1153, amino acids 1173-1218, or amino acids 1231-1297 of SEQ ID NO: 7. In still other aspects of this embodiment, a BoNT/G $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1106-1153, amino acids 1173-1218, or amino acids 1231-1297 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine, 10 or 20 contiguous amino acid additions relative to amino acids 1106-1153, amino acids 1173-1218, or amino acids 1231-1297 of SEQ ID NO: 7.

In another embodiment, a BoNT/G binding domain comprising a BoNT/G $H_{CC}$ binding domain comprises a β4/β5 hairpin turn of a β-trefoil domain of a BoNT/G $H_{CC}$ binding domain or a β8/β9 hairpin turn of a β-trefoil domain of a BoNT/G $H_{CC}$ binding domain. In another aspect of this embodiment, a BoNT/G binding domain comprising a BoNT/G $H_{CC}$ binding domain comprises a modification of amino acids 1154-1172 or amino acids 1219-1230 of SEQ ID NO: 7.

In other aspects of this embodiment, a BoNT/G $H_{CC}$ binding domain comprising a β-trefoil fold domain comprises a polypeptide having, e.g., at least 70% amino acid identity with amino acids 1154-1172 or amino acids 1219-1230 of SEQ ID NO: 7, at least 75% amino acid identity with amino acids 1154-1172 or amino acids 1219-1230 of SEQ ID NO: 7, at least 80% amino acid identity with amino acids 1154-1172 or amino acids 1219-1230 of SEQ ID NO: 7, at least 85% amino acid identity with amino acids 1154-1172 or amino acids 1219-1230 of SEQ ID NO: 7, at least 90% amino acid identity with amino acids 1154-1172 or amino acids 1219-1230 of SEQ ID NO: 7 or at least 95% amino acid identity with amino acids 1154-1172 or amino acids 1219-1230 of SEQ ID NO: 7. In yet other aspects of this embodiment, a BoNT/G $H_{CC}$ binding domain comprising a β-trefoil fold domain comprises a polypeptide having, e.g., at most 70% amino acid identity with amino acids 1154-1172 or amino acids 1219-1230 of SEQ ID NO: 7, at most 75% amino acid identity with amino acids 1154-1172 or amino acids 1219-1230 of SEQ ID NO: 7, at most 80% amino acid identity with amino acids 1154-1172 or amino acids 1219-1230 of SEQ ID NO: 7, at most 85% amino acid identity with amino acids 1154-1172 or amino acids 1219-1230 of SEQ ID NO: 7, at most 90% amino acid identity with amino acids 1154-1172 or amino acids 1219-1230 of SEQ ID NO: 7 or at most 95% amino acid identity with amino acids 1154-1172 or amino acids 1219-1230 of SEQ ID NO: 7.

In other aspects of this embodiment, a BoNT/G $H_{CC}$ binding domain comprising a β-trefoil fold domain comprises a polypeptide having, e.g., at most one, two, three, four, five, six, seven, eight, nine or 10 non-contiguous amino acid substitutions relative to amino acids 1154-1172 or amino acids 1219-1230 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine or 10 non-contiguous amino acid substitutions relative to amino acids 1154-1172 or amino acids 1219-1230 of SEQ ID NO: 7. In other aspects of this embodiment, a non-contiguous amino acid substitution of any amino acid from amino acids 1154-1172 or amino acids 1219-1230 of SEQ ID NO: 7 can be replaced with glycine. In other aspects of this embodiment, a non-contiguous amino acid substitution of any hydrophobic amino acid from amino acids 1154-1172 or amino acids 1219-1230 of SEQ ID NO: 7 can be replaced with phenylalanine. In yet other aspects of this embodiment, a BoNT/G $H_{CC}$ binding domain comprising a β-trefoil fold domain comprises a polypeptide having, e.g., at most one, two, three, four, five, six, seven, eight, nine or 10 non-contiguous amino acid deletions relative to amino acids 1154-1172 or amino acids 1219-1230 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine or 10 non-contiguous amino acid deletions relative to amino acids 1154-1172 or amino acids 1219-1230 of SEQ ID NO: 7. In still other aspects of this embodiment, a BoNT/G $H_{CC}$ binding domain comprising a β-trefoil fold domain comprises a polypeptide having, e.g., at most one, two, three, four, five, six, seven, eight, nine or 10 non-contiguous amino acid additions relative to amino acids 1154-1172 or amino acids 1219-1230 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine or 10 non-contiguous amino acid additions relative to amino acids 1154-1172 or amino acids 1219-1230 of SEQ ID NO: 7.

In other aspects of this embodiment, a BoNT/G $H_{CC}$ binding domain comprising a β-trefoil fold domain comprises a polypeptide having, e.g., at most one, two, three, four, five, six, seven, eight, nine or 10 contiguous amino acid substitutions relative to amino acids 1154-1172 or amino acids 1219-1230 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine or 10 contiguous amino acid substitutions relative to amino acids 1154-1172 or amino acids 1219-1230 of SEQ ID NO: 7. In other aspects of this embodiment, contiguous amino acid substitutions of amino acids from amino acids 1154-1172 or amino acids 1219-1230 of SEQ ID NO: 7 can be replaced with glycine. In other aspects of this embodiment, contiguous amino acid substitutions of hydrophobic amino acids from amino acids 1154-1172 or amino acids 1219-1230 of SEQ ID NO: 7 can be replaced with phenylalanine. In yet other aspects of this embodiment, a BoNT/G $H_{CC}$ binding domain comprising a β-trefoil fold domain comprises a polypeptide having, e.g., at most one, two, three, four, five, six, seven, eight, nine or 10 contiguous amino acid deletions relative to amino acids 1154-1172 or amino acids 1219-1230 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine or 10 contiguous amino acid deletions relative to amino acids 1154-1172 or amino acids 1219-1230 of SEQ ID NO: 7. In still other aspects of this embodiment, a BoNT/G $H_{CC}$ binding domain comprising a β-trefoil fold domain comprises a polypeptide having, e.g., at most one, two, three, four, five, six, seven, eight, nine or 10 contiguous amino acid additions relative to amino acids 1154-1172 or amino acids 1219-1230 of SEQ ID NO: 7. In other aspects of this embodiment, a BoNT/G $H_{CC}$ binding domain comprising a β-trefoil fold domain comprises a polypeptide having, e.g., at least one, two, three, four, five, six, seven, eight, nine or 10 contiguous amino acid additions relative to amino acids 1154-1172 or amino acids 1219-1230 of SEQ ID NO: 7.

In other aspects of this embodiment, a BoNT/G $H_{CC}$ binding domain comprises a substitution of amino acid Trp 1096, Gly 1097, Leu 1100, Tyr 1106, Tyr 1107, Gly 1148, Ile 1153, Asp 1172, Gln 1198, Ile 1245, Ser 1266, Trp 1268, Tyr 1269, Arg 1272, Gly 1283 or Trp 1285, or any combination thereof, the substitution enhancing the binding activity of the BoNT/G $H_{CC}$ binding domain. In other aspects of this embodiment, a BoNT/G $H_{CC}$ binding domain comprises a deletion of amino acid Trp 1096, Gly 1097, Leu 1100, Tyr 1106, Tyr 1107, Gly 1148, Ile 1153, Asp 1172, Gln 1198, Ile 1245, Ser 1266, Trp 1268, Tyr 1269, Arg 1272, Gly 1283 or Trp 1285, or any combination thereof, the deletion enhancing the binding activity of the BoNT/G $H_{CC}$ binding domain.

In another embodiment, a binding domain comprises a TeNT binding domain. In an aspect of this embodiment, a TeNT binding domain comprises a TeNT $H_C$ binding domain. In other aspects of this embodiment, a TeNT binding domain comprising a TeNT $H_C$ binding domain comprises a polypeptide having, e.g., at least 70% amino acid identity with amino acids 882-1315 of SEQ ID NO: 8, at least 75% amino acid identity with amino acids 882-1315 of SEQ ID NO: 8, at least 80% amino acid identity with amino acids 882-1315 of SEQ ID NO: 8, at least 85% amino acid identity with amino acids 882-1315 of SEQ ID NO: 8, at least 90% amino acid identity with amino acids 882-1315 of SEQ ID NO: 8 or at least 95% amino acid identity with amino acids 882-1315 of SEQ ID NO: 8. In yet other aspects of this embodiment, a TeNT binding domain comprising a TeNT $H_C$ binding domain comprises a polypeptide having, e.g., at most 70% amino acid identity with amino acids 882-1315 of SEQ ID NO: 8, at most 75% amino acid identity with amino acids 882-1315 of SEQ ID NO: 8, at most 80% amino acid identity with amino acids 882-1315 of SEQ ID NO: 8, at most 85% amino acid identity with amino acids 882-1315 of SEQ ID NO: 8, at most 90% amino acid identity with amino acids 882-1315 of SEQ ID NO: 8 or at most 95% amino acid identity with amino acids 882-1315 of SEQ ID NO: 8.

In other aspects of this embodiment, a TeNT binding domain comprising a TeNT $H_C$ binding domain comprises a polypeptide having, e.g., at most one, two, three, four, five, six, seven, eight, nine, 10, 20, 30, 40, 50, 100, or 200 non-contiguous amino acid substitutions relative to amino acids 882-1315 of SEQ ID NO: 8. In other aspects of this embodiment, a TeNT binding domain comprising a TeNT $H_C$ binding domain comprises a polypeptide having, e.g., at least one, two, three, four, five, six, seven, eight, nine, 10, 20, 30, 40, 50, 100 or 200 non-contiguous amino acid substitutions relative to amino acids 882-1315 of SEQ ID NO: 8. In yet other aspects of this embodiment, a TeNT binding domain comprising a TeNT $H_C$ binding domain comprises a polypeptide having, e.g., at most one, two, three, four, five, six, seven, eight, nine, 10, 20, 30, 40, 50, 100 or 200 non-contiguous amino acid deletions relative to amino acids 882-1315 of SEQ ID NO: 8. In other aspects of this embodiment, a TeNT binding domain comprising a TeNT $H_C$ binding domain comprises a polypeptide having, e.g., at least one, two, three, four, five, six, seven, eight, nine, 10, 20, 30, 40, 50, 100 or 200 non-contiguous amino acid deletions relative to amino acids 882-1315 of SEQ ID NO: 8. In still other aspects of this embodiment, a TeNT binding domain comprising a TeNT $H_C$ binding domain comprises a polypeptide e having, e.g., at most one, two, three, four, five, six, seven, eight, nine, 10, 20, 30, 40, 50, 100 or 200 non-contiguous amino acid additions relative to amino acids 882-1315 of SEQ ID NO: 8. In other aspects of this embodiment, a TeNT binding domain comprising a TeNT $H_C$ binding domain comprises a polypeptide having, e.g., at least one, two, three, four, five, six, seven, eight, nine, 10, 20, 30, 40, 50, 100 or 200 non-contiguous amino acid additions relative to amino acids 882-1315 of SEQ ID NO: 8.

In other aspects of this embodiment, a TeNT binding domain comprising a TeNT $H_C$ binding domain comprises a polypeptide having, e.g., at most one, two, three, four, five, six, seven, eight, nine, 10, 20, 30, 40, 50, 100 or 200 contiguous amino acid substitutions relative to amino acids 882-1315 of SEQ ID NO: 8. In other aspects of this embodiment, a TeNT binding domain comprising a TeNT $H_C$ binding domain comprises a polypeptide having, e.g., at least one, two, three, four, five, six, seven, eight, nine, 10, 20, 30, 40, 50, 100 or 200 contiguous amino acid substitutions relative to amino acids 882-1315 of SEQ ID NO: 8. In yet other aspects of this embodiment, a TeNT binding domain comprising a TeNT $H_C$ binding domain comprises a polypeptide having, e.g., at most one, two, three, four, five, six, seven, eight, nine, 10, 20, 30, 40, 50, 100 or 200 contiguous amino acid deletions relative to amino acids 882-1315 of SEQ ID NO: 8. In other aspects of this embodiment, a TeNT binding domain comprising a TeNT $H_C$ binding domain comprises a polypeptide having, e.g., at least one, two, three, four, five, six, seven, eight, nine, 10, 20, 30, 40, 50, 100 or 200 contiguous amino acid deletions relative to amino acids 882-1315 of SEQ ID NO: 8. In still other aspects of this embodiment, a TeNT binding domain comprising a TeNT $H_C$ binding domain comprises a polypeptide having, e.g., at most one, two, three, four, five, six, seven, eight, nine, 10, 20, 30, 40, 50, 100 or 200 contiguous amino acid additions relative to amino acids 882-1315 of SEQ ID NO: 8. In other aspects of this embodiment, a TeNT binding domain comprising a TeNT $H_C$ binding domain comprises a polypeptide having, e.g., at least one, two, three, four, five, six, seven, eight, nine, 10, 20, 30, 40, 50, 100 or 200 contiguous amino acid additions relative to amino acids 882-1315 of SEQ ID NO: 8.

In another aspect of this embodiment, a TeNT binding domain comprises a TeNT $H_{CC}$ binding domain. In an aspect of this embodiment, a TeNT binding domain comprising a TeNT $H_{CC}$ binding domain comprises a modification of amino acids 1128-1315 of SEQ ID NO: 8. In another aspect of this embodiment, a TeNT $H_{CC}$ binding domain comprises a α-fold motif of a β-trefoil domain of a TeNT $H_{CC}$ binding domain, a β-fold motif of a β-trefoil domain of a TeNT $H_{CC}$ binding domain, or a γ-fold motif of a β-trefoil domain of a TeNT $H_{CC}$ binding domain. In another aspect of this embodiment, a TeNT binding domain comprising a TeNT $H_{CC}$ binding domain comprises a modification to amino acids 1128-1177, amino acids 1195-1240, or amino acids 1255-1315 of SEQ ID NO: 8.

In other aspects of this embodiment, a TeNT $H_{CC}$ binding domain comprising a β-trefoil fold domain comprises a polypeptide having, e.g., at least 70% amino acid identity with amino acids 1128-1177, amino acids 1195-1240, or amino acids 1255-1315 of SEQ ID NO: 8, at least 75% amino acid identity with amino acids 1128-1177, amino acids 1195-1240, or amino acids 1255-1315 of SEQ ID NO: 8, at least 80% amino acid identity with amino acids 1128-1177, amino acids 1195-1240, or amino acids 1255-1315 of SEQ ID NO: 8, at least 85% amino acid identity with amino acids 1128-1177, amino acids 1195-1240, or amino acids 1255-1315 of SEQ ID NO: 8, at least 90% amino acid identity with amino acids 1128-1177, amino acids 1195-1240, or amino acids 1255-1315 of SEQ ID NO: 8 or at least 95% amino acid identity with amino acids 1128-1177, amino acids 1195-1240, or amino acids 1255-1315 of SEQ ID NO: 8. In yet other aspects of this embodiment, a TeNT $H_{CC}$ binding domain comprising a β-trefoil fold domain comprises a polypeptide having, e.g., at most 70% amino acid identity with amino acids 1128-1177, amino acids 1195-1240, or amino acids 1255-1315 of SEQ ID NO: 8, at most 75% amino acid identity with amino acids 1128-1177, amino acids 1195-1240, or amino acids 1255-1315 of SEQ ID NO: 8, at most 80% amino acid identity with amino acids 1128-1177, amino acids 1195-1240, or amino acids 1255-1315 of SEQ ID NO: 8, at most 85% amino acid identity with amino acids 1128-1177, amino acids 1195-1240, or amino acids 1255-1315 of SEQ ID NO: 8, at most 90% amino acid identity with amino acids 1128-1177, amino acids 1195-1240, or amino acids 1255-1315 of SEQ ID NO: 8 or at most 95% amino acid identity with amino acids 1128-1177, amino acids 1195-1240, or amino acids 1255-1315 of SEQ ID NO: 8.

In other aspects of this embodiment, a TeNT $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1128-1177, amino acids 1195-1240, or amino acids 1255-1315 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine, 10 or 20 non-contiguous amino acid substitutions relative to amino acids 1128-1177, amino acids 1195-1240, or amino acids 1255-1315 of SEQ ID NO: 8. In yet other aspects of this embodiment, a TeNT $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1128-1177, amino acids 1195-1240, or amino acids 1255-1315 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1128-1177, amino acids 1195-1240, or amino acids 1255-1315 of SEQ ID NO: 8. In still other aspects of this embodiment, a TeNT $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1128-1177, amino acids 1195-1240, or amino acids 1255-1315 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1128-1177, amino acids 1195-1240, or amino acids 1255-1315 of SEQ ID NO: 8.

In other aspects of this embodiment, a TeNT $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1128-1177, amino acids 1195-1240, or amino acids 1255-1315 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1128-1177, amino acids 1195-1240, or amino acids 1255-1315 of SEQ ID NO: 8. In yet other aspects of this embodiment, a TeNT $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1128-1177, amino acids 1195-1240, or amino acids 1255-1315 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1128-1177, amino acids 1195-1240, or amino acids 1255-1315 of SEQ ID NO: 8. In still other aspects of this embodiment, a TeNT $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1128-1177, amino acids 1195-1240, or amino acids 1255-1315 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine, 10 or 20 contiguous amino acid additions relative to amino acids 1128-1177, amino acids 1195-1240, or amino acids 1255-1315 of SEQ ID NO: 8.

In another embodiment, a TeNT binding domain comprising a TeNT $H_{CC}$ binding domain comprises a β4/β5 hairpin turn of a β-trefoil domain of a TeNT $H_{CC}$ binding domain or a β8/β9 hairpin turn of a β-trefoil domain of a TeNT $H_{CC}$ binding domain. In another aspect of this embodiment, a TeNT binding domain comprising a TeNT $H_{CC}$ binding domain comprises a modification of amino acids 1178-1194 or amino acids 1241-1254 of SEQ ID NO: 8.

In other aspects of this embodiment, a TeNT $H_{CC}$ binding domain comprising a β-trefoil fold domain comprises a polypeptide having, e.g., at least 70% amino acid identity with amino acids 1178-1194 or amino acids 1241-1254 of SEQ ID NO: 8, at least 75% amino acid identity with amino acids 1178-1194 or amino acids 1241-1254 of SEQ ID NO: 8, at least 80% amino acid identity with amino acids 1178-1194 or amino acids 1241-1254 of SEQ ID NO: 8, at least 85% amino acid identity with amino acids 1178-1194 or amino acids 1241-1254 of SEQ ID NO: 8, at least 90% amino acid identity with amino acids 1178-1194 or amino acids 1241-1254 of SEQ ID NO: 8 or at least 95% amino acid identity with amino acids 1178-1194 or amino acids 1241-1254 of SEQ ID NO: 8. In yet other aspects of this embodiment, a TeNT $H_{CC}$ binding domain comprising a β-trefoil fold domain comprises a polypeptide having, e.g., at most 70% amino acid identity with amino acids 1178-1194 or amino acids 1241-1254 of SEQ ID NO: 8, at most 75% amino acid identity with amino acids 1178-1194 or amino acids 1241-1254 of SEQ ID NO: 8, at most 80% amino acid identity with amino acids 1178-1194 or amino acids 1241-1254 of SEQ ID NO: 8, at most 85% amino acid identity with amino acids 1178-1194 or amino acids 1241-1254 of SEQ ID NO: 8, at most 90% amino acid identity with amino acids 1178-1194 or amino acids 1241-1254 of SEQ ID NO: 8 or at most 95% amino acid identity with amino acids 1178-1194 or amino acids 1241-1254 of SEQ ID NO: 8.

In other aspects of this embodiment, a TeNT $H_{CC}$ binding domain comprising a β-trefoil fold domain comprises a polypeptide having, e.g., at most one, two, three, four, five, six, seven, eight, nine or 10 non-contiguous amino acid substitutions relative to amino acids 1178-1194 or amino acids 1241-1254 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine or 10 non-contiguous amino acid substitutions relative to amino acids 1178-1194 or amino acids 1241-1254 of SEQ ID NO: 8. In other aspects of this embodiment, a non-contiguous amino acid substitution of any amino acid from amino acids 1178-1194 or amino acids 1241-1254 of SEQ ID NO: 8 can be replaced with glycine. In other aspects of this embodiment, a non-contiguous amino acid substitution of any hydrophobic amino acid from amino acids 1178-1194 or amino acids 1241-1254 of SEQ ID NO: 8 can be replaced with phenylalanine. In yet other aspects of this embodiment, a TeNT $H_{CC}$ binding domain comprising a β-trefoil fold domain comprises a polypeptide having, e.g., at most one, two, three, four, five, six, seven, eight, nine or 10 non-contiguous amino acid deletions relative to amino acids 1178-1194 or amino acids 1241-1254 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine or 10 non-contiguous amino acid deletions relative to amino acids 1178-1194 or amino acids 1241-1254 of SEQ ID NO: 8. In still other aspects of this embodiment, a TeNT $H_{CC}$ binding domain comprising a β-trefoil fold domain comprises a polypeptide having, e.g., at most one, two, three, four, five, six, seven, eight, nine or 10 non-contiguous amino acid additions relative to amino acids 1178-1194 or amino acids 1241-1254 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine or 10 non-contiguous amino acid additions relative to amino acids 1178-1194 or amino acids 1241-1254 of SEQ ID NO: 8.

In other aspects of this embodiment, a TeNT $H_{CC}$ binding domain comprising a β-trefoil fold domain comprises a polypeptide having, e.g., at most one, two, three, four, five, six, seven, eight, nine or 10 contiguous amino acid substitutions relative to amino acids 1178-1194 or amino acids 1241-1254 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine or 10 contiguous amino acid substitutions relative to amino acids 1178-1194 or amino acids 1241-1254 of SEQ ID NO: 8. In other aspects of this embodiment, contiguous amino acid substitutions of amino acids from amino acids 1178-1194 or amino acids 1241-1254 of SEQ ID NO: 8 can be replaced with glycine. In other aspects of this embodiment, contiguous amino acid substitutions of hydrophobic amino acids from amino acids 1178-1194 or amino acids 1241-1254 of SEQ ID NO: 8 can be replaced with phenylalanine. In yet other aspects of this embodiment, a TeNT $H_{CC}$ binding domain comprising a β-trefoil fold domain comprises a polypeptide having, e.g., at most one, two, three, four, five, six, seven, eight, nine or 10 contiguous amino acid deletions relative to amino acids 1178-1194 or amino acids 1241-1254 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine or 10 contiguous amino acid deletions relative to amino acids 1178-1194 or amino acids 1241-1254 of SEQ ID NO: 8. In still other aspects of this embodiment, a TeNT $H_{CC}$ binding domain comprising a β-trefoil fold domain comprises a polypeptide having, e.g., at most one, two, three, four, five, six, seven, eight, nine or 10 contiguous amino acid additions relative to amino acids 1178-1194 or amino acids 1241-1254 of SEQ ID NO: 8. In other aspects of this embodiment, a TeNT $H_{CC}$ binding domain comprising a β-trefoil fold domain comprises a polypeptide having, e.g., at least one, two, three, four, five, six, seven, eight, nine or 10 contiguous amino acid additions relative to amino acids 1178-1194 or amino acids 1241-1254 of SEQ ID NO: 8.

In other aspects of this embodiment, a TeNT $H_{CC}$ binding domain comprises a substitution of amino acid Trp 1118, Gly 1119, Leu 1122, Tyr 1128, Tyr 1129, Gly 1172, Ile 1177, Asp 1194, Asp 1222, Thr 1270, Ser 1287, Trp 1289, Tyr 1290, His 1293, Gly 1300 or Trp 1303, or any combination thereof, the substitution enhancing the binding activity of the TeNT $H_{CC}$ binding domain. In other aspects of this embodiment, a TeNT $H_{CC}$ binding domain comprises a deletion of amino acid Trp 1118, Gly 1119, Leu 1122, Tyr 1128, Tyr 1129, Gly 1172, Ile 1177, Asp 1194, Asp 1222, Thr 1270, Ser 1287, Trp 1289, Tyr 1290, His 1293, Gly 1300 or Trp 1303, or any combination thereof, the deletion enhancing the binding activity of the TeNT $H_{CC}$ binding domain.

In another embodiment, a binding domain comprises a BaNT binding domain. In an aspect of this embodiment, a BaNT binding domain comprises a BaNT $H_C$ binding domain. In other aspects of this embodiment, a BaNT binding domain comprising a BaNT $H_C$ binding domain comprises a polypeptide having, e.g., at least 70% amino acid identity with amino acids 858-1268 of SEQ ID NO: 9, at least 75% amino acid identity with amino acids 858-1268 of SEQ ID NO: 9, at least 80% amino acid identity with amino acids 858-1268 of SEQ ID NO: 9, at least 85% amino acid identity with amino acids 858-1268 of SEQ ID NO: 9, at least 90% amino acid identity with amino acids 858-1268 of SEQ ID NO: 9 or at least 95% amino acid identity with amino acids 858-1268 of SEQ ID NO: 9. In yet other aspects of this embodiment, a BaNT binding domain comprising a BaNT $H_C$ binding domain comprises a polypeptide having, e.g., at most 70% amino acid identity with amino acids 858-1268 of SEQ ID NO: 9, at most 75% amino acid identity with amino acids 858-1268 of SEQ ID NO: 9, at most 80% amino acid identity with amino acids 858-1268 of SEQ ID NO: 9, at most 85% amino acid identity with amino acids 858-1268 of SEQ ID NO: 9, at most 90% amino acid identity with amino acids 858-1268 of SEQ ID NO: 9 or at most 95% amino acid identity with amino acids 858-1268 of SEQ ID NO: 9.

In other aspects of this embodiment, a BaNT binding domain comprising a BaNT $H_C$ binding domain comprises a polypeptide having, e.g., at most one, two, three, four, five, six, seven, eight, nine, 10, 20, 30, 40, 50, 100, or 200 non-contiguous amino acid substitutions relative to amino acids 858-1268 of SEQ ID NO: 9. In other aspects of this embodiment, a BaNT binding domain comprising a BaNT $H_C$ binding domain comprises a polypeptide having, e.g., at least one, two, three, four, five, six, seven, eight, nine, 10, 20, 30, 40, 50, 100 or 200 non-contiguous amino acid substitutions relative to amino acids 858-1268 of SEQ ID NO: 9. In yet other aspects of this embodiment, a BaNT binding domain comprising a BaNT $H_C$ binding domain comprises a polypeptide having, e.g., at most one, two, three, four, five, six, seven, eight, nine, 10, 20, 30, 40, 50, 100 or 200 non-contiguous amino acid deletions relative to amino acids 858-1268 of SEQ ID NO: 9. In other aspects of this embodiment, a BaNT binding domain comprising a BaNT $H_C$ binding domain comprises a polypeptide having, e.g., at least one, two, three, four, five, six, seven, eight, nine, 10, 20, 30, 40, 50, 100 or 200 non-contiguous amino acid deletions relative to amino acids 858-1268 of SEQ ID NO: 9. In still other aspects of this embodiment, a BaNT binding domain comprising a BaNT $H_C$ binding domain comprises a polypeptide having, e.g., at most one, two, three, four, five, six, seven, eight, nine, 10, 20, 30, 40, 50, 100 or 200 non-contiguous amino acid additions relative to amino acids 858-1268 of SEQ ID NO: 9. In other aspects of this embodiment, a BaNT binding domain comprising a BaNT $H_C$ binding domain comprises a polypeptide having, e.g., at least one, two, three, four, five, six, seven, eight, nine, 10, 20, 30, 40, 50, 100 or 200 non-contiguous amino acid additions relative to amino acids 858-1268 of SEQ ID NO: 9.

In other aspects of this embodiment, a BaNT binding domain comprising a BaNT $H_C$ binding domain comprises a polypeptide having, e.g., at most one, two, three, four, five, six, seven, eight, nine, 10, 20, 30, 40, 50, 100 or 200 contiguous amino acid substitutions relative to amino acids 858-1268 of SEQ ID NO: 9. In other aspects of this embodiment, a BaNT binding domain comprising a BaNT $H_C$ binding domain comprises a polypeptide having, e.g., at least one, two, three, four, five, six, seven, eight, nine, 10, 20, 30, 40, 50, 100 or 200 contiguous amino acid substitutions relative to amino acids 858-1268 of SEQ ID NO: 9. In yet other aspects of this embodiment, a BaNT binding domain comprising a BaNT $H_C$ binding domain comprises a polypeptide having, e.g., at most one, two, three, four, five, six, seven, eight, nine, 10, 20, 30, 40, 50, 100 or 200 contiguous amino acid deletions relative to amino acids 858-1268 of SEQ ID NO: 9. In other aspects of this embodiment, a BaNT binding domain comprising a BaNT $H_C$ binding domain comprises a polypeptide having, e.g., at least one, two, three, four, five, six, seven, eight, nine, 10, 20, 30, 40, 50, 100 or 200 contiguous amino acid deletions relative to amino acids 858-1268 of SEQ ID NO: 9. In still other aspects of this embodiment, a BaNT binding domain comprising a BaNT $H_C$ binding domain comprises a polypeptide having, e.g., at most one, two, three, four, five, six, seven, eight, nine, 10, 20, 30, 40, 50, 100 or 200 contiguous amino acid additions relative to amino acids 858-1268 of SEQ ID NO: 9. In other aspects of this embodiment, a BaNT binding domain comprising a BaNT $H_C$ binding domain comprises a polypeptide having, e.g., at least one, two, three, four, five, six, seven, eight, nine, 10, 20, 30, 40, 50, 100 or 200 contiguous amino acid additions relative to amino acids 858-1268 of SEQ ID NO: 9.

In another embodiment, a BaNT binding domain comprises a BaNT $H_{CC}$ binding domain. In an aspect of this embodiment, a BaNT binding domain comprising a BaNT $H_{CC}$ binding domain comprises a modification of amino acids 1128-1315 of SEQ ID NO: 8. In another aspect of this embodiment, a BaNT binding domain comprising a BaNT $H_{CC}$ binding domain comprises a α-fold motif of a β-trefoil domain of a BaNT $H_{CC}$ binding domain, a β-fold motif of a β-trefoil domain of a BaNT $H_{CC}$ binding domain, or a γ-fold motif of a β-trefoil domain of a BaNT $H_{CC}$ binding domain. In another aspect of this embodiment, a BaNT binding domain comprising a BaNT $H_{CC}$ binding domain comprises a modification to amino acids 1095-1142, amino acids 1162-1207, or amino acids 1216-1268 of SEQ ID NO: 9.

In other aspects of this embodiment, a BaNT $H_{CC}$ binding domain comprising a β-trefoil fold domain comprises a polypeptide having, e.g., at least 70% amino acid identity with amino acids 1095-1142, amino acids 1162-1207, or amino acids 1216-1268 of SEQ ID NO: 9, at least 75% amino acid identity with amino acids 1095-1142, amino acids 1162-1207, or amino acids 1216-1268 of SEQ ID NO: 9, at least 80% amino acid identity with amino acids 1095-1142, amino acids 1162-1207, or amino acids 1216-1268 of SEQ ID NO: 9, at least 85% amino acid identity with amino acids 1095-1142, amino acids 1162-1207, or amino acids 1216-1268 of SEQ ID NO: 9, at least 90% amino acid identity with amino acids 1095-1142, amino acids 1162-1207, or amino acids 1216-1268 of SEQ ID NO: 9 or at least 95% amino acid identity with amino acids 1095-1142, amino acids 1162-1207, or amino acids 1216-1268 of SEQ ID NO: 9. In yet other aspects of this embodiment, a BaNT $H_{CC}$ binding domain comprising a β-trefoil fold domain comprises a polypeptide having, e.g., at most 70% amino acid identity with amino acids 1095-1142, amino acids 1162-1207, or amino acids 1216-1268 of SEQ ID NO: 9, at most 75% amino acid identity with amino acids 1095-1142, amino acids 1162-1207, or amino acids 1216-1268 of SEQ ID NO: 9, at most 80% amino acid identity with amino acids 1095-1142, amino acids 1162-1207, or amino acids 1216-1268 of SEQ ID NO: 9, at most 85% amino acid identity with amino acids 1095-1142, amino acids 1162-1207, or amino acids 1216-1268 of SEQ ID NO: 9, at most 90% amino acid identity with amino acids 1095-1142, amino acids 1162-1207, or amino acids 1216-1268 of SEQ ID NO: 9 or at most 95% amino acid identity with amino acids 1095-1142, amino acids 1162-1207, or amino acids 1216-1268 of SEQ ID NO: 9.

In other aspects of this embodiment, a BaNT $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1095-1142, amino acids 1162-1207, or amino acids 1216-1268 of SEQ ID NO: 9. In other aspects of this embodiment, a BaNT $H_{CC}$ binding domain comprising a β-trefoil fold domain comprises a polypeptide having, e.g., at least one, two, three, four, five, six, seven, eight, nine, 10 or 20 non-contiguous amino acid substitutions relative to amino acids 1095-1142, amino acids 1162-1207, or amino acids 1216-1268 of SEQ ID NO: 9. In yet other aspects of this embodiment, a BaNT $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1095-1142, amino acids 1162-1207, or amino acids 1216-1268 of SEQ ID NO: 9. In other aspects of this embodiment, a BaNT $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1095-1142, amino acids 1162-1207, or amino acids 1216-1268 of SEQ ID NO: 9. In still other aspects of this embodiment, a BaNT $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1095-1142, amino acids 1162-1207, or amino acids 1216-1268 of SEQ ID NO: 9. In other aspects of this embodiment, a BaNT $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1095-1142, amino acids 1162-1207, or amino acids 1216-1268 of SEQ ID NO: 9.

In other aspects of this embodiment, a BaNT $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1095-1142, amino acids 1162-1207, or amino acids 1216-1268 of SEQ ID NO: 9. In other aspects of this embodiment, a BaNT $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1095-1142, amino acids 1162-1207, or amino acids 1216-1268 of SEQ ID NO: 9. In yet other aspects of this embodiment, a BaNT $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1095-1142, amino acids 1162-1207, or amino acids 1216-1268 of SEQ ID NO: 9. In other aspects of this embodiment, a BaNT $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1095-1142, amino acids 1162-1207, or amino acids 1216-1268 of SEQ ID NO: 9. In still other aspects of this embodiment, a BaNT $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1095-1142, amino acids 1162-1207, or amino acids 1216-1268 of SEQ ID NO: 9. In other aspects of this embodiment, a BaNT $H_{CC}$ binding domain comprising a β-trefoil fold domain comprises a polypeptide having, e.g., at least one, two, three, four, five, six, seven, eight, nine, 10 or 20 contiguous amino acid additions relative to amino acids 1095-1142, amino acids 1162-1207, or amino acids 1216-1268 of SEQ ID NO: 9.

In another embodiment, a BaNT binding domain comprising a BaNT $H_{CC}$ binding domain comprises a β4/β5 hairpin turn of a β-trefoil domain of a BaNT $H_{CC}$ binding domain or a β8/β9 hairpin turn of a β-trefoil domain of a BaNT $H_{CC}$ binding domain. In another aspect of this embodiment, a BaNT binding domain comprising a BaNT H$_{CC}$ binding domain comprises a modification of amino acids 1143-1161 or amino acids 1208-1215 of SEQ ID NO: 9.

In other aspects of this embodiment, a BaNT H$_{CC}$ binding domain comprising a β-trefoil fold domain comprises a polypeptide having, e.g., at least 70% amino acid identity with amino acids 1143-1161 or amino acids 1208-1215 of SEQ ID NO: 9, at least 75% amino acid identity with amino acids 1143-1161 or amino acids 1208-1215 of SEQ ID NO: 9, at least 80% amino acid identity with amino acids 1143-1161 or amino acids 1208-1215 of SEQ ID NO: 9, at least 85% amino acid identity with amino acids 1143-1161 or amino acids 1208-1215 of SEQ ID NO: 9, at least 90% amino acid identity with amino acids 1143-1161 or amino acids 1208-1215 of SEQ ID NO: 9 or at least 95% amino acid identity with amino acids 1143-1161 or amino acids 1208-1215 of SEQ ID NO: 9. In yet other aspects of this embodiment, a BaNT H$_{CC}$ binding domain comprising a β-trefoil fold domain comprises a polypeptide having, e.g., at most 70% amino acid identity with amino acids 1143-1161 or amino acids 1208-1215 of SEQ ID NO: 9, at most 75% amino acid identity with amino acids 1143-1161 or amino acids 1208-1215 of SEQ ID NO: 9, at most 80% amino acid identity with amino acids 1143-1161 or amino acids 1208-1215 of SEQ ID NO: 9, at most 85% amino acid identity with amino acids 1143-1161 or amino acids 1208-1215 of SEQ ID NO: 9, at most 90% amino acid identity with amino acids 1143-1161 or amino acids 1208-1215 of SEQ ID NO: 9 or at most 95% amino acid identity with amino acids 1143-1161 or amino acids 1208-1215 of SEQ ID NO: 9.

In other aspects of this embodiment, a BaNT H$_{CC}$ binding domain comprising a β-trefoil fold domain comprises a polypeptide having, e.g., at most one, two, three, four, five, six, seven, eight, nine or 10 non-contiguous amino acid substitutions relative to amino acids 1143-1161 or amino acids 1208-1215 of SEQ ID NO: 9. In other aspects of this embodiment, a BaNT H$_{CC}$ binding domain comprising a β-trefoil fold domain comprises a polypeptide having, e.g., at least one, two, three, four, five, six, seven, eight, nine or 10 non-contiguous amino acid substitutions relative to amino acids 1143-1161 or amino acids 1208-1215 of SEQ ID NO: 9. In other aspects of this embodiment, a non-contiguous amino acid substitution of any amino acid from amino acids 1143-1161 or amino acids 1208-1215 of SEQ ID NO: 9 can be replaced with glycine. In other aspects of this embodiment, a non-contiguous amino acid substitution of any hydrophobic amino acid from amino acids 1143-1161 or amino acids 1208-1215 of SEQ ID NO: 9 can be replaced with phenylalanine. In yet other aspects of this embodiment, a BaNT H$_{CC}$ binding domain comprising a β-trefoil fold domain comprises a polypeptide having, e.g., at most one, two, three, four, five, six, seven, eight, nine or 10 non-contiguous amino acid deletions relative to amino acids 1143-1161 or amino acids 1208-1215 of SEQ ID NO: 9. In other aspects of this embodiment, a BaNT H$_{CC}$ binding domain comprising a β-trefoil fold domain comprises a polypeptide having, e.g., at least one, two, three, four, five, six, seven, eight, nine or 10 non-contiguous amino acid deletions relative to amino acids 1143-1161 or amino acids 1208-1215 of SEQ ID NO: 9. In still other aspects of this embodiment, a BaNT H$_{CC}$ binding domain comprising a β-trefoil fold domain comprises a polypeptide having, e.g., at most one, two, three, four, five, six, seven, eight, nine or 10 non-contiguous amino acid additions relative to amino acids 1143-1161 or amino acids 1208-1215 of SEQ ID NO: 9. In other aspects of this embodiment, a BaNT H$_{CC}$ binding domain comprising a β-trefoil fold domain comprises a polypeptide having, e.g., at least one, two, three, four, five, six, seven, eight, nine or 10 non-contiguous amino acid additions relative to amino acids 1143-1161 or amino acids 1208-1215 of SEQ ID NO: 9.

In other aspects of this embodiment, a BaNT H$_{CC}$ binding domain comprising a β-trefoil fold domain comprises a polypeptide having, e.g., at most one, two, three, four, five, six, seven, eight, nine or 10 contiguous amino acid substitutions relative to amino acids 1143-1161 or amino acids 1208-1215 of SEQ ID NO: 9. In other aspects of this embodiment, a BaNT H$_{CC}$ binding domain comprising a β-trefoil fold domain comprises a polypeptide having, e.g., at least one, two, three, four, five, six, seven, eight, nine or 10 contiguous amino acid substitutions relative to amino acids 1143-1161 or amino acids 1208-1215 of SEQ ID NO: 9. In other aspects of this embodiment, contiguous amino acid substitutions of amino acids from amino acids 1143-1161 or amino acids 1208-1215 of SEQ ID NO: 9 can be replaced with glycine. In other aspects of this embodiment, contiguous amino acid substitutions of hydrophobic amino acids from amino acids 1143-1161 or amino acids 1208-1215 of SEQ ID NO: 9 can be replaced with phenylalanine. In yet other aspects of this embodiment, a BaNT H$_{CC}$ binding domain comprising a β-trefoil fold domain comprises a polypeptide having, e.g., at most one, two, three, four, five, six, seven, eight, nine or 10 contiguous amino acid deletions relative to amino acids 1143-1161 or amino acids 1208-1215 of SEQ ID NO: 9. In other aspects of this embodiment, a BaNT H$_{CC}$ binding domain comprising a β-trefoil fold domain comprises a polypeptide having, e.g., at least one, two, three, four, five, six, seven, eight, nine or 10 contiguous amino acid deletions relative to amino acids 1143-1161 or amino acids 1208-1215 of SEQ ID NO: 9. In still other aspects of this embodiment, a BaNT H$_{CC}$ binding domain comprising a β-trefoil fold domain comprises a polypeptide having, e.g., at most one, two, three, four, five, six, seven, eight, nine or 10 contiguous amino acid additions relative to amino acids 1143-1161 or amino acids 1208-1215 of SEQ ID NO: 9. In other aspects of this embodiment, a BaNT H$_{CC}$ binding domain comprising a β-trefoil fold domain comprises a polypeptide having, e.g., at least one, two, three, four, five, six, seven, eight, nine or 10 contiguous amino acid additions relative to amino acids 1143-1161 or amino acids 1208-1215 of SEQ ID NO: 9.

In other aspects of this embodiment, a BaNT H$_{CC}$ binding domain comprises a substitution of amino acid Trp 1085, Gly 1086, Leu 1089, Tyr 1095, Tyr 1096, Gly 1137, Ile 1142, Asp 1161, Ile 1189, Phe 1231, Ser 1239, Trp 1241, Tyr 1242, Asn 1245, Gly 1254 or Trp 1257, or any combination thereof, the substitution enhancing the binding activity of the BaNT H$_{CC}$ binding domain. In other aspects of this embodiment, a BaNT H$_{CC}$ binding domain comprises a deletion of amino acid Trp 1085, Gly 1086, Leu 1089, Tyr 1095, Tyr 1096, Gly 1137, Ile 1142, Asp 1161, Ile 1189, Phe 1231, Ser 1239, Trp 1241, Tyr 1242, Asn 1245, Gly 1254 or Trp 1257, or any combination thereof, the deletion enhancing the binding activity of the BaNT H$_{CC}$ binding domain.

In another embodiment, a binding domain comprises a BuNT binding domain. In an aspect of this embodiment, a BuNT binding domain comprises a BuNT H$_C$ binding domain. In other aspects of this embodiment, a BuNT binding domain comprising a BuNT H$_C$ binding domain comprises a polypeptide having, e.g., at least 70% amino acid identity with amino acids 848-1251 of SEQ ID NO: 10, at least 75% amino acid identity with amino acids 848-1251 of SEQ ID NO: 10, at least 80% amino acid identity with amino acids 848-1251 of SEQ ID NO: 10, at least 85% amino acid identity with amino acids 848-1251 of SEQ ID NO: 10, at least 90% amino acid identity with amino acids 848-1251 of SEQ ID NO: 10 or at least 95% amino acid identity with amino acids 848-1251 of SEQ ID NO: 10. In yet other aspects of this embodiment, a BuNT binding domain comprising a BuNT $H_C$ binding domain comprises a polypeptide having, e.g., at most 70% amino acid identity with amino acids 848-1251 of SEQ ID NO: 10, at most 75% amino acid identity with amino acids 848-1251 of SEQ ID NO: 10, at most 80% amino acid identity with amino acids 848-1251 of SEQ ID NO: 10, at most 85% amino acid identity with amino acids 848-1251 of SEQ ID NO: 10, at most 90% amino acid identity with amino acids 848-1251 of SEQ ID NO: 10 or at most 95% amino acid identity with amino acids 848-1251 of SEQ ID NO: 10.

In other aspects of this embodiment, a BuNT binding domain comprising a BuNT $H_C$ binding domain comprises a polypeptide having, e.g., at most one, two, three, four, five, six, seven, eight, nine, 10, 20, 30, 40, 50, 100, or 200 non-contiguous amino acid substitutions relative to amino acids 848-1251 of SEQ ID NO: 10. In other aspects of this embodiment, a BuNT binding domain comprising a BuNT $H_C$ binding domain comprises a polypeptide having, e.g., at least one, two, three, four, five, six, seven, eight, nine, 10, 20, 30, 40, 50, 100 or 200 non-contiguous amino acid substitutions relative to amino acids 848-1251 of SEQ ID NO: 10. In yet other aspects of this embodiment, a BuNT binding domain comprising a BuNT $H_C$ binding domain comprises a polypeptide having, e.g., at most one, two, three, four, five, six, seven, eight, nine, 10, 20, 30, 40, 50, 100 or 200 non-contiguous amino acid deletions relative to amino acids 848-1251 of SEQ ID NO: 10. In other aspects of this embodiment, a BuNT binding domain comprising a BuNT $H_C$ binding domain comprises a polypeptide having, e.g., at least one, two, three, four, five, six, seven, eight, nine, 10, 20, 30, 40, 50, 100 or 200 non-contiguous amino acid deletions relative to amino acids 848-1251 of SEQ ID NO: 10. In still other aspects of this embodiment, a BuNT binding domain comprising a BuNT $H_C$ binding domain comprises a polypeptide having, e.g., at most one, two, three, four, five, six, seven, eight, nine, 10, 20, 30, 40, 50, 100 or 200 non-contiguous amino acid additions relative to amino acids 848-1251 of SEQ ID NO: 10. In other aspects of this embodiment, a BuNT binding domain comprising a BuNT $H_C$ binding domain comprises a polypeptide having, e.g., at least one, two, three, four, five, six, seven, eight, nine, 10, 20, 30, 40, 50, 100 or 200 non-contiguous amino acid additions relative to amino acids 848-1251 of SEQ ID NO: 10.

In other aspects of this embodiment, a BuNT binding domain comprising a BuNT $H_C$ binding domain comprises a polypeptide having, e.g., at most one, two, three, four, five, six, seven, eight, nine, 10, 20, 30, 40, 50, 100 or 200 contiguous amino acid substitutions relative to amino acids 848-1251 of SEQ ID NO: 10. In other aspects of this embodiment, a BuNT binding domain comprising a BuNT $H_C$ binding domain comprises a polypeptide having, e.g., at least one, two, three, four, five, six, seven, eight, nine, 10, 20, 30, 40, 50, 100 or 200 contiguous amino acid substitutions relative to amino acids 848-1251 of SEQ ID NO: 10. In yet other aspects of this embodiment, a BuNT binding domain comprising a BuNT $H_C$ binding domain comprises a polypeptide having, e.g., at most one, two, three, four, five, six, seven, eight, nine, 10, 20, 30, 40, 50, 100 or 200 contiguous amino acid deletions relative to amino acids 848-1251 of SEQ ID NO: 10. In other aspects of this embodiment, a BuNT binding domain comprising a BuNT $H_C$ binding domain comprises a polypeptide having, e.g., at least one, two, three, four, five, six, seven, eight, nine, 10, 20, 30, 40, 50, 100 or 200 contiguous amino acid deletions relative to amino acids 848-1251 of SEQ ID NO: 10. In still other aspects of this embodiment, a BuNT binding domain comprising a BuNT $H_C$ binding domain comprises a polypeptide having, e.g., at most one, two, three, four, five, six, seven, eight, nine, 10, 20, 30, 40, 50, 100 or 200 contiguous amino acid additions relative to amino acids 848-1251 of SEQ ID NO: 10. In other aspects of this embodiment, a BuNT binding domain comprising a BuNT $H_C$ binding domain comprises a polypeptide having, e.g., at least one, two, three, four, five, six, seven, eight, nine, 10, 20, 30, 40, 50, 100 or 200 contiguous amino acid additions relative to amino acids 848-1251 of SEQ ID NO: 10.

In another embodiment, a BuNT binding domain comprises a BuNT $H_{CC}$ binding domain. In an aspect of this embodiment, a BuNT binding domain comprising a BuNT $H_{CC}$ binding domain comprises a modification of amino acids 1128-1315 of SEQ ID NO: 8. In another aspect of this embodiment, a BuNT binding domain comprising a BuNT $H_{CC}$ binding domain comprises a α-fold motif of a β-trefoil domain of a BuNT $H_{CC}$ binding domain, a β-fold motif of a β-trefoil domain of a BuNT $H_{CC}$ binding domain, or a γ-fold motif of a β-trefoil domain of a BuNT $H_{CC}$ binding domain. In another aspect of this embodiment, a BuNT binding domain comprising a BuNT $H_{CC}$ binding domain comprises a modification to amino acids 1086-1129, amino acids 1147-1190, or amino acids 1198-1251 of SEQ ID NO: 10.

In other aspects of this embodiment, a BuNT $H_{CC}$ binding domain comprising a β-trefoil fold domain comprises a polypeptide having, e.g., at least 70% amino acid identity with amino acids 1086-1129, amino acids 1147-1190, or amino acids 1198-1251 of SEQ ID NO: 10, at least 75% amino acid identity with amino acids 1086-1129, amino acids 1147-1190, or amino acids 1198-1251 of SEQ ID NO: 10, at least 80% amino acid identity with amino acids 1086-1129, amino acids 1147-1190, or amino acids 1198-1251 of SEQ ID NO: 10, at least 85% amino acid identity with amino acids 1086-1129, amino acids 1147-1190, or amino acids 1198-1251 of SEQ ID NO: 10, at least 90% amino acid identity with amino acids 1086-1129, amino acids 1147-1190, or amino acids 1198-1251 of SEQ ID NO: 10 or at least 95% amino acid identity with amino acids 1086-1129, amino acids 1147-1190, or amino acids 1198-1251 of SEQ ID NO: 10. In yet other aspects of this embodiment, a BuNT $H_{CC}$ binding domain comprising a β-trefoil fold domain comprises a polypeptide having, e.g., at most 70% amino acid identity with amino acids 1086-1129, amino acids 1147-1190, or amino acids 1198-1251 of SEQ ID NO: 10, at most 75% amino acid identity with amino acids 1086-1129, amino acids 1147-1190, or amino acids 1198-1251 of SEQ ID NO: 10, at most 80% amino acid identity with amino acids 1086-1129, amino acids 1147-1190, or amino acids 1198-1251 of SEQ ID NO: 10, at most 85% amino acid identity with amino acids 1086-1129, amino acids 1147-1190, or amino acids 1198-1251 of SEQ ID NO: 10, at most 90% amino acid identity with amino acids 1086-1129, amino acids 1147-1190, or amino acids 1198-1251 of SEQ ID NO: 10 or at most 95% amino acid identity with amino acids 1086-1129, amino acids 1147-1190, or amino acids 1198-1251 of SEQ ID NO: 10.

In other aspects of this embodiment, a BuNT $H_{CC}$ binding domain comprising a β-trefoil fold domain comprises a polypeptide having, e.g., at most one, two, three, four, five, six, seven, eight, nine, 10 or 20 non-contiguous amino acid substitutions relative to amino acids 1086-1129, amino acids 1147-1190, or amino acids 1198-1251 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine, 10 or 20 non-contiguous amino acid substitutions relative to amino acids 1086-1129, amino acids 1147-1190, or amino acids 1198-1251 of SEQ ID NO: 10. In yet other aspects of this embodiment, a BuNT $H_{CC}$ binding domain comprising a β-trefoil fold domain comprises a polypeptide having, e.g., at most one, two, three, four, five, six, seven, eight, nine, 10 or 20 non-contiguous amino acid deletions relative to amino acids 1086-1129, amino acids 1147-1190, or amino acids 1198-1251 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine, 10 or 20 non-contiguous amino acid deletions relative to amino acids 1086-1129, amino acids 1147-1190, or amino acids 1198-1251 of SEQ ID NO: 10. In still other aspects of this embodiment, a BuNT $H_{CC}$ binding domain comprising a β-trefoil fold domain comprises a polypeptide having, e.g., at most one, two, three, four, five, six, seven, eight, nine, 10 or 20 non-contiguous amino acid additions relative to amino acids 1086-1129, amino acids 1147-1190, or amino acids 1198-1251 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine, 10 or 20 non-contiguous amino acid additions relative to amino acids 1086-1129, amino acids 1147-1190, or amino acids 1198-1251 of SEQ ID NO: 10.

In other aspects of this embodiment, a BuNT $H_{CC}$ binding domain comprising a β-trefoil fold domain comprises a polypeptide having, e.g., at most one, two, three, four, five, six, seven, eight, nine, 10 or 20 contiguous amino acid substitutions relative to amino acids 1086-1129, amino acids 1147-1190, or amino acids 1198-1251 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine, 10 or 20 contiguous amino acid substitutions relative to amino acids 1086-1129, amino acids 1147-1190, or amino acids 1198-1251 of SEQ ID NO: 10. In yet other aspects of this embodiment, a BuNT $H_{CC}$ binding domain comprising a β-trefoil fold domain comprises a polypeptide having, e.g., at most one, two, three, four, five, six, seven, eight, nine, 10 or 20 contiguous amino acid deletions relative to amino acids 1086-1129, amino acids 1147-1190, or amino acids 1198-1251 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine, 10 or 20 contiguous amino acid deletions relative to amino acids 1086-1129, amino acids 1147-1190, or amino acids 1198-1251 of SEQ ID NO: 10. In still other aspects of this embodiment, a BuNT $H_{CC}$ binding domain comprising a β-trefoil fold domain comprises a polypeptide having, e.g., at most one, two, three, four, five, six, seven, eight, nine, 10 or 20 contiguous amino acid additions relative to amino acids 1086-1129, amino acids 1147-1190, or amino acids 1198-1251 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine, 10 or 20 contiguous amino acid additions relative to amino acids 1086-1129, amino acids 1147-1190, or amino acids 1198-1251 of SEQ ID NO: 10.

In another embodiment, a BuNT binding domain comprising a BuNT $H_{CC}$ binding domain comprises a β4/β5 hairpin turn of a β-trefoil domain of a BuNT $H_{CC}$ binding domain or a β8/β9 hairpin turn of a β-trefoil domain of a BuNT $H_{CC}$ binding domain. In another aspect of this embodiment, a BuNT binding domain comprising a BuNT $H_{CC}$ binding domain comprises a modification of amino acids 1130-1146 or amino acids 1191-1197 of SEQ ID NO: 10.

In other aspects of this embodiment, a BuNT $H_{CC}$ binding domain comprising a β-trefoil fold domain comprises a polypeptide having, e.g., at least 70% amino acid identity with amino acids 1130-1146 or amino acids 1191-1197 of SEQ ID NO: 10, at least 75% amino acid identity with amino acids 1130-1146 or amino acids 1191-1197 of SEQ ID NO: 10, at least 80% amino acid identity with amino acids 1130-1146 or amino acids 1191-1197 of SEQ ID NO: 10, at least 85% amino acid identity with amino acids 1130-1146 or amino acids 1191-1197 of SEQ ID NO: 10, at least 90% amino acid identity with amino acids 1130-1146 or amino acids 1191-1197 of SEQ ID NO: 10 or at least 95% amino acid identity with amino acids 1130-1146 or amino acids 1191-1197 of SEQ ID NO: 10. In yet other aspects of this embodiment, a BuNT $H_{CC}$ binding domain comprising a β-trefoil fold domain comprises a polypeptide having, e.g., at most 70% amino acid identity with amino acids 1130-1146 or amino acids 1191-1197 of SEQ ID NO: 10, at most 75% amino acid identity with amino acids 1130-1146 or amino acids 1191-1197 of SEQ ID NO: 10, at most 80% amino acid identity with amino acids 1130-1146 or amino acids 1191-1197 of SEQ ID NO: 10, at most 85% amino acid identity with amino acids 1130-1146 or amino acids 1191-1197 of SEQ ID NO: 10, at most 90% amino acid identity with amino acids 1130-1146 or amino acids 1191-1197 of SEQ ID NO: 10 or at most 95% amino acid identity with amino acids 1130-1146 or amino acids 1191-1197 of SEQ ID NO: 10.

In other aspects of this embodiment, a BuNT $H_{CC}$ binding domain comprising a β-trefoil fold domain comprises a polypeptide having, e.g., at most one, two, three, four, five, six, seven, eight, nine or 10 non-contiguous amino acid substitutions relative to amino acids 1130-1146 or amino acids 1191-1197 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine or 10 non-contiguous amino acid substitutions relative to amino acids 1130-1146 or amino acids 1191-1197 of SEQ ID NO: 10. In other aspects of this embodiment, a non-contiguous amino acid substitution of any amino acid from amino acids 1130-1146 or amino acids 1191-1197 of SEQ ID NO: 10 can be replaced with glycine. In other aspects of this embodiment, a non-contiguous amino acid substitution of any hydrophobic amino acid from amino acids 1130-1146 or amino acids 1191-1197 of SEQ ID NO: 10 can be replaced with phenylalanine. In yet other aspects of this embodiment, a BuNT $H_{CC}$ binding domain comprising a β-trefoil fold domain comprises a polypeptide having, e.g., at most one, two, three, four, five, six, seven, eight, nine or 10 non-contiguous amino acid deletions relative to amino acids 1130-1146 or amino acids 1191-1197 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine or 10 non-contiguous amino acid deletions relative to amino acids 1130-1146 or amino acids 1191-1197 of SEQ ID NO: 10. In still other aspects of this embodiment, a BuNT $H_{CC}$ binding domain comprising a β-trefoil fold domain comprises a polypeptide having, e.g., at most one, two, three, four, five, six, seven, eight, nine or 10 non-contiguous amino acid additions relative to amino acids 1130-1146 or amino acids 1191-1197 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine or 10 non-contiguous amino acid additions relative to amino acids 1130-1146 or amino acids 1191-1197 of SEQ ID NO: 10.

In other aspects of this embodiment, a BuNT $H_{CC}$ binding domain comprising a β-trefoil fold domain comprises a polypeptide having, e.g., at most one, two, three, four, five, six, seven, eight, nine or 10 contiguous amino acid substitutions relative to amino acids 1130-1146 or amino acids 1191-1197 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine or 10 contiguous amino acid substitutions relative to amino acids 1130-1146 or amino acids 1191-1197 of SEQ ID NO: 10. In other aspects of this embodiment, contiguous amino acid substitutions of amino acids from amino acids 1130-1146 or amino acids 1191-1197 of SEQ ID NO: 10 can be replaced with glycine. In other aspects of this embodiment, contiguous amino acid substitutions of hydrophobic amino acids from amino acids 1130-1146 or amino acids 1191-1197 of SEQ ID NO: 10 can be replaced with phenylalanine. In yet other aspects of this embodiment, a BuNT $H_{CC}$ binding domain comprising a β-trefoil fold domain comprises a polypeptide having, e.g., at most one, two, three, four, five, six, seven, eight, nine or 10 contiguous amino acid deletions relative to amino acids 1130-1146 or amino acids 1191-1197 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine or 10 contiguous amino acid deletions relative to amino acids 1130-1146 or amino acids 1191-1197 of SEQ ID NO: 10. In still other aspects of this embodiment, a BuNT $H_{CC}$ binding domain comprising a β-trefoil fold domain comprises a polypeptide having, e.g., at most one, two, three, four, five, six, seven, eight, nine or 10 contiguous amino acid additions relative to amino acids 1130-1146 or amino acids 1191-1197 of SEQ ID NO: 10. In other aspects of this embodiment, a BuNT $H_{CC}$ binding domain comprising a β-trefoil fold domain comprises a polypeptide having, e.g., at least one, two, three, four, five, six, seven, eight, nine or 10 contiguous amino acid additions relative to amino acids 1130-1146 or amino acids 1191-1197 of SEQ ID NO: 10.

In other aspects of this embodiment, a BuNT $H_{CC}$ binding domain comprises a substitution of amino acid Trp 1076, Gly 1077, Leu 1080, Tyr 1086, Tyr 1087, Gly 1124, Ile 1129, Asp 1146, Glu 1172, Phe 1213, Ser 1221, Trp 1223, Tyr 1224, His 1227, Gly 1236 or Trp 1239, or any combination thereof, the substitution enhancing the binding activity of the BuNT $H_{CC}$ binding domain. In other aspects of this embodiment, a BuNT $H_{CC}$ binding domain comprises a deletion of amino acid Trp 1085, Gly 1086, Leu 1089, Trp 1076, Gly 1077, Leu 1080, Tyr 1086, Tyr 1087, Gly 1124, Ile 1129, Asp 1146, Glu 1172, Phe 1213, Ser 1221, Trp 1223, Tyr 1224, His 1227, Gly 1236 or Trp 1239, or any combination thereof, the deletion enhancing the binding activity of the BuNT $H_{CC}$ binding domain.

Another example of a binding domain, includes, without limitation, a Clostridial toxin non-toxin associated protein, such as, e.g., non-toxic non-hemagglutinin (NTNH), hemagglutinin-17 (HA-17), hemagglutinin-33 (HA-33) and hemagglutinin-70 (HA-70). In vivo, Clostridial bacteria produce a toxin complex comprising the approximately 150-kDa Clostridial toxin and other proteins collectively called non-toxin associated proteins (NAPs). Identified NAPs include proteins possessing hemaglutination activity, such, e.g., a hemagglutinin of approximately 17-kDa (HA-17), a hemagglutinin of approximately 33-kDa (HA-33) and a hemagglutinin of approximately 70-kDa (HA-70); as well as non-toxic non-hemagglutinin (NTNH), a protein of approximately 130-kDa, see, e.g., Eric A. Johnson and Marite Bradshaw, *Clostridial botulinum and its Neurotoxins: A Metabolic and Cellular Perspective*, 39 Toxicon 1703-1722 (2001); and Stephanie Raffestin et al., *Organization and Regulation of the Neurotoxin Genes in Clostridium botulinum and Clostridium tetani*, 10 Anaerobe 93-100 (2004). The toxin complex is important for the intoxication process because it provides protection from adverse environmental conditions, resistance to protease digestion, and appears to facilitate internalization and activation of the toxin.

Recent crystallography experiments have revealed that HA-17, HA-33 and NTNH from various Clostridial bacteria contain a region comprising β-trefoil domains very similar to the single β-trefoil domain present in the binding domain of Clostridial toxins, see, e.g., Kaoru Inoue et al., *Structural Analysis by X-Ray Crystallography and Calorimetry of a Haemagglutinin Component (HA 1) of the Progenitor Toxin from Clostridium botulinum*, 149 Microbiol. 3361-3370 (2003); and Joseph W. Arndt et al., *The Structure of the Neurotoxin-Associated Protein HA33/A from Clostridial botulinum Suggests a Reoccurring β-trefoil Fold in the Progenitor Toxin Complex*, 346 J. Mol. Biol. 1083-1093 (2005). For example, HA-33 from *Clostridium botulinum* serotype A has two β-trefoil domains, each of which consists of three potential carbohydrate binding moieties or β-trefoil folds, designated 1α (amino acids 10-55 of SEQ ID NO: 11), 1β (amino acids 56-102 of SEQ ID NO: 11) and 1γ (amino acids 103-144 of SEQ ID NO: 11) for the first β-trefoil domain and 2α (amino acids 151-197 of SEQ ID NO: 11), 2β (amino acids 198-245 of SEQ ID NO: 11) and 2γ (amino acids 246-293 of SEQ ID NO: 11) for the second β-trefoil domain. Mutations in conserved amino acids of the carbohydrate binding moiety result in a loss of carbohydrate binding, see, e.g., Kaoru Inoue et al., *Structural Analysis by X-Ray Crystallography and Calorimetry of a Haemagglutinin Component (HA1) of the Progenitor Toxin from Clostridium botulinum*, 149 Microbiol. 3361-3370 (2003).

TABLE 3

β-trefoil Domains of Clostridial HA-33 Proteins

| Protein | SEQ ID NO: | 1α-fold | 1β4/β5 β-hairpin turn | 1β-fold | 1β8/β9 β-hairpin turn | 1γ-fold |
|---|---|---|---|---|---|---|
| HA-33/A1 | 11 | 10-54 | 55-59 | 60-100 | 101-104 | 105-144 |
| HA-33/A2 | 12 | 10-54 | 55-59 | 60-100 | 101-104 | 105-144 |
| HA-33/A3 | 13 | 10-54 | 55-59 | 60-100 | 101-104 | 105-144 |
| HA-33/A4 | 14 | 10-56 | 57-61 | 62-102 | 103-106 | 107-146 |
| HA-33/A5 | 15 | 10-54 | 55-59 | 60-100 | 101-104 | 105-144 |
| HA-33/B1 | 16 | 10-54 | 55-59 | 60-100 | 101-104 | 105-144 |
| HA-33/B2 | 17 | 10-56 | 57-61 | 62-102 | 103-106 | 107-146 |
| HA-33/C1-1 | 18 | 10-54 | 55-59 | 60-98 | 99-102 | 103-141 |
| HA-33/C1-2 | 19 | 10-54 | 55-59 | 60-98 | 99-102 | 103-141 |
| HA-33/D1 | 20 | 10-54 | 55-59 | 60-98 | 99-102 | 103-141 |

These β-trefoil domains are also found in the HA-33 proteins produced by *Clostridium botulinum* serotype B, serotype C1 and serotype D and sequence alignments revealed that amino acids essential for overall carbohydrate binding are conserved. The amino acids predicted to be essential for carbohydrate binding are as follows Asp 263, Tyr 265, Gln 268, Gln 276, Phe 278 and Gln 286 of HA-33/A1 of SEQ ID NO: 11, HA-33/A2 of SEQ ID NO: 12, HA-33/A3 of SEQ ID NO: 13, HA-33/A5 of SEQ ID NO: 14 and HA-33/B2 of SEQ ID NO: 15; Asp 264, Tyr 266, Gln 269, Gln 277, Phe 279 and Gln 287 of HA-33/A4 of SEQ ID NO: 14; Asp 262, Tyr 264, Gln 267, Gln 275, Phe 277 and Gln 285 of HA-33/B1 of SEQ ID NO: 16; Asp 255, Val 257, Gly 260, Gln 268, Typ 270 and Gln 278 of HA-33/C1 of SEQ ID NO: 18; and Asp 256, Tyr 258, Gln 261, Ile 269, Asp 271 and Gln 279 of HA-33/C2 of SEQ ID NO: 19 and HA-33/D of SEQ ID NO: 20.

Immunoaffinity column chromatography and pull-down assays have shown that HA-33 can bind synaptotagmin II, a putative Clostridial toxin receptor, see, e.g., Yu Zhou et al., *Haemagglutinin-33 of Type Q Botulinum Neurotoxin Complex Binds with Synaptotagmin II*, 272 FEBS Lett. 2717-2726 (2005). The amino acid sequences comprising the β-trefoil domains found in various Clostridial HA-33 proteins are shown in Tables 3 and 4.

Further analysis of the β-trefoil domain sequence of HA-33 also identified β-trefoil domains in HA-17 and NTNH, see, e.g., Joseph W. Arndt et al., *The Structure of the Neurotoxin-Associated Protein HA33/A from Clostridial botulinum Suggests a Reoccurring β-trefoil Fold in the Progenitor Toxin Complex*, 346 J. Mol. Biol. 1083-1093 (2005). The HA-17 comprises a single β-trefoil domain containing three carbohydrate binding moieties or β-trefoil folds. The carbohydrate binding moieties of HA-17 exhibits the greatest sequence similarity with the 2γ carbohydrate binding moiety of HA-33. These R-trefoil domains are also found in the HA-17 proteins produced by *Clostridium botulinum* serotype B, serotype C1 and serotype D and sequence alignments revealed that amino acids essential for overall carbohydrate binding are conserved. The amino acids predicted to be essential for carbohydrate binding are as follows Tyr 110, Typ 112, Tyr 115, Pro 130, Phe 132 and Asn 138 of HA-17/A of SEQ ID NO: 21, HA-17/B of SEQ ID NO: 22, HA-17/C1 of SEQ ID NO: 23 and HA-17/D of SEQ ID NO: 24. The amino acid sequences comprising the β-trefoil domains found in various Clostridial HA-17 proteins are shown in Table 5.

TABLE 4

β-trefoil Domains of Clostridial HA-33 Proteins

| Protein | SEQ ID NO: | 2α-fold | 2β4/β5 β-hairpin turn | 2β-fold | 2β8/β9 β-hairpin turn | 2γ-fold |
|---|---|---|---|---|---|---|
| HA-33/A1 | 11 | 151-195 | 196-199 | 200-242 | 243-248 | 249-293 |
| HA-33/A2 | 12 | 151-195 | 196-199 | 200-242 | 243-248 | 249-293 |
| HA-33/A3 | 13 | 151-195 | 196-199 | 200-242 | 243-248 | 249-293 |
| HA-33/A4 | 14 | 153-197 | 198-201 | 202-243 | 244-249 | 250-294 |
| HA-33/A5 | 15 | 151-195 | 196-199 | 200-242 | 243-248 | 249-279 |
| HA-33/B1 | 16 | 151-195 | 196-199 | 200-241 | 242-247 | 248-292 |
| HA-33/B2 | 17 | 153-197 | 198-201 | 200-242 | 243-248 | 249-291 |
| HA-33/C1-1 | 18 | 148-190 | 191-194 | 195-234 | 235-240 | 241-285 |
| HA-33/C1-2 | 19 | 148-190 | 191-194 | 195-235 | 236-241 | 242-286 |
| HA-33/D1 | 20 | 148-190 | 191-194 | 195-235 | 236-241 | 242-286 |

TABLE 5

β-trefoil Domains of Clostridial HA-17 Proteins

| | | | Amino Acid Sequence Region of Carbohydrate Binding Moieties | | | |
|---|---|---|---|---|---|---|
| Protein | SEQ ID NO: | α-fold | β4/β5 β-hairpin turn | β-fold | β8/β9 β-hairpin turn | γ-fold |
| HA-17/A | 21 | 9-50 | 51-54 | 55-91 | 92-94 | 95-146 |
| HA-17/B | 22 | 9-50 | 51-54 | 55-91 | 92-94 | 95-146 |
| HA-17/C1 | 23 | 9-50 | 51-54 | 55-91 | 92-94 | 95-146 |
| HA-17/D | 24 | 9-50 | 51-54 | 55-91 | 92-94 | 95-146 |

NTNH from various Clostridial bacteria shows significant sequence similarity to the β-trefoil domains present in the cell binding domain of BoNT/A and TeNT. The high degree of structural similarity is interesting in light of the low sequence similarity between NTNH and the Clostridial toxins. Furthermore, since NTNH of the various serotypes have greater sequence similarity than the Clostridial toxins, it is likely that the NTNH produced by other Clostridial strains will also have β-trefoil domains exhibiting high structural similarity with the binding domains of Clostridial toxins. The β-trefoil domains of various Clostridial NTNHs are as follows: amino acids 1050-1193 of NTNH/A1 of SEQ ID NO: 25; amino acids 1050-1198 of NTNH/A2 of SEQ ID NO: 26; amino acids 1050-1193 of NTNH/A3 of SEQ ID NO: 27; amino acids 1049-1197 of NTNH/B of SEQ ID NO: 28; amino acids 1049-1196 of NTNH/C1 of SEQ ID NO: 29; amino acids 1049-1196 of NTNH/D of SEQ ID NO: 30; amino acids 1014-1162 of NTNH/E of SEQ ID NO: 30; amino acids 1016-1159 of NTNH/F1 of SEQ ID NO: 32; amino acids 1017-1165 of NTNH/F2 of SEQ ID NO: 33; and amino acids 1050-1198 of NTNH/G of SEQ ID NO: 34. The amino acid sequences comprising the β-trefoil domains found in various Clostridial NTNH proteins are shown in Table 6.

high prediction of structural similarity of the β-trefoil domains present in HA-33, HA-17 and NTNH relative to the β-trefoil domain found in Clostridial toxins provides a potential source of binding domains useful for developing multivalent Clostridial toxins. As a non-limiting example, a carbohydrate binding moiety or a β-trefoil fold from HA-33, HA-17 or NTNH can be substituted for the naturally occurring carbohydrate binding moiety present in a Clostridial toxin. As another non-limiting example, a carbohydrate binding moiety or a β-trefoil fold from HA-33, HA-17 or NTNH can be added in addition to the naturally occurring carbohydrate binding moiety present in a Clostridial toxin. As yet another non-limiting example, a multiple carbohydrate binding moieties or a β-trefoil folds from HA-33, HA-17 or NTNH can be substituted for the naturally occurring carbohydrate binding moiety present in a Clostridial toxin. As still another non-limiting example, multiple carbohydrate binding moieties or a β-trefoil folds from HA-33, HA-17 or NTNH can be added in addition to the naturally occurring carbohydrate binding moiety present in a Clostridial toxin. As another non-limiting example, multiple carbohydrate binding moieties or a β-trefoil folds from a Clostridial toxin binding

TABLE 6

β-trefoil Domains of Clostridial NTNH Proteins

| | | Amino Acid Sequence Region of Carbohydrate Binding Moieties | | | | |
|---|---|---|---|---|---|---|
| Protein | SEQ ID NO: | α-fold | β4/β5 β-hairpin turn | β-fold | β8/β9 β-hairpin turn | γ-fold |
| NTNH/A1 | 25 | 1050-1097 | 1098-1110 | 1111-1138 | 1139-1148 | 1149-1194 |
| NTNH/A2 | 26 | 1050-1097 | 1098-1110 | 1111-1138 | 1140-1148 | 1149-1199 |
| NTNH/A3 | 27 | 1050-1097 | 1098-1110 | 1111-1138 | 1139-1148 | 1149-1194 |
| NTNH/B | 28 | 1049-1096 | 1097-1109 | 1110-1138 | 1139-1147 | 1148-1198 |
| NTNH/C1 | 29 | 1049-1096 | 1097-1109 | 1110-1138 | 1139-1147 | 1148-1197 |
| NTNH/D | 30 | 1049-1096 | 1097-1109 | 1110-1138 | 1139-1147 | 1148-1197 |
| NTNH/E | 31 | 1014-1061 | 1062-1074 | 1075-1103 | 1104-1113 | 1114-1163 |
| NTNH/F1 | 32 | 1016-1063 | 1064-1076 | 1077-1104 | 1105-1114 | 1115-1160 |
| NTNH/F2 | 33 | 1017-1064 | 1065-1077 | 1078-1106 | 1107-1116 | 1117-1166 |
| NTNH/G | 34 | 1050-1097 | 1098-1110 | 1111-1139 | 1140-1149 | 1150-1199 |

The β-trefoil domains present in the Clostridial toxin, HA-33, HA-17 and NTNH collectively form nearly half the mass of a Clostridial toxin complex and underlies the apparent importance of carbohydrate binding in the cell binding step of the intoxication process. This observation is further enhanced by the fact that a Clostridial toxin alone is not as effective in intoxicating a cell as the entire toxin complex. One potential explanation for this enhanced binding activity is the presence, both in type and in quantity, of the β-trefoil domains present in HA-33, HA-17 and NTNH. Therefore, the domain can be added in addition to the naturally occurring carbohydrate binding moiety present in a Clostridial toxin.

As used herein, the term "Non-toxin Associated Protein" is synonymous with "NAP" and means a Clostridial NAP with selective binding activity, such as, e.g., a binding affinity or a binding specificity, for a Clostridial toxin receptor. It is envisioned that both naturally occurring NAPs as well as non-naturally occurring NAPs can be used as a binding domain. A Clostridial NAP includes, without limitation, naturally occurring Clostridial NAP variants, such as, e.g., Clostridial NAP isoforms and Clostridial NAP subtypes; non-naturally occurring Clostridial NAP variants, such as, e.g., conservative Clostridial NAP variants, non-conservative Clostridial NAP variants, Clostridial NAP chimerics, active Clostridial NAP fragments thereof, or any combination thereof.

As used herein, the term "Clostridial NAP variant," whether naturally-occurring or non-naturally-occurring, means a Clostridial NAP that has at least one amino acid change from the corresponding region of the disclosed reference sequences (see Tables 3-6) and can be described in percent identity to the corresponding region of that reference sequence. Unless expressly indicated, all Clostridial NAP variants disclosed in the present specification are capable of executing the cell binding step of the intoxication process.

It is recognized by those of skill in the art that within each Clostridial bacterium there can be naturally occurring Clostridial NAP variants that differ somewhat in their amino acid sequence, and also in the nucleic acids encoding these proteins. For example, there are presently five BoNT/A HA-33 variants, HA-33/A1, HA-33/A2, HA-33/A3, HA-33/A4 and HA-33/A5 (Tables 3 and 4), with specific HA-33 variants showing various degrees of amino acid divergence when compared to another HA-33 variant. As another example, there are presently three BoNT/A NTNH-33 variants, NTNH/A1, NTNH/A2 and NTNH/A3 (Table 6), with specific NTNH variant showing various degrees of amino acid divergence when compared to another NTNH variant. As used herein, the term "naturally occurring Clostridial NAP variant" means any Clostridial NAP produced by a naturally-occurring process, including, without limitation, Clostridial NAP isoforms produced from alternatively-spliced transcripts, Clostridial NAP isoforms produced by spontaneous mutation and Clostridial NAP subtypes. A naturally occurring Clostridial NAP variant can function in substantially the same manner as the reference Clostridial NAP on which the naturally occurring Clostridial NAP variant is based, and can be substituted for the reference Clostridial NAP in any aspect of the present invention. A naturally occurring Clostridial NAP variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial NAP on which the naturally occurring Clostridial NAP variant is based. A naturally occurring Clostridial NAP variant can also substitute at least 10 contiguous amino acids, at least 15 contiguous amino acids, at least 20 contiguous amino acids, or at least 25 contiguous amino acids from the reference Clostridial NAP on which the naturally occurring Clostridial NAP variant is based, that possess at least 50% amino acid identity, 65% amino acid identity, 75% amino acid identity, 85% amino acid identity or 95% amino acid identity to the reference Clostridial NAP on which the naturally occurring Clostridial NAP variant is based.

A non-limiting examples of a naturally occurring Clostridial NAP variant is a Clostridial NAP isoform such as, e.g., a BoNT/A HA-33 isoform, a *Clostridium botulinum* serotype B HA-33 isoform, a *Clostridium botulinum* serotype C1 HA-33 isoform, a *Clostridium botulinum* serotype D HA-33 isoform, a BoNT/A HA-17 isoform, a *Clostridium botulinum* serotype B HA-17 isoform, a *Clostridium botulinum* serotype C1 HA-17 isoform, a *Clostridium botulinum* serotype D HA-17 isoform, a BoNT/A NTNH isoform, a *Clostridium botulinum* serotype B NTNH isoform, a *Clostridium botulinum* serotype C1 NTNH isoform, a *Clostridium botulinum* serotype D NTNH isoform, a *Clostridium botulinum* serotype E NTNH isoform, a *Clostridium botulinum* serotype F NTNH isoform and a *Clostridium botulinum* serotype G NTNH isoform. A Clostridial NAP isoform can function in substantially the same manner as the reference Clostridial NAP on which the Clostridial NAP isoform is based, and can be substituted for the reference Clostridial NAP in any aspect of the present invention.

Another non-limiting examples of a naturally occurring Clostridial NAP variant is a Clostridial NAP subtype such as, e.g., a BoNT/A HA-33 subtype, a *Clostridium botulinum* serotype B HA-33 subtype, a *Clostridium botulinum* serotype C1 HA-33 subtype, a *Clostridium botulinum* serotype D HA-33 subtype, a BoNT/A HA-17 subtype, a *Clostridium botulinum* serotype B HA-17 subtype, a *Clostridium botulinum* serotype C1 HA-17 subtype, a *Clostridium botulinum* serotype D HA-17 subtype, a BoNT/A NTNH subtype, a *Clostridium botulinum* serotype B NTNH subtype, a *Clostridium botulinum* serotype C1 NTNH subtype, a *Clostridium botulinum* serotype D NTNH subtype, a *Clostridium botulinum* serotype E NTNH subtype, a *Clostridium botulinum* serotype F NTNH subtype and a *Clostridium botulinum* serotype G NTNH subtype. A Clostridial NAP subtype can function in substantially the same manner as the reference Clostridial NAP on which the Clostridial NAP subtype is based, and can be substituted for the reference Clostridial NAP in any aspect of the present invention.

As used herein, the term "non-naturally occurring Clostridial NAP variant" means any Clostridial NAP produced with the aid of human manipulation, including, without limitation, Clostridial NAPs produced by genetic engineering using random mutagenesis or rational design and Clostridial NAPs produced by chemical synthesis. Non-limiting examples of non-naturally occurring Clostridial NAP variants include, e.g., conservative Clostridial NAP variants, non-conservative Clostridial NAP variants, Clostridial NAP chimeric variants and active Clostridial NAP fragments.

As used herein, the term "conservative Clostridial NAP variant" means a Clostridial NAP that has at least one amino acid substituted by another amino acid or an amino acid analog that has at least one property similar to that of the original amino acid from the reference Clostridial NAP sequence (see Tables 3-6). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial NAP variant can function in substantially the same manner as the reference Clostridial NAP on which the conservative Clostridial NAP variant is based, and can be substituted for the reference Clostridial NAP in any aspect of the present invention. A conservative Clostridial NAP variant may substitute one or more amino acids, two or more amino acids, three or more amino acids, four or more amino acids, five or more amino acids, ten or more amino acids, 20 or more amino acids, 30 or more amino acids, 40 or more amino acids or 50 or more amino acids from the reference Clostridial NAP on which the conservative Clostridial NAP variant is based. A conservative Clostridial NAP variant can also substitute at least 10 contiguous amino acids, at least 15 contiguous amino acids, at least 20 contiguous amino acids, or at least 25 contiguous amino acids from the reference Clostridial NAP on which the conservative Clostridial NAP variant is based, that possess at least 50% amino acid identity, 65% amino acid identity, 75% amino acid identity, 85% amino acid identity or 95% amino acid identity to the reference Clostridial NAP on which the conservative Clostridial NAP variant is based. Non-limiting examples of a conservative Clostridial NAP variant include, e.g., a conservative BoNT/A HA-33 variant, a conservative *Clostridium botulinum* serotype B HA-33 variant, a conservative *Clostridium botulinum* serotype C1 HA-33 variant, a conservative *Clostridium botulinum* serotype D HA-33 variant, a conservative BoNT/A HA-17 variant, a conservative *Clostridium botulinum* serotype B HA-17 variant, a conservative *Clostridium botulinum* serotype C1 HA-17 variant, a conservative *Clostridium botulinum* serotype D HA-17 variant, a conservative BoNT/A NTNH variant, a conservative *Clostridium botulinum* serotype B NTNH variant, a conservative *Clostridium botulinum* serotype C1 NTNH variant, a conservative *Clostridium botulinum* serotype D NTNH variant, a conservative *Clostridium botulinum* serotype E NTNH variant, a conservative *Clostridium botulinum* serotype F NTNH variant and a conservative *Clostridium botulinum* serotype G NTNH variant.

As used herein, the term "non-conservative Clostridial NAP variant" means a Clostridial NAP in which 1) at least one amino acid is deleted from the reference Clostridial NAP on which the non-conservative Clostridial NAP variant is based; 2) at least one amino acid added to the reference Clostridial NAP on which the non-conservative Clostridial NAP is based; or 3) at least one amino acid is substituted by another amino acid or an amino acid analog that does not share any property similar to that of the original amino acid from the reference Clostridial NAP sequence (see Tables 3-6). A non-conservative Clostridial NAP variant can function in substantially the same manner as the reference Clostridial NAP on which the non-conservative Clostridial NAP variant is based, and can be substituted for the reference Clostridial NAP in any aspect of the present invention. A non-conservative Clostridial NAP variant can delete one or more amino acids, two or more amino acids, three or more amino acids, four or more amino acids, five or more amino acids, and ten or more amino acids from the reference Clostridial NAP on which the non-conservative Clostridial NAP variant is based. A non-conservative Clostridial NAP variant can add one or more amino acids, two or more amino acids, three or more amino acids, four or more amino acids, five or more amino acids, and ten or more amino acids to the reference Clostridial NAP on which the non-conservative Clostridial NAP variant is based. A non-conservative Clostridial NAP variant may substitute one or more amino acids, two or more amino acids, three or more amino acids, four or more amino acids, five or more amino acids, ten or more amino acids, 20 or more amino acids, 30 or more amino acids, 40 or more amino acids or 50 or more amino acids from the reference Clostridial NAP on which the non-conservative Clostridial NAP variant is based. A non-conservative Clostridial NAP variant can also substitute at least 10 contiguous amino acids, at least 15 contiguous amino acids, at least 20 contiguous amino acids, or at least 25 contiguous amino acids from the reference Clostridial NAP on which the non-conservative Clostridial NAP variant is based, that possess at least 50% amino acid identity, 65% amino acid identity, 75% amino acid identity, 85% amino acid identity or 95% amino acid identity to the reference Clostridial NAP on which the non-conservative Clostridial NAP variant is based. Non-limiting examples of a non-conservative Clostridial NAP variant include, e.g., a non-conservative BoNT/A HA-33 variant, a non-conservative *Clostridium botulinum* serotype B HA-33 variant, a non-conservative *Clostridium botulinum* serotype C1 HA-33 variant, a non-conservative *Clostridium botulinum* serotype D HA-33 variant, a non-conservative BoNT/A HA-17 variant, a non-conservative *Clostridium botulinum* serotype B HA-17 variant, a non-conservative *Clostridium botulinum* serotype C1 HA-17 variant, a non-conservative *Clostridium botulinum* serotype D HA-17 variant, a non-conservative BoNT/A NTNH variant, a non-conservative *Clostridium botulinum* serotype B NTNH variant, a non-conservative *Clostridium botulinum* serotype C1 NTNH variant, a non-conservative *Clostridium botulinum* serotype D NTNH variant, a non-conservative *Clostridium botulinum* serotype E NTNH variant, a non-conservative *Clostridium botulinum* serotype F NTNH variant and a non-conservative *Clostridium botulinum* serotype G NTNH variant.

As used herein, the term "Clostridial NAP chimeric" means a polypeptide comprising at least a portion of a Clostridial NAP and at least a portion of at least one other polypeptide to form an enhanced targeting domain with at least one property different from the reference Clostridial NAP (see Tables 3-6), with the proviso that this Clostridial NAP chimeric can specifically bind to a Clostridial toxin receptor present in a Clostridial toxin target cell, and thus participate in executing the overall cellular mechanism whereby a Clostridial toxin proteolytically cleaves a substrate.

As used herein, the term "active Clostridial NAP fragment" means any of a variety of Clostridial NAP fragments comprising the enhanced targeting domain can be useful in aspects of the present invention with the proviso that these NAP fragments can specifically bind to a Clostridial toxin receptor present in a Clostridial toxin target cell, and thus participate in executing the overall cellular mechanism whereby a Clostridial toxin proteolytically cleaves a substrate.

Thus, in an embodiment, a binding domain comprises a NAP. In aspects of this embodiment, a NAP comprises a β-trefoil domain derived from a NAP.

In another embodiment, a binding domain comprises a β-trefoil domain derived from a Clostridial HA-33. In an aspect of this embodiment, a binding domain comprising a β-trefoil domain derived from a Clostridial HA-33 comprises, e.g., a β-trefoil domain derived from a BoNT/A HA-33, a β-trefoil domain derived from a BoNT/B HA-33, a β-trefoil domain derived from a BoNT/C1 HA-33 or a β-trefoil domain derived from a BoNT/D HA-33. In another aspect of this embodiment, a β-trefoil domain derived from a Clostridial HA-33 comprises a 1α-fold motif of a β-trefoil domain of a BoNT/A HA-33, a 1β-fold motif of a β-trefoil domain of a BoNT/A HA-33, a 1γ-fold motif of a β-trefoil domain of a BoNT/A HA-33, a 2α-fold motif of β-trefoil domain of a BoNT/A HA-33, a 2β-fold motif of a β-trefoil domain of a BoNT/A HA-33, or a 2γ-fold motif of a β-trefoil domain of a BoNT/A HA-33. In another aspect of this embodiment, a β-trefoil domain derived from a Clostridial HA-33 comprises a 1α-fold motif of a β-trefoil domain of a BoNT/B HA-33, a 1β-fold motif of a β-trefoil domain of a BoNT/B HA-33, a 1γ-fold motif of a β-trefoil domain of a BoNT/B HA-33, a 2α-fold motif of a β-trefoil domain of a BoNT/B HA-33, a 2β-fold motif of a β-trefoil domain of a BoNT/B HA-33, or a 2γ-fold motif of a β-trefoil domain of a BoNT/B HA-33. In another aspect of this embodiment, a β-trefoil domain derived from a Clostridial HA-33 comprises a 1α-fold motif of a β-trefoil domain of a BoNT/C1 HA-33, a 1β-fold motif of a β-trefoil domain of a BoNT/C1 HA-33, a 1γ-fold motif of a β-trefoil domain of a BoNT/C1 HA-33, a 2α-fold motif of a β-trefoil domain of a BoNT/C1 HA-33, a 2β-fold motif of a β-trefoil domain of a BoNT/C1 HA-33, or a 2γ-fold motif of a β-trefoil domain of a BoNT/C1 HA-33. In another aspect of this embodiment, a β-trefoil domain derived from a Clostridial HA-33 comprises a 1α-fold motif of a β-trefoil domain of a BoNT/D HA-33, a 1β-fold motif of a β-trefoil domain of a BoNT/D HA-33, a 1γ-fold motif of a β-trefoil domain of a BoNT/D HA-33, a 2α-fold motif of a β-trefoil domain of a BoNT/D HA-33, a 2β-fold motif of a β-trefoil domain of a BoNT/D HA-33, or a 2γ-fold motif of a β-trefoil domain of a BoNT/D HA-33.

In another embodiment, a binding domain comprises a β-trefoil domain derived from a BoNT/A HA-33 of SEQ ID NO: 11. In another embodiment, a binding domain comprising a β-trefoil domain derived from a BoNT/A HA-33 comprises amino acids 10-144 or amino acids 151-293 of SEQ ID NO: 11. In another aspect of this embodiment, a binding domain comprising a β-trefoil domain derived from a BoNT/A HA-33 comprises a 1α-fold motif of a β-trefoil domain of a BoNT/A HA-33, a 1β-fold motif of a β-trefoil domain of a BoNT/A HA-33, a 1γ-fold motif of a β-trefoil domain of a BoNT/A HA-33, a 2α-fold motif of a β-trefoil domain of a BoNT/A HA-33, a 2β-fold motif of a β-trefoil domain of a BoNT/A HA-33, or a 2γ-fold motif of a β-trefoil domain of a BoNT/A HA-33 of SEQ ID NO: 11. In another aspect of this embodiment, a binding domain comprising a β-trefoil domain derived from a BoNT/A HA-33 comprises amino acids 10-54, amino acids 60-100, amino acids 105-144, amino acids 151-195, amino acids 200-242, or amino acids 249-293 of SEQ ID NO: 11.

In other aspects of this embodiment, a binding domain comprising a BoNT/A HA-33 β-trefoil domain comprises a polypeptide having, e.g., at least 70% amino acid identity with amino acids 10-54, amino acids 60-100, amino acids 105-144, amino acids 151-195, amino acids 200-242, or amino acids 249-293 of SEQ ID NO: 11, at least 75% amino acid identity with amino acids 10-54, amino acids 60-100, amino acids 105-144, amino acids 151-195, amino acids 200-242, or amino acids 249-293 of SEQ ID NO: 11, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-54, amino acids 60-100, amino acids 105-144, amino acids 151-195, amino acids 200-242, or amino acids 249-293 of SEQ ID NO: 11, at least 90% amino acid identity with amino acids 10-54, amino acids 60-100, amino acids 105-144, amino acids 151-195, amino acids 200-242, or amino acids 249-293 of SEQ ID NO: 11 or at least 95% amino acid identity with amino acids 10-54, amino acids 60-100, amino acids 105-144, amino acids 151-195, amino acids 200-242, or amino acids 249-293 of SEQ ID NO: 11. In yet other aspects of this embodiment, a binding domain comprising a BoNT/A HA-33 β-trefoil domain comprises a polypeptide having, e.g., at most 70% amino acid identity with amino acids 10-54, amino acids 60-100, amino acids 105-144, amino acids 151-195, amino acids 200-242, or amino acids 249-293 of SEQ ID NO: 11, at most 75% amino acid identity with amino acids 10-54, amino acids 60-100, amino acids 105-144, amino acids 151-195, amino acids 200-242, or amino acids 249-293 of SEQ ID NO: 11, at most 80% amino acid identity with amino acids 10-54, amino acids 60-100, amino acids 105-144, amino acids 151-195, amino acids 200-242, or amino acids 249-293 of SEQ ID NO: 11, at most 85% amino acid identity with amino acids 10-54, amino acids 60-100, amino acids 105-144, amino acids 151-195, amino acids 200-242, or amino acids 249-293 of SEQ ID NO: 11, at most 90% amino acid identity with amino acids 10-54, amino acids 60-100, amino acids 105-144, amino acids 151-195, amino acids 200-242, or amino acids 249-293 of SEQ ID NO: 11 or at most 95% amino acid identity with amino acids 10-54, amino acids 60-100, amino acids 105-144, amino acids 151-195, amino acids 200-242, or amino acids 249-293 of SEQ ID NO: 11.

In other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 11. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 11. In yet other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 11. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 11. In still other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 11. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 11.

In other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 11. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 11. In yet other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 11. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 11. In still other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 11. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 11.

In another embodiment, a binding domain comprising a BoNT/A HA-33 β-trefoil domain comprises a 1β4/β5 hairpin turn of a β-trefoil domain of a BoNT/A HA-33, a 1β8/β9 hairpin turn of a β-trefoil domain of a BoNT/A HA-33, a 2β4/β5 hairpin turn of a β-trefoil domain of a BoNT/A HA-33 or a 2β8/β9 hairpin turn of a β-trefoil domain of a BoNT/A HA-33 of SEQ ID NO: 11. In another aspect of this embodiment, a binding domain comprising a BoNT/A HA-33 β-trefoil domain comprises amino acids 55-59, amino acids 101-104, amino acids 196-199, or amino acids 243-248 of SEQ ID NO: 11.

In other aspects of this embodiment, a binding domain comprising a BoNT/A HA-33 β-trefoil domain comprises a polypeptide having, e.g., at least 70% amino acid identity with amino acids 55-59, amino acids 101-104, amino acids 196-199, or amino acids 243-248 of SEQ ID NO: 11, at least 75% amino acid identity with amino acids 55-59, amino acids 101-104, amino acids 196-199, or amino acids 243-248 of SEQ ID NO: 11, at least 80% amino acid identity with amino acids 55-59, amino acids 101-104, amino acids 196-199, or amino acids 243-248 of SEQ ID NO: 11, at least 85% amino acid identity with amino acids 55-59, amino acids 101-104, amino acids 196-199, or amino acids 243-248 of SEQ ID NO: 11, at least 90% amino acid identity with amino acids 55-59, amino acids 101-104, amino acids 196-199, or amino acids 243-248 of SEQ ID NO: 11 or at least 95% amino acid identity with amino acids 55-59, amino acids 101-104, amino acids 196-199, or amino acids 243-248 of SEQ ID NO: 11. In yet other aspects of this embodiment, a binding domain comprising a BoNT/A HA-33 β-trefoil domain comprises a polypeptide having, e.g., at most 70% amino acid identity with amino acids 55-59, amino acids 101-104, amino acids 196-199, or amino acids 243-248 of SEQ ID NO: 11, at most 75% amino acid identity with amino acids 55-59, amino acids 101-104, amino acids 196-199, or amino acids 243-248 of SEQ ID NO: 11, at most 80% amino acid identity with amino acids 55-59, amino acids 101-104, amino acids 196-199, or amino acids 243-248 of SEQ ID NO: 11, at most 85% amino acid identity with amino acids 55-59, amino acids 101-104, amino acids 196-199, or amino acids 243-248 of SEQ ID NO: 11, at most 90% amino acid identity with amino acids 55-59, amino acids 101-104, amino acids 196-199, or amino acids 243-248 of SEQ ID NO: 11 or at most 95% amino acid identity with amino acids 55-59, amino acids 101-104, amino acids 196-199, or amino acids 243-248 of SEQ ID NO: 11.

In other aspects of this embodiment, a binding domain comprising a BoNT/A HA-33 β-trefoil domain comprises a polypeptide having, e.g., at most one, two, three or four non-contiguous amino acid substitutions relative to amino acids 55-59, amino acids 101-104, amino acids 196-199, or amino acids 243-248 of SEQ ID NO: 11. In other aspects of this embodiment, a binding domain comprising a BoNT/A HA-33 β-trefoil domain comprises a polypeptide having, e.g., at least one, two, three or four non-contiguous amino acid substitutions relative to amino acids 55-59, amino acids 101-104, amino acids 196-199, or amino acids 243-248 of SEQ ID NO: 11. In other aspects of this embodiment, a non-contiguous amino acid substitution of any amino acid from amino acids 55-59, amino acids 101-104, amino acids 196-199, or amino acids 243-248 of SEQ ID NO: 11 can be replaced with glycine. In other aspects of this embodiment, a non-contiguous amino acid substitution of any hydrophobic amino acid from amino acids 55-59, amino acids 101-104, amino acids 196-199, or amino acids 243-248 of SEQ ID NO: 11 can be replaced with phenylalanine. In yet other aspects of this embodiment, a β-trefoil domain with enhanced binding activity derived from a BoNT/A HA-33 comprises a polypeptide having, e.g., at most one, two, three or four non-contiguous amino acid deletions relative to amino acids 55-59, amino acids 101-104, amino acids 196-199, or amino acids 243-248 of SEQ ID NO: 11. In other aspects of this embodiment, a binding domain comprising a BoNT/A HA-33 β-trefoil domain comprises a polypeptide having, e.g., at least one, two, three or four non-contiguous amino acid deletions relative to amino acids 55-59, amino acids 101-104, amino acids 196-199, or amino acids 243-248 of SEQ ID NO: 11. In still other aspects of this embodiment, a binding domain comprising a BoNT/A HA-33 β-trefoil domain comprises a polypeptide having, e.g., at most one, two, three or four non-contiguous amino acid additions relative to amino acids 55-59, amino acids 101-104, amino acids 196-199, or amino acids 243-248 of SEQ ID NO: 11. In other aspects of this embodiment, a binding domain comprising a BoNT/A HA-33 β-trefoil domain comprises a polypeptide having, e.g., at least one, two, three or four non-contiguous amino acid additions relative to amino acids 55-59, amino acids 101-104, amino acids 196-199, or amino acids 243-248 of SEQ ID NO: 11.

In other aspects of this embodiment, a binding domain comprising a BoNT/A HA-33 β-trefoil domain comprises a polypeptide having, e.g., at most one, two, three or four contiguous amino acid substitutions relative to amino acids 55-59, amino acids 101-104, amino acids 196-199, or amino acids 243-248 of SEQ ID NO: 11. In other aspects of this embodiment, a binding domain comprising a BoNT/A HA-33 β-trefoil domain comprises a polypeptide having, e.g., at least one, two, three or four contiguous amino acid substitutions relative to amino acids 55-59, amino acids 101-104, amino acids 196-199, or amino acids 243-248 of SEQ ID NO: 11. In other aspects of this embodiment, contiguous amino acid substitutions of amino acids from amino acids 55-59, amino acids 101-104, amino acids 196-199, or amino acids 243-248 of SEQ ID NO: 11 can be replaced with glycine. In other aspects of this embodiment, contiguous amino acid substitutions of hydrophobic amino acids from amino acids 55-59, amino acids 101-104, amino acids 196-199, or amino acids 243-248 of SEQ ID NO: 11 can be replaced with phenylalanine. In yet other aspects of this embodiment, a binding domain comprising a BoNT/A HA-33 β-trefoil domain comprises a polypeptide having, e.g., at most one, two, three or four contiguous amino acid deletions relative to amino acids 55-59, amino acids 101-104, amino acids 196-199, or amino acids 243-248 of SEQ ID NO: 11. In other aspects of this embodiment, a binding domain comprising a BoNT/A HA-33 β-trefoil domain comprises a polypeptide having, e.g., at least one, two, three or four contiguous amino acid deletions relative to amino acids 55-59, amino acids 101-104, amino acids 196-199, or amino acids 243-248 of SEQ ID NO: 11. In still other aspects of this embodiment, a binding domain comprising a BoNT/A HA-33 β-trefoil domain comprises a polypeptide having, e.g., at most one, two, three or four contiguous amino acid additions relative to amino acids 55-59, amino acids 101-104, amino acids 196-199, or amino acids 243-248 of SEQ ID NO: 11. In other aspects of this embodiment, a binding domain comprising a BoNT/A HA-33 β-trefoil domain comprises a polypeptide having, e.g., at least one, two, three or four contiguous amino acid additions relative to amino acids 55-59, amino acids 101-104, amino acids 196-199, or amino acids 243-248 of SEQ ID NO: 11.

In another embodiment, a binding domain comprises a β-trefoil domain derived from a BoNT/A HA-33 of SEQ ID NO: 12. In another embodiment, a binding domain comprising a β-trefoil domain derived from a BoNT/A HA-33 comprises amino acids 10-144 or amino acids 151-293 of SEQ ID NO: 12. In another aspect of this embodiment, a binding domain comprising a β-trefoil domain derived from a BoNT/A HA-33 comprises a 1α-fold motif of a β-trefoil domain of a BoNT/A HA-33, a 1β-fold motif of a β-trefoil domain of a BoNT/A HA-33, a 1γ-fold motif of a β-trefoil domain of a BoNT/A HA-33, a 2α-fold motif of a β-trefoil domain of a BoNT/A HA-33, a 2β-fold motif of a β-trefoil domain of a BoNT/A HA-33, or a 2γ-fold motif of a β-trefoil domain of a BoNT/A HA-33 of SEQ ID NO: 12. In another aspect of this embodiment, a binding domain comprising a β-trefoil domain derived from a BoNT/A HA-33 comprises amino acids 10-54, amino acids 60-100, amino acids 105-144, amino acids 151-195, amino acids 200-242, or amino acids 249-293 of SEQ ID NO: 12.

In other aspects of this embodiment, a binding domain comprising a BoNT/A HA-33 β-trefoil domain comprises a polypeptide having, e.g., at least 70% amino acid identity with amino acids 10-54, amino acids 60-100, amino acids 105-144, amino acids 151-195, amino acids 200-242, or amino acids 249-293 of SEQ ID NO: 12, at least 75% amino acid identity with amino acids 10-54, amino acids 60-100, amino acids 105-144, amino acids 151-195, amino acids 200-242, or amino acids 249-293 of SEQ ID NO: 12, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-54, amino acids 60-100, amino acids 105-144, amino acids 151-195, amino acids 200-242, or amino acids 249-293 of SEQ ID NO: 12, at least 90% amino acid identity with amino acids 10-54, amino acids 60-100, amino acids 105-144, amino acids 151-195, amino acids 200-242, or amino acids 249-293 of SEQ ID NO: 12 or at least 95% amino acid identity with amino acids 10-54, amino acids 60-100, amino acids 105-144, amino acids 151-195, amino acids 200-242, or amino acids 249-293 of SEQ ID NO: 12. In yet other aspects of this embodiment, a binding domain comprising a BoNT/A HA-33 β-trefoil domain comprises a polypeptide having, e.g., at most 70% amino acid identity with amino acids 10-54, amino acids 60-100, amino acids 105-144, amino acids 151-195, amino acids 200-242, or amino acids 249-293 of SEQ ID NO: 12, at most 75% amino acid identity with amino acids 10-54, amino acids 60-100, amino acids 105-144, amino acids 151-195, amino acids 200-242, or amino acids 249-293 of SEQ ID NO: 12, at most 80% amino acid identity with amino acids 10-54, amino acids 60-100, amino acids 105-144, amino acids 151-195, amino acids 200-242, or amino acids 249-293 of SEQ ID NO: 12, at most 85% amino acid identity with amino acids 10-54, amino acids 60-100, amino acids 105-144, amino acids 151-195, amino acids 200-242, or amino acids 249-293 of SEQ ID NO: 12, at most 90% amino acid identity with amino acids 10-54, amino acids 60-100, amino acids 105-144, amino acids 151-195, amino acids 200-242, or amino acids 249-293 of SEQ ID NO: 12 or at most 95% amino acid identity with amino acids 10-54, amino acids 60-100, amino acids 105-144, amino acids 151-195, amino acids 200-242, or amino acids 249-293 of SEQ ID NO: 12.

In other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 12. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 12. In yet other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 12. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 12. In still other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 12. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 12.

In other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 12. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 12. In yet other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 12. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 12. In still other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 12. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 12.

In another embodiment, a binding domain comprising a BoNT/A HA-33 β-trefoil domain comprises a 1β4/β5 hairpin turn of a β-trefoil domain of a BoNT/A HA-33, a 1β8/β9 hairpin turn of a β-trefoil domain of a BoNT/A HA-33, a 2β4/β5 hairpin turn of a β-trefoil domain of a BoNT/A HA-33 or a 2β8/β9 hairpin turn of a β-trefoil domain of a BoNT/A HA-33 of SEQ ID NO: 12. In another aspect of this embodiment, a binding domain comprising a BoNT/A HA-33 β-trefoil domain comprises amino acids 55-59, amino acids 101-104, amino acids 196-199, or amino acids 243-248 of SEQ ID NO: 12.

In other aspects of this embodiment, a binding domain comprising a BoNT/A HA-33 β-trefoil domain comprises a polypeptide having, e.g., at least 70% amino acid identity with amino acids 55-59, amino acids 101-104, amino acids 196-199, or amino acids 243-248 of SEQ ID NO: 12, at least 75% amino acid identity with amino acids 55-59, amino acids 101-104, amino acids 196-199, or amino acids 243-248 of SEQ ID NO: 12, at least 80% amino acid identity with amino acids 55-59, amino acids 101-104, amino acids 196-199, or amino acids 243-248 of SEQ ID NO: 12, at least 85% amino acid identity with amino acids 55-59, amino acids 101-104, amino acids 196-199, or amino acids 243-248 of SEQ ID NO: 12, at least 90% amino acid identity with amino acids 55-59, amino acids 101-104, amino acids 196-199, or amino acids 243-248 of SEQ ID NO: 12 or at least 95% amino acid identity with amino acids 55-59, amino acids 101-104, amino acids 196-199, or amino acids 243-248 of SEQ ID NO: 12. In yet other aspects of this embodiment, a binding domain comprising a BoNT/A HA-33 β-trefoil domain comprises a polypeptide having, e.g., at most 70% amino acid identity with amino acids 55-59, amino acids 101-104, amino acids 196-199, or amino acids 243-248 of SEQ ID NO: 12, at most 75% amino acid identity with amino acids 55-59, amino acids 101-104, amino acids 196-199, or amino acids 243-248 of SEQ ID NO: 12, at most 80% amino acid identity with amino acids 55-59, amino acids 101-104, amino acids 196-199, or amino acids 243-248 of SEQ ID NO: 12, at most 85% amino acid identity with amino acids 55-59, amino acids 101-104, amino acids 196-199, or amino acids 243-248 of SEQ ID NO: 12, at most 90% amino acid identity with amino acids 55-59, amino acids 101-104, amino acids 196-199, or amino acids 243-248 of SEQ ID NO: 12 or at most 95% amino acid identity with amino acids 55-59, amino acids 101-104, amino acids 196-199, or amino acids 243-248 of SEQ ID NO: 12.

In other aspects of this embodiment, a binding domain comprising a BoNT/A HA-33 β-trefoil domain comprises a polypeptide having, e.g., at most one, two, three or four non-contiguous amino acid substitutions relative to amino acids 55-59, amino acids 101-104, amino acids 196-199, or amino acids 243-248 of SEQ ID NO: 12. In other aspects of this embodiment, a binding domain comprising a BoNT/A HA-33 β-trefoil domain comprises a polypeptide having, e.g., at least one, two, three or four non-contiguous amino acid substitutions relative to amino acids 55-59, amino acids 101-104, amino acids 196-199, or amino acids 243-248 of SEQ ID NO: 12. In other aspects of this embodiment, a non-contiguous amino acid substitution of any amino acid from amino acids 55-59, amino acids 101-104, amino acids 196-199, or amino acids 243-248 of SEQ ID NO: 12 can be replaced with glycine. In other aspects of this embodiment, a non-contiguous amino acid substitution of any hydrophobic amino acid from amino acids 55-59, amino acids 101-104, amino acids 196-199, or amino acids 243-248 of SEQ ID NO: 12 can be replaced with phenylalanine. In yet other aspects of this embodiment, a β-trefoil domain with enhanced binding activity derived from a BoNT/A HA-33 comprises a polypeptide having, e.g., at most one, two, three or four non-contiguous amino acid deletions relative to amino acids 55-59, amino acids 101-104, amino acids 196-199, or amino acids 243-248 of SEQ ID NO: 12. In other aspects of this embodiment, a binding domain comprising a BoNT/A HA-33 β-trefoil domain comprises a polypeptide having, e.g., at least one, two, three or four non-contiguous amino acid deletions relative to amino acids 55-59, amino acids 101-104, amino acids 196-199, or amino acids 243-248 of SEQ ID NO: 12. In still other aspects of this embodiment, a binding domain comprising a BoNT/A HA-33 β-trefoil domain comprises a polypeptide having, e.g., at most one, two, three or four non-contiguous amino acid additions relative to amino acids 55-59, amino acids 101-104, amino acids 196-199, or amino acids 243-248 of SEQ ID NO: 12. In other aspects of this embodiment, a binding domain comprising a BoNT/A HA-33 β-trefoil domain comprises a polypeptide having, e.g., at least one, two, three or four non-contiguous amino acid additions relative to amino acids 55-59, amino acids 101-104, amino acids 196-199, or amino acids 243-248 of SEQ ID NO: 12.

In other aspects of this embodiment, a binding domain comprising a BoNT/A HA-33 β-trefoil domain comprises a polypeptide having, e.g., at most one, two, three or four contiguous amino acid substitutions relative to amino acids 55-59, amino acids 101-104, amino acids 196-199, or amino acids 243-248 of SEQ ID NO: 12. In other aspects of this embodiment, a binding domain comprising a BoNT/A HA-33 β-trefoil domain comprises a polypeptide having, e.g., at least one, two, three or four contiguous amino acid substitutions relative to amino acids 55-59, amino acids 101-104, amino acids 196-199, or amino acids 243-248 of SEQ ID NO: 12. In other aspects of this embodiment, contiguous amino acid substitutions of amino acids from amino acids 55-59, amino acids 101-104, amino acids 196-199, or amino acids 243-248 of SEQ ID NO: 12 can be replaced with glycine. In other aspects of this embodiment, contiguous amino acid substitutions of hydrophobic amino acids from amino acids 55-59, amino acids 101-104, amino acids 196-199, or amino acids 243-248 of SEQ ID NO: 12 can be replaced with phenylalanine. In yet other aspects of this embodiment, a binding domain comprising a BoNT/A HA-33 β-trefoil domain comprises a polypeptide having, e.g., at most one, two, three or four contiguous amino acid deletions relative to amino acids 55-59, amino acids 101-104, amino acids 196-199, or amino acids 243-248 of SEQ ID NO: 12. In other aspects of this embodiment, a binding domain comprising a BoNT/A HA-33 β-trefoil domain comprises a polypeptide having, e.g., at least one, two, three or four contiguous amino acid deletions relative to amino acids 55-59, amino acids 101-104, amino acids 196-199, or amino acids 243-248 of SEQ ID NO: 12. In still other aspects of this embodiment, a binding domain comprising a BoNT/A HA-33 β-trefoil domain comprises a polypeptide having, e.g., at most one, two, three or four contiguous amino acid additions relative to amino acids 55-59, amino acids 101-104, amino acids 196-199, or amino acids 243-248 of SEQ ID NO: 12. In other aspects of this embodiment, a binding domain comprising a BoNT/A HA-33 β-trefoil domain comprises a polypeptide having, e.g., at least one, two, three or four contiguous amino acid additions relative to amino acids 55-59, amino acids 101-104, amino acids 196-199, or amino acids 243-248 of SEQ ID NO: 12.

In another embodiment, a binding domain comprises a β-trefoil domain derived from a BoNT/A HA-33 of SEQ ID NO: 13. In another embodiment, a binding domain comprising a β-trefoil domain derived from a BoNT/A HA-33 comprises amino acids 10-144 or amino acids 151-293 of SEQ ID NO: 13. In another aspect of this embodiment, a binding domain comprising a β-trefoil domain derived from a BoNT/A HA-33 comprises a 1α-fold motif of a β-trefoil domain of a BoNT/A HA-33, a 1β-fold motif of a β-trefoil domain of a BoNT/A HA-33, a 1γ-fold motif of a β-trefoil domain of a BoNT/A HA-33, a 2α-fold motif of a β-trefoil domain of a BoNT/A HA-33, a 2β-fold motif of a β-trefoil domain of a BoNT/A HA-33, or a 2γ-fold motif of a β-trefoil domain of a BoNT/A HA-33 of SEQ ID NO: 13. In another aspect of this embodiment, a binding domain comprising a β-trefoil domain derived from a BoNT/A HA-33 comprises amino acids 10-54, amino acids 60-100, amino acids 105-144, amino acids 151-195, amino acids 200-242, or amino acids 249-293 of SEQ ID NO: 13.

In other aspects of this embodiment, a binding domain comprising a BoNT/A HA-33 β-trefoil domain comprises a polypeptide having, e.g., at least 70% amino acid identity with amino acids 10-54, amino acids 60-100, amino acids 105-144, amino acids 151-195, amino acids 200-242, or amino acids 249-293 of SEQ ID NO: 13, at least 75% amino acid identity with amino acids 10-54, amino acids 60-100, amino acids 105-144, amino acids 151-195, amino acids 200-242, or amino acids 249-293 of SEQ ID NO: 13, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-54, amino acids 60-100, amino acids 105-144, amino acids 151-195, amino acids 200-242, or amino acids 249-293 of SEQ ID NO: 13, at least 90% amino acid identity with amino acids 10-54, amino acids 60-100, amino acids 105-144, amino acids 151-195, amino acids 200-242, or amino acids 249-293 of SEQ ID NO: 13 or at least 95% amino acid identity with amino acids 10-54, amino acids 60-100, amino acids 105-144, amino acids 151-195, amino acids 200-242, or amino acids 249-293 of SEQ ID NO: 13. In yet other aspects of this embodiment, a binding domain comprising a BoNT/A HA-33 β-trefoil domain comprises a polypeptide having, e.g., at most 70% amino acid identity with amino acids 10-54, amino acids 60-100, amino acids 105-144, amino acids 151-195, amino acids 200-242, or amino acids 249-293 of SEQ ID NO: 13, at most 75% amino acid identity with amino acids 10-54, amino acids 60-100, amino acids 105-144, amino acids 151-195, amino acids 200-242, or amino acids 249-293 of SEQ ID NO: 13, at most 80% amino acid identity with amino acids 10-54, amino acids 60-100, amino acids 105-144, amino acids 151-195, amino acids 200-242, or amino acids 249-293 of SEQ ID NO: 13, at most 85% amino acid identity with amino acids 10-54, amino acids 60-100, amino acids 105-144, amino acids 151-195, amino acids 200-242, or amino acids 249-293 of SEQ ID NO: 13, at most 90% amino acid identity with amino acids 10-54, amino acids 60-100, amino acids 105-144, amino acids 151-195, amino acids 200-242, or amino acids 249-293 of SEQ ID NO: 13 or at most 95% amino acid identity with amino acids 10-54, amino acids 60-100, amino acids 105-144, amino acids 151-195, amino acids 200-242, or amino acids 249-293 of SEQ ID NO: 13.

In other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 13. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 13. In yet other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 13. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 13. In still other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 13. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 13.

In other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 13. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 13. In yet other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 13. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 13. In still other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 13. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 13.

In another embodiment, a binding domain comprising a BoNT/A HA-33 β-trefoil domain comprises a 1β4/β5 hairpin turn of a β-trefoil domain of a BoNT/A HA-33, a 1β8/β9 hairpin turn of a β-trefoil domain of a BoNT/A HA-33, a 2β4/β5 hairpin turn of a β-trefoil domain of a BoNT/A HA-33 or a 2β8/β9 hairpin turn of a β-trefoil domain of a BoNT/A HA-33 of SEQ ID NO: 13. In another aspect of this embodiment, a binding domain comprising a BoNT/A HA-33 β-trefoil domain comprises amino acids 55-59, amino acids 101-104, amino acids 196-199, or amino acids 243-248 of SEQ ID NO: 13.

In other aspects of this embodiment, a binding domain comprising a BoNT/A HA-33 β-trefoil domain comprises a polypeptide having, e.g., at least 70% amino acid identity with amino acids 55-59, amino acids 101-104, amino acids 196-199, or amino acids 243-248 of SEQ ID NO: 13, at least 75% amino acid identity with amino acids 55-59, amino acids 101-104, amino acids 196-199, or amino acids 243-248 of SEQ ID NO: 13, at least 80% amino acid identity with amino acids 55-59, amino acids 101-104, amino acids 196-199, or amino acids 243-248 of SEQ ID NO: 13, at least 85% amino acid identity with amino acids 55-59, amino acids 101-104, amino acids 196-199, or amino acids 243-248 of SEQ ID NO: 13, at least 90% amino acid identity with amino acids 55-59, amino acids 101-104, amino acids 196-199, or amino acids 243-248 of SEQ ID NO: 13 or at least 95% amino acid identity with amino acids 55-59, amino acids 101-104, amino acids 196-199, or amino acids 243-248 of SEQ ID NO: 13. In yet other aspects of this embodiment, a binding domain comprising a BoNT/A HA-33 β-trefoil domain comprises a polypeptide having, e.g., at most 70% amino acid identity with amino acids 55-59, amino acids 101-104, amino acids 196-199, or amino acids 243-248 of SEQ ID NO: 13, at most 75% amino acid identity with amino acids 55-59, amino acids 101-104, amino acids 196-199, or amino acids 243-248 of SEQ ID NO: 13, at most 80% amino acid identity with amino acids 55-59, amino acids 101-104, amino acids 196-199, or amino acids 243-248 of SEQ ID NO: 13, at most 85% amino acid identity with amino acids 55-59, amino acids 101-104, amino acids 196-199, or amino acids 243-248 of SEQ ID NO: 13, at most 90% amino acid identity with amino acids 55-59, amino acids 101-104, amino acids 196-199, or amino acids 243-248 of SEQ ID NO: 13 or at most 95% amino acid identity with amino acids 55-59, amino acids 101-104, amino acids 196-199, or amino acids 243-248 of SEQ ID NO: 13.

In other aspects of this embodiment, a binding domain comprising a BoNT/A HA-33 β-trefoil domain comprises a polypeptide having, e.g., at most one, two, three or four non-contiguous amino acid substitutions relative to amino acids 55-59, amino acids 101-104, amino acids 196-199, or amino acids 243-248 of SEQ ID NO: 13. In other aspects of this embodiment, a binding domain comprising a BoNT/A HA-33 β-trefoil domain comprises a polypeptide having, e.g., at least one, two, three or four non-contiguous amino acid substitutions relative to amino acids 55-59, amino acids 101-104, amino acids 196-199, or amino acids 243-248 of SEQ ID NO: 13. In other aspects of this embodiment, a non-contiguous amino acid substitution of any amino acid from amino acids 55-59, amino acids 101-104, amino acids 196-199, or amino acids 243-248 of SEQ ID NO: 13 can be replaced with glycine. In other aspects of this embodiment, a non-contiguous amino acid substitution of any hydrophobic amino acid from amino acids 55-59, amino acids 101-104, amino acids 196-199, or amino acids 243-248 of SEQ ID NO: 13 can be replaced with phenylalanine. In yet other aspects of this embodiment, a β-trefoil domain with enhanced binding activity derived from a BoNT/A HA-33 comprises a polypeptide having, e.g., at most one, two, three or four non-contiguous amino acid deletions relative to amino acids 55-59, amino acids 101-104, amino acids 196-199, or amino acids 243-248 of SEQ ID NO: 13. In other aspects of this embodiment, a binding domain comprising a BoNT/A HA-33 β-trefoil domain comprises a polypeptide having, e.g., at least one, two, three or four non-contiguous amino acid deletions relative to amino acids 55-59, amino acids 101-104, amino acids 196-199, or amino acids 243-248 of SEQ ID NO: 13. In still other aspects of this embodiment, a binding domain comprising a BoNT/A HA-33 β-trefoil domain comprises a polypeptide having, e.g., at most one, two, three or four non-contiguous amino acid additions relative to amino acids 55-59, amino acids 101-104, amino acids 196-199, or amino acids 243-248 of SEQ ID NO: 13. In other aspects of this embodiment, a binding domain comprising a BoNT/A HA-33 β-trefoil domain comprises a polypeptide having, e.g., at least one, two, three or four non-contiguous amino acid additions relative to amino acids 55-59, amino acids 101-104, amino acids 196-199, or amino acids 243-248 of SEQ ID NO: 13.

In other aspects of this embodiment, a binding domain comprising a BoNT/A HA-33 β-trefoil domain comprises a polypeptide having, e.g., at most one, two, three or four contiguous amino acid substitutions relative to amino acids 55-59, amino acids 101-104, amino acids 196-199, or amino acids 243-248 of SEQ ID NO: 13. In other aspects of this embodiment, a binding domain comprising a BoNT/A HA-33 β-trefoil domain comprises a polypeptide having, e.g., at least one, two, three or four contiguous amino acid substitutions relative to amino acids 55-59, amino acids 101-104, amino acids 196-199, or amino acids 243-248 of SEQ ID NO: 13. In other aspects of this embodiment, contiguous amino acid substitutions of amino acids from amino acids 55-59, amino acids 101-104, amino acids 196-199, or amino acids 243-248 of SEQ ID NO: 13 can be replaced with glycine. In other aspects of this embodiment, contiguous amino acid substitutions of hydrophobic amino acids from amino acids 55-59, amino acids 101-104, amino acids 196-199, or amino acids 243-248 of SEQ ID NO: 13 can be replaced with phenylalanine. In yet other aspects of this embodiment, a binding domain comprising a BoNT/A HA-33 β-trefoil domain comprises a polypeptide having, e.g., at most one, two, three or four contiguous amino acid deletions relative to amino acids 55-59, amino acids 101-104, amino acids 196-199, or amino acids 243-248 of SEQ ID NO: 13. In other aspects of this embodiment, a binding domain comprising a BoNT/A HA-33 β-trefoil domain comprises a polypeptide having, e.g., at least one, two, three or four contiguous amino acid deletions relative to amino acids 55-59, amino acids 101-104, amino acids 196-199, or amino acids 243-248 of SEQ ID NO: 13. In still other aspects of this embodiment, a binding domain comprising a BoNT/A HA-33 β-trefoil domain comprises a polypeptide having, e.g., at most one, two, three or four contiguous amino acid additions relative to amino acids 55-59, amino acids 101-104, amino acids 196-199, or amino acids 243-248 of SEQ ID NO: 13. In other aspects of this embodiment, a binding domain comprising a BoNT/A HA-33 β-trefoil domain comprises a polypeptide having, e.g., at least one, two, three or four contiguous amino acid additions relative to amino acids 55-59, amino acids 101-104, amino acids 196-199, or amino acids 243-248 of SEQ ID NO: 13.

In another embodiment, a binding domain comprises a β-trefoil domain derived from a BoNT/A HA-33 of SEQ ID NO: 14. In another embodiment, a binding domain comprising a β-trefoil domain derived from a BoNT/A HA-33 comprises amino acids 10-146 or amino acids 153-294 of SEQ ID NO: 14. In another aspect of this embodiment, a binding domain comprising a β-trefoil domain derived from a BoNT/A HA-33 comprises a 1α-fold motif of a β-trefoil domain of a BoNT/A HA-33, a 1β-fold motif of a β-trefoil domain of a BoNT/A HA-33, a 1γ-fold motif of a β-trefoil domain of a BoNT/A HA-33, a 2α-fold motif of a β-trefoil domain of a BoNT/A HA-33, a 2β-fold motif of a β-trefoil domain of a BoNT/A HA-33, or a 2γ-fold motif of a β-trefoil domain of a BoNT/A HA-33 of SEQ ID NO: 14. In another aspect of this embodiment, a binding domain comprising a β-trefoil domain derived from a BoNT/A HA-33 comprises amino acids 10-56, amino acids 62-102, amino acids 107-146, amino acids 153-197, amino acids 202-243, or amino acids 250-294 of SEQ ID NO: 14.

In other aspects of this embodiment, a binding domain comprising a BoNT/A HA-33 β-trefoil domain comprises a polypeptide having, e.g., at least 70% amino acid identity with amino acids 10-56, amino acids 62-102, amino acids 107-146, amino acids 153-197, amino acids 202-243, or amino acids 250-294 of SEQ ID NO: 14, at least 75% amino acid identity with amino acids 10-56, amino acids 62-102, amino acids 107-146, amino acids 153-197, amino acids 202-243, or amino acids 250-294 of SEQ ID NO: 14, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-56, amino acids 62-102, amino acids 107-146, amino acids 153-197, amino acids 202-243, or amino acids 250-294 of SEQ ID NO: 14, at least 90% amino acid identity with amino acids 10-56, amino acids 62-102, amino acids 107-146, amino acids 153-197, amino acids 202-243, or amino acids 250-294 of SEQ ID NO: 14 or at least 95% amino acid identity with amino acids 10-56, amino acids 62-102, amino acids 107-146, amino acids 153-197, amino acids 202-243, or amino acids 250-294 of SEQ ID NO: 14. In yet other aspects of this embodiment, a binding domain comprising a BoNT/A HA-33 β-trefoil domain comprises a polypeptide having, e.g., at most 70% amino acid identity with amino acids 10-56, amino acids 62-102, amino acids 107-146, amino acids 153-197, amino acids 202-243, or amino acids 250-294 of SEQ ID NO: 14, at most 75% amino acid identity with amino acids 10-56, amino acids 62-102, amino acids 107-146, amino acids 153-197, amino acids 202-243, or amino acids 250-294 of SEQ ID NO: 14, at most 80% amino acid identity with amino acids 10-56, amino acids 62-102, amino acids 107-146, amino acids 153-197, amino acids 202-243, or amino acids 250-294 of SEQ ID NO: 14, at most 85% amino acid identity with amino acids 10-56, amino acids 62-102, amino acids 107-146, amino acids 153-197, amino acids 202-243, or amino acids 250-294 of SEQ ID NO: 14, at most 90% amino acid identity with amino acids 10-56, amino acids 62-102, amino acids 107-146, amino acids 153-197, amino acids 202-243, or amino acids 250-294 of SEQ ID NO: 14 or at most 95% amino acid identity with amino acids 10-56, amino acids 62-102, amino acids 107-146, amino acids 153-197, amino acids 202-243, or amino acids 250-294 of SEQ ID NO: 14.

In other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid substitutions relative to amino acids 10-56, amino acids 62-102, amino acids 107-146, amino acids 153-197, amino acids 202-243, or amino acids 250-294 of SEQ ID NO: 14. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid substitutions relative to amino acids 10-56, amino acids 62-102, amino acids 107-146, amino acids 153-197, amino acids 202-243, or amino acids 250-294 of SEQ ID NO: 14. In yet other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid deletions relative to amino acids 10-56, amino acids 62-102, amino acids 107-146, amino acids 153-197, amino acids 202-243, or amino acids 250-294 of SEQ ID NO: 14. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid deletions relative to amino acids 10-56, amino acids 62-102, amino acids 107-146, amino acids 153-197, amino acids 202-243, or amino acids 250-294 of SEQ ID NO: 14. In still other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid additions relative to amino acids 10-56, amino acids 62-102, amino acids 107-146, amino acids 153-197, amino acids 202-243, or amino acids 250-294 of SEQ ID NO: 14. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid additions relative to amino acids 10-56, amino acids 62-102, amino acids 107-146, amino acids 153-197, amino acids 202-243, or amino acids 250-294 of SEQ ID NO: 14.

In other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid substitutions relative to amino acids 10-56, amino acids 62-102, amino acids 107-146, amino acids 153-197, amino acids 202-243, or amino acids 250-294 of SEQ ID NO: 14. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid substitutions relative to amino acids 10-56, amino acids 62-102, amino acids 107-146, amino acids 153-197, amino acids 202-243, or amino acids 250-294 of SEQ ID NO: 14. In yet other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid deletions relative to amino acids 10-56, amino acids 62-102, amino acids 107-146, amino acids 153-197, amino acids 202-243, or amino acids 250-294 of SEQ ID NO: 14. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid deletions relative to amino acids 10-56, amino acids 62-102, amino acids 107-146, amino acids 153-197, amino acids 202-243, or amino acids 250-294 of SEQ ID NO: 14. In still other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid additions relative to amino acids 10-56, amino acids 62-102, amino acids 107-146, amino acids 153-197, amino acids 202-243, or amino acids 250-294 of SEQ ID NO: 14. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid additions relative to amino acids 10-56, amino acids 62-102, amino acids 107-146, amino acids 153-197, amino acids 202-243, or amino acids 250-294 of SEQ ID NO: 14.

In another embodiment, a binding domain comprising a BoNT/A HA-33 β-trefoil domain comprises a 1β4/β5 hairpin turn of a β-trefoil domain of a BoNT/A HA-33, a 1β8/β9 hairpin turn of a β-trefoil domain of a BoNT/A HA-33, a 2β4/β5 hairpin turn of a β-trefoil domain of a BoNT/A HA-33 or a 2β8/β9 hairpin turn of a β-trefoil domain of a BoNT/A HA-33 of SEQ ID NO: 14. In another aspect of this embodiment, a binding domain comprising a BoNT/A HA-33 β-trefoil domain comprises amino acids 57-61, amino acids 103-106, amino acids 198-201, or amino acids 244-249 of SEQ ID NO: 14.

In other aspects of this embodiment, a binding domain comprising a BoNT/A HA-33 β-trefoil domain comprises a polypeptide having, e.g., at least 70% amino acid identity with amino acids 57-61, amino acids 103-106, amino acids 198-201, or amino acids 244-249 of SEQ ID NO: 14, at least 75% amino acid identity with amino acids 57-61, amino acids 103-106, amino acids 198-201, or amino acids 244-249 of SEQ ID NO: 14, at least 80% amino acid identity with amino acids 57-61, amino acids 103-106, amino acids 198-201, or amino acids 244-249 of SEQ ID NO: 14, at least 85% amino acid identity with amino acids 57-61, amino acids 103-106, amino acids 198-201, or amino acids 244-249 of SEQ ID NO: 14, at least 90% amino acid identity with amino acids 57-61, amino acids 103-106, amino acids 198-201, or amino acids 244-249 of SEQ ID NO: 14 or at least 95% amino acid identity with amino acids 57-61, amino acids 103-106, amino acids 198-201, or amino acids 244-249 of SEQ ID NO: 14. In yet other aspects of this embodiment, a binding domain comprising a BoNT/A HA-33 β-trefoil domain comprises a polypeptide having, e.g., at most 70% amino acid identity with amino acids 57-61, amino acids 103-106, amino acids 198-201, or amino acids 244-249 of SEQ ID NO: 14, at most 75% amino acid identity with amino acids 57-61, amino acids 103-106, amino acids 198-201, or amino acids 244-249 of SEQ ID NO: 14, at most 80% amino acid identity with amino acids 57-61, amino acids 103-106, amino acids 198-201, or amino acids 244-249 of SEQ ID NO: 14, at most 85% amino acid identity with amino acids 57-61, amino acids 103-106, amino acids 198-201, or amino acids 244-249 of SEQ ID NO: 14, at most 90% amino acid identity with amino acids 57-61, amino acids 103-106, amino acids 198-201, or amino acids 244-249 of SEQ ID NO: 14 or at most 95% amino acid identity with amino acids 57-61, amino acids 103-106, amino acids 198-201, or amino acids 244-249 of SEQ ID NO: 14.

In other aspects of this embodiment, a binding domain comprising a BoNT/A HA-33 β-trefoil domain comprises a polypeptide having, e.g., at most one, two, three or four non-contiguous amino acid substitutions relative to amino acids 57-61, amino acids 103-106, amino acids 198-201, or amino acids 244-249 of SEQ ID NO: 14. In other aspects of this embodiment, a binding domain comprising a BoNT/A HA-33 β-trefoil domain comprises a polypeptide having, e.g., at least one, two, three or four non-contiguous amino acid substitutions relative to amino acids 57-61, amino acids 103-106, amino acids 198-201, or amino acids 244-249 of SEQ ID NO: 14. In other aspects of this embodiment, a non-contiguous amino acid substitution of any amino acid from amino acids 57-61, amino acids 103-106, amino acids 198-201, or amino acids 244-249 of SEQ ID NO: 14 can be replaced with glycine. In other aspects of this embodiment, a non-contiguous amino acid substitution of any hydrophobic amino acid from amino acids 57-61, amino acids 103-106, amino acids 198-201, or amino acids 244-249 of SEQ ID NO: 14 can be replaced with phenylalanine. In yet other aspects of this embodiment, a β-trefoil domain with enhanced binding activity derived from a BoNT/A HA-33 comprises a polypeptide having, e.g., at most one, two, three or four non-contiguous amino acid deletions relative to amino acids 57-61, amino acids 103-106, amino acids 198-201, or amino acids 244-249 of SEQ ID NO: 14. In other aspects of this embodiment, a binding domain comprising a BoNT/A HA-33 β-trefoil domain comprises a polypeptide having, e.g., at least one, two, three or four non-contiguous amino acid deletions relative to amino acids 57-61, amino acids 103-106, amino acids 198-201, or amino acids 244-249 of SEQ ID NO: 14. In still other aspects of this embodiment, a binding domain comprising a BoNT/A HA-33 β-trefoil domain comprises a polypeptide having, e.g., at most one, two, three or four non-contiguous amino acid additions relative to amino acids 57-61, amino acids 103-106, amino acids 198-201, or amino acids 244-249 of SEQ ID NO: 14. In other aspects of this embodiment, a binding domain comprising a BoNT/A HA-33 β-trefoil domain comprises a polypeptide having, e.g., at least one, two, three or four non-contiguous amino acid additions relative to amino acids 57-61, amino acids 103-106, amino acids 198-201, or amino acids 244-249 of SEQ ID NO: 14.

In other aspects of this embodiment, a binding domain comprising a BoNT/A HA-33 β-trefoil domain comprises a polypeptide having, e.g., at most one, two, three or four contiguous amino acid substitutions relative to amino acids 57-61, amino acids 103-106, amino acids 198-201, or amino acids 244-249 of SEQ ID NO: 14. In other aspects of this embodiment, a binding domain comprising a BoNT/A HA-33 β-trefoil domain comprises a polypeptide having, e.g., at least one, two, three or four contiguous amino acid substitutions relative to amino acids 57-61, amino acids 103-106, amino acids 198-201, or amino acids 244-249 of SEQ ID NO: 14. In other aspects of this embodiment, contiguous amino acid substitutions of amino acids from amino acids 57-61, amino acids 103-106, amino acids 198-201, or amino acids 244-249 of SEQ ID NO: 14 can be replaced with glycine. In other aspects of this embodiment, contiguous amino acid substitutions of hydrophobic amino acids from amino acids 57-61, amino acids 103-106, amino acids 198-201, or amino acids 244-249 of SEQ ID NO: 14 can be replaced with phenylalanine. In yet other aspects of this embodiment, a binding domain comprising a BoNT/A HA-33 β-trefoil domain comprises a polypeptide having, e.g., at most one, two, three or four contiguous amino acid deletions relative to amino acids 57-61, amino acids 103-106, amino acids 198-201, or amino acids 244-249 of SEQ ID NO: 14. In other aspects of this embodiment, a binding domain comprising a BoNT/A HA-33 β-trefoil domain comprises a polypeptide having, e.g., at least one, two, three or four contiguous amino acid deletions relative to amino acids 57-61, amino acids 103-106, amino acids 198-201, or amino acids 244-249 of SEQ ID NO: 14. In still other aspects of this embodiment, a binding domain comprising a BoNT/A HA-33 β-trefoil domain comprises a polypeptide having, e.g., at most one, two, three or four contiguous amino acid additions relative to amino acids 57-61, amino acids 103-106, amino acids 198-201, or amino acids 244-249 of SEQ ID NO: 14. In other aspects of this embodiment, a binding domain comprising a BoNT/A HA-33 β-trefoil domain comprises a polypeptide having, e.g., at least one, two, three or four contiguous amino acid additions relative to amino acids 57-61, amino acids 103-106, amino acids 198-201, or amino acids 244-249 of SEQ ID NO: 14.

In another embodiment, a binding domain comprises a β-trefoil domain derived from a BoNT/A HA-33 of SEQ ID NO: 15. In another embodiment, a binding domain comprising a β-trefoil domain derived from a BoNT/A HA-33 comprises amino acids 10-144 or amino acids 151-279 of SEQ ID NO: 15. In another aspect of this embodiment, a binding domain comprising a β-trefoil domain derived from a BoNT/A HA-33 comprises a 1α-fold motif of a β-trefoil domain of a BoNT/A HA-33, a 1β-fold motif of a β-trefoil domain of a BoNT/A HA-33, a 1γ-fold motif of a β-trefoil domain of a BoNT/A HA-33, a 2α-fold motif of a β-trefoil domain of a BoNT/A HA-33, a 2β-fold motif of a β-trefoil domain of a BoNT/A HA-33, or a 2γ-fold motif of a β-trefoil domain of a BoNT/A HA-33 of SEQ ID NO: 15. In another aspect of this embodiment, a binding domain comprising a β-trefoil domain derived from a BoNT/A HA-33 comprises amino acids 10-54, amino acids 60-100, amino acids 105-144, amino acids 151-195, amino acids 200-242, or amino acids 249-293 of SEQ ID NO: 15.

In other aspects of this embodiment, a binding domain comprising a BoNT/A HA-33 β-trefoil domain comprises a polypeptide having, e.g., at least 70% amino acid identity with amino acids 10-54, amino acids 60-100, amino acids 105-144, amino acids 151-195, amino acids 200-242, or amino acids 249-293 of SEQ ID NO: 15, at least 75% amino acid identity with amino acids 10-54, amino acids 60-100, amino acids 105-144, amino acids 151-195, amino acids 200-242, or amino acids 249-293 of SEQ ID NO: 15, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-54, amino acids 60-100, amino acids 105-144, amino acids 151-195, amino acids 200-242, or amino acids 249-293 of SEQ ID NO: 15, at least 90% amino acid identity with amino acids 10-54, amino acids 60-100, amino acids 105-144, amino acids 151-195, amino acids 200-242, or amino acids 249-293 of SEQ ID NO: 15 or at least 95% amino acid identity with amino acids 10-54, amino acids 60-100, amino acids 105-144, amino acids 151-195, amino acids 200-242, or amino acids 249-293 of SEQ ID NO: 15. In yet other aspects of this embodiment, a binding domain comprising a BoNT/A HA-33 β-trefoil domain comprises a polypeptide having, e.g., at most 70% amino acid identity with amino acids 10-54, amino acids 60-100, amino acids 105-144, amino acids 151-195, amino acids 200-242, or amino acids 249-293 of SEQ ID NO: 15, at most 75% amino acid identity with amino acids 10-54, amino acids 60-100, amino acids 105-144, amino acids 151-195, amino acids 200-242, or amino acids 249-293 of SEQ ID NO: 15, at most 80% amino acid identity with amino acids 10-54, amino acids 60-100, amino acids 105-144, amino acids 151-195, amino acids 200-242, or amino acids 249-293 of SEQ ID NO: 15, at most 85% amino acid identity with amino acids 10-54, amino acids 60-100, amino acids 105-144, amino acids 151-195, amino acids 200-242, or amino acids 249-293 of SEQ ID NO: 15, at most 90% amino acid identity with amino acids 10-54, amino acids 60-100, amino acids 105-144, amino acids 151-195, amino acids 200-242, or amino acids 249-293 of SEQ ID NO: 15 or at most 95% amino acid identity with amino acids 10-54, amino acids 60-100, amino acids 105-144, amino acids 151-195, amino acids 200-242, or amino acids 249-293 of SEQ ID NO: 15.

In other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 15. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 15. In yet other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 15. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 15. In still other aspects of this embodiment, a binding domain comprising a BoNT/A HA-33 β-trefoil domain comprises a polypeptide having, e.g., at most one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 15. In other aspects of this embodiment, a binding domain comprising a BoNT/A HA-33 β-trefoil domain comprises a polypeptide having, e.g., at least one, two, three, four, five, six, seven, eight, nine, 10 or 20 non-contiguous amino acid additions relative to amino acids 10-54, amino acids 60-100, amino acids 105-

144, amino acids 151-195, amino acids 200-242, or amino acids 249-293 of SEQ ID NO: 15.

In other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 15. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 15. In yet other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 15. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 15. In still other aspects of this embodiment, a binding domain comprising a BoNT/A HA-33 β-trefoil domain comprises a polypeptide having, e.g., at most one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 15. In other aspects of this embodiment, a binding domain comprising a BoNT/A HA-33 β-trefoil domain comprises a polypeptide having, e.g., at least one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 15.

In another embodiment, a binding domain comprising a BoNT/A HA-33 β-trefoil domain comprises a 1β4/β5 hairpin turn of a β-trefoil domain of a BoNT/A HA-33, a 1β8/β9 hairpin turn of a β-trefoil domain of a BoNT/A HA-33, a 2β4/β5 hairpin turn of a β-trefoil domain of a BoNT/A HA-33 or a 2β8/β9 hairpin turn of a β-trefoil domain of a BoNT/A HA-33 of SEQ ID NO: 15. In another aspect of this embodiment, a binding domain comprising a BoNT/A HA-33 β-trefoil domain comprises amino acids 55-59, amino acids 101-104, amino acids 196-199, or amino acids 243-248 of SEQ ID NO: 15.

In other aspects of this embodiment, a binding domain comprising a BoNT/A HA-33 β-trefoil domain comprises a polypeptide having, e.g., at least 70% amino acid identity with amino acids 55-59, amino acids 101-104, amino acids 196-199, or amino acids 243-248 of SEQ ID NO: 15, at least 75% amino acid identity with amino acids 55-59, amino acids 101-104, amino acids 196-199, or amino acids 243-248 of SEQ ID NO: 15, at least 80% amino acid identity with amino acids 55-59, amino acids 101-104, amino acids 196-199, or amino acids 243-248 of SEQ ID NO: 15, at least 85% amino acid identity with amino acids 55-59, amino acids 101-104, amino acids 196-199, or amino acids 243-248 of SEQ ID NO: 15, at least 90% amino acid identity with amino acids 55-59, amino acids 101-104, amino acids 196-199, or amino acids 243-248 of SEQ ID NO: 15 or at least 95% amino acid identity with amino acids 55-59, amino acids 101-104, amino acids 196-199, or amino acids 243-248 of SEQ ID NO: 15. In yet other aspects of this embodiment, a binding domain comprising a BoNT/A HA-33 β-trefoil domain comprises a polypeptide having, e.g., at most 70% amino acid identity with amino acids 55-59, amino acids 101-104, amino acids 196-199, or amino acids 243-248 of SEQ ID NO: 15, at most 75% amino acid identity with amino acids 55-59, amino acids 101-104, amino acids 196-199, or amino acids 243-248 of SEQ ID NO: 15, at most 80% amino acid identity with amino acids 55-59, amino acids 101-104, amino acids 196-199, or amino acids 243-248 of SEQ ID NO: 15, at most 85% amino acid identity with amino acids 55-59, amino acids 101-104, amino acids 196-199, or amino acids 243-248 of SEQ ID NO: 15, at most 90% amino acid identity with amino acids 55-59, amino acids 101-104, amino acids 196-199, or amino acids 243-248 of SEQ ID NO: 15 or at most 95% amino acid identity with amino acids 55-59, amino acids 101-104, amino acids 196-199, or amino acids 243-248 of SEQ ID NO: 15.

In other aspects of this embodiment, a binding domain comprising a BoNT/A HA-33 β-trefoil domain comprises a polypeptide having, e.g., at most one, two, three or four non-contiguous amino acid substitutions relative to amino acids 55-59, amino acids 101-104, amino acids 196-199, or amino acids 243-248 of SEQ ID NO: 15. In other aspects of this embodiment, a binding domain comprising a BoNT/A HA-33 β-trefoil domain comprises a polypeptide having, e.g., at least one, two, three or four non-contiguous amino acid substitutions relative to amino acids 55-59, amino acids 101-104, amino acids 196-199, or amino acids 243-248 of SEQ ID NO: 15. In other aspects of this embodiment, a non-contiguous amino acid substitution of any amino acid from amino acids 55-59, amino acids 101-104, amino acids 196-199, or amino acids 243-248 of SEQ ID NO: 15 can be replaced with glycine. In other aspects of this embodiment, a non-contiguous amino acid substitution of any hydrophobic amino acid from amino acids 55-59, amino acids 101-104, amino acids 196-199, or amino acids 243-248 of SEQ ID NO: 15 can be replaced with phenylalanine. In yet other aspects of this embodiment, a β-trefoil domain with enhanced binding activity derived from a BoNT/A HA-33 comprises a polypeptide having, e.g., at most one, two, three or four non-contiguous amino acid deletions relative to amino acids 55-59, amino acids 101-104, amino acids 196-199, or amino acids 243-248 of SEQ ID NO: 15. In other aspects of this embodiment, a binding domain comprising a BoNT/A HA-33 β-trefoil domain comprises a polypeptide having, e.g., at least one, two, three or four non-contiguous amino acid deletions relative to amino acids 55-59, amino acids 101-104, amino acids 196-199, or amino acids 243-248 of SEQ ID NO: 15. In still other aspects of this embodiment, a binding domain comprising a BoNT/A HA-33 β-trefoil domain comprises a polypeptide having, e.g., at most one, two, three or four non-contiguous amino acid additions relative to amino acids 55-59, amino acids 101-104, amino acids 196-199, or amino acids 243-248 of SEQ ID NO: 15. In other aspects of this embodiment, a binding domain comprising a BoNT/A HA-33 β-trefoil domain comprises a polypeptide having, e.g., at least one, two, three or four non-contiguous amino acid additions relative to amino acids 55-59, amino acids 101-104, amino acids 196-199, or amino acids 243-248 of SEQ ID NO: 15.

In other aspects of this embodiment, a binding domain comprising a BoNT/A HA-33 β-trefoil domain comprises a polypeptide having, e.g., at most one, two, three or four contiguous amino acid substitutions relative to amino acids 55-59, amino acids 101-104, amino acids 196-199, or amino acids 243-248 of SEQ ID NO: 15. In other aspects of this embodiment, a binding domain comprising a BoNT/A HA-33 β-trefoil domain comprises a polypeptide having, e.g., at least one, two, three or four contiguous amino acid substitutions relative to amino acids 55-59, amino acids 101-104, amino acids 196-199, or amino acids 243-248 of SEQ ID NO: 15. In other aspects of this embodiment, contiguous amino acid substitutions of amino acids from amino acids 55-59, amino acids 101-104, amino acids 196-199, or amino acids 243-248 of SEQ ID NO: 15 can be replaced with glycine. In other aspects of this embodiment, contiguous amino acid substitutions of hydrophobic amino acids from amino acids 55-59, amino acids 101-104, amino acids 196-199, or amino acids 243-248 of SEQ ID NO: 15 can be replaced with phenylalanine. In yet other aspects of this embodiment, a binding domain comprising a BoNT/A HA-33 β-trefoil domain comprises a polypeptide having, e.g., at most one, two, three or four contiguous amino acid deletions relative to amino acids 55-59, amino acids 101-104, amino acids 196-199, or amino acids 243-248 of SEQ ID NO: 15. In other aspects of this embodiment, a binding domain comprising a BoNT/A HA-33 β-trefoil domain comprises a polypeptide having, e.g., at least one, two, three or four contiguous amino acid deletions relative to amino acids 55-59, amino acids 101-104, amino acids 196-199, or amino acids 243-248 of SEQ ID NO: 15. In still other aspects of this embodiment, a binding domain comprising a BoNT/A HA-33 β-trefoil domain comprises a polypeptide having, e.g., at most one, two, three or four contiguous amino acid additions relative to amino acids 55-59, amino acids 101-104, amino acids 196-199, or amino acids 243-248 of SEQ ID NO: 15. In other aspects of this embodiment, a binding domain comprising a BoNT/A HA-33 β-trefoil domain comprises a polypeptide having, e.g., at least one, two, three or four contiguous amino acid additions relative to amino acids 55-59, amino acids 101-104, amino acids 196-199, or amino acids 243-248 of SEQ ID NO: 15.

In another embodiment, a binding domain comprises a β-trefoil domain derived from a BoNT/B HA-33 of SEQ ID NO: 16. In another embodiment, a binding domain comprising a β-trefoil domain derived from a BoNT/B HA-33 comprises amino acids 10-144 or amino acids 151-292 of SEQ ID NO: 16. In another aspect of this embodiment, a binding domain comprising a β-trefoil domain derived from a BoNT/B HA-33 comprises a 1α-fold motif of a β-trefoil domain of a BoNT/B HA-33, a 1β-fold motif of a β-trefoil domain of a BoNT/B HA-33, a 1γ-fold motif of a β-trefoil domain of a BoNT/B HA-33, a 2α-fold motif of a β-trefoil domain of a BoNT/B HA-33, a 2β-fold motif of a β-trefoil domain of a BoNT/B HA-33, or a 2γ-fold motif of a β-trefoil domain of a BoNT/B HA-33 of SEQ ID NO: 16. In another aspect of this embodiment, a binding domain comprising a β-trefoil domain derived from a BoNT/B HA-33 comprises amino acids 10-54, amino acids 60-100, amino acids 105-144, amino acids 151-195, amino acids 200-241, or amino acids 248-292 of SEQ ID NO: 16.

In other aspects of this embodiment, a binding domain comprising a BoNT/B HA-33 β-trefoil domain comprises a polypeptide having, e.g., at least 70% amino acid identity with amino acids 10-54, amino acids 60-100, amino acids 105-144, amino acids 151-195, amino acids 200-241, or amino acids 248-292 of SEQ ID NO: 16, at least 75% amino acid identity with amino acids 10-54, amino acids 60-100, amino acids 105-144, amino acids 151-195, amino acids 200-241, or amino acids 248-292 of SEQ ID NO: 16, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-54, amino acids 60-100, amino acids 105-144, amino acids 151-195, amino acids 200-241, or amino acids 248-292 of SEQ ID NO: 16, at least 90% amino acid identity with amino acids 10-54, amino acids 60-100, amino acids 105-144, amino acids 151-195, amino acids 200-241, or amino acids 248-292 of SEQ ID NO: 16 or at least 95% amino acid identity with amino acids 10-54, amino acids 60-100, amino acids 105-144, amino acids 151-195, amino acids 200-241, or amino acids 248-292 of SEQ ID NO: 16. In yet other aspects of this embodiment, a binding domain comprising a BoNT/B HA-33 β-trefoil domain comprises a polypeptide having, e.g., at most 70% amino acid identity with amino acids 10-54, amino acids 60-100, amino acids 105-144, amino acids 151-195, amino acids 200-241, or amino acids 248-292 of SEQ ID NO: 16, at most 75% amino acid identity with amino acids 10-54, amino acids 60-100, amino acids 105-144, amino acids 151-195, amino acids 200-241, or amino acids 248-292 of SEQ ID NO: 16, at most 80% amino acid identity with amino acids 10-54, amino acids 60-100, amino acids 105-144, amino acids 151-195, amino acids 200-241, or amino acids 248-292 of SEQ ID NO: 16, at most 85% amino acid identity with amino acids 10-54, amino acids 60-100, amino acids 105-144, amino acids 151-195, amino acids 200-241, or amino acids 248-292 of SEQ ID NO: 16, at most 90% amino acid identity with amino acids 10-54, amino acids 60-100, amino acids 105-144, amino acids 151-195, amino acids 200-241, or amino acids 248-292 of SEQ ID NO: 16 or at most 95% amino acid identity with amino acids 10-54, amino acids 60-100, amino acids 105-144, amino acids 151-195, amino acids 200-241, or amino acids 248-292 of SEQ ID NO: 16.

In other aspects of this embodiment, a binding domain comprising a BoNT/B HA-33 β-trefoil domain comprises a polypeptide having, e.g., at most one, two, three, four, five, six, seven, eight, nine, 10 or 20 non-contiguous amino acid substitutions relative to amino acids 10-54, amino acids 60-100, amino acids 105-144, amino acids 151-195, amino acids 200-241, or amino acids 248-292 of SEQ ID NO: 16. In other aspects of this embodiment, a binding domain comprising a BoNT/B HA-33 β-trefoil domain comprises a polypeptide having, e.g., at least one, two, three, four, five, six, seven, eight, nine, 10 or 20 non-contiguous amino acid substitutions relative to amino acids 10-54, amino acids 60-100, amino acids 105-144, amino acids 151-195, amino acids 200-241, or amino acids 248-292 of SEQ ID NO: 16. In yet other aspects of this embodiment, a binding domain comprising a BoNT/B HA-33 β-trefoil domain comprises a polypeptide having, e.g., at most one, two, three, four, five, six, seven, eight, nine, 10 or 20 non-contiguous amino acid deletions relative to amino acids 10-54, amino acids 60-100, amino acids 105-144, amino acids 151-195, amino acids 200-241, or amino acids 248-292 of SEQ ID NO: 16. In other aspects of this embodiment, a binding domain comprising a BoNT/B HA-33 β-trefoil domain comprises a polypeptide having, e.g., at least one, two, three, four, five, six, seven, eight, nine, 10 or 20 non-contiguous amino acid deletions relative to amino acids 10-54, amino acids 60-100, amino acids 105-144, amino acids 151-195, amino acids 200-241, or amino acids 248-292 of SEQ ID NO: 16. In still other aspects of this embodiment, a binding domain comprising a BoNT/B HA-33 β-trefoil domain comprises a polypeptide having, e.g., at most one, two, three, four, five, six, seven, eight, nine, 10 or 20 non-contiguous amino acid additions relative to amino acids 10-54, amino acids 60-100, amino acids 105-144, amino acids 151-195, amino acids 200-241, or amino acids 248-292 of SEQ ID NO: 16. In other aspects of this embodiment, a binding domain comprising a BoNT/B HA-33 β-trefoil domain comprises a polypeptide having, e.g., at least one, two, three, four, five, six, seven, eight, nine, 10 or 20 non-contiguous amino acid additions relative to amino acids 10-54, amino acids 60-100, amino acids 105-144, amino acids 151-195, amino acids 200-241, or amino acids 248-292 of SEQ ID NO: 16.

In other aspects of this embodiment, a binding domain comprising a BoNT/B HA-33 β-trefoil domain comprises a polypeptide having, e.g., at most one, two, three, four, five, six, seven, eight, nine, 10 or 20 contiguous amino acid substitutions relative to amino acids 10-54, amino acids 60-100, amino acids 105-144, amino acids 151-195, amino acids 200-241, or amino acids 248-292 of SEQ ID NO: 16. In other aspects of this embodiment, a binding domain comprising a BoNT/B HA-33 β-trefoil domain comprises a polypeptide having, e.g., at least one, two, three, four, five, six, seven, eight, nine, 10 or 20 contiguous amino acid substitutions relative to amino acids 10-54, amino acids 60-100, amino acids 105-144, amino acids 151-195, amino acids 200-241, or amino acids 248-292 of SEQ ID NO: 16. In yet other aspects of this embodiment, a binding domain comprising a BoNT/B HA-33 β-trefoil domain comprises a polypeptide having, e.g., at most one, two, three, four, five, six, seven, eight, nine, 10 or 20 contiguous amino acid deletions relative to amino acids 10-54, amino acids 60-100, amino acids 105-144, amino acids 151-195, amino acids 200-241, or amino acids 248-292 of SEQ ID NO: 16. In other aspects of this embodiment, a binding domain comprising a BoNT/B HA-33 β-trefoil domain comprises a polypeptide having, e.g., at least one, two, three, four, five, six, seven, eight, nine, 10 or 20 contiguous amino acid deletions relative to amino acids 10-54, amino acids 60-100, amino acids 105-144, amino acids 151-195, amino acids 200-241, or amino acids 248-292 of SEQ ID NO: 16. In still other aspects of this embodiment, a binding domain comprising a BoNT/B HA-33 β-trefoil domain comprises a polypeptide having, e.g., at most one, two, three, four, five, six, seven, eight, nine, 10 or 20 contiguous amino acid additions relative to amino acids 10-54, amino acids 60-100, amino acids 105-144, amino acids 151-195, amino acids 200-241, or amino acids 248-292 of SEQ ID NO: 16. In other aspects of this embodiment, a binding domain comprising a BoNT/B HA-33 β-trefoil domain comprises a polypeptide having, e.g., at least one, two, three, four, five, six, seven, eight, nine, 10 or 20 contiguous amino acid additions relative to amino acids 10-54, amino acids 60-100, amino acids 105-144, amino acids 151-195, amino acids 200-241, or amino acids 248-292 of SEQ ID NO: 16.

In another embodiment, a binding domain comprising a BoNT/B HA-33 β-trefoil domain comprises a 1β4/β5 hairpin turn of a β-trefoil domain of a BoNT/B HA-33, a 1β8/β9 hairpin turn of a β-trefoil domain of a BoNT/B HA-33, a 2β4/β5 hairpin turn of a β-trefoil domain of a BoNT/B HA-33 or a 2β8/β9 hairpin turn of a β-trefoil domain of a BoNT/B HA-33 of SEQ ID NO: 16. In another aspect of this embodiment, a binding domain comprising a BoNT/B HA-33 β-trefoil domain comprises amino acids 55-59, amino acids 101-104, amino acids 196-199, or amino acids 242-247 of SEQ ID NO: 16.

In other aspects of this embodiment, a binding domain comprising a BoNT/B HA-33 β-trefoil domain comprises a polypeptide having, e.g., at least 70% amino acid identity with amino acids 55-59, amino acids 101-104, amino acids 196-199, or amino acids 242-247 of SEQ ID NO: 16, at least 75% amino acid identity with amino acids 55-59, amino acids 101-104, amino acids 196-199, or amino acids 242-247 of SEQ ID NO: 16, at least 80% amino acid identity with amino acids 55-59, amino acids 101-104, amino acids 196-199, or amino acids 242-247 of SEQ ID NO: 16, at least 85% amino acid identity with amino acids 55-59, amino acids 101-104, amino acids 196-199, or amino acids 242-247 of SEQ ID NO: 16, at least 90% amino acid identity with amino acids 55-59, amino acids 101-104, amino acids 196-199, or amino acids 242-247 of SEQ ID NO: 16 or at least 95% amino acid identity with amino acids 55-59, amino acids 101-104, amino acids 196-199, or amino acids 242-247 of SEQ ID NO: 16. In yet other aspects of this embodiment, a binding domain comprising a BoNT/B HA-33 β-trefoil domain comprises a polypeptide having, e.g., at most 70% amino acid identity with amino acids 55-59, amino acids 101-104, amino acids 196-199, or amino acids 242-247 of SEQ ID NO: 16, at most 75% amino acid identity with amino acids 55-59, amino acids 101-104, amino acids 196-199, or amino acids 242-247 of SEQ ID NO: 16, at most 80% amino acid identity with amino acids 55-59, amino acids 101-104, amino acids 196-199, or amino acids 242-247 of SEQ ID NO: 16, at most 85% amino acid identity with amino acids 55-59, amino acids 101-104, amino acids 196-199, or amino acids 242-247 of SEQ ID NO: 16, at most 90% amino acid identity with amino acids 55-59, amino acids 101-104, amino acids 196-199, or amino acids 242-247 of SEQ ID NO: 16 or at most 95% amino acid identity with amino acids 55-59, amino acids 101-104, amino acids 196-199, or amino acids 242-247 of SEQ ID NO: 16.

In other aspects of this embodiment, a binding domain comprising a BoNT/B HA-33 β-trefoil domain comprises a polypeptide having, e.g., at most one, two, three or four non-contiguous amino acid substitutions relative to amino acids 55-59, amino acids 101-104, amino acids 196-199, or amino acids 242-247 of SEQ ID NO: 16. In other aspects of this embodiment, a binding domain comprising a BoNT/B HA-33 β-trefoil domain comprises a polypeptide having, e.g., at least one, two, three or four non-contiguous amino acid substitutions relative to amino acids 55-59, amino acids 101-104, amino acids 196-199, or amino acids 242-247 of SEQ ID NO: 16. In other aspects of this embodiment, a non-contiguous amino acid substitution of any amino acid from amino acids 55-59, amino acids 101-104, amino acids 196-199, or amino acids 242-247 of SEQ ID NO: 16 can be replaced with glycine. In other aspects of this embodiment, a non-contiguous amino acid substitution of any hydrophobic amino acid from amino acids 55-59, amino acids 101-104, amino acids 196-199, or amino acids 242-247 of SEQ ID NO: 16 can be replaced with phenylalanine. In yet other aspects of this embodiment, a β-trefoil domain with enhanced binding activity derived from a BoNT/B HA-33 comprises a polypeptide having, e.g., at most one, two, three or four non-contiguous amino acid deletions relative to amino acids 55-59, amino acids 101-104, amino acids 196-199, or amino acids 242-247 of SEQ ID NO: 16. In other aspects of this embodiment, a binding domain comprising a BoNT/B HA-33 β-trefoil domain comprises a polypeptide having, e.g., at least one, two, three or four non-contiguous amino acid deletions relative to amino acids 55-59, amino acids 101-104, amino acids 196-199, or amino acids 242-247 of SEQ ID NO: 16. In still other aspects of this embodiment, a binding domain comprising a BoNT/B HA-33 β-trefoil domain comprises a polypeptide having, e.g., at most one, two, three or four non-contiguous amino acid additions relative to amino acids 55-59, amino acids 101-104, amino acids 196-199, or amino acids 242-247 of SEQ ID NO: 16. In other aspects of this embodiment, a binding domain comprising a BoNT/B HA-33 β-trefoil domain comprises a polypeptide having, e.g., at least one, two, three or four non-contiguous amino acid additions relative to amino acids 55-59, amino acids 101-104, amino acids 196-199, or amino acids 242-247 of SEQ ID NO: 16.

In other aspects of this embodiment, a binding domain comprising a BoNT/B HA-33 β-trefoil domain comprises a polypeptide having, e.g., at most one, two, three or four contiguous amino acid substitutions relative to amino acids 55-59, amino acids 101-104, amino acids 196-199, or amino acids 242-247 of SEQ ID NO: 16. In other aspects of this embodiment, a binding domain comprising a BoNT/B HA-33 β-trefoil domain comprises a polypeptide having, e.g., at least one, two, three or four contiguous amino acid substitutions relative to amino acids 55-59, amino acids 101-104, amino acids 196-199, or amino acids 242-247 of SEQ ID NO: 16. In other aspects of this embodiment, contiguous amino acid substitutions of amino acids from amino acids 55-59, amino acids 101-104, amino acids 196-199, or amino acids 242-247 of SEQ ID NO: 16 can be replaced with glycine. In other aspects of this embodiment, contiguous amino acid substitutions of hydrophobic amino acids from amino acids 55-59, amino acids 101-104, amino acids 196-199, or amino acids 242-247 of SEQ ID NO: 16 can be replaced with phenylalanine. In yet other aspects of this embodiment, a binding domain comprising a BoNT/B HA-33 β-trefoil domain comprises a polypeptide having, e.g., at most one, two, three or four contiguous amino acid deletions relative to amino acids 55-59, amino acids 101-104, amino acids 196-199, or amino acids 242-247 of SEQ ID NO: 16. In other aspects of this embodiment, a binding domain comprising a BoNT/B HA-33 β-trefoil domain comprises a polypeptide having, e.g., at least one, two, three or four contiguous amino acid deletions relative to amino acids 55-59, amino acids 101-104, amino acids 196-199, or amino acids 242-247 of SEQ ID NO: 16. In still other aspects of this embodiment, a binding domain comprising a BoNT/B HA-33 β-trefoil domain comprises a polypeptide having, e.g., at most one, two, three or four contiguous amino acid additions relative to amino acids 55-59, amino acids 101-104, amino acids 196-199, or amino acids 242-247 of SEQ ID NO: 16. In other aspects of this embodiment, a binding domain comprising a BoNT/B HA-33 β-trefoil domain comprises a polypeptide having, e.g., at least one, two, three or four contiguous amino acid additions relative to amino acids 55-59, amino acids 101-104, amino acids 196-199, or amino acids 242-247 of SEQ ID NO: 16.

In another embodiment, a binding domain comprises a β-trefoil domain derived from a BoNT/B HA-33 of SEQ ID NO: 17. In another embodiment, a binding domain comprising a β-trefoil domain derived from a BoNT/B HA-33 comprises amino acids 10-146 or amino acids 153-291 of SEQ ID NO: 17. In another aspect of this embodiment, a binding domain comprising a β-trefoil domain derived from a BoNT/B HA-33 comprises a 1α-fold motif of a β-trefoil domain of a BoNT/B HA-33, a 1β-fold motif of a β-trefoil domain of a BoNT/B HA-33, a 1γ-fold motif of a β-trefoil domain of a BoNT/B HA-33, a 2α-fold motif of a β-trefoil domain of a BoNT/B HA-33, a 2β-fold motif of a β-trefoil domain of a BoNT/B HA-33, or a 2γ-fold motif of a β-trefoil domain of a BoNT/B HA-33 of SEQ ID NO: 17. In another aspect of this embodiment, a binding domain comprising a β-trefoil domain derived from a BoNT/B HA-33 comprises amino acids 10-56, amino acids 62-102, amino acids 107-146, amino acids 153-197, amino acids 200-242, or amino acids 249-291 of SEQ ID NO: 17.

In other aspects of this embodiment, a binding domain comprising a BoNT/B HA-33 β-trefoil domain comprises a polypeptide having, e.g., at least 70% amino acid identity with amino acids 10-56, amino acids 62-102, amino acids 107-146, amino acids 153-197, amino acids 200-242, or amino acids 249-291 of SEQ ID NO: 17, at least 75% amino acid identity with amino acids 10-56, amino acids 62-102, amino acids 107-146, amino acids 153-197, amino acids 200-242, or amino acids 249-291 of SEQ ID NO: 17, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-56, amino acids 62-102, amino acids 107-146, amino acids 153-197, amino acids 200-242, or amino acids 249-291 of SEQ ID NO: 17, at least 90% amino acid identity with amino acids 10-56, amino acids 62-102, amino acids 107-146, amino acids 153-197, amino acids 200-242, or amino acids 249-291 of SEQ ID NO: 17 or at least 95% amino acid identity with amino acids 10-56, amino acids 62-102, amino acids 107-146, amino acids 153-197, amino acids 200-242, or amino acids 249-291 of SEQ ID NO: 17. In yet other aspects of this embodiment, a binding domain comprising a BoNT/B HA-33 β-trefoil domain comprises a polypeptide having, e.g., at most 70% amino acid identity with amino acids 10-56, amino acids 62-102, amino acids 107-146, amino acids 153-197, amino acids 200-242, or amino acids 249-291 of SEQ ID NO: 17, at most 75% amino acid identity with amino acids 10-56, amino acids 62-102, amino acids 107-146, amino acids 153-197, amino acids 200-242, or amino acids 249-291 of SEQ ID NO: 17, at most 80% amino acid identity with amino acids 10-56, amino acids 62-102, amino acids 107-146, amino acids 153-197, amino acids 200-242, or amino acids 249-291 of SEQ ID NO: 17, at most 85% amino acid identity with amino acids 10-56, amino acids 62-102, amino acids 107-146, amino acids 153-197, amino acids 200-242, or amino acids 249-291 of SEQ ID NO: 17, at most 90% amino acid identity with amino acids 10-56, amino acids 62-102, amino acids 107-146, amino acids 153-197, amino acids 200-242, or amino acids 249-291 of SEQ ID NO: 17 or at most 95% amino acid identity with amino acids 10-56, amino acids 62-102, amino acids 107-146, amino acids 153-197, amino acids 200-242, or amino acids 249-291 of SEQ ID NO: 17.

In other aspects of this embodiment, a binding domain comprising a BoNT/B HA-33 β-trefoil domain comprises a polypeptide having, e.g., at most one, two, three, four, five, six, seven, eight, nine, 10 or 20 non-contiguous amino acid substitutions relative to amino acids 10-56, amino acids 62-102, amino acids 107-146, amino acids 153-197, amino acids 200-242, or amino acids 249-291 of SEQ ID NO: 17. In other aspects of this embodiment, a binding domain comprising a BoNT/B HA-33 β-trefoil domain comprises a polypeptide having, e.g., at least one, two, three, four, five, six, seven, eight, nine, 10 or 20 non-contiguous amino acid substitutions relative to amino acids 10-56, amino acids 62-102, amino acids 107-146, amino acids 153-197, amino acids 200-242, or amino acids 249-291 of SEQ ID NO: 17. In yet other aspects of this embodiment, a binding domain comprising a BoNT/B HA-33 β-trefoil domain comprises a polypeptide having, e.g., at most one, two, three, four, five, six, seven, eight, nine, 10 or 20 non-contiguous amino acid deletions relative to amino acids 10-56, amino acids 62-102, amino acids 107-146, amino acids 153-197, amino acids 200-242, or amino acids 249-291 of SEQ ID NO: 17. In other aspects of this embodiment, a binding domain comprising a BoNT/B HA-33 β-trefoil domain comprises a polypeptide having, e.g., at least one, two, three, four, five, six, seven, eight, nine, 10 or 20 non-contiguous amino acid deletions relative to amino acids 10-56, amino acids 62-102, amino acids 107-146, amino acids 153-197, amino acids 200-242, or amino acids 249-291 of SEQ ID NO: 17. In still other aspects of this embodiment, a binding domain comprising a BoNT/B HA-33 β-trefoil domain comprises a polypeptide having, e.g., at most one, two, three, four, five, six, seven, eight, nine, 10 or 20 non-contiguous amino acid additions relative to amino acids 10-56, amino acids 62-102, amino acids 107-146, amino acids 153-197, amino acids 200-242, or amino acids 249-291 of SEQ ID NO: 17. In other aspects of this embodiment, a binding domain comprising a BoNT/B HA-33 β-trefoil domain comprises a polypeptide having, e.g., at least one, two, three, four, five, six, seven, eight, nine, 10 or 20 non-contiguous amino acid additions relative to amino acids 10-56, amino acids 62-102, amino acids 107-146, amino acids 153-197, amino acids 200-242, or amino acids 249-291 of SEQ ID NO: 17.

In other aspects of this embodiment, a binding domain comprising a BoNT/B HA-33 β-trefoil domain comprises a polypeptide having, e.g., at most one, two, three, four, five, six, seven, eight, nine, 10 or 20 contiguous amino acid substitutions relative to amino acids 10-56, amino acids 62-102, amino acids 107-146, amino acids 153-197, amino acids 200-242, or amino acids 249-291 of SEQ ID NO: 17. In other aspects of this embodiment, a binding domain comprising a BoNT/B HA-33 β-trefoil domain comprises a polypeptide having, e.g., at least one, two, three, four, five, six, seven, eight, nine, 10 or 20 contiguous amino acid substitutions relative to amino acids 10-56, amino acids 62-102, amino acids 107-146, amino acids 153-197, amino acids 200-242, or amino acids 249-291 of SEQ ID NO: 17. In yet other aspects of this embodiment, a binding domain comprising a BoNT/B HA-33 β-trefoil domain comprises a polypeptide having, e.g., at most one, two, three, four, five, six, seven, eight, nine, 10 or 20 contiguous amino acid deletions relative to amino acids 10-56, amino acids 62-102, amino acids 107-146, amino acids 153-197, amino acids 200-242, or amino acids 249-291 of SEQ ID NO: 17. In other aspects of this embodiment, a binding domain comprising a BoNT/B HA-33 β-trefoil domain comprises a polypeptide having, e.g., at least one, two, three, four, five, six, seven, eight, nine, 10 or 20 contiguous amino acid deletions relative to amino acids 10-56, amino acids 62-102, amino acids 107-146, amino acids 153-197, amino acids 200-242, or amino acids 249-291 of SEQ ID NO: 17. In still other aspects of this embodiment, a binding domain comprising a BoNT/B HA-33 β-trefoil domain comprises a polypeptide having, e.g., at most one, two, three, four, five, six, seven, eight, nine, 10 or 20 contiguous amino acid additions relative to amino acids 10-56, amino acids 62-102, amino acids 107-146, amino acids 153-197, amino acids 200-242, or amino acids 249-291 of SEQ ID NO: 17. In other aspects of this embodiment, a binding domain comprising a BoNT/B HA-33 β-trefoil domain comprises a polypeptide having, e.g., at least one, two, three, four, five, six, seven, eight, nine, 10 or 20 contiguous amino acid additions relative to amino acids 10-56, amino acids 62-102, amino acids 107-146, amino acids 153-197, amino acids 200-242, or amino acids 249-291 of SEQ ID NO: 17.

In another embodiment, a binding domain comprising a BoNT/B HA-33 β-trefoil domain comprises a 1β4/β5 hairpin turn of a β-trefoil domain of a BoNT/B HA-33, a 1β8/β9 hairpin turn of a β-trefoil domain of a BoNT/B HA-33, a 2β4/β5 hairpin turn of a β-trefoil domain of a BoNT/B HA-33 or a 2β8/β9 hairpin turn of a β-trefoil domain of a BoNT/B HA-33 of SEQ ID NO: 17. In another aspect of this embodiment, a binding domain comprising a BoNT/B HA-33 β-trefoil domain comprises amino acids 56-61, amino acids 103-106, amino acids 198-201, or amino acids 243-248 of SEQ ID NO: 17.

In other aspects of this embodiment, a binding domain comprising a BoNT/B HA-33 β-trefoil domain comprises a polypeptide having, e.g., at least 70% amino acid identity with amino acids 56-61, amino acids 103-106, amino acids 198-201, or amino acids 243-248 of SEQ ID NO: 17, at least 75% amino acid identity with amino acids 56-61, amino acids 103-106, amino acids 198-201, or amino acids 243-248 of SEQ ID NO: 17, at least 80% amino acid identity with amino acids 56-61, amino acids 103-106, amino acids 198-201, or amino acids 243-248 of SEQ ID NO: 17, at least 85% amino acid identity with amino acids 56-61, amino acids 103-106, amino acids 198-201, or amino acids 243-248 of SEQ ID NO: 17, at least 90% amino acid identity with amino acids 56-61, amino acids 103-106, amino acids 198-201, or amino acids 243-248 of SEQ ID NO: 17 or at least 95% amino acid identity with amino acids 56-61, amino acids 103-106, amino acids 198-201, or amino acids 243-248 of SEQ ID NO: 17. In yet other aspects of this embodiment, a binding domain comprising a BoNT/B HA-33 β-trefoil domain comprises a polypeptide having, e.g., at most 70% amino acid identity with amino acids 56-61, amino acids 103-106, amino acids 198-201, or amino acids 243-248 of SEQ ID NO: 17, at most 75% amino acid identity with amino acids 56-61, amino acids 103-106, amino acids 198-201, or amino acids 243-248 of SEQ ID NO: 17, at most 80% amino acid identity with amino acids 56-61, amino acids 103-106, amino acids 198-201, or amino acids 243-248 of SEQ ID NO: 17, at most 85% amino acid identity with amino acids 56-61, amino acids 103-106, amino acids 198-201, or amino acids 243-248 of SEQ ID NO: 17, at most 90% amino acid identity with amino acids 56-61, amino acids 103-106, amino acids 198-201, or amino acids 243-248 of SEQ ID NO: 17 or at most 95% amino acid identity with amino acids 56-61, amino acids 103-106, amino acids 198-201, or amino acids 243-248 of SEQ ID NO: 17.

In other aspects of this embodiment, a binding domain comprising a BoNT/B HA-33 β-trefoil domain comprises a polypeptide having, e.g., at most one, two, three or four non-contiguous amino acid substitutions relative to amino acids 56-61, amino acids 103-106, amino acids 198-201, or amino acids 243-248 of SEQ ID NO: 17. In other aspects of this embodiment, a binding domain comprising a BoNT/B HA-33 β-trefoil domain comprises a polypeptide having, e.g., at least one, two, three or four non-contiguous amino acid substitutions relative to amino acids 56-61, amino acids 103-106, amino acids 198-201, or amino acids 243-248 of SEQ ID NO: 17. In other aspects of this embodiment, a non-contiguous amino acid substitution of any amino acid from amino acids 56-61, amino acids 103-106, amino acids 198-201, or amino acids 243-248 of SEQ ID NO: 17 can be replaced with glycine. In other aspects of this embodiment, a non-contiguous amino acid substitution of any hydrophobic amino acid from amino acids 56-61, amino acids 103-106, amino acids 198-201, or amino acids 243-248 of SEQ ID NO: 17 can be replaced with phenylalanine. In yet other aspects of this embodiment, a β-trefoil domain with enhanced binding activity derived from a BoNT/B HA-33 comprises a polypeptide having, e.g., at most one, two, three or four non-contiguous amino acid deletions relative to amino acids 56-61, amino acids 103-106, amino acids 198-201, or amino acids 243-248 of SEQ ID NO: 17. In other aspects of this embodiment, a binding domain comprising a BoNT/B HA-33 β-trefoil domain comprises a polypeptide having, e.g., at least one, two, three or four non-contiguous amino acid deletions relative to amino acids 56-61, amino acids 103-106, amino acids 198-201, or amino acids 243-248 of SEQ ID NO: 17. In still other aspects of this embodiment, a binding domain comprising a BoNT/B HA-33 β-trefoil domain comprises a polypeptide having, e.g., at most one, two, three or four non-contiguous amino acid additions relative to amino acids 56-61, amino acids 103-106, amino acids 198-201, or amino acids 243-248 of SEQ ID NO: 17. In other aspects of this embodiment, a binding domain comprising a BoNT/B HA-33 β-trefoil domain comprises a polypeptide having, e.g., at least one, two, three or four non-contiguous amino acid additions relative to amino acids 56-61, amino acids 103-106, amino acids 198-201, or amino acids 243-248 of SEQ ID NO: 17.

In other aspects of this embodiment, a binding domain comprising a BoNT/B HA-33 β-trefoil domain comprises a polypeptide having, e.g., at most one, two, three or four contiguous amino acid substitutions relative to amino acids 56-61, amino acids 103-106, amino acids 198-201, or amino acids 243-248 of SEQ ID NO: 17. In other aspects of this embodiment, a binding domain comprising a BoNT/B HA-33 β-trefoil domain comprises a polypeptide having, e.g., at least one, two, three or four contiguous amino acid substitutions relative to amino acids 56-61, amino acids 103-106, amino acids 198-201, or amino acids 243-248 of SEQ ID NO: 17. In other aspects of this embodiment, contiguous amino acid substitutions of amino acids from amino acids 56-61, amino acids 103-106, amino acids 198-201, or amino acids 243-248 of SEQ ID NO: 17 can be replaced with glycine. In other aspects of this embodiment, contiguous amino acid substitutions of hydrophobic amino acids from amino acids 56-61, amino acids 103-106, amino acids 198-201, or amino acids 243-248 of SEQ ID NO: 17 can be replaced with phenylalanine. In yet other aspects of this embodiment, a binding domain comprising a BoNT/B HA-33 β-trefoil domain comprises a polypeptide having, e.g., at most one, two, three or four contiguous amino acid deletions relative to amino acids 56-61, amino acids 103-106, amino acids 198-201, or amino acids 243-248 of SEQ ID NO: 17. In other aspects of this embodiment, a binding domain comprising a BoNT/B HA-33 β-trefoil domain comprises a polypeptide having, e.g., at least one, two, three or four contiguous amino acid deletions relative to amino acids 56-61, amino acids 103-106, amino acids 198-201, or amino acids 243-248 of SEQ ID NO: 17. In still other aspects of this embodiment, a binding domain comprising a BoNT/B HA-33 β-trefoil domain comprises a polypeptide having, e.g., at most one, two, three or four contiguous amino acid additions relative to amino acids 56-61, amino acids 103-106, amino acids 198-201, or amino acids 243-248 of SEQ ID NO: 17. In other aspects of this embodiment, a binding domain comprising a BoNT/B HA-33 β-trefoil domain comprises a polypeptide having, e.g., at least one, two, three or four contiguous amino acid additions relative to amino acids 56-61, amino acids 103-106, amino acids 198-201, or amino acids 243-248 of SEQ ID NO: 17.

In another embodiment, a binding domain comprises a β-trefoil domain derived from a BoNT/C1 HA-33 of SEQ ID NO: 18. In another embodiment, a binding domain comprising a β-trefoil domain derived from a BoNT/C1 HA-33 comprises amino acids 10-141 or amino acids 148-285 of SEQ ID NO: 18. In another aspect of this embodiment, a binding domain comprising a β-trefoil domain derived from a BoNT/C1 HA-33 comprises a 1α-fold motif of a β-trefoil domain of a BoNT/C1 HA-33, a 1β-fold motif of a β-trefoil domain of a BoNT/C1 HA-33, a 1γ-fold motif of a β-trefoil domain of a BoNT/C1 HA-33, a 2α-fold motif of a β-trefoil domain of a BoNT/C1 HA-33, a 2β-fold motif of a β-trefoil domain of a BoNT/C1 HA-33, or a 2γ-fold motif of a β-trefoil domain of a BoNT/C1 HA-33 of SEQ ID NO: 18. In another aspect of this embodiment, a binding domain comprising a β-trefoil domain derived from a BoNT/C1 HA-33 comprises amino acids 10-54, amino acids 60-98, amino acids 103-141, amino acids 148-190, amino acids 195-234, or amino acids 241-285 of SEQ ID NO: 18.

In other aspects of this embodiment, a binding domain comprising a BoNT/C1 HA-33 β-trefoil domain comprises a polypeptide having, e.g., at least 70% amino acid identity with amino acids 10-54, amino acids 60-98, amino acids 103-141, amino acids 148-190, amino acids 195-234, or amino acids 241-285 of SEQ ID NO: 18, at least 75% amino acid identity with amino acids 10-54, amino acids 60-98, amino acids 103-141, amino acids 148-190, amino acids 195-234, or amino acids 241-285 of SEQ ID NO: 18, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-54, amino acids 60-98, amino acids 103-141, amino acids 148-190, amino acids 195-234, or amino acids 241-285 of SEQ ID NO: 18, at least 90% amino acid identity with amino acids 10-54, amino acids 60-98, amino acids 103-141, amino acids 148-190, amino acids 195-234, or amino acids 241-285 of SEQ ID NO: 18 or at least 95% amino acid identity with amino acids 10-54, amino acids 60-98, amino acids 103-141, amino acids 148-190, amino acids 195-234, or amino acids 241-285 of SEQ ID NO: 18. In yet other aspects of this embodiment, a binding domain comprising a BoNT/C1 HA-33 β-trefoil domain comprises a polypeptide having, e.g., at most 70% amino acid identity with amino acids 10-54, amino acids 60-98, amino acids 103-141, amino acids 148-190, amino acids 195-234, or amino acids 241-285 of SEQ ID NO: 18, at most 75% amino acid identity with amino acids 10-54, amino acids 60-98, amino acids 103-141, amino acids 148-190, amino acids 195-234, or amino acids 241-285 of SEQ ID NO: 18, at most 80% amino acid identity with amino acids 10-54, amino acids 60-98, amino acids 103-141, amino acids 148-190, amino acids 195-234, or amino acids 241-285 of SEQ ID NO: 18, at most 85% amino acid identity with amino acids 10-54, amino acids 60-98, amino acids 103-141, amino acids 148-190, amino acids 195-234, or amino acids 241-285 of SEQ ID NO: 18, at most 90% amino acid identity with amino acids 10-54, amino acids 60-98, amino acids 103-141, amino acids 148-190, amino acids 195-234, or amino acids 241-285 of SEQ ID NO: 18 or at most 95% amino acid identity with amino acids 10-54, amino acids 60-98, amino acids 103-141, amino acids 148-190, amino acids 195-234, or amino acids 241-285 of SEQ ID NO: 18.

In other aspects of this embodiment, a binding domain comprising a BoNT/C1 HA-33 β-trefoil domain comprises a polypeptide having, e.g., at most one, two, three, four, five, six, seven, eight, nine, 10 or 20 non-contiguous amino acid substitutions relative to amino acids 10-54, amino acids 60-98, amino acids 103-141, amino acids 148-190, amino acids 195-234, or amino acids 241-285 of SEQ ID NO: 18. In other aspects of this embodiment, a binding domain comprising a BoNT/C1 HA-33 β-trefoil domain comprises a polypeptide having, e.g., at least one, two, three, four, five, six, seven, eight, nine, 10 or 20 non-contiguous amino acid substitutions relative to amino acids 10-54, amino acids 60-98, amino acids 103-141, amino acids 148-190, amino acids 195-234, or amino acids 241-285 of SEQ ID NO: 18. In yet other aspects of this embodiment, a binding domain comprising a BoNT/C1 HA-33 β-trefoil domain comprises a polypeptide having, e.g., at most one, two, three, four, five, six, seven, eight, nine, 10 or 20 non-contiguous amino acid deletions relative to amino acids 10-54, amino acids 60-98, amino acids 103-141, amino acids 148-190, amino acids 195-234, or amino acids 241-285 of SEQ ID NO: 18. In other aspects of this embodiment, a binding domain comprising a BoNT/C1 HA-33 β-trefoil domain comprises a polypeptide having, e.g., at least one, two, three, four, five, six, seven, eight, nine, 10 or 20 non-contiguous amino acid deletions relative to amino acids 10-54, amino acids 60-98, amino acids 103-141, amino acids 148-190, amino acids 195-234, or amino acids 241-285 of SEQ ID NO: 18. In still other aspects of this embodiment, a binding domain comprising a BoNT/C1 HA-33 β-trefoil domain comprises a polypeptide having, e.g., at most one, two, three, four, five, six, seven, eight, nine, 10 or 20 non-contiguous amino acid additions relative to amino acids 10-54, amino acids 60-98, amino acids 103-141, amino acids 148-190, amino acids 195-234, or amino acids 241-285 of SEQ ID NO: 18. In other aspects of this embodiment, a binding domain comprising a BoNT/C1 HA-33 β-trefoil domain comprises a polypeptide having, e.g., at least one, two, three, four, five, six, seven, eight, nine, 10 or 20 non-contiguous amino acid additions relative to amino acids 10-54, amino acids 60-98, amino acids 103-141, amino acids 148-190, amino acids 195-234, or amino acids 241-285 of SEQ ID NO: 18.

In other aspects of this embodiment, a binding domain comprising a BoNT/C1 HA-33 β-trefoil domain comprises a polypeptide having, e.g., at most one, two, three, four, five, six, seven, eight, nine, 10 or 20 contiguous amino acid substitutions relative to amino acids 10-54, amino acids 60-98, amino acids 103-141, amino acids 148-190, amino acids 195-234, or amino acids 241-285 of SEQ ID NO: 18. In other aspects of this embodiment, a binding domain comprising a BoNT/C1 HA-33 β-trefoil domain comprises a polypeptide having, e.g., at least one, two, three, four, five, six, seven, eight, nine, 10 or 20 contiguous amino acid substitutions relative to amino acids 10-54, amino acids 60-98, amino acids 103-141, amino acids 148-190, amino acids 195-234, or amino acids 241-285 of SEQ ID NO: 18. In yet other aspects of this embodiment, a binding domain comprising a BoNT/C1 HA-33 β-trefoil domain comprises a polypeptide having, e.g., at most one, two, three, four, five, six, seven, eight, nine, 10 or 20 contiguous amino acid deletions relative to amino acids 10-54, amino acids 60-98, amino acids 103-141, amino acids 148-190, amino acids 195-234, or amino acids 241-285 of SEQ ID NO: 18. In other aspects of this embodiment, a binding domain comprising a BoNT/C1 HA-33 β-trefoil domain comprises a polypeptide having, e.g., at least one, two, three, four, five, six, seven, eight, nine, 10 or 20 contiguous amino acid deletions relative to amino acids 10-54, amino acids 60-98, amino acids 103-141, amino acids 148-190, amino acids 195-234, or amino acids 241-285 of SEQ ID NO: 18. In still other aspects of this embodiment, a binding domain comprising a BoNT/C1 HA-33 β-trefoil domain comprises a polypeptide having, e.g., at most one, two, three, four, five, six, seven, eight, nine, 10 or 20 contiguous amino acid additions relative to amino acids 10-54, amino acids 60-98, amino acids 103-141, amino acids 148-190, amino acids 195-234, or amino acids 241-285 of SEQ ID NO: 18. In other aspects of this embodiment, a binding domain comprising a BoNT/C1 HA-33 β-trefoil domain comprises a polypeptide having, e.g., at least one, two, three, four, five, six, seven, eight, nine, 10 or 20 contiguous amino acid additions relative to amino acids 10-54, amino acids 60-98, amino acids 103-141, amino acids 148-190, amino acids 195-234, or amino acids 241-285 of SEQ ID NO: 18.

In another embodiment, a binding domain comprising a BoNT/C1 HA-33 β-trefoil domain comprises a 1β4/β5 hairpin turn of a β-trefoil domain of a BoNT/C1 HA-33, a 1β8/β9 hairpin turn of a β-trefoil domain of a BoNT/C1 HA-33, a 2β4/β5 hairpin turn of a β-trefoil domain of a BoNT/C1 HA-33 or a 2β8/β9 hairpin turn of a β-trefoil domain of a BoNT/C1 HA-33 of SEQ ID NO: 18. In another aspect of this embodiment, a binding domain comprising a BoNT/C1 HA-33 β-trefoil domain comprises amino acids 55-59, amino acids 99-102, amino acids 191-194, or amino acids 235-240 of SEQ ID NO: 18.

In other aspects of this embodiment, a binding domain comprising a BoNT/C1 HA-33 β-trefoil domain comprises a polypeptide having, e.g., at least 70% amino acid identity with amino acids 55-59, amino acids 99-102, amino acids 191-194, or amino acids 235-240 of SEQ ID NO: 18, at least 75% amino acid identity with amino acids 55-59, amino acids 99-102, amino acids 191-194, or amino acids 235-240 of SEQ ID NO: 18, at least 80% amino acid identity with amino acids 55-59, amino acids 99-102, amino acids 191-194, or amino acids 235-240 of SEQ ID NO: 18, at least 85% amino acid identity with amino acids 55-59, amino acids 99-102, amino acids 191-194, or amino acids 235-240 of SEQ ID NO: 18, at least 90% amino acid identity with amino acids 55-59, amino acids 99-102, amino acids 191-194, or amino acids 235-240 of SEQ ID NO: 18 or at least 95% amino acid identity with amino acids 55-59, amino acids 99-102, amino acids 191-194, or amino acids 235-240 of SEQ ID NO: 18. In yet other aspects of this embodiment, a binding domain comprising a BoNT/C1 HA-33 β-trefoil domain comprises a polypeptide having, e.g., at most 70% amino acid identity with amino acids 55-59, amino acids 99-102, amino acids 191-194, or amino acids 235-240 of SEQ ID NO: 18, at most 75% amino acid identity with amino acids 55-59, amino acids 99-102, amino acids 191-194, or amino acids 235-240 of SEQ ID NO: 18, at most 80% amino acid identity with amino acids 55-59, amino acids 99-102, amino acids 191-194, or amino acids 235-240 of SEQ ID NO: 18, at most 85% amino acid identity with amino acids 55-59, amino acids 99-102, amino acids 191-194, or amino acids 235-240 of SEQ ID NO: 18, at most 90% amino acid identity with amino acids 55-59, amino acids 99-102, amino acids 191-194, or amino acids 235-240 of SEQ ID NO: 18 or at most 95% amino acid identity with amino acids 55-59, amino acids 99-102, amino acids 191-194, or amino acids 235-240 of SEQ ID NO: 18.

In other aspects of this embodiment, a binding domain comprising a BoNT/C1 HA-33 β-trefoil domain comprises a polypeptide having, e.g., at most one, two, three or four non-contiguous amino acid substitutions relative to amino acids 55-59, amino acids 99-102, amino acids 191-194, or amino acids 235-240 of SEQ ID NO: 18. In other aspects of this embodiment, a binding domain comprising a BoNT/C1 HA-33 β-trefoil domain comprises a polypeptide having, e.g., at least one, two, three or four non-contiguous amino acid substitutions relative to amino acids 55-59, amino acids 99-102, amino acids 191-194, or amino acids 235-240 of SEQ ID NO: 18. In other aspects of this embodiment, a non-contiguous amino acid substitution of any amino acid from amino acids 55-59, amino acids 99-102, amino acids 191-194, or amino acids 235-240 of SEQ ID NO: 18 can be replaced with glycine. In other aspects of this embodiment, a non-contiguous amino acid substitution of any hydrophobic amino acid from amino acids 55-59, amino acids 99-102, amino acids 191-194, or amino acids 235-240 of SEQ ID NO: 18 can be replaced with phenylalanine. In yet other aspects of this embodiment, a β-trefoil domain with enhanced binding activity derived from a BoNT/C1 HA-33 comprises a polypeptide having, e.g., at most one, two, three or four non-contiguous amino acid deletions relative to amino acids 55-59, amino acids 99-102, amino acids 191-194, or amino acids 235-240 of SEQ ID NO: 18. In other aspects of this embodiment, a binding domain comprising a BoNT/C1 HA-33 β-trefoil domain comprises a polypeptide having, e.g., at least one, two, three or four non-contiguous amino acid deletions relative to amino acids 55-59, amino acids 99-102, amino acids 191-194, or amino acids 235-240 of SEQ ID NO: 18. In still other aspects of this embodiment, a binding domain comprising a BoNT/C1 HA-33 β-trefoil domain comprises a polypeptide having, e.g., at most one, two, three or four non-contiguous amino acid additions relative to amino acids 55-59, amino acids 99-102, amino acids 191-194, or amino acids 235-240 of SEQ ID NO: 18. In other aspects of this embodiment, a binding domain comprising a BoNT/C1 HA-33 β-trefoil domain comprises a polypeptide having, e.g., at least one, two, three or four non-contiguous amino acid additions relative to amino acids 55-59, amino acids 99-102, amino acids 191-194, or amino acids 235-240 of SEQ ID NO: 18.

In other aspects of this embodiment, a binding domain comprising a BoNT/C1 HA-33 β-trefoil domain comprises a polypeptide having, e.g., at most one, two, three or four contiguous amino acid substitutions relative to amino acids 55-59, amino acids 99-102, amino acids 191-194, or amino acids 235-240 of SEQ ID NO: 18. In other aspects of this embodiment, a binding domain comprising a BoNT/C1 HA-33 β-trefoil domain comprises a polypeptide having, e.g., at least one, two, three or four contiguous amino acid substitutions relative to amino acids 55-59, amino acids 99-102, amino acids 191-194, or amino acids 235-240 of SEQ ID NO: 18. In other aspects of this embodiment, contiguous amino acid substitutions of amino acids from amino acids 55-59, amino acids 99-102, amino acids 191-194, or amino acids 235-240 of SEQ ID NO: 18 can be replaced with glycine. In other aspects of this embodiment, contiguous amino acid substitutions of hydrophobic amino acids from amino acids 55-59, amino acids 99-102, amino acids 191-194, or amino acids 235-240 of SEQ ID NO: 18 can be replaced with phenylalanine. In yet other aspects of this embodiment, a binding domain comprising a BoNT/C1 HA-33 β-trefoil domain comprises a polypeptide having, e.g., at most one, two, three or four contiguous amino acid deletions relative to amino acids 55-59, amino acids 99-102, amino acids 191-194, or amino acids 235-240 of SEQ ID NO: 18. In other aspects of this embodiment, a binding domain comprising a BoNT/C1 HA-33 β-trefoil domain comprises a polypeptide having, e.g., at least one, two, three or four contiguous amino acid deletions relative to amino acids 55-59, amino acids 99-102, amino acids 191-194, or amino acids 235-240 of SEQ ID NO: 18. In still other aspects of this embodiment, a binding domain comprising a BoNT/C1 HA-33 β-trefoil domain comprises a polypeptide having, e.g., at most one, two, three or four contiguous amino acid additions relative to amino acids 55-59, amino acids 99-102, amino acids 191-194, or amino acids 235-240 of SEQ ID NO: 18. In other aspects of this embodiment, a binding domain comprising a BoNT/C1 HA-33 β-trefoil domain comprises a polypeptide having, e.g., at least one, two, three or four contiguous amino acid additions relative to amino acids 55-59, amino acids 99-102, amino acids 191-194, or amino acids 235-240 of SEQ ID NO: 18.

In another embodiment, a binding domain comprises a β-trefoil domain derived from a BoNT/C1 HA-33 of SEQ ID NO: 19. In another embodiment, a binding domain comprising a β-trefoil domain derived from a BoNT/C1 HA-33 comprises amino acids 10-141 or amino acids 148-286 of SEQ ID NO: 19. In another aspect of this embodiment, a binding domain comprising a β-trefoil domain derived from a BoNT/C1 HA-33 comprises a 1α-fold motif of a β-trefoil domain of a BoNT/C1 HA-33, a 1β-fold motif of a β-trefoil domain of a BoNT/C1 HA-33, a 1γ-fold motif of a β-trefoil domain of a BoNT/C1 HA-33, a 2α-fold motif of a β-trefoil domain of a BoNT/C1 HA-33, a 2α-fold motif of a β-trefoil domain of a BoNT/C1 HA-33, or a 2γ-fold motif of a β-trefoil domain of a BoNT/C1 HA-33 of SEQ ID NO: 19. In another aspect of this embodiment, a binding domain comprising a β-trefoil domain derived from a BoNT/C1 HA-33 comprises amino acids 10-54, amino acids 60-98, amino acids 103-141, amino acids 148-190, amino acids 195-235, or amino acids 242-286 of SEQ ID NO: 19.

In other aspects of this embodiment, a binding domain comprising a BoNT/C1 HA-33 β-trefoil domain comprises a polypeptide having, e.g., at least 70% amino acid identity with amino acids 10-54, amino acids 60-98, amino acids 103-141, amino acids 148-190, amino acids 195-235, or amino acids 242-286 of SEQ ID NO: 19, at least 75% amino acid identity with amino acids 10-54, amino acids 60-98, amino acids 103-141, amino acids 148-190, amino acids 195-235, or amino acids 242-286 of SEQ ID NO: 19, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-54, amino acids 60-98, amino acids 103-141, amino acids 148-190, amino acids 195-235, or amino acids 242-286 of SEQ ID NO: 19, at least 90% amino acid identity with amino acids 10-54, amino acids 60-98, amino acids 103-141, amino acids 148-190, amino acids 195-235, or amino acids 242-286 of SEQ ID NO: 19 or at least 95% amino acid identity with amino acids 10-54, amino acids 60-98, amino acids 103-141, amino acids 148-190, amino acids 195-235, or amino acids 242-286 of SEQ ID NO: 19. In yet other aspects of this embodiment, a binding domain comprising a BoNT/C1 HA-33 β-trefoil domain comprises a polypeptide having, e.g., at most 70% amino acid identity with amino acids 10-54, amino acids 60-98, amino acids 103-141, amino acids 148-190, amino acids 195-235, or amino acids 242-286 of SEQ ID NO: 19, at most 75% amino acid identity with amino acids 10-54, amino acids 60-98, amino acids 103-141, amino acids 148-190, amino acids 195-235, or amino acids 242-286 of SEQ ID NO: 19, at most 80% amino acid identity with amino acids 10-54, amino acids 60-98, amino acids 103-141, amino acids 148-190, amino acids 195-235, or amino acids 242-286 of SEQ ID NO: 19, at most 85% amino acid identity with amino acids 10-54, amino acids 60-98, amino acids 103-141, amino acids 148-190, amino acids 195-235, or amino acids 242-286 of SEQ ID NO: 19, at most 90% amino acid identity with amino acids 10-54, amino acids 60-98, amino acids 103-141, amino acids 148-190, amino acids 195-235, or amino acids 242-286 of SEQ ID NO: 19 or at most 95% amino acid identity with amino acids 10-54, amino acids 60-98, amino acids 103-141, amino acids 148-190, amino acids 195-235, or amino acids 242-286 of SEQ ID NO: 19.

In other aspects of this embodiment, a binding domain comprising a BoNT/C1 HA-33 β-trefoil domain comprises a polypeptide having, e.g., at most one, two, three, four, five, six, seven, eight, nine, 10 or 20 non-contiguous amino acid substitutions relative to amino acids 10-54, amino acids 60-98, amino acids 103-141, amino acids 148-190, amino acids 195-235, or amino acids 242-286 of SEQ ID NO: 19. In other aspects of this embodiment, a binding domain comprising a BoNT/C1 HA-33 β-trefoil domain comprises a polypeptide having, e.g., at least one, two, three, four, five, six, seven, eight, nine, 10 or 20 non-contiguous amino acid substitutions relative to amino acids 10-54, amino acids 60-98, amino acids 103-141, amino acids 148-190, amino acids 195-235, or amino acids 242-286 of SEQ ID NO: 19. In yet other aspects of this embodiment, a binding domain comprising a BoNT/C1 HA-33 β-trefoil domain comprises a polypeptide having, e.g., at most one, two, three, four, five, six, seven, eight, nine, 10 or 20 non-contiguous amino acid deletions relative to amino acids 10-54, amino acids 60-98, amino acids 103-141, amino acids 148-190, amino acids 195-235, or amino acids 242-286 of SEQ ID NO: 19. In other aspects of this embodiment, a binding domain comprising a BoNT/C1 HA-33 β-trefoil domain comprises a polypeptide having, e.g., at least one, two, three, four, five, six, seven, eight, nine, 10 or 20 non-contiguous amino acid deletions relative to amino acids 10-54, amino acids 60-98, amino acids 103-141, amino acids 148-190, amino acids 195-235, or amino acids 242-286 of SEQ ID NO: 19. In still other aspects of this embodiment, a binding domain comprising a BoNT/C1 HA-33 β-trefoil domain comprises a polypeptide having, e.g., at most one, two, three, four, five, six, seven, eight, nine, 10 or 20 non-contiguous amino acid additions relative to amino acids 10-54, amino acids 60-98, amino acids 103-141, amino acids 148-190, amino acids 195-235, or amino acids 242-286 of SEQ ID NO: 19. In other aspects of this embodiment, a binding domain comprising a BoNT/C1 HA-33 β-trefoil domain comprises a polypeptide having, e.g., at least one, two, three, four, five, six, seven, eight, nine, 10 or 20 non-contiguous amino acid additions relative to amino acids 10-54, amino acids 60-98, amino acids 103-141, amino acids 148-190, amino acids 195-235, or amino acids 242-286 of SEQ ID NO: 19.

In other aspects of this embodiment, a binding domain comprising a BoNT/C1 HA-33 β-trefoil domain comprises a polypeptide having, e.g., at most one, two, three, four, five, six, seven, eight, nine, 10 or 20 contiguous amino acid substitutions relative to amino acids 10-54, amino acids 60-98, amino acids 103-141, amino acids 148-190, amino acids 195-235, or amino acids 242-286 of SEQ ID NO: 19. In other aspects of this embodiment, a binding domain comprising a BoNT/C1 HA-33 β-trefoil domain comprises a polypeptide having, e.g., at least one, two, three, four, five, six, seven, eight, nine, 10 or 20 contiguous amino acid substitutions relative to amino acids 10-54, amino acids 60-98, amino acids 103-141, amino acids 148-190, amino acids 195-235, or amino acids 242-286 of SEQ ID NO: 19. In yet other aspects of this embodiment, a binding domain comprising a BoNT/C1 HA-33 β-trefoil domain comprises a polypeptide having, e.g., at most one, two, three, four, five, six, seven, eight, nine, 10 or 20 contiguous amino acid deletions relative to amino acids 10-54, amino acids 60-98, amino acids 103-141, amino acids 148-190, amino acids 195-235, or amino acids 242-286 of SEQ ID NO: 19. In other aspects of this embodiment, a binding domain comprising a BoNT/C1 HA-33 β-trefoil domain comprises a polypeptide having, e.g., at least one, two, three, four, five, six, seven, eight, nine, 10 or 20 contiguous amino acid deletions relative to amino acids 10-54, amino acids 60-98, amino acids 103-141, amino acids 148-190, amino acids 195-235, or amino acids 242-286 of SEQ ID NO: 19. In still other aspects of this embodiment, a binding domain comprising a BoNT/C1 HA-33 β-trefoil domain comprises a polypeptide having, e.g., at most one, two, three, four, five, six, seven, eight, nine, 10 or 20 contiguous amino acid additions relative to amino acids 10-54, amino acids 60-98, amino acids 103-141, amino acids 148-190, amino acids 195-235, or amino acids 242-286 of SEQ ID NO: 19. In other aspects of this embodiment, a binding domain comprising a BoNT/C1 HA-33 β-trefoil domain comprises a polypeptide having, e.g., at least one, two, three, four, five, six, seven, eight, nine, 10 or 20 contiguous amino acid additions relative to amino acids 10-54, amino acids 60-98, amino acids 103-141, amino acids 148-190, amino acids 195-235, or amino acids 242-286 of SEQ ID NO: 19.

In another embodiment, a binding domain comprising a BoNT/C1 HA-33 β-trefoil domain comprises a 1β4/β5 hairpin turn of a β-trefoil domain of a BoNT/C1 HA-33, a 1β8/β9 hairpin turn of a β-trefoil domain of a BoNT/C1 HA-33, a 2β4/β5 hairpin turn of a β-trefoil domain of a BoNT/C1 HA-33 or a 2β8/β9 hairpin turn of a β-trefoil domain of a BoNT/C1 HA-33 of SEQ ID NO: 19. In another aspect of this embodiment, a binding domain comprising a BoNT/C1 HA-33 β-trefoil domain comprises amino acids 55-59, amino acids 99-102, amino acids 191-194, or amino acids 236-241 of SEQ ID NO: 19.

In other aspects of this embodiment, a binding domain comprising a BoNT/C1 HA-33 β-trefoil domain comprises a polypeptide having, e.g., at least 70% amino acid identity with amino acids 55-59, amino acids 99-102, amino acids 191-194, or amino acids 236-241 of SEQ ID NO: 19, at least 75% amino acid identity with amino acids 55-59, amino acids 99-102, amino acids 191-194, or amino acids 236-241 of SEQ ID NO: 19, at least 80% amino acid identity with amino acids 55-59, amino acids 99-102, amino acids 191-194, or amino acids 236-241 of SEQ ID NO: 19, at least 85% amino acid identity with amino acids 55-59, amino acids 99-102, amino acids 191-194, or amino acids 236-241 of SEQ ID NO: 19, at least 90% amino acid identity with amino acids 55-59, amino acids 99-102, amino acids 191-194, or amino acids 236-241 of SEQ ID NO: 19 or at least 95% amino acid identity with amino acids 55-59, amino acids 99-102, amino acids 191-194, or amino acids 236-241 of SEQ ID NO: 19. In yet other aspects of this embodiment, a binding domain comprising a BoNT/C1 HA-33 β-trefoil domain comprises a polypeptide having, e.g., at most 70% amino acid identity with amino acids 55-59, amino acids 99-102, amino acids 191-194, or amino acids 236-241 of SEQ ID NO: 19, at most 75% amino acid identity with amino acids 55-59, amino acids 99-102, amino acids 191-194, or amino acids 236-241 of SEQ ID NO: 19, at most 80% amino acid identity with amino acids 55-59, amino acids 99-102, amino acids 191-194, or amino acids 236-241 of SEQ ID NO: 19, at most 85% amino acid identity with amino acids 55-59, amino acids 99-102, amino acids 191-194, or amino acids 236-241 of SEQ ID NO: 19, at most 90% amino acid identity with amino acids 55-59, amino acids 99-102, amino acids 191-194, or amino acids 236-241 of SEQ ID NO: 19 or at most 95% amino acid identity with amino acids 55-59, amino acids 99-102, amino acids 191-194, or amino acids 236-241 of SEQ ID NO: 19.

In other aspects of this embodiment, a binding domain comprising a BoNT/C1 HA-33 β-trefoil domain comprises a polypeptide having, e.g., at most one, two, three or four non-contiguous amino acid substitutions relative to amino acids 55-59, amino acids 99-102, amino acids 191-194, or amino acids 236-241 of SEQ ID NO: 19. In other aspects of this embodiment, a binding domain comprising a BoNT/C1 HA-33 β-trefoil domain comprises a polypeptide having, e.g., at least one, two, three or four non-contiguous amino acid substitutions relative to amino acids 55-59, amino acids 99-102, amino acids 191-194, or amino acids 236-241 of SEQ ID NO: 19. In other aspects of this embodiment, a non-contiguous amino acid substitution of any amino acid from amino acids 55-59, amino acids 99-102, amino acids 191-194, or amino acids 236-241 of SEQ ID NO: 19 can be replaced with glycine. In other aspects of this embodiment, a non-contiguous amino acid substitution of any hydrophobic amino acid from amino acids 55-59, amino acids 99-102, amino acids 191-194, or amino acids 236-241 of SEQ ID NO: 19 can be replaced with phenylalanine. In yet other aspects of this embodiment, a β-trefoil domain with enhanced binding activity derived from a BoNT/C1 HA-33 comprises a polypeptide having, e.g., at most one, two, three or four non-contiguous amino acid deletions relative to amino acids 55-59, amino acids 99-102, amino acids 191-194, or amino acids 236-241 of SEQ ID NO: 19. In other aspects of this embodiment, a binding domain comprising a BoNT/C1 HA-33 β-trefoil domain comprises a polypeptide having, e.g., at least one, two, three or four non-contiguous amino acid deletions relative to amino acids 55-59, amino acids 99-102, amino acids 191-194, or amino acids 236-241 of SEQ ID NO: 19. In still other aspects of this embodiment, a binding domain comprising a BoNT/C1 HA-33 β-trefoil domain comprises a polypeptide having, e.g., at most one, two, three or four non-contiguous amino acid additions relative to amino acids 55-59, amino acids 99-102, amino acids 191-194, or amino acids 236-241 of SEQ ID NO: 19. In other aspects of this embodiment, a binding domain comprising a BoNT/C1 HA-33 β-trefoil domain comprises a polypeptide having, e.g., at least one, two, three or four non-contiguous amino acid additions relative to amino acids 55-59, amino acids 99-102, amino acids 191-194, or amino acids 236-241 of SEQ ID NO: 19.

In other aspects of this embodiment, a binding domain comprising a BoNT/C1 HA-33 β-trefoil domain comprises a polypeptide having, e.g., at most one, two, three or four contiguous amino acid substitutions relative to amino acids 55-59, amino acids 99-102, amino acids 191-194, or amino acids 236-241 of SEQ ID NO: 19. In other aspects of this embodiment, a binding domain comprising a BoNT/C1 HA-33 β-trefoil domain comprises a polypeptide having, e.g., at least one, two, three or four contiguous amino acid substitutions relative to amino acids 55-59, amino acids 99-102, amino acids 191-194, or amino acids 236-241 of SEQ ID NO: 19. In other aspects of this embodiment, contiguous amino acid substitutions of amino acids from amino acids 55-59, amino acids 99-102, amino acids 191-194, or amino acids 236-241 of SEQ ID NO: 19 can be replaced with glycine. In other aspects of this embodiment, contiguous amino acid substitutions of hydrophobic amino acids from amino acids 55-59, amino acids 99-102, amino acids 191-194, or amino acids 236-241 of SEQ ID NO: 19 can be replaced with phenylalanine. In yet other aspects of this embodiment, a binding domain comprising a BoNT/C1 HA-33 β-trefoil domain comprises a polypeptide having, e.g., at most one, two, three or four contiguous amino acid deletions relative to amino acids 55-59, amino acids 99-102, amino acids 191-194, or amino acids 236-241 of SEQ ID NO: 19. In other aspects of this embodiment, a binding domain comprising a BoNT/C1 HA-33 β-trefoil domain comprises a polypeptide having, e.g., at least one, two, three or four contiguous amino acid deletions relative to amino acids 55-59, amino acids 99-102, amino acids 191-194, or amino acids 236-241 of SEQ ID NO: 19. In still other aspects of this embodiment, a binding domain comprising a BoNT/C1 HA-33 β-trefoil domain comprises a polypeptide having, e.g., at most one, two, three or four contiguous amino acid additions relative to amino acids 55-59, amino acids 99-102, amino acids 191-194, or amino acids 236-241 of SEQ ID NO: 19. In other aspects of this embodiment, a binding domain comprising a BoNT/C1 HA-33 β-trefoil domain comprises a polypeptide having, e.g., at least one, two, three or four contiguous amino acid additions relative to amino acids 55-59, amino acids 99-102, amino acids 191-194, or amino acids 236-241 of SEQ ID NO: 19.

In another embodiment, a binding domain comprises a β-trefoil domain derived from a BoNT/D HA-33 of SEQ ID NO: 20. In another embodiment, a binding domain comprising a β-trefoil domain derived from a BoNT/D HA-33 comprises amino acids 10-141 or amino acids 148-286 of SEQ ID NO: 20. In another aspect of this embodiment, a binding domain comprising a β-trefoil domain derived from a BoNT/D HA-33 comprises a 1α-fold motif of a β-trefoil domain of a BoNT/D HA-33, a 1β-fold motif of a β-trefoil domain of a BoNT/D HA-33, a 1γ-fold motif of a β-trefoil domain of a BoNT/D HA-33, a 2α-fold motif of a β-trefoil domain of a BoNT/D HA-33, a 2α-fold motif of a β-trefoil domain of a BoNT/D HA-33, or a 2γ-fold motif of a β-trefoil domain of a BoNT/D HA-33 of SEQ ID NO: 20. In another aspect of this embodiment, a binding domain comprising a β-trefoil domain derived from a BoNT/D HA-33 comprises amino acids 10-54, amino acids 60-98, amino acids 103-141, amino acids 148-190, amino acids 195-235, or amino acids 242-286 of SEQ ID NO: 20.

In other aspects of this embodiment, a binding domain comprising a BoNT/D HA-33 β-trefoil domain comprises a polypeptide having, e.g., at least 70% amino acid identity with amino acids 10-54, amino acids 60-98, amino acids 103-141, amino acids 148-190, amino acids 195-235, or amino acids 242-286 of SEQ ID NO: 20, at least 75% amino acid identity with amino acids 10-54, amino acids 60-98, amino acids 103-141, amino acids 148-190, amino acids 195-235, or amino acids 242-286 of SEQ ID NO: 20, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-54, amino acids 60-98, amino acids 103-141, amino acids 148-190, amino acids 195-235, or amino acids 242-286 of SEQ ID NO: 20, at least 90% amino acid identity with amino acids 10-54, amino acids 60-98, amino acids 103-141, amino acids 148-190, amino acids 195-235, or amino acids 242-286 of SEQ ID NO: 20 or at least 95% amino acid identity with amino acids 10-54, amino acids 60-98, amino acids 103-141, amino acids 148-190, amino acids 195-235, or amino acids 242-286 of SEQ ID NO: 20. In yet other aspects of this embodiment, a binding domain comprising a BoNT/D HA-33 β-trefoil domain comprises a polypeptide having, e.g., at most 70% amino acid identity with amino acids 10-54, amino acids 60-98, amino acids 103-141, amino acids 148-190, amino acids 195-235, or amino acids 242-286 of SEQ ID NO: 20, at most 75% amino acid identity with amino acids 10-54, amino acids 60-98, amino acids 103-141, amino acids 148-190, amino acids 195-235, or amino acids 242-286 of SEQ ID NO: 20, at most 80% amino acid identity with amino acids 10-54, amino acids 60-98, amino acids 103-141, amino acids 148-190, amino acids 195-235, or amino acids 242-286 of SEQ ID NO: 20, at most 85% amino acid identity with amino acids 10-54, amino acids 60-98, amino acids 103-141, amino acids 148-190, amino acids 195-235, or amino acids 242-286 of SEQ ID NO: 20, at most 90% amino acid identity with amino acids 10-54, amino acids 60-98, amino acids 103-141, amino acids 148-190, amino acids 195-235, or amino acids 242-286 of SEQ ID NO: 20 or at most 95% amino acid identity with amino acids 10-54, amino acids 60-98, amino acids 103-141, amino acids 148-190, amino acids 195-235, or amino acids 242-286 of SEQ ID NO: 20.

In other aspects of this embodiment, a binding domain comprising a BoNT/D HA-33 β-trefoil domain comprises a polypeptide having, e.g., at most one, two, three, four, five, six, seven, eight, nine, 10 or 20 non-contiguous amino acid substitutions relative to amino acids 10-54, amino acids 60-98, amino acids 103-141, amino acids 148-190, amino acids 195-235, or amino acids 242-286 of SEQ ID NO: 20. In other aspects of this embodiment, a binding domain comprising a BoNT/D HA-33 β-trefoil domain comprises a polypeptide having, e.g., at least one, two, three, four, five, six, seven, eight, nine, 10 or 20 non-contiguous amino acid substitutions relative to amino acids 10-54, amino acids 60-98, amino acids 103-141, amino acids 148-190, amino acids 195-235, or amino acids 242-286 of SEQ ID NO: 20. In yet other aspects of this embodiment, a binding domain comprising a BoNT/D HA-33 β-trefoil domain comprises a polypeptide having, e.g., at most one, two, three, four, five, six, seven, eight, nine, 10 or 20 non-contiguous amino acid deletions relative to amino acids 10-54, amino acids 60-98, amino acids 103-141, amino acids 148-190, amino acids 195-235, or amino acids 242-286 of SEQ ID NO: 20. In other aspects of this embodiment, a binding domain comprising a BoNT/D HA-33 β-trefoil domain comprises a polypeptide having, e.g., at least one, two, three, four, five, six, seven, eight, nine, 10 or 20 non-contiguous amino acid deletions relative to amino acids 10-54, amino acids 60-98, amino acids 103-141, amino acids 148-190, amino acids 195-235, or amino acids 242-286 of SEQ ID NO: 20. In still other aspects of this embodiment, a binding domain comprising a BoNT/D HA-33 β-trefoil domain comprises a polypeptide having, e.g., at most one, two, three, four, five, six, seven, eight, nine, 10 or 20 non-contiguous amino acid additions relative to amino acids 10-54, amino acids 60-98, amino acids 103-141, amino acids 148-190, amino acids 195-235, or amino acids 242-286 of SEQ ID NO: 20. In other aspects of this embodiment, a binding domain comprising a BoNT/D HA-33 β-trefoil domain comprises a polypeptide having, e.g., at least one, two, three, four, five, six, seven, eight, nine, 10 or 20 non-contiguous amino acid additions relative to amino acids 10-54, amino acids 60-98, amino acids 103-141, amino acids 148-190, amino acids 195-235, or amino acids 242-286 of SEQ ID NO: 20.

In other aspects of this embodiment, a binding domain comprising a BoNT/D HA-33 β-trefoil domain comprises a polypeptide having, e.g., at most one, two, three, four, five, six, seven, eight, nine, 10 or 20 contiguous amino acid substitutions relative to amino acids 10-54, amino acids 60-98, amino acids 103-141, amino acids 148-190, amino acids 195-235, or amino acids 242-286 of SEQ ID NO: 20. In other aspects of this embodiment, a binding domain comprising a BoNT/D HA-33 β-trefoil domain comprises a polypeptide having, e.g., at least one, two, three, four, five, six, seven, eight, nine, 10 or 20 contiguous amino acid substitutions relative to amino acids 10-54, amino acids 60-98, amino acids 103-141, amino acids 148-190, amino acids 195-235, or amino acids 242-286 of SEQ ID NO: 20. In yet other aspects of this embodiment, a binding domain comprising a BoNT/D HA-33 β-trefoil domain comprises a polypeptide having, e.g., at most one, two, three, four, five, six, seven, eight, nine, 10 or 20 contiguous amino acid deletions relative to amino acids 10-54, amino acids 60-98, amino acids 103-141, amino acids 148-190, amino acids 195-235, or amino acids 242-286 of SEQ ID NO: 20. In other aspects of this embodiment, a binding domain comprising a BoNT/D HA-33 β-trefoil domain comprises a polypeptide having, e.g., at least one, two, three, four, five, six, seven, eight, nine, 10 or 20 contiguous amino acid deletions relative to amino acids 10-54, amino acids 60-98, amino acids 103-141, amino acids 148-190, amino acids 195-235, or amino acids 242-286 of SEQ ID NO: 20. In still other aspects of this embodiment, a binding domain comprising a BoNT/D HA-33 β-trefoil domain comprises a polypeptide having, e.g., at most one, two, three, four, five, six, seven, eight, nine, 10 or 20 contiguous amino acid additions relative to amino acids 10-54, amino acids 60-98, amino acids 103-141, amino acids 148-190, amino acids 195-235, or amino acids 242-286 of SEQ ID NO: 20. In other aspects of this embodiment, a binding domain comprising a BoNT/D HA-33 β-trefoil domain comprises a polypeptide having, e.g., at least one, two, three, four, five, six, seven, eight, nine, 10 or 20 contiguous amino acid additions relative to amino acids 10-54, amino acids 60-98, amino acids 103-141, amino acids 148-190, amino acids 195-235, or amino acids 242-286 of SEQ ID NO: 20.

In another embodiment, a binding domain comprising a BoNT/D HA-33 β-trefoil domain comprises a 1β4/β5 hairpin turn of a β-trefoil domain of a BoNT/D HA-33, a 1β8/β9 hairpin turn of a β-trefoil domain of a BoNT/D HA-33, a 2β4/β5 hairpin turn of a β-trefoil domain of a BoNT/D HA-33 or a 2β8/β9 hairpin turn of a β-trefoil domain of a BoNT/D HA-33 of SEQ ID NO: 20. In another aspect of this embodiment, a binding domain comprising a BoNT/D HA-33 β-trefoil domain comprises amino acids 55-59, amino acids 99-102, amino acids 191-194, or amino acids 236-241 of SEQ ID NO: 20.

In other aspects of this embodiment, a binding domain comprising a BoNT/D HA-33 β-trefoil domain comprises a polypeptide having, e.g., at least 70% amino acid identity with amino acids 55-59, amino acids 99-102, amino acids 191-194, or amino acids 236-241 of SEQ ID NO: 20, at least 75% amino acid identity with amino acids 55-59, amino acids 99-102, amino acids 191-194, or amino acids 236-241 of SEQ ID NO: 20, at least 80% amino acid identity with amino acids 55-59, amino acids 99-102, amino acids 191-194, or amino acids 236-241 of SEQ ID NO: 20, at least 85% amino acid identity with amino acids 55-59, amino acids 99-102, amino acids 191-194, or amino acids 236-241 of SEQ ID NO: 20, at least 90% amino acid identity with amino acids 55-59, amino acids 99-102, amino acids 191-194, or amino acids 236-241 of SEQ ID NO: 20 or at least 95% amino acid identity with amino acids 55-59, amino acids 99-102, amino acids 191-194, or amino acids 236-241 of SEQ ID NO: 20. In yet other aspects of this embodiment, a binding domain comprising a BoNT/D HA-33 β-trefoil domain comprises a polypeptide having, e.g., at most 70% amino acid identity with amino acids 55-59, amino acids 99-102, amino acids 191-194, or amino acids 236-241 of SEQ ID NO: 20, at most 75% amino acid identity with amino acids 55-59, amino acids 99-102, amino acids 191-194, or amino acids 236-241 of SEQ ID NO: 20, at most 80% amino acid identity with amino acids 55-59, amino acids 99-102, amino acids 191-194, or amino acids 236-241 of SEQ ID NO: 20, at most 85% amino acid identity with amino acids 55-59, amino acids 99-102, amino acids 191-194, or amino acids 236-241 of SEQ ID NO: 20, at most 90% amino acid identity with amino acids 55-59, amino acids 99-102, amino acids 191-194, or amino acids 236-241 of SEQ ID NO: 20 or at most 95% amino acid identity with amino acids 55-59, amino acids 99-102, amino acids 191-194, or amino acids 236-241 of SEQ ID NO: 20.

In other aspects of this embodiment, a binding domain comprising a BoNT/D HA-33 β-trefoil domain comprises a polypeptide having, e.g., at most one, two, three or four non-contiguous amino acid substitutions relative to amino acids 55-59, amino acids 99-102, amino acids 191-194, or amino acids 236-241 of SEQ ID NO: 20. In other aspects of this embodiment, a binding domain comprising a BoNT/D HA-33 β-trefoil domain comprises a polypeptide having, e.g., at least one, two, three or four non-contiguous amino acid substitutions relative to amino acids 55-59, amino acids 99-102, amino acids 191-194, or amino acids 236-241 of SEQ ID NO: 20. In other aspects of this embodiment, a non-contiguous amino acid substitution of any amino acid from amino acids 55-59, amino acids 99-102, amino acids 191-194, or amino acids 236-241 of SEQ ID NO: 20 can be replaced with glycine. In other aspects of this embodiment, a non-contiguous amino acid substitution of any hydrophobic amino acid from amino acids 55-59, amino acids 99-102, amino acids 191-194, or amino acids 236-241 of SEQ ID NO: 20 can be replaced with phenylalanine. In yet other aspects of this embodiment, a β-trefoil domain with enhanced binding activity derived from a BoNT/D HA-33 comprises a polypeptide having, e.g., at most one, two, three or four non-contiguous amino acid deletions relative to amino acids 55-59, amino acids 99-102, amino acids 191-194, or amino acids 236-241 of SEQ ID NO: 20. In other aspects of this embodiment, a binding domain comprising a BoNT/D HA-33 β-trefoil domain comprises a polypeptide having, e.g., at least one, two, three or four non-contiguous amino acid deletions relative to amino acids 55-59, amino acids 99-102, amino acids 191-194, or amino acids 236-241 of SEQ ID NO: 20. In still other aspects of this embodiment, a binding domain comprising a BoNT/D HA-33 β-trefoil domain comprises a polypeptide having, e.g., at most one, two, three or four non-contiguous amino acid additions relative to amino acids 55-59, amino acids 99-102, amino acids 191-194, or amino acids 236-241 of SEQ ID NO: 20. In other aspects of this embodiment, a binding domain comprising a BoNT/D HA-33 β-trefoil domain comprises a polypeptide having, e.g., at least one, two, three or four non-contiguous amino acid additions relative to amino acids 55-59, amino acids 99-102, amino acids 191-194, or amino acids 236-241 of SEQ ID NO: 20.

In other aspects of this embodiment, a binding domain comprising a BoNT/D HA-33 β-trefoil domain comprises a polypeptide having, e.g., at most one, two, three or four contiguous amino acid substitutions relative to amino acids 55-59, amino acids 99-102, amino acids 191-194, or amino acids 236-241 of SEQ ID NO: 20. In other aspects of this embodiment, a binding domain comprising a BoNT/D HA-33 β-trefoil domain comprises a polypeptide having, e.g., at least one, two, three or four contiguous amino acid substitutions relative to amino acids 55-59, amino acids 99-102, amino acids 191-194, or amino acids 236-241 of SEQ ID NO: 20. In other aspects of this embodiment, contiguous amino acid substitutions of amino acids from amino acids 55-59, amino acids 99-102, amino acids 191-194, or amino acids 236-241 of SEQ ID NO: 20 can be replaced with glycine. In other aspects of this embodiment, contiguous amino acid substitutions of hydrophobic amino acids from amino acids 55-59, amino acids 99-102, amino acids 191-194, or amino acids 236-241 of SEQ ID NO: 20 can be replaced with phenylalanine. In yet other aspects of this embodiment, a binding domain comprising a BoNT/D HA-33 β-trefoil domain comprises a polypeptide having, e.g., at most one, two, three or four contiguous amino acid deletions relative to amino acids 55-59, amino acids 99-102, amino acids 191-194, or amino acids 236-241 of SEQ ID NO: 20. In other aspects of this embodiment, a binding domain comprising a BoNT/D HA-33 β-trefoil domain comprises a polypeptide having, e.g., at least one, two, three or four contiguous amino acid deletions relative to amino acids 55-59, amino acids 99-102, amino acids 191-194, or amino acids 236-241 of SEQ ID NO: 20. In still other aspects of this embodiment, a binding domain comprising a BoNT/D HA-33 β-trefoil domain comprises a polypeptide having, e.g., at most one, two, three or four contiguous amino acid additions relative to amino acids 55-59, amino acids 99-102, amino acids 191-194, or amino acids 236-241 of SEQ ID NO: 20. In other aspects of this embodiment, a binding domain comprising a BoNT/D HA-33 β-trefoil domain comprises a polypeptide having, e.g., at least one, two, three or four contiguous amino acid additions relative to amino acids 55-59, amino acids 99-102, amino acids 191-194, or amino acids 236-241 of SEQ ID NO: 20.

In another embodiment, a binding domain comprises a β-trefoil domain derived from a Clostridial HA-17. In an aspect of this embodiment, a β-trefoil domain derived from a Clostridial HA-17 comprises, e.g., a β-trefoil domain derived from a BoNT/A HA-17, a β-trefoil domain derived from a BoNT/B HA-17, a β-trefoil domain derived from a BoNT/C1 HA-17 or a β-trefoil domain derived from a BoNT/D HA-17. In another aspect of this embodiment, a β-trefoil domain derived from a Clostridial HA-17 comprises an α-fold motif of a β-trefoil domain of a BoNT/A HA-17, a β-fold motif of a β-trefoil domain of a BoNT/A HA-17, or a γ-fold motif of a β-trefoil domain of a BoNT/A HA-17. In another aspect of this embodiment, a β-trefoil domain derived from a Clostridial HA-17 comprises an α-fold motif of a β-trefoil domain of a BoNT/B HA-17, a β-fold motif of a β-trefoil domain of a BoNT/B HA-17, or a γ-fold motif of a β-trefoil domain of a BoNT/B HA-17. In another aspect of this embodiment, a β-trefoil domain derived from a Clostridial HA-17 comprises an α-fold motif of a β-trefoil domain of a BoNT/C1 HA-17, a β-fold motif of a β-trefoil domain of a BoNT/C1 HA-17, or a γ-fold motif of a β-trefoil domain of a BoNT/C1 HA-17. In another aspect of this embodiment, a β-trefoil domain derived from a Clostridial HA-17 comprises an α-fold motif of a β-trefoil domain of a BoNT/D HA-17, a β-fold motif of a β-trefoil domain of a BoNT/D HA-17, or a γ-fold motif of a β-trefoil domain of a BoNT/D HA-17.

In another embodiment, a binding domain comprises a β-trefoil domain derived from a BoNT/A HA-17 of SEQ ID NO: 21. In another embodiment, a binding domain comprising a β-trefoil domain derived from a BoNT/A HA-17 comprises amino acids 9-146 of SEQ ID NO: 21. In another aspect of this embodiment, a binding domain comprising a β-trefoil domain derived from a BoNT/A HA-17 comprises a α-fold motif of a β-trefoil domain of a BoNT/A HA-17, a β-fold motif of a β-trefoil domain of a BoNT/A HA-17 or a γ-fold motif of a β-trefoil domain of a BoNT/A HA-17 of SEQ ID NO: 21. In another aspect of this embodiment, a β-trefoil domain derived from a BoNT/A HA-17 comprises amino acids 9-50, amino acids 55-91, or amino acids 95-146 of SEQ ID NO: 21.

In other aspects of this embodiment, a binding domain comprising a BoNT/A HA-17 β-trefoil domain comprises a polypeptide having, e.g., at least 70% amino acid identity with amino acids 9-50, amino acids 55-91, or amino acids 95-146 of SEQ ID NO: 21, at least 75% amino acid identity with amino acids 9-50, amino acids 55-91, or amino acids 95-146 of SEQ ID NO: 21, at least 80% amino acid identity with amino acids 9-50, amino acids 55-91, or amino acids 95-146 of SEQ ID NO: 21, at least 85% amino acid identity with amino acids 9-50, amino acids 55-91, or amino acids 95-146 of SEQ ID NO: 21, at least 90% amino acid identity with amino acids 9-50, amino acids 55-91, or amino acids 95-146 of SEQ ID NO: 21 or at least 95% amino acid identity with amino acids 9-50, amino acids 55-91, or amino acids 95-146 of SEQ ID NO: 21. In yet other aspects of this embodiment, a binding domain comprising a BoNT/A HA-17 β-trefoil domain comprises a polypeptide having, e.g., at most 70% amino acid identity with amino acids 9-50, amino acids 55-91, or amino acids 95-146 of SEQ ID NO: 21, at most 75% amino acid identity with amino acids 9-50, amino acids 55-91, or amino acids 95-146 of SEQ ID NO: 21, at most 80% amino acid identity with amino acids 9-50, amino acids 55-91, or amino acids 95-146 of SEQ ID NO: 21, at most 85% amino acid identity with amino acids 9-50, amino acids 55-91, or amino acids 95-146 of SEQ ID NO: 21, at most 90% amino acid identity with amino acids 9-50, amino acids 55-91, or amino acids 95-146 of SEQ ID NO: 21 or at most 95% amino acid identity with amino acids 9-50, amino acids 55-91, or amino acids 95-146 of SEQ ID NO: 21.

In other aspects of this embodiment, a binding domain comprising a BoNT/A HA-17 β-trefoil domain comprises a polypeptide having, e.g., at most one, two, three, four, five, six, seven, eight, nine, 10 or 20 non-contiguous amino acid substitutions relative to amino acids 9-50, amino acids 55-91, or amino acids 95-146 of SEQ ID NO: 21. In other aspects of this embodiment, a binding domain comprising a BoNT/A HA-17 β-trefoil domain comprises a polypeptide having, e.g., at least one, two, three, four, five, six, seven, eight, nine, 10 or 20 non-contiguous amino acid substitutions relative to amino acids 9-50, amino acids 55-91, or amino acids 95-146 of SEQ ID NO: 21. In yet other aspects of this embodiment, a binding domain comprising a BoNT/A HA-17 β-trefoil domain comprises a polypeptide having, e.g., at most one, two, three, four, five, six, seven, eight, nine, 10 or 20 non-contiguous amino acid deletions relative to amino acids 9-50, amino acids 55-91, or amino acids 95-146 of SEQ ID NO: 21. In other aspects of this embodiment, a binding domain comprising a BoNT/A HA-17 β-trefoil domain comprises a polypeptide having, e.g., at least one, two, three, four, five, six, seven, eight, nine, 10 or 20 non-contiguous amino acid deletions relative to amino acids 9-50, amino acids 55-91, or amino acids 95-146 of SEQ ID NO: 21. In still other aspects of this embodiment, a binding domain comprising a BoNT/A HA-17 β-trefoil domain comprises a polypeptide having, e.g., at most one, two, three, four, five, six, seven, eight, nine, 10 or 20 non-contiguous amino acid additions relative to amino acids 9-50, amino acids 55-91, or amino acids 95-146 of SEQ ID NO: 21. In other aspects of this embodiment, a binding domain comprising a BoNT/A HA-17 β-trefoil domain comprises a polypeptide having, e.g., at least one, two, three, four, five, six, seven, eight, nine, 10 or 20 non-contiguous amino acid additions relative to amino acids 9-50, amino acids 55-91, or amino acids 95-146 of SEQ ID NO: 21.

In other aspects of this embodiment, a binding domain comprising a BoNT/A HA-17 β-trefoil domain comprises a polypeptide having, e.g., at most one, two, three, four, five, six, seven, eight, nine, 10 or 20 contiguous amino acid substitutions relative to amino acids 9-50, amino acids 55-91, or amino acids 95-146 of SEQ ID NO: 21. In other aspects of this embodiment, a binding domain comprising a BoNT/A HA-17 β-trefoil domain comprises a polypeptide having, e.g., at least one, two, three, four, five, six, seven, eight, nine, 10 or 20 contiguous amino acid substitutions relative to amino acids 9-50, amino acids 55-91, or amino acids 95-146 of SEQ ID NO: 21. In yet other aspects of this embodiment, a binding domain comprising a BoNT/A HA-17 β-trefoil domain comprises a polypeptide having, e.g., at most one, two, three, four, five, six, seven, eight, nine, 10 or 20 contiguous amino acid deletions relative to amino acids 9-50, amino acids 55-91, or amino acids 95-146 of SEQ ID NO: 21. In other aspects of this embodiment, a binding domain comprising a BoNT/A HA-17 β-trefoil domain comprises a polypeptide having, e.g., at least one, two, three, four, five, six, seven, eight, nine, 10 or 20 contiguous amino acid deletions relative to amino acids 9-50, amino acids 55-91, or amino acids 95-146 of SEQ ID NO: 21. In still other aspects of this embodiment, a binding domain comprising a BoNT/A HA-17 β-trefoil domain comprises a polypeptide having, e.g., at most one, two, three, four, five, six, seven, eight, nine, 10 or 20 contiguous amino acid additions relative to amino acids 9-50, amino acids 55-91, or amino acids 95-146 of SEQ ID NO: 21. In other aspects of this embodiment, a binding domain comprising a BoNT/A HA-17 β-trefoil domain comprises a polypeptide having, e.g., at least one, two, three, four, five, six, seven, eight, nine, 10 or 20 contiguous amino acid additions relative to amino acids 9-50, amino acids 55-91, or amino acids 95-146 of SEQ ID NO: 21.

In another embodiment, a binding domain comprising a BoNT/A HA-17 β-trefoil domain comprises a β4/β5 hairpin turn of a β-trefoil domain of a BoNT/A HA-17 or a β8/β9 hairpin turn of a β-trefoil domain of a BoNT/A HA-17 of SEQ ID NO: 21. In another aspect of this embodiment, a binding domain comprising a BoNT/A HA-17 β-trefoil domain comprises amino acids 51-54 or amino acids 92-94 of SEQ ID NO: 21.

In other aspects of this embodiment, a binding domain comprising a BoNT/A HA-17 β-trefoil domain comprises a polypeptide having, e.g., at least 70% amino acid identity with amino acids 51-54 or amino acids 92-94 of SEQ ID NO: 21, at least 75% amino acid identity with amino acids 51-54 or amino acids 92-94 of SEQ ID NO: 21, at least 80% amino acid identity with amino acids 51-54 or amino acids 92-94 of SEQ ID NO: 21, at least 85% amino acid identity with amino acids 51-54 or amino acids 92-94 of SEQ ID NO: 21, at least 90% amino acid identity with amino acids 51-54 or amino acids 92-94 of SEQ ID NO: 21 or at least 95% amino acid identity with amino acids 51-54 or amino acids 92-94 of SEQ ID NO: 21. In yet other aspects of this embodiment, a binding domain comprising a BoNT/A HA-17 β-trefoil domain comprises a polypeptide having, e.g., at most 70% amino acid identity with amino acids 51-54 or amino acids 92-94 of SEQ ID NO: 21, at most 75% amino acid identity with amino acids 51-54 or amino acids 92-94 of SEQ ID NO: 21, at most 80% amino acid identity with amino acids 51-54 or amino acids 92-94 of SEQ ID NO: 21, at most 85% amino acid identity with amino acids 51-54 or amino acids 92-94 of SEQ ID NO: 21, at most 90% amino acid identity with amino acids 51-54 or amino acids 92-94 of SEQ ID NO: 21 or at most 95% amino acid identity with amino acids 51-54 or amino acids 92-94 of SEQ ID NO: 21.

In other aspects of this embodiment, a binding domain comprising a BoNT/A HA-17 β-trefoil domain comprises a polypeptide having, e.g., at most one, two, three or four non-contiguous amino acid substitutions relative to amino acids 51-54 or amino acids 92-94 of SEQ ID NO: 21. In other aspects of this embodiment, a binding domain comprising a BoNT/A HA-17 β-trefoil domain comprises a polypeptide having, e.g., at least one, two, three or four non-contiguous amino acid substitutions relative to amino acids 51-54 or amino acids 92-94 of SEQ ID NO: 21. In other aspects of this embodiment, a non-contiguous amino acid substitution of any amino acid from amino acids 51-54 or amino acids 92-94 of SEQ ID NO: 21 can be replaced with glycine. In other aspects of this embodiment, a non-contiguous amino acid substitution of any hydrophobic amino acid from amino acids 51-54 or amino acids 92-94 of SEQ ID NO: 21 can be replaced with phenylalanine. In yet other aspects of this embodiment, a binding domain comprising a BoNT/A HA-17 β-trefoil domain comprises a polypeptide having, e.g., at most one, two, three or four non-contiguous amino acid deletions relative to amino acids 51-54 or amino acids 92-94 of SEQ ID NO: 21. In other aspects of this embodiment, a binding domain comprising a BoNT/A HA-17 β-trefoil domain comprises a polypeptide having, e.g., at least one, two, three or four non-contiguous amino acid deletions relative to amino acids 51-54 or amino acids 92-94 of SEQ ID NO: 21. In still other aspects of this embodiment, a binding domain comprising a BoNT/A HA-17 β-trefoil domain comprises a polypeptide having, e.g., at most one, two, three or four non-contiguous amino acid additions relative to amino acids 51-54 or amino acids 92-94 of SEQ ID NO: 21. In other aspects of this embodiment, a binding domain comprising a BoNT/A HA-17 β-trefoil domain comprises a polypeptide having, e.g., at least one, two, three or four non-contiguous amino acid additions relative to amino acids 51-54 or amino acids 92-94 of SEQ ID NO: 21.

In other aspects of this embodiment, a binding domain comprising a BoNT/A HA-17 β-trefoil domain comprises a polypeptide having, e.g., at most one, two, three or four contiguous amino acid substitutions relative to amino acids 51-54 or amino acids 92-94 of SEQ ID NO: 21. In other aspects of this embodiment, a binding domain comprising a BoNT/A HA-17 β-trefoil domain comprises a polypeptide having, e.g., at least one, two, three or four contiguous amino acid substitutions relative to amino acids 51-54 or amino acids 92-94 of SEQ ID NO: 21. In other aspects of this embodiment, contiguous amino acid substitutions of amino acids from amino acids 51-54 or amino acids 92-94 of SEQ ID NO: 21 can be replaced with glycine. In other aspects of this embodiment, contiguous amino acid substitutions of hydrophobic amino acids from amino acids 51-54 or amino acids 92-94 of SEQ ID NO: 21 can be replaced with phenylalanine. In yet other aspects of this embodiment, a β-trefoil domain with enhanced binding activity derived from a BoNT/A HA-17 comprises a polypeptide having, e.g., at most one, two, three or four contiguous amino acid deletions relative to amino acids 51-54 or amino acids 92-94 of SEQ ID NO: 21. In other aspects of this embodiment, a binding domain comprising a BoNT/A HA-17 β-trefoil domain comprises a polypeptide having, e.g., at least one, two, three or four contiguous amino acid deletions relative to amino acids 51-54 or amino acids 92-94 of SEQ ID NO: 21. In still other aspects of this embodiment, a binding domain comprising a BoNT/A HA-17 β-trefoil domain comprises a polypeptide having, e.g., at most one, two, three or four contiguous amino acid additions relative to amino acids 51-54 or amino acids 92-94 of SEQ ID NO: 21. In other aspects of this embodiment, a binding domain comprising a BoNT/A HA-17 β-trefoil domain comprises a polypeptide having, e.g., at least one, two, three or four contiguous amino acid additions relative to amino acids 51-54 or amino acids 92-94 of SEQ ID NO: 21.

In another embodiment, a binding domain comprises a β-trefoil domain derived from a BoNT/B HA-17 of SEQ ID NO: 22. In another embodiment, a binding domain comprising a β-trefoil domain derived from a BoNT/B HA-17 comprises amino acids 9-146 of SEQ ID NO: 22. In another aspect of this embodiment, a binding domain comprising a β-trefoil domain derived from a BoNT/B HA-17 comprises a α-fold motif of a β-trefoil domain of a BoNT/B HA-17, a β-fold motif of a β-trefoil domain of a BoNT/B HA-17 or a γ-fold motif of a β-trefoil domain of a BoNT/B HA-17 of SEQ ID NO: 22. In another aspect of this embodiment, a β-trefoil domain derived from a BoNT/B HA-17 comprises amino acids 9-50, amino acids 55-91, or amino acids 95-146 of SEQ ID NO: 22.

In other aspects of this embodiment, a binding domain comprising a BoNT/B HA-17 β-trefoil domain comprises a polypeptide having, e.g., at least 70% amino acid identity with amino acids 9-50, amino acids 55-91, or amino acids 95-146 of SEQ ID NO: 22, at least 75% amino acid identity with amino acids 9-50, amino acids 55-91, or amino acids 95-146 of SEQ ID NO: 22, at least 80% amino acid identity with amino acids 9-50, amino acids 55-91, or amino acids 95-146 of SEQ ID NO: 22, at least 85% amino acid identity with amino acids 9-50, amino acids 55-91, or amino acids 95-146 of SEQ ID NO: 22, at least 90% amino acid identity with amino acids 9-50, amino acids 55-91, or amino acids 95-146 of SEQ ID NO: 22 or at least 95% amino acid identity with amino acids 9-50, amino acids 55-91, or amino acids 95-146 of SEQ ID NO: 22. In yet other aspects of this embodiment, a binding domain comprising a BoNT/B HA-17 β-trefoil domain comprises a polypeptide having, e.g., at most 70% amino acid identity with amino acids 9-50, amino acids 55-91, or amino acids 95-146 of SEQ ID NO: 22, at most 75% amino acid identity with amino acids 9-50, amino acids 55-91, or amino acids 95-146 of SEQ ID NO: 22, at most 80% amino acid identity with amino acids 9-50, amino acids 55-91, or amino acids 95-146 of SEQ ID NO: 22, at most 85% amino acid identity with amino acids 9-50, amino acids 55-91, or amino acids 95-146 of SEQ ID NO: 22, at most 90% amino acid identity with amino acids 9-50, amino acids 55-91, or amino acids 95-146 of SEQ ID NO: 22 or at most 95% amino acid identity with amino acids 9-50, amino acids 55-91, or amino acids 95-146 of SEQ ID NO: 22.

In other aspects of this embodiment, a binding domain comprising a BoNT/B HA-17 β-trefoil domain comprises a polypeptide having, e.g., at most one, two, three, four, five, six, seven, eight, nine, 10 or 20 non-contiguous amino acid substitutions relative to amino acids 9-50, amino acids 55-91, or amino acids 95-146 of SEQ ID NO: 22. In other aspects of this embodiment, a binding domain comprising a BoNT/B HA-17 β-trefoil domain comprises a polypeptide having, e.g., at least one, two, three, four, five, six, seven, eight, nine, 10 or 20 non-contiguous amino acid substitutions relative to amino acids 9-50, amino acids 55-91, or amino acids 95-146 of SEQ ID NO: 22. In yet other aspects of this embodiment, a binding domain comprising a BoNT/B HA-17 β-trefoil domain comprises a polypeptide having, e.g., at most one, two, three, four, five, six, seven, eight, nine, 10 or 20 non-contiguous amino acid deletions relative to amino acids 9-50, amino acids 55-91, or amino acids 95-146 of SEQ ID NO: 22. In other aspects of this embodiment, a binding domain comprising a BoNT/B HA-17 β-trefoil domain comprises a polypeptide having, e.g., at least one, two, three, four, five, six, seven, eight, nine, 10 or 20 non-contiguous amino acid deletions relative to amino acids 9-50, amino acids 55-91, or amino acids 95-146 of SEQ ID NO: 22. In still other aspects of this embodiment, a binding domain comprising a BoNT/B HA-17 β-trefoil domain comprises a polypeptide having, e.g., at most one, two, three, four, five, six, seven, eight, nine, 10 or 20 non-contiguous amino acid additions relative to amino acids 9-50, amino acids 55-91, or amino acids 95-146 of SEQ ID NO: 22. In other aspects of this embodiment, a binding domain comprising a BoNT/B HA-17 β-trefoil domain comprises a polypeptide having, e.g., at least one, two, three, four, five, six, seven, eight, nine, 10 or 20 non-contiguous amino acid additions relative to amino acids 9-50, amino acids 55-91, or amino acids 95-146 of SEQ ID NO: 22.

In other aspects of this embodiment, a binding domain comprising a BoNT/B HA-17 β-trefoil domain comprises a polypeptide having, e.g., at most one, two, three, four, five, six, seven, eight, nine, 10 or 20 contiguous amino acid substitutions relative to amino acids 9-50, amino acids 55-91, or amino acids 95-146 of SEQ ID NO: 22. In other aspects of this embodiment, a binding domain comprising a BoNT/B HA-17 β-trefoil domain comprises a polypeptide having, e.g., at least one, two, three, four, five, six, seven, eight, nine, 10 or 20 contiguous amino acid substitutions relative to amino acids 9-50, amino acids 55-91, or amino acids 95-146 of SEQ ID NO: 22. In yet other aspects of this embodiment, a binding domain comprising a BoNT/B HA-17 β-trefoil domain comprises a polypeptide having, e.g., at most one, two, three, four, five, six, seven, eight, nine, 10 or 20 contiguous amino acid deletions relative to amino acids 9-50, amino acids 55-91, or amino acids 95-146 of SEQ ID NO: 22. In other aspects of this embodiment, a binding domain comprising a BoNT/B HA-17 β-trefoil domain comprises a polypeptide having, e.g., at least one, two, three, four, five, six, seven, eight, nine, 10 or 20 contiguous amino acid deletions relative to amino acids 9-50, amino acids 55-91, or amino acids 95-146 of SEQ ID NO: 22. In still other aspects of this embodiment, a binding domain comprising a BoNT/B HA-17 β-trefoil domain comprises a polypeptide having, e.g., at most one, two, three, four, five, six, seven, eight, nine, 10 or 20 contiguous amino acid additions relative to amino acids 9-50, amino acids 55-91, or amino acids 95-146 of SEQ ID NO: 22. In other aspects of this embodiment, a binding domain comprising a BoNT/B HA-17 β-trefoil domain comprises a polypeptide having, e.g., at least one, two, three, four, five, six, seven, eight, nine, 10 or 20 contiguous amino acid additions relative to amino acids 9-50, amino acids 55-91, or amino acids 95-146 of SEQ ID NO: 22.

In another embodiment, a binding domain comprising a BoNT/B HA-17 β-trefoil domain comprises a β4/β5 hairpin turn of a β-trefoil domain of a BoNT/B HA-17 or a β8/β9 hairpin turn of a β-trefoil domain of a BoNT/B HA-17 of SEQ ID NO: 22. In another aspect of this embodiment, a binding domain comprising a BoNT/B HA-17 β-trefoil domain comprises amino acids 51-54 or amino acids 92-94 of SEQ ID NO: 22.

In other aspects of this embodiment, a binding domain comprising a BoNT/B HA-17 β-trefoil domain comprises a polypeptide having, e.g., at least 70% amino acid identity with amino acids 51-54 or amino acids 92-94 of SEQ ID NO: 22, at least 75% amino acid identity with amino acids 51-54 or amino acids 92-94 of SEQ ID NO: 22, at least 80% amino acid identity with amino acids 51-54 or amino acids 92-94 of SEQ ID NO: 22, at least 85% amino acid identity with amino acids 51-54 or amino acids 92-94 of SEQ ID NO: 22, at least 90% amino acid identity with amino acids 51-54 or amino acids 92-94 of SEQ ID NO: 22 or at least 95% amino acid identity with amino acids 51-54 or amino acids 92-94 of SEQ ID NO: 22. In yet other aspects of this embodiment, a binding domain comprising a BoNT/B HA-17 β-trefoil domain comprises a polypeptide having, e.g., at most 70% amino acid identity with amino acids 51-54 or amino acids 92-94 of SEQ ID NO: 22, at most 75% amino acid identity with amino acids 51-54 or amino acids 92-94 of SEQ ID NO: 22, at most 80% amino acid identity with amino acids 51-54 or amino acids 92-94 of SEQ ID NO: 22, at most 85% amino acid identity with amino acids 51-54 or amino acids 92-94 of SEQ ID NO: 22, at most 90% amino acid identity with amino acids 51-54 or amino acids 92-94 of SEQ ID NO: 22 or at most 95% amino acid identity with amino acids 51-54 or amino acids 92-94 of SEQ ID NO: 22.

In other aspects of this embodiment, a binding domain comprising a BoNT/B HA-17 β-trefoil domain comprises a polypeptide having, e.g., at most one, two, three or four non-contiguous amino acid substitutions relative to amino acids 51-54 or amino acids 92-94 of SEQ ID NO: 22. In other aspects of this embodiment, a binding domain comprising a BoNT/B HA-17 β-trefoil domain comprises a polypeptide having, e.g., at least one, two, three or four non-contiguous amino acid substitutions relative to amino acids 51-54 or amino acids 92-94 of SEQ ID NO: 22. In other aspects of this embodiment, a non-contiguous amino acid substitution of any amino acid from amino acids 51-54 or amino acids 92-94 of SEQ ID NO: 22 can be replaced with glycine. In other aspects of this embodiment, a non-contiguous amino acid substitution of any hydrophobic amino acid from amino acids 51-54 or amino acids 92-94 of SEQ ID NO: 22 can be replaced with phenylalanine. In yet other aspects of this embodiment, a binding domain comprising a BoNT/B HA-17 β-trefoil domain comprises a polypeptide having, e.g., at most one, two, three or four non-contiguous amino acid deletions relative to amino acids 51-54 or amino acids 92-94 of SEQ ID NO: 22. In other aspects of this embodiment, a binding domain comprising a BoNT/B HA-17 β-trefoil domain comprises a polypeptide having, e.g., at least one, two, three or four non-contiguous amino acid deletions relative to amino acids 51-54 or amino acids 92-94 of SEQ ID NO: 22. In still other aspects of this embodiment, a binding domain comprising a BoNT/B HA-17 β-trefoil domain comprises a polypeptide having, e.g., at most one, two, three or four non-contiguous amino acid additions relative to amino acids 51-54 or amino acids 92-94 of SEQ ID NO: 22. In other aspects of this embodiment, a binding domain comprising a BoNT/B HA-17 β-trefoil domain comprises a polypeptide having, e.g., at least one, two, three or four non-contiguous amino acid additions relative to amino acids 51-54 or amino acids 92-94 of SEQ ID NO: 22.

In other aspects of this embodiment, a binding domain comprising a BoNT/B HA-17 β-trefoil domain comprises a polypeptide having, e.g., at most one, two, three or four contiguous amino acid substitutions relative to amino acids 51-54 or amino acids 92-94 of SEQ ID NO: 22. In other aspects of this embodiment, a binding domain comprising a BoNT/B HA-17 β-trefoil domain comprises a polypeptide having, e.g., at least one, two, three or four contiguous amino acid substitutions relative to amino acids 51-54 or amino acids 92-94 of SEQ ID NO: 22. In other aspects of this embodiment, contiguous amino acid substitutions of amino acids from amino acids 51-54 or amino acids 92-94 of SEQ ID NO: 22 can be replaced with glycine. In other aspects of this embodiment, contiguous amino acid substitutions of hydrophobic amino acids from amino acids 51-54 or amino acids 92-94 of SEQ ID NO: 22 can be replaced with phenylalanine. In yet other aspects of this embodiment, a β-trefoil domain with enhanced binding activity derived from a BoNT/B HA-17 comprises a polypeptide having, e.g., at most one, two, three or four contiguous amino acid deletions relative to amino acids 51-54 or amino acids 92-94 of SEQ ID NO: 22. In other aspects of this embodiment, a binding domain comprising a BoNT/B HA-17 β-trefoil domain comprises a polypeptide having, e.g., at least one, two, three or four contiguous amino acid deletions relative to amino acids 51-54 or amino acids 92-94 of SEQ ID NO: 22. In still other aspects of this embodiment, a binding domain comprising a BoNT/B HA-17 β-trefoil domain comprises a polypeptide having, e.g., at most one, two, three or four contiguous amino acid additions relative to amino acids 51-54 or amino acids 92-94 of SEQ ID NO: 22. In other aspects of this embodiment, a binding domain comprising a BoNT/B HA-17 β-trefoil domain comprises a polypeptide having, e.g., at least one, two, three or four contiguous amino acid additions relative to amino acids 51-54 or amino acids 92-94 of SEQ ID NO: 22.

In another embodiment, a binding domain comprises a β-trefoil domain derived from a BoNT/C1 HA-17 of SEQ ID NO: 23. In another embodiment, a binding domain comprising a β-trefoil domain derived from a BoNT/C1 HA-17 comprises amino acids 9-146 of SEQ ID NO: 23. In another aspect of this embodiment, a binding domain comprising a β-trefoil domain derived from a BoNT/C1 HA-17 comprises a α-fold motif of a β-trefoil domain of a BoNT/C1 HA-17, a β-fold motif of a β-trefoil domain of a BoNT/C1 HA-17 or a γ-fold motif of a β-trefoil domain of a BoNT/C1 HA-17 of SEQ ID NO: 23. In another aspect of this embodiment, a β-trefoil domain derived from a BoNT/C1 HA-17 comprises amino acids 9-50, amino acids 55-91, or amino acids 95-146 of SEQ ID NO: 23.

In other aspects of this embodiment, a binding domain comprising a BoNT/C1 HA-17 β-trefoil domain comprises a polypeptide having, e.g., at least 70% amino acid identity with amino acids 9-50, amino acids 55-91, or amino acids 95-146 of SEQ ID NO: 23, at least 75% amino acid identity with amino acids 9-50, amino acids 55-91, or amino acids 95-146 of SEQ ID NO: 23, at least 80% amino acid identity with amino acids 9-50, amino acids 55-91, or amino acids 95-146 of SEQ ID NO: 23, at least 85% amino acid identity with amino acids 9-50, amino acids 55-91, or amino acids 95-146 of SEQ ID NO: 23, at least 90% amino acid identity with amino acids 9-50, amino acids 55-91, or amino acids 95-146 of SEQ ID NO: 23 or at least 95% amino acid identity with amino acids 9-50, amino acids 55-91, or amino acids 95-146 of SEQ ID NO: 23. In yet other aspects of this embodiment, a binding domain comprising a BoNT/C1 HA-17 β-trefoil domain comprises a polypeptide having, e.g., at most 70% amino acid identity with amino acids 9-50, amino acids 55-91, or amino acids 95-146 of SEQ ID NO: 23, at most 75% amino acid identity with amino acids 9-50, amino acids 55-91, or amino acids 95-146 of SEQ ID NO: 23, at most 80% amino acid identity with amino acids 9-50, amino acids 55-91, or amino acids 95-146 of SEQ ID NO: 23, at most 85% amino acid identity with amino acids 9-50, amino acids 55-91, or amino acids 95-146 of SEQ ID NO: 23, at most 90% amino acid identity with amino acids 9-50, amino acids 55-91, or amino acids 95-146 of SEQ ID NO: 23 or at most 95% amino acid identity with amino acids 9-50, amino acids 55-91, or amino acids 95-146 of SEQ ID NO: 23.

In other aspects of this embodiment, a binding domain comprising a BoNT/C1 HA-17 β-trefoil domain comprises a polypeptide having, e.g., at most one, two, three, four, five, six, seven, eight, nine, 10 or 20 non-contiguous amino acid substitutions relative to amino acids 9-50, amino acids 55-91, or amino acids 95-146 of SEQ ID NO: 23. In other aspects of this embodiment, a binding domain comprising a BoNT/C1 HA-17 β-trefoil domain comprises a polypeptide having, e.g., at least one, two, three, four, five, six, seven, eight, nine, 10 or 20 non-contiguous amino acid substitutions relative to amino acids 9-50, amino acids 55-91, or amino acids 95-146 of SEQ ID NO: 23. In yet other aspects of this embodiment, a binding domain comprising a BoNT/C1 HA-17 β-trefoil domain comprises a polypeptide having, e.g., at most one, two, three, four, five, six, seven, eight, nine, 10 or 20 non-contiguous amino acid deletions relative to amino acids 9-50, amino acids 55-91, or amino acids 95-146 of SEQ ID NO: 23. In other aspects of this embodiment, a binding domain comprising a BoNT/C1 HA-17 β-trefoil domain comprises a polypeptide having, e.g., at least one, two, three, four, five, six, seven, eight, nine, 10 or 20 non-contiguous amino acid deletions relative to amino acids 9-50, amino acids 55-91, or amino acids 95-146 of SEQ ID NO: 23. In still other aspects of this embodiment, a binding domain comprising a BoNT/C1 HA-17 β-trefoil domain comprises a polypeptide having, e.g., at most one, two, three, four, five, six, seven, eight, nine, 10 or 20 non-contiguous amino acid additions relative to amino acids 9-50, amino acids 55-91, or amino acids 95-146 of SEQ ID NO: 23. In other aspects of this embodiment, a binding domain comprising a BoNT/C1 HA-17 β-trefoil domain comprises a polypeptide having, e.g., at least one, two, three, four, five, six, seven, eight, nine, 10 or 20 non-contiguous amino acid additions relative to amino acids 9-50, amino acids 55-91, or amino acids 95-146 of SEQ ID NO: 23.

In other aspects of this embodiment, a binding domain comprising a BoNT/C1 HA-17 β-trefoil domain comprises a polypeptide having, e.g., at most one, two, three, four, five, six, seven, eight, nine, 10 or 20 contiguous amino acid substitutions relative to amino acids 9-50, amino acids 55-91, or amino acids 95-146 of SEQ ID NO: 23. In other aspects of this embodiment, a binding domain comprising a BoNT/C1 HA-17 β-trefoil domain comprises a polypeptide having, e.g., at least one, two, three, four, five, six, seven, eight, nine, 10 or 20 contiguous amino acid substitutions relative to amino acids 9-50, amino acids 55-91, or amino acids 95-146 of SEQ ID NO: 23. In yet other aspects of this embodiment, a binding domain comprising a BoNT/C1 HA-17 β-trefoil domain comprises a polypeptide having, e.g., at most one, two, three, four, five, six, seven, eight, nine, 10 or 20 contiguous amino acid deletions relative to amino acids 9-50, amino acids 55-91, or amino acids 95-146 of SEQ ID NO: 23. In other aspects of this embodiment, a binding domain comprising a BoNT/C1 HA-17 β-trefoil domain comprises a polypeptide having, e.g., at least one, two, three, four, five, six, seven, eight, nine, 10 or 20 contiguous amino acid deletions relative to amino acids 9-50, amino acids 55-91, or amino acids 95-146 of SEQ ID NO: 23. In still other aspects of this embodiment, a binding domain comprising a BoNT/C1 HA-17 β-trefoil domain comprises a polypeptide having, e.g., at most one, two, three, four, five, six, seven, eight, nine, 10 or 20 contiguous amino acid additions relative to amino acids 9-50, amino acids 55-91, or amino acids 95-146 of SEQ ID NO: 23. In other aspects of this embodiment, a binding domain comprising a BoNT/C1 HA-17 β-trefoil domain comprises a polypeptide having, e.g., at least one, two, three, four, five, six, seven, eight, nine, 10 or 20 contiguous amino acid additions relative to amino acids 9-50, amino acids 55-91, or amino acids 95-146 of SEQ ID NO: 23.

In another embodiment, a binding domain comprising a BoNT/C1 HA-17 β-trefoil domain comprises a β4/β5 hairpin turn of a β-trefoil domain of a BoNT/C1 HA-17 or a β8/β9 hairpin turn of a β-trefoil domain of a BoNT/C1 HA-17 of SEQ ID NO: 23. In another aspect of this embodiment, a binding domain comprising a BoNT/C1 HA-17 β-trefoil domain comprises amino acids 51-54 or amino acids 92-94 of SEQ ID NO: 23.

In other aspects of this embodiment, a binding domain comprising a BoNT/C1 HA-17 β-trefoil domain comprises a polypeptide having, e.g., at least 70% amino acid identity with amino acids 51-54 or amino acids 92-94 of SEQ ID NO: 23, at least 75% amino acid identity with amino acids 51-54 or amino acids 92-94 of SEQ ID NO: 23, at least 80% amino acid identity with amino acids 51-54 or amino acids 92-94 of SEQ ID NO: 23, at least 85% amino acid identity with amino acids 51-54 or amino acids 92-94 of SEQ ID NO: 23, at least 90% amino acid identity with amino acids 51-54 or amino acids 92-94 of SEQ ID NO: 23 or at least 95% amino acid identity with amino acids 51-54 or amino acids 92-94 of SEQ ID NO: 23. In yet other aspects of this embodiment, a binding domain comprising a BoNT/C1 HA-17 β-trefoil domain comprises a polypeptide having, e.g., at most 70% amino acid identity with amino acids 51-54 or amino acids 92-94 of SEQ ID NO: 23, at most 75% amino acid identity with amino acids 51-54 or amino acids 92-94 of SEQ ID NO: 23, at most 80% amino acid identity with amino acids 51-54 or amino acids 92-94 of SEQ ID NO: 23, at most 85% amino acid identity with amino acids 51-54 or amino acids 92-94 of SEQ ID NO: 23, at most 90% amino acid identity with amino acids 51-54 or amino acids 92-94 of SEQ ID NO: 23 or at most 95% amino acid identity with amino acids 51-54 or amino acids 92-94 of SEQ ID NO: 23.

In other aspects of this embodiment, a binding domain comprising a BoNT/C1 HA-17 β-trefoil domain comprises a polypeptide having, e.g., at most one, two, three or four non-contiguous amino acid substitutions relative to amino acids 51-54 or amino acids 92-94 of SEQ ID NO: 23. In other aspects of this embodiment, a binding domain comprising a BoNT/C1 HA-17 β-trefoil domain comprises a polypeptide having, e.g., at least one, two, three or four non-contiguous amino acid substitutions relative to amino acids 51-54 or amino acids 92-94 of SEQ ID NO: 23. In other aspects of this embodiment, a non-contiguous amino acid substitution of any amino acid from amino acids 51-54 or amino acids 92-94 of SEQ ID NO: 23 can be replaced with glycine. In other aspects of this embodiment, a non-contiguous amino acid substitution of any hydrophobic amino acid from amino acids 51-54 or amino acids 92-94 of SEQ ID NO: 23 can be replaced with phenylalanine. In yet other aspects of this embodiment, a binding domain comprising a BoNT/C1 HA-17 β-trefoil domain comprises a polypeptide having, e.g., at most one, two, three or four non-contiguous amino acid deletions relative to amino acids 51-54 or amino acids 92-94 of SEQ ID NO: 23. In other aspects of this embodiment, a binding domain comprising a BoNT/C1 HA-17 β-trefoil domain comprises a polypeptide having, e.g., at least one, two, three or four non-contiguous amino acid deletions relative to amino acids 51-54 or amino acids 92-94 of SEQ ID NO: 23. In still other aspects of this embodiment, a binding domain comprising a BoNT/C1 HA-17 β-trefoil domain comprises a polypeptide having, e.g., at most one, two, three or four non-contiguous amino acid additions relative to amino acids 51-54 or amino acids 92-94 of SEQ ID NO: 23. In other aspects of this embodiment, a binding domain comprising a BoNT/C1 HA-17 β-trefoil domain comprises a polypeptide having, e.g., at least one, two, three or four non-contiguous amino acid additions relative to amino acids 51-54 or amino acids 92-94 of SEQ ID NO: 23.

In other aspects of this embodiment, a binding domain comprising a BoNT/C1 HA-17 β-trefoil domain comprises a polypeptide having, e.g., at most one, two, three or four contiguous amino acid substitutions relative to amino acids 51-54 or amino acids 92-94 of SEQ ID NO: 23. In other aspects of this embodiment, a binding domain comprising a BoNT/C1 HA-17 β-trefoil domain comprises a polypeptide having, e.g., at least one, two, three or four contiguous amino acid substitutions relative to amino acids 51-54 or amino acids 92-94 of SEQ ID NO: 23. In other aspects of this embodiment, contiguous amino acid substitutions of amino acids from amino acids 51-54 or amino acids 92-94 of SEQ ID NO: 23 can be replaced with glycine. In other aspects of this embodiment, contiguous amino acid substitutions of hydrophobic amino acids from amino acids 51-54 or amino acids 92-94 of SEQ ID NO: 23 can be replaced with phenylalanine. In yet other aspects of this embodiment, a β-trefoil domain with enhanced binding activity derived from a BoNT/C1 HA-17 comprises a polypeptide having, e.g., at most one, two, three or four contiguous amino acid deletions relative to amino acids 51-54 or amino acids 92-94 of SEQ ID NO: 23. In other aspects of this embodiment, a binding domain comprising a BoNT/C1 HA-17 β-trefoil domain comprises a polypeptide having, e.g., at least one, two, three or four contiguous amino acid deletions relative to amino acids 51-54 or amino acids 92-94 of SEQ ID NO: 23. In still other aspects of this embodiment, a binding domain comprising a BoNT/C1 HA-17 β-trefoil domain comprises a polypeptide having, e.g., at most one, two, three or four contiguous amino acid additions relative to amino acids 51-54 or amino acids 92-94 of SEQ ID NO: 23. In other aspects of this embodiment, a binding domain comprising a BoNT/C1 HA-17 β-trefoil domain comprises a polypeptide having, e.g., at least one, two, three or four contiguous amino acid additions relative to amino acids 51-54 or amino acids 92-94 of SEQ ID NO: 23.

In another embodiment, a binding domain comprises a β-trefoil domain derived from a BoNT/D HA-17 of SEQ ID NO: 24. In another embodiment, a binding domain comprising a β-trefoil domain derived from a BoNT/D HA-17 comprises amino acids 9-146 of SEQ ID NO: 24. In another aspect of this embodiment, a binding domain comprising a β-trefoil domain derived from a BoNT/D HA-17 comprises a α-fold motif of a β-trefoil domain of a BoNT/D HA-17, a β-fold motif of a β-trefoil domain of a BoNT/D HA-17 or a γ-fold motif of a β-trefoil domain of a BoNT/D HA-17 of SEQ ID NO: 24. In another aspect of this embodiment, a β-trefoil domain derived from a BoNT/D HA-17 comprises amino acids 9-50, amino acids 55-91, or amino acids 95-146 of SEQ ID NO: 24.

In other aspects of this embodiment, a binding domain comprising a BoNT/D HA-17 β-trefoil domain comprises a polypeptide having, e.g., at least 70% amino acid identity with amino acids 9-50, amino acids 55-91, or amino acids 95-146 of SEQ ID NO: 24, at least 75% amino acid identity with amino acids 9-50, amino acids 55-91, or amino acids 95-146 of SEQ ID NO: 24, at least 80% amino acid identity with amino acids 9-50, amino acids 55-91, or amino acids 95-146 of SEQ ID NO: 24, at least 85% amino acid identity with amino acids 9-50, amino acids 55-91, or amino acids 95-146 of SEQ ID NO: 24, at least 90% amino acid identity with amino acids 9-50, amino acids 55-91, or amino acids 95-146 of SEQ ID NO: 24 or at least 95% amino acid identity with amino acids 9-50, amino acids 55-91, or amino acids 95-146 of SEQ ID NO: 24. In yet other aspects of this embodiment, a binding domain comprising a BoNT/D HA-17 β-trefoil domain comprises a polypeptide having, e.g., at most 70% amino acid identity with amino acids 9-50, amino acids 55-91, or amino acids 95-146 of SEQ ID NO: 24, at most 75% amino acid identity with amino acids 9-50, amino acids 55-91, or amino acids 95-146 of SEQ ID NO: 24, at most 80% amino acid identity with amino acids 9-50, amino acids 55-91, or amino acids 95-146 of SEQ ID NO: 24, at most 85% amino acid identity with amino acids 9-50, amino acids 55-91, or amino acids 95-146 of SEQ ID NO: 24, at most 90% amino acid identity with amino acids 9-50, amino acids 55-91, or amino acids 95-146 of SEQ ID NO: 24 or at most 95% amino acid identity with amino acids 9-50, amino acids 55-91, or amino acids 95-146 of SEQ ID NO: 24.

In other aspects of this embodiment, a binding domain comprising a BoNT/D HA-17 β-trefoil domain comprises a polypeptide having, e.g., at most one, two, three, four, five, six, seven, eight, nine, 10 or 20 non-contiguous amino acid substitutions relative to amino acids 9-50, amino acids 55-91, or amino acids 95-146 of SEQ ID NO: 24. In other aspects of this embodiment, a binding domain comprising a BoNT/D HA-17 β-trefoil domain comprises a polypeptide having, e.g., at least one, two, three, four, five, six, seven, eight, nine, 10 or 20 non-contiguous amino acid substitutions relative to amino acids 9-50, amino acids 55-91, or amino acids 95-146 of SEQ ID NO: 24. In yet other aspects of this embodiment, a binding domain comprising a BoNT/D HA-17 β-trefoil domain comprises a polypeptide having, e.g., at most one, two, three, four, five, six, seven, eight, nine, 10 or 20 non-contiguous amino acid deletions relative to amino acids 9-50, amino acids 55-91, or amino acids 95-146 of SEQ ID NO: 24. In other aspects of this embodiment, a binding domain comprising a BoNT/D HA-17 β-trefoil domain comprises a polypeptide having, e.g., at least one, two, three, four, five, six, seven, eight, nine, 10 or 20 non-contiguous amino acid deletions relative to amino acids 9-50, amino acids 55-91, or amino acids 95-146 of SEQ ID NO: 24. In still other aspects of this embodiment, a binding domain comprising a BoNT/D HA-17 β-trefoil domain comprises a polypeptide having, e.g., at most one, two, three, four, five, six, seven, eight, nine, 10 or 20 non-contiguous amino acid additions relative to amino acids 9-50, amino acids 55-91, or amino acids 95-146 of SEQ ID NO: 24. In other aspects of this embodiment, a binding domain comprising a BoNT/D HA-17 β-trefoil domain comprises a polypeptide having, e.g., at least one, two, three, four, five, six, seven, eight, nine, 10 or 20 non-contiguous amino acid additions relative to amino acids 9-50, amino acids 55-91, or amino acids 95-146 of SEQ ID NO: 24.

In other aspects of this embodiment, a binding domain comprising a BoNT/D HA-17 β-trefoil domain comprises a polypeptide having, e.g., at most one, two, three, four, five, six, seven, eight, nine, 10 or 20 contiguous amino acid substitutions relative to amino acids 9-50, amino acids 55-91, or amino acids 95-146 of SEQ ID NO: 24. In other aspects of this embodiment, a binding domain comprising a BoNT/D HA-17 β-trefoil domain comprises a polypeptide having, e.g., at least one, two, three, four, five, six, seven, eight, nine, 10 or 20 contiguous amino acid substitutions relative to amino acids 9-50, amino acids 55-91, or amino acids 95-146 of SEQ ID NO: 24. In yet other aspects of this embodiment, a binding domain comprising a BoNT/D HA-17 β-trefoil domain comprises a polypeptide having, e.g., at most one, two, three, four, five, six, seven, eight, nine, 10 or 20 contiguous amino acid deletions relative to amino acids 9-50, amino acids 55-91, or amino acids 95-146 of SEQ ID NO: 24. In other aspects of this embodiment, a binding domain comprising a BoNT/D HA-17 β-trefoil domain comprises a polypeptide having, e.g., at least one, two, three, four, five, six, seven, eight, nine, 10 or 20 contiguous amino acid deletions relative to amino acids 9-50, amino acids 55-91, or amino acids 95-146 of SEQ ID NO: 24. In still other aspects of this embodiment, a binding domain comprising a BoNT/D HA-17 β-trefoil domain comprises a polypeptide having, e.g., at most one, two, three, four, five, six, seven, eight, nine, 10 or 20 contiguous amino acid additions relative to amino acids 9-50, amino acids 55-91, or amino acids 95-146 of SEQ ID NO: 24. In other aspects of this embodiment, a binding domain comprising a BoNT/D HA-17 β-trefoil domain comprises a polypeptide having, e.g., at least one, two, three, four, five, six, seven, eight, nine, 10 or 20 contiguous amino acid additions relative to amino acids 9-50, amino acids 55-91, or amino acids 95-146 of SEQ ID NO: 24.

In another embodiment, a binding domain comprising a BoNT/D HA-17 β-trefoil domain comprises a β4/β5 hairpin turn of a β-trefoil domain of a BoNT/D HA-17 or a β8/β9 hairpin turn of a β-trefoil domain of a BoNT/D HA-17 of SEQ ID NO: 24. In another aspect of this embodiment, a binding domain comprising a BoNT/D HA-17 β-trefoil domain comprises amino acids 51-54 or amino acids 92-94 of SEQ ID NO: 24.

In other aspects of this embodiment, a binding domain comprising a BoNT/D HA-17 β-trefoil domain comprises a polypeptide having, e.g., at least 70% amino acid identity with amino acids 51-54 or amino acids 92-94 of SEQ ID NO: 24, at least 75% amino acid identity with amino acids 51-54 or amino acids 92-94 of SEQ ID NO: 24, at least 80% amino acid identity with amino acids 51-54 or amino acids 92-94 of SEQ ID NO: 24, at least 85% amino acid identity with amino acids 51-54 or amino acids 92-94 of SEQ ID NO: 24, at least 90% amino acid identity with amino acids 51-54 or amino acids 92-94 of SEQ ID NO: 24 or at least 95% amino acid identity with amino acids 51-54 or amino acids 92-94 of SEQ ID NO: 24. In yet other aspects of this embodiment, a binding domain comprising a BoNT/D HA-17 β-trefoil domain comprises a polypeptide having, e.g., at most 70% amino acid identity with amino acids 51-54 or amino acids 92-94 of SEQ ID NO: 24, at most 75% amino acid identity with amino acids 51-54 or amino acids 92-94 of SEQ ID NO: 24, at most 80% amino acid identity with amino acids 51-54 or amino acids 92-94 of SEQ ID NO: 24, at most 85% amino acid identity with amino acids 51-54 or amino acids 92-94 of SEQ ID NO: 24, at most 90% amino acid identity with amino acids 51-54 or amino acids 92-94 of SEQ ID NO: 24 or at most 95% amino acid identity with amino acids 51-54 or amino acids 92-94 of SEQ ID NO: 24.

In other aspects of this embodiment, a binding domain comprising a BoNT/D HA-17 β-trefoil domain comprises a polypeptide having, e.g., at most one, two, three or four non-contiguous amino acid substitutions relative to amino acids 51-54 or amino acids 92-94 of SEQ ID NO: 24. In other aspects of this embodiment, a binding domain comprising a BoNT/D HA-17 β-trefoil domain comprises a polypeptide having, e.g., at least one, two, three or four non-contiguous amino acid substitutions relative to amino acids 51-54 or amino acids 92-94 of SEQ ID NO: 24. In other aspects of this embodiment, a non-contiguous amino acid substitution of any amino acid from amino acids 51-54 or amino acids 92-94 of SEQ ID NO: 24 can be replaced with glycine. In other aspects of this embodiment, a non-contiguous amino acid substitution of any hydrophobic amino acid from amino acids 51-54 or amino acids 92-94 of SEQ ID NO: 24 can be replaced with phenylalanine. In yet other aspects of this embodiment, a binding domain comprising a BoNT/D HA-17 β-trefoil domain comprises a polypeptide having, e.g., at most one, two, three or four non-contiguous amino acid deletions relative to amino acids 51-54 or amino acids 92-94 of SEQ ID NO: 24. In other aspects of this embodiment, a binding domain comprising a BoNT/D HA-17 β-trefoil domain comprises a polypeptide having, e.g., at least one, two, three or four non-contiguous amino acid deletions relative to amino acids 51-54 or amino acids 92-94 of SEQ ID NO: 24. In still other aspects of this embodiment, a binding domain comprising a BoNT/D HA-17 β-trefoil domain comprises a polypeptide having, e.g., at most one, two, three or four non-contiguous amino acid additions relative to amino acids 51-54 or amino acids 92-94 of SEQ ID NO: 24. In other aspects of this embodiment, a binding domain comprising a BoNT/D HA-17 β-trefoil domain comprises a polypeptide having, e.g., at least one, two, three or four non-contiguous amino acid additions relative to amino acids 51-54 or amino acids 92-94 of SEQ ID NO: 24.

In other aspects of this embodiment, a binding domain comprising a BoNT/D HA-17 β-trefoil domain comprises a polypeptide having, e.g., at most one, two, three or four contiguous amino acid substitutions relative to amino acids 51-54 or amino acids 92-94 of SEQ ID NO: 24. In other aspects of this embodiment, a binding domain comprising a BoNT/D HA-17 β-trefoil domain comprises a polypeptide having, e.g., at least one, two, three or four contiguous amino acid substitutions relative to amino acids 51-54 or amino acids 92-94 of SEQ ID NO: 24. In other aspects of this embodiment, contiguous amino acid substitutions of amino acids from amino acids 51-54 or amino acids 92-94 of SEQ ID NO: 24 can be replaced with glycine. In other aspects of this embodiment, contiguous amino acid substitutions of hydrophobic amino acids from amino acids 51-54 or amino acids 92-94 of SEQ ID NO: 24 can be replaced with phenylalanine. In yet other aspects of this embodiment, a β-trefoil domain with enhanced binding activity derived from a BoNT/D HA-17 comprises a polypeptide having, e.g., at most one, two, three or four contiguous amino acid deletions relative to amino acids 51-54 or amino acids 92-94 of SEQ ID NO: 24. In other aspects of this embodiment, a binding domain comprising a BoNT/D HA-17 β-trefoil domain comprises a polypeptide having, e.g., at least one, two, three or four contiguous amino acid deletions relative to amino acids 51-54 or amino acids 92-94 of SEQ ID NO: 24. In still other aspects of this embodiment, a binding domain comprising a BoNT/D HA-17 β-trefoil domain comprises a polypeptide having, e.g., at most one, two, three or four contiguous amino acid additions relative to amino acids 51-54 or amino acids 92-94 of SEQ ID NO: 24. In other aspects of this embodiment, a binding domain comprising a BoNT/D HA-17 β-trefoil domain comprises a polypeptide having, e.g., at least one, two, three or four contiguous amino acid additions relative to amino acids 51-54 or amino acids 92-94 of SEQ ID NO: 24.

In another embodiment, a binding domain comprises a β-trefoil domain derived from a Clostridial NTNH. In an aspect of this embodiment, a binding domain comprising a β-trefoil domain derived from a Clostridial NTNH comprises, e.g., a β-trefoil domain derived from a BoNT/A NTNH, a β-trefoil domain derived from a BoNT/B NTNH, a β-trefoil domain derived from a BoNT/C1 NTNH, a β-trefoil domain derived from a BoNT/D NTNH, a β-trefoil domain derived from a BoNT/E NTNH, a β-trefoil domain derived from a BoNT/F NTNH, or a β-trefoil domain derived from a BoNT/G NTNH. In another aspect of this embodiment, a β-trefoil domain derived from a Clostridial NTNH comprises an α-fold motif of a β-trefoil domain of a BoNT/A NTNH, β-fold motif of β-trefoil domain of a BoNT/A NTNH, or a γ-fold motif of a β-trefoil domain of a BoNT/A NTNH. In another aspect of this embodiment, a β-trefoil domain derived from a Clostridial NTNH comprises an α-fold motif of a β-trefoil domain of a BoNT/B NTNH, a β-fold motif of a β-trefoil domain of a BoNT/B NTNH, or a γ-fold motif of a β-trefoil domain of a BoNT/B NTNH. In another aspect of this embodiment, a β-trefoil domain derived from a Clostridial NTNH comprises an α-fold motif of a β-trefoil domain of a BoNT/C1 NTNH, a β-fold motif of a β-trefoil domain of a BoNT/C1 NTNH, or a γ-fold motif of a β-trefoil domain of a BoNT/C1 NTNH. In another aspect of this embodiment, a β-trefoil domain derived from a Clostridial NTNH comprises an β-fold motif of a β-trefoil domain of a BoNT/D NTNH, a β-fold motif of a β-trefoil domain of a BoNT/D NTNH, or a γ-fold motif of a β-trefoil domain of a BoNT/D NTNH. In another aspect of this embodiment, a β-trefoil domain derived from a Clostridial NTNH comprises an β-fold motif of a β-trefoil domain of a BoNT/E NTNH, a β-fold motif of a β-trefoil domain of a BoNT/E NTNH, or a γ-fold motif of a β-trefoil domain of a BoNT/E NTNH. In another aspect of this embodiment, a β-trefoil domain derived from a Clostridial NTNH comprises an α-fold motif of a β-trefoil domain of a BoNT/F NTNH, a β-fold motif of a β-trefoil domain of a BoNT/F NTNH, or a γ-fold motif of a β-trefoil domain of a BoNT/F NTNH. In another aspect of this embodiment, a β-trefoil domain derived from a Clostridial NTNH comprises an α-fold motif of a β-trefoil domain of a BoNT/G NTNH, a β-fold motif of a β-trefoil domain of a BoNT/G NTNH, or a γ-fold motif of a β-trefoil domain of a BoNT/G NTNH.

In another embodiment, a binding domain comprises a β-trefoil domain derived from a BoNT/A NTNH of SEQ ID NO: 25. In another embodiment, a binding domain comprising a β-trefoil domain derived from a BoNT/A NTNH comprises amino acids 1050-1194 of SEQ ID NO: 25. In another aspect of this embodiment, a binding domain comprising a β-trefoil domain derived from a BoNT/A NTNH comprises a α-fold motif of a β-trefoil domain of a BoNT/A NTNH, a β-fold motif of a β-trefoil domain of a BoNT/A NTNH or a γ-fold motif of a β-trefoil domain of a BoNT/A NTNH of SEQ ID NO: 24. In another aspect of this embodiment, a β-trefoil domain derived from a BoNT/A NTNH comprises amino acids 1050-1097, amino acids 1111-1138, or amino acids 1149-1194 of SEQ ID NO: 25.

In other aspects of this embodiment, a binding domain comprising a BoNT/A NTNH β-trefoil domain comprises a polypeptide having, e.g., at least 70% amino acid identity with amino acids 1050-1097, amino acids 1111-1138, or amino acids 1149-1194 of SEQ ID NO: 25, at least 75% amino acid identity with amino acids 1050-1097, amino acids 1111-1138, or amino acids 1149-1194 of SEQ ID NO: 25, at least 80% amino acid identity with amino acids 1050-1097, amino acids 1111-1138, or amino acids 1149-1194 of SEQ ID NO: 25, at least 85% amino acid identity with amino acids 1050-1097, amino acids 1111-1138, or amino acids 1149-1194 of SEQ ID NO: 25, at least 90% amino acid identity with amino acids 1050-1097, amino acids 1111-1138, or amino acids 1149-1194 of SEQ ID NO: 25 or at least 95% amino acid identity with amino acids 1050-1097, amino acids 1111-1138, or amino acids 1149-1194 of SEQ ID NO: 25. In yet other aspects of this embodiment, a binding domain comprising a BoNT/A NTNH β-trefoil domain comprises a polypeptide having, e.g., at most 70% amino acid identity with amino acids 1050-1097, amino acids 1111-1138, or amino acids 1149-1194 of SEQ ID NO: 25, at most 75% amino acid identity with amino acids 1050-1097, amino acids 1111-1138, or amino acids 1149-1194 of SEQ ID NO: 25, at most 80% amino acid identity with amino acids 1050-1097, amino acids 1111-1138, or amino acids 1149-1194 of SEQ ID NO: 25, at most 85% amino acid identity with amino acids 1050-1097, amino acids 1111-1138, or amino acids 1149-1194 of SEQ ID NO: 25, at most 90% amino acid identity with amino acids 1050-1097, amino acids 1111-1138, or amino acids 1149-1194 of SEQ ID NO: 25 or at most 95% amino acid identity with amino acids 1050-1097, amino acids 1111-1138, or amino acids 1149-1194 of SEQ ID NO: 25.

In other aspects of this embodiment, a binding domain comprising a BoNT/A NTNH β-trefoil domain comprises a polypeptide having, e.g., at most one, two, three, four, five, six, seven, eight, nine, 10 or 20 non-contiguous amino acid substitutions relative to amino acids 1050-1097, amino acids 1111-1138, or amino acids 1149-1194 of SEQ ID NO: 25. In other aspects of this embodiment, a binding domain comprising a BoNT/A NTNH β-trefoil domain comprises a polypeptide having, e.g., at least one, two, three, four, five, six, seven, eight, nine, 10 or 20 non-contiguous amino acid substitutions relative to amino acids 1050-1097, amino acids 1111-1138, or amino acids 1149-1194 of SEQ ID NO: 25. In yet other aspects of this embodiment, a binding domain comprising a BoNT/A NTNH β-trefoil domain comprises a polypeptide having, e.g., at most one, two, three, four, five, six, seven, eight, nine, 10 or 20 non-contiguous amino acid deletions relative to amino acids 1050-1097, amino acids 1111-1138, or amino acids 1149-1194 of SEQ ID NO: 25. In other aspects of this embodiment, a binding domain comprising a BoNT/A NTNH β-trefoil domain comprises a polypeptide having, e.g., at least one, two, three, four, five, six, seven, eight, nine, 10 or 20 non-contiguous amino acid deletions relative to amino acids 1050-1097, amino acids 1111-1138, or amino acids 1149-1194 of SEQ ID NO: 25. In still other aspects of this embodiment, a binding domain comprising a BoNT/A NTNH β-trefoil domain comprises a polypeptide having, e.g., at most one, two, three, four, five, six, seven, eight, nine, 10 or 20 non-contiguous amino acid additions relative to amino acids 1050-1097, amino acids 1111-1138, or amino acids 1149-1194 of SEQ ID NO: 25. In other aspects of this embodiment, a binding domain comprising a BoNT/A NTNH β-trefoil domain comprises a polypeptide having, e.g., at least one, two, three, four, five, six, seven, eight, nine, 10 or 20 non-contiguous amino acid additions relative to amino acids 1050-1097, amino acids 1111-1138, or amino acids 1149-1194 of SEQ ID NO: 25.

In other aspects of this embodiment, a binding domain comprising a BoNT/A NTNH β-trefoil domain comprises a polypeptide having, e.g., at most one, two, three, four, five, six, seven, eight, nine, 10 or 20 contiguous amino acid substitutions relative to amino acids 1050-1097, amino acids 1111-1138, or amino acids 1149-1194 of SEQ ID NO: 25. In other aspects of this embodiment, a binding domain comprising a BoNT/A NTNH β-trefoil domain comprises a polypeptide having, e.g., at least one, two, three, four, five, six, seven, eight, nine, 10 or 20 contiguous amino acid substitutions relative to amino acids 1050-1097, amino acids 1111-1138, or amino acids 1149-1194 of SEQ ID NO: 25. In yet other aspects of this embodiment, a binding domain comprising a BoNT/A NTNH β-trefoil domain comprises a polypeptide having, e.g., at most one, two, three, four, five, six, seven, eight, nine, 10 or 20 contiguous amino acid deletions relative to amino acids 1050-1097, amino acids 1111-1138, or amino acids 1149-1194 of SEQ ID NO: 25. In other aspects of this embodiment, a binding domain comprising a BoNT/A NTNH β-trefoil domain comprises a polypeptide having, e.g., at least one, two, three, four, five, six, seven, eight, nine, 10 or 20 contiguous amino acid deletions relative to amino acids 1050-1097, amino acids 1111-1138, or amino acids 1149-1194 of SEQ ID NO: 25. In still other aspects of this embodiment, a binding domain comprising a BoNT/A NTNH β-trefoil domain comprises a polypeptide having, e.g., at most one, two, three, four, five, six, seven, eight, nine, 10 or 20 contiguous amino acid additions relative to amino acids 1050-1097, amino acids 1111-1138, or amino acids 1149-1194 of SEQ ID NO: 25. In other aspects of this embodiment, a binding domain comprising a BoNT/A NTNH β-trefoil domain comprises a polypeptide having, e.g., at least one, two, three, four, five, six, seven, eight, nine, 10 or 20 contiguous amino acid additions relative to amino acids 1050-1097, amino acids 1111-1138, or amino acids 1149-1194 of SEQ ID NO: 25.

In another embodiment, a binding domain comprising a BoNT/A NTNH β-trefoil domain comprises a β4/β5 hairpin turn of a β-trefoil domain of a BoNT/A NTNH or a β8/β9 hairpin turn of a β-trefoil domain of a BoNT/A NTNH of SEQ ID NO: 24. In another aspect of this embodiment, a binding domain comprising a BoNT/A NTNH β-trefoil domain comprises amino acids 1098-1110 or amino acids 1139-1148 of SEQ ID NO: 25.

In other aspects of this embodiment, a binding domain comprising a BoNT/A NTNH β-trefoil domain comprises a polypeptide having, e.g., at least 70% amino acid identity with amino acids 1098-1110 or amino acids 1139-1148 of SEQ ID NO: 25, at least 75% amino acid identity with amino acids 1098-1110 or amino acids 1139-1148 of SEQ ID NO: 25, at least 80% amino acid identity with amino acids 1098-1110 or amino acids 1139-1148 of SEQ ID NO: 25, at least 85% amino acid identity with amino acids 1098-1110 or amino acids 1139-1148 of SEQ ID NO: 25, at least 90% amino acid identity with amino acids 1098-1110 or amino acids 1139-1148 of SEQ ID NO: 25 or at least 95% amino acid identity with amino acids 1098-1110 or amino acids 1139-1148 of SEQ ID NO: 25. In yet other aspects of this embodiment, a binding domain comprising a BoNT/A NTNH β-trefoil domain comprises a polypeptide having, e.g., at most 70% amino acid identity with amino acids 1098-1110 or amino acids 1139-1148 of SEQ ID NO: 25, at most 75% amino acid identity with amino acids 1098-1110 or amino acids 1139-1148 of SEQ ID NO: 25, at most 80% amino acid identity with amino acids 1098-1110 or amino acids 1139-1148 of SEQ ID NO: 25, at most 85% amino acid identity with amino acids 1098-1110 or amino acids 1139-1148 of SEQ ID NO: 25, at most 90% amino acid identity with amino acids 1098-1110 or amino acids 1139-1148 of SEQ ID NO: 25 or at most 95% amino acid identity with amino acids 1098-1110 or amino acids 1139-1148 of SEQ ID NO: 25.

In other aspects of this embodiment, a binding domain comprising a BoNT/A NTNH β-trefoil domain comprises a polypeptide having, e.g., at most one, two, three or four non-contiguous amino acid substitutions relative to amino acids 1098-1110 or amino acids 1139-1148 of SEQ ID NO: 25. In other aspects of this embodiment, a binding domain comprising a BoNT/A NTNH β-trefoil domain comprises a polypeptide having, e.g., at least one, two, three or four non-contiguous amino acid substitutions relative to amino acids 1098-1110 or amino acids 1139-1148 of SEQ ID NO: 25. In other aspects of this embodiment, a non-contiguous amino acid substitution of any amino acid from amino acids 1098-1110 or amino acids 1139-1148 of SEQ ID NO: 25 can be replaced with glycine. In other aspects of this embodiment, a non-contiguous amino acid substitution of any hydrophobic amino acid from amino acids 1098-1110 or amino acids 1139-1148 of SEQ ID NO: 25 can be replaced with phenylalanine. In yet other aspects of this embodiment, a binding domain comprising a BoNT/A NTNH β-trefoil domain comprises a polypeptide having, e.g., at most one, two, three or four non-contiguous amino acid deletions relative to amino acids 1098-1110 or amino acids 1139-1148 of SEQ ID NO: 25. In other aspects of this embodiment, a binding domain comprising a BoNT/A NTNH β-trefoil domain comprises a polypeptide having, e.g., at least one, two, three or four non-contiguous amino acid deletions relative to amino acids 1098-1110 or amino acids 1139-1148 of SEQ ID NO: 25. In still other aspects of this embodiment, a binding domain comprising a BoNT/A NTNH β-trefoil domain comprises a polypeptide having, e.g., at most one, two, three or four non-contiguous amino acid additions relative to amino acids 1098-1110 or amino acids 1139-1148 of SEQ ID NO: 25. In other aspects of this embodiment, a binding domain comprising a BoNT/A NTNH β-trefoil domain comprises a polypeptide having, e.g., at least one, two, three or four non-contiguous amino acid additions relative to amino acids 1098-1110 or amino acids 1139-1148 of SEQ ID NO: 25.

In other aspects of this embodiment, a binding domain comprising a BoNT/A NTNH β-trefoil domain comprises a polypeptide having, e.g., at most one, two, three or four contiguous amino acid substitutions relative to amino acids 1098-1110 or amino acids 1139-1148 of SEQ ID NO: 25. In other aspects of this embodiment, a binding domain comprising a BoNT/A NTNH β-trefoil domain comprises a polypeptide having, e.g., at least one, two, three or four contiguous amino acid substitutions relative to amino acids 1098-1110 or amino acids 1139-1148 of SEQ ID NO: 25. In other aspects of this embodiment, contiguous amino acid substitutions of amino acids from amino acids 1098-1110 or amino acids 1139-1148 of SEQ ID NO: 25 can be replaced with glycine. In other aspects of this embodiment, contiguous amino acid substitutions of hydrophobic amino acids from amino acids 1098-1110 or amino acids 1139-1148 of SEQ ID NO: 25 can be replaced with phenylalanine. In yet other aspects of this embodiment, a β-trefoil domain with enhanced binding activity derived from a BoNT/A NTNH comprises a polypeptide having, e.g., at most one, two, three or four contiguous amino acid deletions relative to amino acids 1098-1110 or amino acids 1139-1148 of SEQ ID NO: 25. In other aspects of this embodiment, a binding domain comprising a BoNT/A NTNH β-trefoil domain comprises a polypeptide having, e.g., at least one, two, three or four contiguous amino acid deletions relative to amino acids 1098-1110 or amino acids 1139-1148 of SEQ ID NO: 25. In still other aspects of this embodiment, a binding domain comprising a BoNT/A NTNH β-trefoil domain comprises a polypeptide having, e.g., at most one, two, three or four contiguous amino acid additions relative to amino acids 1098-1110 or amino acids 1139-1148 of SEQ ID NO: 25. In other aspects of this embodiment, a binding domain comprising a BoNT/A NTNH β-trefoil domain comprises a polypeptide having, e.g., at least one, two, three or four contiguous amino acid additions relative to amino acids 1098-1110 or amino acids 1139-1148 of SEQ ID NO: 25.

In another embodiment, a binding domain comprises a β-trefoil domain derived from a BoNT/A NTNH of SEQ ID NO: 26. In another embodiment, a binding domain comprising a β-trefoil domain derived from a BoNT/A NTNH comprises amino acids 1050-1199 of SEQ ID NO: 26. In another aspect of this embodiment, a binding domain comprising a β-trefoil domain derived from a BoNT/A NTNH comprises a α-fold motif of a β-trefoil domain of a BoNT/A NTNH, a β-fold motif of a β-trefoil domain of a BoNT/A NTNH or a γ-fold motif of a β-trefoil domain of a BoNT/A NTNH of SEQ ID NO: 24. In another aspect of this embodiment, a β-trefoil domain derived from a BoNT/A NTNH comprises amino acids 1050-1097, amino acids 1111-1139, or amino acids 1149-1199 of SEQ ID NO: 26.

In other aspects of this embodiment, a binding domain comprising a BoNT/A NTNH β-trefoil domain comprises a polypeptide having, e.g., at least 70% amino acid identity with amino acids 1050-1097, amino acids 1111-1139, or amino acids 1149-1199 of SEQ ID NO: 26, at least 75% amino acid identity with amino acids 1050-1097, amino acids 1111-1139, or amino acids 1149-1199 of SEQ ID NO: 26, at least 80% amino acid identity with amino acids 1050-1097, amino acids 1111-1139, or amino acids 1149-1199 of SEQ ID NO: 26, at least 85% amino acid identity with amino acids 1050-1097, amino acids 1111-1139, or amino acids 1149-1199 of SEQ ID NO: 26, at least 90% amino acid identity with amino acids 1050-1097, amino acids 1111-1139, or amino acids 1149-1199 of SEQ ID NO: 26 or at least 95% amino acid identity with amino acids 1050-1097, amino acids 1111-1139, or amino acids 1149-1199 of SEQ ID NO: 26. In yet other aspects of this embodiment, a binding domain comprising a BoNT/A NTNH β-trefoil domain comprises a polypeptide having, e.g., at most 70% amino acid identity with amino acids 1050-1097, amino acids 1111-1139, or amino acids 1149-1199 of SEQ ID NO: 26, at most 75% amino acid identity with amino acids 1050-1097, amino acids 1111-1139, or amino acids 1149-1199 of SEQ ID NO: 26, at most 80% amino acid identity with amino acids 1050-1097, amino acids 1111-1139, or amino acids 1149-1199 of SEQ ID NO: 26, at most 85% amino acid identity with amino acids 1050-1097, amino acids 1111-1139, or amino acids 1149-1199 of SEQ ID NO: 26, at most 90% amino acid identity with amino acids 1050-1097, amino acids 1111-1139, or amino acids 1149-1199 of SEQ ID NO: 26 or at most 95% amino acid identity with amino acids 1050-1097, amino acids 1111-1139, or amino acids 1149-1199 of SEQ ID NO: 26.

In other aspects of this embodiment, a binding domain comprising a BoNT/A NTNH β-trefoil domain comprises a polypeptide having, e.g., at most one, two, three, four, five, six, seven, eight, nine, 10 or 20 non-contiguous amino acid substitutions relative to amino acids 1050-1097, amino acids 1111-1139, or amino acids 1149-1199 of SEQ ID NO: 26. In other aspects of this embodiment, a binding domain comprising a BoNT/A NTNH β-trefoil domain comprises a polypeptide having, e.g., at least one, two, three, four, five, six, seven, eight, nine, 10 or 20 non-contiguous amino acid substitutions relative to amino acids 1050-1097, amino acids 1111-1139, or amino acids 1149-1199 of SEQ ID NO: 26. In yet other aspects of this embodiment, a binding domain comprising a BoNT/A NTNH β-trefoil domain comprises a polypeptide having, e.g., at most one, two, three, four, five, six, seven, eight, nine, 10 or 20 non-contiguous amino acid deletions relative to amino acids 1050-1097, amino acids 1111-1139, or amino acids 1149-1199 of SEQ ID NO: 26. In other aspects of this embodiment, a binding domain comprising a BoNT/A NTNH β-trefoil domain comprises a polypeptide having, e.g., at least one, two, three, four, five, six, seven, eight, nine, 10 or 20 non-contiguous amino acid deletions relative to amino acids 1050-1097, amino acids 1111-1139, or amino acids 1149-1199 of SEQ ID NO: 26. In still other aspects of this embodiment, a binding domain comprising a BoNT/A NTNH β-trefoil domain comprises a polypeptide having, e.g., at most one, two, three, four, five, six, seven, eight, nine, 10 or 20 non-contiguous amino acid additions relative to amino acids 1050-1097, amino acids 1111-1139, or amino acids 1149-1199 of SEQ ID NO: 26. In other aspects of this embodiment, a binding domain comprising a BoNT/A NTNH β-trefoil domain comprises a polypeptide having, e.g., at least one, two, three, four, five, six, seven, eight, nine, 10 or 20 non-contiguous amino acid additions relative to amino acids 1050-1097, amino acids 1111-1139, or amino acids 1149-1199 of SEQ ID NO: 26.

In other aspects of this embodiment, a binding domain comprising a BoNT/A NTNH β-trefoil domain comprises a polypeptide having, e.g., at most one, two, three, four, five, six, seven, eight, nine, 10 or 20 contiguous amino acid substitutions relative to amino acids 1050-1097, amino acids 1111-1139, or amino acids 1149-1199 of SEQ ID NO: 26. In other aspects of this embodiment, a binding domain comprising a BoNT/A NTNH β-trefoil domain comprises a polypeptide having, e.g., at least one, two, three, four, five, six, seven, eight, nine, 10 or 20 contiguous amino acid substitutions relative to amino acids 1050-1097, amino acids 1111-1139, or amino acids 1149-1199 of SEQ ID NO: 26. In yet other aspects of this embodiment, a binding domain comprising a BoNT/A NTNH β-trefoil domain comprises a polypeptide having, e.g., at most one, two, three, four, five, six, seven, eight, nine, 10 or 20 contiguous amino acid deletions relative to amino acids 1050-1097, amino acids 1111-1139, or amino acids 1149-1199 of SEQ ID NO: 26. In other aspects of this embodiment, a binding domain comprising a BoNT/A NTNH β-trefoil domain comprises a polypeptide having, e.g., at least one, two, three, four, five, six, seven, eight, nine, 10 or 20 contiguous amino acid deletions relative to amino acids 1050-1097, amino acids 1111-1139, or amino acids 1149-1199 of SEQ ID NO: 26. In still other aspects of this embodiment, a binding domain comprising a BoNT/A NTNH β-trefoil domain comprises a polypeptide having, e.g., at most one, two, three, four, five, six, seven, eight, nine, 10 or 20 contiguous amino acid additions relative to amino acids 1050-1097, amino acids 1111-1139, or amino acids 1149-1199 of SEQ ID NO: 26. In other aspects of this embodiment, a binding domain comprising a BoNT/A NTNH β-trefoil domain comprises a polypeptide having, e.g., at least one, two, three, four, five, six, seven, eight, nine, 10 or 20 contiguous amino acid additions relative to amino acids 1050-1097, amino acids 1111-1139, or amino acids 1149-1199 of SEQ ID NO: 26.

In another embodiment, a binding domain comprising a BoNT/A NTNH β-trefoil domain comprises a β4/β5 hairpin turn of a β-trefoil domain of a BoNT/A NTNH or a β8/β9 hairpin turn of a β-trefoil domain of a BoNT/A NTNH of SEQ ID NO: 24. In another aspect of this embodiment, a binding domain comprising a BoNT/A NTNH β-trefoil domain comprises amino acids 1098-1110 or amino acids 1140-1148 of SEQ ID NO: 26.

In other aspects of this embodiment, a binding domain comprising a BoNT/A NTNH β-trefoil domain comprises a polypeptide having, e.g., at least 70% amino acid identity with amino acids 1098-1110 or amino acids 1140-1148 of SEQ ID NO: 26, at least 75% amino acid identity with amino acids 1098-1110 or amino acids 1140-1148 of SEQ ID NO: 26, at least 80% amino acid identity with amino acids 1098-1110 or amino acids 1140-1148 of SEQ ID NO: 26, at least 85% amino acid identity with amino acids 1098-1110 or amino acids 1140-1148 of SEQ ID NO: 26, at least 90% amino acid identity with amino acids 1098-1110 or amino acids 1140-1148 of SEQ ID NO: 26 or at least 95% amino acid identity with amino acids 1098-1110 or amino acids 1140-1148 of SEQ ID NO: 26. In yet other aspects of this embodiment, a binding domain comprising a BoNT/A NTNH β-trefoil domain comprises a polypeptide having, e.g., at most 70% amino acid identity with amino acids 1098-1110 or amino acids 1140-1148 of SEQ ID NO: 26, at most 75% amino acid identity with amino acids 1098-1110 or amino acids 1140-1148 of SEQ ID NO: 26, at most 80% amino acid identity with amino acids 1098-1110 or amino acids 1140-1148 of SEQ ID NO: 26, at most 85% amino acid identity with amino acids 1098-1110 or amino acids 1140-1148 of SEQ ID NO: 26, at most 90% amino acid identity with amino acids 1098-1110 or amino acids 1140-1148 of SEQ ID NO: 26 or at most 95% amino acid identity with amino acids 1098-1110 or amino acids 1140-1148 of SEQ ID NO: 26.

In other aspects of this embodiment, a binding domain comprising a BoNT/A NTNH β-trefoil domain comprises a polypeptide having, e.g., at most one, two, three or four non-contiguous amino acid substitutions relative to amino acids 1098-1110 or amino acids 1140-1148 of SEQ ID NO: 26. In other aspects of this embodiment, a binding domain comprising a BoNT/A NTNH β-trefoil domain comprises a polypeptide having, e.g., at least one, two, three or four non-contiguous amino acid substitutions relative to amino acids 1098-1110 or amino acids 1140-1148 of SEQ ID NO: 26. In other aspects of this embodiment, a non-contiguous amino acid substitution of any amino acid from amino acids 1098-1110 or amino acids 1140-1148 of SEQ ID NO: 26 can be replaced with glycine. In other aspects of this embodiment, a non-contiguous amino acid substitution of any hydrophobic amino acid from amino acids 1098-1110 or amino acids 1140-1148 of SEQ ID NO: 26 can be replaced with phenylalanine. In yet other aspects of this embodiment, a binding domain comprising a BoNT/A NTNH β-trefoil domain comprises a polypeptide having, e.g., at most one, two, three or four non-contiguous amino acid deletions relative to amino acids 1098-1110 or amino acids 1140-1148 of SEQ ID NO: 26. In other aspects of this embodiment, a binding domain comprising a BoNT/A NTNH β-trefoil domain comprises a polypeptide having, e.g., at least one, two, three or four non-contiguous amino acid deletions relative to amino acids 1098-1110 or amino acids 1140-1148 of SEQ ID NO: 26. In still other aspects of this embodiment, a binding domain comprising a BoNT/A NTNH β-trefoil domain comprises a polypeptide having, e.g., at most one, two, three or four non-contiguous amino acid additions relative to amino acids 1098-1110 or amino acids 1140-1148 of SEQ ID NO: 26. In other aspects of this embodiment, a binding domain comprising a BoNT/A NTNH β-trefoil domain comprises a polypeptide having, e.g., at least one, two, three or four non-contiguous amino acid additions relative to amino acids 1098-1110 or amino acids 1140-1148 of SEQ ID NO: 26.

In other aspects of this embodiment, a binding domain comprising a BoNT/A NTNH β-trefoil domain comprises a polypeptide having, e.g., at most one, two, three or four contiguous amino acid substitutions relative to amino acids 1098-1110 or amino acids 1140-1148 of SEQ ID NO: 26. In other aspects of this embodiment, a binding domain comprising a BoNT/A NTNH β-trefoil domain comprises a polypeptide having, e.g., at least one, two, three or four contiguous amino acid substitutions relative to amino acids 1098-1110 or amino acids 1140-1148 of SEQ ID NO: 26. In other aspects of this embodiment, contiguous amino acid substitutions of amino acids from amino acids 1098-1110 or amino acids 1140-1148 of SEQ ID NO: 26 can be replaced with glycine. In other aspects of this embodiment, contiguous amino acid substitutions of hydrophobic amino acids from amino acids 1098-1110 or amino acids 1140-1148 of SEQ ID NO: 26 can be replaced with phenylalanine. In yet other aspects of this embodiment, a β-trefoil domain with enhanced binding activity derived from a BoNT/A NTNH comprises a polypeptide having, e.g., at most one, two, three or four contiguous amino acid deletions relative to amino acids 1098-1110 or amino acids 1140-1148 of SEQ ID NO: 26. In other aspects of this embodiment, a binding domain comprising a BoNT/A NTNH β-trefoil domain comprises a polypeptide having, e.g., at least one, two, three or four contiguous amino acid deletions relative to amino acids 1098-1110 or amino acids 1140-1148 of SEQ ID NO: 26. In still other aspects of this embodiment, a binding domain comprising a BoNT/A NTNH β-trefoil domain comprises a polypeptide having, e.g., at most one, two, three or four contiguous amino acid additions relative to amino acids 1098-1110 or amino acids 1140-1148 of SEQ ID NO: 26. In other aspects of this embodiment, a binding domain comprising a BoNT/A NTNH β-trefoil domain comprises a polypeptide having, e.g., at least one, two, three or four contiguous amino acid additions relative to amino acids 1098-1110 or amino acids 1140-1148 of SEQ ID NO: 26.

In another embodiment, a binding domain comprises a β-trefoil domain derived from a BoNT/A NTNH of SEQ ID NO: 27. In another embodiment, a binding domain comprising a β-trefoil domain derived from a BoNT/A NTNH comprises amino acids 1050-1194 of SEQ ID NO: 27. In another aspect of this embodiment, a binding domain comprising a β-trefoil domain derived from a BoNT/A NTNH comprises a α-fold motif of a β-trefoil domain of a BoNT/A NTNH, a β-fold motif of a β-trefoil domain of a BoNT/A NTNH or a γ-fold motif of a β-trefoil domain of a BoNT/A NTNH of SEQ ID NO: 24. In another aspect of this embodiment, a β-trefoil domain derived from a BoNT/A NTNH comprises amino acids 1050-1097, amino acids 1111-1138, or amino acids 1149-1194 of SEQ ID NO: 27.

In other aspects of this embodiment, a binding domain comprising a BoNT/A NTNH β-trefoil domain comprises a polypeptide having, e.g., at least 70% amino acid identity with amino acids 1050-1097, amino acids 1111-1138, or amino acids 1149-1194 of SEQ ID NO: 27, at least 75% amino acid identity with amino acids 1050-1097, amino acids 1111-1138, or amino acids 1149-1194 of SEQ ID NO: 27, at least 80% amino acid identity with amino acids 1050-1097, amino acids 1111-1138, or amino acids 1149-1194 of SEQ ID NO: 27, at least 85% amino acid identity with amino acids 1050-1097, amino acids 1111-1138, or amino acids 1149-1194 of SEQ ID NO: 27, at least 90% amino acid identity with amino acids 1050-1097, amino acids 1111-1138, or amino acids 1149-1194 of SEQ ID NO: 27 or at least 95% amino acid identity with amino acids 1050-1097, amino acids 1111-1138, or amino acids 1149-1194 of SEQ ID NO: 27. In yet other aspects of this embodiment, a binding domain comprising a BoNT/A NTNH β-trefoil domain comprises a polypeptide having, e.g., at most 70% amino acid identity with amino acids 1050-1097, amino acids 1111-1138, or amino acids 1149-1194 of SEQ ID NO: 27, at most 75% amino acid identity with amino acids 1050-1097, amino acids 1111-1138, or amino acids 1149-1194 of SEQ ID NO: 27, at most 80% amino acid identity with amino acids 1050-1097, amino acids 1111-1138, or amino acids 1149-1194 of SEQ ID NO: 27, at most 85% amino acid identity with amino acids 1050-1097, amino acids 1111-1138, or amino acids 1149-1194 of SEQ ID NO: 27, at most 90% amino acid identity with amino acids 1050-1097, amino acids 1111-1138, or amino acids 1149-1194 of SEQ ID NO: 27 or at most 95% amino acid identity with amino acids 1050-1097, amino acids 1111-1138, or amino acids 1149-1194 of SEQ ID NO: 27.

In other aspects of this embodiment, a binding domain comprising a BoNT/A NTNH β-trefoil domain comprises a polypeptide having, e.g., at most one, two, three, four, five, six, seven, eight, nine, 10 or 20 non-contiguous amino acid substitutions relative to amino acids 1050-1097, amino acids 1111-1138, or amino acids 1149-1194 of SEQ ID NO: 27. In other aspects of this embodiment, a binding domain comprising a BoNT/A NTNH β-trefoil domain comprises a polypeptide having, e.g., at least one, two, three, four, five, six, seven, eight, nine, 10 or 20 non-contiguous amino acid substitutions relative to amino acids 1050-1097, amino acids 1111-1138, or amino acids 1149-1194 of SEQ ID NO: 27. In yet other aspects of this embodiment, a binding domain comprising a BoNT/A NTNH β-trefoil domain comprises a polypeptide having, e.g., at most one, two, three, four, five, six, seven, eight, nine, 10 or 20 non-contiguous amino acid deletions relative to amino acids 1050-1097, amino acids 1111-1138, or amino acids 1149-1194 of SEQ ID NO: 27. In other aspects of this embodiment, a binding domain comprising a BoNT/A NTNH β-trefoil domain comprises a polypeptide having, e.g., at least one, two, three, four, five, six, seven, eight, nine, 10 or 20 non-contiguous amino acid deletions relative to amino acids 1050-1097, amino acids 1111-1138, or amino acids 1149-1194 of SEQ ID NO: 27. In still other aspects of this embodiment, a binding domain comprising a BoNT/A NTNH β-trefoil domain comprises a polypeptide having, e.g., at most one, two, three, four, five, six, seven, eight, nine, 10 or 20 non-contiguous amino acid additions relative to amino acids 1050-1097, amino acids 1111-1138, or amino acids 1149-1194 of SEQ ID NO: 27. In other aspects of this embodiment, a binding domain comprising a BoNT/A NTNH β-trefoil domain comprises a polypeptide having, e.g., at least one, two, three, four, five, six, seven, eight, nine, 10 or 20 non-contiguous amino acid additions relative to amino acids 1050-1097, amino acids 1111-1138, or amino acids 1149-1194 of SEQ ID NO: 27.

In other aspects of this embodiment, a binding domain comprising a BoNT/A NTNH β-trefoil domain comprises a polypeptide having, e.g., at most one, two, three, four, five, six, seven, eight, nine, 10 or 20 contiguous amino acid substitutions relative to amino acids 1050-1097, amino acids 1111-1138, or amino acids 1149-1194 of SEQ ID NO: 27. In other aspects of this embodiment, a binding domain comprising a BoNT/A NTNH β-trefoil domain comprises a polypeptide having, e.g., at least one, two, three, four, five, six, seven, eight, nine, 10 or 20 contiguous amino acid substitutions relative to amino acids 1050-1097, amino acids 1111-1138, or amino acids 1149-1194 of SEQ ID NO: 27. In yet other aspects of this embodiment, a binding domain comprising a BoNT/A NTNH β-trefoil domain comprises a polypeptide having, e.g., at most one, two, three, four, five, six, seven, eight, nine, 10 or 20 contiguous amino acid deletions relative to amino acids 1050-1097, amino acids 1111-1138, or amino acids 1149-1194 of SEQ ID NO: 27. In other aspects of this embodiment, a binding domain comprising a BoNT/A NTNH β-trefoil domain comprises a polypeptide having, e.g., at least one, two, three, four, five, six, seven, eight, nine, 10 or 20 contiguous amino acid deletions relative to amino acids 1050-1097, amino acids 1111-1138, or amino acids 1149-1194 of SEQ ID NO: 27. In still other aspects of this embodiment, a binding domain comprising a BoNT/A NTNH β-trefoil domain comprises a polypeptide having, e.g., at most one, two, three, four, five, six, seven, eight, nine, 10 or 20 contiguous amino acid additions relative to amino acids 1050-1097, amino acids 1111-1138, or amino acids 1149-1194 of SEQ ID NO: 27. In other aspects of this embodiment, a binding domain comprising a BoNT/A NTNH β-trefoil domain comprises a polypeptide having, e.g., at least one, two, three, four, five, six, seven, eight, nine, 10 or 20 contiguous amino acid additions relative to amino acids 1050-1097, amino acids 1111-1138, or amino acids 1149-1194 of SEQ ID NO: 27.

In another embodiment, a binding domain comprising a BoNT/A NTNH β-trefoil domain comprises a β4/β5 hairpin turn of a β-trefoil domain of a BoNT/A NTNH or a β8/β9 hairpin turn of a β-trefoil domain of a BoNT/A NTNH of SEQ ID NO: 24. In another aspect of this embodiment, a binding domain comprising a BoNT/A NTNH β-trefoil domain comprises amino acids 1098-1110 or amino acids 1139-1148 of SEQ ID NO: 27.

In other aspects of this embodiment, a binding domain comprising a BoNT/A NTNH β-trefoil domain comprises a polypeptide having, e.g., at least 70% amino acid identity with amino acids 1098-1110 or amino acids 1139-1148 of SEQ ID NO: 27, at least 75% amino acid identity with amino acids 1098-1110 or amino acids 1139-1148 of SEQ ID NO: 27, at least 80% amino acid identity with amino acids 1098-1110 or amino acids 1139-1148 of SEQ ID NO: 27, at least 85% amino acid identity with amino acids 1098-1110 or amino acids 1139-1148 of SEQ ID NO: 27, at least 90% amino acid identity with amino acids 1098-1110 or amino acids 1139-1148 of SEQ ID NO: 27 or at least 95% amino acid identity with amino acids 1098-1110 or amino acids 1139-1148 of SEQ ID NO: 27. In yet other aspects of this embodiment, a binding domain comprising a BoNT/A NTNH β-trefoil domain comprises a polypeptide having, e.g., at most 70% amino acid identity with amino acids 1098-1110 or amino acids 1139-1148 of SEQ ID NO: 27, at most 75% amino acid identity with amino acids 1098-1110 or amino acids 1139-1148 of SEQ ID NO: 27, at most 80% amino acid identity with amino acids 1098-1110 or amino acids 1139-1148 of SEQ ID NO: 27, at most 85% amino acid identity with amino acids 1098-1110 or amino acids 1139-1148 of SEQ ID NO: 27, at most 90% amino acid identity with amino acids 1098-1110 or amino acids 1139-1148 of SEQ ID NO: 27 or at most 95% amino acid identity with amino acids 1098-1110 or amino acids 1139-1148 of SEQ ID NO: 27.

In other aspects of this embodiment, a binding domain comprising a BoNT/A NTNH β-trefoil domain comprises a polypeptide having, e.g., at most one, two, three or four non-contiguous amino acid substitutions relative to amino acids 1098-1110 or amino acids 1139-1148 of SEQ ID NO: 27. In other aspects of this embodiment, a binding domain comprising a BoNT/A NTNH β-trefoil domain comprises a polypeptide having, e.g., at least one, two, three or four non-contiguous amino acid substitutions relative to amino acids 1098-1110 or amino acids 1139-1148 of SEQ ID NO: 27. In other aspects of this embodiment, a non-contiguous amino acid substitution of any amino acid from amino acids 1098-1110 or amino acids 1139-1148 of SEQ ID NO: 27 can be replaced with glycine. In other aspects of this embodiment, a non-contiguous amino acid substitution of any hydrophobic amino acid from amino acids 1098-1110 or amino acids 1139-1148 of SEQ ID NO: 27 can be replaced with phenylalanine. In yet other aspects of this embodiment, a binding domain comprising a BoNT/A NTNH β-trefoil domain comprises a polypeptide having, e.g., at most one, two, three or four non-contiguous amino acid deletions relative to amino acids 1098-1110 or amino acids 1139-1148 of SEQ ID NO: 27. In other aspects of this embodiment, a binding domain comprising a BoNT/A NTNH β-trefoil domain comprises a polypeptide having, e.g., at least one, two, three or four non-contiguous amino acid deletions relative to amino acids 1098-1110 or amino acids 1139-1148 of SEQ ID NO: 27. In still other aspects of this embodiment, a binding domain comprising a BoNT/A NTNH β-trefoil domain comprises a polypeptide having, e.g., at most one, two, three or four non-contiguous amino acid additions relative to amino acids 1098-1110 or amino acids 1139-1148 of SEQ ID NO: 27. In other aspects of this embodiment, a binding domain comprising a BoNT/A NTNH β-trefoil domain comprises a polypeptide having, e.g., at least one, two, three or four non-contiguous amino acid additions relative to amino acids 1098-1110 or amino acids 1139-1148 of SEQ ID NO: 27.

In other aspects of this embodiment, a binding domain comprising a BoNT/A NTNH β-trefoil domain comprises a polypeptide having, e.g., at most one, two, three or four contiguous amino acid substitutions relative to amino acids 1098-1110 or amino acids 1139-1148 of SEQ ID NO: 27. In other aspects of this embodiment, a binding domain comprising a BoNT/A NTNH β-trefoil domain comprises a polypeptide having, e.g., at least one, two, three or four contiguous amino acid substitutions relative to amino acids 1098-1110 or amino acids 1139-1148 of SEQ ID NO: 27. In other aspects of this embodiment, contiguous amino acid substitutions of amino acids from amino acids 1098-1110 or amino acids 1139-1148 of SEQ ID NO: 27 can be replaced with glycine. In other aspects of this embodiment, contiguous amino acid substitutions of hydrophobic amino acids from amino acids 1098-1110 or amino acids 1139-1148 of SEQ ID NO: 27 can be replaced with phenylalanine. In yet other aspects of this embodiment, a β-trefoil domain with enhanced binding activity derived from a BoNT/A NTNH comprises a polypeptide having, e.g., at most one, two, three or four contiguous amino acid deletions relative to amino acids 1098-1110 or amino acids 1139-1148 of SEQ ID NO: 27. In other aspects of this embodiment, a binding domain comprising a BoNT/A NTNH β-trefoil domain comprises a polypeptide having, e.g., at least one, two, three or four contiguous amino acid deletions relative to amino acids 1098-1110 or amino acids 1139-1148 of SEQ ID NO: 27. In still other aspects of this embodiment, a binding domain comprising a BoNT/A NTNH β-trefoil domain comprises a polypeptide having, e.g., at most one, two, three or four contiguous amino acid additions relative to amino acids 1098-1110 or amino acids 1139-1148 of SEQ ID NO: 27. In other aspects of this embodiment, a binding domain comprising a BoNT/A NTNH β-trefoil domain comprises a polypeptide having, e.g., at least one, two, three or four contiguous amino acid additions relative to amino acids 1098-1110 or amino acids 1139-1148 of SEQ ID NO: 27.

In another embodiment, a binding domain comprises a β-trefoil domain derived from a BoNT/B NTNH of SEQ ID NO: 28. In another embodiment, a binding domain comprising a β-trefoil domain derived from a BoNT/B NTNH comprises amino acids 1049-1198 of SEQ ID NO: 28. In another aspect of this embodiment, a binding domain comprising a β-trefoil domain derived from a BoNT/B NTNH comprises a α-fold motif of a β-trefoil domain of a BoNT/B NTNH, a β-fold motif of a β-trefoil domain of a BoNT/B NTNH or a γ-fold motif of a β-trefoil domain of a BoNT/B NTNH of SEQ ID NO: 24. In another aspect of this embodiment, a β-trefoil domain derived from a BoNT/B NTNH comprises amino acids 1049-1096, amino acids 1110-1138, or amino acids 1148-1198 of SEQ ID NO: 28.

In other aspects of this embodiment, a binding domain comprising a BoNT/B NTNH β-trefoil domain comprises a polypeptide having, e.g., at least 70% amino acid identity with amino acids 1049-1096, amino acids 1110-1138, or amino acids 1148-1198 of SEQ ID NO: 28, at least 75% amino acid identity with amino acids 1049-1096, amino acids 1110-1138, or amino acids 1148-1198 of SEQ ID NO: 28, at least 80% amino acid identity with amino acids 1049-1096, amino acids 1110-1138, or amino acids 1148-1198 of SEQ ID NO: 28, at least 85% amino acid identity with amino acids 1049-1096, amino acids 1110-1138, or amino acids 1148-1198 of SEQ ID NO: 28, at least 90% amino acid identity with amino acids 1049-1096, amino acids 1110-1138, or amino acids 1148-1198 of SEQ ID NO: 28 or at least 95% amino acid identity with amino acids 1049-1096, amino acids 1110-1138, or amino acids 1148-1198 of SEQ ID NO: 28. In yet other aspects of this embodiment, a binding domain comprising a BoNT/B NTNH β-trefoil domain comprises a polypeptide having, e.g., at most 70% amino acid identity with amino acids 1049-1096, amino acids 1110-1138, or amino acids 1148-1198 of SEQ ID NO: 28, at most 75% amino acid identity with amino acids 1049-1096, amino acids 1110-1138, or amino acids 1148-1198 of SEQ ID NO: 28, at most 80% amino acid identity with amino acids 1049-1096, amino acids 1110-1138, or amino acids 1148-1198 of SEQ ID NO: 28, at most 85% amino acid identity with amino acids 1049-1096, amino acids 1110-1138, or amino acids 1148-1198 of SEQ ID NO: 28, at most 90% amino acid identity with amino acids 1049-1096, amino acids 1110-1138, or amino acids 1148-1198 of SEQ ID NO: 28 or at most 95% amino acid identity with amino acids 1049-1096, amino acids 1110-1138, or amino acids 1148-1198 of SEQ ID NO: 28.

In other aspects of this embodiment, a binding domain comprising a BoNT/B NTNH β-trefoil domain comprises a polypeptide having, e.g., at most one, two, three, four, five, six, seven, eight, nine, 10 or 20 non-contiguous amino acid substitutions relative to amino acids 1049-1096, amino acids 1110-1138, or amino acids 1148-1198 of SEQ ID NO: 28. In other aspects of this embodiment, a binding domain comprising a BoNT/B NTNH β-trefoil domain comprises a polypeptide having, e.g., at least one, two, three, four, five, six, seven, eight, nine, 10 or 20 non-contiguous amino acid substitutions relative to amino acids 1049-1096, amino acids 1110-1138, or amino acids 1148-1198 of SEQ ID NO: 28. In yet other aspects of this embodiment, a binding domain comprising a BoNT/B NTNH β-trefoil domain comprises a polypeptide having, e.g., at most one, two, three, four, five, six, seven, eight, nine, 10 or 20 non-contiguous amino acid deletions relative to amino acids 1049-1096, amino acids 1110-1138, or amino acids 1148-1198 of SEQ ID NO: 28. In other aspects of this embodiment, a binding domain comprising a BoNT/B NTNH β-trefoil domain comprises a polypeptide having, e.g., at least one, two, three, four, five, six, seven, eight, nine, 10 or 20 non-contiguous amino acid deletions relative to amino acids 1049-1096, amino acids 1110-1138, or amino acids 1148-1198 of SEQ ID NO: 28. In still other aspects of this embodiment, a binding domain comprising a BoNT/B NTNH β-trefoil domain comprises a polypeptide having, e.g., at most one, two, three, four, five, six, seven, eight, nine, 10 or 20 non-contiguous amino acid additions relative to amino acids 1049-1096, amino acids 1110-1138, or amino acids 1148-1198 of SEQ ID NO: 28. In other aspects of this embodiment, a binding domain comprising a BoNT/B NTNH β-trefoil domain comprises a polypeptide having, e.g., at least one, two, three, four, five, six, seven, eight, nine, 10 or 20 non-contiguous amino acid additions relative to amino acids 1049-1096, amino acids 1110-1138, or amino acids 1148-1198 of SEQ ID NO: 28.

In other aspects of this embodiment, a binding domain comprising a BoNT/B NTNH β-trefoil domain comprises a polypeptide having, e.g., at most one, two, three, four, five, six, seven, eight, nine, 10 or 20 contiguous amino acid substitutions relative to amino acids 1049-1096, amino acids 1110-1138, or amino acids 1148-1198 of SEQ ID NO: 28. In other aspects of this embodiment, a binding domain comprising a BoNT/B NTNH β-trefoil domain comprises a polypeptide having, e.g., at least one, two, three, four, five, six, seven, eight, nine, 10 or 20 contiguous amino acid substitutions relative to amino acids 1049-1096, amino acids 1110-1138, or amino acids 1148-1198 of SEQ ID NO: 28. In yet other aspects of this embodiment, a binding domain comprising a BoNT/B NTNH β-trefoil domain comprises a polypeptide having, e.g., at most one, two, three, four, five, six, seven, eight, nine, 10 or 20 contiguous amino acid deletions relative to amino acids 1049-1096, amino acids 1110-1138, or amino acids 1148-1198 of SEQ ID NO: 28. In other aspects of this embodiment, a binding domain comprising a BoNT/B NTNH β-trefoil domain comprises a polypeptide having, e.g., at least one, two, three, four, five, six, seven, eight, nine, 10 or 20 contiguous amino acid deletions relative to amino acids 1049-1096, amino acids 1110-1138, or amino acids 1148-1198 of SEQ ID NO: 28. In still other aspects of this embodiment, a binding domain comprising a BoNT/B NTNH β-trefoil domain comprises a polypeptide having, e.g., at most one, two, three, four, five, six, seven, eight, nine, 10 or 20 contiguous amino acid additions relative to amino acids 1049-1096, amino acids 1110-1138, or amino acids 1148-1198 of SEQ ID NO: 28. In other aspects of this embodiment, a binding domain comprising a BoNT/B NTNH β-trefoil domain comprises a polypeptide having, e.g., at least one, two, three, four, five, six, seven, eight, nine, 10 or 20 contiguous amino acid additions relative to amino acids 1049-1096, amino acids 1110-1138, or amino acids 1148-1198 of SEQ ID NO: 28.

In another embodiment, a binding domain comprising a BoNT/B NTNH β-trefoil domain comprises a β4/β5 hairpin turn of a β-trefoil domain of a BoNT/B NTNH or a β8/β9 hairpin turn of a β-trefoil domain of a BoNT/B NTNH of SEQ ID NO: 24. In another aspect of this embodiment, a binding domain comprising a BoNT/B NTNH β-trefoil domain comprises amino acids 1097-1109 or amino acids 1139-1147 of SEQ ID NO: 28.

In other aspects of this embodiment, a binding domain comprising a BoNT/B NTNH β-trefoil domain comprises a polypeptide having, e.g., at least 70% amino acid identity with amino acids 1097-1109 or amino acids 1139-1147 of SEQ ID NO: 28, at least 75% amino acid identity with amino acids 1097-1109 or amino acids 1139-1147 of SEQ ID NO: 28, at least 80% amino acid identity with amino acids 1097-1109 or amino acids 1139-1147 of SEQ ID NO: 28, at least 85% amino acid identity with amino acids 1097-1109 or amino acids 1139-1147 of SEQ ID NO: 28, at least 90% amino acid identity with amino acids 1097-1109 or amino acids 1139-1147 of SEQ ID NO: 28 or at least 95% amino acid identity with amino acids 1097-1109 or amino acids 1139-1147 of SEQ ID NO: 28. In yet other aspects of this embodiment, a binding domain comprising a BoNT/B NTNH β-trefoil domain comprises a polypeptide having, e.g., at most 70% amino acid identity with amino acids 1097-1109 or amino acids 1139-1147 of SEQ ID NO: 28, at most 75% amino acid identity with amino acids 1097-1109 or amino acids 1139-1147 of SEQ ID NO: 28, at most 80% amino acid identity with amino acids 1097-1109 or amino acids 1139-1147 of SEQ ID NO: 28, at most 85% amino acid identity with amino acids 1097-1109 or amino acids 1139-1147 of SEQ ID NO: 28, at most 90% amino acid identity with amino acids 1097-1109 or amino acids 1139-1147 of SEQ ID NO: 28 or at most 95% amino acid identity with amino acids 1097-1109 or amino acids 1139-1147 of SEQ ID NO: 28.

In other aspects of this embodiment, a binding domain comprising a BoNT/B NTNH β-trefoil domain comprises a polypeptide having, e.g., at most one, two, three or four non-contiguous amino acid substitutions relative to amino acids 1097-1109 or amino acids 1139-1147 of SEQ ID NO: 28. In other aspects of this embodiment, a binding domain comprising a BoNT/B NTNH β-trefoil domain comprises a polypeptide having, e.g., at least one, two, three or four non-contiguous amino acid substitutions relative to amino acids 1097-1109 or amino acids 1139-1147 of SEQ ID NO: 28. In other aspects of this embodiment, a non-contiguous amino acid substitution of any amino acid from amino acids 1097-1109 or amino acids 1139-1147 of SEQ ID NO: 28 can be replaced with glycine. In other aspects of this embodiment, a non-contiguous amino acid substitution of any hydrophobic amino acid from amino acids 1097-1109 or amino acids 1139-1147 of SEQ ID NO: 28 can be replaced with phenylalanine. In yet other aspects of this embodiment, a binding domain comprising a BoNT/B NTNH β-trefoil domain comprises a polypeptide having, e.g., at most one, two, three or four non-contiguous amino acid deletions relative to amino acids 1097-1109 or amino acids 1139-1147 of SEQ ID NO: 28. In other aspects of this embodiment, a binding domain comprising a BoNT/B NTNH β-trefoil domain comprises a polypeptide having, e.g., at least one, two, three or four non-contiguous amino acid deletions relative to amino acids 1097-1109 or amino acids 1139-1147 of SEQ ID NO: 28. In still other aspects of this embodiment, a binding domain comprising a BoNT/B NTNH β-trefoil domain comprises a polypeptide having, e.g., at most one, two, three or four non-contiguous amino acid additions relative to amino acids 1097-1109 or amino acids 1139-1147 of SEQ ID NO: 28. In other aspects of this embodiment, a binding domain comprising a BoNT/B NTNH β-trefoil domain comprises a polypeptide having, e.g., at least one, two, three or four non-contiguous amino acid additions relative to amino acids 1097-1109 or amino acids 1139-1147 of SEQ ID NO: 28.

In other aspects of this embodiment, a binding domain comprising a BoNT/B NTNH β-trefoil domain comprises a polypeptide having, e.g., at most one, two, three or four contiguous amino acid substitutions relative to amino acids 1097-1109 or amino acids 1139-1147 of SEQ ID NO: 28. In other aspects of this embodiment, a binding domain comprising a BoNT/B NTNH β-trefoil domain comprises a polypeptide having, e.g., at least one, two, three or four contiguous amino acid substitutions relative to amino acids 1097-1109 or amino acids 1139-1147 of SEQ ID NO: 28. In other aspects of this embodiment, contiguous amino acid substitutions of amino acids from amino acids 1097-1109 or amino acids 1139-1147 of SEQ ID NO: 28 can be replaced with glycine. In other aspects of this embodiment, contiguous amino acid substitutions of hydrophobic amino acids from amino acids 1097-1109 or amino acids 1139-1147 of SEQ ID NO: 28 can be replaced with phenylalanine. In yet other aspects of this embodiment, a β-trefoil domain with enhanced binding activity derived from a BoNT/B NTNH comprises a polypeptide having, e.g., at most one, two, three or four contiguous amino acid deletions relative to amino acids 1097-1109 or amino acids 1139-1147 of SEQ ID NO: 28. In other aspects of this embodiment, a binding domain comprising a BoNT/B NTNH β-trefoil domain comprises a polypeptide having, e.g., at least one, two, three or four contiguous amino acid deletions relative to amino acids 1097-1109 or amino acids 1139-1147 of SEQ ID NO: 28. In still other aspects of this embodiment, a binding domain comprising a BoNT/B NTNH β-trefoil domain comprises a polypeptide having, e.g., at most one, two, three or four contiguous amino acid additions relative to amino acids 1097-1109 or amino acids 1139-1147 of SEQ ID NO: 28. In other aspects of this embodiment, a binding domain comprising a BoNT/B NTNH β-trefoil domain comprises a polypeptide having, e.g., at least one, two, three or four contiguous amino acid additions relative to amino acids 1097-1109 or amino acids 1139-1147 of SEQ ID NO: 28.

In another embodiment, a binding domain comprises a β-trefoil domain derived from a BoNT/C1 NTNH of SEQ ID NO: 29. In another embodiment, a binding domain comprising a β-trefoil domain derived from a BoNT/C1 NTNH comprises amino acids 1049-1197 of SEQ ID NO: 29. In another aspect of this embodiment, a binding domain comprising a β-trefoil domain derived from a BoNT/C1 NTNH comprises a α-fold motif of a β-trefoil domain of a BoNT/C1 NTNH, a β-fold motif of a β-trefoil domain of a BoNT/C1 NTNH or a γ-fold motif of a β-trefoil domain of a BoNT/C1 NTNH of SEQ ID NO: 24. In another aspect of this embodiment, a β-trefoil domain derived from a BoNT/C1 NTNH comprises amino acids 1049-1096, amino acids 1110-1138, or amino acids 1148-1197 of SEQ ID NO: 29.

In other aspects of this embodiment, a binding domain comprising a BoNT/C1 NTNH β-trefoil domain comprises a polypeptide having, e.g., at least 70% amino acid identity with amino acids 1049-1096, amino acids 1110-1138, or amino acids 1148-1197 of SEQ ID NO: 29, at least 75% amino acid identity with amino acids 1049-1096, amino acids 1110-1138, or amino acids 1148-1197 of SEQ ID NO: 29, at least 80% amino acid identity with amino acids 1049-1096, amino acids 1110-1138, or amino acids 1148-1197 of SEQ ID NO: 29, at least 85% amino acid identity with amino acids 1049-1096, amino acids 1110-1138, or amino acids 1148-1197 of SEQ ID NO: 29, at least 90% amino acid identity with amino acids 1049-1096, amino acids 1110-1138, or amino acids 1148-1197 of SEQ ID NO: 29 or at least 95% amino acid identity with amino acids 1049-1096, amino acids 1110-1138, or amino acids 1148-1197 of SEQ ID NO: 29. In yet other aspects of this embodiment, a binding domain comprising a BoNT/C1 NTNH β-trefoil domain comprises a polypeptide having, e.g., at most 70% amino acid identity with amino acids 1049-1096, amino acids 1110-1138, or amino acids 1148-1197 of SEQ ID NO: 29, at most 75% amino acid identity with amino acids 1049-1096, amino acids 1110-1138, or amino acids 1148-1197 of SEQ ID NO: 29, at most 80% amino acid identity with amino acids 1049-1096, amino acids 1110-1138, or amino acids 1148-1197 of SEQ ID NO: 29, at most 85% amino acid identity with amino acids 1049-1096, amino acids 1110-1138, or amino acids 1148-1197 of SEQ ID NO: 29, at most 90% amino acid identity with amino acids 1049-1096, amino acids 1110-1138, or amino acids 1148-1197 of SEQ ID NO: 29 or at most 95% amino acid identity with amino acids 1049-1096, amino acids 1110-1138, or amino acids 1148-1197 of SEQ ID NO: 29.

In other aspects of this embodiment, a binding domain comprising a BoNT/C1 NTNH β-trefoil domain comprises a polypeptide having, e.g., at most one, two, three, four, five, six, seven, eight, nine, 10 or 20 non-contiguous amino acid substitutions relative to amino acids 1049-1096, amino acids 1110-1138, or amino acids 1148-1197 of SEQ ID NO: 29. In other aspects of this embodiment, a binding domain comprising a BoNT/C1 NTNH β-trefoil domain comprises a polypeptide having, e.g., at least one, two, three, four, five, six, seven, eight, nine, 10 or 20 non-contiguous amino acid substitutions relative to amino acids 1049-1096, amino acids 1110-1138, or amino acids 1148-1197 of SEQ ID NO: 29. In yet other aspects of this embodiment, a binding domain comprising a BoNT/C1 NTNH β-trefoil domain comprises a polypeptide having, e.g., at most one, two, three, four, five, six, seven, eight, nine, 10 or 20 non-contiguous amino acid deletions relative to amino acids 1049-1096, amino acids 1110-1138, or amino acids 1148-1197 of SEQ ID NO: 29. In other aspects of this embodiment, a binding domain comprising a BoNT/C1 NTNH β-trefoil domain comprises a polypeptide having, e.g., at least one, two, three, four, five, six, seven, eight, nine, 10 or 20 non-contiguous amino acid deletions relative to amino acids 1049-1096, amino acids 1110-1138, or amino acids 1148-1197 of SEQ ID NO: 29. In still other aspects of this embodiment, a binding domain comprising a BoNT/C1 NTNH β-trefoil domain comprises a polypeptide having, e.g., at most one, two, three, four, five, six, seven, eight, nine, 10 or 20 non-contiguous amino acid additions relative to amino acids 1049-1096, amino acids 1110-1138, or amino acids 1148-1197 of SEQ ID NO: 29. In other aspects of this embodiment, a binding domain comprising a BoNT/C1 NTNH β-trefoil domain comprises a polypeptide having, e.g., at least one, two, three, four, five, six, seven, eight, nine, 10 or 20 non-contiguous amino acid additions relative to amino acids 1049-1096, amino acids 1110-1138, or amino acids 1148-1197 of SEQ ID NO: 29.

In other aspects of this embodiment, a binding domain comprising a BoNT/C1 NTNH β-trefoil domain comprises a polypeptide having, e.g., at most one, two, three, four, five, six, seven, eight, nine, 10 or 20 contiguous amino acid substitutions relative to amino acids 1049-1096, amino acids 1110-1138, or amino acids 1148-1197 of SEQ ID NO: 29. In other aspects of this embodiment, a binding domain comprising a BoNT/C1 NTNH β-trefoil domain comprises a polypeptide having, e.g., at least one, two, three, four, five, six, seven, eight, nine, 10 or 20 contiguous amino acid substitutions relative to amino acids 1049-1096, amino acids 1110-1138, or amino acids 1148-1197 of SEQ ID NO: 29. In yet other aspects of this embodiment, a binding domain comprising a BoNT/C1 NTNH β-trefoil domain comprises a polypeptide having, e.g., at most one, two, three, four, five, six, seven, eight, nine, 10 or 20 contiguous amino acid deletions relative to amino acids 1049-1096, amino acids 1110-1138, or amino acids 1148-1197 of SEQ ID NO: 29. In other aspects of this embodiment, a binding domain comprising a BoNT/C1 NTNH β-trefoil domain comprises a polypeptide having, e.g., at least one, two, three, four, five, six, seven, eight, nine, 10 or 20 contiguous amino acid deletions relative to amino acids 1049-1096, amino acids 1110-1138, or amino acids 1148-1197 of SEQ ID NO: 29. In still other aspects of this embodiment, a binding domain comprising a BoNT/C1 NTNH β-trefoil domain comprises a polypeptide having, e.g., at most one, two, three, four, five, six, seven, eight, nine, 10 or 20 contiguous amino acid additions relative to amino acids 1049-1096, amino acids 1110-1138, or amino acids 1148-1197 of SEQ ID NO: 29. In other aspects of this embodiment, a binding domain comprising a BoNT/C1 NTNH β-trefoil domain comprises a polypeptide having, e.g., at least one, two, three, four, five, six, seven, eight, nine, 10 or 20 contiguous amino acid additions relative to amino acids 1049-1096, amino acids 1110-1138, or amino acids 1148-1197 of SEQ ID NO: 29.

In another embodiment, a binding domain comprising a BoNT/C1 NTNH β-trefoil domain comprises a β4/β5 hairpin turn of a β-trefoil domain of a BoNT/C1 NTNH or a β8/β9 hairpin turn of a β-trefoil domain of a BoNT/C1 NTNH of SEQ ID NO: 24. In another aspect of this embodiment, a binding domain comprising a BoNT/C1 NTNH β-trefoil domain comprises amino acids 1097-1109 or amino acids 1139-1147 of SEQ ID NO: 29.

In other aspects of this embodiment, a binding domain comprising a BoNT/C1 NTNH β-trefoil domain comprises a polypeptide having, e.g., at least 70% amino acid identity with amino acids 1097-1109 or amino acids 1139-1147 of SEQ ID NO: 29, at least 75% amino acid identity with amino acids 1097-1109 or amino acids 1139-1147 of SEQ ID NO: 29, at least 80% amino acid identity with amino acids 1097-1109 or amino acids 1139-1147 of SEQ ID NO: 29, at least 85% amino acid identity with amino acids 1097-1109 or amino acids 1139-1147 of SEQ ID NO: 29, at least 90% amino acid identity with amino acids 1097-1109 or amino acids 1139-1147 of SEQ ID NO: 29 or at least 95% amino acid identity with amino acids 1097-1109 or amino acids 1139-1147 of SEQ ID NO: 29. In yet other aspects of this embodiment, a binding domain comprising a BoNT/C1 NTNH β-trefoil domain comprises a polypeptide having, e.g., at most 70% amino acid identity with amino acids 1097-1109 or amino acids 1139-1147 of SEQ ID NO: 29, at most 75% amino acid identity with amino acids 1097-1109 or amino acids 1139-1147 of SEQ ID NO: 29, at most 80% amino acid identity with amino acids 1097-1109 or amino acids 1139-1147 of SEQ ID NO: 29, at most 85% amino acid identity with amino acids 1097-1109 or amino acids 1139-1147 of SEQ ID NO: 29, at most 90% amino acid identity with amino acids 1097-1109 or amino acids 1139-1147 of SEQ ID NO: 29 or at most 95% amino acid identity with amino acids 1097-1109 or amino acids 1139-1147 of SEQ ID NO: 29.

In other aspects of this embodiment, a binding domain comprising a BoNT/C1 NTNH β-trefoil domain comprises a polypeptide having, e.g., at most one, two, three or four non-contiguous amino acid substitutions relative to amino acids 1097-1109 or amino acids 1139-1147 of SEQ ID NO: 29. In other aspects of this embodiment, a binding domain comprising a BoNT/C1 NTNH β-trefoil domain comprises a polypeptide having, e.g., at least one, two, three or four non-contiguous amino acid substitutions relative to amino acids 1097-1109 or amino acids 1139-1147 of SEQ ID NO: 29. In other aspects of this embodiment, a non-contiguous amino acid substitution of any amino acid from amino acids 1097-1109 or amino acids 1139-1147 of SEQ ID NO: 29 can be replaced with glycine. In other aspects of this embodiment, a non-contiguous amino acid substitution of any hydrophobic amino acid from amino acids 1097-1109 or amino acids 1139-1147 of SEQ ID NO: 29 can be replaced with phenylalanine. In yet other aspects of this embodiment, a binding domain comprising a BoNT/C1 NTNH β-trefoil domain comprises a polypeptide having, e.g., at most one, two, three or four non-contiguous amino acid deletions relative to amino acids 1097-1109 or amino acids 1139-1147 of SEQ ID NO: 29. In other aspects of this embodiment, a binding domain comprising a BoNT/C1 NTNH β-trefoil domain comprises a polypeptide having, e.g., at least one, two, three or four non-contiguous amino acid deletions relative to amino acids 1097-1109 or amino acids 1139-1147 of SEQ ID NO: 29. In still other aspects of this embodiment, a binding domain comprising a BoNT/C1 NTNH β-trefoil domain comprises a polypeptide having, e.g., at most one, two, three or four non-contiguous amino acid additions relative to amino acids 1097-1109 or amino acids 1139-1147 of SEQ ID NO: 29. In other aspects of this embodiment, a binding domain comprising a BoNT/C1 NTNH β-trefoil domain comprises a polypeptide having, e.g., at least one, two, three or four non-contiguous amino acid additions relative to amino acids 1097-1109 or amino acids 1139-1147 of SEQ ID NO: 29.

In other aspects of this embodiment, a binding domain comprising a BoNT/C1 NTNH β-trefoil domain comprises a polypeptide having, e.g., at most one, two, three or four contiguous amino acid substitutions relative to amino acids 1097-1109 or amino acids 1139-1147 of SEQ ID NO: 29. In other aspects of this embodiment, a binding domain comprising a BoNT/C1 NTNH β-trefoil domain comprises a polypeptide having, e.g., at least one, two, three or four contiguous amino acid substitutions relative to amino acids 1097-1109 or amino acids 1139-1147 of SEQ ID NO: 29. In other aspects of this embodiment, contiguous amino acid substitutions of amino acids from amino acids 1097-1109 or amino acids 1139-1147 of SEQ ID NO: 29 can be replaced with glycine. In other aspects of this embodiment, contiguous amino acid substitutions of hydrophobic amino acids from amino acids 1097-1109 or amino acids 1139-1147 of SEQ ID NO: 29 can be replaced with phenylalanine. In yet other aspects of this embodiment, a β-trefoil domain with enhanced binding activity derived from a BoNT/C1 NTNH comprises a polypeptide having, e.g., at most one, two, three or four contiguous amino acid deletions relative to amino acids 1097-1109 or amino acids 1139-1147 of SEQ ID NO: 29. In other aspects of this embodiment, a binding domain comprising a BoNT/C1 NTNH β-trefoil domain comprises a polypeptide having, e.g., at least one, two, three or four contiguous amino acid deletions relative to amino acids 1097-1109 or amino acids 1139-1147 of SEQ ID NO: 29. In still other aspects of this embodiment, a binding domain comprising a BoNT/C1 NTNH β-trefoil domain comprises a polypeptide having, e.g., at most one, two, three or four contiguous amino acid additions relative to amino acids 1097-1109 or amino acids 1139-1147 of SEQ ID NO: 29. In other aspects of this embodiment, a binding domain comprising a BoNT/C1 NTNH β-trefoil domain comprises a polypeptide having, e.g., at least one, two, three or four contiguous amino acid additions relative to amino acids 1097-1109 or amino acids 1139-1147 of SEQ ID NO: 29.

In another embodiment, a binding domain comprises a β-trefoil domain derived from a BoNT/D NTNH of SEQ ID NO: 30. In another embodiment, a binding domain comprising a β-trefoil domain derived from a BoNT/D NTNH comprises amino acids 1049-1197 of SEQ ID NO: 30. In another aspect of this embodiment, a binding domain comprising a β-trefoil domain derived from a BoNT/D NTNH comprises a α-fold motif of a β-trefoil domain of a BoNT/D NTNH, a β-fold motif of a β-trefoil domain of a BoNT/D NTNH or a γ-fold motif of a β-trefoil domain of a BoNT/D NTNH of SEQ ID NO: 24. In another aspect of this embodiment, a β-trefoil domain derived from a BoNT/D NTNH comprises amino acids 1049-1096, amino acids 1110-1138, or amino acids 1148-1197 of SEQ ID NO: 30.

In other aspects of this embodiment, a binding domain comprising a BoNT/D NTNH β-trefoil domain comprises a polypeptide having, e.g., at least 70% amino acid identity with amino acids 1049-1096, amino acids 1110-1138, or amino acids 1148-1197 of SEQ ID NO: 30, at least 75% amino acid identity with amino acids 1049-1096, amino acids 1110-1138, or amino acids 1148-1197 of SEQ ID NO: 30, at least 80% amino acid identity with amino acids 1049-1096, amino acids 1110-1138, or amino acids 1148-1197 of SEQ ID NO: 30, at least 85% amino acid identity with amino acids 1049-1096, amino acids 1110-1138, or amino acids 1148-1197 of SEQ ID NO: 30, at least 90% amino acid identity with amino acids 1049-1096, amino acids 1110-1138, or amino acids 1148-1197 of SEQ ID NO: 30 or at least 95% amino acid identity with amino acids 1049-1096, amino acids 1110-1138, or amino acids 1148-1197 of SEQ ID NO: 30. In yet other aspects of this embodiment, a binding domain comprising a BoNT/D NTNH β-trefoil domain comprises a polypeptide having, e.g., at most 70% amino acid identity with amino acids 1049-1096, amino acids 1110-1138, or amino acids 1148-1197 of SEQ ID NO: 30, at most 75% amino acid identity with amino acids 1049-1096, amino acids 1110-1138, or amino acids 1148-1197 of SEQ ID NO: 30, at most 80% amino acid identity with amino acids 1049-1096, amino acids 1110-1138, or amino acids 1148-1197 of SEQ ID NO: 30, at most 85% amino acid identity with amino acids 1049-1096, amino acids 1110-1138, or amino acids 1148-1197 of SEQ ID NO: 30, at most 90% amino acid identity with amino acids 1049-1096, amino acids 1110-1138, or amino acids 1148-1197 of SEQ ID NO: 30 or at most 95% amino acid identity with amino acids 1049-1096, amino acids 1110-1138, or amino acids 1148-1197 of SEQ ID NO: 30.

In other aspects of this embodiment, a binding domain comprising a BoNT/D NTNH β-trefoil domain comprises a polypeptide having, e.g., at most one, two, three, four, five, six, seven, eight, nine, 10 or 20 non-contiguous amino acid substitutions relative to amino acids 1049-1096, amino acids 1110-1138, or amino acids 1148-1197 of SEQ ID NO: 30. In other aspects of this embodiment, a binding domain comprising a BoNT/D NTNH β-trefoil domain comprises a polypeptide having, e.g., at least one, two, three, four, five, six, seven, eight, nine, 10 or 20 non-contiguous amino acid substitutions relative to amino acids 1049-1096, amino acids 1110-1138, or amino acids 1148-1197 of SEQ ID NO: 30. In yet other aspects of this embodiment, a binding domain comprising a BoNT/D NTNH β-trefoil domain comprises a polypeptide having, e.g., at most one, two, three, four, five, six, seven, eight, nine, 10 or 20 non-contiguous amino acid deletions relative to amino acids 1049-1096, amino acids 1110-1138, or amino acids 1148-1197 of SEQ ID NO: 30. In other aspects of this embodiment, a binding domain comprising a BoNT/D NTNH β-trefoil domain comprises a polypeptide having, e.g., at least one, two, three, four, five, six, seven, eight, nine, 10 or 20 non-contiguous amino acid deletions relative to amino acids 1049-1096, amino acids 1110-1138, or amino acids 1148-1197 of SEQ ID NO: 30. In still other aspects of this embodiment, a binding domain comprising a BoNT/D NTNH β-trefoil domain comprises a polypeptide having, e.g., at most one, two, three, four, five, six, seven, eight, nine, 10 or 20 non-contiguous amino acid additions relative to amino acids 1049-1096, amino acids 1110-1138, or amino acids 1148-1197 of SEQ ID NO: 30. In other aspects of this embodiment, a binding domain comprising a BoNT/D NTNH β-trefoil domain comprises a polypeptide having, e.g., at least one, two, three, four, five, six, seven, eight, nine, 10 or 20 non-contiguous amino acid additions relative to amino acids 1049-1096, amino acids 1110-1138, or amino acids 1148-1197 of SEQ ID NO: 30.

In other aspects of this embodiment, a binding domain comprising a BoNT/D NTNH β-trefoil domain comprises a polypeptide having, e.g., at most one, two, three, four, five, six, seven, eight, nine, 10 or 20 contiguous amino acid substitutions relative to amino acids 1049-1096, amino acids 1110-1138, or amino acids 1148-1197 of SEQ ID NO: 30. In other aspects of this embodiment, a binding domain comprising a BoNT/D NTNH β-trefoil domain comprises a polypeptide having, e.g., at least one, two, three, four, five, six, seven, eight, nine, 10 or 20 contiguous amino acid substitutions relative to amino acids 1049-1096, amino acids 1110-1138, or amino acids 1148-1197 of SEQ ID NO: 30. In yet other aspects of this embodiment, a binding domain comprising a BoNT/D NTNH β-trefoil domain comprises a polypeptide having, e.g., at most one, two, three, four, five, six, seven, eight, nine, 10 or 20 contiguous amino acid deletions relative to amino acids 1049-1096, amino acids 1110-1138, or amino acids 1148-1197 of SEQ ID NO: 30. In other aspects of this embodiment, a binding domain comprising a BoNT/D NTNH β-trefoil domain comprises a polypeptide having, e.g., at least one, two, three, four, five, six, seven, eight, nine, 10 or 20 contiguous amino acid deletions relative to amino acids 1049-1096, amino acids 1110-1138, or amino acids 1148-1197 of SEQ ID NO: 30. In still other aspects of this embodiment, a binding domain comprising a BoNT/D NTNH β-trefoil domain comprises a polypeptide having, e.g., at most one, two, three, four, five, six, seven, eight, nine, 10 or 20 contiguous amino acid additions relative to amino acids 1049-1096, amino acids 1110-1138, or amino acids 1148-1197 of SEQ ID NO: 30. In other aspects of this embodiment, a binding domain comprising a BoNT/D NTNH β-trefoil domain comprises a polypeptide having, e.g., at least one, two, three, four, five, six, seven, eight, nine, 10 or 20 contiguous amino acid additions relative to amino acids 1049-1096, amino acids 1110-1138, or amino acids 1148-1197 of SEQ ID NO: 30.

In another embodiment, a binding domain comprising a BoNT/D NTNH β-trefoil domain comprises a β4/β5 hairpin turn of a β-trefoil domain of a BoNT/D NTNH or a β8/β9 hairpin turn of a β-trefoil domain of a BoNT/D NTNH of SEQ ID NO: 24. In another aspect of this embodiment, a binding domain comprising a BoNT/D NTNH β-trefoil domain comprises amino acids 1097-1109 or amino acids 1139-1147 of SEQ ID NO: 30.

In other aspects of this embodiment, a binding domain comprising a BoNT/D NTNH β-trefoil domain comprises a polypeptide having, e.g., at least 70% amino acid identity with amino acids 1097-1109 or amino acids 1139-1147 of SEQ ID NO: 30, at least 75% amino acid identity with amino acids 1097-1109 or amino acids 1139-1147 of SEQ ID NO: 30, at least 80% amino acid identity with amino acids 1097-1109 or amino acids 1139-1147 of SEQ ID NO: 30, at least 85% amino acid identity with amino acids 1097-1109 or amino acids 1139-1147 of SEQ ID NO: 30, at least 90% amino acid identity with amino acids 1097-1109 or amino acids 1139-1147 of SEQ ID NO: 30 or at least 95% amino acid identity with amino acids 1097-1109 or amino acids 1139-1147 of SEQ ID NO: 30. In yet other aspects of this embodiment, a binding domain comprising a BoNT/D NTNH β-trefoil domain comprises a polypeptide having, e.g., at most 70% amino acid identity with amino acids 1097-1109 or amino acids 1139-1147 of SEQ ID NO: 30, at most 75% amino acid identity with amino acids 1097-1109 or amino acids 1139-1147 of SEQ ID NO: 30, at most 80% amino acid identity with amino acids 1097-1109 or amino acids 1139-1147 of SEQ ID NO: 30, at most 85% amino acid identity with amino acids 1097-1109 or amino acids 1139-1147 of SEQ ID NO: 30, at most 90% amino acid identity with amino acids 1097-1109 or amino acids 1139-1147 of SEQ ID NO: 30 or at most 95% amino acid identity with amino acids 1097-1109 or amino acids 1139-1147 of SEQ ID NO: 30.

In other aspects of this embodiment, a binding domain comprising a BoNT/D NTNH β-trefoil domain comprises a polypeptide having, e.g., at most one, two, three or four non-contiguous amino acid substitutions relative to amino acids 1097-1109 or amino acids 1139-1147 of SEQ ID NO: 30. In other aspects of this embodiment, a binding domain comprising a BoNT/D NTNH β-trefoil domain comprises a polypeptide having, e.g., at least one, two, three or four non-contiguous amino acid substitutions relative to amino acids 1097-1109 or amino acids 1139-1147 of SEQ ID NO: 30. In other aspects of this embodiment, a non-contiguous amino acid substitution of any amino acid from amino acids 1097-1109 or amino acids 1139-1147 of SEQ ID NO: 30 can be replaced with glycine. In other aspects of this embodiment, a non-contiguous amino acid substitution of any hydrophobic amino acid from amino acids 1097-1109 or amino acids 1139-1147 of SEQ ID NO: 30 can be replaced with phenylalanine. In yet other aspects of this embodiment, a binding domain comprising a BoNT/D NTNH β-trefoil domain comprises a polypeptide having, e.g., at most one, two, three or four non-contiguous amino acid deletions relative to amino acids 1097-1109 or amino acids 1139-1147 of SEQ ID NO: 30. In other aspects of this embodiment, a binding domain comprising a BoNT/D NTNH β-trefoil domain comprises a polypeptide having, e.g., at least one, two, three or four non-contiguous amino acid deletions relative to amino acids 1097-1109 or amino acids 1139-1147 of SEQ ID NO: 30. In still other aspects of this embodiment, a binding domain comprising a BoNT/D NTNH β-trefoil domain comprises a polypeptide having, e.g., at most one, two, three or four non-contiguous amino acid additions relative to amino acids 1097-1109 or amino acids 1139-1147 of SEQ ID NO: 30. In other aspects of this embodiment, a binding domain comprising a BoNT/D NTNH β-trefoil domain comprises a polypeptide having, e.g., at least one, two, three or four non-contiguous amino acid additions relative to amino acids 1097-1109 or amino acids 1139-1147 of SEQ ID NO: 30.

In other aspects of this embodiment, a binding domain comprising a BoNT/D NTNH β-trefoil domain comprises a polypeptide having, e.g., at most one, two, three or four contiguous amino acid substitutions relative to amino acids 1097-1109 or amino acids 1139-1147 of SEQ ID NO: 30. In other aspects of this embodiment, a binding domain comprising a BoNT/D NTNH β-trefoil domain comprises a polypeptide having, e.g., at least one, two, three or four contiguous amino acid substitutions relative to amino acids 1097-1109 or amino acids 1139-1147 of SEQ ID NO: 30. In other aspects of this embodiment, contiguous amino acid substitutions of amino acids from amino acids 1097-1109 or amino acids 1139-1147 of SEQ ID NO: 30 can be replaced with glycine. In other aspects of this embodiment, contiguous amino acid substitutions of hydrophobic amino acids from amino acids 1097-1109 or amino acids 1139-1147 of SEQ ID NO: 30 can be replaced with phenylalanine. In yet other aspects of this embodiment, a β-trefoil domain with enhanced binding activity derived from a BoNT/D NTNH comprises a polypeptide having, e.g., at most one, two, three or four contiguous amino acid deletions relative to amino acids 1097-1109 or amino acids 1139-1147 of SEQ ID NO: 30. In other aspects of this embodiment, a binding domain comprising a BoNT/D NTNH β-trefoil domain comprises a polypeptide having, e.g., at least one, two, three or four contiguous amino acid deletions relative to amino acids 1097-1109 or amino acids 1139-1147 of SEQ ID NO: 30. In still other aspects of this embodiment, a binding domain comprising a BoNT/D NTNH β-trefoil domain comprises a polypeptide having, e.g., at most one, two, three or four contiguous amino acid additions relative to amino acids 1097-1109 or amino acids 1139-1147 of SEQ ID NO: 30. In other aspects of this embodiment, a binding domain comprising a BoNT/D NTNH β-trefoil domain comprises a polypeptide having, e.g., at least one, two, three or four contiguous amino acid additions relative to amino acids 1097-1109 or amino acids 1139-1147 of SEQ ID NO: 30.

In another embodiment, a binding domain comprises a β-trefoil domain derived from a BoNT/E NTNH of SEQ ID NO: 31. In another embodiment, a binding domain comprising a β-trefoil domain derived from a BoNT/E NTNH comprises amino acids 1014-1163 of SEQ ID NO: 31. In another aspect of this embodiment, a binding domain comprising a β-trefoil domain derived from a BoNT/E NTNH comprises a α-fold motif of a β-trefoil domain of a BoNT/E NTNH, a β-fold motif of a β-trefoil domain of a BoNT/E NTNH or a γ-fold motif of a β-trefoil domain of a BoNT/E NTNH of SEQ ID NO: 24. In another aspect of this embodiment, a β-trefoil domain derived from a BoNT/E NTNH comprises amino acids 1014-1061, amino acids 1075-1103, or amino acids 1114-1163 of SEQ ID NO: 31.

In other aspects of this embodiment, a binding domain comprising a BoNT/E NTNH β-trefoil domain comprises a polypeptide having, e.g., at least 70% amino acid identity with amino acids 1014-1061, amino acids 1075-1103, or amino acids 1114-1163 of SEQ ID NO: 31, at least 75% amino acid identity with amino acids 1014-1061, amino acids 1075-1103, or amino acids 1114-1163 of SEQ ID NO: 31, at least 80% amino acid identity with amino acids 1014-1061, amino acids 1075-1103, or amino acids 1114-1163 of SEQ ID NO: 31, at least 85% amino acid identity with amino acids 1014-1061, amino acids 1075-1103, or amino acids 1114-1163 of SEQ ID NO: 31, at least 90% amino acid identity with amino acids 1014-1061, amino acids 1075-1103, or amino acids 1114-1163 of SEQ ID NO: 31 or at least 95% amino acid identity with amino acids 1014-1061, amino acids 1075-1103, or amino acids 1114-1163 of SEQ ID NO: 31. In yet other aspects of this embodiment, a binding domain comprising a BoNT/E NTNH β-trefoil domain comprises a polypeptide having, e.g., at most 70% amino acid identity with amino acids 1014-1061, amino acids 1075-1103, or amino acids 1114-1163 of SEQ ID NO: 31, at most 75% amino acid identity with amino acids 1014-1061, amino acids 1075-1103, or amino acids 1114-1163 of SEQ ID NO: 31, at most 80% amino acid identity with amino acids 1014-1061, amino acids 1075-1103, or amino acids 1114-1163 of SEQ ID NO: 31, at most 85% amino acid identity with amino acids 1014-1061, amino acids 1075-1103, or amino acids 1114-1163 of SEQ ID NO: 31, at most 90% amino acid identity with amino acids 1014-1061, amino acids 1075-1103, or amino acids 1114-1163 of SEQ ID NO: 31 or at most 95% amino acid identity with amino acids 1014-1061, amino acids 1075-1103, or amino acids 1114-1163 of SEQ ID NO: 31.

In other aspects of this embodiment, a binding domain comprising a BoNT/E NTNH β-trefoil domain comprises a polypeptide having, e.g., at most one, two, three, four, five, six, seven, eight, nine, 10 or 20 non-contiguous amino acid substitutions relative to amino acids 1014-1061, amino acids 1075-1103, or amino acids 1114-1163 of SEQ ID NO: 31. In other aspects of this embodiment, a binding domain comprising a BoNT/E NTNH β-trefoil domain comprises a polypeptide having, e.g., at least one, two, three, four, five, six, seven, eight, nine, 10 or 20 non-contiguous amino acid substitutions relative to amino acids 1014-1061, amino acids 1075-1103, or amino acids 1114-1163 of SEQ ID NO: 31. In yet other aspects of this embodiment, a binding domain comprising a BoNT/E NTNH β-trefoil domain comprises a polypeptide having, e.g., at most one, two, three, four, five, six, seven, eight, nine, 10 or 20 non-contiguous amino acid deletions relative to amino acids 1014-1061, amino acids 1075-1103, or amino acids 1114-1163 of SEQ ID NO: 31. In other aspects of this embodiment, a binding domain comprising a BoNT/E NTNH β-trefoil domain comprises a polypeptide having, e.g., at least one, two, three, four, five, six, seven, eight, nine, 10 or 20 non-contiguous amino acid deletions relative to amino acids 1014-1061, amino acids 1075-1103, or amino acids 1114-1163 of SEQ ID NO: 31. In still other aspects of this embodiment, a binding domain comprising a BoNT/E NTNH β-trefoil domain comprises a polypeptide having, e.g., at most one, two, three, four, five, six, seven, eight, nine, 10 or 20 non-contiguous amino acid additions relative to amino acids 1014-1061, amino acids 1075-1103, or amino acids 1114-1163 of SEQ ID NO: 31. In other aspects of this embodiment, a binding domain comprising a BoNT/E NTNH β-trefoil domain comprises a polypeptide having, e.g., at least one, two, three, four, five, six, seven, eight, nine, 10 or 20 non-contiguous amino acid additions relative to amino acids 1014-1061, amino acids 1075-1103, or amino acids 1114-1163 of SEQ ID NO: 31.

In other aspects of this embodiment, a binding domain comprising a BoNT/E NTNH β-trefoil domain comprises a polypeptide having, e.g., at most one, two, three, four, five, six, seven, eight, nine, 10 or 20 contiguous amino acid substitutions relative to amino acids 1014-1061, amino acids 1075-1103, or amino acids 1114-1163 of SEQ ID NO: 31. In other aspects of this embodiment, a binding domain comprising a BoNT/E NTNH β-trefoil domain comprises a polypeptide having, e.g., at least one, two, three, four, five, six, seven, eight, nine, 10 or 20 contiguous amino acid substitutions relative to amino acids 1014-1061, amino acids 1075-1103, or amino acids 1114-1163 of SEQ ID NO: 31. In yet other aspects of this embodiment, a binding domain comprising a BoNT/E NTNH β-trefoil domain comprises a polypeptide having, e.g., at most one, two, three, four, five, six, seven, eight, nine, 10 or 20 contiguous amino acid deletions relative to amino acids 1014-1061, amino acids 1075-1103, or amino acids 1114-1163 of SEQ ID NO: 31. In other aspects of this embodiment, a binding domain comprising a BoNT/E NTNH β-trefoil domain comprises a polypeptide having, e.g., at least one, two, three, four, five, six, seven, eight, nine, 10 or 20 contiguous amino acid deletions relative to amino acids 1014-1061, amino acids 1075-1103, or amino acids 1114-1163 of SEQ ID NO: 31. In still other aspects of this embodiment, a binding domain comprising a BoNT/E NTNH β-trefoil domain comprises a polypeptide having, e.g., at most one, two, three, four, five, six, seven, eight, nine, 10 or 20 contiguous amino acid additions relative to amino acids 1014-1061, amino acids 1075-1103, or amino acids 1114-1163 of SEQ ID NO: 31. In other aspects of this embodiment, a binding domain comprising a BoNT/E NTNH β-trefoil domain comprises a polypeptide having, e.g., at least one, two, three, four, five, six, seven, eight, nine, 10 or 20 contiguous amino acid additions relative to amino acids 1014-1061, amino acids 1075-1103, or amino acids 1114-1163 of SEQ ID NO: 31.

In another embodiment, a binding domain comprising a BoNT/E NTNH β-trefoil domain comprises a β4/β5 hairpin turn of β-trefoil domain of a BoNT/E NTNH or a β8/β9 hairpin turn of a β-trefoil domain of a BoNT/E NTNH of SEQ ID NO: 24. In another aspect of this embodiment, a binding domain comprising a BoNT/E NTNH β-trefoil domain comprises amino acids 1062-1074 or amino acids 1104-1113 of SEQ ID NO: 31.

In other aspects of this embodiment, a binding domain comprising a BoNT/E NTNH β-trefoil domain comprises a polypeptide having, e.g., at least 70% amino acid identity with amino acids 1062-1074 or amino acids 1104-1113 of SEQ ID NO: 31, at least 75% amino acid identity with amino acids 1062-1074 or amino acids 1104-1113 of SEQ ID NO: 31, at least 80% amino acid identity with amino acids 1062-1074 or amino acids 1104-1113 of SEQ ID NO: 31, at least 85% amino acid identity with amino acids 1062-1074 or amino acids 1104-1113 of SEQ ID NO: 31, at least 90% amino acid identity with amino acids 1062-1074 or amino acids 1104-1113 of SEQ ID NO: 31 or at least 95% amino acid identity with amino acids 1062-1074 or amino acids 1104-1113 of SEQ ID NO: 31. In yet other aspects of this embodiment, a binding domain comprising a BoNT/E NTNH β-trefoil domain comprises a polypeptide having, e.g., at most 70% amino acid identity with amino acids 1062-1074 or amino acids 1104-1113 of SEQ ID NO: 31, at most 75% amino acid identity with amino acids 1062-1074 or amino acids 1104-1113 of SEQ ID NO: 31, at most 80% amino acid identity with amino acids 1062-1074 or amino acids 1104-1113 of SEQ ID NO: 31, at most 85% amino acid identity with amino acids 1062-1074 or amino acids 1104-1113 of SEQ ID NO: 31, at most 90% amino acid identity with amino acids 1062-1074 or amino acids 1104-1113 of SEQ ID NO: 31 or at most 95% amino acid identity with amino acids 1062-1074 or amino acids 1104-1113 of SEQ ID NO: 31.

In other aspects of this embodiment, a binding domain comprising a BoNT/E NTNH β-trefoil domain comprises a polypeptide having, e.g., at most one, two, three or four non-contiguous amino acid substitutions relative to amino acids 1062-1074 or amino acids 1104-1113 of SEQ ID NO: 31. In other aspects of this embodiment, a binding domain comprising a BoNT/E NTNH β-trefoil domain comprises a polypeptide having, e.g., at least one, two, three or four non-contiguous amino acid substitutions relative to amino acids 1062-1074 or amino acids 1104-1113 of SEQ ID NO: 31. In other aspects of this embodiment, a non-contiguous amino acid substitution of any amino acid from amino acids 1062-1074 or amino acids 1104-1113 of SEQ ID NO: 31 can be replaced with glycine. In other aspects of this embodiment, a non-contiguous amino acid substitution of any hydrophobic amino acid from amino acids 1062-1074 or amino acids 1104-1113 of SEQ ID NO: 31 can be replaced with phenylalanine. In yet other aspects of this embodiment, a binding domain comprising a BoNT/E NTNH β-trefoil domain comprises a polypeptide having, e.g., at most one, two, three or four non-contiguous amino acid deletions relative to amino acids 1062-1074 or amino acids 1104-1113 of SEQ ID NO: 31. In other aspects of this embodiment, a binding domain comprising a BoNT/E NTNH β-trefoil domain comprises a polypeptide having, e.g., at least one, two, three or four non-contiguous amino acid deletions relative to amino acids 1062-

1074 or amino acids 1104-1113 of SEQ ID NO: 31. In still other aspects of this embodiment, a binding domain comprising a BoNT/E NTNH β-trefoil domain comprises a polypeptide having, e.g., at most one, two, three or four non-contiguous amino acid additions relative to amino acids 1062-1074 or amino acids 1104-1113 of SEQ ID NO: 31. In other aspects of this embodiment, a binding domain comprising a BoNT/E NTNH β-trefoil domain comprises a polypeptide having, e.g., at least one, two, three or four non-contiguous amino acid additions relative to amino acids 1062-1074 or amino acids 1104-1113 of SEQ ID NO: 31.

In other aspects of this embodiment, a binding domain comprising a BoNT/E NTNH β-trefoil domain comprises a polypeptide having, e.g., at most one, two, three or four contiguous amino acid substitutions relative to amino acids 1062-1074 or amino acids 1104-1113 of SEQ ID NO: 31. In other aspects of this embodiment, a binding domain comprising a BoNT/E NTNH β-trefoil domain comprises a polypeptide having, e.g., at least one, two, three or four contiguous amino acid substitutions relative to amino acids 1062-1074 or amino acids 1104-1113 of SEQ ID NO: 31. In other aspects of this embodiment, contiguous amino acid substitutions of amino acids from amino acids 1062-1074 or amino acids 1104-1113 of SEQ ID NO: 31 can be replaced with glycine. In other aspects of this embodiment, contiguous amino acid substitutions of hydrophobic amino acids from amino acids 1062-1074 or amino acids 1104-1113 of SEQ ID NO: 31 can be replaced with phenylalanine. In yet other aspects of this embodiment, a β-trefoil domain with enhanced binding activity derived from a BoNT/E NTNH comprises a polypeptide having, e.g., at most one, two, three or four contiguous amino acid deletions relative to amino acids 1062-1074 or amino acids 1104-1113 of SEQ ID NO: 31. In other aspects of this embodiment, a binding domain comprising a BoNT/E NTNH β-trefoil domain comprises a polypeptide having, e.g., at least one, two, three or four contiguous amino acid deletions relative to amino acids 1062-1074 or amino acids 1104-1113 of SEQ ID NO: 31. In still other aspects of this embodiment, a binding domain comprising a BoNT/E NTNH β-trefoil domain comprises a polypeptide having, e.g., at most one, two, three or four contiguous amino acid additions relative to amino acids 1062-1074 or amino acids 1104-1113 of SEQ ID NO: 31. In other aspects of this embodiment, a binding domain comprising a BoNT/E NTNH β-trefoil domain comprises a polypeptide having, e.g., at least one, two, three or four contiguous amino acid additions relative to amino acids 1062-1074 or amino acids 1104-1113 of SEQ ID NO: 31.

In another embodiment, a binding domain comprises a β-trefoil domain derived from a BoNT/F NTNH of SEQ ID NO: 32. In another embodiment, a binding domain comprising a β-trefoil domain derived from a BoNT/F NTNH comprises amino acids 1016-1160 of SEQ ID NO: 32. In another aspect of this embodiment, a binding domain comprising a β-trefoil domain derived from a BoNT/F NTNH comprises a α-fold motif of a β-trefoil domain of a BoNT/F NTNH, a β-fold motif of a β-trefoil domain of a BoNT/F NTNH or a γ-fold motif of a β-trefoil domain of a BoNT/F NTNH of SEQ ID NO: 24. In another aspect of this embodiment, a β-trefoil domain derived from a BoNT/F NTNH comprises amino acids 1016-1063, amino acids 1077-1104, or amino acids 1115-1160 of SEQ ID NO: 32.

In other aspects of this embodiment, a binding domain comprising a BoNT/F NTNH β-trefoil domain comprises a polypeptide having, e.g., at least 70% amino acid identity with amino acids 1016-1063, amino acids 1077-1104, or amino acids 1115-1160 of SEQ ID NO: 32, at least 75% amino acid identity with amino acids 1016-1063, amino acids 1077-1104, or amino acids 1115-1160 of SEQ ID NO: 32, at least 80% amino acid identity with amino acids 1016-1063, amino acids 1077-1104, or amino acids 1115-1160 of SEQ ID NO: 32, at least 85% amino acid identity with amino acids 1016-1063, amino acids 1077-1104, or amino acids 1115-1160 of SEQ ID NO: 32, at least 90% amino acid identity with amino acids 1016-1063, amino acids 1077-1104, or amino acids 1115-1160 of SEQ ID NO: 32 or at least 95% amino acid identity with amino acids 1016-1063, amino acids 1077-1104, or amino acids 1115-1160 of SEQ ID NO: 32. In yet other aspects of this embodiment, a binding domain comprising a BoNT/F NTNH β-trefoil domain comprises a polypeptide having, e.g., at most 70% amino acid identity with amino acids 1016-1063, amino acids 1077-1104, or amino acids 1115-1160 of SEQ ID NO: 32, at most 75% amino acid identity with amino acids 1016-1063, amino acids 1077-1104, or amino acids 1115-1160 of SEQ ID NO: 32, at most 80% amino acid identity with amino acids 1016-1063, amino acids 1077-1104, or amino acids 1115-1160 of SEQ ID NO: 32, at most 85% amino acid identity with amino acids 1016-1063, amino acids 1077-1104, or amino acids 1115-1160 of SEQ ID NO: 32, at most 90% amino acid identity with amino acids 1016-1063, amino acids 1077-1104, or amino acids 1115-1160 of SEQ ID NO: 32 or at most 95% amino acid identity with amino acids 1016-1063, amino acids 1077-1104, or amino acids 1115-1160 of SEQ ID NO: 32.

In other aspects of this embodiment, a binding domain comprising a BoNT/F NTNH β-trefoil domain comprises a polypeptide having, e.g., at most one, two, three, four, five, six, seven, eight, nine, 10 or 20 non-contiguous amino acid substitutions relative to amino acids 1016-1063, amino acids 1077-1104, or amino acids 1115-1160 of SEQ ID NO: 32. In other aspects of this embodiment, a binding domain comprising a BoNT/F NTNH β-trefoil domain comprises a polypeptide having, e.g., at least one, two, three, four, five, six, seven, eight, nine, 10 or 20 non-contiguous amino acid substitutions relative to amino acids 1016-1063, amino acids 1077-1104, or amino acids 1115-1160 of SEQ ID NO: 32. In yet other aspects of this embodiment, a binding domain comprising a BoNT/F NTNH β-trefoil domain comprises a polypeptide having, e.g., at most one, two, three, four, five, six, seven, eight, nine, 10 or 20 non-contiguous amino acid deletions relative to amino acids 1016-1063, amino acids 1077-1104, or amino acids 1115-1160 of SEQ ID NO: 32. In other aspects of this embodiment, a binding domain comprising a BoNT/F NTNH β-trefoil domain comprises a polypeptide having, e.g., at least one, two, three, four, five, six, seven, eight, nine, 10 or 20 non-contiguous amino acid deletions relative to amino acids 1016-1063, amino acids 1077-1104, or amino acids 1115-1160 of SEQ ID NO: 32. In still other aspects of this embodiment, a binding domain comprising a BoNT/F NTNH β-trefoil domain comprises a polypeptide having, e.g., at most one, two, three, four, five, six, seven, eight, nine, 10 or 20 non-contiguous amino acid additions relative to amino acids 1016-1063, amino acids 1077-1104, or amino acids 1115-1160 of SEQ ID NO: 32. In other aspects of this embodiment, a binding domain comprising a BoNT/F NTNH β-trefoil domain comprises a polypeptide having, e.g., at least one, two, three, four, five, six, seven, eight, nine, 10 or 20 non-contiguous amino acid additions relative to amino acids 1016-1063, amino acids 1077-1104, or amino acids 1115-1160 of SEQ ID NO: 32.

In other aspects of this embodiment, a binding domain comprising a BoNT/F NTNH β-trefoil domain comprises a polypeptide having, e.g., at most one, two, three, four, five, six, seven, eight, nine, 10 or 20 contiguous amino acid substitutions relative to amino acids 1016-1063, amino acids 1077-1104, or amino acids 1115-1160 of SEQ ID NO: 32. In other aspects of this embodiment, a binding domain comprising a BoNT/F NTNH β-trefoil domain comprises a polypeptide having, e.g., at least one, two, three, four, five, six, seven, eight, nine, 10 or 20 contiguous amino acid substitutions relative to amino acids 1016-1063, amino acids 1077-1104, or amino acids 1115-1160 of SEQ ID NO: 32. In yet other aspects of this embodiment, a binding domain comprising a BoNT/F NTNH β-trefoil domain comprises a polypeptide having, e.g., at most one, two, three, four, five, six, seven, eight, nine, 10 or 20 contiguous amino acid deletions relative to amino acids 1016-1063, amino acids 1077-1104, or amino acids 1115-1160 of SEQ ID NO: 32. In other aspects of this embodiment, a binding domain comprising a BoNT/F NTNH β-trefoil domain comprises a polypeptide having, e.g., at least one, two, three, four, five, six, seven, eight, nine, 10 or 20 contiguous amino acid deletions relative to amino acids 1016-1063, amino acids 1077-1104, or amino acids 1115-1160 of SEQ ID NO: 32. In still other aspects of this embodiment, a binding domain comprising a BoNT/F NTNH β-trefoil domain comprises a polypeptide having, e.g., at most one, two, three, four, five, six, seven, eight, nine, 10 or 20 contiguous amino acid additions relative to amino acids 1016-1063, amino acids 1077-1104, or amino acids 1115-1160 of SEQ ID NO: 32. In other aspects of this embodiment, a binding domain comprising a BoNT/F NTNH β-trefoil domain comprises a polypeptide having, e.g., at least one, two, three, four, five, six, seven, eight, nine, 10 or 20 contiguous amino acid additions relative to amino acids 1016-1063, amino acids 1077-1104, or amino acids 1115-1160 of SEQ ID NO: 32.

In another embodiment, a binding domain comprising a BoNT/F NTNH β-trefoil domain comprises a β4/β5 hairpin turn of a β-trefoil domain of a BoNT/F NTNH or a β8/β9 hairpin turn of a β-trefoil domain of a BoNT/F NTNH of SEQ ID NO: 24. In another aspect of this embodiment, a binding domain comprising a BoNT/F NTNH β-trefoil domain comprises amino acids 1064-1076 or amino acids 1105-1114 of SEQ ID NO: 32.

In other aspects of this embodiment, a binding domain comprising a BoNT/F NTNH β-trefoil domain comprises a polypeptide having, e.g., at least 70% amino acid identity with amino acids 1064-1076 or amino acids 1105-1114 of SEQ ID NO: 32, at least 75% amino acid identity with amino acids 1064-1076 or amino acids 1105-1114 of SEQ ID NO: 32, at least 80% amino acid identity with amino acids 1064-1076 or amino acids 1105-1114 of SEQ ID NO: 32, at least 85% amino acid identity with amino acids 1064-1076 or amino acids 1105-1114 of SEQ ID NO: 32, at least 90% amino acid identity with amino acids 1064-1076 or amino acids 1105-1114 of SEQ ID NO: 32 or at least 95% amino acid identity with amino acids 1064-1076 or amino acids 1105-1114 of SEQ ID NO: 32. In yet other aspects of this embodiment, a binding domain comprising a BoNT/F NTNH β-trefoil domain comprises a polypeptide having, e.g., at most 70% amino acid identity with amino acids 1064-1076 or amino acids 1105-1114 of SEQ ID NO: 32, at most 75% amino acid identity with amino acids 1064-1076 or amino acids 1105-1114 of SEQ ID NO: 32, at most 80% amino acid identity with amino acids 1064-1076 or amino acids 1105-1114 of SEQ ID NO: 32, at most 85% amino acid identity with amino acids 1064-1076 or amino acids 1105-1114 of SEQ ID NO: 32, at most 90% amino acid identity with amino acids 1064-1076 or amino acids 1105-1114 of SEQ ID NO: 32 or at most 95% amino acid identity with amino acids 1064-1076 or amino acids 1105-1114 of SEQ ID NO: 32.

In other aspects of this embodiment, a binding domain comprising a BoNT/F NTNH β-trefoil domain comprises a polypeptide having, e.g., at most one, two, three or four non-contiguous amino acid substitutions relative to amino acids 1064-1076 or amino acids 1105-1114 of SEQ ID NO: 32. In other aspects of this embodiment, a binding domain comprising a BoNT/F NTNH β-trefoil domain comprises a polypeptide having, e.g., at least one, two, three or four non-contiguous amino acid substitutions relative to amino acids 1064-1076 or amino acids 1105-1114 of SEQ ID NO: 32. In other aspects of this embodiment, a non-contiguous amino acid substitution of any amino acid from amino acids 1064-1076 or amino acids 1105-1114 of SEQ ID NO: 32 can be replaced with glycine. In other aspects of this embodiment, a non-contiguous amino acid substitution of any hydrophobic amino acid from amino acids 1064-1076 or amino acids 1105-1114 of SEQ ID NO: 32 can be replaced with phenylalanine. In yet other aspects of this embodiment, a binding domain comprising a BoNT/F NTNH β-trefoil domain comprises a polypeptide having, e.g., at most one, two, three or four non-contiguous amino acid deletions relative to amino acids 1064-1076 or amino acids 1105-1114 of SEQ ID NO: 32. In other aspects of this embodiment, a binding domain comprising a BoNT/F NTNH β-trefoil domain comprises a polypeptide having, e.g., at least one, two, three or four non-contiguous amino acid deletions relative to amino acids 1064-1076 or amino acids 1105-1114 of SEQ ID NO: 32. In still other aspects of this embodiment, a binding domain comprising a BoNT/F NTNH β-trefoil domain comprises a polypeptide having, e.g., at most one, two, three or four non-contiguous amino acid additions relative to amino acids 1064-1076 or amino acids 1105-1114 of SEQ ID NO: 32. In other aspects of this embodiment, a binding domain comprising a BoNT/F NTNH β-trefoil domain comprises a polypeptide having, e.g., at least one, two, three or four non-contiguous amino acid additions relative to amino acids 1064-1076 or amino acids 1105-1114 of SEQ ID NO: 32.

In other aspects of this embodiment, a binding domain comprising a BoNT/F NTNH β-trefoil domain comprises a polypeptide having, e.g., at most one, two, three or four contiguous amino acid substitutions relative to amino acids 1064-1076 or amino acids 1105-1114 of SEQ ID NO: 32. In other aspects of this embodiment, a binding domain comprising a BoNT/F NTNH β-trefoil domain comprises a polypeptide having, e.g., at least one, two, three or four contiguous amino acid substitutions relative to amino acids 1064-1076 or amino acids 1105-1114 of SEQ ID NO: 32. In other aspects of this embodiment, contiguous amino acid substitutions of amino acids from amino acids 1064-1076 or amino acids 1105-1114 of SEQ ID NO: 32 can be replaced with glycine. In other aspects of this embodiment, contiguous amino acid substitutions of hydrophobic amino acids from amino acids 1064-1076 or amino acids 1105-1114 of SEQ ID NO: 32 can be replaced with phenylalanine. In yet other aspects of this embodiment, a β-trefoil domain with enhanced binding activity derived from a BoNT/F NTNH comprises a polypeptide having, e.g., at most one, two, three or four contiguous amino acid deletions relative to amino acids 1064-1076 or amino acids 1105-1114 of SEQ ID NO: 32. In other aspects of this embodiment, a binding domain comprising a BoNT/F NTNH β-trefoil domain comprises a polypeptide having, e.g., at least one, two, three or four contiguous amino acid deletions relative to amino acids 1064-1076 or amino acids 1105-1114 of SEQ ID NO: 32. In still other aspects of this embodiment, a binding domain comprising a BoNT/F NTNH β-trefoil domain comprises a polypeptide having, e.g., at most one, two, three or four contiguous amino acid additions relative to amino acids 1064-1076 or amino acids 1105-1114 of SEQ ID NO: 32. In other aspects of this embodiment, a binding domain comprising a BoNT/F NTNH β-trefoil domain comprises a polypeptide having, e.g., at least one, two, three or four contiguous amino acid additions relative to amino acids 1064-1076 or amino acids 1105-1114 of SEQ ID NO: 32.

In another embodiment, a binding domain comprises a β-trefoil domain derived from a BoNT/F NTNH of SEQ ID NO: 33. In another embodiment, a binding domain comprising a β-trefoil domain derived from a BoNT/F NTNH comprises amino acids 1017-1166 of SEQ ID NO: 33. In another aspect of this embodiment, a binding domain comprising a β-trefoil domain derived from a BoNT/F NTNH comprises a α-fold motif of a β-trefoil domain of a BoNT/F NTNH, a β-fold motif of a β-trefoil domain of a BoNT/F NTNH or a γ-fold motif of a β-trefoil domain of a BoNT/F NTNH of SEQ ID NO: 24. In another aspect of this embodiment, a β-trefoil domain derived from a BoNT/F NTNH comprises amino acids 1017-1064, amino acids 1078-1106, or amino acids 1117-1166 of SEQ ID NO: 33.

In other aspects of this embodiment, a binding domain comprising a BoNT/F NTNH β-trefoil domain comprises a polypeptide having, e.g., at least 70% amino acid identity with amino acids 1017-1064, amino acids 1078-1106, or amino acids 1117-1166 of SEQ ID NO: 33, at least 75% amino acid identity with amino acids 1017-1064, amino acids 1078-1106, or amino acids 1117-1166 of SEQ ID NO: 33, at least 80% amino acid identity with amino acids 1017-1064, amino acids 1078-1106, or amino acids 1117-1166 of SEQ ID NO: 33, at least 85% amino acid identity with amino acids 1017-1064, amino acids 1078-1106, or amino acids 1117-1166 of SEQ ID NO: 33, at least 90% amino acid identity with amino acids 1017-1064, amino acids 1078-1106, or amino acids 1117-1166 of SEQ ID NO: 33 or at least 95% amino acid identity with amino acids 1017-1064, amino acids 1078-1106, or amino acids 1117-1166 of SEQ ID NO: 33. In yet other aspects of this embodiment, a binding domain comprising a BoNT/F NTNH β-trefoil domain comprises a polypeptide having, e.g., at most 70% amino acid identity with amino acids 1017-1064, amino acids 1078-1106, or amino acids 1117-1166 of SEQ ID NO: 33, at most 75% amino acid identity with amino acids 1017-1064, amino acids 1078-1106, or amino acids 1117-1166 of SEQ ID NO: 33, at most 80% amino acid identity with amino acids 1017-1064, amino acids 1078-1106, or amino acids 1117-1166 of SEQ ID NO: 33, at most 85% amino acid identity with amino acids 1017-1064, amino acids 1078-1106, or amino acids 1117-1166 of SEQ ID NO: 33, at most 90% amino acid identity with amino acids 1017-1064, amino acids 1078-1106, or amino acids 1117-1166 of SEQ ID NO: 33 or at most 95% amino acid identity with amino acids 1017-1064, amino acids 1078-1106, or amino acids 1117-1166 of SEQ ID NO: 33.

In other aspects of this embodiment, a binding domain comprising a BoNT/F NTNH β-trefoil domain comprises a polypeptide having, e.g., at most one, two, three, four, five, six, seven, eight, nine, 10 or 20 non-contiguous amino acid substitutions relative to amino acids 1017-1064, amino acids 1078-1106, or amino acids 1117-1166 of SEQ ID NO: 33. In other aspects of this embodiment, a binding domain comprising a BoNT/F NTNH β-trefoil domain comprises a polypeptide having, e.g., at least one, two, three, four, five, six, seven, eight, nine, 10 or 20 non-contiguous amino acid substitutions relative to amino acids 1017-1064, amino acids 1078-1106, or amino acids 1117-1166 of SEQ ID NO: 33. In yet other aspects of this embodiment, a binding domain comprising a BoNT/F NTNH β-trefoil domain comprises a polypeptide having, e.g., at most one, two, three, four, five, six, seven, eight, nine, 10 or 20 non-contiguous amino acid deletions relative to amino acids 1017-1064, amino acids 1078-1106, or amino acids 1117-1166 of SEQ ID NO: 33. In other aspects of this embodiment, a binding domain comprising a BoNT/F NTNH β-trefoil domain comprises a polypeptide having, e.g., at least one, two, three, four, five, six, seven, eight, nine, 10 or 20 non-contiguous amino acid deletions relative to amino acids 1017-1064, amino acids 1078-1106, or amino acids 1117-1166 of SEQ ID NO: 33. In still other aspects of this embodiment, a binding domain comprising a BoNT/F NTNH β-trefoil domain comprises a polypeptide having, e.g., at most one, two, three, four, five, six, seven, eight, nine, 10 or 20 non-contiguous amino acid additions relative to amino acids 1017-1064, amino acids 1078-1106, or amino acids 1117-1166 of SEQ ID NO: 33. In other aspects of this embodiment, a binding domain comprising a BoNT/F NTNH β-trefoil domain comprises a polypeptide having, e.g., at least one, two, three, four, five, six, seven, eight, nine, 10 or 20 non-contiguous amino acid additions relative to amino acids 1017-1064, amino acids 1078-1106, or amino acids 1117-1166 of SEQ ID NO: 33.

In other aspects of this embodiment, a binding domain comprising a BoNT/F NTNH β-trefoil domain comprises a polypeptide having, e.g., at most one, two, three, four, five, six, seven, eight, nine, 10 or 20 contiguous amino acid substitutions relative to amino acids 1017-1064, amino acids 1078-1106, or amino acids 1117-1166 of SEQ ID NO: 33. In other aspects of this embodiment, a binding domain comprising a BoNT/F NTNH β-trefoil domain comprises a polypeptide having, e.g., at least one, two, three, four, five, six, seven, eight, nine, 10 or 20 contiguous amino acid substitutions relative to amino acids 1017-1064, amino acids 1078-1106, or amino acids 1117-1166 of SEQ ID NO: 33. In yet other aspects of this embodiment, a binding domain comprising a BoNT/F NTNH β-trefoil domain comprises a polypeptide having, e.g., at most one, two, three, four, five, six, seven, eight, nine, 10 or 20 contiguous amino acid deletions relative to amino acids 1017-1064, amino acids 1078-1106, or amino acids 1117-1166 of SEQ ID NO: 33. In other aspects of this embodiment, a binding domain comprising a BoNT/F NTNH β-trefoil domain comprises a polypeptide having, e.g., at least one, two, three, four, five, six, seven, eight, nine, 10 or 20 contiguous amino acid deletions relative to amino acids 1017-1064, amino acids 1078-1106, or amino acids 1117-1166 of SEQ ID NO: 33. In still other aspects of this embodiment, a binding domain comprising a BoNT/F NTNH β-trefoil domain comprises a polypeptide having, e.g., at most one, two, three, four, five, six, seven, eight, nine, 10 or 20 contiguous amino acid additions relative to amino acids 1017-1064, amino acids 1078-1106, or amino acids 1117-1166 of SEQ ID NO: 33. In other aspects of this embodiment, a binding domain comprising a BoNT/F NTNH β-trefoil domain comprises a polypeptide having, e.g., at least one, two, three, four, five, six, seven, eight, nine, 10 or 20 contiguous amino acid additions relative to amino acids 1017-1064, amino acids 1078-1106, or amino acids 1117-1166 of SEQ ID NO: 33.

In another embodiment, a binding domain comprising a BoNT/F NTNH β-trefoil domain comprises a β4/β5 hairpin turn of a β-trefoil domain of a BoNT/F NTNH or a β8/β9 hairpin turn of a β-trefoil domain of a BoNT/F NTNH of SEQ ID NO: 24. In another aspect of this embodiment, a binding domain comprising a BoNT/F NTNH β-trefoil domain comprises amino acids 1065-1077 or amino acids 1107-1116 of SEQ ID NO: 33.

In other aspects of this embodiment, a binding domain comprising a BoNT/F NTNH β-trefoil domain comprises a polypeptide having, e.g., at least 70% amino acid identity with amino acids 1065-1077 or amino acids 1107-1116 of SEQ ID NO: 33, at least 75% amino acid identity with amino acids 1065-1077 or amino acids 1107-1116 of SEQ ID NO: 33, at least 80% amino acid identity with amino acids 1065-1077 or amino acids 1107-1116 of SEQ ID NO: 33, at least 85% amino acid identity with amino acids 1065-1077 or amino acids 1107-1116 of SEQ ID NO: 33, at least 90% amino acid identity with amino acids 1065-1077 or amino acids 1107-1116 of SEQ ID NO: 33 or at least 95% amino acid identity with amino acids 1065-1077 or amino acids 1107-1116 of SEQ ID NO: 33. In yet other aspects of this embodiment, a binding domain comprising a BoNT/F NTNH β-trefoil domain comprises a polypeptide having, e.g., at most 70% amino acid identity with amino acids 1065-1077 or amino acids 1107-1116 of SEQ ID NO: 33, at most 75% amino acid identity with amino acids 1065-1077 or amino acids 1107-1116 of SEQ ID NO: 33, at most 80% amino acid identity with amino acids 1065-1077 or amino acids 1107-1116 of SEQ ID NO: 33, at most 85% amino acid identity with amino acids 1065-1077 or amino acids 1107-1116 of SEQ ID NO: 33, at most 90% amino acid identity with amino acids 1065-1077 or amino acids 1107-1116 of SEQ ID NO: 33 or at most 95% amino acid identity with amino acids 1065-1077 or amino acids 1107-1116 of SEQ ID NO: 33.

In other aspects of this embodiment, a binding domain comprising a BoNT/F NTNH β-trefoil domain comprises a polypeptide having, e.g., at most one, two, three or four non-contiguous amino acid substitutions relative to amino acids 1065-1077 or amino acids 1107-1116 of SEQ ID NO: 33. In other aspects of this embodiment, a binding domain comprising a BoNT/F NTNH β-trefoil domain comprises a polypeptide having, e.g., at least one, two, three or four non-contiguous amino acid substitutions relative to amino acids 1065-1077 or amino acids 1107-1116 of SEQ ID NO: 33. In other aspects of this embodiment, a non-contiguous amino acid substitution of any amino acid from amino acids 1065-1077 or amino acids 1107-1116 of SEQ ID NO: 33 can be replaced with glycine. In other aspects of this embodiment, a non-contiguous amino acid substitution of any hydrophobic amino acid from amino acids 1065-1077 or amino acids 1107-1116 of SEQ ID NO: 33 can be replaced with phenylalanine. In yet other aspects of this embodiment, a binding domain comprising a BoNT/F NTNH β-trefoil domain comprises a polypeptide having, e.g., at most one, two, three or four non-contiguous amino acid deletions relative to amino acids 1065-1077 or amino acids 1107-1116 of SEQ ID NO: 33. In other aspects of this embodiment, a binding domain comprising a BoNT/F NTNH β-trefoil domain comprises a polypeptide having, e.g., at least one, two, three or four non-contiguous amino acid deletions relative to amino acids 1065-1077 or amino acids 1107-1116 of SEQ ID NO: 33. In still other aspects of this embodiment, a binding domain comprising a BoNT/F NTNH β-trefoil domain comprises a polypeptide having, e.g., at most one, two, three or four non-contiguous amino acid additions relative to amino acids 1065-1077 or amino acids 1107-1116 of SEQ ID NO: 33. In other aspects of this embodiment, a binding domain comprising a BoNT/F NTNH β-trefoil domain comprises a polypeptide having, e.g., at least one, two, three or four non-contiguous amino acid additions relative to amino acids 1065-1077 or amino acids 1107-1116 of SEQ ID NO: 33.

In other aspects of this embodiment, a binding domain comprising a BoNT/F NTNH β-trefoil domain comprises a polypeptide having, e.g., at most one, two, three or four contiguous amino acid substitutions relative to amino acids 1065-1077 or amino acids 1107-1116 of SEQ ID NO: 33. In other aspects of this embodiment, a binding domain comprising a BoNT/F NTNH β-trefoil domain comprises a polypeptide having, e.g., at least one, two, three or four contiguous amino acid substitutions relative to amino acids 1065-1077 or amino acids 1107-1116 of SEQ ID NO: 33. In other aspects of this embodiment, contiguous amino acid substitutions of amino acids from amino acids 1065-1077 or amino acids 1107-1116 of SEQ ID NO: 33 can be replaced with glycine. In other aspects of this embodiment, contiguous amino acid substitutions of hydrophobic amino acids from amino acids 1065-1077 or amino acids 1107-1116 of SEQ ID NO: 33 can be replaced with phenylalanine. In yet other aspects of this embodiment, a β-trefoil domain with enhanced binding activity derived from a BoNT/F NTNH comprises a polypeptide having, e.g., at most one, two, three or four contiguous amino acid deletions relative to amino acids 1065-1077 or amino acids 1107-1116 of SEQ ID NO: 33. In other aspects of this embodiment, a binding domain comprising a BoNT/F NTNH β-trefoil domain comprises a polypeptide having, e.g., at least one, two, three or four contiguous amino acid deletions relative to amino acids 1065-1077 or amino acids 1107-1116 of SEQ ID NO: 33. In still other aspects of this embodiment, a binding domain comprising a BoNT/F NTNH β-trefoil domain comprises a polypeptide having, e.g., at most one, two, three or four contiguous amino acid additions relative to amino acids 1065-1077 or amino acids 1107-1116 of SEQ ID NO: 33. In other aspects of this embodiment, a binding domain comprising a BoNT/F NTNH β-trefoil domain comprises a polypeptide having, e.g., at least one, two, three or four contiguous amino acid additions relative to amino acids 1065-1077 or amino acids 1107-1116 of SEQ ID NO: 33.

In another embodiment, a binding domain comprising a β-trefoil domain derived from a BoNT/G NTNH of SEQ ID NO: 34. In another embodiment, a binding domain comprising a β-trefoil domain derived from a BoNT/G NTNH comprises amino acids 1050-1199 of SEQ ID NO: 34. In another aspect of this embodiment, a binding domain comprising a β-trefoil domain derived from a BoNT/G NTNH comprises a α-fold motif of a β-trefoil domain of a BoNT/G NTNH, a β-fold motif of a β-trefoil domain of a BoNT/G NTNH or a γ-fold motif of a β-trefoil domain of a BoNT/G NTNH of SEQ ID NO: 24. In another aspect of this embodiment, a β-trefoil domain derived from a BoNT/G NTNH comprises amino acids 1050-1097, amino acids 1111-1139, or amino acids 1150-1199 of SEQ ID NO: 34.

In other aspects of this embodiment, a binding domain comprising a BoNT/G NTNH β-trefoil domain comprises a polypeptide having, e.g., at least 70% amino acid identity with amino acids 1050-1097, amino acids 1111-1139, or amino acids 1150-1199 of SEQ ID NO: 34, at least 75% amino acid identity with amino acids 1050-1097, amino acids 1111-1139, or amino acids 1150-1199 of SEQ ID NO: 34, at least 80% amino acid identity with amino acids 1050-1097, amino acids 1111-1139, or amino acids 1150-1199 of SEQ ID NO: 34, at least 85% amino acid identity with amino acids 1050-1097, amino acids 1111-1139, or amino acids 1150-1199 of SEQ ID NO: 34, at least 90% amino acid identity with amino acids 1050-1097, amino acids 1111-1139, or amino acids 1150-1199 of SEQ ID NO: 34 or at least 95% amino acid identity with amino acids 1050-1097, amino acids 1111-1139, or amino acids 1150-1199 of SEQ ID NO: 34. In yet other aspects of this embodiment, a binding domain comprising a BoNT/G NTNH β-trefoil domain comprises a polypeptide having, e.g., at most 70% amino acid identity with amino acids 1050-1097, amino acids 1111-1139, or amino acids 1150-1199 of SEQ ID NO: 34, at most 75% amino acid identity with amino acids 1050-1097, amino acids 1111-1139, or amino acids 1150-1199 of SEQ ID NO: 34, at most 80% amino acid identity with amino acids 1050-1097, amino acids 1111-1139, or amino acids 1150-1199 of SEQ ID NO:

34, at most 85% amino acid identity with amino acids 1050-1097, amino acids 1111-1139, or amino acids 1150-1199 of SEQ ID NO: 34, at most 90% amino acid identity with amino acids 1050-1097, amino acids 1111-1139, or amino acids 1150-1199 of SEQ ID NO: 34 or at most 95% amino acid identity with amino acids 1050-1097, amino acids 1111-1139, or amino acids 1150-1199 of SEQ ID NO: 34.

In other aspects of this embodiment, a binding domain comprising a BoNT/G NTNH β-trefoil domain comprises a polypeptide having, e.g., at most one, two, three, four, five, six, seven, eight, nine, 10 or 20 non-contiguous amino acid substitutions relative to amino acids 1050-1097, amino acids 1111-1139, or amino acids 1150-1199 of SEQ ID NO: 34. In other aspects of this embodiment, a binding domain comprising a BoNT/G NTNH β-trefoil domain comprises a polypeptide having, e.g., at least one, two, three, four, five, six, seven, eight, nine, 10 or 20 non-contiguous amino acid substitutions relative to amino acids 1050-1097, amino acids 1111-1139, or amino acids 1150-1199 of SEQ ID NO: 34. In yet other aspects of this embodiment, a binding domain comprising a BoNT/G NTNH β-trefoil domain comprises a polypeptide having, e.g., at most one, two, three, four, five, six, seven, eight, nine, 10 or 20 non-contiguous amino acid deletions relative to amino acids 1050-1097, amino acids 1111-1139, or amino acids 1150-1199 of SEQ ID NO: 34. In other aspects of this embodiment, a binding domain comprising a BoNT/G NTNH β-trefoil domain comprises a polypeptide having, e.g., at least one, two, three, four, five, six, seven, eight, nine, 10 or 20 non-contiguous amino acid deletions relative to amino acids 1050-1097, amino acids 1111-1139, or amino acids 1150-1199 of SEQ ID NO: 34. In still other aspects of this embodiment, a binding domain comprising a BoNT/G NTNH β-trefoil domain comprises a polypeptide having, e.g., at most one, two, three, four, five, six, seven, eight, nine, 10 or 20 non-contiguous amino acid additions relative to amino acids 1050-1097, amino acids 1111-1139, or amino acids 1150-1199 of SEQ ID NO: 34. In other aspects of this embodiment, a binding domain comprising a BoNT/G NTNH β-trefoil domain comprises a polypeptide having, e.g., at least one, two, three, four, five, six, seven, eight, nine, 40 10 or 20 non-contiguous amino acid additions relative to amino acids 1050-1097, amino acids 1111-1139, or amino acids 1150-1199 of SEQ ID NO: 34.

In other aspects of this embodiment, a binding domain comprising a BoNT/G NTNH β-trefoil domain comprises a polypeptide having, e.g., at most one, two, three, four, five, six, seven, eight, nine, 10 or 20 contiguous amino acid substitutions relative to amino acids 1050-1097, amino acids 1111-1139, or amino acids 1150-1199 of SEQ ID NO: 34. In other aspects of this embodiment, a binding domain comprising a BoNT/G NTNH β-trefoil domain comprises a polypeptide having, e.g., at least one, two, three, four, five, six, seven, eight, nine, 10 or 20 contiguous amino acid substitutions relative to amino acids 1050-1097, amino acids 1111-1139, or amino acids 1150-1199 of SEQ ID NO: 34. In yet other aspects of this embodiment, a binding domain comprising a BoNT/G NTNH β-trefoil domain comprises a polypeptide having, e.g., at most one, two, three, four, five, six, seven, eight, nine, 10 or 20 contiguous amino acid deletions relative to amino acids 1050-1097, amino acids 1111-1139, or amino acids 1150-1199 of SEQ ID NO: 34. In other aspects of this embodiment, a binding domain comprising a BoNT/G NTNH β-trefoil domain comprises a polypeptide having, e.g., at least one, two, three, four, five, six, seven, eight, nine, 10 or 20 contiguous amino acid deletions relative to amino acids 1050-1097, amino acids 1111-1139, or amino acids 1150-1199 of SEQ ID NO: 34. In still other aspects of this embodiment, a binding domain comprising a BoNT/G NTNH β-trefoil domain comprises a polypeptide having, e.g., at most one, two, three, four, five, six, seven, eight, nine, 10 or 20 contiguous amino acid additions relative to amino acids 1050-1097, amino acids 1111-1139, or amino acids 1150-1199 of SEQ ID NO: 34. In other aspects of this embodiment, a binding domain comprising a BoNT/G NTNH β-trefoil domain comprises a polypeptide having, e.g., at least one, two, three, four, five, six, seven, eight, nine, 10 or 20 contiguous amino acid additions relative to amino acids 1050-1097, amino acids 1111-1139, or amino acids 1150-1199 of SEQ ID NO: 34.

In another embodiment, a binding domain comprising a BoNT/G NTNH β-trefoil domain comprises a β4/β5 hairpin turn of a β-trefoil domain of a BoNT/G NTNH or a β8/β9 hairpin turn of a β-trefoil domain of a BoNT/G NTNH of SEQ ID NO: 24. In another aspect of this embodiment, a binding domain comprising a BoNT/G NTNH β-trefoil domain comprises amino acids 1098-1110 or amino acids 1140-1149 of SEQ ID NO: 34.

In other aspects of this embodiment, a binding domain comprising a BoNT/G NTNH β-trefoil domain comprises a polypeptide having, e.g., at least 70% amino acid identity with amino acids 1098-1110 or amino acids 1140-1149 of SEQ ID NO: 34, at least 75% amino acid identity with amino acids 1098-1110 or amino acids 1140-1149 of SEQ ID NO: 34, at least 80% amino acid identity with amino acids 1098-1110 or amino acids 1140-1149 of SEQ ID NO: 34, at least 85% amino acid identity with amino acids 1098-1110 or amino acids 1140-1149 of SEQ ID NO: 34, at least 90% amino acid identity with amino acids 1098-1110 or amino acids 1140-1149 of SEQ ID NO: 34 or at least 95% amino acid identity with amino acids 1098-1110 or amino acids 1140-1149 of SEQ ID NO: 34. In yet other aspects of this embodiment, a binding domain comprising a BoNT/G NTNH β-trefoil domain comprises a polypeptide having, e.g., at most 70% amino acid identity with amino acids 1098-1110 or amino acids 1140-1149 of SEQ ID NO: 34, at most 75% amino acid identity with amino acids 1098-1110 or amino acids 1140-1149 of SEQ ID NO: 34, at most 80% amino acid identity with amino acids 1098-1110 or amino acids 1140-1149 of SEQ ID NO: 34, at most 85% amino acid identity with amino acids 1098-1110 or amino acids 1140-1149 of SEQ ID NO: 34, at most 90% amino acid identity with amino acids 1098-1110 or amino acids 1140-1149 of SEQ ID NO: 34 or at most 95% amino acid identity with amino acids 1098-1110 or amino acids 1140-1149 of SEQ ID NO: 34.

In other aspects of this embodiment, a binding domain comprising a BoNT/G NTNH β-trefoil domain comprises a polypeptide having, e.g., at most one, two, three or four non-contiguous amino acid substitutions relative to amino acids 1098-1110 or amino acids 1140-1149 of SEQ ID NO: 34. In other aspects of this embodiment, a binding domain comprising a BoNT/G NTNH β-trefoil domain comprises a polypeptide having, e.g., at least one, two, three or four non-contiguous amino acid substitutions relative to amino acids 1098-1110 or amino acids 1140-1149 of SEQ ID NO: 34. In other aspects of this embodiment, a non-contiguous amino acid substitution of any amino acid from amino acids 1098-1110 or amino acids 1140-1149 of SEQ ID NO: 34 can be replaced with glycine. In other aspects of this embodiment, a non-contiguous amino acid substitution of any hydrophobic amino acid from amino acids 1098-1110 or amino acids 1140-1149 of SEQ ID NO: 34 can be replaced with phenylalanine. In yet other aspects of this embodiment, a binding domain comprising a BoNT/G NTNH β-trefoil domain comprises a polypeptide having, e.g., at most one, two, three or four non-contiguous amino acid deletions relative to amino acids 1098-1110 or amino acids 1140-1149 of SEQ ID NO: 34. In other aspects of this embodiment, a binding domain comprising a BoNT/G NTNH β-trefoil domain comprises a polypeptide having, e.g., at least one, two, three or four non-contiguous amino acid deletions relative to amino acids 1098-1110 or amino acids 1140-1149 of SEQ ID NO: 34. In still other aspects of this embodiment, a binding domain comprising a BoNT/G NTNH β-trefoil domain comprises a polypeptide having, e.g., at most one, two, three or four non-contiguous amino acid additions relative to amino acids 1098-1110 or amino acids 1140-1149 of SEQ ID NO: 34. In other aspects of this embodiment, a binding domain comprising a BoNT/G NTNH β-trefoil domain comprises a polypeptide having, e.g., at least one, two, three or four non-contiguous amino acid additions relative to amino acids 1098-1110 or amino acids 1140-1149 of SEQ ID NO: 34.

In other aspects of this embodiment, a binding domain comprising a BoNT/G NTNH β-trefoil domain comprises a polypeptide having, e.g., at most one, two, three or four contiguous amino acid substitutions relative to amino acids 1098-1110 or amino acids 1140-1149 of SEQ ID NO: 34. In other aspects of this embodiment, a binding domain comprising a BoNT/G NTNH β-trefoil domain comprises a polypeptide having, e.g., at least one, two, three or four contiguous amino acid substitutions relative to amino acids 1098-1110 or amino acids 1140-1149 of SEQ ID NO: 34. In other aspects of this embodiment, contiguous amino acid substitutions of amino acids from amino acids 1098-1110 or amino acids 1140-1149 of SEQ ID NO: 34 can be replaced with glycine. In other aspects of this embodiment, contiguous amino acid substitutions of hydrophobic amino acids from amino acids 1098-1110 or amino acids 1140-1149 of SEQ ID NO: 34 can be replaced with phenylalanine. In yet other aspects of this embodiment, a β-trefoil domain with enhanced binding activity derived from a BoNT/G NTNH comprises a polypeptide having, e.g., at most one, two, three or four contiguous amino acid deletions relative to amino acids 1098-1110 or amino acids 1140-1149 of SEQ ID NO: 34. In other aspects of this embodiment, a binding domain comprising a BoNT/G NTNH β-trefoil domain comprises a polypeptide having, e.g., at least one, two, three or four contiguous amino acid deletions relative to amino acids 1098-1110 or amino acids 1140-1149 of SEQ ID NO: 34. In still other aspects of this embodiment, a binding domain comprising a BoNT/G NTNH β-trefoil domain comprises a polypeptide having, e.g., at most one, two, three or four contiguous amino acid additions relative to amino acids 1098-1110 or amino acids 1140-1149 of SEQ ID NO: 34. In other aspects of this embodiment, a binding domain comprising a BoNT/G NTNH β-trefoil domain comprises a polypeptide having, e.g., at least one, two, three or four contiguous amino acid additions relative to amino acids 1098-1110 or amino acids 1140-1149 of SEQ ID NO: 34.

Another example of a binding domain, includes, without limitation, ligands that bind the same receptors as does the naturally-occurring Clostridial toxins. Recent studies are revealing components of the endogenous receptors used by a Clostridial toxin during the intoxication process. As a non-limiting example, fibroblast growth factor 3 receptor (FGFR3) serves as a BoNT/A receptor, see, e.g., Ester Fernandez-Salas et al., Botulinum Toxin Screening Assays, PCT Patent Application No. 2005/006421 (Sep. 9, 2005). As another non-limiting example, synaptotagmin I serves as a BoNT/B receptor and as a BoNT/G receptor, see, e.g., Min Dong et al., Synaptotagmins I and II mediate entry of botulinum neurotoxin B into cells, 162(7) J. Cell Biol. 1293-1303 (2003); and Andreas Rummel et al., Synaptotagmins I and II act as nerve cell receptors for botulinum neurotoxin G, 279 (29) J. Biol. Chem. 30865-30870 (2004). As yet another non-limiting example, synaptotagmin II serves as a BoNT/B receptor and as a BoNT/G receptor, see, e.g., Min Dong et al., supra, (2003); and Andreas Rummel et al., supra, (2004). The selection of a binding domain will depend on the Clostridial toxin being modified. As non-limiting examples, ligands that selectively bind to a FGFR3 could be used as a binding domain for a modified BoNT/A, whereas ligands that selectively bind a Synaptotagmin I or Synaptotagmin II could be used as a binding domain for a modified BoNT/B or a modified BoNT/G.

In addition to its enhanced targeting activity, replacement of a naturally-occurring binding domain with, e.g., an FGF ligand, has an added advantage of reducing the likelihood of the modified toxin from eliciting an immunogenic response. Regions found in the $H_{CC}$ targeting domain are bound by neutralizing anti-BoNT/A antibodies, see, e.g., M. Zouhair Atassi et al., Mapping of the Antibody-binding Regions on Botulinum Neurotoxin H-chain Domain 855-1296 with Anti-toxin Antibodies from Three Host Species, 15 J. PROT. CHEM. 691-700, (1996); M. Zouhair Atassi & Behzod Z. Dolimbek, Mapping of the Antibody-binding Profile on Botulinum Neurotoxin A $H_N$-domain (residues 449-859) with Anti-toxin Antibodies from Four Host Species. Antigenic Profile of the Entire H-chain of Botulinum Neurotoxin A, 23(1) PROTEIN J. 39-52, (2004). Therefore, elimination of this binding domain will reduce the likelihood of an immunogenic response because 1) the Clostridial toxin $H_{CC}$ binding domain is absent; 2) a human FGF binding domain will most likely not elicit an immunogenic response in a patient because it is a human polypeptide.

Fibroblast growth factors (FGF) participate in many developmental, differentiation and growth and repair processes of cells through complex combinatorial signaling pathways. Presently, at least 23 ligands (FGF1-23) are known to signal through a family of five transmembrane tyrosine kinase FGF receptors (FGFR1-5). Affinity of FGFRs for their ligands is highly diverse with different affinities for each family member of growth factors, see, e.g., C. J. Powers et al., Fibroblast growth factors, their receptors and signaling, 7(3) Endocr. Relat. Cancer. 165-197 (2000). This diversity is achieved in part by the generation of alternatively spliced variants encoding distinct receptor isoforms, see, e.g., Bernhard Reuss & Oliver von Bohlen und Halbach, Fibroblast growth factors and their receptors in the central nervous system, 313(2) Cell Tissue Res. 139-157 (2003). The protein region that appears to have the highest influence on ligand binding selectivity is a portion of the IgIII domain, for which isoforms encoded by three different splice variants have been identified. These three isoforms, designated IgIIIa, IgIIIb and IgIIIc, have relative binding affinities for different FGFR family members. Alternative splicing in the FGFR ligand binding domain, designated a and b, generates additional receptor isoforms with novel ligand affinities. Isoforms for IgIIIa, IgIIIb and IgIIIc have been identified for both FGFR1 and FGFR2. Thus far, the IgIIIa isoform of FGFR3 and the IgIIIa and IgIIIb isoforms of FGFR4 and FGFR5 have not been reported.

Currently, several FGFs have been shown to selectively bind FGFR3, such as, e.g., FGF-1, FGF-2, FGF-4, FGF-8, FGF-9, FGF-17 and FGF-18, see, e.g., Hecht et al., 1995; Ornitz et al., 1996; and Xu et al., 2000. Additional studies have revealed that FGF-1 and FGF9 preferentially bind FGFR3IIIb, whereas FGF-1 FGF-2, FGF-4, FGF-8, and FGF9 preferentially bind FGFR3IIIc. Studies have shown that each of these ligands is present in various vertebrate species with a high degree of sequence identity which suggests functional equivalence or similarity. As a non-limiting example, FGF-8 is found in fish, birds and mammals and each of these FGF-8 ligands have over 80% amino acid sequence identity. As another non-limiting example, FGF-18 is found in fish, birds and mammals and each of these FGF-18 ligands have over 70% amino acid sequence identity. Crystallographic studies have revealed that all FGFs are structurally organized into β-trefoil domain. The amino acid sequences comprising the β-trefoil domains found in various FGF ligands that bind FGFR3 are shown in Table 7.

TABLE 7

β-trefoil Domains of FGFs

| | | | Amino Acid Sequence Region of Carbohydrate Binding Moieties | | | |
|---|---|---|---|---|---|---|
| Ligand | SEQ ID NO: | α-fold | β4/β5 β-hairpin turn | β-fold | β8/β9 β-hairpin turn | γ-fold |
| FGF-1 | 35 | 26-64 | 65-67 | 68-105 | 106-108 | 109-155 |
| FGF-2 | 36 | 29-67 | 68-70 | 71-111 | 112-114 | 115-155 |
| FGF-4 | 37 | 83-121 | 122-124 | 125-162 | 163-165 | 166-206 |
| FGF-8 | 38 | 43-80 | 81-83 | 84-123 | 124-126 | 127-172 |
| FGF-9 | 39 | 63-100 | 101-103 | 104-144 | 145-147 | 148-196 |
| FGF-17 | 40 | 55-91 | 92-94 | 95-134 | 135-137 | 138-183 |
| FGF-18 | 41 | 54-91 | 92-94 | 95-134 | 135-137 | 138-183 |

As used herein, the term "Fibroblast Growth Factor" is synonymous with "FGF" and means a polypeptide with selective binding activity, such as, e.g., a binding affinity or a binding specificity, for a receptor, including endogenous Clostridial toxin receptors such as, e.g., a receptor comprising FGFR3. It is envisioned that both naturally occurring FGFs as well as non-naturally occurring FGFs can be used as a binding domain. Any of a variety of sequence alignment methods can be used to determine percent identity of a non-naturally occurring FGF relative to a naturally-occurring FGF, including, without limitation, global methods, local methods and hybrid methods, such as, e.g., segment approach methods. Protocols to determine percent identity are routine procedures within the scope of one skilled in the art and from the teaching herein.

Approaches well known to one skilled in the art on how to modify a FGF in order to increase its binding activity for an endogenous Clostridial toxin receptor present on a naturally-occurring Clostridial toxin target cell. As described above, one approach involves identifying amino acids using computational protein design algorithms; changing specifically-identified amino acids using, without limitation, site-directed mutagenesis, oligonucleotide-directed mutagenesis and site-specific mutagenesis; and testing the binding activity of multivalent Clostridial toxins comprising a modified FGF with enhanced binding activity using, e.g., heterogeneous assays, homogeneous assays and non-separating homogeneous assays. It is further envisioned that the binding activity of a multivalent Clostridial toxin disclosed in the present specification can be determined by affinity chromatography using immobilized receptors and interfacial optical assays. In another approach described above, a binding activity of a modified FGF for a naturally-occurring Clostridial toxin receptor present on a naturally-occurring Clostridial toxin target cell can be achieved using directed-evolution methods.

A FGF includes, without limitation, naturally occurring FGF variants, such as, e.g., FGF isoforms and FGF subtypes; non-naturally occurring FGF variants, such as, e.g., conservative FGF variants, non-conservative FGF variants, FGF chimerics, active FGF fragments thereof, or any combination thereof.

As used herein, the term "FGF variant," whether naturally-occurring or non-naturally-occurring, means a FGF that has at least one amino acid change from the corresponding region of the disclosed reference sequences (see Table 7) and can be described in percent identity to the corresponding region of that reference sequence. Unless expressly indicated, all FGF variants disclosed in the present specification are capable of executing the cell binding step of the intoxication process.

It is recognized by those of skill in the art that there can be naturally occurring FGF variants that differ somewhat in their amino acid sequence, and also in the nucleic acids encoding these proteins. For example, there are presently at least four FGF-8 variants, FGF-8A, FGF-8A, FGF-8B, FGF-8E and FGF-8F, with specific FGF-8 variants showing various degrees of amino acid divergence when compared to another FGF-8 variant. As another example, there are presently at least two FGF-2 variants, FGF-2-1 and FGF-2-1, with the FGF-2-1 variant showing an amino acid divergence when compared to the FGF-2-2 variant. As used herein, the term "naturally occurring FGF variant" means any FGF produced by a naturally-occurring process, including, without limitation, FGF isoforms produced from alternatively-spliced transcripts, FGF isoforms produced by spontaneous mutation and FGF subtypes. A naturally occurring FGF variant can function in substantially the same manner as the reference FGF on which the naturally occurring FGF variant is based, and can be substituted for the reference FGF in any aspect of the present invention. A naturally occurring FGF variant may substitute one or more amino acids, two or more amino acids, three or more amino acids, four or more amino acids, five or more amino acids, ten or more amino acids, 20 or more amino acids, 30 or more amino acids, 40 or more amino acids, or 50 or more amino acids from the reference FGF on which the naturally occurring FGF variant is based. A naturally occurring FGF variant can also substitute at least 10 contiguous amino acids, at least 15 contiguous amino acids, at least 20 contiguous amino acids, or at least 25 contiguous amino acids from the reference FGF on which the naturally occurring FGF variant is based, that possess at least 50% amino acid identity, 65% amino acid identity, 75% amino acid identity, 85% amino acid identity or 95% amino acid identity to the reference FGF on which the naturally occurring FGF variant is based.

A non-limiting examples of a naturally occurring FGF variant is a FGF isoform such as, e.g., a FGF-1 isoform, a FGF-2 isoform, a FGF-4 isoform, a FGF-8 isoform, a FGF-9 isoform, a FGF-17 isoform and a FGF-18 isoform. A FGF isoform can function in substantially the same manner as the reference FGF on which the FGF isoform is based, and can be substituted for the reference FGF in any aspect of the present invention.

Another non-limiting examples of a naturally occurring FGF variant is a FGF subtype such as, e.g., a FGF-1 subtype, a FGF-2 subtype, a FGF-4 subtype, a FGF-8 subtype, a FGF-9 subtype, a FGF-17 subtype and a FGF-18 subtype. A FGF subtype can function in substantially the same manner as the reference FGF on which the FGF subtype is based, and can be substituted for the reference FGF in any aspect of the present invention.

As used herein, the term "non-naturally occurring FGF variant" means any FGF produced with the aid of human manipulation, including, without limitation, FGFs produced by genetic engineering using random mutagenesis or rational design and FGFs produced by chemical synthesis. Non-limiting examples of non-naturally occurring FGF variants include, e.g., conservative FGF variants, non-conservative FGF variants, FGF chimeric variants and active FGF fragments.

As used herein, the term "conservative FGF variant" means a FGF that has at least one amino acid substituted by another amino acid or an amino acid analog that has at least one property similar to that of the original amino acid from the reference FGF sequence (see Table 7). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative FGF variant can function in substantially the same manner as the reference FGF on which the conservative FGF variant is based, and can be substituted for the reference FGF in any aspect of the present invention. A conservative FGF variant may substitute one or more amino acids, two or more amino acids, three or more amino acids, four or more amino acids, five or more amino acids, ten or more amino acids, 20 or more amino acids, 30 or more amino acids, 40 or more amino acids or 50 or more amino acids from the reference FGF on which the conservative FGF variant is based. A conservative FGF variant can also substitute at least 10 contiguous amino acids, at least 15 contiguous amino acids, at least 20 contiguous amino acids, or at least 25 contiguous amino acids from the reference FGF on which the conservative FGF variant is based, that possess at least 50% amino acid identity, 65% amino acid identity, 75% amino acid identity, 85% amino acid identity or 95% amino acid identity to the reference FGF on which the conservative FGF variant is based. Non-limiting examples of a conservative FGF variant include, e.g., a conservative FGF-1 variant, a conservative FGF-2 variant, a conservative FGF-4 variant, a conservative FGF-8 variant, a conservative FGF-9 variant, a conservative FGF-17 variant and a conservative FGF-18 variant.

As used herein, the term "non-conservative FGF variant" means a FGF in which 1) at least one amino acid is deleted from the reference FGF on which the non-conservative FGF variant is based; 2) at least one amino acid added to the reference FGF on which the non-conservative FGF is based; or 3) at least one amino acid is substituted by another amino acid or an amino acid analog that does not share any property similar to that of the original amino acid from the reference FGF sequence (see Table 7). A non-conservative FGF variant can function in substantially the same manner as the reference FGF on which the non-conservative FGF variant is based, and can be substituted for the reference FGF in any aspect of the present invention. A non-conservative FGF variant can delete one or more amino acids, two or more amino acids, three or more amino acids, four or more amino acids, five or more amino acids, and ten or more amino acids from the reference FGF on which the non-conservative FGF variant is based. A non-conservative FGF variant can add one or more amino acids, two or more amino acids, three or more amino acids, four or more amino acids, five or more amino acids, and ten or more amino acids to the reference FGF on which the non-conservative FGF variant is based. A non-conservative FGF variant may substitute one or more amino acids, two or more amino acids, three or more amino acids, four or more amino acids, five or more amino acids, ten or more amino acids, 20 or more amino acids, 30 or more amino acids, 40 or more amino acids or 50 or more amino acids from the reference FGF on which the non-conservative FGF variant is based. A non-conservative FGF variant can also substitute at least 10 contiguous amino acids, at least 15 contiguous amino acids, at least 20 contiguous amino acids, or at least 25 contiguous amino acids from the reference FGF on which the non-conservative FGF variant is based, that possess at least 50% amino acid identity, 65% amino acid identity, 75% amino acid identity, 85% amino acid identity or 95% amino acid identity to the reference FGF on which the non-conservative FGF variant is based. Non-limiting examples of a non-conservative FGF variant include, e.g., a non-conservative FGF-1 variant, a non-conservative FGF-2 variant, a non-conservative FGF-4 variant, a non-conservative FGF-8 variant, a non-conservative FGF-9 variant, a non-conservative FGF-17 variant and a non-conservative FGF-18 variant.

As used herein, the term "FGF chimeric" means a polypeptide comprising at least a portion of a FGF and at least a portion of at least one other polypeptide to form an enhanced targeting domain with at least one property different from the reference FGF (see Table 7), with the proviso that this FGF chimeric can specifically bind to an endogenous Clostridial toxin receptor present in a Clostridial toxin target cell, and thus participate in executing the overall cellular mechanism whereby a Clostridial toxin proteolytically cleaves a substrate.

Thus, in an embodiment, a binding domain comprises a FGF. In aspects of this embodiment, a FGF comprises a β-trefoil domain derived from a FGF. In an aspect of this embodiment, a β-trefoil domain derived from a FGF comprises, e.g., a β-trefoil domain derived from a FGF-1, a β-trefoil domain derived from a FGF-2, a β-trefoil domain derived from FGF-4, a β-trefoil domain derived from a FGF-8, a β-trefoil domain derived from a FGF-9, a β-trefoil domain derived from a FGF-17 or a β-trefoil domain derived from a FGF-18. In another aspect of this embodiment, a β-trefoil domain derived from a FGF comprises a α-fold motif of a β-trefoil domain of a FGF, a β-fold motif of a β-trefoil domain of a FGF or a γ-fold motif of a β-trefoil domain of a FGF.

In another embodiment, a binding domain comprises a β-trefoil domain derived a FGF-1 of SEQ ID NO: 35. In another embodiment, a binding domain comprising a β-trefoil domain derived from a FGF-1 comprises amino acids 26-155 of SEQ ID NO: 35. In another aspect of this embodiment, a binding domain comprising a β-trefoil domain derived from a FGF-1 comprises an α-fold motif of a β-trefoil domain of a FGF-1, a β-fold motif of a β-trefoil domain of a FGF-1 or a γ-fold motif of a β-trefoil domain of a FGF-1 of SEQ ID NO: 35. In another aspect of this embodiment, a β-trefoil domain derived from a FGF-1 comprises amino acids 26-64, amino acids 68-105, or amino acids 109-155 of SEQ ID NO: 35.

In other aspects of this embodiment, a binding domain comprising a FGF-1 β-trefoil domain comprises a polypeptide having, e.g., at least 70% amino acid identity with amino acids 26-64, amino acids 68-105, or amino acids 109-155 of SEQ ID NO: 35, at least 75% amino acid identity with amino acids 26-64, amino acids 68-105, or amino acids 109-155 of SEQ ID NO: 35, at least 80% amino acid identity with amino acids 26-64, amino acids 68-105, or amino acids 109-155 of SEQ ID NO: 35, at least 85% amino acid identity with amino acids 26-64, amino acids 68-105, or amino acids 109-155 of SEQ ID NO: 35, at least 90% amino acid identity with amino acids 26-64, amino acids 68-105, or amino acids 109-155 of SEQ ID NO: 35 or at least 95% amino acid identity with amino acids 26-64, amino acids 68-105, or amino acids 109-155 of SEQ ID NO: 35. In yet other aspects of this embodiment, a binding domain comprising a FGF-1 β-trefoil domain comprises a polypeptide having, e.g., at most 70% amino acid identity with amino acids 26-64, amino acids 68-105, or amino acids 109-155 of SEQ ID NO: 35, at most 75% amino acid identity with amino acids 26-64, amino acids 68-105, or amino acids 109-155 of SEQ ID NO: 35, at most 80% amino acid identity with amino acids 26-64, amino acids 68-105, or amino acids 109-155 of SEQ ID NO: 35, at most 85% amino acid identity with amino acids 26-64, amino acids 68-105, or amino acids 109-155 of SEQ ID NO: 35, at most 90% amino acid identity with amino acids 26-64, amino acids 68-105, or amino acids 109-155 of SEQ ID NO: 35 or at most 95% amino acid identity with amino acids 26-64, amino acids 68-105, or amino acids 109-155 of SEQ ID NO: 35.

In other aspects of this embodiment, a binding domain comprising a FGF-1 β-trefoil domain comprises a polypeptide having, e.g., at most one, two, three, four, five, six, seven, eight, nine, 10 or 20 non-contiguous amino acid substitutions relative to amino acids 26-64, amino acids 68-105, or amino acids 109-155 of SEQ ID NO: 35. In other aspects of this embodiment, a binding domain comprising a FGF-1 β-trefoil domain comprises a polypeptide having, e.g., at least one, two, three, four, five, six, seven, eight, nine, 10 or 20 non-contiguous amino acid substitutions relative to amino acids 26-64, amino acids 68-105, or amino acids 109-155 of SEQ ID NO: 35. In yet other aspects of this embodiment, a binding domain comprising a FGF-1 β-trefoil domain comprises a polypeptide having, e.g., at most one, two, three, four, five, six, seven, eight, nine, 10 or 20 non-contiguous amino acid deletions relative to amino acids 26-64, amino acids 68-105, or amino acids 109-155 of SEQ ID NO: 35. In other aspects of this embodiment, a binding domain comprising a FGF-1 β-trefoil domain comprises a polypeptide having, e.g., at least one, two, three, four, five, six, seven, eight, nine, 10 or 20 non-contiguous amino acid deletions relative to amino acids 26-64, amino acids 68-105, or amino acids 109-155 of SEQ ID NO: 35. In still other aspects of this embodiment, a binding domain comprising a FGF-1 β-trefoil domain comprises a polypeptide having, e.g., at most one, two, three, four, five, six, seven, eight, nine, 10 or 20 non-contiguous amino acid additions relative to amino acids 26-64, amino acids 68-105, or amino acids 109-155 of SEQ ID NO: 35. In other aspects of this embodiment, a binding domain comprising a FGF-1 β-trefoil domain comprises a polypeptide having, e.g., at least one, two, three, four, five, six, seven, eight, nine, 10 or 20 non-contiguous amino acid additions relative to amino acids 26-64, amino acids 68-105, or amino acids 109-155 of SEQ ID NO: 35.

In other aspects of this embodiment, a binding domain comprising a FGF-1 β-trefoil domain comprises a polypeptide having, e.g., at most one, two, three, four, five, six, seven, eight, nine, 10 or 20 contiguous amino acid substitutions relative to amino acids 26-64, amino acids 68-105, or amino acids 109-155 of SEQ ID NO: 35. In other aspects of this embodiment, a binding domain comprising a FGF-1 β-trefoil domain comprises a polypeptide having, e.g., at least one, two, three, four, five, six, seven, eight, nine, 10 or 20 contiguous amino acid substitutions relative to amino acids 26-64, amino acids 68-105, or amino acids 109-155 of SEQ ID NO: 35. In yet other aspects of this embodiment, a binding domain comprising a FGF-1 β-trefoil domain comprises a polypeptide having, e.g., at most one, two, three, four, five, six, seven, eight, nine, 10 or 20 contiguous amino acid deletions relative to amino acids 26-64, amino acids 68-105, or amino acids 109-155 of SEQ ID NO: 35. In other aspects of this embodiment, a binding domain comprising a FGF-1 β-trefoil domain comprises a polypeptide having, e.g., at least one, two, three, four, five, six, seven, eight, nine, 10 or 20 contiguous amino acid deletions relative to amino acids 26-64, amino acids 68-105, or amino acids 109-155 of SEQ ID NO: 35. In still other aspects of this embodiment, a binding domain comprising a FGF-1 β-trefoil domain comprises a polypeptide having, e.g., at most one, two, three, four, five, six, seven, eight, nine, 10 or 20 contiguous amino acid additions relative to amino acids 26-64, amino acids 68-105, or amino acids 109-155 of SEQ ID NO: 35. In other aspects of this embodiment, a binding domain comprising a FGF-1 β-trefoil domain comprises a polypeptide having, e.g., at least one, two, three, four, five, six, seven, eight, nine, 10 or 20 contiguous amino acid additions relative to amino acids 26-64, amino acids 68-105, or amino acids 109-155 of SEQ ID NO: 35.

In another embodiment, a binding domain comprising a FGF-1 β-trefoil domain comprises a β4/β5 hairpin turn of a β-trefoil domain of a FGF-1 or a β8/β9 hairpin turn of a β-trefoil domain of a FGF-1 of SEQ ID NO: 35. In another aspect of this embodiment, a binding domain comprising a FGF-1 β-trefoil domain comprises amino acids 65-67 or amino acids 106-108 of SEQ ID NO: 35.

In other aspects of this embodiment, a binding domain comprising a FGF-1 β-trefoil domain comprises a polypeptide having, e.g., at least 70% amino acid identity with amino acids 65-67 or amino acids 106-108 of SEQ ID NO: 35, at least 75% amino acid identity with amino acids 65-67 or amino acids 106-108 of SEQ ID NO: 35, at least 80% amino acid identity with amino acids 65-67 or amino acids 106-108 of SEQ ID NO: 35, at least 85% amino acid identity with amino acids 65-67 or amino acids 106-108 of SEQ ID NO: 35, at least 90% amino acid identity with amino acids 65-67 or amino acids 106-108 of SEQ ID NO: 35 or at least 95% amino acid identity with amino acids 65-67 or amino acids 106-108 of SEQ ID NO: 35. In yet other aspects of this embodiment, a binding domain comprising a FGF-1 β-trefoil domain comprises a polypeptide having, e.g., at most 70% amino acid identity with amino acids 65-67 or amino acids 106-108 of SEQ ID NO: 35, at most 75% amino acid identity with amino acids 65-67 or amino acids 106-108 of SEQ ID NO: 35, at most 80% amino acid identity with amino acids 65-67 or amino acids 106-108 of SEQ ID NO: 35, at most 85% amino acid identity with amino acids 65-67 or amino acids 106-108 of SEQ ID NO: 35, at most 90% amino acid identity with amino acids 65-67 or amino acids 106-108 of SEQ ID NO: 35 or at most 95% amino acid identity with amino acids 65-67 or amino acids 106-108 of SEQ ID NO: 35.

In other aspects of this embodiment, a binding domain comprising a FGF-1 β-trefoil domain comprises a polypeptide having, e.g., at most one, two, three or four non-contiguous amino acid substitutions relative to amino acids 65-67 or amino acids 106-108 of SEQ ID NO: 35. In other aspects of this embodiment, a binding domain comprising a FGF-1 β-trefoil domain comprises a polypeptide having, e.g., at least one, two, three or four non-contiguous amino acid substitutions relative to amino acids 65-67 or amino acids 106-108 of SEQ ID NO: 35. In other aspects of this embodiment, a non-contiguous amino acid substitution of any amino acid from amino acids 65-67 or amino acids 106-108 of SEQ ID NO: 35 can be replaced with glycine. In other aspects of this embodiment, a non-contiguous amino acid substitution of any hydrophobic amino acid from amino acids 65-67 or amino acids 106-108 of SEQ ID NO: 35 can be replaced with phenylalanine. In yet other aspects of this embodiment, a binding domain comprising a FGF-1 β-trefoil domain comprises a polypeptide having, e.g., at most one, two, three or four non-contiguous amino acid deletions relative to amino acids 65-67 or amino acids 106-108 of SEQ ID NO: 35. In other aspects of this embodiment, a binding domain comprising a FGF-1 β-trefoil domain comprises a polypeptide having, e.g., at least one, two, three or four non-contiguous amino acid deletions relative to amino acids 65-67 or amino acids 106-108 of SEQ ID NO: 35. In still other aspects of this embodiment, a binding domain comprising a FGF-1 β-trefoil domain comprises a polypeptide having, e.g., at most one, two, three or four non-contiguous amino acid additions relative to amino acids 65-67 or amino acids 106-108 of SEQ ID NO: 35. In other aspects of this embodiment, a binding domain comprising a FGF-1 β-trefoil domain comprises a polypeptide having, e.g., at least one, two, three or four non-contiguous amino acid additions relative to amino acids 65-67 or amino acids 106-108 of SEQ ID NO: 35.

In other aspects of this embodiment, a binding domain comprising a FGF-1 β-trefoil domain comprises a polypeptide having, e.g., at most one, two, three or four contiguous amino acid substitutions relative to amino acids 65-67 or amino acids 106-108 of SEQ ID NO: 35. In other aspects of this embodiment, a binding domain comprising a FGF-1 β-trefoil domain comprises a polypeptide having, e.g., at least one, two, three or four contiguous amino acid substitutions relative to amino acids 65-67 or amino acids 106-108 of SEQ ID NO: 35. In other aspects of this embodiment, contiguous amino acid substitutions of amino acids from amino acids 65-67 or amino acids 106-108 of SEQ ID NO: 35 can be replaced with glycine. In other aspects of this embodiment, contiguous amino acid substitutions of hydrophobic amino acids from amino acids 65-67 or amino acids 106-108 of SEQ ID NO: 35 can be replaced with phenylalanine. In yet other aspects of this embodiment, a binding domain comprising a FGF-1 β-trefoil domain comprises a polypeptide having, e.g., at most one, two, three or four contiguous amino acid deletions relative to amino acids 65-67 or amino acids 106-108 of SEQ ID NO: 35. In other aspects of this embodiment, a binding domain comprising a FGF-1 β-trefoil domain comprises a polypeptide having, e.g., at least one, two, three or four contiguous amino acid deletions relative to amino acids 65-67 or amino acids 106-108 of SEQ ID NO: 35. In still other aspects of this embodiment, a binding domain comprising a FGF-1 β-trefoil domain comprises a polypeptide having, e.g., at most one, two, three or four contiguous amino acid additions relative to amino acids 65-67 or amino acids 106-108 of SEQ ID NO: 35. In other aspects of this embodiment, a binding domain comprising a FGF-1 β-trefoil domain comprises a polypeptide having, e.g., at least one, two, three or four contiguous amino acid additions relative to amino acids 65-67 or amino acids 106-108 of SEQ ID NO: 35.

In another embodiment, a binding domain comprises a β-trefoil domain derived a FGF-2 of SEQ ID NO: 36. In another embodiment, a binding domain comprising a β-trefoil domain derived from a FGF-2 comprises amino acids 29-155 of SEQ ID NO: 36. In another aspect of this embodiment, a binding domain comprising a β-trefoil domain derived from a FGF-2 comprises an α-fold motif of a β-trefoil domain of a FGF-2, a β-fold motif of a β-trefoil domain of a FGF-2 or a γ-fold motif of a β-trefoil domain of a FGF-2 of SEQ ID NO: 36. In another aspect of this embodiment, a β-trefoil domain derived from a FGF-2 comprises amino acids 29-67, amino acids 71-111, or amino acids 115-155 of SEQ ID NO: 36.

In other aspects of this embodiment, a binding domain comprising a FGF-2 β-trefoil domain comprises a polypeptide having, e.g., at least 70% amino acid identity with amino acids 29-67, amino acids 71-111, or amino acids 115-155 of SEQ ID NO: 36, at least 75% amino acid identity with amino acids 29-67, amino acids 71-111, or amino acids 115-155 of SEQ ID NO: 36, at least 80% amino acid identity with amino acids 29-67, amino acids 71-111, or amino acids 115-155 of SEQ ID NO: 36, at least 85% amino acid identity with amino acids 29-67, amino acids 71-111, or amino acids 115-155 of SEQ ID NO: 36, at least 90% amino acid identity with amino acids 29-67, amino acids 71-111, or amino acids 115-155 of SEQ ID NO: 36 or at least 95% amino acid identity with amino acids 29-67, amino acids 71-111, or amino acids 115-155 of SEQ ID NO: 36. In yet other aspects of this embodiment, a binding domain comprising a FGF-2 β-trefoil domain comprises a polypeptide having, e.g., at most 70% amino acid identity with amino acids 29-67, amino acids 71-111, or amino acids 115-155 of SEQ ID NO: 36, at most 75% amino acid identity with amino acids 29-67, amino acids 71-111, or amino acids 115-155 of SEQ ID NO: 36, at most 80% amino acid identity with amino acids 29-67, amino acids 71-111, or amino acids 115-155 of SEQ ID NO: 36, at most 85% amino acid identity with amino acids 29-67, amino acids 71-111, or amino acids 115-155 of SEQ ID NO: 36, at most 90% amino acid identity with amino acids 29-67, amino acids 71-111, or amino acids 115-155 of SEQ ID NO: 36 or at most 95% amino acid identity with amino acids 29-67, amino acids 71-111, or amino acids 115-155 of SEQ ID NO: 36.

In other aspects of this embodiment, a binding domain comprising a FGF-2 β-trefoil domain comprises a polypeptide having, e.g., at most one, two, three, four, five, six, seven, eight, nine, 10 or 20 non-contiguous amino acid substitutions relative to amino acids 29-67, amino acids 71-111, or amino acids 115-155 of SEQ ID NO: 36. In other aspects of this embodiment, a binding domain comprising a FGF-2 β-trefoil domain comprises a polypeptide having, e.g., at least one, two, three, four, five, six, seven, eight, nine, 10 or 20 non-contiguous amino acid substitutions relative to amino acids 29-67, amino acids 71-111, or amino acids 115-155 of SEQ ID NO: 36. In yet other aspects of this embodiment, a binding domain comprising a FGF-2 β-trefoil domain comprises a polypeptide having, e.g., at most one, two, three, four, five, six, seven, eight, nine, 10 or 20 non-contiguous amino acid deletions relative to amino acids 29-67, amino acids 71-111, or amino acids 115-155 of SEQ ID NO: 36. In other aspects of this embodiment, a binding domain comprising a FGF-2 β-trefoil domain comprises a polypeptide having, e.g., at least one, two, three, four, five, six, seven, eight, nine, 10 or 20 non-contiguous amino acid deletions relative to amino acids 29-67, amino acids 71-111, or amino acids 115-155 of SEQ ID NO: 36. In still other aspects of this embodiment, a binding domain comprising a FGF-2 β-trefoil domain comprises a polypeptide having, e.g., at most one, two, three, four, five, six, seven, eight, nine, 10 or 20 non-contiguous amino acid additions relative to amino acids 29-67, amino acids 71-111, or amino acids 115-155 of SEQ ID NO: 36. In other aspects of this embodiment, a binding domain comprising a FGF-2 β-trefoil domain comprises a polypeptide having, e.g., at least one, two, three, four, five, six, seven, eight, nine, 10 or 20 non-contiguous amino acid additions relative to amino acids 29-67, amino acids 71-111, or amino acids 115-155 of SEQ ID NO: 36.

In other aspects of this embodiment, a binding domain comprising a FGF-2 β-trefoil domain comprises a polypeptide having, e.g., at most one, two, three, four, five, six, seven, eight, nine, 10 or 20 contiguous amino acid substitutions relative to amino acids 29-67, amino acids 71-111, or amino acids 115-155 of SEQ ID NO: 36. In other aspects of this embodiment, a binding domain comprising a FGF-2 β-trefoil domain comprises a polypeptide having, e.g., at least one, two, three, four, five, six, seven, eight, nine, 10 or 20 contiguous amino acid substitutions relative to amino acids 29-67, amino acids 71-111, or amino acids 115-155 of SEQ ID NO: 36. In yet other aspects of this embodiment, a binding domain comprising a FGF-2 β-trefoil domain comprises a polypeptide having, e.g., at most one, two, three, four, five, six, seven, eight, nine, 10 or 20 contiguous amino acid deletions relative to amino acids 29-67, amino acids 71-111, or amino acids 115-155 of SEQ ID NO: 36. In other aspects of this embodiment, a binding domain comprising a FGF-2 β-trefoil domain comprises a polypeptide having, e.g., at least one, two, three, four, five, six, seven, eight, nine, 10 or 20 contiguous amino acid deletions relative to amino acids 29-67, amino acids 71-111, or amino acids 115-155 of SEQ ID NO: 36. In still other aspects of this embodiment, a binding domain comprising a FGF-2 β-trefoil domain comprises a polypeptide having, e.g., at most one, two, three, four, five, six, seven, eight, nine, 10 or 20 contiguous amino acid additions relative to amino acids 29-67, amino acids 71-111, or amino acids 115-155 of SEQ ID NO: 36. In other aspects of this embodiment, a binding domain comprising a FGF-2 β-trefoil domain comprises a polypeptide having, e.g., at least one, two, three, four, five, six, seven, eight, nine, 10 or 20 contiguous amino acid additions relative to amino acids 29-67, amino acids 71-111, or amino acids 115-155 of SEQ ID NO: 36.

In another embodiment, a binding domain comprising a FGF-2 β-trefoil domain comprises a β4/β5 hairpin turn of a β-trefoil domain of a FGF-2 or a β8/β9 hairpin turn of a β-trefoil domain of a FGF-2 of SEQ ID NO: 35. In another aspect of this embodiment, a binding domain comprising a FGF-2 β-trefoil domain comprises amino acids 68-70 or amino acids 112-114 of SEQ ID NO: 36.

In other aspects of this embodiment, a binding domain comprising a FGF-2 β-trefoil domain comprises a polypeptide having, e.g., at least 70% amino acid identity with amino acids 68-70 or amino acids 112-114 of SEQ ID NO: 36, at least 75% amino acid identity with amino acids 68-70 or amino acids 112-114 of SEQ ID NO: 36, at least 80% amino acid identity with amino acids 68-70 or amino acids 112-114 of SEQ ID NO: 36, at least 85% amino acid identity with amino acids 68-70 or amino acids 112-114 of SEQ ID NO: 36, at least 90% amino acid identity with amino acids 68-70 or amino acids 112-114 of SEQ ID NO: 36 or at least 95% amino acid identity with amino acids 68-70 or amino acids 112-114 of SEQ ID NO: 36. In yet other aspects of this embodiment, a binding domain comprising a FGF-2 β-trefoil domain comprises a polypeptide having, e.g., at most 70% amino acid identity with amino acids 68-70 or amino acids 112-114 of SEQ ID NO: 36, at most 75% amino acid identity with amino acids 68-70 or amino acids 112-114 of SEQ ID NO: 36, at most 80% amino acid identity with amino acids 68-70 or amino acids 112-114 of SEQ ID NO: 36, at most 85% amino acid identity with amino acids 68-70 or amino acids 112-114 of SEQ ID NO: 36, at most 90% amino acid identity with amino acids 68-70 or amino acids 112-114 of SEQ ID NO: 36 or at most 95% amino acid identity with amino acids 68-70 or amino acids 112-114 of SEQ ID NO: 36.

In other aspects of this embodiment, a binding domain comprising a FGF-2 β-trefoil domain comprises a polypeptide having, e.g., at most one, two, three or four non-contiguous amino acid substitutions relative to amino acids 68-70 or amino acids 112-114 of SEQ ID NO: 36. In other aspects of this embodiment, a binding domain comprising a FGF-2 β-trefoil domain comprises a polypeptide having, e.g., at least one, two, three or four non-contiguous amino acid substitutions relative to amino acids 68-70 or amino acids 112-114 of SEQ ID NO: 36. In other aspects of this embodiment, a non-contiguous amino acid substitution of any amino acid from amino acids 68-70 or amino acids 112-114 of SEQ ID NO: 36 can be replaced with glycine. In other aspects of this embodiment, a non-contiguous amino acid substitution of any hydrophobic amino acid from amino acids 68-70 or amino acids 112-114 of SEQ ID NO: 36 can be replaced with phenylalanine. In yet other aspects of this embodiment, a binding domain comprising a FGF-2 β-trefoil domain comprises a polypeptide having, e.g., at most one, two, three or four non-contiguous amino acid deletions relative to amino acids 68-70 or amino acids 112-114 of SEQ ID NO: 36. In other aspects of this embodiment, a binding domain comprising a FGF-2 β-trefoil domain comprises a polypeptide having, e.g., at least one, two, three or four non-contiguous amino acid deletions relative to amino acids 68-70 or amino acids 112-114 of SEQ ID NO: 36. In still other aspects of this embodiment, a binding domain comprising a FGF-2 β-trefoil domain comprises a polypeptide having, e.g., at most one, two, three or four non-contiguous amino acid additions relative to amino acids 68-70 or amino acids 112-114 of SEQ ID NO: 36. In other aspects of this embodiment, a binding domain comprising a FGF-2 β-trefoil domain comprises a polypeptide having, e.g., at least one, two, three or four non-contiguous amino acid additions relative to amino acids 68-70 or amino acids 112-114 of SEQ ID NO: 36.

In other aspects of this embodiment, a binding domain comprising a FGF-2 β-trefoil domain comprises a polypeptide having, e.g., at most one, two, three or four contiguous amino acid substitutions relative to amino acids 68-70 or amino acids 112-114 of SEQ ID NO: 36. In other aspects of this embodiment, a binding domain comprising a FGF-2 β-trefoil domain comprises a polypeptide having, e.g., at least one, two, three or four contiguous amino acid substitutions relative to amino acids 68-70 or amino acids 112-114 of SEQ ID NO: 36. In other aspects of this embodiment, contiguous amino acid substitutions of amino acids from amino acids 68-70 or amino acids 112-114 of SEQ ID NO: 36 can be replaced with glycine. In other aspects of this embodiment, contiguous amino acid substitutions of hydrophobic amino acids from amino acids 68-70 or amino acids 112-114 of SEQ ID NO: 36 can be replaced with phenylalanine. In yet other aspects of this embodiment, a binding domain comprising a FGF-2 β-trefoil domain comprises a polypeptide having, e.g., at most one, two, three or four contiguous amino acid deletions relative to amino acids 68-70 or amino acids 112-114 of SEQ ID NO: 36. In other aspects of this embodiment, a binding domain comprising a FGF-2 β-trefoil domain comprises a polypeptide having, e.g., at least one, two, three or four contiguous amino acid deletions relative to amino acids 68-70 or amino acids 112-114 of SEQ ID NO: 36. In still other aspects of this embodiment, a binding domain comprising a FGF-2 β-trefoil domain comprises a polypeptide having, e.g., at most one, two, three or four contiguous amino acid additions relative to amino acids 68-70 or amino acids 112-114 of SEQ ID NO: 36. In other aspects of this embodiment, a binding domain comprising a FGF-2 β-trefoil domain comprises a polypeptide having, e.g., at least one, two, three or four contiguous amino acid additions relative to amino acids 68-70 or amino acids 112-114 of SEQ ID NO: 36.

In another embodiment, a binding domain comprises a β-trefoil domain derived a FGF-4 of SEQ ID NO: 37. In another embodiment, a binding domain comprising a β-trefoil domain derived from a FGF-4 comprises amino acids 83-206 of SEQ ID NO: 37. In another aspect of this embodiment, a binding domain comprising a β-trefoil domain derived from a FGF-4 comprises an α-fold motif of a β-trefoil domain of a FGF-4, a β-fold motif of a β-trefoil domain of a FGF-4 or a γ-fold motif of a β-trefoil domain of a FGF-4 of SEQ ID NO: 37. In another aspect of this embodiment, a β-trefoil domain derived from a FGF-4 comprises amino acids 83-121, amino acids 125-162, or amino acids 166-206 of SEQ ID NO: 37.

In other aspects of this embodiment, a binding domain comprising a FGF-4 β-trefoil domain comprises a polypeptide having, e.g., at least 70% amino acid identity with amino acids 83-121, amino acids 125-162, or amino acids 166-206 of SEQ ID NO: 37, at least 75% amino acid identity with amino acids 83-121, amino acids 125-162, or amino acids 166-206 of SEQ ID NO: 37, at least 80% amino acid identity with amino acids 83-121, amino acids 125-162, or amino acids 166-206 of SEQ ID NO: 37, at least 85% amino acid identity with amino acids 83-121, amino acids 125-162, or amino acids 166-206 of SEQ ID NO: 37, at least 90% amino acid identity with amino acids 83-121, amino acids 125-162, or amino acids 166-206 of SEQ ID NO: 37 or at least 95% amino acid identity with amino acids 83-121, amino acids 125-162, or amino acids 166-206 of SEQ ID NO: 37. In yet other aspects of this embodiment, a binding domain comprising a FGF-4 β-trefoil domain comprises a polypeptide having, e.g., at most 70% amino acid identity with amino acids 83-121, amino acids 125-162, or amino acids 166-206 of SEQ ID NO: 37, at most 75% amino acid identity with amino acids 83-121, amino acids 125-162, or amino acids 166-206 of SEQ ID NO: 37, at most 80% amino acid identity with amino acids 83-121, amino acids 125-162, or amino acids 166-206 of SEQ ID NO: 37, at most 85% amino acid identity with amino acids 83-121, amino acids 125-162, or amino acids 166-206 of SEQ ID NO: 37, at most 90% amino acid identity with amino acids 83-121, amino acids 125-162, or amino acids 166-206 of SEQ ID NO: 37 or at most 95% amino acid identity with amino acids 83-121, amino acids 125-162, or amino acids 166-206 of SEQ ID NO: 37.

In other aspects of this embodiment, a binding domain comprising a FGF-4 β-trefoil domain comprises a polypeptide having, e.g., at most one, two, three, four, five, six, seven, eight, nine, 10 or 20 non-contiguous amino acid substitutions relative to amino acids 83-121, amino acids 125-162, or amino acids 166-206 of SEQ ID NO: 37. In other aspects of this embodiment, a binding domain comprising a FGF-4 β-trefoil domain comprises a polypeptide having, e.g., at least one, two, three, four, five, six, seven, eight, nine, 10 or 20 non-contiguous amino acid substitutions relative to amino acids 83-121, amino acids 125-162, or amino acids 166-206 of SEQ ID NO: 37. In yet other aspects of this embodiment, a binding domain comprising a FGF-4 β-trefoil domain comprises a polypeptide having, e.g., at most one, two, three, four, five, six, seven, eight, nine, 10 or 20 non-contiguous amino acid deletions relative to amino acids 83-121, amino acids 125-162, or amino acids 166-206 of SEQ ID NO: 37. In other aspects of this embodiment, a binding domain comprising a FGF-4 β-trefoil domain comprises a polypeptide having, e.g., at least one, two, three, four, five, six, seven, eight, nine, 10 or 20 non-contiguous amino acid deletions relative to amino acids 83-121, amino acids 125-162, or amino acids 166-206 of SEQ ID NO: 37. In still other aspects of this embodiment, a binding domain comprising a FGF-4 β-trefoil domain comprises a polypeptide having, e.g., at most one, two, three, four, five, six, seven, eight, nine, 10 or 20 non-contiguous amino acid additions relative to amino acids 83-121, amino acids 125-162, or amino acids 166-206 of SEQ ID NO: 37. In other aspects of this embodiment, a binding domain comprising a FGF-4 β-trefoil domain comprises a polypeptide having, e.g., at least one, two, three, four, five, six, seven, eight, nine, 10 or 20 non-contiguous amino acid additions relative to amino acids 83-121, amino acids 125-162, or amino acids 166-206 of SEQ ID NO: 37.

In other aspects of this embodiment, a binding domain comprising a FGF-4 β-trefoil domain comprises a polypeptide having, e.g., at most one, two, three, four, five, six, seven, eight, nine, 10 or 20 contiguous amino acid substitutions relative to amino acids 83-121, amino acids 125-162, or amino acids 166-206 of SEQ ID NO: 37. In other aspects of this embodiment, a binding domain comprising a FGF-4 β-trefoil domain comprises a polypeptide having, e.g., at least one, two, three, four, five, six, seven, eight, nine, 10 or 20 contiguous amino acid substitutions relative to amino acids 83-121, amino acids 125-162, or amino acids 166-206 of SEQ ID NO: 37. In yet other aspects of this embodiment, a binding domain comprising a FGF-4 β-trefoil domain comprises a polypeptide having, e.g., at most one, two, three, four, five, six, seven, eight, nine, 10 or 20 contiguous amino acid deletions relative to amino acids 83-121, amino acids 125-162, or amino acids 166-206 of SEQ ID NO: 37. In other aspects of this embodiment, a binding domain comprising a FGF-4 β-trefoil domain comprises a polypeptide having, e.g., at least one, two, three, four, five, six, seven, eight, nine, 10 or 20 contiguous amino acid deletions relative to amino acids 83-121, amino acids 125-162, or amino acids 166-206 of SEQ ID NO: 37. In still other aspects of this embodiment, a binding domain comprising a FGF-4 β-trefoil domain comprises a polypeptide having, e.g., at most one, two, three, four, five, six, seven, eight, nine, 10 or 20 contiguous amino acid additions relative to amino acids 83-121, amino acids 125-162, or amino acids 166-206 of SEQ ID NO: 37. In other aspects of this embodiment, a binding domain comprising a FGF-4 β-trefoil domain comprises a polypeptide having, e.g., at least one, two, three, four, five, six, seven, eight, nine, 10 or 20 contiguous amino acid additions relative to amino acids 83-121, amino acids 125-162, or amino acids 166-206 of SEQ ID NO: 37.

In another embodiment, a binding domain comprising a FGF-4 β-trefoil domain comprises a β4/β5 hairpin turn of a β-trefoil domain of a FGF-4 or a β8/β9 hairpin turn of a β-trefoil domain of a FGF-4 of SEQ ID NO: 35. In another aspect of this embodiment, a binding domain comprising a FGF-4 β-trefoil domain comprises amino acids 122-124 or amino acids 163-165 of SEQ ID NO: 37.

In other aspects of this embodiment, a binding domain comprising a FGF-4 β-trefoil domain comprises a polypeptide having, e.g., at least 70% amino acid identity with amino acids 122-124 or amino acids 163-165 of SEQ ID NO: 37, at least 75% amino acid identity with amino acids 122-124 or amino acids 163-165 of SEQ ID NO: 37, at least 80% amino acid identity with amino acids 122-124 or amino acids 163-165 of SEQ ID NO: 37, at least 85% amino acid identity with amino acids 122-124 or amino acids 163-165 of SEQ ID NO:

37, at least 90% amino acid identity with amino acids 122-124 or amino acids 163-165 of SEQ ID NO: 37 or at least 95% amino acid identity with amino acids 122-124 or amino acids 163-165 of SEQ ID NO: 37. In yet other aspects of this embodiment, a binding domain comprising a FGF-4 β-trefoil domain comprises a polypeptide having, e.g., at most 70% amino acid identity with amino acids 122-124 or amino acids 163-165 of SEQ ID NO: 37, at most 75% amino acid identity with amino acids 122-124 or amino acids 163-165 of SEQ ID NO: 37, at most 80% amino acid identity with amino acids 122-124 or amino acids 163-165 of SEQ ID NO: 37, at most 85% amino acid identity with amino acids 122-124 or amino acids 163-165 of SEQ ID NO: 37, at most 90% amino acid identity with amino acids 122-124 or amino acids 163-165 of SEQ ID NO: 37 or at most 95% amino acid identity with amino acids 122-124 or amino acids 163-165 of SEQ ID NO: 37.

In other aspects of this embodiment, a binding domain comprising a FGF-4 β-trefoil domain comprises a polypeptide having, e.g., at most one, two, three or four non-contiguous amino acid substitutions relative to amino acids 122-124 or amino acids 163-165 of SEQ ID NO: 37. In other aspects of this embodiment, a binding domain comprising a FGF-4 β-trefoil domain comprises a polypeptide having, e.g., at least one, two, three or four non-contiguous amino acid substitutions relative to amino acids 122-124 or amino acids 163-165 of SEQ ID NO: 37. In other aspects of this embodiment, a non-contiguous amino acid substitution of any amino acid from amino acids 122-124 or amino acids 163-165 of SEQ ID NO: 37 can be replaced with glycine. In other aspects of this embodiment, a non-contiguous amino acid substitution of any hydrophobic amino acid from amino acids 122-124 or amino acids 163-165 of SEQ ID NO: 37 can be replaced with phenylalanine. In yet other aspects of this embodiment, a binding domain comprising a FGF-4 β-trefoil domain comprises a polypeptide having, e.g., at most one, two, three or four non-contiguous amino acid deletions relative to amino acids 122-124 or amino acids 163-165 of SEQ ID NO: 37. In other aspects of this embodiment, a binding domain comprising a FGF-4 β-trefoil domain comprises a polypeptide having, e.g., at least one, two, three or four non-contiguous amino acid deletions relative to amino acids 122-124 or amino acids 163-165 of SEQ ID NO: 37. In still other aspects of this embodiment, a binding domain comprising a FGF-4 β-trefoil domain comprises a polypeptide having, e.g., at most one, two, three or four non-contiguous amino acid additions relative to amino acids 122-124 or amino acids 163-165 of SEQ ID NO: 37. In other aspects of this embodiment, a binding domain comprising a FGF-4 β-trefoil domain comprises a polypeptide having, e.g., at least one, two, three or four non-contiguous amino acid additions relative to amino acids 122-124 or amino acids 163-165 of SEQ ID NO: 37.

In other aspects of this embodiment, a binding domain comprising a FGF-4 β-trefoil domain comprises a polypeptide having, e.g., at most one, two, three or four contiguous amino acid substitutions relative to amino acids 122-124 or amino acids 163-165 of SEQ ID NO: 37. In other aspects of this embodiment, a binding domain comprising a FGF-4 β-trefoil domain comprises a polypeptide having, e.g., at least one, two, three or four contiguous amino acid substitutions relative to amino acids 122-124 or amino acids 163-165 of SEQ ID NO: 37. In other aspects of this embodiment, contiguous amino acid substitutions of amino acids from amino acids 122-124 or amino acids 163-165 of SEQ ID NO: 37 can be replaced with glycine. In other aspects of this embodiment, contiguous amino acid substitutions of hydrophobic amino acids from amino acids 122-124 or amino acids 163-165 of SEQ ID NO: 37 can be replaced with phenylalanine. In yet other aspects of this embodiment, a binding domain comprising a FGF-4 β-trefoil domain comprises a polypeptide having, e.g., at most one, two, three or four contiguous amino acid deletions relative to amino acids 122-124 or amino acids 163-165 of SEQ ID NO: 37. In other aspects of this embodiment, a binding domain comprising a FGF-4 β-trefoil domain comprises a polypeptide having, e.g., at least one, two, three or four contiguous amino acid deletions relative to amino acids 122-124 or amino acids 163-165 of SEQ ID NO: 37. In still other aspects of this embodiment, a binding domain comprising a FGF-4 β-trefoil domain comprises a polypeptide having, e.g., at most one, two, three or four contiguous amino acid additions relative to amino acids 122-124 or amino acids 163-165 of SEQ ID NO: 37. In other aspects of this embodiment, a binding domain comprising a FGF-4 β-trefoil domain comprises a polypeptide having, e.g., at least one, two, three or four contiguous amino acid additions relative to amino acids 122-124 or amino acids 163-165 of SEQ ID NO: 37.

In another embodiment, a binding domain comprises a β-trefoil domain derived a FGF-8 of SEQ ID NO: 38. In another embodiment, a binding domain comprising a β-trefoil domain derived from a FGF-8 comprises amino acids 43-172 of SEQ ID NO: 38. In another aspect of this embodiment, a binding domain comprising a β-trefoil domain derived from a FGF-8 comprises an α-fold motif of a β-trefoil domain of a FGF-8, a β-fold motif of a β-trefoil domain of a FGF-8 or a γ-fold motif of a β-trefoil domain of a FGF-8 of SEQ ID NO: 38. In another aspect of this embodiment, a β-trefoil domain derived from a FGF-8 comprises amino acids 43-80, amino acids 84-123, or amino acids 127-172 of SEQ ID NO: 38.

In other aspects of this embodiment, a binding domain comprising a FGF-8 β-trefoil domain comprises a polypeptide having, e.g., at least 70% amino acid identity with amino acids 43-80, amino acids 84-123, or amino acids 127-172 of SEQ ID NO: 38, at least 75% amino acid identity with amino acids 43-80, amino acids 84-123, or amino acids 127-172 of SEQ ID NO: 38, at least 80% amino acid identity with amino acids 43-80, amino acids 84-123, or amino acids 127-172 of SEQ ID NO: 38, at least 85% amino acid identity with amino acids 43-80, amino acids 84-123, or amino acids 127-172 of SEQ ID NO: 38, at least 90% amino acid identity with amino acids 43-80, amino acids 84-123, or amino acids 127-172 of SEQ ID NO: 38 or at least 95% amino acid identity with amino acids 43-80, amino acids 84-123, or amino acids 127-172 of SEQ ID NO: 38. In yet other aspects of this embodiment, a binding domain comprising a FGF-8 β-trefoil domain comprises a polypeptide having, e.g., at most 70% amino acid identity with amino acids 43-80, amino acids 84-123, or amino acids 127-172 of SEQ ID NO: 38, at most 75% amino acid identity with amino acids 43-80, amino acids 84-123, or amino acids 127-172 of SEQ ID NO: 38, at most 80% amino acid identity with amino acids 43-80, amino acids 84-123, or amino acids 127-172 of SEQ ID NO: 38, at most 85% amino acid identity with amino acids 43-80, amino acids 84-123, or amino acids 127-172 of SEQ ID NO: 38, at most 90% amino acid identity with amino acids 43-80, amino acids 84-123, or amino acids 127-172 of SEQ ID NO: 38 or at most 95% amino acid identity with amino acids 43-80, amino acids 84-123, or amino acids 127-172 of SEQ ID NO: 38.

In other aspects of this embodiment, a binding domain comprising a FGF-8 β-trefoil domain comprises a polypeptide having, e.g., at most one, two, three, four, five, six, seven, eight, nine, 10 or 20 non-contiguous amino acid substitutions relative to amino acids 43-80, amino acids 84-123, or amino acids 127-172 of SEQ ID NO: 38. In other aspects of this embodiment, a binding domain comprising a FGF-8 β-trefoil domain comprises a polypeptide having, e.g., at least one, two, three, four, five, six, seven, eight, nine, 10 or 20 non-contiguous amino acid substitutions relative to amino acids 43-80, amino acids 84-123, or amino acids 127-172 of SEQ ID NO: 38. In yet other aspects of this embodiment, a binding domain comprising a FGF-8 β-trefoil domain comprises a polypeptide having, e.g., at most one, two, three, four, five, six, seven, eight, nine, 10 or 20 non-contiguous amino acid deletions relative to amino acids 43-80, amino acids 84-123, or amino acids 127-172 of SEQ ID NO: 38. In other aspects of this embodiment, a binding domain comprising a FGF-8 β-trefoil domain comprises a polypeptide having, e.g., at least one, two, three, four, five, six, seven, eight, nine, 10 or 20 non-contiguous amino acid deletions relative to amino acids 43-80, amino acids 84-123, or amino acids 127-172 of SEQ ID NO: 38. In still other aspects of this embodiment, a binding domain comprising a FGF-8 β-trefoil domain comprises a polypeptide having, e.g., at most one, two, three, four, five, six, seven, eight, nine, 10 or 20 non-contiguous amino acid additions relative to amino acids 43-80, amino acids 84-123, or amino acids 127-172 of SEQ ID NO: 38. In other aspects of this embodiment, a binding domain comprising a FGF-8 β-trefoil domain comprises a polypeptide having, e.g., at least one, two, three, four, five, six, seven, eight, nine, 10 or 20 non-contiguous amino acid additions relative to amino acids 43-80, amino acids 84-123, or amino acids 127-172 of SEQ ID NO: 38.

In other aspects of this embodiment, a binding domain comprising a FGF-8 β-trefoil domain comprises a polypeptide having, e.g., at most one, two, three, four, five, six, seven, eight, nine, 10 or 20 contiguous amino acid substitutions relative to amino acids 43-80, amino acids 84-123, or amino acids 127-172 of SEQ ID NO: 38. In other aspects of this embodiment, a binding domain comprising a FGF-8 β-trefoil domain comprises a polypeptide having, e.g., at least one, two, three, four, five, six, seven, eight, nine, 10 or 20 contiguous amino acid substitutions relative to amino acids 43-80, amino acids 84-123, or amino acids 127-172 of SEQ ID NO: 38. In yet other aspects of this embodiment, a binding domain comprising a FGF-8 β-trefoil domain comprises a polypeptide having, e.g., at most one, two, three, four, five, six, seven, eight, nine, 10 or 20 contiguous amino acid deletions relative to amino acids 43-80, amino acids 84-123, or amino acids 127-172 of SEQ ID NO: 38. In other aspects of this embodiment, a binding domain comprising a FGF-8 β-trefoil domain comprises a polypeptide having, e.g., at least one, two, three, four, five, six, seven, eight, nine, 10 or 20 contiguous amino acid deletions relative to amino acids 43-80, amino acids 84-123, or amino acids 127-172 of SEQ ID NO: 38. In still other aspects of this embodiment, a binding domain comprising a FGF-8 β-trefoil domain comprises a polypeptide having, e.g., at most one, two, three, four, five, six, seven, eight, nine, 10 or 20 contiguous amino acid additions relative to amino acids 43-80, amino acids 84-123, or amino acids 127-172 of SEQ ID NO: 38. In other aspects of this embodiment, a binding domain comprising a FGF-8 β-trefoil domain comprises a polypeptide having, e.g., at least one, two, three, four, five, six, seven, eight, nine, 10 or 20 contiguous amino acid additions relative to amino acids 43-80, amino acids 84-123, or amino acids 127-172 of SEQ ID NO: 38.

In another embodiment, a binding domain comprising a FGF-8 β-trefoil domain comprises a β4/β5 hairpin turn of a β-trefoil domain of a FGF-8 or a β8/β9 hairpin turn of a β-trefoil domain of a FGF-8 of SEQ ID NO: 35. In another aspect of this embodiment, a binding domain comprising a FGF-8 β-trefoil domain comprises amino acids 81-83 or amino acids 124-126 of SEQ ID NO: 38.

In other aspects of this embodiment, a binding domain comprising a FGF-8 β-trefoil domain comprises a polypeptide having, e.g., at least 70% amino acid identity with amino acids 81-83 or amino acids 124-126 of SEQ ID NO: 38, at least 75% amino acid identity with amino acids 81-83 or amino acids 124-126 of SEQ ID NO: 38, at least 80% amino acid identity with amino acids 81-83 or amino acids 124-126 of SEQ ID NO: 38, at least 85% amino acid identity with amino acids 81-83 or amino acids 124-126 of SEQ ID NO: 38, at least 90% amino acid identity with amino acids 81-83 or amino acids 124-126 of SEQ ID NO: 38 or at least 95% amino acid identity with amino acids 81-83 or amino acids 124-126 of SEQ ID NO: 38. In yet other aspects of this embodiment, a binding domain comprising a FGF-8 β-trefoil domain comprises a polypeptide having, e.g., at most 70% amino acid identity with amino acids 81-83 or amino acids 124-126 of SEQ ID NO: 38, at most 75% amino acid identity with amino acids 81-83 or amino acids 124-126 of SEQ ID NO: 38, at most 80% amino acid identity with amino acids 81-83 or amino acids 124-126 of SEQ ID NO: 38, at most 85% amino acid identity with amino acids 81-83 or amino acids 124-126 of SEQ ID NO: 38, at most 90% amino acid identity with amino acids 81-83 or amino acids 124-126 of SEQ ID NO: 38 or at most 95% amino acid identity with amino acids 81-83 or amino acids 124-126 of SEQ ID NO: 38.

In other aspects of this embodiment, a binding domain comprising a FGF-8 β-trefoil domain comprises a polypeptide having, e.g., at most one, two, three or four non-contiguous amino acid substitutions relative to amino acids 81-83 or amino acids 124-126 of SEQ ID NO: 38. In other aspects of this embodiment, a binding domain comprising a FGF-8 β-trefoil domain comprises a polypeptide having, e.g., at least one, two, three or four non-contiguous amino acid substitutions relative to amino acids 81-83 or amino acids 124-126 of SEQ ID NO: 38. In other aspects of this embodiment, a non-contiguous amino acid substitution of any amino acid from amino acids 81-83 or amino acids 124-126 of SEQ ID NO: 38 can be replaced with glycine. In other aspects of this embodiment, a non-contiguous amino acid substitution of any hydrophobic amino acid from amino acids 81-83 or amino acids 124-126 of SEQ ID NO: 38 can be replaced with phenylalanine. In yet other aspects of this embodiment, a binding domain comprising a FGF-8 β-trefoil domain comprises a polypeptide having, e.g., at most one, two, three or four non-contiguous amino acid deletions relative to amino acids 81-83 or amino acids 124-126 of SEQ ID NO: 38. In other aspects of this embodiment, a binding domain comprising a FGF-8 β-trefoil domain comprises a polypeptide having, e.g., at least one, two, three or four non-contiguous amino acid deletions relative to amino acids 81-83 or amino acids 124-126 of SEQ ID NO: 38. In still other aspects of this embodiment, a binding domain comprising a FGF-8 β-trefoil domain comprises a polypeptide having, e.g., at most one, two, three or four non-contiguous amino acid additions relative to amino acids 81-83 or amino acids 124-126 of SEQ ID NO: 38. In other aspects of this embodiment, a binding domain comprising a FGF-8 β-trefoil domain comprises a polypeptide having, e.g., at least one, two, three or four non-contiguous amino acid additions relative to amino acids 81-83 or amino acids 124-126 of SEQ ID NO: 38.

In other aspects of this embodiment, a binding domain comprising a FGF-8 β-trefoil domain comprises a polypeptide having, e.g., at most one, two, three or four contiguous amino acid substitutions relative to amino acids 81-83 or amino acids 124-126 of SEQ ID NO: 38. In other aspects of this embodiment, a binding domain comprising a FGF-8 β-trefoil domain comprises a polypeptide having, e.g., at least one, two, three or four contiguous amino acid substitutions relative to amino acids 81-83 or amino acids 124-126 of SEQ ID NO: 38. In other aspects of this embodiment, contiguous amino acid substitutions of amino acids from amino acids 81-83 or amino acids 124-126 of SEQ ID NO: 38 can be replaced with glycine. In other aspects of this embodiment, contiguous amino acid substitutions of hydrophobic amino acids from amino acids 81-83 or amino acids 124-126 of SEQ ID NO: 38 can be replaced with phenylalanine. In yet other aspects of this embodiment, a binding domain comprising a FGF-8 β-trefoil domain comprises a polypeptide having, e.g., at most one, two, three or four contiguous amino acid deletions relative to amino acids 81-83 or amino acids 124-126 of SEQ ID NO: 38. In other aspects of this embodiment, a binding domain comprising a FGF-8 β-trefoil domain comprises a polypeptide having, e.g., at least one, two, three or four contiguous amino acid deletions relative to amino acids 81-83 or amino acids 124-126 of SEQ ID NO: 38. In still other aspects of this embodiment, a binding domain comprising a FGF-8 β-trefoil domain comprises a polypeptide having, e.g., at most one, two, three or four contiguous amino acid additions relative to amino acids 81-83 or amino acids 124-126 of SEQ ID NO: 38. In other aspects of this embodiment, a binding domain comprising a FGF-8 β-trefoil domain comprises a polypeptide having, e.g., at least one, two, three or four contiguous amino acid additions relative to amino acids 81-83 or amino acids 124-126 of SEQ ID NO: 38.

In another embodiment, a binding domain comprises a β-trefoil domain derived a FGF-9 of SEQ ID NO: 39. In another embodiment, a binding domain comprising a β-trefoil domain derived from a FGF-9 comprises amino acids 63-196 of SEQ ID NO: 39. In another aspect of this embodiment, a binding domain comprising a β-trefoil domain derived from a FGF-9 comprises an α-fold motif of a β-trefoil domain of a FGF-9, a β-fold motif of a β-trefoil domain of a FGF-9 or a γ-fold motif of a β-trefoil domain of a FGF-9 of SEQ ID NO: 39. In another aspect of this embodiment, a β-trefoil domain derived from a FGF-9 comprises amino acids 63-100, amino acids 104-144, or amino acids 148-196 of SEQ ID NO: 39.

In other aspects of this embodiment, a binding domain comprising a FGF-9 β-trefoil domain comprises a polypeptide having, e.g., at least 70% amino acid identity with amino acids 63-100, amino acids 104-144, or amino acids 148-196 of SEQ ID NO: 39, at least 75% amino acid identity with amino acids 63-100, amino acids 104-144, or amino acids 148-196 of SEQ ID NO: 39, at least 80% amino acid identity with amino acids 63-100, amino acids 104-144, or amino acids 148-196 of SEQ ID NO: 39, at least 85% amino acid identity with amino acids 63-100, amino acids 104-144, or amino acids 148-196 of SEQ ID NO: 39, at least 90% amino acid identity with amino acids 63-100, amino acids 104-144, or amino acids 148-196 of SEQ ID NO: 39 or at least 95% amino acid identity with amino acids 63-100, amino acids 104-144, or amino acids 148-196 of SEQ ID NO: 39. In yet other aspects of this embodiment, a binding domain comprising a FGF-9 β-trefoil domain comprises a polypeptide having, e.g., at most 70% amino acid identity with amino acids 63-100, amino acids 104-144, or amino acids 148-196 of SEQ ID NO: 39, at most 75% amino acid identity with amino acids 63-100, amino acids 104-144, or amino acids 148-196 of SEQ ID NO: 39, at most 80% amino acid identity with amino acids 63-100, amino acids 104-144, or amino acids 148-196 of SEQ ID NO: 39, at most 85% amino acid identity with amino acids 63-100, amino acids 104-144, or amino acids 148-196 of SEQ ID NO: 39, at most 90% amino acid identity with amino acids 63-100, amino acids 104-144, or amino acids 148-196 of SEQ ID NO: 39 or at most 95% amino acid identity with amino acids 63-100, amino acids 104-144, or amino acids 148-196 of SEQ ID NO: 39.

In other aspects of this embodiment, a binding domain comprising a FGF-9 β-trefoil domain comprises a polypeptide having, e.g., at most one, two, three, four, five, six, seven, eight, nine, 10 or 20 non-contiguous amino acid substitutions relative to amino acids 63-100, amino acids 104-144, or amino acids 148-196 of SEQ ID NO: 39. In other aspects of this embodiment, a binding domain comprising a FGF-9 β-trefoil domain comprises a polypeptide having, e.g., at least one, two, three, four, five, six, seven, eight, nine, 10 or 20 non-contiguous amino acid substitutions relative to amino acids 63-100, amino acids 104-144, or amino acids 148-196 of SEQ ID NO: 39. In yet other aspects of this embodiment, a binding domain comprising a FGF-9 β-trefoil domain comprises a polypeptide having, e.g., at most one, two, three, four, five, six, seven, eight, nine, 10 or 20 non-contiguous amino acid deletions relative to amino acids 63-100, amino acids 104-144, or amino acids 148-196 of SEQ ID NO: 39. In other aspects of this embodiment, a binding domain comprising a FGF-9 β-trefoil domain comprises a polypeptide having, e.g., at least one, two, three, four, five, six, seven, eight, nine, 10 or 20 non-contiguous amino acid deletions relative to amino acids 63-100, amino acids 104-144, or amino acids 148-196 of SEQ ID NO: 39. In still other aspects of this embodiment, a binding domain comprising a FGF-9 β-trefoil domain comprises a polypeptide having, e.g., at most one, two, three, four, five, six, seven, eight, nine, 10 or 20 non-contiguous amino acid additions relative to amino acids 63-100, amino acids 104-144, or amino acids 148-196 of SEQ ID NO: 39. In other aspects of this embodiment, a binding domain comprising a FGF-9 β-trefoil domain comprises a polypeptide having, e.g., at least one, two, three, four, five, six, seven, eight, nine, 10 or 20 non-contiguous amino acid additions relative to amino acids 63-100, amino acids 104-144, or amino acids 148-196 of SEQ ID NO: 39.

In other aspects of this embodiment, a binding domain comprising a FGF-9 β-trefoil domain comprises a polypeptide having, e.g., at most one, two, three, four, five, six, seven, eight, nine, 10 or 20 contiguous amino acid substitutions relative to amino acids 63-100, amino acids 104-144, or amino acids 148-196 of SEQ ID NO: 39. In other aspects of this embodiment, a binding domain comprising a FGF-9 β-trefoil domain comprises a polypeptide having, e.g., at least one, two, three, four, five, six, seven, eight, nine, 10 or 20 contiguous amino acid substitutions relative to amino acids 63-100, amino acids 104-144, or amino acids 148-196 of SEQ ID NO: 39. In yet other aspects of this embodiment, a binding domain comprising a FGF-9 β-trefoil domain comprises a polypeptide having, e.g., at most one, two, three, four, five, six, seven, eight, nine, 10 or 20 contiguous amino acid deletions relative to amino acids 63-100, amino acids 104-144, or amino acids 148-196 of SEQ ID NO: 39. In other aspects of this embodiment, a binding domain comprising a FGF-9 β-trefoil domain comprises a polypeptide having, e.g., at least one, two, three, four, five, six, seven, eight, nine, 10 or 20 contiguous amino acid deletions relative to amino acids 63-100, amino acids 104-144, or amino acids 148-196 of SEQ ID NO: 39. In still other aspects of this embodiment, a binding domain comprising a FGF-9 β-trefoil domain comprises a polypeptide having, e.g., at most one, two, three, four, five, six, seven, eight, nine, 10 or 20 contiguous amino acid additions relative to amino acids 63-100, amino acids 104-

144, or amino acids 148-196 of SEQ ID NO: 39. In other aspects of this embodiment, a binding domain comprising a FGF-9 β-trefoil domain comprises a polypeptide having, e.g., at least one, two, three, four, five, six, seven, eight, nine, 10 or 20 contiguous amino acid additions relative to amino acids 63-100, amino acids 104-144, or amino acids 148-196 of SEQ ID NO: 39.

In another embodiment, a binding domain comprising a FGF-9 β-trefoil domain comprises a β4/β5 hairpin turn of a β-trefoil domain of a FGF-9 or a β8/β9 hairpin turn of a β-trefoil domain of a FGF-9 of SEQ ID NO: 35. In another aspect of this embodiment, a binding domain comprising a FGF-9 β-trefoil domain comprises amino acids 101-103 or amino acids 145-147 of SEQ ID NO: 39.

In other aspects of this embodiment, a binding domain comprising a FGF-9 β-trefoil domain comprises a polypeptide having, e.g., at least 70% amino acid identity with amino acids 101-103 or amino acids 145-147 of SEQ ID NO: 39, at least 75% amino acid identity with amino acids 101-103 or amino acids 145-147 of SEQ ID NO: 39, at least 80% amino acid identity with amino acids 101-103 or amino acids 145-147 of SEQ ID NO: 39, at least 85% amino acid identity with amino acids 101-103 or amino acids 145-147 of SEQ ID NO: 39, at least 90% amino acid identity with amino acids 101-103 or amino acids 145-147 of SEQ ID NO: 39 or at least 95% amino acid identity with amino acids 101-103 or amino acids 145-147 of SEQ ID NO: 39. In yet other aspects of this embodiment, a binding domain comprising a FGF-9 β-trefoil domain comprises a polypeptide having, e.g., at most 70% amino acid identity with amino acids 101-103 or amino acids 145-147 of SEQ ID NO: 39, at most 75% amino acid identity with amino acids 101-103 or amino acids 145-147 of SEQ ID NO: 39, at most 80% amino acid identity with amino acids 101-103 or amino acids 145-147 of SEQ ID NO: 39, at most 85% amino acid identity with amino acids 101-103 or amino acids 145-147 of SEQ ID NO: 39, at most 90% amino acid identity with amino acids 101-103 or amino acids 145-147 of SEQ ID NO: 39 or at most 95% amino acid identity with amino acids 101-103 or amino acids 145-147 of SEQ ID NO: 39.

In other aspects of this embodiment, a binding domain comprising a FGF-9 β-trefoil domain comprises a polypeptide having, e.g., at most one, two, three or four non-contiguous amino acid substitutions relative to amino acids 101-103 or amino acids 145-147 of SEQ ID NO: 39. In other aspects of this embodiment, a binding domain comprising a FGF-9 β-trefoil domain comprises a polypeptide having, e.g., at least one, two, three or four non-contiguous amino acid substitutions relative to amino acids 101-103 or amino acids 145-147 of SEQ ID NO: 39. In other aspects of this embodiment, a non-contiguous amino acid substitution of any amino acid from amino acids 101-103 or amino acids 145-147 of SEQ ID NO: 39 can be replaced with glycine. In other aspects of this embodiment, a non-contiguous amino acid substitution of any hydrophobic amino acid from amino acids 101-103 or amino acids 145-147 of SEQ ID NO: 39 can be replaced with phenylalanine. In yet other aspects of this embodiment, a binding domain comprising a FGF-9 β-trefoil domain comprises a polypeptide having, e.g., at most one, two, three or four non-contiguous amino acid deletions relative to amino acids 101-103 or amino acids 145-147 of SEQ ID NO: 39. In other aspects of this embodiment, a binding domain comprising a FGF-9 β-trefoil domain comprises a polypeptide having, e.g., at least one, two, three or four non-contiguous amino acid deletions relative to amino acids 101-103 or amino acids 145-147 of SEQ ID NO: 39. In still other aspects of this embodiment, a binding domain comprising a FGF-9 β-trefoil domain comprises a polypeptide having, e.g., at most one, two, three or four non-contiguous amino acid additions relative to amino acids 101-103 or amino acids 145-147 of SEQ ID NO: 39. In other aspects of this embodiment, a binding domain comprising a FGF-9 β-trefoil domain comprises a polypeptide having, e.g., at least one, two, three or four non-contiguous amino acid additions relative to amino acids 101-103 or amino acids 145-147 of SEQ ID NO: 39.

In other aspects of this embodiment, a binding domain comprising a FGF-9 β-trefoil domain comprises a polypeptide having, e.g., at most one, two, three or four contiguous amino acid substitutions relative to amino acids 101-103 or amino acids 145-147 of SEQ ID NO: 39. In other aspects of this embodiment, a binding domain comprising a FGF-9 β-trefoil domain comprises a polypeptide having, e.g., at least one, two, three or four contiguous amino acid substitutions relative to amino acids 101-103 or amino acids 145-147 of SEQ ID NO: 39. In other aspects of this embodiment, contiguous amino acid substitutions of amino acids from amino acids 101-103 or amino acids 145-147 of SEQ ID NO: 39 can be replaced with glycine. In other aspects of this embodiment, contiguous amino acid substitutions of hydrophobic amino acids from amino acids 101-103 or amino acids 145-147 of SEQ ID NO: 39 can be replaced with phenylalanine. In yet other aspects of this embodiment, a binding domain comprising a FGF-9 β-trefoil domain comprises a polypeptide having, e.g., at most one, two, three or four contiguous amino acid deletions relative to amino acids 101-103 or amino acids 145-147 of SEQ ID NO: 39. In other aspects of this embodiment, a binding domain comprising a FGF-9 β-trefoil domain comprises a polypeptide having, e.g., at least one, two, three or four contiguous amino acid deletions relative to amino acids 101-103 or amino acids 145-147 of SEQ ID NO: 39. In still other aspects of this embodiment, a binding domain comprising a FGF-9 β-trefoil domain comprises a polypeptide having, e.g., at most one, two, three or four contiguous amino acid additions relative to amino acids 101-103 or amino acids 145-147 of SEQ ID NO: 39. In other aspects of this embodiment, a binding domain comprising a FGF-9 β-trefoil domain comprises a polypeptide having, e.g., at least one, two, three or four contiguous amino acid additions relative to amino acids 101-103 or amino acids 145-147 of SEQ ID NO: 39.

In another embodiment, a binding domain comprises β-trefoil domain derived a FGF-17 of SEQ ID NO: 40. In another embodiment, a binding domain comprising a β-trefoil domain derived from a FGF-17 comprises amino acids 55-183 of SEQ ID NO: 40. In another aspect of this embodiment, a binding domain comprising a β-trefoil domain derived from a FGF-17 comprises an α-fold motif of a β-trefoil domain of a FGF-17, a β-fold motif of a β-trefoil domain of a FGF-17 or a γ-fold motif of a β-trefoil domain of a FGF-17 of SEQ ID NO: 40. In another aspect of this embodiment, a β-trefoil domain derived from a FGF-17 comprises amino acids 55-91, amino acids 95-134, or amino acids 138-183 of SEQ ID NO: 40.

In other aspects of this embodiment, a binding domain comprising a FGF-17 β-trefoil domain comprises a polypeptide having, e.g., at least 70% amino acid identity with amino acids 55-91, amino acids 95-134, or amino acids 138-183 of SEQ ID NO: 40, at least 75% amino acid identity with amino acids 55-91, amino acids 95-134, or amino acids 138-183 of SEQ ID NO: 40, at least 80% amino acid identity with amino acids 55-91, amino acids 95-134, or amino acids 138-183 of SEQ ID NO: 40, at least 85% amino acid identity with amino acids 55-91, amino acids 95-134, or amino acids 138-183 of SEQ ID NO: 40, at least 90% amino acid identity with amino acids 55-91, amino acids 95-134, or amino acids 138-183 of SEQ ID NO: 40 or at least 95% amino acid identity with amino acids 55-91, amino acids 95-134, or amino acids 138-183 of SEQ ID NO: 40. In yet other aspects of this embodiment, a binding domain comprising a FGF-17 β-trefoil domain comprises a polypeptide having, e.g., at most 70% amino acid identity with amino acids 55-91, amino acids 95-134, or amino acids 138-183 of SEQ ID NO: 40, at most 75% amino acid identity with amino acids 55-91, amino acids 95-134, or amino acids 138-183 of SEQ ID NO: 40, at most 80% amino acid identity with amino acids 55-91, amino acids 95-134, or amino acids 138-183 of SEQ ID NO: 40, at most 85% amino acid identity with amino acids 55-91, amino acids 95-134, or amino acids 138-183 of SEQ ID NO: 40, at most 90% amino acid identity with amino acids 55-91, amino acids 95-134, or amino acids 138-183 of SEQ ID NO: 40 or at most 95% amino acid identity with amino acids 55-91, amino acids 95-134, or amino acids 138-183 of SEQ ID NO: 40.

In other aspects of this embodiment, a binding domain comprising a FGF-17 β-trefoil domain comprises a polypeptide having, e.g., at most one, two, three, four, five, six, seven, eight, nine, 10 or 20 non-contiguous amino acid substitutions relative to amino acids 55-91, amino acids 95-134, or amino acids 138-183 of SEQ ID NO: 40. In other aspects of this embodiment, a binding domain comprising a FGF-17 β-trefoil domain comprises a polypeptide having, e.g., at least one, two, three, four, five, six, seven, eight, nine, 10 or 20 non-contiguous amino acid substitutions relative to amino acids 55-91, amino acids 95-134, or amino acids 138-183 of SEQ ID NO: 40. In yet other aspects of this embodiment, a binding domain comprising a FGF-17 β-trefoil domain comprises a polypeptide having, e.g., at most one, two, three, four, five, six, seven, eight, nine, 10 or 20 non-contiguous amino acid deletions relative to amino acids 55-91, amino acids 95-134, or amino acids 138-183 of SEQ ID NO: 40. In other aspects of this embodiment, a binding domain comprising a FGF-17 β-trefoil domain comprises a polypeptide having, e.g., at least one, two, three, four, five, six, seven, eight, nine, 10 or 20 non-contiguous amino acid deletions relative to amino acids 55-91, amino acids 95-134, or amino acids 138-183 of SEQ ID NO: 40. In still other aspects of this embodiment, a binding domain comprising a FGF-17 β-trefoil domain comprises a polypeptide having, e.g., at most one, two, three, four, five, six, seven, eight, nine, 10 or 20 non-contiguous amino acid additions relative to amino acids 55-91, amino acids 95-134, or amino acids 138-183 of SEQ ID NO: 40. In other aspects of this embodiment, a binding domain comprising a FGF-17 β-trefoil domain comprises a polypeptide having, e.g., at least one, two, three, four, five, six, seven, eight, nine, 10 or 20 non-contiguous amino acid additions relative to amino acids 55-91, amino acids 95-134, or amino acids 138-183 of SEQ ID NO: 40.

In other aspects of this embodiment, a binding domain comprising a FGF-17 β-trefoil domain comprises a polypeptide having, e.g., at most one, two, three, four, five, six, seven, eight, nine, 10 or 20 contiguous amino acid substitutions relative to amino acids 55-91, amino acids 95-134, or amino acids 138-183 of SEQ ID NO: 40. In other aspects of this embodiment, a binding domain comprising a FGF-17 β-trefoil domain comprises a polypeptide having, e.g., at least one, two, three, four, five, six, seven, eight, nine, 10 or 20 contiguous amino acid substitutions relative to amino acids 55-91, amino acids 95-134, or amino acids 138-183 of SEQ ID NO: 40. In yet other aspects of this embodiment, a binding domain comprising a FGF-17 β-trefoil domain comprises a polypeptide having, e.g., at most one, two, three, four, five, six, seven, eight, nine, 10 or 20 contiguous amino acid deletions relative to amino acids 55-91, amino acids 95-134, or amino acids 138-183 of SEQ ID NO: 40. In other aspects of this embodiment, a binding domain comprising a FGF-17 β-trefoil domain comprises a polypeptide having, e.g., at least one, two, three, four, five, six, seven, eight, nine, 10 or 20 contiguous amino acid deletions relative to amino acids 55-91, amino acids 95-134, or amino acids 138-183 of SEQ ID NO: 40. In still other aspects of this embodiment, a binding domain comprising a FGF-17 β-trefoil domain comprises a polypeptide having, e.g., at most one, two, three, four, five, six, seven, eight, nine, 10 or 20 contiguous amino acid additions relative to amino acids 55-91, amino acids 95-134, or amino acids 138-183 of SEQ ID NO: 40. In other aspects of this embodiment, a binding domain comprising a FGF-17 β-trefoil domain comprises a polypeptide having, e.g., at least one, two, three, four, five, six, seven, eight, nine, 10 or 20 contiguous amino acid additions relative to amino acids 55-91, amino acids 95-134, or amino acids 138-183 of SEQ ID NO: 40.

In another embodiment, a binding domain comprising a FGF-17 β-trefoil domain comprises a β4/β5 hairpin turn of a β-trefoil domain of a FGF-17 or a β8/β9 hairpin turn of a β-trefoil domain of a FGF-17 of SEQ ID NO: 35. In another aspect of this embodiment, a binding domain comprising a FGF-17 β-trefoil domain comprises amino acids 92-94 or amino acids 135-137 of SEQ ID NO: 40.

In other aspects of this embodiment, a binding domain comprising a FGF-17 β-trefoil domain comprises a polypeptide having, e.g., at least 70% amino acid identity with amino acids 92-94 or amino acids 135-137 of SEQ ID NO: 40, at least 75% amino acid identity with amino acids 92-94 or amino acids 135-137 of SEQ ID NO: 40, at least 80% amino acid identity with amino acids 92-94 or amino acids 135-137 of SEQ ID NO: 40, at least 85% amino acid identity with amino acids 92-94 or amino acids 135-137 of SEQ ID NO: 40, at least 90% amino acid identity with amino acids 92-94 or amino acids 135-137 of SEQ ID NO: 40 or at least 95% amino acid identity with amino acids 92-94 or amino acids 135-137 of SEQ ID NO: 40. In yet other aspects of this embodiment, a binding domain comprising a FGF-17 β-trefoil domain comprises a polypeptide having, e.g., at most 70% amino acid identity with amino acids 92-94 or amino acids 135-137 of SEQ ID NO: 40, at most 75% amino acid identity with amino acids 92-94 or amino acids 135-137 of SEQ ID NO: 40, at most 80% amino acid identity with amino acids 92-94 or amino acids 135-137 of SEQ ID NO: 40, at most 85% amino acid identity with amino acids 92-94 or amino acids 135-137 of SEQ ID NO: 40, at most 90% amino acid identity with amino acids 92-94 or amino acids 135-137 of SEQ ID NO: 40 or at most 95% amino acid identity with amino acids 92-94 or amino acids 135-137 of SEQ ID NO: 40.

In other aspects of this embodiment, a binding domain comprising a FGF-17 β-trefoil domain comprises a polypeptide having, e.g., at most one, two, three or four non-contiguous amino acid substitutions relative to amino acids 92-94 or amino acids 135-137 of SEQ ID NO: 40. In other aspects of this embodiment, a binding domain comprising a FGF-17 β-trefoil domain comprises a polypeptide having, e.g., at least one, two, three or four non-contiguous amino acid substitutions relative to amino acids 92-94 or amino acids 135-137 of SEQ ID NO: 40. In other aspects of this embodiment, a non-contiguous amino acid substitution of any amino acid from amino acids 92-94 or amino acids 135-137 of SEQ ID NO: 40 can be replaced with glycine. In other aspects of this embodiment, a non-contiguous amino acid substitution of any hydrophobic amino acid from amino acids 92-94 or amino acids 135-137 of SEQ ID NO: 40 can be replaced with phenylalanine. In yet other aspects of this embodiment, a binding domain comprising a FGF-17 β-trefoil domain comprises a polypeptide having, e.g., at most one, two, three or four non-contiguous amino acid deletions relative to amino acids 92-94 or amino acids 135-137 of SEQ ID NO: 40. In other aspects of this embodiment, a binding domain comprising a FGF-17 β-trefoil domain comprises a polypeptide having, e.g., at least one, two, three or four non-contiguous amino acid deletions relative to amino acids 92-94 or amino acids 135-137 of SEQ ID NO: 40. In still other aspects of this embodiment, a binding domain comprising a FGF-17 β-trefoil domain comprises a polypeptide having, e.g., at most one, two, three or four non-contiguous amino acid additions relative to amino acids 92-94 or amino acids 135-137 of SEQ ID NO: 40. In other aspects of this embodiment, a binding domain comprising a FGF-17 β-trefoil domain comprises a polypeptide having, e.g., at least one, two, three or four non-contiguous amino acid additions relative to amino acids 92-94 or amino acids 135-137 of SEQ ID NO: 40.

In other aspects of this embodiment, a binding domain comprising a FGF-17 β-trefoil domain comprises a polypeptide having, e.g., at most one, two, three or four contiguous amino acid substitutions relative to amino acids 92-94 or amino acids 135-137 of SEQ ID NO: 40. In other aspects of this embodiment, a binding domain comprising a FGF-17 β-trefoil domain comprises a polypeptide having, e.g., at least one, two, three or four contiguous amino acid substitutions relative to amino acids 92-94 or amino acids 135-137 of SEQ ID NO: 40. In other aspects of this embodiment, contiguous amino acid substitutions of amino acids from amino acids 92-94 or amino acids 135-137 of SEQ ID NO: 40 can be replaced with glycine. In other aspects of this embodiment, contiguous amino acid substitutions of hydrophobic amino acids from amino acids 92-94 or amino acids 135-137 of SEQ ID NO: 40 can be replaced with phenylalanine. In yet other aspects of this embodiment, a binding domain comprising a FGF-17 β-trefoil domain comprises a polypeptide having, e.g., at most one, two, three or four contiguous amino acid deletions relative to amino acids 92-94 or amino acids 135-137 of SEQ ID NO: 40. In other aspects of this embodiment, a binding domain comprising a FGF-17 β-trefoil domain comprises a polypeptide having, e.g., at least one, two, three or four contiguous amino acid deletions relative to amino acids 92-94 or amino acids 135-137 of SEQ ID NO: 40. In still other aspects of this embodiment, a binding domain comprising a FGF-17 β-trefoil domain comprises a polypeptide having, e.g., at most one, two, three or four contiguous amino acid additions relative to amino acids 92-94 or amino acids 135-137 of SEQ ID NO: 40. In other aspects of this embodiment, a binding domain comprising a FGF-17 β-trefoil domain comprises a polypeptide having, e.g., at least one, two, three or four contiguous amino acid additions relative to amino acids 92-94 or amino acids 135-137 of SEQ ID NO: 40.

In another embodiment, a binding domain comprises β-trefoil domain derived a FGF-18 of SEQ ID NO: 41. In another embodiment, a binding domain comprising a β-trefoil domain derived from a FGF-18 comprises amino acids 54-183 of SEQ ID NO: 41. In another aspect of this embodiment, a binding domain comprising a β-trefoil domain derived from a FGF-18 comprises an α-fold motif of a β-trefoil domain of a FGF-18, a β-fold motif of a β-trefoil domain of a FGF-18 or a γ-fold motif of a β-trefoil domain of a FGF-18 of SEQ ID NO: 41. In another aspect of this embodiment, a β-trefoil domain derived from a FGF-18 comprises amino acids 55-91, amino acids 95-134, or amino acids 138-183 of SEQ ID NO: 41.

In other aspects of this embodiment, a binding domain comprising a FGF-18 β-trefoil domain comprises a polypeptide having, e.g., at least 70% amino acid identity with amino acids 55-91, amino acids 95-134, or amino acids 138-183 of SEQ ID NO: 41, at least 75% amino acid identity with amino acids 55-91, amino acids 95-134, or amino acids 138-183 of SEQ ID NO: 41, at least 80% amino acid identity with amino acids 55-91, amino acids 95-134, or amino acids 138-183 of SEQ ID NO: 41, at least 85% amino acid identity with amino acids 55-91, amino acids 95-134, or amino acids 138-183 of SEQ ID NO: 41, at least 90% amino acid identity with amino acids 55-91, amino acids 95-134, or amino acids 138-183 of SEQ ID NO: 41 or at least 95% amino acid identity with amino acids 55-91, amino acids 95-134, or amino acids 138-183 of SEQ ID NO: 41. In yet other aspects of this embodiment, a binding domain comprising a FGF-18 β-trefoil domain comprises a polypeptide having, e.g., at most 70% amino acid identity with amino acids 55-91, amino acids 95-134, or amino acids 138-183 of SEQ ID NO: 41, at most 75% amino acid identity with amino acids 55-91, amino acids 95-134, or amino acids 138-183 of SEQ ID NO: 41, at most 80% amino acid identity with amino acids 55-91, amino acids 95-134, or amino acids 138-183 of SEQ ID NO: 41, at most 85% amino acid identity with amino acids 55-91, amino acids 95-134, or amino acids 138-183 of SEQ ID NO: 41, at most 90% amino acid identity with amino acids 55-91, amino acids 95-134, or amino acids 138-183 of SEQ ID NO: 41 or at most 95% amino acid identity with amino acids 55-91, amino acids 95-134, or amino acids 138-183 of SEQ ID NO: 41.

In other aspects of this embodiment, a binding domain comprising a FGF-18 β-trefoil domain comprises a polypeptide having, e.g., at most one, two, three, four, five, six, seven, eight, nine, 10 or 20 non-contiguous amino acid substitutions relative to amino acids 55-91, amino acids 95-134, or amino acids 138-183 of SEQ ID NO: 41. In other aspects of this embodiment, a binding domain comprising a FGF-18 β-trefoil domain comprises a polypeptide having, e.g., at least one, two, three, four, five, six, seven, eight, nine, 10 or 20 non-contiguous amino acid substitutions relative to amino acids 55-91, amino acids 95-134, or amino acids 138-183 of SEQ ID NO: 41. In yet other aspects of this embodiment, a binding domain comprising a FGF-18 β-trefoil domain comprises a polypeptide having, e.g., at most one, two, three, four, five, six, seven, eight, nine, 10 or 20 non-contiguous amino acid deletions relative to amino acids 55-91, amino acids 95-134, or amino acids 138-183 of SEQ ID NO: 41. In other aspects of this embodiment, a binding domain comprising a FGF-18 β-trefoil domain comprises a polypeptide having, e.g., at least one, two, three, four, five, six, seven, eight, nine, 10 or 20 non-contiguous amino acid deletions relative to amino acids 55-91, amino acids 95-134, or amino acids 138-183 of SEQ ID NO: 41. In still other aspects of this embodiment, a binding domain comprising a FGF-18 β-trefoil domain comprises a polypeptide having, e.g., at most one, two, three, four, five, six, seven, eight, nine, 10 or 20 non-contiguous amino acid additions relative to amino acids 55-91, amino acids 95-134, or amino acids 138-183 of SEQ ID NO: 41. In other aspects of this embodiment, a binding domain comprising a FGF-18 β-trefoil domain comprises a polypeptide having, e.g., at least one, two, three, four, five, six, seven, eight, nine, 10 or 20 non-contiguous amino acid additions relative to amino acids 55-91, amino acids 95-134, or amino acids 138-183 of SEQ ID NO: 41.

In other aspects of this embodiment, a binding domain comprising a FGF-18 β-trefoil domain comprises a polypeptide having, e.g., at most one, two, three, four, five, six, seven, eight, nine, 10 or 20 contiguous amino acid substitutions relative to amino acids 55-91, amino acids 95-134, or amino acids 138-183 of SEQ ID NO: 41. In other aspects of this embodiment, a binding domain comprising a FGF-18 β-trefoil domain comprises a polypeptide having, e.g., at least one, two, three, four, five, six, seven, eight, nine, 10 or 20 contiguous amino acid substitutions relative to amino acids 55-91, amino acids 95-134, or amino acids 138-183 of SEQ ID NO: 41. In yet other aspects of this embodiment, a binding domain comprising a FGF-18 β-trefoil domain comprises a polypeptide having, e.g., at most one, two, three, four, five, six, seven, eight, nine, 10 or 20 contiguous amino acid deletions relative to amino acids 55-91, amino acids 95-134, or amino acids 138-183 of SEQ ID NO: 41. In other aspects of this embodiment, a binding domain comprising a FGF-18 β-trefoil domain comprises a polypeptide having, e.g., at least one, two, three, four, five, six, seven, eight, nine, 10 or 20 contiguous amino acid deletions relative to amino acids 55-91, amino acids 95-134, or amino acids 138-183 of SEQ ID NO: 41. In still other aspects of this embodiment, a binding domain comprising a FGF-18 β-trefoil domain comprises a polypeptide having, e.g., at most one, two, three, four, five, six, seven, eight, nine, 10 or 20 contiguous amino acid additions relative to amino acids 55-91, amino acids 95-134, or amino acids 138-183 of SEQ ID NO: 41. In other aspects of this embodiment, a binding domain comprising a FGF-18 β-trefoil domain comprises a polypeptide having, e.g., at least one, two, three, four, five, six, seven, eight, nine, 10 or 20 contiguous amino acid additions relative to amino acids 55-91, amino acids 95-134, or amino acids 138-183 of SEQ ID NO: 41.

In another embodiment, a binding domain comprising a FGF-18 β-trefoil domain comprises a β4/β5 hairpin turn of a β-trefoil domain of a FGF-18 or a β8/β9 hairpin turn of a β-trefoil domain of a FGF-18 of SEQ ID NO: 35. In another aspect of this embodiment, a binding domain comprising a FGF-18 β-trefoil domain comprises amino acids 92-94 or amino acids 135-137 of SEQ ID NO: 41.

In other aspects of this embodiment, a binding domain comprising a FGF-18 β-trefoil domain comprises a polypeptide having, e.g., at least 70% amino acid identity with amino acids 92-94 or amino acids 135-137 of SEQ ID NO: 41, at least 75% amino acid identity with amino acids 92-94 or amino acids 135-137 of SEQ ID NO: 41, at least 80% amino acid identity with amino acids 92-94 or amino acids 135-137 of SEQ ID NO: 41, at least 85% amino acid identity with amino acids 92-94 or amino acids 135-137 of SEQ ID NO: 41, at least 90% amino acid identity with amino acids 92-94 or amino acids 135-137 of SEQ ID NO: 41 or at least 95% amino acid identity with amino acids 92-94 or amino acids 135-137 of SEQ ID NO: 41. In yet other aspects of this embodiment, a binding domain comprising a FGF-18 β-trefoil domain comprises a polypeptide having, e.g., at most 70% amino acid identity with amino acids 92-94 or amino acids 135-137 of SEQ ID NO: 41, at most 75% amino acid identity with amino acids 92-94 or amino acids 135-137 of SEQ ID NO: 41, at most 80% amino acid identity with amino acids 92-94 or amino acids 135-137 of SEQ ID NO: 41, at most 85% amino acid identity with amino acids 92-94 or amino acids 135-137 of SEQ ID NO: 41, at most 90% amino acid identity with amino acids 92-94 or amino acids 135-137 of SEQ ID NO: 41 or at most 95% amino acid identity with amino acids 92-94 or amino acids 135-137 of SEQ ID NO: 41.

In other aspects of this embodiment, a binding domain comprising a FGF-18 β-trefoil domain comprises a polypeptide having, e.g., at most one, two, three or four non-contiguous amino acid substitutions relative to amino acids 92-94 or amino acids 135-137 of SEQ ID NO: 41. In other aspects of this embodiment, a binding domain comprising a FGF-18 β-trefoil domain comprises a polypeptide having, e.g., at least one, two, three or four non-contiguous amino acid substitutions relative to amino acids 92-94 or amino acids 135-137 of SEQ ID NO: 41. In other aspects of this embodiment, a non-contiguous amino acid substitution of any amino acid from amino acids 92-94 or amino acids 135-137 of SEQ ID NO: 41 can be replaced with glycine. In other aspects of this embodiment, a non-contiguous amino acid substitution of any hydrophobic amino acid from amino acids 92-94 or amino acids 135-137 of SEQ ID NO: 41 can be replaced with phenylalanine. In yet other aspects of this embodiment, a binding domain comprising a FGF-18 β-trefoil domain comprises a polypeptide having, e.g., at most one, two, three or four non-contiguous amino acid deletions relative to amino acids 92-94 or amino acids 135-137 of SEQ ID NO: 41. In other aspects of this embodiment, a binding domain comprising a FGF-18 β-trefoil domain comprises a polypeptide having, e.g., at least one, two, three or four non-contiguous amino acid deletions relative to amino acids 92-94 or amino acids 135-137 of SEQ ID NO: 41. In still other aspects of this embodiment, a binding domain comprising a FGF-18 β-trefoil domain comprises a polypeptide having, e.g., at most one, two, three or four non-contiguous amino acid additions relative to amino acids 92-94 or amino acids 135-137 of SEQ ID NO: 41. In other aspects of this embodiment, a binding domain comprising a FGF-18 β-trefoil domain comprises a polypeptide having, e.g., at least one, two, three or four non-contiguous amino acid additions relative to amino acids 92-94 or amino acids 135-137 of SEQ ID NO: 41.

In other aspects of this embodiment, a binding domain comprising a FGF-18 β-trefoil domain comprises a polypeptide having, e.g., at most one, two, three or four contiguous amino acid substitutions relative to amino acids 92-94 or amino acids 135-137 of SEQ ID NO: 41. In other aspects of this embodiment, a binding domain comprising a FGF-18 β-trefoil domain comprises a polypeptide having, e.g., at least one, two, three or four contiguous amino acid substitutions relative to amino acids 92-94 or amino acids 135-137 of SEQ ID NO: 41. In other aspects of this embodiment, contiguous amino acid substitutions of amino acids from amino acids 92-94 or amino acids 135-137 of SEQ ID NO: 41 can be replaced with glycine. In other aspects of this embodiment, contiguous amino acid substitutions of hydrophobic amino acids from amino acids 92-94 or amino acids 135-137 of SEQ ID NO: 41 can be replaced with phenylalanine. In yet other aspects of this embodiment, a binding domain comprising a FGF-18 β-trefoil domain comprises a polypeptide having, e.g., at most one, two, three or four contiguous amino acid deletions relative to amino acids 92-94 or amino acids 135-137 of SEQ ID NO: 41. In other aspects of this embodiment, a binding domain comprising a FGF-18 β-trefoil domain comprises a polypeptide having, e.g., at least one, two, three or four contiguous amino acid deletions relative to amino acids 92-94 or amino acids 135-137 of SEQ ID NO: 41. In still other aspects of this embodiment, a binding domain comprising a FGF-18 β-trefoil domain comprises a polypeptide having, e.g., at most one, two, three or four contiguous amino acid additions relative to amino acids 92-94 or amino acids 135-137 of SEQ ID NO: 41. In other aspects of this embodiment, a binding domain comprising a FGF-18 β-trefoil domain comprises a polypeptide having, e.g., at least one, two, three or four contiguous amino acid additions relative to amino acids 92-94 or amino acids 135-137 of SEQ ID NO: 41.

Because of the modular nature of the β-trefoil domain, it is envisioned that any combination of α-folds, β-folds, γ-folds, β4/β5 β-hairpin turns, β8/β9 β-hairpin turns, or any combination thereof from a β-trefoil domain of a Clostridial toxin binding domain, a β-trefoil domain of a NAP or a β-trefoil domain, a β-trefoil domain of an FGF ligand, or any combination thereof, can be used to practice aspect of the present invention. As a non-limiting example, a multivalent Clostridial toxin disclosed in the present specification can comprise a binding domain comprising a α-fold from a BoNT/A binding domain, a β-fold from a FGF-18 and a 2γ-fold from a BoNT/A HA-33. As another non-limiting example, a multivalent Clostridial toxin disclosed in the present specification can comprise a binding domain comprising a α-fold from a BoNT/A HA-17, a β-fold from a *Clostridium botulinum* serotype E NTNH and a γ-fold from a modified BoNT/C1 binding domain with enhanced binding activity.

Thus, in an embodiment, a binding domain comprises a glycogen-like peptide. In another embodiment, a binding domain comprises a glycogen-like peptide of SEQ ID NO: 42. In another embodiment, a binding domain is derived from a glycogen-like peptide. In another embodiment, a binding domain is derived from a glycogen-like peptide of SEQ ID NO: 42. In aspects of this embodiment, a binding domain is derived from a glycogen-like peptide comprises a GRPP, a GLP-1, a GLP-2, a glucagon or an oxyntomodulin. In aspects of this embodiment, a binding domain is derived from a glycogen-like peptide comprising amino acids 21-50, amino acids 53-81, amino acids 53-89, amino acids 98-124, or amino acids 146-178 of SEQ ID NO: 42.

In other aspects of this embodiment, a glycogen-like peptide comprises a polypeptide having, e.g., at least 70% amino acid identity with amino acids 21-50, amino acids 53-81, amino acids 53-89, amino acids 98-124, or amino acids 146-178 of SEQ ID NO: 42, at least 75% amino acid identity with amino acids 21-50, amino acids 53-81, amino acids 53-89, amino acids 98-124, or amino acids 146-178 of SEQ ID NO: 42, at least 80% amino acid identity with amino acids 21-50, amino acids 53-81, amino acids 53-89, amino acids 98-124, or amino acids 146-178 of SEQ ID NO: 42, at least 85% amino acid identity with amino acids 21-50, amino acids 53-81, amino acids 53-89, amino acids 98-124, or amino acids 146-178 of SEQ ID NO: 42, at least 90% amino acid identity with amino acids 21-50, amino acids 53-81, amino acids 53-89, amino acids 98-124, or amino acids 146-178 of SEQ ID NO: 42 or at least 95% amino acid identity with amino acids 21-50, amino acids 53-81, amino acids 53-89, amino acids 98-124, or amino acids 146-178 of SEQ ID NO: 42. In yet other aspects of this embodiment, a glycogen-like peptide comprises a polypeptide having, e.g., at most 70% amino acid identity with amino acids 21-50, amino acids 53-81, amino acids 53-89, amino acids 98-124, or amino acids 146-178 of SEQ ID NO: 42, at most 75% amino acid identity with amino acids 21-50, amino acids 53-81, amino acids 53-89, amino acids 98-124, or amino acids 146-178 of SEQ ID NO: 42, at most 80% amino acid identity with amino acids 21-50, amino acids 53-81, amino acids 53-89, amino acids 98-124, or amino acids 146-178 of SEQ ID NO: 42, at most 85% amino acid identity with amino acids 21-50, amino acids 53-81, amino acids 53-89, amino acids 98-124, or amino acids 146-178 of SEQ ID NO: 42, at most 90% amino acid identity with amino acids 21-50, amino acids 53-81, amino acids 53-89, amino acids 98-124, or amino acids 146-178 of SEQ ID NO: 42 or at most 95% amino acid identity with amino acids 21-50, amino acids 53-81, amino acids 53-89, amino acids 98-124, or amino acids 146-178 of SEQ ID NO: 42.

In other aspects of this embodiment, a glycogen-like peptide comprises a polypeptide having, e.g., at most one, two, three, four, five, six, seven, eight, nine, 10 or 20 non-contiguous amino acid substitutions relative to amino acids 21-50, amino acids 53-81, amino acids 53-89, amino acids 98-124, or amino acids 146-178 of SEQ ID NO: 42. In other aspects of this embodiment, a glycogen-like peptide comprises a polypeptide having, e.g., at least one, two, three, four, five, six, seven, eight, nine, 10 or 20 non-contiguous amino acid substitutions relative to amino acids 21-50, amino acids 53-81, amino acids 53-89, amino acids 98-124, or amino acids 146-178 of SEQ ID NO: 42. In yet other aspects of this embodiment, a glycogen-like peptide comprises a polypeptide having, e.g., at most one, two, three, four, five, six, seven, eight, nine, 10 or 20 non-contiguous amino acid deletions relative to amino acids 21-50, amino acids 53-81, amino acids 53-89, amino acids 98-124, or amino acids 146-178 of SEQ ID NO: 42. In other aspects of this embodiment, a glycogen-like peptide comprises a polypeptide having, e.g., at least one, two, three, four, five, six, seven, eight, nine, 10 or 20 non-contiguous amino acid deletions relative to amino acids 21-50, amino acids 53-81, amino acids 53-89, amino acids 98-124, or amino acids 146-178 of SEQ ID NO: 42. In still other aspects of this embodiment, a glycogen-like peptide comprises a polypeptide having, e.g., at most one, two, three, four, five, six, seven, eight, nine, 10 or 20 non-contiguous amino acid additions relative to amino acids 21-50, amino acids 53-81, amino acids 53-89, amino acids 98-124, or amino acids 146-178 of SEQ ID NO: 42. In other aspects of this embodiment, a glycogen-like peptide comprises a polypeptide having, e.g., at least one, two, three, four, five, six, seven, eight, nine, 10 or 20 non-contiguous amino acid additions relative to amino acids 21-50, amino acids 53-81, amino acids 53-89, amino acids 98-124, or amino acids 146-178 of SEQ ID NO: 42.

In other aspects of this embodiment, a glycogen-like peptide comprises a polypeptide having, e.g., at most one, two, three, four, five, six, seven, eight, nine, 10 or 20 contiguous amino acid substitutions relative to amino acids 21-50, amino acids 53-81, amino acids 53-89, amino acids 98-124, or amino acids 146-178 of SEQ ID NO: 42. In other aspects of this embodiment, a glycogen-like peptide comprises a polypeptide having, e.g., at least one, two, three, four, five, six, seven, eight, nine, 10 or 20 contiguous amino acid substitutions relative to amino acids 21-50, amino acids 53-81, amino acids 53-89, amino acids 98-124, or amino acids 146-178 of SEQ ID NO: 42. In yet other aspects of this embodiment, a glycogen-like peptide comprises a polypeptide having, e.g., at most one, two, three, four, five, six, seven, eight, nine, 10 or 20 contiguous amino acid deletions relative to amino acids 21-50, amino acids 53-81, amino acids 53-89, amino acids 98-124, or amino acids 146-178 of SEQ ID NO: 42. In other aspects of this embodiment, a glycogen-like peptide comprises a polypeptide having, e.g., at least one, two, three, four, five, six, seven, eight, nine, 10 or 20 contiguous amino acid deletions relative to amino acids 21-50, amino acids 53-81, amino acids 53-89, amino acids 98-124, or amino acids 146-178 of SEQ ID NO: 42. In still other aspects of this embodiment, a glycogen-like peptide comprises a polypeptide having, e.g., at most one, two, three, four, five, six, seven, eight, nine, 10 or 20 contiguous amino acid additions relative to amino acids 21-50, amino acids 53-81, amino acids 53-89, amino acids 98-124, or amino acids 146-178 of SEQ ID NO: 42. In other aspects of this embodiment, a glycogen-like peptide comprises a polypeptide having, e.g., at least one, two, three, four, five, six, seven, eight, nine, 10 or 20 contiguous amino acid additions relative to amino acids 21-50, amino acids 53-81, amino acids 53-89, amino acids 98-124, or amino acids 146-178 of SEQ ID NO: 42.

In an embodiment, a binding domain comprises a PACAP. In another embodiment, a binding domain comprises a PACAP of SEQ ID NO: 43. In another embodiment, a binding domain is derived from a PACAP. In another embodiment, a binding domain is derived from a PACAP of SEQ ID NO: 43. In an aspect of this embodiment, a binding domain is derived from a PACAP comprising amino acids 132-158 of SEQ ID NO: 43.

In other aspects of this embodiment, a PACAP comprises a polypeptide having, e.g., at least 70% amino acid identity with amino acids 132-158 of SEQ ID NO: 43, at least 75% amino acid identity with amino acids 132-158 of SEQ ID NO: 43, at least 80% amino acid identity with amino acids 132-158 of SEQ ID NO: 43, at least 85% amino acid identity with amino acids 132-158 of SEQ ID NO: 43, at least 90% amino acid identity with amino acids 132-158 of SEQ ID NO: 43 or at least 95% amino acid identity with amino acids 132-158 of SEQ ID NO: 43. In yet other aspects of this embodiment, a PACAP comprises a polypeptide having, e.g., at most 70% amino acid identity with amino acids 132-158 of SEQ ID NO: 43, at most 75% amino acid identity with amino acids 132-158 of SEQ ID NO: 43, at most 80% amino acid identity with amino acids 132-158 of SEQ ID NO: 43, at most 85% amino acid identity with amino acids 132-158 of SEQ ID NO: 43, at most 90% amino acid identity with amino acids 132-158 of SEQ ID NO: 43 or at most 95% amino acid identity with amino acids 132-158 of SEQ ID NO: 43.

In other aspects of this embodiment, a PACAP comprises a polypeptide having, e.g., at most one, two, three, four, five, six, seven, eight, nine, 10 or 20 non-contiguous amino acid substitutions relative to amino acids 132-158 of SEQ ID NO: 43. In other aspects of this embodiment, a PACAP comprises a polypeptide having, e.g., at least one, two, three, four, five, six, seven, eight, nine, 10 or 20 non-contiguous amino acid substitutions relative to amino acids 132-158 of SEQ ID NO: 43. In yet other aspects of this embodiment, a PACAP comprises a polypeptide having, e.g., at most one, two, three, four, five, six, seven, eight, nine, 10 or 20 non-contiguous amino acid deletions relative to amino acids 132-158 of SEQ ID NO: 43. In other aspects of this embodiment, a PACAP comprises a polypeptide having, e.g., at least one, two, three, four, five, six, seven, eight, nine, 10 or 20 non-contiguous amino acid deletions relative to amino acids 132-158 of SEQ ID NO: 43. In still other aspects of this embodiment, a PACAP comprises a polypeptide having, e.g., at most one, two, three, four, five, six, seven, eight, nine, 10 or 20 non-contiguous amino acid additions relative to amino acids 132-158 of SEQ ID NO: 43. In other aspects of this embodiment, a PACAP comprises a polypeptide having, e.g., at least one, two, three, four, five, six, seven, eight, nine, 10 or 20 non-contiguous amino acid additions relative to amino acids 132-158 of SEQ ID NO: 43.

In other aspects of this embodiment, a PACAP comprises a polypeptide having, e.g., at most one, two, three, four, five, six, seven, eight, nine, 10 or 20 contiguous amino acid substitutions relative to amino acids 132-158 of SEQ ID NO: 43. In other aspects of this embodiment, a PACAP comprises a polypeptide having, e.g., at least one, two, three, four, five, six, seven, eight, nine, 10 or 20 contiguous amino acid substitutions relative to amino acids 132-158 of SEQ ID NO: 43. In yet other aspects of this embodiment, a PACAP comprises a polypeptide having, e.g., at most one, two, three, four, five, six, seven, eight, nine, 10 or 20 contiguous amino acid deletions relative to amino acids 132-158 of SEQ ID NO: 43. In other aspects of this embodiment, a PACAP comprises a polypeptide having, e.g., at least one, two, three, four, five, six, seven, eight, nine, 10 or 20 contiguous amino acid deletions relative to amino acids 132-158 of SEQ ID NO: 43. In still other aspects of this embodiment, a PACAP comprises a polypeptide having, e.g., at most one, two, three, four, five, six, seven, eight, nine, 10 or 20 contiguous amino acid additions relative to amino acids 132-158 of SEQ ID NO: 43. In other aspects of this embodiment, a PACAP comprises a polypeptide having, e.g., at least one, two, three, four, five, six, seven, eight, nine, 10 or 20 contiguous amino acid additions relative to amino acids 132-158 of SEQ ID NO: 43.

In an embodiment, a binding domain comprises a GHRH. In another embodiment, a binding domain comprises a GHRH of SEQ ID NO: 44. In another embodiment, a binding domain is derived from a GHRH. In another embodiment, a binding domain is derived from a GHRH of SEQ ID NO: 44. In aspects of this embodiment, a binding domain is derived from a GHRH comprising amino acids 32-58 or amino acids 32-75 of SEQ ID NO: 44.

In other aspects of this embodiment, a GHRH comprises a polypeptide having, e.g., at least 70% amino acid identity with amino acids 32-58 or amino acids 32-75 of SEQ ID NO: 44, at least 75% amino acid identity with amino acids 32-58 or amino acids 32-75 of SEQ ID NO: 44, at least 80% amino acid identity with amino acids 32-58 or amino acids 32-75 of SEQ ID NO: 44, at least 85% amino acid identity with amino acids 32-58 or amino acids 32-75 of SEQ ID NO: 44, at least 90% amino acid identity with amino acids 32-58 or amino acids 32-75 of SEQ ID NO: 44 or at least 95% amino acid identity with amino acids 32-58 or amino acids 32-75 of SEQ ID NO: 44. In yet other aspects of this embodiment, a GHRH comprises a polypeptide having, e.g., at most 70% amino acid identity with amino acids 32-58 or amino acids 32-75 of SEQ ID NO: 44, at most 75% amino acid identity with amino acids 32-58 or amino acids 32-75 of SEQ ID NO: 44, at most 80% amino acid identity with amino acids 32-58 or amino acids 32-75 of SEQ ID NO: 44, at most 85% amino acid identity with amino acids 32-58 or amino acids 32-75 of SEQ ID NO: 44, at most 90% amino acid identity with amino acids 32-58 or amino acids 32-75 of SEQ ID NO: 44 or at most 95% amino acid identity with amino acids 32-58 or amino acids 32-75 of SEQ ID NO: 44.

In other aspects of this embodiment, a GHRH comprises a polypeptide having, e.g., at most one, two, three, four, five, six, seven, eight, nine, 10 or 20 non-contiguous amino acid substitutions relative to amino acids 32-58 or amino acids 32-75 of SEQ ID NO: 44. In other aspects of this embodiment, a GHRH comprises a polypeptide having, e.g., at least one, two, three, four, five, six, seven, eight, nine, 10 or 20 non-contiguous amino acid substitutions relative to amino acids 32-58 or amino acids 32-75 of SEQ ID NO: 44. In yet other aspects of this embodiment, a GHRH comprises a polypeptide having, e.g., at most one, two, three, four, five, six, seven, eight, nine, 10 or 20 non-contiguous amino acid deletions relative to amino acids 32-58 or amino acids 32-75 of SEQ ID NO: 44. In other aspects of this embodiment, a GHRH comprises a polypeptide having, e.g., at least one, two, three, four, five, six, seven, eight, nine, 10 or 20 non-contiguous amino acid deletions relative to amino acids 32-58 or amino acids 32-75 of SEQ ID NO: 44. In still other aspects of this embodiment, a GHRH comprises a polypeptide having, e.g., at most one, two, three, four, five, six, seven, eight, nine, 10 or 20 non-contiguous amino acid additions relative to amino acids 32-58 or amino acids 32-75 of SEQ ID NO: 44. In other aspects of this embodiment, a GHRH comprises a polypeptide having, e.g., at least one, two, three, four, five, six, seven, eight, nine, 10 or 20 non-contiguous amino acid additions relative to amino acids 32-58 or amino acids 32-75 of SEQ ID NO: 44.

In other aspects of this embodiment, a GHRH comprises a polypeptide having, e.g., at most one, two, three, four, five, six, seven, eight, nine, 10 or 20 contiguous amino acid substitutions relative to amino acids 32-58 or amino acids 32-75 of SEQ ID NO: 44. In other aspects of this embodiment, a GHRH comprises a polypeptide having, e.g., at least one, two, three, four, five, six, seven, eight, nine, 10 or 20 contiguous amino acid substitutions relative to amino acids 32-58 or amino acids 32-75 of SEQ ID NO: 44. In yet other aspects of this embodiment, a GHRH comprises a polypeptide having, e.g., at most one, two, three, four, five, six, seven, eight, nine, 10 or 20 contiguous amino acid deletions relative to amino acids 32-58 or amino acids 32-75 of SEQ ID NO: 44. In other aspects of this embodiment, a GHRH comprises a polypeptide having, e.g., at least one, two, three, four, five, six, seven, eight, nine, 10 or 20 contiguous amino acid deletions relative to amino acids 32-58 or amino acids 32-75 of SEQ ID NO: 44. In still other aspects of this embodiment, a GHRH comprises a polypeptide having, e.g., at most one, two, three, four, five, six, seven, eight, nine, 10 or 20 contiguous amino acid additions relative to amino acids 32-58 or amino acids 32-75 of SEQ ID NO: 44. In other aspects of this embodiment, a GHRH comprises a polypeptide having, e.g., at least one, two, three, four, five, six, seven, eight, nine, 10 or 20 contiguous amino acid additions relative to amino acids 32-58 or amino acids 32-75 of SEQ ID NO: 44.

In an embodiment, a binding domain comprises a VIP1. In another embodiment, a binding domain comprises a VIP1 of SEQ ID NO: 45. In another embodiment, a binding domain is derived from a VIP1. In another embodiment, a binding domain is derived from a VIP1 of SEQ ID NO: 45. In aspects of this embodiment, a binding domain is derived from a VIP1 comprising amino acids 81-107 or amino acids 125-151 of SEQ ID NO: 45.

In other aspects of this embodiment, a VIP1 comprises a polypeptide having, e.g., at least 70% amino acid identity with amino acids 81-107 or amino acids 125-151 of SEQ ID NO: 45, at least 75% amino acid identity with amino acids 81-107 or amino acids 125-151 of SEQ ID NO: 45, at least 80% amino acid identity with amino acids 81-107 or amino acids 125-151 of SEQ ID NO: 45, at least 85% amino acid identity with amino acids 81-107 or amino acids 125-151 of SEQ ID NO: 45, at least 90% amino acid identity with amino acids 81-107 or amino acids 125-151 of SEQ ID NO: 45 or at least 95% amino acid identity with amino acids 81-107 or amino acids 125-151 of SEQ ID NO: 45. In yet other aspects of this embodiment, a VIP1 comprises a polypeptide having, e.g., at most 70% amino acid identity with amino acids 81-107 or amino acids 125-151 of SEQ ID NO: 45, at most 75% amino acid identity with amino acids 81-107 or amino acids 125-151 of SEQ ID NO: 45, at most 80% amino acid identity with amino acids 81-107 or amino acids 125-151 of SEQ ID NO: 45, at most 85% amino acid identity with amino acids 81-107 or amino acids 125-151 of SEQ ID NO: 45, at most 90% amino acid identity with amino acids 81-107 or amino acids 125-151 of SEQ ID NO: 45 or at most 95% amino acid identity with amino acids 81-107 or amino acids 125-151 of SEQ ID NO: 45.

In other aspects of this embodiment, a VIP1 comprises a polypeptide having, e.g., at most one, two, three, four, five, six, seven, eight, nine, 10 or 20 non-contiguous amino acid substitutions relative to amino acids 81-107 or amino acids 125-151 of SEQ ID NO: 45. In other aspects of this embodiment, a VIP1 comprises a polypeptide having, e.g., at least one, two, three, four, five, six, seven, eight, nine, 10 or 20 non-contiguous amino acid substitutions relative to amino acids 81-107 or amino acids 125-151 of SEQ ID NO: 45. In yet other aspects of this embodiment, a VIP1 comprises a polypeptide having, e.g., at most one, two, three, four, five, six, seven, eight, nine, 10 or 20 non-contiguous amino acid deletions relative to amino acids 81-107 or amino acids 125-151 of SEQ ID NO: 45. In other aspects of this embodiment, a VIP1 comprises a polypeptide having, e.g., at least one, two, three, four, five, six, seven, eight, nine, 10 or 20 non-contiguous amino acid deletions relative to amino acids 81-107 or amino acids 125-151 of SEQ ID NO: 45. In still other aspects of this embodiment, a VIP1 comprises a polypeptide having, e.g., at most one, two, three, four, five, six, seven, eight, nine, 10 or 20 non-contiguous amino acid additions relative to amino acids 81-107 or amino acids 125-151 of SEQ ID NO: 45. In other aspects of this embodiment, a VIP1 comprises a polypeptide having, e.g., at least one, two, three, four, five, six, seven, eight, nine, 10 or 20 non-contiguous amino acid additions relative to amino acids 81-107 or amino acids 125-151 of SEQ ID NO: 45.

In other aspects of this embodiment, a VIP1 comprises a polypeptide having, e.g., at most one, two, three, four, five, six, seven, eight, nine, 10 or 20 contiguous amino acid substitutions relative to amino acids 81-107 or amino acids 125-151 of SEQ ID NO: 45. In other aspects of this embodiment, a VIP1 comprises a polypeptide having, e.g., at least one, two, three, four, five, six, seven, eight, nine, 10 or 20 contiguous amino acid substitutions relative to amino acids 81-107 or amino acids 125-151 of SEQ ID NO: 45. In yet other aspects of this embodiment, a VIP1 comprises a polypeptide having, e.g., at most one, two, three, four, five, six, seven, eight, nine, 10 or 20 contiguous amino acid deletions relative to amino acids 81-107 or amino acids 125-151 of SEQ ID NO: 45. In other aspects of this embodiment, a VIP1 comprises a polypeptide having, e.g., at least one, two, three, four, five, six, seven, eight, nine, 10 or 20 contiguous amino acid deletions relative to amino acids 81-107 or amino acids 125-151 of SEQ ID NO: 45. In still other aspects of this embodiment, a VIP1 comprises a polypeptide having, e.g., at most one, two, three, four, five, six, seven, eight, nine, 10 or 20 contiguous amino acid additions relative to amino acids 81-107 or amino acids 125-151 of SEQ ID NO: 45. In other aspects of this embodiment, a VIP1 comprises a polypeptide having, e.g., at least one, two, three, four, five, six, seven, eight, nine, 10 or 20 contiguous amino acid additions relative to amino acids 81-107 or amino acids 125-151 of SEQ ID NO: 45.

In an embodiment, a binding domain comprises a VIP2. In another embodiment, a binding domain comprises a VIP2 of SEQ ID NO: 46. In another embodiment, a binding domain is derived from a VIP2. In another embodiment, a binding domain is derived from a VIP2 of SEQ ID NO: 46. In aspects of this embodiment, a binding domain is derived from a VIP2 comprising amino acids 81-107 or amino acids 124-150 of SEQ ID NO: 46.

In other aspects of this embodiment, a VIP2 comprises a polypeptide having, e.g., at least 70% amino acid identity with amino acids 81-107 or amino acids 124-150 of SEQ ID NO: 46, at least 75% amino acid identity with amino acids 81-107 or amino acids 124-150 of SEQ ID NO: 46, at least 80% amino acid identity with amino acids 81-107 or amino acids 124-150 of SEQ ID NO: 46, at least 85% amino acid identity with amino acids 81-107 or amino acids 124-150 of SEQ ID NO: 46, at least 90% amino acid identity with amino acids 81-107 or amino acids 124-150 of SEQ ID NO: 46 or at least 95% amino acid identity with amino acids 81-107 or amino acids 124-150 of SEQ ID NO: 46. In yet other aspects of this embodiment, a VIP2 comprises a polypeptide having, e.g., at most 70% amino acid identity with amino acids 81-107 or amino acids 124-150 of SEQ ID NO: 46, at most 75% amino acid identity with amino acids 81-107 or amino acids 124-150 of SEQ ID NO: 46, at most 80% amino acid identity with amino acids 81-107 or amino acids 124-150 of SEQ ID NO: 46, at most 85% amino acid identity with amino acids 81-107 or amino acids 124-150 of SEQ ID NO: 46, at most 90% amino acid identity with amino acids 81-107 or amino acids 124-150 of SEQ ID NO: 46 or at most 95% amino acid identity with amino acids 81-107 or amino acids 124-150 of SEQ ID NO: 46.

In other aspects of this embodiment, a VIP2 comprises a polypeptide having, e.g., at most one, two, three, four, five, six, seven, eight, nine, 10 or 20 non-contiguous amino acid substitutions relative to amino acids 81-107 or amino acids 124-150 of SEQ ID NO: 46. In other aspects of this embodiment, a VIP2 comprises a polypeptide having, e.g., at least one, two, three, four, five, six, seven, eight, nine, 10 or 20 non-contiguous amino acid substitutions relative to amino acids 81-107 or amino acids 124-150 of SEQ ID NO: 46. In yet other aspects of this embodiment, a VIP2 comprises a polypeptide having, e.g., at most one, two, three, four, five, six, seven, eight, nine, 10 or 20 non-contiguous amino acid deletions relative to amino acids 81-107 or amino acids 124-150 of SEQ ID NO: 46. In other aspects of this embodiment, a VIP2 comprises a polypeptide having, e.g., at least one, two, three, four, five, six, seven, eight, nine, 10 or 20 non-contiguous amino acid deletions relative to amino acids 81-107 or amino acids 124-150 of SEQ ID NO: 46. In still other aspects of this embodiment, a VIP2 comprises a polypeptide having, e.g., at most one, two, three, four, five, six, seven, eight, nine, 10 or 20 non-contiguous amino acid additions relative to amino acids 81-107 or amino acids 124-150 of SEQ ID NO: 46. In other aspects of this embodiment, a VIP2 comprises a polypeptide having, e.g., at least one, two, three, four, five, six, seven, eight, nine, 10 or 20 non-contiguous amino acid additions relative to amino acids 81-107 or amino acids 124-150 of SEQ ID NO: 46.

In other aspects of this embodiment, a VIP2 comprises a polypeptide having, e.g., at most one, two, three, four, five, six, seven, eight, nine, 10 or 20 contiguous amino acid substitutions relative to amino acids 81-107 or amino acids 124-150 of SEQ ID NO: 46. In other aspects of this embodiment, a VIP2 comprises a polypeptide having, e.g., at least one, two, three, four, five, six, seven, eight, nine, 10 or 20 contiguous amino acid substitutions relative to amino acids 81-107 or amino acids 124-150 of SEQ ID NO: 46. In yet other aspects of this embodiment, a VIP2 comprises a polypeptide having, e.g., at most one, two, three, four, five, six, seven, eight, nine, 10 or 20 contiguous amino acid deletions relative to amino acids 81-107 or amino acids 124-150 of SEQ ID NO: 46. In other aspects of this embodiment, a VIP2 comprises a polypeptide having, e.g., at least one, two, three, four, five, six, seven, eight, nine, 10 or 20 contiguous amino acid deletions relative to amino acids 81-107 or amino acids 124-150 of SEQ ID NO: 46. In still other aspects of this embodiment, a VIP2 comprises a polypeptide having, e.g., at most one, two, three, four, five, six, seven, eight, nine, 10 or 20 contiguous amino acid additions relative to amino acids 81-107 or amino acids 124-150 of SEQ ID NO: 46. In other aspects of this embodiment, a VIP2 comprises a polypeptide having, e.g., at least one, two, three, four, five, six, seven, eight, nine, 10 or 20 contiguous amino acid additions relative to amino acids 81-107 or amino acids 124-150 of SEQ ID NO: 46.

In an embodiment, a binding domain comprises a GIP. In another embodiment, a binding domain comprises a GIP of SEQ ID NO: 47. In another embodiment, a binding domain is derived from a GIP. In another embodiment, a binding domain is derived from a GIP of SEQ ID NO: 47. In aspects of this embodiment, a binding domain is derived from a GIP comprising amino acids 52-78 or amino acids 52-93 of SEQ ID NO: 47.

In other aspects of this embodiment, a GIP comprises a polypeptide having, e.g., at least 70% amino acid identity with amino acids 52-78 or amino acids 52-93 of SEQ ID NO: 47, at least 75% amino acid identity with amino acids 52-78 or amino acids 52-93 of SEQ ID NO: 47, at least 80% amino acid identity with amino acids 52-78 or amino acids 52-93 of SEQ ID NO: 47, at least 85% amino acid identity with amino acids 52-78 or amino acids 52-93 of SEQ ID NO: 47, at least 90% amino acid identity with amino acids 52-78 or amino acids 52-93 of SEQ ID NO: 47 or at least 95% amino acid identity with amino acids 52-78 or amino acids 52-93 of SEQ ID NO: 47. In yet other aspects of this embodiment, a GIP comprises a polypeptide having, e.g., at most 70% amino acid identity with amino acids 52-78 or amino acids 52-93 of SEQ ID NO: 47, at most 75% amino acid identity with amino acids 52-78 or amino acids 52-93 of SEQ ID NO: 47, at most 80% amino acid identity with amino acids 52-78 or amino acids 52-93 of SEQ ID NO: 47, at most 85% amino acid identity with amino acids 52-78 or amino acids 52-93 of SEQ ID NO: 47, at most 90% amino acid identity with amino acids 52-78 or amino acids 52-93 of SEQ ID NO: 47 or at most 95% amino acid identity with amino acids 52-78 or amino acids 52-93 of SEQ ID NO: 47.

In other aspects of this embodiment, a GIP comprises a polypeptide having, e.g., at most one, two, three, four, five, six, seven, eight, nine, 10 or 20 non-contiguous amino acid substitutions relative to amino acids 52-78 or amino acids 52-93 of SEQ ID NO: 47. In other aspects of this embodiment, a GIP comprises a polypeptide having, e.g., at least one, two, three, four, five, six, seven, eight, nine, 10 or 20 non-contiguous amino acid substitutions relative to amino acids 52-78 or amino acids 52-93 of SEQ ID NO: 47. In yet other aspects of this embodiment, a GIP comprises a polypeptide having, e.g., at most one, two, three, four, five, six, seven, eight, nine, 10 or 20 non-contiguous amino acid deletions relative to amino acids 52-78 or amino acids 52-93 of SEQ ID NO: 47. In other aspects of this embodiment, a GIP comprises a polypeptide having, e.g., at least one, two, three, four, five, six, seven, eight, nine, 10 or 20 non-contiguous amino acid deletions relative to amino acids 52-78 or amino acids 52-93 of SEQ ID NO: 47. In still other aspects of this embodiment, a GIP comprises a polypeptide having, e.g., at most one, two, three, four, five, six, seven, eight, nine, 10 or 20 non-contiguous amino acid additions relative to amino acids 52-78 or amino acids 52-93 of SEQ ID NO: 47. In other aspects of this embodiment, a GIP comprises a polypeptide having, e.g., at least one, two, three, four, five, six, seven, eight, nine, 10 or 20 non-contiguous amino acid additions relative to amino acids 52-78 or amino acids 52-93 of SEQ ID NO: 47.

In other aspects of this embodiment, a GIP comprises a polypeptide having, e.g., at most one, two, three, four, five, six, seven, eight, nine, 10 or 20 contiguous amino acid substitutions relative to amino acids 52-78 or amino acids 52-93 of SEQ ID NO: 47. In other aspects of this embodiment, a GIP comprises a polypeptide having, e.g., at least one, two, three, four, five, six, seven, eight, nine, 10 or 20 contiguous amino acid substitutions relative to amino acids 52-78 or amino acids 52-93 of SEQ ID NO: 47. In yet other aspects of this embodiment, a GIP comprises a polypeptide having, e.g., at most one, two, three, four, five, six, seven, eight, nine, 10 or 20 contiguous amino acid deletions relative to amino acids 52-78 or amino acids 52-93 of SEQ ID NO: 47. In other aspects of this embodiment, a GIP comprises a polypeptide having, e.g., at least one, two, three, four, five, six, seven, eight, nine, 10 or 20 contiguous amino acid deletions relative to amino acids 52-78 or amino acids 52-93 of SEQ ID NO: 47. In still other aspects of this embodiment, a GIP comprises a polypeptide having, e.g., at most one, two, three, four, five, six, seven, eight, nine, 10 or 20 contiguous amino acid additions relative to amino acids 52-78 or amino acids 52-93 of SEQ ID NO: 47. In other aspects of this embodiment, a GIP comprises a polypeptide having, e.g., at least one, two, three, four, five, six, seven, eight, nine, 10 or 20 contiguous amino acid additions relative to amino acids 52-78 or amino acids 52-93 of SEQ ID NO: 47.

In an embodiment, a binding domain comprises a Secretin. In another embodiment, a binding domain comprises a Secretin of SEQ ID NO: 48. In another embodiment, a binding domain is derived from a Secretin. In another embodiment, a binding domain is derived from a Secretin of SEQ ID NO: 48. In an aspect of this embodiment, a binding domain is derived from a Secretin comprising amino acids 28-54 of SEQ ID NO: 48.

In other aspects of this embodiment, a Secretin comprises a polypeptide having, e.g., at least 70% amino acid identity with amino acids 28-54 of SEQ ID NO: 48, at least 75% amino acid identity with amino acids 28-54 of SEQ ID NO: 48, at least 80% amino acid identity with amino acids 28-54 of SEQ ID NO: 48, at least 85% amino acid identity with amino acids 28-54 of SEQ ID NO: 48, at least 90% amino acid identity with amino acids 28-54 of SEQ ID NO: 48 or at least 95% amino acid identity with amino acids 28-54 of SEQ ID NO: 48. In yet other aspects of this embodiment, a Secretin comprises a polypeptide having, e.g., at most 70% amino acid identity with amino acids 28-54 of SEQ ID NO: 48, at most 75% amino acid identity with amino acids 28-54 of SEQ ID NO: 48, at most 80% amino acid identity with amino acids 28-54 of SEQ ID NO: 48, at most 85% amino acid identity with amino acids 28-54 of SEQ ID NO: 48, at most 90% amino acid identity with amino acids 28-54 of SEQ ID NO: 48 or at most 95% amino acid identity with amino acids 28-54 of SEQ ID NO: 48.

In other aspects of this embodiment, a Secretin comprises a polypeptide having, e.g., at most one, two, three, four, five, six, seven, eight, nine, 10 or 20 non-contiguous amino acid substitutions relative to amino acids 28-54 of SEQ ID NO: 48. In other aspects of this embodiment, a Secretin comprises a polypeptide having, e.g., at least one, two, three, four, five, six, seven, eight, nine, 10 or 20 non-contiguous amino acid substitutions relative to amino acids 28-54 of SEQ ID NO: 48. In yet other aspects of this embodiment, a Secretin comprises a polypeptide having, e.g., at most one, two, three, four, five, six, seven, eight, nine, 10 or 20 non-contiguous amino acid deletions relative to amino acids 28-54 of SEQ ID NO: 48. In other aspects of this embodiment, a Secretin comprises a polypeptide having, e.g., at least one, two, three, four, five, six, seven, eight, nine, 10 or 20 non-contiguous amino acid deletions relative to amino acids 28-54 of SEQ ID NO: 48. In still other aspects of this embodiment, a Secretin comprises a polypeptide having, e.g., at most one, two, three, four, five, six, seven, eight, nine, 10 or 20 non-contiguous amino acid additions relative to amino acids 28-54 of SEQ ID NO: 48. In other aspects of this embodiment, a Secretin comprises a polypeptide having, e.g., at least one, two, three, four, five, six, seven, eight, nine, 10 or 20 non-contiguous amino acid additions relative to amino acids 28-54 of SEQ ID NO: 48.

In other aspects of this embodiment, a Secretin comprises a polypeptide having, e.g., at most one, two, three, four, five, six, seven, eight, nine, 10 or 20 contiguous amino acid substitutions relative to amino acids 28-54 of SEQ ID NO: 48. In other aspects of this embodiment, a Secretin comprises a polypeptide having, e.g., at least one, two, three, four, five, six, seven, eight, nine, 10 or 20 contiguous amino acid substitutions relative to amino acids 28-54 of SEQ ID NO: 48. In yet other aspects of this embodiment, a Secretin comprises a polypeptide having, e.g., at most one, two, three, four, five, six, seven, eight, nine, 10 or 20 contiguous amino acid deletions relative to amino acids 28-54 of SEQ ID NO: 48. In other aspects of this embodiment, a Secretin comprises a polypeptide having, e.g., at least one, two, three, four, five, six, seven, eight, nine, 10 or 20 contiguous amino acid deletions relative to amino acids 28-54 of SEQ ID NO: 48. In still other aspects of this embodiment, a Secretin comprises a polypeptide having, e.g., at most one, two, three, four, five, six, seven, eight, nine, 10 or 20 contiguous amino acid additions relative to amino acids 28-54 of SEQ ID NO: 48. In other aspects of this embodiment, a Secretin comprises a polypeptide having, e.g., at least one, two, three, four, five, six, seven, eight, nine, 10 or 20 contiguous amino acid additions relative to amino acids 28-54 of SEQ ID NO: 48.

In an embodiment, a binding domain comprises a Gastrin. In another embodiment, a binding domain comprises a Gastrin of SEQ ID NO: 49. In another embodiment, a binding domain is derived from a Gastrin. In another embodiment, a binding domain is derived from a Gastrin of SEQ ID NO: 49. In aspects of this embodiment, a binding domain is derived from a Gastrin comprising amino acids 76-92 or amino acids 59-92 of SEQ ID NO: 49.

In other aspects of this embodiment, a Gastrin comprises a polypeptide having, e.g., at least 70% amino acid identity with amino acids 76-92 or amino acids 59-92 of SEQ ID NO: 49, at least 75% amino acid identity with amino acids 76-92 or amino acids 59-92 of SEQ ID NO: 49, at least 80% amino acid identity with amino acids 76-92 or amino acids 59-92 of SEQ ID NO: 49, at least 85% amino acid identity with amino acids 76-92 or amino acids 59-92 of SEQ ID NO: 49, at least 90% amino acid identity with amino acids 76-92 or amino acids 59-92 of SEQ ID NO: 49 or at least 95% amino acid identity with amino acids 76-92 or amino acids 59-92 of SEQ ID NO: 49. In yet other aspects of this embodiment, a Gastrin comprises a polypeptide having, e.g., at most 70% amino acid identity with amino acids 76-92 or amino acids 59-92 of SEQ ID NO: 49, at most 75% amino acid identity with amino acids 76-92 or amino acids 59-92 of SEQ ID NO: 49, at most 80% amino acid identity with amino acids 76-92 or amino acids 59-92 of SEQ ID NO: 49, at most 85% amino acid identity with amino acids 76-92 or amino acids 59-92 of SEQ ID NO: 49, at most 90% amino acid identity with amino acids 76-92 or amino acids 59-92 of SEQ ID NO: 49 or at most 95% amino acid identity with amino acids 76-92 or amino acids 59-92 of SEQ ID NO: 49.

In other aspects of this embodiment, a Gastrin comprises a polypeptide having, e.g., at most one, two, three, four, five, six, seven, eight, nine, 10 or 20 non-contiguous amino acid substitutions relative to amino acids 76-92 or amino acids 59-92 of SEQ ID NO: 49. In other aspects of this embodiment, a Gastrin comprises a polypeptide having, e.g., at least one, two, three, four, five, six, seven, eight, nine, 10 or 20 non-contiguous amino acid substitutions relative to amino acids 76-92 or amino acids 59-92 of SEQ ID NO: 49. In yet other aspects of this embodiment, a Gastrin comprises a polypeptide having, e.g., at most one, two, three, four, five, six, seven, eight, nine, 10 or 20 non-contiguous amino acid deletions relative to amino acids 76-92 or amino acids 59-92 of SEQ ID NO: 49. In other aspects of this embodiment, a Gastrin comprises a polypeptide having, e.g., at least one, two, three, four, five, six, seven, eight, nine, 10 or 20 non-contiguous amino acid deletions relative to amino acids 76-92 or amino acids 59-92 of SEQ ID NO: 49. In still other aspects of this embodiment, a Gastrin comprises a polypeptide having, e.g., at most one, two, three, four, five, six, seven, eight, nine, 10 or 20 non-contiguous amino acid additions relative to amino acids 76-92 or amino acids 59-92 of SEQ ID NO: 49. In other aspects of this embodiment, a Gastrin comprises a polypeptide having, e.g., at least one, two, three, four, five, six, seven, eight, nine, 10 or 20 non-contiguous amino acid additions relative to amino acids 76-92 or amino acids 59-92 of SEQ ID NO: 49.

In other aspects of this embodiment, a Gastrin comprises a polypeptide having, e.g., at most one, two, three, four, five, six, seven, eight, nine, 10 or 20 contiguous amino acid substitutions relative to amino acids 76-92 or amino acids 59-92 of SEQ ID NO: 49. In other aspects of this embodiment, a Gastrin comprises a polypeptide having, e.g., at least one, two, three, four, five, six, seven, eight, nine, 10 or 20 contiguous amino acid substitutions relative to amino acids 76-92 or amino acids 59-92 of SEQ ID NO: 49. In yet other aspects of this embodiment, a Gastrin comprises a polypeptide having, e.g., at most one, two, three, four, five, six, seven, eight, nine, 10 or 20 contiguous amino acid deletions relative to amino acids 76-92 or amino acids 59-92 of SEQ ID NO: 49. In other aspects of this embodiment, a Gastrin comprises a polypeptide having, e.g., at least one, two, three, four, five, six, seven, eight, nine, 10 or 20 contiguous amino acid deletions relative to amino acids 76-92 or amino acids 59-92 of SEQ ID NO: 49. In still other aspects of this embodiment, a Gastrin comprises a polypeptide having, e.g., at most one, two, three, four, five, six, seven, eight, nine, 10 or 20 contiguous amino acid additions relative to amino acids 76-92 or amino acids 59-92 of SEQ ID NO: 49. In other aspects of this embodiment, a Gastrin comprises a polypeptide having, e.g., at least one, two, three, four, five, six, seven, eight, nine, 10 or 20 contiguous amino acid additions relative to amino acids 76-92 or amino acids 59-92 of SEQ ID NO: 49.

In an embodiment, a binding domain comprises a GRP. In another embodiment, a binding domain comprises a GRP of SEQ ID NO: 50. In another embodiment, a binding domain is derived from a GRP. In another embodiment, a binding domain is derived from a GRP of SEQ ID NO: 50. In aspects of this embodiment, a binding domain is derived from a GRP comprising amino acids 41-50 or amino acids 24-50 of SEQ ID NO: 50.

In other aspects of this embodiment, a GRP comprises a polypeptide having, e.g., at least 70% amino acid identity with amino acids 41-50 or amino acids 24-50 of SEQ ID NO: 50, at least 75% amino acid identity with amino acids 41-50 or amino acids 24-50 of SEQ ID NO: 50, at least 80% amino acid identity with amino acids 41-50 or amino acids 24-50 of SEQ ID NO: 50, at least 85% amino acid identity with amino acids 41-50 or amino acids 24-50 of SEQ ID NO: 50, at least 90% amino acid identity with amino acids 41-50 or amino acids 24-50 of SEQ ID NO: 50 or at least 95% amino acid identity with amino acids 41-50 or amino acids 24-50 of SEQ ID NO: 50. In yet other aspects of this embodiment, a GRP comprises a polypeptide having, e.g., at most 70% amino acid identity with amino acids 41-50 or amino acids 24-50 of SEQ ID NO: 50, at most 75% amino acid identity with amino acids 41-50 or amino acids 24-50 of SEQ ID NO: 50, at most 80% amino acid identity with amino acids 41-50 or amino acids 24-50 of SEQ ID NO: 50, at most 85% amino acid identity with amino acids 41-50 or amino acids 24-50 of SEQ ID NO: 50, at most 90% amino acid identity with amino acids 41-50 or amino acids 24-50 of SEQ ID NO: 50 or at most 95% amino acid identity with amino acids 41-50 or amino acids 24-50 of SEQ ID NO: 50.

In other aspects of this embodiment, a GRP comprises a polypeptide having, e.g., at most one, two, three, four, five, six, seven, eight, nine, 10 or 20 non-contiguous amino acid substitutions relative to amino acids 41-50 or amino acids 24-50 of SEQ ID NO: 50. In other aspects of this embodiment, a GRP comprises a polypeptide having, e.g., at least one, two, three, four, five, six, seven, eight, nine, 10 or 20 non-contiguous amino acid substitutions relative to amino acids 41-50 or amino acids 24-50 of SEQ ID NO: 50. In yet other aspects of this embodiment, a GRP comprises a polypeptide having, e.g., at most one, two, three, four, five, six, seven, eight, nine, 10 or 20 non-contiguous amino acid deletions relative to amino acids 41-50 or amino acids 24-50 of SEQ ID NO: 50. In other aspects of this embodiment, a GRP comprises a polypeptide having, e.g., at least one, two, three, four, five, six, seven, eight, nine, 10 or 20 non-contiguous amino acid deletions relative to amino acids 41-50 or amino acids 24-50 of SEQ ID NO: 50. In still other aspects of this embodiment, a GRP comprises a polypeptide having, e.g., at most one, two, three, four, five, six, seven, eight, nine, 10 or 20 non-contiguous amino acid additions relative to amino acids 41-50 or amino acids 24-50 of SEQ ID NO: 50. In other aspects of this embodiment, a GRP comprises a polypeptide having, e.g., at least one, two, three, four, five, six, seven, eight, nine, 10 or 20 non-contiguous amino acid additions relative to amino acids 41-50 or amino acids 24-50 of SEQ ID NO: 50.

In other aspects of this embodiment, a GRP comprises a polypeptide having, e.g., at most one, two, three, four, five, six, seven, eight, nine, 10 or 20 contiguous amino acid substitutions relative to amino acids 41-50 or amino acids 24-50 of SEQ ID NO: 50. In other aspects of this embodiment, a GRP comprises a polypeptide having, e.g., at least one, two, three, four, five, six, seven, eight, nine, 10 or 20 contiguous amino acid substitutions relative to amino acids 41-50 or amino acids 24-50 of SEQ ID NO: 50. In yet other aspects of this embodiment, a GRP comprises a polypeptide having, e.g., at most one, two, three, four, five, six, seven, eight, nine, 10 or 20 contiguous amino acid deletions relative to amino acids 41-50 or amino acids 24-50 of SEQ ID NO: 50. In other aspects of this embodiment, a GRP comprises a polypeptide having, e.g., at least one, two, three, four, five, six, seven, eight, nine, 10 or 20 contiguous amino acid deletions relative to amino acids 41-50 or amino acids 24-50 of SEQ ID NO: 50. In still other aspects of this embodiment, a GRP comprises a polypeptide having, e.g., at most one, two, three, four, five, six, seven, eight, nine, 10 or 20 contiguous amino acid additions relative to amino acids 41-50 or amino acids 24-50 of SEQ ID NO: 50. In other aspects of this embodiment, a GRP comprises a polypeptide having, e.g., at least one, two, three, four, five, six, seven, eight, nine, 10 or 20 contiguous amino acid additions relative to amino acids 41-50 or amino acids 24-50 of SEQ ID NO: 50.

In an embodiment, a binding domain comprises a CCK. In another embodiment, a binding domain comprises a CCK of SEQ ID NO: 51. In another embodiment, a binding domain is derived from a CCK. In another embodiment, a binding domain is derived from a CCK of SEQ ID NO: 51. In an aspect of this embodiment, a binding domain is derived from a CCK comprising amino acids 99-112 of SEQ ID NO: 51.

In other aspects of this embodiment, a CCK comprises a polypeptide having, e.g., at least 70% amino acid identity with amino acids 99-112 of SEQ ID NO: 51, at least 75% amino acid identity with amino acids 99-112 of SEQ ID NO:

51, at least 80% amino acid identity with amino acids 99-112 of SEQ ID NO: 51, at least 85% amino acid identity with amino acids 99-112 of SEQ ID NO: 51, at least 90% amino acid identity with amino acids 99-112 of SEQ ID NO: 51 or at least 95% amino acid identity with amino acids 99-112 of SEQ ID NO: 51. In yet other aspects of this embodiment, a CCK comprises a polypeptide having, e.g., at most 70% amino acid identity with amino acids 99-112 of SEQ ID NO: 51, at most 75% amino acid identity with amino acids 99-112 of SEQ ID NO: 51, at most 80% amino acid identity with amino acids 99-112 of SEQ ID NO: 51, at most 85% amino acid identity with amino acids 99-112 of SEQ ID NO: 51, at most 90% amino acid identity with amino acids 99-112 of SEQ ID NO: 51 or at most 95% amino acid identity with amino acids 99-112 of SEQ ID NO: 51.

In other aspects of this embodiment, a CCK comprises a polypeptide having, e.g., at most one, two, three, four, five, six, seven, eight, nine, 10 or 20 non-contiguous amino acid substitutions relative to amino acids 99-112 of SEQ ID NO: 51. In other aspects of this embodiment, a CCK comprises a polypeptide having, e.g., at least one, two, three, four, five, six, seven, eight, nine, 10 or 20 non-contiguous amino acid substitutions relative to amino acids 99-112 of SEQ ID NO: 51. In yet other aspects of this embodiment, a CCK comprises a polypeptide having, e.g., at most one, two, three, four, five, six, seven, eight, nine, 10 or 20 non-contiguous amino acid deletions relative to amino acids 99-112 of SEQ ID NO: 51. In other aspects of this embodiment, a CCK comprises a polypeptide having, e.g., at least one, two, three, four, five, six, seven, eight, nine, 10 or 20 non-contiguous amino acid deletions relative to amino acids 99-112 of SEQ ID NO: 51. In still other aspects of this embodiment, a CCK comprises a polypeptide having, e.g., at most one, two, three, four, five, six, seven, eight, nine, 10 or 20 non-contiguous amino acid additions relative to amino acids 99-112 of SEQ ID NO: 51. In other aspects of this embodiment, a CCK comprises a polypeptide having, e.g., at least one, two, three, four, five, six, seven, eight, nine, 10 or 20 non-contiguous amino acid additions relative to amino acids 99-112 of SEQ ID NO: 51.

In other aspects of this embodiment, a CCK comprises a polypeptide having, e.g., at most one, two, three, four, five, six, seven, eight, nine, 10 or 20 contiguous amino acid substitutions relative to amino acids 99-112 of SEQ ID NO: 51. In other aspects of this embodiment, a CCK comprises a polypeptide having, e.g., at least one, two, three, four, five, six, seven, eight, nine, 10 or 20 contiguous amino acid substitutions relative to amino acids 99-112 of SEQ ID NO: 51. In yet other aspects of this embodiment, a CCK comprises a polypeptide having, e.g., at most one, two, three, four, five, six, seven, eight, nine, 10 or 20 contiguous amino acid deletions relative to amino acids 99-112 of SEQ ID NO: 51. In other aspects of this embodiment, a CCK comprises a polypeptide having, e.g., at least one, two, three, four, five, six, seven, eight, nine, 10 or 20 contiguous amino acid deletions relative to amino acids 99-112 of SEQ ID NO: 51. In still other aspects of this embodiment, a CCK comprises a polypeptide having, e.g., at most one, two, three, four, five, six, seven, eight, nine, 10 or 20 contiguous amino acid additions relative to amino acids 99-112 of SEQ ID NO: 51. In other aspects of this embodiment, a CCK comprises a polypeptide having, e.g., at least one, two, three, four, five, six, seven, eight, nine, 10 or 20 contiguous amino acid additions relative to amino acids 99-112 of SEQ ID NO: 51.

Another example of a binding domain disclosed in the present specification is, e.g., neurohormones, such as, e.g., corticotropin-releasing hormone (CCRH) or parathyroid hormone (PTH).

Thus, in an embodiment, a binding domain comprises a CCRH. In another embodiment, a binding domain comprises a CCRH of SEQ ID NO: 52. In another embodiment, a binding domain is derived from a CCRH. In another embodiment, a binding domain is derived from a CCRH of SEQ ID NO: 52. In aspects of this embodiment, a binding domain is derived from a CCRH comprising amino acids 159-193 or amino acids 154-194 of SEQ ID NO: 52.

In other aspects of this embodiment, a CCRH comprises a polypeptide having, e.g., at least 70% amino acid identity with amino acids 159-193 or amino acids 154-194 of SEQ ID NO: 52, at least 75% amino acid identity with amino acids 159-193 or amino acids 154-194 of SEQ ID NO: 52, at least 80% amino acid identity with amino acids 159-193 or amino acids 154-194 of SEQ ID NO: 52, at least 85% amino acid identity with amino acids 159-193 or amino acids 154-194 of SEQ ID NO: 52, at least 90% amino acid identity with amino acids 159-193 or amino acids 154-194 of SEQ ID NO: 52 or at least 95% amino acid identity with amino acids 159-193 or amino acids 154-194 of SEQ ID NO: 52. In yet other aspects of this embodiment, a CCRH comprises a polypeptide having, e.g., at most 70% amino acid identity with amino acids 159-193 or amino acids 154-194 of SEQ ID NO: 52, at most 75% amino acid identity with amino acids 159-193 or amino acids 154-194 of SEQ ID NO: 52, at most 80% amino acid identity with amino acids 159-193 or amino acids 154-194 of SEQ ID NO: 52, at most 85% amino acid identity with amino acids 159-193 or amino acids 154-194 of SEQ ID NO: 52, at most 90% amino acid identity with amino acids 159-193 or amino acids 154-194 of SEQ ID NO: 52 or at most 95% amino acid identity with amino acids 159-193 or amino acids 154-194 of SEQ ID NO: 52.

In other aspects of this embodiment, a CCRH comprises a polypeptide having, e.g., at most one, two, three, four, five, six, seven, eight, nine, 10 or 20 non-contiguous amino acid substitutions relative to amino acids 159-193 or amino acids 154-194 of SEQ ID NO: 52. In other aspects of this embodiment, a CCRH comprises a polypeptide having, e.g., at least one, two, three, four, five, six, seven, eight, nine, 10 or 20 non-contiguous amino acid substitutions relative to amino acids 159-193 or amino acids 154-194 of SEQ ID NO: 52. In yet other aspects of this embodiment, a CCRH comprises a polypeptide having, e.g., at most one, two, three, four, five, six, seven, eight, nine, 10 or 20 non-contiguous amino acid deletions relative to amino acids 159-193 or amino acids 154-194 of SEQ ID NO: 52. In other aspects of this embodiment, a CCRH comprises a polypeptide having, e.g., at least one, two, three, four, five, six, seven, eight, nine, 10 or 20 non-contiguous amino acid deletions relative to amino acids 159-193 or amino acids 154-194 of SEQ ID NO: 52. In still other aspects of this embodiment, a CCRH comprises a polypeptide having, e.g., at most one, two, three, four, five, six, seven, eight, nine, 10 or 20 non-contiguous amino acid additions relative to amino acids 159-193 or amino acids 154-194 of SEQ ID NO: 52. In other aspects of this embodiment, a CCRH comprises a polypeptide having, e.g., at least one, two, three, four, five, six, seven, eight, nine, 10 or 20 non-contiguous amino acid additions relative to amino acids 159-193 or amino acids 154-194 of SEQ ID NO: 52.

In other aspects of this embodiment, a CCRH comprises a polypeptide having, e.g., at most one, two, three, four, five, six, seven, eight, nine, 10 or 20 contiguous amino acid substitutions relative to amino acids 154-194 of SEQ ID NO: 52. In other aspects of this embodiment, a CCRH comprises a polypeptide having, e.g., at least one, two, three, four, five, six, seven, eight, nine, 10 or 20 contiguous amino acid substitutions relative to amino acids 159-193 or amino acids 154-194 of SEQ ID NO: 52. In yet other aspects of this embodiment, a CCRH comprises a polypeptide having, e.g., at most one, two, three, four, five, six, seven, eight, nine, 10 or 20 contiguous amino acid deletions relative to amino acids 159-193 or amino acids 154-194 of SEQ ID NO: 52. In other aspects of this embodiment, a CCRH comprises a polypeptide having, e.g., at least one, two, three, four, five, six, seven, eight, nine, 10 or 20 contiguous amino acid deletions relative to amino acids 159-193 or amino acids 154-194 of SEQ ID NO: 52. In still other aspects of this embodiment, a CCRH comprises a polypeptide having, e.g., at most one, two, three, four, five, six, seven, eight, nine, 10 or 20 contiguous amino acid additions relative to amino acids 159-193 or amino acids 154-194 of SEQ ID NO: 52. In other aspects of this embodiment, a CCRH comprises a polypeptide having, e.g., at least one, two, three, four, five, six, seven, eight, nine, 10 or 20 contiguous amino acid additions relative to amino acids 159-193 or amino acids 154-194 of SEQ ID NO: 52.

In an embodiment, a binding domain comprises a PTH. In another embodiment, a binding domain comprises a PTH of SEQ ID NO: 53. In another embodiment, a binding domain is derived from a PTH. In another embodiment, a binding domain is derived from a PTH of SEQ ID NO: 53. In aspects of this embodiment, a binding domain is derived from a PTH comprising amino acids 35-70 or amino acids 145-177 of SEQ ID NO: 53.

In other aspects of this embodiment, a PTH comprises a polypeptide having, e.g., at least 70% amino acid identity with amino acids 35-70 or amino acids 145-177 of SEQ ID NO: 53, at least 75% amino acid identity with amino acids 35-70 or amino acids 145-177 of SEQ ID NO: 53, at least 80% amino acid identity with amino acids 35-70 or amino acids 145-177 of SEQ ID NO: 53, at least 85% amino acid identity with amino acids 35-70 or amino acids 145-177 of SEQ ID NO: 53, at least 90% amino acid identity with amino acids 35-70 or amino acids 145-177 of SEQ ID NO: 53 or at least 95% amino acid identity with amino acids 35-70 or amino acids 145-177 of SEQ ID NO: 53. In yet other aspects of this embodiment, a PTH comprises a polypeptide having, e.g., at most 70% amino acid identity with amino acids 35-70 or amino acids 145-177 of SEQ ID NO: 53, at most 75% amino acid identity with amino acids 35-70 or amino acids 145-177 of SEQ ID NO: 53, at most 80% amino acid identity with amino acids 35-70 or amino acids 145-177 of SEQ ID NO: 53, at most 85% amino acid identity with amino acids 35-70 or amino acids 145-177 of SEQ ID NO: 53, at most 90% amino acid identity with amino acids 35-70 or amino acids 145-177 of SEQ ID NO: 53 or at most 95% amino acid identity with amino acids 35-70 or amino acids 145-177 of SEQ ID NO: 53.

In other aspects of this embodiment, a PTH comprises a polypeptide having, e.g., at most one, two, three, four, five, six, seven, eight, nine, 10 or 20 non-contiguous amino acid substitutions relative to amino acids 35-70 or amino acids 145-177 of SEQ ID NO: 53. In other aspects of this embodiment, a PTH comprises a polypeptide having, e.g., at least one, two, three, four, five, six, seven, eight, nine, 10 or 20 non-contiguous amino acid substitutions relative to amino acids 35-70 or amino acids 145-177 of SEQ ID NO: 53. In yet other aspects of this embodiment, a PTH comprises a polypeptide having, e.g., at most one, two, three, four, five, six, seven, eight, nine, 10 or 20 non-contiguous amino acid deletions relative to amino acids 35-70 or amino acids 145-177 of SEQ ID NO: 53. In other aspects of this embodiment, a PTH comprises a polypeptide having, e.g., at least one, two, three, four, five, six, seven, eight, nine, 10 or 20 non-contiguous amino acid deletions relative to amino acids 35-70 or amino acids 145-177 of SEQ ID NO: 53. In still other aspects of this embodiment, a PTH comprises a polypeptide having, e.g., at most one, two, three, four, five, six, seven, eight, nine, 10 or 20 non-contiguous amino acid additions relative to amino acids 35-70 or amino acids 145-177 of SEQ ID NO: 53. In other aspects of this embodiment, a PTH comprises a polypeptide having, e.g., at least one, two, three, four, five, six, seven, eight, nine, 10 or 20 non-contiguous amino acid additions relative to amino acids 35-70 or amino acids 145-177 of SEQ ID NO: 53.

In other aspects of this embodiment, a PTH comprises a polypeptide having, e.g., at most one, two, three, four, five, six, seven, eight, nine, 10 or 20 contiguous amino acid substitutions relative to amino acids 35-70 or amino acids 145-177 of SEQ ID NO: 53. In other aspects of this embodiment, a PTH comprises a polypeptide having, e.g., at least one, two, three, four, five, six, seven, eight, nine, 10 or 20 contiguous amino acid substitutions relative to amino acids 35-70 or amino acids 145-177 of SEQ ID NO: 53. In yet other aspects of this embodiment, a PTH comprises a polypeptide having, e.g., at most one, two, three, four, five, six, seven, eight, nine, 10 or 20 contiguous amino acid deletions relative to amino acids 35-70 or amino acids 145-177 of SEQ ID NO: 53. In other aspects of this embodiment, a PTH comprises a polypeptide having, e.g., at least one, two, three, four, five, six, seven, eight, nine, 10 or 20 contiguous amino acid deletions relative to amino acids 35-70 or amino acids 145-177 of SEQ ID NO: 53. In still other aspects of this embodiment, a PTH comprises a polypeptide having, e.g., at most one, two, three, four, five, six, seven, eight, nine, 10 or 20 contiguous amino acid additions relative to amino acids 35-70 or amino acids 145-177 of SEQ ID NO: 53. In other aspects of this embodiment, a PTH comprises a polypeptide having, e.g., at least one, two, three, four, five, six, seven, eight, nine, 10 or 20 contiguous amino acid additions relative to amino acids 35-70 or amino acids 145-177 of SEQ ID NO: 53.

Another example of a binding domain disclosed in the present specification is, e.g., neuroregulatory cytokines, such as, e.g., ciliary neurotrophic factor (CNTF), glycophorin-A (GPA), leukemia inhibitory factor (LIF), also known as cholinergic differentiation factor (CDF), interleukins (ILs), like IL1, IL2, IL6, IL8 and IL10, onostatin M, cardiotrophin-1 (CT-1), cardiotrophin-like cytokine (CLC), or neuroleukin, also known as glucose phosphate isomerase (GPI), autocrine motility factor (AMF), maturation and differentiation factor (MF).

Thus, in an embodiment, a binding domain comprises a CNTF. In another embodiment, a binding domain comprises a CNTF of SEQ ID NO: 54. In another embodiment, a binding domain is derived from a CNTF. In another embodiment, a binding domain is derived from a CNTF of SEQ ID NO: 54. In aspects of this embodiment, a CNTF comprises a polypeptide having, e.g., at least 70% amino acid identity with the amino acid sequence of SEQ ID NO: 54, at least 75% amino acid identity with the amino acid sequence of SEQ ID NO: 54, at least 80% amino acid identity with the amino acid sequence of SEQ ID NO: 54, at least 85% amino acid identity with the amino acid sequence of SEQ ID NO: 54, at least 90% amino acid identity with the amino acid sequence of SEQ ID NO: 54 or at least 95% amino acid identity with the amino acid sequence of SEQ ID NO: 54. In yet other aspects of this embodiment, a CNTF comprises a polypeptide having, e.g., at most 70% amino acid identity with the amino acid sequence of SEQ ID NO: 54, at most 75% amino acid identity with the amino acid sequence of SEQ ID NO: 54, at most 80% amino acid identity with the amino acid sequence of SEQ ID NO: 54, at most 85% amino acid identity with the amino acid sequence of SEQ ID NO: 54, at most 90% amino acid identity with the amino acid sequence of SEQ ID NO: 54 or at most 95% amino acid identity with the amino acid sequence of SEQ ID NO: 54.

In other aspects of this embodiment, a CNTF comprises a polypeptide having, e.g., at most one, two, three, four, five, six, seven, eight, nine, 10 or 20 non-contiguous amino acid substitutions relative to the amino acid sequence of SEQ ID NO: 54. In other aspects of this embodiment, a CNTF comprises a polypeptide having, e.g., at least one, two, three, four, five, six, seven, eight, nine, 10 or 20 non-contiguous amino acid substitutions relative to the amino acid sequence of SEQ ID NO: 54. In yet other aspects of this embodiment, a CNTF comprises a polypeptide having, e.g., at most one, two, three, four, five, six, seven, eight, nine, 10 or 20 non-contiguous amino acid deletions relative to the amino acid sequence of SEQ ID NO: 54. In other aspects of this embodiment, a CNTF comprises a polypeptide having, e.g., at least one, two, three, four, five, six, seven, eight, nine, 10 or 20 non-contiguous amino acid deletions relative to the amino acid sequence of SEQ ID NO: 54. In still other aspects of this embodiment, a CNTF comprises a polypeptide having, e.g., at most one, two, three, four, five, six, seven, eight, nine, 10 or 20 non-contiguous amino acid additions relative to the amino acid sequence of SEQ ID NO: 54. In other aspects of this embodiment, a CNTF comprises a polypeptide having, e.g., at least one, two, three, four, five, six, seven, eight, nine, 10 or 20 non-contiguous amino acid additions relative to the amino acid sequence of SEQ ID NO: 54.

In other aspects of this embodiment, a CNTF comprises a polypeptide having, e.g., at most one, two, three, four, five, six, seven, eight, nine, 10 or 20 contiguous amino acid substitutions relative to the amino acid sequence of SEQ ID NO: 54. In other aspects of this embodiment, a CNTF comprises a polypeptide having, e.g., at least one, two, three, four, five, six, seven, eight, nine, 10 or 20 contiguous amino acid substitutions relative to the amino acid sequence of SEQ ID NO: 54. In yet other aspects of this embodiment, a CNTF comprises a polypeptide having, e.g., at most one, two, three, four, five, six, seven, eight, nine, 10 or 20 contiguous amino acid deletions relative to the amino acid sequence of SEQ ID NO: 54. In other aspects of this embodiment, a CNTF comprises a polypeptide having, e.g., at least one, two, three, four, five, six, seven, eight, nine, 10 or 20 contiguous amino acid deletions relative to the amino acid sequence of SEQ ID NO: 54. In still other aspects of this embodiment, a CNTF comprises a polypeptide having, e.g., at most one, two, three, four, five, six, seven, eight, nine, 10 or 20 contiguous amino acid additions relative to the amino acid sequence of SEQ ID NO: 54. In other aspects of this embodiment, a CNTF comprises a polypeptide having, e.g., at least one, two, three, four, five, six, seven, eight, nine, 10 or 20 contiguous amino acid additions relative to the amino acid sequence of SEQ ID NO: 54.

In an embodiment, a binding domain comprises a GPA. In another embodiment, a binding domain comprises a GPA of SEQ ID NO: 55. In another embodiment, a binding domain is derived from a GPA. In another embodiment, a binding domain is derived from a GPA of SEQ ID NO: 55. In aspects of this embodiment, a GPA comprises a polypeptide having, e.g., at least 70% amino acid identity with the amino acid sequence of SEQ ID NO: 55, at least 75% amino acid identity with the amino acid sequence of SEQ ID NO: 55, at least 80% amino acid identity with the amino acid sequence of SEQ ID NO: 55, at least 85% amino acid identity with the amino acid sequence of SEQ ID NO: 55, at least 90% amino acid identity with the amino acid sequence of SEQ ID NO: 55 or at least 95% amino acid identity with the amino acid sequence of SEQ ID NO: 55. In yet other aspects of this embodiment, a GPA comprises a polypeptide having, e.g., at most 70% amino acid identity with the amino acid sequence of SEQ ID NO: 55, at most 75% amino acid identity with the amino acid sequence of SEQ ID NO: 55, at most 80% amino acid identity with the amino acid sequence of SEQ ID NO: 55, at most 85% amino acid identity with the amino acid sequence of SEQ ID NO: 55, at most 90% amino acid identity with the amino acid sequence of SEQ ID NO: 55 or at most 95% amino acid identity with the amino acid sequence of SEQ ID NO: 55.

In other aspects of this embodiment, a GPA comprises a polypeptide having, e.g., at most one, two, three, four, five, six, seven, eight, nine, 10 or 20 non-contiguous amino acid substitutions relative to the amino acid sequence of SEQ ID NO: 55. In other aspects of this embodiment, a GPA comprises a polypeptide having, e.g., at least one, two, three, four, five, six, seven, eight, nine, 10 or 20 non-contiguous amino acid substitutions relative to the amino acid sequence of SEQ ID NO: 55. In yet other aspects of this embodiment, a GPA comprises a polypeptide having, e.g., at most one, two, three, four, five, six, seven, eight, nine, 10 or 20 non-contiguous amino acid deletions relative to the amino acid sequence of SEQ ID NO: 55. In other aspects of this embodiment, a GPA comprises a polypeptide having, e.g., at least one, two, three, four, five, six, seven, eight, nine, 10 or 20 non-contiguous amino acid deletions relative to the amino acid sequence of SEQ ID NO: 55. In still other aspects of this embodiment, a GPA comprises a polypeptide having, e.g., at most one, two, three, four, five, six, seven, eight, nine, 10 or 20 non-contiguous amino acid additions relative to the amino acid sequence of SEQ ID NO: 55. In other aspects of this embodiment, a GPA comprises a polypeptide having, e.g., at least one, two, three, four, five, six, seven, eight, nine, 10 or 20 non-contiguous amino acid additions relative to the amino acid sequence of SEQ ID NO: 55.

In other aspects of this embodiment, a GPA comprises a polypeptide having, e.g., at most one, two, three, four, five, six, seven, eight, nine, 10 or 20 contiguous amino acid substitutions relative to the amino acid sequence of SEQ ID NO: 55. In other aspects of this embodiment, a GPA comprises a polypeptide having, e.g., at least one, two, three, four, five, six, seven, eight, nine, 10 or 20 contiguous amino acid substitutions relative to the amino acid sequence of SEQ ID NO: 55. In yet other aspects of this embodiment, a GPA comprises a polypeptide having, e.g., at most one, two, three, four, five, six, seven, eight, nine, 10 or 20 contiguous amino acid deletions relative to the amino acid sequence of SEQ ID NO: 55. In other aspects of this embodiment, a GPA comprises a polypeptide having, e.g., at least one, two, three, four, five, six, seven, eight, nine, 10 or 20 contiguous amino acid deletions relative to the amino acid sequence of SEQ ID NO: 55. In still other aspects of this embodiment, a GPA comprises a polypeptide having, e.g., at most one, two, three, four, five, six, seven, eight, nine, 10 or 20 contiguous amino acid additions relative to the amino acid sequence of SEQ ID NO: 55. In other aspects of this embodiment, a GPA comprises a polypeptide having, e.g., at least one, two, three, four, five, six, seven, eight, nine, 10 or 20 contiguous amino acid additions relative to the amino acid sequence of SEQ ID NO: 55.

In an embodiment, a binding domain comprises a LIF. In another embodiment, a binding domain comprises a LIF of SEQ ID NO: 56. In another embodiment, a binding domain is derived from a LIF. In another embodiment, a binding domain is derived from a LIF of SEQ ID NO: 56. In aspects of this embodiment, a LIF comprises a polypeptide having, e.g., at least 70% amino acid identity with the amino acid sequence of SEQ ID NO: 56, at least 75% amino acid identity with the amino acid sequence of SEQ ID NO: 56, at least 80% amino acid identity with the amino acid sequence of SEQ ID NO: 56, at least 85% amino acid identity with the amino acid sequence of SEQ ID NO: 56, at least 90% amino acid identity with the amino acid sequence of SEQ ID NO: 56 or at least 95% amino acid identity with the amino acid sequence of SEQ ID NO: 56. In yet other aspects of this embodiment, a LIF comprises a polypeptide having, e.g., at most 70% amino acid identity with the amino acid sequence of SEQ ID NO: 56, at most 75% amino acid identity with the amino acid sequence of SEQ ID NO: 56, at most 80% amino acid identity with the amino acid sequence of SEQ ID NO: 56, at most 85% amino acid identity with the amino acid sequence of SEQ ID NO: 56, at most 90% amino acid identity with the amino acid sequence of SEQ ID NO: 56 or at most 95% amino acid identity with the amino acid sequence of SEQ ID NO: 56.

In other aspects of this embodiment, a LIF comprises a polypeptide having, e.g., at most one, two, three, four, five, six, seven, eight, nine, 10 or 20 non-contiguous amino acid substitutions relative to the amino acid sequence of SEQ ID NO: 56. In other aspects of this embodiment, a LIF comprises a polypeptide having, e.g., at least one, two, three, four, five, six, seven, eight, nine, 10 or 20 non-contiguous amino acid substitutions relative to the amino acid sequence of SEQ ID NO: 56. In yet other aspects of this embodiment, a LIF comprises a polypeptide having, e.g., at most one, two, three, four, five, six, seven, eight, nine, 10 or 20 non-contiguous amino acid deletions relative to the amino acid sequence of SEQ ID NO: 56. In other aspects of this embodiment, a LIF comprises a polypeptide having, e.g., at least one, two, three, four, five, six, seven, eight, nine, 10 or 20 non-contiguous amino acid deletions relative to the amino acid sequence of SEQ ID NO: 56. In still other aspects of this embodiment, a LIF comprises a polypeptide having, e.g., at most one, two, three, four, five, six, seven, eight, nine, 10 or 20 non-contiguous amino acid additions relative to the amino acid sequence of SEQ ID NO: 56. In other aspects of this embodiment, a LIF comprises a polypeptide having, e.g., at least one, two, three, four, five, six, seven, eight, nine, 10 or 20 non-contiguous amino acid additions relative to the amino acid sequence of SEQ ID NO: 56.

In other aspects of this embodiment, a LIF comprises a polypeptide having, e.g., at most one, two, three, four, five, six, seven, eight, nine, 10 or 20 contiguous amino acid substitutions relative to the amino acid sequence of SEQ ID NO: 56. In other aspects of this embodiment, a LIF comprises a polypeptide having, e.g., at least one, two, three, four, five, six, seven, eight, nine, 10 or 20 contiguous amino acid substitutions relative to the amino acid sequence of SEQ ID NO: 56. In yet other aspects of this embodiment, a LIF comprises a polypeptide having, e.g., at most one, two, three, four, five, six, seven, eight, nine, 10 or 20 contiguous amino acid deletions relative to the amino acid sequence of SEQ ID NO: 56. In other aspects of this embodiment, a LIF comprises a polypeptide having, e.g., at least one, two, three, four, five, six, seven, eight, nine, 10 or 20 contiguous amino acid deletions relative to the amino acid sequence of SEQ ID NO: 56. In still other aspects of this embodiment, a LIF comprises a polypeptide having, e.g., at most one, two, three, four, five, six, seven, eight, nine, 10 or 20 contiguous amino acid additions relative to the amino acid sequence of SEQ ID NO: 56. In other aspects of this embodiment, a LIF comprises a polypeptide having, e.g., at least one, two, three, four, five, six, seven, eight, nine, 10 or 20 contiguous amino acid additions relative to the amino acid sequence of SEQ ID NO: 56.

In an embodiment, a binding domain comprises a CT-1. In another embodiment, a binding domain comprises a CT-1 of SEQ ID NO: 57. In another embodiment, a binding domain is derived from a CT-1. In another embodiment, a binding domain is derived from a CT-1 of SEQ ID NO: 57. In aspects of this embodiment, a CT-1 comprises a polypeptide having, e.g., at least 70% amino acid identity with the amino acid sequence of SEQ ID NO: 57, at least 75% amino acid identity with the amino acid sequence of SEQ ID NO: 57, at least 80% amino acid identity with the amino acid sequence of SEQ ID NO: 57, at least 85% amino acid identity with the amino acid sequence of SEQ ID NO: 57, at least 90% amino acid identity with the amino acid sequence of SEQ ID NO: 57 or at least 95% amino acid identity with the amino acid sequence of SEQ ID NO: 57. In yet other aspects of this embodiment, a CT-1 comprises a polypeptide having, e.g., at most 70% amino acid identity with the amino acid sequence of SEQ ID NO: 57, at most 75% amino acid identity with the amino acid sequence of SEQ ID NO: 57, at most 80% amino acid identity with the amino acid sequence of SEQ ID NO: 57, at most 85% amino acid identity with the amino acid sequence of SEQ ID NO: 57, at most 90% amino acid identity with the amino acid sequence of SEQ ID NO: 57 or at most 95% amino acid identity with the amino acid sequence of SEQ ID NO: 57.

In other aspects of this embodiment, a CT-1 comprises a polypeptide having, e.g., at most one, two, three, four, five, six, seven, eight, nine, 10 or 20 non-contiguous amino acid substitutions relative to the amino acid sequence of SEQ ID NO: 57. In other aspects of this embodiment, a CT-1 comprises a polypeptide having, e.g., at least one, two, three, four, five, six, seven, eight, nine, 10 or 20 non-contiguous amino acid substitutions relative to the amino acid sequence of SEQ ID NO: 57. In yet other aspects of this embodiment, a CT-1 comprises a polypeptide having, e.g., at most one, two, three, four, five, six, seven, eight, nine, 10 or 20 non-contiguous amino acid deletions relative to the amino acid sequence of SEQ ID NO: 57. In other aspects of this embodiment, a CT-1 comprises a polypeptide having, e.g., at least one, two, three, four, five, six, seven, eight, nine, 10 or 20 non-contiguous amino acid deletions relative to the amino acid sequence of SEQ ID NO: 57. In still other aspects of this embodiment, a CT-1 comprises a polypeptide having, e.g., at most one, two, three, four, five, six, seven, eight, nine, 10 or 20 non-contiguous amino acid additions relative to the amino acid sequence of SEQ ID NO: 57. In other aspects of this embodiment, a CT-1 comprises a polypeptide having, e.g., at least one, two, three, four, five, six, seven, eight, nine, 10 or 20 non-contiguous amino acid additions relative to the amino acid sequence of SEQ ID NO: 57.

In other aspects of this embodiment, a CT-1 comprises a polypeptide having, e.g., at most one, two, three, four, five, six, seven, eight, nine, 10 or 20 contiguous amino acid substitutions relative to the amino acid sequence of SEQ ID NO: 57. In other aspects of this embodiment, a CT-1 comprises a polypeptide having, e.g., at least one, two, three, four, five, six, seven, eight, nine, 10 or 20 contiguous amino acid substitutions relative to the amino acid sequence of SEQ ID NO: 57. In yet other aspects of this embodiment, a CT-1 comprises a polypeptide having, e.g., at most one, two, three, four, five, six, seven, eight, nine, 10 or 20 contiguous amino acid deletions relative to the amino acid sequence of SEQ ID NO: 57. In other aspects of this embodiment, a CT-1 comprises a polypeptide having, e.g., at least one, two, three, four, five, six, seven, eight, nine, 10 or 20 contiguous amino acid deletions relative to the amino acid sequence of SEQ ID NO: 57. In still other aspects of this embodiment, a CT-1 comprises a polypeptide having, e.g., at most one, two, three, four, five, six, seven, eight, nine, 10 or 20 contiguous amino acid additions relative to the amino acid sequence of SEQ ID NO: 57. In other aspects of this embodiment, a CT-1 comprises a polypeptide having, e.g., at least one, two, three, four, five, six, seven, eight, nine, 10 or 20 contiguous amino acid additions relative to the amino acid sequence of SEQ ID NO: 57.

In an embodiment, a binding domain comprises a CLC. In another embodiment, a binding domain comprises a CLC of SEQ ID NO: 58. In another embodiment, a binding domain is derived from a CLC. In another embodiment, a binding domain is derived from a CLC of SEQ ID NO: 58. In aspects of this embodiment, a CLC comprises a polypeptide having, e.g., at least 70% amino acid identity with the amino acid sequence of SEQ ID NO: 58, at least 75% amino acid identity with the amino acid sequence of SEQ ID NO: 58, at least 80% amino acid identity with the amino acid sequence of SEQ ID NO: 58, at least 85% amino acid identity with the amino acid sequence of SEQ ID NO: 58, at least 90% amino acid identity with the amino acid sequence of SEQ ID NO: 58 or at least 95% amino acid identity with the amino acid sequence of SEQ ID NO: 58. In yet other aspects of this embodiment, a CLC comprises a polypeptide having, e.g., at most 70% amino acid identity with the amino acid sequence of SEQ ID NO: 58, at most 75% amino acid identity with the amino acid sequence of SEQ ID NO: 58, at most 80% amino acid identity with the amino acid sequence of SEQ ID NO: 58, at most 85% amino acid identity with the amino acid sequence of SEQ ID NO: 58, at most 90% amino acid identity with the amino acid sequence of SEQ ID NO: 58 or at most 95% amino acid identity with the amino acid sequence of SEQ ID NO: 58.

In other aspects of this embodiment, a CLC comprises a polypeptide having, e.g., at most one, two, three, four, five, six, seven, eight, nine, 10 or 20 non-contiguous amino acid substitutions relative to the amino acid sequence of SEQ ID NO: 58. In other aspects of this embodiment, a CLC comprises a polypeptide having, e.g., at least one, two, three, four, five, six, seven, eight, nine, 10 or 20 non-contiguous amino acid substitutions relative to the amino acid sequence of SEQ ID NO: 58. In yet other aspects of this embodiment, a CLC comprises a polypeptide having, e.g., at most one, two, three, four, five, six, seven, eight, nine, 10 or 20 non-contiguous amino acid deletions relative to the amino acid sequence of SEQ ID NO: 58. In other aspects of this embodiment, a CLC comprises a polypeptide having, e.g., at least one, two, three, four, five, six, seven, eight, nine, 10 or 20 non-contiguous amino acid deletions relative to the amino acid sequence of SEQ ID NO: 58. In still other aspects of this embodiment, a CLC comprises a polypeptide having, e.g., at most one, two, three, four, five, six, seven, eight, nine, 10 or 20 non-contiguous amino acid additions relative to the amino acid sequence of SEQ ID NO: 58. In other aspects of this embodiment, a CLC comprises a polypeptide having, e.g., at least one, two, three, four, five, six, seven, eight, nine, 10 or 20 non-contiguous amino acid additions relative to the amino acid sequence of SEQ ID NO: 58.

In other aspects of this embodiment, a CLC comprises a polypeptide having, e.g., at most one, two, three, four, five, six, seven, eight, nine, 10 or 20 contiguous amino acid substitutions relative to the amino acid sequence of SEQ ID NO: 58. In other aspects of this embodiment, a CLC comprises a polypeptide having, e.g., at least one, two, three, four, five, six, seven, eight, nine, 10 or 20 contiguous amino acid substitutions relative to the amino acid sequence of SEQ ID NO: 58. In yet other aspects of this embodiment, a CLC comprises a polypeptide having, e.g., at most one, two, three, four, five, six, seven, eight, nine, 10 or 20 contiguous amino acid deletions relative to the amino acid sequence of SEQ ID NO: 58. In other aspects of this embodiment, a CLC comprises a polypeptide having, e.g., at least one, two, three, four, five, six, seven, eight, nine, 10 or 20 contiguous amino acid deletions relative to the amino acid sequence of SEQ ID NO: 58. In still other aspects of this embodiment, a CLC comprises a polypeptide having, e.g., at most one, two, three, four, five, six, seven, eight, nine, 10 or 20 contiguous amino acid additions relative to the amino acid sequence of SEQ ID NO: 58. In other aspects of this embodiment, a CLC comprises a polypeptide having, e.g., at least one, two, three, four, five, six, seven, eight, nine, 10 or 20 contiguous amino acid additions relative to the amino acid sequence of SEQ ID NO: 58.

In an embodiment, a binding domain comprises a IL-1. In another embodiment, a binding domain comprises a IL-1 of SEQ ID NO: 59. In another embodiment, a binding domain is derived from an IL-1. In another embodiment, a binding domain is derived from an IL-1 of SEQ ID NO: 59. In an aspect of this embodiment, a binding domain is derived from an IL-1 comprising amino acids 123-265 of SEQ ID NO: 59.

In other aspects of this embodiment, an IL-1 comprises a polypeptide having, e.g., at least 70% amino acid identity with amino acids 123-265 of SEQ ID NO: 59, at least 75% amino acid identity with amino acids 123-265 of SEQ ID NO: 59, at least 80% amino acid identity with amino acids 123-265 of SEQ ID NO: 59, at least 85% amino acid identity with amino acids 123-265 of SEQ ID NO: 59, at least 90% amino acid identity with amino acids 123-265 of SEQ ID NO: 59 or at least 95% amino acid identity with amino acids 123-265 of SEQ ID NO: 59. In yet other aspects of this embodiment, an IL-1 comprises a polypeptide having, e.g., at most 70% amino acid identity with amino acids 123-265 of SEQ ID NO: 59, at most 75% amino acid identity with amino acids 123-265 of SEQ ID NO: 59, at most 80% amino acid identity with amino acids 123-265 of SEQ ID NO: 59, at most 85% amino acid identity with amino acids 123-265 of SEQ ID NO: 59, at most 90% amino acid identity with amino acids 123-265 of SEQ ID NO: 59 or at most 95% amino acid identity with amino acids 123-265 of SEQ ID NO: 59.

In other aspects of this embodiment, an IL-1 comprises a polypeptide having, e.g., at most one, two, three, four, five, six, seven, eight, nine, 10 or 20 non-contiguous amino acid substitutions relative to amino acids 123-265 of SEQ ID NO: 59. In other aspects of this embodiment, an IL-1 comprises a polypeptide having, e.g., at least one, two, three, four, five, six, seven, eight, nine, 10 or 20 non-contiguous amino acid substitutions relative to amino acids 123-265 of SEQ ID NO: 59. In yet other aspects of this embodiment, an IL-1 comprises a polypeptide having, e.g., at most one, two, three, four, five, six, seven, eight, nine, 10 or 20 non-contiguous amino acid deletions relative to amino acids 123-265 of SEQ ID NO: 59. In other aspects of this embodiment, an IL-1 comprises a polypeptide having, e.g., at least one, two, three, four, five, six, seven, eight, nine, 10 or 20 non-contiguous amino acid deletions relative to amino acids 123-265 of SEQ ID NO: 59. In still other aspects of this embodiment, an IL-1 comprises a polypeptide having, e.g., at most one, two, three, four, five, six, seven, eight, nine, 10 or 20 non-contiguous amino acid additions relative to amino acids 123-265 of SEQ ID NO: 59. In other aspects of this embodiment, an IL-1 comprises a polypeptide having, e.g., at least one, two, three, four, five, six, seven, eight, nine, 10 or 20 non-contiguous amino acid additions relative to amino acids 123-265 of SEQ ID NO: 59.

In other aspects of this embodiment, an IL-1 comprises a polypeptide having, e.g., at most one, two, three, four, five, six, seven, eight, nine, 10 or 20 contiguous amino acid substitutions relative to amino acids 123-265 of SEQ ID NO: 59. In other aspects of this embodiment, an IL-1 comprises a polypeptide having, e.g., at least one, two, three, four, five, six, seven, eight, nine, 10 or 20 contiguous amino acid substitutions relative to amino acids 123-265 of SEQ ID NO: 59. In yet other aspects of this embodiment, an IL-1 comprises a polypeptide having, e.g., at most one, two, three, four, five, six, seven, eight, nine, 10 or 20 contiguous amino acid deletions relative to amino acids 123-265 of SEQ ID NO: 59. In other aspects of this embodiment, an IL-1 comprises a polypeptide having, e.g., at least one, two, three, four, five, six, seven, eight, nine, 10 or 20 contiguous amino acid deletions relative to amino acids 123-265 of SEQ ID NO: 59. In still other aspects of this embodiment, an IL-1 comprises a polypeptide having, e.g., at most one, two, three, four, five, six, seven, eight, nine, 10 or 20 contiguous amino acid additions relative to amino acids 123-265 of SEQ ID NO: 59. In other aspects of this embodiment, an IL-1 comprises a polypeptide having, e.g., at least one, two, three, four, five, six, seven, eight, nine, 10 or 20 contiguous amino acid additions relative to amino acids 123-265 of SEQ ID NO: 59.

In an embodiment, a binding domain comprises a IL-2. In another embodiment, a binding domain comprises a IL-2 of SEQ ID NO: 60. In another embodiment, a binding domain is derived from an IL-2. In another embodiment, a binding domain is derived from an IL-2 of SEQ ID NO: 60. In an aspect of this embodiment, a binding domain is derived from an IL-2 comprising amino acids 21-153 of SEQ ID NO: 60.

In other aspects of this embodiment, an IL-2 comprises a polypeptide having, e.g., at least 70% amino acid identity with amino acids 21-153 of SEQ ID NO: 60, at least 75% amino acid identity with amino acids 21-153 of SEQ ID NO: 60, at least 80% amino acid identity with amino acids 21-153 of SEQ ID NO: 60, at least 85% amino acid identity with amino acids 21-153 of SEQ ID NO: 60, at least 90% amino acid identity with amino acids 21-153 of SEQ ID NO: 60 or at least 95% amino acid identity with amino acids 21-153 of SEQ ID NO: 60. In yet other aspects of this embodiment, an IL-2 comprises a polypeptide having, e.g., at most 70% amino acid identity with amino acids 21-153 of SEQ ID NO: 60, at most 75% amino acid identity with amino acids 21-153 of SEQ ID NO: 60, at most 80% amino acid identity with amino acids 21-153 of SEQ ID NO: 60, at most 85% amino acid identity with amino acids 21-153 of SEQ ID NO: 60, at most 90% amino acid identity with amino acids 21-153 of SEQ ID NO: 60 or at most 95% amino acid identity with amino acids 21-153 of SEQ ID NO: 60.

In other aspects of this embodiment, an IL-2 comprises a polypeptide having, e.g., at most one, two, three, four, five, six, seven, eight, nine, 10 or 20 non-contiguous amino acid substitutions relative to amino acids 21-153 of SEQ ID NO: 60. In other aspects of this embodiment, an IL-2 comprises a polypeptide having, e.g., at least one, two, three, four, five, six, seven, eight, nine, 10 or 20 non-contiguous amino acid substitutions relative to amino acids 21-153 of SEQ ID NO: 60. In yet other aspects of this embodiment, an IL-2 comprises a polypeptide having, e.g., at most one, two, three, four, five, six, seven, eight, nine, 10 or 20 non-contiguous amino acid deletions relative to amino acids 21-153 of SEQ ID NO: 60. In other aspects of this embodiment, an IL-2 comprises a polypeptide having, e.g., at least one, two, three, four, five, six, seven, eight, nine, 10 or 20 non-contiguous amino acid deletions relative to amino acids 21-153 of SEQ ID NO: 60. In still other aspects of this embodiment, an IL-2 comprises a polypeptide having, e.g., at most one, two, three, four, five, six, seven, eight, nine, 10 or 20 non-contiguous amino acid additions relative to amino acids 21-153 of SEQ ID NO: 60. In other aspects of this embodiment, an IL-2 comprises a polypeptide having, e.g., at least one, two, three, four, five, six, seven, eight, nine, 10 or 20 non-contiguous amino acid additions relative to amino acids 21-153 of SEQ ID NO: 60.

In other aspects of this embodiment, an IL-2 comprises a polypeptide having, e.g., at most one, two, three, four, five, six, seven, eight, nine, 10 or 20 contiguous amino acid substitutions relative to amino acids 21-153 of SEQ ID NO: 60. In other aspects of this embodiment, an IL-2 comprises a polypeptide having, e.g., at least one, two, three, four, five, six, seven, eight, nine, 10 or 20 contiguous amino acid substitutions relative to amino acids 21-153 of SEQ ID NO: 60. In yet other aspects of this embodiment, an IL-2 comprises a polypeptide having, e.g., at most one, two, three, four, five, six, seven, eight, nine, 10 or 20 contiguous amino acid deletions relative to amino acids 21-153 of SEQ ID NO: 60. In other aspects of this embodiment, an IL-2 comprises a polypeptide having, e.g., at least one, two, three, four, five, six, seven, eight, nine, 10 or 20 contiguous amino acid deletions relative to amino acids 21-153 of SEQ ID NO: 60. In still other aspects of this embodiment, an IL-2 comprises a polypeptide having, e.g., at most one, two, three, four, five, six, seven, eight, nine, 10 or 20 contiguous amino acid additions relative to amino acids 21-153 of SEQ ID NO: 60. In other aspects of this embodiment, an IL-2 comprises a polypeptide having, e.g., at least one, two, three, four, five, six, seven, eight, nine, 10 or 20 contiguous amino acid additions relative to amino acids 21-153 of SEQ ID NO: 60.

In an embodiment, a binding domain comprises a IL-6. In another embodiment, a binding domain comprises a IL-6 of SEQ ID NO: 61. In another embodiment, a binding domain is derived from an IL-6. In another embodiment, a binding domain is derived from an IL-6 of SEQ ID NO: 61. In an aspect of this embodiment, a binding domain is derived from an IL-6 comprising amino acids 57-210 of SEQ ID NO: 61.

In other aspects of this embodiment, an IL-6 comprises a polypeptide having, e.g., at least 70% amino acid identity with amino acids 57-210 of SEQ ID NO: 61, at least 75% amino acid identity with amino acids 57-210 of SEQ ID NO: 61, at least 80% amino acid identity with amino acids 57-210 of SEQ ID NO: 61, at least 85% amino acid identity with amino acids 57-210 of SEQ ID NO: 61, at least 90% amino acid identity with amino acids 57-210 of SEQ ID NO: 61 or at least 95% amino acid identity with amino acids 57-210 of SEQ ID NO: 61. In yet other aspects of this embodiment, an IL-6 comprises a polypeptide having, e.g., at most 70% amino acid identity with amino acids 57-210 of SEQ ID NO: 61, at most 75% amino acid identity with amino acids 57-210 of SEQ ID NO: 61, at most 80% amino acid identity with amino acids 57-210 of SEQ ID NO: 61, at most 85% amino acid identity with amino acids 57-210 of SEQ ID NO: 61, at most 90% amino acid identity with amino acids 57-210 of SEQ ID NO: 61 or at most 95% amino acid identity with amino acids 57-210 of SEQ ID NO: 61.

In other aspects of this embodiment, an IL-6 comprises a polypeptide having, e.g., at most one, two, three, four, five, six, seven, eight, nine, 10 or 20 non-contiguous amino acid substitutions relative to amino acids 57-210 of SEQ ID NO: 61. In other aspects of this embodiment, an IL-6 comprises a polypeptide having, e.g., at least one, two, three, four, five, six, seven, eight, nine, 10 or 20 non-contiguous amino acid substitutions relative to amino acids 57-210 of SEQ ID NO: 61. In yet other aspects of this embodiment, an IL-6 comprises a polypeptide having, e.g., at most one, two, three, four, five, six, seven, eight, nine, 10 or 20 non-contiguous amino acid deletions relative to amino acids 57-210 of SEQ ID NO: 61. In other aspects of this embodiment, an IL-6 comprises a polypeptide having, e.g., at least one, two, three, four, five, six, seven, eight, nine, 10 or 20 non-contiguous amino acid deletions relative to amino acids 57-210 of SEQ ID NO: 61. In still other aspects of this embodiment, an IL-6 comprises a polypeptide having, e.g., at most one, two, three, four, five, six, seven, eight, nine, 10 or 20 non-contiguous amino acid additions relative to amino acids 57-210 of SEQ ID NO: 61. In other aspects of this embodiment, an IL-6 comprises a polypeptide having, e.g., at least one, two, three, four, five, six, seven, eight, nine, 10 or 20 non-contiguous amino acid additions relative to amino acids 57-210 of SEQ ID NO: 61.

In other aspects of this embodiment, an IL-6 comprises a polypeptide having, e.g., at most one, two, three, four, five, six, seven, eight, nine, 10 or 20 contiguous amino acid substitutions relative to amino acids 57-210 of SEQ ID NO: 61. In other aspects of this embodiment, an IL-6 comprises a polypeptide having, e.g., at least one, two, three, four, five, six, seven, eight, nine, 10 or 20 contiguous amino acid substitutions relative to amino acids 57-210 of SEQ ID NO: 61. In yet other aspects of this embodiment, an IL-6 comprises a polypeptide having, e.g., at most one, two, three, four, five, six, seven, eight, nine, 10 or 20 contiguous amino acid deletions relative to amino acids 57-210 of SEQ ID NO: 61. In other aspects of this embodiment, an IL-6 comprises a polypeptide having, e.g., at least one, two, three, four, five, six, seven, eight, nine, 10 or 20 contiguous amino acid deletions relative to amino acids 57-210 of SEQ ID NO: 61. In still other aspects of this embodiment, an IL-6 comprises a polypeptide having, e.g., at most one, two, three, four, five, six, seven, eight, nine, 10 or 20 contiguous amino acid additions relative to amino acids 57-210 of SEQ ID NO: 61. In other aspects of this embodiment, an IL-6 comprises a polypeptide having, e.g., at least one, two, three, four, five, six, seven, eight, nine, 10 or 20 contiguous amino acid additions relative to amino acids 57-210 of SEQ ID NO: 61.

In an embodiment, a binding domain comprises a IL-8. In another embodiment, a binding domain comprises a IL-8 of SEQ ID NO: 62. In another embodiment, a binding domain is derived from an IL-8. In another embodiment, a binding domain is derived from an IL-8 of SEQ ID NO: 62. In an aspect of this embodiment, a binding domain is derived from an IL-8 comprising amino acids 21-99 or amino acids 31-94 of SEQ ID NO: 62.

In other aspects of this embodiment, an IL-8 comprises a polypeptide having, e.g., at least 70% amino acid identity with amino acids 21-99 or amino acids 31-94 of SEQ ID NO: 62, at least 75% amino acid identity with amino acids 21-99 or amino acids 31-94 of SEQ ID NO: 62, at least 80% amino acid identity with amino acids 21-99 or amino acids 31-94 of SEQ ID NO: 62, at least 85% amino acid identity with amino acids 21-99 or amino acids 31-94 of SEQ ID NO: 62, at least 90% amino acid identity with amino acids 21-99 or amino acids 31-94 of SEQ ID NO: 62 or at least 95% amino acid identity with amino acids 21-99 or amino acids 31-94 of SEQ ID NO: 62. In yet other aspects of this embodiment, an IL-8 comprises a polypeptide having, e.g., at most 70% amino acid identity with amino acids 21-99 or amino acids 31-94 of SEQ ID NO: 62, at most 75% amino acid identity with amino acids 21-99 or amino acids 31-94 of SEQ ID NO: 62, at most 80% amino acid identity with amino acids 21-99 or amino acids 31-94 of SEQ ID NO: 62, at most 85% amino acid identity with amino acids 21-99 or amino acids 31-94 of SEQ ID NO: 62, at most 90% amino acid identity with amino acids 21-99 or amino acids 31-94 of SEQ ID NO: 62 or at most 95% amino acid identity with amino acids 21-99 or amino acids 31-94 of SEQ ID NO: 62.

In other aspects of this embodiment, an IL-8 comprises a polypeptide having, e.g., at most one, two, three, four, five, six, seven, eight, nine, 10 or 20 non-contiguous amino acid substitutions relative to amino acids 21-99 or amino acids 31-94 of SEQ ID NO: 62. In other aspects of this embodiment, an IL-8 comprises a polypeptide having, e.g., at least one, two, three, four, five, six, seven, eight, nine, 10 or 20 non-contiguous amino acid substitutions relative to amino acids 21-99 or amino acids 31-94 of SEQ ID NO: 62. In yet other aspects of this embodiment, an IL-8 comprises a polypeptide having, e.g., at most one, two, three, four, five, six, seven, eight, nine, 10 or 20 non-contiguous amino acid deletions relative to amino acids 21-99 or amino acids 31-94 of SEQ ID NO: 62. In other aspects of this embodiment, an IL-8 comprises a polypeptide having, e.g., at least one, two, three, four, five, six, seven, eight, nine, 10 or 20 non-contiguous amino acid deletions relative to amino acids 21-99 or amino acids 31-94 of SEQ ID NO: 62. In still other aspects of this embodiment, an IL-8 comprises a polypeptide having, e.g., at most one, two, three, four, five, six, seven, eight, nine, 10 or 20 non-contiguous amino acid additions relative to amino acids 21-99 or amino acids 31-94 of SEQ ID NO: 62. In other aspects of this embodiment, an IL-8 comprises a polypeptide having, e.g., at least one, two, three, four, five, six, seven, eight, nine, 10 or 20 non-contiguous amino acid additions relative to amino acids 21-99 or amino acids 31-94 of SEQ ID NO: 62.

In other aspects of this embodiment, an IL-8 comprises a polypeptide having, e.g., at most one, two, three, four, five, six, seven, eight, nine, 10 or 20 contiguous amino acid substitutions relative to amino acids 21-99 or amino acids 31-94 of SEQ ID NO: 62. In other aspects of this embodiment, an IL-8 comprises a polypeptide having, e.g., at least one, two, three, four, five, six, seven, eight, nine, 10 or 20 contiguous amino acid substitutions relative to amino acids 21-99 or amino acids 31-94 of SEQ ID NO: 62. In yet other aspects of this embodiment, an IL-8 comprises a polypeptide having, e.g., at most one, two, three, four, five, six, seven, eight, nine, 10 or 20 contiguous amino acid deletions relative to amino acids 21-99 or amino acids 31-94 of SEQ ID NO: 62. In other aspects of this embodiment, an IL-8 comprises a polypeptide having, e.g., at least one, two, three, four, five, six, seven, eight, nine, 10 or 20 contiguous amino acid deletions relative to amino acids 21-99 or amino acids 31-94 of SEQ ID NO: 62. In still other aspects of this embodiment, an IL-8 comprises a polypeptide having, e.g., at most one, two, three, four, five, six, seven, eight, nine, 10 or 20 contiguous amino acid additions relative to amino acids 21-99 or amino acids 31-94 of SEQ ID NO: 62. In other aspects of this embodiment, an IL-8 comprises a polypeptide having, e.g., at least one, two, three, four, five, six, seven, eight, nine, 10 or 20 contiguous amino acid additions relative to amino acids 21-99 or amino acids 31-94 of SEQ ID NO: 62.

In an embodiment, a binding domain comprises a IL-10. In another embodiment, a binding domain comprises a IL-10 of SEQ ID NO: 63. In another embodiment, a binding domain is derived from an IL-10. In another embodiment, a binding domain is derived from an IL-10 of SEQ ID NO: 63. In an aspect of this embodiment, a binding domain is derived from an IL-10 comprising amino acids 37-173 or amino acids 19-178 of SEQ ID NO: 63.

In other aspects of this embodiment, an IL-10 comprises a polypeptide having, e.g., at least 70% amino acid identity with amino acids 37-173 or amino acids 19-178 of SEQ ID NO: 63, at least 75% amino acid identity with amino acids 37-173 or amino acids 19-178 of SEQ ID NO: 63, at least 80% amino acid identity with amino acids 37-173 or amino acids 19-178 of SEQ ID NO: 63, at least 85% amino acid identity with amino acids 37-173 or amino acids 19-178 of SEQ ID NO: 63, at least 90% amino acid identity with amino acids 37-173 or amino acids 19-178 of SEQ ID NO: 63 or at least 95% amino acid identity with amino acids 37-173 or amino acids 19-178 of SEQ ID NO: 63. In yet other aspects of this embodiment, an IL-10 comprises a polypeptide having, e.g., at most 70% amino acid identity with amino acids 37-173 or amino acids 19-178 of SEQ ID NO: 63, at most 75% amino acid identity with amino acids 37-173 or amino acids 19-178 of SEQ ID NO: 63, at most 80% amino acid identity with amino acids 37-173 or amino acids 19-178 of SEQ ID NO: 63, at most 85% amino acid identity with amino acids 37-173 or amino acids 19-178 of SEQ ID NO: 63, at most 90% amino acid identity with amino acids 37-173 or amino acids 19-178 of SEQ ID NO: 63 or at most 95% amino acid identity with amino acids 37-173 or amino acids 19-178 of SEQ ID NO: 63.

In other aspects of this embodiment, an IL-10 comprises a polypeptide having, e.g., at most one, two, three, four, five, six, seven, eight, nine, 10 or 20 non-contiguous amino acid substitutions relative to amino acids 37-173 or amino acids 19-178 of SEQ ID NO: 63. In other aspects of this embodiment, an IL-10 comprises a polypeptide having, e.g., at least one, two, three, four, five, six, seven, eight, nine, 10 or 20 non-contiguous amino acid substitutions relative to amino acids 37-173 or amino acids 19-178 of SEQ ID NO: 63. In yet other aspects of this embodiment, an IL-10 comprises a polypeptide having, e.g., at most one, two, three, four, five, six, seven, eight, nine, 10 or 20 non-contiguous amino acid deletions relative to amino acids 37-173 or amino acids 19-178 of SEQ ID NO: 63. In other aspects of this embodiment, an IL-10 comprises a polypeptide having, e.g., at least one, two, three, four, five, six, seven, eight, nine, 10 or 20 non-contiguous amino acid deletions relative to amino acids 37-173 or amino acids 19-178 of SEQ ID NO: 63. In still other aspects of this embodiment, an IL-10 comprises a polypeptide having, e.g., at most one, two, three, four, five, six, seven, eight, nine, 10 or 20 non-contiguous amino acid additions relative to amino acids 37-173 or amino acids 19-178 of SEQ ID NO: 63. In other aspects of this embodiment, an IL-10 comprises a polypeptide having, e.g., at least one, two, three, four, five, six, seven, eight, nine, 10 or 20 non-contiguous amino acid additions relative to amino acids 37-173 or amino acids 19-178 of SEQ ID NO: 63.

In other aspects of this embodiment, an IL-10 comprises a polypeptide having, e.g., at most one, two, three, four, five, six, seven, eight, nine, 10 or 20 contiguous amino acid substitutions relative to amino acids 37-173 or amino acids 19-178 of SEQ ID NO: 63. In other aspects of this embodiment, an IL-10 comprises a polypeptide having, e.g., at least one, two, three, four, five, six, seven, eight, nine, 10 or 20 contiguous amino acid substitutions relative to amino acids 37-173 or amino acids 19-178 of SEQ ID NO: 63. In yet other aspects of this embodiment, an IL-10 comprises a polypeptide having, e.g., at most one, two, three, four, five, six, seven, eight, nine, 10 or 20 contiguous amino acid deletions relative to amino acids 37-173 or amino acids 19-178 of SEQ ID NO: 63. In other aspects of this embodiment, an IL-10 comprises a polypeptide having, e.g., at least one, two, three, four, five, six, seven, eight, nine, 10 or 20 contiguous amino acid deletions relative to amino acids 37-173 or amino acids 19-178 of SEQ ID NO: 63. In still other aspects of this embodiment, an IL-10 comprises a polypeptide having, e.g., at most one, two, three, four, five, six, seven, eight, nine, 10 or 20 contiguous amino acid additions relative to amino acids 37-173 or amino acids 19-178 of SEQ ID NO: 63. In other aspects of this embodiment, an IL-10 comprises a polypeptide having, e.g., at least one, two, three, four, five, six, seven, eight, nine, 10 or 20 contiguous amino acid additions relative to amino acids 37-173 or amino acids 19-178 of SEQ ID NO: 63.

In an embodiment, a binding domain comprises a neuroleukin. In another embodiment, a binding domain comprises a neuroleukin of SEQ ID NO: 64. In another embodiment, a binding domain is derived from a neuroleukin. In another embodiment, a binding domain is derived from a neuroleukin of SEQ ID NO: 64. In aspects of this embodiment, a neuroleukin comprises a polypeptide having, e.g., at least 70% amino acid identity with the amino acid sequence of SEQ ID NO: 64, at least 75% amino acid identity with the amino acid sequence of SEQ ID NO: 64, at least 80% amino acid identity with the amino acid sequence of SEQ ID NO: 64, at least 85% amino acid identity with the amino acid sequence of SEQ ID NO: 64, at least 90% amino acid identity with the amino acid sequence of SEQ ID NO: 64 or at least 95% amino acid identity with the amino acid sequence of SEQ ID NO: 64. In yet other aspects of this embodiment, a neuroleukin comprises a polypeptide having, e.g., at most 70% amino acid identity with the amino acid sequence of SEQ ID NO: 64, at most 75% amino acid identity with the amino acid sequence of SEQ ID NO: 64, at most 80% amino acid identity with the amino acid sequence of SEQ ID NO: 64, at most 85% amino acid identity with the amino acid sequence of SEQ ID NO: 64, at most 90% amino acid identity with the amino acid sequence of SEQ ID NO: 64 or at most 95% amino acid identity with the amino acid sequence of SEQ ID NO: 64.

In other aspects of this embodiment, a neuroleukin comprises a polypeptide having, e.g., at most one, two, three, four, five, six, seven, eight, nine, 10 or 20 non-contiguous amino acid substitutions relative to the amino acid sequence of SEQ ID NO: 64. In other aspects of this embodiment, a neuroleukin comprises a polypeptide having, e.g., at least one, two, three, four, five, six, seven, eight, nine, 10 or 20 non-contiguous amino acid substitutions relative to the amino acid sequence of SEQ ID NO: 64. In yet other aspects of this embodiment, a neuroleukin comprises a polypeptide having, e.g., at most one, two, three, four, five, six, seven, eight, nine, 10 or 20 non-contiguous amino acid deletions relative to the amino acid sequence of SEQ ID NO: 64. In other aspects of this embodiment, a neuroleukin comprises a polypeptide having, e.g., at least one, two, three, four, five, six, seven, eight, nine, 10 or 20 non-contiguous amino acid deletions relative to the amino acid sequence of SEQ ID NO: 64. In still other aspects of this embodiment, a neuroleukin comprises a polypeptide having, e.g., at most one, two, three, four, five, six, seven, eight, nine, 10 or 20 non-contiguous amino acid additions relative to the amino acid sequence of SEQ ID NO: 64. In other aspects of this embodiment, a neuroleukin comprises a polypeptide having, e.g., at least one, two, three, four, five, six, seven, eight, nine, 10 or 20 non-contiguous amino acid additions relative to the amino acid sequence of SEQ ID NO: 64.

In other aspects of this embodiment, a neuroleukin comprises a polypeptide having, e.g., at most one, two, three, four, five, six, seven, eight, nine, 10 or 20 contiguous amino acid substitutions relative to the amino acid sequence of SEQ ID NO: 64. In other aspects of this embodiment, a neuroleukin comprises a polypeptide having, e.g., at least one, two, three, four, five, six, seven, eight, nine, 10 or 20 contiguous amino acid substitutions relative to the amino acid sequence of SEQ ID NO: 64. In yet other aspects of this embodiment, a neuroleukin comprises a polypeptide having, e.g., at most one, two, three, four, five, six, seven, eight, nine, 10 or 20 contiguous amino acid deletions relative to the amino acid sequence of SEQ ID NO: 64. In other aspects of this embodiment, a neuroleukin comprises a polypeptide having, e.g., at least one, two, three, four, five, six, seven, eight, nine, 10 or 20 contiguous amino acid deletions relative to the amino acid sequence of SEQ ID NO: 64. In still other aspects of this embodiment, a neuroleukin comprises a polypeptide having, e.g., at most one, two, three, four, five, six, seven, eight, nine, 10 or 20 contiguous amino acid additions relative to the amino acid sequence of SEQ ID NO: 64. In other aspects of this embodiment, a neuroleukin comprises a polypeptide having, e.g., at least one, two, three, four, five, six, seven, eight, nine, 10 or 20 contiguous amino acid additions relative to the amino acid sequence of SEQ ID NO: 64.

In an embodiment, a binding domain comprises a VEGF. In another embodiment, a binding domain comprises a VEGF of SEQ ID NO: 65. In another embodiment, a binding domain is derived from a VEGF. In another embodiment, a binding domain is derived from a VEGF of SEQ ID NO: 65. In aspects of this embodiment, a VEGF comprises a polypeptide having, e.g., at least 70% amino acid identity with the amino acid sequence of SEQ ID NO: 65, at least 75% amino acid identity with the amino acid sequence of SEQ ID NO: 65, at least 80% amino acid identity with the amino acid sequence of SEQ ID NO: 65, at least 85% amino acid identity with the amino acid sequence of SEQ ID NO: 65, at least 90% amino acid identity with the amino acid sequence of SEQ ID NO: 65 or at least 95% amino acid identity with the amino acid sequence of SEQ ID NO: 65. In yet other aspects of this embodiment, a VEGF comprises a polypeptide having, e.g., at most 70% amino acid identity with the amino acid sequence of SEQ ID NO: 65, at most 75% amino acid identity with the amino acid sequence of SEQ ID NO: 65, at most 80% amino acid identity with the amino acid sequence of SEQ ID NO: 65, at most 85% amino acid identity with the amino acid sequence of SEQ ID NO: 65, at most 90% amino acid identity with the amino acid sequence of SEQ ID NO: 65 or at most 95% amino acid identity with the amino acid sequence of SEQ ID NO: 65.

In other aspects of this embodiment, a VEGF comprises a polypeptide having, e.g., at most one, two, three, four, five, six, seven, eight, nine, 10 or 20 non-contiguous amino acid substitutions relative to the amino acid sequence of SEQ ID NO: 65. In other aspects of this embodiment, a VEGF comprises a polypeptide having, e.g., at least one, two, three, four, five, six, seven, eight, nine, 10 or 20 non-contiguous amino acid substitutions relative to the amino acid sequence of SEQ ID NO: 65. In yet other aspects of this embodiment, a VEGF comprises a polypeptide having, e.g., at most one, two, three, four, five, six, seven, eight, nine, 10 or 20 non-contiguous amino acid deletions relative to the amino acid sequence of SEQ ID NO: 65. In other aspects of this embodiment, a VEGF comprises a polypeptide having, e.g., at least one, two, three, four, five, six, seven, eight, nine, 10 or 20 non-contiguous amino acid deletions relative to the amino acid sequence of SEQ ID NO: 65. In still other aspects of this embodiment, a VEGF comprises a polypeptide having, e.g., at most one, two, three, four, five, six, seven, eight, nine, 10 or 20 non-contiguous amino acid additions relative to the amino acid sequence of SEQ ID NO: 65. In other aspects of this embodiment, a VEGF comprises a polypeptide having, e.g., at least one, two, three, four, five, six, seven, eight, nine, 10 or 20 non-contiguous amino acid additions relative to the amino acid sequence of SEQ ID NO: 65.

In other aspects of this embodiment, a VEGF comprises a polypeptide having, e.g., at most one, two, three, four, five, six, seven, eight, nine, 10 or 20 contiguous amino acid substitutions relative to the amino acid sequence of SEQ ID NO: 65. In other aspects of this embodiment, a VEGF comprises a polypeptide having, e.g., at least one, two, three, four, five, six, seven, eight, nine, 10 or 20 contiguous amino acid substitutions relative to the amino acid sequence of SEQ ID NO: 65. In yet other aspects of this embodiment, a VEGF comprises a polypeptide having, e.g., at most one, two, three, four, five, six, seven, eight, nine, 10 or 20 contiguous amino acid deletions relative to the amino acid sequence of SEQ ID NO: 65. In other aspects of this embodiment, a VEGF comprises a polypeptide having, e.g., at least one, two, three, four, five, six, seven, eight, nine, 10 or 20 contiguous amino acid deletions relative to the amino acid sequence of SEQ ID NO: 65. In still other aspects of this embodiment, a VEGF comprises a polypeptide having, e.g., at most one, two, three, four, five, six, seven, eight, nine, 10 or 20 contiguous amino acid additions relative to the amino acid sequence of SEQ ID NO: 65. In other aspects of this embodiment, a VEGF comprises a polypeptide having, e.g., at least one, two, three, four, five, six, seven, eight, nine, 10 or 20 contiguous amino acid additions relative to the amino acid sequence of SEQ ID NO: 65.

In an embodiment, a binding domain comprises a IGF-1. In another embodiment, a binding domain comprises a IGF-1 of SEQ ID NO: 66. In another embodiment, a binding domain is derived from an IGF-1. In another embodiment, a binding domain is derived from an IGF-1 of SEQ ID NO: 66. In an aspect of this embodiment, a binding domain is derived from an IGF-1 comprising amino acids 52-109 or amino acids 49-118 of SEQ ID NO: 66.

In other aspects of this embodiment, an IGF-1 comprises a polypeptide having, e.g., at least 70% amino acid identity with amino acids 52-109 or amino acids 49-118 of SEQ ID NO: 66, at least 75% amino acid identity with amino acids 52-109 or amino acids 49-118 of SEQ ID NO: 66, at least 80% amino acid identity with amino acids 52-109 or amino acids 49-118 of SEQ ID NO: 66, at least 85% amino acid identity with amino acids 52-109 or amino acids 49-118 of SEQ ID NO: 66, at least 90% amino acid identity with amino acids 52-109 or amino acids 49-118 of SEQ ID NO: 66 or at least 95% amino acid identity with amino acids 52-109 or amino acids 49-118 of SEQ ID NO: 66. In yet other aspects of this embodiment, an IGF-1 comprises a polypeptide having, e.g., at most 70% amino acid identity with amino acids 52-109 or amino acids 49-118 of SEQ ID NO: 66, at most 75% amino acid identity with amino acids 52-109 or amino acids 49-118 of SEQ ID NO: 66, at most 80% amino acid identity with amino acids 52-109 or amino acids 49-118 of SEQ ID NO: 66, at most 85% amino acid identity with amino acids 52-109 or amino acids 49-118 of SEQ ID NO: 66, at most 90% amino acid identity with amino acids 52-109 or amino acids 49-118 of SEQ ID NO: 66 or at most 95% amino acid identity with amino acids 52-109 or amino acids 49-118 of SEQ ID NO: 66.

In other aspects of this embodiment, an IGF-1 comprises a polypeptide having, e.g., at most one, two, three, four, five, six, seven, eight, nine, 10 or 20 non-contiguous amino acid substitutions relative to amino acids 52-109 or amino acids 49-118 of SEQ ID NO: 66. In other aspects of this embodiment, an IGF-1 comprises a polypeptide having, e.g., at least one, two, three, four, five, six, seven, eight, nine, 10 or 20 non-contiguous amino acid substitutions relative to amino acids 52-109 or amino acids 49-118 of SEQ ID NO: 66. In yet other aspects of this embodiment, an IGF-1 comprises a polypeptide having, e.g., at most one, two, three, four, five, six, seven, eight, nine, 10 or 20 non-contiguous amino acid deletions relative to amino acids 52-109 or amino acids 49-118 of SEQ ID NO: 66. In other aspects of this embodiment, an IGF-1 comprises a polypeptide having, e.g., at least one, two, three, four, five, six, seven, eight, nine, 10 or 20 non-contiguous amino acid deletions relative to amino acids 52-109 or amino acids 49-118 of SEQ ID NO: 66. In still other aspects of this embodiment, an IGF-1 comprises a polypeptide having, e.g., at most one, two, three, four, five, six, seven, eight, nine, 10 or 20 non-contiguous amino acid additions relative to amino acids 52-109 or amino acids 49-118 of SEQ ID NO: 66. In other aspects of this embodiment, an IGF-1 comprises a polypeptide having, e.g., at least one, two, three, four, five, six, seven, eight, nine, 10 or 20 non-contiguous amino acid additions relative to amino acids 52-109 or amino acids 49-118 of SEQ ID NO: 66.

In other aspects of this embodiment, an IGF-1 comprises a polypeptide having, e.g., at most one, two, three, four, five, six, seven, eight, nine, 10 or 20 contiguous amino acid substitutions relative to amino acids 52-109 or amino acids 49-118 of SEQ ID NO: 66. In other aspects of this embodiment, an IGF-1 comprises a polypeptide having, e.g., at least one, two, three, four, five, six, seven, eight, nine, 10 or 20 contiguous amino acid substitutions relative to amino acids 52-109 or amino acids 49-118 of SEQ ID NO: 66. In yet other aspects of this embodiment, an IGF-1 comprises a polypeptide having, e.g., at most one, two, three, four, five, six, seven, eight, nine, 10 or 20 contiguous amino acid deletions relative to amino acids 52-109 or amino acids 49-118 of SEQ ID NO: 66. In other aspects of this embodiment, an IGF-1 comprises a polypeptide having, e.g., at least one, two, three, four, five, six, seven, eight, nine, 10 or 20 contiguous amino acid deletions relative to amino acids 52-109 or amino acids 49-118 of SEQ ID NO: 66. In still other aspects of this embodiment, an IGF-1 comprises a polypeptide having, e.g., at most one, two, three, four, five, six, seven, eight, nine, 10 or 20 contiguous amino acid additions relative to amino acids 52-109 or amino acids 49-118 of SEQ ID NO: 66. In other aspects of this embodiment, an IGF-1 comprises a polypeptide having, e.g., at least one, two, three, four, five, six, seven, eight, nine, 10 or 20 contiguous amino acid additions relative to amino acids 52-109 or amino acids 49-118 of SEQ ID NO: 66.

In an embodiment, a binding domain comprises a IGF-2. In another embodiment, a binding domain comprises a IGF-2 of SEQ ID NO: 67. In another embodiment, a binding domain is derived from an IGF-2. In another embodiment, a binding domain is derived from an IGF-2 of SEQ ID NO: 67. In an aspect of this embodiment, a binding domain is derived from an IGF-2 comprising amino acids 31-84 or amino acids 25-180 of SEQ ID NO: 67.

In other aspects of this embodiment, an IGF-2 comprises a polypeptide having, e.g., at least 70% amino acid identity with amino acids 31-84 or amino acids 25-180 of SEQ ID NO: 67, at least 75% amino acid identity with amino acids 31-84 or amino acids 25-180 of SEQ ID NO: 67, at least 80% amino acid identity with amino acids 31-84 or amino acids 25-180 of SEQ ID NO: 67, at least 85% amino acid identity with amino acids 31-84 or amino acids 25-180 of SEQ ID NO: 67, at least 90% amino acid identity with amino acids 31-84 or amino acids 25-180 of SEQ ID NO: 67 or at least 95% amino acid identity with amino acids 31-84 or amino acids 25-180 of SEQ ID NO: 67. In yet other aspects of this embodiment, an IGF-2 comprises a polypeptide having, e.g., at most 70% amino acid identity with amino acids 31-84 or amino acids 25-180 of SEQ ID NO: 67, at most 75% amino acid identity with amino acids 31-84 or amino acids 25-180 of SEQ ID NO: 67, at most 80% amino acid identity with amino acids 31-84 or amino acids 25-180 of SEQ ID NO: 67, at most 85% amino acid identity with amino acids 31-84 or amino acids 25-180 of SEQ ID NO: 67, at most 90% amino acid identity with amino acids 31-84 or amino acids 25-180 of SEQ ID NO: 67 or at most 95% amino acid identity with amino acids 31-84 or amino acids 25-180 of SEQ ID NO: 67.

In other aspects of this embodiment, an IGF-2 comprises a polypeptide having, e.g., at most one, two, three, four, five, six, seven, eight, nine, 10 or 20 non-contiguous amino acid substitutions relative to amino acids 31-84 or amino acids 25-180 of SEQ ID NO: 67. In other aspects of this embodiment, an IGF-2 comprises a polypeptide having, e.g., at least one, two, three, four, five, six, seven, eight, nine, 10 or 20 non-contiguous amino acid substitutions relative to amino acids 31-84 or amino acids 25-180 of SEQ ID NO: 67. In yet other aspects of this embodiment, an IGF-2 comprises a polypeptide having, e.g., at most one, two, three, four, five, six, seven, eight, nine, 10 or 20 non-contiguous amino acid deletions relative to amino acids 31-84 or amino acids 25-180 of SEQ ID NO: 67. In other aspects of this embodiment, an IGF-2 comprises a polypeptide having, e.g., at least one, two, three, four, five, six, seven, eight, nine, 10 or 20 non-contiguous amino acid deletions relative to amino acids 31-84 or amino acids 25-180 of SEQ ID NO: 67. In still other aspects of this embodiment, an IGF-2 comprises a polypeptide having, e.g., at most one, two, three, four, five, six, seven, eight, nine, 10 or 20 non-contiguous amino acid additions relative to amino acids 31-84 or amino acids 25-180 of SEQ ID NO: 67. In other aspects of this embodiment, an IGF-2 comprises a polypeptide having, e.g., at least one, two, three, four, five, six, seven, eight, nine, 10 or 20 non-contiguous amino acid additions relative to amino acids 31-84 or amino acids 25-180 of SEQ ID NO: 67.

In other aspects of this embodiment, an IGF-2 comprises a polypeptide having, e.g., at most one, two, three, four, five, six, seven, eight, nine, 10 or 20 contiguous amino acid substitutions relative to amino acids 31-84 or amino acids 25-180 of SEQ ID NO: 67. In other aspects of this embodiment, an IGF-2 comprises a polypeptide having, e.g., at least one, two, three, four, five, six, seven, eight, nine, 10 or 20 contiguous amino acid substitutions relative to amino acids 31-84 or amino acids 25-180 of SEQ ID NO: 67. In yet other aspects of this embodiment, an IGF-2 comprises a polypeptide having, e.g., at most one, two, three, four, five, six, seven, eight, nine, 10 or 20 contiguous amino acid deletions relative to amino acids 31-84 or amino acids 25-180 of SEQ ID NO: 67. In other aspects of this embodiment, an IGF-2 comprises a polypeptide having, e.g., at least one, two, three, four, five, six, seven, eight, nine, 10 or 20 contiguous amino acid deletions relative to amino acids 31-84 or amino acids 25-180 of SEQ ID NO: 67. In still other aspects of this embodiment, an IGF-2 comprises a polypeptide having, e.g., at most one, two, three, four, five, six, seven, eight, nine, 10 or 20 contiguous amino acid additions relative to amino acids 31-84 or amino acids 25-180 of SEQ ID NO: 67. In other aspects of this embodiment, an IGF-2 comprises a polypeptide having, e.g., at least one, two, three, four, five, six, seven, eight, nine, 10 or 20 contiguous amino acid additions relative to amino acids 31-84 or amino acids 25-180 of SEQ ID NO: 67.

In an embodiment, a binding domain comprises a EGF. In another embodiment, a binding domain comprises a EGF of SEQ ID NO: 68. In another embodiment, a binding domain is derived from an EGF. In another embodiment, a binding domain is derived from an EGF of SEQ ID NO: 68. In aspects of this embodiment, an EGF comprises a polypeptide having, e.g., at least 70% amino acid identity with the amino acid sequence of SEQ ID NO: 68, at least 75% amino acid identity with the amino acid sequence of SEQ ID NO: 68, at least 80% amino acid identity with the amino acid sequence of SEQ ID NO: 68, at least 85% amino acid identity with the amino acid sequence of SEQ ID NO: 68, at least 90% amino acid identity with the amino acid sequence of SEQ ID NO: 68 or at least 95% amino acid identity with the amino acid sequence of SEQ ID NO: 68. In yet other aspects of this embodiment, an EGF comprises a polypeptide having, e.g., at most 70% amino acid identity with the amino acid sequence of SEQ ID NO: 68, at most 75% amino acid identity with the amino acid sequence of SEQ ID NO: 68, at most 80% amino acid identity with the amino acid sequence of SEQ ID NO: 68, at most 85% amino acid identity with the amino acid sequence of SEQ ID NO: 68, at most 90% amino acid identity with the amino acid sequence of SEQ ID NO: 68 or at most 95% amino acid identity with the amino acid sequence of SEQ ID NO: 68.

In other aspects of this embodiment, an EGF comprises a polypeptide having, e.g., at most one, two, three, four, five, six, seven, eight, nine, 10 or 20 non-contiguous amino acid substitutions relative to the amino acid sequence of SEQ ID NO: 68. In other aspects of this embodiment, an EGF comprises a polypeptide having, e.g., at least one, two, three, four, five, six, seven, eight, nine, 10 or 20 non-contiguous amino acid substitutions relative to the amino acid sequence of SEQ ID NO: 68. In yet other aspects of this embodiment, an EGF comprises a polypeptide having, e.g., at most one, two, three, four, five, six, seven, eight, nine, 10 or 20 non-contiguous amino acid deletions relative to the amino acid sequence of SEQ ID NO: 68. In other aspects of this embodiment, an EGF comprises a polypeptide having, e.g., at least one, two, three, four, five, six, seven, eight, nine, 10 or 20 non-contiguous amino acid deletions relative to the amino acid sequence of SEQ ID NO: 68. In still other aspects of this embodiment, an EGF comprises a polypeptide having, e.g., at most one, two, three, four, five, six, seven, eight, nine, 10 or 20 non-contiguous amino acid additions relative to the amino acid sequence of SEQ ID NO: 68. In other aspects of this embodiment, an EGF comprises a polypeptide having, e.g., at least one, two, three, four, five, six, seven, eight, nine, 10 or 20 non-contiguous amino acid additions relative to the amino acid sequence of SEQ ID NO: 68.

In other aspects of this embodiment, an EGF comprises a polypeptide having, e.g., at most one, two, three, four, five, six, seven, eight, nine, 10 or 20 contiguous amino acid substitutions relative to the amino acid sequence of SEQ ID NO: 68. In other aspects of this embodiment, an EGF comprises a polypeptide having, e.g., at least one, two, three, four, five, six, seven, eight, nine, 10 or 20 contiguous amino acid substitutions relative to the amino acid sequence of SEQ ID NO: 68. In yet other aspects of this embodiment, an EGF comprises a polypeptide having, e.g., at most one, two, three, four, five, six, seven, eight, nine, 10 or 20 contiguous amino acid deletions relative to the amino acid sequence of SEQ ID NO: 68. In other aspects of this embodiment, an EGF comprises a polypeptide having, e.g., at least one, two, three, four, five, six, seven, eight, nine, 10 or 20 contiguous amino acid deletions relative to the amino acid sequence of SEQ ID NO: 68. In still other aspects of this embodiment, an EGF comprises a polypeptide having, e.g., at most one, two, three, four, five, six, seven, eight, nine, 10 or 20 contiguous amino acid additions relative to the amino acid sequence of SEQ ID NO: 68. In other aspects of this embodiment, an EGF comprises a polypeptide having, e.g., at least one, two, three, four, five, six, seven, eight, nine, 10 or 20 contiguous amino acid additions relative to the amino acid sequence of SEQ ID NO: 68.

Another example of a binding domain disclosed in the present specification is, e.g., a neurotrophin, such as, e.g., a NGF, a BDNF, a NT-3 or a NT-5.

Thus, in an embodiment, a binding domain comprises a NGF. In another embodiment, a binding domain comprises a NGF of SEQ ID NO: 69. In another embodiment, a binding domain is derived from a NGF. In another embodiment, a binding domain is derived from a NGF of SEQ ID NO: 69. In an aspect of this embodiment, a binding domain is derived from a NGF comprising amino acids 139-257 of SEQ ID NO: 69.

In other aspects of this embodiment, a NGF comprises a polypeptide having, e.g., at least 70% amino acid identity with amino acids 139-257 of SEQ ID NO: 69, at least 75% amino acid identity with amino acids 139-257 of SEQ ID NO: 69, at least 80% amino acid identity with amino acids 139-257 of SEQ ID NO: 69, at least 85% amino acid identity with amino acids 139-257 of SEQ ID NO: 69, at least 90% amino acid identity with amino acids 139-257 of SEQ ID NO: 69 or at least 95% amino acid identity with amino acids 139-257 of SEQ ID NO: 69. In yet other aspects of this embodiment, a NGF comprises a polypeptide having, e.g., at most 70% amino acid identity with amino acids 139-257 of SEQ ID NO: 69, at most 75% amino acid identity with amino acids 139-257 of SEQ ID NO: 69, at most 80% amino acid identity with amino acids 139-257 of SEQ ID NO: 69, at most 85% amino acid identity with amino acids 139-257 of SEQ ID NO: 69, at most 90% amino acid identity with amino acids 139-257 of SEQ ID NO: 69 or at most 95% amino acid identity with amino acids 139-257 of SEQ ID NO: 69.

In other aspects of this embodiment, a NGF comprises a polypeptide having, e.g., at most one, two, three, four, five, six, seven, eight, nine, 10 or 20 non-contiguous amino acid substitutions relative to amino acids 139-257 of SEQ ID NO: 69. In other aspects of this embodiment, a NGF comprises a polypeptide having, e.g., at least one, two, three, four, five, six, seven, eight, nine, 10 or 20 non-contiguous amino acid substitutions relative to amino acids 139-257 of SEQ ID NO: 69. In yet other aspects of this embodiment, a NGF comprises a polypeptide having, e.g., at most one, two, three, four, five, six, seven, eight, nine, 10 or 20 non-contiguous amino acid deletions relative to amino acids 139-257 of SEQ ID NO: 69. In other aspects of this embodiment, a NGF comprises a polypeptide having, e.g., at least one, two, three, four, five, six, seven, eight, nine, 10 or 20 non-contiguous amino acid deletions relative to amino acids 139-257 of SEQ ID NO: 69. In still other aspects of this embodiment, a NGF comprises a polypeptide having, e.g., at most one, two, three, four, five, six, seven, eight, nine, 10 or 20 non-contiguous amino acid additions relative to amino acids 139-257 of SEQ ID NO: 69. In other aspects of this embodiment, a NGF comprises a polypeptide having, e.g., at least one, two, three, four, five, six, seven, eight, nine, 10 or 20 non-contiguous amino acid additions relative to amino acids 139-257 of SEQ ID NO: 69.

In other aspects of this embodiment, a NGF comprises a polypeptide having, e.g., at most one, two, three, four, five, six, seven, eight, nine, 10 or 20 contiguous amino acid substitutions relative to amino acids 139-257 of SEQ ID NO: 69. In other aspects of this embodiment, a NGF comprises a polypeptide having, e.g., at least one, two, three, four, five, six, seven, eight, nine, 10 or 20 contiguous amino acid substitutions relative to amino acids 139-257 of SEQ ID NO: 69. In yet other aspects of this embodiment, a NGF comprises a polypeptide having, e.g., at most one, two, three, four, five, six, seven, eight, nine, 10 or 20 contiguous amino acid deletions relative to amino acids 139-257 of SEQ ID NO: 69. In other aspects of this embodiment, a NGF comprises a polypeptide having, e.g., at least one, two, three, four, five, six, seven, eight, nine, 10 or 20 contiguous amino acid deletions relative to amino acids 139-257 of SEQ ID NO: 69. In still other aspects of this embodiment, a NGF comprises a polypeptide having, e.g., at most one, two, three, four, five, six, seven, eight, nine, 10 or 20 contiguous amino acid additions relative to amino acids 139-257 of SEQ ID NO: 69. In other aspects of this embodiment, a NGF comprises a polypeptide having, e.g., at least one, two, three, four, five, six, seven, eight, nine, 10 or 20 contiguous amino acid additions relative to amino acids 139-257 of SEQ ID NO: 69.

In an embodiment, a binding domain comprises a BDGF. In another embodiment, a binding domain comprises a BDGF of SEQ ID NO: 70. In another embodiment, a binding domain is derived from a BDGF. In another embodiment, a binding domain is derived from a BDGF of SEQ ID NO: 70. In an aspect of this embodiment, a binding domain is derived from a BDGF comprising amino acids 133-240 or amino acids 129-247 of SEQ ID NO: 70.

In other aspects of this embodiment, a BDGF comprises a polypeptide having, e.g., at least 70% amino acid identity with amino acids 133-240 or amino acids 129-247 of SEQ ID NO: 70, at least 75% amino acid identity with amino acids 133-240 or amino acids 129-247 of SEQ ID NO: 70, at least 80% amino acid identity with amino acids 133-240 or amino acids 129-247 of SEQ ID NO: 70, at least 85% amino acid identity with amino acids 133-240 or amino acids 129-247 of SEQ ID NO: 70, at least 90% amino acid identity with amino acids 133-240 or amino acids 129-247 of SEQ ID NO: 70 or at least 95% amino acid identity with amino acids 133-240 or amino acids 129-247 of SEQ ID NO: 70. In yet other aspects of this embodiment, a BDGF comprises a polypeptide having, e.g., at most 70% amino acid identity with amino acids 133-240 or amino acids 129-247 of SEQ ID NO: 70, at most 75% amino acid identity with amino acids 133-240 or amino acids 129-247 of SEQ ID NO: 70, at most 80% amino acid identity with amino acids 133-240 or amino acids 129-247 of SEQ ID NO: 70, at most 85% amino acid identity with amino acids 133-240 or amino acids 129-247 of SEQ ID NO: 70, at most 90% amino acid identity with amino acids 133-240 or amino acids 129-247 of SEQ ID NO: 70 or at most 95% amino acid identity with amino acids 133-240 or amino acids 129-247 of SEQ ID NO: 70.

In other aspects of this embodiment, a BDGF comprises a polypeptide having, e.g., at most one, two, three, four, five, six, seven, eight, nine, 10 or 20 non-contiguous amino acid substitutions relative to amino acids 133-240 or amino acids 129-247 of SEQ ID NO: 70. In other aspects of this embodiment, a BDGF comprises a polypeptide having, e.g., at least one, two, three, four, five, six, seven, eight, nine, 10 or 20 non-contiguous amino acid substitutions relative to amino acids 133-240 or amino acids 129-247 of SEQ ID NO: 70. In yet other aspects of this embodiment, a BDGF comprises a polypeptide having, e.g., at most one, two, three, four, five, six, seven, eight, nine, 10 or 20 non-contiguous amino acid deletions relative to amino acids 133-240 or amino acids 129-247 of SEQ ID NO: 70. In other aspects of this embodiment, a BDGF comprises a polypeptide having, e.g., at least one, two, three, four, five, six, seven, eight, nine, 10 or 20 non-contiguous amino acid deletions relative to amino acids 133-240 or amino acids 129-247 of SEQ ID NO: 70. In still other aspects of this embodiment, a BDGF comprises a polypeptide having, e.g., at most one, two, three, four, five, six, seven, eight, nine, 10 or 20 non-contiguous amino acid additions relative to amino acids 133-240 or amino acids 129-247 of SEQ ID NO: 70. In other aspects of this embodiment, a BDGF comprises a polypeptide having, e.g., at least one, two, three, four, five, six, seven, eight, nine, 10 or 20 non-contiguous amino acid additions relative to amino acids 133-240 or amino acids 129-247 of SEQ ID NO: 70.

In other aspects of this embodiment, a BDGF comprises a polypeptide having, e.g., at most one, two, three, four, five, six, seven, eight, nine, 10 or 20 contiguous amino acid substitutions relative to amino acids 133-240 or amino acids 129-247 of SEQ ID NO: 70. In other aspects of this embodiment, a BDGF comprises a polypeptide having, e.g., at least one, two, three, four, five, six, seven, eight, nine, 10 or 20 contiguous amino acid substitutions relative to amino acids 133-240 or amino acids 129-247 of SEQ ID NO: 70. In yet other aspects of this embodiment, a BDGF comprises a polypeptide having, e.g., at most one, two, three, four, five, six, seven, eight, nine, 10 or 20 contiguous amino acid deletions relative to amino acids 133-240 or amino acids 129-247 of SEQ ID NO: 70. In other aspects of this embodiment, a BDGF comprises a polypeptide having, e.g., at least one, two, three, four, five, six, seven, eight, nine, 10 or 20 contiguous amino acid deletions relative to amino acids 133-240 or amino acids 129-247 of SEQ ID NO: 70. In still other aspects of this embodiment, a BDGF comprises a polypeptide having, e.g., at most one, two, three, four, five, six, seven, eight, nine, 10 or 20 contiguous amino acid additions relative to amino acids 133-240 or amino acids 129-247 of SEQ ID NO: 70. In other aspects of this embodiment, a BDGF comprises a polypeptide having, e.g., at least one, two, three, four, five, six, seven, eight, nine, 10 or 20 contiguous amino acid additions relative to amino acids 133-240 or amino acids 129-247 of SEQ ID NO: 70.

In an embodiment, a binding domain comprises a NT-3. In another embodiment, a binding domain comprises a NT-3 of SEQ ID NO: 71. In another embodiment, a binding domain is derived from a NT-3. In another embodiment, a binding domain is derived from a NT-3 of SEQ ID NO: 71. In an aspect of this embodiment, a binding domain is derived from a NT-3 comprising amino acids 144-249 or amino acids 19-257 of SEQ ID NO: 71.

In other aspects of this embodiment, a NT-3 comprises a polypeptide having, e.g., at least 70% amino acid identity with amino acids 144-249 or amino acids 19-257 of SEQ ID NO: 71, at least 75% amino acid identity with amino acids 144-249 or amino acids 19-257 of SEQ ID NO: 71, at least 80% amino acid identity with amino acids 144-249 or amino acids 19-257 of SEQ ID NO: 71, at least 85% amino acid identity with amino acids 144-249 or amino acids 19-257 of SEQ ID NO: 71, at least 90% amino acid identity with amino acids 144-249 or amino acids 19-257 of SEQ ID NO: 71 or at least 95% amino acid identity with amino acids 144-249 or amino acids 19-257 of SEQ ID NO: 71. In yet other aspects of this embodiment, a NT-3 comprises a polypeptide having, e.g., at most 70% amino acid identity with amino acids 144-249 or amino acids 19-257 of SEQ ID NO: 71, at most 75% amino acid identity with amino acids 144-249 or amino acids 19-257 of SEQ ID NO: 71, at most 80% amino acid identity with amino acids 144-249 or amino acids 19-257 of SEQ ID NO: 71, at most 85% amino acid identity with amino acids 144-249 or amino acids 19-257 of SEQ ID NO: 71, at most 90% amino acid identity with amino acids 144-249 or amino acids 19-257 of SEQ ID NO: 71 or at most 95% amino acid identity with amino acids 144-249 or amino acids 19-257 of SEQ ID NO: 71.

In other aspects of this embodiment, a NT-3 comprises a polypeptide having, e.g., at most one, two, three, four, five, six, seven, eight, nine, 10 or 20 non-contiguous amino acid substitutions relative to amino acids 144-249 or amino acids 19-257 of SEQ ID NO: 71. In other aspects of this embodiment, a NT-3 comprises a polypeptide having, e.g., at least one, two, three, four, five, six, seven, eight, nine, 10 or 20 non-contiguous amino acid substitutions relative to amino acids 144-249 or amino acids 19-257 of SEQ ID NO: 71. In yet other aspects of this embodiment, a NT-3 comprises a polypeptide having, e.g., at most one, two, three, four, five, six, seven, eight, nine, 10 or 20 non-contiguous amino acid deletions relative to amino acids 144-249 or amino acids 19-257 of SEQ ID NO: 71. In other aspects of this embodiment, a NT-3 comprises a polypeptide having, e.g., at least one, two, three, four, five, six, seven, eight, nine, 10 or 20 non-contiguous amino acid deletions relative to amino acids 144-249 or amino acids 19-257 of SEQ ID NO: 71. In still other aspects of this embodiment, a NT-3 comprises a polypeptide having, e.g., at most one, two, three, four, five, six, seven, eight, nine, 10 or 20 non-contiguous amino acid additions relative to amino acids 144-249 or amino acids 19-257 of SEQ ID NO: 71. In other aspects of this embodiment, a NT-3 comprises a polypeptide having, e.g., at least one, two, three, four, five, six, seven, eight, nine, 10 or 20 non-contiguous amino acid additions relative to amino acids 144-249 or amino acids 19-257 of SEQ ID NO: 71.

In other aspects of this embodiment, a NT-3 comprises a polypeptide having, e.g., at most one, two, three, four, five, six, seven, eight, nine, 10 or 20 contiguous amino acid substitutions relative to amino acids 144-249 or amino acids 19-257 of SEQ ID NO: 71. In other aspects of this embodiment, a NT-3 comprises a polypeptide having, e.g., at least one, two, three, four, five, six, seven, eight, nine, 10 or 20 contiguous amino acid substitutions relative to amino acids 144-249 or amino acids 19-257 of SEQ ID NO: 71. In yet other aspects of this embodiment, a NT-3 comprises a polypeptide having, e.g., at most one, two, three, four, five, six, seven, eight, nine, 10 or 20 contiguous amino acid deletions relative to amino acids 144-249 or amino acids 19-257 of SEQ ID NO: 71. In other aspects of this embodiment, a NT-3 comprises a polypeptide having, e.g., at least one, two, three, four, five, six, seven, eight, nine, 10 or 20 contiguous amino acid deletions relative to amino acids 144-249 or amino acids 19-257 of SEQ ID NO: 71. In still other aspects of this embodiment, a NT-3 comprises a polypeptide having, e.g., at most one, two, three, four, five, six, seven, eight, nine, 10 or 20 contiguous amino acid additions relative to amino acids 144-249 or amino acids 19-257 of SEQ ID NO: 71. In other aspects of this embodiment, a NT-3 comprises a polypeptide having, e.g., at least one, two, three, four, five, six, seven, eight, nine, 10 or 20 contiguous amino acid additions relative to amino acids 144-249 or amino acids 19-257 of SEQ ID NO: 71.

In an embodiment, a binding domain comprises a NT-4/5. In another embodiment, a binding domain comprises a NT-4/5 of SEQ ID NO: 72. In another embodiment, a binding domain is derived from a NT-4/5. In another embodiment, a binding domain is derived from a NT-4/5 of SEQ ID NO: 72. In an aspect of this embodiment, a binding domain is derived from a NT-4/5 comprising amino acids 89-202 or amino acids 81-210 of SEQ ID NO: 72.

In other aspects of this embodiment, a NT-4/5 comprises a polypeptide having, e.g., at least 70% amino acid identity with amino acids 89-202 or amino acids 81-210 of SEQ ID NO: 72, at least 75% amino acid identity with amino acids 89-202 or amino acids 81-210 of SEQ ID NO: 72, at least 80% amino acid identity with amino acids 89-202 or amino acids 81-210 of SEQ ID NO: 72, at least 85% amino acid identity with amino acids 89-202 or amino acids 81-210 of SEQ ID NO: 72, at least 90% amino acid identity with amino acids 89-202 or amino acids 81-210 of SEQ ID NO: 72 or at least 95% amino acid identity with amino acids 89-202 or amino acids 81-210 of SEQ ID NO: 72. In yet other aspects of this embodiment, a NT-4/5 comprises a polypeptide having, e.g., at most 70% amino acid identity with amino acids 89-202 or amino acids 81-210 of SEQ ID NO: 72, at most 75% amino acid identity with amino acids 89-202 or amino acids 81-210 of SEQ ID NO: 72, at most 80% amino acid identity with amino acids 89-202 or amino acids 81-210 of SEQ ID NO: 72, at most 85% amino acid identity with amino acids 89-202 or amino acids 81-210 of SEQ ID NO: 72, at most 90% amino acid identity with amino acids 89-202 or amino acids 81-210 of SEQ ID NO: 72 or at most 95% amino acid identity with amino acids 89-202 or amino acids 81-210 of SEQ ID NO: 72.

In other aspects of this embodiment, a NT-4/5 comprises a polypeptide having, e.g., at most one, two, three, four, five, six, seven, eight, nine, 10 or 20 non-contiguous amino acid substitutions relative to amino acids 89-202 or amino acids 81-210 of SEQ ID NO: 72. In other aspects of this embodiment, a NT-4/5 comprises a polypeptide having, e.g., at least one, two, three, four, five, six, seven, eight, nine, 10 or 20 non-contiguous amino acid substitutions relative to amino acids 89-202 or amino acids 81-210 of SEQ ID NO: 72. In yet other aspects of this embodiment, a NT-4/5 comprises a polypeptide having, e.g., at most one, two, three, four, five, six, seven, eight, nine, 10 or 20 non-contiguous amino acid deletions relative to amino acids 89-202 or amino acids 81-210 of SEQ ID NO: 72. In other aspects of this embodiment, a NT-4/5 comprises a polypeptide having, e.g., at least one, two, three, four, five, six, seven, eight, nine, 10 or 20 non-contiguous amino acid deletions relative to amino acids 89-202 or amino acids 81-210 of SEQ ID NO: 72. In still other aspects of this embodiment, a NT-4/5 comprises a polypeptide having, e.g., at most one, two, three, four, five, six, seven, eight, nine, 10 or 20 non-contiguous amino acid additions relative to amino acids 89-202 or amino acids 81-210 of SEQ ID NO: 72. In other aspects of this embodiment, a NT-4/5 comprises a polypeptide having, e.g., at least one, two, three, four, five, six, seven, eight, nine, 10 or 20 non-contiguous amino acid additions relative to amino acids 89-202 or amino acids 81-210 of SEQ ID NO: 72.

In other aspects of this embodiment, a NT-4/5 comprises a polypeptide having, e.g., at most one, two, three, four, five, six, seven, eight, nine, 10 or 20 contiguous amino acid substitutions relative to amino acids 89-202 or amino acids 81-210 of SEQ ID NO: 72. In other aspects of this embodiment, a NT-4/5 comprises a polypeptide having, e.g., at least one, two, three, four, five, six, seven, eight, nine, 10 or 20 contiguous amino acid substitutions relative to amino acids 89-202 or amino acids 81-210 of SEQ ID NO: 72. In yet other aspects of this embodiment, a NT-4/5 comprises a polypeptide having, e.g., at most one, two, three, four, five, six, seven, eight, nine, 10 or 20 contiguous amino acid deletions relative to amino acids 89-202 or amino acids 81-210 of SEQ ID NO: 72. In other aspects of this embodiment, a NT-4/5 comprises a polypeptide having, e.g., at least one, two, three, four, five, six, seven, eight, nine, 10 or 20 contiguous amino acid deletions relative to amino acids 89-202 or amino acids 81-210 of SEQ ID NO: 72. In still other aspects of this embodiment, a NT-4/5 comprises a polypeptide having, e.g., at most one, two, three, four, five, six, seven, eight, nine, 10 or 20 contiguous amino acid additions relative to amino acids 89-202 or amino acids 81-210 of SEQ ID NO: 72. In other aspects of this embodiment, a NT-4/5 comprises a polypeptide having, e.g., at least one, two, three, four, five, six, seven, eight, nine, 10 or 20 contiguous amino acid additions relative to amino acids 89-202 or amino acids 81-210 of SEQ ID NO: 72.

Another example of a binding domain disclosed in the present specification is, e.g., a GDNF, a neurturin, a persephrin or an artemin.

Thus, in an embodiment, a binding domain comprises a GDNF. In another embodiment, a binding domain comprises a GDNF of SEQ ID NO: 73. In another embodiment, a binding domain is derived from a GDNF. In another embodiment, a binding domain is derived from a GDNF of SEQ ID NO: 73.

In an aspect of this embodiment, a binding domain is derived from a GDNF comprising amino acids 118-211 of SEQ ID NO: 73.

In other aspects of this embodiment, a GDNF comprises a polypeptide having, e.g., at least 70% amino acid identity with amino acids 118-211 of SEQ ID NO: 73, at least 75% amino acid identity with amino acids 118-211 of SEQ ID NO: 73, at least 80% amino acid identity with amino acids 118-211 of SEQ ID NO: 73, at least 85% amino acid identity with amino acids 118-211 of SEQ ID NO: 73, at least 90% amino acid identity with amino acids 118-211 of SEQ ID NO: 73 or at least 95% amino acid identity with amino acids 118-211 of SEQ ID NO: 73. In yet other aspects of this embodiment, a GDNF comprises a polypeptide having, e.g., at most 70% amino acid identity with amino acids 118-211 of SEQ ID NO: 73, at most 75% amino acid identity with amino acids 118-211 of SEQ ID NO: 73, at most 80% amino acid identity with amino acids 118-211 of SEQ ID NO: 73, at most 85% amino acid identity with amino acids 118-211 of SEQ ID NO: 73, at most 90% amino acid identity with amino acids 118-211 of SEQ ID NO: 73 or at most 95% amino acid identity with amino acids 118-211 of SEQ ID NO: 73.

In other aspects of this embodiment, a GDNF comprises a polypeptide having, e.g., at most one, two, three, four, five, six, seven, eight, nine, 10 or 20 non-contiguous amino acid substitutions relative to amino acids 118-211 of SEQ ID NO: 73. In other aspects of this embodiment, a GDNF comprises a polypeptide having, e.g., at least one, two, three, four, five, six, seven, eight, nine, 10 or 20 non-contiguous amino acid substitutions relative to amino acids 118-211 of SEQ ID NO: 73. In yet other aspects of this embodiment, a GDNF comprises a polypeptide having, e.g., at most one, two, three, four, five, six, seven, eight, nine, 10 or 20 non-contiguous amino acid deletions relative to amino acids 118-211 of SEQ ID NO: 73. In other aspects of this embodiment, a GDNF comprises a polypeptide having, e.g., at least one, two, three, four, five, six, seven, eight, nine, 10 or 20 non-contiguous amino acid deletions relative to amino acids 118-211 of SEQ ID NO: 73. In still other aspects of this embodiment, a GDNF comprises a polypeptide having, e.g., at most one, two, three, four, five, six, seven, eight, nine, 10 or 20 non-contiguous amino acid additions relative to amino acids 118-211 of SEQ ID NO: 73. In other aspects of this embodiment, a GDNF comprises a polypeptide having, e.g., at least one, two, three, four, five, six, seven, eight, nine, 10 or 20 non-contiguous amino acid additions relative to amino acids 118-211 of SEQ ID NO: 73.

In other aspects of this embodiment, a GDNF comprises a polypeptide having, e.g., at most one, two, three, four, five, six, seven, eight, nine, 10 or 20 contiguous amino acid substitutions relative to amino acids 118-211 of SEQ ID NO: 73. In other aspects of this embodiment, a GDNF comprises a polypeptide having, e.g., at least one, two, three, four, five, six, seven, eight, nine, 10 or 20 contiguous amino acid substitutions relative to amino acids 118-211 of SEQ ID NO: 73. In yet other aspects of this embodiment, a GDNF comprises a polypeptide having, e.g., at most one, two, three, four, five, six, seven, eight, nine, 10 or 20 contiguous amino acid deletions relative to amino acids 118-211 of SEQ ID NO: 73. In other aspects of this embodiment, a GDNF comprises a polypeptide having, e.g., at least one, two, three, four, five, six, seven, eight, nine, 10 or 20 contiguous amino acid deletions relative to amino acids 118-211 of SEQ ID NO: 73. In still other aspects of this embodiment, a GDNF comprises a polypeptide having, e.g., at most one, two, three, four, five, six, seven, eight, nine, 10 or 20 contiguous amino acid additions relative to amino acids 118-211 of SEQ ID NO: 73. In other aspects of this embodiment, a GDNF comprises a polypeptide having, e.g., at least one, two, three, four, five, six, seven, eight, nine, 10 or 20 contiguous amino acid additions relative to amino acids 118-211 of SEQ ID NO: 73.

In an embodiment, a binding domain comprises a Neurturin. In another embodiment, a binding domain comprises a Neurturin of SEQ ID NO: 74. In another embodiment, a binding domain is derived from a Neurturin. In another embodiment, a binding domain is derived from a Neurturin of SEQ ID NO: 74. In an aspect of this embodiment, a binding domain is derived from a Neurturin comprising amino acids 107-196 or amino acids 96-197 of SEQ ID NO: 74.

In other aspects of this embodiment, a Neurturin comprises a polypeptide having, e.g., at least 70% amino acid identity with amino acids 107-196 or amino acids 96-197 of SEQ ID NO: 74, at least 75% amino acid identity with amino acids 107-196 or amino acids 96-197 of SEQ ID NO: 74, at least 80% amino acid identity with amino acids 107-196 or amino acids 96-197 of SEQ ID NO: 74, at least 85% amino acid identity with amino acids 107-196 or amino acids 96-197 of SEQ ID NO: 74, at least 90% amino acid identity with amino acids 107-196 or amino acids 96-197 of SEQ ID NO: 74 or at least 95% amino acid identity with amino acids 107-196 or amino acids 96-197 of SEQ ID NO: 74. In yet other aspects of this embodiment, a Neurturin comprises a polypeptide having, e.g., at most 70% amino acid identity with amino acids 107-196 or amino acids 96-197 of SEQ ID NO: 74, at most 75% amino acid identity with amino acids 107-196 or amino acids 96-197 of SEQ ID NO: 74, at most 80% amino acid identity with amino acids 107-196 or amino acids 96-197 of SEQ ID NO: 74, at most 85% amino acid identity with amino acids 107-196 or amino acids 96-197 of SEQ ID NO: 74, at most 90% amino acid identity with amino acids 107-196 or amino acids 96-197 of SEQ ID NO: 74 or at most 95% amino acid identity with amino acids 107-196 or amino acids 96-197 of SEQ ID NO: 74.

In other aspects of this embodiment, a Neurturin comprises a polypeptide having, e.g., at most one, two, three, four, five, six, seven, eight, nine, 10 or 20 non-contiguous amino acid substitutions relative to amino acids 107-196 or amino acids 96-197 of SEQ ID NO: 74. In other aspects of this embodiment, a Neurturin comprises a polypeptide having, e.g., at least one, two, three, four, five, six, seven, eight, nine, 10 or 20 non-contiguous amino acid substitutions relative to amino acids 107-196 or amino acids 96-197 of SEQ ID NO: 74. In yet other aspects of this embodiment, a Neurturin comprises a polypeptide having, e.g., at most one, two, three, four, five, six, seven, eight, nine, 10 or 20 non-contiguous amino acid deletions relative to amino acids 107-196 or amino acids 96-197 of SEQ ID NO: 74. In other aspects of this embodiment, a Neurturin comprises a polypeptide having, e.g., at least one, two, three, four, five, six, seven, eight, nine, 10 or 20 non-contiguous amino acid deletions relative to amino acids 107-196 or amino acids 96-197 of SEQ ID NO: 74. In still other aspects of this embodiment, a Neurturin comprises a polypeptide having, e.g., at most one, two, three, four, five, six, seven, eight, nine, 10 or 20 non-contiguous amino acid additions relative to amino acids 107-196 or amino acids 96-197 of SEQ ID NO: 74. In other aspects of this embodiment, a Neurturin comprises a polypeptide having, e.g., at least one, two, three, four, five, six, seven, eight, nine, 10 or 20 non-contiguous amino acid additions relative to amino acids 107-196 or amino acids 96-197 of SEQ ID NO: 74.

In other aspects of this embodiment, a Neurturin comprises a polypeptide having, e.g., at most one, two, three, four, five, six, seven, eight, nine, 10 or 20 contiguous amino acid substitutions relative to amino acids 107-196 or amino acids 96-197 of SEQ ID NO: 74. In other aspects of this embodiment, a Neurturin comprises a polypeptide having, e.g., at least one, two, three, four, five, six, seven, eight, nine, 10 or 20 contiguous amino acid substitutions relative to amino acids 107-196 or amino acids 96-197 of SEQ ID NO: 74. In yet other aspects of this embodiment, a Neurturin comprises a polypeptide having, e.g., at most one, two, three, four, five, six, seven, eight, nine, 10 or 20 contiguous amino acid deletions relative to amino acids 107-196 or amino acids 96-197 of SEQ ID NO: 74. In other aspects of this embodiment, a Neurturin comprises a polypeptide having, e.g., at least one, two, three, four, five, six, seven, eight, nine, 10 or 20 contiguous amino acid deletions relative to amino acids 107-196 or amino acids 96-197 of SEQ ID NO: 74. In still other aspects of this embodiment, a Neurturin comprises a polypeptide having, e.g., at most one, two, three, four, five, six, seven, eight, nine, 10 or 20 contiguous amino acid additions relative to amino acids 107-196 or amino acids 96-197 of SEQ ID NO: 74. In other aspects of this embodiment, a Neurturin comprises a polypeptide having, e.g., at least one, two, three, four, five, six, seven, eight, nine, 10 or 20 contiguous amino acid additions relative to amino acids 107-196 or amino acids 96-197 of SEQ ID NO: 74.

In an embodiment, a binding domain comprises a Persephrin. In another embodiment, a binding domain comprises a Persephrin of SEQ ID NO: 75. In another embodiment, a binding domain is derived from a Persephrin. In another embodiment, a binding domain is derived from a Persephrin of SEQ ID NO: 75. In an aspect of this embodiment, a binding domain is derived from a Persephrin comprising amino acids 66-155 of SEQ ID NO: 75.

In other aspects of this embodiment, a Persephrin comprises a polypeptide having, e.g., at least 70% amino acid identity with amino acids 66-155 of SEQ ID NO: 75, at least 75% amino acid identity with amino acids 66-155 of SEQ ID NO: 75, at least 80% amino acid identity with amino acids 66-155 of SEQ ID NO: 75, at least 85% amino acid identity with amino acids 66-155 of SEQ ID NO: 75, at least 90% amino acid identity with amino acids 66-155 of SEQ ID NO: 75 or at least 95% amino acid identity with amino acids 66-155 of SEQ ID NO: 75. In yet other aspects of this embodiment, a Persephrin comprises a polypeptide having, e.g., at most 70% amino acid identity with amino acids 66-155 of SEQ ID NO: 75, at most 75% amino acid identity with amino acids 66-155 of SEQ ID NO: 75, at most 80% amino acid identity with amino acids 66-155 of SEQ ID NO: 75, at most 85% amino acid identity with amino acids 66-155 of SEQ ID NO: 75, at most 90% amino acid identity with amino acids 66-155 of SEQ ID NO: 75 or at most 95% amino acid identity with amino acids 66-155 of SEQ ID NO: 75.

In other aspects of this embodiment, a Persephrin comprises a polypeptide having, e.g., at most one, two, three, four, five, six, seven, eight, nine, 10 or 20 non-contiguous amino acid substitutions relative to amino acids 66-155 of SEQ ID NO: 75. In other aspects of this embodiment, a Persephrin comprises a polypeptide having, e.g., at least one, two, three, four, five, six, seven, eight, nine, 10 or 20 non-contiguous amino acid substitutions relative to amino acids 66-155 of SEQ ID NO: 75. In yet other aspects of this embodiment, a Persephrin comprises a polypeptide having, e.g., at most one, two, three, four, five, six, seven, eight, nine, 10 or 20 non-contiguous amino acid deletions relative to amino acids 66-155 of SEQ ID NO: 75. In other aspects of this embodiment, a Persephrin comprises a polypeptide having, e.g., at least one, two, three, four, five, six, seven, eight, nine, 10 or 20 non-contiguous amino acid deletions relative to amino acids 66-155 of SEQ ID NO: 75. In still other aspects of this embodiment, a Persephrin comprises a polypeptide having, e.g., at most one, two, three, four, five, six, seven, eight, nine, 10 or 20 non-contiguous amino acid additions relative to amino acids 66-155 of SEQ ID NO: 75. In other aspects of this embodiment, a Persephrin comprises a polypeptide having, e.g., at least one, two, three, four, five, six, seven, eight, nine, 10 or 20 non-contiguous amino acid additions relative to amino acids 66-155 of SEQ ID NO: 75.

In other aspects of this embodiment, a Persephrin comprises a polypeptide having, e.g., at most one, two, three, four, five, six, seven, eight, nine, 10 or 20 contiguous amino acid substitutions relative to amino acids 66-155 of SEQ ID NO: 75. In other aspects of this embodiment, a Persephrin comprises a polypeptide having, e.g., at least one, two, three, four, five, six, seven, eight, nine, 10 or 20 contiguous amino acid substitutions relative to amino acids 66-155 of SEQ ID NO: 75. In yet other aspects of this embodiment, a Persephrin comprises a polypeptide having, e.g., at most one, two, three, four, five, six, seven, eight, nine, 10 or 20 contiguous amino acid deletions relative to amino acids 66-155 of SEQ ID NO: 75. In other aspects of this embodiment, a Persephrin comprises a polypeptide having, e.g., at least one, two, three, four, five, six, seven, eight, nine, 10 or 20 contiguous amino acid deletions relative to amino acids 66-155 of SEQ ID NO: 75. In still other aspects of this embodiment, a Persephrin comprises a polypeptide having, e.g., at most one, two, three, four, five, six, seven, eight, nine, 10 or 20 contiguous amino acid additions relative to amino acids 66-155 of SEQ ID NO: 75. In other aspects of this embodiment, a Persephrin comprises a polypeptide having, e.g., at least one, two, three, four, five, six, seven, eight, nine, 10 or 20 contiguous amino acid additions relative to amino acids 66-155 of SEQ ID NO: 75.

In an embodiment, a binding domain comprises an Artemin. In another embodiment, a binding domain comprises an Artemin of SEQ ID NO: 76. In another embodiment, a binding domain is derived from an Artemin. In another embodiment, a binding domain is derived from an Artemin of SEQ ID NO: 76. In an aspect of this embodiment, a binding domain is derived from an Artemin comprising amino acids 123-218 of SEQ ID NO: 76.

In other aspects of this embodiment, an Artemin comprises a polypeptide having, e.g., at least 70% amino acid identity with amino acids 123-218 of SEQ ID NO: 76, at least 75% amino acid identity with amino acids 123-218 of SEQ ID NO: 76, at least 80% amino acid identity with amino acids 123-218 of SEQ ID NO: 76, at least 85% amino acid identity with amino acids 123-218 of SEQ ID NO: 76, at least 90% amino acid identity with amino acids 123-218 of SEQ ID NO: 76 or at least 95% amino acid identity with amino acids 123-218 of SEQ ID NO: 76. In yet other aspects of this embodiment, an Artemin comprises a polypeptide having, e.g., at most 70% amino acid identity with amino acids 123-218 of SEQ ID NO: 76, at most 75% amino acid identity with amino acids 123-218 of SEQ ID NO: 76, at most 80% amino acid identity with amino acids 123-218 of SEQ ID NO: 76, at most 85% amino acid identity with amino acids 123-218 of SEQ ID NO: 76, at most 90% amino acid identity with amino acids 123-218 of SEQ ID NO: 76 or at most 95% amino acid identity with amino acids 123-218 of SEQ ID NO: 76.

In other aspects of this embodiment, an Artemin comprises a polypeptide having, e.g., at most one, two, three, four, five, six, seven, eight, nine, 10 or 20 non-contiguous amino acid substitutions relative to amino acids 123-218 of SEQ ID NO: 76. In other aspects of this embodiment, an Artemin comprises a polypeptide having, e.g., at least one, two, three, four, five, six, seven, eight, nine, 10 or 20 non-contiguous amino acid substitutions relative to amino acids 123-218 of SEQ ID NO: 76. In yet other aspects of this embodiment, an Artemin comprises a polypeptide having, e.g., at most one, two, three, four, five, six, seven, eight, nine, 10 or 20 non-contiguous amino acid deletions relative to amino acids 123-218 of SEQ ID NO: 76. In other aspects of this embodiment, an Artemin comprises a polypeptide having, e.g., at least one, two, three, four, five, six, seven, eight, nine, 10 or 20 non-contiguous amino acid deletions relative to amino acids 123-218 of SEQ ID NO: 76. In still other aspects of this embodiment, an Artemin comprises a polypeptide having, e.g., at most one, two, three, four, five, six, seven, eight, nine, 10 or 20 non-contiguous amino acid additions relative to amino acids 123-218 of SEQ ID NO: 76. In other aspects of this embodiment, an Artemin comprises a polypeptide having, e.g., at least one, two, three, four, five, six, seven, eight, nine, 10 or 20 non-contiguous amino acid additions relative to amino acids 123-218 of SEQ ID NO: 76.

In other aspects of this embodiment, an Artemin comprises a polypeptide having, e.g., at most one, two, three, four, five, six, seven, eight, nine, 10 or 20 contiguous amino acid substitutions relative to amino acids 123-218 of SEQ ID NO: 76. In other aspects of this embodiment, an Artemin comprises a polypeptide having, e.g., at least one, two, three, four, five, six, seven, eight, nine, 10 or 20 contiguous amino acid substitutions relative to amino acids 123-218 of SEQ ID NO: 76. In yet other aspects of this embodiment, an Artemin comprises a polypeptide having, e.g., at most one, two, three, four, five, six, seven, eight, nine, 10 or 20 contiguous amino acid deletions relative to amino acids 123-218 of SEQ ID NO: 76. In other aspects of this embodiment, an Artemin comprises a polypeptide having, e.g., at least one, two, three, four, five, six, seven, eight, nine, 10 or 20 contiguous amino acid deletions relative to amino acids 123-218 of SEQ ID NO: 76. In still other aspects of this embodiment, an Artemin comprises a polypeptide having, e.g., at most one, two, three, four, five, six, seven, eight, nine, 10 or 20 contiguous amino acid additions relative to amino acids 123-218 of SEQ ID NO: 76. In other aspects of this embodiment, an Artemin comprises a polypeptide having, e.g., at least one, two, three, four, five, six, seven, eight, nine, 10 or 20 contiguous amino acid additions relative to amino acids 123-218 of SEQ ID NO: 76.

Another example of a binding domain disclosed in the present specification is, e.g., a TGFβs, such as, e.g., TGFβ1, TGFβ2, TGFβ3 or TGFβ4.

Thus, in an embodiment, a binding domain comprises a TGFβ1. In another embodiment, a binding domain comprises a TGFβ1 of SEQ ID NO: 77. In another embodiment, a binding domain is derived from a TGFβ1. In another embodiment, a binding domain is derived from a TGFβ1 of SEQ ID NO: 77. In an aspect of this embodiment, a binding domain is derived from a TGFβ1 comprising amino acids 293-390 of SEQ ID NO: 77.

In other aspects of this embodiment, a TGFβ1 comprises a polypeptide having, e.g., at least 70% amino acid identity with amino acids 293-390 of SEQ ID NO: 77, at least 75% amino acid identity with amino acids 293-390 of SEQ ID NO: 77, at least 80% amino acid identity with amino acids 293-390 of SEQ ID NO: 77, at least 85% amino acid identity with amino acids 293-390 of SEQ ID NO: 77, at least 90% amino acid identity with amino acids 293-390 of SEQ ID NO: 77 or at least 95% amino acid identity with amino acids 293-390 of SEQ ID NO: 77. In yet other aspects of this embodiment, a TGFβ1 comprises a polypeptide having, e.g., at most 70% amino acid identity with amino acids 293-390 of SEQ ID NO: 77, at most 75% amino acid identity with amino acids 293-390 of SEQ ID NO: 77, at most 80% amino acid identity with amino acids 293-390 of SEQ ID NO: 77, at most 85% amino acid identity with amino acids 293-390 of SEQ ID NO: 77, at most 90% amino acid identity with amino acids 293-390 of SEQ ID NO: 77 or at most 95% amino acid identity with amino acids 293-390 of SEQ ID NO: 77.

In other aspects of this embodiment, a TGFβ1 comprises a polypeptide having, e.g., at most one, two, three, four, five, six, seven, eight, nine, 10 or 20 non-contiguous amino acid substitutions relative to amino acids 293-390 of SEQ ID NO: 77. In other aspects of this embodiment, a TGFβ1 comprises a polypeptide having, e.g., at least one, two, three, four, five, six, seven, eight, nine, 10 or 20 non-contiguous amino acid substitutions relative to amino acids 293-390 of SEQ ID NO: 77. In yet other aspects of this embodiment, a TGFβ1 comprises a polypeptide having, e.g., at most one, two, three, four, five, six, seven, eight, nine, 10 or 20 non-contiguous amino acid deletions relative to amino acids 293-390 of SEQ ID NO: 77. In other aspects of this embodiment, a TGFβ1 comprises a polypeptide having, e.g., at least one, two, three, four, five, six, seven, eight, nine, 10 or 20 non-contiguous amino acid deletions relative to amino acids 293-390 of SEQ ID NO: 77. In still other aspects of this embodiment, a TGFβ1 comprises a polypeptide having, e.g., at most one, two, three, four, five, six, seven, eight, nine, 10 or 20 non-contiguous amino acid additions relative to amino acids 293-390 of SEQ ID NO: 77. In other aspects of this embodiment, a TGFβ1 comprises a polypeptide having, e.g., at least one, two, three, four, five, six, seven, eight, nine, 10 or 20 non-contiguous amino acid additions relative to amino acids 293-390 of SEQ ID NO: 77.

In other aspects of this embodiment, a TGFβ1 comprises a polypeptide having, e.g., at most one, two, three, four, five, six, seven, eight, nine, 10 or 20 contiguous amino acid substitutions relative to amino acids 293-390 of SEQ ID NO: 77. In other aspects of this embodiment, a TGFβ1 comprises a polypeptide having, e.g., at least one, two, three, four, five, six, seven, eight, nine, 10 or 20 contiguous amino acid substitutions relative to amino acids 293-390 of SEQ ID NO: 77. In yet other aspects of this embodiment, a TGFβ1 comprises a polypeptide having, e.g., at most one, two, three, four, five, six, seven, eight, nine, 10 or 20 contiguous amino acid deletions relative to amino acids 293-390 of SEQ ID NO: 77. In other aspects of this embodiment, a TGFβ1 comprises a polypeptide having, e.g., at least one, two, three, four, five, six, seven, eight, nine, 10 or 20 contiguous amino acid deletions relative to amino acids 293-390 of SEQ ID NO: 77. In still other aspects of this embodiment, a TGFβ1 comprises a polypeptide having, e.g., at most one, two, three, four, five, six, seven, eight, nine, 10 or 20 contiguous amino acid additions relative to amino acids 293-390 of SEQ ID NO: 77. In other aspects of this embodiment, a TGFβ1 comprises a polypeptide having, e.g., at least one, two, three, four, five, six, seven, eight, nine, 10 or 20 contiguous amino acid additions relative to amino acids 293-390 of SEQ ID NO: 77.

In an embodiment, a binding domain comprises a TGFβ2. In another embodiment, a binding domain comprises a TGFβ2 of SEQ ID NO: 78. In another embodiment, a binding domain is derived from a TGFβ2. In another embodiment, a binding domain is derived from a TGFβ2 of SEQ ID NO: 77. In an aspect of this embodiment, a binding domain is derived from a TGFβ2 comprising amino acids 317-414 of SEQ ID NO: 78.

In other aspects of this embodiment, a TGFβ2 comprises a polypeptide having, e.g., at least 70% amino acid identity with amino acids 317-414 of SEQ ID NO: 78, at least 75% amino acid identity with amino acids 317-414 of SEQ ID NO: 78, at least 80% amino acid identity with amino acids 317-414 of SEQ ID NO: 78, at least 85% amino acid identity with amino acids 317-414 of SEQ ID NO: 78, at least 90% amino acid identity with amino acids 317-414 of SEQ ID NO: 78 or at least 95% amino acid identity with amino acids 317-414 of SEQ ID NO: 78. In yet other aspects of this embodiment, a TGFβ2 comprises a polypeptide having, e.g., at most 70% amino acid identity with amino acids 317-414 of SEQ ID NO: 78, at most 75% amino acid identity with amino acids 317-414 of SEQ ID NO: 78, at most 80% amino acid identity with amino acids 317-414 of SEQ ID NO: 78, at most 85% amino acid identity with amino acids 317-414 of SEQ ID NO: 78, at most 90% amino acid identity with amino acids 317-414 of SEQ ID NO: 78 or at most 95% amino acid identity with amino acids 317-414 of SEQ ID NO: 78.

In other aspects of this embodiment, a TGFβ2 comprises a polypeptide having, e.g., at most one, two, three, four, five, six, seven, eight, nine, 10 or 20 non-contiguous amino acid substitutions relative to amino acids 317-414 of SEQ ID NO: 78. In other aspects of this embodiment, a TGFβ2 comprises a polypeptide having, e.g., at least one, two, three, four, five, six, seven, eight, nine, 10 or 20 non-contiguous amino acid substitutions relative to amino acids 317-414 of SEQ ID NO: 78. In yet other aspects of this embodiment, a TGFβ2 comprises a polypeptide having, e.g., at most one, two, three, four, five, six, seven, eight, nine, 10 or 20 non-contiguous amino acid deletions relative to amino acids 317-414 of SEQ ID NO: 78. In other aspects of this embodiment, a TGFβ2 comprises a polypeptide having, e.g., at least one, two, three, four, five, six, seven, eight, nine, 10 or 20 non-contiguous amino acid deletions relative to amino acids 317-414 of SEQ ID NO: 78. In still other aspects of this embodiment, a TGFβ2 comprises a polypeptide having, e.g., at most one, two, three, four, five, six, seven, eight, nine, 10 or 20 non-contiguous amino acid additions relative to amino acids 317-414 of SEQ ID NO: 78. In other aspects of this embodiment, a TGFβ2 comprises a polypeptide having, e.g., at least one, two, three, four, five, six, seven, eight, nine, 10 or 20 non-contiguous amino acid additions relative to amino acids 317-414 of SEQ ID NO: 78.

In other aspects of this embodiment, a TGFβ2 comprises a polypeptide having, e.g., at most one, two, three, four, five, six, seven, eight, nine, 10 or 20 contiguous amino acid substitutions relative to amino acids 317-414 of SEQ ID NO: 78. In other aspects of this embodiment, a TGFβ2 comprises a polypeptide having, e.g., at least one, two, three, four, five, six, seven, eight, nine, 10 or 20 contiguous amino acid substitutions relative to amino acids 317-414 of SEQ ID NO: 78. In yet other aspects of this embodiment, a TGFβ2 comprises a polypeptide having, e.g., at most one, two, three, four, five, six, seven, eight, nine, 10 or 20 contiguous amino acid deletions relative to amino acids 317-414 of SEQ ID NO: 78. In other aspects of this embodiment, a TGFβ2 comprises a polypeptide having, e.g., at least one, two, three, four, five, six, seven, eight, nine, 10 or 20 contiguous amino acid deletions relative to amino acids 317-414 of SEQ ID NO: 78. In still other aspects of this embodiment, a TGFβ2 comprises a polypeptide having, e.g., at most one, two, three, four, five, six, seven, eight, nine, 10 or 20 contiguous amino acid additions relative to amino acids 317-414 of SEQ ID NO: 78. In other aspects of this embodiment, a TGFβ2 comprises a polypeptide having, e.g., at least one, two, three, four, five, six, seven, eight, nine, 10 or 20 contiguous amino acid additions relative to amino acids 317-414 of SEQ ID NO: 78.

In an embodiment, a binding domain comprises a TGFβ3. In another embodiment, a binding domain comprises a TGFβ3 of SEQ ID NO: 79. In another embodiment, a binding domain is derived from a TGFβ3. In another embodiment, a binding domain is derived from a TGFβ3 of SEQ ID NO: 77. In an aspect of this embodiment, a binding domain is derived from a TGFβ3 comprising amino acids 315-412 of SEQ ID NO: 79.

In other aspects of this embodiment, a TGFβ3 comprises a polypeptide having, e.g., at least 70% amino acid identity with amino acids 315-412 of SEQ ID NO: 79, at least 75% amino acid identity with amino acids 315-412 of SEQ ID NO: 79, at least 80% amino acid identity with amino acids 315-412 of SEQ ID NO: 79, at least 85% amino acid identity with amino acids 315-412 of SEQ ID NO: 79, at least 90% amino acid identity with amino acids 315-412 of SEQ ID NO: 79 or at least 95% amino acid identity with amino acids 315-412 of SEQ ID NO: 79. In yet other aspects of this embodiment, a TGFβ3 comprises a polypeptide having, e.g., at most 70% amino acid identity with amino acids 315-412 of SEQ ID NO: 79, at most 75% amino acid identity with amino acids 315-412 of SEQ ID NO: 79, at most 80% amino acid identity with amino acids 315-412 of SEQ ID NO: 79, at most 85% amino acid identity with amino acids 315-412 of SEQ ID NO: 79, at most 90% amino acid identity with amino acids 315-412 of SEQ ID NO: 79 or at most 95% amino acid identity with amino acids 315-412 of SEQ ID NO: 79.

In other aspects of this embodiment, a TGFβ3 comprises a polypeptide having, e.g., at most one, two, three, four, five, six, seven, eight, nine, 10 or 20 non-contiguous amino acid substitutions relative to amino acids 315-412 of SEQ ID NO: 79. In other aspects of this embodiment, a TGFβ3 comprises a polypeptide having, e.g., at least one, two, three, four, five, six, seven, eight, nine, 10 or 20 non-contiguous amino acid substitutions relative to amino acids 315-412 of SEQ ID NO: 79. In yet other aspects of this embodiment, a TGFβ3 comprises a polypeptide having, e.g., at most one, two, three, four, five, six, seven, eight, nine, 10 or 20 non-contiguous amino acid deletions relative to amino acids 315-412 of SEQ ID NO: 79. In other aspects of this embodiment, a TGFβ3 comprises a polypeptide having, e.g., at least one, two, three, four, five, six, seven, eight, nine, 10 or 20 non-contiguous amino acid deletions relative to amino acids 315-412 of SEQ ID NO: 79. In still other aspects of this embodiment, a TGFβ3 comprises a polypeptide having, e.g., at most one, two, three, four, five, six, seven, eight, nine, 10 or 20 non-contiguous amino acid additions relative to amino acids 315-412 of SEQ ID NO: 79. In other aspects of this embodiment, a TGFβ3 comprises a polypeptide having, e.g., at least one, two, three, four, five, six, seven, eight, nine, 10 or 20 non-contiguous amino acid additions relative to amino acids 315-412 of SEQ ID NO: 79.

In other aspects of this embodiment, a TGFβ3 comprises a polypeptide having, e.g., at most one, two, three, four, five, six, seven, eight, nine, 10 or 20 contiguous amino acid substitutions relative to amino acids 315-412 of SEQ ID NO: 79. In other aspects of this embodiment, a TGFβ3 comprises a polypeptide having, e.g., at least one, two, three, four, five, six, seven, eight, nine, 10 or 20 contiguous amino acid substitutions relative to amino acids 315-412 of SEQ ID NO: 79. In yet other aspects of this embodiment, a TGFβ3 comprises a polypeptide having, e.g., at most one, two, three, four, five, six, seven, eight, nine, 10 or 20 contiguous amino acid deletions relative to amino acids 315-412 of SEQ ID NO: 79. In other aspects of this embodiment, a TGFβ3 comprises a polypeptide having, e.g., at least one, two, three, four, five, six, seven, eight, nine, 10 or 20 contiguous amino acid deletions relative to amino acids 315-412 of SEQ ID NO: 79. In still other aspects of this embodiment, a TGFβ3 comprises a polypeptide having, e.g., at most one, two, three, four, five, six, seven, eight, nine, 10 or 20 contiguous amino acid additions relative to amino acids 315-412 of SEQ ID NO: 79. In other aspects of this embodiment, a TGFβ3 comprises a polypeptide having, e.g., at least one, two, three, four, five, six, seven, eight, nine, 10 or 20 contiguous amino acid additions relative to amino acids 315-412 of SEQ ID NO: 79.

In an embodiment, a binding domain comprises a TGFβ4. In another embodiment, a binding domain comprises a TGFβ4 of SEQ ID NO: 80. In another embodiment, a binding domain is derived from a TGFβ4. In another embodiment, a binding domain is derived from a TGFβ4 of SEQ ID NO: 77. In an aspect of this embodiment, a binding domain is derived from a TGFβ4 comprising amino acids 276-373 of SEQ ID NO: 80.

In other aspects of this embodiment, a TGFβ4 comprises a polypeptide having, e.g., at least 70% amino acid identity with amino acids 276-373 of SEQ ID NO: 80, at least 75% amino acid identity with amino acids 276-373 of SEQ ID NO: 80, at least 80% amino acid identity with amino acids 276-373 of SEQ ID NO: 80, at least 85% amino acid identity with amino acids 276-373 of SEQ ID NO: 80, at least 90% amino acid identity with amino acids 276-373 of SEQ ID NO: 80 or at least 95% amino acid identity with amino acids 276-373 of SEQ ID NO: 80. In yet other aspects of this embodiment, a TGFβ4 comprises a polypeptide having, e.g., at most 70% amino acid identity with amino acids 276-373 of SEQ ID NO: 80, at most 75% amino acid identity with amino acids 276-373 of SEQ ID NO: 80, at most 80% amino acid identity with amino acids 276-373 of SEQ ID NO: 80, at most 85% amino acid identity with amino acids 276-373 of SEQ ID NO: 80, at most 90% amino acid identity with amino acids 276-373 of SEQ ID NO: 80 or at most 95% amino acid identity with amino acids 276-373 of SEQ ID NO: 80.

In other aspects of this embodiment, a TGFβ4 comprises a polypeptide having, e.g., at most one, two, three, four, five, six, seven, eight, nine, 10 or 20 non-contiguous amino acid substitutions relative to amino acids 276-373 of SEQ ID NO: 80. In other aspects of this embodiment, a TGFβ4 comprises a polypeptide having, e.g., at least one, two, three, four, five, six, seven, eight, nine, 10 or 20 non-contiguous amino acid substitutions relative to amino acids 276-373 of SEQ ID NO: 80. In yet other aspects of this embodiment, a TGFβ4 comprises a polypeptide having, e.g., at most one, two, three, four, five, six, seven, eight, nine, 10 or 20 non-contiguous amino acid deletions relative to amino acids 276-373 of SEQ ID NO: 80. In other aspects of this embodiment, a TGFβ4 comprises a polypeptide having, e.g., at least one, two, three, four, five, six, seven, eight, nine, 10 or 20 non-contiguous amino acid deletions relative to amino acids 276-373 of SEQ ID NO: 80. In still other aspects of this embodiment, a TGFβ4 comprises a polypeptide having, e.g., at most one, two, three, four, five, six, seven, eight, nine, 10 or 20 non-contiguous amino acid additions relative to amino acids 276-373 of SEQ ID NO: 80. In other aspects of this embodiment, a TGFβ4 comprises a polypeptide having, e.g., at least one, two, three, four, five, six, seven, eight, nine, 10 or 20 non-contiguous amino acid additions relative to amino acids 276-373 of SEQ ID NO: 80.

In other aspects of this embodiment, a TGFβ4 comprises a polypeptide having, e.g., at least one, two, three, four, five, six, seven, eight, nine, 10 or 20 contiguous amino acid substitutions relative to amino acids 276-373 of SEQ ID NO: 80. In other aspects of this embodiment, a TGFβ4 comprises a polypeptide having, e.g., at least one, two, three, four, five, six, seven, eight, nine, 10 or 20 contiguous amino acid substitutions relative to amino acids 276-373 of SEQ ID NO: 80. In yet other aspects of this embodiment, a TGFβ4 comprises a polypeptide having, e.g., at most one, two, three, four, five, six, seven, eight, nine, 10 or 20 contiguous amino acid deletions relative to amino acids 276-373 of SEQ ID NO: 80. In other aspects of this embodiment, a TGFβ4 comprises a polypeptide having, e.g., at least one, two, three, four, five, six, seven, eight, nine, 10 or 20 contiguous amino acid deletions relative to amino acids 276-373 of SEQ ID NO: 80. In still other aspects of this embodiment, a TGFβ4 comprises a polypeptide having, e.g., at most one, two, three, four, five, six, seven, eight, nine, 10 or 20 contiguous amino acid additions relative to amino acids 276-373 of SEQ ID NO: 80. In other aspects of this embodiment, a TGFβ4 comprises a polypeptide having, e.g., at least one, two, three, four, five, six, seven, eight, nine, 10 or 20 contiguous amino acid additions relative to amino acids 276-373 of SEQ ID NO: 80.

Another example of a binding domain disclosed in the present specification is, e.g., a BMPs, such as, e.g., BMP2, BMP3, BMP4, BMP5, BMP6, BMP7, BMP8 or BMP10.

Thus, in an embodiment, a binding domain comprises a BMP2. In another embodiment, a binding domain comprises a BMP2 of SEQ ID NO: 81. In another embodiment, a binding domain is derived from a BMP2. In another embodiment, a binding domain is derived from a BMP2 of SEQ ID NO: 81. In an aspect of this embodiment, a binding domain is derived from a BMP2 comprising amino acids 296-396 of SEQ ID NO: 81.

In other aspects of this embodiment, a BMP2 comprises a polypeptide having, e.g., at least 70% amino acid identity with amino acids 296-396 of SEQ ID NO: 81, at least 75% amino acid identity with amino acids 296-396 of SEQ ID NO: 81, at least 80% amino acid identity with amino acids 296-396 of SEQ ID NO: 81, at least 85% amino acid identity with amino acids 296-396 of SEQ ID NO: 81, at least 90% amino acid identity with amino acids 296-396 of SEQ ID NO: 81 or at least 95% amino acid identity with amino acids 296-396 of SEQ ID NO: 81. In yet other aspects of this embodiment, a BMP2 comprises a polypeptide having, e.g., at most 70% amino acid identity with amino acids 296-396 of SEQ ID NO: 81, at most 75% amino acid identity with amino acids 296-396 of SEQ ID NO: 81, at most 80% amino acid identity with amino acids 296-396 of SEQ ID NO: 81, at most 85% amino acid identity with amino acids 296-396 of SEQ ID NO: 81, at most 90% amino acid identity with amino acids 296-396 of SEQ ID NO: 81 or at most 95% amino acid identity with amino acids 296-396 of SEQ ID NO: 81.

In other aspects of this embodiment, a BMP2 comprises a polypeptide having, e.g., at most one, two, three, four, five, six, seven, eight, nine, 10 or 20 non-contiguous amino acid substitutions relative to amino acids 296-396 of SEQ ID NO: 81. In other aspects of this embodiment, a BMP2 comprises a polypeptide having, e.g., at least one, two, three, four, five, six, seven, eight, nine, 10 or 20 non-contiguous amino acid substitutions relative to amino acids 296-396 of SEQ ID NO: 81. In yet other aspects of this embodiment, a BMP2 comprises a polypeptide having, e.g., at most one, two, three, four, five, six, seven, eight, nine, 10 or 20 non-contiguous amino acid deletions relative to amino acids 296-396 of SEQ ID NO: 81. In other aspects of this embodiment, a BMP2 comprises a polypeptide having, e.g., at least one, two, three, four, five, six, seven, eight, nine, 10 or 20 non-contiguous amino acid deletions relative to amino acids 296-396 of SEQ ID NO: 81. In still other aspects of this embodiment, a BMP2 comprises a polypeptide having, e.g., at most one, two, three, four, five, six, seven, eight, nine, 10 or 20 non-contiguous amino acid additions relative to amino acids 296-396 of SEQ ID NO: 81. In other aspects of this embodiment, a BMP2 comprises a polypeptide having, e.g., at least one, two, three, four, five, six, seven, eight, nine, 10 or 20 non-contiguous amino acid additions relative to amino acids 296-396 of SEQ ID NO: 81.

In other aspects of this embodiment, a BMP2 comprises a polypeptide having, e.g., at most one, two, three, four, five, six, seven, eight, nine, 10 or 20 contiguous amino acid substitutions relative to amino acids 296-396 of SEQ ID NO: 81. In other aspects of this embodiment, a BMP2 comprises a polypeptide having, e.g., at least one, two, three, four, five, six, seven, eight, nine, 10 or 20 contiguous amino acid substitutions relative to amino acids 296-396 of SEQ ID NO: 81. In yet other aspects of this embodiment, a BMP2 comprises a polypeptide having, e.g., at most one, two, three, four, five, six, seven, eight, nine, 10 or 20 contiguous amino acid deletions relative to amino acids 296-396 of SEQ ID NO: 81. In other aspects of this embodiment, a BMP2 comprises a polypeptide having, e.g., at least one, two, three, four, five, six, seven, eight, nine, 10 or 20 contiguous amino acid deletions relative to amino acids 296-396 of SEQ ID NO: 81. In still other aspects of this embodiment, a BMP2 comprises a polypeptide having, e.g., at most one, two, three, four, five, six, seven, eight, nine, 10 or 20 contiguous amino acid additions relative to amino acids 296-396 of SEQ ID NO: 81. In other aspects of this embodiment, a BMP2 comprises a polypeptide having, e.g., at least one, two, three, four, five, six, seven, eight, nine, 10 or 20 contiguous amino acid additions relative to amino acids 296-396 of SEQ ID NO: 81.

In an embodiment, a binding domain comprises a BMP3. In another embodiment, a binding domain comprises a BMP3 of SEQ ID NO: 82. In another embodiment, a binding domain is derived from a BMP3. In another embodiment, a binding domain is derived from a BMP3 of SEQ ID NO: 82. In an aspect of this embodiment, a binding domain is derived from a BMP3 comprising amino acids 370-472 of SEQ ID NO: 82.

In other aspects of this embodiment, a BMP3 comprises a polypeptide having, e.g., at least 70% amino acid identity with amino acids 370-472 of SEQ ID NO: 82, at least 75% amino acid identity with amino acids 370-472 of SEQ ID NO: 82, at least 80% amino acid identity with amino acids 370-472 of SEQ ID NO: 82, at least 85% amino acid identity with amino acids 370-472 of SEQ ID NO: 82, at least 90% amino acid identity with amino acids 370-472 of SEQ ID NO: 82 or at least 95% amino acid identity with amino acids 370-472 of SEQ ID NO: 82. In yet other aspects of this embodiment, a BMP3 comprises a polypeptide having, e.g., at most 70% amino acid identity with amino acids 370-472 of SEQ ID NO: 82, at most 75% amino acid identity with amino acids 370-472 of SEQ ID NO: 82, at most 80% amino acid identity with amino acids 370-472 of SEQ ID NO: 82, at most 85% amino acid identity with amino acids 370-472 of SEQ ID NO: 82, at most 90% amino acid identity with amino acids 370-472 of SEQ ID NO: 82 or at most 95% amino acid identity with amino acids 370-472 of SEQ ID NO: 82.

In other aspects of this embodiment, a BMP3 comprises a polypeptide having, e.g., at most one, two, three, four, five, six, seven, eight, nine, 10 or 20 non-contiguous amino acid substitutions relative to amino acids 370-472 of SEQ ID NO: 82. In other aspects of this embodiment, a BMP3 comprises a polypeptide having, e.g., at least one, two, three, four, five, six, seven, eight, nine, 10 or 20 non-contiguous amino acid substitutions relative to amino acids 370-472 of SEQ ID NO: 82. In yet other aspects of this embodiment, a BMP3 comprises a polypeptide having, e.g., at most one, two, three, four, five, six, seven, eight, nine, 10 or 20 non-contiguous amino acid deletions relative to amino acids 370-472 of SEQ ID NO: 82. In other aspects of this embodiment, a BMP3 comprises a polypeptide having, e.g., at least one, two, three, four, five, six, seven, eight, nine, 10 or 20 non-contiguous amino acid deletions relative to amino acids 370-472 of SEQ ID NO: 82. In still other aspects of this embodiment, a BMP3 comprises a polypeptide having, e.g., at most one, two, three, four, five, six, seven, eight, nine, 10 or 20 non-contiguous amino acid additions relative to amino acids 370-472 of SEQ ID NO: 82. In other aspects of this embodiment, a BMP3 comprises a polypeptide having, e.g., at least one, two, three, four, five, six, seven, eight, nine, 10 or 20 non-contiguous amino acid additions relative to amino acids 370-472 of SEQ ID NO: 82.

In other aspects of this embodiment, a BMP3 comprises a polypeptide having, e.g., at most one, two, three, four, five, six, seven, eight, nine, 10 or 20 contiguous amino acid substitutions relative to amino acids 370-472 of SEQ ID NO: 82. In other aspects of this embodiment, a BMP3 comprises a polypeptide having, e.g., at least one, two, three, four, five, six, seven, eight, nine, 10 or 20 contiguous amino acid substitutions relative to amino acids 370-472 of SEQ ID NO: 82. In yet other aspects of this embodiment, a BMP3 comprises a polypeptide having, e.g., at most one, two, three, four, five, six, seven, eight, nine, 10 or 20 contiguous amino acid deletions relative to amino acids 370-472 of SEQ ID NO: 82. In other aspects of this embodiment, a BMP3 comprises a polypeptide having, e.g., at least one, two, three, four, five, six, seven, eight, nine, 10 or 20 contiguous amino acid deletions relative to amino acids 370-472 of SEQ ID NO: 82. In still other aspects of this embodiment, a BMP3 comprises a polypeptide having, e.g., at most one, two, three, four, five, six, seven, eight, nine, 10 or 20 contiguous amino acid additions relative to amino acids 370-472 of SEQ ID NO: 82. In other aspects of this embodiment, a BMP3 comprises a polypeptide having, e.g., at least one, two, three, four, five, six, seven, eight, nine, 10 or 20 contiguous amino acid additions relative to amino acids 370-472 of SEQ ID NO: 82.

In an embodiment, a binding domain comprises a BMP4. In another embodiment, a binding domain comprises a BMP4 of SEQ ID NO: 83. In another embodiment, a binding domain is derived from a BMP4. In another embodiment, a binding domain is derived from a BMP4 of SEQ ID NO: 83. In an aspect of this embodiment, a binding domain is derived from a BMP4 comprising amino acids 309-409 of SEQ ID NO: 83.

In other aspects of this embodiment, a BMP4 comprises a polypeptide having, e.g., at least 70% amino acid identity with amino acids 309-409 of SEQ ID NO: 83, at least 75% amino acid identity with amino acids 309-409 of SEQ ID NO: 83, at least 80% amino acid identity with amino acids 309-409 of SEQ ID NO: 83, at least 85% amino acid identity with amino acids 309-409 of SEQ ID NO: 83, at least 90% amino acid identity with amino acids 309-409 of SEQ ID NO: 83 or at least 95% amino acid identity with amino acids 309-409 of SEQ ID NO: 83. In yet other aspects of this embodiment, a BMP4 comprises a polypeptide having, e.g., at most 70% amino acid identity with amino acids 309-409 of SEQ ID NO: 83, at most 75% amino acid identity with amino acids 309-409 of SEQ ID NO: 83, at most 80% amino acid identity with amino acids 309-409 of SEQ ID NO: 83, at most 85% amino acid identity with amino acids 309-409 of SEQ ID NO: 83, at most 90% amino acid identity with amino acids 309-409 of SEQ ID NO: 83 or at most 95% amino acid identity with amino acids 309-409 of SEQ ID NO: 83.

In other aspects of this embodiment, a BMP4 comprises a polypeptide having, e.g., at most one, two, three, four, five, six, seven, eight, nine, 10 or 20 non-contiguous amino acid substitutions relative to amino acids 309-409 of SEQ ID NO: 83. In other aspects of this embodiment, a BMP4 comprises a polypeptide having, e.g., at least one, two, three, four, five, six, seven, eight, nine, 10 or 20 non-contiguous amino acid substitutions relative to amino acids 309-409 of SEQ ID NO: 83. In yet other aspects of this embodiment, a BMP4 comprises a polypeptide having, e.g., at most one, two, three, four, five, six, seven, eight, nine, 10 or 20 non-contiguous amino acid deletions relative to amino acids 309-409 of SEQ ID NO: 83. In other aspects of this embodiment, a BMP4 comprises a polypeptide having, e.g., at least one, two, three, four, five, six, seven, eight, nine, 10 or 20 non-contiguous amino acid deletions relative to amino acids 309-409 of SEQ ID NO: 83. In still other aspects of this embodiment, a BMP4 comprises a polypeptide having, e.g., at most one, two, three, four, five, six, seven, eight, nine, 10 or 20 non-contiguous amino acid additions relative to amino acids 309-409 of SEQ ID NO: 83. In other aspects of this embodiment, a BMP4 comprises a polypeptide having, e.g., at least one, two, three, four, five, six, seven, eight, nine, 10 or 20 non-contiguous amino acid additions relative to amino acids 309-409 of SEQ ID NO: 83.

In other aspects of this embodiment, a BMP4 comprises a polypeptide having, e.g., at most one, two, three, four, five, six, seven, eight, nine, 10 or 20 contiguous amino acid substitutions relative to amino acids 309-409 of SEQ ID NO: 83. In other aspects of this embodiment, a BMP4 comprises a polypeptide having, e.g., at least one, two, three, four, five, six, seven, eight, nine, 10 or 20 contiguous amino acid substitutions relative to amino acids 309-409 of SEQ ID NO: 83. In yet other aspects of this embodiment, a BMP4 comprises a polypeptide having, e.g., at most one, two, three, four, five, six, seven, eight, nine, 10 or 20 contiguous amino acid deletions relative to amino acids 309-409 of SEQ ID NO: 83. In other aspects of this embodiment, a BMP4 comprises a polypeptide having, e.g., at least one, two, three, four, five, six, seven, eight, nine, 10 or 20 contiguous amino acid deletions relative to amino acids 309-409 of SEQ ID NO: 83. In still other aspects of this embodiment, a BMP4 comprises a polypeptide having, e.g., at most one, two, three, four, five, six, seven, eight, nine, 10 or 20 contiguous amino acid additions relative to amino acids 309-409 of SEQ ID NO: 83. In other aspects of this embodiment, a BMP4 comprises a polypeptide having, e.g., at least one, two, three, four, five, six, seven, eight, nine, 10 or 20 contiguous amino acid additions relative to amino acids 309-409 of SEQ ID NO: 83.

In an embodiment, a binding domain comprises a BMP5. In another embodiment, a binding domain comprises a BMP5 of SEQ ID NO: 84. In another embodiment, a binding domain is derived from a BMP5. In another embodiment, a binding domain is derived from a BMP5 of SEQ ID NO: 84. In an aspect of this embodiment, a binding domain is derived from a BMP5 comprising amino acids 353-454 or amino acids 323-454 of SEQ ID NO: 84.

In other aspects of this embodiment, a BMP5 comprises a polypeptide having, e.g., at least 70% amino acid identity with amino acids 353-454 or amino acids 323-454 of SEQ ID NO: 84, at least 75% amino acid identity with amino acids 353-454 or amino acids 323-454 of SEQ ID NO: 84, at least 80% amino acid identity with amino acids 353-454 or amino acids 323-454 of SEQ ID NO: 84, at least 85% amino acid identity with amino acids 353-454 or amino acids 323-454 of SEQ ID NO: 84, at least 90% amino acid identity with amino acids 353-454 or amino acids 323-454 of SEQ ID NO: 84 or at least 95% amino acid identity with amino acids 353-454 or amino acids 323-454 of SEQ ID NO: 84. In yet other aspects of this embodiment, a BMP5 comprises a polypeptide having, e.g., at most 70% amino acid identity with amino acids 353-454 or amino acids 323-454 of SEQ ID NO: 84, at most 75% amino acid identity with amino acids 353-454 or amino acids 323-454 of SEQ ID NO: 84, at most 80% amino acid identity with amino acids 353-454 or amino acids 323-454 of SEQ ID NO: 84, at most 85% amino acid identity with amino acids 353-454 or amino acids 323-454 of SEQ ID NO: 84, at most 90% amino acid identity with amino acids 353-454 or amino acids 323-454 of SEQ ID NO: 84 or at most 95% amino acid identity with amino acids 353-454 or amino acids 323-454 of SEQ ID NO: 84.

In other aspects of this embodiment, a BMP5 comprises a polypeptide having, e.g., at most one, two, three, four, five, six, seven, eight, nine, 10 or 20 non-contiguous amino acid substitutions relative to amino acids 353-454 or amino acids 323-454 of SEQ ID NO: 84. In other aspects of this embodiment, a BMP5 comprises a polypeptide having, e.g., at least one, two, three, four, five, six, seven, eight, nine, 10 or 20 non-contiguous amino acid substitutions relative to amino acids 353-454 or amino acids 323-454 of SEQ ID NO: 84. In yet other aspects of this embodiment, a BMP5 comprises a polypeptide having, e.g., at most one, two, three, four, five, six, seven, eight, nine, 10 or 20 non-contiguous amino acid deletions relative to amino acids 353-454 or amino acids 323-454 of SEQ ID NO: 84. In other aspects of this embodiment, a BMP5 comprises a polypeptide having, e.g., at least one, two, three, four, five, six, seven, eight, nine, 10 or 20 non-contiguous amino acid deletions relative to amino acids 353-454 or amino acids 323-454 of SEQ ID NO: 84. In still other aspects of this embodiment, a BMP5 comprises a polypeptide having, e.g., at most one, two, three, four, five, six, seven, eight, nine, 10 or 20 non-contiguous amino acid additions relative to amino acids 353-454 or amino acids 323-454 of SEQ ID NO: 84. In other aspects of this embodiment, a BMP5 comprises a polypeptide having, e.g., at least one, two, three, four, five, six, seven, eight, nine, 10 or 20 non-contiguous amino acid additions relative to amino acids 353-454 or amino acids 323-454 of SEQ ID NO: 84.

In other aspects of this embodiment, a BMP5 comprises a polypeptide having, e.g., at most one, two, three, four, five, six, seven, eight, nine, 10 or 20 contiguous amino acid substitutions relative to amino acids 353-454 or amino acids 323-454 of SEQ ID NO: 84. In other aspects of this embodiment, a BMP5 comprises a polypeptide having, e.g., at least one, two, three, four, five, six, seven, eight, nine, 10 or 20 contiguous amino acid substitutions relative to amino acids 353-454 or amino acids 323-454 of SEQ ID NO: 84. In yet other aspects of this embodiment, a BMP5 comprises a polypeptide having, e.g., at most one, two, three, four, five, six, seven, eight, nine, 10 or 20 contiguous amino acid deletions relative to amino acids 353-454 or amino acids 323-454 of SEQ ID NO: 84. In other aspects of this embodiment, a BMP5 comprises a polypeptide having, e.g., at least one, two, three, four, five, six, seven, eight, nine, 10 or 20 contiguous amino acid deletions relative to amino acids 353-454 or amino acids 323-454 of SEQ ID NO: 84. In still other aspects of this embodiment, a BMP5 comprises a polypeptide having, e.g., at most one, two, three, four, five, six, seven, eight, nine, 10 or 20 contiguous amino acid additions relative to amino acids 353-454 or amino acids 323-454 of SEQ ID NO: 84. In other aspects of this embodiment, a BMP5 comprises a polypeptide having, e.g., at least one, two, three, four, five, six, seven, eight, nine, 10 or 20 contiguous amino acid additions relative to amino acids 353-454 or amino acids 323-454 of SEQ ID NO: 84.

In an embodiment, a binding domain comprises a BMP6. In another embodiment, a binding domain comprises a BMP6 of SEQ ID NO: 85. In another embodiment, a binding domain is derived from a BMP6. In another embodiment, a binding domain is derived from a BMP6 of SEQ ID NO: 85. In an aspect of this embodiment, a binding domain is derived from a BMP6 comprising amino acids 412-513 or amino acids 374-513 of SEQ ID NO: 85.

In other aspects of this embodiment, a BMP6 comprises a polypeptide having, e.g., at least 70% amino acid identity with amino acids 412-513 or amino acids 374-513 of SEQ ID NO: 85, at least 75% amino acid identity with amino acids 412-513 or amino acids 374-513 of SEQ ID NO: 85, at least 80% amino acid identity with amino acids 412-513 or amino acids 374-513 of SEQ ID NO: 85, at least 85% amino acid identity with amino acids 412-513 or amino acids 374-513 of SEQ ID NO: 85, at least 90% amino acid identity with amino acids 412-513 or amino acids 374-513 of SEQ ID NO: 85 or at least 95% amino acid identity with amino acids 412-513 or amino acids 374-513 of SEQ ID NO: 85. In yet other aspects of this embodiment, a BMP6 comprises a polypeptide having, e.g., at most 70% amino acid identity with amino acids 412-513 or amino acids 374-513 of SEQ ID NO: 85, at most 75% amino acid identity with amino acids 412-513 or amino acids 374-513 of SEQ ID NO: 85, at most 80% amino acid identity with amino acids 412-513 or amino acids 374-513 of SEQ ID NO: 85, at most 85% amino acid identity with amino acids 412-513 or amino acids 374-513 of SEQ ID NO: 85, at most 90% amino acid identity with amino acids 412-513 or amino acids 374-513 of SEQ ID NO: 85 or at most 95% amino acid identity with amino acids 412-513 or amino acids 374-513 of SEQ ID NO: 85.

In other aspects of this embodiment, a BMP6 comprises a polypeptide having, e.g., at most one, two, three, four, five, six, seven, eight, nine, 10 or 20 non-contiguous amino acid substitutions relative to amino acids 412-513 or amino acids 374-513 of SEQ ID NO: 85. In other aspects of this embodiment, a BMP6 comprises a polypeptide having, e.g., at least one, two, three, four, five, six, seven, eight, nine, 10 or 20 non-contiguous amino acid substitutions relative to amino acids 412-513 or amino acids 374-513 of SEQ ID NO: 85. In yet other aspects of this embodiment, a BMP6 comprises a polypeptide having, e.g., at most one, two, three, four, five, six, seven, eight, nine, 10 or 20 non-contiguous amino acid deletions relative to amino acids 412-513 or amino acids 374-513 of SEQ ID NO: 85. In other aspects of this embodiment, a BMP6 comprises a polypeptide having, e.g., at least one, two, three, four, five, six, seven, eight, nine, 10 or 20 non-contiguous amino acid deletions relative to amino acids 412-513 or amino acids 374-513 of SEQ ID NO: 85. In still other aspects of this embodiment, a BMP6 comprises a polypeptide having, e.g., at most one, two, three, four, five, six, seven, eight, nine, 10 or 20 non-contiguous amino acid additions relative to amino acids 412-513 or amino acids 374-513 of SEQ ID NO: 85. In other aspects of this embodiment, a BMP6 comprises a polypeptide having, e.g., at least one, two, three, four, five, six, seven, eight, nine, 10 or 20 non-contiguous amino acid additions relative to amino acids 412-513 or amino acids 374-513 of SEQ ID NO: 85.

In other aspects of this embodiment, a BMP6 comprises a polypeptide having, e.g., at most one, two, three, four, five, six, seven, eight, nine, 10 or 20 contiguous amino acid substitutions relative to amino acids 412-513 or amino acids 374-513 of SEQ ID NO: 85. In other aspects of this embodiment, a BMP6 comprises a polypeptide having, e.g., at least one, two, three, four, five, six, seven, eight, nine, 10 or 20 contiguous amino acid substitutions relative to amino acids 412-513 or amino acids 374-513 of SEQ ID NO: 85. In yet other aspects of this embodiment, a BMP6 comprises a polypeptide having, e.g., at most one, two, three, four, five, six, seven, eight, nine, 10 or 20 contiguous amino acid deletions relative to amino acids 412-513 or amino acids 374-513 of SEQ ID NO: 85. In other aspects of this embodiment, a BMP6 comprises a polypeptide having, e.g., at least one, two, three, four, five, six, seven, eight, nine, 10 or 20 contiguous amino acid deletions relative to amino acids 412-513 or amino acids 374-513 of SEQ ID NO: 85. In still other aspects of this embodiment, a BMP6 comprises a polypeptide having, e.g., at most one, two, three, four, five, six, seven, eight, nine, 10 or 20 contiguous amino acid additions relative to amino acids 412-513 or amino acids 374-513 of SEQ ID NO: 85. In other aspects of this embodiment, a BMP6 comprises a polypeptide having, e.g., at least one, two, three, four, five, six, seven, eight, nine, 10 or 20 contiguous amino acid additions relative to amino acids 412-513 or amino acids 374-513 of SEQ ID NO: 85.

In an embodiment, a binding domain comprises a BMP7. In another embodiment, a binding domain comprises a BMP7 of SEQ ID NO: 86. In another embodiment, a binding domain is derived from a BMP7. In another embodiment, a binding domain is derived from a BMP7 of SEQ ID NO: 86. In an aspect of this embodiment, a binding domain is derived from a BMP7 comprising amino acids 330-431 or amino acids 293-431 of SEQ ID NO: 86.

In other aspects of this embodiment, a BMP7 comprises a polypeptide having, e.g., at least 70% amino acid identity with amino acids 330-431 or amino acids 293-431 of SEQ ID NO: 86, at least 75% amino acid identity with amino acids 330-431 or amino acids 293-431 of SEQ ID NO: 86, at least 80% amino acid identity with amino acids 330-431 or amino acids 293-431 of SEQ ID NO: 86, at least 85% amino acid identity with amino acids 330-431 or amino acids 293-431 of SEQ ID NO: 86, at least 90% amino acid identity with amino acids 330-431 or amino acids 293-431 of SEQ ID NO: 86 or at least 95% amino acid identity with amino acids 330-431 or amino acids 293-431 of SEQ ID NO: 86. In yet other aspects of this embodiment, a BMP7 comprises a polypeptide having, e.g., at most 70% amino acid identity with amino acids 330-431 or amino acids 293-431 of SEQ ID NO: 86, at most 75% amino acid identity with amino acids 330-431 or amino acids 293-431 of SEQ ID NO: 86, at most 80% amino acid identity with amino acids 330-431 or amino acids 293-431 of SEQ ID NO: 86, at most 85% amino acid identity with amino acids 330-431 or amino acids 293-431 of SEQ ID NO: 86, at most 90% amino acid identity with amino acids 330-431 or amino acids 293-431 of SEQ ID NO: 86 or at most 95% amino acid identity with amino acids 330-431 or amino acids 293-431 of SEQ ID NO: 86.

In other aspects of this embodiment, a BMP7 comprises a polypeptide having, e.g., at most one, two, three, four, five, six, seven, eight, nine, 10 or 20 non-contiguous amino acid substitutions relative to amino acids 330-431 or amino acids 293-431 of SEQ ID NO: 86. In other aspects of this embodiment, a BMP7 comprises a polypeptide having, e.g., at least one, two, three, four, five, six, seven, eight, nine, 10 or 20 non-contiguous amino acid substitutions relative to amino acids 330-431 or amino acids 293-431 of SEQ ID NO: 86. In yet other aspects of this embodiment, a BMP7 comprises a polypeptide having, e.g., at most one, two, three, four, five, six, seven, eight, nine, 10 or 20 non-contiguous amino acid deletions relative to amino acids 330-431 or amino acids 293-431 of SEQ ID NO: 86. In other aspects of this embodiment, a BMP7 comprises a polypeptide having, e.g., at least one, two, three, four, five, six, seven, eight, nine, 10 or 20 non-contiguous amino acid deletions relative to amino acids 330-431 or amino acids 293-431 of SEQ ID NO: 86. In still other aspects of this embodiment, a BMP7 comprises a polypeptide having, e.g., at most one, two, three, four, five, six, seven, eight, nine, 10 or 20 non-contiguous amino acid additions relative to amino acids 330-431 or amino acids 293-431 of SEQ ID NO: 86. In other aspects of this embodiment, a BMP7 comprises a polypeptide having, e.g., at least one, two, three, four, five, six, seven, eight, nine, 10 or 20 non-contiguous amino acid additions relative to amino acids 330-431 or amino acids 293-431 of SEQ ID NO: 86.

In other aspects of this embodiment, a BMP7 comprises a polypeptide having, e.g., at most one, two, three, four, five, six, seven, eight, nine, 10 or 20 contiguous amino acid substitutions relative to amino acids 330-431 or amino acids 293-431 of SEQ ID NO: 86. In other aspects of this embodiment, a BMP7 comprises a polypeptide having, e.g., at least one, two, three, four, five, six, seven, eight, nine, 10 or 20 contiguous amino acid substitutions relative to amino acids 330-431 or amino acids 293-431 of SEQ ID NO: 86. In yet other aspects of this embodiment, a BMP7 comprises a polypeptide having, e.g., at most one, two, three, four, five, six, seven, eight, nine, 10 or 20 contiguous amino acid deletions relative to amino acids 330-431 or amino acids 293-431 of SEQ ID NO: 86. In other aspects of this embodiment, a BMP7 comprises a polypeptide having, e.g., at least one, two, three, four, five, six, seven, eight, nine, 10 or 20 contiguous amino acid deletions relative to amino acids 330-431 or amino acids 293-431 of SEQ ID NO: 86. In still other aspects of this embodiment, a BMP7 comprises a polypeptide having, e.g., at most one, two, three, four, five, six, seven, eight, nine, 10 or 20 contiguous amino acid additions relative to amino acids 330-431 or amino acids 293-431 of SEQ ID NO: 86. In other aspects of this embodiment, a BMP7 comprises a polypeptide having, e.g., at least one, two, three, four, five, six, seven, eight, nine, 10 or 20 contiguous amino acid additions relative to amino acids 330-431 or amino acids 293-431 of SEQ ID NO: 86.

In an embodiment, a binding domain comprises a BMP8. In another embodiment, a binding domain comprises a BMP8 of SEQ ID NO: 87. In another embodiment, a binding domain is derived from a BMP8. In another embodiment, a binding domain is derived from a BMP8 of SEQ ID NO: 87. In an aspect of this embodiment, a binding domain is derived from a BMP8 comprising amino acids 301-402 of SEQ ID NO: 87.

In other aspects of this embodiment, a BMP8 comprises a polypeptide having, e.g., at least 70% amino acid identity with amino acids 301-402 of SEQ ID NO: 87, at least 75% amino acid identity with amino acids 301-402 of SEQ ID NO: 87, at least 80% amino acid identity with amino acids 301-402 of SEQ ID NO: 87, at least 85% amino acid identity with amino acids 301-402 of SEQ ID NO: 87, at least 90% amino acid identity with amino acids 301-402 of SEQ ID NO: 87 or at least 95% amino acid identity with amino acids 301-402 of SEQ ID NO: 87. In yet other aspects of this embodiment, a BMP8 comprises a polypeptide having, e.g., at most 70% amino acid identity with amino acids 301-402 of SEQ ID NO: 87, at most 75% amino acid identity with amino acids 301-402 of SEQ ID NO: 87, at most 80% amino acid identity with amino acids 301-402 of SEQ ID NO: 87, at most 85% amino acid identity with amino acids 301-402 of SEQ ID NO: 87, at most 90% amino acid identity with amino acids 301-402 of SEQ ID NO: 87 or at most 95% amino acid identity with amino acids 301-402 of SEQ ID NO: 87.

In other aspects of this embodiment, a BMP8 comprises a polypeptide having, e.g., at most one, two, three, four, five, six, seven, eight, nine, 10 or 20 non-contiguous amino acid substitutions relative to amino acids 301-402 of SEQ ID NO: 87. In other aspects of this embodiment, a BMP8 comprises a polypeptide having, e.g., at least one, two, three, four, five, six, seven, eight, nine, 10 or 20 non-contiguous amino acid substitutions relative to amino acids 301-402 of SEQ ID NO: 87. In yet other aspects of this embodiment, a BMP8 comprises a polypeptide having, e.g., at most one, two, three, four, five, six, seven, eight, nine, 10 or 20 non-contiguous amino acid deletions relative to amino acids 301-402 of SEQ ID NO: 87. In other aspects of this embodiment, a BMP8 comprises a polypeptide having, e.g., at least one, two, three, four, five, six, seven, eight, nine, 10 or 20 non-contiguous amino acid deletions relative to amino acids 301-402 of SEQ ID NO: 87. In still other aspects of this embodiment, a BMP8 comprises a polypeptide having, e.g., at most one, two, three, four, five, six, seven, eight, nine, 10 or 20 non-contiguous amino acid additions relative to amino acids 301-402 of SEQ ID NO: 87. In other aspects of this embodiment, a BMP8 comprises a polypeptide having, e.g., at least one, two, three, four, five, six, seven, eight, nine, 10 or 20 non-contiguous amino acid additions relative to amino acids 301-402 of SEQ ID NO: 87.

In other aspects of this embodiment, a BMP8 comprises a polypeptide having, e.g., at most one, two, three, four, five, six, seven, eight, nine, 10 or 20 contiguous amino acid substitutions relative to amino acids 301-402 of SEQ ID NO: 87. In other aspects of this embodiment, a BMP8 comprises a polypeptide having, e.g., at least one, two, three, four, five, six, seven, eight, nine, 10 or 20 contiguous amino acid substitutions relative to amino acids 301-402 of SEQ ID NO: 87. In yet other aspects of this embodiment, a BMP8 comprises a polypeptide having, e.g., at most one, two, three, four, five, six, seven, eight, nine, 10 or 20 contiguous amino acid deletions relative to amino acids 301-402 of SEQ ID NO: 87. In other aspects of this embodiment, a BMP8 comprises a polypeptide having, e.g., at least one, two, three, four, five, six, seven, eight, nine, 10 or 20 contiguous amino acid deletions relative to amino acids 301-402 of SEQ ID NO: 87. In still other aspects of this embodiment, a BMP8 comprises a polypeptide having, e.g., at most one, two, three, four, five, six, seven, eight, nine, 10 or 20 contiguous amino acid additions relative to amino acids 301-402 of SEQ ID NO: 87. In other aspects of this embodiment, a BMP8 comprises a polypeptide having, e.g., at least one, two, three, four, five, six, seven, eight, nine, 10 or 20 contiguous amino acid additions relative to amino acids 301-402 of SEQ ID NO: 87.

In an embodiment, a binding domain comprises a BMP10. In another embodiment, a binding domain comprises a BMP10 of SEQ ID NO: 88. In another embodiment, a binding domain is derived from a BMP10. In another embodiment, a binding domain is derived from a BMP10 of SEQ ID NO: 88. In an aspect of this embodiment, a binding domain is derived from a BMP10 comprising amino acids 323-424 of SEQ ID NO: 88.

In other aspects of this embodiment, a BMP10 comprises a polypeptide having, e.g., at least 70% amino acid identity with amino acids 323-424 of SEQ ID NO: 88, at least 75% amino acid identity with amino acids 323-424 of SEQ ID NO: 88, at least 80% amino acid identity with amino acids 323-424 of SEQ ID NO: 88, at least 85% amino acid identity with amino acids 323-424 of SEQ ID NO: 88, at least 90% amino acid identity with amino acids 323-424 of SEQ ID NO: 88 or at least 95% amino acid identity with amino acids 323-424 of SEQ ID NO: 88. In yet other aspects of this embodiment, a BMP10 comprises a polypeptide having, e.g., at most 70% amino acid identity with amino acids 323-424 of SEQ ID NO: 88, at most 75% amino acid identity with amino acids 323-424 of SEQ ID NO: 88, at most 80% amino acid identity with amino acids 323-424 of SEQ ID NO: 88, at most 85% amino acid identity with amino acids 323-424 of SEQ ID NO: 88, at most 90% amino acid identity with amino acids 323-424 of SEQ ID NO: 88 or at most 95% amino acid identity with amino acids 323-424 of SEQ ID NO: 88.

In other aspects of this embodiment, a BMP10 comprises a polypeptide having, e.g., at most one, two, three, four, five, six, seven, eight, nine, 10 or 20 non-contiguous amino acid substitutions relative to amino acids 323-424 of SEQ ID NO: 88. In other aspects of this embodiment, a BMP10 comprises a polypeptide having, e.g., at least one, two, three, four, five, six, seven, eight, nine, 10 or 20 non-contiguous amino acid substitutions relative to amino acids 323-424 of SEQ ID NO: 88. In yet other aspects of this embodiment, a BMP10 comprises a polypeptide having, e.g., at most one, two, three, four, five, six, seven, eight, nine, 10 or 20 non-contiguous amino acid deletions relative to amino acids 323-424 of SEQ ID NO: 88. In other aspects of this embodiment, a BMP10 comprises a polypeptide having, e.g., at least one, two, three, four, five, six, seven, eight, nine, 10 or 20 non-contiguous amino acid deletions relative to amino acids 323-424 of SEQ ID NO: 88. In still other aspects of this embodiment, a BMP10 comprises a polypeptide having, e.g., at most one, two, three, four, five, six, seven, eight, nine, 10 or 20 non-contiguous amino acid additions relative to amino acids 323-424 of SEQ ID NO: 88. In other aspects of this embodiment, a BMP10 comprises a polypeptide having, e.g., at least one, two, three, four, five, six, seven, eight, nine, 10 or 20 non-contiguous amino acid additions relative to amino acids 323-424 of SEQ ID NO: 88.

In other aspects of this embodiment, a BMP10 comprises a polypeptide having, e.g., at most one, two, three, four, five, six, seven, eight, nine, 10 or 20 contiguous amino acid substitutions relative to amino acids 323-424 of SEQ ID NO: 88. In other aspects of this embodiment, a BMP10 comprises a polypeptide having, e.g., at least one, two, three, four, five, six, seven, eight, nine, 10 or 20 contiguous amino acid substitutions relative to amino acids 323-424 of SEQ ID NO: 88. In yet other aspects of this embodiment, a BMP10 comprises a polypeptide having, e.g., at most one, two, three, four, five, six, seven, eight, nine, 10 or 20 contiguous amino acid deletions relative to amino acids 323-424 of SEQ ID NO: 88. In other aspects of this embodiment, a BMP10 comprises a polypeptide having, e.g., at least one, two, three, four, five, six, seven, eight, nine, 10 or 20 contiguous amino acid deletions relative to amino acids 323-424 of SEQ ID NO: 88. In still other aspects of this embodiment, a BMP10 comprises a polypeptide having, e.g., at most one, two, three, four, five, six, seven, eight, nine, 10 or 20 contiguous amino acid additions relative to amino acids 323-424 of SEQ ID NO: 88. In other aspects of this embodiment, a BMP10 comprises a polypeptide having, e.g., at least one, two, three, four, five, six, seven, eight, nine, 10 or 20 contiguous amino acid additions relative to amino acids 323-424 of SEQ ID NO: 88.

Another example of a binding domain disclosed in the present specification is, e.g., a GFPs, such as, e.g., GDF1, GDF2, GDF3, GDF5, GDF6, GDF7, GDF8, GDF10, GDF11 or GDF15.

Thus, in an embodiment, a binding domain comprises a GDF1. In another embodiment, a binding domain comprises a GDF1 of SEQ ID NO: 89. In another embodiment, a binding domain is derived from a GDF1. In another embodiment, a binding domain is derived from a GDF1 of SEQ ID NO: 89. In an aspect of this embodiment, a binding domain is derived from a GDF1 comprising amino acids 267-372 of SEQ ID NO: 89.

In other aspects of this embodiment, a GDF1 comprises a polypeptide having, e.g., at least 70% amino acid identity with amino acids 267-372 of SEQ ID NO: 89, at least 75% amino acid identity with amino acids 267-372 of SEQ ID NO: 89, at least 80% amino acid identity with amino acids 267-372 of SEQ ID NO: 89, at least 85% amino acid identity with amino acids 267-372 of SEQ ID NO: 89, at least 90% amino acid identity with amino acids 267-372 of SEQ ID NO: 89 or at least 95% amino acid identity with amino acids 267-372 of SEQ ID NO: 89. In yet other aspects of this embodiment, a GDF1 comprises a polypeptide having, e.g., at most 70% amino acid identity with amino acids 267-372 of SEQ ID NO: 89, at most 75% amino acid identity with amino acids 267-372 of SEQ ID NO: 89, at most 80% amino acid identity with amino acids 267-372 of SEQ ID NO: 89, at most 85% amino acid identity with amino acids 267-372 of SEQ ID NO: 89, at most 90% amino acid identity with amino acids 267-372 of SEQ ID NO: 89 or at most 95% amino acid identity with amino acids 267-372 of SEQ ID NO: 89.

In other aspects of this embodiment, a GDF1 comprises a polypeptide having, e.g., at most one, two, three, four, five, six, seven, eight, nine, 10 or 20 non-contiguous amino acid substitutions relative to amino acids 267-372 of SEQ ID NO: 89. In other aspects of this embodiment, a GDF1 comprises a polypeptide having, e.g., at least one, two, three, four, five, six, seven, eight, nine, 10 or 20 non-contiguous amino acid substitutions relative to amino acids 267-372 of SEQ ID NO: 89. In yet other aspects of this embodiment, a GDF1 comprises a polypeptide having, e.g., at most one, two, three, four, five, six, seven, eight, nine, 10 or 20 non-contiguous amino acid deletions relative to amino acids 267-372 of SEQ ID NO: 89. In other aspects of this embodiment, a GDF1 comprises a polypeptide having, e.g., at least one, two, three, four, five, six, seven, eight, nine, 10 or 20 non-contiguous amino acid deletions relative to amino acids 267-372 of SEQ ID NO: 89. In still other aspects of this embodiment, a GDF1 comprises a polypeptide having, e.g., at most one, two, three, four, five, six, seven, eight, nine, 10 or 20 non-contiguous amino acid additions relative to amino acids 267-372 of SEQ ID NO: 89. In other aspects of this embodiment, a GDF1 comprises a polypeptide having, e.g., at least one, two, three, four, five, six, seven, eight, nine, 10 or 20 non-contiguous amino acid additions relative to amino acids 267-372 of SEQ ID NO: 89.

In other aspects of this embodiment, a GDF1 comprises a polypeptide having, e.g., at most one, two, three, four, five, six, seven, eight, nine, 10 or 20 contiguous amino acid substitutions relative to amino acids 267-372 of SEQ ID NO: 89. In other aspects of this embodiment, a GDF1 comprises a polypeptide having, e.g., at least one, two, three, four, five, six, seven, eight, nine, 10 or 20 contiguous amino acid substitutions relative to amino acids 267-372 of SEQ ID NO: 89. In yet other aspects of this embodiment, a GDF1 comprises a polypeptide having, e.g., at most one, two, three, four, five, six, seven, eight, nine, 10 or 20 contiguous amino acid deletions relative to amino acids 267-372 of SEQ ID NO: 89. In other aspects of this embodiment, a GDF1 comprises a polypeptide having, e.g., at least one, two, three, four, five, six, seven, eight, nine, 10 or 20 contiguous amino acid deletions relative to amino acids 267-372 of SEQ ID NO: 89. In still other aspects of this embodiment, a GDF1 comprises a polypeptide having, e.g., at most one, two, three, four, five, six, seven, eight, nine, 10 or 20 contiguous amino acid additions relative to amino acids 267-372 of SEQ ID NO: 89. In other aspects of this embodiment, a GDF1 comprises a polypeptide having, e.g., at least one, two, three, four, five, six, seven, eight, nine, 10 or 20 contiguous amino acid additions relative to amino acids 267-372 of SEQ ID NO: 89.

In an embodiment, a binding domain comprises a GDF2. In another embodiment, a binding domain comprises a GDF2 of SEQ ID NO: 90. In another embodiment, a binding domain is derived from a GDF2. In another embodiment, a binding domain is derived from a GDF2 of SEQ ID NO: 90. In an aspect of this embodiment, a binding domain is derived from a GDF2 comprising amino acids 327-429 of SEQ ID NO: 90.

In other aspects of this embodiment, a GDF2 comprises a polypeptide having, e.g., at least 70% amino acid identity with amino acids 327-429 of SEQ ID NO: 90, at least 75% amino acid identity with amino acids 327-429 of SEQ ID NO: 90, at least 80% amino acid identity with amino acids 327-429 of SEQ ID NO: 90, at least 85% amino acid identity with amino acids 327-429 of SEQ ID NO: 90, at least 90% amino acid identity with amino acids 327-429 of SEQ ID NO: 90 or at least 95% amino acid identity with amino acids 327-429 of SEQ ID NO: 90. In yet other aspects of this embodiment, a GDF2 comprises a polypeptide having, e.g., at most 70% amino acid identity with amino acids 327-429 of SEQ ID NO: 90, at most 75% amino acid identity with amino acids 327-429 of SEQ ID NO: 90, at most 80% amino acid identity with amino acids 327-429 of SEQ ID NO: 90, at most 85% amino acid identity with amino acids 327-429 of SEQ ID NO: 90, at most 90% amino acid identity with amino acids 327-429 of SEQ ID NO: 90 or at most 95% amino acid identity with amino acids 327-429 of SEQ ID NO: 90.

In other aspects of this embodiment, a GDF2 comprises a polypeptide having, e.g., at most one, two, three, four, five, six, seven, eight, nine, 10 or 20 non-contiguous amino acid substitutions relative to amino acids 327-429 of SEQ ID NO: 90. In other aspects of this embodiment, a GDF2 comprises a polypeptide having, e.g., at least one, two, three, four, five, six, seven, eight, nine, 10 or 20 non-contiguous amino acid substitutions relative to amino acids 327-429 of SEQ ID NO: 90. In yet other aspects of this embodiment, a GDF2 comprises a polypeptide having, e.g., at most one, two, three, four, five, six, seven, eight, nine, 10 or 20 non-contiguous amino acid deletions relative to amino acids 327-429 of SEQ ID NO: 90. In other aspects of this embodiment, a GDF2 comprises a polypeptide having, e.g., at least one, two, three, four, five, six, seven, eight, nine, 10 or 20 non-contiguous amino acid deletions relative to amino acids 327-429 of SEQ ID NO: 90. In still other aspects of this embodiment, a GDF2 comprises a polypeptide having, e.g., at most one, two, three, four, five, six, seven, eight, nine, 10 or 20 non-contiguous amino acid additions relative to amino acids 327-429 of SEQ ID NO: 90. In other aspects of this embodiment, a GDF2 comprises a polypeptide having, e.g., at least one, two, three, four, five, six, seven, eight, nine, 10 or 20 non-contiguous amino acid additions relative to amino acids 327-429 of SEQ ID NO: 90.

In other aspects of this embodiment, a GDF2 comprises a polypeptide having, e.g., at most one, two, three, four, five, six, seven, eight, nine, 10 or 20 contiguous amino acid substitutions relative to amino acids 327-429 of SEQ ID NO: 90. In other aspects of this embodiment, a GDF2 comprises a polypeptide having, e.g., at least one, two, three, four, five, six, seven, eight, nine, 10 or 20 contiguous amino acid substitutions relative to amino acids 327-429 of SEQ ID NO: 90. In yet other aspects of this embodiment, a GDF2 comprises a polypeptide having, e.g., at most one, two, three, four, five, six, seven, eight, nine, 10 or 20 contiguous amino acid deletions relative to amino acids 327-429 of SEQ ID NO: 90. In other aspects of this embodiment, a GDF2 comprises a polypeptide having, e.g., at least one, two, three, four, five, six, seven, eight, nine, 10 or 20 contiguous amino acid deletions relative to amino acids 327-429 of SEQ ID NO: 90. In still other aspects of this embodiment, a GDF2 comprises a polypeptide having, e.g., at most one, two, three, four, five, six, seven, eight, nine, 10 or 20 contiguous amino acid additions relative to amino acids 327-429 of SEQ ID NO: 90. In other aspects of this embodiment, a GDF2 comprises a polypeptide having, e.g., at least one, two, three, four, five, six, seven, eight, nine, 10 or 20 contiguous amino acid additions relative to amino acids 327-429 of SEQ ID NO: 90.

In an embodiment, a binding domain comprises a GDF3. In another embodiment, a binding domain comprises a GDF3 of SEQ ID NO: 91. In another embodiment, a binding domain is derived from a GDF3. In another embodiment, a binding domain is derived from a GDF3 of SEQ ID NO: 91. In an aspect of this embodiment, a binding domain is derived from a GDF3 comprising amino acids 264-364 of SEQ ID NO: 91.

In other aspects of this embodiment, a GDF3 comprises a polypeptide having, e.g., at least 70% amino acid identity with amino acids 264-364 of SEQ ID NO: 91, at least 75% amino acid identity with amino acids 264-364 of SEQ ID NO: 91, at least 80% amino acid identity with amino acids 264-364 of SEQ ID NO: 91, at least 85% amino acid identity with amino acids 264-364 of SEQ ID NO: 91, at least 90% amino acid identity with amino acids 264-364 of SEQ ID NO: 91 or at least 95% amino acid identity with amino acids 264-364 of SEQ ID NO: 91. In yet other aspects of this embodiment, a GDF3 comprises a polypeptide having, e.g., at most 70% amino acid identity with amino acids 264-364 of SEQ ID NO: 91, at most 75% amino acid identity with amino acids 264-364 of SEQ ID NO: 91, at most 80% amino acid identity with amino acids 264-364 of SEQ ID NO: 91, at most 85% amino acid identity with amino acids 264-364 of SEQ ID NO: 91, at most 90% amino acid identity with amino acids 264-364 of SEQ ID NO: 91 or at most 95% amino acid identity with amino acids 264-364 of SEQ ID NO: 91.

In other aspects of this embodiment, a GDF3 comprises a polypeptide having, e.g., at most one, two, three, four, five, six, seven, eight, nine, 10 or 20 non-contiguous amino acid substitutions relative to amino acids 264-364 of SEQ ID NO: 91. In other aspects of this embodiment, a GDF3 comprises a polypeptide having, e.g., at least one, two, three, four, five, six, seven, eight, nine, 10 or 20 non-contiguous amino acid substitutions relative to amino acids 264-364 of SEQ ID NO: 91. In yet other aspects of this embodiment, a GDF3 comprises a polypeptide having, e.g., at most one, two, three, four, five, six, seven, eight, nine, 10 or 20 non-contiguous amino acid deletions relative to amino acids 264-364 of SEQ ID NO: 91. In other aspects of this embodiment, a GDF3 comprises a polypeptide having, e.g., at least one, two, three, four, five, six, seven, eight, nine, 10 or 20 non-contiguous amino acid deletions relative to amino acids 264-364 of SEQ ID NO: 91. In still other aspects of this embodiment, a GDF3 comprises a polypeptide having, e.g., at most one, two, three, four, five, six, seven, eight, nine, 10 or 20 non-contiguous amino acid additions relative to amino acids 264-364 of SEQ ID NO: 91. In other aspects of this embodiment, a GDF3 comprises a polypeptide having, e.g., at least one, two, three, four, five, six, seven, eight, nine, 10 or 20 non-contiguous amino acid additions relative to amino acids 264-364 of SEQ ID NO: 91.

In other aspects of this embodiment, a GDF3 comprises a polypeptide having, e.g., at most one, two, three, four, five, six, seven, eight, nine, 10 or 20 contiguous amino acid substitutions relative to amino acids 264-364 of SEQ ID NO: 91. In other aspects of this embodiment, a GDF3 comprises a polypeptide having, e.g., at least one, two, three, four, five, six, seven, eight, nine, 10 or 20 contiguous amino acid substitutions relative to amino acids 264-364 of SEQ ID NO: 91. In yet other aspects of this embodiment, a GDF3 comprises a polypeptide having, e.g., at most one, two, three, four, five, six, seven, eight, nine, 10 or 20 contiguous amino acid deletions relative to amino acids 264-364 of SEQ ID NO: 91. In other aspects of this embodiment, a GDF3 comprises a polypeptide having, e.g., at least one, two, three, four, five, six, seven, eight, nine, 10 or 20 contiguous amino acid deletions relative to amino acids 264-364 of SEQ ID NO: 91. In still other aspects of this embodiment, a GDF3 comprises a polypeptide having, e.g., at most one, two, three, four, five, six, seven, eight, nine, 10 or 20 contiguous amino acid additions relative to amino acids 264-364 of SEQ ID NO: 91. In other aspects of this embodiment, a GDF3 comprises a polypeptide having, e.g., at least one, two, three, four, five, six, seven, eight, nine, 10 or 20 contiguous amino acid additions relative to amino acids 264-364 of SEQ ID NO: 91.

In an embodiment, a binding domain comprises a GDF5. In another embodiment, a binding domain comprises a GDF5 of SEQ ID NO: 92. In another embodiment, a binding domain is derived from a GDF5. In another embodiment, a binding domain is derived from a GDF5 of SEQ ID NO: 92. In an aspect of this embodiment, a binding domain is derived from a GDF5 comprising amino acids 400-501 of SEQ ID NO: 92.

In other aspects of this embodiment, a GDF5 comprises a polypeptide having, e.g., at least 70% amino acid identity with amino acids 400-501 of SEQ ID NO: 92, at least 75% amino acid identity with amino acids 400-501 of SEQ ID NO: 92, at least 80% amino acid identity with amino acids 400-501 of SEQ ID NO: 92, at least 85% amino acid identity with amino acids 400-501 of SEQ ID NO: 92, at least 90% amino acid identity with amino acids 400-501 of SEQ ID NO: 92 or at least 95% amino acid identity with amino acids 400-501 of SEQ ID NO: 92. In yet other aspects of this embodiment, a GDF5 comprises a polypeptide having, e.g., at most 70% amino acid identity with amino acids 400-501 of SEQ ID NO: 92, at most 75% amino acid identity with amino acids 400-501 of SEQ ID NO: 92, at most 80% amino acid identity with amino acids 400-501 of SEQ ID NO: 92, at most 85% amino acid identity with amino acids 400-501 of SEQ ID NO: 92, at most 90% amino acid identity with amino acids 400-501 of SEQ ID NO: 92 or at most 95% amino acid identity with amino acids 400-501 of SEQ ID NO: 92.

In other aspects of this embodiment, a GDF5 comprises a polypeptide having, e.g., at most one, two, three, four, five, six, seven, eight, nine, 10 or 20 non-contiguous amino acid substitutions relative to amino acids 400-501 of SEQ ID NO: 92. In other aspects of this embodiment, a GDF5 comprises a polypeptide having, e.g., at least one, two, three, four, five, six, seven, eight, nine, 10 or 20 non-contiguous amino acid substitutions relative to amino acids 400-501 of SEQ ID NO: 92. In yet other aspects of this embodiment, a GDF5 comprises a polypeptide having, e.g., at most one, two, three, four, five, six, seven, eight, nine, 10 or 20 non-contiguous amino acid deletions relative to amino acids 400-501 of SEQ ID NO: 92. In other aspects of this embodiment, a GDF5 comprises a polypeptide having, e.g., at least one, two, three, four, five, six, seven, eight, nine, 10 or 20 non-contiguous amino acid deletions relative to amino acids 400-501 of SEQ ID NO: 92. In still other aspects of this embodiment, a GDF5 comprises a polypeptide having, e.g., at most one, two, three, four, five, six, seven, eight, nine, 10 or 20 non-contiguous amino acid additions relative to amino acids 400-501 of SEQ ID NO: 92. In other aspects of this embodiment, a GDF5 comprises a polypeptide having, e.g., at least one, two, three, four, five, six, seven, eight, nine, 10 or 20 non-contiguous amino acid additions relative to amino acids 400-501 of SEQ ID NO: 92.

In other aspects of this embodiment, a GDF5 comprises a polypeptide having, e.g., at most one, two, three, four, five, six, seven, eight, nine, 10 or 20 contiguous amino acid substitutions relative to amino acids 400-501 of SEQ ID NO: 92. In other aspects of this embodiment, a GDF5 comprises a polypeptide having, e.g., at least one, two, three, four, five, six, seven, eight, nine, 10 or 20 contiguous amino acid substitutions relative to amino acids 400-501 of SEQ ID NO: 92. In yet other aspects of this embodiment, a GDF5 comprises a polypeptide having, e.g., at most one, two, three, four, five, six, seven, eight, nine, 10 or 20 contiguous amino acid deletions relative to amino acids 400-501 of SEQ ID NO: 92. In other aspects of this embodiment, a GDF5 comprises a polypeptide having, e.g., at least one, two, three, four, five, six, seven, eight, nine, 10 or 20 contiguous amino acid deletions relative to amino acids 400-501 of SEQ ID NO: 92. In still other aspects of this embodiment, a GDF5 comprises a polypeptide having, e.g., at most one, two, three, four, five, six, seven, eight, nine, 10 or 20 contiguous amino acid additions relative to amino acids 400-501 of SEQ ID NO: 92. In other aspects of this embodiment, a GDF5 comprises a polypeptide having, e.g., at least one, two, three, four, five, six, seven, eight, nine, 10 or 20 contiguous amino acid additions relative to amino acids 400-501 of SEQ ID NO: 92.

In an embodiment, a binding domain comprises a GDF6. In another embodiment, a binding domain comprises a GDF6 of SEQ ID NO: 93. In another embodiment, a binding domain is derived from a GDF6. In another embodiment, a binding domain is derived from a GDF6 of SEQ ID NO: 93. In an aspect of this embodiment, a binding domain is derived from a GDF6 comprising amino acids 354-455 of SEQ ID NO: 93.

In other aspects of this embodiment, a GDF6 comprises a polypeptide having, e.g., at least 70% amino acid identity with amino acids 354-455 of SEQ ID NO: 93, at least 75% amino acid identity with amino acids 354-455 of SEQ ID NO: 93, at least 80% amino acid identity with amino acids 354-455 of SEQ ID NO: 93, at least 85% amino acid identity with amino acids 354-455 of SEQ ID NO: 93, at least 90% amino acid identity with amino acids 354-455 of SEQ ID NO: 93 or at least 95% amino acid identity with amino acids 354-455 of SEQ ID NO: 93. In yet other aspects of this embodiment, a GDF6 comprises a polypeptide having, e.g., at most 70% amino acid identity with amino acids 354-455 of SEQ ID NO: 93, at most 75% amino acid identity with amino acids 354-455 of SEQ ID NO: 93, at most 80% amino acid identity with amino acids 354-455 of SEQ ID NO: 93, at most 85% amino acid identity with amino acids 354-455 of SEQ ID NO: 93, at most 90% amino acid identity with amino acids 354-455 of SEQ ID NO: 93 or at most 95% amino acid identity with amino acids 354-455 of SEQ ID NO: 93.

In other aspects of this embodiment, a GDF6 comprises a polypeptide having, e.g., at most one, two, three, four, five, six, seven, eight, nine, 10 or 20 non-contiguous amino acid substitutions relative to amino acids 354-455 of SEQ ID NO: 93. In other aspects of this embodiment, a GDF6 comprises a polypeptide having, e.g., at least one, two, three, four, five, six, seven, eight, nine, 10 or 20 non-contiguous amino acid substitutions relative to amino acids 354-455 of SEQ ID NO: 93. In yet other aspects of this embodiment, a GDF6 comprises a polypeptide having, e.g., at most one, two, three, four, five, six, seven, eight, nine, 10 or 20 non-contiguous amino acid deletions relative to amino acids 354-455 of SEQ ID NO: 93. In other aspects of this embodiment, a GDF6 comprises a polypeptide having, e.g., at least one, two, three, four, five, six, seven, eight, nine, 10 or 20 non-contiguous amino acid deletions relative to amino acids 354-455 of SEQ ID NO: 93. In still other aspects of this embodiment, a GDF6 comprises a polypeptide having, e.g., at most one, two, three, four, five, six, seven, eight, nine, 10 or 20 non-contiguous amino acid additions relative to amino acids 354-455 of SEQ ID NO: 93. In other aspects of this embodiment, a GDF6 comprises a polypeptide having, e.g., at least one, two, three, four, five, six, seven, eight, nine, 10 or 20 non-contiguous amino acid additions relative to amino acids 354-455 of SEQ ID NO: 93.

In other aspects of this embodiment, a GDF6 comprises a polypeptide having, e.g., at most one, two, three, four, five, six, seven, eight, nine, 10 or 20 contiguous amino acid substitutions relative to amino acids 354-455 of SEQ ID NO: 93. In other aspects of this embodiment, a GDF6 comprises a polypeptide having, e.g., at least one, two, three, four, five, six, seven, eight, nine, 10 or 20 contiguous amino acid substitutions relative to amino acids 354-455 of SEQ ID NO: 93. In yet other aspects of this embodiment, a GDF6 comprises a polypeptide having, e.g., at most one, two, three, four, five, six, seven, eight, nine, 10 or 20 contiguous amino acid deletions relative to amino acids 354-455 of SEQ ID NO: 93. In other aspects of this embodiment, a GDF6 comprises a polypeptide having, e.g., at least one, two, three, four, five, six, seven, eight, nine, 10 or 20 contiguous amino acid deletions relative to amino acids 354-455 of SEQ ID NO: 93. In still other aspects of this embodiment, a GDF6 comprises a polypeptide having, e.g., at most one, two, three, four, five, six, seven, eight, nine, 10 or 20 contiguous amino acid additions relative to amino acids 354-455 of SEQ ID NO: 93. In other aspects of this embodiment, a GDF6 comprises a polypeptide having, e.g., at least one, two, three, four, five, six, seven, eight, nine, 10 or 20 contiguous amino acid additions relative to amino acids 354-455 of SEQ ID NO: 93.

In an embodiment, a binding domain comprises a GDF7. In another embodiment, a binding domain comprises a GDF7 of SEQ ID NO: 94. In another embodiment, a binding domain is derived from a GDF7. In another embodiment, a binding domain is derived from a GDF7 of SEQ ID NO: 94. In an aspect of this embodiment, a binding domain is derived from a GDF7 comprising amino acids 352-450 of SEQ ID NO: 94.

In other aspects of this embodiment, a GDF7 comprises a polypeptide having, e.g., at least 70% amino acid identity with amino acids 352-450 of SEQ ID NO: 94, at least 75% amino acid identity with amino acids 352-450 of SEQ ID NO: 94, at least 80% amino acid identity with amino acids 352-450 of SEQ ID NO: 94, at least 85% amino acid identity with amino acids 352-450 of SEQ ID NO: 94, at least 90% amino acid identity with amino acids 352-450 of SEQ ID NO: 94 or at least 95% amino acid identity with amino acids 352-450 of SEQ ID NO: 94. In yet other aspects of this embodiment, a GDF7 comprises a polypeptide having, e.g., at most 70% amino acid identity with amino acids 352-450 of SEQ ID NO: 94, at most 75% amino acid identity with amino acids 352-450 of SEQ ID NO: 94, at most 80% amino acid identity with amino acids 352-450 of SEQ ID NO: 94, at most 85% amino acid identity with amino acids 352-450 of SEQ ID NO: 94, at most 90% amino acid identity with amino acids 352-450 of SEQ ID NO: 94 or at most 95% amino acid identity with amino acids 352-450 of SEQ ID NO: 94.

In other aspects of this embodiment, a GDF7 comprises a polypeptide having, e.g., at most one, two, three, four, five, six, seven, eight, nine, 10 or 20 non-contiguous amino acid substitutions relative to amino acids 352-450 of SEQ ID NO: 94. In other aspects of this embodiment, a GDF7 comprises a polypeptide having, e.g., at least one, two, three, four, five, six, seven, eight, nine, 10 or 20 non-contiguous amino acid substitutions relative to amino acids 352-450 of SEQ ID NO: 94. In yet other aspects of this embodiment, a GDF7 comprises a polypeptide having, e.g., at most one, two, three, four, five, six, seven, eight, nine, 10 or 20 non-contiguous amino acid deletions relative to amino acids 352-450 of SEQ ID NO: 94. In other aspects of this embodiment, a GDF7 comprises a polypeptide having, e.g., at least one, two, three, four, five, six, seven, eight, nine, 10 or 20 non-contiguous amino acid deletions relative to amino acids 352-450 of SEQ ID NO: 94. In still other aspects of this embodiment, a GDF7 comprises a polypeptide having, e.g., at most one, two, three, four, five, six, seven, eight, nine, 10 or 20 non-contiguous amino acid additions relative to amino acids 352-450 of SEQ ID NO: 94. In other aspects of this embodiment, a GDF7 comprises a polypeptide having, e.g., at least one, two, three, four, five, six, seven, eight, nine, 10 or 20 non-contiguous amino acid additions relative to amino acids 352-450 of SEQ ID NO: 94.

In other aspects of this embodiment, a GDF7 comprises a polypeptide having, e.g., at most one, two, three, four, five, six, seven, eight, nine, 10 or 20 contiguous amino acid substitutions relative to amino acids 352-450 of SEQ ID NO: 94. In other aspects of this embodiment, a GDF7 comprises a polypeptide having, e.g., at least one, two, three, four, five, six, seven, eight, nine, 10 or 20 contiguous amino acid substitutions relative to amino acids 352-450 of SEQ ID NO: 94. In yet other aspects of this embodiment, a GDF7 comprises a polypeptide having, e.g., at most one, two, three, four, five, six, seven, eight, nine, 10 or 20 contiguous amino acid deletions relative to amino acids 352-450 of SEQ ID NO: 94. In other aspects of this embodiment, a GDF7 comprises a polypeptide having, e.g., at least one, two, three, four, five, six, seven, eight, nine, 10 or 20 contiguous amino acid deletions relative to amino acids 352-450 of SEQ ID NO: 94. In still other aspects of this embodiment, a GDF7 comprises a polypeptide having, e.g., at most one, two, three, four, five, six, seven, eight, nine, 10 or 20 contiguous amino acid additions relative to amino acids 352-450 of SEQ ID NO: 94. In other aspects of this embodiment, a GDF7 comprises a polypeptide having, e.g., at least one, two, three, four, five, six, seven, eight, nine, 10 or 20 contiguous amino acid additions relative to amino acids 352-450 of SEQ ID NO: 94.

In an embodiment, a binding domain comprises a GDF8. In another embodiment, a binding domain comprises a GDF8 of SEQ ID NO: 95. In another embodiment, a binding domain is derived from a GDF8. In another embodiment, a binding domain is derived from a GDF8 of SEQ ID NO: 95. In an aspect of this embodiment, a binding domain is derived from a GDF8 comprising amino acids 281-375 of SEQ ID NO: 95.

In other aspects of this embodiment, a GDF8 comprises a polypeptide having, e.g., at least 70% amino acid identity with amino acids 281-375 of SEQ ID NO: 95, at least 75% amino acid identity with amino acids 281-375 of SEQ ID NO: 95, at least 80% amino acid identity with amino acids 281-375 of SEQ ID NO: 95, at least 85% amino acid identity with amino acids 281-375 of SEQ ID NO: 95, at least 90% amino acid identity with amino acids 281-375 of SEQ ID NO: 95 or at least 95% amino acid identity with amino acids 281-375 of SEQ ID NO: 95. In yet other aspects of this embodiment, a GDF8 comprises a polypeptide having, e.g., at most 70% amino acid identity with amino acids 281-375 of SEQ ID NO: 95, at most 75% amino acid identity with amino acids 281-375 of SEQ ID NO: 95, at most 80% amino acid identity with amino acids 281-375 of SEQ ID NO: 95, at most 85% amino acid identity with amino acids 281-375 of SEQ ID NO: 95, at most 90% amino acid identity with amino acids 281-375 of SEQ ID NO: 95 or at most 95% amino acid identity with amino acids 281-375 of SEQ ID NO: 95.

In other aspects of this embodiment, a GDF8 comprises a polypeptide having, e.g., at most one, two, three, four, five, six, seven, eight, nine, 10 or 20 non-contiguous amino acid substitutions relative to amino acids 281-375 of SEQ ID NO: 95. In other aspects of this embodiment, a GDF8 comprises a polypeptide having, e.g., at least one, two, three, four, five, six, seven, eight, nine, 10 or 20 non-contiguous amino acid substitutions relative to amino acids 281-375 of SEQ ID NO: 95. In yet other aspects of this embodiment, a GDF8 comprises a polypeptide having, e.g., at most one, two, three, four, five, six, seven, eight, nine, 10 or 20 non-contiguous amino acid deletions relative to amino acids 281-375 of SEQ ID NO: 95. In other aspects of this embodiment, a GDF8 comprises a polypeptide having, e.g., at least one, two, three, four, five, six, seven, eight, nine, 10 or 20 non-contiguous amino acid deletions relative to amino acids 281-375 of SEQ ID NO: 95. In still other aspects of this embodiment, a GDF8 comprises a polypeptide having, e.g., at most one, two, three, four, five, six, seven, eight, nine, 10 or 20 non-contiguous amino acid additions relative to amino acids 281-375 of SEQ ID NO: 95. In other aspects of this embodiment, a GDF8 comprises a polypeptide having, e.g., at least one, two, three, four, five, six, seven, eight, nine, 10 or 20 non-contiguous amino acid additions relative to amino acids 281-375 of SEQ ID NO: 95.

In other aspects of this embodiment, a GDF8 comprises a polypeptide having, e.g., at most one, two, three, four, five, six, seven, eight, nine, 10 or 20 contiguous amino acid substitutions relative to amino acids 281-375 of SEQ ID NO: 95. In other aspects of this embodiment, a GDF8 comprises a polypeptide having, e.g., at least one, two, three, four, five, six, seven, eight, nine, 10 or 20 contiguous amino acid substitutions relative to amino acids 281-375 of SEQ ID NO: 95. In yet other aspects of this embodiment, a GDF8 comprises a polypeptide having, e.g., at most one, two, three, four, five, six, seven, eight, nine, 10 or 20 contiguous amino acid deletions relative to amino acids 281-375 of SEQ ID NO: 95. In other aspects of this embodiment, a GDF8 comprises a polypeptide having, e.g., at least one, two, three, four, five, six, seven, eight, nine, 10 or 20 contiguous amino acid deletions relative to amino acids 281-375 of SEQ ID NO: 95. In still other aspects of this embodiment, a GDF8 comprises a polypeptide having, e.g., at most one, two, three, four, five, six, seven, eight, nine, 10 or 20 contiguous amino acid additions relative to amino acids 281-375 of SEQ ID NO: 95. In other aspects of this embodiment, a GDF8 comprises a polypeptide having, e.g., at least one, two, three, four, five, six, seven, eight, nine, 10 or 20 contiguous amino acid additions relative to amino acids 281-375 of SEQ ID NO: 95.

In an embodiment, a binding domain comprises a GDF10. In another embodiment, a binding domain comprises a GDF19 of SEQ ID NO: 96. In another embodiment, a binding domain is derived from a GDF10. In another embodiment, a binding domain is derived from a GDF10 of SEQ ID NO: 96. In an aspect of this embodiment, a binding domain is derived from a GDF10 comprising amino acids 376-478 of SEQ ID NO: 96.

In other aspects of this embodiment, a GDF10 comprises a polypeptide having, e.g., at least 70% amino acid identity with amino acids 376-478 of SEQ ID NO: 96, at least 75% amino acid identity with amino acids 376-478 of SEQ ID NO: 96, at least 80% amino acid identity with amino acids 376-478 of SEQ ID NO: 96, at least 85% amino acid identity with amino acids 376-478 of SEQ ID NO: 96, at least 90% amino acid identity with amino acids 376-478 of SEQ ID NO: 96 or at least 95% amino acid identity with amino acids 376-478 of SEQ ID NO: 96. In yet other aspects of this embodiment, a GDF10 comprises a polypeptide having, e.g., at most 70% amino acid identity with amino acids 376-478 of SEQ ID NO: 96, at most 75% amino acid identity with amino acids 376-478 of SEQ ID NO: 96, at most 80% amino acid identity with amino acids 376-478 of SEQ ID NO: 96, at most 85% amino acid identity with amino acids 376-478 of SEQ ID NO: 96, at most 90% amino acid identity with amino acids 376-478 of SEQ ID NO: 96 or at most 95% amino acid identity with amino acids 376-478 of SEQ ID NO: 96.

In other aspects of this embodiment, a GDF10 comprises a polypeptide having, e.g., at most one, two, three, four, five, six, seven, eight, nine, 10 or 20 non-contiguous amino acid substitutions relative to amino acids 376-478 of SEQ ID NO: 96. In other aspects of this embodiment, a GDF10 comprises a polypeptide having, e.g., at least one, two, three, four, five, six, seven, eight, nine, 10 or 20 non-contiguous amino acid substitutions relative to amino acids 376-478 of SEQ ID NO: 96. In yet other aspects of this embodiment, a GDF10 comprises a polypeptide having, e.g., at most one, two, three, four, five, six, seven, eight, nine, 10 or 20 non-contiguous amino acid deletions relative to amino acids 376-478 of SEQ ID NO: 96. In other aspects of this embodiment, a GDF10 comprises a polypeptide having, e.g., at least one, two, three, four, five, six, seven, eight, nine, 10 or 20 non-contiguous amino acid deletions relative to amino acids 376-478 of SEQ ID NO: 96. In still other aspects of this embodiment, a GDF10 comprises a polypeptide having, e.g., at most one, two, three, four, five, six, seven, eight, nine, 10 or 20 non-contiguous amino acid additions relative to amino acids 376-478 of SEQ ID NO: 96. In other aspects of this embodiment, a GDF10 comprises a polypeptide having, e.g., at least one, two, three, four, five, six, seven, eight, nine, 10 or 20 non-contiguous amino acid additions relative to amino acids 376-478 of SEQ ID NO: 96.

In other aspects of this embodiment, a GDF10 comprises a polypeptide having, e.g., at most one, two, three, four, five, six, seven, eight, nine, 10 or 20 contiguous amino acid substitutions relative to amino acids 376-478 of SEQ ID NO: 96. In other aspects of this embodiment, a GDF10 comprises a polypeptide having, e.g., at least one, two, three, four, five, six, seven, eight, nine, 10 or 20 contiguous amino acid substitutions relative to amino acids 376-478 of SEQ ID NO: 96. In yet other aspects of this embodiment, a GDF10 comprises a polypeptide having, e.g., at most one, two, three, four, five, six, seven, eight, nine, 10 or 20 contiguous amino acid deletions relative to amino acids 376-478 of SEQ ID NO: 96. In other aspects of this embodiment, a GDF10 comprises a polypeptide having, e.g., at least one, two, three, four, five, six, seven, eight, nine, 10 or 20 contiguous amino acid deletions relative to amino acids 376-478 of SEQ ID NO: 96. In still other aspects of this embodiment, a GDF10 comprises a polypeptide having, e.g., at most one, two, three, four, five, six, seven, eight, nine, 10 or 20 contiguous amino acid additions relative to amino acids 376-478 of SEQ ID NO: 96. In other aspects of this embodiment, a GDF10 comprises a polypeptide having, e.g., at least one, two, three, four, five, six, seven, eight, nine, 10 or 20 contiguous amino acid additions relative to amino acids 376-478 of SEQ ID NO: 96.

In an embodiment, a binding domain comprises a GDF11. In another embodiment, a binding domain comprises a GDF11 of SEQ ID NO: 97. In another embodiment, a binding domain is derived from a GDF11. In another embodiment, a binding domain is derived from a GDF11 of SEQ ID NO: 97. In an aspect of this embodiment, a binding domain is derived from a GDF11 comprising amino acids 313-407 of SEQ ID NO: 97.

In other aspects of this embodiment, a GDF11 comprises a polypeptide having, e.g., at least 70% amino acid identity with amino acids 313-407 of SEQ ID NO: 97, at least 75% amino acid identity with amino acids 313-407 of SEQ ID NO: 97, at least 80% amino acid identity with amino acids 313-407 of SEQ ID NO: 97, at least 85% amino acid identity with amino acids 313-407 of SEQ ID NO: 97, at least 90% amino acid identity with amino acids 313-407 of SEQ ID NO: 97 or at least 95% amino acid identity with amino acids 313-407 of SEQ ID NO: 97. In yet other aspects of this embodiment, a GDF11 comprises a polypeptide having, e.g., at most 70% amino acid identity with amino acids 313-407 of SEQ ID NO: 97, at most 75% amino acid identity with amino acids 313-407 of SEQ ID NO: 97, at most 80% amino acid identity with amino acids 313-407 of SEQ ID NO: 97, at most 85% amino acid identity with amino acids 313-407 of SEQ ID NO: 97, at most 90% amino acid identity with amino acids 313-407 of SEQ ID NO: 97 or at most 95% amino acid identity with amino acids 313-407 of SEQ ID NO: 97.

In other aspects of this embodiment, a GDF11 comprises a polypeptide having, e.g., at most one, two, three, four, five, six, seven, eight, nine, 10 or 20 non-contiguous amino acid substitutions relative to amino acids 313-407 of SEQ ID NO: 97. In other aspects of this embodiment, a GDF11 comprises a polypeptide having, e.g., at least one, two, three, four, five, six, seven, eight, nine, 10 or 20 non-contiguous amino acid substitutions relative to amino acids 313-407 of SEQ ID NO: 97. In yet other aspects of this embodiment, a GDF11 comprises a polypeptide having, e.g., at most one, two, three, four, five, six, seven, eight, nine, 10 or 20 non-contiguous amino acid deletions relative to amino acids 313-407 of SEQ ID NO: 97. In other aspects of this embodiment, a GDF11 comprises a polypeptide having, e.g., at least one, two, three, four, five, six, seven, eight, nine, 10 or 20 non-contiguous amino acid deletions relative to amino acids 313-407 of SEQ ID NO: 97. In still other aspects of this embodiment, a GDF11 comprises a polypeptide having, e.g., at most one, two, three, four, five, six, seven, eight, nine, 10 or 20 non-contiguous amino acid additions relative to amino acids 313-407 of SEQ ID NO: 97. In other aspects of this embodiment, a GDF11 comprises a polypeptide having, e.g., at least one, two, three, four, five, six, seven, eight, nine, 10 or 20 non-contiguous amino acid additions relative to amino acids 313-407 of SEQ ID NO: 97.

In other aspects of this embodiment, a GDF11 comprises a polypeptide having, e.g., at most one, two, three, four, five, six, seven, eight, nine, 10 or 20 contiguous amino acid substitutions relative to amino acids 313-407 of SEQ ID NO: 97. In other aspects of this embodiment, a GDF11 comprises a polypeptide having, e.g., at least one, two, three, four, five, six, seven, eight, nine, 10 or 20 contiguous amino acid substitutions relative to amino acids 313-407 of SEQ ID NO: 97. In yet other aspects of this embodiment, a GDF11 comprises a polypeptide having, e.g., at most one, two, three, four, five, six, seven, eight, nine, 10 or 20 contiguous amino acid deletions relative to amino acids 313-407 of SEQ ID NO: 97. In other aspects of this embodiment, a GDF11 comprises a polypeptide having, e.g., at least one, two, three, four, five, six, seven, eight, nine, 10 or 20 contiguous amino acid deletions relative to amino acids 313-407 of SEQ ID NO: 97. In still other aspects of this embodiment, a GDF11 comprises a polypeptide having, e.g., at most one, two, three, four, five, six, seven, eight, nine, 10 or 20 contiguous amino acid additions relative to amino acids 313-407 of SEQ ID NO: 97. In other aspects of this embodiment, a GDF11 comprises a polypeptide having, e.g., at least one, two, three, four, five, six, seven, eight, nine, 10 or 20 contiguous amino acid additions relative to amino acids 313-407 of SEQ ID NO: 97.

In an embodiment, a binding domain comprises a GDF15. In another embodiment, a binding domain comprises a GDF15 of SEQ ID NO: 98. In another embodiment, a binding domain is derived from a GDF15. In another embodiment, a binding domain is derived from a GDF15 of SEQ ID NO: 98. In an aspect of this embodiment, a binding domain is derived from a GDF15 comprising amino acids 211-308 of SEQ ID NO: 98.

In other aspects of this embodiment, a GDF15 comprises a polypeptide having, e.g., at least 70% amino acid identity with amino acids 211-308 of SEQ ID NO: 98, at least 75% amino acid identity with amino acids 211-308 of SEQ ID NO: 98, at least 80% amino acid identity with amino acids 211-308 of SEQ ID NO: 98, at least 85% amino acid identity with amino acids 211-308 of SEQ ID NO: 98, at least 90% amino acid identity with amino acids 211-308 of SEQ ID NO: 98 or at least 95% amino acid identity with amino acids 211-308 of SEQ ID NO: 98. In yet other aspects of this embodiment, a GDF15 comprises a polypeptide having, e.g., at most 70% amino acid identity with amino acids 211-308 of SEQ ID NO: 98, at most 75% amino acid identity with amino acids 211-308 of SEQ ID NO: 98, at most 80% amino acid identity with amino acids 211-308 of SEQ ID NO: 98, at most 85% amino acid identity with amino acids 211-308 of SEQ ID NO: 98, at most 90% amino acid identity with amino acids 211-308 of SEQ ID NO: 98 or at most 95% amino acid identity with amino acids 211-308 of SEQ ID NO: 98.

In other aspects of this embodiment, a GDF15 comprises a polypeptide having, e.g., at most one, two, three, four, five, six, seven, eight, nine, 10 or 20 non-contiguous amino acid substitutions relative to amino acids 211-308 of SEQ ID NO: 98. In other aspects of this embodiment, a GDF15 comprises a polypeptide having, e.g., at least one, two, three, four, five, six, seven, eight, nine, 10 or 20 non-contiguous amino acid substitutions relative to amino acids 211-308 of SEQ ID NO: 98. In yet other aspects of this embodiment, a GDF15 comprises a polypeptide having, e.g., at most one, two, three, four, five, six, seven, eight, nine, 10 or 20 non-contiguous amino acid deletions relative to amino acids 211-308 of SEQ ID NO: 98. In other aspects of this embodiment, a GDF15 comprises a polypeptide having, e.g., at least one, two, three, four, five, six, seven, eight, nine, 10 or 20 non-contiguous amino acid deletions relative to amino acids 211-308 of SEQ ID NO: 98. In still other aspects of this embodiment, a GDF15 comprises a polypeptide having, e.g., at most one, two, three, four, five, six, seven, eight, nine, 10 or 20 non-contiguous amino acid additions relative to amino acids 211-308 of SEQ ID NO: 98. In other aspects of this embodiment, a GDF15 comprises a polypeptide having, e.g., at least one, two, three, four, five, six, seven, eight, nine, 10 or 20 non-contiguous amino acid additions relative to amino acids 211-308 of SEQ ID NO: 98.

In other aspects of this embodiment, a GDF15 comprises a polypeptide having, e.g., at most one, two, three, four, five, six, seven, eight, nine, 10 or 20 contiguous amino acid substitutions relative to amino acids 211-308 of SEQ ID NO: 98. In other aspects of this embodiment, a GDF15 comprises a polypeptide having, e.g., at least one, two, three, four, five, six, seven, eight, nine, 10 or 20 contiguous amino acid substitutions relative to amino acids 211-308 of SEQ ID NO: 98. In yet other aspects of this embodiment, a GDF15 comprises a polypeptide having, e.g., at most one, two, three, four, five, six, seven, eight, nine, 10 or 20 contiguous amino acid deletions relative to amino acids 211-308 of SEQ ID NO: 98. In other aspects of this embodiment, a GDF15 comprises a polypeptide having, e.g., at least one, two, three, four, five, six, seven, eight, nine, 10 or 20 contiguous amino acid deletions relative to amino acids 211-308 of SEQ ID NO: 98. In still other aspects of this embodiment, a GDF15 comprises a polypeptide having, e.g., at most one, two, three, four, five, six, seven, eight, nine, 10 or 20 contiguous amino acid additions relative to amino acids 211-308 of SEQ ID NO: 98. In other aspects of this embodiment, a GDF15 comprises a polypeptide having, e.g., at least one, two, three, four, five, six, seven, eight, nine, 10 or 20 contiguous amino acid additions relative to amino acids 211-308 of SEQ ID NO: 98.

Another example of a binding domain disclosed in the present specification is, e.g., an activin A, an activin B, an activin C, an activin E or an inhibin A.

Thus. in an embodiment, a binding domain comprises an Activin A. In another embodiment, a binding domain comprises an Activin A of SEQ ID NO: 99. In another embodiment, a binding domain is derived from an Activin A. In another embodiment, a binding domain is derived from an Activin A of SEQ ID NO: 99. In an aspect of this embodiment, a binding domain is derived from an Activin A comprising amino acids 321-426 of SEQ ID NO: 99.

In other aspects of this embodiment, an Activin A comprises a polypeptide having, e.g., at least 70% amino acid identity with amino acids 321-426 of SEQ ID NO: 99, at least 75% amino acid identity with amino acids 321-426 of SEQ ID NO: 99, at least 80% amino acid identity with amino acids 321-426 of SEQ ID NO: 99, at least 85% amino acid identity with amino acids 321-426 of SEQ ID NO: 99, at least 90% amino acid identity with amino acids 321-426 of SEQ ID NO: 99 or at least 95% amino acid identity with amino acids 321-426 of SEQ ID NO: 99. In yet other aspects of this embodiment, an Activin A comprises a polypeptide having, e.g., at most 70% amino acid identity with amino acids 321-426 of SEQ ID NO: 99, at most 75% amino acid identity with amino acids 321-426 of SEQ ID NO: 99, at most 80% amino acid identity with amino acids 321-426 of SEQ ID NO: 99, at most 85% amino acid identity with amino acids 321-426 of SEQ ID NO: 99, at most 90% amino acid identity with amino acids 321-426 of SEQ ID NO: 99 or at most 95% amino acid identity with amino acids 321-426 of SEQ ID NO: 99.

In other aspects of this embodiment, an Activin A comprises a polypeptide having, e.g., at most one, two, three, four, five, six, seven, eight, nine, 10 or 20 non-contiguous amino acid substitutions relative to amino acids 321-426 of SEQ ID NO: 99. In other aspects of this embodiment, an Activin A comprises a polypeptide having, e.g., at least one, two, three, four, five, six, seven, eight, nine, 10 or 20 non-contiguous amino acid substitutions relative to amino acids 321-426 of SEQ ID NO: 99. In yet other aspects of this embodiment, an Activin A comprises a polypeptide having, e.g., at most one, two, three, four, five, six, seven, eight, nine, 10 or 20 non-contiguous amino acid deletions relative to amino acids 321-426 of SEQ ID NO: 99. In other aspects of this embodiment, an Activin A comprises a polypeptide having, e.g., at least one, two, three, four, five, six, seven, eight, nine, 10 or 20 non-contiguous amino acid deletions relative to amino acids 321-426 of SEQ ID NO: 99. In still other aspects of this embodiment, an Activin A comprises a polypeptide having, e.g., at most one, two, three, four, five, six, seven, eight, nine, 10 or 20 non-contiguous amino acid additions relative to amino acids 321-426 of SEQ ID NO: 99. In other aspects of this embodiment, an Activin A comprises a polypeptide having, e.g., at least one, two, three, four, five, six, seven, eight, nine, 10 or 20 non-contiguous amino acid additions relative to amino acids 321-426 of SEQ ID NO: 99.

In other aspects of this embodiment, an Activin A comprises a polypeptide having, e.g., at most one, two, three, four, five, six, seven, eight, nine, 10 or 20 contiguous amino acid substitutions relative to amino acids 321-426 of SEQ ID NO: 99. In other aspects of this embodiment, an Activin A comprises a polypeptide having, e.g., at least one, two, three, four, five, six, seven, eight, nine, 10 or 20 contiguous amino acid substitutions relative to amino acids 321-426 of SEQ ID NO: 99. In yet other aspects of this embodiment, an Activin A comprises a polypeptide having, e.g., at most one, two, three, four, five, six, seven, eight, nine, 10 or 20 contiguous amino acid deletions relative to amino acids 321-426 of SEQ ID NO: 99. In other aspects of this embodiment, an Activin A comprises a polypeptide having, e.g., at least one, two, three, four, five, six, seven, eight, nine, 10 or 20 contiguous amino acid deletions relative to amino acids 321-426 of SEQ ID NO: 99. In still other aspects of this embodiment, an Activin A comprises a polypeptide having, e.g., at most one, two, three, four, five, six, seven, eight, nine, 10 or 20 contiguous amino acid additions relative to amino acids 321-426 of SEQ ID NO: 99. In other aspects of this embodiment, an Activin A comprises a polypeptide having, e.g., at least one, two, three, four, five, six, seven, eight, nine, 10 or 20 contiguous amino acid additions relative to amino acids 321-426 of SEQ ID NO: 99.

In an embodiment, a binding domain comprises an Activin B. In another embodiment, a binding domain comprises an Activin B of SEQ ID NO: 100. In another embodiment, a binding domain is derived from an Activin B. In another embodiment, a binding domain is derived from an Activin B of SEQ ID NO: 100. In an aspect of this embodiment, a binding domain is derived from an Activin B comprising amino acids 303-406 of SEQ ID NO: 100.

In other aspects of this embodiment, an Activin B comprises a polypeptide having, e.g., at least 70% amino acid identity with amino acids 303-406 of SEQ ID NO: 100, at least 75% amino acid identity with amino acids 303-406 of SEQ ID NO: 100, at least 80% amino acid identity with amino acids 303-406 of SEQ ID NO: 100, at least 85% amino acid identity with amino acids 303-406 of SEQ ID NO: 100, at least 90% amino acid identity with amino acids 303-406 of SEQ ID NO: 100 or at least 95% amino acid identity with amino acids 303-406 of SEQ ID NO: 100. In yet other aspects of this embodiment, an Activin B comprises a polypeptide having, e.g., at most 70% amino acid identity with amino acids 303-406 of SEQ ID NO: 100, at most 75% amino acid identity with amino acids 303-406 of SEQ ID NO: 100, at most 80% amino acid identity with amino acids 303-406 of SEQ ID NO: 100, at most 85% amino acid identity with amino acids 303-406 of SEQ ID NO: 100, at most 90% amino acid identity with amino acids 303-406 of SEQ ID NO: 100 or at most 95% amino acid identity with amino acids 303-406 of SEQ ID NO: 100.

In other aspects of this embodiment, an Activin B comprises a polypeptide having, e.g., at most one, two, three, four, five, six, seven, eight, nine, 10 or 20 non-contiguous amino acid substitutions relative to amino acids 303-406 of SEQ ID NO: 100. In other aspects of this embodiment, an Activin B comprises a polypeptide having, e.g., at least one, two, three, four, five, six, seven, eight, nine, 10 or 20 non-contiguous amino acid substitutions relative to amino acids 303-406 of SEQ ID NO: 100. In yet other aspects of this embodiment, an Activin B comprises a polypeptide having, e.g., at most one, two, three, four, five, six, seven, eight, nine, 10 or 20 non-contiguous amino acid deletions relative to amino acids 303-406 of SEQ ID NO: 100. In other aspects of this embodiment, an Activin B comprises a polypeptide having, e.g., at least one, two, three, four, five, six, seven, eight, nine, 10 or 20 non-contiguous amino acid deletions relative to amino acids 303-406 of SEQ ID NO: 100. In still other aspects of this embodiment, an Activin B comprises a polypeptide having, e.g., at most one, two, three, four, five, six, seven, eight, nine, 10 or 20 non-contiguous amino acid additions relative to amino acids 303-406 of SEQ ID NO: 100. In other aspects of this embodiment, an Activin B comprises a polypeptide having, e.g., at least one, two, three, four, five, six, seven, eight, nine, 10 or 20 non-contiguous amino acid additions relative to amino acids 303-406 of SEQ ID NO: 100.

In other aspects of this embodiment, an Activin B comprises a polypeptide having, e.g., at most one, two, three, four, five, six, seven, eight, nine, 10 or 20 contiguous amino acid substitutions relative to amino acids 303-406 of SEQ ID NO: 100. In other aspects of this embodiment, an Activin B comprises a polypeptide having, e.g., at least one, two, three, four, five, six, seven, eight, nine, 10 or 20 contiguous amino acid substitutions relative to amino acids 303-406 of SEQ ID NO: 100. In yet other aspects of this embodiment, an Activin B comprises a polypeptide having, e.g., at most one, two, three, four, five, six, seven, eight, nine, 10 or 20 contiguous amino acid deletions relative to amino acids 303-406 of SEQ ID NO: 100. In other aspects of this embodiment, an Activin B comprises a polypeptide having, e.g., at least one, two, three, four, five, six, seven, eight, nine, 10 or 20 contiguous amino acid deletions relative to amino acids 303-406 of SEQ ID NO: 100. In still other aspects of this embodiment, an Activin B comprises a polypeptide having, e.g., at most one, two, three, four, five, six, seven, eight, nine, 10 or 20 contiguous amino acid additions relative to amino acids 303-406 of SEQ ID NO: 100. In other aspects of this embodiment, an Activin B comprises a polypeptide having, e.g., at least one, two, three, four, five, six, seven, eight, nine, 10 or 20 contiguous amino acid additions relative to amino acids 303-406 of SEQ ID NO: 100.

In an embodiment, a binding domain comprises an Activin C. In another embodiment, a binding domain comprises an Activin C of SEQ ID NO: 101. In another embodiment, a binding domain is derived from an Activin C. In another embodiment, a binding domain is derived from an Activin C of SEQ ID NO: 101. In an aspect of this embodiment, a binding domain is derived from an Activin C comprising amino acids 247-352 or amino acids 237-352 of SEQ ID NO: 101.

In other aspects of this embodiment, an Activin C comprises a polypeptide having, e.g., at least 70% amino acid identity with amino acids 247-352 or amino acids 237-352 of SEQ ID NO: 101, at least 75% amino acid identity with amino acids 247-352 or amino acids 237-352 of SEQ ID NO: 101, at least 80% amino acid identity with amino acids 247-352 or amino acids 237-352 of SEQ ID NO: 101, at least 85% amino acid identity with amino acids 247-352 or amino acids 237-352 of SEQ ID NO: 101, at least 90% amino acid identity with amino acids 247-352 or amino acids 237-352 of SEQ ID NO: 101 or at least 95% amino acid identity with amino acids 247-352 or amino acids 237-352 of SEQ ID NO: 101. In yet other aspects of this embodiment, an Activin C comprises a polypeptide having, e.g., at most 70% amino acid identity with amino acids 247-352 or amino acids 237-352 of SEQ ID NO: 101, at most 75% amino acid identity with amino acids 247-352 or amino acids 237-352 of SEQ ID NO: 101, at most 80% amino acid identity with amino acids 247-352 or amino acids 237-352 of SEQ ID NO: 101, at most 85% amino acid identity with amino acids 247-352 or amino acids 237-352 of SEQ ID NO: 101, at most 90% amino acid identity with amino acids 247-352 or amino acids 237-352 of SEQ ID NO: 101 or at most 95% amino acid identity with amino acids 247-352 or amino acids 237-352 of SEQ ID NO: 101.

In other aspects of this embodiment, an Activin C comprises a polypeptide having, e.g., at most one, two, three, four, five, six, seven, eight, nine, 10 or 20 non-contiguous amino acid substitutions relative to amino acids 247-352 or amino acids 237-352 of SEQ ID NO: 101. In other aspects of this embodiment, an Activin C comprises a polypeptide having, e.g., at least one, two, three, four, five, six, seven, eight, nine, 10 or 20 non-contiguous amino acid substitutions relative to amino acids 247-352 or amino acids 237-352 of SEQ ID NO: 101. In yet other aspects of this embodiment, an Activin C comprises a polypeptide having, e.g., at most one, two, three, four, five, six, seven, eight, nine, 10 or 20 non-contiguous amino acid deletions relative to amino acids 247-352 or amino acids 237-352 of SEQ ID NO: 101. In other aspects of this embodiment, an Activin C comprises a polypeptide having, e.g., at least one, two, three, four, five, six, seven, eight, nine, 10 or 20 non-contiguous amino acid deletions relative to amino acids 247-352 or amino acids 237-352 of SEQ ID NO: 101. In still other aspects of this embodiment, an Activin C comprises a polypeptide having, e.g., at most one, two, three, four, five, six, seven, eight, nine, 10 or 20 non-contiguous amino acid additions relative to amino acids 247-352 or amino acids 237-352 of SEQ ID NO: 101. In other aspects of this embodiment, an Activin C comprises a polypeptide having, e.g., at least one, two, three, four, five, six, seven, eight, nine, 10 or 20 non-contiguous amino acid additions relative to amino acids 247-352 or amino acids 237-352 of SEQ ID NO: 101.

In other aspects of this embodiment, an Activin C comprises a polypeptide having, e.g., at most one, two, three, four, five, six, seven, eight, nine, 10 or 20 contiguous amino acid substitutions relative to amino acids 247-352 or amino acids 237-352 of SEQ ID NO: 101. In other aspects of this embodiment, an Activin C comprises a polypeptide having, e.g., at least one, two, three, four, five, six, seven, eight, nine, 10 or 20 contiguous amino acid substitutions relative to amino acids 247-352 or amino acids 237-352 of SEQ ID NO: 101. In yet other aspects of this embodiment, an Activin C comprises a polypeptide having, e.g., at most one, two, three, four, five, six, seven, eight, nine, 10 or 20 contiguous amino acid deletions relative to amino acids 247-352 or amino acids 237-352 of SEQ ID NO: 101. In other aspects of this embodiment, an Activin C comprises a polypeptide having, e.g., at least one, two, three, four, five, six, seven, eight, nine, 10 or 20 contiguous amino acid deletions relative to amino acids 247-352 or amino acids 237-352 of SEQ ID NO: 101. In still other aspects of this embodiment, an Activin C comprises a polypeptide having, e.g., at most one, two, three, four, five, six, seven, eight, nine, 10 or 20 contiguous amino acid additions relative to amino acids 247-352 or amino acids 237-352 of SEQ ID NO: 101. In other aspects of this embodiment, an Activin C comprises a polypeptide having, e.g., at least one, two, three, four, five, six, seven, eight, nine, 10 or 20 contiguous amino acid additions relative to amino acids 247-352 or amino acids 237-352 of SEQ ID NO: 101.

In an embodiment, a binding domain comprises an Activin D. In another embodiment, a binding domain comprises an Activin D of SEQ ID NO: 102. In another embodiment, a binding domain is derived from an Activin E. In another embodiment, a binding domain is derived from an Activin E of SEQ ID NO: 102. In an aspect of this embodiment, a binding domain is derived from an Activin E comprising amino acids 247-350 of SEQ ID NO: 102.

In other aspects of this embodiment, an Activin E comprises a polypeptide having, e.g., at least 70% amino acid identity with amino acids 247-350 of SEQ ID NO: 102, at least 75% amino acid identity with amino acids 247-350 of SEQ ID NO: 102, at least 80% amino acid identity with amino acids 247-350 of SEQ ID NO: 102, at least 85% amino acid identity with amino acids 247-350 of SEQ ID NO: 102, at least 90% amino acid identity with amino acids 247-350 of SEQ ID NO: 102 or at least 95% amino acid identity with amino acids 247-350 of SEQ ID NO: 102. In yet other aspects of this embodiment, an Activin E comprises a polypeptide having, e.g., at most 70% amino acid identity with amino acids 247-350 of SEQ ID NO: 102, at most 75% amino acid identity with amino acids 247-350 of SEQ ID NO: 102, at most 80% amino acid identity with amino acids 247-350 of SEQ ID NO: 102, at most 85% amino acid identity with amino acids 247-350 of SEQ ID NO: 102, at most 90% amino acid identity with amino acids 247-350 of SEQ ID NO: 102 or at most 95% amino acid identity with amino acids 247-350 of SEQ ID NO: 102.

In other aspects of this embodiment, an Activin E comprises a polypeptide having, e.g., at most one, two, three, four, five, six, seven, eight, nine, 10 or 20 non-contiguous amino acid substitutions relative to amino acids 247-350 of SEQ ID NO: 102. In other aspects of this embodiment, an Activin E comprises a polypeptide having, e.g., at least one, two, three, four, five, six, seven, eight, nine, 10 or 20 non-contiguous amino acid substitutions relative to amino acids 247-350 of SEQ ID NO: 102. In yet other aspects of this embodiment, an Activin E comprises a polypeptide having, e.g., at most one, two, three, four, five, six, seven, eight, nine, 10 or 20 non-contiguous amino acid deletions relative to amino acids 247-

350 of SEQ ID NO: 102. In other aspects of this embodiment, an Activin E comprises a polypeptide having, e.g., at least one, two, three, four, five, six, seven, eight, nine, 10 or 20 non-contiguous amino acid deletions relative to amino acids 247-350 of SEQ ID NO: 102. In still other aspects of this embodiment, an Activin E comprises a polypeptide having, e.g., at most one, two, three, four, five, six, seven, eight, nine, 10 or 20 non-contiguous amino acid additions relative to amino acids 247-350 of SEQ ID NO: 102. In other aspects of this embodiment, an Activin E comprises a polypeptide having, e.g., at least one, two, three, four, five, six, seven, eight, nine, 10 or 20 non-contiguous amino acid additions relative to amino acids 247-350 of SEQ ID NO: 102.

In other aspects of this embodiment, an Activin E comprises a polypeptide having, e.g., at most one, two, three, four, five, six, seven, eight, nine, 10 or 20 contiguous amino acid substitutions relative to amino acids 247-350 of SEQ ID NO: 102. In other aspects of this embodiment, an Activin E comprises a polypeptide having, e.g., at least one, two, three, four, five, six, seven, eight, nine, 10 or 20 contiguous amino acid substitutions relative to amino acids 247-350 of SEQ ID NO: 102. In yet other aspects of this embodiment, an Activin E comprises a polypeptide having, e.g., at most one, two, three, four, five, six, seven, eight, nine, 10 or 20 contiguous amino acid deletions relative to amino acids 247-350 of SEQ ID NO: 102. In other aspects of this embodiment, an Activin E comprises a polypeptide having, e.g., at least one, two, three, four, five, six, seven, eight, nine, 10 or 20 contiguous amino acid deletions relative to amino acids 247-350 of SEQ ID NO: 102. In still other aspects of this embodiment, an Activin E comprises a polypeptide having, e.g., at most one, two, three, four, five, six, seven, eight, nine, 10 or 20 contiguous amino acid additions relative to amino acids 247-350 of SEQ ID NO: 102. In other aspects of this embodiment, an Activin E comprises a polypeptide having, e.g., at least one, two, three, four, five, six, seven, eight, nine, 10 or 20 contiguous amino acid additions relative to amino acids 247-350 of SEQ ID NO: 102.

In an embodiment, a binding domain comprises an Inhibin A. In another embodiment, a binding domain comprises an Inhibin A of SEQ ID NO: 103. In another embodiment, a binding domain is derived from an Inhibin A. In another embodiment, a binding domain is derived from an Inhibin A of SEQ ID NO: 103. In an aspect of this embodiment, a binding domain is derived from an Inhibin A comprising amino acids 262-366 or amino acids 233-366 of SEQ ID NO: 103.

In other aspects of this embodiment, an Inhibin A comprises a polypeptide having, e.g., at least 70% amino acid identity with amino acids 262-366 or amino acids 233-366 of SEQ ID NO: 103, at least 75% amino acid identity with amino acids 262-366 or amino acids 233-366 of SEQ ID NO: 103, at least 80% amino acid identity with amino acids 262-366 or amino acids 233-366 of SEQ ID NO: 103, at least 85% amino acid identity with amino acids 262-366 or amino acids 233-366 of SEQ ID NO: 103, at least 90% amino acid identity with amino acids 262-366 or amino acids 233-366 of SEQ ID NO: 103 or at least 95% amino acid identity with amino acids 262-366 or amino acids 233-366 of SEQ ID NO: 103. In yet other aspects of this embodiment, an Inhibin A comprises a polypeptide having, e.g., at most 70% amino acid identity with amino acids 262-366 or amino acids 233-366 of SEQ ID NO: 103, at most 75% amino acid identity with amino acids 262-366 or amino acids 233-366 of SEQ ID NO: 103, at most 80% amino acid identity with amino acids 262-366 or amino acids 233-366 of SEQ ID NO: 103, at most 85% amino acid identity with amino acids 262-366 or amino acids 233-366 of SEQ ID NO: 103, at most 90% amino acid identity with amino acids 262-366 or amino acids 233-366 of SEQ ID NO: 103 or at most 95% amino acid identity with amino acids 262-366 or amino acids 233-366 of SEQ ID NO: 103.

In other aspects of this embodiment, an Inhibin A comprises a polypeptide having, e.g., at most one, two, three, four, five, six, seven, eight, nine, 10 or 20 non-contiguous amino acid substitutions relative to amino acids 262-366 or amino acids 233-366 of SEQ ID NO: 103. In other aspects of this embodiment, an Inhibin A comprises a polypeptide having, e.g., at least one, two, three, four, five, six, seven, eight, nine, 10 or 20 non-contiguous amino acid substitutions relative to amino acids 262-366 or amino acids 233-366 of SEQ ID NO: 103. In yet other aspects of this embodiment, an Inhibin A comprises a polypeptide having, e.g., at most one, two, three, four, five, six, seven, eight, nine, 10 or 20 non-contiguous amino acid deletions relative to amino acids 262-366 or amino acids 233-366 of SEQ ID NO: 103. In other aspects of this embodiment, an Inhibin A comprises a polypeptide having, e.g., at least one, two, three, four, five, six, seven, eight, nine, 10 or 20 non-contiguous amino acid deletions relative to amino acids 262-366 or amino acids 233-366 of SEQ ID NO: 103. In still other aspects of this embodiment, an Inhibin A comprises a polypeptide having, e.g., at most one, two, three, four, five, six, seven, eight, nine, 10 or 20 non-contiguous amino acid additions relative to amino acids 262-366 or amino acids 233-366 of SEQ ID NO: 103. In other aspects of this embodiment, an Inhibin A comprises a polypeptide having, e.g., at least one, two, three, four, five, six, seven, eight, nine, 10 or 20 non-contiguous amino acid additions relative to amino acids 262-366 or amino acids 233-366 of SEQ ID NO: 103.

In other aspects of this embodiment, an Inhibin A comprises a polypeptide having, e.g., at most one, two, three, four, five, six, seven, eight, nine, 10 or 20 contiguous amino acid substitutions relative to amino acids 262-366 or amino acids 233-366 of SEQ ID NO: 103. In other aspects of this embodiment, an Inhibin A comprises a polypeptide having, e.g., at least one, two, three, four, five, six, seven, eight, nine, 10 or 20 contiguous amino acid substitutions relative to amino acids 262-366 or amino acids 233-366 of SEQ ID NO: 103. In yet other aspects of this embodiment, an Inhibin A comprises a polypeptide having, e.g., at most one, two, three, four, five, six, seven, eight, nine, 10 or 20 contiguous amino acid deletions relative to amino acids 262-366 or amino acids 233-366 of SEQ ID NO: 103. In other aspects of this embodiment, an Inhibin A comprises a polypeptide having, e.g., at least one, two, three, four, five, six, seven, eight, nine, 10 or 20 contiguous amino acid deletions relative to amino acids 262-366 or amino acids 233-366 of SEQ ID NO: 103. In still other aspects of this embodiment, an Inhibin A comprises a polypeptide having, e.g., at most one, two, three, four, five, six, seven, eight, nine, 10 or 20 contiguous amino acid additions relative to amino acids 262-366 or amino acids 233-366 of SEQ ID NO: 103. In other aspects of this embodiment, an Inhibin A comprises a polypeptide having, e.g., at least one, two, three, four, five, six, seven, eight, nine, 10 or 20 contiguous amino acid additions relative to amino acids 262-366 or amino acids 233-366 of SEQ ID NO: 103.

Another example of a binding domain includes, without limitation, a opioid peptide, such as, e.g., an enkephalin, an endomorphin, an endorphin, a dynorphin, a nociceptin or a hemorphin. Thus, in an embodiment, a binding domain comprises an opioid peptide. In another embodiment, a binding domain is derived from an opioid peptide.

In another embodiment, an opioid binding domain comprises an enkephalin peptide. In aspects of this embodiment, an opioid binding domain is derived from an enkephalin peptide. In other aspects of this embodiment, an enkephalin binding domain is derived from a Leu-enkephalin, a Met-enkephalin, a Met-enkephalin MRGL or a Met-enkephalin MRF. In other aspects of this embodiment, an enkephalin binding domain comprises SEQ ID NO: 104, SEQ ID NO: 105, SEQ ID NO: 106 or SEQ ID NO: 107.

In other aspects of this embodiment, an enkephalin binding domain comprises a polypeptide having, e.g., at least 70% amino acid identity with SEQ ID NO: 104, SEQ ID NO: 105, SEQ ID NO: 106 or SEQ ID NO: 107, at least 75% amino acid identity with SEQ ID NO: 104, SEQ ID NO: 105, SEQ ID NO: 106 or SEQ ID NO: 107, at least 80% amino acid identity with SEQ ID NO: 104, SEQ ID NO: 105, SEQ ID NO: 106 or SEQ ID NO: 107, at least 85% amino acid identity with SEQ ID NO: 104, SEQ ID NO: 105, SEQ ID NO: 106 or SEQ ID NO: 107, at least 90% amino acid identity with SEQ ID NO: 104, SEQ ID NO: 105, SEQ ID NO: 106 or SEQ ID NO: 107 or at least 95% amino acid identity with SEQ ID NO: 104, SEQ ID NO: 105, SEQ ID NO: 106 or SEQ ID NO: 107. In yet other aspects of this embodiment, an enkephalin binding domain comprises a polypeptide having, e.g., at most 70% amino acid identity with SEQ ID NO: 104, SEQ ID NO: 105, SEQ ID NO: 106 or SEQ ID NO: 107, at most 75% amino acid identity with SEQ ID NO: 104, SEQ ID NO: 105, SEQ ID NO: 106 or SEQ ID NO: 107, at most 80% amino acid identity with SEQ ID NO: 104, SEQ ID NO: 105, SEQ ID NO: 106 or SEQ ID NO: 107, at most 85% amino acid identity with SEQ ID NO: 104, SEQ ID NO: 105, SEQ ID NO: 106 or SEQ ID NO: 107, at most 90% amino acid identity with SEQ ID NO: 104, SEQ ID NO: 105, SEQ ID NO: 106 or SEQ ID NO: 107 or at most 95% amino acid identity with SEQ ID NO: 104, SEQ ID NO: 105, SEQ ID NO: 106 or SEQ ID NO: 107.

In other aspects of this embodiment, an enkephalin binding domain comprises a polypeptide having, e.g., at least one, two or three non-contiguous amino acid substitutions relative to SEQ ID NO: 104, SEQ ID NO: 105, SEQ ID NO: 106 or SEQ ID NO: 107. In other aspects of this embodiment, an enkephalin binding domain comprises a polypeptide having, e.g., at most one, two or three non-contiguous amino acid substitutions relative to SEQ ID NO: 104, SEQ ID NO: 105, SEQ ID NO: 106 or SEQ ID NO: 107. In yet other aspects of this embodiment, an enkephalin binding domain comprises a polypeptide having, e.g., at least one, two or three non-contiguous amino acid deletions relative to SEQ ID NO: 104, SEQ ID NO: 105, SEQ ID NO: 106 or SEQ ID NO: 107. In yet other aspects of this embodiment, an enkephalin binding domain comprises a polypeptide having, e.g., at most one, two or three non-contiguous amino acid deletions relative to SEQ ID NO: 104, SEQ ID NO: 105, SEQ ID NO: 106 or SEQ ID NO: 107. In still other aspects of this embodiment, an enkephalin binding domain comprises a polypeptide having, e.g., at least one, two or three non-contiguous amino acid additions relative to SEQ ID NO: 104, SEQ ID NO: 105, SEQ ID NO: 106 or SEQ ID NO: 107. In yet other aspects of this embodiment, an enkephalin binding domain comprises a polypeptide having, e.g., at most one, two or three non-contiguous amino acid additions relative to SEQ ID NO: 104, SEQ ID NO: 105, SEQ ID NO: 106 or SEQ ID NO: 107.

In other aspects of this embodiment, an enkephalin binding domain comprises a polypeptide having, e.g., at least one, two or three contiguous amino acid substitutions relative to SEQ ID NO: 104, SEQ ID NO: 105, SEQ ID NO: 106 or SEQ ID NO: 107. In other aspects of this embodiment, an enkephalin binding domain comprises a polypeptide having, e.g., at most one, two or three contiguous amino acid substitutions relative to SEQ ID NO: 104, SEQ ID NO: 105, SEQ ID NO: 106 or SEQ ID NO: 107. In yet other aspects of this embodiment, an enkephalin binding domain comprises a polypeptide having, e.g., at least one, two or three contiguous amino acid deletions relative to SEQ ID NO: 104, SEQ ID NO: 105, SEQ ID NO: 106 or SEQ ID NO: 107. In yet other aspects of this embodiment, an enkephalin binding domain comprises a polypeptide having, e.g., at most one, two or three contiguous amino acid deletions relative to SEQ ID NO: 104, SEQ ID NO: 105, SEQ ID NO: 106 or SEQ ID NO: 107. In still other aspects of this embodiment, an enkephalin binding domain comprises a polypeptide having, e.g., at least one, two or three contiguous amino acid additions relative to SEQ ID NO: 104, SEQ ID NO: 105, SEQ ID NO: 106 or SEQ ID NO: 107. In yet other aspects of this embodiment, an enkephalin binding domain comprises a polypeptide having, e.g., at most one, two or three contiguous amino acid additions relative to SEQ ID NO: 104, SEQ ID NO: 105, SEQ ID NO: 106 or SEQ ID NO: 107.

In another embodiment, an opioid binding domain comprises a bovine adrenomedullary-22 (BAM22) peptide. In aspects of this embodiment, an opioid binding domain comprising a BAM22 peptide is derived from a BAM22 peptide (1-12), a BAM22 peptide (6-22), a BAM22 peptide (8-22) or a BAM22 peptide (1-22). In other aspects of this embodiment, a BAM22 binding domain comprises amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112 or amino acids 1-12, amino acids 6-22, amino acids 8-22 or amino acids 1-22 of SEQ ID NO: 113.

In other aspects of this embodiment, a BAM22 binding domain comprises a polypeptide having, e.g., at least 70% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113, at least 75% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113, at least 80% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113, at least 85% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113, at least 90% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113 or at least 95% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113.

In yet other aspects of this embodiment, a BAM22 binding domain comprises a polypeptide having, e.g., at most 70% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113, at most 75% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113, at most 80% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113, at most 85% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113, at most 90% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113 or at most 95% amino acid identity with amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113.

In other aspects of this embodiment, a BAM22 binding domain comprises a polypeptide having, e.g., at least one, two, three, four or five non-contiguous amino acid substitutions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In other aspects of this embodiment, a BAM22 binding domain comprises a polypeptide having, e.g., at most one, two, three, four or five non-contiguous amino acid substitutions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In yet other aspects of this embodiment, a BAM22 binding domain comprises a polypeptide having, e.g., at least one, two, three, four or five non-contiguous amino acid deletions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In yet other aspects of this embodiment, a BAM22 binding domain comprises a polypeptide having, e.g., at most one, two, three, four or five non-contiguous amino acid deletions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In still other aspects of this embodiment, a BAM22 binding domain comprises a polypeptide having, e.g., at least one, two, three, four or five non-contiguous amino acid additions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In yet other aspects of this embodiment, a BAM22 binding domain comprises a polypeptide having, e.g., at most one, two, three, four or five non-contiguous amino acid additions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113.

In other aspects of this embodiment, a BAM22 binding domain comprises a polypeptide having, e.g., at least one, two, three, four or five contiguous amino acid substitutions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In other aspects of this embodiment, a BAM22 binding domain comprises a polypeptide having, e.g., at most one, two, three, four or five contiguous amino acid substitutions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In yet other aspects of this embodiment, a BAM22 binding domain comprises a polypeptide having, e.g., at least one, two, three, four or five contiguous amino acid deletions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In yet other aspects of this embodiment, a BAM22 binding domain comprises a polypeptide having, e.g., at most one, two, three, four or five contiguous amino acid deletions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In still other aspects of this embodiment, a BAM22 binding domain comprises a polypeptide having, e.g., at least one, two, three, four or five contiguous amino acid additions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113. In yet other aspects of this embodiment, a BAM22 binding domain comprises a polypeptide having, e.g., at most one, two, three, four or five contiguous amino acid additions relative to amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; or amino acids 1-12, amino acids 6-22, amino acids 8-22 or amino acids 1-22 of SEQ ID NO: 113.

In another embodiment, an opioid binding domain comprises an endomorphin peptide. In another embodiment, an opioid binding domain is derived from an endomorphin peptide. In aspects of this embodiment, an endomorphin binding domain comprises an endomorphin-1 or an endomorphin-2. In other aspects of this embodiment, an endomorphin binding domain comprises SEQ ID NO: 114 or SEQ ID NO: 115.

In other aspects of this embodiment, an endomorphin binding domain comprises a polypeptide having, e.g., at least 70% amino acid identity with SEQ ID NO: 114 or SEQ ID NO: 115, at least 75% amino acid identity with SEQ ID NO: 114 or SEQ ID NO: 115, at least 80% amino acid identity with SEQ ID NO: 114 or SEQ ID NO: 115, at least 85% amino acid identity with SEQ ID NO: 114 or SEQ ID NO: 115, at least 90% amino acid identity with SEQ ID NO: 114 or SEQ ID NO: 115 or at least 95% amino acid identity with SEQ ID NO:

114 or SEQ ID NO: 115. In yet other aspects of this embodiment, an endomorphin binding domain comprises a polypeptide having, e.g., at most 70% amino acid identity with SEQ ID NO: 114 or SEQ ID NO: 115, at most 75% amino acid identity with SEQ ID NO: 114 or SEQ ID NO: 115, at most 80% amino acid identity with SEQ ID NO: 114 or SEQ ID NO: 115, at most 85% amino acid identity with SEQ ID NO: 114 or SEQ ID NO: 115, at most 90% amino acid identity with SEQ ID NO: 114 or SEQ ID NO: 115 or at most 95% amino acid identity with SEQ ID NO: 114 or SEQ ID NO: 115.

In other aspects of this embodiment, an endomorphin binding domain comprises a polypeptide having, e.g., at least one, two or three non-contiguous amino acid substitutions relative to SEQ ID NO: 114 or SEQ ID NO: 115. In other aspects of this embodiment, an endomorphin binding domain comprises a polypeptide having, e.g., at most one, two or three non-contiguous amino acid substitutions relative to SEQ ID NO: 114 or SEQ ID NO: 115. In yet other aspects of this embodiment, an endomorphin binding domain comprises a polypeptide having, e.g., at least one, two or three non-contiguous amino acid deletions relative to SEQ ID NO: 114 or SEQ ID NO: 115. In yet other aspects of this embodiment, an endomorphin binding domain comprises a polypeptide having, e.g., at most one, two or three non-contiguous amino acid deletions relative to SEQ ID NO: 114 or SEQ ID NO: 115. In still other aspects of this embodiment, an endomorphin binding domain comprises a polypeptide having, e.g., at least one, two or three non-contiguous amino acid additions relative to SEQ ID NO: 114 or SEQ ID NO: 115. In yet other aspects of this embodiment, an endomorphin binding domain comprises a polypeptide having, e.g., at most one, two or three non-contiguous amino acid additions relative to SEQ ID NO: 114 or SEQ ID NO: 115.

In other aspects of this embodiment, an endomorphin binding domain comprises a polypeptide having, e.g., at least one, two or three contiguous amino acid substitutions relative to SEQ ID NO: 114 or SEQ ID NO: 115. In other aspects of this embodiment, an endomorphin binding domain comprises a polypeptide having, e.g., at most one, two or three contiguous amino acid substitutions relative to SEQ ID NO: 114 or SEQ ID NO: 115. In yet other aspects of this embodiment, an endomorphin binding domain comprises a polypeptide having, e.g., at least one, two or three contiguous amino acid deletions relative to SEQ ID NO: 114 or SEQ ID NO: 115. In yet other aspects of this embodiment, an endomorphin binding domain comprises a polypeptide having, e.g., at most one, two or three contiguous amino acid deletions relative to SEQ ID NO: 114 or SEQ ID NO: 115. In still other aspects of this embodiment, an endomorphin binding domain comprises a polypeptide having, e.g., at least one, two or three contiguous amino acid additions relative to SEQ ID NO: 114 or SEQ ID NO: 115. In yet other aspects of this embodiment, an endomorphin binding domain comprises a polypeptide having, e.g., at most one, two or three contiguous amino acid additions relative to SEQ ID NO: 114 or SEQ ID NO: 115.

In another embodiment, an opioid binding domain comprises an endorphin peptide. In aspects of this embodiment, an opioid binding domain comprises is derived from an endorphin peptide. In other aspects, an endorphin binding domain comprises an endorphin-α, a neoendorphin-α, an endorphin-β, a neoendorphin-β or an endorphin-γ. In other aspects of this embodiment, an endorphin binding domain comprises SEQ ID NO: 291, SEQ ID NO: 116, SEQ ID NO: 117, SEQ ID NO: 118, SEQ ID NO: 119 or SEQ ID NO: 120.

In other aspects of this embodiment, an endorphin binding domain comprises a polypeptide having, e.g., at least 70% amino acid identity with SEQ ID NO: 291, SEQ ID NO: 116, SEQ ID NO: 117, SEQ ID NO: 118, SEQ ID NO: 119 or SEQ ID NO: 120, at least 75% amino acid identity with SEQ ID NO: 291, SEQ ID NO: 116, SEQ ID NO: 117, SEQ ID NO: 118, SEQ ID NO: 119 or SEQ ID NO: 120, at least 80% amino acid identity with SEQ ID NO: 291, SEQ ID NO: 116, SEQ ID NO: 117, SEQ ID NO: 118, SEQ ID NO: 119 or SEQ ID NO: 120, at least 85% amino acid identity with SEQ ID NO: 291, SEQ ID NO: 116, SEQ ID NO: 117, SEQ ID NO: 118, SEQ ID NO: 119 or SEQ ID NO: 120, at least 90% amino acid identity with SEQ ID NO: 291, SEQ ID NO: 116, SEQ ID NO: 117, SEQ ID NO: 118, SEQ ID NO: 119 or SEQ ID NO: 120 or at least 95% amino acid identity with SEQ ID NO: 291, SEQ ID NO: 116, SEQ ID NO: 117, SEQ ID NO: 118, SEQ ID NO: 119 or SEQ ID NO: 120. In yet other aspects of this embodiment, an endorphin binding domain comprises a polypeptide having, e.g., at most 70% amino acid identity with SEQ ID NO: 291, SEQ ID NO: 116, SEQ ID NO: 117, SEQ ID NO: 118, SEQ ID NO: 119 or SEQ ID NO: 120, at most 75% amino acid identity with SEQ ID NO: 291, SEQ ID NO: 116, SEQ ID NO: 117, SEQ ID NO: 118, SEQ ID NO: 119 or SEQ ID NO: 120, at most 80% amino acid identity with SEQ ID NO: 291, SEQ ID NO: 116, SEQ ID NO: 117, SEQ ID NO: 118, SEQ ID NO: 119 or SEQ ID NO: 120, at most 85% amino acid identity with SEQ ID NO: 291, SEQ ID NO: 116, SEQ ID NO: 117, SEQ ID NO: 118, SEQ ID NO: 119 or SEQ ID NO: 120, at most 90% amino acid identity with SEQ ID NO: 291, SEQ ID NO: 116, SEQ ID NO: 117, SEQ ID NO: 118, SEQ ID NO: 119 or SEQ ID NO: 120 or at most 95% amino acid identity with SEQ ID NO: 291, SEQ ID NO: 116, SEQ ID NO: 117, SEQ ID NO: 118, SEQ ID NO: 119 or SEQ ID NO: 120.

In other aspects of this embodiment, an endorphin binding domain comprises a polypeptide having, e.g., at least one, two, three, four or five non-contiguous amino acid substitutions relative to SEQ ID NO: 291, SEQ ID NO: 116, SEQ ID NO: 117, SEQ ID NO: 118, SEQ ID NO: 119 or SEQ ID NO: 120. In other aspects of this embodiment, an endorphin binding domain comprises a polypeptide having, e.g., at most one, two, three, four or five non-contiguous amino acid substitutions relative to SEQ ID NO: 291, SEQ ID NO: 116, SEQ ID NO: 117, SEQ ID NO: 118, SEQ ID NO: 119 or SEQ ID NO: 120. In yet other aspects of this embodiment, an endorphin binding domain comprises a polypeptide having, e.g., at least one, two, three, four or five non-contiguous amino acid deletions relative to SEQ ID NO: 291, SEQ ID NO: 116, SEQ ID NO: 117, SEQ ID NO: 118, SEQ ID NO: 119 or SEQ ID NO: 120. In yet other aspects of this embodiment, an endorphin binding domain comprises a polypeptide having, e.g., at most one, two, three, four or five non-contiguous amino acid deletions relative to SEQ ID NO: 291, SEQ ID NO: 116, SEQ ID NO: 117, SEQ ID NO: 118, SEQ ID NO: 119 or SEQ ID NO: 120. In still other aspects of this embodiment, an endorphin binding domain comprises a polypeptide having, e.g., at least one, two, three, four or five non-contiguous amino acid additions relative to SEQ ID NO: 291, SEQ ID NO: 116, SEQ ID NO: 117, SEQ ID NO: 118, SEQ ID NO: 119 or SEQ ID NO: 120. In yet other aspects of this embodiment, an endorphin binding domain comprises a polypeptide having, e.g., at most one, two, three, four or five non-contiguous amino acid additions relative to SEQ ID NO: 291, SEQ ID NO: 116, SEQ ID NO: 117, SEQ ID NO: 118, SEQ ID NO: 119 or SEQ ID NO: 120.

In other aspects of this embodiment, an endorphin binding domain comprises a polypeptide having, e.g., at least one, two, three, four or five contiguous amino acid substitutions relative to SEQ ID NO: 291, SEQ ID NO: 116, SEQ ID NO:

117, SEQ ID NO: 118, SEQ ID NO: 119 or SEQ ID NO: 120. In other aspects of this embodiment, an endorphin binding domain comprises a polypeptide having, e.g., at most one, two, three, four or five contiguous amino acid substitutions relative to SEQ ID NO: 291, SEQ ID NO: 116, SEQ ID NO: 117, SEQ ID NO: 118, SEQ ID NO: 119 or SEQ ID NO: 120. In yet other aspects of this embodiment, an endorphin binding domain comprises a polypeptide having, e.g., at least one, two, three, four or five contiguous amino acid deletions relative to SEQ ID NO: 291, SEQ ID NO: 116, SEQ ID NO: 117, SEQ ID NO: 118, SEQ ID NO: 119 or SEQ ID NO: 120. In yet other aspects of this embodiment, an endorphin binding domain comprises a polypeptide having, e.g., at most one, two, three, four or five contiguous amino acid deletions relative to SEQ ID NO: 291, SEQ ID NO: 116, SEQ ID NO: 117, SEQ ID NO: 118, SEQ ID NO: 119 or SEQ ID NO: 120. In still other aspects of this embodiment, an endorphin binding domain comprises a polypeptide having, e.g., at least one, two, three, four or five contiguous amino acid additions relative to SEQ ID NO: 291, SEQ ID NO: 116, SEQ ID NO: 117, SEQ ID NO: 118, SEQ ID NO: 119 or SEQ ID NO: 120. In yet other aspects of this embodiment, an endorphin binding domain comprises a polypeptide having, e.g., at most one, two, three, four or five contiguous amino acid additions relative to SEQ ID NO: 291, SEQ ID NO: 116, SEQ ID NO: 117, SEQ ID NO: 118, SEQ ID NO: 119 or SEQ ID NO: 120.

In another embodiment, an opioid binding domain comprises a dynorphin peptide. In another embodiment, an opioid binding domain is derived from a dynorphin peptide. In aspects of this embodiment, a dynorphin binding domain comprises a dynorphin A, a dynorphin B (leumorphin) or a rimorphin. In other aspects of this embodiment, a dynorphin binding domain comprises SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150 or SEQ ID NO: 151.

In other aspects of this embodiment, a dynorphin binding domain comprises a polypeptide having, e.g., at least 70% amino acid identity with SEQ ID NO: 121, SEQ ID NO: 130 or SEQ ID NO: 146, at least 75% amino acid identity with SEQ ID NO: 121, SEQ ID NO: 130 or SEQ ID NO: 146, at least 80% amino acid identity with SEQ ID NO: 121, SEQ ID NO: 130 or SEQ ID NO: 146, at least 85% amino acid identity with SEQ ID NO: 121, SEQ ID NO: 130 or SEQ ID NO: 146, at least 90% amino acid identity with SEQ ID NO: 121, SEQ ID NO: 130 or SEQ ID NO: 146 or at least 95% amino acid identity with SEQ ID NO: 121, SEQ ID NO: 130 or SEQ ID NO: 146. In yet other aspects of this embodiment, a dynorphin binding domain comprises a polypeptide having, e.g., at most 70% amino acid identity with SEQ ID NO: 121, SEQ ID NO: 130 or SEQ ID NO: 146, at most 75% amino acid identity with SEQ ID NO: 121, SEQ ID NO: 130 or SEQ ID NO: 146, at most 80% amino acid identity with SEQ ID NO: 121, SEQ ID NO: 130 or SEQ ID NO: 146, at most 85% amino acid identity with SEQ ID NO: 121, SEQ ID NO: 130 or SEQ ID NO: 146, at most 90% amino acid identity with SEQ ID NO: 121, SEQ ID NO: 130 or SEQ ID NO: 146 or at most 95% amino acid identity with SEQ ID NO: 121, SEQ ID NO: 130 or SEQ ID NO: 146.

In other aspects of this embodiment, a dynorphin binding domain comprises a polypeptide having, e.g., at least one, two, three, four, five, six, seven, eight, nine or ten non-contiguous amino acid substitutions relative to SEQ ID NO: 121, SEQ ID NO: 130 or SEQ ID NO: 146. In other aspects of this embodiment, a dynorphin binding domain comprises a polypeptide having, e.g., at most one, two, three, four, five, six, seven, eight, nine or ten non-contiguous amino acid substitutions relative to SEQ ID NO: 121, SEQ ID NO: 130 or SEQ ID NO: 146. In yet other aspects of this embodiment, a dynorphin binding domain comprises a polypeptide having, e.g., at least one, two, three, four, five, six, seven, eight, nine or ten non-contiguous amino acid deletions relative to SEQ ID NO: 121, SEQ ID NO: 130 or SEQ ID NO: 146. In yet other aspects of this embodiment, a dynorphin binding domain comprises a polypeptide having, e.g., at most one, two, three, four, five, six, seven, eight, nine or ten non-contiguous amino acid deletions relative to SEQ ID NO: 121, SEQ ID NO: 130 or SEQ ID NO: 146. In still other aspects of this embodiment, a dynorphin binding domain comprises a polypeptide having, e.g., at least one, two, three, four, five, six, seven, eight, nine or ten non-contiguous amino acid additions relative to SEQ ID NO: 121, SEQ ID NO: 130 or SEQ ID NO: 146. In yet other aspects of this embodiment, a dynorphin binding domain comprises a polypeptide having, e.g., at most one, two, three, four, five, six, seven, eight, nine or ten non-contiguous amino acid additions relative to SEQ ID NO: 121, SEQ ID NO: 130 or SEQ ID NO: 146.

In other aspects of this embodiment, a dynorphin binding domain comprises a polypeptide having, e.g., at least one, two, three, four, five, six, seven, eight, nine or ten contiguous amino acid substitutions relative to SEQ ID NO: 121, SEQ ID NO: 130 or SEQ ID NO: 146. In other aspects of this embodiment, a dynorphin binding domain comprises a polypeptide having, e.g., at most one, two, three, four, five, six, seven, eight, nine or ten contiguous amino acid substitutions relative to SEQ ID NO: 121, SEQ ID NO: 130 or SEQ ID NO: 146. In yet other aspects of this embodiment, a dynorphin binding domain comprises a polypeptide having, e.g., at least one, two, three, four, five, six, seven, eight, nine or ten contiguous amino acid deletions relative to SEQ ID NO: 121, SEQ ID NO: 130 or SEQ ID NO: 146. In yet other aspects of this embodiment, a dynorphin binding domain comprises a polypeptide having, e.g., at most one, two, three, four, five, six, seven, eight, nine or ten contiguous amino acid deletions relative to SEQ ID NO: 121, SEQ ID NO: 130 or SEQ ID NO: 146. In still other aspects of this embodiment, a dynorphin binding domain comprises a polypeptide having, e.g., at least one, two, three, four, five, six, seven, eight, nine or ten contiguous amino acid additions relative to SEQ ID NO: 121, SEQ ID NO: 130 or SEQ ID NO: 146. In yet other aspects of this embodiment, a dynorphin binding domain comprises a polypeptide having, e.g., at most one, two, three, four, five, six, seven, eight, nine or ten contiguous amino acid additions relative to SEQ ID NO: 121, SEQ ID NO: 130 or SEQ ID NO: 146.

In another embodiment, an opioid binding domain comprises a nociceptin peptide. In another embodiment, an opioid binding domain is derived from a nociceptin peptide. In aspects of this embodiment, a nociceptin binding domain comprises a nociceptin RK, a nociceptin, a neuropeptide 1, a neuropeptide 2 or a neuropeptide 3. In other aspects of this embodiment, a nociceptin binding domain comprises SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160 or SEQ ID NO: 161.

In other aspects of this embodiment, a nociceptin binding domain comprises a polypeptide having, e.g., at least 70% amino acid identity with SEQ ID NO: 152, SEQ ID NO: 159, SEQ ID NO: 160 or SEQ ID NO: 161, at least 75% amino acid identity with SEQ ID NO: 152, SEQ ID NO: 159, SEQ ID NO: 160 or SEQ ID NO: 161, at least 80% amino acid identity with SEQ ID NO: 152, SEQ ID NO: 159, SEQ ID NO: 160 or SEQ ID NO: 161, at least 85% amino acid identity with SEQ ID NO: 152, SEQ ID NO: 159, SEQ ID NO: 160 or SEQ ID NO: 161, at least 90% amino acid identity with SEQ ID NO: 152, SEQ ID NO: 159, SEQ ID NO: 160 or SEQ ID NO: 161 or at least 95% amino acid identity with SEQ ID NO: 152, SEQ ID NO: 159, SEQ ID NO: 160 or SEQ ID NO: 161. In yet other aspects of this embodiment, a nociceptin binding domain comprises a polypeptide having, e.g., at most 70% amino acid identity with SEQ ID NO: 152, SEQ ID NO: 159, SEQ ID NO: 160 or SEQ ID NO: 161, at most 75% amino acid identity with SEQ ID NO: 152, SEQ ID NO: 159, SEQ ID NO: 160 or SEQ ID NO: 161, at most 80% amino acid identity with SEQ ID NO: 152, SEQ ID NO: 159, SEQ ID NO: 160 or SEQ ID NO: 161, at most 85% amino acid identity with SEQ ID NO: 152, SEQ ID NO: 159, SEQ ID NO: 160 or SEQ ID NO: 161, at most 90% amino acid identity with SEQ ID NO: 152, SEQ ID NO: 159, SEQ ID NO: 160 or SEQ ID NO: 161 or at most 95% amino acid identity with SEQ ID NO: 152, SEQ ID NO: 159, SEQ ID NO: 160 or SEQ ID NO: 161.

In other aspects of this embodiment, a nociceptin binding domain comprises a polypeptide having, e.g., at least one, two, three, four, five, six, seven, eight, nine or ten non-contiguous amino acid substitutions relative to SEQ ID NO: 152, SEQ ID NO: 159, SEQ ID NO: 160 or SEQ ID NO: 161. In other aspects of this embodiment, a nociceptin binding domain comprises a polypeptide having, e.g., at most one, two, three, four, five, six, seven, eight, nine or ten non-contiguous amino acid substitutions relative to SEQ ID NO: 152, SEQ ID NO: 159, SEQ ID NO: 160 or SEQ ID NO: 161. In yet other aspects of this embodiment, a nociceptin binding domain comprises a polypeptide having, e.g., at least one, two, three, four, five, six, seven, eight, nine or ten non-contiguous amino acid deletions relative to SEQ ID NO: 152, SEQ ID NO: 159, SEQ ID NO: 160 or SEQ ID NO: 161. In yet other aspects of this embodiment, a nociceptin binding domain comprises a polypeptide having, e.g., at most one, two, three, four, five, six, seven, eight, nine or ten non-contiguous amino acid deletions relative to SEQ ID NO: 152, SEQ ID NO: 159, SEQ ID NO: 160 or SEQ ID NO: 161. In still other aspects of this embodiment, a nociceptin binding domain comprises a polypeptide having, e.g., at least one, two, three, four, five, six, seven, eight, nine or ten non-contiguous amino acid additions relative to SEQ ID NO: 152, SEQ ID NO: 159, SEQ ID NO: 160 or SEQ ID NO: 161. In yet other aspects of this embodiment, a nociceptin binding domain comprises a polypeptide having, e.g., at most one, two, three, four, five, six, seven, eight, nine or ten non-contiguous amino acid additions relative to SEQ ID NO: 152, SEQ ID NO: 159, SEQ ID NO: 160 or SEQ ID NO: 161.

In other aspects of this embodiment, a nociceptin binding domain comprises a polypeptide having, e.g., at least one, two, three, four, five, six, seven, eight, nine or ten contiguous amino acid substitutions relative to SEQ ID NO: 152, SEQ ID NO: 159, SEQ ID NO: 160 or SEQ ID NO: 161. In other aspects of this embodiment, a nociceptin binding domain comprises a polypeptide having, e.g., at most one, two, three, four, five, six, seven, eight, nine or ten contiguous amino acid substitutions relative to SEQ ID NO: 152, SEQ ID NO: 159, SEQ ID NO: 160 or SEQ ID NO: 161. In yet other aspects of this embodiment, a nociceptin binding domain comprises a polypeptide having, e.g., at least one, two, three, four, five, six, seven, eight, nine or ten contiguous amino acid deletions relative to SEQ ID NO: 152, SEQ ID NO: 159, SEQ ID NO: 160 or SEQ ID NO: 161. In yet other aspects of this embodiment, a nociceptin binding domain comprises a polypeptide having, e.g., at most one, two, three, four, five, six, seven, eight, nine or ten contiguous amino acid deletions relative to SEQ ID NO: 152, SEQ ID NO: 159, SEQ ID NO: 160 or SEQ ID NO: 161. In still other aspects of this embodiment, a nociceptin binding domain comprises a polypeptide having, e.g., at least one, two, three, four, five, six, seven, eight, nine or ten contiguous amino acid additions relative to SEQ ID NO: 152, SEQ ID NO: 159, SEQ ID NO: 160 or SEQ ID NO: 161. In yet other aspects of this embodiment, a nociceptin binding domain comprises a polypeptide having, e.g., at most one, two, three, four, five, six, seven, eight, nine or ten contiguous amino acid additions relative to SEQ ID NO: 152, SEQ ID NO: 159, SEQ ID NO: 160 or SEQ ID NO: 161.

Another example of a binding domain disclosed in the present specification is, e.g., a melanocortin peptide, such as, e.g., a melanocyte stimulating hormone, an adrenocorticotropin, a Corticotropin-like intermediary peptide) or a lipotropin. Thus, in an embodiment, a binding domain is derived from a melanocortin peptide.

In another embodiment, a binding domain comprises a melanocortin peptide. In another embodiment, a binding domain is derived from a melanocortin peptide. In an aspect of this embodiment, a melanocortin peptide binding domain comprises a melanocyte stimulating hormone. In an aspect of this embodiment, a melanocortin peptide binding domain comprises is derived from a melanocyte stimulating hormone. In aspects of this embodiment, a melanocyte stimulating hormone binding domain comprises an α-melanocyte stimulating hormones (α-MSH), a β-melanocyte stimulating hormones (β-MSH), a γ-melanocyte stimulating hormones (γ-MSH). In other aspects of this embodiment, a melanocyte stimulating hormone binding domain comprises SEQ ID NO: 162, SEQ ID NO: 163 or SEQ ID NO: 164.

In other aspects of this embodiment, a melanocyte stimulating hormone binding domain comprises a polypeptide having, e.g., at least 70% amino acid identity with SEQ ID NO: 162, SEQ ID NO: 163 or SEQ ID NO: 164, at least 75% amino acid identity with SEQ ID NO: 162, SEQ ID NO: 163 or SEQ ID NO: 164, at least 80% amino acid identity with SEQ ID NO: 162, SEQ ID NO: 163 or SEQ ID NO: 164, at least 85% amino acid identity with SEQ ID NO: 162, SEQ ID NO: 163 or SEQ ID NO: 164, at least 90% amino acid identity with SEQ ID NO: 162, SEQ ID NO: 163 or SEQ ID NO: 164 or at least 95% amino acid identity with SEQ ID NO: 162, SEQ ID NO: 163 or SEQ ID NO: 164. In yet other aspects of this embodiment, a melanocyte stimulating hormone binding domain comprises a polypeptide having, e.g., at most 70% amino acid identity with SEQ ID NO: 162, SEQ ID NO: 163 or SEQ ID NO: 164, at most 75% amino acid identity with SEQ ID NO: 162, SEQ ID NO: 163 or SEQ ID NO: 164, at most 80% amino acid identity with SEQ ID NO: 162, SEQ ID NO: 163 or SEQ ID NO: 164, at most 85% amino acid identity with SEQ ID NO: 162, SEQ ID NO: 163 or SEQ ID NO: 164, at most 90% amino acid identity with SEQ ID NO: 162, SEQ ID NO: 163 or SEQ ID NO: 164 or at most 95% amino acid identity with SEQ ID NO: 162, SEQ ID NO: 163 or SEQ ID NO: 164.

In other aspects of this embodiment, a melanocyte stimulating hormone binding domain comprises a polypeptide having, e.g., at least one, two, three, four or five non-contiguous amino acid substitutions relative to SEQ ID NO: 162, SEQ ID NO: 163 or SEQ ID NO: 164. In other aspects of this embodiment, a melanocyte stimulating hormone binding domain comprises a polypeptide having, e.g., at most one, two, three, four or five non-contiguous amino acid substitutions relative to SEQ ID NO: 162, SEQ ID NO: 163 or SEQ ID NO: 164. In yet other aspects of this embodiment, a melanocyte stimulating hormone binding domain comprises a polypeptide having, e.g., at least one, two, three, four or five non-contiguous amino acid deletions relative to SEQ ID NO: 162, SEQ ID NO: 163 or SEQ ID NO: 164. In yet other aspects of this embodiment, a melanocyte stimulating hormone binding domain comprises a polypeptide having, e.g., at most one, two, three, four or five non-contiguous amino acid deletions relative to SEQ ID NO: 162, SEQ ID NO: 163 or SEQ ID NO: 164. In still other aspects of this embodiment, a melanocyte stimulating hormone binding domain comprises a polypeptide having, e.g., at least one, two, three, four or five non-contiguous amino acid additions relative to SEQ ID NO: 162, SEQ ID NO: 163 or SEQ ID NO: 164. In yet other aspects of this embodiment, a melanocyte stimulating hormone binding domain comprises a polypeptide having, e.g., at most one, two, three, four or five non-contiguous amino acid additions relative to SEQ ID NO: 162, SEQ ID NO: 163 or SEQ ID NO: 164.

In other aspects of this embodiment, a melanocyte stimulating hormone binding domain comprises a polypeptide having, e.g., at least one, two, three, four or five contiguous amino acid substitutions relative to SEQ ID NO: 162, SEQ ID NO: 163 or SEQ ID NO: 164. In other aspects of this embodiment, a melanocyte stimulating hormone binding domain comprises a polypeptide having, e.g., at most one, two, three, four or five contiguous amino acid substitutions relative to SEQ ID NO: 162, SEQ ID NO: 163 or SEQ ID NO: 164. In yet other aspects of this embodiment, a melanocyte stimulating hormone binding domain comprises a polypeptide having, e.g., at least one, two, three, four or five contiguous amino acid deletions relative to SEQ ID NO: 162, SEQ ID NO: 163 or SEQ ID NO: 164. In yet other aspects of this embodiment, a melanocyte stimulating hormone binding domain comprises a polypeptide having, e.g., at most one, two, three, four or five contiguous amino acid deletions relative to SEQ ID NO: 162, SEQ ID NO: 163 or SEQ ID NO: 164. In still other aspects of this embodiment, a melanocyte stimulating hormone binding domain comprises a polypeptide having, e.g., at least one, two, three, four or five contiguous amino acid additions relative to SEQ ID NO: 162, SEQ ID NO: 163 or SEQ ID NO: 164. In yet other aspects of this embodiment, a melanocyte stimulating hormone binding domain comprises a polypeptide having, e.g., at most one, two, three, four or five contiguous amino acid additions relative to SEQ ID NO: 162, SEQ ID NO: 163 or SEQ ID NO: 164.

In another embodiment, a melanocortin peptide binding domain comprises an adrenocorticotropin. In another embodiment, a melanocortin peptide binding domain is derived from an adrenocorticotropin. In aspects of this embodiment, an adrenocorticotropin binding domain comprises an adrenocorticotropin (ACTH) or a Corticotropin-like intermediary peptide (CLIP). In other aspects of this embodiment, an adrenocorticotropin binding domain comprises SEQ ID NO: 165 or SEQ ID NO: 166.

In other aspects of this embodiment, an adrenocorticotropin binding domain comprises a polypeptide having, e.g., at least 70% amino acid identity with SEQ ID NO: 165 or SEQ ID NO: 166, at least 75% amino acid identity with SEQ ID NO: 165 or SEQ ID NO: 166, at least 80% amino acid identity with SEQ ID NO: 165 or SEQ ID NO: 166, at least 85% amino acid identity with SEQ ID NO: 165 or SEQ ID NO: 166, at least 90% amino acid identity with SEQ ID NO: 165 or SEQ ID NO: 166 or at least 95% amino acid identity with SEQ ID NO: 165 or SEQ ID NO: 166. In yet other aspects of this embodiment, an adrenocorticotropin binding domain comprises a polypeptide having, e.g., at most 70% amino acid identity with SEQ ID NO: 165 or SEQ ID NO: 166, at most 75% amino acid identity with SEQ ID NO: 165 or SEQ ID NO: 166, at most 80% amino acid identity with SEQ ID NO: 165 or SEQ ID NO: 166, at most 85% amino acid identity with SEQ ID NO: 165 or SEQ ID NO: 166, at most 90% amino acid identity with SEQ ID NO: 165 or SEQ ID NO: 166 or at most 95% amino acid identity with SEQ ID NO: 165 or SEQ ID NO: 166.

In other aspects of this embodiment, an adrenocorticotropin binding domain comprises a polypeptide having, e.g., at least one, two, three, four or five non-contiguous amino acid substitutions relative to SEQ ID NO: 165 or SEQ ID NO: 166. In other aspects of this embodiment, an adrenocorticotropin binding domain comprises a polypeptide having, e.g., at most one, two, three, four or five non-contiguous amino acid substitutions relative to SEQ ID NO: 165 or SEQ ID NO: 166. In yet other aspects of this embodiment, an adrenocorticotropin binding domain comprises a polypeptide having, e.g., at least one, two, three, four or five non-contiguous amino acid deletions relative to SEQ ID NO: 165 or SEQ ID NO: 166. In yet other aspects of this embodiment, an adrenocorticotropin binding domain comprises a polypeptide having, e.g., at most one, two, three, four or five non-contiguous amino acid deletions relative to SEQ ID NO: 165 or SEQ ID NO: 166. In still other aspects of this embodiment, an adrenocorticotropin binding domain comprises a polypeptide having, e.g., at least one, two, three, four or five non-contiguous amino acid additions relative to SEQ ID NO: 165 or SEQ ID NO: 166. In yet other aspects of this embodiment, an adrenocorticotropin binding domain comprises a polypeptide having, e.g., at most one, two, three, four or five non-contiguous amino acid additions relative to SEQ ID NO: 165 or SEQ ID NO: 166.

In other aspects of this embodiment, an adrenocorticotropin binding domain comprises a polypeptide having, e.g., at least one, two, three, four or five contiguous amino acid substitutions relative to SEQ ID NO: 165 or SEQ ID NO: 166. In other aspects of this embodiment, an adrenocorticotropin binding domain comprises a polypeptide having, e.g., at most one, two, three, four or five contiguous amino acid substitutions relative to SEQ ID NO: 165 or SEQ ID NO: 166. In yet other aspects of this embodiment, an adrenocorticotropin binding domain comprises a polypeptide having, e.g., at least one, two, three, four or five contiguous amino acid deletions relative to SEQ ID NO: 165 or SEQ ID NO: 166. In yet other aspects of this embodiment, an adrenocorticotropin binding domain comprises a polypeptide having, e.g., at most one, two, three, four or five contiguous amino acid deletions relative to SEQ ID NO: 165 or SEQ ID NO: 166. In still other aspects of this embodiment, an adrenocorticotropin binding domain comprises a polypeptide having, e.g., at least one, two, three, four or five contiguous amino acid additions relative to SEQ ID NO: 165 or SEQ ID NO: 166. In yet other aspects of this embodiment, an adrenocorticotropin binding domain comprises a polypeptide having, e.g., at most one, two, three, four or five contiguous amino acid additions relative to SEQ ID NO: 165 or SEQ ID NO: 166.

In another embodiment, a melanocortin peptide binding domain comprises a lipotropin. In another embodiment, a melanocortin peptide binding domain is derived from a lipotropin. In aspects of this embodiment, a lipotropin binding domain comprises a β-lipotropin (β-LPH) or a γ-lipotropin (γ-LPH). In other aspects of this embodiment, a lipotropin binding domain comprises SEQ ID NO: 167 or SEQ ID NO: 168.

In other aspects of this embodiment, a lipotropin binding domain comprises a polypeptide having, e.g., at least 70% amino acid identity with SEQ ID NO: 167 or SEQ ID NO: 168, at least 75% amino acid identity with SEQ ID NO: 167 or SEQ ID NO: 168, at least 80% amino acid identity with SEQ ID NO: 167 or SEQ ID NO: 168, at least 85% amino acid identity with SEQ ID NO: 167 or SEQ ID NO: 168, at least 90% amino acid identity with SEQ ID NO: 167 or SEQ ID NO: 168 or at least 95% amino acid identity with SEQ ID NO: 167 or SEQ ID NO: 168. In yet other aspects of this embodiment, a lipotropin binding domain comprises a polypeptide having, e.g., at most 70% amino acid identity with SEQ ID NO: 167 or SEQ ID NO: 168, at most 75% amino acid identity with SEQ ID NO: 167 or SEQ ID NO: 168, at most 80% amino acid identity with SEQ ID NO: 167 or SEQ ID NO: 168, at most 85% amino acid identity with SEQ ID NO: 167 or SEQ ID NO: 168, at most 90% amino acid identity with SEQ ID NO: 167 or SEQ ID NO: 168 or at most 95% amino acid identity with SEQ ID NO: 167 or SEQ ID NO: 168.

In other aspects of this embodiment, a lipotropin binding domain comprises a polypeptide having, e.g., at least one, two, three, four, five, six, seven, eight, nine or ten non-contiguous amino acid substitutions relative to SEQ ID NO: 167 or SEQ ID NO: 168. In other aspects of this embodiment, a lipotropin binding domain comprises a polypeptide having, e.g., at most one, two, three, four, five, six, seven, eight, nine or ten non-contiguous amino acid substitutions relative to SEQ ID NO: 167 or SEQ ID NO: 168. In yet other aspects of this embodiment, a lipotropin binding domain comprises a polypeptide having, e.g., at least one, two, three, four, five, six, seven, eight, nine or ten non-contiguous amino acid deletions relative to SEQ ID NO: 167 or SEQ ID NO: 168. In yet other aspects of this embodiment, a lipotropin binding domain comprises a polypeptide having, e.g., at most one, two, three, four, five, six, seven, eight, nine or ten non-contiguous amino acid deletions relative to SEQ ID NO: 167 or SEQ ID NO: 168. In still other aspects of this embodiment, a lipotropin binding domain comprises a polypeptide having, e.g., at least one, two, three, four, five, six, seven, eight, nine or ten non-contiguous amino acid additions relative to SEQ ID NO: 167 or SEQ ID NO: 168. In yet other aspects of this embodiment, a lipotropin binding domain comprises a polypeptide having, e.g., at most one, two, three, four, five, six, seven, eight, nine or ten non-contiguous amino acid additions relative to SEQ ID NO: 167 or SEQ ID NO: 168.

In other aspects of this embodiment, a lipotropin binding domain comprises a polypeptide having, e.g., at least one, two, three, four, five, six, seven, eight, nine or ten contiguous amino acid substitutions relative to SEQ ID NO: 167 or SEQ ID NO: 168. In other aspects of this embodiment, a lipotropin binding domain comprises a polypeptide having, e.g., at most one, two, three, four, five, six, seven, eight, nine or ten contiguous amino acid substitutions relative to SEQ ID NO: 167 or SEQ ID NO: 168. In yet other aspects of this embodiment, a lipotropin binding domain comprises a polypeptide having, e.g., at least one, two, three, four, five, six, seven, eight, nine or ten contiguous amino acid deletions relative to SEQ ID NO: 167 or SEQ ID NO: 168. In yet other aspects of this embodiment, a lipotropin binding domain comprises a polypeptide having, e.g., at most one, two, three, four, five, six, seven, eight, nine or ten contiguous amino acid deletions relative to SEQ ID NO: 167 or SEQ ID NO: 168. In still other aspects of this embodiment, a lipotropin binding domain comprises a polypeptide having, e.g., at least one, two, three, four, five, six, seven, eight, nine or ten contiguous amino acid additions relative to SEQ ID NO: 167 or SEQ ID NO: 168. In yet other aspects of this embodiment, a lipotropin binding domain comprises a polypeptide having, e.g., at most one, two, three, four, five, six, seven, eight, nine or ten contiguous amino acid additions relative to SEQ ID NO: 167 or SEQ ID NO: 168.

In another embodiment, a melanocortin peptide binding domain comprises a neuropeptide derived from a melanocortin peptide. In another embodiment, a melanocortin peptide binding domain is derived from a neuropeptide derived from a melanocortin peptide. In aspects of this embodiment, a melanocortin peptide derived neuropeptide binding domain comprises SEQ ID NO: 169, SEQ ID NO: 170 or SEQ ID NO: 171.

In other aspects of this embodiment, a melanocortin peptide derived neuropeptide binding domain comprises a polypeptide having, e.g., at least 70% amino acid identity with SEQ ID NO: 169, SEQ ID NO: 170 or SEQ ID NO: 171, at least 75% amino acid identity with SEQ ID NO: 169, SEQ ID NO: 170 or SEQ ID NO: 171, at least 80% amino acid identity with SEQ ID NO: 169, SEQ ID NO: 170 or SEQ ID NO: 171, at least 85% amino acid identity with SEQ ID NO: 169, SEQ ID NO: 170 or SEQ ID NO: 171, at least 90% amino acid identity with SEQ ID NO: 169, SEQ ID NO: 170 or SEQ ID NO: 171 or at least 95% amino acid identity with SEQ ID NO: 169, SEQ ID NO: 170 or SEQ ID NO: 171. In yet other aspects of this embodiment, a melanocortin peptide derived neuropeptide binding domain comprises a polypeptide having, e.g., at most 70% amino acid identity with SEQ ID NO: 169, SEQ ID NO: 170 or SEQ ID NO: 171, at most 75% amino acid identity with SEQ ID NO: 169, SEQ ID NO: 170 or SEQ ID NO: 171, at most 80% amino acid identity with SEQ ID NO: 169, SEQ ID NO: 170 or SEQ ID NO: 171, at most 85% amino acid identity with SEQ ID NO: 169, SEQ ID NO: 170 or SEQ ID NO: 171, at most 90% amino acid identity with SEQ ID NO: 169, SEQ ID NO: 170 or SEQ ID NO: 171 or at most 95% amino acid identity with SEQ ID NO: 169, SEQ ID NO: 170 or SEQ ID NO: 171.

In other aspects of this embodiment, a melanocortin peptide derived neuropeptide binding domain comprises a polypeptide having, e.g., at least one, two, three, four, five, six, seven, eight, nine or ten non-contiguous amino acid substitutions relative to SEQ ID NO: 169, SEQ ID NO: 170 or SEQ ID NO: 171. In other aspects of this embodiment, a melanocortin peptide derived neuropeptide binding domain comprises a polypeptide having, e.g., at most one, two, three, four, five, six, seven, eight, nine or ten non-contiguous amino acid substitutions relative to SEQ ID NO: 169, SEQ ID NO: 170 or SEQ ID NO: 171. In yet other aspects of this embodiment, a melanocortin peptide derived neuropeptide binding domain comprises a polypeptide having, e.g., at least one, two, three, four, five, six, seven, eight, nine or ten non-contiguous amino acid deletions relative to SEQ ID NO: 169, SEQ ID NO: 170 or SEQ ID NO: 171. In yet other aspects of this embodiment, a melanocortin peptide derived neuropeptide binding domain comprises a polypeptide having, e.g., at most one, two, three, four, five, six, seven, eight, nine or ten non-contiguous amino acid deletions relative to SEQ ID NO: 169, SEQ ID NO: 170 or SEQ ID NO: 171. In still other aspects of this embodiment, a melanocortin peptide derived neuropeptide binding domain comprises a polypeptide having, e.g., at least one, two, three, four, five, six, seven, eight, nine or ten non-contiguous amino acid additions relative to SEQ ID NO: 169, SEQ ID NO: 170 or SEQ ID NO: 171. In yet other aspects of this embodiment, a melanocortin peptide derived neuropeptide binding domain comprises a polypeptide having, e.g., at most one, two, three, four, five, six, seven, eight, nine or ten non-contiguous amino acid additions relative to SEQ ID NO: 169, SEQ ID NO: 170 or SEQ ID NO: 171.

In other aspects of this embodiment, a melanocortin peptide derived neuropeptide binding domain comprises a polypeptide having, e.g., at least one, two, three, four, five, six, seven, eight, nine or ten contiguous amino acid substitutions relative to SEQ ID NO: 169, SEQ ID NO: 170 or SEQ ID NO: 171. In other aspects of this embodiment, a melanocortin peptide derived neuropeptide binding domain comprises a polypeptide having, e.g., at most one, two, three, four, five, six, seven, eight, nine or ten contiguous amino acid substitutions relative to SEQ ID NO: 169, SEQ ID NO: 170 or SEQ ID NO: 171. In yet other aspects of this embodiment, a melanocortin peptide derived neuropeptide binding domain comprises a polypeptide having, e.g., at least one, two, three, four, five, six, seven, eight, nine or ten contiguous amino acid deletions relative to SEQ ID NO: 169, SEQ ID NO: 170 or SEQ ID NO: 171. In yet other aspects of this embodiment, a melanocortin peptide derived neuropeptide binding domain comprises a polypeptide having, e.g., at most one, two, three, four, five, six, seven, eight, nine or ten contiguous amino acid deletions relative to SEQ ID NO: 169, SEQ ID NO: 170 or SEQ ID NO: 171. In still other aspects of this embodiment, a melanocortin peptide derived neuropeptide binding domain comprises a polypeptide having, e.g., at least one, two, three, four, five, six, seven, eight, nine or ten contiguous amino acid additions relative to SEQ ID NO: 169, SEQ ID NO: 170 or SEQ ID NO: 171. In yet other aspects of this embodiment, a melanocortin peptide derived neuropeptide binding domain comprises a polypeptide having, e.g., at most one, two, three, four, five, six, seven, eight, nine or ten contiguous amino acid additions relative to SEQ ID NO: 169, SEQ ID NO: 170 or SEQ ID NO: 171.

In another embodiment, a binding domain comprises a galanin. In another embodiment, a binding domain is derived from a galanin. In aspects of this embodiment, a galanin binding domain comprises a galanin or a galanin message-associated peptide (GMAP). In other aspects of this embodiment, a galanin binding domain comprises SEQ ID NO: 172 or SEQ ID NO: 173.

In other aspects of this embodiment, a galanin binding domain comprises a polypeptide having, e.g., at least 70% amino acid identity with SEQ ID NO: 172 or SEQ ID NO: 173, at least 75% amino acid identity with SEQ ID NO: 172 or SEQ ID NO: 173, at least 80% amino acid identity with SEQ ID NO: 172 or SEQ ID NO: 173, at least 85% amino acid identity with SEQ ID NO: 172 or SEQ ID NO: 173, at least 90% amino acid identity with SEQ ID NO: 172 or SEQ ID NO: 173 or at least 95% amino acid identity with SEQ ID NO: 172 or SEQ ID NO: 173. In yet other aspects of this embodiment, a galanin binding domain comprises a polypeptide having, e.g., at most 70% amino acid identity with SEQ ID NO: 172 or SEQ ID NO: 173, at most 75% amino acid identity with SEQ ID NO: 172 or SEQ ID NO: 173, at most 80% amino acid identity with SEQ ID NO: 172 or SEQ ID NO: 173, at most 85% amino acid identity with SEQ ID NO: 172 or SEQ ID NO: 173, at most 90% amino acid identity with SEQ ID NO: 172 or SEQ ID NO: 173 or at most 95% amino acid identity with SEQ ID NO: 172 or SEQ ID NO: 173.

In other aspects of this embodiment, a galanin binding domain comprises a polypeptide having, e.g., at least one, two, three, four, five, six, seven, eight, nine or ten non-contiguous amino acid substitutions relative to SEQ ID NO: 172 or SEQ ID NO: 173. In other aspects of this embodiment, a galanin binding domain comprises a polypeptide having, e.g., at most one, two, three, four, five, six, seven, eight, nine or ten non-contiguous amino acid substitutions relative to SEQ ID NO: 172 or SEQ ID NO: 173. In yet other aspects of this embodiment, a galanin binding domain comprises a polypeptide having, e.g., at least one, two, three, four, five, six, seven, eight, nine or ten non-contiguous amino acid deletions relative to SEQ ID NO: 172 or SEQ ID NO: 173. In yet other aspects of this embodiment, a galanin binding domain comprises a polypeptide having, e.g., at most one, two, three, four, five, six, seven, eight, nine or ten non-contiguous amino acid deletions relative to SEQ ID NO: 172 or SEQ ID NO: 173. In still other aspects of this embodiment, a galanin binding domain comprises a polypeptide having, e.g., at least one, two, three, four, five, six, seven, eight, nine or ten non-contiguous amino acid additions relative to SEQ ID NO: 172 or SEQ ID NO: 173. In yet other aspects of this embodiment, a galanin binding domain comprises a polypeptide having, e.g., at most one, two, three, four, five, six, seven, eight, nine or ten non-contiguous amino acid additions relative to SEQ ID NO: 172 or SEQ ID NO: 173.

In other aspects of this embodiment, a galanin binding domain comprises a polypeptide having, e.g., at least one, two, three, four, five, six, seven, eight, nine or ten contiguous amino acid substitutions relative to SEQ ID NO: 172 or SEQ ID NO: 173. In other aspects of this embodiment, a galanin binding domain comprises a polypeptide having, e.g., at most one, two, three, four, five, six, seven, eight, nine or ten contiguous amino acid substitutions relative to SEQ ID NO: 172 or SEQ ID NO: 173. In yet other aspects of this embodiment, a galanin binding domain comprises a polypeptide having, e.g., at least one, two, three, four, five, six, seven, eight, nine or ten contiguous amino acid deletions relative to SEQ ID NO: 172 or SEQ ID NO: 173. In yet other aspects of this embodiment, a galanin binding domain comprises a polypeptide having, e.g., at most one, two, three, four, five, six, seven, eight, nine or ten contiguous amino acid deletions relative to SEQ ID NO: 172 or SEQ ID NO: 173. In still other aspects of this embodiment, a galanin binding domain comprises a polypeptide having, e.g., at least one, two, three, four, five, six, seven, eight, nine or ten contiguous amino acid additions relative to SEQ ID NO: 172 or SEQ ID NO: 173. In yet other aspects of this embodiment, a galanin binding domain comprises a polypeptide having, e.g., at most one, two, three, four, five, six, seven, eight, nine or ten contiguous amino acid additions relative to SEQ ID NO: 172 or SEQ ID NO: 173.

Another example of a binding domain disclosed in the present specification is, e.g., a granin peptide, such as, e.g., a chromogranin A, a chromogranin B (secretogranin 1) or a chromogranin C (secretogranin II). Thus, in an embodiment, a binding domain comprises a granin peptide. In another embodiment, a binding domain is derived from a granin peptide.

In another embodiment, a granin peptide binding domain comprises a chromogranin A peptide. In another embodiment, a granin peptide binding domain is derived from a chromogranin A peptide. In aspects of this embodiment, a chromogranin A peptide binding domain comprises a β-granin, a vasostatin, a chromostatin, a pancreastatin, a WE-14, a catestatin, a parastatin or a GE-25. In other aspects of this embodiment, a chromogranin A peptide binding domain comprises SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181.

In other aspects of this embodiment, a chromogranin A peptide binding domain comprises a polypeptide having, e.g., at least 70% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181, at least 75% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181, at least 80% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181, at least 85% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181, at least 90% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181 or at least 95% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In yet other aspects of this embodiment, a chromogranin A peptide binding domain comprises a polypeptide having, e.g., at most 70% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181, at most 75% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181, at most 80% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181, at most 85% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181, at most 90% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181 or at most 95% amino acid identity with SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181.

In other aspects of this embodiment, a chromogranin A peptide binding domain comprises a polypeptide having, e.g., at least one, two, three, four, five, six, seven, eight, nine or ten non-contiguous amino acid substitutions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In other aspects of this embodiment, a chromogranin A peptide binding domain comprises a polypeptide having, e.g., at most one, two, three, four, five, six, seven, eight, nine or ten non-contiguous amino acid substitutions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In yet other aspects of this embodiment, a chromogranin A peptide binding domain comprises a polypeptide having, e.g., at least one, two, three, four, five, six, seven, eight, nine or ten non-contiguous amino acid deletions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In yet other aspects of this embodiment, a chromogranin A peptide binding domain comprises a polypeptide having, e.g., at most one, two, three, four, five, six, seven, eight, nine or ten non-contiguous amino acid deletions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In still other aspects of this embodiment, a chromogranin A peptide binding domain comprises a polypeptide having, e.g., at least one, two, three, four, five, six, seven, eight, nine or ten non-contiguous amino acid additions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In yet other aspects of this embodiment, a chromogranin A peptide binding domain comprises a polypeptide having, e.g., at most one, two, three, four, five, six, seven, eight, nine or ten non-contiguous amino acid additions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181.

In other aspects of this embodiment, a chromogranin A peptide binding domain comprises a polypeptide having, e.g., at least one, two, three, four, five, six, seven, eight, nine or ten contiguous amino acid substitutions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In other aspects of this embodiment, a chromogranin A peptide binding domain comprises a polypeptide having, e.g., at most one, two, three, four, five, six, seven, eight, nine or ten contiguous amino acid substitutions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In yet other aspects of this embodiment, a chromogranin A peptide binding domain comprises a polypeptide having, e.g., at least one, two, three, four, five, six, seven, eight, nine or ten contiguous amino acid deletions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In yet other aspects of this embodiment, a chromogranin A peptide binding domain comprises a polypeptide having, e.g., at most one, two, three, four, five, six, seven, eight, nine or ten contiguous amino acid deletions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In still other aspects of this embodiment, a chromogranin A peptide binding domain comprises a polypeptide having, e.g., at least one, two, three, four, five, six, seven, eight, nine or ten contiguous amino acid additions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181. In yet other aspects of this embodiment, a chromogranin A peptide binding domain comprises a polypeptide having, e.g., at most one, two, three, four, five, six, seven, eight, nine or ten contiguous amino acid additions relative to SEQ ID NO: 174, SEQ ID NO: 175, SEQ ID NO: 176, SEQ ID NO: 177, SEQ ID NO: 178, SEQ ID NO: 179, SEQ ID NO: 180 or SEQ ID NO: 181.

In another embodiment, a granin peptide binding domain comprises a chromogranin B peptide. In another embodiment, a granin peptide binding domain is derived from a chromogranin B peptide. In aspects of this embodiment, a chromogranin B peptide binding domain comprises a GAWK peptide, an adrenomedullary peptide or a secretolytin. In other aspects of this embodiment, a chromogranin B peptide binding domain comprises SEQ ID NO: 182, SEQ ID NO: 183, SEQ ID NO: 184, SEQ ID NO: 185 or SEQ ID NO: 186.

In other aspects of this embodiment, a chromogranin B peptide binding domain comprises a polypeptide having, e.g., at least 70% amino acid identity with SEQ ID NO: 182, SEQ ID NO: 183, SEQ ID NO: 184, SEQ ID NO: 185 or SEQ ID NO: 186, at least 75% amino acid identity with SEQ ID NO: 182, SEQ ID NO: 183, SEQ ID NO: 184, SEQ ID NO: 185 or SEQ ID NO: 186, at least 80% amino acid identity with SEQ ID NO: 182, SEQ ID NO: 183, SEQ ID NO: 184, SEQ ID NO: 185 or SEQ ID NO: 186, at least 85% amino acid identity with SEQ ID NO: 182, SEQ ID NO: 183, SEQ ID NO: 184, SEQ ID NO: 185 or SEQ ID NO: 186, at least 90% amino acid identity with SEQ ID NO: 182, SEQ ID NO: 183, SEQ ID NO: 184, SEQ ID NO: 185 or SEQ ID NO: 186 or at least 95% amino acid identity with SEQ ID NO: 182, SEQ ID NO: 183, SEQ ID NO: 184, SEQ ID NO: 185 or SEQ ID NO: 186. In yet other aspects of this embodiment, a chromogranin B peptide binding domain comprises a polypeptide having, e.g., at most 70% amino acid identity with SEQ ID NO: 182, SEQ ID NO: 183, SEQ ID NO: 184, SEQ ID NO: 185 or SEQ ID NO: 186, at most 75% amino acid identity with SEQ ID NO: 182, SEQ ID NO: 183, SEQ ID NO: 184, SEQ ID NO: 185 or SEQ ID NO: 186, at most 80% amino acid identity with SEQ ID NO: 182, SEQ ID NO: 183, SEQ ID NO: 184, SEQ ID NO: 185 or SEQ ID NO: 186, at most 85% amino acid identity with SEQ ID NO: 182, SEQ ID NO: 183, SEQ ID NO: 184, SEQ ID NO: 185 or SEQ ID NO: 186, at most 90% amino acid identity with SEQ ID NO: 182, SEQ ID NO: 183, SEQ ID NO: 184, SEQ ID NO: 185 or SEQ ID NO: 186 or at most 95% amino acid identity with SEQ ID NO: 182, SEQ ID NO: 183, SEQ ID NO: 184, SEQ ID NO: 185 or SEQ ID NO: 186.

In other aspects of this embodiment, a chromogranin B peptide binding domain comprises a polypeptide having, e.g., at least one, two, three, four, five, six, seven, eight, nine or ten non-contiguous amino acid substitutions relative to SEQ ID NO: 182, SEQ ID NO: 183, SEQ ID NO: 184, SEQ ID NO: 185 or SEQ ID NO: 186. In other aspects of this embodiment, a chromogranin B peptide binding domain comprises a polypeptide having, e.g., at most one, two, three, four, five, six, seven, eight, nine or ten non-contiguous amino acid substitutions relative to SEQ ID NO: 182, SEQ ID NO: 183, SEQ ID NO: 184, SEQ ID NO: 185 or SEQ ID NO: 186. In yet other aspects of this embodiment, a chromogranin B peptide binding domain comprises a polypeptide having, e.g., at least one, two, three, four, five, six, seven, eight, nine or ten non-contiguous amino acid deletions relative to SEQ ID NO: 182, SEQ ID NO: 183, SEQ ID NO: 184, SEQ ID NO: 185 or SEQ ID NO: 186. In yet other aspects of this embodiment, a chromogranin B peptide binding domain comprises a polypeptide having, e.g., at most one, two, three, four, five, six, seven, eight, nine or ten non-contiguous amino acid deletions relative to SEQ ID NO: 182, SEQ ID NO: 183, SEQ ID NO: 184, SEQ ID NO: 185 or SEQ ID NO: 186. In still other aspects of this embodiment, a chromogranin B peptide binding domain comprises a polypeptide having, e.g., at least one, two, three, four, five, six, seven, eight, nine or ten non-contiguous amino acid additions relative to SEQ ID NO: 182, SEQ ID NO: 183, SEQ ID NO: 184, SEQ ID NO: 185 or SEQ ID NO: 186. In yet other aspects of this embodiment, a chromogranin B peptide binding domain comprises a polypeptide having, e.g., at most one, two, three, four, five, six, seven, eight, nine or ten non-contiguous amino acid additions relative to SEQ ID NO: 182, SEQ ID NO: 183, SEQ ID NO: 184, SEQ ID NO: 185 or SEQ ID NO: 186.

In other aspects of this embodiment, a chromogranin B peptide binding domain comprises a polypeptide having, e.g., at least one, two, three, four, five, six, seven, eight, nine or ten contiguous amino acid substitutions relative to SEQ ID NO: 182, SEQ ID NO: 183, SEQ ID NO: 184, SEQ ID NO: 185 or SEQ ID NO: 186. In other aspects of this embodiment, a chromogranin B peptide binding domain comprises a polypeptide having, e.g., at most one, two, three, four, five, six, seven, eight, nine or ten contiguous amino acid substitutions relative to SEQ ID NO: 182, SEQ ID NO: 183, SEQ ID NO: 184, SEQ ID NO: 185 or SEQ ID NO: 186. In yet other aspects of this embodiment, a chromogranin B peptide binding domain comprises a polypeptide having, e.g., at least one, two, three, four, five, six, seven, eight, nine or ten contiguous amino acid deletions relative to SEQ ID NO: 182, SEQ ID NO: 183, SEQ ID NO: 184, SEQ ID NO: 185 or SEQ ID NO: 186. In yet other aspects of this embodiment, a chromogranin B peptide binding domain comprises a polypeptide having, e.g., at most one, two, three, four, five, six, seven, eight, nine or ten contiguous amino acid deletions relative to SEQ ID NO: 182, SEQ ID NO: 183, SEQ ID NO: 184, SEQ ID NO: 185 or SEQ ID NO: 186. In still other aspects of this embodiment, a chromogranin B peptide binding domain comprises a polypeptide having, e.g., at least one, two, three, four, five, six, seven, eight, nine or ten contiguous amino acid additions relative to SEQ ID NO: 182, SEQ ID NO: 183, SEQ ID NO: 184, SEQ ID NO: 185 or SEQ ID NO: 186. In yet other aspects of this embodiment, a chromogranin B peptide binding domain comprises a polypeptide having, e.g., at most one, two, three, four, five, six, seven, eight, nine or ten contiguous amino acid additions relative to SEQ ID NO: 182, SEQ ID NO: 183, SEQ ID NO: 184, SEQ ID NO: 185 or SEQ ID NO: 186.

In another embodiment, a granin peptide binding domain comprises a chromogranin C peptide. In another embodiment, a granin peptide binding domain is derived from a chromogranin C peptide. In aspects of this embodiment, a chromogranin C peptide binding domain comprises a secretoneurin. In other aspects of this embodiment, a chromogranin C peptide binding domain comprises SEQ ID NO: 187.

In other aspects of this embodiment, a chromogranin C peptide binding domain comprises a polypeptide having, e.g., at least 70% amino acid identity with SEQ ID NO: 187, at least 75% amino acid identity with SEQ ID NO: 187, at least 80% amino acid identity with SEQ ID NO: 187, at least 85% amino acid identity with SEQ ID NO: 187, at least 90% amino acid identity with SEQ ID NO: 187 or at least 95% amino acid identity with SEQ ID NO: 187. In yet other aspects of this embodiment, a chromogranin C peptide binding domain comprises a polypeptide having, e.g., at most 70% amino acid identity with SEQ ID NO: 187, at most 75% amino acid identity with SEQ ID NO: 187, at most 80% amino acid identity with SEQ ID NO: 187, at most 85% amino acid identity with SEQ ID NO: 187, at most 90% amino acid identity with SEQ ID NO: 187 or at most 95% amino acid identity with SEQ ID NO: 187.

In other aspects of this embodiment, a chromogranin C peptide binding domain comprises a polypeptide having, e.g., at least one, two, three, four, five, six, seven, eight, nine or ten non-contiguous amino acid substitutions relative to SEQ ID NO: 187. In other aspects of this embodiment, a chromogranin C peptide binding domain comprises a polypeptide having, e.g., at most one, two, three, four, five, six, seven, eight, nine or ten non-contiguous amino acid substitutions relative to SEQ ID NO: 187. In yet other aspects of this embodiment, a chromogranin C peptide binding domain comprises a polypeptide having, e.g., at least one, two, three, four, five, six, seven, eight, nine or ten non-contiguous amino acid deletions relative to SEQ ID NO: 187. In yet other aspects of this embodiment, a chromogranin C peptide binding domain comprises a polypeptide having, e.g., at most one, two, three, four, five, six, seven, eight, nine or ten non-contiguous amino acid deletions relative to SEQ ID NO: 187. In still other aspects of this embodiment, a chromogranin C peptide binding domain comprises a polypeptide having, e.g., at least one, two, three, four, five, six, seven, eight, nine or ten non-contiguous amino acid additions relative to SEQ ID NO: 187. In yet other aspects of this embodiment, a chromogranin C peptide binding domain comprises a polypeptide having, e.g., at most one, two, three, four, five, six, seven, eight, nine or ten non-contiguous amino acid additions relative to SEQ ID NO: 187.

In other aspects of this embodiment, a chromogranin C peptide binding domain comprises a polypeptide having, e.g., at least one, two, three, four, five, six, seven, eight, nine or ten contiguous amino acid substitutions relative to SEQ ID NO: 187. In other aspects of this embodiment, a chromogranin C peptide binding domain comprises a polypeptide having, e.g., at most one, two, three, four, five, six, seven, eight, nine or ten contiguous amino acid substitutions relative to SEQ ID NO: 187. In yet other aspects of this embodiment, a chromogranin C peptide binding domain comprises a polypeptide having, e.g., at least one, two, three, four, five, six, seven, eight, nine or ten contiguous amino acid deletions relative to SEQ ID NO: 187. In yet other aspects of this embodiment, a chromogranin C peptide binding domain comprises a polypeptide having, e.g., at most one, two, three, four, five, six, seven, eight, nine or ten contiguous amino acid deletions relative to SEQ ID NO: 187. In still other aspects of this embodiment, a chromogranin C peptide binding domain comprises a polypeptide having, e.g., at least one, two, three, four, five, six, seven, eight, nine or ten contiguous amino acid additions relative to SEQ ID NO: 187. In yet other aspects of this embodiment, a chromogranin C peptide binding domain comprises a polypeptide having, e.g., at most one, two, three, four, five, six, seven, eight, nine or ten contiguous amino acid additions relative to SEQ ID NO: 187.

Another example of a binding domain disclosed in the present specification is, e.g., a tachykinin peptide, such as, e.g., a Substance P, a neuropeptide K (NPK), a neuropeptide gamma (NP gamma), a neurokinin A (NKA; Substance K, neurokinin alpha, neuromedin L), a neurokinin B (NKB), a hemokinin or a endokinin. Thus, in an embodiment, a binding domain comprises a tachykinin peptide. In an embodiment, a binding domain is derived from a tachykinin peptide.

In aspects of this embodiment, a tachykinin peptide binding domain comprises a Substance P, a neuropeptide K (NPK), a neuropeptide gamma (NP gamma), a neurokinin A (NKA; Substance K, neurokinin alpha, neuromedin L), a neurokinin B (NKB), a hemokinin or a endokinin. In aspects of this embodiment, a tachykinin peptide binding domain is derived from a Substance P, a neuropeptide K (NPK), a neuropeptide gamma (NP gamma), a neurokinin A (NKA; Substance K, neurokinin alpha, neuromedin L), a neurokinin B (NKB), a hemokinin or a endokinin. In other aspects of this embodiment, a tachykinin peptide binding domain comprises SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 or SEQ ID NO: 199.

In other aspects of this embodiment, a tachykinin peptide binding domain comprises a polypeptide having, e.g., at least 70% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199, at least 75% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199, at least 80% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199, at least 85% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199, at least 90% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199 or at least 95% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In yet other aspects of this embodiment, a tachykinin peptide binding domain comprises a polypeptide having, e.g., at most 70% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199, at most 75% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199, at most 80% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199, at most 85% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199, at most 90% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199 or at most 95% amino acid identity with SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199.

In other aspects of this embodiment, a tachykinin peptide binding domain comprises a polypeptide having, e.g., at least one, two, three, four or five non-contiguous amino acid substitutions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In other aspects of this embodiment, a tachykinin peptide binding domain comprises a polypeptide having, e.g., at most one, two, three, four or five non-contiguous amino acid substitutions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In yet other aspects of this embodiment, a tachykinin peptide binding domain comprises a polypeptide having, e.g., at least one, two, three, four or five non-contiguous amino acid deletions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In yet other aspects of this embodiment, a tachykinin peptide binding domain comprises a polypeptide having, e.g., at most one, two, three, four or five non-contiguous amino acid deletions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In still other aspects of this embodiment, a tachykinin peptide binding domain comprises a polypeptide having, e.g., at least one, two, three, four or five non-contiguous amino acid additions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In yet other aspects of this embodiment, a tachykinin peptide binding domain comprises a polypeptide having, e.g., at most one, two, three, four or five non-contiguous amino acid additions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199.

In other aspects of this embodiment, a tachykinin peptide binding domain comprises a polypeptide having, e.g., at least one, two, three, four or five contiguous amino acid substitutions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In other aspects of this embodiment, a tachykinin peptide binding domain comprises a polypeptide having, e.g., at most one, two, three, four or five contiguous amino acid substitutions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In yet other aspects of this embodiment, a tachykinin peptide binding domain comprises a polypeptide having, e.g., at least one, two, three, four or five contiguous amino acid deletions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In yet other aspects of this embodiment, a tachykinin peptide binding domain comprises a polypeptide having, e.g., at most one, two, three, four or five contiguous amino acid deletions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In still other aspects of this embodiment, a tachykinin peptide binding domain comprises a polypeptide having, e.g., at least one, two, three, four or five contiguous amino acid additions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199. In yet other aspects of this embodiment, a tachykinin peptide binding domain comprises a polypeptide having, e.g., at most one, two, three, four or five contiguous amino acid additions relative to SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 OR SEQ ID NO: 199.

Another example of a binding domain disclosed in the present specification is, e.g., a cholecystokinin peptide, such as, e.g., a cholecystokinin 58, a cholecystokinin 39, a cholecystokinin 33, a cholecystokinin 12 or a cholecystokinin 8. Thus, in an embodiment, a binding domain comprises a cholecystokinin peptide. In another embodiment, a binding domain is derived from a cholecystokinin peptide.

In aspects of this embodiment, a cholecystokinin peptide binding domain comprises a cholecystokinin 58, a cholecystokinin 39, a cholecystokinin 33, a cholecystokinin 12 or a cholecystokinin 8. In other aspects of this embodiment, a cholecystokinin peptide comprising a binding domain is SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In still other aspects of this embodiment, a cholecystokinin peptide binding domain comprises amino acids 20-58 of SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In yet other aspects of this embodiment, a cholecystokinin peptide binding domain comprises amino acids 26-58 of SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In still further other aspects of this embodiment, a cholecystokinin peptide binding domain comprises amino acids 47-58 of SEQ ID NO: 200, SEQ ID NO: 210 or SEQ ID NO: 214. In yet further aspects of this embodiment, a cholecystokinin peptide binding domain comprises amino acids 51-58 of SEQ ID NO: 200.

In other aspects of this embodiment, a cholecystokinin peptide binding domain comprises a polypeptide having, e.g., at least 70% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215, at least 75% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215, at least 80% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215, at least 85% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215, at least 90% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215 or at least 95% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In yet other aspects of this embodiment, a cholecystokinin peptide binding domain comprises a polypeptide having, e.g., at most 70% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215, at most 75% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215, at most 80% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215, at most 85% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215, at most 90% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215 or at most 95% amino acid identity with SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215.

In other aspects of this embodiment, a cholecystokinin peptide binding domain comprises a polypeptide having, e.g., at least one, two, three, four, five, six, seven, eight, nine or ten non-contiguous amino acid substitutions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In other aspects of this embodiment, a cholecystokinin peptide binding domain comprises a polypeptide having, e.g., at most one, two, three, four, five, six, seven, eight, nine or ten non-contiguous amino acid substitutions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In yet other aspects of this embodiment, a cholecystokinin peptide binding domain comprises a polypeptide having, e.g., at least one, two, three, four, five, six, seven, eight, nine or ten non-contiguous amino acid deletions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In yet other aspects of this embodiment, a cholecystokinin peptide binding domain comprises a polypeptide having, e.g., at most one, two, three, four, five, six, seven, eight, nine or ten non-contiguous amino acid deletions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In still other aspects of this embodiment, a cholecystokinin peptide binding domain comprises a polypeptide having, e.g., at least one, two, three, four, five, six, seven, eight, nine or ten non-contiguous amino acid additions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In yet other aspects of this embodiment, a cholecystokinin peptide binding domain comprises a polypeptide having, e.g., at most one, two, three, four, five, six, seven, eight, nine or ten non-contiguous amino acid additions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215.

In other aspects of this embodiment, a cholecystokinin peptide binding domain comprises a polypeptide having, e.g., at least one, two, three, four, five, six, seven, eight, nine or ten contiguous amino acid substitutions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In other aspects of this embodiment, a cholecystokinin peptide binding domain comprises a polypeptide having, e.g., at most one, two, three, four, five, six, seven, eight, nine or ten contiguous amino acid substitutions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In yet other aspects of this embodiment, a cholecystokinin peptide binding domain comprises a polypeptide having, e.g., at least one, two, three, four, five, six, seven, eight, nine or ten contiguous amino acid deletions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In yet other aspects of this embodiment, a cholecystokinin peptide binding domain comprises a polypeptide having, e.g., at most one, two, three, four, five, six, seven, eight, nine or ten contiguous amino acid deletions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In still other aspects of this embodiment, a cholecystokinin peptide binding domain comprises a polypeptide having, e.g., at least one, two, three, four, five, six, seven, eight, nine or ten contiguous amino acid additions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215. In yet other aspects of this embodiment, a cholecystokinin peptide binding domain comprises a polypeptide having, e.g., at most one, two, three, four, five, six, seven, eight, nine or ten contiguous amino acid additions relative to SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215.

In still other aspects of this embodiment, a cholecystokinin peptide binding domain comprises a polypeptide having, e.g., at least 70% amino acid identity with amino acids 20-58 of SEQ ID NO: 200 or amino acids 26-58 of SEQ ID NO: 200, at least 75% amino acid identity with amino acids 20-58 of SEQ ID NO: 200 or amino acids 26-58 of SEQ ID NO: 200, at least 80% amino acid identity with amino acids 20-58 of SEQ ID NO: 200 or amino acids 26-58 of SEQ ID NO: 200, at least 85% amino acid identity with amino acids 20-58 of SEQ ID NO: 200 or amino acids 26-58 of SEQ ID NO: 200, at least 90% amino acid identity with amino acids 20-58 of SEQ ID NO: 200 or amino acids 26-58 of SEQ ID NO: 200 or at least 95% amino acid identity with amino acids 20-58 of SEQ ID NO: 200 or amino acids 26-58 of SEQ ID NO: 200. In yet other aspects of this embodiment, a cholecystokinin peptide binding domain comprises a polypeptide having, e.g., at most 70% amino acid identity with amino acids 20-58 of SEQ ID NO: 200 or amino acids 26-58 of SEQ ID NO: 200, at most 75% amino acid identity with amino acids 20-58 of SEQ ID NO: 200 or amino acids 26-58 of SEQ ID NO: 200, at most 80% amino acid identity with amino acids 20-58 of SEQ ID NO: 200 or amino acids 26-58 of SEQ ID NO: 200, at most 85% amino acid identity with amino acids 20-58 of SEQ ID NO: 200 or amino acids 26-58 of SEQ ID NO: 200, at most 90% amino acid identity with amino acids 20-58 of SEQ ID NO: 200 or amino acids 26-58 of SEQ ID NO: 200 or at most 95% amino acid identity with amino acids 20-58 of SEQ ID NO: 200 or amino acids 26-58 of SEQ ID NO: 200.

In still other aspects of this embodiment, a cholecystokinin peptide binding domain comprises a polypeptide having, e.g., at least one, two, three, four, five, six, seven, eight, nine or ten non-contiguous amino acid substitutions relative to amino acids 20-58 of SEQ ID NO: 200 or amino acids 26-58 of SEQ ID NO: 200. In other aspects of this embodiment, a cholecystokinin peptide binding domain comprises a polypeptide having, e.g., at most one, two, three, four, five, six, seven, eight, nine or ten non-contiguous amino acid substitutions relative to amino acids 20-58 of SEQ ID NO: 200 or amino acids 26-58 of SEQ ID NO: 200. In yet other aspects of this embodiment, a cholecystokinin peptide binding domain comprises a polypeptide having, e.g., at least one, two, three, four, five, six, seven, eight, nine or ten non-contiguous amino acid deletions relative to amino acids 20-58 of SEQ ID NO: 200 or amino acids 26-58 of SEQ ID NO: 200. In yet other aspects of this embodiment, a cholecystokinin peptide binding domain comprises a polypeptide having, e.g., at most one, two, three, four, five, six, seven, eight, nine or ten non-contiguous amino acid deletions relative to amino acids 20-58 of SEQ ID NO: 200 or amino acids 26-58 of SEQ ID NO: 200. In still other aspects of this embodiment, a cholecystokinin peptide binding domain comprises a polypeptide having, e.g., at least one, two, three, four, five, six, seven, eight, nine or ten non-contiguous amino acid additions relative to amino acids 20-58 of SEQ ID NO: 200 or amino acids 26-58 of SEQ ID NO: 200. In yet other aspects of this embodiment, a cholecystokinin peptide binding domain comprises a polypeptide having, e.g., at most one, two, three, four, five, six, seven, eight, nine or ten non-contiguous amino acid additions relative to amino acids 20-58 of SEQ ID NO: 200 or amino acids 26-58 of SEQ ID NO: 200.

In still other aspects of this embodiment, a cholecystokinin peptide binding domain comprises a polypeptide having, e.g., at least one, two, three, four, five, six, seven, eight, nine or ten contiguous amino acid substitutions relative to amino acids 20-58 of SEQ ID NO: 200 or amino acids 26-58 of SEQ ID NO: 200. In other aspects of this embodiment, a cholecystokinin peptide binding domain comprises a polypeptide having, e.g., at most one, two, three, four, five, six, seven, eight, nine or ten contiguous amino acid substitutions relative to amino acids 20-58 of SEQ ID NO: 200 or amino acids 26-58 of SEQ ID NO: 200. In yet other aspects of this embodiment, a cholecystokinin peptide binding domain comprises a polypeptide having, e.g., at least one, two, three, four, five, six, seven, eight, nine or ten contiguous amino acid deletions relative to amino acids 20-58 of SEQ ID NO: 200 or amino acids 26-58 of SEQ ID NO: 200. In yet other aspects of this embodiment, a cholecystokinin peptide binding domain comprises a polypeptide having, e.g., at most one, two, three, four, five, six, seven, eight, nine or ten contiguous amino acid deletions relative to amino acids 20-58 of SEQ ID NO: 200 or amino acids 26-58 of SEQ ID NO: 200. In still other aspects of this embodiment, a cholecystokinin peptide binding domain comprises a polypeptide having, e.g., at least one, two, three, four, five, six, seven, eight, nine or ten contiguous amino acid additions relative to amino acids 20-58 of SEQ ID NO: 200 or amino acids 26-58 of SEQ ID NO: 200. In yet other aspects of this embodiment, a cholecystokinin peptide binding domain comprises a polypeptide having, e.g., at most one, two, three, four, five, six, seven, eight, nine or ten contiguous amino acid additions relative to amino acids 20-58 of SEQ ID NO: 200 or amino acids 26-58 of SEQ ID NO: 200.

In other aspects of this embodiment, a cholecystokinin peptide binding domain comprises a polypeptide having, e.g., at least 70% amino acid identity with amino acids 47-58 of SEQ ID NO: 200 or amino acids 51-58 of SEQ ID NO: 200, at least 75% amino acid identity with amino acids 47-58 of SEQ ID NO: 200 or amino acids 51-58 of SEQ ID NO: 200, at least 80% amino acid identity with amino acids 47-58 of SEQ ID NO: 200 or amino acids 51-58 of SEQ ID NO: 200, at least 85% amino acid identity with amino acids 47-58 of SEQ ID NO: 200 or amino acids 51-58 of SEQ ID NO: 200, at least 90% amino acid identity with amino acids 47-58 of SEQ ID NO: 200 or amino acids 51-58 of SEQ ID NO: 200 or at least 95% amino acid identity with amino acids 47-58 of SEQ ID NO: 200 or amino acids 51-58 of SEQ ID NO: 200. In yet other aspects of this embodiment, a cholecystokinin peptide binding domain comprises a polypeptide having, e.g., at most 70% amino acid identity with amino acids 47-58 of SEQ ID NO: 200 or amino acids 51-58 of SEQ ID NO: 200, at most 75% amino acid identity with amino acids 47-58 of SEQ ID NO: 200 or amino acids 51-58 of SEQ ID NO: 200, at most 80% amino acid identity with amino acids 47-58 of SEQ ID NO: 200 or amino acids 51-58 of SEQ ID NO: 200, at most 85% amino acid identity with amino acids 47-58 of SEQ ID NO: 200 or amino acids 51-58 of SEQ ID NO: 200, at most 90% amino acid identity with amino acids 47-58 of SEQ ID NO: 200 or amino acids 51-58 of SEQ ID NO: 200 or at most 95% amino acid identity with amino acids 47-58 of SEQ ID NO: 200 or amino acids 51-58 of SEQ ID NO: 200.

In other aspects of this embodiment, a cholecystokinin peptide binding domain comprises a polypeptide having, e.g., at least one, two, three or four non-contiguous amino acid substitutions relative to amino acids 47-58 of SEQ ID NO: 200 or amino acids 51-58 of SEQ ID NO: 200. In other aspects of this embodiment, a cholecystokinin peptide binding domain comprises a polypeptide having, e.g., at most one, two, three or four non-contiguous amino acid substitutions relative to amino acids 47-58 of SEQ ID NO: 200 or amino acids 51-58 of SEQ ID NO: 200. In yet other aspects of this embodiment, a cholecystokinin peptide binding domain comprises a polypeptide having, e.g., at least one, two, three or four non-contiguous amino acid deletions relative to amino acids 47-58 of SEQ ID NO: 200 or amino acids 51-58 of SEQ ID NO: 200. In yet other aspects of this embodiment, a cholecystokinin peptide binding domain comprises a polypeptide having, e.g., at most one, two, three or four non-contiguous amino acid deletions relative to amino acids 47-58 of SEQ ID NO: 200 or amino acids 51-58 of SEQ ID NO: 200. In still other aspects of this embodiment, a cholecystokinin peptide binding domain comprises a polypeptide having, e.g., at least one, two, three or four non-contiguous amino acid additions relative to amino acids 47-58 of SEQ ID NO: 200 or amino acids 51-58 of SEQ ID NO: 200. In yet other aspects of this embodiment, a cholecystokinin peptide binding domain comprises a polypeptide having, e.g., at most one, two, three or four non-contiguous amino acid additions relative to amino acids 47-58 of SEQ ID NO: 200 or amino acids 51-58 of SEQ ID NO: 200.

In other aspects of this embodiment, a cholecystokinin peptide binding domain comprises a polypeptide having, e.g., at least one, two, three or four contiguous amino acid substitutions relative to amino acids 47-58 of SEQ ID NO: 200 or amino acids 51-58 of SEQ ID NO: 200. In other aspects of this embodiment, a cholecystokinin peptide binding domain comprises a polypeptide having, e.g., at most one, two, three or four contiguous amino acid substitutions relative to amino acids 47-58 of SEQ ID NO: 200 or amino acids 51-58 of SEQ ID NO: 200. In yet other aspects of this embodiment, a cholecystokinin peptide binding domain comprises a polypeptide having, e.g., at least one, two, three or four contiguous amino acid deletions relative to amino acids 47-58 of SEQ ID NO: 200 or amino acids 51-58 of SEQ ID NO: 200. In yet other aspects of this embodiment, a cholecystokinin peptide binding domain comprises a polypeptide having, e.g., at most one, two, three or four contiguous amino acid deletions relative to amino acids 47-58 of SEQ ID NO: 200 or amino acids 51-58 of SEQ ID NO: 200. In still other aspects of this embodiment, a cholecystokinin peptide binding domain comprises a polypeptide having, e.g., at least one, two, three or four contiguous amino acid additions relative to amino acids 47-58 of SEQ ID NO: 200 or amino acids 51-58 of SEQ ID NO: 200. In yet other aspects of this embodiment, a cholecystokinin peptide binding domain comprises a polypeptide having, e.g., at most one, two, three or four contiguous amino acid additions relative to amino acids 47-58 of SEQ ID NO: 200 or amino acids 51-58 of SEQ ID NO: 200.

Another example of a binding domain disclosed in the present specification is, e.g., a Neuropeptide Y related peptide, such as, e.g., a Neuropeptide Y (NPY), a Peptide YY (PYY), Pancreatic peptide (PP) or a Pancreatic icosapeptide (PIP). Thus, in an embodiment, a binding domain comprises a Neuropeptide Y related peptide. In another embodiment, a binding domain is derived from a Neuropeptide Y related peptide.

In aspects of this embodiment, a Neuropeptide Y related peptide binding domain comprises a Neuropeptide Y (NPY), a Peptide YY (PYY), Pancreatic peptide (PP) or a Pancreatic icosapeptide (PIP). In other aspects of this embodiment, a Neuropeptide Y related peptide binding domain comprises SEQ ID NO: 216, SEQ ID NO: 217, SEQ ID NO: 218, SEQ ID NO: 219 or SEQ ID NO: 220.

In other aspects of this embodiment, a Neuropeptide Y related peptide binding domain comprises a polypeptide having, e.g., at least 70% amino acid identity with SEQ ID NO: 216, SEQ ID NO: 217, SEQ ID NO: 218, SEQ ID NO: 219 or SEQ ID NO: 220, at least 75% amino acid identity with SEQ ID NO: 216, SEQ ID NO: 217, SEQ ID NO: 218, SEQ ID NO: 219 or SEQ ID NO: 220, at least 80% amino acid identity with SEQ ID NO: 216, SEQ ID NO: 217, SEQ ID NO: 218, SEQ ID NO: 219 or SEQ ID NO: 220, at least 85% amino acid identity with SEQ ID NO: 216, SEQ ID NO: 217, SEQ ID NO: 218, SEQ ID NO: 219 or SEQ ID NO: 220, at least 90% amino acid identity with SEQ ID NO: 216, SEQ ID NO: 217, SEQ ID NO: 218, SEQ ID NO: 219 or SEQ ID NO: 220 or at least 95% amino acid identity with SEQ ID NO: 216, SEQ ID NO: 217, SEQ ID NO: 218, SEQ ID NO: 219 or SEQ ID NO: 220. In yet other aspects of this embodiment, a Neuropeptide Y related peptide binding domain comprises a polypeptide having, e.g., at most 70% amino acid identity with SEQ ID NO: 216, SEQ ID NO: 217, SEQ ID NO: 218, SEQ ID NO: 219 or SEQ ID NO: 220, at most 75% amino acid identity with SEQ ID NO: 216, SEQ ID NO: 217, SEQ ID NO: 218, SEQ ID NO: 219 or SEQ ID NO: 220, at most 80% amino acid identity with SEQ ID NO: 216, SEQ ID NO: 217, SEQ ID NO: 218, SEQ ID NO: 219 or SEQ ID NO: 220, at most 85% amino acid identity with SEQ ID NO: 216, SEQ ID NO: 217, SEQ ID NO: 218, SEQ ID NO: 219 or SEQ ID NO: 220, at most 90% amino acid identity with SEQ ID NO: 216, SEQ ID NO: 217, SEQ ID NO: 218, SEQ ID NO: 219 or SEQ ID NO: 220 or at most 95% amino acid identity with SEQ ID NO: 216, SEQ ID NO: 217, SEQ ID NO: 218, SEQ ID NO: 219 or SEQ ID NO: 220.

In other aspects of this embodiment, a Neuropeptide Y related peptide binding domain comprises a polypeptide having, e.g., at least one, two, three, four, five, six, seven, eight, nine or ten non-contiguous amino acid substitutions relative to SEQ ID NO: 216, SEQ ID NO: 217, SEQ ID NO: 218, SEQ ID NO: 219 or SEQ ID NO: 220. In other aspects of this embodiment, a Neuropeptide Y related peptide binding domain comprises a polypeptide having, e.g., at most one, two, three, four, five, six, seven, eight, nine or ten non-contiguous amino acid substitutions relative to SEQ ID NO: 216, SEQ ID NO: 217, SEQ ID NO: 218, SEQ ID NO: 219 or SEQ ID NO: 220. In yet other aspects of this embodiment, a Neuropeptide Y related peptide binding domain comprises a polypeptide having, e.g., at least one, two, three, four, five, six, seven, eight, nine or ten non-contiguous amino acid deletions relative to SEQ ID NO: 216, SEQ ID NO: 217, SEQ ID NO: 218, SEQ ID NO: 219 or SEQ ID NO: 220. In yet other aspects of this embodiment, a Neuropeptide Y related peptide binding domain comprises a polypeptide having, e.g., at most one, two, three, four, five, six, seven, eight, nine or ten non-contiguous amino acid deletions relative to SEQ ID NO: 216, SEQ ID NO: 217, SEQ ID NO: 218, SEQ ID NO: 219 or SEQ ID NO: 220. In still other aspects of this embodiment, a Neuropeptide Y related peptide binding domain comprises a polypeptide having, e.g., at least one, two, three, four, five, six, seven, eight, nine or ten non-contiguous amino acid additions relative to SEQ ID NO: 216, SEQ ID NO: 217, SEQ ID NO: 218, SEQ ID NO: 219 or SEQ ID NO: 220. In yet other aspects of this embodiment, a Neuropeptide Y related peptide binding domain comprises a polypeptide having, e.g., at most one, two, three, four, five, six, seven, eight, nine or ten non-contiguous amino acid additions relative to SEQ ID NO: 216, SEQ ID NO: 217, SEQ ID NO: 218, SEQ ID NO: 219 or SEQ ID NO: 220.

In other aspects of this embodiment, a Neuropeptide Y related peptide binding domain comprises a polypeptide having, e.g., at least one, two, three, four, five, six, seven, eight, nine or ten contiguous amino acid substitutions relative to SEQ ID NO: 216, SEQ ID NO: 217, SEQ ID NO: 218, SEQ ID NO: 219 or SEQ ID NO: 220. In other aspects of this embodiment, a Neuropeptide Y related peptide binding domain comprises a polypeptide having, e.g., at most one, two, three, four, five, six, seven, eight, nine or ten contiguous amino acid substitutions relative to SEQ ID NO: 216, SEQ ID NO: 217, SEQ ID NO: 218, SEQ ID NO: 219 or SEQ ID NO: 220. In yet other aspects of this embodiment, a Neuropeptide Y related peptide binding domain comprises a polypeptide having, e.g., at least one, two, three, four, five, six, seven, eight, nine or ten contiguous amino acid deletions relative to SEQ ID NO: 216, SEQ ID NO: 217, SEQ ID NO: 218, SEQ ID NO: 219 or SEQ ID NO: 220. In yet other aspects of this embodiment, a Neuropeptide Y related peptide binding domain comprises a polypeptide having, e.g., at most one, two, three, four, five, six, seven, eight, nine or ten contiguous amino acid deletions relative to SEQ ID NO: 216, SEQ ID NO: 217, SEQ ID NO: 218, SEQ ID NO: 219 or SEQ ID NO: 220. In still other aspects of this embodiment, a Neuropeptide Y related peptide binding domain comprises a polypeptide having, e.g., at least one, two, three, four, five, six, seven, eight, nine or ten contiguous amino acid additions relative to SEQ ID NO: 216, SEQ ID NO: 217, SEQ ID NO: 218, SEQ ID NO: 219 or SEQ ID NO: 220. In yet other aspects of this embodiment, a Neuropeptide Y related peptide binding domain comprises a polypeptide having, e.g., at most one, two, three, four, five, six, seven, eight, nine or ten contiguous amino acid additions relative to SEQ ID NO: 216, SEQ ID NO: 217, SEQ ID NO: 218, SEQ ID NO: 219 or SEQ ID NO: 220.

Another example of a binding domain disclosed in the present specification is, e.g., a corticotropin-releasing hormone, a thyrotropin-releasing hormone, somatostatin, a leukemia inhibitor factor (LIF) or an interleukin-1 (IL1). Thus, in an embodiment, a binding domain comprises a corticotropin-releasing hormone. In an embodiment, a binding domain is derived from a corticotropin-releasing hormone. In another embodiment, a binding domain comprises a thyrotropin-releasing hormone. In another embodiment, a binding domain is derived from a thyrotropin-releasing hormone. In another embodiment, a binding domain comprises a somatostatin. In another embodiment, a binding domain is derived from a somatostatin. In another embodiment, a binding domain comprises a LIF. In another embodiment, a binding domain is derived from a LIF. In another embodiment, a binding domain comprises an IL1. In another embodiment, a binding domain is derived from an IL1. In aspects of this embodiment, a binding domain comprises SEQ ID NO: 221, SEQ ID NO: 222, SEQ ID NO: 223, SEQ ID NO: 224, SEQ ID NO: 225 or SEQ ID NO: 226.

In other aspects of this embodiment, a binding domain comprises a polypeptide having, e.g., at least 70% amino acid identity with SEQ ID NO: 221, SEQ ID NO: 222, SEQ ID NO: 223, SEQ ID NO: 224, SEQ ID NO: 225, or SEQ ID NO: 226, at least 75% amino acid identity with SEQ ID NO: 221, SEQ ID NO: 222, SEQ ID NO: 223, SEQ ID NO: 224, SEQ ID NO: 225 or SEQ ID NO: 226, at least 80% amino acid identity with SEQ ID NO: 221, SEQ ID NO: 222, SEQ ID NO: 223, SEQ ID NO: 224, SEQ ID NO: 225 or SEQ ID NO: 226, at least 85% amino acid identity with SEQ ID NO: 221, SEQ ID NO: 222, SEQ ID NO: 223, SEQ ID NO: 224, SEQ ID NO: 225 or SEQ ID NO: 226, at least 90% amino acid identity with SEQ ID NO: 221, SEQ ID NO: 222, SEQ ID NO: 223, SEQ ID NO: 224, SEQ ID NO: 225 or SEQ ID NO: 226 or at least 95% amino acid identity with SEQ ID NO: 221, SEQ ID NO: 222, SEQ ID NO: 223, SEQ ID NO: 224, SEQ ID NO: 225 or SEQ ID NO: 226. In yet other aspects of this embodiment, a binding domain comprises a polypeptide having, e.g., at most 70% amino acid identity with SEQ ID NO: 221, SEQ ID NO: 222, SEQ ID NO: 223, SEQ ID NO: 224, SEQ ID NO: 225 or SEQ ID NO: 226, at most 75% amino acid identity with SEQ ID NO: 221, SEQ ID NO: 222, SEQ ID NO: 223, SEQ ID NO: 224, SEQ ID NO: 225 or SEQ ID NO: 226, at most 80% amino acid identity with SEQ ID NO: 221, SEQ ID NO: 222, SEQ ID NO: 223, SEQ ID NO: 224, SEQ ID NO: 225 or SEQ ID NO: 226, at most 85% amino acid identity with SEQ ID NO: 221, SEQ ID NO: 222, SEQ ID NO: 223, SEQ ID NO: 224, SEQ ID NO: 225 or SEQ ID NO: 226, at most 90% amino acid identity with SEQ ID NO: 221, SEQ ID NO: 222, SEQ ID NO: 223, SEQ ID NO: 224, SEQ ID NO: 225 or SEQ ID NO: 226 or at most 95% amino acid identity with SEQ ID NO: 221, SEQ ID NO: 222, SEQ ID NO: 223, SEQ ID NO: 224, SEQ ID NO: 225 or SEQ ID NO: 226.

In other aspects of this embodiment, a binding domain comprises a polypeptide having, e.g., at least one, two, three, four or five non-contiguous amino acid substitutions relative to SEQ ID NO: 221, SEQ ID NO: 222, SEQ ID NO: 223, SEQ ID NO: 224, SEQ ID NO: 225 or SEQ ID NO: 226. In other aspects of this embodiment, a binding domain comprises a polypeptide having, e.g., at most one, two, three, four or five non-contiguous amino acid substitutions relative to SEQ ID NO: 221, SEQ ID NO: 222, SEQ ID NO: 223, SEQ ID NO: 224, SEQ ID NO: 225 or SEQ ID NO: 226. In yet other aspects of this embodiment, a binding domain comprises a polypeptide having, e.g., at least one, two, three, four or five non-contiguous amino acid deletions relative to SEQ ID NO: 221, SEQ ID NO: 222, SEQ ID NO: 223, SEQ ID NO: 224, SEQ ID NO: 225 or SEQ ID NO: 226. In yet other aspects of this embodiment, a binding domain comprises a polypeptide having, e.g., at most one, two, three, four or five non-contiguous amino acid deletions relative to SEQ ID NO: 221, SEQ ID NO: 222, SEQ ID NO: 223, SEQ ID NO: 224, SEQ ID NO: 225 or SEQ ID NO: 226. In still other aspects of this embodiment, a binding domain comprises a polypeptide having, e.g., at least one, two, three, four or five non-contiguous amino acid additions relative to SEQ ID NO: 221, SEQ ID NO: 222, SEQ ID NO: 223, SEQ ID NO: 224, SEQ ID NO: 225 or SEQ ID NO: 226. In yet other aspects of this embodiment, a binding domain comprises a polypeptide having, e.g., at most one, two, three, four or five non-contiguous amino acid additions relative to SEQ ID NO: 221, SEQ ID NO: 222, SEQ ID NO: 223, SEQ ID NO: 224, SEQ ID NO: 225 or SEQ ID NO: 226.

In other aspects of this embodiment, a binding domain comprises a polypeptide having, e.g., at least one, two, three, four or five contiguous amino acid substitutions relative to SEQ ID NO: 221, SEQ ID NO: 222, SEQ ID NO: 223, SEQ ID NO: 224, SEQ ID NO: 225 or SEQ ID NO: 226. In other aspects of this embodiment, a binding domain comprises a polypeptide having, e.g., at most one, two, three, four or five contiguous amino acid substitutions relative to SEQ ID NO: 221, SEQ ID NO: 222, SEQ ID NO: 223, SEQ ID NO: 224, SEQ ID NO: 225 or SEQ ID NO: 226. In yet other aspects of this embodiment, a binding domain comprises a polypeptide having, e.g., at least one, two, three, four or five contiguous amino acid deletions relative to SEQ ID NO: 221, SEQ ID NO: 222, SEQ ID NO: 223, SEQ ID NO: 224, SEQ ID NO: 225 or SEQ ID NO: 226. In yet other aspects of this embodiment, a binding domain comprises a polypeptide having, e.g., at most one, two, three, four or five contiguous amino acid deletions relative to SEQ ID NO: 221, SEQ ID NO: 222, SEQ ID NO: 223, SEQ ID NO: 224, SEQ ID NO: 225 or SEQ ID NO: 226. In still other aspects of this embodiment, a binding domain comprises a polypeptide having, e.g., at least one, two, three, four or five contiguous amino acid additions relative to SEQ ID NO: 221, SEQ ID NO: 222, SEQ ID NO: 223, SEQ ID NO: 224, SEQ ID NO: 225 or SEQ ID NO: 226. In yet other aspects of this embodiment, a binding domain comprises a polypeptide having, e.g., at most one, two, three, four or five contiguous amino acid additions relative to SEQ ID NO: 221, SEQ ID NO: 222, SEQ ID NO: 223, SEQ ID NO: 224, SEQ ID NO: 225 or SEQ ID NO: 226.

Another example of a binding domain disclosed in the present specification is a kinin peptide, such as, e.g., a bradykinin, a kallidin, a desArg$^9$ bradykinin and a desArg$^{10}$ bradykinin. Thus, in an embodiment, a binding domain comprises a kinin peptide. In another embodiment, a binding domain is derived from a kinin peptide. In aspects of this embodiment, a kinin peptide binding domain comprises a bradykinin, a kallidin, a desArg⁹ bradykinin and a desArg¹⁰ bradykinin. In other aspects of this embodiment, a kinin peptide binding domain comprises SEQ ID NO: 227, SEQ ID NO: 228, SEQ ID NO: 229 or SEQ ID NO: 230.

In other aspects of this embodiment, a kinin peptide binding domain comprises a polypeptide having, e.g., at least 70% amino acid identity with SEQ ID NO: 227, SEQ ID NO: 228, SEQ ID NO: 229 or SEQ ID NO: 230, at least 75% amino acid identity with SEQ ID NO: 227, SEQ ID NO: 228, SEQ ID NO: 229 or SEQ ID NO: 230, at least 80% amino acid identity with SEQ ID NO: 227, SEQ ID NO: 228, SEQ ID NO: 229 or SEQ ID NO: 230, at least 85% amino acid identity with SEQ ID NO: 227, SEQ ID NO: 228, SEQ ID NO: 229 or SEQ ID NO: 230, at least 90% amino acid identity with SEQ ID NO: 227, SEQ ID NO: 228, SEQ ID NO: 229 or SEQ ID NO: 230 or at least 95% amino acid identity with SEQ ID NO: 227, SEQ ID NO: 228, SEQ ID NO: 229 or SEQ ID NO: 230. In yet other aspects of this embodiment, a kinin peptide binding domain comprises a polypeptide having, e.g., at most 70% amino acid identity with SEQ ID NO: 227, SEQ ID NO: 228, SEQ ID NO: 229 or SEQ ID NO: 230, at most 75% amino acid identity with SEQ ID NO: 227, SEQ ID NO: 228, SEQ ID NO: 229 or SEQ ID NO: 230, at most 80% amino acid identity with SEQ ID NO: 227, SEQ ID NO: 228, SEQ ID NO: 229 or SEQ ID NO: 230, at most 85% amino acid identity with SEQ ID NO: 227, SEQ ID NO: 228, SEQ ID NO: 229 or SEQ ID NO: 230, at most 90% amino acid identity with SEQ ID NO: 227, SEQ ID NO: 228, SEQ ID NO: 229 or SEQ ID NO: 230 or at most 95% amino acid identity with SEQ ID NO: 227, SEQ ID NO: 228, SEQ ID NO: 229 or SEQ ID NO: 230.

In other aspects of this embodiment, a kinin peptide binding domain comprises a polypeptide having, e.g., at least one, two, three, four, five, six, seven, eight, nine or ten non-contiguous amino acid substitutions relative to SEQ ID NO: 227, SEQ ID NO: 228, SEQ ID NO: 229 or SEQ ID NO: 230. In other aspects of this embodiment, a kinin peptide binding domain comprises a polypeptide having, e.g., at most one, two, three, four, five, six, seven, eight, nine or ten non-contiguous amino acid substitutions relative to SEQ ID NO: 227, SEQ ID NO: 228, SEQ ID NO: 229 or SEQ ID NO: 230. In yet other aspects of this embodiment, a kinin peptide binding domain comprises a polypeptide having, e.g., at least one, two, three, four, five, six, seven, eight, nine or ten non-contiguous amino acid deletions relative to SEQ ID NO: 227, SEQ ID NO: 228, SEQ ID NO: 229 or SEQ ID NO: 230. In yet other aspects of this embodiment, a kinin peptide binding domain comprises a polypeptide having, e.g., at most one, two, three, four, five, six, seven, eight, nine or ten non-contiguous amino acid deletions relative to SEQ ID NO: 227, SEQ ID NO: 228, SEQ ID NO: 229 or SEQ ID NO: 230. In still other aspects of this embodiment, a kinin peptide binding domain comprises a polypeptide having, e.g., at least one, two, three, four, five, six, seven, eight, nine or ten non-contiguous amino acid additions relative to SEQ ID NO: 227, SEQ ID NO: 228, SEQ ID NO: 229 or SEQ ID NO: 230. In yet other aspects of this embodiment, a kinin peptide binding domain comprises a polypeptide having, e.g., at most one, two, three, four, five, six, seven, eight, nine or ten non-contiguous amino acid additions relative to SEQ ID NO: 227, SEQ ID NO: 228, SEQ ID NO: 229 or SEQ ID NO: 230.

In other aspects of this embodiment, a kinin peptide binding domain comprises a polypeptide having, e.g., at least one, two, three, four, five, six, seven, eight, nine or ten contiguous amino acid substitutions relative to SEQ ID NO: 227, SEQ ID NO: 228, SEQ ID NO: 229 or SEQ ID NO: 230. In other aspects of this embodiment, a kinin peptide binding domain comprises a polypeptide having, e.g., at most one, two, three, four, five, six, seven, eight, nine or ten contiguous amino acid substitutions relative to SEQ ID NO: 227, SEQ ID NO: 228, SEQ ID NO: 229 or SEQ ID NO: 230. In yet other aspects of this embodiment, a kinin peptide binding domain comprises a polypeptide having, e.g., at least one, two, three, four, five, six, seven, eight, nine or ten contiguous amino acid deletions relative to SEQ ID NO: 227, SEQ ID NO: 228, SEQ ID NO: 229 or SEQ ID NO: 230. In yet other aspects of this embodiment, a kinin peptide binding domain comprises a polypeptide having, e.g., at most one, two, three, four, five, six, seven, eight, nine or ten contiguous amino acid deletions relative to SEQ ID NO: 227, SEQ ID NO: 228, SEQ ID NO: 229 or SEQ ID NO: 230. In still other aspects of this embodiment, a kinin peptide binding domain comprises a polypeptide having, e.g., at least one, two, three, four, five, six, seven, eight, nine or ten contiguous amino acid additions relative to SEQ ID NO: 227, SEQ ID NO: 228, SEQ ID NO: 229 or SEQ ID NO: 230. In yet other aspects of this embodiment, a kinin peptide binding domain comprises a polypeptide having, e.g., at most one, two, three, four, five, six, seven, eight, nine or ten contiguous amino acid additions relative to SEQ ID NO: 227, SEQ ID NO: 228, SEQ ID NO: 229 or SEQ ID NO: 230.

Another example of a binding domain disclosed in the present specification is a PAR peptide, such as, e.g., a PAR1 peptide, a PAR2 peptide, a PAR3 peptide and a PAR4 peptide. Thus, in an embodiment, a binding domain comprises a PAR peptide. In another embodiment, a binding domain is derived from a PAR peptide. In aspects of this embodiment, a PAR peptide binding domain comprises a PAR1 peptide, a PAR2 peptide, a PAR3 peptide or a PAR4 peptide. In other aspects of this embodiment, a PAR peptide binding domain comprises amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234.

In other aspects of this embodiment, a PAR peptide binding domain comprises a polypeptide having, e.g., at least 70% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234, at least 75% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234, at least 80% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234, at least 85% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234, at least 90% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234 or at least 95% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234.

In yet other aspects of this embodiment, a PAR peptide binding domain comprises a polypeptide having, e.g., at most 70% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234, at most 75% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234, at most 80% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234, at most 85% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234, at most 90% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234 or at most 95% amino acid identity with amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234.

In other aspects of this embodiment, a PAR peptide binding domain comprises a polypeptide having, e.g., at least one, two, three, four or five non-contiguous amino acid substitutions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234. In other aspects of this embodiment, a PAR peptide binding domain comprises a polypeptide having, e.g., at most one, two, three, four or five non-contiguous amino acid substitutions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234. In yet other aspects of this embodiment, a PAR peptide binding domain comprises a polypeptide having, e.g., at least one, two, three, four or five non-contiguous amino acid deletions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234. In yet other aspects of this embodiment, a PAR peptide binding domain comprises a polypeptide having, e.g., at most one, two, three, four or five non-contiguous amino acid deletions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234. In still other aspects of this embodiment, a PAR peptide binding domain comprises a polypeptide having, e.g., at least one, two, three, four or five non-contiguous amino acid additions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234. In yet other aspects of this embodiment, a PAR peptide binding domain comprises a polypeptide having, e.g., at most one, two, three, four or five non-contiguous amino acid additions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234.

In other aspects of this embodiment, a PAR peptide binding domain comprises a polypeptide having, e.g., at least one, two, three, four or five contiguous amino acid substitutions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO:

233; amino acids 48-53, amino acids 48-61, amino acids 35-70 or amino acids 1-70 of SEQ ID NO: 234. In other aspects of this embodiment, a PAR peptide binding domain comprises a polypeptide having, e.g., at most one, two, three, four or five contiguous amino acid substitutions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234. In yet other aspects of this embodiment, a PAR peptide binding domain comprises a polypeptide having, e.g., at least one, two, three, four or five contiguous amino acid deletions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234. In yet other aspects of this embodiment, a PAR peptide binding domain comprises a polypeptide having, e.g., at most one, two, three, four or five contiguous amino acid deletions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234. In still other aspects of this embodiment, a PAR peptide binding domain comprises a polypeptide having, e.g., at least one, two, three, four or five contiguous amino acid additions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234. In yet other aspects of this embodiment, a PAR peptide binding domain comprises a polypeptide having, e.g., at most one, two, three or five contiguous amino acid additions relative to amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234.

Another example of a binding domain, includes, without limitation, a translocator, such as, e.g., a protein translocation domain (PTD), like, a herpes simplex virus type 1 VP22 protein translocating sequence, a SV-40 virus large T translocating sequence, a TAT translocating sequence, an adenovirus translocating sequence, a synthetic integrin binding domain translocating sequence, a Kaposi fibroblast growth factor membrane translocating sequence, a nuclear localization signal, a Transportan translocating sequence, a ciliary neurotrophic factor translocating sequence, a caveolin, an interleukin 1-β translocating sequence, a thioredoxin translocating sequence, a fibroblast growth factor-1 translocating sequence, a fibroblast growth factor-2 translocating sequence, an integrin β1 translocating sequence, an integrin β3 translocating sequence, a lactoferrin translocating sequence, a homeodomain translocating sequence, like, a penetratin translocating sequence, an Engrailed-1 translocating sequence, an Engrailed-2 translocating sequence, a Hoxa-5 translocating sequence, a Hoxb-4 translocating sequence, a Hoxc-8 translocating sequence.

Without wishing to limit the invention to any theory or mechanism of operation, it is believed that the translocator comprises a protein translocation domain (PTD). Further, it is believed that the PTD is primarily responsible for the translocation of the neurotoxin across a cell membrane. PTDs are amino acid sequence domains that have been shown to cross biological membranes efficiently and independently of transporters or specific receptors. See e.g., Morris M. C. et al., NATURE BIOTECHNOLOGY, 19:1173-1176 (December 2001), the disclosure of which is herein incorporated by reference in its entirety.

For example, herpes simplex virus type 1 viral protein 22 (HSV-1 VP 22) protein is a transcription factor that concentrates in the nucleus and binds chromatin. It has been shown that HSV-1 VP 22 comprises a translocating sequence that mediates trafficking across the membrane via non-classical endocytosis and can enter cells regardless of GAP junctions and physical contacts. If HSV-1 VP 22 is expressed in a small population of cells in culture, it will reach 100% of the cells in that culture. Fusion proteins with HSV-1 VP 22 and for example p53, GFP, thymidine kinase, β-galactosidase and others have been generated. It has been demonstrated that the fusion proteins are taken up by several kinds of cells including terminally differentiated cells suggesting that mitosis is not a requirement for efficient entry. In addition, HSV-1 VP 22-GFP fusion showed that the protein can shuttle in and out of the cells and enter cells that were not exposed to HSV-1 VP 22.

As another example, the trans-activator gene product (TAT) from the lentivirus HIV-1 was one of the earliest described cell-permeating proteins comprising a translocating sequence. A receptor-mediated event appears not to be required for HIV TAT to pass into a neighboring cell; thus for selective cell targeting, a PTD is preferably used in conjunction with a more target cell-selective binding domain in the multivalent Clostridial toxin derivative of the present invention. It is now known that many other lentiviruses, encodes a potent TAT protein. Embury et al., DIABETES 50:1706-1713, 2001 discuss the use the TAT PTD to transduce anti-apoptotic proteins into pancreatic islet cells. The PTD of TAT is a small peptide comprising amino acids 47-57 of the TAT protein; the PTD sequence comprises the amino acid sequence YGRKKRRQRRR (SEQ ID NO 41) or at least the nonapeptide comprising TAT amino acids 49-57. Fusion proteins comprising this peptide can transit the plasma membrane in vitro and in vivo. E.g., Schwartz, J. J. et al., Peptide-mediated cellular delivery, Curr. Opin. Mol. Therapeutics. 2000, 2:162-7. The disclosures of these references are incorporated in their entirety by reference herein.

As another example, a translocating sequence may be derived from a homeoprotein. Homeoproteins are helix turn helix proteins that contain a 60 amino acid DNA-binding domain, the homeodomain. a translocating sequence may be derived from the homeodomain. One kind of translocating sequence may be derived from the family of Drosophila homeoproteins. Drosophila homeoproteins are involved in developmental processes and are able to translocate across neuronal membranes. The third helix of the homeodomain of just 16 amino acids, known as penetratin, is able to translocate molecules into live cells. When added to several cell types in culture, 100% of the cells were able to uptake the peptide. Internalization occurs both at 37° C. and 4° C., and thus appears to be neither receptor-mediated nor energy-dependent. Several penetrating peptides, including those of the penetratin family, have been developed and used to internalize cargo molecules into the cytoplasm and nucleus of several cell types in vivo and in vitro. The results suggest that the entry of penetratin peptides is mediated by tryptophan, phenylalanine, and/or glutamine residues. In addition, the retro-inverse and all D-amino acid forms are also translocated efficiently using the penetratins, and non-α-helical structures are also internalized. See Prochiantz, A., Messenger proteins: homeoproteins, TAT and others, *Curr Opin Cell Biol* 2000, 12:400-6; and Schwartz, J J et al., Peptide-mediated cellular delivery, *Curr Opin Mol Therapeutics* 2000, 2:162-7. The disclosures of these references are incorporated in their entirety by reference herein.

Furthermore, PTD-transported proteins and peptides, such as fusion peptides, have been shown to generally retain their biological properties and functions once inside the cells. Further, the TAT is able to carry a variety of cargo molecules including nucleic acid molecules (DNA and RNA), and therapeutic drugs. The capability of this sequence to promote internalization of the peptide (and any cargo peptide) appears to be related to the strongly positive charge of the PTD sequence, and not to be inhibited at 4° C. or in the presence of endocytosis inhibitors. Thus, the PTD appears not to be dependent upon active transport or receptor mediated endocytosis for this activity. The PTD sequence is able to mediate the transduction of its cargo in a concentration dependent and receptor-, transporter-, and endocytosis-independent manner to 100% of the target cells in a given tissue or culture. Of special interest are the studies demonstrating that the PTD of TAT is able to deliver proteins in vivo to several different tissues when injected into animals.

A PTD may comprise a synthetic translocating sequence, such as, e.g., the synthetic translocating sequence disclosed in, e.g., WO 99/29721 and Ho, A. et al., *Synthetic PTDs: enhanced transduction potential in vitro and in vivo*, CANCER RES 2001, 61, 474-7. In addition, it has been demonstrated that a 9-mer of L-Arginine is 20 fold more efficient than the TAT-PTD at cellular uptake, and when a D-arginine oligomer was used the rate enhancement was >100 fold. See Wender, P A et al., *The Design, Synthesis, And Evaluation Of Molecules That Enable Or Enhance Cellular Uptake: Peptoid Molecular Transporters*, PROC. NATL. ACAD. SCI. USA 2000, 97:13003-13008. These data suggested that the guanidinium groups of TAT-PTD play a greater role than charge or backbone structure in mediating cellular uptake. Thus, a peptoid analogue containing a six-methylene spacer between the guanidine head group and backbone was synthesized. This peptoid exhibited enhanced cellular uptake when compared to TAT-PTD and even to the D-Arg peptide.

In addition to the proteins and peptides discussed above, other peptide-mediated delivery systems have been described and are well-known to those of skill in the art. These PTD-containing proteins and peptides include: MPG, SCWKn, (LARL)n, HA2, RGD, AlkCWK$_{18}$, DiCWK$_{18}$, DipaLytic, K$_{16}$RGD, Plae and Kplae. See Schwartz, J J et al., Peptide-mediated cellular delivery, *Curr Opin Mol Therapeutics* 2000, 2:162-7. The disclosure of which is incorporated in its entirety by reference herein. In some embodiments, these proteins and peptides may be used as translocators in accordance with the present invention.

A number of PTDs have now been characterized and are well-known in the art. The amino acid sequences of exemplary translocators are shown in Table 8.

TABLE 8

| Translocator Peptides Useful as Binding Domains | | |
|---|---|---|
| PTD | Translocating Sequence | SEQ ID NO: |
| SV-40 virus large T | CGGGPKKKRKVGG | 235 |
| TAT | YGRKKRRQRRR | 236 |
| Adenovirus | CGGFSTSLRARKA | 237 |
| Integrin binding domain | CKKKKKKGGRGDMFG | 238 |
| Kaposi FGF membrane translocating sequence | AAVALLPAVLLALLAP | 239 |
| Nuclear Localization Signal | TPPKKKRKVEDP | 240 |
| Transportan | GWTLNSAGYLLGKINLKALAALAKKIL | 241 |
| HSV-1 VP 22 | DAATATRGRSAASRPTERPRAPARSASRPRRPVE | 242 |
| Penetratin 43-58 | RQIKIWFQNRRMKWKK | 243 |
| Penetratin 58-43 | KKWKMRRNQFWIKIQR | 244 |
| Penetratin 43-58 | RQIKIWFQNRRMKWKK | 245 |
| Penetratin Pro50 | RQIKIWFPNRRMKWKK | 246 |
| Penetratin 3Pro | RQPKIWFPNRRMPWKK | 247 |
| Penetratin Met-Arg | RQIKIWFQNMRRKWKK | 248 |
| Penetratin 7Arg | RQIRIWFQNRRMRWRR | 249 |
| Penetratin W/R | RRWRRWWRRWWRRWRR | 250 |
| Penetratin-1 | RQIKIFFQNRRMKFKK | 251 |

TABLE 8-continued

Translocator Peptides Useful as Binding Domains

| PTD | Translocating Sequence | SEQ ID NO: |
|---|---|---|
| Penetratin-2 | TERQIKIWFQNRRMK | 252 |
| Penetratin-3 | KIWFQNRRMKWKKEN | 253 |

As used herein, a "translocator" of the present invention comprises a polypeptide or a peptidomimetic that facilitates the transport of a molecule across a cell membrane. It is envisioned that both naturally occurring translocators as well as non-naturally occurring translocators can be used as a binding domain. A translocator includes, without limitation, naturally occurring translocator variants, such as, e.g., translocator isoforms and translocator subtypes; non-naturally occurring translocator variants, such as, e.g., conservative translocator variants, non-conservative translocator variants, translocator chimerics, active translocator fragments thereof, or any combination thereof.

As used herein, the term "translocator variant," whether naturally-occurring or non-naturally-occurring, means a translocator that has at least one amino acid change from the corresponding region of the disclosed reference sequences (see Table 8) and can be described in percent identity to the corresponding region of that reference sequence. Unless expressly indicated, all translocator variants disclosed in the present specification are capable of executing the cell binding step of the intoxication process.

It is recognized by those of skill in the art that there can be naturally occurring translocator variants that differ somewhat in their amino acid sequence, and also in the nucleic acids encoding these proteins. For example, HSV-1 VP22 protein variants, TAT variants, and penetratin variants. As used herein, the term "naturally occurring translocator variant" means any translocator produced by a naturally-occurring process, including, without limitation, translocator isoforms produced from alternatively-spliced transcripts, translocator isoforms produced by spontaneous mutation and translocator subtypes. A naturally occurring translocator variant can function in substantially the same manner as the reference translocator on which the naturally occurring translocator variant is based, and can be substituted for the reference translocator in any aspect of the present invention. A naturally occurring translocator variant may substitute one or more amino acids, two or more amino acids, three or more amino acids, four or more amino acids, five or more amino acids, six or more amino acids, seven or more amino acids, eight or more amino acids, nine or more amino acids, or ten or more amino acids from the reference translocator on which the naturally occurring translocator variant is based. A naturally occurring translocator variant can also substitute at least 2 contiguous amino acids, at least 3 contiguous amino acids, at least 4 contiguous amino acids, at least 5 contiguous amino acids, at least 6 contiguous amino acids, at least 7 contiguous amino acids, at least 8 contiguous amino acids, at least 9 contiguous amino acids, or at least 10 contiguous amino acids from the reference translocator on which the naturally occurring translocator variant is based, that possess at least 50% amino acid identity, 65% amino acid identity, 75% amino acid identity, 85% amino acid identity or 95% amino acid identity to the reference translocator on which the naturally occurring translocator variant is based.

A non-limiting examples of a naturally occurring translocator variant is a translocator isoform such as, e.g., a HSV-1 VP22 protein isoform, a SV-40 virus large T isoform, a TAT isoform, an adenovirus isoform, a synthetic integrin binding domain isoform, a Kaposi fibroblast growth factor membrane isoform, a nuclear localization signal, a Transportan isoform, a ciliary neurotrophic factor isoform, a caveolin, an interleukin 1-β isoform, a thioredoxin isoform, a fibroblast growth factor-1 isoform, a fibroblast growth factor-2 isoform, an integrin β1 isoform, an integrin β3 isoform, a lactoferrin isoform, a homeodomain isoform, like, a penetratin isoform, an Engrailed-1 isoform, an Engrailed-2 isoform, a Hoxa-5 isoform, a Hoxb-4 isoform, a Hoxc-8 isoform. A translocator isoform can function in substantially the same manner as the reference translocator on which the translocator isoform is based, and can be substituted for the reference translocator in any aspect of the present invention.

Another non-limiting examples of a naturally occurring translocator variant is a translocator subtype such as, e.g., a HSV-1 VP22 protein subtype, a SV-40 virus large T subtype, a TAT subtype, an adenovirus subtype, a synthetic integrin binding domain subtype, a Kaposi fibroblast growth factor membrane subtype, a nuclear localization signal, a Transportan subtype, a ciliary neurotrophic factor subtype, a caveolin, an interleukin 1-β subtype, a thioredoxin subtype, a fibroblast growth factor-1 subtype, a fibroblast growth factor-2 subtype, an integrin β1 subtype, an integrin β3 subtype, a lactoferrin subtype, a homeodomain subtype, like, a penetratin subtype, an Engrailed-1 subtype, an Engrailed-2 subtype, a Hoxa-5 subtype, a Hoxb-4 subtype, a Hoxc-8 subtype. A translocator subtype can function in substantially the same manner as the reference translocator on which the translocator subtype is based, and can be substituted for the reference translocator in any aspect of the present invention.

As used herein, the term "non-naturally occurring translocator variant" means any translocator produced with the aid of human manipulation, including, without limitation, translocators produced by genetic engineering using random mutagenesis or rational design and translocators produced by chemical synthesis. Non-limiting examples of non-naturally occurring translocator variants include, e.g., conservative translocator variants, non-conservative translocator variants, translocator chimeric variants and active translocator fragments.

As used herein, the term "conservative translocator variant" means a translocator that has at least one amino acid substituted by another amino acid or an amino acid analog that has at least one property similar to that of the original amino acid from the reference translocator sequence (see Table 8). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative translocator variant can function in substantially the same manner as the reference translocator on which the conservative translocator variant is based, and can be substituted for the reference translocator in any aspect of the present invention. A conservative translocator variant may substitute one or more amino acids, two or more amino acids, three or more amino acids, four or more amino acids, five or more amino acids, six or more amino acids, seven or more amino acids, eight or more amino acids, nine or more amino acids, or ten or more amino acids from the reference translocator on which the conservative translocator variant is based. A conservative translocator variant can also substitute at least 2 contiguous amino acids, at least 3 contiguous amino acids, at least 4 contiguous amino acids, at least 5 contiguous amino acids, at least 6 contiguous amino acids, at least 7 contiguous amino acids, at least 8 contiguous amino acids, at least 9 contiguous amino acids, or at least 10 contiguous amino acids from the reference translocator on which the conservative translocator variant is based, that possess at least 50% amino acid identity, 65% amino acid identity, 75% amino acid identity, 85% amino acid identity or 95% amino acid identity to the reference translocator on which the conservative translocator variant is based. Non-limiting examples of a conservative translocator variant include, e.g., a conservative HSV-1 VP22 protein variant, a conservative SV-40 virus large T variant, a conservative TAT variant, an adenovirus variant, a conservative synthetic integrin binding domain variant, a conservative Kaposi fibroblast growth factor membrane variant, a conservative nuclear localization signal, a conservative Transportan variant, a conservative ciliary neurotrophic factor variant, a conservative caveolin, an interleukin 1-β variant, a conservative thioredoxin variant, a conservative fibroblast growth factor-1 variant, a conservative fibroblast growth factor-2 variant, an integrin β1 variant, an integrin β3 variant, a conservative lactoferrin variant, a conservative homeodomain variant, like, a conservative penetratin variant, an Engrailed-1 variant, an Engrailed-2 variant, a conservative Hoxa-5 variant, a conservative Hoxb-4 variant, a conservative Hoxc-8 variant.

As used herein, the term "non-conservative translocator variant" means a translocator in which 1) at least one amino acid is deleted from the reference translocator on which the non-conservative translocator variant is based; 2) at least one amino acid added to the reference translocator on which the non-conservative translocator is based; or 3) at least one amino acid is substituted by another amino acid or an amino acid analog that does not share any property similar to that of the original amino acid from the reference translocator sequence (see Table 8). A non-conservative translocator variant can function in substantially the same manner as the reference translocator on which the non-conservative translocator variant is based, and can be substituted for the reference translocator in any aspect of the present invention. A non-conservative translocator variant can delete one or more amino acids, two or more amino acids, three or more amino acids, four or more amino acids, five or more amino acids, and ten or more amino acids from the reference translocator on which the non-conservative translocator variant is based. A non-conservative translocator variant can add one or more amino acids, two or more amino acids, three or more amino acids, four or more amino acids, five or more amino acids, and ten or more amino acids to the reference translocator on which the non-conservative translocator variant is based. A non-conservative translocator variant may substitute one or more amino acids, two or more amino acids, three or more amino acids, four or more amino acids, five or more amino acids, six or more amino acids, seven or more amino acids, eight or more amino acids, nine or more amino acids, or ten or more amino acids from the reference translocator on which the non-conservative translocator variant is based. A non-conservative translocator variant can also substitute at least 2 contiguous amino acids, at least 3 contiguous amino acids, at least 4 contiguous amino acids, at least 5 contiguous amino acids, at least 6 contiguous amino acids, at least 7 contiguous amino acids, at least 8 contiguous amino acids, at least 9 contiguous amino acids, or at least 10 contiguous amino acids from the reference translocator on which the non-conservative translocator variant is based, that possess at least 50% amino acid identity, 65% amino acid identity, 75% amino acid identity, 85% amino acid identity or 95% amino acid identity to the reference translocator on which the non-conservative translocator variant is based. Non-limiting examples of a non-conservative translocator variant include, e.g., a non-conservative HSV-1 VP22 protein variant, a non-conservative SV-40 virus large T variant, a non-conservative TAT variant, an adenovirus variant, a non-conservative synthetic integrin binding domain variant, a non-conservative Kaposi fibroblast growth factor membrane variant, a non-conservative nuclear localization signal, a non-conservative Transportan variant, a non-conservative ciliary neurotrophic factor variant, a non-conservative caveolin, an interleukin 1-β variant, a non-conservative thioredoxin variant, a non-conservative fibroblast growth factor-1 variant, a non-conservative fibroblast growth factor-2 variant, an integrin β1 variant, an integrin β3 variant, a non-conservative lactoferrin variant, a non-conservative homeodomain variant, like, a non-conservative penetratin variant, an Engrailed-1 variant, an Engrailed-2 variant, a non-conservative Hoxa-5 variant, a non-conservative Hoxb-4 variant, a non-conservative Hoxc-8 variant.

As used herein, the term "translocator chimeric" means a polypeptide comprising at least a portion of a translocator and at least a portion of at least one other polypeptide to form an enhanced targeting domain with at least one property different from the reference translocator (see Table 8), with the proviso that this translocator chimeric can facilitate the transport of a molecule across a cell membrane.

As used herein, the term "active translocator fragment" means any of a variety of translocator fragments comprising the enhanced targeting domain can be useful in aspects of the present invention with the proviso that these NAP fragments can facilitate the transport of a molecule across a cell membrane.

In some embodiments, the translocator may function independently of cell surface transporters or specific receptors, and therefore non-specifically. In this embodiment the multivalent Clostridial toxin will also comprise at least one target cell selective ligand. In some embodiments, one or more binding domain of the multivalent Clostridial toxin may comprise a translocator. In other embodiments, a translocator may comprise a peptide or peptidomimetic selective for a cell surface transporter, feature, or receptor; in such an embodiment the multivalent Clostridial toxin may comprise two or more identical binding domains, or may comprise at least one target cell selective domain and at least one target cell non-selective binding domain, so long as the number of binding domains totals at least two.

In an embodiment, a binding domain comprises a translocator. In aspects of this embodiment, a translocator comprises a PTD.

In another embodiment, a binding domain comprises a translocating sequence comprises a SV-40 virus large T translocating sequence. In another embodiment, a binding domain comprises a translocating sequence derived from a SV-40 virus large T translocating sequence. In an aspect of this embodiment, a binding domain comprises a SV-40 virus large T translocating sequence comprises SEQ ID NO: 235. In another aspect of this embodiment, a binding domain comprises a SV-40 virus large T translocating sequence derived from SEQ ID NO: 235.

In other aspects of this embodiment, a SV-40 virus large T translocating sequence comprises a polypeptide having, e.g., at least 70% amino acid identity with SEQ ID NO: 235, at least 75% amino acid identity with SEQ ID NO: 235, at least 80% amino acid identity with SEQ ID NO: 235, at least 85% amino acid identity with SEQ ID NO: 235, at least 90% amino acid identity with SEQ ID NO: 235 or at least 95% amino acid identity with SEQ ID NO: 235. In yet other aspects of this embodiment, a SV-40 virus large T translocating sequence comprises a polypeptide having, e.g., at most 70% amino acid identity with SEQ ID NO: 235, at most 75% amino acid identity with SEQ ID NO: 235, at most 80% amino acid identity with SEQ ID NO: 235, at most 85% amino acid identity with SEQ ID NO: 235, at most 90% amino acid identity with SEQ ID NO: 235 or at most 95% amino acid identity with SEQ ID NO: 235.

In other aspects of this embodiment, a SV-40 virus large T translocating sequence comprises a polypeptide having, e.g., at most one, two, three, four, five, six, seven, eight, nine, or 10 non-contiguous amino acid substitutions relative to SEQ ID NO: 235. In other aspects of this embodiment, a SV-40 virus large T translocating sequence comprises a polypeptide having, e.g., at least one, two, three, four, five, six, seven, eight, nine, or 10 non-contiguous amino acid substitutions relative to SEQ ID NO: 235. In yet other aspects of this embodiment, a SV-40 virus large T translocating sequence comprises a polypeptide having, e.g., at most one, two, three, four, five, six, seven, eight, nine, or 10 non-contiguous amino acid deletions relative to SEQ ID NO: 235. In other aspects of this embodiment, a SV-40 virus large T translocating sequence comprises a polypeptide having, e.g., at least one, two, three, four, five, six, seven, eight, nine, or 10 non-contiguous amino acid deletions relative to SEQ ID NO: 235. In still other aspects of this embodiment, a SV-40 virus large T translocating sequence comprises a polypeptide having, e.g., at most one, two, three, four, five, six, seven, eight, nine, or 10 non-contiguous amino acid additions relative to SEQ ID NO: 235. In other aspects of this embodiment, a SV-40 virus large T translocating sequence comprises a polypeptide having, e.g., at least one, two, three, four, five, six, seven, eight, nine, or 10 non-contiguous amino acid additions relative to SEQ ID NO: 235.

In other aspects of this embodiment, a SV-40 virus large T translocating sequence comprises a polypeptide having, e.g., at most one, two, three, four, five, six, seven, eight, nine, or 10 contiguous amino acid substitutions relative to SEQ ID NO: 235. In other aspects of this embodiment, a SV-40 virus large T translocating sequence comprises a polypeptide having, e.g., at least one, two, three, four, five, six, seven, eight, nine, or 10 contiguous amino acid substitutions relative to SEQ ID NO: 235. In yet other aspects of this embodiment, a SV-40 virus large T translocating sequence comprises a polypeptide having, e.g., at most one, two, three, four, five, six, seven, eight, nine, or 10 contiguous amino acid deletions relative to SEQ ID NO: 235. In other aspects of this embodiment, a SV-40 virus large T translocating sequence comprises a polypeptide having, e.g., at least one, two, three, four, five, six, seven, eight, nine, or 10 contiguous amino acid deletions relative to SEQ ID NO: 235. In still other aspects of this embodiment, a SV-40 virus large T translocating sequence comprises a polypeptide having, e.g., at most one, two, three, four, five, six, seven, eight, nine, or 10 contiguous amino acid additions relative to SEQ ID NO: 235. In other aspects of this embodiment, a SV-40 virus large T translocating sequence comprises a polypeptide having, e.g., at least one, two, three, four, five, six, seven, eight, nine, or 10 contiguous amino acid additions relative to SEQ ID NO: 235.

In another embodiment, a binding domain comprises a translocating sequence comprises a TAT translocating sequence. In another embodiment, a binding domain comprises a translocating sequence derived from a TAT translocating sequence. In an aspect of this embodiment, a binding domain comprises a TAT translocating sequence comprises SEQ ID NO: 236. In another aspect of this embodiment, a binding domain comprises a TAT translocating sequence derived from SEQ ID NO: 236.

In other aspects of this embodiment, a TAT translocating sequence comprises a polypeptide having, e.g., at least 70% amino acid identity with SEQ ID NO: 236, at least 75% amino acid identity with SEQ ID NO: 236, at least 80% amino acid identity with SEQ ID NO: 236, at least 85% amino acid identity with SEQ ID NO: 236, at least 90% amino acid identity with SEQ ID NO: 236 or at least 95% amino acid identity with SEQ ID NO: 236. In yet other aspects of this embodiment, a TAT translocating sequence comprises a polypeptide having, e.g., at most 70% amino acid identity with SEQ ID NO: 236, at most 75% amino acid identity with SEQ ID NO: 236, at most 80% amino acid identity with SEQ ID NO: 236, at most 85% amino acid identity with SEQ ID NO: 236, at most 90% amino acid identity with SEQ ID NO: 236 or at most 95% amino acid identity with SEQ ID NO: 236.

In other aspects of this embodiment, a TAT translocating sequence comprises a polypeptide having, e.g., at most one, two, three, four, five, six, seven, eight, nine, or 10 non-contiguous amino acid substitutions relative to SEQ ID NO: 236. In other aspects of this embodiment, a TAT translocating sequence comprises a polypeptide having, e.g., at least one, two, three, four, five, six, seven, eight, nine, or 10 non-contiguous amino acid substitutions relative to SEQ ID NO: 236. In yet other aspects of this embodiment, a TAT translocating sequence comprises a polypeptide having, e.g., at most one, two, three, four, five, six, seven, eight, nine, or 10 non-contiguous amino acid deletions relative to SEQ ID NO: 236. In other aspects of this embodiment, a TAT translocating sequence comprises a polypeptide having, e.g., at least one, two, three, four, five, six, seven, eight, nine, or 10 non-contiguous amino acid deletions relative to SEQ ID NO: 236. In still other aspects of this embodiment, a TAT translocating sequence comprises a polypeptide having, e.g., at most one, two, three, four, five, six, seven, eight, nine, or 10 non-contiguous amino acid additions relative to SEQ ID NO: 236. In other aspects of this embodiment, a TAT translocating sequence comprises a polypeptide having, e.g., at least one, two, three, four, five, six, seven, eight, nine, or 10 non-contiguous amino acid additions relative to SEQ ID NO: 236.

In other aspects of this embodiment, a TAT translocating sequence comprises a polypeptide having, e.g., at most one, two, three, four, five, six, seven, eight, nine, or 10 contiguous amino acid substitutions relative to SEQ ID NO: 236. In other aspects of this embodiment, a TAT translocating sequence comprises a polypeptide having, e.g., at least one, two, three, four, five, six, seven, eight, nine, or 10 contiguous amino acid substitutions relative to SEQ ID NO: 236. In yet other aspects of this embodiment, a TAT translocating sequence comprises a polypeptide having, e.g., at most one, two, three, four, five, six, seven, eight, nine, or 10 contiguous amino acid deletions relative to SEQ ID NO: 236. In other aspects of this embodiment, a TAT translocating sequence comprises a polypeptide having, e.g., at least one, two, three, four, five, six, seven, eight, nine, or 10 contiguous amino acid deletions relative to SEQ ID NO: 236. In still other aspects of this embodiment, a TAT translocating sequence comprises a polypeptide having, e.g., at most one, two, three, four, five, six, seven, eight, nine, or 10 contiguous amino acid additions relative to SEQ ID NO: 236. In other aspects of this embodiment, a TAT translocating sequence comprises a polypeptide having, e.g., at least one, two, three, four, five, six, seven, eight, nine, or 10 contiguous amino acid additions relative to SEQ ID NO: 236.

In another embodiment, a binding domain comprises a translocating sequence comprises an adenovirus translocating sequence. In another embodiment, a binding domain comprises a translocating sequence derived from an adenovirus translocating sequence. In an aspect of this embodiment, a binding domain comprises an adenovirus translocating sequence comprises SEQ ID NO: 237. In another aspect of this embodiment, a binding domain comprises an adenovirus translocating sequence derived from SEQ ID NO: 237.

In other aspects of this embodiment, an adenovirus translocating sequence comprises a polypeptide having, e.g., at least 70% amino acid identity with SEQ ID NO: 237, at least 75% amino acid identity with SEQ ID NO: 237, at least 80% amino acid identity with SEQ ID NO: 237, at least 85% amino acid identity with SEQ ID NO: 237, at least 90% amino acid identity with SEQ ID NO: 237 or at least 95% amino acid identity with SEQ ID NO: 237. In yet other aspects of this embodiment, an adenovirus translocating sequence comprises a polypeptide having, e.g., at most 70% amino acid identity with SEQ ID NO: 237, at most 75% amino acid identity with SEQ ID NO: 237, at most 80% amino acid identity with SEQ ID NO: 237, at most 85% amino acid identity with SEQ ID NO: 237, at most 90% amino acid identity with SEQ ID NO: 237 or at most 95% amino acid identity with SEQ ID NO: 237.

In other aspects of this embodiment, an adenovirus translocating sequence comprises a polypeptide having, e.g., at most one, two, three, four, five, six, seven, eight, nine, or 10 non-contiguous amino acid substitutions relative to SEQ ID NO: 237. In other aspects of this embodiment, an adenovirus translocating sequence comprises a polypeptide having, e.g., at least one, two, three, four, five, six, seven, eight, nine, or 10 non-contiguous amino acid substitutions relative to SEQ ID NO: 237. In yet other aspects of this embodiment, an adenovirus translocating sequence comprises a polypeptide having, e.g., at most one, two, three, four, five, six, seven, eight, nine, or 10 non-contiguous amino acid deletions relative to SEQ ID NO: 237. In other aspects of this embodiment, an adenovirus translocating sequence comprises a polypeptide having, e.g., at least one, two, three, four, five, six, seven, eight, nine, or 10 non-contiguous amino acid deletions relative to SEQ ID NO: 237. In still other aspects of this embodiment, an adenovirus translocating sequence comprises a polypeptide having, e.g., at most one, two, three, four, five, six, seven, eight, nine, or 10 non-contiguous amino acid additions relative to SEQ ID NO: 237. In other aspects of this embodiment, an adenovirus translocating sequence comprises a polypeptide having, e.g., at least one, two, three, four, five, six, seven, eight, nine, or 10 non-contiguous amino acid additions relative to SEQ ID NO: 237.

In other aspects of this embodiment, an adenovirus translocating sequence comprises a polypeptide having, e.g., at most one, two, three, four, five, six, seven, eight, nine, or 10 contiguous amino acid substitutions relative to SEQ ID NO: 237. In other aspects of this embodiment, an adenovirus translocating sequence comprises a polypeptide having, e.g., at least one, two, three, four, five, six, seven, eight, nine, or 10 contiguous amino acid substitutions relative to SEQ ID NO: 237. In yet other aspects of this embodiment, an adenovirus translocating sequence comprises a polypeptide having, e.g., at most one, two, three, four, five, six, seven, eight, nine, or 10 contiguous amino acid deletions relative to SEQ ID NO: 237. In other aspects of this embodiment, an adenovirus translocating sequence comprises a polypeptide having, e.g., at least one, two, three, four, five, six, seven, eight, nine, or 10 contiguous amino acid deletions relative to SEQ ID NO: 237. In still other aspects of this embodiment, an adenovirus translocating sequence comprises a polypeptide having, e.g., at most one, two, three, four, five, six, seven, eight, nine, or 10 contiguous amino acid additions relative to SEQ ID NO: 237. In other aspects of this embodiment, an adenovirus translocating sequence comprises a polypeptide having, e.g., at least one, two, three, four, five, six, seven, eight, nine, or 10 contiguous amino acid additions relative to SEQ ID NO: 237.

In another embodiment, a binding domain comprises a translocating sequence comprises an integrin binding domain translocating sequence. In another embodiment, a binding domain comprises a translocating sequence derived from an integrin binding domain translocating sequence. In an aspect of this embodiment, a binding domain comprises an integrin binding domain translocating sequence comprises SEQ ID NO: 238. In another aspect of this embodiment, a binding domain comprises an integrin binding domain translocating sequence derived from SEQ ID NO: 238.

In other aspects of this embodiment, an integrin binding domain translocating sequence comprises a polypeptide having, e.g., at least 70% amino acid identity with SEQ ID NO: 238, at least 75% amino acid identity with SEQ ID NO: 238, at least 80% amino acid identity with SEQ ID NO: 238, at least 85% amino acid identity with SEQ ID NO: 238, at least 90% amino acid identity with SEQ ID NO: 238 or at least 95% amino acid identity with SEQ ID NO: 238. In yet other aspects of this embodiment, an integrin binding domain translocating sequence comprises a polypeptide having, e.g., at most 70% amino acid identity with SEQ ID NO: 238, at most 75% amino acid identity with SEQ ID NO: 238, at most 80% amino acid identity with SEQ ID NO: 238, at most 85% amino acid identity with SEQ ID NO: 238, at most 90% amino acid identity with SEQ ID NO: 238 or at most 95% amino acid identity with SEQ ID NO: 238.

In other aspects of this embodiment, an integrin binding domain translocating sequence comprises a polypeptide having, e.g., at most one, two, three, four, five, six, seven, eight, nine, or 10 non-contiguous amino acid substitutions relative to SEQ ID NO: 238. In other aspects of this embodiment, an integrin binding domain translocating sequence comprises a polypeptide having, e.g., at least one, two, three, four, five, six, seven, eight, nine, or 10 non-contiguous amino acid substitutions relative to SEQ ID NO: 238. In yet other aspects of this embodiment, an integrin binding domain translocating sequence comprises a polypeptide having, e.g., at most one, two, three, four, five, six, seven, eight, nine, or 10 non-contiguous amino acid deletions relative to SEQ ID NO: 238. In other aspects of this embodiment, an integrin binding domain translocating sequence comprises a polypeptide having, e.g., at least one, two, three, four, five, six, seven, eight, nine, or 10 non-contiguous amino acid deletions relative to SEQ ID NO: 238. In still other aspects of this embodiment, an integrin binding domain translocating sequence comprises a polypeptide having, e.g., at most one, two, three, four, five, six, seven, eight, nine, or 10 non-contiguous amino acid additions relative to SEQ ID NO: 238. In other aspects of this embodiment, an integrin binding domain translocating sequence comprises a polypeptide having, e.g., at least one, two, three, four, five, six, seven, eight, nine, or 10 non-contiguous amino acid additions relative to SEQ ID NO: 238.

In other aspects of this embodiment, an integrin binding domain translocating sequence comprises a polypeptide having, e.g., at most one, two, three, four, five, six, seven, eight, nine, or 10 contiguous amino acid substitutions relative to SEQ ID NO: 238. In other aspects of this embodiment, an integrin binding domain translocating sequence comprises a polypeptide having, e.g., at least one, two, three, four, five, six, seven, eight, nine, or 10 contiguous amino acid substitutions relative to SEQ ID NO: 238. In yet other aspects of this embodiment, an integrin binding domain translocating sequence comprises a polypeptide having, e.g., at most one, two, three, four, five, six, seven, eight, nine, or 10 contiguous amino acid deletions relative to SEQ ID NO: 238. In other aspects of this embodiment, an integrin binding domain translocating sequence comprises a polypeptide having, e.g., at least one, two, three, four, five, six, seven, eight, nine, or 10 contiguous amino acid deletions relative to SEQ ID NO: 238. In still other aspects of this embodiment, an integrin binding domain translocating sequence comprises a polypeptide having, e.g., at most one, two, three, four, five, six, seven, eight, nine, or 10 contiguous amino acid additions relative to SEQ ID NO: 238. In other aspects of this embodiment, an integrin binding domain translocating sequence comprises a polypeptide having, e.g., at least one, two, three, four, five, six, seven, eight, nine, or 10 contiguous amino acid additions relative to SEQ ID NO: 238.

In another embodiment, a binding domain comprises a translocating sequence comprises a Kaposi FGF membrane translocating sequence. In another embodiment, a binding domain comprises a translocating sequence derived from a Kaposi FGF membrane translocating sequence. In an aspect of this embodiment, a binding domain comprises a Kaposi FGF membrane translocating sequence comprises SEQ ID NO: 239. In another aspect of this embodiment, a binding domain comprises a Kaposi FGF membrane translocating sequence derived from SEQ ID NO: 239.

In other aspects of this embodiment, a Kaposi FGF membrane translocating sequence comprises a polypeptide having, e.g., at least 70% amino acid identity with SEQ ID NO: 239, at least 75% amino acid identity with SEQ ID NO: 239, at least 80% amino acid identity with SEQ ID NO: 239, at least 85% amino acid identity with SEQ ID NO: 239, at least 90% amino acid identity with SEQ ID NO: 239 or at least 95% amino acid identity with SEQ ID NO: 239. In yet other aspects of this embodiment, a Kaposi FGF membrane translocating sequence comprises a polypeptide having, e.g., at most 70% amino acid identity with SEQ ID NO: 239, at most 75% amino acid identity with SEQ ID NO: 239, at most 80% amino acid identity with SEQ ID NO: 239, at most 85% amino acid identity with SEQ ID NO: 239, at most 90% amino acid identity with SEQ ID NO: 239 or at most 95% amino acid identity with SEQ ID NO: 239.

In other aspects of this embodiment, a Kaposi FGF membrane translocating sequence comprises a polypeptide having, e.g., at most one, two, three, four, five, six, seven, eight, nine, or 10 non-contiguous amino acid substitutions relative to SEQ ID NO: 239. In other aspects of this embodiment, a Kaposi FGF membrane translocating sequence comprises a polypeptide having, e.g., at least one, two, three, four, five, six, seven, eight, nine, or 10 non-contiguous amino acid substitutions relative to SEQ ID NO: 239. In yet other aspects of this embodiment, a Kaposi FGF membrane translocating sequence comprises a polypeptide having, e.g., at most one, two, three, four, five, six, seven, eight, nine, or 10 non-contiguous amino acid deletions relative to SEQ ID NO: 239. In other aspects of this embodiment, a Kaposi FGF membrane translocating sequence comprises a polypeptide having, e.g., at least one, two, three, four, five, six, seven, eight, nine, or 10 non-contiguous amino acid deletions relative to SEQ ID NO: 239. In still other aspects of this embodiment, a Kaposi FGF membrane translocating sequence comprises a polypeptide having, e.g., at most one, two, three, four, five, six, seven, eight, nine, or 10 non-contiguous amino acid additions relative to SEQ ID NO: 239. In other aspects of this embodiment, a Kaposi FGF membrane translocating sequence comprises a polypeptide having, e.g., at least one, two, three, four, five, six, seven, eight, nine, or 10 non-contiguous amino acid additions relative to SEQ ID NO: 239.

In other aspects of this embodiment, a Kaposi FGF membrane translocating sequence comprises a polypeptide having, e.g., at most one, two, three, four, five, six, seven, eight, nine, or 10 contiguous amino acid substitutions relative to SEQ ID NO: 239. In other aspects of this embodiment, a Kaposi FGF membrane translocating sequence comprises a polypeptide having, e.g., at least one, two, three, four, five, six, seven, eight, nine, or 10 contiguous amino acid substitutions relative to SEQ ID NO: 239. In yet other aspects of this embodiment, a Kaposi FGF membrane translocating sequence comprises a polypeptide having, e.g., at most one, two, three, four, five, six, seven, eight, nine, or 10 contiguous amino acid deletions relative to SEQ ID NO: 239. In other aspects of this embodiment, a Kaposi FGF membrane translocating sequence comprises a polypeptide having, e.g., at least one, two, three, four, five, six, seven, eight, nine, or 10 contiguous amino acid deletions relative to SEQ ID NO: 239. In still other aspects of this embodiment, a Kaposi FGF membrane translocating sequence comprises a polypeptide having, e.g., at most one, two, three, four, five, six, seven, eight, nine, or 10 contiguous amino acid additions relative to SEQ ID NO: 239. In other aspects of this embodiment, a Kaposi FGF membrane translocating sequence comprises a polypeptide having, e.g., at least one, two, three, four, five, six, seven, eight, nine, or 10 contiguous amino acid additions relative to SEQ ID NO: 239.

In another embodiment, a binding domain comprises a translocating sequence comprises a Nuclear Localization Signal translocating sequence. In another embodiment, a binding domain comprises a translocating sequence derived from a Nuclear Localization Signal translocating sequence. In an aspect of this embodiment, a binding domain comprises a Nuclear Localization Signal translocating sequence comprises SEQ ID NO: 240. In another aspect of this embodiment, a binding domain comprises a Nuclear Localization Signal translocating sequence derived from SEQ ID NO: 240.

In other aspects of this embodiment, a Nuclear Localization Signal translocating sequence comprises a polypeptide having, e.g., at least 70% amino acid identity with SEQ ID NO: 240, at least 75% amino acid identity with SEQ ID NO: 240, at least 80% amino acid identity with SEQ ID NO: 240, at least 85% amino acid identity with SEQ ID NO: 240, at least 90% amino acid identity with SEQ ID NO: 240 or at least 95% amino acid identity with SEQ ID NO: 240. In yet other aspects of this embodiment, a Nuclear Localization Signal translocating sequence comprises a polypeptide having, e.g., at most 70% amino acid identity with SEQ ID NO: 240, at most 75% amino acid identity with SEQ ID NO: 240, at most 80% amino acid identity with SEQ ID NO: 240, at most 85% amino acid identity with SEQ ID NO: 240, at most 90% amino acid identity with SEQ ID NO: 240 or at most 95% amino acid identity with SEQ ID NO: 240.

In other aspects of this embodiment, a Nuclear Localization Signal translocating sequence comprises a polypeptide having, e.g., at most one, two, three, four, five, six, seven, eight, nine, or 10 non-contiguous amino acid substitutions relative to SEQ ID NO: 240. In other aspects of this embodiment, a Nuclear Localization Signal translocating sequence comprises a polypeptide having, e.g., at least one, two, three, four, five, six, seven, eight, nine, or 10 non-contiguous amino acid substitutions relative to SEQ ID NO: 240. In yet other aspects of this embodiment, a Nuclear Localization Signal translocating sequence comprises a polypeptide having, e.g., at most one, two, three, four, five, six, seven, eight, nine, or 10 non-contiguous amino acid deletions relative to SEQ ID NO: 240. In other aspects of this embodiment, a Nuclear Localization Signal translocating sequence comprises a polypeptide having, e.g., at least one, two, three, four, five, six, seven, eight, nine, or 10 non-contiguous amino acid deletions relative to SEQ ID NO: 240. In still other aspects of this embodiment, a Nuclear Localization Signal translocating sequence comprises a polypeptide having, e.g., at most one, two, three, four, five, six, seven, eight, nine, or 10 non-contiguous amino acid additions relative to SEQ ID NO: 240. In other aspects of this embodiment, a Nuclear Localization Signal translocating sequence comprises a polypeptide having, e.g., at least one, two, three, four, five, six, seven, eight, nine, or 10 non-contiguous amino acid additions relative to SEQ ID NO: 240.

In other aspects of this embodiment, a Nuclear Localization Signal translocating sequence comprises a polypeptide having, e.g., at most one, two, three, four, five, six, seven, eight, nine, or 10 contiguous amino acid substitutions relative to SEQ ID NO: 240. In other aspects of this embodiment, a Nuclear Localization Signal translocating sequence comprises a polypeptide having, e.g., at least one, two, three, four, five, six, seven, eight, nine, or 10 contiguous amino acid substitutions relative to SEQ ID NO: 240. In yet other aspects of this embodiment, a Nuclear Localization Signal translocating sequence comprises a polypeptide having, e.g., at most one, two, three, four, five, six, seven, eight, nine, or 10 contiguous amino acid deletions relative to SEQ ID NO: 240. In other aspects of this embodiment, a Nuclear Localization Signal translocating sequence comprises a polypeptide having, e.g., at least one, two, three, four, five, six, seven, eight, nine, or 10 contiguous amino acid deletions relative to SEQ ID NO: 240. In still other aspects of this embodiment, a Nuclear Localization Signal translocating sequence comprises a polypeptide having, e.g., at most one, two, three, four, five, six, seven, eight, nine, or 10 contiguous amino acid additions relative to SEQ ID NO: 240. In other aspects of this embodiment, a Nuclear Localization Signal translocating sequence comprises a polypeptide having, e.g., at least one, two, three, four, five, six, seven, eight, nine, or 10 contiguous amino acid additions relative to SEQ ID NO: 240.

In another embodiment, a binding domain comprises a translocating sequence comprises a Transportan translocating sequence. In another embodiment, a binding domain comprises a translocating sequence derived from a Transportan translocating sequence. In an aspect of this embodiment, a binding domain comprises a Transportan translocating sequence comprises SEQ ID NO: 241. In another aspect of this embodiment, a binding domain comprises a Transportan translocating sequence derived from SEQ ID NO: 241.

In other aspects of this embodiment, a Transportan translocating sequence comprises a polypeptide having, e.g., at least 70% amino acid identity with SEQ ID NO: 241, at least 75% amino acid identity with SEQ ID NO: 241, at least 80% amino acid identity with SEQ ID NO: 241, at least 85% amino acid identity with SEQ ID NO: 241, at least 90% amino acid identity with SEQ ID NO: 241 or at least 95% amino acid identity with SEQ ID NO: 241. In yet other aspects of this embodiment, a Transportan translocating sequence comprises a polypeptide having, e.g., at most 70% amino acid identity with SEQ ID NO: 241, at most 75% amino acid identity with SEQ ID NO: 241, at most 80% amino acid identity with SEQ ID NO: 241, at most 85% amino acid identity with SEQ ID NO: 241, at most 90% amino acid identity with SEQ ID NO: 241 or at most 95% amino acid identity with SEQ ID NO: 241.

In other aspects of this embodiment, a Transportan translocating sequence comprises a polypeptide having, e.g., at most one, two, three, four, five, six, seven, eight, nine, or 10 non-contiguous amino acid substitutions relative to SEQ ID NO: 241. In other aspects of this embodiment, a Transportan translocating sequence comprises a polypeptide having, e.g., at least one, two, three, four, five, six, seven, eight, nine, or 10 non-contiguous amino acid substitutions relative to SEQ ID NO: 241. In yet other aspects of this embodiment, a Transportan translocating sequence comprises a polypeptide having, e.g., at most one, two, three, four, five, six, seven, eight, nine, or 10 non-contiguous amino acid deletions relative to SEQ ID NO: 241. In other aspects of this embodiment, a Transportan translocating sequence comprises a polypeptide having, e.g., at least one, two, three, four, five, six, seven, eight, nine, or 10 non-contiguous amino acid deletions relative to SEQ ID NO: 241. In still other aspects of this embodiment, a Transportan translocating sequence comprises a polypeptide having, e.g., at most one, two, three, four, five, six, seven, eight, nine, or 10 non-contiguous amino acid additions relative to SEQ ID NO: 241. In other aspects of this embodiment, a Transportan translocating sequence comprises a polypeptide having, e.g., at least one, two, three, four, five, six, seven, eight, nine, or 10 non-contiguous amino acid additions relative to SEQ ID NO: 241.

In other aspects of this embodiment, a Transportan translocating sequence comprises a polypeptide having, e.g., at most one, two, three, four, five, six, seven, eight, nine, or 10 contiguous amino acid substitutions relative to SEQ ID NO: 241. In other aspects of this embodiment, a Transportan translocating sequence comprises a polypeptide having, e.g., at least one, two, three, four, five, six, seven, eight, nine, or 10 contiguous amino acid substitutions relative to SEQ ID NO: 241. In yet other aspects of this embodiment, a Transportan translocating sequence comprises a polypeptide having, e.g., at most one, two, three, four, five, six, seven, eight, nine, or 10 contiguous amino acid deletions relative to SEQ ID NO: 241. In other aspects of this embodiment, a Transportan translocating sequence comprises a polypeptide having, e.g., at least one, two, three, four, five, six, seven, eight, nine, or 10 contiguous amino acid deletions relative to SEQ ID NO: 241. In still other aspects of this embodiment, a Transportan translocating sequence comprises a polypeptide having, e.g., at most one, two, three, four, five, six, seven, eight, nine, or 10 contiguous amino acid additions relative to SEQ ID NO: 241. In other aspects of this embodiment, a Transportan translocating sequence comprises a polypeptide having, e.g., at least one, two, three, four, five, six, seven, eight, nine, or 10 contiguous amino acid additions relative to SEQ ID NO: 241.

In another embodiment, a binding domain comprises a translocating sequence comprises a HSV-1 VP 22 translocating sequence. In another embodiment, a binding domain comprises a translocating sequence derived from a HSV-1 VP 22 translocating sequence. In an aspect of this embodiment, a binding domain comprises a HSV-1 VP 22 translocating sequence comprises SEQ ID NO: 242. In another aspect of this embodiment, a binding domain comprises a HSV-1 VP 22 translocating sequence derived from SEQ ID NO: 242.

In other aspects of this embodiment, a HSV-1 VP 22 translocating sequence comprises a polypeptide having, e.g., at least 70% amino acid identity with SEQ ID NO: 242, at least 75% amino acid identity with SEQ ID NO: 242, at least 80% amino acid identity with SEQ ID NO: 242, at least 85% amino acid identity with SEQ ID NO: 242, at least 90% amino acid identity with SEQ ID NO: 242 or at least 95% amino acid identity with SEQ ID NO: 242. In yet other aspects of this embodiment, a HSV-1 VP 22 translocating sequence comprises a polypeptide having, e.g., at most 70% amino acid identity with SEQ ID NO: 242, at most 75% amino acid identity with SEQ ID NO: 242, at most 80% amino acid identity with SEQ ID NO: 242, at most 85% amino acid identity with SEQ ID NO: 242, at most 90% amino acid identity with SEQ ID NO: 242 or at most 95% amino acid identity with SEQ ID NO: 242.

In other aspects of this embodiment, a HSV-1 VP 22 translocating sequence comprises a polypeptide having, e.g., at most one, two, three, four, five, six, seven, eight, nine, or 10 non-contiguous amino acid substitutions relative to SEQ ID NO: 242. In other aspects of this embodiment, a HSV-1 VP 22 translocating sequence comprises a polypeptide having, e.g., at least one, two, three, four, five, six, seven, eight, nine, or 10 non-contiguous amino acid substitutions relative to SEQ ID NO: 242. In yet other aspects of this embodiment, a HSV-1 VP 22 translocating sequence comprises a polypeptide having, e.g., at most one, two, three, four, five, six, seven, eight, nine, or 10 non-contiguous amino acid deletions relative to SEQ ID NO: 242. In other aspects of this embodiment, a HSV-1 VP 22 translocating sequence comprises a polypeptide having, e.g., at least one, two, three, four, five, six, seven, eight, nine, or 10 non-contiguous amino acid deletions relative to SEQ ID NO: 242. In still other aspects of this embodiment, a HSV-1 VP 22 translocating sequence comprises a polypeptide having, e.g., at most one, two, three, four, five, six, seven, eight, nine, or 10 non-contiguous amino acid additions relative to SEQ ID NO: 242. In other aspects of this embodiment, a HSV-1 VP 22 translocating sequence comprises a polypeptide having, e.g., at least one, two, three, four, five, six, seven, eight, nine, or 10 non-contiguous amino acid additions relative to SEQ ID NO: 242.

In other aspects of this embodiment, a HSV-1 VP 22 translocating sequence comprises a polypeptide having, e.g., at most one, two, three, four, five, six, seven, eight, nine, or 10 contiguous amino acid substitutions relative to SEQ ID NO: 242. In other aspects of this embodiment, a HSV-1 VP 22 translocating sequence comprises a polypeptide having, e.g., at least one, two, three, four, five, six, seven, eight, nine, or 10 contiguous amino acid substitutions relative to SEQ ID NO: 242. In yet other aspects of this embodiment, a HSV-1 VP 22 translocating sequence comprises a polypeptide having, e.g., at most one, two, three, four, five, six, seven, eight, nine, or 10 contiguous amino acid deletions relative to SEQ ID NO: 242. In other aspects of this embodiment, a HSV-1 VP 22 translocating sequence comprises a polypeptide having, e.g., at least one, two, three, four, five, six, seven, eight, nine, or 10 contiguous amino acid deletions relative to SEQ ID NO: 242. In still other aspects of this embodiment, a HSV-1 VP 22 translocating sequence comprises a polypeptide having, e.g., at most one, two, three, four, five, six, seven, eight, nine, or 10 contiguous amino acid additions relative to SEQ ID NO: 242. In other aspects of this embodiment, a HSV-1 VP 22 translocating sequence comprises a polypeptide having, e.g., at least one, two, three, four, five, six, seven, eight, nine, or 10 contiguous amino acid additions relative to SEQ ID NO: 242.

In another embodiment, a binding domain comprises a translocating sequence comprises a Penetratin translocating sequence. In another embodiment, a binding domain comprises a translocating sequence derived from a Penetratin translocating sequence. In an aspect of this embodiment, a binding domain comprises a Penetratin translocating sequence comprises SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252 or SEQ ID NO: 253. In another aspect of this embodiment, a binding domain comprises a Penetratin translocating sequence derived from SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252 or SEQ ID NO: 253.

In other aspects of this embodiment, a Penetratin translocating sequence comprises a polypeptide having, e.g., at least 70% amino acid identity with SEQ ID NO: 243, at least 75% amino acid identity with SEQ ID NO: 243, at least 80% amino acid identity with SEQ ID NO: 243, at least 85% amino acid identity with SEQ ID NO: 243, at least 90% amino acid identity with SEQ ID NO: 243 or at least 95% amino acid identity with SEQ ID NO: 243. In yet other aspects of this embodiment, a Penetratin translocating sequence comprises a polypeptide having, e.g., at most 70% amino acid identity with SEQ ID NO: 243, at most 75% amino acid identity with SEQ ID NO: 243, at most 80% amino acid identity with SEQ ID NO: 243, at most 85% amino acid identity with SEQ ID NO: 243, at most 90% amino acid identity with SEQ ID NO: 243 or at most 95% amino acid identity with SEQ ID NO: 243.

In other aspects of this embodiment, a Penetratin translocating sequence comprises a polypeptide having, e.g., at most one, two, three, four, five, six, seven, eight, nine, or 10 non-contiguous amino acid substitutions relative to SEQ ID NO: 243. In other aspects of this embodiment, a Penetratin translocating sequence comprises a polypeptide having, e.g., at least one, two, three, four, five, six, seven, eight, nine, or 10 non-contiguous amino acid substitutions relative to SEQ ID NO: 243. In yet other aspects of this embodiment, a Penetratin translocating sequence comprises a polypeptide having, e.g., at most one, two, three, four, five, six, seven, eight, nine, or 10 non-contiguous amino acid deletions relative to SEQ ID NO: 243. In other aspects of this embodiment, a Penetratin translocating sequence comprises a polypeptide having, e.g., at least one, two, three, four, five, six, seven, eight, nine, or 10 non-contiguous amino acid deletions relative to SEQ ID NO: 243. In still other aspects of this embodiment, a Penetratin translocating sequence comprises a polypeptide having, e.g., at most one, two, three, four, five, six, seven, eight, nine, or 10 non-contiguous amino acid additions relative to SEQ ID NO: 243. In other aspects of this embodiment, a Penetratin translocating sequence comprises a polypeptide having, e.g., at least one, two, three, four, five, six, seven, eight, nine, or 10 non-contiguous amino acid additions relative to SEQ ID NO: 243.

In other aspects of this embodiment, a Penetratin translocating sequence comprises a polypeptide having, e.g., at most one, two, three, four, five, six, seven, eight, nine, or 10 contiguous amino acid substitutions relative to SEQ ID NO: 243. In other aspects of this embodiment, a Penetratin translocating sequence comprises a polypeptide having, e.g., at least one, two, three, four, five, six, seven, eight, nine, or 10 contiguous amino acid substitutions relative to SEQ ID NO: 243. In yet other aspects of this embodiment, a Penetratin translocating sequence comprises a polypeptide having, e.g., at most one, two, three, four, five, six, seven, eight, nine, or 10 contiguous amino acid deletions relative to SEQ ID NO: 243. In other aspects of this embodiment, a Penetratin translocating sequence comprises a polypeptide having, e.g., at least one, two, three, four, five, six, seven, eight, nine, or 10 contiguous amino acid deletions relative to SEQ ID NO: 243. In still other aspects of this embodiment, a Penetratin translocating sequence comprises a polypeptide having, e.g., at most one, two, three, four, five, six, seven, eight, nine, or 10 contiguous amino acid additions relative to SEQ ID NO: 243. In other aspects of this embodiment, a Penetratin translocating sequence comprises a polypeptide having, e.g., at least one, two, three, four, five, six, seven, eight, nine, or 10 contiguous amino acid additions relative to SEQ ID NO: 243.

Another example of a binding domain, includes, without limitation, an antibody to a coated pit protein, such as, e.g., a clatherin antibody and an Adaptor Protein-2 (adaptin) antibody; an antibody to a caveolae-associated protein, such as, e.g., a caveolin-1 antibody and a GPI-linked receptor protein antibody.

One major route of receptor-mediated endocytosis is by means of endocytotic coated pits. These specialized sites on the plasma membrane of eukaryotic cells are responsible for internalization of many cell surface receptors, usually after ligand binding. The coated pits serve in part to concentrate the receptors for internalization within far fewer endosomes than would be the case if each receptor were individually internalized. Coated pits consist largely of two major proteins: clatherin and the adaptor protein (adaptin) Adaptor Protein-2 (AP-2). Assembly of the coated pit is thought to be initiated by the binding of AP-2 molecules to a receptor or ligand-docking site in the membrane. The receptor:AP-2 complex then recruits the structural protein clatherin.

Sorting signals present in many membrane proteins, such as cell surface receptors, provide for recognition and binding of AP-2 to these proteins as the initial step of coated pit formation. One common sorting signal is the amino acid sequence YXXΦ (wherein Φ is an amino acid with a bulky hydrophobic side chain, such as leucine, phenylalanine, methionine and valine), which provides a signal for rapid internalization. This signal is recognized by and binds to the μ2 subunit of AP-2, and mediates rapid internalization by mammalian cells. Preferably, the signal is present ion such a way as to be displayed on the cytosolic side of the membrane. See e.g., Bonifacino et al., J. Cell Biol. 145: 923 (May 31, 1999).

At least one binding domain of a multivalent Clostridial toxin of the present invention may comprise at least one sorting signal for an adaptin, preferably AP-2. Preferably, the binding site comprising this sorting signal is present in addition to another distinct binding domain which will directly bind a cell surface receptor.

In certain embodiments, a multivalent Clostridial toxin of the present invention comprising two or more pancreatic acinar cell targeting moieties may be administered to treat pancreatitis; the use of CCK forms and derivatives capable of selective binding to CCK receptors of pancreatic acinar cells is disclosed in U.S. Pat. No. 6,843,998. In one preferred embodiment of this aspect of the present invention, two or more binding moieties of the present invention are independently a CCK or CCK derivative.

In another embodiment of the invention for treatment of, e.g., acute or chronic pancreatitis, at least one binding moiety of the multivalent Clostridial toxin is a CCK or CCK derivative, and at least one additional binding region comprises a region of a glycosyl phosphatylinositol (GPI)-linked membrane protein that directly or indirectly binds caveolin-1 binding. Alternatively, the additional binding region may comprise a ligand capable of binding a GPI-linked membrane protein, particularly a membrane associated cell surface receptor, as the CCK receptor, like the TNF and other known receptors, is known to be concentrated and recruited for internalization by caveolae.

Caveolae are discrete membrane domains present in many cell types; they are not thought to be present in neural cells. Caveolae are comprised largely of detergent-insoluble lipids and lipid associated proteins, including a major protein, caveolin-1. Caveolae are also known to recruit and concentrate GPI-linked membrane proteins, a family of membrane proteins that includes cell surface receptors. Further, caveolae appear to participate in a non clatherin-associated form of endocytosis, and experiments have been reported in which gene transfer vectors have been directed to GPI-linked receptor proteins to facilitate gene transfer.

Thus, for example, the urokinase plasminogen activator receptor (uPAR) is a GPI-linked membrane protein that appears to facilitate endocytosis upon binding of its cognate ligand urokinase plasminigen activator (uPA). See e.g., Drapkin et al., J. CLIN. INVEST. 105: 589-596 (Mar. 1, 2000), incorporated by reference as part of this specification. uPA is a 55 KDa protein secreted by alveolar epithelial cells that cleaves plasminogen to plasmin and is known to degrade the extracellular matrix in alveoli. Targeting such cells, which also display the uPAR, with the multivalent Clostridial toxin of the present invention comprising, for example, two or more binding domains comprising a uPAR-binding region derived from, for example, uPA or an anti-uPAR antibody may be of therapeutic use in the treatment of respiratory and lung diseases such as e.g., cystic fibrosis, since the ligand-bound receptor is subject to endocytosis in a ligand dependent manner. Thus, for example, a patent may be administered a mist or dispersion comprising such multivalent Clostridial toxin as a delivery mechanism.

In certain embodiments the target cell may comprise a cell comprising a membrane protein that displays an antibody variable region at the cell surface. In such a case the multivalent Clostridial toxin comprises two or more binding domains, with at least one binding domain comprising an antigen able to selectively bind the antibody variable region. In a preferred embodiment, the multivalent Clostridial toxin may comprise more than one binding region comprising an antigen able to selectively bind to said antibody variable region.

Alternatively, the multivalent Clostridial toxin of the present invention (comprising more than one binding domain), may have at least one binding domain comprising an antigen-binding portion of an antibody H or L chain, wherein the antigen comprises a cell surface marker for a target cell. For example, and without limitation, the multivalent Clostridial toxin of the present invention may comprise at least one binding domain comprising an antibody variable region that selectively binds to an eosinophil cell surface marker (for example, the cell surface markers CD 44 and CD 69), thereby aiding in alleviating the symptoms of allergy. The nomenclature "CD" is derived from the use of monoclonal antibodies directed towards a given cell type, and stands for "Cluster of Differentiation".

In another example, the multivalent Clostridial toxin derivative may be used to inhibit or decrease the rate of infection of T helper cells by the human immunodeficiency virus (HIV). T helper cells are commonly identified by virtue of their display of the cell surface marker CD4. The HIV virus uses the CD4 marker to gain entry into and thereby infect T helper cells, and appears to employ viral fusion proteins sharing remarkable similarity to the SNARE system to invade cells through a membrane fusion mechanism. See e.g., Duman & Forte, AM. J. PHYSIOL. CELL PHYSIOL. 285: C237-C249 (2003). A multivalent Clostridial toxin of the present invention comprising at least one, and preferably two or more, anti-CD4 antibody domain or similar CD4 "addressable"

binding domain would permit the neurotoxin protease domain to deny the virus use of the SNARE proteins for entry and/or exit of the cell. Moreover, alteration of the toxin proteolytic domain to selectively recognize and cleave one or more of the HIV viral fusion proteins, using such techniques as directed evolution, site directed mutagenesis or other well known molecular biology methods, could provide a method of reducing the extent of, or eliminating, HIV infection.

In another aspect of the invention, a multivalent Clostridial toxin comprises, in part, a protease cleavage site. As used herein, the term "protease cleavage site" means a scissile bond together with adjacent or non-adjacent recognition elements, or both, sufficient for detectable proteolysis at the scissile bond by a protease under conditions suitable for protease activity. A protease cleavage site can be an endogenous protease cleavage site or an exogenous protease cleavage site. One function of the protease cleavage site may be to convert the single-chain polypeptide form of a Clostridial toxin into the di-chain form. Another role of a protease cleavage site may be change the conformational structure of a binding domain, thereby facilitating the binding domain's ability to bind to its cognate receptor, e.g., a binding domain may function only as a dimer, like the binding domains from the TGFβ superfamily; or exposing the amino terminal end of a binding domain, like the binding domains of opiod family members. Likewise, the location and kind of protease cleavage site may be critical because certain targeting domains require a free amino-terminal or carboxyl-terminal amino acid. For example, when a targeting domain is placed between two other domains, one criterion for selection of a protease cleavage site could be whether the protease that cleaves its site leaves a flush cut, exposing the free amino-terminal or carboxyl-terminal of the altered targeting domain necessary for selective binding of the targeting domain to its receptor. The selection and placement of a protease cleavage site is well known in the art.

It is envisioned that a multivalent Clostridial toxin may comprise one protease cleavage site. It is also envisioned that a multivalent Clostridial toxin may comprise a plurality of protease cleavage sites. Thus. in an embodiment, a multivalent Clostridial toxin may comprise one protease cleavage site. In another embodiment, a multivalent Clostridial toxin may comprise a plurality protease cleavage site. In aspects of this embodiment, a multivalent Clostridial toxin may comprise, e.g., at least one protease cleavage site, at least two protease cleavage sites, at least three protease cleavage sites, at least four protease cleavage sites, or at least five protease cleavage sites. In other aspects of this embodiment, a multivalent Clostridial toxin may comprise, e.g., at most one protease cleavage site, at most two protease cleavage sites, at most three protease cleavage sites, at most four protease cleavage sites, or at most five protease cleavage sites. In still other aspects of this embodiment, a multivalent Clostridial toxin may comprise, e.g., one protease cleavage site, two protease cleavage sites, three protease cleavage sites, four protease cleavage sites, or five protease cleavage sites.

It is envisioned that a multivalent Clostridial toxin can comprise an endogenous protease cleavage. As used herein, the term "endogenous protease cleavage site" is synonymous with "di-chain loop protease cleavage site," "naturally occurring Clostridial toxin di-chain loop protease cleavage site" or "naturally occurring Clostridial toxin protease cleavage site" and means a naturally occurring Clostridial toxin protease cleavage site found within the di-chain loop region of a naturally occurring Clostridial toxin and includes, without limitation, naturally occurring Clostridial toxin di-chain loop protease cleavage site variants, such as, e.g., Clostridial toxin di-chain loop protease cleavage site isoforms and Clostridial toxin di-chain loop protease cleavage site subtypes. Non-limiting examples of an endogenous protease cleavage site, include, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

As mentioned above, Clostridial toxins are translated as a single-chain polypeptide of approximately 150 kDa that is subsequently cleaved by proteolytic scission within a disulfide loop by a naturally-occurring protease. This posttranslational processing yields a di-chain molecule comprising an approximately 50 kDa light chain (LC) and an approximately 100 kDa heavy chain (HC) held together by a single disulphide bond and noncovalent interactions. While the identity of the protease is currently unknown, the di-chain loop protease cleavage site for many Clostridial toxins has been proposed. In BoNTs, cleavage at K448-A449 converts the single polypeptide form of BoNT/A into the di-chain form; cleavage at K441-A442 converts the single polypeptide form of BoNT/B into the di-chain form; cleavage at K449-T450 converts the single polypeptide form of BoNT/C1 into the di-chain form; cleavage at R445-D446 converts the single polypeptide form of BoNT/D into the di-chain form; cleavage at R422-K423 converts the single polypeptide form of BoNT/E into the di-chain form; cleavage at K439-A440 converts the single polypeptide form of BoNT/F into the di-chain form; and cleavage at K446-S447 converts the single polypeptide form of BoNT/G into the di-chain form. Proteolytic cleavage of the single polypeptide form of TeNT at A457-S458 results in the di-chain form. Such a di-chain loop protease cleavage site is operably-linked in-frame to a multivalent Clostridial toxin as a fusion protein.

However, it should also be noted that additional cleavage sites within the di-chain loop also appear to be cleaved resulting in the generation of a small peptide fragment being lost. As a non-limiting example, BoNT/A single-chain polypeptide cleave ultimately results in the loss of a ten amino acid fragment within the di-chain loop. Thus, in BoNTs, cleavage at S441-L442 converts the single polypeptide form of BoNT/A into the di-chain form; cleavage at G444-1445 converts the single polypeptide form of BoNT/B into the di-chain form; cleavage at S445-L446 converts the single polypeptide form of BoNT/C1 into the di-chain form; cleavage at K442-N443 converts the single polypeptide form of BoNT/D into the di-chain form; cleavage at K419-G420 converts the single polypeptide form of BoNT/E into the di-chain form; cleavage at K423-S424 converts the single polypeptide form of BoNT/E into the di-chain form; cleavage at K436-G437 converts the single polypeptide form of BoNT/F into the di-chain form; cleavage at T444-G445 converts the single polypeptide form of BoNT/G into the di-chain form; and cleavage at E448-Q449 converts the single polypeptide form of BoNT/G into the di-chain form.

As used herein, the term "di-chain loop region" means the amino acid sequence of a Clostridial toxin containing a protease cleavage site used to convert the single-chain form of a Clostridial toxin into the di-chain form. Non-limiting examples of a Clostridial toxin di-chain loop region, include, a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; and a di-chain loop region of TeNT comprising amino acids 439-467 of SEQ ID NO: 8 (Table 9).

ring Clostridial toxin. Non-limiting examples of exogenous protease cleavage sites include, e.g., an enterokinase cleavage site (Table 10); a Thrombin cleavage site (Table 10); a Factor Xa cleavage site (Table 10); a human rhinovirus 3C protease cleavage site (Table 10); a tobacco etch virus (TEV) protease cleavage site (Table 10); a dipeptidyl aminopeptidase cleavage site; a small ubiquitin-like modifier (SUMO)/ubiquitin-

TABLE 9

Di-chain Loop Region of Clostridial Toxins

| Toxin | SEQ ID NO: | Light Chain Region | Di-chain Loop Region Containing the Naturally-occurring Protease Cleavage Site | Heavy Chain Region |
|---|---|---|---|---|
| BoNT/A | 1 | NMNFTKLKNFTGLFEFYKLL | CVRGIITSKTKSLDKGYNK*----ALNDLC | IKVNNWDL |
| BoNT/B | 2 | KQAYEEISKEHLAVYKIQM | CKSVK*------------------APGIC | IDVDNEDL |
| BoNT/C1 | 3 | PALRKVNPENMLYLFTKF | CHKAIDGRSLYNK*------------TLDC | RELLVKNTDL |
| BoNT/D | 4 | PALQKLSSESVVDLFTKV | CLRLTKNSR*---------------DDSTC | IKVKNNRL |
| BoNT/E | 5 | IITPITGRGLVKKIIRF | CKNIVSVKGIR*--------------KSIC | IEINNGEL |
| BoNT/F | 6 | IIDSIPDKGLVEKIVKF | CKSVIPRKGTK*------------APPRLC | IRVNNSEL |
| BoNT/G | 7 | KEAYEEISLEHLVIYRIAM | CKPVMYKNTGK*--------------SEQC | IIVNNEDL |
| TeNT | 8 | TNAFRNVDGSGLVSKLIGL | CKKIIPPTNIRENLYNRTA*SLTDLGGELC | IKIKNEDL |

The amino acid sequence displayed are as follows: BoNT/A, residues 325-462 of SEQ ID No: 1; BoNT/B, residues 332-454 of SEQ ID No: 2; BoNT/C1, residues 334-463 of SEQ ID No: 3; BoNT/D, residues 334-458 of SEQ ID No: 4; BoNT/E, residues 311-434 of SEQ ID No: 5; BoNT/F, residues 328-453 of SEQ ID No: 6; BoNT/G, residues 331-458 of SEQ ID No: 7; and TeNT, residues 334-474 of SEQ ID No: 8.
An asterisks (*) indicates a peptide bond that is cleaved by a Clostridial toxin protease.

Thus, in an embodiment, a multivalent Clostridial toxin comprising a protease cleavage site comprises an endogenous protease cleavage site. In aspects of this embodiment, an endogenous protease cleavage site comprises, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site or a TeNT di-chain loop protease cleavage site.

In other aspects of this embodiment, an endogenous protease cleavage site comprises, e.g., a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; or a di-chain loop region of TeNT comprising amino acids 439-467 of SEQ ID NO: 8.

It is also envisioned that a multivalent Clostridial toxin can comprise an exogenous protease cleavage. As used herein, the term "exogenous protease cleavage site" is synonymous with a "non-naturally occurring Clostridial toxin protease cleavage site" and means a protease cleavage site that is not normally present in a di-chain loop region from a naturally occurring Clostridial toxin. Non-limiting examples of exogenous protease cleavage sites include, e.g., an enterokinase cleavage site (Table 10); a Thrombin cleavage site (Table 10); a Factor Xa cleavage site (Table 10); a human rhinovirus 3C protease cleavage site (Table 10); a tobacco etch virus (TEV) protease cleavage site (Table 10); a dipeptidyl aminopeptidase cleavage site; a small ubiquitin-like modifier (SUMO)/ubiquitin-like protein-1(ULP-1) protease cleavage site, such as, e.g., MADSEVNQEAKPEVKPEVKPETHIN-LKVSDGSSEIFFKI KKTTPLRRLMEAFAKRQGKEMD-SLRFLYDGIRIQADQTPEDLDMEDNDIIEAHREQIGG (SEQ ID. NO: 271); and a Clostridial toxin substrate cleavage site.

As mentioned above, a Clostridial toxin is converted from a single polypeptide form into a di-chain molecule by proteolytic cleavage. While the naturally-occurring protease is currently not known, cleavage occurs within the di-chain loop region between the two cysteine residues that form the disulfide bridge (see Table 9). Replacement of an endogenous protease cleavage site with an exogenous protease cleavage site will enable cleavage of a multivalent Clostridial toxin disclosed in the present specification when expressed in an organism that does not produce the naturally-occurring protease used to cleave the di-chain loop region of a toxin. Similarly, an addition of an exogenous protease cleavage site in the di-chain loop region will also enable cleavage of a multivalent Clostridial toxin disclosed in the present specification when expressed in an organism that does not produce the naturally-occurring protease used to cleave the di-chain loop region of a toxin. Furthermore, cleavage at an exogenous protease cleavage site can facilitate a change in the conformational structure of a binding domain, thereby facilitating the binding domain's ability to bind to its cognate receptor, e.g., a binding domain may function only as a dimer, like the binding domains from the TGFβ superfamily; or exposing the amino terminal end of a binding domain, like the binding domains of opiod family members.

TABLE 10

Exogenous Protease Cleavage Sites

| Protease Cleavage Site | Consensus Sequence | Non-limiting Examples | SEQ ID NO: |
|---|---|---|---|
| Bovine enterokinase | DDDDK* | DDDDK* | 254 |
| Tobacco Etch Virus (TEV) | E $P^5$ $P^4YP^2Q*(G/S)$, where $P^2$, $P^4$ and $P^5$ can be any amino acid | ENLYFQ*G | 255 |
| | | ENLYFQ*S | 256 |
| | | ENIYTQ*G | 257 |
| | | ENIYTQ*S | 258 |
| | | ENIYLQ*G | 259 |
| | | ENIYLQ*S | 260 |
| | | ENVYFQ*G | 261 |
| | | ENVYSQ*S | 262 |
| | | ENVYSQ*G | 263 |
| | | ENVYSQ*S | 264 |
| Human Rhinovirus 3C | $P^5P^4LFQ*GP$ where $P^4$ is G, A, V, L, I, M, S or T and $P^5$ can any amino acid, with D or E preferred. | EALFQ*GP | 265 |
| | | EVLFQ*GP | 266 |
| | | ELLFQ*GP | 267 |
| | | DALFQ*GP | 268 |
| | | DVLFQ*GP | 269 |
| | | DLLFQ*GP | 270 |
| SUMO/ULP-1 | Tertiary structure | polypeptide-G* | 271 |
| Thrombin | $P^3P^2(R/K)*P^{1'}$, where $P^3$ is any amino acid and $P^2$ or $P^{1'}$ is G with the other position being any amino acid | GVR*G | 272 |
| | | SAR*G | 273 |
| | | SLR*G | 274 |
| | | DGR*I | 275 |
| | | QGK*I | 276 |
| Thrombin | $P^4P^3(R/K)*P^{1'}P^{2'}$ where $P^{1'}$ and $P^{2'}$ can be any amino acid except for acidic amino acids like D or E; and $P^3$ and $P^4$ are hydrophobic amino acids like F, L, I, Y, W, V, M, P, C or A | LVPR*GS | 277 |
| | | LVPK*GS | 278 |
| | | FIPR*TF | 279 |
| | | VLPR*SF | 280 |
| | | IVPR*SF | 281 |
| | | IVPR*GY | 282 |
| | | VVPR*GV | 283 |
| | | VLPR*LI | 284 |
| | | VMPR*SL | 285 |
| | | MFPR*SL | 286 |
| Coagulation Factor Xa | I(E/D)GR* | IDGR* | 287 |
| | | IEGR* | 288 |

An asterisks (*) indicates the peptide bond that is cleaved by the indicated protease.

It is envisioned that an exogenous protease cleavage site of any and all lengths can be useful in aspects of the present invention with the proviso that the exogenous protease cleavage site is capable of being cleaved by its respective protease. Thus, in aspects of this embodiment, an exogenous protease cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, an exogenous protease cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

In aspects of this embodiment, a di-chain loop region can be modified to substitute a naturally-occurring protease cleavage site for an exogenous protease cleavage site. In this type of modification, the naturally-occurring protease cleavage site is made inoperable and thus can not be cleaved by its protease. Only the exogenous protease cleavage site can be cleaved by its corresponding exogenous protease. In this type of modification, the exogenous protease site is operably-linked in-frame to a multivalent Clostridial toxin as a fusion protein and the site can be cleaved by its respective exogenous protease. As a non-limiting example, a single-chain modified BoNT/A comprising an exogenous protease cleavage site in the di-chain loop region can be cleaved by its respective exogenous protease to produce the di-chain form of the toxin.

In other aspects of this embodiment, a di-chain loop region can be modified to include an exogenous protease cleavage site in addition to the naturally-occurring protease cleavage site. In this type of modification, both cleavage sites are operably-linked in-frame to a multivalent Clostridial toxin as a fusion protein and both sites can be cleaved by their respective proteases. As a non-limiting example, a single-chain modified BoNT/A that comprises a di-chain loop containing both the naturally-occurring BoNT/A di-chain loop protease cleavage site and an exogenous protease cleavage site can be cleaved by either the naturally occurring di-chain loop protease or by the appropriate exogenous protease to produce the di-chain form of the toxin.

A naturally-occurring protease cleavage site can be made inoperable by altering at least the two amino acids flanking the peptide bond cleaved by the naturally-occurring di-chain loop protease. More extensive alterations can be made, with the proviso that the two cysteine residues of the di-chain loop region remain intact and can still form the disulfide bridge. Non-limiting examples of an amino acid alteration include deletion of an amino acid or replacement of the original amino acid with a different amino acid. Thus, in one embodiment, a naturally-occurring protease cleavage site is made inoperable by altering the two amino acids flanking the peptide bond cleaved by a naturally-occurring protease. In other aspects of this embodiment, a naturally-occurring protease cleavage site is made inoperable by altering, e.g., at least three amino acids including the two amino acids flanking the peptide bond cleaved by a naturally-occurring protease; at least four amino acids including the two amino acids flanking the peptide bond cleaved by a naturally-occurring protease; at least five amino acids including the two amino acids flanking the peptide bond cleaved by a naturally-occurring protease; at least six amino acids including the two amino acids flanking the peptide bond cleaved by a naturally-occurring protease; at least seven amino acids including the two amino acids flanking the peptide bond cleaved by a naturally-occurring protease; at least eight amino acids including the two amino acids flanking the peptide bond cleaved by a naturally-occurring protease; at least nine amino acids including the two amino acids flanking the peptide bond cleaved by a naturally-occurring protease; at least ten amino acids including the two amino acids flanking the peptide bond cleaved by a naturally-occurring protease; at least 15 amino acids including the two amino acids flanking the peptide bond cleaved by a naturally-occurring protease; or at least 20 amino acids including the two amino acids flanking the peptide bond cleaved by a naturally-occurring protease.

In still other aspects of this embodiment, a naturally-occurring di-chain protease cleavage site is made inoperable by altering, e.g., at most three amino acids including the two amino acids flanking the peptide bond cleaved by a naturally-occurring protease; at most four amino acids including the two amino acids flanking the peptide bond cleaved by a naturally-occurring protease; at most five amino acids including the two amino acids flanking the peptide bond cleaved by a naturally-occurring protease; at most six amino acids including the two amino acids flanking the peptide bond cleaved by a naturally-occurring protease; at most seven amino acids including the two amino acids flanking the peptide bond cleaved by a naturally-occurring protease; at most eight amino acids including the two amino acids flanking the peptide bond cleaved by a naturally-occurring protease; at most nine amino acids including the two amino acids flanking the peptide bond cleaved by a naturally-occurring protease; at most ten amino acids including the two amino acids flanking the peptide bond cleaved by a naturally-occurring protease; at most 15 amino acids including the two amino acids flanking the peptide bond cleaved by a naturally-occurring protease; or at most 20 amino acids including the two amino acids flanking the peptide bond cleaved by a naturally-occurring protease.

In an embodiment, an exogenous protease cleavage site is located within the di-chain loop of a multivalent Clostridial toxin. In aspects of this embodiment, a multivalent Clostridial toxin comprises an exogenous protease cleavage site comprises, e.g., a bovine enterokinase protease cleavage site, a Tobacco Etch Virus protease cleavage site, a Human Rhinovirus 3C protease cleavage site, a SUMO/ULP-1 protease cleavage site, a Thrombin protease cleavage site or a Factor Xa protease cleavage site. In other aspects of this embodiment, an exogenous protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In an aspect of this embodiment, an exogenous protease cleavage site can be, e.g., a bovine enterokinase cleavage site is located within the di-chain loop of a multivalent Clostridial toxin. In other aspects of the embodiment, an exogenous protease cleavage site can be, e.g., a bovine enterokinase protease cleavage site located within the di-chain loop of a multivalent Clostridial toxin comprises SEQ ID NO: 254. Is still other aspects of this embodiment, a bovine enterokinase protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In another aspect of this embodiment, an exogenous protease cleavage site can be, e.g., a Tobacco Etch Virus protease cleavage site is located within the di-chain loop of a multivalent Clostridial toxin. In other aspects of the embodiment, an exogenous protease cleavage site can be, e.g., a Tobacco Etch Virus protease cleavage site located within the di-chain loop of a multivalent Clostridial toxin comprises SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263 or SEQ ID NO: 264. Is still other aspects of this embodiment, a Tobacco Etch Virus protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In still another aspect of this embodiment, an exogenous protease cleavage site can be, e.g., a Human Rhinovirus 3C protease cleavage site is located within the di-chain loop of a multivalent Clostridial toxin. In other aspects of the embodiment, an exogenous protease cleavage site can be, e.g., a Human Rhinovirus 3C protease cleavage site located within the di-chain loop of a multivalent Clostridial toxin comprises SEQ ID NO: 265, SEQ ID NO: 266, SEQ ID NO: 267, SEQ ID NO: 268, SEQ ID NO: 269 or SEQ ID NO: 270. Is still other aspects of this embodiment, a Human Rhinovirus 3C protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In yet another aspect of this embodiment, an exogenous protease cleavage site can be, e.g., a SUMO/ULP-1 protease cleavage site is located within the di-chain loop of a multivalent Clostridial toxin. In other aspects of the embodiment, an exogenous protease cleavage site can be, e.g., a SUMO/ULP-1 protease cleavage site located within the di-chain loop of a multivalent Clostridial toxin comprises SEQ ID NO: 271. Is still other aspects of this embodiment, a SUMO/ULP-1 protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In a further aspect of this embodiment, an exogenous protease cleavage site can be, e.g., a Thrombin protease cleavage site is located within the di-chain loop of a multivalent Clostridial toxin. In other aspects of the embodiment, an exogenous protease cleavage site can be, e.g., a Thrombin protease cleavage site located within the di-chain loop of a multivalent Clostridial toxin comprises SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285 or SEQ ID NO: 286. Is still other aspects of this embodiment, a Thrombin protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In another aspect of this embodiment, an exogenous protease cleavage site can be, e.g., a Coagulation Factor Xa protease cleavage site is located within the di-chain loop of a multivalent Clostridial toxin. In other aspects of the embodiment, an exogenous protease cleavage site can be, e.g., a Coagulation Factor Xa protease cleavage site located within the di-chain loop of a multivalent Clostridial toxin comprises SEQ ID NO: 287 or SEQ ID NO: 288. Is still other aspects of this embodiment, a Coagulation Factor Xa protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In another embodiment, an exogenous protease site comprises a Clostridial toxin substrate cleavage site. As used herein, the term "Clostridial toxin substrate cleavage site" means a scissile bond together with adjacent or non-adjacent recognition elements, or both, sufficient for detectable proteolysis at the scissile bond by a Clostridial toxin under conditions suitable for Clostridial toxin protease activity. By definition, a Clostridial toxin substrate cleavage site is susceptible to cleavage by at least one Clostridial toxin under conditions suitable for Clostridial toxin protease activity. Non-limiting examples of Clostridial toxin substrate cleavage site are disclosed in, e.g., Steward, L. E. et al., Self-Activating Clostridial Toxins, U.S. Patent Application 60/718,616 (Sep. 19, 2005).

It is understood that a multivalent Clostridial toxin disclosed in the present specification can optionally include one or more additional components. As a non-limiting example of an optional component, a multivalent Clostridial toxin can further comprise a flexible region comprising a flexible spacer. Non-limiting examples of a flexible spacer include, e.g., a G-spacer GGGGS (SEQ ID NO: 289) or an A-spacer EAAAK (SEQ ID NO: 290). A flexible region comprising flexible spacers can be used to adjust the length of a polypeptide region in order to optimize a characteristic, attribute or property of a polypeptide. Such a flexible region is operably-linked in-frame to the multivalent Clostridial toxin as a fusion protein. As a non-limiting example, a polypeptide region comprising one or more flexible spacers in tandem can be use to better expose a protease cleavage site thereby facilitating cleavage of that site by a protease. As another non-limiting example, a polypeptide region comprising one or more flexible spacers in tandem can be use to better present an enhanced targeting domain, thereby facilitating the binding of that enhanced targeting domain to its receptor.

Thus, in an embodiment, a multivalent Clostridial toxin disclosed in the present specification can further comprise a flexible region comprising a flexible spacer. In another embodiment, a multivalent Clostridial toxin disclosed in the present specification can further comprise flexible region comprising a plurality of flexible spacers in tandem. In aspects of this embodiment, a flexible region can comprise in tandem, e.g., at least 1 G-spacer, at least 2 G-spacers, at least 3 G-spacers, at least 4 G-spacers or at least 5 G-spacers. In other aspects of this embodiment, a flexible region can comprise in tandem, e.g., at most 1 G-spacer, at most 2 G-spacers, at most 3 G-spacers, at most 4 G-spacers or at most 5 G-spacers. In still other aspects of this embodiment, a flexible region can comprise in tandem, e.g., at least 1 A-spacer, at least 2 A-spacers, at least 3 A-spacers, at least 4 A-spacers or at least 5 A-spacers. In still other aspects of this embodiment, a flexible region can comprise in tandem, e.g., at most 1 A-spacer, at most 2 A-spacers, at most 3 A-spacers, at most 4 A-spacers or at most 5 A-spacers. In another aspect of this embodiment, a multivalent Clostridial toxin can comprise a flexible region comprising one or more copies of the same flexible spacers, one or more copies of different flexible-spacer regions, or any combination thereof.

In aspects of this embodiment, a multivalent Clostridial toxin comprising a flexible spacer can be, e.g., a modified BoNT/A, a modified BoNT/B, a modified BoNT/C1, a modified BoNT/D, a modified BoNT/E, a modified BoNT/F, a modified BoNT/G or a modified TeNT.

It is envisioned that a multivalent Clostridial toxin disclosed in the present specification can comprise a flexible spacer in any and all locations with the proviso that multivalent Clostridial toxin is capable of performing the intoxication process. In aspects of this embodiment, a flexible spacer is positioned between, e.g., an enzymatic domain and a translocation domain, an enzymatic domain and a binding domain, an enzymatic domain and a protease cleavage site. In other aspects of this embodiment, a G-spacer is positioned between, e.g., an enzymatic domain and a translocation domain, an enzymatic domain and a binding domain, an enzymatic domain and a protease cleavage site. In other aspects of this embodiment, a A-spacer is positioned between, e.g., an enzymatic domain and a translocation domain, an enzymatic domain and a binding domain, an enzymatic domain and a protease cleavage site.

In other aspects of this embodiment, a flexible spacer is positioned between, e.g., a binding domain and a translocation domain, a binding domain and an enzymatic domain, a binding domain and a protease cleavage site. In other aspects of this embodiment, a G-spacer is positioned between, e.g., a binding domain and a translocation domain, a binding domain and an enzymatic domain, a binding domain and a protease cleavage site. In other aspects of this embodiment, a A-spacer is positioned between, e.g., a binding domain and a translocation domain, a binding domain and an enzymatic domain, a binding domain and a protease cleavage site.

In yet other aspects of this embodiment, a flexible spacer is positioned between, e.g., a translocation domain and an enzymatic domain, an translocation domain and a binding domain, an translocation domain and a protease cleavage site. In other aspects of this embodiment, a G-spacer is positioned between, e.g., a translocation domain and an enzymatic domain, an translocation domain and a binding domain, an translocation domain and a protease cleavage site. In other aspects of this embodiment, a A-spacer is positioned between, e.g., a translocation domain and an enzymatic domain, an translocation domain and a binding domain, a translocation domain and a protease cleavage site.

Figure 6A:
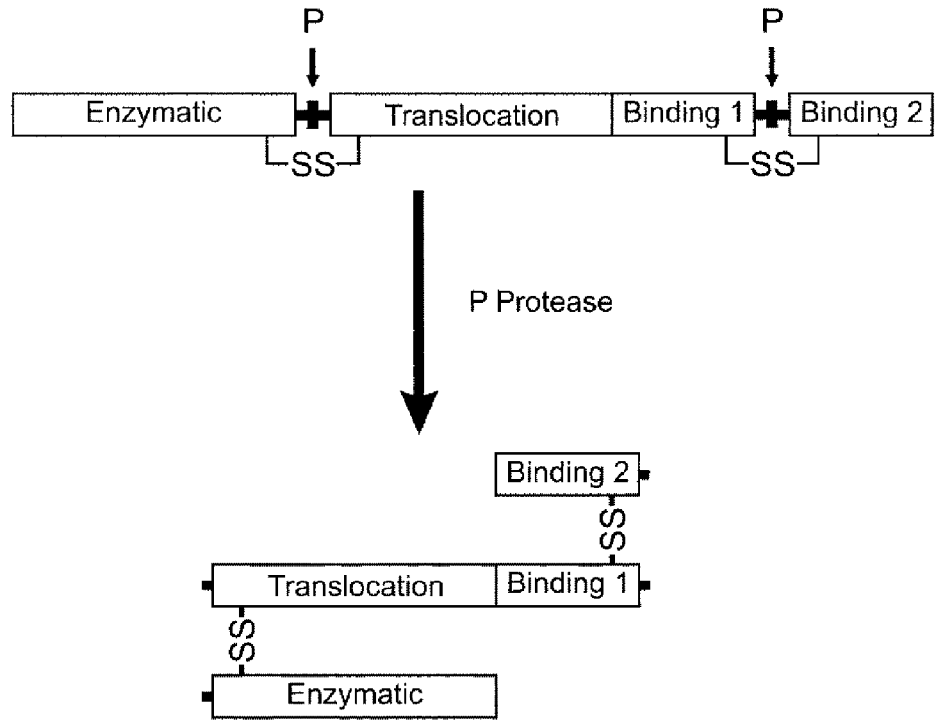
FIG. 6A depicts the single polypeptide form of a multivalent Clostridial toxin with an amino to carboxyl linear organization comprising an enzymatic domain, a translocation domain, a binding domain 1 and a binding domain 2, with the di-chain loop region depicted by the double SS bracket. A first protease cleavage site (P) within a di-chain loop region is located between the enzymatic domain and translocation domain. A second protease cleavage site (P) is located between the binding domain 1 and binding domain 2. Upon proteolytic cleavage with a P protease, the single chain form of the toxin is converted to the tri-chain form. The P protease site can be a Clostridial toxin endogenous protease cleavage site or a non-Clostridial toxin exogenous protease cleavage site. Additionally, the first and second proteolytic cleavage sites can be the same site cleaved by the same protease or different sites cleaved by different proteases. Spacers can be placed between the enzymatic domain and translocation domain, the translocation domain and binding domain 1, the binding domain 1 and binding domain 2, or any combination thereof.
Figure 6B:
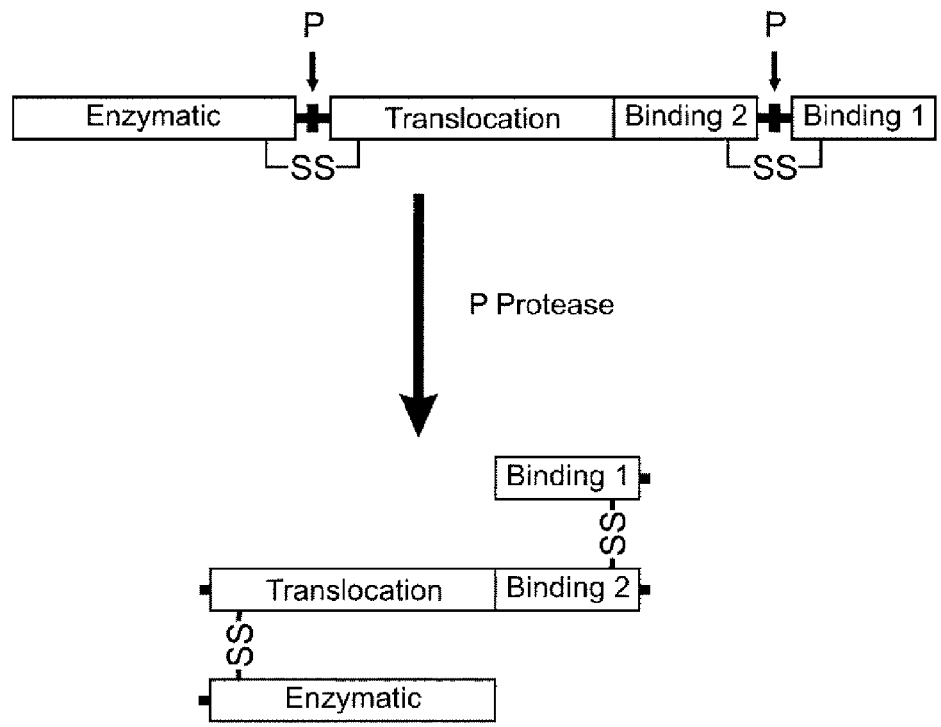
FIG. 6B depicts the single polypeptide form of a multivalent Clostridial toxin with an amino to carboxyl linear organization comprising an enzymatic domain, a translocation domain, a binding domain 2 and a binding domain 1, with the di-chain loop region depicted by the double SS bracket. A first protease cleavage site (P) within a di-chain loop region is located between the enzymatic domain and translocation domain. A second protease cleavage site (P) is located between the binding domain 2 and binding domain 1. Upon proteolytic cleavage with a P protease, the single chain form of the toxin is converted to the tri-chain form. The P protease cleavage site can be a Clostridial toxin endogenous protease cleavage site or a non-Clostridial toxin exogenous protease cleavage site. Additionally, the first and second protease cleavage sites can be the same site cleaved by the same protease or different sites cleaved by different proteases. Spacers can be placed between the enzymatic domain and translocation domain, the translocation domain and binding domain 2, the binding domain 2 and binding domain 1, or any combination thereof.

It is envisioned that a multivalent Clostridial toxin disclosed in the present specification can comprise a binding domain 1 and a binding domain 2 in any and all locations with the proviso that multivalent Clostridial toxin is capable of performing the intoxication process. Non-limiting examples are depicted in FIG. 4), FIG. 5, and FIG. 6. The enzymatic domain of naturally-occurring Clostridial toxins contains the native start methionine. Thus, in domain organizations where the enzymatic domain is not in the amino-terminal location an amino acid sequence comprising the start methionine should be placed in front of the amino-terminal domain. Likewise, where a binding domain is in the amino-terminal position, an amino acid sequence comprising a start methionine and a protease cleavage site may be operably-linked in situations in which the enhanced targeting domain requires a free amino terminus, see, e.g., Shengwen Li et al., *Degradable Clostridial Toxins*, International Patent Application Publication WO 2006/026780 (Mar. 9, 2006). In addition, it is known in the art that when adding a polypeptide that is operably-linked to the amino terminus of another polypeptide comprising the start methionine that the original methionine residue can be deleted.

Thus, in an embodiment, a multivalent Clostridial toxin can comprise an amino to carboxyl linear organization comprising a binding domain 1, a translocation domain, a binding domain 2 and an enzymatic domain. In an aspect of this embodiment, a multivalent Clostridial toxin can comprise an amino to carboxyl linear organization comprising a binding domain 1, a translocation domain, a binding domain 2, a protease cleavage site and an enzymatic domain. In another aspect of this embodiment, a multivalent Clostridial toxin can comprise an amino to carboxyl linear organization comprising a binding domain 1, a translocation domain, a binding domain 2, an endogenous protease cleavage site and an enzymatic domain. In another aspect of this embodiment, a multivalent Clostridial toxin can comprise an amino to carboxyl linear organization comprising a binding domain 1, a translocation domain, a binding domain 2, an exogenous protease cleavage site and an enzymatic domain.

In another embodiment, a multivalent Clostridial toxin can comprise an amino to carboxyl linear organization comprising an enzymatic domain, a binding domain 1, a translocation domain and a binding domain 2. In an aspect of this embodiment, a multivalent Clostridial toxin can comprise an amino to carboxyl linear organization comprising an enzymatic domain, a protease cleavage site, a binding domain 1, a translocation domain and a binding domain 2. In another aspect of this embodiment, a multivalent Clostridial toxin can comprise an amino to carboxyl linear organization comprising an enzymatic domain, an endogenous protease cleavage site, a binding domain 1, a translocation domain and a binding domain 2. In another aspect of this embodiment, a multivalent Clostridial toxin can comprise an amino to carboxyl linear organization comprising an enzymatic domain, an exogenous protease cleavage site, a binding domain 1, a translocation domain and a binding domain 2.

In another embodiment, a multivalent Clostridial toxin can comprise an amino to carboxyl linear organization comprising an enzymatic domain, a translocation domain, a binding domain 1 and a binding domain 2. In an aspect of this embodiment, a multivalent Clostridial toxin can comprise an amino to carboxyl linear organization comprising an enzymatic domain, a protease cleavage site, a translocation domain, a binding domain 1 and a binding domain 2. In another aspect of this embodiment, a multivalent Clostridial toxin can comprise an amino to carboxyl linear organization comprising an enzymatic domain, an endogenous protease cleavage site, a translocation domain, a binding domain 1 and a binding domain 2. In another aspect of this embodiment, a multivalent Clostridial toxin can comprise an amino to carboxyl linear organization comprising an enzymatic domain, an exogenous protease cleavage site, a translocation domain, a binding domain 1 and a binding domain 2.

In another embodiment, a multivalent Clostridial toxin can comprise an amino to carboxyl linear organization comprising an enzymatic domain, a translocation domain, a binding domain 2 and a binding domain 1. In an aspect of this embodiment, a multivalent Clostridial toxin can comprise an amino to carboxyl linear organization comprising an enzymatic domain, a protease cleavage site, a translocation domain, a binding domain 2 and a binding domain 1. In another aspect of this embodiment, a multivalent Clostridial toxin can comprise an amino to carboxyl linear organization comprising an enzymatic domain, an endogenous protease cleavage site, a translocation domain, a binding domain 2 and a binding domain 1. In another aspect of this embodiment, a multivalent Clostridial toxin can comprise an amino to carboxyl linear organization comprising an enzymatic domain, an exogenous protease cleavage site, a translocation domain, a binding domain 2 and a binding domain 1.

In another embodiment, a multivalent Clostridial toxin can comprise an amino to carboxyl linear organization comprising a binding domain 1, an enzymatic domain, a translocation domain and a binding domain 2. In an aspect of this embodiment, a multivalent Clostridial toxin can comprise an amino to carboxyl linear organization comprising a binding domain 1, an enzymatic domain, a protease cleavage site, a translocation domain and a binding domain 2. In an aspect of this embodiment, a multivalent Clostridial toxin can comprise an amino to carboxyl linear organization comprising a binding domain 1, an enzymatic domain, an endogenous protease cleavage site, a translocation domain and a binding domain 2. In an aspect of this embodiment, a multivalent Clostridial toxin can comprise an amino to carboxyl linear organization comprising a binding domain 1, an enzymatic domain, an exogenous protease cleavage site, a translocation domain and a binding domain 2.

In another embodiment, a multivalent Clostridial toxin can comprise an amino to carboxyl linear organization comprising a translocation domain, a binding domain 2, a binding domain 1 and an enzymatic domain. In an aspect of this embodiment, a multivalent Clostridial toxin can comprise an amino to carboxyl linear organization comprising a translocation domain, a binding domain 2, a protease cleavage site, a binding domain 1 and an enzymatic domain. In another aspect of this embodiment, a multivalent Clostridial toxin can comprise an amino to carboxyl linear organization comprising a translocation domain, a binding domain 2, an endogenous protease cleavage site, a binding domain 1 and an enzymatic domain. In another aspect of this embodiment, a multivalent Clostridial toxin can comprise an amino to carboxyl linear organization comprising a translocation domain, a binding domain 2, an exogenous protease cleavage site, a binding domain 1 and an enzymatic domain.

In another embodiment, a multivalent Clostridial toxin can comprise an amino to carboxyl linear organization comprising a translocation domain, a binding domain 2, an enzymatic domain and a binding domain 1. In an aspect of this embodiment, a multivalent Clostridial toxin can comprise an amino to carboxyl linear organization comprising a translocation domain, a binding domain 2, a protease cleavage site, an enzymatic domain and a binding domain 1. In another aspect of this embodiment, a multivalent Clostridial toxin can comprise an amino to carboxyl linear organization comprising a translocation domain, a binding domain 2, an endogenous protease cleavage site, an enzymatic domain and a binding domain 1. In another aspect of this embodiment, a multivalent Clostridial toxin can comprise an amino to carboxyl linear organization comprising a translocation domain, a binding domain 2, an exogenous protease cleavage site, an enzymatic domain and a binding domain 1.

In another embodiment, a multivalent Clostridial toxin can comprise an amino to carboxyl linear organization comprising a binding domain 2, a translocation domain, a binding domain 1 and an enzymatic domain. In an aspect of this embodiment, a multivalent Clostridial toxin can comprise an amino to carboxyl linear organization comprising a binding domain 2, a translocation domain, a protease cleavage site, a binding domain 1 and an enzymatic domain. In another aspect of this embodiment, a multivalent Clostridial toxin can comprise an amino to carboxyl linear organization comprising a binding domain 2, a translocation domain, an endogenous cleavage protease site, a binding domain 1 and an enzymatic domain. In another aspect of this embodiment, a multivalent Clostridial toxin can comprise an amino to carboxyl linear organization comprising a binding domain 2, a translocation domain, an exogenous protease cleavage site, a binding domain 1 and an enzymatic domain.

In another embodiment, a multivalent Clostridial toxin can comprise an amino to carboxyl linear organization comprising an enzymatic domain, a translocation domain, a binding domain 1 and a binding domain 2. In an aspect of this embodiment, a multivalent Clostridial toxin can comprise an amino to carboxyl linear organization comprising an enzymatic domain, a first protease cleavage site, a translocation domain, a binding domain 1, a second protease cleavage site, and a binding domain 2. In another aspect of this embodiment, a multivalent Clostridial toxin can comprise an amino to carboxyl linear organization comprising an enzymatic domain, a first endogenous protease cleavage site, a translocation domain, a binding domain 1, a second endogenous protease cleavage site, and a binding domain 2. In another aspect of this embodiment, a multivalent Clostridial toxin can comprise an amino to carboxyl linear organization comprising an enzymatic domain, a first exogenous protease cleavage site, a translocation domain, a binding domain 1, a second exogenous protease cleavage site, and a binding domain 2.

In another embodiment, a multivalent Clostridial toxin can comprise an amino to carboxyl linear organization comprising an enzymatic domain, a translocation domain, a binding domain 2 and a binding domain 1. In an aspect of this embodiment, a multivalent Clostridial toxin can comprise an amino to carboxyl linear organization comprising an enzymatic domain, a first protease cleavage site, a translocation domain, a binding domain 2, a second protease cleavage site, and a binding domain 1. In another aspect of this embodiment, a multivalent Clostridial toxin can comprise an amino to carboxyl linear organization comprising an enzymatic domain, a first endogenous protease cleavage site, a translocation domain, a binding domain 2, a second endogenous protease cleavage site, and a binding domain 1. In another aspect of this embodiment, a multivalent Clostridial toxin can comprise an amino to carboxyl linear organization comprising an enzymatic domain, a first exogenous protease cleavage site, a translocation domain, a binding domain 2, a second exogenous protease cleavage site, and a binding domain 1.

Aspects of the present invention provide, in part multivalent Clostridial toxins. Non-limiting examples of Clostridial toxin modifications disclosed in the present specification include, e.g., addition of a binding domain 1, addition of a binding domain 2, addition of a protease cleavage site, rearrangement of the enzymatic, translocation and binding domains and addition of a spacer region. It is understood that all such modifications do not substantially affect the ability of a multivalent Clostridial toxin to intoxicate a cell. As used herein, the term "do not substantially affect" means a multivalent Clostridial toxin can still execute the overall cellular mechanism whereby a Clostridial toxin enters a neuron and inhibits neurotransmitter release and encompasses the binding of a Clostridial toxin to a low or high affinity receptor complex, the internalization of the toxin/receptor complex, the translocation of the Clostridial toxin light chain into the cytoplasm and the enzymatic modification of a Clostridial toxin substrate. In aspects of this embodiment, the multivalent Clostridial toxin is, e.g., at least 10% as toxic as a naturally-occurring Clostridial toxin, at least 20% as toxic as a naturally-occurring Clostridial toxin, at least 30% as toxic as a naturally-occurring Clostridial toxin, at least 40% as toxic as a naturally-occurring Clostridial toxin, at least 50% as toxic as a naturally-occurring Clostridial toxin, at least 60% as toxic as a naturally-occurring Clostridial toxin, at least 70% as toxic as a naturally-occurring Clostridial toxin, at least 80% as toxic as a naturally-occurring Clostridial toxin, at least 90% as toxic as a naturally-occurring Clostridial toxin or at least 95% as toxic as a naturally-occurring Clostridial toxin. In aspects of this embodiment, the multivalent Clostridial toxin is, e.g., at most 10% as toxic as a naturally-occurring Clostridial toxin, at most 20% as toxic as a naturally-occurring Clostridial toxin, at most 30% as toxic as a naturally-occurring Clostridial toxin, at most 40% as toxic as a naturally-occurring Clostridial toxin, at most 50% as toxic as a naturally-occurring Clostridial toxin, at most 60% as toxic as a naturally-occurring Clostridial toxin, at most 70% as toxic as a naturally-occurring Clostridial toxin, at most 80% as toxic as a naturally-occurring Clostridial toxin, at most 90% as toxic as a naturally-occurring Clostridial toxin or at most 95% as toxic as a naturally-occurring Clostridial toxin.

Another aspect of the present invention provides polynucleotide molecules encoding multivalent Clostridial toxins disclosed in the present specification. It is envisioned that any and all multivalent Clostridial toxin disclosed in the present specification can be encoded by a polynucleotide molecule.

Aspects of the present invention provide, in part polynucleotide molecules. As used herein, the term "polynucleotide molecule" is synonymous with "nucleic acid molecule" and means a polymeric form of nucleotides, such as, e.g., ribonucleotides and deoxyribonucleotides, of any length. It is envisioned that any and all polynucleotide molecules that can encode a multivalent Clostridial toxin disclosed in the present specification can be useful, including, without limitation naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagmid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

Well-established molecular biology techniques that may be necessary to make a polynucleotide molecule encoding a multivalent Clostridial toxin disclosed in the present specification including, but not limited to, procedures involving polymerase chain reaction (PCR) amplification, restriction enzyme reactions, agarose gel electrophoresis, nucleic acid ligation, bacterial transformation, nucleic acid purification, nucleic acid sequencing and recombination-based techniques are routine procedures well within the scope of one skilled in the art and from the teaching herein. Non-limiting examples of specific protocols necessary to make a polynucleotide molecule encoding a multivalent Clostridial toxin are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004). Additionally, a variety of commercially available products useful for making a polynucleotide molecule encoding a multivalent Clostridial toxin are widely available. These protocols are routine procedures well within the scope of one skilled in the art and from the teaching herein.

Another aspect of the present invention provides a method of producing a multivalent Clostridial toxin disclosed in the present specification, such method comprising the step of expressing a polynucleotide molecule encoding a multivalent Clostridial toxin in a cell. Another aspect of the present invention provides a method of producing a multivalent Clostridial toxin disclosed in the present specification, such method comprising the steps of introducing an expression construct comprising a polynucleotide molecule encoding a multivalent Clostridial toxin into a cell and expressing the expression construct in the cell.

The methods disclosed in the present specification include, in part, a multivalent Clostridial toxin. It is envisioned that any and all multivalent Clostridial toxins disclosed in the present specification can be produced using the methods disclosed in the present specification. It is also envisioned that any and all polynucleotide molecules encoding a multivalent Clostridial toxins disclosed in the present specification can be useful in producing a multivalent Clostridial toxins disclosed in the present specification using the methods disclosed in the present specification.

The methods disclosed in the present specification include, in part, an expression construct. An expression construct comprises a polynucleotide molecule disclosed in the present specification operably-linked to an expression vector useful for expressing the polynucleotide molecule in a cell or cell-free extract. A wide variety of expression vectors can be employed for expressing a polynucleotide molecule encoding a multivalent Clostridial toxin, including, without limitation, a viral expression vector; a prokaryotic expression vector; eukaryotic expression vectors, such as, e.g., a yeast expression vector, an insect expression vector and a mammalian expression vector; and a cell-free extract expression vector. It is further understood that expression vectors useful to practice aspects of these methods may include those which express a multivalent Clostridial toxin under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

Thus, aspects of this embodiment include, without limitation, a viral expression vector operably-linked to a polynucleotide molecule encoding a multivalent Clostridial toxin; a prokaryotic expression vector operably-linked to a polynucleotide molecule encoding a multivalent Clostridial toxin; a yeast expression vector operably-linked to a polynucleotide molecule encoding a multivalent Clostridial toxin; an insect expression vector operably-linked to a polynucleotide molecule encoding a multivalent Clostridial toxin; and a mammalian expression vector operably-linked to a polynucleotide molecule encoding a multivalent Clostridial toxin. Other aspects of this embodiment include, without limitation, expression constructs suitable for expressing a multivalent Clostridial toxin disclosed in the present specification using a cell-free extract comprising a cell-free extract expression vector operably linked to a polynucleotide molecule encoding a multivalent Clostridial toxin.

The methods disclosed in the present specification include, in part, a cell. It is envisioned that any and all cells can be used. Thus, aspects of this embodiment include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridia perfringens, Clostridia difficile, Caulobacter crescentus, Lactococcus lactis, Methylobacterium extorquens, Neisseria meningirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, $4^{th}$ ed. 2000); ANIMAL CELL CULTURE: A PRACTICAL APPROACH (John R. W. Masters ed., Oxford University Press, $3^{rd}$ ed. 2000); MOLECULAR CLONING A LABORATORY MANUAL, supra, (2001); BASIC CELL CULTURE: A PRACTICAL APPROACH (John M. Davis, Oxford Press, $2^{nd}$ ed. 2002); and CURRENT PROTOCOLS IN MOLECULAR BIOLOGY, supra, (2004). These protocols are routine procedures within the scope of one skilled in the art and from the teaching herein.

The methods disclosed in the present specification include, in part, introducing into a cell a polynucleotide molecule. A polynucleotide molecule introduced into a cell can be transiently or stably maintained by that cell. Stably-maintained polynucleotide molecules may be extra-chromosomal and replicate autonomously, or they may be integrated into the chromosomal material of the cell and replicate non-autonomously. It is envisioned that any and all methods for introducing a polynucleotide molecule disclosed in the present specification into a cell can be used. Methods useful for introducing a nucleic acid molecule into a cell include, without limitation, chemical-mediated transfection such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated transfection, such as, e.g., biolistic particle delivery, microinjection, protoplast fusion and electroporation; and viral-mediated transfection, such as, e.g., retroviral-mediated transfection, see, e.g., Introducing Cloned Genes into Cultured Mammalian Cells, pp. 16.1-16.62 (Sambrook & Russell, eds., Molecular Cloning A Laboratory Manual, Vol. 3, $3^{rd}$ ed. 2001). One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein.

In an aspect of this embodiment, a chemical-mediated method, termed transfection, is used to introduce a polynucleotide molecule encoding a multivalent Clostridial toxin into a cell. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, Transfection of adherent and suspended cells by calcium phosphate, 33(2) Methods 136-143 (2004); diethyl-aminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., Polyethylenimine strategies for plasmid delivery to brain-derived cells, 33(2) Methods 144-150 (2004). Such chemical-mediated delivery systems can be prepared by standard methods and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

In another aspect of this embodiment, a physical-mediated method is used to introduce a polynucleotide molecule encoding a multivalent Clostridial toxin into a cell. Physical techniques include, without limitation, electroporation, biolistic and microinjection. Biolistics and microinjection techniques perforate the cell wall in order to introduce the nucleic acid molecule into the cell, see, e.g., Jeike E. Biewenga et al., Plasmid-mediated gene transfer in neurons using the biolistics technique, 71(1) J. Neurosci. Methods. 67-75 (1997); and John O'Brien & Sarah C. R. Lummis, Biolistic and diolistic transfection: using the gene gun to deliver DNA and lipophilic dyes into mammalian cells, 33(2) Methods 121-125 (2004). Electroporation, also termed electropermeabilization, uses brief, high-voltage, electrical pulses to create transient pores in the membrane through which the nucleic acid molecules enter and can be used effectively for stable and transient transfections of all cell types, see, e.g., M. Golzio et al., In vitro and in vivo electric field-mediated permeabilization, gene transfer, and expression, 33(2) Methods 126-135 (2004); and Oliver Gresch et al., New non-viral method for gene transfer into primary cells, 33(2) Methods 151-163 (2004).

In another aspect of this embodiment, a viral-mediated method, termed transduction, is used to introduce a polynucleotide molecule encoding a multivalent Clostridial toxin into a cell. In viral-mediated methods of transient transduction, the process by which viral particles infect and replicate in a host cell has been manipulated in order to use this mechanism to introduce a nucleic acid molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, Lentiviral and MLV based retroviral vectors for ex vivo and in vivo gene transfer, 33(2) Methods 164-172 (2004); and Maurizio Federico, From lentiviruses to lentivirus vectors, 229 Methods Mol. Biol. 3-15 (2003); E. M. Poeschla, Non-primate lentiviral vectors, 5(5) Curr. Opin. Mol. Ther. 529-540 (2003); Karim Benihoud et al, Adenovirus vectors for gene delivery, 10(5) Curr. Opin. Biotechnol. 440-447 (1999); H. Bueler, Adeno-associated viral vectors for gene transfer and gene therapy, 380(6) Biol. Chem. 613-622 (1999); Chooi M. Lai et al., Adenovirus and adeno-associated virus vectors, 21(12) DNA Cell Biol. 895-913 (2002); Edward A. Burton et al., Gene delivery using herpes simplex virus vectors, 21(12) DNA Cell Biol. 915-936 (2002); Paola Grandi et al., Targeting HSV amplicon vectors, 33(2) Methods 179-186 (2004); Ilya Frolov et al., Alphavirus-based expression vectors: strategies and applications, 93(21) Proc. Natl. Acad. Sci. U.S.A. 11371-11377 (1996); Markus U. Ehrengruber, Alphaviral gene transfer in neurobiology, 59(1) Brain Res. Bull. 13-22 (2002); Thomas A. Kost & J. Patrick Condreay, Recombinant baculoviruses as mammalian cell gene-delivery vectors, 20(4) Trends Biotechnol. 173-180 (2002); and A. Huser & C. Hofmann, Baculovirus vectors: novel mammalian cell gene-delivery vehicles and their applications, 3(1) Am. J. Pharmacogenomics 53-63 (2003).

Adenoviruses, which are non-enveloped, double-stranded DNA viruses, are often selected for mammalian cell transduction because adenoviruses handle relatively large polynucleotide molecules of about 36 kb, are produced at high titer, and can efficiently infect a wide variety of both dividing and non-dividing cells, see, e.g., Wim T. J. M. C. Hermens et al., Transient gene transfer to neurons and glia: analysis of adenoviral vector performance in the CNS and PNS, 71(1) J. Neurosci. Methods 85-98 (1997); and Hiroyuki Mizuguchi et al., Approaches for generating recombinant adenovirus vectors, 52(3) Adv. Drug Deliv. Rev. 165-176 (2001). Transduction using adenoviral-based system do not support prolonged protein expression because the nucleic acid molecule is carried from an episome in the cell nucleus, rather than being integrated into the host cell chromosome. Adenoviral vector systems and specific protocols for how to use such vectors are disclosed in, e.g., ViraPower™ Adenoviral Expression System (Invitrogen, Inc., Carlsbad, Calif.) and ViraPower™ Adenoviral Expression System Instruction Manual 25-0543 version A, Invitrogen, Inc., (Jul. 15, 2002); and AdEasy™ Adenoviral Vector System (Stratagene, Inc., La Jolla, Calif.) and AdEasy™ Adenoviral Vector System Instruction Manual 064004f, Stratagene, Inc.

Nucleic acid molecule delivery can also use single-stranded RNA retroviruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., Transient production of retroviral- and lentiviral-based vectors for the transduction of Mammalian cells, 285 Methods Mol. Biol. 141-148 (2004); Armin Blesch, Lentiviral and MLV based retroviral vectors for ex vivo and in vivo gene transfer, 33(2) Methods 164-172 (2004); Félix Recillas-Targa, Gene transfer and expression in mammalian cell lines and transgenic animals, 267 Methods Mol. Biol. 417-433 (2004); and Roland Wolkowicz et al., Lentiviral vectors for the delivery of DNA into mammalian cells, 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persistent expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., In vivo gene delivery and stable transduction of non-dividing cells by a lentiviral vector, 272 (5259) Science 263-267 (1996). The Oncoretroviruses-derived vector systems, such as, e.g., Moloney murine leukemia virus (MoMLV), are widely used and infect many different non-dividing cells. Lentiviruses can also infect many different cell types, including dividing and non-dividing cells and possess complex envelope proteins, which allows for highly specific cellular targeting.

Retroviral vectors and specific protocols for how to use such vectors are disclosed in, e.g., U.S. patent Nos. Manfred Gossen & Hermann Bujard, Tight control of gene expression in eukaryotic cells by tetracycline-responsive promoters, U.S. Pat. No. 5,464,758 (Nov. 7, 1995) and Hermann Bujard & Manfred Gossen, Methods for regulating gene expression, U.S. Pat. No. 5,814,618 (Sep. 29, 1998) David S. Hogness, Polynucleotides encoding insect steroid hormone receptor polypeptides and cells transformed with same, U.S. Pat. No. 5,514,578 (May 7, 1996) and David S. Hogness, Polynucleotide encoding insect ecdysone receptor, U.S. Pat. No. 6,245,531 (Jun. 12, 2001); Elisabetta Vegeto et al., Progesterone receptor having C. terminal hormone binding domain truncations, U.S. Pat. No. 5,364,791 (Nov. 15, 1994), Elisabetta Vegeto et al., Mutated steroid hormone receptors, methods for their use and molecular switch for gene therapy, U.S. Pat. No. 5,874,534 (Feb. 23, 1999) and Elisabetta Vegeto et al., Mutated steroid hormone receptors, methods for their use and molecular switch for gene therapy, U.S. Pat. No. 5,935,934 (Aug. 10, 1999). Furthermore, such viral delivery systems can be prepared by standard methods and are commercially available, see, e.g., BD™ Tet-Off and Tet-On Gene Expression Systems (BD Biosciences-Clonetech, Palo Alto, Calif.) and BD™ Tet-Off and Tet-On Gene Expression Systems User Manual, PT3001-1, BD Biosciences Clonetech, (Mar. 14, 2003), GeneSwitch™ System (Invitrogen, Inc., Carlsbad, Calif.) and GeneSwitch™ System A Mifepristone-Regulated Expression System for Mammalian Cells version D, 25-0313, Invitrogen, Inc., (Nov. 4, 2002); ViraPower™ Lentiviral Expression System (Invitrogen, Inc., Carlsbad, Calif.) and ViraPower™ Lentiviral Expression System Instruction Manual 25-0501 version E, Invitrogen, Inc., (Dec. 8, 2003); and Complete Control® Retroviral Inducible Mammalian Expression System (Stratagene, La Jolla, Calif.) and Complete Control® Retroviral Inducible Mammalian Expression System Instruction Manual, 064005e.

The methods disclosed in the present specification include, in part, expressing a multivalent Clostridial toxin from a polynucleotide molecule. It is envisioned that any of a variety of expression systems may be useful for expressing a multivalent Clostridial toxin from a polynucleotide molecule disclosed in the present specification, including, without limitation, cell-based systems and cell-free expression systems. Cell-based systems include, without limitation, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts and generally are equivalent to the method disclosed herein. Expression of a polynucleotide molecule using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins,* 80(9) CURRENT SCIENCE 1121-1128, (2001). These protocols are routine procedures well within the scope of one skilled in the art and from the teaching herein.

A variety of cell-based expression procedures are useful for expressing a multivalent Clostridial toxin encoded by polynucleotide molecule disclosed in the present specification. Examples included, without limitation, viral expression systems, prokaryotic expression systems, yeast expression systems, baculoviral expression systems, insect expression systems and mammalian expression systems. Viral expression systems include, without limitation, the ViraPower™ Lentiviral (Invitrogen, Inc., Carlsbad, Calif.), the Adenoviral Expression Systems (Invitrogen, Inc., Carlsbad, Calif.), the AdEasy™ XL Adenoviral Vector System (Stratagene, La Jolla, Calif.) and the ViraPort® Retroviral Gene Expression System (Stratagene, La Jolla, Calif.). Non-limiting examples of prokaryotic expression systems include the Champion™ pET Expression System (EMD Biosciences-Novagen, Madison, Wis.), the TriEx™ Bacterial Expression System (EMD Biosciences-Novagen, Madison, Wis.), the QIAexpress® Expression System (QIAGEN, Inc.), and the Affinity® Protein Expression and Purification System (Stratagene, La Jolla, Calif.). Yeast expression systems include, without limitation, the EasySelect™ *Pichia* Expression Kit (Invitrogen, Inc., Carlsbad, Calif.), the YES-Echo™ Expression Vector Kits (Invitrogen, Inc., Carlsbad, Calif.) and the SpECTRA™ *S. pombe* Expression System (Invitrogen, Inc., Carlsbad, Calif.). Non-limiting examples of baculoviral expression systems include the BaculoDirect™ (Invitrogen, Inc., Carlsbad, Calif.), the Bac-to-Bac® (Invitrogen, Inc., Carlsbad, Calif.), and the BD BaculoGold™ (BD Biosciences-Pharmigen, San Diego, Calif.). Insect expression systems include, without limitation, the *Drosophila* Expression System (DES®) (Invitrogen, Inc., Carlsbad, Calif.), InsectSelect™ System (Invitrogen, Inc., Carlsbad, Calif.) and InsectDirect™ System (EMD Biosciences-Novagen, Madison, Wis.). Non-limiting examples of mammalian expression systems include the T-REx™ (Tetracycline-Regulated Expression) System (Invitrogen, Inc., Carlsbad, Calif.), the Flp-In™ T-REx™ System (Invitrogen, Inc., Carlsbad, Calif.), the pcDNA™ system (Invitrogen, Inc., Carlsbad, Calif.), the pSecTag2 system (Invitrogen, Inc., Carlsbad, Calif.), the Exchanger® System, InterPlay™ Mammalian TAP System (Stratagene, La Jolla, Calif.), Complete Control® Inducible Mammalian Expression System (Stratagene, La Jolla, Calif.) and LacSwitch® II Inducible Mammalian Expression System (Stratagene, La Jolla, Calif.).

Another procedure of expressing a multivalent Clostridial toxin encoded by polynucleotide molecule disclosed in the present specification employs a cell-free expression system such as, without limitation, prokaryotic extracts and eukaryotic extracts. Non-limiting examples of prokaryotic cell extracts include the RTS 100 *E. coli* HY Kit (Roche Applied Science, Indianapolis, Ind.), the ActivePro In Vitro Translation Kit (Ambion, Inc., Austin, Tex.), the EcoPro™ System (EMD Biosciences-Novagen, Madison, Wis.) and the Expressway™ Plus Expression System (Invitrogen, Inc., Carlsbad, Calif.). Eukaryotic cell extract include, without limitation, the RTS 100 Wheat Germ CECF Kit (Roche Applied Science, Indianapolis, Ind.), the TnT® Coupled Wheat Germ Extract Systems (Promega Corp., Madison, Wis.), the Wheat Germ IVT™ Kit (Ambion, Inc., Austin, Tex.), the Retic Lysate IVT™ Kit (Ambion, Inc., Austin, Tex.), the PROTEINscript® II System (Ambion, Inc., Austin, Tex.) and the TnT® Coupled Reticulocyte Lysate Systems (Promega Corp., Madison, Wis.).

Aspects of the present invention can also be described as follows:

1. A polypeptide comprising an endopeptidase domain; a translocation domain effective to facilitate the movement of said endopeptidase domain across an endosomal membrane; and at least two binding domains, wherein: a first binding domain comprises a first ligand binding, under physiological conditions, to a first cell surface receptor displayed by the target cell; and a second binding domain comprises a second ligand binding, under physiological conditions, to a second cell surface receptor displayed by the target cell; wherein said target cell internalizes said polypeptide upon binding of said polypeptide to said target cell.
2. The polypeptide of 1 wherein said second cell surface receptor comprises a caveolin-binding domain.
3. The polypeptide of 1 wherein said second cell surface receptor comprises TNFR-1.
4. The polypeptide of 3 wherein said second ligand comprises a TNFR-1 binding protein selected from the group consisting of TNF-α and a TNF-α derivative comprising a TNFR-1-binding domain.
5. The polypeptide of 2 wherein said second ligand binds a glycosyl phosphatylinositol (GPI)-linked membrane protein.
6. The polypeptide of 1 wherein said second cell surface receptor comprises an antibody variable (V) domain region.
7. The polypeptide of 6 wherein said second ligand comprises an antigen that selectively binds the antibody variable domain region of said second cell surface receptor.
8. The polypeptide of 1 wherein said second cell surface receptor directly binds clatherin.
9. The polypeptide of 1 wherein said second cell surface receptor indirectly binds clatherin.
10. The polypeptide of 9 wherein the second cell surface receptor has the amino acid sequence tyrosine-X-arginine-phenylalanine near the carboxy terminus.
11. The polypeptide of 9 wherein the second cell surface receptor binds an adaptin.
12. The polypeptide of claim 11 wherein the second cell surface receptor binds Adaptor Protein-2.
13. The polypeptide of 1 wherein the first ligand selectively binds a Clostridial neurotoxin-binding cell surface receptor.
14. The polypeptide of 13 wherein the first ligand comprises a Clostridial neurotoxin binding domain.
15. The polypeptide of 15 wherein the first ligand comprises a Clostridial neurotoxin binding domain selected from the group consisting of a TeNT receptor binding domain, a BoNT-A receptor binding domain, a BoNT-B receptor binding domain, a BoNT-C receptor binding domain, a BoNT-C1 receptor binding domain, a BoNT-D receptor binding domain, a BoNT-E receptor binding domain, a BoNT-F receptor binding domain, a BoNT-G receptor binding domain HA or NTNH β-trefoil domain of a neurotoxin associated protein (NAP) associated with any Clostridial neurotoxin, and variants and isoforms of any of the above.
16. The polypeptide of 1 wherein first or second ligand comprises a receptor-binding domain selected from the group consisting of: a nerve growth factor (NGF) receptor binding domain; a leukemia inhibitory factor (LIF) receptor binding domain; a basic fibroblast growth factor (bFGF) receptor binding domain; a brain-derived neurotrophic factor (BDNF) receptor binding domain; a neurotrophin-3 (NT-3) receptor binding domain; a hydra head activator peptide (HHAP) receptor binding domain; a transforming growth factor 1 (TGF-1) receptor binding domain; a transforming growth factor 2 (TGF-2) receptor binding domain; a transforming growth factor 3 (TGF-3) receptor binding domain; an epidermal growth factor (EGF) receptor binding domain; a ciliary neurotrophic factor (CNTF) receptor binding domain; a tumor necrosis factor (TNF-) receptor binding domain; an interleukin-1 (IL-1) receptor binding domain; an interleukin-1 (IL-1) receptor binding domain; an interleukin-8 (IL-8) receptor binding domain; a bradykinin receptor binding domain; a dynorphin receptor binding domain; a β-endorphin receptor binding domain; an etorphine receptor binding domain; an endomorphin-1 receptor binding domain; an endomorphin-2 receptor binding domain; a leu-enkephalin receptor binding domain; a met-enkephalin receptor binding domain; a galanin receptor binding domain; a lofentanil receptor binding domain; a nociceptin receptor binding domain; an antigen-binding variable region of an antibody against the lactoseries carbohydrate epitopes found on the surface of dorsal root ganglion neurons; an antigen-binding variable region of an antibody binding any of the receptors for the binding domains given above and an antibody against the surface expressed antigen Thyl.
17. The polypeptide of 16 wherein said first and second cell surface receptors are identical.
18. The polypeptide of 17 wherein the first and second ligands are identical.
19. The polypeptide of 16 wherein said first and second ligands are different.
20. The polypeptide of 15 wherein said second ligand comprises a receptor-binding domain selected from the group consisting of: a nerve growth factor (NGF) receptor binding domain; a leukemia inhibitory factor (LIF) receptor binding domain; a basic fibroblast growth factor (bFGF) receptor binding domain; a brain-derived neurotrophic factor (BDNF) receptor binding domain; a neurotrophin-3 (NT-3) receptor binding domain; a hydra head activator peptide (HHAP) receptor binding domain; a transforming growth factor 1 (TGF-1) receptor binding domain; a transforming growth factor 2 (TGF-2) receptor binding domain; a transforming growth factor 3 (TGF-3) receptor binding domain; an epidermal growth factor (EGF) receptor binding domain; a ciliary neurotrophic factor (CNTF) receptor binding domain; a tumor necrosis factor (TNF-) receptor binding domain; an interleukin-1 (IL-1) receptor binding domain; an interleukin-1 (IL-1) receptor binding domain; an interleukin-8 (IL-8) receptor binding domain; a bradykinin receptor binding domain; a dynorphin receptor binding domain; a β-endorphin receptor binding domain; an etorphine receptor binding domain; an endomorphin-1 receptor binding domain; an endomorphin-2 receptor binding domain; a leu-enkephalin receptor binding domain; a met-enkephalin receptor binding domain; a galanin receptor binding domain; a lofentanil receptor binding domain; a nociceptin receptor binding domain; an antigen-binding variable region of an antibody against the lactoseries carbohydrate epitopes found on the surface of dorsal root ganglion neurons; an antigen-binding variable region of an antibody binding any of the receptors for the binding domains given above and an antibody against the surface expressed antigen Thy1.

21. The polypeptide of 16 wherein said second cell surface receptor comprises a caveolin-binding domain.

22. The polypeptide of 16 wherein said second cell surface receptor comprises TNFR-1.

23. The polypeptide of 22 wherein said second ligand comprises a TNFR-1 binding protein selected from the group consisting of TNF-α and a TNF-α derivative comprising a TNFR-1-binding domain.

24. The polypeptide of 21 wherein said second ligand binds a glycosyl phosphatylinositol (GPI)-linked membrane protein.

25. The polypeptide of 16 wherein said second cell surface receptor comprises an antibody variable (V) domain region.

26. The polypeptide of 25 wherein said second ligand comprises an antigen that selectively binds the antibody variable domain region of said second cell surface receptor.

27. The polypeptide of 16 wherein said second cell surface receptor directly or indirectly binds clatherin.

28. The polypeptide of 27 wherein said second cell surface receptor indirectly binds clatherin.

29. The polypeptide of 27 wherein the second cell surface receptor has the amino acid sequence tyrosine-X-arginine-phenylalanine near the carboxy terminus.

30. The polypeptide of 27 wherein the second cell surface receptor directly binds an adaptin.

31. The polypeptide of 30 wherein the second cell surface receptor binds Adaptor Protein-2.

32. A method for inhibiting or decreasing exocytosis or secretion in a target cell comprising contacting said target cell under physiological conditions with an effective dose of a multivalent Clostridial toxin composition comprising: an endopeptidase domain; a translocation domain effective to facilitate the movement of said endopeptidase domain from an endocytotic vesicle to the cytoplasm of said target cell; and at least two binding domains, wherein: a first binding domain comprises a first ligand selectively binding under physiological conditions to a first cell surface receptor selectively displayed by the target cell; and a second binding domain comprises a second ligand binding, under physiological conditions, to a second cell surface receptor displayed by the target cell; wherein said endopeptidase domain catalyzes cleavage of a intracellular SNARE protein within the target cell, thereby inhibiting or decreasing exocytosis or secretion by said cell.

33. The method of 32 wherein said second cell surface receptor comprises a caveolin-binding domain.

34. The method of 32 wherein said second cell surface receptor comprises TNFR-1.

35. The method of 34 wherein said second ligand comprises a TNFR-1 binding protein selected from the group consisting of TNF-α and a TNF-α derivative comprising a TNFR-1-binding domain.

36. The method of 33 wherein said second ligand binds a glycosyl phosphatylinositol (GPI)-linked membrane protein.

37. The method of 32 wherein said second cell surface receptor comprises an antibody variable (V) domain region.

38. The method of 37 wherein said second ligand comprises an antigen that selectively binds the antibody variable domain region of said second cell surface receptor.

39. The method of 32 wherein said second cell surface receptor directly binds clatherin.

40. The method of 32 wherein said second cell surface receptor indirectly binds clatherin.

41. The method of 39 wherein the second cell surface receptor has the amino acid sequence tyrosine-X-arginine-phenylalanine near the carboxy terminus.

42. The method of 39 wherein the second cell surface receptor binds an adaptin.

43. The method of 42 wherein the second cell surface receptor binds Adaptor Protein-2.

44. The method of 32 wherein the first ligand selectively binds a Clostridial neurotoxin-binding cell surface receptor.

45. The method of 44 wherein the first ligand comprises a clostridial neurotoxin binding domain.

46. The method of 45 wherein the first ligand comprises a clostridial neurotoxin binding domain selected from the group consisting of a TeNT receptor binding domain, a BoNT-A receptor binding domain, a BoNT-B receptor binding domain, a BoNT-C receptor binding domain, a BoNT-C1 receptor binding domain, a BoNT-D receptor binding domain, a BoNT-E receptor binding domain, a BoNT-F receptor binding domain, a BoNT-G receptor binding domain HA or NTNH β trefoil domain of a neurotoxin associated protein (NAP) associated 47. The method of 32 wherein first or second ligand comprises a receptor-binding domain selected from the group consisting of: a nerve growth factor (NGF) receptor binding domain; a leukemia inhibitory factor (LIF) receptor binding domain; a basic fibroblast growth factor (bFGF) receptor binding domain; a brain-derived neurotrophic factor (BDNF) receptor binding domain; a neurotrophin-3 (NT-3) receptor binding domain; a hydra head activator peptide (HHAP) receptor binding domain; a transforming growth factor 1 (TGF-1) receptor binding domain; a transforming growth factor 2 (TGF-2) receptor binding domain; a transforming growth factor 3 (TGF-3) receptor binding domain; an epidermal growth factor (EGF) receptor binding domain; a ciliary neurotrophic factor (CNTF) receptor binding domain; a tumor necrosis factor (TNF-) receptor binding domain; an interleukin-1 (IL-1) receptor binding domain; an interleukin-1 (IL-1) receptor binding domain; an interleukin-8 (IL-8) receptor binding domain; a bradykinin receptor binding domain; a dynorphin receptor binding domain; a β-endorphin receptor binding domain; an etorphine receptor binding domain; an endomorphin-1 receptor binding domain; an endomorphin-2 receptor binding domain; a leu-enkephalin receptor binding domain; a met-enkephalin receptor binding domain; a galanin receptor binding domain; a lofentanil receptor binding domain; a nociceptin receptor binding domain; an antigen-binding variable region of an antibody against the lactoseries carbohydrate epitopes found on the surface of dorsal root ganglion neurons; an antigen-binding variable region of an antibody binding any of the receptors for the binding domains given above and an antibody against the surface expressed antigen Thy1.

48. The method of 47 wherein said first and second cell surface receptors are identical.
49. The method of 48 wherein the first and second ligands are identical.
50. The method of 47 wherein said first and second ligands are different.
51. The method of 46 wherein said second ligand comprises a receptor-binding domain selected from the group consisting of: a nerve growth factor (NGF) receptor binding domain; a leukemia inhibitory factor (LIF) receptor binding domain; a basic fibroblast growth factor (bFGF) receptor binding domain; a brain-derived neurotrophic factor (BDNF) receptor binding domain; a neurotrophin-3 (NT-3) receptor binding domain; a hydra head activator peptide (HHAP) receptor binding domain; a transforming growth factor 1 (TGF-1) receptor binding domain; a transforming growth factor 2 (TGF-2) receptor binding domain; a transforming growth factor 3 (TGF-3) receptor binding domain; an epidermal growth factor (EGF) receptor binding domain; a ciliary neurotrophic factor (CNTF) receptor binding domain; a tumor necrosis factor (TNF-) receptor binding domain; an interleukin-1 (IL-1) receptor binding domain; an interleukin-1 (IL-1) receptor binding domain; an interleukin-8 (IL-8) receptor binding domain; a bradykinin receptor binding domain; a dynorphin receptor binding domain; β-endorphin receptor binding domain; an etorphine receptor binding domain; an endomorphin-1 receptor binding domain; an endomorphin-2 receptor binding domain; a leu-enkephalin receptor binding domain; a met-enkephalin receptor binding domain; a galanin receptor binding domain; a lofentanil receptor binding domain; a nociceptin receptor binding domain; an antigen-binding variable region of an antibody against the lactoseries carbohydrate epitopes found on the surface of dorsal root ganglion neurons; an antigen-binding variable region of an antibody binding any of the receptors for the binding domains given above and an antibody against the surface expressed antigen Thy1.
52. The method of 47 wherein said second cell surface receptor comprises a caveolin-binding domain.
53. The method of 46 wherein said second cell surface receptor comprises TNFR-1.
54. The method of 53 wherein said second ligand comprises a TNFR-1 binding protein selected from the group consisting of TNF-α and a TNF-α derivative comprising a TNFR-1-binding domain.
55. The method of 52 wherein said second ligand binds a glycosyl phosphatylinositol (GPI)-linked membrane protein.
56. The method of 16 wherein said second cell surface receptor comprises an antibody variable (V) domain region.
57. The method of 56 wherein said second ligand comprises an antigen that selectively binds the antibody variable domain region of said second cell surface receptor.
58. The method of 47 wherein said second cell surface receptor directly or indirectly binds clatherin.
59. The method of 58 wherein said second cell surface receptor indirectly binds clatherin.
60. The method of 58 wherein the second cell surface receptor has the amino acid sequence tyrosine-X-arginine-phenylalanine near the carboxy terminus.
61. The method of 58 wherein the second cell surface receptor directly binds an adaptin.
62. The method of 61 wherein the second cell surface receptor binds Adaptor Protein-2.
63. The method of 32 wherein said exocytosis or secretion is associated with a pathological condition related to a condition selected from the group consisting of a movement disorder, a disorder of the sensory nervous system, acute or chronic pain, cancer, pancreatitis, hyperhydrosis, glandular disorders, viral infections, and cystic fibrosis.
64. The method of 32 wherein the multivalent Clostridial toxin is administered by injection.
65. A nucleic acid molecule encoding a polypeptide according to any one of 1-31.

Aspects of the present invention can also be described as follows:

1. A multivalent Clostridial toxin comprising:
   a) a Clostridial toxin enzymatic domain capable of executing an enzymatic target modification step of a Clostridial toxin intoxication process;
   b) a Clostridial toxin translocation domain capable of executing a translocation step of a Clostridial toxin intoxication process;
   c) a first binding domain capable of executing a cell binding step of a Clostridial toxin intoxication process by selectively binding a first cell surface receptor displayed by the target cell; and
   d) a second binding domain capable of executing a cell binding step of a Clostridial toxin intoxication process by selectively binding a second cell surface receptor displayed by the target cell; and
   e) a protease cleavage site, wherein cleavage of the protease cleavage site converts the single-chain form of the modified Clostridial toxin into the di-chain form.
2. The multivalent Clostridial toxin according to 1, wherein the multivalent Clostridial toxin comprises amino to carboxyl linear organization comprising a binding domain 1, a translocation domain, a binding domain 2, a protease cleavage site and an enzymatic domain.
3. The multivalent Clostridial toxin according to 1, wherein the multivalent Clostridial toxin comprises an amino to carboxyl linear organization comprising an enzymatic domain, a protease cleavage site, a binding domain 1, a translocation domain and a binding domain 2
4. The multivalent Clostridial toxin according to 1, wherein the multivalent Clostridial toxin comprises an amino to carboxyl linear organization comprising an enzymatic domain, a protease cleavage site, a translocation domain, a binding domain 1 and a binding domain 2
5. The multivalent Clostridial toxin according to 1, wherein the multivalent Clostridial toxin comprises an amino to carboxyl linear organization comprising an enzymatic domain, a protease cleavage site, a translocation domain, a binding domain 2 and a binding domain 1
6. The multivalent Clostridial toxin according to 1, wherein the multivalent Clostridial toxin comprises an amino to carboxyl linear organization comprising a binding domain 1, an enzymatic domain, a protease cleavage site, a translocation domain and a binding domain 2
7. The multivalent Clostridial toxin according to 1, wherein the multivalent Clostridial toxin comprises amino to carboxyl linear organization comprising a translocation domain, a binding domain 2, a protease cleavage site, a binding domain 1 and an enzymatic domain
8. The multivalent Clostridial toxin according to 1, wherein the multivalent Clostridial toxin comprises an amino to carboxyl linear organization comprising a translocation domain, a binding domain 2, a protease cleavage site, an enzymatic domain and a binding domain 1

9. The multivalent Clostridial toxin according to 1, wherein the multivalent Clostridial toxin comprises an amino to carboxyl linear organization comprising a binding domain 2, a translocation domain, a protease cleavage site, a binding domain 1 and an enzymatic domain 10. The multivalent Clostridial toxin according to 1, wherein the protease cleavage site is an endogenous protease cleavage site or an exogenous protease cleavage site.

11. The multivalent Clostridial toxin according to 10, wherein the endogenous protease cleavage site is selected from the group consisting of a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

12. The multivalent Clostridial toxin according to 10, wherein the exogenous protease cleavage site is selected from the group consisting of a bovine enterokinase protease cleavage site, a Tobacco Etch Virus protease cleavage site, a Human Rhinovirus 3C protease cleavage site, a SUMO/ULP-1 protease cleavage site, a Thrombin protease cleavage site, and a Factor Xa protease cleavage site.

13. A multivalent Clostridial toxin comprising:
   a) a Clostridial toxin enzymatic domain capable of executing an enzymatic target modification step of a Clostridial toxin intoxication process;
   b) a Clostridial toxin translocation domain capable of executing a translocation step of a Clostridial toxin intoxication process;
   c) a first binding domain capable of executing a cell binding step of a Clostridial toxin intoxication process by selectively binding a first cell surface receptor displayed by the target cell;
   d) a second binding domain capable of executing a cell binding step of a Clostridial toxin intoxication process by selectively binding a second cell surface receptor displayed by the target cell;
   e) a first protease cleavage site, wherein cleavage of the first protease cleavage site converts the single-chain form of the modified Clostridial toxin into the di-chain form; and
   f) a second protease cleavage site; wherein cleavage of the second protease causes a structural confirmation in the first and second binding domains which facilitates the selectively binding activity of the first binding domain, the second binding domain, or both the first and second binding domains.

14. The multivalent Clostridial toxin according to 13, wherein the multivalent Clostridial toxin comprises an amino to carboxyl linear organization comprising an enzymatic domain, a first protease cleavage site, a translocation domain, a binding domain 1, a second protease cleavage site and a binding domain 2

15. The multivalent Clostridial toxin according to 13, wherein the multivalent Clostridial toxin comprises an amino to carboxyl linear organization comprising an enzymatic domain, a first protease cleavage site, a translocation domain, a binding domain 2, a second protease cleavage site and a binding domain 1

16. The modified Clostridial toxin according to 13, wherein the first protease cleavage site is an endogenous protease cleavage site or an exogenous protease cleavage site.

17. The multivalent Clostridial toxin according to 16, wherein the endogenous protease cleavage site is selected from the group consisting of a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

18. The multivalent Clostridial toxin according to 16, wherein the exogenous protease cleavage site is selected from the group consisting of a bovine enterokinase protease cleavage site, a Tobacco Etch Virus protease cleavage site, a Human Rhinovirus 3C protease cleavage site, a SUMO/ULP-1 protease cleavage site, a Thrombin protease cleavage site, and a Factor Xa protease cleavage site.

19. The modified Clostridial toxin according to 13, wherein the second protease cleavage site is an endogenous protease cleavage site or an exogenous protease cleavage site.

20. The multivalent Clostridial toxin according to 19, wherein the endogenous protease cleavage site is selected from the group consisting of a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

21. The multivalent Clostridial toxin according to 19, wherein the exogenous protease cleavage site is selected from the group consisting of a bovine enterokinase protease cleavage site, a Tobacco Etch Virus protease cleavage site, a Human Rhinovirus 3C protease cleavage site, a SUMO/ULP-1 protease cleavage site, a Thrombin protease cleavage site, and a Factor Xa protease cleavage site.

22. The multivalent Clostridial toxin according to either 1 or 13, wherein the Clostridial toxin enzymatic domain is selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain and a BuNT enzymatic domain.

23. The multivalent Clostridial toxin according to 22, wherein the Clostridial toxin enzymatic domain comprises an amino acid sequence selected from the group consisting of amino acids 1-448 of SEQ ID NO: 1, amino acids 1-441 SEQ ID NO: 2, amino acids 1-449 of SEQ ID NO: 3, amino acids 1-445 of SEQ ID NO: 4, amino acids 1-422 of SEQ ID NO: 5, amino acids 1-439 of SEQ ID NO: 6, amino acids 1-446 of SEQ ID NO: 7, amino acid 1-457 of SEQ ID NO: 8, amino acid 1-431 of SEQ ID NO: 9, and amino acid 1-422 of SEQ ID NO: 10.

24. The multivalent Clostridial toxin according either 1 or 13, wherein the Clostridial toxin translocation domain is selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain and a BuNT translocation domain.

25. The multivalent Clostridial toxin according to 24, wherein the Clostridial toxin translocation domain comprises an amino acid sequence selected from the group consisting of amino acids 449-873 of SEQ ID NO: 1, amino acids 442-860 SEQ ID NO: 2, amino acids 450-868 of SEQ ID NO: 3, amino acids 446-864 of SEQ ID NO: 4, amino acids 423-847 of SEQ ID NO: 5, amino acids 440-866 of SEQ ID NO: 6, amino acids 447-865 of SEQ ID NO: 7, amino acid 458-881 of SEQ ID NO: 8, amino acid 432-857 of SEQ ID NO: 9, and amino acid 423-847 of SEQ ID NO: 10.

26. The multivalent Clostridial toxin according either 1 or 13, wherein the first binding domain comprises a binding domain selected from the group consisting of a Clostridial toxin binding domain, a Clostridial non-toxin associated protein β-trefoil domain and an FGF β-trefoil domain.

27. The multivalent Clostridial toxin according to 26, wherein the Clostridial toxin binding domain is selected from the group consisting of a BoNT/A binding domain, a BoNT/B binding domain, a BoNT/C1 binding domain, a BoNT/D binding domain, a BoNT/E binding domain, a BoNT/F binding domain, a BoNT/G binding domain, a TeNT binding domain, a BaNT binding domain, and a BuNT binding domain.

28. The multivalent Clostridial toxin according to 26, wherein the Clostridial toxin binding domain comprises a BoNT/A $H_C$ binding domain, a BoNT/B $H_C$ binding domain, a BoNT/C1 $H_C$ binding domain, a BoNT/D $H_C$ binding domain, a BoNT/E $H_C$ binding domain, a BoNT/F $H_C$ binding domain, a BoNT/G $H_C$ binding domain, a TeNT $H_C$ binding domain, a BaNT $H_C$ binding domain, and a BuNT $H_C$ binding domain.

29. The multivalent Clostridial toxin according to 28, wherein the Clostridial toxin binding domain comprises an amino acid sequence selected from the group consisting of amino acids 874-1296 of SEQ ID NO: 1, amino acids 861-1291 SEQ ID NO: 2, amino acids 869-1291 of SEQ ID NO: 3, amino acids 865-1276 of SEQ ID NO: 4, amino acids 848-1252 of SEQ ID NO: 5, amino acids 867-1274 of SEQ ID NO: 6, amino acids 866-1297 of SEQ ID NO: 7, amino acid 882-1315 of SEQ ID NO: 8, amino acid 858-1268 of SEQ ID NO: 9, and amino acid 848-1251 of SEQ ID NO: 10.

30. The multivalent Clostridial toxin according to 26, wherein the Clostridial toxin binding domain comprises a BoNT/A $H_{CC}$ binding domain, a BoNT/B $H_{CC}$ binding domain, a BoNT/C1 $H_{CC}$ binding domain, a BoNT/D $H_{CC}$ binding domain, a BoNT/E $H_{CC}$ binding domain, a BoNT/F $H_{CC}$ binding domain, a BoNT/G $H_{CC}$ binding domain, a TeNT $H_{CC}$ binding domain, a BaNT $H_{CC}$ binding domain, and a BuNT $H_{CC}$ binding domain.

31. The multivalent Clostridial toxin according to 30, wherein the Clostridial toxin binding domain comprises an amino acid sequence selected from the group consisting of amino acids 874-1110 of SEQ ID NO: 1, amino acids 861-1097 SEQ ID NO: 2, amino acids 869-1111 of SEQ ID NO: 3, amino acids 865-1098 of SEQ ID NO: 4, amino acids 848-1085 of SEQ ID NO: 5, amino acids 867-1105 of SEQ ID NO: 6, amino acids 866-1105 of SEQ ID NO: 7, amino acid 882-1127 of SEQ ID NO: 8, amino acid 858-1094 of SEQ ID NO: 9, and amino acid 848-1085 of SEQ ID NO: 10.

32. The multivalent Clostridial toxin according to 26, wherein the Clostridial non-toxin associated protein β-trefoil domain is selected from the group consisting of a BoNT/A HA-33 β-trefoil domain, a BoNT/B HA-33 β-trefoil domain, a BoNT/C1 HA-33 β-trefoil domain, a BoNT/D HA-33 β-trefoil domain, a BoNT/A HA-17 β-trefoil domain, a BoNT/B HA-17 β-trefoil domain, a BoNT/C1 HA-17 β-trefoil domain, a BoNT/D HA-17 β-trefoil domain, a BoNT/A NTNH β-trefoil domain, a BoNT/B NTNH β-trefoil domain, a BoNT/C1 NTNH β-trefoil domain, a BoNT/D NTNH β-trefoil domain, a BoNT/E NTNH β-trefoil domain, a BoNT/F NTNH β-trefoil domain, AND a BoNT/G NTNH β-trefoil domain.

33. The multivalent Clostridial toxin according to 32, wherein the BoNT/A HA-33 β-trefoil domain comprises amino acids 10-144 of SEQ ID NO: 11, amino acids 151-293 of SEQ ID NO: 11, amino acids 10-144 or amino acids 151-293 of SEQ ID NO: 12, amino acids 10-144 of SEQ ID NO: 13, amino acids 151-293 of SEQ ID NO: 13, amino acids 10-146 of SEQ ID NO: 14, amino acids 153-294 of SEQ ID NO: 14, amino acids 10-144 of SEQ ID NO: 15, or amino acids 151-279 of SEQ ID NO: 15.

34. The multivalent Clostridial toxin according to 32, wherein the BoNT/B HA-33 β-trefoil domain comprises amino acids 10-144 of SEQ ID NO: 16, amino acids 151-292 of SEQ ID NO: 16, amino acids 10-146 of SEQ ID NO: 17, or amino acids 153-291 of SEQ ID NO: 17.

35. The multivalent Clostridial toxin according to 32, wherein the BoNT/C1 HA-33 β-trefoil domain comprises amino acids 10-141 of SEQ ID NO: 18, amino acids 148-285 of SEQ ID NO: 18, amino acids 10-141 of SEQ ID NO: 19, or amino acids 148-286 of SEQ ID NO: 19.

36. The multivalent Clostridial toxin according to 32, wherein the BoNT/D HA-33 β-trefoil domain comprises amino acids 10-141 of SEQ ID NO: 20, or amino acids 148-286 of SEQ ID NO: 20.

37. The multivalent Clostridial toxin according to 32, wherein the BoNT/A HA-17 β-trefoil domain comprises amino acids 9-146 of SEQ ID NO: 21.

38. The multivalent Clostridial toxin according to 32, wherein the BoNT/B HA-17 β-trefoil domain comprises amino acids 9-146 of SEQ ID NO: 22.

39. The multivalent Clostridial toxin according to 32, wherein the BoNT/C1 HA-17 β-trefoil domain comprises amino acids 9-146 of SEQ ID NO: 23.

40. The multivalent Clostridial toxin according to 32, wherein the BoNT/D HA-17 β-trefoil domain comprises amino acids 9-146 of SEQ ID NO: 24.

41. The multivalent Clostridial toxin according to 32, wherein the BoNT/A NTNH β-trefoil domain comprises amino acids 1050-1194 of SEQ ID NO: 25, amino acids 1050-1199 of SEQ ID NO: 26, or amino acids 1050-1194 of SEQ ID NO: 27.

42. The multivalent Clostridial toxin according to 32, wherein the BoNT/B NTNH β-trefoil domain comprises amino acids 1049-1198 of SEQ ID NO: 28.

43. The multivalent Clostridial toxin according to 32, wherein the BoNT/C1 NTNH β-trefoil domain comprises amino acids 1049-1197 of SEQ ID NO:29.

44. The multivalent Clostridial toxin according to 32, wherein the BoNT/D NTNH β-trefoil domain comprises amino acids 1049-1197 of SEQ ID NO: 30.

45. The multivalent Clostridial toxin according to 32, wherein the BoNT/E NTNH β-trefoil domain comprises amino acids 1014-1163 of SEQ ID NO: 31.

46. The multivalent Clostridial toxin according to 32, wherein the BoNT/F NTNH β-trefoil domain comprises amino acids 1016-1160 of SEQ ID NO: 32, or amino acids 1017-1166 of SEQ ID NO: 33.

47. The multivalent Clostridial toxin according to 32, wherein the BoNT/G NTNH β-trefoil domain comprises amino acids 1050-1197 of SEQ ID NO: 34.

48. The multivalent Clostridial toxin according to 26, wherein the FGF β-trefoil domain is selected from the group consisting of a FGF-1 β-trefoil domain, a FGF-2 β-trefoil domain, a FGF-4 β-trefoil domain, a FGF-8 β-trefoil domain, a FGF-9 β-trefoil domain, a FGF-17 β-trefoil domain and a FGF-18 β-trefoil domain.

49. The multivalent Clostridial toxin according to 26, wherein the FGF β-trefoil domain is selected from the group consisting of amino acids 26-155 of SEQ ID NO: 35, amino acids 29-155 of SEQ ID NO: 36, amino acids 83-206 of SEQ ID NO: 37, amino acids 43-172 of SEQ ID NO: 38, amino acids 63-196 of SEQ ID NO: 39, amino acids 55-183 of SEQ ID NO: 40 and amino acids 54-183 of SEQ ID NO: 41.

50. The multivalent Clostridial toxin according either 1 or 13, wherein the first binding domain comprises a binding domain selected from the group consisting of a glucagon like hormone, a neurohormone, a neuroregulatory cytokine, a neurotrophin, a growth factor, and an axon guidance signaling molecule.

51. The multivalent Clostridial toxin according to 50, wherein the glucagon like hormone is selected from the group consisting of a GRPP, a glucagon-like peptide-1 (GLP-1), a glucagon-like peptide-2 (GLP-2), a glucagon, an oxyntomodulin (OXY), pituitary adenylate cyclase activating peptide (PACAP), GHRH, vasoactive intestinal peptide-1 (VIP-1), vasoactive intestinal peptide-2 (VIP-2), gastric inhibitory polypeptide (GIP), secretin, gastrin, GRP, Ghrelin (GHS), glicentin, glicentin-related polypeptide (GRPP), and a calcitonin-related peptidesvisceral gut peptide.

52. The multivalent Clostridial toxin according to 50, wherein the glucagon like hormone comprises amino acids 21-50 of SEQ ID NO: 42, amino acids 53-81 of SEQ ID NO: 42, amino acids 53-89 of SEQ ID NO: 42, amino acids 98-124 of SEQ ID NO: 42, amino acids 146-178 of SEQ ID NO: 42, amino acids 132-158 of SEQ ID NO: 43, amino acids 32-58, of SEQ ID NO: 44, amino acids 32-75 of SEQ ID NO: 44, amino acids 81-107 of SEQ ID NO: 45, amino acids 125-151 of SEQ ID NO: 45, amino acids 81-107 of SEQ ID NO: 46, amino acids 124-150 of SEQ ID NO: 46, amino acids 52-78 of SEQ ID NO: 47, amino acids 52-93 of SEQ ID NO: 47, amino acids 28-54 of SEQ ID NO: 48, amino acids 76-92 of SEQ ID NO: 49, amino acids 59-92 of SEQ ID NO: 49, amino acids 41-50 of SEQ ID NO: 50, amino acids 24-50 of SEQ ID NO: 50, or amino acids 99-112 of SEQ ID NO: 51.

53. The multivalent Clostridial toxin according to 50, wherein the neurohormone is selected from the group consisting of corticotropin-releasing hormone (CCRH) and parathyroid hormone (PTH).

54. The multivalent Clostridial toxin according to 50, wherein the neurohormone comprises a amino acids 159-193 of SEQ ID NO: 52, amino acids 154-194 of SEQ ID NO: 52, amino acids 35-70 of SEQ ID NO: 53 and amino acids 145-177 of SEQ ID NO: 53.

55. The multivalent Clostridial toxin according to 50, wherein the neuroregulatory cytokine is selected from the group consisting of ciliary neurotrophic factor (CNTF), glycophorin-A (GPA), leukemia inhibitory factor (LIF), an interleukin (IL), onostatin M (OSM), cardiotrophin-1 (CT-1), cardiotrophin-like cytokine (CLC), neuroleukin (NL), VEGF, insulin-like growth factor-1 (IGF-1), insulin-like growth factor-2 (IGF-2) and epidermal growth factor (EGF).

56. The multivalent Clostridial toxin according to 50, wherein the neurohormone comprises SEQ ID NO: 54, SEQ ID NO: 55, SEQ ID NO: 56, SEQ ID NO: 57, SEQ ID NO: 58, amino acids 123-265 of SEQ ID NO: 59, amino acids 21-153 of SEQ ID NO: 60, amino acids 57-210 of SEQ ID NO: 61, amino acids 21-99 of SEQ ID NO: 62, amino acids 31-94 of SEQ ID NO: 62, amino acids 37-173 of SEQ ID NO: 63, amino acids 19-178 of SEQ ID NO: 63, SEQ ID NO: 64, SEQ ID NO: 65, amino acids 52-109 of SEQ ID NO: 66, amino acids 49-118 of SEQ ID NO: 66, amino acids 31-84 of SEQ ID NO: 67, amino acids 25-180 of SEQ ID NO: 67 or SEQ ID NO: 68.

57. The multivalent Clostridial toxin according to 50, wherein the neurotrophin is selected from the group consisting of nerve growth factor (NGF), brain-derived growth factor (BDNF), neurotrophin-3 (NT-3) and neurotrophin-4/5 (NT-4/5).

58. The multivalent Clostridial toxin according to 50, wherein the neurotrophin comprises amino acids 139-257 of SEQ ID NO: 69, amino acids 133-240 of SEQ ID NO: 70, amino acids 129-247 of SEQ ID NO: 70, amino acids 144-249 of SEQ ID NO: 71, amino acids 19-257 of SEQ ID NO: 71, amino acids 89-202 of SEQ ID NO: 72 and amino acids 81-210 of SEQ ID NO: 72.

59. The multivalent Clostridial toxin according to 50, wherein the growth factor is selected from the group consisting of glial cell derived neurotrophic factor (GDNF), neurturin (NRTN), persephrin (PSPN), artemin (ARTN), TGFβ1, TGFβ2, TGFβ3, TGFβ4, BMP2, BMP3, BMP4, BMP5, BMP6, BMP7, BMP8, BMP10, GDF1, GDF2, GDF3, GDF5, GDF6, GDF7, GDF8, GDF10, GDF11, GDF15, activin A, activin B, activin C, activin E and inhibin A.

60. The multivalent Clostridial toxin according to 50, wherein the growth factor selected from the group consisting of amino acids 118-211 of SEQ ID NO: 73, amino acids 107-196 of SEQ ID NO: 74, amino acids 96-197 of SEQ ID NO: 74, amino acids 66-155 of SEQ ID NO: 75, amino acids 123-218 of SEQ ID NO: 76, amino acids 293-390 of SEQ ID NO: 77, amino acids 317-414 of SEQ ID NO: 78, amino acids 315-412 of SEQ ID NO: 79, amino acids 276-373 of SEQ ID NO: 80, amino acids 296-396 of SEQ ID NO: 81, amino acids 370-472 of SEQ ID NO: 82, amino acids 309-409 of SEQ ID NO: 83, amino acids 353-454 of SEQ ID NO: 84, amino acids 323-454 of SEQ ID NO: 84, amino acids 412-513 of SEQ ID NO: 85, amino acids 374-513 of SEQ ID NO: 85, amino acids 330-431 of SEQ ID NO: 86, amino acids 293-431 of SEQ ID NO: 86, amino acids 301-402 of SEQ ID NO: 87, amino acids 323-424 of SEQ ID NO: 88, amino acids 267-372 of SEQ ID NO: 89, amino acids 327-429 of SEQ ID NO: 90, amino acids 264-364 of SEQ ID NO: 91, amino acids 400-501 of SEQ ID NO: 92, amino acids 354-455 of SEQ ID NO: 93, amino acids 352-450 of SEQ ID NO: 94, amino acids 281-375 of SEQ ID NO: 95; amino acids 376-478 of SEQ ID NO: 96; amino acids 313-407 of SEQ ID NO: 97; amino acids 211-308 of SEQ ID NO: 98; amino acids 321-426 of SEQ ID NO: 99; amino acids 303-406 of SEQ ID NO: 100; amino acids 247-352 of SEQ ID NO: 101; amino acids 237-352 of SEQ ID NO: 101; amino acids 247-350 of SEQ ID NO: 102; amino acids 262-366 of SEQ ID NO: 103; or amino acids 233-366 of SEQ ID NO: 103.

61. The multivalent Clostridial toxin according either 1 or 13, wherein the first binding domain comprises a binding domain selected from the group consisting of an opioid peptide, a melanocortin peptide, a galanin peptide, a granin peptide, a tachykinin peptide, a cholecystokinin peptide, a Neuropeptide Y related peptide, a kinin peptide, a protease activated receptor (PAR) peptide, a somatostatin peptide, a leukemia inhibitor factor peptide, and an interleukin-1 peptide.

62. The multivalent Clostridial toxin according to 61, wherein the opioid peptide is selected from the group consisting of an enkephalin peptide, a BAM22 peptide, an endomorphin peptide, an endorphin peptide, a dynorphin peptide, a nociceptin peptide and a hemorphin peptide.

63. The multivalent Clostridial toxin according to 62, wherein the enkephalin peptide is selected from the group consisting of a Leu-enkephalin, a Met-enkephalin, a Met-enkephalin MRGL and a Met-enkephalin MRF 64. The multivalent Clostridial toxin according to 62, wherein the enkephalin peptide comprises SEQ ID NO: 104, SEQ ID NO: 105, SEQ ID NO: 106 or SEQ ID NO: 107.

65. The multivalent Clostridial toxin according to 62, wherein the BAM22 peptide is selected from the group consisting of a BAM22 peptide (1-12), a BAM22 peptide (6-22), a BAM22 peptide (8-22) or a BAM22 peptide (1-22).

66. The multivalent Clostridial toxin according to 62, wherein the BAM22 peptide comprises amino acids 1-12 of SEQ ID NO: 108, amino acids 6-22 of SEQ ID NO: 108, amino acids 8-22 of SEQ ID NO: 108, amino acids 1-22 of SEQ ID NO: 108, amino acids 1-12 of SEQ ID NO: 109, amino acids 6-22 of SEQ ID NO: 109, amino acids 8-22 of SEQ ID NO: 109, amino acids 1-22 of SEQ ID NO: 109, amino acids 1-12 of SEQ ID NO: 110, amino acids 6-22 of SEQ ID NO: 110, amino acids 8-22 of SEQ ID NO: 110, amino acids 1-22 of SEQ ID NO: 110, amino acids 1-12 of SEQ ID NO: 111, amino acids 6-22 of SEQ ID NO: 111, amino acids 8-22 of SEQ ID NO: 111, amino acids 1-22 of SEQ ID NO: 111, amino acids 1-12 of SEQ ID NO: 112, amino acids 6-22 of SEQ ID NO: 112, amino acids 8-22 of SEQ ID NO: 112, amino acids 1-22 of SEQ ID NO: 112, amino acids 1-12 of SEQ ID NO: 113, amino acids 6-22 of SEQ ID NO: 113, amino acids 8-22 of SEQ ID NO: 113, or amino acids 1-22 of SEQ ID NO: 113.

67. The multivalent Clostridial toxin according to 62, wherein the endomorphin peptide is selected from the group consisting of an endomorphin-1 and an endomorphin-2.

68. The multivalent Clostridial toxin according to 62, wherein the endomorphin peptide comprises SEQ ID NO: 114, or SEQ ID NO: 115.

69. The multivalent Clostridial toxin according to 62, wherein the endorphin peptide is selected from the group consisting of an endorphin-α, a neoendorphin-α, an endorphin-β, a neoendorphin-β or an endorphin-γ.

70. The multivalent Clostridial toxin according to 62, wherein the altered targeting domain comprises an endorphin selected from the group consisting of SEQ ID NO: 291, SEQ ID NO: 116, SEQ ID NO: 117, SEQ ID NO: 118, SEQ ID NO: 119, or SEQ ID NO: 120.

71. The multivalent Clostridial toxin according to 62, wherein the dynorphin peptide is selected from the group consisting of a dynorphin A, a dynorphin B and a rimorphin.

72. The multivalent Clostridial toxin according to 62, wherein the dynorphin peptide comprises SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, or SEQ ID NO: 151.

73. The multivalent Clostridial toxin according to 62, wherein the nociceptin peptide selected from the group consisting of a nociceptin RK, a nociceptin, a neuropeptide 1, a neuropeptide 2 or a neuropeptide 3.

74. The multivalent Clostridial toxin according to 62, wherein the nociceptin peptide comprises SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, or SEQ ID NO: 161.

75. The multivalent Clostridial toxin according to 61, wherein the melanocortin peptide is selected from the group consisting of an α-melanocyte stimulating hormones (α-MSH), α-melanocyte stimulating hormones (β-MSH), a γ-melanocyte stimulating hormones (γ-MSH), an adrenocorticotropin (ACTH), a Corticotropin-like intermediary peptide (CLIP), a β-lipotropin (β-LPH) and a γ-lipotropin (γ-LPH).

76. The multivalent Clostridial toxin according to 61, wherein the melanocortin peptide is selected from the group consisting SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, or SEQ ID NO: 171.

77. The multivalent Clostridial toxin according to 61, wherein the galanin peptide is selected from the group consisting of a galanin and a galanin message-associated peptide (GMAP).

78. The multivalent Clostridial toxin according to 61, wherein the galanin peptide comprises SEQ ID NO: 172, or SEQ ID NO: 173.

79. The multivalent Clostridial toxin according to 61, wherein the grainin peptide is selected from the group consisting of a chromogranin A peptide, a chromogranin B peptide and a chromogranin C peptide.

80. The multivalent Clostridial toxin according to 79, wherein the chromogranin A peptide is selected from the group consisting of a β-granin, a vasostatin, a chromostatin, a pancreastatin, a WE-14, a catestatin, a parastatin and a GE-25.

81. The modified Clostridial toxin according to 79, wherein the chromogranin A peptide comprises SEQ ID NO: 174, SEQ ID NO: 175, SEQ ID NO: 176, SEQ ID NO: 177, SEQ ID NO: 178, SEQ ID NO: 179, SEQ ID NO: 180, or SEQ ID NO: 181.

82. The multivalent Clostridial toxin according to 79, wherein the chromogranin B peptide is selected from the group consisting of a GAWK peptide, an adrenomedullary peptide and a secretolytin.

83. The multivalent Clostridial toxin according to 79, wherein the chromogranin B peptide comprises SEQ ID NO: 182, SEQ ID NO: 183, SEQ ID NO: 184, SEQ ID NO: 185, or SEQ ID NO: 186

84. The multivalent Clostridial toxin according to 79, wherein the chromogranin C peptide is selected from the group consisting of a secretoneurin, a EM66 and a manserin.

85. The multivalent Clostridial toxin according to 79, wherein the chromogranin C peptide comprises SEQ ID NO: 187.

86. The multivalent Clostridial toxin according to 61, wherein the tachykinin peptide is selected from the group consisting of a Substance P, a neuropeptide K (NPK), a neuropeptide gamma, a neurokinin A, a neurokinin B, a hemokinin and a endokinin.

87. The multivalent Clostridial toxin according to 61, wherein the tachykinin peptide comprises SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198 and SEQ ID NO: 199.

88. The multivalent Clostridial toxin according to 61, wherein the cholecystokinin peptide is selected from the group consisting of a cholecystokinin 58, a cholecystokinin 39, a cholecystokinin 33, a cholecystokinin 12 and a cholecystokinin 8.

89. The multivalent Clostridial toxin according to 88, wherein the cholecystokinin 58 is selected from the group consisting of SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, or SEQ ID NO: 215.

90. The multivalent Clostridial toxin according to 88, wherein the cholecystokinin 39 is selected from the group consisting of amino acids 20-58 of SEQ ID NO: 200, amino acids 20-58 of SEQ ID NO: 201, amino acids 20-58 of SEQ ID NO: 202, amino acids 20-58 of SEQ ID NO: 203, amino acids 20-58 of SEQ ID NO: 204, amino acids 20-58 of SEQ ID NO: 205, amino acids 20-58 of SEQ ID NO: 207, amino acids 20-58 of SEQ ID NO: 208, amino acids 20-58 of SEQ ID NO: 209, amino acids 20-58 of SEQ ID NO: 210, amino acids 20-58 of SEQ ID NO: 211, amino acids 20-58 of SEQ ID NO: 212, amino acids 20-58 of SEQ ID NO: 213, amino acids 20-58 of SEQ ID NO: 214, or amino acids 20-58 of SEQ ID NO: 215.

91. The multivalent Clostridial toxin according to 88, wherein the cholecystokinin 33 is selected from the group consisting of amino acids 26-58 of SEQ ID NO: 200, amino acids 26-58 of SEQ ID NO: 201, amino acids 26-58 of SEQ ID NO: 202, amino acids 26-58 of SEQ ID NO: 203, amino acids 26-58 of SEQ ID NO: 204, amino acids 26-58 of SEQ ID NO: 205, amino acids 26-58 of SEQ ID NO: 207, amino acids 26-58 of SEQ ID NO: 208, amino acids 26-58 of SEQ ID NO: 209, amino acids 26-58 of SEQ ID NO: 210, amino acids 26-58 of SEQ ID NO: 211, amino acids 26-58 of SEQ ID NO: 212, amino acids 26-58 of SEQ ID NO: 213, amino acids 26-58 of SEQ ID NO: 214 or amino acids 26-58 of SEQ ID NO: 215.

92. The multivalent Clostridial toxin according to 88, wherein the cholecystokinin 12 is selected from the group consisting of amino acids 47-58 of SEQ ID NO: 200, amino acids 47-58 of SEQ ID NO: 210 or amino acids 47-58 of SEQ ID NO: 214.

93. The multivalent Clostridial toxin according to 88, wherein the cholecystokinin 8 is amino acids 51-58 of SEQ ID NO: 200.

94. The multivalent Clostridial toxin according to 61, wherein the Neuropeptide Y related peptide is selected from the group consisting of a Neuropeptide Y (NPY), a Peptide YY (PYY), a Pancreatic peptide (PP) and a Pancreatic icosapeptide (PIP).

95. The multivalent Clostridial toxin according to 61, wherein the Neuropeptide Y related peptide comprises SEQ ID NO: 216, SEQ ID NO: 217, SEQ ID NO: 218, SEQ ID NO: 219, or SEQ ID NO: 220.

96. The multivalent Clostridial toxin according to 61, wherein the kinin peptide is selected from the group consisting of a bradykinin, a kallidin, a desArg$^9$ bradykinin and a desArg$^{10}$ bradykinin.

97. The multivalent Clostridial toxin according to 61, wherein the kinin peptide comprises SEQ ID NO: 227, SEQ ID NO: 228, SEQ ID NO: 229, or SEQ ID NO: 230.

98. The multivalent Clostridial toxin according to 61, wherein the PAR peptide is selected from the group consisting of a PAR1 peptide, a PAR2 peptide, a PAR3 peptide and a PAR4 peptide.

99. The modified Clostridial toxin according to 61, wherein the PAR peptide comprises amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234.

100. The multivalent Clostridial toxin according either 1 or 13, wherein the first binding domain comprises a binding domain selected from the group consisting of a PTD.

101. The multivalent Clostridial toxin according to 100, wherein the PTD is selected from the group consisting of a herpes simplex virus type 1 VP22 protein translocating sequence, a SV-40 virus large T translocating sequence, a TAT translocating sequence, an adenovirus translocating sequence, a synthetic integrin binding domain translocating sequence, a Kaposi fibroblast growth factor membrane translocating sequence, a nuclear localization signal, a Transportan translocating sequence, a ciliary neurotrophic factor translocating sequence, a caveolin, an interleukin 1-β translocating sequence, a thioredoxin translocating sequence, a fibroblast growth factor-1 translocating sequence, a fibroblast growth factor-2 translocating sequence, an integrin β1 translocating sequence, an integrin β3 translocating sequence, a lactoferrin translocating sequence, a homeodomain translocating sequence, like, a penetratin translocating sequence, an Engrailed-1 translocating sequence, an Engrailed-2 translocating sequence, a Hoxa-5 translocating sequence, a Hoxb-4 translocating sequence, and a Hoxc-8 translocating sequence.

102. The multivalent Clostridial toxin according to 100, wherein the PTD comprises SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, or SEQ ID NO: 253.

103. A polynucleotide molecule encoding a multivalent Clostridial toxin according to any one of Claims 1-102.

104. The polynucleotide molecule according to Claims 103, wherein the polynucleotide molecule is an expression construct.

105. A method of producing a multivalent Clostridial toxin comprising the step of expressing in a cell a polynucleotide according to 52

106. A method of producing a multivalent Clostridial toxin comprising the steps of
   a) introducing in a cell an expression construct comprising a polynucleotide according to 52; and
   b) expressing the expression construct in the cell.

EXAMPLES

Example 1

Construction of a Multivalent Clostridial Neurotoxin Comprising Two Clostridial Toxin Binding Domains This example illustrates how to make a multivalent Clostridial toxin comprising two modified Clostridial toxin binding domains with enhanced binding activity using site-directed mutagenesis.

A polynucleotide molecule encoding BoNT/A (SEQ ID NO: 1) and further comprising a polynucleotide sequence comprising a repeat of amino acids 874-1296 of the binding domain of BoNT/A at the amino terminus is synthesized using standard procedures (BlueHeron® Biotechnology, Bothell, Wash.). The basic strategy is set forth in FIG. 5A. Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/multivalent Clostridial toxin(AA)1. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression-optimized polynucleotide molecule encoding BoNT/A (SEQ ID NO: 1) can be synthesized in order to improve expression in an *Escherichia coli* strain. The polynucleotide molecule encoding the BoNT/A can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, PCT Patent Serial No. 2005/020578 (Jun. 9, 2005); Lance E. Steward et al. Optimizing Expression of Active Botulinum Toxin Type A, PCT Patent Serial No. 2005/027917 (Aug. 3, 2005). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/multivalent Clostridial toxin1/(AA)1:ECopt. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). Is so desired, optimization to a different organism, such as, e.g., a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005).

A similar cloning strategy is used to make pUCBHB1 cloning constructs comprising a polynucleotide molecule encoding BoNT/B of SEQ ID NO: 2; a polynucleotide molecule encoding BoNT/C1 of SEQ ID NO: 3; a polynucleotide molecule encoding BoNT/D of SEQ ID NO: 4; a polynucleotide molecule encoding BoNT/E of SEQ ID NO: 5; a polynucleotide molecule encoding BoNT/F of SEQ ID NO: 6; a polynucleotide molecule encoding BoNT/G of SEQ ID NO: 7; a polynucleotide molecule encoding TeNT of SEQ ID NO: 8; a polynucleotide molecule encoding BaNT of SEQ ID NO: 9; a polynucleotide molecule encoding BuNT of SEQ ID NO: 10; wherein the additional binding domain can be selected from, e.g., any of the $H_C$ or $H_{CC}$ binding domains listed in Table 1. In addition, one skilled in the art can modify Clostridial toxins, such as, e.g., to include an exogenous protease cleavage site within the di-chain loop region, or flexible spacer regions. Likewise, a similar cloning strategy can be used to make other domain orientations as, e.g., as set forth in FIG. 4A, 4B, 4C, 4D, 5B, 5C, 5D, 6A or 6B.

To construct pET29/multivalent Clostridial toxin/A(AA)1, a pUCBHB1/multivalent Clostridial toxin(AA)1 construct is digested with restriction endonucleases that 1) excise the insert comprising the open reading frame of SEQ ID NO: 1 (with the added nucleotide sequence encoding the N terminal Binding 1 site) encoding the multivalent Clostridial toxin (AA)1; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/multivalent Clostridial toxin/A(AA)1. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 µg/mL of Kanamycin, and placed in a 37° C. incubator for overnight growth. Bacteria containing expression constructs are identified as kanamycin resistant colonies. Candidate constructs are isolated using an alkaline lysis plasmid mini-preparation procedure and analyzed by restriction endonuclease digest mapping to determine the presence and orientation of the insert. This cloning strategy yields a pET29 expression construct comprising the polynucleotide molecule encoding the BoNT/A of SEQ ID NO: 1 operably-linked to an additional N-terminal binding site comprising the native binding region of BoNT/A.

A similar cloning strategy is used to make pET29 expression constructs comprising polynucleotide molecule encoding the multivalent Clostridial toxins discussed above comprising BoNT/B of SEQ ID NO: 2; a polynucleotide molecule encoding BoNT/C1 of SEQ ID NO: 3; a polynucleotide molecule encoding BoNT/D of SEQ ID NO: 4; a polynucleotide molecule encoding BoNT/E of SEQ ID NO: 5; a polynucleotide molecule encoding BoNT/F of SEQ ID NO: 6; a polynucleotide molecule encoding BoNT/G of SEQ ID NO: 7; a polynucleotide molecule encoding TeNT of SEQ ID NO: 8, a polynucleotide molecule encoding BaNT of SEQ ID NO: 9 and a polynucleotide molecule encoding BuNT of SEQ ID NO: 10, each with an additional binding site.

To construct a multivalent Clostridial toxin comprising one or more modified binding domain with enhanced binding activity, specific amino acids influencing binding activity will be changed. For example, it is already known that amino acids Trp 1101, Gly 1102, Leu 1105, Tyr 1111, Tyr 1112, Gly 1158, Ile 1163, Asp 1179, Glu 1203, Phe 1252, Ser 1264, Trp 1266, Tyr 1267, Gln 1270, Gly 1279 and Trp 1282 of SEQ ID NO: 1 (within the binding site) are important for function. To determine which amino acid substitutions could enhance the binding activity of a BoNT/A binding domain, computational protein design algorithms will generate novel binding domains with optimized properties. The crystal structure of a BoNT/A binding domain will be used as the starting template for computational calculations. Potential amino acid candidates will be identified using a combined output from Protein Design Automation® (PDA®) and Sequence Prediction Algorithm™ (SPA™) calculations. For PDA calculations, the conformations of amino acids at variable positions will be represented as a set of backbone-independent side chain rotamers derived from the rotamer library. The energies of all possible combinations of the considered amino acids at the chosen variable positions will be calculated using a force field containing terms describing van der Waals, solvation, electrostatic, and hydrogen bond interactions. The optimal (ground state) sequence will be determined using a Dead End Elimination (DEE) algorithm, and a Monte Carlo (MC) algorithm will be used to evaluate the energies of similar sequences around the predicted ground state. SPA calculations utilize a genetic algorithm to screen for low energy sequences, with energies being calculated during each round of "evolution" for those sequences being sampled. The conformations of amino acids will be represented as a set of side chain rotamers derived from a backbone-independent rotamer library using a flexible rotamer model. SPA calculations will generate sequences which will be subsequently clustered computationally into groups of similar sequences using a nearest neighbor single linkage hierarchical clustering algorithm. Critical contact amino acids will be fixed in both sequence and conformation and calculations will be carried out to evaluate single and combinatorial substitutions at variable amino acids. All amino acids in contact with these residues will be floated, that is the amino acid conformation but not the amino acid identity will be allowed to vary to allow for conformational adjustments. Final experimental substitutions will be chosen based on their predicted energies relative to the naturally occurring BoNT/A binding domain and their occupancy, that is the number times the substitution occurred in the set of 1000 MC or genetic algorithm sequences. Two sets of design calculations will be carried out using Rosetta to identify substitutions predicted to stabilize the BoNT/A binding domain. In the first round, only single amino acid substitutions will be modeled. In a second round, interface amino acids will be allowed to change to all 20 naturally occurring amino acids including the native amino acid type, but excluding cysteine, simultaneously. In each case, amino acid side chains contacting the substituted amino acid side chains will be repacked (allowing all rotamers of the native amino acid type). Sequences and conformations with low energies will be selected using a Monte-Carlo simulated annealing procedure. All resulting protein complex models will be rescored by computing a predicted binding energy. Final sequences are selected for the lowest binding energy.

To use this information to generate one or more modified Clostridial neurotoxin binding domain, candidate amino acids identified as described above will be changed using site-directed in vitro mutagenesis. A 50 µL reaction will be assembled using pET29/multivalent Clostridial toxin/A (AA)1 as a template, sense and antisense oligonucleotides encoding the desired amino acid change identified above, and reagents included with the QuickChange® II XL Site-Directed Mutagenesis kit (Stratagene, La Jolla, Calif.). The polymerase chain reaction (PCR) mix will contain 5 µL of 10× Buffer, 1 µL of deoxyribonucleotides (dNTPs), 1 µL of PfuUltra™ High Fidelity DNA polymerase (2.5 units/µL), 125 ng of each primer, 100 ng of template DNA, and nuclease-free water to a final volume of 50 µL. The thermocycler conditions will be: one cycle of 95° C. for 60 seconds; 16 cycles of 95° C. for 30 seconds, 55° C. for 60 seconds, and 72° C. for 10 minutes; one cycle of 72° C. for 5 minutes; and 4° C. to hold. Following thermocycling, 1 µL of DpnI restriction enzyme (Stratagene, La Jolla, Calif.) will be added to the reaction and will be incubated for 1 hour at 37° C. to digest the template DNA. The reaction will be purified by QIAquick kit (QIAGEN, Inc., Valencia, Calif.) and will be analysis by agarose gel electrophoresis to determine that the reaction produced full-length plasmid. The mutagenesis products will be transformed into chemically competent E. coli DH5α cells (Invitrogen, Inc, Carlsbad, Calif.) using a heat shock method, plated on 1.5% Luria-Bertani agar plates (pH 7.0) containing 100 µg/mL of Ampicillin, and will be placed in a 37° C. incubator for overnight growth. Candidate mutagenesis constructs will be isolated as Ampicillin resistant colonies and will be analyzed using an alkaline lysis plasmid mini-preparation procedure to isolate the expression construct and restriction endonuclease digests to determine the presence of the insert. The incorporation of the point mutation will be determined by sequence analysis of candidate plasmid constructs.

To test the binding activity of multivalent Clostridial toxins comprising binding domains derived from BoNT/A, the soluble portion of FGFR3 will be expressed recombinantly for use in surface plasmon resonance (SPR) binding assays, e.g., Biacore® (Biacore Inc., Piscataway, N.J.). The soluble portion of FGFR3 will be expressed as a fusion to streptavidin and the receptor will then be immobilized on an appropriate sensor chip. Utilizing a Biacore® instrument, changes in local refractive index as a result of receptor binding will be measured as a change in the SPR angle. The rates of change in the SPR angle will then be analyzed to determine association rate ($K_{on}$), dissociation rate ($K_{off}$) and the dissociation equilibrium constant ($K_D = K_{off}/K_{on}$). Multivalent Clostridial neurotoxin derivatives comprising binding domains derived from BoNT/A exhibit either an increased association rate, a decreased dissociation rate, both an increased association rate and a decreased dissociation rate, or a decreased dissociation equilibrium constant relative to the measurements obtained from the naturally occurring BoNT/A from which the multivalent Clostridial toxin is derived.

The same methods and rationale may be used to make and test the affinity of any multivalent Clostridial toxin comprising additional binding domain derived from a Clostridial toxin. Generally, but not exclusively, a multivalent Clostridial toxin is tested relative to the Clostridial toxin with which it shares the greatest homology, particularly in the binding domains.

Example 2

Construction of a Multivalent Clostridial Neurotoxin Comprising a Non-Toxin Associated Protein A polynucleotide molecule encoding BoNT/A-Nterm33/A is synthesized using standard procedures (BlueHeron® Biotechnology, Bothell, Wash.), as described in Example 1. BoNT/A-Nterm33/A is a BoNT/A modified to replace amino acids in the second binding domain (the N-terminal binding region of the multivalent Clostridial toxin described in Example 1) corresponding to amino acids 1111-1296 of SEQ ID NO: 1, a BoNT/A β-trefoil domain, with amino acids 151 to 293 of SEQ ID NO: 9, a HA-33 β-trefoil domain from a Clostridial botulinum serotype A strain. If desired, an expression optimized polynucleotide molecule encoding BoNT/A-Nterm33/A can be synthesized in order to improve expression in to a different organism, such as, e.g., an Escherichia coli strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for multivalent Clostridial toxin BoNT/B-Nterm33/A, a multivalent Clostridial toxin based on BoNT/B where amino acids 1098-1291 of SEQ ID NO: 2 are replaced with amino acids 151 to 293 of SEQ ID NO: 11; multivalent Clostridial toxin BoNT/C1-Nterm33/A, a multivalent Clostridial toxin based on BoNT/C1 where amino acids 1112-1291 of SEQ ID NO: 3 are replaced with amino acids 151 to 293 of SEQ ID NO: 11; multivalent Clostridial toxin BoNT/D-Nterm33/A, a multivalent Clostridial toxin based on BoNT/D where amino acids 1099-1276 of SEQ ID NO: 4 are replaced with amino acids 151 to 293 of SEQ ID NO: 11; multivalent Clostridial toxin BoNT/E-Nterm33/A, a multivalent Clostridial toxin based on BoNT/E where amino acids 1086-1252 of SEQ ID NO: 5 are replaced with amino acids 151 to 293 of SEQ ID NO: 11; multivalent Clostridial toxin BoNT/F-Nterm33/A, a multivalent Clostridial toxin based on BoNT/F where amino acids 1106-1274 of SEQ ID NO: 6 are replaced with amino acids 151 to 293 of SEQ ID NO: 11; multivalent Clostridial toxin BoNT/G-Nterm33/A, a multivalent Clostridial toxin based on BoNT/G where amino acids 1106-1297 of SEQ ID NO: 7 are replaced with amino acids 151 to 293 of SEQ ID NO: 11; and multivalent Clostridial toxin TeNT-Nterm33/A, a modified TeNT where amino acids 1128-1315 of SEQ ID NO: 8 are replaced with amino acids 151 to 293 of SEQ ID NO: 11.

Similarly, the β-trefoil domain from a Clostridial toxin indicated above can be replaced with a non-toxin associated protein β-trefoil domain comprising amino acids 10-144 of SEQ ID NO: 11; amino acids 10-144 of SEQ ID NO: 12; amino acids 10-144 of SEQ ID NO: 13; amino acids 10-146 of SEQ ID NO: 14; amino acids 10-144 of SEQ ID NO: 15; amino acids 10-144 of SEQ ID NO: 16; amino acids 10-146 of SEQ ID NO: 17; amino acids 10-141 of SEQ ID NO: 18; amino acids 10-141 of SEQ ID NO: 19; amino acids 10-141 of SEQ ID NO: 20; amino acids 151-293 of SEQ ID NO: 12; amino acids 151-293 of SEQ ID NO: 13; amino acids 153-294 of SEQ ID NO: 14; amino acids 151-279 of SEQ ID NO: 15; amino acids 151-292 of SEQ ID NO: 16; amino acids 153-291 of SEQ ID NO: 17; amino acids 148-285 of SEQ ID NO: 18; amino acids 148-286 of SEQ ID NO: 19; amino acids 148-286 of SEQ ID NO: 20; amino acids 9-146 of SEQ ID NO: 21; amino acids 9-146 of SEQ ID NO: 22; amino acids 9-146 of SEQ ID NO: 23; amino acids 9-146 of SEQ ID NO: 24; amino acids 1050-1194 of SEQ ID NO: 25; amino acids 1050-1199 of SEQ ID NO: 26; amino acids 1050-1194 of SEQ ID NO: 27; amino acids 1049-1198 of SEQ ID NO: 28; amino acids 1049-1197 of SEQ ID NO: 29; amino acids 1049-1197 of SEQ ID NO: 30; amino acids 1014-1163 of SEQ ID NO: 31; amino acids 1016-1160 of SEQ ID NO: 32; amino acids 1017-1166 of SEQ ID NO: 33; and amino acids 1050-1199 of SEQ ID NO: 34.

To construct pET29/multivalent Clostridial toxin/BoNT/A-Nterm33/A, a pUCBHB1/BoNT/A-33/A construct is digested with restriction endonucleases that 1) excise the insert comprising the open reading frame encoding the BoNT/A-Nterm33/A; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-Nterm33/A. The ligation mixture is transformed into chemically competent E. coli DH5α cells (Invitrogen, Inc, Carlsbad, Calif.) using a heat shock method, plated on 1.5% Luria-Bertani agar plates (pH 7.0) containing 50 μg/mL of kanamycin, and placed in a 37° C. incubator for overnight growth. Bacteria containing expression constructs are identified as kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding a multivalent Clostridial toxin BoNT/A-Nterm33/A operably-linked to a carboxyl terminal polyhistidine affinity binding peptide.

A similar cloning strategy is used to make pET29 expression constructs comprising a polynucleotide molecule encoding for BoNT/B-33/A, BoNT/C1-33/A, BoNT/D-33/A, BoNT/E-33/A, BoNT/F-33/A, BoNT/G-33/A, TeNT-33/A, as well as the modified Clostridial toxin indicated above comprising amino acids 10-144 of SEQ ID NO: 11; amino acids 10-144 of SEQ ID NO: 12; amino acids 10-144 of SEQ ID NO: 13; amino acids 10-146 of SEQ ID NO: 14; amino acids 10-144 of SEQ ID NO: 15; amino acids 10-144 of SEQ ID NO: 16; amino acids 10-146 of SEQ ID NO: 17; amino acids 10-141 of SEQ ID NO: 18; amino acids 10-141 of SEQ ID NO: 19; amino acids 10-141 of SEQ ID NO: 20; amino acids 151-293 of SEQ ID NO: 12; amino acids 151-293 of SEQ ID NO: 13; amino acids 153-294 of SEQ ID NO: 14; amino acids 151-279 of SEQ ID NO: 15; amino acids 151-292 of SEQ ID NO: 16; amino acids 153-291 of SEQ ID NO: 17; amino acids 148-285 of SEQ ID NO: 18; amino acids 148-286 of SEQ ID NO: 19; amino acids 148-286 of SEQ ID NO: 20; amino acids 9-146 of SEQ ID NO: 21; amino acids 9-146 of SEQ ID NO: 22; amino acids 9-146 of SEQ ID NO: 23; amino acids 9-146 of SEQ ID NO: 24; amino acids 1050-1194 of SEQ ID NO: 25; amino acids 1050-1199 of SEQ ID NO: 26; amino acids 1050-1194 of SEQ ID NO: 27; amino acids 1049-1198 of SEQ ID NO: 28; amino acids 1049-1197 of SEQ ID NO: 29; amino acids 1049-1197 of SEQ ID NO: 30; amino acids 1014-1163 of SEQ ID NO: 31; amino acids 1016-1160 of SEQ ID NO: 32; amino acids 1017-1166 of SEQ ID NO: 33; and amino acids 1050-1199 of SEQ ID NO: 34.

Example 3

Construction of a Multivalent Clostridial Toxin Comprising an FGF

A polynucleotide molecule encoding BoNT/A-F18 is synthesized using standard procedures (BlueHeron® Biotechnology, Bothell, Wash.), as described in Example 1. BoNT/A-F18 is a BoNT/A modified to replace amino acids 1111-1296 of SEQ ID NO: 1, a BoNT/A β-trefoil domain, with amino acids 54 to 183 of SEQ ID NO: 39, a FGF-18 β-trefoil domain. If desired, an expression optimized polynucleotide molecule encoding BoNT/A-F18 can be synthesized in order to improve expression in to a different organism, such as, e.g., an Escherichia coli strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A polynucleotide molecule encoding BoNT/A-NtermF18 is synthesized using standard procedures (BlueHeron® Biotechnology, Bothell, Wash.), as described in Example 1. BoNT/A-NtermF18 is a BoNT/A modified to replace amino acids in the second binding domain (the N-terminal binding region of the multivalent Clostridial toxin described in Example 1) corresponding to amino acids 1111-1296 of SEQ ID NO: 1, a BoNT/A β-trefoil domain, with amino acids 54 to 183 of SEQ ID NO: 41, a FGF-18 β-trefoil domain. If desired, an expression optimized polynucleotide molecule encoding BoNT/A-NtermF18 can be synthesized in order to improve expression in to a different organism, such as, e.g., an Escherichia coli strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1

(Applied Biosystems, Foster City, Calif.) and an ABI 3100 sequencer (Applied Biosystems, Foster City, Calif.).

A similar cloning strategy is used to make pUCBHB1 cloning constructs for multivalent Clostridial toxin BoNT/B-F18, a modified BoNT/B where amino acids 1098-1291 of SEQ ID NO: 2 are replaced with amino acids 54 to 183 of SEQ ID NO: 41; multivalent Clostridial toxin BoNT/C1-F18, a modified BoNT/C1 where amino acids 1112-1291 of SEQ ID NO: 3 are replaced with amino acids 54 to 183 of SEQ ID NO: 41; BoNT/D-F18, multivalent Clostridial toxin BoNT/D where amino acids 1099-1276 of SEQ ID NO: 4 are replaced with amino acids 54 to 183 of SEQ ID NO: 41; BoNT/E-F18, multivalent Clostridial toxin BoNT/E where amino acids 1086-1252 of SEQ ID NO: 5 are replaced with amino acids 54 to 183 of SEQ ID NO: 41; BoNT/F-F18, multivalent Clostridial toxin BoNT/F where amino acids 1106-1274 of SEQ ID NO: 6 are replaced with amino acids 54 to 183 of SEQ ID NO: 41; BoNT/G-F18, multivalent Clostridial toxin BoNT/G where amino acids 1106-1297 of SEQ ID NO: 7 are replaced with amino acids 54 to 183 of SEQ ID NO: 41; multivalent Clostridial toxin TeNT-F18, TeNT where amino acids 1128-1315 of SEQ ID NO: 8 are replaced with amino acids 54 to 183 of SEQ ID NO: 41; multivalent Clostridial toxin BaNT-F18, BaNT where amino acids 1095-1268 of SEQ ID NO: 9 are replaced with amino acids 54 to 183 of SEQ ID NO: 41; multivalent Clostridial toxin BuNT-F18, BuNT where amino acids 1086-1251 of SEQ ID NO: 10 are replaced with amino acids 54 to 183 of SEQ ID NO: 41. Similarly, the β-trefoil domain from a Clostridial toxin indicated above can be replaced with a FGF β-trefoil domain comprising amino acids 26-155 of SEQ ID NO: 35; amino acids 29-155 of SEQ ID NO: 36; amino acids 83-206 of SEQ ID NO: 37; amino acids 43-172 of SEQ ID NO: 38; amino acids 63-196 of SEQ ID NO: 39; and amino acids 55-183 of SEQ ID NO: 40.

To construct pET29/multivalent Clostridial toxin/BoNT/A-NtermF18, a pUCBHB1/BoNT/A-F18 construct is digested with restriction endonucleases that 1) excise the insert comprising the open reading frame encoding BoNT/A-NtermF18; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-NtermF18. The ligation mixture is transformed into chemically competent E. coli DH5α cells (Invitrogen, Inc, Carlsbad, Calif.) using a heat shock method, plated on 1.5% Luria-Bertani agar plates (pH 7.0) containing 50 µg/mL of kanamycin, and placed in a 37° C. incubator for overnight growth. Bacteria containing expression constructs are identified as kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding the multivalent Clostridial toxin BoNT/A-NtermF18 operably-linked to a carboxyl terminal polyhistidine affinity binding peptide.

A similar cloning strategy is used to make pET29 expression constructs comprising a polynucleotide molecule encoding multivalent Clostridial toxins BoNT/B-F18, BoNT/C1-F18, BoNT/D-F18, BoNT/E-F18, BoNT/F-F18, BoNT/G-F18, TeNT-F18, as well as multivalent Clostridial toxin indicated above comprising amino acids 26-155 of SEQ ID NO: 35; amino acids 29-155 of SEQ ID NO: 36; amino acids 83-206 of SEQ ID NO: 37; amino acids 43-172 of SEQ ID NO: 38; amino acids 63-196 of SEQ ID NO: 39; and amino acids 55-183 of SEQ ID NO: 40.

Example 4

Construction of a Multivalent Clostridial Neurotoxin Comprising a Binding Domain A polynucleotide molecule encoding BoNT/A-NtermGRPP is synthesized using standard procedures (Blue-Heron® Biotechnology, Bothell, Wash.), as described in Example 1. BoNT/A-NtermGRPP is a BoNT/A modified to replace amino acids in the second binding domain (the N-terminal binding region of the multivalent Clostridial toxin described in Example 1) corresponding to amino acids 1111-1296 of SEQ ID NO: 1, a BoNT/A β-trefoil domain, with amino acids 21 to 50 of SEQ ID NO: 42, a GRPP binding domain. If desired, an expression optimized polynucleotide molecule encoding BoNT/A-NtermGRPP can be synthesized in order to improve expression in to a different organism, such as, e.g., an Escherichia coli strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for multivalent Clostridial toxin BoNT/B-GRPP, a modified BoNT/B where amino acids 1098-1291 of SEQ ID NO: 2 are replaced with amino acids 21 to 50 of SEQ ID NO: 42; multivalent Clostridial toxin BoNT/C1-GRPP, a modified BoNT/C1 where amino acids 1112-1291 of SEQ ID NO: 3 are replaced with amino acids 21 to 50 of SEQ ID NO: 42; BoNT/D-GRPP, multivalent Clostridial toxin BoNT/D where amino acids 1099-1276 of SEQ ID NO: 4 are replaced with amino acids 21 to 50 of SEQ ID NO: 42; BoNT/E-GRPP, multivalent Clostridial toxin BoNT/E where amino acids 1086-1252 of SEQ ID NO: 5 are replaced with amino acids 21 to 50 of SEQ ID NO: 42; BoNT/F-GRPP, multivalent Clostridial toxin BoNT/F where amino acids 1106-1274 of SEQ ID NO: 6 are replaced with amino acids 21 to 50 of SEQ ID NO: 42; BoNT/G-GRPP, multivalent Clostridial toxin BoNT/G where amino acids 1106-1297 of SEQ ID NO: 7 are replaced with amino acids 21 to 50 of SEQ ID NO: 42; multivalent Clostridial toxin TeNT-GRPP, TeNT where amino acids 1128-1315 of SEQ ID NO: 8 are replaced with amino acids 21 to 50 of SEQ ID NO: 42; multivalent Clostridial toxin BaNT-GRPP, BaNT where amino acids 1095-1268 of SEQ ID NO: 9 are replaced with amino acids 21 to 50 of SEQ ID NO: 42; multivalent Clostridial toxin BuNT-GRPP, BuNT where amino acids 1086-1251 of SEQ ID NO: 10 are replaced with amino acids 21 to 50 of SEQ ID NO: 42.

Similarly, the β-trefoil domain from a Clostridial toxin indicated above can be replaced with a binding domain comprising, e.g., amino acids 53-81 of SEQ ID NO: 42; amino acids 53-89 of SEQ ID NO: 9; amino acids 98-124 of SEQ ID NO: 42; amino acids 146-178 of SEQ ID NO: 42; amino acids 132-158 of SEQ ID NO: 43; amino acids 32-58 of SEQ ID NO: 44; amino acids 32-75 of SEQ ID NO: 44; amino acids 81-107 of SEQ ID NO: 45; amino acids 125-151 of SEQ ID NO: 45; amino acids 81-107 of SEQ ID NO: 46; amino acids 124-150 of SEQ ID NO: 46; amino acids 52-78 of SEQ ID NO: 47; amino acids 52-93 of SEQ ID NO: 47; amino acids 28-54 of SEQ ID NO: 48; amino acids 76-92 of SEQ ID NO:

49; amino acids 59-92 of SEQ ID NO: 49; amino acids 41-50 of SEQ ID NO: 50; amino acids 24-50 of SEQ ID NO: 50; amino acids 99-112 of SEQ ID NO: 51; amino acids 159-193 of SEQ ID NO: 52; amino acids 154-194 of SEQ ID NO: 52; amino acids 35-70 of SEQ ID NO: 53; amino acids 145-177 of SEQ ID NO: 53; amino acids 1-200 of SEQ ID NO: 54; amino acids 1-150 of SEQ ID NO: 55; amino acids 1-202 of SEQ ID NO: 56; amino acids 1-201 of SEQ ID NO: 57; amino acids 1-225 of SEQ ID NO: 58; amino acids 123-265 of SEQ ID NO: 59; amino acids 21-153 of SEQ ID NO: 60; amino acids 57-210 of SEQ ID NO: 61; amino acids 21-99 of SEQ ID NO: 62; amino acids 31-94 of SEQ ID NO: 62; amino acids 19-178 of SEQ ID NO: 63; amino acids 1-558 of SEQ ID NO: 64; amino acids 1-371 of SEQ ID NO: 65; amino acids 49-118 of SEQ ID NO: 66; amino acids 25-180 of SEQ ID NO: 67; amino acids 1-54 of SEQ ID NO: 68; amino acids 139-257 of SEQ ID NO: 69; amino acids 129-247 of SEQ ID NO: 70; amino acids 19-257 of SEQ ID NO: 71; amino acids 81-210 of SEQ ID NO: 72; amino acids 118-211 of SEQ ID NO: 73; amino acids 107-196 of SEQ ID NO: 74; amino acids 96-197 of SEQ ID NO: 74; amino acids 66-155 of SEQ ID NO: 75; amino acids 123-218 of SEQ ID NO: 76; amino acids 293-390 of SEQ ID NO: 77; amino acids 317-414 of SEQ ID NO: 78; amino acids 315-412 of SEQ ID NO: 79; amino acids 276-373 of SEQ ID NO: 80; amino acids 296-396 of SEQ ID NO: 81; amino acids 370-472 of SEQ ID NO: 82; amino acids 309-409 of SEQ ID NO: 83; amino acids 323-454 of SEQ ID NO: 84; amino acids 412-513 of SEQ ID NO: 85; amino acids 374-513 of SEQ ID NO: 85; amino acids 330-431 of SEQ ID NO: 86; amino acids 293-431 of SEQ ID NO: 86; amino acids 301-402 of SEQ ID NO: 87; amino acids 323-424 of SEQ ID NO: 88; amino acids 267-372 of SEQ ID NO: 89; amino acids 327-429 of SEQ ID NO: 90; amino acids 264-364 of SEQ ID NO: 91; amino acids 400-501 of SEQ ID NO: 92; amino acids 354-455 of SEQ ID NO: 93; amino acids 352-450 of SEQ ID NO: 94; amino acids 281-375 of SEQ ID NO: 95; amino acids 376-478 of SEQ ID NO: 96; amino acids 313-407 of SEQ ID NO: 97; amino acids 211-308 of SEQ ID NO: 98; amino acids 321-426 of SEQ ID NO: 99; amino acids 303-406 of SEQ ID NO: 100; amino acids 247-352 of SEQ ID NO: 101; amino acids 237-352 of SEQ ID NO: 101; amino acids 247-350 of SEQ ID NO: 102; amino acids 262-366 of SEQ ID NO: 103; or amino acids 233-366 of SEQ ID NO: 103.

To construct pET29/multivalent Clostridial toxin/BoNT/A-NtermGRPP, a pUCBHB1/BoNT/A-GRPP construct is digested with restriction endonucleases that 1) excise the insert comprising the open reading frame encoding the BoNT/A-NtermGRPP; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-NtermGRPP. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 µg/mL of kanamycin, and placed in a 37° C. incubator for overnight growth. Bacteria containing expression constructs are identified as kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding the multivalent Clostridial toxin BoNT/A-NtermGRPP operably-linked to a carboxyl terminal polyhistidine affinity binding peptide.

A similar cloning strategy is used to make pET29 expression constructs comprising a polynucleotide molecule encoding multivalent Clostridial toxins BoNT/B-GRPP, BoNT/C1-GRPP, BoNT/D-GRPP, BoNT/E-GRPP, BoNT/F-GRPP, BoNT/G-GRPP, TeNT-GRPP, BaNT-GRPP, BuNT-GRPP, as well as multivalent Clostridial toxin indicated above comprising, e.g., amino acids 53-81 of SEQ ID NO: 42; amino acids 53-89 of SEQ ID NO: 9; amino acids 98-124 of SEQ ID NO: 42; amino acids 146-178 of SEQ ID NO: 42; amino acids 132-158 of SEQ ID NO: 43; amino acids 32-58 of SEQ ID NO: 44; amino acids 32-75 of SEQ ID NO: 44; amino acids 81-107 of SEQ ID NO: 45; amino acids 125-151 of SEQ ID NO: 45; amino acids 81-107 of SEQ ID NO: 46; amino acids 124-150 of SEQ ID NO: 46; amino acids 52-78 of SEQ ID NO: 47; amino acids 52-93 of SEQ ID NO: 47; amino acids 28-54 of SEQ ID NO: 48; amino acids 76-92 of SEQ ID NO: 49; amino acids 59-92 of SEQ ID NO: 49; amino acids 41-50 of SEQ ID NO: 50; amino acids 24-50 of SEQ ID NO: 50; amino acids 99-112 of SEQ ID NO: 51; amino acids 159-193 of SEQ ID NO: 52; amino acids 154-194 of SEQ ID NO: 52; amino acids 35-70 of SEQ ID NO: 53; amino acids 145-177 of SEQ ID NO: 53; amino acids 1-200 of SEQ ID NO: 54; amino acids 1-150 of SEQ ID NO: 55; amino acids 1-202 of SEQ ID NO: 56; amino acids 1-201 of SEQ ID NO: 57; amino acids 1-225 of SEQ ID NO: 58; amino acids 123-265 of SEQ ID NO: 59; amino acids 21-153 of SEQ ID NO: 60; amino acids 57-210 of SEQ ID NO: 61; amino acids 21-99 of SEQ ID NO: 62; amino acids 31-94 of SEQ ID NO: 62; amino acids 19-178 of SEQ ID NO: 63; amino acids 1-558 of SEQ ID NO: 64; amino acids 1-371 of SEQ ID NO: 65; amino acids 49-118 of SEQ ID NO: 66; amino acids 25-180 of SEQ ID NO: 67; amino acids 1-54 of SEQ ID NO: 68; amino acids 139-257 of SEQ ID NO: 69; amino acids 129-247 of SEQ ID NO: 70; amino acids 19-257 of SEQ ID NO: 71; amino acids 81-210 of SEQ ID NO: 72; amino acids 118-211 of SEQ ID NO: 73; amino acids 107-196 of SEQ ID NO: 74; amino acids 96-197 of SEQ ID NO: 74; amino acids 66-155 of SEQ ID NO: 75; amino acids 123-218 of SEQ ID NO: 76; amino acids 293-390 of SEQ ID NO: 77; amino acids 317-414 of SEQ ID NO: 78; amino acids 315-412 of SEQ ID NO: 79; amino acids 276-373 of SEQ ID NO: 80; amino acids 296-396 of SEQ ID NO: 81; amino acids 370-472 of SEQ ID NO: 82; amino acids 309-409 of SEQ ID NO: 83; amino acids 323-454 of SEQ ID NO: 84; amino acids 412-513 of SEQ ID NO: 85; amino acids 374-513 of SEQ ID NO: 85; amino acids 330-431 of SEQ ID NO: 86; amino acids 293-431 of SEQ ID NO: 86; amino acids 301-402 of SEQ ID NO: 87; amino acids 323-424 of SEQ ID NO: 88; amino acids 267-372 of SEQ ID NO: 89; amino acids 327-429 of SEQ ID NO: 90; amino acids 264-364 of SEQ ID NO: 91; amino acids 400-501 of SEQ ID NO: 92; amino acids 354-455 of SEQ ID NO: 93; amino acids 352-450 of SEQ ID NO: 94; amino acids 281-375 of SEQ ID NO: 95; amino acids 376-478 of SEQ ID NO: 96; amino acids 313-407 of SEQ ID NO: 97; amino acids 211-308 of SEQ ID NO: 98; amino acids 321-426 of SEQ ID NO: 99; amino acids 303-406 of SEQ ID NO: 100; amino acids 247-352 of SEQ ID NO: 101; amino acids 237-352 of SEQ ID NO: 101; amino acids 247-350 of SEQ ID NO: 102; amino acids 262-366 of SEQ ID NO: 103; or amino acids 233-366 of SEQ ID NO: 103.

Example 5

Construction of a Multivalent Clostridial Neurotoxin Comprising a Binding Domain A polynucleotide molecule encoding BoNT/A-Noci is synthesized using standard procedures (BlueHeron® Biotechnology, Bothell, Wash.), as described in Example 1. BoNT/A-Noci is a BoNT/A modified to replace amino acids 874-1296 of SEQ ID NO: 1, a BoNT/A β-trefoil domain, with a nociceptin-RK targeting domain. If desired, an expression optimized polynucleotide molecule encoding BoNT/A-Noci can be synthesized in order to improve expression in to a different organism, such as, e.g., an *Escherichia coli* strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A polynucleotide molecule encoding BoNT/A-NtermNoci is synthesized using standard procedures (BlueHeron® Biotechnology, Bothell, Wash.), as described in Example 1. BoNT/A-NtermNoci is a BoNT/A modified to replace amino acids in the second binding domain (the N-terminal binding region of the multivalent Clostridial toxin described in Example 1) corresponding to amino acids 874-1296 of SEQ ID NO: 1, a BoNT/A β-trefoil domain, with SEQ ID NO: 152, a nociceptin-RK binding domain. If desired, an expression optimized polynucleotide molecule encoding BoNT/A-NtermNoci can be synthesized in order to improve expression in to a different organism, such as, e.g., an *Escherichia coli* strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for multivalent Clostridial toxin BoNT/B-Noci, a modified BoNT/B where amino acids 861-1291 of SEQ ID NO: 2 are replaced with SEQ ID NO: 152; multivalent Clostridial toxin BoNT/C1-Noci, a modified BoNT/C1 where amino acids 869-1291 of SEQ ID NO: 3 are replaced with SEQ ID NO: 152; BoNT/D-Noci, multivalent Clostridial toxin BoNT/D where amino acids 865-1276 of SEQ ID NO: 4 are replaced with SEQ ID NO: 152; BoNT/E-Noci, multivalent Clostridial toxin BoNT/E where amino acids 848-1252 of SEQ ID NO: 5 are replaced with SEQ ID NO: 152; BoNT/F-Noci, multivalent Clostridial toxin BoNT/F where amino acids 867-1274 of SEQ ID NO: 6 are replaced with SEQ ID NO: 152; BoNT/G-Noci, multivalent Clostridial toxin BoNT/G where amino acids 866-1297 of SEQ ID NO: 7 are replaced with SEQ ID NO: 152; multivalent Clostridial toxin TeNT-Noci, TeNT where amino acids 882-1315 of SEQ ID NO: 8 are replaced with SEQ ID NO: 152; multivalent Clostridial toxin BaNT-Noci, BaNT where amino acids 858-1268 of SEQ ID NO: 9 are replaced with SEQ ID NO: 152; multivalent Clostridial toxin BuNT-Noci, BuNT where amino acids 848-1251 of SEQ ID NO: 10 are replaced with SEQ ID NO: 152.

Similarly, the β-trefoil domain from a Clostridial toxin indicated above can be replaced with a binding domain comprising, e.g., SEQ ID NO: 104; SEQ ID NO: 105, SEQ ID NO: 106, SEQ ID NO: 107, SEQ ID NO: 114, SEQ ID NO: 115, SEQ ID NO: 291, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, or SEQ ID NO: 253.

Similarly, the β-trefoil domain from a Clostridial toxin indicated above can be replaced with a binding domain comprising, e.g., amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; amino acids 1-12, amino acids 6-22, amino acids 8-22 or amino acids 1-22 of SEQ ID NO: 113; amino acids 20-58 of SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215; amino acids 26-58 of SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215; amino acids 47-58 of SEQ ID NO: 200, SEQ ID NO: 210 or SEQ ID NO: 214; or amino acids 51-58 of SEQ ID NO: 200; amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234.

To construct pET29/multivalent Clostridial toxin/BoNT/A-NtermGRPP, a pUCBHB1/BoNT/A-Noci construct is digested with restriction endonucleases that 1) excise the insert comprising the open reading frame encoding the BoNT/A-NtermNoci; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-NtermNoci. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of kanamycin, and placed in a 37° C. incubator for overnight growth. Bacteria containing expression constructs are identified as kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding the multivalent Clostridial toxin BoNT/A-NtermNoci operably-linked to a carboxyl terminal polyhistidine affinity binding peptide.

A similar cloning strategy is used to make pET29 expression constructs comprising a polynucleotide molecule encoding multivalent Clostridial toxins BoNT/B-Noci, BoNT/C1-Noci, BoNT/D-Noci, BoNT/E-Noci, BoNT/F-Noci, BoNT/G-Noci, TeNT-Noci, BaNT-Noci, BuNT-Noci, as well as multivalent Clostridial toxin indicated above comprising, e.g., SEQ ID NO: 104; SEQ ID NO: 105, SEQ ID NO: 106, SEQ ID NO: 107, SEQ ID NO: 114, SEQ ID NO: 115, SEQ ID NO: 291, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253; amino acids 1-12, amino acids 6-22, amino acids 8-22 or amino acids 1-22 of SEQ ID NO: 108; amino acids 1-12, amino acids 6-22, amino acids 8-22 or amino acids 1-22 of SEQ ID NO: 109; amino acids 1-12, amino acids 6-22, amino acids 8-22 or amino acids 1-22 of SEQ ID NO: 110; amino acids 1-12, amino acids 6-22, amino acids 8-22 or amino acids 1-22 of SEQ ID NO: 111; amino acids 1-12, amino acids 6-22, amino acids 8-22 or amino acids 1-22 of SEQ ID NO: 112; amino acids 1-12, amino acids 6-22, amino acids 8-22 or amino acids 1-22 of SEQ ID NO: 113; amino acids 20-58 of SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215; amino acids 26-58 of SEQ ID NO: 200, SEQ ID NO: 201, SEQ ID NO: 202, SEQ ID NO: 203, SEQ ID NO: 204, SEQ ID NO: 205, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214 or SEQ ID NO: 215; amino acids 47-58 of SEQ ID NO: 200, SEQ ID NO: 210 or SEQ ID NO: 214; or amino acids 51-58 of SEQ ID NO: 200; amino acids 42-47, amino acids 42-55, amino acids 29-64 or amino acids 1-64 of SEQ ID NO: 231; amino acids 35-40, amino acids 35-48, amino acids 24-59 or amino acids 1-59 of SEQ ID NO: 232; amino acids 39-44, amino acids 39-52, amino acids 26-60 or amino acids 1-60 of SEQ ID NO: 233; amino acids 48-53, amino acids 48-61, amino acids 35-70 or amino acids 1-70 of SEQ ID NO: 234

Example 6

Construction of a Multivalent Clostridial Neurotoxin Comprising Three CCK-A Binding Sites The following example illustrates how to make a retargeted multivalent Clostridial toxin comprising three CCK-A binding sites.

A polynucleotide molecule is constructed as described in Example 1 above, encoding BoNT/A with the native binding site replaced with 10 repeats of the CCK 58 amino acid sequence (see U.S. Pat. No. 6,843,998, hereby incorporated by reference herein in its entirety) and with the same CCK 58 sequence repeated twice at the N-terminus of the single chain. The two N-terminal repeats are constructed to be separated by a short amino acid region comprising the loop region of BoNT/A, and two cysteine residues spanning the protease sensitive site. The multivalent Clostridial toxin is termed multivalent Clostridial toxin BoNT/A/C(CCK)N(CCKx2). The basic architecture of the amino acid construct is given in FIG. 2A.

If desired, an expression-optimized polynucleotide molecule encoding multivalent Clostridial toxin BoNT/A/C(CCK)N(CCKx2) can be synthesized in order to improve expression in to a different organism, such as, e.g., an *Escherichia coli* strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for C(CCK)N(CCKx2) multivalent Clostridial toxin's in which the translocation and endopeptidase domains are independently selected from BoNT/B, C1, D, E, F, G, or TeNT.

To construct pET29/multivalent Clostridial toxin BoNT/A/C(CCK)N(CCKx2), a pUCBHB1/multivalent Clostridial toxin BoNT/A/C(CCK)N(CCKx2) construct is digested with restriction endonucleases that 1) excise the insert comprising the open reading frame encoding multivalent Clostridial toxin BoNT/A/C(CCK)N(CCKx2); and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/multivalent Clostridial toxin BoNT/A/C(CCK)N(CCKx2). The ligation mixture is transformed into chemically competent E. coli DH5α cells (Invitrogen, Inc, Carlsbad, Calif.) using a heat shock method, plated on 1.5% Luria-Bertani agar plates (pH 7.0) containing 50 µg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding multivalent Clostridial toxin BoNT/A/C(CCK)N(CCKx2), operably-linked to a carboxyl terminal polyhistidine affinity binding peptide.

A similar cloning strategy is used to make pET29 expression constructs comprising a polynucleotide molecule encoding any combination of translocation and endopeptidase domains derived from BoNT/A, B, C1, D, E, F, G or TeNT with CCK 58 domains similar positioned as in multivalent Clostridial toxin BoNT/A/C(CCK)N(CCKx2).

Example 7

Purification and Quantification of Modified Clostridial Toxins

The following example illustrates methods useful for purification and quantification of any modified Clostridial toxins disclosed in the present specification.

For immobilized metal affinity chromatography (IMAC) protein purification, E. coli BL21 (DE3) cell pellets used to express a modified Clostridial toxin, as described in Example 7, are resuspended in Column Binding Buffer (25 mM N-(2-hydroxyethyl)piperazine-N'-(2-ethanesulfonic acid) (HEPES), pH 7.8; 500 mM sodium chloride; 10 mM imidazole; 2x Protease Inhibitor Cocktail Set III (EMD Biosciences-Calbiochem, San Diego Calif.); 5 units/mL of Benzonase (EMD Biosciences-Novagen, Madison, Wis.); 0.1% (v/v) Triton-X® 100, 4-octylphenol polyethoxylate; 10% (v/v) glycerol), and then are transferred to a cold Oakridge centrifuge tube. The cell suspension is sonicated on ice (10-12 pulses of 10 seconds at 40% amplitude with 60 seconds cooling intervals on a Branson Digital Sonifier) in order to lyse the cells and then is centrifuged (16,000 rpm at 4° C. for 20 minutes) to clarify the lysate. An immobilized metal affinity chromatography column is prepared using a 20 mL Econo-Pac column support (Bio-Rad Laboratories, Hercules, Calif.) packed with 2.5-5.0 mL of TALON™ SuperFlow $Co^{2+}$ affinity resin (BD Biosciences-Clontech, Palo Alto, Calif.), which is then equilibrated by rinsing with 5 column volumes of deionized, distilled water, followed by 5 column volumes of Column Binding Buffer. The clarified lysate is applied slowly to the equilibrated column by gravity flow (approximately 0.25-0.3 mL/minute). The column is then washed with 5 column volumes of Column Wash Buffer (N-(2-hydroxyethyl)piperazine-N'-(2-ethanesulfonic acid) (HEPES), pH 7.8; 500 mM sodium chloride; 10 mM imidazole; 0.1% (v/v) Triton-X® 100, 4-octylphenol polyethoxylate; 10% (v/v) glycerol). The modified Clostridial toxin is eluted with 20-30 mL of Column Elution Buffer (25 mM N-(2-hydroxyethyl)piperazine-N'-(2-ethanesulfonic acid) (HEPES), pH 7.8; 500 mM sodium chloride; 500 mM imidazole; 0.1% (v/v) Triton-X® 100, 4-octylphenol polyethoxylate; 10% (v/v) glycerol) and is collected in approximately twelve 1 mL fractions. The amount of modified Clostridial toxin contained in each elution fraction is determined by a Bradford dye assay. In this procedure, 20 µL aliquots of each 1.0 mL fraction is combined with 200 µL of Bio-Rad Protein Reagent (Bio-Rad Laboratories, Hercules, Calif.), diluted 1 to 4 with deionized, distilled water, and then the intensity of the colorimetric signal is measured using a spectrophotometer. The five fractions with the strongest signal are considered the elution peak and are combined together. Total protein yield is determined by estimating the total protein concentration of the pooled peak elution fractions using bovine gamma globulin as a standard (Bio-Rad Laboratories, Hercules, Calif.).

For purification of a modified Clostridial toxin using a FPLC desalting column, a HiPrep™ 26/10 size exclusion column (Amersham Biosciences, Piscataway, N.J.) is pre-equilibrated with 80 mL of 4° C. Column Buffer (50 mM sodium phosphate, pH 6.5). After the column is equilibrated, a modified Clostridial toxin sample is applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted modified Clostridial toxin sample is collected as a single fraction of approximately 7-12 mL.

For purification of a modified Clostridial toxin using a FPLC ion exchange column, a modified Clostridial toxin sample that has been desalted following elution from an IMAC column is applied to a 1 mL Q1™ anion exchange column (Bio-Rad Laboratories, Hercules, Calif.) using a Bio-Logic DuoFlow chromatography system (Bio-Rad Laboratories, Hercules, Calif.). The sample is applied to the column in 4° C. Column Buffer (50 mM sodium phosphate, pH 6.5) and is eluted by linear gradient with 4° C. Elution Buffer (50 mM sodium phosphate, 1 M sodium chloride, pH 6.5) as follows: step 1, 5.0 mL of 5% Elution Buffer at a flow rate of 1 mL/minute; step 2, 20.0 mL of 5-30% Elution Buffer at a flow rate of 1 mL/minute; step 3, 2.0 mL of 50% Elution Buffer at a flow rate of 1.0 mL/minute; step 4, 4.0 mL of 100% Elution Buffer at a flow rate of 1.0 mL/minute; and step 5, 5.0 mL of 0% Elution Buffer at a flow rate of 1.0 mL/minute. Elution of modified Clostridial toxin from the column is monitored at 280, 260, and 214 nm, and peaks absorbing above a minimum threshold (0.01 au) at 280 nm are collected. Most of the modified Clostridial toxin will elute at a sodium chloride concentration of approximately 100 to 200 mM. Average total yields of modified Clostridial toxin will be determined by a Bradford assay.

Expression of a modified Clostridial toxin is analyzed by polyacrylamide gel electrophoresis. Samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Gels are stained with SYPRO® Ruby (Bio-Rad Laboratories, Hercules, Calif.) and the separated polypeptides are imaged using a Fluor-S MAX MultiImager (Bio-Rad Laboratories, Hercules, Calif.) for quantification of modified Clostridial toxin expression levels. The size and amount of modified Clostridial toxin is determined by comparison to MagicMark™ protein molecular weight standards (Invitrogen, Inc, Carlsbad, Calif.).

Expression of modified Clostridial toxin is also analyzed by Western blot analysis. Protein samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated polypeptides are transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes are blocked by incubating at room temperature for 2 hours in a solution containing 25 mM Tris-Buffered Saline (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes are incubated at 4° C. for overnight in Tris-Buffered Saline TWEEN-20® (25 mM Tris-Buffered Saline, 0.1% TWEEN-20®, polyoxyethylene (20) sorbitan monolaureate) containing appropriate primary antibodies as a probe. Primary antibody probed blots are washed three times for 15 minutes each time in Tris-Buffered Saline TWEEN-20. Washed membranes are incubated at room temperature for 2 hours in Tris-Buffered Saline TWEEN-20® containing an appropriate immunoglobulin G antibody conjugated to horseradish peroxidase as a secondary antibody. Secondary antibody-probed blots are washed three times for 15 minutes each time in Tris-Buffered Saline TWEEN-20®. Signal detection of the labeled modified Clostridial toxin are visualized using the ECL Plus™ Western Blot Detection System (Amersham Biosciences, Piscataway, N.J.) and are imaged with a Typhoon 9410 Variable Mode Imager (Amersham Biosciences, Piscataway, N.J.) for quantification of modified Clostridial toxin expression levels.

Example 8

Treatment of Hyperhidrosis Using a Multivalent Clostridial Toxin

A 32-year-old woman presents complaining with chronic and excessive perspiring under the arms and in the palm of the hands. Clinical examination reveals a high degree of sweating under the arms, and stains on clothing in the same area.

The patient is injected in the eccrine glands under one arm with an approximately minimum effective dose (15 drops) of BOTOX®. The same patient is injected in the eccrine glands under the other arm with 7 drops of the Multivalent Clostridial Neurotoxin Derivative of Example 1.

The patient is observed one week later. Examination reveals that excessive sweating under the arms has been deceased by 85-95% in both cases, despite the fact that the multivalent Clostridial toxin was administered at less than 50% of the BOTOX® dosage.

Example 9

Treatment of Acute Pancreatitis with a Multivalent Clostridial Toxin

A 55 year-old man with a history of alcoholism presents with nausea, loss of appetite and severe abdominal pain radiating to the back. Examination reveals that the patient suffers from acute pancreatitis with a Balthazar Score of Grade D (with fluid collection in a single pancreatic location). The acute and advancing pancreatic necrosis threatens the patient's life.

The patient is administered the multivalent Clostridial toxin of Example 3 in an effective dose by injection directly into the pancreatic acini. Within 48 hours, there is a halt in the progression of the patient's deterioration. Within two weeks the acute pain has been relieved and the patient is able to take oral nourishment.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

Any and all patents, publications, patent applications, and nucleotide and/or amino acid sequences referred to by accession numbers cited in this specification are hereby incorporated by reference as part of this specification.

Each and every feature described herein, and each and every combination of two or more of such features, is included within the scope of the present invention provided that the features included in such a combination are not mutually inconsistent.

These and other aspects of the present invention are set forth in the following claims.

What is claimed is:

1. A multivalent Clostridial toxin comprising:

a) a Clostridial toxin enzymatic domain capable of executing an enzymatic target modification step of a Clostridial toxin intoxication process;

b) a Clostridial toxin translocation domain capable of executing a translocation step of a Clostridial toxin intoxication process;

c) a first binding domain capable of executing a cell binding step of a Clostridial toxin intoxication process by selectively binding a first cell surface receptor displayed by the target cell;

d) a second binding domain capable of executing a cell binding step of a Clostridial toxin intoxication process by selectively binding a second cell surface receptor displayed by the target cell; and e) a protease cleavage site, wherein cleavage of the protease cleavage site converts the single-chain form of the modified Clostridial toxin into the di-chain form.

2. The multivalent Clostridial toxin according to claim 1, wherein the multivalent Clostridial toxin comprises amino to carboxyl linear organization comprising a) a first binding domain, a translocation domain, a second binding domain, a protease cleavage site and an enzymatic domain, b) an enzymatic domain, a protease cleavage site, a first binding domain, a translocation domain and a second binding domain, c) an enzymatic domain, a protease cleavage site, a translocation domain, a first binding domain and a second binding domain, d) an enzymatic domain, a protease cleavage site, a translocation domain, a second binding domain and a first binding domain, e) a first binding domain, an enzymatic domain, a protease cleavage site, a translocation domain and a second binding domain, f) a translocation domain, a second binding domain, a protease cleavage site, a first binding domain and an enzymatic domain, g) a translocation domain, a second binding domain, a protease cleavage site, an enzymatic domain and a first binding domain, or h) a second binding domain, a translocation domain, a protease cleavage site, a first binding domain and an enzymatic domain.

3. The multivalent Clostridial toxin according to claim 1, wherein the protease cleavage site is an endogenous protease cleavage site or an exogenous protease cleavage site.

4. The multivalent Clostridial toxin according to claim 3, wherein the endogenous protease cleavage site is selected from the group consisting of a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

5. The multivalent Clostridial toxin according to claim 3, wherein the exogenous protease cleavage site is selected from the group consisting of a bovine enterokinase protease cleavage site, a Tobacco Etch Virus protease cleavage site, a Human Rhinovirus 3C protease cleavage site, a SUMO/ULP-1 protease cleavage site, a Thrombin protease cleavage site, and a Factor Xa protease cleavage site.

6. The multivalent Clostridial toxin according to claim 1, wherein the Clostridial toxin enzymatic domain is selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain and a BuNT enzymatic domain.

7. The multivalent Clostridial toxin according claim 1, wherein the Clostridial toxin translocation domain is selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain and a BuNT translocation domain.

8. The multivalent Clostridial toxin according claim 1, wherein the first binding domain comprises a binding domain selected from the group consisting of a Clostridial toxin binding domain, a Clostridial non-toxin associated protein β-trefoil domain and an FGF β-trefoil domain.

9. The multivalent Clostridial toxin according claim 1, wherein the first binding domain comprises a binding domain selected from the group consisting of a glucagon like hormone, a neurohormone, a neuroregulatory cytokine, a neurotrophin, a growth factor, and an axon guidance signaling molecule.

10. The multivalent Clostridial toxin according claim 1, wherein the first binding domain comprises a binding domain selected from the group consisting of an opioid peptide, a melanocortin peptide, a galanin peptide, a granin peptide, a tachykinin peptide, a cholecystokinin peptide, a Neuropeptide Y related peptide, a kinin peptide, a protease activated receptor (PAR) peptide, a somatostatin peptide, a leukemia inhibitor factor peptide, and an interleukin-1 peptide.

11. The multivalent Clostridial toxin according claim 1, wherein the first binding domain comprises a protein translocation domain.

12. The multivalent Clostridial toxin according to claim 11, wherein the PTD is selected from the group consisting of a herpes simplex virus type 1 VP22 protein translocating sequence, a SV-40 virus large T translocating sequence, a TAT translocating sequence, an adenovirus translocating sequence, a synthetic integrin binding domain translocating sequence, a Kaposi fibroblast growth factor membrane translocating sequence, a nuclear localization signal, a Transportan translocating sequence, a ciliary neurotrophic factor translocating sequence, a caveolin, an interleukin 1-β translocating sequence, a thioredoxin translocating sequence, a fibroblast growth factor-1 translocating sequence, a fibroblast growth factor-2 translocating sequence, an integrin β1 translocating sequence, an integrin β3 translocating sequence, a lactoferrin translocating sequence, a homeodomain translocating sequence, like, a penetratin translocating sequence, an Engrailed-1 translocating sequence, an Engrailed-2 translocating sequence, a Hoxa-5 translocating sequence, a Hoxb-4 translocating sequence, and a Hoxc-8 translocating sequence.

* * * * *

UNITED STATES PATENT AND TRADEMARK OFFICE
CERTIFICATE OF CORRECTION

PATENT NO. : 7,811,584 B2
APPLICATION NO. : 12/210770
DATED : October 12, 2010
INVENTOR(S) : Lance E. Steward et al.

It is certified that error appears in the above-identified patent and that said Letters Patent is hereby corrected as shown below:

On page 2, in column 2, under "Other Publications", line 40, delete "specifiic" and insert -- specific --, therefor.

On page 2, in column 2, under "Other Publications", line 40, delete "interation" and insert -- interaction --, therefor.

In column 33, line 49, delete "multiivalent" and insert -- multivalent --, therefor.

In column 33, line 52, delete "multiivalent" and insert -- multivalent --, therefor.

In column 33, line 56, delete "multiivalent" and insert -- multivalent --, therefor.

In column 34, line 30-31, delete "onostatin" and insert -- oncostatin --, therefor.

In column 34, line 42, delete "semaphrorings" and insert -- semaphorins --, therefor.

In column 35, line 18, delete "kallidan" and insert -- kallidin --, therefor.

In column 35, line 45, after "sequence" insert -- . --.

In column 36, line 14, after "domain" insert -- . --.

In column 51, line 57, delete "H" and insert -- $H_{CC}$ --, therefor.

In column 68, line 27, delete "H" and insert -- $H_{CC}$ -- therefor.

Signed and Sealed this
Twelfth Day of April, 2011

David J. Kappos
*Director of the United States Patent and Trademark Office*

CERTIFICATE OF CORRECTION (continued)

In column 95, line 40-47, delete "Immunoaffinity column chromatography and pull-down assays have shown that HA-33 can bind synaptotagmin II, a putative Clostridial toxin receptor, see, e.g., Yu Zhou et al., Haemagglutinin-33 of Type Q Botulinum Neurotoxin Complex Binds with Synaptotagmin II, 272 FEBS Lett. 2717-2726 (2005). The amino acid sequences comprising the β-trefoil domains found in various Clostridial HA-33 proteins are shown in Tables 3 and 4." and insert the same on Col. 95, Line 39 after "SEQ ID NO: 20." as a continuation of the paragraph.

In column 96, line 35, delete "R-trefoil" and insert -- β-trefoil --, therefor.

In column 234, line 43, delete "onostatin" and insert -- oncostatin --, therefor.

In column 310, line 47, delete "1)" and insert -- I) --, therefor.

In column 349, line 60, delete "phosphatylinositol" and insert -- phosphatidylinositol --, therefor.

In column 351, line 25, delete "opiod" and insert -- opioid --, therefor.

In column 354, line 67, delete "opiod" and insert -- opioid --, therefor.

In column 371, line 46, delete "phosphatylinositol" and insert -- phosphatidylinositol --, therefor.

In column 373, line 27, delete "phosphatylinositol" and insert -- phosphatidylinositol --, therefor.

In column 374, line 6, delete "phosphatylinositol" and insert -- phosphatidylinositol --, therefor.

In column 374, line 38, after "associated" insert -- . --.

In column 375, line 51, delete "phosphatylinositol" and insert -- phosphatidylinositol --, therefor.

In column 381, line 55, delete "onostatin" and insert -- oncostatin --, therefor.

In column 384, line 25, delete "grainin" and insert -- granin --, therefor.

In column 403, line 27, delete "monolaureate" and insert -- monolaurate --, therefor.

In column 403, line 31, delete "monolaureate" and insert -- monolaurate --, therefor.

In column 729, line 35, in claim 7, delete "according" and insert -- according to --, therefor.

CERTIFICATE OF CORRECTION (continued)
U.S. Pat. No. 7,811,584 B2

In column 730, line 1, in claim 8, delete "according" and insert -- according to --, therefor.

In column 730, line 6, in claim 9, delete "according" and insert -- according to --, therefor.

In column 730, line 12, in claim 10, delete "according" and insert -- according to --, therefor.

In column 730, line 20, in claim 11, delete "according" and insert -- according to --, therefor.

SEQUENCE LISTING

<160> NUMBER OF SEQ ID NOS: 291

<210> SEQ ID NO 1
<211> LENGTH: 1296
<212> TYPE: PRT
<213> ORGANISM: Clostridium botulinum serotype A

<400> SEQUENCE: 1

-continued

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
```

-continued

```
                420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
        450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
        515                 520                 525
Glu Leu Met Pro Asn Ile Glu Arg Phe Pro Asn Gly Lys Lys Tyr Glu
    530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
        595                 600                 605
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
        675                 680                 685
Val Leu Thr Val Gln Thr Ile Asp Asn Ala Leu Ser Lys Arg Asn Glu
    690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
            740                 745                 750
Gln Tyr Thr Glu Glu Glu Lys Asn Asn Ile Asn Phe Asn Ile Asp Asp
        755                 760                 765
Leu Ser Ser Lys Leu Asn Glu Ser Ile Asn Lys Ala Met Ile Asn Ile
    770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                805                 810                 815
Asp Ala Leu Leu Lys Tyr Ile Tyr Asp Asn Arg Gly Thr Leu Ile Gly
            820                 825                 830
Gln Val Asp Arg Leu Lys Asp Lys Val Asn Asn Thr Leu Ser Thr Asp
        835                 840                 845
```

-continued

```
Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
                1060                1065                1070

Asn Leu Phe Asp Lys Glu Leu Asn Glu Lys Glu Ile Lys Asp Leu Tyr
            1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
                1140                1145                1150

Ser Leu Tyr Arg Gly Thr Lys Phe Ile Ile Lys Lys Tyr Ala Ser Gly
            1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
            1235                1240                1245

Phe Ile Gly Phe His Gln Phe Asn Asn Ile Ala Lys Leu Val Ala Ser
    1250                1255                1260
```

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

<210> SEQ ID NO 2
<211> LENGTH: 1291
<212> TYPE: PRT
<213> ORGANISM: Clostridium botulinum serotype B

<400> SEQUENCE: 2

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
        130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
                180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
        210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
                260                 265                 270

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
        290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

-continued

```
Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Lys Ser Asn Ile Asn Ile Asp
            740                 745                 750

Phe Asn Asp Ile Asn Ser Lys Leu Asn Glu Gly Ile Asn Gln Ala Ile
            755                 760                 765
```

-continued

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
        995                 1000                1005

Asn Asn Leu Asn Asn Ala Lys Ile Tyr Ile Asn Gly Lys Leu Glu Ser
    1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Glu
            1060                1065                1070

Glu Arg Tyr Lys Ile Gln Ser Tyr Ser Glu Tyr Leu Lys Asp Phe Trp
        1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
            1140                1145                1150

Ser Gln Ser Ile Asn Asp Asp Ile Val Arg Lys Glu Asp Tyr Ile Tyr
        1155                1160                1165

Leu Asp Phe Phe Asn Leu Asn Gln Glu Trp Arg Val Tyr Thr Tyr Lys
    1170                1175                1180

Tyr Phe Lys Lys Glu Glu Glu Lys Leu Phe Leu Ala Pro Ile Ser Asp

-continued

```
              1185              1190              1195              1200
Ser Asp Glu Phe Tyr Asn Thr Ile Gln Ile Lys Glu Tyr Asp Glu Gln
                    1205              1210              1215
Pro Thr Tyr Ser Cys Gln Leu Leu Phe Lys Lys Asp Glu Glu Ser Thr
                    1220              1225              1230
Asp Glu Ile Gly Leu Ile Gly Ile His Arg Phe Tyr Glu Ser Gly Ile
            1235              1240              1245
Val Phe Glu Glu Tyr Lys Asp Tyr Phe Cys Ile Ser Lys Trp Tyr Leu
        1250              1255              1260
Lys Glu Val Lys Arg Lys Pro Tyr Asn Leu Lys Leu Gly Cys Asn Trp
1265              1270              1275              1280
Gln Phe Ile Pro Lys Asp Glu Gly Trp Thr Glu
                    1285              1290

<210> SEQ ID NO 3
<211> LENGTH: 1291
<212> TYPE: PRT
<213> ORGANISM: Clostridium botulinum serotype C1

<400> SEQUENCE: 3

Met Pro Ile Thr Ile Asn Asn Phe Asn Tyr Ser Asp Pro Val Asp Asn
 1               5                  10                  15
Lys Asn Ile Leu Tyr Leu Asp Thr His Leu Asn Thr Leu Ala Asn Glu
                20                  25                  30
Pro Glu Lys Ala Phe Arg Ile Thr Gly Asn Ile Trp Val Ile Pro Asp
            35                  40                  45
Arg Phe Ser Arg Asn Ser Asn Pro Asn Leu Asn Lys Pro Pro Arg Val
        50                  55                  60
Thr Ser Pro Lys Ser Gly Tyr Tyr Asp Pro Asn Tyr Leu Ser Thr Asp
 65                 70                  75                  80
Ser Asp Lys Asp Pro Phe Leu Lys Glu Ile Ile Lys Leu Phe Lys Arg
                    85                  90                  95
Ile Asn Ser Arg Glu Ile Gly Glu Glu Leu Ile Tyr Arg Leu Ser Thr
                100                 105                 110
Asp Ile Pro Phe Pro Gly Asn Asn Asn Thr Pro Ile Asn Thr Phe Asp
            115                 120                 125
Phe Asp Val Asp Phe Asn Ser Val Asp Val Lys Thr Arg Gln Gly Asn
        130                 135                 140
Asn Trp Val Lys Thr Gly Ser Ile Asn Pro Ser Val Ile Ile Thr Gly
145                 150                 155                 160
Pro Arg Glu Asn Ile Ile Asp Pro Glu Thr Ser Thr Phe Lys Leu Thr
                    165                 170                 175
Asn Asn Thr Phe Ala Ala Gln Glu Gly Phe Gly Ala Leu Ser Ile Ile
                180                 185                 190
Ser Ile Ser Pro Arg Phe Met Leu Thr Tyr Ser Asn Ala Thr Asn Asp
            195                 200                 205
Val Gly Glu Gly Arg Phe Ser Lys Ser Glu Phe Cys Met Asp Pro Ile
        210                 215                 220
Leu Ile Leu Met His Glu Leu Asn His Ala Met His Asn Leu Tyr Gly
225                 230                 235                 240
Ile Ala Ile Pro Asn Asp Gln Thr Ile Ser Ser Val Thr Ser Asn Ile
                    245                 250                 255
Phe Tyr Ser Gln Tyr Asn Val Lys Leu Glu Tyr Ala Glu Ile Tyr Ala
                260                 265                 270
```

-continued

Phe Gly Gly Pro Thr Ile Asp Leu Ile Pro Lys Ser Ala Arg Lys Tyr
           275                 280                 285

Phe Glu Glu Lys Ala Leu Asp Tyr Tyr Arg Ser Ile Ala Lys Arg Leu
       290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
                340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
                420                 425                 430

Phe Thr Lys Phe Cys His Lys Ala Ile Asp Gly Arg Ser Leu Tyr Asn
            435                 440                 445

Lys Thr Leu Asp Cys Arg Glu Leu Leu Val Lys Asn Thr Asp Leu Pro
        450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
        500                 505                 510

Asp Leu Leu Tyr Pro Ser Ile Asp Ser Glu Ser Glu Ile Leu Pro Gly
    515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser

-continued

```
            690                 695                 700
Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
                740                 745                 750

Asp Lys Glu Asn Ile Lys Ser Gln Val Glu Asn Leu Lys Asn Ser Leu
            755                 760                 765

Asp Val Lys Ile Ser Glu Ala Met Asn Ile Asn Lys Phe Ile Arg
770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
                820                 825                 830

Lys Ala Lys Val Asn Asn Ser Phe Gln Asn Thr Ile Pro Phe Asn Ile
            835                 840                 845

Phe Ser Tyr Thr Asn Asn Ser Leu Leu Lys Asp Ile Ile Asn Glu Tyr
            850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
                900                 905                 910

Ser Ser Gly Glu Asp Arg Gly Lys Val Ile Val Thr Gln Asn Glu Asn
            915                 920                 925

Ile Val Tyr Asn Ser Met Tyr Glu Ser Phe Ser Ile Ser Phe Trp Ile
            930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
                980                 985                 990

Phe Ser Tyr Asp Ile Ser Asn Asn Ala Pro Gly Tyr Asn Lys Trp Phe
            995                 1000                1005

Phe Val Thr Val Thr Asn Asn Met Met Gly Asn Met Lys Ile Tyr Ile
            1010                1015                1020

Asn Gly Lys Leu Ile Asp Thr Ile Lys Val Lys Glu Leu Thr Gly Ile
1025                1030                1035                1040

Asn Phe Ser Lys Thr Ile Thr Phe Glu Ile Asn Lys Ile Pro Asp Thr
            1045                1050                1055

Gly Leu Ile Thr Ser Asp Ser Asp Asn Ile Asn Met Trp Ile Arg Asp
            1060                1065                1070

Phe Tyr Ile Phe Ala Lys Glu Leu Asp Gly Lys Asp Ile Asn Ile Leu
            1075                1080                1085

Phe Asn Ser Leu Gln Tyr Thr Asn Val Val Lys Asp Tyr Trp Gly Asn
            1090                1095                1100

Asp Leu Arg Tyr Asn Lys Glu Tyr Tyr Met Val Asn Ile Asp Tyr Leu
1105                1110                1115                1120
```

```
Asn Arg Tyr Met Tyr Ala Asn Ser Arg Gln Ile Val Phe Asn Thr Arg
                1125                1130                1135

Arg Asn Asn Asp Phe Asn Glu Gly Tyr Lys Ile Ile Ile Lys Arg
            1140                1145                1150

Ile Arg Gly Asn Thr Asn Asp Thr Arg Val Arg Gly Gly Asp Ile Leu
            1155                1160                1165

Tyr Phe Asp Met Thr Ile Asn Asn Lys Ala Tyr Asn Leu Phe Met Lys
    1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
                1205                1210                1215

Gln Ile Gln Pro Met Asn Asn Thr Tyr Tyr Ala Ser Gln Ile Phe
            1220                1225                1230

Lys Ser Asn Phe Asn Gly Glu Asn Ile Ser Gly Ile Cys Ser Ile Gly
                1235                1240                1245

Thr Tyr Arg Phe Arg Leu Gly Gly Asp Trp Tyr Arg His Asn Tyr Leu
    1250                1255                1260

Val Pro Thr Val Lys Gln Gly Asn Tyr Ala Ser Leu Leu Glu Ser Thr
1265                1270                1275                1280

Ser Thr His Trp Gly Phe Val Pro Val Ser Glu
                1285                1290

<210> SEQ ID NO 4
<211> LENGTH: 1276
<212> TYPE: PRT
<213> ORGANISM: Clostridium botulinum serotype D

<400> SEQUENCE: 4

Met Thr Trp Pro Val Lys Asp Phe Asn Tyr Ser Asp Pro Val Asn Asp
 1               5                  10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
```

-continued

```
                195                 200                 205
Gln Ser Ser Ala Val Leu Gly Lys Ser Ile Phe Cys Met Asp Pro Val
210                 215                 220
Ile Ala Leu Met His Glu Leu Thr His Ser Leu His Gln Leu Tyr Gly
225                 230                 235                 240
Ile Asn Ile Pro Ser Asp Lys Arg Ile Arg Pro Gln Val Ser Glu Gly
                245                 250                 255
Phe Phe Ser Gln Asp Gly Pro Asn Val Gln Phe Glu Glu Leu Tyr Thr
                260                 265                 270
Phe Gly Gly Leu Asp Val Glu Ile Ile Pro Gln Ile Glu Arg Ser Gln
                275                 280                 285
Leu Arg Glu Lys Ala Leu Gly His Tyr Lys Asp Ile Ala Lys Arg Leu
290                 295                 300
Asn Asn Ile Asn Lys Thr Ile Pro Ser Ser Trp Ile Ser Asn Ile Asp
305                 310                 315                 320
Lys Tyr Lys Lys Ile Phe Ser Glu Lys Tyr Asn Phe Asp Lys Asp Asn
                325                 330                 335
Thr Gly Asn Phe Val Val Asn Ile Asp Lys Phe Asn Ser Leu Tyr Ser
                340                 345                 350
Asp Leu Thr Asn Val Met Ser Glu Val Val Tyr Ser Ser Gln Tyr Asn
                355                 360                 365
Val Lys Asn Arg Thr His Tyr Phe Ser Arg His Tyr Leu Pro Val Phe
370                 375                 380
Ala Asn Ile Leu Asp Asp Asn Ile Tyr Thr Ile Arg Asp Gly Phe Asn
385                 390                 395                 400
Leu Thr Asn Lys Gly Phe Asn Ile Glu Asn Ser Gly Gln Asn Ile Glu
                405                 410                 415
Arg Asn Pro Ala Leu Gln Lys Leu Ser Ser Glu Ser Val Val Asp Leu
                420                 425                 430
Phe Thr Lys Val Cys Leu Arg Leu Thr Lys Asn Ser Arg Asp Asp Ser
                435                 440                 445
Thr Cys Ile Lys Val Lys Asn Asn Arg Leu Pro Tyr Val Ala Asp Lys
450                 455                 460
Asp Ser Ile Ser Gln Glu Ile Phe Glu Asn Lys Ile Ile Thr Asp Glu
465                 470                 475                 480
Thr Asn Val Gln Asn Tyr Ser Asp Lys Phe Ser Leu Asp Glu Ser Ile
                485                 490                 495
Leu Asp Gly Gln Val Pro Ile Asn Pro Glu Ile Val Asp Pro Leu Leu
                500                 505                 510
Pro Asn Val Asn Met Glu Pro Leu Asn Leu Pro Gly Glu Glu Ile Val
                515                 520                 525
Phe Tyr Asp Asp Ile Thr Lys Tyr Val Asp Tyr Leu Asn Ser Tyr Tyr
                530                 535                 540
Tyr Leu Glu Ser Gln Lys Leu Ser Asn Asn Val Glu Asn Ile Thr Leu
545                 550                 555                 560
Thr Thr Ser Val Glu Glu Ala Leu Gly Tyr Ser Asn Lys Ile Tyr Thr
                565                 570                 575
Phe Leu Pro Ser Leu Ala Glu Lys Val Asn Lys Gly Val Gln Ala Gly
                580                 585                 590
Leu Phe Leu Asn Trp Ala Asn Glu Val Val Glu Asp Phe Thr Thr Asn
                595                 600                 605
Ile Met Lys Lys Asp Thr Leu Asp Lys Ile Ser Asp Val Ser Val Ile
610                 615                 620
```

```
Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
            645                 650                 655

Glu Gly Phe Pro Glu Phe Thr Ile Pro Ala Leu Gly Val Phe Thr Phe
                660                 665                 670

Tyr Ser Ser Ile Gln Glu Arg Glu Lys Ile Ile Lys Thr Ile Glu Asn
            675                 680                 685

Cys Leu Glu Gln Arg Val Lys Arg Trp Lys Asp Ser Tyr Gln Trp Met
690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
                740                 745                 750

Ile Lys Ser Gln Val Glu Asn Leu Lys Asn Ser Leu Asp Val Lys Ile
            755                 760                 765

Ser Glu Ala Met Asn Asn Ile Asn Lys Phe Ile Arg Glu Cys Ser Val
770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
                835                 840                 845

Asn Asn Ser Leu Leu Lys Asp Ile Ile Asn Glu Tyr Phe Asn Ser Ile
850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
            915                 920                 925

Glu Asn Ser Ser Val Ser Phe Trp Ile Lys Ile Ser Lys Asp Leu Thr
            930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
            995                 1000                1005

Asn Asn Ile Met Gly Tyr Met Lys Leu Tyr Ile Asn Gly Glu Leu Lys
            1010                1015                1020

Gln Ser Gln Lys Ile Glu Asp Leu Asp Glu Val Lys Leu Asp Lys Thr
1025                1030                1035                1040
```

```
Ile Val Phe Gly Ile Asp Glu Asn Ile Asp Glu Asn Gln Met Leu Trp
                1045                1050                1055

Ile Arg Asp Phe Asn Ile Phe Ser Lys Glu Leu Ser Asn Glu Asp Ile
                1060                1065                1070

Asn Ile Val Tyr Glu Gly Gln Ile Leu Arg Asn Val Ile Lys Asp Tyr
            1075                1080                1085

Trp Gly Asn Pro Leu Lys Phe Asp Thr Glu Tyr Tyr Ile Ile Asn Asp
        1090                1095                1100

Asn Tyr Ile Asp Arg Tyr Ile Ala Pro Glu Ser Asn Val Leu Val Leu
1105                1110                1115                1120

Val Gln Tyr Pro Asp Arg Ser Lys Leu Tyr Thr Gly Asn Pro Ile Thr
                1125                1130                1135

Ile Lys Ser Val Ser Asp Lys Asn Pro Tyr Ser Arg Ile Leu Asn Gly
                1140                1145                1150

Asp Asn Ile Ile Leu His Met Leu Tyr Asn Ser Arg Lys Tyr Met Ile
        1155                1160                1165

Ile Arg Asp Thr Asp Thr Ile Tyr Ala Thr Gln Gly Gly Glu Cys Ser
        1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
                1205                1210                1215

Cys Ser Gln Ile Phe Ser Ser Phe Arg Glu Asn Thr Met Leu Leu Ala
                1220                1225                1230

Asp Ile Tyr Lys Pro Trp Arg Phe Ser Phe Lys Asn Ala Tyr Thr Pro
            1235                1240                1245

Val Ala Val Thr Asn Tyr Glu Thr Lys Leu Leu Ser Thr Ser Ser Phe
        1250                1255                1260

Trp Lys Phe Ile Ser Arg Asp Pro Gly Trp Val Glu
1265                1270                1275

<210> SEQ ID NO 5
<211> LENGTH: 1252
<212> TYPE: PRT
<213> ORGANISM: Clostridium botulinum serotype E

<400> SEQUENCE: 5

Met Pro Lys Ile Asn Ser Phe Asn Tyr Asn Asp Pro Val Asn Asp Arg
  1               5                  10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140
```

-continued

```
Leu Pro Asn Val Ile Ile Met Gly Ala Glu Pro Asp Leu Phe Glu Thr
145                 150                 155                 160

Asn Ser Ser Asn Ile Ser Leu Arg Asn Tyr Met Pro Ser Asn His
            165                 170                 175

Gly Phe Gly Ser Ile Ala Ile Val Thr Phe Ser Pro Glu Tyr Ser Phe
                180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
        210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
        290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
        370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
                420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
        530                 535                 540

Leu Leu Glu Gln Pro Lys Ile Tyr Thr Phe Phe Ser Ser Glu Phe Ile
545                 550                 555                 560
```

-continued

```
Asn Asn Val Asn Lys Pro Val Gln Ala Ala Leu Phe Val Ser Trp Ile
            565             570                 575
Gln Gln Val Leu Val Asp Phe Thr Thr Glu Ala Asn Gln Lys Ser Thr
        580                 585                 590
Val Asp Lys Ile Ala Asp Ile Ser Ile Val Val Pro Tyr Ile Gly Leu
        595                 600                 605
Ala Leu Asn Ile Gly Asn Glu Ala Gln Lys Gly Asn Phe Lys Asp Ala
    610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
            660                 665                 670
Glu Arg Asp Glu Lys Trp Lys Glu Val Tyr Ser Phe Ile Val Ser Asn
        675                 680                 685
Trp Met Thr Lys Ile Asn Thr Gln Phe Asn Lys Arg Lys Glu Gln Met
690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
                725                 730                 735
Lys Tyr Asp Ile Lys Gln Ile Glu Asn Glu Leu Asn Gln Lys Val Ser
            740                 745                 750
Ile Ala Met Asn Asn Ile Asp Arg Phe Leu Thr Glu Ser Ser Ile Ser
        755                 760                 765
Tyr Leu Met Lys Leu Ile Asn Glu Val Lys Ile Asn Lys Leu Arg Glu
    770                 775                 780
Tyr Asp Glu Asn Val Lys Thr Tyr Leu Leu Asn Tyr Ile Ile Gln His
785                 790                 795                 800
Gly Ser Ile Leu Gly Glu Ser Gln Gln Glu Leu Asn Ser Met Val Thr
                805                 810                 815
Asp Thr Leu Asn Asn Ser Ile Pro Phe Lys Leu Ser Ser Tyr Thr Asp
            820                 825                 830
Asp Lys Ile Leu Ile Ser Tyr Phe Asn Lys Phe Phe Lys Arg Ile Lys
        835                 840                 845
Ser Ser Ser Val Leu Asn Met Arg Tyr Lys Asn Asp Lys Tyr Val Asp
    850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                885                 890                 895
Glu Val Asn Ile Ser Gln Asn Asp Tyr Ile Ile Tyr Asp Asn Lys Tyr
            900                 905                 910
Lys Asn Phe Ser Ile Ser Phe Trp Val Arg Ile Pro Asn Tyr Asp Asn
        915                 920                 925
Lys Ile Val Asn Val Asn Asn Glu Tyr Thr Ile Ile Asn Cys Met Arg
    930                 935                 940
Asp Asn Asn Ser Gly Trp Lys Val Ser Leu Asn His Asn Glu Ile Ile
945                 950                 955                 960
Trp Thr Leu Gln Asp Asn Ala Gly Ile Asn Gln Lys Leu Ala Phe Asn
                965                 970                 975
Tyr Gly Asn Ala Asn Gly Ile Ser Asp Tyr Ile Asn Lys Trp Ile Phe
```

```
                   980                 985                 990
Val Thr Ile Thr Asn Asp Arg Leu Gly Asp Ser Lys Leu Tyr Ile Asn
            995                1000                1005

Gly Asn Leu Ile Asp Gln Lys Ser Ile Leu Asn Leu Gly Asn Ile His
       1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
            1045                1050                1055

Thr Glu Ile Gln Thr Leu Tyr Ser Asn Glu Pro Asn Thr Asn Ile Leu
       1060                1065                1070

Lys Asp Phe Trp Gly Asn Tyr Leu Leu Tyr Asp Lys Glu Tyr Tyr Leu
            1075                1080                1085

Leu Asn Val Leu Lys Pro Asn Asn Phe Ile Asp Arg Arg Lys Asp Ser
       1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
            1125                1130                1135

Thr Asn Asp Asn Leu Val Arg Lys Asn Asp Gln Val Tyr Ile Asn Phe
       1140                1145                1150

Val Ala Ser Lys Thr His Leu Phe Pro Leu Tyr Ala Asp Thr Ala Thr
       1155                1160                1165

Thr Asn Lys Glu Lys Thr Ile Lys Ile Ser Ser Ser Gly Asn Arg Phe
       1170                1175                1180

Asn Gln Val Val Val Met Asn Ser Val Gly Asn Asn Cys Thr Met Asn
1185                1190                1195                1200

Phe Lys Asn Asn Asn Gly Asn Asn Ile Gly Leu Leu Gly Phe Lys Ala
            1205                1210                1215

Asp Thr Val Val Ala Ser Thr Trp Tyr Tyr Thr His Met Arg Asp His
       1220                1225                1230

Thr Asn Ser Asn Gly Cys Phe Trp Asn Phe Ile Ser Glu Glu His Gly
       1235                1240                1245

Trp Gln Glu Lys
    1250

<210> SEQ ID NO 6
<211> LENGTH: 1274
<212> TYPE: PRT
<213> ORGANISM: Clostridium botulinum serotype F

<400> SEQUENCE: 6

Met Pro Val Ala Ile Asn Ser Phe Asn Tyr Asn Asp Pro Val Asn Asp
 1               5                  10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95
```

-continued

```
Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Ser Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
```

-continued

```
            515                 520                 525
Glu Glu Tyr Asp Val Val Asp Phe Asn Val Phe Phe Tyr Leu His Ala
            530                 535                 540
Gln Lys Val Pro Glu Gly Glu Thr Asn Ile Ser Leu Thr Ser Ser Ile
545                 550                 555                 560
Asp Thr Ala Leu Leu Glu Glu Ser Lys Asp Ile Phe Phe Ser Ser Glu
                565                 570                 575
Phe Ile Asp Thr Ile Asn Lys Pro Val Asn Ala Ala Leu Phe Ile Asp
                580                 585                 590
Trp Ile Ser Lys Val Ile Arg Asp Phe Thr Thr Glu Ala Thr Gln Lys
                595                 600                 605
Ser Thr Val Asp Lys Ile Ala Asp Ile Ser Leu Ile Val Pro Tyr Val
            610                 615                 620
Gly Leu Ala Leu Asn Ile Ile Glu Ala Glu Lys Gly Asn Phe Glu
625                 630                 635                 640
Glu Ala Phe Glu Leu Leu Gly Val Gly Ile Leu Leu Glu Phe Val Pro
                645                 650                 655
Glu Leu Thr Ile Pro Val Ile Leu Val Phe Thr Ile Lys Ser Tyr Ile
                660                 665                 670
Asp Ser Tyr Glu Asn Lys Asn Lys Ala Ile Lys Ala Ile Asn Asn Ser
            675                 680                 685
Leu Ile Glu Arg Glu Ala Lys Trp Lys Glu Ile Tyr Ser Trp Ile Val
            690                 695                 700
Ser Asn Trp Leu Thr Arg Ile Asn Thr Gln Phe Asn Lys Arg Lys Glu
705                 710                 715                 720
Gln Met Tyr Gln Ala Leu Gln Asn Gln Val Asp Ala Ile Lys Thr Ala
                725                 730                 735
Ile Glu Tyr Lys Tyr Asn Asn Tyr Thr Ser Asp Glu Lys Asn Arg Leu
                740                 745                 750
Glu Ser Glu Tyr Asn Ile Asn Asn Ile Glu Glu Glu Leu Asn Lys Lys
            755                 760                 765
Val Ser Leu Ala Met Lys Asn Ile Glu Arg Phe Met Thr Glu Ser Ser
770                 775                 780
Ile Ser Tyr Leu Met Lys Leu Ile Asn Glu Ala Lys Val Gly Lys Leu
785                 790                 795                 800
Lys Lys Tyr Asp Asn His Val Lys Ser Asp Leu Leu Asn Tyr Ile Leu
                805                 810                 815
Asp His Arg Ser Ile Leu Gly Glu Gln Thr Asn Glu Leu Ser Asp Leu
                820                 825                 830
Val Thr Ser Thr Leu Asn Ser Ser Ile Pro Phe Glu Leu Ser Ser Tyr
            835                 840                 845
Thr Asn Asp Lys Ile Leu Ile Ile Tyr Phe Asn Arg Leu Tyr Lys Lys
850                 855                 860
Ile Lys Asp Ser Ser Ile Leu Asp Met Arg Tyr Glu Asn Asn Lys Phe
865                 870                 875                 880
Ile Asp Ile Ser Gly Tyr Gly Ser Asn Ile Ser Ile Asn Gly Asn Val
                885                 890                 895
Tyr Ile Tyr Ser Thr Asn Arg Asn Gln Phe Gly Ile Tyr Asn Ser Arg
                900                 905                 910
Leu Ser Glu Val Asn Ile Ala Gln Asn Asn Asp Ile Ile Tyr Asn Ser
            915                 920                 925
Arg Tyr Gln Asn Phe Ser Ile Ser Phe Trp Val Arg Ile Pro Lys His
            930                 935                 940
```

```
Tyr Lys Pro Met Asn His Asn Arg Glu Tyr Thr Ile Ile Asn Cys Met
945                 950                 955                 960

Gly Asn Asn Ser Gly Trp Lys Ile Ser Leu Arg Thr Val Arg Asp
            965                 970                 975

Cys Glu Ile Ile Trp Thr Leu Gln Asp Thr Ser Gly Asn Lys Glu Asn
                980                 985                 990

Leu Ile Phe Arg Tyr Glu Glu Leu Asn Arg Ile Ser Asn Tyr Ile Asn
                995                 1000                1005

Lys Trp Ile Phe Val Thr Ile Thr Asn Asn Arg Leu Gly Asn Ser Arg
            1010                1015                1020

Ile Tyr Ile Asn Gly Asn Leu Ile Val Glu Lys Ser Ile Ser Asn Leu
1025                1030                1035                1040

Gly Asp Ile His Val Ser Asp Asn Ile Leu Phe Lys Ile Val Gly Cys
                1045                1050                1055

Asp Asp Glu Thr Tyr Val Gly Ile Arg Tyr Phe Lys Val Phe Asn Thr
                1060                1065                1070

Glu Leu Asp Lys Thr Glu Ile Glu Thr Leu Tyr Ser Asn Glu Pro Asp
                1075                1080                1085

Pro Ser Ile Leu Lys Asn Tyr Trp Gly Asn Tyr Leu Leu Tyr Asn Lys
            1090                1095                1100

Lys Tyr Tyr Leu Phe Asn Leu Leu Arg Lys Asp Lys Tyr Ile Thr Leu
1105                1110                1115                1120

Asn Ser Gly Ile Leu Asn Ile Asn Gln Gln Arg Gly Val Thr Glu Gly
                1125                1130                1135

Ser Val Phe Leu Asn Tyr Lys Leu Tyr Glu Gly Val Glu Val Ile Ile
                1140                1145                1150

Arg Lys Asn Gly Pro Ile Asp Ile Ser Asn Thr Asp Asn Phe Val Arg
                1155                1160                1165

Lys Asn Asp Leu Ala Tyr Ile Asn Val Val Asp Arg Gly Val Glu Tyr
            1170                1175                1180

Arg Leu Tyr Ala Asp Thr Lys Ser Glu Lys Glu Lys Ile Ile Arg Thr
1185                1190                1195                1200

Ser Asn Leu Asn Asp Ser Leu Gly Gln Ile Ile Val Met Asp Ser Ile
                1205                1210                1215

Gly Asn Asn Cys Thr Met Asn Phe Gln Asn Asn Asn Gly Ser Asn Ile
                1220                1225                1230

Gly Leu Leu Gly Phe His Ser Asn Asn Leu Val Ala Ser Ser Trp Tyr
            1235                1240                1245

Tyr Asn Asn Ile Arg Arg Asn Thr Ser Ser Asn Gly Cys Phe Trp Ser
1250                1255                1260

Ser Ile Ser Lys Glu Asn Gly Trp Lys Glu
1265                1270

<210> SEQ ID NO 7
<211> LENGTH: 1297
<212> TYPE: PRT
<213> ORGANISM: Clostridium botulinum serotype G

<400> SEQUENCE: 7

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
                20                  25                  30

Tyr Tyr Lys Ala Phe Arg Ile Ile Asp Arg Ile Trp Ile Val Pro Glu
```

-continued

```
                35                  40                  45
Arg Phe Thr Tyr Gly Phe Gln Pro Asp Gln Phe Asn Ala Ser Thr Gly
 50                  55                  60
Val Phe Ser Lys Asp Val Tyr Glu Tyr Asp Pro Thr Tyr Leu Lys
 65                  70                  75                  80
Thr Asp Ala Glu Lys Asp Lys Phe Leu Lys Thr Met Ile Lys Leu Phe
                 85                  90                  95
Asn Arg Ile Asn Ser Lys Pro Ser Gly Gln Arg Leu Leu Asp Met Ile
                100                 105                 110
Val Asp Ala Ile Pro Tyr Leu Gly Asn Ala Ser Thr Pro Pro Asp Lys
                115                 120                 125
Phe Ala Ala Asn Val Ala Asn Val Ser Ile Asn Lys Lys Ile Ile Gln
130                 135                 140
Pro Gly Ala Glu Asp Gln Ile Lys Gly Leu Met Thr Asn Leu Ile Ile
145                 150                 155                 160
Phe Gly Pro Gly Pro Val Leu Ser Asp Asn Phe Thr Asp Ser Met Ile
                165                 170                 175
Met Asn Gly His Ser Pro Ile Ser Glu Gly Phe Gly Ala Arg Met Met
                180                 185                 190
Ile Arg Phe Cys Pro Ser Cys Leu Asn Val Phe Asn Asn Val Gln Glu
                195                 200                 205
Asn Lys Asp Thr Ser Ile Phe Ser Arg Arg Ala Tyr Phe Ala Asp Pro
                210                 215                 220
Ala Leu Thr Leu Met His Glu Leu Ile His Val Leu His Gly Leu Tyr
225                 230                 235                 240
Gly Ile Lys Ile Ser Asn Leu Pro Ile Thr Pro Asn Thr Lys Glu Phe
                245                 250                 255
Phe Met Gln His Ser Asp Pro Val Gln Ala Glu Glu Leu Tyr Thr Phe
                260                 265                 270
Gly Gly His Asp Pro Ser Val Ile Ser Pro Ser Thr Asp Met Asn Ile
                275                 280                 285
Tyr Asn Lys Ala Leu Gln Asn Phe Gln Asp Ile Ala Asn Arg Leu Asn
                290                 295                 300
Ile Val Ser Ser Ala Gln Gly Ser Gly Ile Asp Ile Ser Leu Tyr Lys
305                 310                 315                 320
Gln Ile Tyr Lys Asn Lys Tyr Asp Phe Val Glu Asp Pro Asn Gly Lys
                325                 330                 335
Tyr Ser Val Asp Lys Asp Lys Phe Asp Lys Leu Tyr Lys Ala Leu Met
                340                 345                 350
Phe Gly Phe Thr Glu Thr Asn Leu Ala Gly Glu Tyr Gly Ile Lys Thr
                355                 360                 365
Arg Tyr Ser Tyr Phe Ser Glu Tyr Leu Pro Pro Ile Lys Thr Glu Lys
                370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
                405                 410                 415
Lys Glu Ala Tyr Glu Glu Ile Ser Leu Glu His Leu Val Ile Tyr Arg
                420                 425                 430
Ile Ala Met Cys Lys Pro Val Met Tyr Lys Asn Thr Gly Lys Ser Glu
                435                 440                 445
Gln Cys Ile Ile Val Asn Asn Glu Asp Leu Phe Phe Ile Ala Asn Lys
                450                 455                 460
```

-continued

```
Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Lys Val Tyr Thr
                565                 570                 575

Phe Phe Ser Thr Asn Leu Val Glu Lys Ala Asn Thr Val Val Gly Ala
                580                 585                 590

Ser Leu Phe Val Asn Trp Val Lys Gly Val Ile Asp Asp Phe Thr Ser
            595                 600                 605

Glu Ser Thr Gln Lys Ser Thr Ile Asp Lys Val Ser Asp Val Ser Ile
        610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
                660                 665                 670

Leu Glu Ser Tyr Val Gly Asn Lys Gly His Ile Ile Met Thr Ile Ser
            675                 680                 685

Asn Ala Leu Lys Lys Arg Asp Gln Lys Trp Thr Asp Met Tyr Gly Leu
            690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
                740                 745                 750

Asn Ile Asn Ile Asp Phe Asn Asp Ile Asp Phe Lys Leu Asn Gln Ser
            755                 760                 765

Ile Asn Leu Ala Ile Asn Asn Ile Asp Asp Phe Ile Asn Gln Cys Ser
            770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
                820                 825                 830

Val Asn Arg His Leu Lys Asp Ser Ile Pro Phe Asp Leu Ser Leu Tyr
            835                 840                 845

Thr Lys Asp Thr Ile Leu Ile Gln Val Phe Asn Asn Tyr Ile Ser Asn
            850                 855                 860

Ile Ser Ser Asn Ala Ile Leu Ser Leu Ser Tyr Arg Gly Gly Arg Leu
865                 870                 875                 880
```

-continued

```
Ile Asp Ser Ser Gly Tyr Gly Ala Thr Met Asn Val Gly Ser Asp Val
            885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
            915                 920                 925

Met Phe Asp Asn Phe Ser Ile Asn Phe Trp Val Arg Thr Pro Lys Tyr
            930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
            965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
            995                 1000                1005

Trp Phe Ser Ile Thr Ile Thr Asn Asp Arg Leu Gly Asn Ala Asn Ile
            1010                1015                1020

Tyr Ile Asn Gly Ser Leu Lys Lys Ser Glu Lys Ile Leu Asn Leu Asp
1025                1030                1035                1040

Arg Ile Asn Ser Ser Asn Asp Ile Asp Phe Lys Leu Ile Asn Cys Thr
            1045                1050                1055

Asp Thr Thr Lys Phe Val Trp Ile Lys Asp Phe Asn Ile Phe Gly Arg
            1060                1065                1070

Glu Leu Asn Ala Thr Glu Val Ser Ser Leu Tyr Trp Ile Gln Ser Ser
            1075                1080                1085

Thr Asn Thr Leu Lys Asp Phe Trp Gly Asn Pro Leu Arg Tyr Asp Thr
            1090                1095                1100

Gln Tyr Tyr Leu Phe Asn Gln Gly Met Gln Asn Ile Tyr Ile Lys Tyr
1105                1110                1115                1120

Phe Ser Lys Ala Ser Met Gly Glu Thr Ala Pro Arg Thr Asn Phe Asn
            1125                1130                1135

Asn Ala Ala Ile Asn Tyr Gln Asn Leu Tyr Leu Gly Leu Arg Phe Ile
            1140                1145                1150

Ile Lys Lys Ala Ser Asn Ser Arg Asn Ile Asn Asn Asp Asn Ile Val
            1155                1160                1165

Arg Glu Gly Asp Tyr Ile Tyr Leu Asn Ile Asp Asn Ile Ser Asp Glu
            1170                1175                1180

Ser Tyr Arg Val Tyr Val Leu Val Asn Ser Lys Glu Ile Gln Thr Gln
1185                1190                1195                1200

Leu Phe Leu Ala Pro Ile Asn Asp Asp Pro Thr Phe Tyr Asp Val Leu
            1205                1210                1215

Gln Ile Lys Lys Tyr Tyr Glu Lys Thr Thr Tyr Asn Cys Gln Ile Leu
            1220                1225                1230

Cys Glu Lys Asp Thr Lys Thr Phe Gly Leu Phe Gly Ile Gly Lys Phe
            1235                1240                1245

Val Lys Asp Tyr Gly Tyr Val Trp Asp Thr Tyr Asp Asn Tyr Phe Cys
            1250                1255                1260

Ile Ser Gln Trp Tyr Leu Arg Arg Ile Ser Glu Asn Ile Asn Lys Leu
1265                1270                1275                1280

Arg Leu Gly Cys Asn Trp Gln Phe Ile Pro Val Asp Glu Gly Trp Thr
            1285                1290                1295

Glu
```

-continued

```
<210> SEQ ID NO 8
<211> LENGTH: 1315
<212> TYPE: PRT
<213> ORGANISM: Clostridium teteni

<400> SEQUENCE: 8
```

| Met | Pro | Ile | Thr | Ile | Asn | Asn | Phe | Arg | Tyr | Ser | Asp | Pro | Val | Asn | Asn |
|---|---|---|---|---|---|---|---|---|---|---|---|---|---|---|---|
| 1 | | | | 5 | | | | | 10 | | | | | 15 | |

| Asp | Thr | Ile | Ile | Met | Met | Glu | Pro | Pro | Tyr | Cys | Lys | Gly | Leu | Asp | Ile |
| | | | 20 | | | | | 25 | | | | | 30 | | |

| Tyr | Tyr | Lys | Ala | Phe | Lys | Ile | Thr | Asp | Arg | Ile | Trp | Ile | Val | Pro | Glu |
| | | 35 | | | | | 40 | | | | | 45 | | | |

| Arg | Tyr | Glu | Phe | Gly | Thr | Lys | Pro | Glu | Asp | Phe | Asn | Pro | Pro | Ser | Ser |
| | 50 | | | | | 55 | | | | | 60 | | | | |

| Leu | Ile | Glu | Gly | Ala | Ser | Glu | Tyr | Tyr | Asp | Pro | Asn | Tyr | Leu | Arg | Thr |
| 65 | | | | | 70 | | | | | 75 | | | | | 80 |

| Asp | Ser | Asp | Lys | Asp | Arg | Phe | Leu | Gln | Thr | Met | Val | Lys | Leu | Phe | Asn |
| | | | | 85 | | | | | 90 | | | | | 95 | |

| Arg | Ile | Lys | Asn | Asn | Val | Ala | Gly | Glu | Ala | Leu | Leu | Asp | Lys | Ile | Ile |
| | | | 100 | | | | | 105 | | | | | 110 | | |

| Asn | Ala | Ile | Pro | Tyr | Leu | Gly | Asn | Ser | Tyr | Ser | Leu | Leu | Asp | Lys | Phe |
| | | 115 | | | | | 120 | | | | | 125 | | | |

| Asp | Thr | Asn | Ser | Asn | Ser | Val | Ser | Phe | Asn | Leu | Leu | Glu | Gln | Asp | Pro |
| | 130 | | | | | 135 | | | | | 140 | | | | |

| Ser | Gly | Ala | Thr | Thr | Lys | Ser | Ala | Met | Leu | Thr | Asn | Leu | Ile | Ile | Phe |
| 145 | | | | | 150 | | | | | 155 | | | | | 160 |

| Gly | Pro | Gly | Pro | Val | Leu | Asn | Lys | Asn | Glu | Val | Arg | Gly | Ile | Val | Leu |
| | | | | 165 | | | | | 170 | | | | | 175 | |

| Arg | Val | Asp | Asn | Lys | Asn | Tyr | Phe | Pro | Cys | Arg | Asp | Gly | Phe | Gly | Ser |
| | | | 180 | | | | | 185 | | | | | 190 | | |

| Ile | Met | Gln | Met | Ala | Phe | Cys | Pro | Glu | Tyr | Val | Pro | Thr | Phe | Asp | Asn |
| | | 195 | | | | | 200 | | | | | 205 | | | |

| Val | Ile | Glu | Asn | Ile | Thr | Ser | Leu | Thr | Ile | Gly | Lys | Ser | Lys | Tyr | Phe |
| | 210 | | | | | 215 | | | | | 220 | | | | |

| Gln | Asp | Pro | Ala | Leu | Leu | Leu | Met | His | Glu | Leu | Ile | His | Val | Leu | His |
| 225 | | | | | 230 | | | | | 235 | | | | | 240 |

| Gly | Leu | Tyr | Gly | Met | Gln | Val | Ser | Ser | His | Glu | Ile | Ile | Pro | Ser | Lys |
| | | | 245 | | | | | 250 | | | | | 255 | | |

| Gln | Glu | Ile | Tyr | Met | Gln | His | Thr | Tyr | Pro | Ile | Ser | Ala | Glu | Glu | Leu |
| | | 260 | | | | | 265 | | | | | 270 | | | |

| Phe | Thr | Phe | Gly | Gly | Gln | Asp | Ala | Asn | Leu | Ile | Ser | Ile | Asp | Ile | Lys |
| | 275 | | | | | 280 | | | | | 285 | | | | |

| Asn | Asp | Leu | Tyr | Glu | Lys | Thr | Leu | Asn | Asp | Tyr | Lys | Ala | Ile | Ala | Asn |
| 290 | | | | | 295 | | | | | 300 | | | | | |

| Lys | Leu | Ser | Gln | Val | Thr | Ser | Cys | Asn | Asp | Pro | Asn | Ile | Asp | Ile | Asp |
| 305 | | | | | 310 | | | | | 315 | | | | | 320 |

| Ser | Tyr | Lys | Gln | Ile | Tyr | Gln | Gln | Lys | Tyr | Gln | Phe | Asp | Lys | Asp | Ser |
| | | | 325 | | | | | 330 | | | | | 335 | | |

| Asn | Gly | Gln | Tyr | Ile | Val | Asn | Glu | Asp | Lys | Phe | Gln | Ile | Leu | Tyr | Asn |
| | | | 340 | | | | | 345 | | | | | 350 | | |

| Ser | Ile | Met | Tyr | Gly | Phe | Thr | Glu | Ile | Glu | Leu | Gly | Lys | Lys | Phe | Asn |
| | | 355 | | | | | 360 | | | | | 365 | | | |

| Ile | Lys | Thr | Arg | Leu | Ser | Tyr | Phe | Ser | Met | Asn | His | Asp | Pro | Val | Lys |

-continued

```
            370                 375                 380
Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
        450                 455                 460

Glu Leu Cys Ile Lys Ile Lys Asn Glu Asp Leu Thr Phe Ile Ala Glu
465                 470                 475                 480

Lys Asn Ser Phe Ser Glu Pro Phe Gln Asp Ile Val Ser Tyr
                485                 490                 495

Asn Thr Lys Asn Lys Pro Leu Asn Phe Asn Tyr Ser Leu Asp Lys Ile
                500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
        530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
        610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
                660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
        690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
        770                 775                 780

Lys Ala Asn Lys Ala Met Ile Asn Ile Asn Ile Phe Met Arg Glu Ser
785                 790                 795                 800
```

-continued

```
Ser Arg Ser Phe Leu Val Asn Gln Met Ile Asn Glu Ala Lys Lys Gln
            805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
            850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
            930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe Asn
            1010                1015                1020

Ala Tyr Leu Ala Asn Lys Trp Val Phe Ile Thr Ile Thr Asn Asp Arg
1025                1030                1035                1040

Leu Ser Ser Ala Asn Leu Tyr Ile Asn Gly Val Leu Met Gly Ser Ala
            1045                1050                1055

Glu Ile Thr Gly Leu Gly Ala Ile Arg Glu Asp Asn Asn Ile Thr Leu
            1060                1065                1070

Lys Leu Asp Arg Cys Asn Asn Asn Asn Gln Tyr Val Ser Ile Asp Lys
            1075                1080                1085

Phe Arg Ile Phe Cys Lys Ala Leu Asn Pro Lys Glu Ile Glu Lys Leu
            1090                1095                1100

Tyr Thr Ser Tyr Leu Ser Ile Thr Phe Leu Arg Asp Phe Trp Gly Asn
1105                1110                1115                1120

Pro Leu Arg Tyr Asp Thr Glu Tyr Tyr Leu Ile Pro Val Ala Ser Ser
            1125                1130                1135

Ser Lys Asp Val Gln Leu Lys Asn Ile Thr Asp Tyr Met Tyr Leu Thr
            1140                1145                1150

Asn Ala Pro Ser Tyr Thr Asn Gly Lys Leu Asn Ile Tyr Tyr Arg Arg
            1155                1160                1165

Leu Tyr Asn Gly Leu Lys Phe Ile Ile Lys Arg Tyr Thr Pro Asn Asn
            1170                1175                1180

Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
            1205                1210                1215
```

```
Ala Phe Asn Asn Leu Asp Arg Ile Leu Arg Val Gly Tyr Asn Ala Pro
        1220                1225                1230

Gly Ile Pro Leu Tyr Lys Lys Met Glu Ala Val Lys Leu Arg Asp Leu
        1235                1240                1245

Lys Thr Tyr Ser Val Gln Leu Lys Leu Tyr Asp Lys Asn Ala Ser
        1250                1255                1260

Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
            1285                1290                1295

Lys Ile Leu Gly Cys Asp Trp Tyr Phe Val Pro Thr Asp Glu Gly Trp
        1300                1305                1310

Thr Asn Asp
        1315
```

<210> SEQ ID NO 9
<211> LENGTH: 1268
<212> TYPE: PRT
<213> ORGANISM: Clostridium baratii

<400> SEQUENCE: 9

```
Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
                20                  25                  30

Tyr Tyr Lys Ala Phe Glu Ile Met Asp Asn Val Trp Ile Ile Pro Glu
            35                  40                  45

Arg Asn Ile Ile Gly Lys Lys Pro Ser Asp Phe Tyr Pro Pro Ile Ser
        50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
    210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
            260                 265                 270
```

-continued

```
Ser Thr Asn Gln Lys Ile Tyr Val Ile Leu Leu Ser Asn Tyr Thr Ala
        275                 280                 285

Ile Ala Ser Arg Leu Ser Gln Val Asn Arg Asn Asn Ser Ala Leu Asn
290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
            340                 345                 350

Gln Val Lys Asn Arg Ser Asn Tyr Leu Phe His Phe Lys Pro Phe Arg
        355                 360                 365

Leu Leu Asp Leu Leu Asp Asp Asn Ile Tyr Ser Ile Ser Glu Gly Phe
    370                 375                 380

Asn Ile Gly Ser Leu Arg Val Asn Asn Asn Gly Gln Asn Ile Asn Leu
385                 390                 395                 400

Asn Ser Arg Ile Val Gly Pro Ile Pro Asp Asn Gly Leu Val Glu Arg
                405                 410                 415

Phe Val Gly Leu Cys Lys Ser Ile Val Ser Lys Lys Gly Thr Lys Asn
            420                 425                 430

Ser Leu Cys Ile Lys Val Asn Asn Arg Asp Leu Phe Phe Val Ala Ser
        435                 440                 445

Glu Ser Ser Tyr Asn Glu Asn Gly Ile Asn Ser Pro Lys Glu Ile Asp
    450                 455                 460

Asp Thr Thr Ile Thr Asn Asn Asn Tyr Lys Lys Asn Leu Asp Glu Val
465                 470                 475                 480

Ile Leu Asp Tyr Asn Ser Asp Ala Ile Pro Asn Leu Ser Ser Arg Leu
                485                 490                 495

Leu Asn Thr Thr Ala Gln Asn Asp Ser Tyr Val Pro Lys Tyr Asp Ser
            500                 505                 510

Asn Gly Thr Ser Glu Ile Lys Glu Tyr Thr Val Asp Lys Leu Asn Val
        515                 520                 525

Phe Phe Tyr Leu Tyr Ala Gln Lys Ala Pro Glu Gly Glu Ser Ala Ile
    530                 535                 540

Ser Leu Thr Ser Ser Val Asn Thr Ala Leu Leu Asp Ala Ser Lys Val
545                 550                 555                 560

Tyr Thr Phe Phe Ser Ser Asp Phe Ile Asn Thr Val Asn Lys Pro Val
                565                 570                 575

Gln Ala Ala Leu Phe Ile Ser Trp Ile Gln Gln Val Ile Asn Asp Phe
            580                 585                 590

Thr Thr Glu Ala Thr Gln Lys Ser Thr Ile Asp Lys Ile Ala Asp Ile
        595                 600                 605

Ser Leu Ile Val Pro Tyr Val Gly Leu Ala Leu Asn Ile Gly Asn Glu
    610                 615                 620

Val Gln Lys Gly Asn Phe Lys Glu Ala Ile Glu Leu Leu Gly Ala Gly
625                 630                 635                 640

Ile Leu Leu Glu Phe Val Pro Glu Leu Leu Ile Pro Thr Ile Leu Val
                645                 650                 655

Phe Thr Ile Lys Ser Phe Ile Asn Ser Asp Asp Ser Lys Asn Lys Ile
            660                 665                 670

Ile Lys Ala Ile Asn Asn Ala Leu Arg Glu Arg Glu Leu Lys Trp Lys
        675                 680                 685
```

-continued

```
Glu Val Tyr Ser Trp Ile Val Ser Asn Trp Leu Thr Arg Ile Asn Thr
    690                 695                 700

Gln Phe Asn Lys Arg Lys Glu Gln Met Tyr Gln Ala Leu Gln Asn Gln
705                 710                 715                 720

Val Asp Gly Ile Lys Lys Ile Ile Glu Tyr Lys Tyr Asn Asn Tyr Thr
                725                 730                 735

Leu Asp Glu Lys Asn Arg Leu Arg Ala Glu Tyr Asn Ile Tyr Ser Ile
            740                 745                 750

Lys Glu Glu Leu Asn Lys Lys Val Ser Leu Ala Met Gln Asn Ile Asp
        755                 760                 765

Arg Phe Leu Thr Glu Ser Ser Ile Ser Tyr Leu Met Lys Leu Ile Asn
770                 775                 780

Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Ser Thr Leu Gly Thr Ser
                805                 810                 815

Ser Val Pro Glu Leu Asn Asn Leu Val Ser Asn Thr Leu Asn Asn Ser
            820                 825                 830

Ile Pro Phe Glu Leu Ser Glu Tyr Thr Asn Asp Lys Ile Leu Ile His
        835                 840                 845

Ile Leu Ile Arg Phe Tyr Lys Arg Ile Asp Ser Ser Ile Leu Asn
850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                885                 890                 895

Gln Phe Gly Ile Tyr Ser Ser Arg Leu Ser Glu Val Asn Ile Thr Gln
            900                 905                 910

Asn Asn Thr Ile Ile Tyr Asn Ser Arg Tyr Gln Asn Phe Ser Val Ser
        915                 920                 925

Phe Trp Val Arg Ile Pro Lys Tyr Asn Asn Leu Lys Asn Leu Asn Asn
930                 935                 940

Glu Tyr Thr Ile Ile Asn Cys Met Arg Asn Asn Asn Ser Gly Trp Lys
945                 950                 955                 960

Ile Ser Leu Asn Tyr Asn Asn Ile Ile Trp Thr Leu Gln Asp Thr Thr
                965                 970                 975

Gly Asn Asn Gln Lys Leu Val Phe Asn Tyr Thr Gln Met Ile Asp Ile
            980                 985                 990

Ser Asp Tyr Ile Asn Lys Trp Thr Phe Val Thr Ile Thr Asn Asn Arg
        995                 1000                1005

Leu Gly His Ser Lys Leu Tyr Ile Asn Gly Asn Leu Thr Asp Gln Lys
    1010                1015                1020

Ser Ile Leu Asn Leu Gly Asn Ile His Val Asp Asp Asn Ile Leu Phe
1025                1030                1035                1040

Lys Ile Val Gly Cys Asn Asp Thr Arg Tyr Val Gly Ile Arg Tyr Phe
                1045                1050                1055

Lys Ile Phe Asn Met Glu Leu Asp Lys Thr Glu Ile Glu Thr Leu Tyr
            1060                1065                1070

His Ser Glu Pro Asp Ser Thr Ile Leu Lys Asp Phe Trp Gly Asn Tyr
        1075                1080                1085

Leu Leu Tyr Asn Lys Lys Tyr Tyr Leu Leu Asn Leu Leu Lys Pro Asn
    1090                1095                1100

Met Ser Val Thr Lys Asn Ser Asp Ile Leu Asn Ile Asn Arg Gln Arg
```

-continued

```
              1105                1110                1115                1120
Gly Ile Tyr Ser Lys Thr Asn Ile Phe Ser Asn Ala Arg Leu Tyr Thr
                    1125                1130                1135
Gly Val Glu Val Ile Ile Arg Lys Val Gly Ser Thr Asp Thr Ser Asn
                1140                1145                1150
Thr Asp Asn Phe Val Arg Lys Asn Asp Thr Val Tyr Ile Asn Val Val
            1155                1160                1165
Asp Gly Asn Ser Glu Tyr Gln Leu Tyr Ala Asp Val Ser Thr Ser Ala
        1170                1175                1180
Val Glu Lys Thr Ile Lys Leu Arg Arg Ile Ser Asn Ser Asn Tyr Asn
1185                1190                1195                1200
Ser Asn Gln Met Ile Ile Met Asp Ser Ile Gly Asp Asn Cys Thr Met
                    1205                1210                1215
Asn Phe Lys Thr Asn Asn Gly Asn Asp Ile Gly Leu Leu Gly Phe His
                1220                1225                1230
Leu Asn Asn Leu Val Ala Ser Ser Trp Tyr Tyr Lys Asn Ile Arg Asn
            1235                1240                1245
Asn Thr Arg Asn Asn Gly Cys Phe Trp Ser Phe Ile Ser Lys Glu His
        1250                1255                1260
Gly Trp Gln Glu
1265

<210> SEQ ID NO 10
<211> LENGTH: 1251
<212> TYPE: PRT
<213> ORGANISM: Clostridium butyricum

<400> SEQUENCE: 10

Met Pro Thr Ile Asn Ser Phe Asn Tyr Asn Asp Pro Val Asn Asn Arg
 1               5                  10                  15
Thr Ile Leu Tyr Ile Lys Pro Gly Gly Cys Gln Gln Phe Tyr Lys Ser
                20                  25                  30
Phe Asn Ile Met Lys Asn Ile Trp Ile Ile Pro Glu Arg Asn Val Ile
            35                  40                  45
Gly Thr Ile Pro Gln Asp Phe Leu Pro Pro Thr Ser Leu Lys Asn Gly
        50                  55                  60
Asp Ser Ser Tyr Tyr Asp Pro Asn Tyr Leu Gln Ser Asp Gln Glu Lys
    65                  70                  75                  80
Asp Lys Phe Leu Lys Ile Val Thr Lys Ile Phe Asn Arg Ile Asn Asp
                85                  90                  95
Asn Leu Ser Gly Arg Ile Leu Leu Glu Glu Leu Ser Lys Ala Asn Pro
            100                 105                 110
Tyr Leu Gly Asn Asp Asn Thr Pro Asp Gly Asp Phe Ile Ile Asn Asp
        115                 120                 125
Ala Ser Ala Val Pro Ile Gln Phe Ser Asn Gly Ser Gln Ser Ile Leu
    130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                165                 170                 175
Gly Phe Gly Ser Ile Ala Ile Val Thr Phe Ser Pro Glu Tyr Ser Phe
            180                 185                 190
Arg Phe Lys Asp Asn Ser Met Asn Glu Phe Ile Gln Asp Pro Ala Leu
        195                 200                 205
```

```
Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Gly Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
```

-continued

```
           625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
                660                 665                 670
Glu Arg Asp Glu Lys Trp Lys Glu Val Tyr Ser Phe Ile Val Ser Asn
                675                 680                 685
Trp Met Thr Lys Ile Asn Thr Gln Phe Asn Lys Arg Lys Glu Gln Met
            690                 695                 700
Tyr Gln Ala Leu Gln Asn Gln Val Asn Ala Leu Lys Ala Ile Ile Glu
705                 710                 715                 720
Ser Lys Tyr Asn Ser Tyr Thr Leu Glu Glu Lys Asn Glu Leu Thr Asn
                725                 730                 735
Lys Tyr Asp Ile Glu Gln Ile Glu Asn Glu Leu Asn Gln Lys Val Ser
                740                 745                 750
Ile Ala Met Asn Asn Ile Asp Arg Phe Leu Thr Glu Ser Ser Ile Ser
            755                 760                 765
Tyr Leu Met Lys Leu Ile Asn Glu Val Lys Ile Asn Lys Leu Arg Glu
770                 775                 780
Tyr Asp Glu Asn Val Lys Thr Tyr Leu Leu Asp Tyr Ile Ile Lys His
785                 790                 795                 800
Gly Ser Ile Leu Gly Glu Ser Gln Gln Glu Leu Asn Ser Met Val Ile
                805                 810                 815
Asp Thr Leu Asn Asn Ser Ile Pro Phe Lys Leu Ser Ser Tyr Thr Asp
                820                 825                 830
Asp Lys Ile Leu Ile Ser Tyr Phe Asn Lys Phe Phe Lys Arg Ile Lys
                835                 840                 845
Ser Ser Val Leu Asn Met Arg Tyr Lys Asn Asp Lys Tyr Val Asp
850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                885                 890                 895
Glu Val Asn Ile Ser Gln Asn Asp Tyr Ile Ile Tyr Asp Asn Lys Tyr
                900                 905                 910
Lys Asn Phe Ser Ile Ser Phe Trp Val Arg Ile Pro Asn Tyr Asp Asn
            915                 920                 925
Lys Ile Val Asn Val Asn Asn Glu Tyr Thr Ile Ile Asn Cys Met Arg
            930                 935                 940
Asp Asn Asn Ser Gly Trp Lys Val Ser Leu Asn His Asn Glu Ile Ile
945                 950                 955                 960
Trp Thr Leu Gln Asp Asn Ser Gly Ile Asn Gln Lys Leu Ala Phe Asn
                965                 970                 975
Tyr Gly Asn Ala Asn Gly Ile Ser Asp Tyr Ile Asn Lys Trp Ile Phe
            980                 985                 990
Val Thr Ile Thr Asn Asp Arg Leu Gly Asp Ser Lys Leu Tyr Ile Asn
            995                 1000                1005
Gly Asn Leu Ile Asp Lys Lys Ser Ile Leu Asn Leu Gly Asn Ile His
        1010                1015                1020
Val Ser Asp Asn Ile Leu Phe Lys Ile Val Asn Cys Ser Tyr Thr Arg
1025                1030                1035                1040
Tyr Ile Gly Ile Arg Tyr Phe Asn Ile Phe Asp Lys Glu Leu Asp Glu
                1045                1050                1055
```

-continued

```
Thr Glu Ile Gln Thr Leu Tyr Asn Asn Glu Pro Asn Ala Asn Ile Leu
                1060                1065                1070

Lys Asp Phe Trp Gly Asn Tyr Leu Leu Tyr Asp Lys Glu Tyr Tyr Leu
            1075                1080                1085

Leu Asn Val Leu Lys Pro Asn Asn Phe Ile Asn Arg Arg Thr Asp Ser
        1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
            1140                1145                1150

Val Ala Ser Lys Thr His Leu Leu Pro Leu Tyr Ala Asp Thr Ala Thr
        1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Cys Thr Met Asn Phe
1185                1190                1195                1200

Lys Asn Asn Asn Gly Asn Asn Ile Gly Leu Leu Gly Phe Lys Ala Asp
                1205                1210                1215

Thr Val Val Ala Ser Thr Trp Tyr Tyr Thr His Met Arg Asp Asn Thr
            1220                1225                1230

Asn Ser Asn Gly Phe Phe Trp Asn Phe Ile Ser Glu Glu His Gly Trp
        1235                1240                1245

Gln Glu Lys
    1250

<210> SEQ ID NO 11
<211> LENGTH: 293
<212> TYPE: PRT
<213> ORGANISM: Clostridium botulinum serotype A

<400> SEQUENCE: 11

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
        35                  40                  45

Arg Leu Ile Tyr Asp Ser Asn Lys Ala Ala Tyr Lys Ile Lys Ser Met
    50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
                85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Ile Glu Asp
    130                 135                 140

Tyr Ile Ile Ser Asp Leu Asn Asn Phe Thr Cys Lys Ile Ser Pro Ile
145                 150                 155                 160

Leu Asp Leu Asn Lys Val Val Gln Gln Val Asp Val Thr Asn Leu Asn
```

```
                165                 170                 175
Val Asn Leu Tyr Thr Trp Asp Tyr Gly Arg Asn Gln Lys Trp Thr Ile
        180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
        210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
            245                 250                 255

Asp Thr Thr Lys Ala Leu Asp Leu Tyr Gly Gly Gln Thr Ala Asn Gly
        260                 265                 270

Thr Ala Ile Gln Val Phe Asn Tyr His Gly Asp Asp Asn Gln Lys Trp
        275                 280                 285

Asn Ile Arg Asn Pro
        290

<210> SEQ ID NO 12
<211> LENGTH: 293
<212> TYPE: PRT
<213> ORGANISM: Clostridium botulinum serotype A

<400> SEQUENCE: 12

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
        35                  40                  45

Arg Leu Ile Tyr Asp Ser Asn Lys Ala Ala Tyr Lys Ile Lys Ser Met
    50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
                85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Ile Glu Asp
    130                 135                 140

Tyr Ile Ile Ser Asp Leu Asn Asn Phe Thr Cys Lys Ile Ser Pro Ile
145                 150                 155                 160

Leu Asp Arg Asn Lys Val Val Gln Gln Val Asp Met Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
    210                 215                 220

Val Ser Ser Ser Asn Asp Gln Asn Asn Asp Ala Gln Tyr Trp Leu Ile
225                 230                 235                 240
```

```
Asn Pro Val Ser Asp Thr Asp Glu Thr Tyr Thr Ile Thr Asn Leu Arg
            245                 250                 255

Asp Thr Thr Lys Ala Leu Asp Leu Tyr Asn Ser Gln Thr Ala Asn Gly
            260                 265                 270

Thr Ala Ile Gln Val Phe Asn Tyr His Gly Asp Asn Gln Lys Trp
            275                 280             285

Asn Ile Arg Asn Pro
    290

<210> SEQ ID NO 13
<211> LENGTH: 293
<212> TYPE: PRT
<213> ORGANISM: Clostridium botulinum serotype A

<400> SEQUENCE: 13

Met Glu His Tyr Ser Val Ile Gln Asn Ser Leu Asn Asp Lys Ile Val
  1               5                  10                  15

Thr Ile Ser Cys Arg Ala Asp Thr Asn Leu Phe Phe Tyr Gln Val Ala
             20                  25                  30

Gly Asn Val Ser Leu Phe Gln Gln Thr Arg Asn Tyr Leu Glu Arg Trp
         35                  40                  45

Arg Ile Ile Tyr Asp Ser Asn Lys Ala Ala Tyr Lys Ile Lys Ser Met
 50                  55                  60

Asp Ile His Asn Thr Asn Leu Val Leu Thr Trp Asn Ala Pro Thr His
 65                  70                  75                  80

Asn Ile Ser Thr Gln Gln Asp Ser Asn Ala Asp Asn Gln Tyr Trp Leu
             85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
            115                 120                 125

Leu Ser Thr Leu Asn Asn Ser Asn Tyr Ile Lys Phe Ile Ile Glu Asp
        130                 135                 140

Tyr Ile Ile Ser Asp Phe Asn Asn Phe Thr Cys Lys Ile Ser Pro Ile
145                 150                 155                 160

Leu Asp Arg Asn Lys Val Val Gln Gln Val Ala Thr Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
    210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Asn Ser Gln Thr Ala Asn Gly
            260                 265                 270

Thr Ala Ile Gln Val Phe Asn Ser Gly Gly Asp Asn Gln Lys Trp
            275                 280             285

Asn Ile Arg Asn Pro
    290

<210> SEQ ID NO 14
```

```
<211> LENGTH: 294
<212> TYPE: PRT
<213> ORGANISM: Clostridium botulinum serotype A

<400> SEQUENCE: 14

Met Glu His Tyr Ser Thr Ile Gln Asn Ser Leu Asn Asp Lys Ile Val
1               5                   10                  15

Thr Ile Ser Cys Lys Ala Asn Thr Asp Leu Phe Phe Tyr Gln Val Pro
            20                  25                  30

Gly Asn Gly Asn Val Ser Leu Phe Gln Gln Thr Arg Asn Tyr Leu Glu
        35                  40                  45

Arg Trp Arg Ile Ile Tyr Asp Ser Asn Lys Ala Ala Tyr Lys Ile Lys
50                  55                  60

Ser Met Asn Ile Tyr Asn Thr Asn Leu Val Leu Thr Trp Asn Ala Pro
65                  70                  75                  80

Thr His Asn Ile Ser Ala Gln Gln Asp Ser Asn Ala Asp Asn Gln Tyr
                85                  90                  95

Trp Leu Leu Leu Lys Asp Ile Gly Asn Asn Ser Phe Ile Ile Ala Ser
            100                 105                 110

Tyr Lys Asn Pro Asn Leu Val Leu Tyr Ala Asp Thr Val Ala Arg Asn
        115                 120                 125

Leu Lys Leu Ser Thr Leu Asn Asn Ser Ser Tyr Ile Lys Phe Ile Ile
130                 135                 140

Glu Asp Tyr Val Ile Ser Asp Phe Lys Asn Phe Thr Cys Arg Ile Ser
145                 150                 155                 160

Pro Ile Leu Ala Gly Gly Lys Val Val Gln Gln Val Ser Met Thr Asn
                165                 170                 175

Leu Ala Val Asn Leu Tyr Ile Trp Asn Asn Asp Leu Asn Gln Lys Trp
            180                 185                 190

Thr Ile Ile Tyr Asn Glu Glu Lys Ala Ala Tyr Gln Phe Phe Asn Lys
        195                 200                 205

Ile Leu Ser Asn Gly Val Leu Thr Trp Ile Phe Ser Asp Gly Asn Thr
210                 215                 220

Val Arg Val Ser Ser Ala Gln Asn Asn Asp Ala Gln Tyr Trp Leu
225                 230                 235                 240

Ile Asn Pro Val Ser Asp Asn Tyr Asp Arg Tyr Thr Ile Thr Asn Leu
                245                 250                 255

Arg Asp Lys Thr Lys Val Leu Asp Leu Tyr Gly Gly Gln Thr Ala Asp
            260                 265                 270

Gly Thr Thr Ile Gln Val Phe Asn Ser Asn Gly Gly Asp Asn Gln Ile
        275                 280                 285

Trp Thr Met Ser Asn Pro
    290

<210> SEQ ID NO 15
<211> LENGTH: 279
<212> TYPE: PRT
<213> ORGANISM: Clostridium botulinum serotype A

<400> SEQUENCE: 15

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
        35                  40                  45
```

```
Arg Leu Ile Tyr Asp Ser Asn Lys Ala Ala Tyr Lys Ile Lys Ser Met
        50                  55                  60

Asp Ile His Asn Thr Asn Leu Val Leu Thr Trp Asn Ala Pro Thr His
 65              70                  75                  80

Asn Ile Ser Thr Gln Gln Asp Ser Asn Ala Asp Asn Gln Tyr Trp Leu
                85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
            115                 120                 125

Leu Ser Thr Leu Asn Asn Ser Asn Tyr Ile Lys Phe Ile Ile Glu Asp
130                 135                 140

Tyr Ile Ile Ser Asp Leu Asn Asn Phe Thr Cys Lys Ile Ser Pro Ile
145                 150                 155                 160

Leu Asp Arg Asn Lys Val Val Gln Gln Val Asp Met Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
            195                 200                 205

Ser Asn Gly Val Leu Thr Trp Ile Phe Ser Asn Gly Asn Thr Val Arg
210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Asn Ser Gln Thr Ala Asn Gly
                260                 265                 270

Thr Ala Ile Gln Val Phe Asn
        275

<210> SEQ ID NO 16
<211> LENGTH: 292
<212> TYPE: PRT
<213> ORGANISM: Clostridium botulinum serotype B

<400> SEQUENCE: 16

Met Glu His Tyr Ser Val Ile Gln Asn Ser Leu Asn Asp Glu Ile Val
  1               5                  10                  15

Thr Ile Ser Cys Lys Ala Asp Thr Asn Leu Phe Phe Tyr Gln Thr Val
                20                  25                  30

Gly Asn Val Ser Leu Phe Gln Gln Thr Arg Asn Tyr Leu Glu Arg Trp
            35                  40                  45

Arg Leu Ile Tyr Asp Ala Asn Lys Ala Ala Tyr Lys Ile Lys Ser Met
        50                  55                  60

Asp Ser His Asn Thr Asn Leu Val Leu Thr Trp Asn Ala Pro Thr His
 65              70                  75                  80

Asn Ile Ser Ala Gln Gln Asp Ser Asn Ala Asp Asn Gln Tyr Trp Leu
                85                  90                  95

Leu Leu Lys Asp Ile Gly Ser Asn Ser Phe Ile Ile Ala Ser Tyr Lys
            100                 105                 110

Asn Pro Asn Leu Val Leu Tyr Ala Asp Thr Val Ala Arg Asn Leu Lys
            115                 120                 125

Leu Ser Thr Leu Asn Asn Ser Ser Tyr Ile Lys Phe Ile Ile Glu Asp
```

-continued

```
                130                 135                 140
Tyr Met Ile Ser Asp Phe Asn Asn Phe Thr Cys Lys Ile Ser Pro Ile
145                 150                 155                 160

Leu Asp Ser Ser Lys Val Val Gln Gln Val Ala Met Thr Asp Leu Ser
                165                 170                 175

Val Asn Leu Tyr Thr Trp Asp Tyr Gly Arg Asn Gln Lys Trp Thr Ile
                180                 185                 190

Lys Tyr Asn Lys Glu Lys Ser Ala Tyr Gln Phe Phe Asn Thr Ile Leu
                195                 200                 205

Ser Asn Gly Val Leu Thr Trp Ile Ser Ser Asn Gly Asn Thr Val Arg
            210                 215                 220

Val Ser Ser Ile Ala Gln Asn Asn Asp Ala Gln Tyr Trp Leu Ile Asn
225                 230                 235                 240

Pro Val Ser Asn Ala Tyr Glu Thr Tyr Thr Ile Thr Asn Leu His Asp
                245                 250                 255

Thr Thr Lys Ala Leu Asp Leu Tyr Asn Ser Gln Thr Ala Asn Gly Thr
                260                 265                 270

Thr Ile Gln Val Phe Asn Tyr His Gly Asp Asp Asn Gln Lys Trp Phe
            275                 280                 285

Ile Arg Asn Pro
        290

<210> SEQ ID NO 17
<211> LENGTH: 285
<212> TYPE: PRT
<213> ORGANISM: Clostridium botulinum serotype C1

<400> SEQUENCE: 17

Met Ser Gln Thr Asn Ala Asn Asp Leu Arg Asn Asn Glu Val Phe Phe
  1               5                  10                  15

Ile Ser Pro Ser Asn Asn Thr Asn Lys Val Leu Asp Lys Ile Ser Gln
                 20                  25                  30

Ser Glu Val Lys Leu Trp Asn Lys Leu Ser Gly Ala Asn Gln Lys Trp
             35                  40                  45

Arg Leu Ile Tyr Asp Thr Asn Lys Gln Ala Tyr Lys Ile Lys Val Met
 50                  55                  60

Asp Asn Thr Ser Leu Ile Leu Thr Trp Asn Ala Pro Leu Ser Ser Val
 65                  70                  75                  80

Ser Val Lys Thr Asp Thr Asn Gly Asp Asn Gln Tyr Trp Tyr Leu Leu
                 85                  90                  95

Gln Asn Tyr Ile Ser Arg Asn Val Ile Ile Arg Asn Tyr Met Asn Pro
                100                 105                 110

Asn Leu Val Leu Gln Tyr Asn Ile Asp Asp Thr Leu Met Val Ser Thr
            115                 120                 125

Gln Thr Ser Ser Asn Gln Phe Phe Lys Phe Ser Asn Cys Ile Tyr
            130                 135                 140

Glu Ser Phe Asn Asn Ser Thr Cys Lys Ile Gln Thr Ser Leu Thr Ile
145                 150                 155                 160

Lys Phe Ile Asp Lys Asn Gln Asn Ser Asn Asn Val Thr Ile Trp Ser
                165                 170                 175

Trp Asn Asn Gly Asp Asn Gln Lys Trp Lys Ile Leu Tyr Asn Glu Ser
                180                 185                 190

Lys Met Ala Tyr Thr Leu Thr Cys Ile Lys Asn Asn Glu Tyr Leu Thr
                195                 200                 205
```

Trp Phe Ser Ser Ile Gly Asn Asn Val Gly Thr Tyr Arg Thr Glu Gly
210                 215                 220

Asn Asn Asp Gln Tyr Trp Phe Ile Asn Tyr Leu Asn Asn Asp Ala Ser
225                 230                 235                 240

Met Tyr Thr Ile Ser Asn Phe Ser Asn Gln Ser Lys Phe Leu Asp Val
                245                 250                 255

Val Asn Ser Gly Leu Ala Asp Gly Thr Asn Val Gln Val Trp Asp Ser
                260                 265                 270

Asn Gly Thr Ser Ala Gln Lys Trp Ile Ile Thr Arg Leu
            275                 280                 285

<210> SEQ ID NO 18
<211> LENGTH: 286
<212> TYPE: PRT
<213> ORGANISM: Clostridium botulinum serotype C1

<400> SEQUENCE: 18

Met Ser Gln Thr Asn Ala Asn Asp Leu Arg Asn Asn Glu Val Phe Phe
1               5                   10                  15

Ile Ser Pro Ser Asn Asn Thr Asn Lys Val Leu Asp Lys Ile Ser Gln
                20                  25                  30

Ser Glu Val Lys Leu Trp Asn Lys Leu Ser Gly Ala Asn Gln Lys Trp
            35                  40                  45

Arg Leu Ile Tyr Asp Thr Asn Lys Gln Ala Tyr Lys Ile Lys Val Met
        50                  55                  60

Asp Asn Thr Ser Leu Ile Leu Thr Trp Asn Ala Pro Leu Ser Ser Val
65                  70                  75                  80

Ser Val Lys Thr Asp Thr Asn Gly Asp Asn Gln Tyr Trp Tyr Leu Leu
                85                  90                  95

Gln Asn Tyr Ile Ser Arg Asn Val Ile Ile Arg Asn Tyr Met Asn Pro
                100                 105                 110

Asn Leu Val Leu Gln Tyr Asn Ile Asp Asp Thr Leu Met Val Ser Thr
            115                 120                 125

Gln Thr Ser Ser Asn Gln Phe Phe Lys Phe Ser Asn Cys Ile Tyr
        130                 135                 140

Glu Ala Leu Asn Asn Arg Asn Cys Lys Leu Gln Thr Gln Leu Asn Ser
145                 150                 155                 160

Asp Arg Phe Leu Ser Lys Asn Leu Asn Ser Gln Ile Ile Val Leu Trp
                165                 170                 175

Gln Trp Phe Asp Ser Ser Arg Gln Lys Trp Ile Ile Glu Tyr Asn Glu
            180                 185                 190

Thr Lys Ser Ala Tyr Thr Leu Lys Cys Gln Glu Asn Asn Arg Tyr Leu
        195                 200                 205

Thr Trp Ile Gln Asn Ser Asn Asn Tyr Val Glu Thr Tyr Gln Ser Thr
210                 215                 220

Asp Ser Leu Ile Gln Tyr Trp Asn Ile Asn Tyr Leu Asp Asn Asp Ala
225                 230                 235                 240

Ser Lys Tyr Ile Leu Tyr Asn Leu Gln Asp Thr Asn Arg Val Leu Asp
                245                 250                 255

Val Tyr Asn Ser Gln Ile Ala Asn Gly Thr His Val Ile Val Asp Ser
                260                 265                 270

Tyr His Gly Asn Thr Asn Gln Gln Trp Ile Ile Asn Leu Ile
            275                 280                 285

<210> SEQ ID NO 19

```
<211> LENGTH: 285
<212> TYPE: PRT
<213> ORGANISM: Clostridium botulinum serotype C1

<400> SEQUENCE: 19
```

| | | | | | | | | | | | | | |
|---|---|---|---|---|---|---|---|---|---|---|---|---|---|
| Met | Ser | Gln | Thr | Asn | Ala | Asn | Asp | Leu | Arg | Asn | Asn | Glu | Val | Phe | Phe |
| 1 | | | | 5 | | | | | 10 | | | | | 15 |
| Ile | Ser | Pro | Ser | Asn | Asn | Thr | Asn | Lys | Val | Leu | Asp | Lys | Ile | Ser | Gln |
| | | | 20 | | | | | 25 | | | | | 30 | | |
| Ser | Glu | Val | Lys | Leu | Trp | Asn | Lys | Leu | Ser | Gly | Ala | Asn | Gln | Lys | Trp |
| | | 35 | | | | | 40 | | | | | 45 | | | |
| Arg | Leu | Ile | Tyr | Asp | Thr | Asn | Lys | Gln | Ala | Tyr | Lys | Ile | Lys | Val | Met |
| | 50 | | | | | 55 | | | | | 60 | | | | |
| Asp | Asn | Thr | Ser | Leu | Ile | Leu | Thr | Trp | Asn | Ala | Pro | Leu | Ser | Ser | Val |
| 65 | | | | | 70 | | | | | 75 | | | | | 80 |
| Ser | Val | Lys | Thr | Asp | Thr | Asn | Gly | Asp | Asn | Gln | Tyr | Trp | Tyr | Leu | Leu |
| | | | | 85 | | | | | 90 | | | | | 95 | |
| Gln | Asn | Tyr | Ile | Ser | Arg | Asn | Val | Ile | Ile | Arg | Asn | Tyr | Met | Asn | Pro |
| | | | 100 | | | | | 105 | | | | | 110 | | |
| Asn | Leu | Val | Leu | Gln | Tyr | Asn | Ile | Asp | Asp | Thr | Leu | Met | Val | Ser | Thr |
| | | | 115 | | | | | 120 | | | | | 125 | | |
| Gln | Thr | Ser | Ser | Ser | Asn | Gln | Phe | Phe | Lys | Phe | Ser | Asn | Cys | Ile | Tyr |
| | 130 | | | | | 135 | | | | | 140 | | | | |
| Glu | Ser | Phe | Asn | Asn | Ser | Thr | Cys | Lys | Ile | Gln | Thr | Ser | Leu | Thr | Ile |
| 145 | | | | | 150 | | | | | 155 | | | | | 160 |
| Lys | Phe | Ile | Asp | Lys | Asn | Gln | Asn | Ser | Asn | Asn | Val | Thr | Ile | Trp | Ser |
| | | | | 165 | | | | | 170 | | | | | 175 | |
| Trp | Asn | Asn | Gly | Asp | Asn | Gln | Lys | Trp | Lys | Ile | Leu | Tyr | Asn | Glu | Ser |
| | | | 180 | | | | | 185 | | | | | 190 | | |
| Lys | Met | Ala | Tyr | Thr | Leu | Thr | Cys | Ile | Lys | Asn | Asn | Glu | Tyr | Leu | Thr |
| | | | 195 | | | | | 200 | | | | | 205 | | |
| Trp | Phe | Ser | Ser | Ile | Gly | Asn | Asn | Val | Gly | Thr | Tyr | Arg | Thr | Glu | Gly |
| | 210 | | | | | 215 | | | | | 220 | | | | |
| Asn | Asn | Asp | Gln | Tyr | Trp | Phe | Ile | Asn | Tyr | Leu | Asn | Asn | Asp | Ala | Ser |
| 225 | | | | | 230 | | | | | 235 | | | | | 240 |
| Met | Tyr | Thr | Ile | Ser | Asn | Phe | Ser | Asn | Gln | Ser | Lys | Phe | Leu | Asp | Val |
| | | | | 245 | | | | | 250 | | | | | 255 | |
| Val | Asn | Ser | Gly | Leu | Ala | Asp | Gly | Thr | Asn | Val | Gln | Val | Trp | Asp | Ser |
| | | | 260 | | | | | 265 | | | | | 270 | | |
| Asn | Gly | Thr | Ser | Ala | Gln | Lys | Trp | Ile | Ile | Thr | Arg | Leu | | | |
| | | | 275 | | | | | 280 | | | | | 285 | | |

```
<210> SEQ ID NO 20
<211> LENGTH: 286
<212> TYPE: PRT
<213> ORGANISM: Clostridium botulinum serotype D

<400> SEQUENCE: 20
```

| | | | | | | | | | | | | | | | |
|---|---|---|---|---|---|---|---|---|---|---|---|---|---|---|---|
| Met | Ser | Gln | Thr | Asn | Ala | Asn | Asp | Leu | Arg | Asn | Asn | Glu | Val | Phe | Phe |
| 1 | | | | 5 | | | | | 10 | | | | | 15 | |
| Ile | Ser | Pro | Ser | Asn | Asn | Thr | Asn | Lys | Val | Leu | Asp | Lys | Ile | Ser | Gln |
| | | | 20 | | | | | 25 | | | | | 30 | | |
| Ser | Glu | Val | Lys | Leu | Trp | Asn | Lys | Leu | Ser | Gly | Ala | Asn | Gln | Lys | Trp |
| | | 35 | | | | | 40 | | | | | 45 | | | |
| Arg | Leu | Ile | Tyr | Asp | Thr | Asn | Lys | Gln | Ala | Tyr | Thr | Ile | Lys | Val | Met |
| | 50 | | | | | 55 | | | | | 60 | | | | |

```
Asp Asn Thr Ser Leu Ile Leu Thr Trp Asp Ala Pro Leu Ser Ser Val
 65                  70                  75                  80

Ser Val Lys Thr Asp Thr Asn Thr Asn Asn Gln Tyr Trp Tyr Leu Leu
             85                  90                  95

Gln Asp Tyr Ile Ser Arg Asn Val Ile Leu Arg Asn Tyr Met Asn Pro
            100                 105                 110

Asn Leu Val Leu Gln Tyr Asn Thr Asp Thr Leu Ile Val Ser Thr
            115                 120                 125

Gln Thr Asn Ser Asn Asn Gln Phe Phe Lys Phe Ser Asn Cys Ile Tyr
130                 135                 140

Glu Ala Leu Asn Asn Arg Asn Cys Lys Leu Gln Thr Gln Leu Asn Ser
145                 150                 155                 160

Asp Arg Phe Leu Ser Lys Asn Leu Asn Ser Gln Ile Ile Val Leu Trp
                165                 170                 175

Gln Trp Phe Asp Ser Ser Arg Gln Lys Trp Thr Ile Glu Tyr Asn Glu
            180                 185                 190

Thr Lys Ser Ala Tyr Thr Leu Lys Cys Gln Glu Asn Asn Arg Tyr Leu
            195                 200                 205

Thr Trp Ile Gln Asn Ser Asn Asn Tyr Val Glu Thr Tyr Gln Ser Thr
210                 215                 220

Asp Ser Leu Ile Gln Tyr Trp Asn Ile Asn Tyr Leu Asp Asn Asp Ala
225                 230                 235                 240

Ser Lys Tyr Ile Leu Tyr Asn Leu Gln Asp Thr Asn Arg Val Leu Asp
                245                 250                 255

Val Tyr Asn Ser Gln Thr Ala Asn Gly Thr His Val Ile Val Asp Ser
            260                 265                 270

Tyr His Gly Asn Thr Asn Gln Gln Trp Ile Ile Asn Leu Ile
            275                 280                 285

<210> SEQ ID NO 21
<211> LENGTH: 146
<212> TYPE: PRT
<213> ORGANISM: Clostridium botulinum serotype A

<400> SEQUENCE: 21

Met Ser Val Glu Arg Thr Phe Leu Pro Asn Gly Asn Tyr Asn Ile Lys
 1               5                  10                  15

Ser Ile Phe Ser Gly Ser Leu Tyr Leu Asn Pro Val Ser Lys Ser Leu
            20                  25                  30

Thr Phe Ser Asn Glu Ser Ser Ala Asn Asn Gln Lys Trp Asn Val Glu
        35                  40                  45

Tyr Met Ala Glu Asn Arg Cys Phe Lys Ile Ser Asn Val Ala Glu Pro
 50                  55                  60

Asn Lys Tyr Leu Ser Tyr Asp Asn Phe Gly Phe Ile Ser Leu Asp Ser
 65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
            100                 105                 110

Asp Ile Tyr Asp Thr Asn Glu Asn Ile Leu Ser Gln Pro Leu Leu Leu
            115                 120                 125

Leu Pro Asn Phe Asp Ile Tyr Asn Ser Asn Gln Met Phe Lys Leu Glu
130                 135                 140

Lys Ile
```

<210> SEQ ID NO 22
<211> LENGTH: 146
<212> TYPE: PRT
<213> ORGANISM: Clostridium botulinum serotype B

<400> SEQUENCE: 22

Met Ser Ala Glu Arg Thr Phe Leu Pro Asn Gly Asn Tyr Asn Ile Lys
1               5                   10                  15

Ser Ile Phe Ser Gly Ser Leu Tyr Leu Ser Pro Val Ser Gly Ser Leu
            20                  25                  30

Thr Phe Ser Asn Glu Ser Ser Ala Asn Asn Gln Lys Trp Asn Val Glu
        35                  40                  45

Tyr Met Ala Glu Asn Arg Cys Phe Lys Ile Ser Val Ala Glu Pro
50                  55                  60

Asn Lys Tyr Leu Ser Tyr Asp Asn Phe Gly Phe Ile Ser Leu Asp Ser
65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
            100                 105                 110

Asp Ile Tyr Asp Thr Asn Glu Asn Ile Leu Ser Gln Pro Leu Leu Leu
        115                 120                 125

Leu Pro Asn Phe Asp Ile Tyr Asn Ser Asn Gln Met Phe Lys Leu Glu
    130                 135                 140

Lys Ile
145

<210> SEQ ID NO 23
<211> LENGTH: 146
<212> TYPE: PRT
<213> ORGANISM: Clostridium botulinum serotype C1

<400> SEQUENCE: 23

Met Ser Ser Glu Arg Thr Phe Leu Pro Asn Gly Asn Tyr Lys Ile Lys
1               5                   10                  15

Ser Leu Phe Ser Asn Ser Leu Tyr Leu Thr Tyr Ser Ser Gly Ala Leu
            20                  25                  30

Ser Phe Ser Asn Thr Ser Ser Leu Asp Asn Gln Lys Trp Lys Leu Glu
        35                  40                  45

Tyr Ile Ser Ser Ser Asn Gly Phe Arg Phe Ser Asn Val Ala Glu Pro
50                  55                  60

Asn Lys Tyr Leu Ala Tyr Asn Asp Tyr Gly Phe Ile Tyr Leu Ser Ser
65                  70                  75                  80

Ser Ser Asn Asn Ser Leu Trp Asn Pro Ile Lys Ile Ala Ile Asn Ser
                85                  90                  95

Tyr Ile Ile Cys Thr Leu Ser Ile Val Asn Val Thr Asp Tyr Ala Trp
            100                 105                 110

Thr Ile Tyr Asp Asn Asn Asn Ile Thr Asp Gln Pro Ile Leu Asn
        115                 120                 125

Leu Pro Asn Phe Asp Ile Asn Asn Ser Asn Gln Ile Leu Lys Leu Glu
    130                 135                 140

Lys Leu
145

<210> SEQ ID NO 24
<211> LENGTH: 146
<212> TYPE: PRT
<213> ORGANISM: Clostridium botulinum serotype D

<400> SEQUENCE: 24

Met Ser Ser Glu Arg Thr Phe Leu Pro Asn Gly Asn Tyr Lys Ile Lys
1               5                   10                  15

Ser Leu Phe Ser Asp Ser Leu Tyr Leu Thr Tyr Ser Ser Gly Ser Leu
            20                  25                  30

Ser Phe Leu Asn Thr Ser Ser Leu Asp Asn Gln Lys Trp Lys Leu Glu
        35                  40                  45

Tyr Ile Ser Ser Ser Asn Gly Phe Arg Phe Ser Asn Val Ala Glu Pro
    50                  55                  60

Asn Lys Tyr Leu Ala Tyr Asn Asp Tyr Gly Phe Ile Tyr Leu Ser Ser
65                  70                  75                  80

Ser Ser Asn Asn Ser Leu Trp Asn Pro Ile Lys Ile Ala Ile Asn Ser
                85                  90                  95

Tyr Ile Ile Cys Thr Leu Ser Ile Val Asn Val Thr Asp Tyr Ala Trp
            100                 105                 110

Thr Ile Tyr Asp Asn Asn Asn Asn Ile Thr Asp Gln Pro Ile Leu Asn
        115                 120                 125

Leu Pro Asn Phe Asp Ile Asn Asn Ser Asn Gln Ile Leu Lys Leu Glu
    130                 135                 140

Lys Leu
145

<210> SEQ ID NO 25
<211> LENGTH: 1193
<212> TYPE: PRT
<213> ORGANISM: Clostridium botulinum serotype A

<400> SEQUENCE: 25

Met Asn Ile Asn Asp Asn Leu Ser Ile Asn Ser Pro Val Asp Asn Lys
1               5                   10                  15

Asn Val Val Val Val Arg Ala Arg Lys Thr Asp Thr Val Phe Lys Ala
            20                  25                  30

Phe Lys Val Ala Pro Asn Ile Trp Val Ala Pro Glu Arg Tyr Tyr Gly
        35                  40                  45

Glu Ser Leu Ser Ile Asp Glu Glu Tyr Lys Val Asp Gly Gly Ile Tyr
    50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

Pro Lys Ser Asn Lys Lys Leu Asn Ser Leu Ile Ser Ser Thr Ile Pro
    130                 135                 140

Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu

-continued

```
                180                 185                 190
Asn Gly Met Gly Thr Met Thr Glu Ile Trp Phe Gln Pro Phe Leu Thr
            195                 200                 205
Tyr Lys Tyr Asp Glu Phe Tyr Ile Asp Pro Ala Ile Glu Leu Ile Lys
        210                 215                 220
Cys Leu Ile Lys Ser Leu Tyr Phe Leu Tyr Gly Ile Lys Pro Ser Asp
225                 230                 235                 240
Asp Leu Val Ile Pro Tyr Arg Leu Arg Ser Glu Leu Glu Asn Ile Glu
                245                 250                 255
Tyr Ser Gln Leu Asn Ile Val Asp Leu Leu Val Ser Gly Gly Ile Asp
            260                 265                 270
Pro Lys Phe Ile Asn Thr Asp Pro Tyr Trp Phe Thr Asp Asn Tyr Phe
        275                 280                 285
Ser Asn Ala Lys Lys Val Phe Glu Asp His Arg Asn Ile Tyr Glu Thr
    290                 295                 300
Glu Ile Glu Gly Asn Asn Ala Ile Gly Asn Asp Ile Lys Leu Arg Leu
305                 310                 315                 320
Lys Gln Lys Phe Arg Ile Asn Ile Asn Asp Ile Trp Glu Leu Asn Leu
                325                 330                 335
Asn Tyr Phe Ser Lys Glu Phe Ser Ile Met Met Pro Asp Arg Phe Asn
            340                 345                 350
Asn Ala Leu Lys His Phe Tyr Arg Lys Gln Tyr Tyr Lys Ile Asp Tyr
        355                 360                 365
Pro Glu Asn Tyr Ser Ile Asn Gly Phe Val Asn Gly Gln Ile Asn Ala
    370                 375                 380
Gln Leu Ser Leu Ser Asp Arg Asn Gln Asp Ile Ile Asn Lys Pro Glu
385                 390                 395                 400
Glu Ile Ile Asn Leu Leu Asn Gly Asn Asn Val Ser Leu Met Arg Ser
                405                 410                 415
Asn Ile Tyr Gly Asp Gly Leu Lys Ser Thr Val Asp Asp Phe Tyr Ser
            420                 425                 430
Asn Tyr Lys Ile Pro Tyr Asn Arg Ala Tyr Glu Tyr His Phe Asn Asn
        435                 440                 445
Ser Asn Asp Ser Ser Leu Asp Asn Val Asn Ile Gly Val Ile Asp Asn
    450                 455                 460
Ile Pro Glu Ile Ile Asp Val Asn Pro Tyr Lys Glu Asn Cys Asp Lys
465                 470                 475                 480
Phe Ser Pro Val Gln Lys Ile Thr Ser Thr Arg Glu Ile Asn Thr Asn
                485                 490                 495
Ile Pro Trp Pro Ile Asn Tyr Leu Gln Ala Gln Asn Thr Asn Asn Glu
            500                 505                 510
Lys Phe Ser Leu Ser Ser Asp Phe Val Glu Val Ser Ser Lys Asp
        515                 520                 525
Lys Ser Leu Val Tyr Ser Phe Leu Ser Asn Val Met Phe Tyr Leu Asp
    530                 535                 540
Ser Ile Lys Asp Asn Ser Pro Ile Asp Thr Asp Lys Lys Tyr Tyr Leu
545                 550                 555                 560
Trp Leu Arg Glu Ile Phe Arg Asn Tyr Ser Phe Asp Ile Thr Ala Thr
                565                 570                 575
Gln Glu Ile Asn Thr Asn Cys Gly Ile Asn Lys Val Val Thr Trp Phe
            580                 585                 590
Gly Lys Ala Leu Asn Ile Leu Asn Thr Ser Asp Ser Phe Val Glu Glu
        595                 600                 605
```

-continued

```
Phe Gln Asn Leu Gly Ala Ile Ser Leu Ile Asn Lys Lys Glu Asn Leu
    610                 615                 620

Ser Met Pro Ile Ile Glu Ser Tyr Glu Ile Pro Asn Asp Met Leu Gly
625                 630                 635                 640

Leu Pro Leu Asn Asp Leu Asn Glu Lys Leu Phe Asn Ile Tyr Ser Lys
                    645                 650                 655

Asn Thr Ala Tyr Phe Lys Lys Ile Tyr Tyr Asn Phe Leu Asp Gln Trp
                660                 665                 670

Trp Thr Gln Tyr Tyr Ser Gln Tyr Phe Asp Leu Ile Cys Met Ala Lys
            675                 680                 685

Arg Ser Val Leu Ala Gln Glu Thr Leu Ile Lys Arg Ile Ile Gln Lys
        690                 695                 700

Lys Leu Ser Tyr Leu Ile Gly Asn Ser Asn Ile Ser Ser Asp Asn Leu
705                 710                 715                 720

Ala Leu Met Asn Leu Thr Thr Thr Asn Thr Leu Arg Asp Ile Ser Asn
                    725                 730                 735

Glu Ser Gln Ile Ala Met Asn Asn Val Asp Ser Phe Leu Asn Asn Ala
                740                 745                 750

Ala Ile Cys Val Phe Glu Ser Asn Ile Tyr Pro Lys Phe Ile Ser Phe
            755                 760                 765

Met Glu Gln Cys Ile Asn Asn Ile Asn Ile Lys Thr Lys Glu Phe Ile
        770                 775                 780

Gln Lys Cys Thr Asn Ile Asn Glu Asp Glu Lys Leu Gln Leu Ile Asn
785                 790                 795                 800

Gln Asn Val Phe Asn Ser Leu Asp Phe Glu Phe Leu Asn Ile Gln Asn
                    805                 810                 815

Met Lys Ser Leu Phe Ser Ser Glu Thr Ala Leu Leu Ile Lys Glu Glu
                820                 825                 830

Thr Trp Pro Tyr Glu Leu Val Leu Tyr Ala Phe Lys Glu Pro Gly Asn
            835                 840                 845

Asn Val Ile Gly Asp Ala Ser Gly Lys Asn Thr Ser Ile Glu Tyr Ser
        850                 855                 860

Lys Asp Ile Gly Leu Val Tyr Gly Ile Asn Ser Asp Ala Leu Tyr Leu
865                 870                 875                 880

Asn Gly Ser Asn Gln Ser Ile Ser Phe Ser Asp Phe Phe Glu Asn
                    885                 890                 895

Gly Leu Thr Asn Ser Phe Ser Ile Tyr Phe Trp Leu Arg Asn Leu Gly
                900                 905                 910

Lys Asp Thr Ile Lys Ser Lys Leu Ile Gly Ser Lys Glu Asp Asn Cys
            915                 920                 925

Gly Trp Glu Ile Tyr Phe Gln Asp Thr Gly Leu Val Phe Asn Met Ile
        930                 935                 940

Asp Ser Asn Gly Asn Glu Lys Asn Ile Tyr Leu Ser Asp Val Ser Asn
945                 950                 955                 960

Asn Ser Trp His Tyr Ile Thr Ile Ser Val Asp Arg Leu Lys Glu Gln
                    965                 970                 975

Leu Leu Ile Phe Ile Asp Asp Asn Leu Val Ala Asn Glu Ser Ile Lys
                980                 985                 990

Glu Ile Leu Asn Ile Tyr Ser Ser Asn Ile Ser Leu Leu Ser Glu
            995                 1000                1005

Asn Asn Pro Ser Tyr Ile Glu Gly Leu Thr Ile Leu Asn Lys Pro Thr
        1010                1015                1020
```

```
Thr Ser Gln Glu Val Leu Ser Asn Tyr Phe Glu Val Leu Asn Asn Ser
1025                1030                1035                1040

Tyr Ile Arg Asp Ser Asn Glu Glu Arg Leu Glu Tyr Asn Lys Thr Tyr
            1045                1050                1055

Gln Leu Tyr Asn Tyr Val Phe Ser Asp Lys Pro Ile Cys Glu Val Lys
        1060                1065                1070

Gln Asn Asn Asn Ile Tyr Leu Thr Ile Asn Asn Thr Asn Asn Leu Asn
    1075                1080                1085

Leu Gln Ala Ser Lys Phe Lys Leu Leu Ser Ile Asn Pro Asn Lys Gln
1090                1095                1100

Tyr Val Gln Lys Leu Asp Glu Val Ile Ile Ser Val Leu Asp Asn Met
1105                1110                1115                1120

Glu Lys Tyr Ile Asp Ile Ser Glu Asp Asn Arg Leu Gln Leu Ile Asp
                1125                1130                1135

Asn Lys Asn Asn Ala Lys Lys Met Ile Ile Ser Asn Asp Ile Phe Ile
            1140                1145                1150

Ser Asn Cys Leu Thr Leu Ser Tyr Asn Gly Lys Tyr Ile Cys Leu Ser
        1155                1160                1165

Met Lys Asp Glu Asn His Asn Trp Met Ile Cys Asn Asn Asp Met Ser
    1170                1175                1180

Lys Tyr Leu Tyr Leu Trp Ser Phe Lys
1185                1190

<210> SEQ ID NO 26
<211> LENGTH: 1198
<212> TYPE: PRT
<213> ORGANISM: Clostridium botulinum serotype A

<400> SEQUENCE: 26

Met Asn Ile Asn Asp Asn Leu Ser Ile Asn Ser Pro Val Asp Asn Lys
1               5                   10                  15

Asn Val Val Val Val Arg Ala Arg Lys Thr Asp Thr Val Phe Lys Ala
                20                  25                  30

Phe Lys Val Ala Pro Asn Ile Trp Val Ala Pro Glu Arg Tyr Tyr Gly
            35                  40                  45

Glu Ser Leu Ser Ile Asp Glu Glu Tyr Lys Val Asp Gly Gly Ile Tyr
        50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

Pro Lys Ser Asn Lys Lys Leu Asn Ser Leu Ile Ser Ser Thr Ile Pro
    130                 135                 140

Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Thr Glu Ile Trp Phe Gln Pro Phe Leu Thr
        195                 200                 205
```

-continued

```
Tyr Lys Tyr Asp Glu Phe Tyr Ile Asp Pro Ala Ile Glu Leu Ile Lys
    210                 215                 220

Cys Leu Ile Lys Ser Leu Tyr Phe Leu Tyr Gly Ile Lys Pro Ser Asp
225                 230                 235                 240

Asp Leu Val Ile Pro Tyr Arg Leu Arg Ser Glu Leu Glu Asn Ile Glu
                245                 250                 255

Tyr Ser Gln Leu Asn Ile Val Asp Leu Val Ser Gly Gly Ile Asp
            260                 265                 270

Pro Lys Phe Ile Asn Thr Asp Pro Tyr Trp Phe Ile Asp Asn Tyr Phe
        275                 280                 285

Ser Asn Ala Lys Lys Val Phe Glu Asp His Arg Asn Ile Tyr Glu Thr
    290                 295                 300

Glu Ile Glu Gly Asn Asn Ala Ile Gly Asn Asp Ile Lys Leu Arg Leu
305                 310                 315                 320

Lys Gln Lys Phe Arg Ile Asn Ile Asn Asp Ile Trp Glu Leu Asn Leu
                325                 330                 335

Asn Tyr Phe Ser Lys Glu Phe Ser Ile Met Met Pro Asp Arg Phe Asn
            340                 345                 350

Asn Ala Leu Lys His Phe Tyr Arg Lys Gln Tyr Tyr Lys Ile Asp Tyr
        355                 360                 365

Pro Glu Asn Tyr Ser Ile Asn Gly Phe Val Asn Gly Gln Ile Asn Ala
    370                 375                 380

Gln Leu Ser Leu Ser Asp Arg Asn Gln Asp Ile Ile Asn Lys Pro Glu
385                 390                 395                 400

Glu Ile Ile Asn Leu Leu Asn Gly Asn Asn Val Ser Leu Met Arg Ser
                405                 410                 415

Asn Ile Tyr Gly Asp Gly Leu Lys Ser Thr Val Asp Asp Phe Tyr Ser
            420                 425                 430

Asn Tyr Lys Ile Pro Tyr Asn Arg Ala Tyr Glu Tyr His Phe Asn Asn
        435                 440                 445

Ser Asn Asp Ser Ser Leu Asp Asn Val Asn Ile Gly Val Ile Asp Asn
    450                 455                 460

Ile Pro Glu Ile Ile Asp Val Asn Pro Tyr Lys Glu Asn Cys Asp Lys
465                 470                 475                 480

Phe Ser Pro Val Gln Lys Ile Thr Ser Thr Arg Glu Ile Asn Thr Asn
                485                 490                 495

Ile Pro Trp Pro Ile Asn Tyr Leu Gln Ala Gln Asn Thr Asn Asn Glu
            500                 505                 510

Lys Phe Ser Leu Ser Ser Asp Phe Val Glu Val Ser Ser Lys Asp
        515                 520                 525

Lys Ser Leu Val Tyr Ser Phe Leu Ser Asn Val Met Phe Tyr Leu Asp
    530                 535                 540

Ser Ile Lys Asp Asn Ser Pro Ile Asp Thr Asp Lys Lys Tyr Tyr Leu
545                 550                 555                 560

Trp Leu Arg Glu Ile Phe Arg Asn Tyr Ser Phe Asp Ile Thr Ala Thr
                565                 570                 575

Gln Glu Ile Asn Thr Asp Cys Gly Ile Asn Lys Val Val Thr Trp Phe
            580                 585                 590

Gly Lys Ala Leu Asn Ile Leu Asn Thr Ser Asp Ser Phe Val Glu Glu
        595                 600                 605

Phe Gln Asn Leu Gly Pro Ile Ser Leu Ile Asn Lys Lys Glu Asn Leu
    610                 615                 620
```

-continued

```
Ser Met Pro Lys Ile Glu Ile Asp Glu Ile Pro Asn Ser Met Leu Asn
625                 630                 635                 640

Leu Ser Phe Lys Asp Leu Ser Glu Asn Leu Phe Asn Ile Phe Ser Lys
                645                 650                 655

Asn Asn Ser Tyr Phe Glu Lys Ile Tyr Tyr Asp Phe Leu Asp Gln Trp
            660                 665                 670

Trp Thr Gln Tyr Tyr Ser Gln Tyr Phe Asp Leu Ile Cys Met Ala Lys
        675                 680                 685

Arg Ser Val Leu Ala Gln Ser Leu Ile Lys Lys Ile Ile Gln Lys
690                 695                 700

Lys Leu Ser Tyr Leu Ile Gly Asn Ser Asn Ile Ser Ser Asp Asn Leu
705                 710                 715                 720

Ala Leu Met Asn Leu Thr Thr Asn Thr Leu Arg Asp Ile Ser Asn
                725                 730                 735

Glu Ser Gln Ile Ala Met Asn Asn Val Asn Asn Phe Leu Asn Asn Val
            740                 745                 750

Ala Ile Cys Val Phe Gln Thr Asn Ile Tyr Pro Lys Phe Ile Ser Phe
        755                 760                 765

Met Glu Gln Cys Ile Asn Asn Ile Asn Lys Asn Thr Arg Glu Phe Ile
770                 775                 780

Gln Lys Cys Thr Asn Ile Thr Glu Asn Glu Lys Leu Gln Leu Ile Asn
785                 790                 795                 800

Gln Asn Ile Phe Ser Ser Leu Asp Phe Asp Phe Leu Asn Ile Glu Asn
                805                 810                 815

Leu Lys Ser Leu Phe Asn Ser Glu Thr Gly Leu Leu Ile Lys Glu Glu
            820                 825                 830

Thr Ser Pro Tyr Glu Leu Val Leu Tyr Ala Phe Gln Glu Pro Gly Asn
        835                 840                 845

Asn Ala Ile Gly Asp Ala Ser Gly Lys Asn Thr Ser Ile Glu Tyr Ser
850                 855                 860

Lys Asp Ile Gly Leu Val Tyr Gly Ile Asn Ser Asp Ala Leu Tyr Leu
865                 870                 875                 880

Asn Gly Ser Asn Gln Ser Ile Ser Phe Ser Asn Asp Phe Phe Glu Asn
                885                 890                 895

Gly Leu Thr Asn Ser Phe Ser Ile Tyr Phe Trp Leu Arg Asn Leu Gly
            900                 905                 910

Lys Asp Thr Ile Lys Ser Lys Leu Ile Gly Ser Lys Glu Asp Asn Cys
        915                 920                 925

Gly Trp Glu Ile Tyr Phe Gln Asp Thr Gly Leu Val Phe Asn Met Ile
930                 935                 940

Asp Ser Asn Gly Asn Glu Lys Asn Ile Tyr Leu Ser Asp Val Ser Asn
945                 950                 955                 960

Asn Ser Trp His Tyr Ile Thr Ile Ser Val Asp Arg Leu Lys Glu Gln
                965                 970                 975

Leu Leu Ile Phe Ile Asp Asp Asn Leu Val Ala Asn Glu Ser Ile Lys
            980                 985                 990

Glu Ile Leu Asn Ile Tyr Ser Ser Asn Thr Ile Ser Leu Val Asn Glu
        995                 1000                1005

Asn Asn Pro Ile Tyr Val Glu Gly Leu Ser Ile Leu Asn Arg Ser Ile
1010                1015                1020

Thr Ser Glu Glu Val Val Asn Asn Tyr Phe Thr Tyr Leu Asn Asn Ser
1025                1030                1035                1040

Tyr Ile Arg Asp Ile Ser Gly Glu Arg Leu Glu Tyr Asn Lys Thr Tyr
```

```
                    1045                1050                1055
Glu Leu Tyr Asn Tyr Val Phe Pro Glu Ser Ser Leu Tyr Glu Val Thr
                1060                1065                1070

Glu Asn Asn Asn Ile Tyr Leu Ser Ile Lys Asn Thr Asn Asn Leu Asn
            1075                1080                1085

Ile Gln Gly Ala Lys Phe Lys Leu Ile Asn Ile Asp Ala Asn Lys Gln
        1090                1095                1100

Tyr Val Gln Lys Trp Asp Glu Gly Val Val Cys Leu Leu Gly Asp Glu
1105                1110                1115                1120

Glu Lys Tyr Val Asp Ile Ser Ser Glu Asn Asn Arg Ile Gln Leu Val
            1125                1130                1135

Ser Ser Lys Asp Thr Ala Lys Arg Ile Ile Phe Asn Asn Asp Ile Phe
        1140                1145                1150

Arg Pro Asn Cys Leu Thr Phe Ala Tyr Asn Asn Lys Tyr Leu Ser Leu
        1155                1160                1165

Ser Leu Arg Asp Arg Asn Tyr Asn Trp Met Ile Cys Asn Asn Asn Asp
        1170                1175                1180

Asn Ile Pro Lys Ala Ala His Leu Trp Ala Leu Lys Gly Ile
1185                1190                1195

<210> SEQ ID NO 27
<211> LENGTH: 1193
<212> TYPE: PRT
<213> ORGANISM: Clostridium botulinum serotype A

<400> SEQUENCE: 27

Met Asp Ile Asn Asp Asp Leu Asn Ile Asn Ser Pro Val Asp Asn Lys
 1               5                  10                  15

Asn Val Val Ile Val Arg Ala Arg Lys Thr Asn Thr Phe Phe Lys Ala
                20                  25                  30

Phe Lys Val Ala Pro Asn Ile Trp Val Ala Pro Glu Arg Tyr Tyr Gly
            35                  40                  45

Glu Pro Leu His Ile Ala Glu Glu Tyr Lys Leu Asp Gly Gly Ile Tyr
        50                  55                  60

Asp Ser Asn Phe Leu Ser Gln Asp Ser Glu Arg Glu Asn Phe Leu Gln
 65                  70                  75                  80

Ala Ile Ile Ile Leu Leu Lys Arg Ile Asn Asn Thr Ile Ser Gly Lys
                85                  90                  95

Gln Leu Leu Ser Leu Ile Ser Thr Ala Ile Pro Phe Pro Tyr Gly Tyr
            100                 105                 110

Ile Gly Gly Gly Tyr Ser Ser Pro Asn Ile Phe Thr Phe Gly Lys Thr
        115                 120                 125

Pro Arg Thr Asn Lys Lys Leu Asn Ser Leu Val Thr Ser Thr Ile Pro
130                 135                 140

Phe Pro Phe Gly Gly Tyr Arg Glu Thr Asn Tyr Ile Glu Ser Gln Asn
145                 150                 155                 160

Asn Lys Asn Phe Tyr Ala Ser Asn Ile Ile Phe Gly Pro Gly Ser
                165                 170                 175

Asn Ile Val Glu Asn Asn Val Ile Tyr Tyr Lys Lys Asn Asp Ala Glu
            180                 185                 190

Asn Gly Met Gly Thr Met Ala Glu Ile Val Phe Gln Pro Leu Leu Thr
        195                 200                 205

Tyr Lys Tyr Asn Lys Phe Tyr Ile Asp Pro Ala Met Glu Leu Thr Lys
    210                 215                 220
```

-continued

```
Cys Leu Ile Lys Ser Leu Tyr Phe Leu Tyr Gly Ile Lys Pro Ser Gly
225                 230                 235                 240

Asn Leu Val Val Pro Tyr Arg Leu Arg Thr Glu Leu Asp Asn Lys Gln
            245                 250                 255

Phe Ser Gln Leu Asn Ile Ile Asp Leu Leu Ile Ser Gly Gly Val Asp
        260                 265                 270

Leu Glu Phe Ile Asn Thr Asn Pro Tyr Trp Phe Thr Asn Ser Tyr Phe
    275                 280                 285

Pro Asn Ser Ile Lys Met Phe Glu Lys Tyr Lys Asn Ile Tyr Lys Thr
290                 295                 300

Glu Ile Glu Gly Asn Asn Ala Ile Gly Asn Asp Ile Lys Leu Arg Leu
305                 310                 315                 320

Lys Gln Lys Phe Gln Ile Asn Val Gln Asp Ile Trp Asn Leu Asn Leu
            325                 330                 335

Asn Tyr Phe Cys Gln Ser Phe Asn Ser Ile Ile Pro Asp Arg Phe Ser
        340                 345                 350

Asn Ala Leu Lys His Phe Tyr Arg Lys Gln Tyr Tyr Thr Met Asp Tyr
    355                 360                 365

Thr Asp Asn Tyr Asn Ile Asn Gly Phe Val Asn Gly Gln Ile Asn Thr
370                 375                 380

Lys Leu Pro Leu Ser Asn Lys Asn Thr Asn Ile Ile Ser Lys Pro Glu
385                 390                 395                 400

Lys Val Val Asn Leu Val Asn Glu Asn Asn Ile Ser Leu Met Lys Ser
            405                 410                 415

Asn Ile Tyr Gly Asp Gly Leu Lys Gly Thr Thr Glu Asp Phe Tyr Ser
        420                 425                 430

Thr Tyr Lys Ile Pro Tyr Asp Glu Glu Tyr Glu Tyr Arg Phe Asn Asp
    435                 440                 445

Ser Asp Asn Phe Pro Leu Asn Asn Ile Ser Ile Glu Glu Val Asp Ser
450                 455                 460

Ile Pro Glu Ile Ile Asp Ile Asn Pro Tyr Lys Asp Asn Ser Asp Asn
465                 470                 475                 480

Leu Val Phe Thr Gln Ile Thr Ser Met Thr Glu Glu Val Thr Thr His
            485                 490                 495

Thr Ala Leu Ser Ile Asn Tyr Leu Gln Ala Gln Ile Thr Asn Asn Glu
        500                 505                 510

Asn Phe Thr Leu Ser Ser Asp Phe Ser Lys Val Val Ser Ser Lys Asp
    515                 520                 525

Lys Ser Leu Val Tyr Ser Phe Leu Asp Asn Leu Met Ser Tyr Leu Glu
530                 535                 540

Thr Ile Lys Asn Asp Arg Pro Ile His Thr Asp Lys Tyr Tyr Leu
545                 550                 555                 560

Trp Leu Lys Glu Val Phe Lys Asn Tyr Ser Phe Asp Ile Asn Leu Thr
            565                 570                 575

Gln Glu Ile Asp Ser Met Cys Gly Ile Asn Gln Val Val Leu Trp Phe
        580                 585                 590

Gly Lys Ala Leu Asn Ile Leu Asn Thr Ser Asn Ser Phe Val Glu Glu
    595                 600                 605

Tyr Gln Asp Ser Gly Ala Ile Ser Leu Ile Ser Lys Lys Asp Asn Leu
610                 615                 620

Arg Glu Pro Asn Ile Glu Ile Asp Asp Ile Ser Asp Ser Leu Leu Gly
625                 630                 635                 640

Leu Ser Phe Lys Asp Leu Asn Asn Lys Leu Tyr Glu Ile Tyr Ser Lys
```

-continued

```
                    645                 650                 655
Asn Ile Val Tyr Phe Lys Lys Ile Tyr Phe Ser Phe Leu Asp Gln Trp
                660                 665                 670
Trp Thr Gln Tyr Tyr Ser Gln Tyr Phe Asp Leu Ile Cys Met Ala Lys
                675                 680                 685
Lys Ser Ile Leu Ala Gln Glu Thr Leu Ile Lys Ile Ile Gln Lys
            690                 695                 700
Lys Leu Ser Tyr Leu Ile Gly Asn Ser Asn Ile Ser Ser Asp Asn Leu
705                 710                 715                 720
Ala Leu Met Asn Leu Thr Thr Thr Asn Thr Leu Arg Asp Ile Ser Asn
                725                 730                 735
Glu Ser Gln Ile Ala Met Asn Asn Val Asp Ser Phe Leu Asn Ser Ala
                740                 745                 750
Ala Ile Cys Val Phe Glu Gly Asn Ile Tyr Pro Lys Phe Ile Ser Phe
                755                 760                 765
Met Glu Gln Cys Ile Asn Ile Asn Lys Asn Thr Arg Glu Phe Ile
            770                 775                 780
Gln Lys Cys Thr Asn Ile Thr Glu Asn Glu Lys Leu Gln Leu Ile Asn
785                 790                 795                 800
Gln Asn Ile Phe Ser Ser Leu Asp Phe Asp Phe Leu Asn Ile Glu Asn
                805                 810                 815
Leu Lys Ser Leu Phe Ser Ser Glu Thr Ala Leu Leu Ile Lys Glu Glu
                820                 825                 830
Thr Ser Pro Tyr Glu Leu Val Leu Tyr Ala Phe Gln Glu Pro Asp Asn
                835                 840                 845
Asn Ala Ile Gly Asp Ala Ser Ala Lys Asn Thr Ser Ile Glu Tyr Ser
850                 855                 860
Lys Asp Ile Asp Leu Val Tyr Gly Ile Asn Ser Asp Ala Leu Tyr Leu
865                 870                 875                 880
Asn Gly Ser Asn Gln Ser Ile Ser Phe Ser Asn Asp Phe Phe Glu Asn
                885                 890                 895
Gly Leu Thr Asn Ser Phe Ser Ile Tyr Phe Trp Leu Arg Asn Leu Gly
                900                 905                 910
Lys Asp Thr Ile Lys Ser Lys Leu Ile Gly Ser Lys Gly Asp Asn Cys
            915                 920                 925
Gly Trp Glu Ile Tyr Phe Gln Asp Thr Gly Leu Val Phe Asn Met Ile
            930                 935                 940
Asp Ser Asn Gly Asn Glu Lys Asn Ile Tyr Leu Ser Asp Val Ser Asn
945                 950                 955                 960
Asn Ser Trp His Tyr Ile Thr Ile Ser Val Asp Arg Leu Lys Glu Gln
                965                 970                 975
Leu Leu Ile Phe Ile Asp Asp Asn Leu Val Ala Asn Glu Ser Ile Lys
            980                 985                 990
Glu Ile Leu Asn Ile Tyr Ser Ser Asn Ile Ser Leu Leu Ser Glu
            995                 1000                1005
Asn Asn Pro Ser Tyr Ile Glu Gly Leu Thr Ile Leu Asn Lys Pro Thr
        1010                1015                1020
Thr Ser Gln Glu Val Leu Asn Asn Tyr Phe Lys Val Leu Asn Asn Ser
1025                1030                1035                1040
Tyr Ile Arg Asp Ser Asn Glu Glu Arg Leu Glu Tyr Asn Lys Thr Tyr
                1045                1050                1055
Gln Leu Tyr Asn Tyr Val Phe Ser Asp Lys Pro Ile Cys Glu Val Lys
                1060                1065                1070
```

```
Gln Asn Asn Asn Ile Tyr Leu Thr Ile Asn Asn Thr Asn Asn Leu Asn
        1075                1080                1085

Leu Gln Pro Ser Lys Phe Lys Leu Leu Ser Ile Asn Pro Asn Lys Gln
    1090                1095                1100

Tyr Val Gln Lys Leu Asp Glu Val Ile Ile Ser Val Leu Gly Asn Met
1105                1110                1115                1120

Glu Lys Tyr Ile Asp Ile Ser Glu Asp Asn Arg Leu Gln Leu Ile Asp
                1125                1130                1135

Asn Lys Asn Gly Ala Lys Lys Met Ile Ile Ser Asn Asp Met Phe Ile
            1140                1145                1150

Ser Asn Cys Leu Thr Leu Ser Cys Gly Gly Lys Tyr Ile Cys Leu Ser
        1155                1160                1165

Met Lys Asp Glu Asn His Asn Trp Met Ile Cys Asn Asn Asp Met Ser
    1170                1175                1180

Lys Tyr Leu Tyr Leu Trp Ser Phe Lys
1185                1190
```

<210> SEQ ID NO 28
<211> LENGTH: 1197
<212> TYPE: PRT
<213> ORGANISM: Clostridium botulinum serotype B

<400> SEQUENCE: 28

```
Met Asn Ile Asn Asp Asn Leu Ser Ile Asn Ser Pro Val Asp Asn Lys
1               5                   10                  15

Asn Val Val Val Arg Ala Arg Lys Thr Asp Thr Val Phe Lys Ala
                20                  25                  30

Phe Lys Val Ala Pro Asn Ile Trp Val Ala Pro Glu Arg Tyr Tyr Gly
            35                  40                  45

Glu Ser Leu Ser Ile Asp Glu Glu Tyr Lys Val Asp Gly Gly Ile Tyr
        50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

Pro Lys Ser Asn Lys Lys Leu Asn Ser Leu Ile Ser Ser Thr Ile Pro
130                 135                 140

Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Thr Glu Ile Trp Phe Gln Pro Phe Leu Thr
        195                 200                 205

Tyr Lys Tyr Asp Glu Phe Tyr Ile Asp Pro Ala Ile Glu Leu Ile Lys
    210                 215                 220

Cys Leu Ile Lys Ser Leu Tyr Phe Leu Tyr Gly Ile Lys Pro Ser Asp
225                 230                 235                 240

Asp Leu Val Ile Pro Tyr Arg Leu Arg Ser Glu Leu Glu Asn Ile Glu
```

-continued

```
                245                 250                 255
Tyr Ser Gln Leu Asn Ile Val Asp Leu Leu Val Ser Gly Gly Ile Asp
                260                 265                 270
Pro Lys Phe Ile Asn Thr Asp Pro Tyr Trp Phe Thr Asp Asn Tyr Phe
                275                 280                 285
Ser Asn Ala Lys Lys Val Phe Glu Asp His Arg Asn Ile Tyr Glu Thr
                290                 295                 300
Gln Ile Glu Gly Asn Asn Ala Ile Gly Asn Asp Ile Lys Leu Arg Leu
305                 310                 315                 320
Lys Gln Lys Phe Arg Ile Asn Ile Asn Asp Ile Trp Glu Leu Asn Leu
                325                 330                 335
Asn Tyr Phe Ser Lys Glu Phe Ser Ile Met Met Pro Asp Arg Phe Asn
                340                 345                 350
Asn Ala Leu Lys His Phe Tyr Arg Lys Gln Tyr Tyr Lys Ile Asp Tyr
                355                 360                 365
Pro Glu Asn Tyr Ser Ile Asn Gly Phe Val Asn Gly Gln Ile Asn Val
                370                 375                 380
Gln Leu Ser Leu Ser Asp Arg Asn Gln Asp Ile Ile Asn Lys Pro Glu
385                 390                 395                 400
Glu Ile Ile Asn Leu Leu Asn Gly Asn Asn Val Ser Leu Met Arg Ser
                405                 410                 415
Asn Ile Tyr Gly Asp Gly Leu Lys Ser Thr Val Asp Asp Phe Tyr Ser
                420                 425                 430
Asn Tyr Lys Ile Pro Tyr Asn Arg Ala Tyr Glu Tyr His Phe Asn Asn
                435                 440                 445
Ser Asn Asp Ser Ser Leu Asp Asn Val Asn Ile Gly Val Ile Asp Asn
                450                 455                 460
Ile Pro Glu Ile Ile Asp Val Asn Pro Tyr Lys Glu Asn Cys Asp Lys
465                 470                 475                 480
Phe Ser Pro Val Gln Lys Ile Thr Ser Thr Arg Glu Ile Asn Thr Asn
                485                 490                 495
Ile Pro Trp Pro Ile Asn Tyr Leu Gln Ala Gln Asn Thr Asn Asn Glu
                500                 505                 510
Lys Phe Ser Leu Ser Ser Asp Phe Val Glu Val Ser Ser Lys Asp
                515                 520                 525
Lys Ser Leu Val Tyr Ser Phe Leu Ser Asn Val Met Phe Tyr Leu Asp
530                 535                 540
Ser Ile Lys Asp Asn Ser Pro Ile Asp Thr Asp Lys Lys Tyr Tyr Leu
545                 550                 555                 560
Trp Leu Arg Glu Ile Phe Arg Asn Tyr Ser Phe Asp Ile Thr Ala Thr
                565                 570                 575
Gln Glu Ile Asn Thr Asp Cys Gly Ile Asn Lys Val Val Thr Trp Phe
                580                 585                 590
Gly Lys Ala Leu Asn Ile Leu Asn Thr Ser Asp Ser Phe Val Glu Glu
                595                 600                 605
Phe Gln Asn Leu Gly Pro Ile Ser Leu Ile Asn Lys Lys Glu Asn Leu
                610                 615                 620
Ser Met Pro Ile Ile Glu Ile Tyr Gly Ile Pro Asn Asp Met Leu Gly
625                 630                 635                 640
Leu Pro Leu Asn Asp Leu Asn Glu Lys Leu Phe Asn Ile Tyr Leu Lys
                645                 650                 655
Asn Ile Leu Tyr Phe Lys Lys Val Tyr Phe Asn Phe Leu Asp Gln Trp
                660                 665                 670
```

```
Trp Thr Glu Tyr Tyr Ser Gln Tyr Phe Asp Leu Ile Cys Met Ala Lys
            675                 680                 685

Gln Ser Ile Leu Ala Gln Glu Lys Leu Ile Lys Gln Ile Ile Gln Asn
        690                 695                 700

Lys Leu Gln Asp Leu Phe Lys Ala Asp Ile Ser Met Asp Lys Leu Asn
705                 710                 715                 720

Leu Met Asn Leu Ala Thr Glu Lys Thr Phe Ile Asp Leu Ser Asn Glu
                725                 730                 735

Ser Gln Ile Ala Ile Asn Asn Ile Asn Asp Phe Leu Asn Lys Ser Ala
            740                 745                 750

Ile Cys Val Phe Asp Thr Asn Ile Tyr Pro Lys Phe Ile Ser Phe Met
        755                 760                 765

Glu Gln Cys Ile Asn Ser Val Asn Ser Asn Val Thr Ala Phe Ile Gln
        770                 775                 780

Lys Cys Thr Asn Ile Thr Glu Asp Glu Lys Leu Gln Leu Ile Lys Leu
785                 790                 795                 800

Asn Thr Phe Met Asn Ile Asp Phe Glu Phe Phe Asp Ile Gln Ser Ile
                805                 810                 815

Lys Asp Leu Ile Thr Ser Glu Thr Asp Leu Ile Lys Glu Glu Lys Glu
            820                 825                 830

Ser Asp Tyr Asn Leu Phe Leu Phe Thr Leu Gln Glu Asp Asn Asn Lys
        835                 840                 845

Val Ile Glu Asp Ile Ser Gly Lys Asn Thr Leu Val Lys Tyr Ser Asp
850                 855                 860

Ser Ile Ser Leu Val Tyr Gly Val Asn Gly Asp Ala Leu Tyr Leu Lys
865                 870                 875                 880

Glu Pro Asp Glu Ser Val Ser Phe Ser Asn Lys Ala Phe Glu Asn Gly
                885                 890                 895

Leu Thr Asn Ser Phe Ser Ile Cys Phe Trp Leu Arg Asn Leu Gly Glu
            900                 905                 910

Asp Ile Ile Thr Ser Lys Leu Ile Glu Asn Lys Ala Asp Asn Cys Gly
        915                 920                 925

Trp Glu Ile Tyr Phe Glu Asn Asn Gly Leu Val Phe Ser Ile Val Asp
        930                 935                 940

Cys Asn Gly Asn Glu Glu Asn Ile Tyr Leu Ser Asp Val Ile Ser Lys
945                 950                 955                 960

Asn Trp Tyr Tyr Ile Ser Ile Ser Ile Asp Arg Leu Arg Asn Gln Leu
                965                 970                 975

Leu Ile Phe Ile Asn Asp Lys Leu Ile Ala Asn Gln Ser Ile Glu Gln
            980                 985                 990

Ile Leu Asn Ile Tyr Ser Ser Asn Thr Ile Ser Leu Val Asn Glu Asn
        995                 1000                1005

Asn Pro Ile Tyr Ile Glu Gly Leu Ser Ile Leu Asn Arg Ser Ile Thr
        1010                1015                1020

Ser Glu Glu Val Val Asn Asn Tyr Phe Ser Tyr Leu Asn Asn Ser Tyr
1025                1030                1035                1040

Ile Arg Asp Ile Ser Gly Glu Arg Leu Glu Tyr Asn Lys Thr Tyr Glu
                1045                1050                1055

Leu Tyr Asn Tyr Val Phe Pro Glu Asn Ser Leu Tyr Glu Val Thr Glu
            1060                1065                1070

Asn Asn Asn Ile Tyr Leu Ser Ile Lys Asp Thr Asn Asn Leu Asn Ile
        1075                1080                1085
```

```
Gln Gly Ala Lys Phe Lys Leu Ile Asn Ile Asp Ala Asn Lys Gln Tyr
    1090                1095                1100

Val Gln Lys Trp Asp Glu Gly Val Val Cys Leu Leu Gly Asp Glu Glu
1105                1110                1115                1120

Lys Tyr Val Asp Ile Ser Ser Glu Asn Asn Arg Ile Gln Leu Val Asn
                1125                1130                1135

Ser Lys Asp Thr Ala Lys Arg Ile Ile Phe Asn Asn Asp Ile Phe Met
            1140                1145                1150

Pro Asn Cys Leu Thr Phe Ala Tyr Asn Asn Lys Tyr Leu Ser Leu Ser
            1155                1160                1165

Leu Arg Asp Arg Asn Tyr Asn Trp Met Ile Cys Asn Asn Asp Asn
        1170                1175                1180

Ile Pro Lys Ala Ala His Leu Trp Ala Leu Lys Gly Ile
1185                1190                1195

<210> SEQ ID NO 29
<211> LENGTH: 1196
<212> TYPE: PRT
<213> ORGANISM: Clostridium botulinum serotype C1

<400> SEQUENCE: 29

Met Asp Ile Asn Asp Asp Leu Asn Ile Asn Ser Pro Val Asp Asn Lys
1               5                   10                  15

Asn Val Val Ile Val Arg Ala Arg Lys Thr Asn Thr Phe Phe Lys Ala
                20                  25                  30

Phe Lys Val Ala Pro Asn Ile Trp Val Ala Pro Glu Arg Tyr Tyr Gly
            35                  40                  45

Glu Pro Leu Asp Ile Ala Glu Glu Tyr Lys Leu Asp Gly Gly Ile Tyr
50                  55                  60

Asp Ser Asn Phe Leu Ser Gln Asp Ser Glu Arg Glu Asn Phe Leu Gln
65                  70                  75                  80

Ala Ile Ile Ile Leu Leu Lys Arg Ile Asn Asn Thr Ile Ser Gly Lys
                85                  90                  95

Gln Leu Leu Ser Leu Ile Ser Thr Ala Ile Pro Phe Pro Tyr Gly Tyr
                100                 105                 110

Ile Gly Gly Gly Tyr Ser Ser Pro Asn Ile Phe Thr Phe Gly Lys Thr
            115                 120                 125

Pro Lys Ser Asn Lys Lys Leu Asn Ser Leu Val Thr Ser Thr Ile Pro
130                 135                 140

Phe Pro Phe Gly Gly Tyr Arg Glu Thr Asn Tyr Ile Glu Ser Gln Asn
145                 150                 155                 160

Asn Lys Asn Phe Tyr Ala Ser Asn Ile Ile Phe Gly Pro Gly Ser
                165                 170                 175

Asn Ile Val Glu Asn Asn Val Ile Tyr Tyr Lys Lys Asn Asp Ala Glu
            180                 185                 190

Asn Gly Met Gly Thr Met Ala Glu Ile Val Phe Gln Pro Leu Leu Thr
            195                 200                 205

Tyr Lys Tyr Asn Lys Phe Tyr Ile Asp Pro Ala Met Glu Leu Thr Lys
210                 215                 220

Cys Leu Ile Lys Ser Leu Tyr Phe Leu Tyr Gly Ile Lys Pro Ser Asp
225                 230                 235                 240

Asn Leu Val Val Pro Tyr Arg Leu Arg Thr Glu Leu Asp Asn Lys Gln
                245                 250                 255

Phe Ser Gln Leu Asn Ile Ile Asp Leu Leu Ile Ser Gly Gly Val Asp
                260                 265                 270
```

-continued

```
Leu Glu Phe Ile Asn Thr Asn Pro Tyr Trp Phe Thr Asn Ser Tyr Phe
            275                 280                 285

Pro Asn Ser Ile Lys Met Phe Glu Lys Tyr Lys Asn Ile Tyr Lys Thr
        290                 295                 300

Glu Ile Glu Gly Asn Asn Ala Ile Gly Asn Asp Ile Lys Leu Arg Leu
305                 310                 315                 320

Lys Gln Lys Phe Gln Ile Asn Val Gln Asp Ile Trp Asn Leu Asn Leu
                325                 330                 335

Asn Tyr Phe Cys Gln Ser Phe Asn Ser Ile Ile Pro Asp Arg Phe Ser
            340                 345                 350

Asn Ala Leu Lys His Phe Tyr Arg Lys Gln Tyr Tyr Thr Met Asp Tyr
        355                 360                 365

Thr Asp Asn Tyr Asn Ile Asn Gly Phe Val Asn Gly Gln Ile Asn Thr
370                 375                 380

Lys Leu Pro Leu Ser Asn Lys Asn Thr Asn Ile Ile Ser Lys Pro Glu
385                 390                 395                 400

Lys Val Val Asn Leu Val Asn Glu Asn Asn Ile Ser Leu Met Lys Ser
                405                 410                 415

Asn Ile Tyr Gly Asp Gly Leu Lys Gly Thr Thr Glu Asp Phe Tyr Ser
            420                 425                 430

Thr Tyr Lys Ile Pro Tyr Asn Glu Glu Tyr Glu Tyr Arg Phe Asn Asp
        435                 440                 445

Ser Asp Asn Phe Pro Leu Asn Asn Ile Ser Ile Glu Glu Val Asp Ser
450                 455                 460

Ile Pro Glu Ile Ile Asp Ile Asn Pro Tyr Lys Asp Asn Ser Asp Asn
465                 470                 475                 480

Leu Val Phe Thr Gln Ile Thr Ser Met Thr Glu Val Thr Thr His
                485                 490                 495

Thr Ala Leu Ser Ile Asn Tyr Leu Gln Ala Gln Ile Thr Asn Asn Glu
            500                 505                 510

Asn Phe Thr Leu Ser Ser Asp Phe Ser Lys Val Val Ser Ser Lys Asp
        515                 520                 525

Lys Ser Leu Val Tyr Ser Phe Leu Asp Asn Leu Met Ser Tyr Leu Glu
530                 535                 540

Thr Ile Lys Asn Asp Gly Pro Ile Asp Thr Asp Lys Lys Tyr Tyr Leu
545                 550                 555                 560

Trp Leu Lys Glu Val Phe Lys Asn Tyr Ser Phe Asp Ile Asn Leu Thr
                565                 570                 575

Gln Glu Ile Asp Ser Met Cys Gly Ile Asn Glu Val Val Leu Trp Phe
            580                 585                 590

Gly Lys Ala Leu Asn Ile Leu Asn Thr Ser Asn Ser Phe Val Glu Glu
        595                 600                 605

Tyr Gln Asp Ser Gly Ala Ile Ser Leu Ile Ser Lys Lys Asp Asn Leu
610                 615                 620

Arg Glu Pro Asn Ile Glu Ile Asp Asp Ile Ser Asp Ser Leu Leu Gly
625                 630                 635                 640

Leu Ser Phe Lys Asp Leu Asn Asn Lys Leu Tyr Glu Ile Tyr Ser Lys
                645                 650                 655

Asn Ile Val Tyr Phe Lys Lys Ile Tyr Phe Ser Phe Leu Asp Gln Trp
            660                 665                 670

Trp Thr Glu Tyr Tyr Ser Gln Tyr Phe Glu Leu Ile Cys Met Ala Lys
        675                 680                 685
```

-continued

```
Gln Ser Ile Leu Ala Gln Glu Ser Leu Val Lys Gln Ile Val Gln Asn
    690                 695                 700
Lys Phe Thr Asp Leu Ser Lys Ala Ser Ile Pro Pro Asp Thr Leu Lys
705                 710                 715                 720
Leu Ile Arg Glu Thr Thr Glu Lys Thr Phe Ile Asp Leu Ser Asn Glu
                725                 730                 735
Ser Gln Ile Ser Met Asn Arg Val Asp Asn Phe Leu Asn Lys Ala Ser
                740                 745                 750
Ile Cys Val Phe Val Glu Asp Ile Tyr Pro Lys Phe Ile Ser Tyr Met
                755                 760                 765
Glu Lys Tyr Ile Asn Asn Ile Asn Lys Thr Arg Glu Phe Ile Gln
770                 775                 780
Arg Cys Thr Asn Ile Asn Asp Asn Glu Lys Ser Ile Leu Ile Asn Ser
785                 790                 795                 800
Tyr Thr Phe Lys Thr Ile Asp Phe Lys Phe Leu Asp Ile Gln Ser Ile
                805                 810                 815
Lys Asn Phe Phe Asn Ser Gln Val Glu Gln Val Met Lys Glu Ile Leu
                820                 825                 830
Ser Pro Tyr Gln Leu Leu Leu Phe Ala Ser Lys Gly Pro Asn Ser Asn
                835                 840                 845
Ile Ile Glu Asp Ile Ser Gly Lys Asn Thr Leu Ile Gln Tyr Thr Glu
                850                 855                 860
Ser Ile Glu Leu Val Tyr Gly Val Asn Gly Glu Ser Leu Tyr Leu Lys
865                 870                 875                 880
Ser Pro Asn Glu Thr Ile Lys Phe Ser Asn Lys Phe Phe Thr Asn Gly
                885                 890                 895
Leu Thr Asn Asn Phe Thr Ile Cys Phe Trp Leu Arg Phe Thr Gly Lys
                900                 905                 910
Asn Asp Asp Lys Thr Arg Leu Ile Gly Asn Lys Val Asn Asn Cys Gly
                915                 920                 925
Trp Glu Ile Tyr Phe Glu Asp Asn Gly Leu Val Phe Glu Ile Ile Asp
                930                 935                 940
Ser Asn Gly Asn Gln Glu Ser Val Tyr Leu Ser Asn Ile Ile Asn Asp
945                 950                 955                 960
Asn Trp Tyr Tyr Ile Ser Ile Ser Val Asp Arg Leu Lys Asp Gln Leu
                965                 970                 975
Leu Ile Phe Ile Asn Asp Lys Asn Val Ala Asn Val Ser Ile Asp Gln
                980                 985                 990
Ile Leu Ser Ile Tyr Ser Thr Asn Ile Ile Ser Leu Val Asn Lys Asn
        995                 1000                1005
Asn Ser Ile Tyr Val Glu Leu Ser Val Leu Asp Asn Pro Ile Thr
        1010                1015                1020
Ser Glu Glu Val Ile Arg Asn Tyr Phe Ser Tyr Leu Asp Asn Ser Tyr
1025                1030                1035                1040
Ile Arg Asp Ser Ser Lys Ser Leu Leu Glu Tyr Asn Lys Asn Tyr Gln
        1045                1050                1055
Leu Tyr Asn Tyr Val Phe Pro Glu Thr Ser Leu Tyr Glu Val Asn Asp
        1060                1065                1070
Asn Asn Lys Ser Tyr Leu Ser Leu Lys Asn Thr Asp Gly Ile Asn Ile
        1075                1080                1085
Ser Ser Val Lys Phe Lys Leu Ile Asn Ile Asp Glu Ser Lys Val Tyr
        1090                1095                1100
Val Gln Lys Trp Asp Glu Cys Ile Ile Cys Val Leu Asp Gly Thr Glu
```

```
1105                1110               1115               1120
Lys Tyr Leu Asp Ile Ser Pro Glu Asn Asn Arg Ile Gln Leu Val Ser
                    1125                1130                1135

Ser Lys Asp Asn Ala Lys Lys Ile Thr Val Asn Thr Asp Leu Phe Arg
                    1140                1145                1150

Pro Asp Cys Ile Thr Phe Ser Tyr Asn Asp Lys Tyr Phe Ser Leu Ser
        1155                1160                1165

Leu Arg Asp Gly Asp Tyr Asn Trp Met Ile Cys Asn Asp Asn Asn Lys
    1170                1175                1180

Val Pro Lys Gly Ala His Leu Trp Ile Leu Glu Ser
1185                1190                1195

<210> SEQ ID NO 30
<211> LENGTH: 1196
<212> TYPE: PRT
<213> ORGANISM: Clostridium botulinum serotype D

<400> SEQUENCE: 30

Met Asp Ile Asn Asp Asp Leu Asn Ile Asn Ser Pro Val Asp Asn Lys
 1               5                  10                  15

Asn Val Val Ile Val Arg Ala Arg Lys Thr Asn Thr Phe Phe Lys Ala
                20                  25                  30

Phe Lys Val Ala Pro Asn Ile Trp Val Ala Pro Glu Arg Tyr Tyr Gly
            35                  40                  45

Glu Pro Leu Asp Ile Ala Glu Glu Tyr Lys Leu Asp Gly Gly Ile Tyr
        50                  55                  60

Asp Ser Asn Phe Leu Ser Gln Asp Ser Glu Arg Glu Asn Phe Leu Gln
65                  70                  75                  80

Ala Ile Ile Thr Leu Leu Lys Arg Ile Asn Asn Thr Ile Ser Gly Lys
                85                  90                  95

Gln Leu Leu Ser Leu Ile Ser Thr Ala Ile Pro Phe Pro Tyr Gly Tyr
            100                 105                 110

Val Gly Gly Gly Tyr Ser Ser Pro Asn Ile Phe Thr Phe Gly Lys Thr
        115                 120                 125

Pro Lys Ser Asn Lys Lys Leu Asn Ser Leu Val Thr Ser Thr Ile Pro
130                 135                 140

Phe Pro Phe Gly Gly Tyr Arg Glu Thr Asn Tyr Ile Glu Ser Gln Asn
145                 150                 155                 160

Asn Lys Asn Phe Tyr Ala Ser Asn Ile Val Ile Phe Gly Pro Gly Ser
                165                 170                 175

Asn Ile Val Glu Asn Asn Val Ile Cys Tyr Lys Lys Asn Asp Ala Glu
            180                 185                 190

Asn Gly Met Gly Thr Met Ala Glu Ile Leu Phe Gln Pro Leu Leu Thr
        195                 200                 205

Tyr Lys Tyr Asn Lys Phe Tyr Ile Asp Pro Ala Met Glu Leu Thr Lys
    210                 215                 220

Cys Leu Ile Lys Ser Leu Tyr Phe Leu Tyr Gly Ile Lys Pro Ser Asp
225                 230                 235                 240

Asp Leu Val Val Pro Tyr Arg Leu Arg Thr Glu Leu Asp Asn Lys Gln
                245                 250                 255

Phe Ser Gln Leu Asn Ile Ile Asp Leu Leu Ile Ser Gly Gly Val Asp
            260                 265                 270

Leu Glu Phe Ile Asn Thr Asn Pro Tyr Trp Phe Thr Asn Ser Tyr Phe
        275                 280                 285
```

-continued

```
Ser Asn Ser Ile Lys Met Phe Glu Lys Tyr Lys Asn Ile Tyr Glu Thr
290                 295                 300

Glu Ile Glu Gly Asn Asn Ala Ile Gly Asn Asp Ile Lys Leu Arg Leu
305                 310                 315                 320

Lys Gln Lys Phe Gln Asn Ser Val Gln Asp Ile Trp Asn Leu Asn Leu
                325                 330                 335

Asn Tyr Phe Ser Lys Glu Phe Asn Ser Ile Ile Pro Asp Arg Phe Ser
                340                 345                 350

Asn Ala Leu Lys His Phe Tyr Arg Lys Gln Tyr Tyr Thr Met Asp Tyr
                355                 360                 365

Gly Asp Asn Tyr Asn Ile Asn Gly Phe Val Asn Gly Gln Ile Asn Thr
370                 375                 380

Lys Leu Pro Leu Ser Asp Lys Asn Thr Asn Ile Ile Ser Lys Pro Glu
385                 390                 395                 400

Lys Val Val Asn Leu Val Asn Ala Asn Asn Ile Ser Leu Met Lys Ser
                405                 410                 415

Asn Ile Tyr Gly Asp Gly Leu Lys Gly Thr Thr Glu Asp Phe Tyr Ser
                420                 425                 430

Thr Tyr Lys Ile Pro Tyr Asn Glu Glu Tyr Glu Tyr Arg Phe Asn Asp
                435                 440                 445

Ser Asp Asn Phe Pro Leu Asn Asn Ile Ser Ile Glu Glu Val Asp Ser
450                 455                 460

Ile Pro Glu Ile Ile Asp Ile Asn Pro Tyr Lys Asp Asn Ser Asp Asp
465                 470                 475                 480

Leu Leu Phe Thr Gln Ile Thr Ser Thr Thr Glu Val Ile Thr His
                485                 490                 495

Thr Ala Leu Pro Val Asn Tyr Leu Gln Ala Gln Ile Ile Thr Asn Glu
                500                 505                 510

Asn Phe Thr Leu Ser Ser Asp Phe Ser Lys Val Val Ser Ser Lys Asp
                515                 520                 525

Lys Ser Leu Val Tyr Ser Phe Leu Asp Asn Leu Met Ser Tyr Leu Glu
530                 535                 540

Thr Ile Lys Asn Asp Gly Pro Ile Asp Thr Asp Lys Lys Tyr Tyr Leu
545                 550                 555                 560

Trp Leu Lys Glu Val Phe Lys Asn Tyr Ser Phe Asp Ile Asn Leu Thr
                565                 570                 575

Gln Glu Ile Asp Ser Ser Cys Gly Ile Asn Glu Val Val Ile Trp Phe
                580                 585                 590

Gly Lys Ala Leu Asn Ile Leu Asn Thr Ser Asn Ser Phe Val Glu Glu
                595                 600                 605

Tyr Gln Asn Ser Gly Pro Ile Ser Leu Ile Ser Lys Lys Asp Asn Leu
610                 615                 620

Ser Glu Pro Asn Ile Glu Ile Asp Asp Ile Pro Asp Ser Leu Leu Gly
625                 630                 635                 640

Leu Ser Phe Lys Asp Leu Asn Asn Lys Leu Tyr Glu Ile Tyr Ser Lys
                645                 650                 655

Asn Arg Val Tyr Phe Arg Lys Ile Tyr Phe Asn Phe Leu Asp Gln Trp
                660                 665                 670

Trp Thr Glu Tyr Tyr Ser Gln Tyr Phe Glu Leu Ile Cys Met Ala Lys
                675                 680                 685

Gln Ser Ile Leu Ala Gln Glu Ser Val Val Lys Gln Ile Ile Gln Asn
                690                 695                 700

Lys Phe Thr Asp Leu Ser Lys Ala Ser Ile Pro Pro Asp Thr Leu Lys
```

-continued

```
            705                 710                 715                 720
        Leu Ile Lys Glu Thr Thr Glu Lys Thr Phe Ile Asp Leu Ser Asn Glu
                        725                 730                 735

Ser Gln Ile Ser Met Asn Arg Val Asp Asn Phe Leu Asn Lys Ala Ser
                        740                 745                 750

Ile Cys Val Phe Val Glu Asp Ile Tyr Pro Lys Phe Ile Ser Tyr Met
                        755                 760                 765

Glu Lys Tyr Ile Asn Asn Ile Asn Ile Lys Thr Arg Glu Phe Ile Gln
                        770                 775                 780

Arg Cys Thr Asn Ile Asn Asp Asn Glu Lys Ser Ile Leu Ile Asn Ser
        785                 790                 795                 800

Tyr Thr Phe Lys Thr Ile Asp Phe Lys Phe Leu Asn Ile Gln Ala Ile
                        805                 810                 815

Lys Asn Phe Phe Asn Ser Gln Val Glu Gln Val Met Lys Glu Met Leu
                        820                 825                 830

Ser Pro Tyr Gln Leu Leu Phe Ala Thr Arg Gly Pro Asn Ser Asn
                        835                 840                 845

Ile Ile Glu Asp Ile Ser Gly Lys Asn Thr Leu Ile Gln Tyr Thr Glu
        850                 855                 860

Ser Val Glu Leu Val Tyr Gly Val Asn Gly Glu Ser Leu Tyr Leu Lys
        865                 870                 875                 880

Ser Pro Asn Glu Thr Val Glu Phe Ser Asn Asn Phe Phe Thr Asn Gly
                        885                 890                 895

Leu Thr Asn Asn Phe Thr Ile Cys Phe Trp Leu Arg Phe Thr Gly Lys
                        900                 905                 910

Asp Asp Asp Lys Thr Arg Leu Ile Gly Asn Lys Val Asn Asn Cys Gly
                        915                 920                 925

Trp Glu Ile Tyr Phe Glu Asp Asn Gly Leu Val Phe Glu Ile Ile Asp
                        930                 935                 940

Ser Asn Gly Asn Gln Glu Ser Val Tyr Leu Ser Asn Val Ile Asn Asn
        945                 950                 955                 960

Asn Trp Tyr Tyr Ile Ser Ile Ser Val Asp Arg Leu Lys Asp Gln Leu
                        965                 970                 975

Leu Ile Phe Ile Asn Asp Lys Asn Val Ala Asn Val Ser Ile Glu Gln
                        980                 985                 990

Ile Leu Asn Ile Tyr Ser Thr Asn Val Ile Ser Leu Val Asn Lys Asn
                        995                 1000                1005

Asn Ser Ile Tyr Val Glu Leu Ser Val Leu Asp Lys Pro Val Ala
                        1010                1015                1020

Ser Glu Glu Val Ile Arg Asn Tyr Phe Ser Tyr Leu Asp Asn Ser Tyr
        1025                1030                1035                1040

Ile Arg Asp Ser Ser Lys Ser Leu Leu Glu Tyr Asn Lys Asn Tyr Gln
                        1045                1050                1055

Leu Tyr Asn Tyr Val Phe Pro Glu Thr Ser Leu Tyr Glu Val Asn Asp
                        1060                1065                1070

Asn Asn Lys Ser Tyr Leu Ser Leu Lys Asn Thr Asp Gly Ile Asn Ile
                        1075                1080                1085

Pro Ser Val Lys Phe Lys Leu Ile Asn Ile Asp Glu Ser Lys Gly Tyr
                        1090                1095                1100

Val Gln Lys Trp Asp Glu Cys Ile Ile Cys Val Ser Asp Gly Thr Glu
        1105                1110                1115                1120

Lys Tyr Leu Asp Ile Ser Pro Glu Asn Asn Arg Ile Gln Leu Val Ser
                        1125                1130                1135
```

-continued

Ser Lys Asp Asn Ala Lys Lys Ile Thr Val Asn Thr Asp Leu Phe Arg
            1140                1145                1150

Pro Asp Cys Ile Thr Phe Ser Tyr Asn Asp Lys Tyr Phe Ser Leu Ser
        1155                1160                1165

Leu Arg Asp Gly Asp Tyr Asn Trp Met Ile Cys Asn Asp Asn Asn Lys
    1170                1175                1180

Val Pro Lys Gly Ala His Leu Trp Ile Leu Lys Ser
1185                1190                1195

<210> SEQ ID NO 31
<211> LENGTH: 1162
<212> TYPE: PRT
<213> ORGANISM: Clostridium botulinum serotype E

<400> SEQUENCE: 31

Met Lys Ile Asn Gly Asn Leu Asn Ile Asp Ser Pro Val Asp Asn Lys
 1               5                  10                  15

Asn Val Ala Ile Val Arg Ser Arg Asn Gln Met Phe Phe Lys Ala Phe
                20                  25                  30

Gln Val Ala Pro Asn Ile Trp Ile Val Pro Glu Arg Tyr Tyr Gly Glu
            35                  40                  45

Ser Leu Lys Ile Asn Glu Asp Gln Lys Phe Asp Gly Gly Ile Tyr Asp
        50                  55                  60

Ser Asn Phe Leu Ser Thr Asn Asn Glu Lys Asp Asp Phe Leu Gln Ala
65                  70                  75                  80

Thr Ile Lys Leu Leu Gln Arg Ile Asn Asn Asn Val Val Gly Ala Lys
                85                  90                  95

Leu Leu Ser Leu Ile Ser Thr Ala Ile Pro Phe Pro Tyr Glu Asn Asn
            100                 105                 110

Thr Glu Asp Tyr Arg Gln Thr Asn Tyr Leu Ser Ser Lys Asn Asn Glu
        115                 120                 125

His Tyr Tyr Thr Ala Asn Leu Val Ile Phe Gly Pro Gly Ser Asn Ile
    130                 135                 140

Ile Lys Asn Asn Val Ile Tyr Tyr Lys Lys Glu Tyr Ala Glu Ser Gly
145                 150                 155                 160

Met Gly Thr Met Leu Glu Ile Trp Phe Gln Pro Phe Leu Thr His Lys
                165                 170                 175

Tyr Asp Glu Phe Tyr Val Asp Pro Ala Leu Glu Leu Ile Lys Cys Leu
            180                 185                 190

Ile Lys Ser Leu Tyr Tyr Leu Tyr Gly Ile Lys Pro Asn Asp Asn Leu
        195                 200                 205

Asn Ile Pro Tyr Arg Leu Arg Asn Glu Phe Asn Ser Leu Glu Tyr Ser
    210                 215                 220

Glu Leu Asn Met Ile Asp Phe Leu Ile Ser Gly Gly Ile Asp Tyr Lys
225                 230                 235                 240

Leu Leu Asn Thr Asn Pro Tyr Trp Phe Ile Asp Lys Tyr Phe Ile Asp
                245                 250                 255

Thr Ser Lys Asn Phe Glu Lys Tyr Lys Asn Asp Tyr Glu Ile Lys Ile
            260                 265                 270

Lys Asn Asn Asn Tyr Ile Ala Asn Ser Ile Lys Leu Tyr Leu Glu Gln
        275                 280                 285

Lys Phe Lys Ile Asn Val Lys Asp Ile Trp Glu Leu Asn Leu Ser Tyr
    290                 295                 300

Phe Ser Lys Glu Phe Gln Ile Met Met Pro Glu Arg Tyr Asn Asn Ala

```
                305                 310                 315                 320
Leu Asn His Tyr Tyr Arg Lys Glu Phe Tyr Val Ile Asp Tyr Phe Lys
                    325                 330                 335
Asn Tyr Asn Ile Asn Gly Phe Lys Asn Gly Gln Ile Lys Thr Lys Leu
                    340                 345                 350
Pro Leu Ser Lys Tyr Asn Lys Glu Ile Ile Asn Lys Pro Glu Leu Ile
                    355                 360                 365
Val Asn Leu Ile Asn Gln Asn Thr Val Leu Met Lys Ser Asn Ile
                    370                 375                 380
Tyr Gly Asp Gly Leu Lys Gly Thr Val Asp Asn Phe Tyr Ser Asn Tyr
385                 390                 395                 400
Ile Ile Pro Tyr Asn Leu Asn Tyr Glu His Ser Ile Asn Tyr Phe Tyr
                    405                 410                 415
Leu Asp Asn Val Asn Ile Glu Glu Ile Glu Lys Ile Pro Pro Ile Asn
                    420                 425                 430
Asp Glu Asp Ile Tyr Pro Tyr Arg Lys Asn Ala Asp Thr Phe Ile Pro
                    435                 440                 445
Val Tyr Asn Ile Thr Lys Ala Lys Glu Ile Asn Thr Thr Thr Pro Leu
                    450                 455                 460
Pro Val Asn Tyr Leu Gln Ala Gln Met Ile Asp Ser Asn Asp Ile Asn
465                 470                 475                 480
Leu Ser Ser Asp Phe Leu Lys Val Ile Ser Ser Lys Gly Ser Leu Val
                    485                 490                 495
Tyr Ser Phe Leu Asn Asn Thr Met Asp Tyr Leu Glu Phe Ile Lys Tyr
                    500                 505                 510
Asp Lys Pro Ile Asp Thr Asp Lys Lys Tyr Tyr Lys Trp Leu Lys Ala
                    515                 520                 525
Ile Phe Arg Asn Tyr Ser Leu Asp Ile Thr Glu Thr Gln Glu Ile Ser
                    530                 535                 540
Asn Gln Phe Gly Asp Thr Lys Ile Ile Pro Trp Ile Gly Arg Ala Leu
545                 550                 555                 560
Asn Ile Leu Asn Thr Asn Asn Ser Phe Val Glu Glu Phe Lys Asn Leu
                    565                 570                 575
Gly Pro Ile Ser Leu Ile Asn Lys Lys Glu Asn Ile Thr Ile Pro Lys
                    580                 585                 590
Ile Lys Ile Asp Glu Ile Pro Ser Ser Met Leu Asn Phe Ser Phe Lys
                    595                 600                 605
Asp Leu Ser Glu Asn Leu Phe Asn Ile Tyr Cys Lys Asn Asn Phe Tyr
                    610                 615                 620
Leu Lys Lys Ile Tyr Tyr Asn Phe Leu Asp Gln Trp Trp Thr Gln Tyr
625                 630                 635                 640
Tyr Ser Gln Tyr Phe Asp Leu Ile Cys Met Ala Ser Lys Ser Val Leu
                    645                 650                 655
Ala Gln Glu Lys Leu Ile Lys Lys Leu Ile Gln Lys Gln Leu Arg Tyr
                    660                 665                 670
Leu Met Glu Asn Ser Asn Ile Ser Ser Thr Asn Leu Ile Leu Ile Asn
                    675                 680                 685
Leu Thr Thr Thr Asn Thr Leu Arg Asp Ile Ser Asn Gln Ser Gln Ile
                    690                 695                 700
Ala Ile Asn Asn Ile Asp Lys Phe Phe Asn Asn Ala Ala Met Cys Val
705                 710                 715                 720
Phe Glu Asn Asn Ile Tyr Pro Lys Phe Thr Ser Phe Met Glu Gln Cys
                    725                 730                 735
```

-continued

```
Ile Lys Asn Ile Asn Lys Ser Thr Lys Glu Phe Ile Leu Lys Cys Thr
            740                 745                 750

Asn Ile Asn Glu Thr Glu Lys Ser His Leu Ile Met Gln Asn Ser Phe
            755                 760                 765

Ser Asn Leu Asp Phe Asp Phe Leu Asp Ile Gln Asn Met Lys Asn Leu
            770                 775                 780

Phe Asn Leu Tyr Thr Glu Leu Leu Ile Lys Glu Gln Thr Ser Pro Tyr
785                 790                 795                 800

Glu Leu Ser Leu Tyr Ala Phe Gln Gln Asp Asn Asn Val Ile Gly
                805                 810                 815

Asp Thr Ser Gly Lys Asn Thr Leu Val Glu Tyr Pro Lys Asp Ile Gly
            820                 825                 830

Leu Val Tyr Gly Ile Asn Asn Ala Ile His Leu Thr Gly Ala Asn
                835                 840                 845

Gln Asn Ile Lys Phe Thr Asn Asp Tyr Phe Asn Gly Leu Thr Asn
            850                 855                 860

Asn Phe Ser Ile Tyr Phe Trp Leu Arg Asn Leu Lys Gln Asn Thr Ile
865                 870                 875                 880

Lys Ser Lys Leu Ile Gly Ser Lys Glu Asp Asn Cys Gly Trp Glu Ile
                885                 890                 895

Tyr Phe Glu Asn Asp Gly Leu Val Phe Asn Ile Ile Asp Ser Asn Gly
                900                 905                 910

Asn Glu Lys Asn Ile Tyr Leu Ser Asn Ile Ser Asn Lys Ser Trp His
            915                 920                 925

Tyr Ile Val Ile Ser Ile Asn Arg Leu Lys Asp Gln Leu Leu Ile Phe
            930                 935                 940

Ile Asp Asn Ile Leu Val Ala Asn Glu Asp Ile Lys Glu Ile Leu Asn
945                 950                 955                 960

Ile Tyr Ser Ser Asp Ile Ile Ser Leu Leu Ser Asp Asn Asn Asn Val
                965                 970                 975

Tyr Ile Glu Gly Leu Ser Val Leu Asn Lys Thr Ile Asn Ser Asn Glu
                980                 985                 990

Ile Leu Thr Asp Tyr Phe Ser Asp Leu Asn Asn Ser Tyr Ile Arg Asn
            995                 1000                1005

Phe Asp Glu Glu Ile Leu Gln Tyr Asn Arg Thr Tyr Glu Leu Phe Asn
            1010                1015                1020

Tyr Val Phe Pro Glu Ile Ala Ile Asn Lys Ile Glu Gln Asn Asn Asn
1025                1030                1035                1040

Ile Tyr Leu Ser Ile Asn Asn Glu Asn Asn Leu Asn Phe Lys Pro Leu
            1045                1050                1055

Lys Phe Lys Leu Leu Asn Thr Asn Pro Asn Lys Gln Tyr Val Gln Lys
            1060                1065                1070

Trp Asp Glu Val Ile Phe Ser Val Leu Asp Gly Thr Gly Lys Tyr Leu
            1075                1080                1085

Asp Ile Ser Thr Thr Asn Asn Arg Ile Gln Leu Val Asp Asn Lys Asn
            1090                1095                1100

Asn Ala Gln Ile Phe Ile Ile Asn Asn Asp Ile Phe Ile Ser Asn Cys
1105                1110                1115                1120

Leu Thr Leu Thr Tyr Asn Asn Val Asn Val Tyr Leu Ser Ile Lys Asn
                1125                1130                1135

Gln Asp Tyr Asn Trp Val Ile Cys Asp Leu Asn His Asp Ile Pro Lys
            1140                1145                1150
```

```
Lys Ser Tyr Leu Trp Ile Leu Lys Asn Ile
        1155                1160
```

<210> SEQ ID NO 32
<211> LENGTH: 1159
<212> TYPE: PRT
<213> ORGANISM: Clostridium botulinum serotype F

<400> SEQUENCE: 32

```
Met Lys Ile Asn Asn Phe Asn Ile Asp Ser Leu Ile Asp Asn Arg
 1               5                  10                  15

Asp Val Ala Ile Val Arg Gly Arg Lys Thr Asp Thr Phe Phe Lys Val
                20                  25                  30

Phe Gln Val Ala Pro Asn Ile Trp Ile Ala Pro Glu Arg Tyr Tyr Gly
            35                  40                  45

Glu Ser Leu Asn Ile Asn Glu Asp Gln Lys Ser Asp Gly Gly Ile Tyr
        50                  55                  60

Asp Ser Asn Phe Leu Ser Thr Asn Asp Glu Lys Asp Glu Phe Leu Gln
65                  70                  75                  80

Ala Thr Val Lys Ile Leu Gln Arg Ile Asn Asn Asn Val Ile Gly Ala
                85                  90                  95

Lys Leu Leu Ser Leu Ile Ser Thr Ala Ile Pro Phe Pro Tyr Glu Tyr
            100                 105                 110

Lys Pro Gly Asp Tyr Arg Gln Thr Asn Tyr Leu Val Ser Lys Asp Asn
        115                 120                 125

Gln His Tyr Tyr Thr Ala Asn Leu Val Ile Phe Gly Pro Gly Thr Asn
    130                 135                 140

Ile Val Glu Asn Asn Ala Ile Tyr Tyr Lys Lys Glu Asp Ser Glu Asn
145                 150                 155                 160

Gly Met Gly Thr Met Ser Glu Ile Trp Phe Gln Pro Phe Leu Thr Tyr
                165                 170                 175

Lys Tyr Gly Gln Phe Tyr Val Asp Pro Ala Leu Glu Leu Ile Lys Cys
            180                 185                 190

Leu Ile Lys Ser Leu Tyr Tyr Leu Tyr Gly Ile Lys Pro Ser Asp Asp
        195                 200                 205

Leu Ser Ile Pro Tyr Arg Leu Arg Ser Glu Leu Asn Ser Phe Glu Tyr
    210                 215                 220

Ser Glu Leu Asp Met Ile Asp Phe Leu Ile Ser Gly Gly Thr Glu Tyr
225                 230                 235                 240

Lys Leu Leu Asp Thr Asn Pro Tyr Trp Phe Thr Asp Asn Tyr Phe Ile
                245                 250                 255

Asp Ala Pro Lys Asn Phe Glu Lys Tyr Lys Asn Asp Tyr Glu Thr Lys
            260                 265                 270

Ile Lys Asn Asn Asn Asp Ile Ala Asn Ser Ile Lys Leu Tyr Leu Glu
        275                 280                 285

Gln Lys Phe Lys Thr Asn Ala Gln Asp Ile Trp Glu Leu Asn Leu Ser
    290                 295                 300

Tyr Phe Ser Thr Glu Phe Glu Ile Met Met Pro Glu Ile Phe Asn Asn
305                 310                 315                 320

Ala Leu Asn His Tyr Tyr Arg Lys Glu Tyr Tyr Val Ile Asp Tyr Phe
                325                 330                 335

Lys Asn Tyr Asn Ile Asn Gly Phe Ile Asn Gly Gln Ile Lys Thr Ile
            340                 345                 350

Leu Pro Leu Ser Lys Tyr Asn Lys Asn Ile Ile Asn Lys Pro Glu Leu
        355                 360                 365
```

-continued

```
Val Val Asn Leu Ile Asn Glu Asn Asn Thr Val Leu Met Lys Ser Asn
    370                 375                 380

Val Tyr Gly Asp Gly Leu Lys Gly Thr Met Asp Asn Phe Tyr Ala Ala
385                 390                 395                 400

Tyr Lys Ile Pro Tyr Asn Ile Gly Asp Glu Tyr His Ile Asn Tyr Ser
                405                 410                 415

Tyr Leu Asn Asn Val Asn Val Glu Glu Ile Asn Asn Ile Pro Pro Ile
                420                 425                 430

Asn Asp Ala Asp Ile Tyr Pro Tyr Arg Lys Asn Ser Asp Pro Phe Ile
            435                 440                 445

Pro Val Tyr Asn Ile Thr Glu Thr Lys Glu Ile Asn Thr Thr Thr Pro
    450                 455                 460

Leu Ser Val Asn Tyr Leu Gln Ala Gln Val Thr Asn Ser Asn Asp Ile
465                 470                 475                 480

Ser Leu Ser Ser Asp Phe Ser Lys Val Ile Ser Ser Lys Asp Arg Ser
                485                 490                 495

Leu Val Tyr Ser Phe Leu Asp Asn Thr Ile Asp Tyr Leu Asp Ser Ile
                500                 505                 510

Lys Tyr Asp Glu Pro Ile Asp Thr Asp Lys Lys Tyr Tyr Leu Trp Leu
            515                 520                 525

Lys Glu Ile Phe Arg Asn Tyr Ser Phe Asp Met Thr Glu Thr Gln Glu
    530                 535                 540

Val Asn Thr Pro Cys Gly Ile Asn Lys Val Val Pro Trp Leu Gly Lys
545                 550                 555                 560

Ala Leu Asn Ile Leu Asn Thr Gly Asn Ser Phe Ile Glu Glu Phe Lys
                565                 570                 575

Ser Leu Gly Pro Ile Ser Leu Ile Asn Lys Lys Glu Asn Ile Thr Met
                580                 585                 590

Pro Lys Ile Glu Ile Asp Glu Ile Pro Asn Ser Met Leu Asn Leu Ser
            595                 600                 605

Phe Lys Asp Leu Ser Glu Asn Leu Phe Asn Arg Phe Ser Lys Asn Asn
    610                 615                 620

Ser Tyr Phe Glu Lys Ile Tyr Tyr Asp Phe Leu Asp Gln Trp Trp Thr
625                 630                 635                 640

Gln Tyr Tyr Ser Gln Tyr Phe Asp Leu Ile Cys Met Ala Lys Lys Ser
                645                 650                 655

Ile Leu Ala Gln Glu Thr Leu Ile Lys Lys Ile Ile Gln Lys Lys Leu
                660                 665                 670

Ser Tyr Leu Ile Gly Asn Ser Asn Ile Ser Ser Asp Asn Leu Ala Leu
            675                 680                 685

Met Asn Leu Thr Thr Thr Asn Thr Leu Arg Asp Ile Ser Asn Glu Ser
    690                 695                 700

Gln Ile Ala Met Asn Asn Val Asp Ser Phe Leu Asn Ser Ala Ala Ile
705                 710                 715                 720

Cys Val Phe Glu Gly Asn Ile Tyr Ser Lys Phe Ile Ser Phe Met Glu
                725                 730                 735

Gln Cys Ile Asn Asn Ile Asn Lys Asn Thr Arg Glu Phe Ile Gln Lys
                740                 745                 750

Cys Thr Asn Ile Thr Glu Asn Glu Lys Leu Gln Leu Ile Asn Gln Asn
            755                 760                 765

Ile Phe Ser Ser Leu Asp Phe Asp Phe Leu Asn Ile Glu Asn Leu Lys
    770                 775                 780
```

-continued

```
Ser Leu Phe Ser Ser Glu Thr Ala Leu Leu Ile Lys Glu Glu Thr Ser
785                 790                 795                 800

Pro Tyr Glu Leu Val Leu Tyr Ala Phe Gln Glu Pro Asp Asn Asn Ala
            805                 810                 815

Ile Gly Asp Ala Ser Ala Lys Asn Thr Ser Ile Glu Tyr Ser Lys Asp
        820                 825                 830

Ile Asp Leu Val Tyr Gly Ile Asn Ser Asp Ala Leu Tyr Leu Asn Gly
    835                 840                 845

Ser Asn Gln Ser Ile Ser Phe Ser Asn Asp Phe Phe Glu Asn Gly Leu
850                 855                 860

Thr Asn Ser Phe Ser Ile Tyr Phe Trp Leu Arg Asn Leu Gly Lys Asp
865                 870                 875                 880

Thr Ile Lys Tyr Lys Leu Ile Gly Ser Lys Glu Asp Asn Cys Gly Trp
            885                 890                 895

Glu Ile Tyr Phe Gln Asp Thr Gly Leu Val Phe Asn Met Ile Asp Ser
        900                 905                 910

Asn Gly Asn Glu Lys Asn Ile Tyr Leu Ser Asp Val Ser Asn Asn Ser
    915                 920                 925

Trp His Tyr Ile Thr Ile Ser Val Asp Arg Leu Lys Glu Gln Leu Leu
930                 935                 940

Ile Phe Ile Asp Asp Asn Leu Val Ala Asn Glu Ser Ile Lys Glu Ile
945                 950                 955                 960

Leu Asn Ile Tyr Ser Ser Asn Ile Ile Ser Leu Leu Ser Glu Asn Lys
            965                 970                 975

Pro Ser Tyr Ile Glu Gly Leu Thr Ile Leu Asn Lys Pro Thr Thr Ser
        980                 985                 990

Gln Glu Val Leu Asn Asn Tyr Phe Lys Val Leu Asn Asn Ser Tyr Ile
    995                 1000                1005

Arg Asp Ser Asn Glu Glu Arg Leu Glu Tyr His Lys Thr Tyr Gln Leu
1010                1015                1020

Asp Asn Tyr Val Phe Ser Asp Lys Pro Ile Cys Glu Val Lys Gln Asn
1025                1030                1035                1040

Asn Asn Ile Tyr Leu Thr Ile Asn Asn Thr Asn Leu Asn Leu Gln
            1045                1050                1055

Pro Ser Lys Phe Lys Leu Leu Ser Ile Asn Ser Asn Lys Gln Tyr Val
        1060                1065                1070

Gln Lys Phe Asp Glu Val Ile Ile Ser Ile Leu Gly Asn Met Glu Lys
    1075                1080                1085

Tyr Ile Asp Ile Ser Glu Asp Asn Arg Leu Gln Leu Ile Asp Asn Lys
    1090                1095                1100

Asn Gly Ala Lys Lys Met Ile Ile Ser Asn Asp Met Phe Ile Ser Asn
1105                1110                1115                1120

Cys Leu Thr Leu Ser Cys Gly Gly Lys Tyr Ile Cys Leu Ser Met Lys
            1125                1130                1135

Asp Glu Asn His Asn Trp Met Ile Cys Asn Asn Asp Met Ser Lys Tyr
        1140                1145                1150

Leu Tyr Leu Trp Ser Phe Lys
        1155

<210> SEQ ID NO 33
<211> LENGTH: 1165
<212> TYPE: PRT
<213> ORGANISM: Clostridium botulinum serotype F

<400> SEQUENCE: 33
```

```
Met Lys Ile Asn Asp Asp Leu Asn Ile Asn Ser Pro Val Asp Asn Lys
  1               5                   10                  15

Asn Val Val Ile Val Arg Ala Arg Lys Thr Asn Ile Phe Phe Lys Ala
             20                  25                  30

Phe Gln Val Ala Pro Asn Ile Trp Val Ala Pro Glu Arg Tyr Tyr Gly
             35                  40                  45

Glu Pro Leu Asn Ile Ser Asp Gln Glu Lys Ser Asp Gly Gly Ile Tyr
 50                  55                  60

Asp Glu Asn Phe Leu Lys Glu Asn Ser Glu Lys Glu Glu Phe Leu Gln
 65                  70                  75                  80

Ala Ile Ile Leu Leu Leu Lys Arg Ile Asn Asn Asn Ile Ile Gly Gln
                 85                  90                  95

Lys Leu Leu Ser Leu Met Cys Thr Ser Ile Pro Phe Leu His Glu Tyr
                100                 105                 110

Lys Gln Gly Asp Tyr Arg Gln Ser Asn Tyr Leu Gly Ser Lys Asn Ser
                115                 120                 125

Glu Tyr Leu Tyr Ser Ala Asn Ile Val Ile Phe Gly Pro Gly Ser Asn
130                 135                 140

Ile Val Lys Asn Asn Thr Ile Tyr Tyr Lys Lys Asn Phe Ala Glu Asn
145                 150                 155                 160

Gly Met Gly Thr Met Ala Glu Ile Leu Phe Gln Pro Phe Leu Thr Tyr
                165                 170                 175

Lys Tyr Asn Gln Phe Tyr Ala Asp Pro Ala Leu Glu Leu Ile Lys Cys
                180                 185                 190

Leu Ile Lys Ala Ile Tyr Phe Leu Tyr Gly Ile Lys Pro Asn Asp Asn
                195                 200                 205

Leu Asn Ile Pro Tyr Arg Leu Arg Asn Glu Phe Ser Asn Val Glu Tyr
210                 215                 220

Ser Glu Leu Asn Ile Ile Asp Phe Leu Ile Ser Gly Gly Ile Asp Tyr
225                 230                 235                 240

Lys Phe Ile Asn Thr Asn Pro Tyr Trp Phe Ile Asp Asn Tyr Phe Ile
                245                 250                 255

Asp Val Pro Lys Val Phe Glu Lys His Lys Asn Asp Tyr Glu Ile Asn
                260                 265                 270

Ile Lys Asn Asn Ser Glu Ile Gly Thr Ser Ile Lys Leu Tyr Leu Glu
                275                 280                 285

Gln Lys Phe Lys Thr Asn Val Gln Asp Ile Trp Glu Leu Asn Leu Ser
                290                 295                 300

Tyr Phe Ser Lys Glu Phe Gln Ile Met Met Pro Glu Lys His Asn Asn
305                 310                 315                 320

Ala Leu Lys His Tyr Tyr Arg Lys Glu Tyr Tyr Lys Ile Asn Tyr Ser
                325                 330                 335

Lys Gln Tyr Asp Ile Asn Gly Phe Val Asn Gly Gln Ile Ala Thr Lys
                340                 345                 350

Leu Leu Leu Ser Glu Lys Asn Gln Tyr Ile Ile Asn Lys Pro Gln Leu
                355                 360                 365

Ile Ile Asn Leu Ile Asn Lys Ser Asn Asn Ser Leu Leu Met Lys Ser
                370                 375                 380

Asn Ile Tyr Gly Asp Gly Leu Asn Gly Thr Thr Asp Asn Phe Tyr Arg
385                 390                 395                 400

Asn Tyr Lys Ile Pro Asp Asn Ile Ala Tyr Gln Tyr His Pro Asn Asn
                405                 410                 415
```

```
Thr Tyr Leu Asp Asn Val Asn Ile Glu Glu Ile Asn Asn Ile Pro Gln
            420                 425                 430

Ile Thr Asp Ala Asp Ile Tyr Pro Tyr Thr Asn Asn Cys Asp Thr Phe
            435                 440                 445

Ile Pro Ile Tyr Asn Ile Thr Gln Ser Arg Glu Ile Asn Thr Thr Val
            450                 455                 460

Pro Tyr Ser Ile Asn Tyr Leu Gln Ser Gln Ile Met Asn Ser Asp Asp
465                 470                 475                 480

Ile Thr Leu Ser Ser Asp Phe Trp Glu Val Val Cys Ser Asn Asp Lys
            485                 490                 495

Ser Leu Val Tyr Ser Tyr Leu Asp Asn Val Ile Asn Tyr Leu Asp Ser
            500                 505                 510

Ile Lys Asn Asn Thr Pro Ile Asn Thr Asp Lys Lys Tyr Tyr Leu Trp
            515                 520                 525

Leu Lys Glu Ile Phe Arg Asn Tyr Ser Phe Asp Ile Thr Ala Thr Glu
            530                 535                 540

Glu Ile Thr Thr Glu Cys Gly Ile Asn Lys Ile Val Ser Trp Phe Gly
545                 550                 555                 560

Lys Ala Phe Asn Ile Leu Asn Thr Asp Asn Ser Phe Lys Ile Glu Phe
            565                 570                 575

Gln Asn Ser Gly Ala Ile Ala Leu Ile Asn Lys Lys Asp Asn Ile Ile
            580                 585                 590

Ile Pro Lys Ile Glu Ile Asp Glu Met Pro Asn Ser Met Leu Asn Leu
            595                 600                 605

Ser Phe Glu Asp Leu Asn Glu Gln Leu Tyr Ser Ile Tyr Ser Lys Asn
            610                 615                 620

Ile Thr Tyr Phe Lys Lys Ile Tyr Tyr Asn Phe Leu Asp Gln Trp Trp
625                 630                 635                 640

Thr Glu Tyr Tyr Ser Gln Tyr Phe Asp Leu Ile Cys Met Ala Lys Lys
            645                 650                 655

Ser Ile Leu Ala Gln Glu Asn Leu Ile Lys Lys Ile Gln Lys Lys
            660                 665                 670

Ile Ser Tyr Leu Ile Gly Ala Ser Asn Ile Pro Asp Asp Ile Leu Ala
            675                 680                 685

Val Met Arg Leu Thr Thr Thr Asn Thr Leu Arg Asp Ile Ser Val Glu
            690                 695                 700

Ser Gln Ile Ala Met Asn Asn Leu Asn Asn Phe Leu Asn Lys Ala Ala
705                 710                 715                 720

Met Cys Val Phe Gln Ser Asn Ile Tyr Pro Lys Phe Ile Ser Phe Met
            725                 730                 735

Glu Gln Cys Ile Lys His Ile Asn Lys Ser Thr Lys Glu Phe Ile Gln
            740                 745                 750

Lys Cys Thr Asn Ile Asn Glu Thr Glu Lys Leu Gln Leu Ile Met Gln
            755                 760                 765

Asn Ser Phe Ser Asn Leu Asp Phe Asp Phe Leu Asp Ile Gln Asn Met
            770                 775                 780

Lys Asn Leu Phe Asn Ser Tyr Thr Glu Leu Leu Ile Lys Glu Gln Thr
785                 790                 795                 800

Ser Pro Tyr Glu Leu Ser Leu Tyr Ala Phe Glu Glu Gln Asp Asn Asn
            805                 810                 815

Val Ile Gly Asp Ala Ser Gly Lys Asn Thr Leu Val Glu Tyr Pro Lys
            820                 825                 830

Gly Ile Glu Leu Val Tyr Gly Ile Asn Asn Ser Ala Leu Tyr Leu Asn
```

```
                835                 840                 845
Gly Ser Asn Gln Ser Ile Ile Phe Thr Asn Asp Tyr Phe Glu Asn Gly
    850                 855                 860
Leu Thr Asn Ser Phe Ser Ile Tyr Phe Trp Leu Arg Asn Leu Gly Gln
865                 870                 875                 880
Asp Thr Ile Lys Ser Lys Leu Ile Gly Ser Lys Glu Tyr Asn Cys Gly
                885                 890                 895
Trp Glu Ile Tyr Phe Gln Glu Ile Gly His Val Phe Asn Met Ile Asp
            900                 905                 910
Ser Asn Gly Asn Glu Lys Asn Ile Tyr Leu Ser Asp Val Ser Asn Asn
                915                 920                 925
Ser Trp His Tyr Ile Thr Ile Ser Val Asp Arg Leu Lys Glu Gln Leu
        930                 935                 940
Leu Ile Phe Ile Asp Asp Asn Leu Val Val Asn Glu Ser Ile Lys Asp
945                 950                 955                 960
Ile Leu Asn Ile Tyr Ser Ser Asn Ile Ile Ser Leu Ser Asp Asn
                965                 970                 975
Lys Ala Ser Tyr Ile Glu Gly Leu Thr Ile Leu Asn Lys Pro Thr Thr
            980                 985                 990
Gly Glu Glu Val Leu Arg Asn Tyr Phe Lys Asn Leu Asn Asn Ser Tyr
        995                1000                1005
Val Arg Asp Ser Asn Asp Glu Arg Leu Glu Tyr Asn Lys Thr Tyr Gln
        1010                1015                1020
Leu Tyr Asp Tyr Val Phe Pro Asp Asn Pro Ile Cys Glu Val Lys Gln
1025                1030                1035                1040
Asp Asn Asn Ile Tyr Leu Thr Ile Asn Asn Ile Asn Asn Leu Asn Met
                1045                1050                1055
Lys Pro Cys Lys Phe Lys Leu Leu Ser Ile Asn Ser Asn Lys Gln Tyr
            1060                1065                1070
Val Gln Lys Trp Asp Glu Val Ile Ile Ser Val Leu Tyr Asp Thr Glu
        1075                1080                1085
Lys Tyr Val Cys Ile Ser Asn Glu Asn Asn Arg Val Lys Ile Ile Asp
        1090                1095                1100
Asn Lys Ile Met Gln Val Lys Phe Ile Ile Ser Asn Asp Ile Phe Ile
1105                1110                1115                1120
Ser Asn Cys Leu Thr His Ala His Asn Asn Lys Tyr Ile Cys Leu Ser
                1125                1130                1135
Met Lys Asp Glu Asn Tyr Asn Trp Met Ile Cys Asn Asn Glu Ser Asn
            1140                1145                1150
Ile Pro Lys Lys Ala Tyr Leu Trp Ile Leu Lys Glu Val
        1155                1160                1165

<210> SEQ ID NO 34
<211> LENGTH: 1198
<212> TYPE: PRT
<213> ORGANISM: Clostridium botulinum serotype G

<400> SEQUENCE: 34

Met Lys Ile Asn Ser Asn Leu Thr Ile Asn Ser Pro Ile Asp Asn Lys
1               5                  10                  15
Asn Val Val Ile Val Arg Ala Arg Glu Thr Ser Lys Phe Phe Lys Ala
                20                  25                  30
Phe Lys Val Ala Pro Asn Ile Trp Val Ala Pro Glu Arg Tyr Tyr Gly
        35                  40                  45
```

-continued

```
Glu Ser Leu Ser Ile Glu Glu Ser Lys Lys Val Asn Gly Gly Val Tyr
 50                  55                  60

Asp Ser Asn Phe Leu Ser Gln Asn Asn Glu Lys Asp Lys Phe Leu Gln
 65                  70                  75                  80

Ala Ile Ile Thr Leu Leu Lys Arg Ile Asn Ser Asn Ile Ala Gly Glu
                 85                  90                  95

Lys Leu Leu Ser Leu Val Ser Thr Ala Ile Pro Phe Pro Tyr Gly Tyr
                100                 105                 110

Ile Gly Gly Gly Tyr Tyr Cys Pro Asn Ile Val Thr Phe Gly Ser Thr
                115                 120                 125

Ile Lys Tyr Asn Lys Lys Ile Asn Ser Leu Ile Ser Thr Thr Ile Pro
130                 135                 140

Phe Pro Tyr Gly Gly Tyr Arg Glu Thr Asn Tyr Leu Ser Ser Lys Asp
145                 150                 155                 160

Thr Glu Asn Phe Tyr Ala Ala Asn Ile Val Ile Phe Gly Pro Gly Ala
                165                 170                 175

Asn Ile Val Glu Asn Asn Thr Val Phe Tyr Lys Lys Glu Asp Ala Glu
                180                 185                 190

Asn Gly Met Gly Thr Met Ala Glu Ile Cys Phe Gln Pro Phe Leu Thr
                195                 200                 205

Tyr Lys Tyr Asp Gln Phe Tyr Val Asp Pro Ala Leu Glu Leu Met Glu
210                 215                 220

Cys Leu Ile Lys Ser Leu Tyr Phe Leu Tyr Gly Ile Lys Pro Asn Asn
225                 230                 235                 240

Asn Leu Thr Val Pro Tyr Arg Leu Arg Asn Glu Leu Ser Asn Ile Glu
                245                 250                 255

Phe Ser Gln Leu Ser Ile Val Asp Leu Leu Ile Ser Gly Gly Ile Asp
                260                 265                 270

Ser Lys Phe Ile Asn Thr Asp Pro Tyr Trp Phe Ile Asp Ser Tyr Phe
                275                 280                 285

Ser Asn Ala Lys Thr Thr Phe Glu Glu His Lys Ser Ile Tyr Glu Thr
290                 295                 300

Glu Ile Lys Gly Asn Asn Ala Ile Gly Asn Asp Ile Lys Leu Arg Leu
305                 310                 315                 320

Lys Gln Lys Phe Gln Thr Thr Val His Asp Ile Trp Gln Leu Asn Leu
                325                 330                 335

Asp Tyr Phe Ser Lys Glu Phe Gln Ile Met Met Pro Tyr Arg Phe Asn
                340                 345                 350

Asn Ala Leu Lys Tyr Tyr Arg Lys Glu Tyr Tyr Lys Ile Asp Tyr
                355                 360                 365

Pro Glu Lys Tyr Ser Ile Ala Gly Phe Val Asp Gly Gln Leu Asn Thr
                370                 375                 380

Gln Leu Ser Leu Ser Asp Lys Asn Gln Tyr Ile Ile Asn Lys Pro Glu
385                 390                 395                 400

Leu Ile Val Asn Leu Ile Ser Glu Asn Asn Ile Ser Leu Met Arg Ser
                405                 410                 415

Asn Ile Tyr Gly Asp Gly Leu Lys Tyr Thr Thr Asp Asn Phe Tyr Ser
                420                 425                 430

Thr Tyr Lys Ile Pro Tyr Asn Arg Ala Tyr Glu Tyr His Phe Asn Asn
                435                 440                 445

Ser Ser Thr Ser Ser Leu Glu Asn Val Asn Val Glu Glu Ile Ser Asn
450                 455                 460

Ile Pro Glu Ile Ile Asp Ile Asn Pro Tyr Arg Glu Asn Ser Asp Ile
```

-continued

```
            465                 470                 475                 480

Phe Ser Pro Val Glu Asn Ile Ile Glu Thr Lys Glu Val Asn Thr Lys
                        485                 490                 495

Thr Pro Trp Pro Ile Asn Tyr Leu Gln Ala Gln Ile Pro Asn Asn Glu
                        500                 505                 510

Glu Phe Thr Leu Ser Ser Asp Phe Ser Gln Val Val Ser Tyr Lys Thr
                        515                 520                 525

Gln Ser Leu Val Tyr Ser Phe Leu Ser Asn Val Ile Ser Tyr Leu Asp
                        530                 535                 540

Ser Val Lys Asp Thr Asn Pro Ile Asp Thr Asp Glu Lys Tyr Tyr Leu
        545                 550                 555                 560

Trp Leu Arg Glu Ile Phe Arg Asn Tyr Ser Phe Asp Ile Thr Ala Ile
                        565                 570                 575

Glu Glu Ile Asn Thr Ser Cys Gly Ile Asn Lys Val Val Ser Trp Phe
                        580                 585                 590

Gly Lys Ala Leu Asn Ile Leu Asn Thr Ser Asn Ser Phe Val Lys Glu
                        595                 600                 605

Phe Lys Asn Leu Gly Pro Ile Ser Leu Ile Asn Lys Lys Glu Asn Leu
                        610                 615                 620

Ser Met Pro Ile Ile Glu Val Asn Glu Ile Pro Asn Asp Met Leu Gly
        625                 630                 635                 640

Leu Ser Leu Lys Asp Leu Asn Glu Lys Leu Phe Asn Ile Tyr Leu Lys
                        645                 650                 655

Asn Ile Leu Tyr Phe Lys Lys Val Tyr Phe Ser Phe Leu Asp Gln Trp
                        660                 665                 670

Trp Thr Glu Tyr Tyr Ser Gln Tyr Phe Gly Leu Ile Cys Met Ala Lys
                        675                 680                 685

Gln Ser Ile Leu Ala Gln Glu Asn Leu Ile Lys Lys Ile Val Gln Lys
                        690                 695                 700

Lys Leu Ser Asp Leu Ser Lys Gln Ser Asn Ile Ser Asn Glu Lys Leu
        705                 710                 715                 720

Asn Leu Met Asn Leu Thr Thr Glu Lys Thr Phe Ile Asp Leu Ser Asn
                        725                 730                 735

Gln Ser Gln Ile Ala Met Asn Asn Ile Asn Asn Phe Leu Asn Lys Ala
                        740                 745                 750

Ala Ile Cys Val Phe Glu Ser Asn Ile Tyr Pro Lys Phe Ile Ser Phe
                        755                 760                 765

Met Glu Gln Tyr Ile Asn Asn Ile Asn Ile Lys Thr Thr Ala Phe Ile
                        770                 775                 780

Arg Lys Cys Thr Asn Ile Thr Glu Lys Glu Lys Leu Gln Leu Ile Asn
        785                 790                 795                 800

Gln Asn Thr Phe Asn Asn Leu Asp Phe Glu Phe Phe Asp Ile Gln Thr
                        805                 810                 815

Ile Glu Asn Leu Leu Thr Ser Glu Thr Asn Leu Ile Ile Lys Glu Lys
                        820                 825                 830

Thr Ser Pro Tyr Asp Leu Leu Leu Phe Ser Leu Gln Glu Ala Asp Arg
                        835                 840                 845

Lys Val Ile Lys Asp Ile Ser Gly Lys Asp Thr Leu Val Gln Tyr Ser
                        850                 855                 860

Asp Thr Ile Asp Leu Ser Tyr Gly Val Asn Gly Asp Ala Leu Tyr Leu
        865                 870                 875                 880

Lys Glu Pro Asn Gln Ser Val Asn Phe Ser Asn Ile Phe Glu Asn
                        885                 890                 895
```

-continued

```
Gly Leu Thr Asn Ser Phe Ser Ile Cys Phe Trp Leu Arg Asn Leu Gly
            900                 905                 910

Gln Asp Asn Leu Ser Ser Asn Leu Ile Gly Asn Ile Val Asn Asn Cys
        915                 920                 925

Gly Trp Gln Ile Tyr Phe Glu Asn Asn Gly Leu Val Phe Ser Met Val
    930                 935                 940

Asp Cys Asn Gly Asn Glu Lys Asn Ile Tyr Leu Ser Asp Val Leu Ser
945                 950                 955                 960

Lys Tyr Trp Tyr Tyr Ile Ser Val Ser Val Asp Arg Leu Arg Asn Lys
                965                 970                 975

Leu Leu Ile Phe Ile Asn Asp Lys Leu Ile Val Asn Glu Ser Ile Glu
            980                 985                 990

Gln Ile Leu Asn Ile Tyr Ser Ser Asn Ile Ile Ser Leu Val Asn Glu
        995                 1000                1005

Asn Asn Pro Ile Cys Ile Glu Glu Leu Ser Ile Leu Asn Lys Ala Leu
    1010                1015                1020

Thr Ser Glu Glu Val Leu Asn Ser Tyr Phe Thr Asn Leu Asn Asn Ser
1025                1030                1035                1040

Tyr Ile Arg Asp Ser Tyr Gly Ala Arg Leu Glu Tyr Asn Lys Asn Tyr
                1045                1050                1055

Glu Leu Tyr Asn Tyr Val Phe Pro Glu Asn Ser Leu Tyr Glu Val Ile
            1060                1065                1070

Glu Asn Asn Asn Met Tyr Leu Ser Ile Lys Asn Ile Lys Asn Thr Asn
        1075                1080                1085

Ile Leu Gly Ala Lys Phe Lys Leu Ile Asn Thr Asp Glu Ser Lys Gln
    1090                1095                1100

Tyr Val Gln Lys Trp Asp Glu Val Ile Ile Cys Val Leu Gly Asp Thr
1105                1110                1115                1120

Glu Lys Tyr Ala Asp Ile Gln Ala Gly Asn Asn Arg Ile Gln Leu Val
                1125                1130                1135

Asn Ser Lys Asp Asn Ala Arg Lys Ile Ile Val Asn Asn Asn Ile Phe
            1140                1145                1150

Arg Pro Asn Cys Val Leu Phe Ser Tyr Asn Asn Lys Tyr Leu Ser Leu
        1155                1160                1165

Ser Leu Arg Asn Arg Asn Tyr Asn Trp Met Ile Cys Asn Asp Asn Ser
    1170                1175                1180

Phe Ile Pro Lys His Ala His Leu Trp Ile Leu Lys Lys Ile
1185                1190                1195

<210> SEQ ID NO 35
<211> LENGTH: 155
<212> TYPE: PRT
<213> ORGANISM: Homo sapiens

<400> SEQUENCE: 35

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
```

```
                 65                  70                  75                  80
Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 36
<211> LENGTH: 155
<212> TYPE: PRT
<213> ORGANISM: Homo sapiens

<400> SEQUENCE: 36

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 37
<211> LENGTH: 206
<212> TYPE: PRT
<213> ORGANISM: Homo sapiens

<400> SEQUENCE: 37

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
```

-continued

```
                 85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205

<210> SEQ ID NO 38
<211> LENGTH: 204
<212> TYPE: PRT
<213> ORGANISM: Homo sapiens

<400> SEQUENCE: 38

Met Gly Ser Pro Arg Ser Ala Leu Ser Cys Leu Leu His Leu Leu
1               5                   10                  15

Val Leu Cys Leu Gln Ala Gln His Val Arg Glu Gln Ser Leu Val Thr
            20                  25                  30

Asp Gln Leu Ser Arg Arg Leu Ile Arg Thr Tyr Gln Leu Tyr Ser Arg
        35                  40                  45

Thr Ser Gly Lys His Val Gln Val Leu Ala Asn Lys Arg Ile Asn Ala
    50                  55                  60

Met Ala Glu Asp Gly Asp Pro Phe Ala Lys Leu Ile Val Glu Thr Asp
65                  70                  75                  80

Thr Phe Gly Ser Arg Val Arg Val Arg Gly Ala Glu Thr Gly Leu Tyr
                85                  90                  95

Ile Cys Met Asn Lys Lys Gly Lys Leu Ile Ala Lys Ser Asn Gly Lys
            100                 105                 110

Gly Lys Asp Cys Val Phe Thr Glu Ile Val Leu Glu Asn Asn Tyr Thr
        115                 120                 125

Ala Leu Gln Asn Ala Lys Tyr Glu Gly Trp Tyr Met Ala Phe Thr Arg
    130                 135                 140

Lys Gly Arg Pro Arg Lys Gly Ser Lys Thr Arg Gln His Gln Arg Glu
145                 150                 155                 160

Val His Phe Met Lys Arg Leu Pro Arg Gly His His Thr Thr Glu Gln
                165                 170                 175

Ser Leu Arg Phe Glu Phe Leu Asn Tyr Pro Pro Phe Thr Arg Ser Leu
            180                 185                 190

Arg Gly Ser Gln Arg Thr Trp Ala Pro Glu Pro Arg
        195                 200

<210> SEQ ID NO 39
<211> LENGTH: 208
<212> TYPE: PRT
<213> ORGANISM: Homo sapiens

<400> SEQUENCE: 39

Met Ala Pro Leu Gly Glu Val Gly Asn Tyr Phe Gly Val Gln Asp Ala
```

-continued

```
                1               5                      10                      15
Val Pro Phe Gly Asn Val Pro Val Leu Pro Val Asp Ser Pro Val Leu
                   20                      25                      30

Leu Ser Asp His Leu Gly Gln Ser Glu Ala Gly Gly Leu Pro Arg Gly
                   35                      40                      45

Pro Ala Val Thr Asp Leu Asp His Leu Lys Gly Ile Leu Arg Arg Arg
             50                      55                      60

Gln Leu Tyr Cys Arg Thr Gly Phe His Leu Glu Ile Phe Pro Asn Gly
65                      70                      75                      80

Thr Ile Gln Gly Thr Arg Lys Asp His Ser Arg Phe Gly Ile Leu Glu
                   85                      90                      95

Phe Ile Ser Ile Ala Val Gly Leu Val Ser Ile Arg Gly Val Asp Ser
                   100                     105                     110

Gly Leu Tyr Leu Gly Met Asn Glu Lys Gly Glu Leu Tyr Gly Ser Glu
                   115                     120                     125

Lys Leu Thr Gln Glu Cys Val Phe Arg Glu Gln Phe Glu Glu Asn Trp
             130                     135                     140

Tyr Asn Thr Tyr Ser Ser Asn Leu Tyr Lys His Val Asp Thr Gly Arg
145                     150                     155                     160

Arg Tyr Tyr Val Ala Leu Asn Lys Asp Gly Thr Pro Arg Glu Gly Thr
                   165                     170                     175

Arg Thr Lys Arg His Gln Lys Phe Thr His Phe Leu Pro Arg Pro Val
                   180                     185                     190

Asp Pro Asp Lys Val Pro Glu Leu Tyr Lys Asp Ile Leu Ser Gln Ser
             195                     200                     205
```

<210> SEQ ID NO 40
<211> LENGTH: 216
<212> TYPE: PRT
<213> ORGANISM: Homo sapiens

<400> SEQUENCE: 40

```
Met Gly Ala Ala Arg Leu Leu Pro Asn Leu Thr Leu Cys Leu Gln Leu
1               5                       10                      15

Leu Ile Leu Cys Cys Gln Thr Gln Gly Glu Asn His Pro Ser Pro Asn
                   20                      25                      30

Phe Asn Gln Tyr Val Arg Asp Gln Gly Ala Met Thr Asp Gln Leu Ser
                   35                      40                      45

Arg Arg Gln Ile Arg Glu Tyr Gln Leu Tyr Ser Arg Thr Ser Gly Lys
             50                      55                      60

His Val Gln Val Thr Gly Arg Arg Ile Ser Ala Thr Ala Glu Asp Gly
65                      70                      75                      80

Asn Lys Phe Ala Lys Leu Ile Val Glu Thr Asp Thr Phe Gly Ser Arg
                   85                      90                      95

Val Arg Ile Lys Gly Ala Glu Ser Glu Lys Tyr Ile Cys Met Asn Lys
                   100                     105                     110

Arg Gly Lys Leu Ile Gly Lys Pro Ser Gly Lys Ser Lys Asp Cys Val
                   115                     120                     125

Phe Thr Glu Ile Val Leu Glu Asn Asn Tyr Thr Ala Phe Gln Asn Ala
             130                     135                     140

Arg His Glu Gly Trp Phe Met Ala Phe Thr Arg Gln Gly Arg Pro Arg
145                     150                     155                     160

Gln Ala Ser Arg Ser Arg Gln Asn Gln Arg Glu Ala His Phe Ile Lys
                   165                     170                     175
```

```
Arg Leu Tyr Gln Gly Gln Leu Pro Phe Pro Asn His Ala Glu Lys Gln
                175                 180                 185                 190

Lys Gln Phe Glu Phe Val Gly Ser Ala Pro Thr Arg Thr Lys Arg
        195                 200                 205

Thr Arg Arg Pro Gln Pro Leu Thr
    210                 215

<210> SEQ ID NO 41
<211> LENGTH: 207
<212> TYPE: PRT
<213> ORGANISM: Homo sapiens

<400> SEQUENCE: 41

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 42
<211> LENGTH: 180
<212> TYPE: PRT
<213> ORGANISM: Homo sapiens

<400> SEQUENCE: 42

Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
50                  55                  60

Tyr Leu Asp Ser Arg Arg Ala Gln Asp Phe Val Gln Trp Leu Met Asn
65                  70                  75                  80
```

```
Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 43
<211> LENGTH: 176
<212> TYPE: PRT
<213> ORGANISM: Homo sapiens

<400> SEQUENCE: 43

Met Thr Met Cys Ser Gly Ala Arg Leu Ala Leu Leu Val Tyr Gly Ile
1               5                   10                  15

Ile Met His Ser Ser Val Tyr Ser Ser Pro Ala Ala Gly Leu Arg
                20                  25                  30

Phe Pro Gly Ile Arg Pro Glu Glu Glu Ala Tyr Gly Glu Asp Gly Asn
            35                  40                  45

Pro Leu Pro Asp Phe Asp Gly Ser Glu Pro Pro Gly Ala Gly Ser Pro
    50                  55                  60

Ala Ser Ala Pro Arg Ala Ala Ala Trp Tyr Arg Pro Ala Gly Arg
65                  70                  75                  80

Arg Asp Val Ala His Gly Ile Leu Asn Glu Ala Tyr Arg Lys Val Leu
                85                  90                  95

Asp Gln Leu Ser Ala Gly Lys His Leu Gln Ser Leu Val Ala Arg Gly
            100                 105                 110

Val Gly Gly Ser Leu Gly Gly Gly Ala Gly Asp Asp Ala Glu Pro Leu
        115                 120                 125

Ser Lys Arg His Ser Asp Gly Ile Phe Thr Asp Ser Tyr Ser Arg Tyr
    130                 135                 140

Arg Lys Gln Met Ala Val Lys Lys Tyr Leu Ala Ala Val Leu Gly Lys
145                 150                 155                 160

Arg Tyr Lys Gln Arg Val Lys Asn Lys Gly Arg Arg Ile Ala Tyr Leu
                165                 170                 175

<210> SEQ ID NO 44
<211> LENGTH: 108
<212> TYPE: PRT
<213> ORGANISM: Homo sapiens

<400> SEQUENCE: 44

Met Pro Leu Trp Val Phe Phe Val Ile Leu Thr Leu Ser Asn Ser
1               5                   10                  15

Ser His Cys Ser Pro Pro Pro Leu Thr Leu Arg Met Arg Arg Tyr
                20                  25                  30

Ala Asp Ala Ile Phe Thr Asn Ser Tyr Arg Lys Val Leu Gly Gln Leu
            35                  40                  45
```

```
Ser Ala Arg Lys Leu Leu Gln Asp Ile Met Ser Arg Gln Gln Gly Glu
    50                  55                  60

Ser Asn Gln Glu Arg Gly Ala Arg Ala Arg Leu Gly Arg Gln Val Asp
65                  70                  75                  80

Ser Met Trp Ala Glu Gln Lys Gln Met Glu Leu Glu Ser Ile Leu Val
                85                  90                  95

Ala Leu Leu Gln Lys His Ser Arg Asn Ser Gln Gly
            100                 105

<210> SEQ ID NO 45
<211> LENGTH: 170
<212> TYPE: PRT
<213> ORGANISM: Homo sapiens

<400> SEQUENCE: 45

Met Asp Thr Arg Asn Lys Ala Gln Leu Leu Val Leu Leu Thr Leu Leu
1               5                   10                  15

Ser Val Leu Phe Ser Gln Thr Ser Ala Trp Pro Leu Tyr Arg Ala Pro
                20                  25                  30

Ser Ala Leu Arg Leu Gly Asp Arg Ile Pro Phe Glu Gly Ala Asn Glu
            35                  40                  45

Pro Asp Gln Val Ser Leu Lys Glu Asp Ile Asp Met Leu Gln Asn Ala
    50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95

Leu Ser Ala Lys Lys Tyr Leu Glu Ser Leu Met Gly Lys Arg Val Ser
            100                 105                 110

Ser Asn Ile Ser Glu Asp Pro Val Pro Val Lys Arg His Ser Asp Ala
        115                 120                 125

Val Phe Thr Asp Asn Tyr Thr Arg Leu Arg Lys Gln Met Ala Val Lys
    130                 135                 140

Lys Tyr Leu Asn Ser Ile Leu Asn Gly Lys Arg Ser Ser Glu Gly Glu
145                 150                 155                 160

Ser Pro Asp Phe Pro Glu Glu Leu Glu Lys
                165                 170

<210> SEQ ID NO 46
<211> LENGTH: 169
<212> TYPE: PRT
<213> ORGANISM: Homo sapiens

<400> SEQUENCE: 46

Met Asp Thr Arg Asn Lys Ala Gln Leu Leu Val Leu Leu Thr Leu Leu
1               5                   10                  15

Ser Val Leu Phe Ser Gln Thr Ser Ala Trp Pro Leu Tyr Arg Ala Pro
                20                  25                  30

Ser Ala Leu Arg Leu Gly Asp Arg Ile Pro Phe Glu Gly Ala Asn Glu
            35                  40                  45

Pro Asp Gln Val Ser Leu Lys Glu Asp Ile Asp Met Leu Gln Asn Ala
    50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95
```

Leu Ser Ala Lys Lys Tyr Leu Glu Ser Leu Met Gly Lys Arg Val Ser
            100                 105                 110

Asn Ile Ser Glu Asp Pro Val Pro Val Lys Arg His Ser Asp Ala Val
        115                 120                 125

Phe Thr Asp Asn Tyr Thr Arg Leu Arg Lys Gln Met Ala Val Lys Lys
    130                 135                 140

Tyr Leu Asn Ser Ile Leu Asn Gly Lys Arg Ser Ser Glu Gly Glu Ser
145                 150                 155                 160

Pro Asp Phe Pro Glu Glu Leu Glu Lys
                165

<210> SEQ ID NO 47
<211> LENGTH: 153
<212> TYPE: PRT
<213> ORGANISM: Homo sapiens

<400> SEQUENCE: 47

Met Val Ala Thr Lys Thr Phe Ala Leu Leu Leu Ser Leu Phe Leu
 1               5                  10                  15

Ala Val Gly Leu Gly Glu Lys Lys Glu Gly His Phe Ser Ala Leu Pro
            20                  25                  30

Ser Leu Pro Val Gly Ser His Ala Lys Val Ser Ser Pro Gln Pro Arg
        35                  40                  45

Gly Pro Arg Tyr Ala Glu Gly Thr Phe Ile Ser Asp Tyr Ser Ile Ala
    50                  55                  60

Met Asp Lys Ile His Gln Gln Asp Phe Val Asn Trp Leu Leu Ala Gln
65                  70                  75                  80

Lys Gly Lys Lys Asn Asp Trp Lys His Asn Ile Thr Gln Arg Glu Ala
                85                  90                  95

Arg Ala Leu Glu Leu Ala Ser Gln Ala Asn Arg Lys Glu Glu Glu Ala
            100                 105                 110

Val Glu Pro Gln Ser Ser Pro Ala Lys Asn Pro Ser Asp Glu Asp Leu
        115                 120                 125

Leu Arg Asp Leu Leu Ile Gln Glu Leu Leu Ala Cys Leu Leu Asp Gln
    130                 135                 140

Thr Asn Leu Cys Arg Leu Arg Ser Arg
145                 150

<210> SEQ ID NO 48
<211> LENGTH: 121
<212> TYPE: PRT
<213> ORGANISM: Homo sapiens

<400> SEQUENCE: 48

Met Ala Pro Arg Pro Leu Leu Leu Leu Leu Leu Leu Gly Gly Ser
 1               5                  10                  15

Ala Ala Arg Pro Ala Pro Pro Arg Ala Arg His Ser Asp Gly Thr
            20                  25                  30

Phe Thr Ser Glu Leu Ser Arg Leu Arg Glu Gly Ala Arg Leu Gln Arg
        35                  40                  45

Leu Leu Gln Gly Leu Val Gly Lys Arg Ser Glu Gln Asp Ala Glu Asn
    50                  55                  60

Ser Met Ala Trp Thr Arg Leu Ser Ala Gly Leu Leu Cys Pro Ser Gly
65                  70                  75                  80

Ser Asn Met Pro Ile Leu Gln Ala Trp Met Pro Leu Asp Gly Thr Trp
                85                  90                  95

```
Ser Pro Trp Leu Pro Pro Gly Pro Met Val Ser Glu Pro Ala Gly Ala
                100                 105                 110

Ala Ala Glu Gly Thr Leu Arg Pro Arg
            115                 120

<210> SEQ ID NO 49
<211> LENGTH: 101
<212> TYPE: PRT
<213> ORGANISM: Homo sapiens

<400> SEQUENCE: 49

Met Gln Arg Leu Cys Val Tyr Val Leu Ile Phe Ala Leu Ala Leu Ala
  1               5                  10                  15

Ala Phe Ser Glu Ala Ser Trp Lys Pro Arg Ser Gln Gln Pro Asp Ala
             20                  25                  30

Pro Leu Gly Thr Gly Ala Asn Arg Asp Leu Glu Leu Pro Trp Leu Glu
         35                  40                  45

Gln Gln Gly Pro Ala Ser His His Arg Arg Gln Leu Gly Pro Gln Gly
     50                  55                  60

Pro Pro His Leu Val Ala Asp Pro Ser Lys Lys Gln Gly Pro Trp Leu
 65                  70                  75                  80

Glu Glu Glu Glu Glu Ala Tyr Gly Trp Met Asp Phe Gly Arg Arg Ser
                 85                  90                  95

Ala Glu Asp Glu Asn
            100

<210> SEQ ID NO 50
<211> LENGTH: 148
<212> TYPE: PRT
<213> ORGANISM: Homo sapiens

<400> SEQUENCE: 50

Met Arg Gly Arg Glu Leu Pro Leu Val Leu Ala Leu Val Leu Cys
  1               5                  10                  15

Leu Ala Pro Arg Gly Arg Ala Val Pro Leu Pro Ala Gly Gly Gly Thr
             20                  25                  30

Val Leu Thr Lys Met Tyr Pro Arg Gly Asn His Trp Ala Val Gly His
         35                  40                  45

Leu Met Gly Lys Lys Ser Thr Gly Glu Ser Ser Val Ser Glu Arg
     50                  55                  60

Gly Ser Leu Lys Gln Gln Leu Arg Glu Tyr Ile Arg Trp Glu Glu Ala
 65                  70                  75                  80

Ala Arg Asn Leu Leu Gly Leu Ile Glu Ala Lys Glu Asn Arg Asn His
                 85                  90                  95

Gln Pro Pro Gln Pro Lys Ala Leu Gly Asn Gln Gln Pro Ser Trp Asp
                100                 105                 110

Ser Glu Asp Ser Ser Asn Phe Lys Asp Val Gly Ser Lys Gly Lys Val
            115                 120                 125

Gly Arg Leu Ser Ala Pro Gly Ser Gln Arg Glu Gly Arg Asn Pro Gln
        130                 135                 140

Leu Asn Gln Gln
145

<210> SEQ ID NO 51
<211> LENGTH: 115
<212> TYPE: PRT
<213> ORGANISM: Homo sapiens
```

```
<400> SEQUENCE: 51

Met Asn Ser Gly Val Cys Leu Cys Val Leu Met Ala Val Leu Ala Ala
1               5                   10                  15

Gly Ala Leu Thr Gln Pro Val Pro Pro Ala Asp Pro Ala Gly Ser Gly
            20                  25                  30

Leu Gln Arg Ala Glu Glu Ala Pro Arg Arg Gln Leu Arg Val Ser Gln
        35                  40                  45

Arg Thr Asp Gly Glu Ser Arg Ala His Leu Gly Ala Leu Leu Ala Arg
    50                  55                  60

Tyr Ile Gln Gln Ala Arg Lys Ala Pro Ser Gly Arg Met Ser Ile Val
65                  70                  75                  80

Lys Asn Leu Gln Asn Leu Asp Pro Ser His Arg Ile Ser Asp Arg Asp
                85                  90                  95

Tyr Met Gly Trp Met Asp Phe Gly Arg Arg Ser Ala Glu Glu Tyr Glu
            100                 105                 110

Tyr Pro Ser
        115

<210> SEQ ID NO 52
<211> LENGTH: 196
<212> TYPE: PRT
<213> ORGANISM: Homo sapiens

<400> SEQUENCE: 52

Met Arg Leu Pro Leu Leu Val Ser Ala Gly Val Leu Val Ala Leu
1               5                   10                  15

Leu Pro Cys Pro Pro Cys Arg Ala Leu Leu Ser Arg Gly Pro Val Pro
            20                  25                  30

Gly Ala Arg Gln Ala Pro Gln His Pro Gln Pro Leu Asp Phe Phe Gln
        35                  40                  45

Pro Pro Pro Gln Ser Glu Gln Pro Gln Gln Pro Gln Ala Arg Pro Val
    50                  55                  60

Leu Leu Arg Met Gly Glu Glu Tyr Phe Leu Arg Leu Gly Asn Leu Asn
65                  70                  75                  80

Lys Ser Pro Ala Ala Pro Leu Ser Pro Ala Ser Ser Leu Leu Ala Gly
                85                  90                  95

Gly Ser Gly Ser Arg Pro Ser Pro Glu Gln Ala Thr Ala Asn Phe Phe
            100                 105                 110

Arg Val Leu Leu Gln Gln Leu Leu Pro Arg Arg Ser Leu Asp Ser
        115                 120                 125

Pro Ala Ala Leu Ala Glu Arg Gly Ala Arg Asn Ala Leu Gly Gly His
    130                 135                 140

Gln Glu Ala Pro Glu Arg Arg Ser Glu Glu Pro Pro Ile Ser
145                 150                 155                 160

Leu Asp Leu Thr Phe His Leu Leu Arg Glu Val Leu Glu Met Ala Arg
                165                 170                 175

Ala Glu Gln Leu Ala Gln Gln Ala His Ser Asn Arg Lys Leu Met Glu
            180                 185                 190

Ile Ile Gly Lys
        195

<210> SEQ ID NO 53
<211> LENGTH: 177
<212> TYPE: PRT
<213> ORGANISM: Homo sapiens
```

```
<400> SEQUENCE: 53

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
                20                  25                  30

Arg Leu Lys Arg Ala Val Ser Glu His Gln Leu Leu His Asp Lys Gly
            35                  40                  45

Lys Ser Ile Gln Asp Leu Arg Arg Phe Phe Leu His His Leu Ile
        50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
                100                 105                 110

Thr Tyr Lys Glu Gln Pro Leu Lys Thr Pro Gly Lys Lys Lys Lys Gly
                115                 120                 125

Lys Pro Gly Lys Arg Lys Glu Gln Glu Lys Lys Lys Arg Arg Thr Arg
                130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                    165                 170                 175

His

<210> SEQ ID NO 54
<211> LENGTH: 200
<212> TYPE: PRT
<213> ORGANISM: Homo sapiens

<400> SEQUENCE: 54

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
                115                 120                 125

Leu Leu Glu Tyr Lys Ile Pro Arg Asn Glu Ala Asp Gly Met Pro Ile
                130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                    165                 170                 175

Arg Phe Ile Ser Ser His Gln Thr Gly Ile Pro Ala Arg Gly Ser His
```

180                 185                 190
Tyr Ile Ala Asn Asn Lys Lys Met
        195                 200

<210> SEQ ID NO 55
<211> LENGTH: 150
<212> TYPE: PRT
<213> ORGANISM: Homo sapiens

<400> SEQUENCE: 55

Met Tyr Gly Lys Ile Ile Phe Val Leu Leu Leu Ser Ala Ile Val Ser
1               5                   10                  15

Ile Ser Ala Ser Ser Thr Thr Gly Val Ala Met His Thr Ser Thr Ser
                20                  25                  30

Ser Ser Val Thr Lys Ser Tyr Ile Ser Ser Gln Thr Asn Asp Thr His
            35                  40                  45

Lys Arg Asp Thr Tyr Ala Ala Thr Pro Arg Ala His Glu Val Ser Glu
    50                  55                  60

Ile Ser Val Arg Thr Val Tyr Pro Pro Glu Glu Glu Thr Gly Glu Arg
65                  70                  75                  80

Val Gln Leu Ala His His Phe Ser Glu Pro Glu Ile Thr Leu Ile Ile
                85                  90                  95

Phe Gly Val Met Ala Gly Val Ile Gly Thr Ile Leu Leu Ile Ser Tyr
            100                 105                 110

Gly Ile Arg Arg Leu Ile Lys Lys Ser Pro Ser Asp Val Lys Pro Leu
        115                 120                 125

Pro Ser Pro Asp Thr Asp Val Pro Leu Ser Ser Val Glu Ile Glu Asn
    130                 135                 140

Pro Glu Thr Ser Asp Gln
145                 150

<210> SEQ ID NO 56
<211> LENGTH: 202
<212> TYPE: PRT
<213> ORGANISM: Homo sapiens

<400> SEQUENCE: 56

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
                20                  25                  30

Thr Cys Ala Ile Arg His Pro Cys His Asn Asn Leu Met Asn Gln Ile
            35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His

```
                145                 150                 155                 160
Val Gly His Val Asp Val Thr Tyr Gly Pro Asp Thr Ser Gly Lys Asp
                    165                 170                 175

Val Phe Gln Lys Lys Leu Gly Cys Gln Leu Leu Gly Lys Tyr Lys
                180                 185                 190

Gln Ile Ile Ala Val Leu Ala Gln Ala Phe
            195                 200

<210> SEQ ID NO 57
<211> LENGTH: 201
<212> TYPE: PRT
<213> ORGANISM: Homo sapiens

<400> SEQUENCE: 57

Met Ser Arg Arg Glu Gly Ser Leu Glu Asp Pro Gln Thr Asp Ser Ser
  1               5                  10                  15

Val Ser Leu Leu Pro His Leu Glu Ala Lys Ile Arg Gln Thr His Ser
                 20                  25                  30

Leu Ala His Leu Leu Thr Lys Tyr Ala Glu Gln Leu Leu Gln Glu Tyr
             35                  40                  45

Val Gln Leu Gln Gly Asp Pro Phe Gly Leu Pro Ser Phe Ser Pro Pro
         50                  55                  60

Arg Leu Pro Val Ala Gly Leu Ser Ala Pro Ala Pro Ser His Ala Gly
 65                  70                  75                  80

Leu Pro Val His Glu Arg Leu Arg Leu Asp Ala Ala Leu Ala Ala
                 85                  90                  95

Leu Pro Pro Leu Leu Asp Ala Val Cys Arg Arg Gln Ala Glu Leu Asn
            100                 105                 110

Pro Arg Ala Pro Arg Leu Leu Arg Arg Leu Glu Asp Ala Ala Arg Gln
            115                 120                 125

Ala Arg Ala Leu Gly Ala Ala Val Glu Ala Leu Leu Ala Ala Leu Gly
        130                 135                 140

Ala Ala Asn Arg Gly Pro Arg Ala Glu Pro Ala Ala Thr Ala Ser
145                 150                 155                 160

Ala Ala Ser Ala Thr Gly Val Phe Pro Ala Lys Val Leu Gly Leu Arg
                165                 170                 175

Val Cys Gly Leu Tyr Arg Glu Trp Leu Ser Arg Thr Glu Gly Asp Leu
            180                 185                 190

Gly Gln Leu Leu Pro Gly Gly Ser Ala
        195                 200

<210> SEQ ID NO 58
<211> LENGTH: 225
<212> TYPE: PRT
<213> ORGANISM: Homo sapiens

<400> SEQUENCE: 58

Met Asp Leu Arg Ala Gly Asp Ser Trp Gly Met Leu Ala Cys Leu Cys
  1               5                  10                  15

Thr Val Leu Trp His Leu Pro Ala Val Pro Ala Leu Asn Arg Thr Gly
                 20                  25                  30

Asp Pro Gly Pro Gly Pro Ser Ile Gln Lys Thr Tyr Asp Leu Thr Arg
             35                  40                  45

Tyr Leu Glu His Gln Leu Arg Ser Leu Ala Gly Thr Tyr Leu Asn Tyr
         50                  55                  60

Leu Gly Pro Pro Phe Asn Glu Pro Asp Phe Asn Pro Pro Arg Leu Gly
```

-continued

```
                65                  70                  75                  80
Ala Glu Thr Leu Pro Arg Ala Thr Val Asp Leu Glu Val Trp Arg Ser
                    85                  90                  95

Leu Asn Asp Lys Leu Arg Leu Thr Gln Asn Tyr Glu Ala Tyr Ser His
                100                 105                 110

Leu Leu Cys Tyr Leu Arg Gly Leu Asn Arg Gln Ala Ala Thr Ala Glu
                115                 120                 125

Leu Arg Arg Ser Leu Ala His Phe Cys Thr Ser Leu Gln Gly Leu Leu
            130                 135                 140

Gly Ser Ile Ala Gly Val Met Ala Ala Leu Gly Tyr Pro Leu Pro Gln
145                 150                 155                 160

Pro Leu Pro Gly Thr Glu Pro Thr Trp Thr Pro Gly Pro Ala His Ser
                165                 170                 175

Asp Phe Leu Gln Lys Met Asp Asp Phe Trp Leu Leu Lys Glu Leu Gln
                180                 185                 190

Thr Trp Leu Trp Arg Ser Ala Lys Asp Phe Asn Arg Leu Lys Lys Lys
                195                 200                 205

Met Gln Pro Pro Ala Ala Ala Val Thr Leu His Leu Gly Ala His Gly
    210                 215                 220

Phe
225

<210> SEQ ID NO 59
<211> LENGTH: 269
<212> TYPE: PRT
<213> ORGANISM: Homo sapiens

<400> SEQUENCE: 59

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205
```

```
Lys Lys Met Glu Lys Arg Phe Val Phe Asn Lys Ile Glu Ile Asn Asn
210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
                260                 265

<210> SEQ ID NO 60
<211> LENGTH: 153
<212> TYPE: PRT
<213> ORGANISM: Homo sapiens

<400> SEQUENCE: 60

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
                20                  25                  30

Gln Leu Glu His Leu Leu Leu Asp Leu Gln Met Ile Leu Asn Gly Ile
                35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
                115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr
145                 150

<210> SEQ ID NO 61
<211> LENGTH: 212
<212> TYPE: PRT
<213> ORGANISM: Homo sapiens

<400> SEQUENCE: 61

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
                35                  40                  45

Ser Ser Glu Arg Ile Asp Lys Gln Ile Arg Tyr Ile Leu Asp Gly Ile
        50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
                100                 105                 110
```

Val Lys Ile Ile Thr Gly Leu Leu Glu Phe Glu Val Tyr Leu Glu Tyr
            115                 120                 125

Leu Gln Asn Arg Phe Glu Ser Ser Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 62
<211> LENGTH: 99
<212> TYPE: PRT
<213> ORGANISM: Homo sapiens

<400> SEQUENCE: 62

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 63
<211> LENGTH: 178
<212> TYPE: PRT
<213> ORGANISM: Homo sapiens

<400> SEQUENCE: 63

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg

-continued

```
            115                 120                 125
Phe Leu Pro Cys Glu Asn Lys Ser Lys Ala Val Glu Gln Val Lys Asn
130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 64
<211> LENGTH: 558
<212> TYPE: PRT
<213> ORGANISM: Homo sapiens

<400> SEQUENCE: 64

Met Ala Ala Leu Thr Arg Asp Pro Gln Phe Gln Lys Leu Gln Gln Trp
  1               5                  10                  15

Tyr Arg Glu His Arg Ser Glu Leu Asn Leu Arg Arg Leu Phe Asp Ala
                 20                  25                  30

Asn Lys Asp Arg Phe Asn His Phe Ser Leu Thr Leu Asn Thr Asn His
             35                  40                  45

Gly His Ile Leu Val Asp Tyr Ser Lys Asn Leu Val Thr Glu Asp Val
 50                  55                  60

Met Arg Met Leu Val Asp Leu Ala Lys Ser Arg Gly Val Glu Ala Ala
 65                  70                  75                  80

Arg Glu Arg Met Phe Asn Gly Glu Lys Ile Asn Tyr Thr Glu Gly Arg
                 85                  90                  95

Ala Val Leu His Val Ala Leu Arg Asn Arg Ser Asn Thr Pro Ile Leu
            100                 105                 110

Val Asp Gly Lys Asp Val Met Pro Glu Val Asn Lys Val Leu Asp Lys
            115                 120                 125

Met Lys Ser Phe Cys Gln Arg Val Arg Ser Gly Asp Trp Lys Gly Tyr
130                 135                 140

Thr Gly Lys Thr Ile Thr Asp Val Ile Asn Ile Gly Ile Gly Gly Ser
145                 150                 155                 160

Asp Leu Gly Pro Leu Met Val Thr Glu Ala Leu Lys Pro Tyr Ser Ser
                165                 170                 175

Gly Gly Pro Arg Val Trp Tyr Val Ser Asn Ile Asp Gly Thr His Ile
            180                 185                 190

Ala Lys Thr Leu Ala Gln Leu Asn Pro Glu Ser Ser Leu Phe Ile Ile
        195                 200                 205

Ala Ser Lys Thr Phe Thr Thr Gln Glu Thr Ile Thr Asn Ala Glu Thr
210                 215                 220

Ala Lys Glu Trp Phe Leu Gln Ala Ala Lys Asp Pro Ser Ala Val Ala
225                 230                 235                 240

Lys His Phe Val Ala Leu Ser Thr Asn Thr Thr Lys Val Lys Glu Phe
                245                 250                 255

Gly Ile Asp Pro Gln Asn Met Phe Glu Phe Trp Asp Trp Val Gly Gly
            260                 265                 270

Arg Tyr Ser Leu Trp Ser Ala Ile Gly Leu Ser Ile Ala Leu His Val
        275                 280                 285

Gly Phe Asp Asn Phe Glu Gln Leu Leu Ser Gly Ala His Trp Met Asp
290                 295                 300

Gln His Phe Arg Thr Thr Pro Leu Glu Lys Asn Ala Pro Val Leu Leu
```

```
                305                 310                 315                 320

Ala Leu Leu Gly Ile Trp Tyr Ile Asn Cys Phe Gly Cys Glu Thr His
                325                 330                 335

Ala Met Leu Pro Tyr Asp Gln Tyr Leu His Arg Phe Ala Ala Tyr Phe
                340                 345                 350

Gln Gln Gly Asp Met Glu Ser Asn Gly Lys Tyr Ile Thr Lys Ser Gly
                355                 360                 365

Thr Arg Val Asp His Gln Thr Gly Pro Ile Val Trp Gly Glu Pro Gly
                370                 375                 380

Thr Asn Gly Gln His Ala Phe Tyr Gln Leu Ile His Gln Gly Thr Lys
385                 390                 395                 400

Met Ile Pro Cys Asp Phe Leu Ile Pro Val Gln Thr Gln His Pro Ile
                405                 410                 415

Arg Lys Gly Leu His His Lys Ile Leu Leu Ala Asn Phe Leu Ala Gln
                420                 425                 430

Thr Glu Ala Leu Met Arg Gly Lys Ser Thr Glu Glu Ala Arg Lys Glu
                435                 440                 445

Leu Gln Ala Ala Gly Lys Ser Pro Glu Asp Leu Glu Arg Leu Leu Pro
            450                 455                 460

His Lys Val Phe Glu Gly Asn Arg Pro Thr Asn Ser Ile Val Phe Thr
465                 470                 475                 480

Lys Leu Thr Pro Phe Met Leu Gly Ala Leu Ala Met Tyr Glu His
                485                 490                 495

Lys Ile Phe Val Gln Gly Ile Ile Trp Asp Ile Asn Ser Phe Asp Gln
                500                 505                 510

Trp Gly Val Glu Leu Gly Lys Gln Leu Ala Lys Lys Ile Glu Pro Glu
                515                 520                 525

Leu Asp Gly Ser Ala Gln Val Thr Ser His Asp Ala Ser Thr Asn Gly
            530                 535                 540

Leu Ile Asn Phe Ile Lys Gln Gln Arg Glu Ala Arg Val Gln
545                 550                 555

<210> SEQ ID NO 65
<211> LENGTH: 371
<212> TYPE: PRT
<213> ORGANISM: Homo sapiens

<400> SEQUENCE: 65

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
                115                 120                 125
```

Ser Ala Pro Ala Ala Arg Ala Pro Gln Ala Leu Ala Arg Ala Ser Gly
            130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
            245                 250                 255

Cys Val Pro Leu Met Arg Cys Gly Gly Cys Cys Asn Asp Glu Gly Leu
        260                 265                 270

Glu Cys Val Pro Thr Glu Glu Ser Asn Ile Thr Met Gln Ile Met Arg
    275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
            325                 330                 335

Asp Pro Gln Thr Cys Lys Cys Ser Cys Lys Asn Thr Asp Ser Arg Cys
        340                 345                 350

Lys Ala Arg Gln Leu Glu Leu Asn Glu Arg Thr Cys Arg Ser Leu Thr
    355                 360                 365

Arg Lys Asp
    370

<210> SEQ ID NO 66
<211> LENGTH: 153
<212> TYPE: PRT
<213> ORGANISM: Homo sapiens

<400> SEQUENCE: 66

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 67
<211> LENGTH: 180
<212> TYPE: PRT
<213> ORGANISM: Homo sapiens

<400> SEQUENCE: 67

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180

<210> SEQ ID NO 68
<211> LENGTH: 54
<212> TYPE: PRT
<213> ORGANISM: Homo sapiens

<400> SEQUENCE: 68

Met Asn Ser Asp Ser Glu Cys Pro Leu Ser His Asp Gly Tyr Cys Leu
1               5                   10                  15

His Asp Gly Val Cys Met Tyr Ile Glu Ala Leu Asp Lys Tyr Ala Cys
            20                  25                  30

Asn Cys Val Val Gly Tyr Ile Gly Glu Arg Cys Gln Tyr Arg Asp Leu
        35                  40                  45

Lys Trp Trp Glu Leu Arg
    50

<210> SEQ ID NO 69
<211> LENGTH: 257
<212> TYPE: PRT
<213> ORGANISM: Homo sapiens

<400> SEQUENCE: 69

```
Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
            115                 120                 125

Val Ala Asn Arg Thr Ser Arg Arg Lys Arg Tyr Ala Glu His Lys Ser
130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
            195                 200                 205

Asp Asp Lys His Trp Asn Ser Gln Cys Lys Thr Ser Gln Thr Tyr Val
210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 70
<211> LENGTH: 247
<212> TYPE: PRT
<213> ORGANISM: Homo sapiens

<400> SEQUENCE: 70

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110
```

```
Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
            245

<210> SEQ ID NO 71
<211> LENGTH: 257
<212> TYPE: PRT
<213> ORGANISM: Homo sapiens

<400> SEQUENCE: 71

Met Ser Ile Leu Phe Tyr Val Ile Phe Leu Ala Tyr Leu Arg Gly Ile
  1               5                  10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
 50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
    210                 215                 220

Arg Ala Leu Thr Ser Glu Asn Asn Lys Leu Val Gly Trp Arg Trp Ile
225                 230                 235                 240
```

```
Arg Ile Asp Thr Ser Cys Val Cys Ala Leu Ser Arg Lys Ile Gly Arg
            245                 250                 255

Thr

<210> SEQ ID NO 72
<211> LENGTH: 210
<212> TYPE: PRT
<213> ORGANISM: Homo sapiens

<400> SEQUENCE: 72

Met Leu Pro Leu Pro Ser Cys Ser Leu Pro Ile Leu Leu Phe Leu
  1               5                  10                  15

Leu Pro Ser Val Pro Ile Glu Ser Gln Pro Pro Ser Thr Leu Pro
                 20                  25                  30

Pro Phe Leu Ala Pro Glu Trp Asp Leu Leu Ser Pro Arg Val Val Leu
                 35                  40                  45

Ser Arg Gly Ala Pro Ala Gly Pro Pro Leu Leu Phe Leu Leu Glu Ala
 50                      55                  60

Gly Ala Phe Arg Glu Ser Ala Gly Ala Pro Ala Asn Arg Ser Arg Arg
 65                      70                  75                  80

Gly Val Ser Glu Thr Ala Pro Ala Ser Arg Arg Gly Glu Leu Ala Val
                 85                  90                  95

Cys Asp Ala Val Ser Gly Trp Val Thr Asp Arg Arg Thr Ala Val Asp
                100                 105                 110

Leu Arg Gly Arg Glu Val Glu Val Leu Gly Glu Val Pro Ala Ala Gly
                115                 120                 125

Gly Ser Pro Leu Arg Gln Tyr Phe Phe Glu Thr Arg Cys Lys Ala Asp
130                     135                 140

Asn Ala Glu Glu Gly Gly Pro Gly Ala Gly Gly Gly Cys Arg Gly
145                     150                 155                 160

Val Asp Arg Arg His Trp Val Ser Glu Cys Lys Ala Lys Gln Ser Tyr
                165                 170                 175

Val Arg Ala Leu Thr Ala Asp Ala Gln Gly Arg Val Gly Trp Arg Trp
                180                 185                 190

Ile Arg Ile Asp Thr Ala Cys Val Cys Thr Leu Leu Ser Arg Thr Gly
                195                 200                 205

Arg Ala
    210

<210> SEQ ID NO 73
<211> LENGTH: 211
<212> TYPE: PRT
<213> ORGANISM: Homo sapiens

<400> SEQUENCE: 73

Met Lys Leu Trp Asp Val Val Ala Val Cys Leu Val Leu Leu His Thr
  1               5                  10                  15

Ala Ser Ala Phe Pro Leu Pro Ala Gly Lys Arg Pro Pro Glu Ala Pro
                 20                  25                  30

Ala Glu Asp Arg Ser Leu Gly Arg Arg Arg Ala Pro Phe Ala Leu Ser
                 35                  40                  45

Ser Asp Ser Asn Met Pro Glu Asp Tyr Pro Asp Gln Phe Asp Asp Val
 50                      55                  60

Met Asp Phe Ile Gln Ala Thr Ile Lys Arg Leu Lys Arg Ser Pro Asp
 65                      70                  75                  80
```

```
Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Leu Ser Phe Leu Asp
            180                 185                 190

Asp Asn Leu Val Tyr His Ile Leu Arg Lys His Ser Ala Lys Arg Cys
            195                 200                 205

Gly Cys Ile
        210

<210> SEQ ID NO 74
<211> LENGTH: 197
<212> TYPE: PRT
<213> ORGANISM: Homo sapiens

<400> SEQUENCE: 74

Met Gln Arg Trp Lys Ala Ala Leu Ala Ser Val Leu Cys Ser Ser
 1               5                  10                  15

Val Leu Ser Ile Trp Met Cys Arg Glu Gly Leu Leu Leu Ser His Arg
                20                  25                  30

Leu Gly Pro Ala Leu Val Pro Leu His Arg Leu Pro Arg Thr Leu Asp
            35                  40                  45

Ala Arg Ile Ala Arg Leu Ala Gln Tyr Arg Ala Leu Leu Gln Gly Ala
        50                  55                  60

Pro Asp Ala Met Glu Leu Arg Glu Leu Thr Pro Trp Ala Gly Arg Pro
65                  70                  75                  80

Pro Gly Pro Arg Arg Ala Gly Pro Arg Arg Arg Ala Arg Ala
                85                  90                  95

Arg Leu Gly Ala Arg Pro Cys Gly Leu Arg Glu Leu Glu Val Arg Val
            100                 105                 110

Ser Glu Leu Gly Leu Gly Tyr Ala Ser Asp Glu Thr Val Leu Phe Arg
        115                 120                 125

Tyr Cys Ala Gly Ala Cys Glu Ala Ala Ala Arg Val Tyr Asp Leu Gly
    130                 135                 140

Leu Arg Arg Leu Arg Gln Arg Arg Arg Leu Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
            180                 185                 190

Glu Cys Ala Cys Val
        195

<210> SEQ ID NO 75
<211> LENGTH: 156
<212> TYPE: PRT
<213> ORGANISM: Homo sapiens
```

```
<400> SEQUENCE: 75

Met Ala Val Gly Lys Phe Leu Leu Gly Ser Leu Leu Leu Leu Ser Leu
1               5                   10                  15

Gln Leu Gly Gln Gly Trp Gly Pro Asp Ala Arg Gly Val Pro Val Ala
            20                  25                  30

Asp Gly Glu Phe Ser Ser Glu Gln Val Ala Lys Ala Gly Gly Thr Trp
        35                  40                  45

Leu Gly Thr His Arg Pro Leu Ala Arg Leu Arg Ala Leu Ser Gly
    50                  55                  60

Pro Cys Gln Leu Trp Ser Leu Thr Leu Ser Val Ala Glu Leu Gly Leu
65                  70                  75                  80

Gly Tyr Ala Ser Glu Glu Lys Val Ile Phe Arg Tyr Cys Ala Gly Ser
                85                  90                  95

Cys Pro Arg Gly Ala Arg Thr Gln His Gly Leu Ala Leu Ala Arg Leu
            100                 105                 110

Gln Gly Gln Gly Arg Ala His Gly Gly Pro Cys Cys Arg Pro Thr Arg
            115                 120                 125

Tyr Thr Asp Val Ala Phe Leu Asp Asp Arg His Arg Trp Gln Arg Leu
            130                 135                 140

Pro Gln Leu Ser Ala Ala Ala Cys Gly Cys Gly Gly
145                 150                 155

<210> SEQ ID NO 76
<211> LENGTH: 220
<212> TYPE: PRT
<213> ORGANISM: Homo sapiens

<400> SEQUENCE: 76

Met Glu Leu Gly Leu Gly Gly Leu Ser Thr Leu Ser His Cys Pro Trp
1               5                   10                  15

Pro Arg Gln Gln Pro Ala Leu Trp Pro Thr Leu Ala Ala Leu Ala Leu
            20                  25                  30

Leu Ser Ser Val Ala Glu Ala Ser Leu Gly Ser Ala Pro Arg Ser Pro
        35                  40                  45

Ala Pro Arg Glu Gly Pro Pro Val Leu Ala Ser Pro Ala Gly His
    50                  55                  60

Leu Pro Gly Gly Arg Thr Ala Arg Trp Cys Ser Gly Arg Ala Arg Arg
65                  70                  75                  80

Pro Pro Pro Gln Pro Ser Arg Pro Ala Pro Pro Ala Pro Pro
                85                  90                  95

Ser Ala Leu Pro Arg Gly Gly Arg Ala Ala Arg Ala Gly Gly Pro Gly
            100                 105                 110

Ser Arg Ala Arg Ala Ala Gly Ala Arg Gly Cys Arg Leu Arg Ser Gln
            115                 120                 125

Leu Val Pro Val Arg Ala Leu Gly Leu Gly His Arg Ser Asp Glu Leu
            130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
            165                 170                 175

Pro Pro Gly Ser Arg Pro Val Ser Gln Pro Cys Cys Arg Pro Thr Arg
            180                 185                 190

Tyr Glu Ala Val Ser Phe Met Asp Val Asn Ser Thr Trp Arg Thr Val
            195                 200                 205
```

```
Asp Arg Leu Ser Ala Thr Ala Cys Gly Cys Leu Gly
    210                 215                 220
```

<210> SEQ ID NO 77
<211> LENGTH: 390
<212> TYPE: PRT
<213> ORGANISM: Homo sapiens

<400> SEQUENCE: 77

```
Met Pro Pro Ser Gly Leu Arg Leu Leu Leu Leu Leu Pro Leu Leu
 1               5                  10                  15

Trp Leu Leu Val Leu Thr Pro Gly Arg Pro Ala Ala Gly Leu Ser Thr
                 20                  25                  30

Cys Lys Thr Ile Asp Met Glu Leu Val Lys Arg Lys Arg Ile Glu Ala
             35                  40                  45

Ile Arg Gly Gln Ile Leu Ser Lys Leu Arg Leu Ala Ser Pro Pro Ser
 50                  55                  60

Gln Gly Glu Val Pro Pro Gly Pro Leu Pro Glu Ala Val Leu Ala Leu
 65                  70                  75                  80

Tyr Asn Ser Thr Arg Asp Arg Val Ala Gly Glu Ser Ala Glu Pro Glu
                 85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
            290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
```

```
                355                 360                 365
Tyr Val Gly Arg Lys Pro Lys Val Glu Gln Leu Ser Asn Met Ile Val
    370                 375                 380
Arg Ser Cys Lys Cys Ser
385                 390

<210> SEQ ID NO 78
<211> LENGTH: 413
<212> TYPE: PRT
<213> ORGANISM: Homo sapiens

<400> SEQUENCE: 78

Met His Tyr Cys Val Leu Ser Ala Phe Leu Ile Leu His Leu Val Thr
  1               5                  10                  15

Val Ala Leu Ser Leu Ser Thr Cys Ser Thr Leu Asp Met Asp Gln Phe
             20                  25                  30

Met Arg Lys Arg Ile Glu Ala Ile Arg Gly Gln Ile Leu Ser Lys Leu
         35                  40                  45

Lys Leu Thr Ser Pro Pro Glu Asp Tyr Pro Glu Pro Glu Glu Val Pro
     50                  55                  60

Pro Glu Val Ile Ser Ile Tyr Asn Ser Thr Arg Asp Leu Leu Gln Glu
 65                  70                  75                  80

Lys Ala Ser Arg Arg Ala Ala Ala Cys Glu Arg Glu Arg Ser Asp Glu
                 85                  90                  95

Glu Tyr Tyr Ala Lys Glu Val Tyr Lys Ile Asp Met Pro Pro Phe Phe
            100                 105                 110

Pro Ser Glu Ala Ile Pro Pro Thr Phe Tyr Arg Pro Tyr Phe Arg Ile
        115                 120                 125

Val Arg Phe Asp Val Ser Ala Met Glu Lys Asn Ala Ser Asn Leu Val
    130                 135                 140

Lys Ala Glu Phe Arg Val Phe Arg Leu Gln Asn Pro Lys Ala Arg Val
145                 150                 155                 160

Pro Glu Gln Arg Ile Glu Leu Tyr Gln Ile Leu Lys Ser Lys Asp Leu
                165                 170                 175

Thr Ser Pro Thr Gln Arg Tyr Ile Asp Ser Lys Val Val Lys Thr Arg
            180                 185                 190

Ala Glu Gly Glu Trp Leu Ser Phe Asp Val Thr Asp Ala Val His Glu
        195                 200                 205

Trp Leu His His Lys Asp Arg Asn Leu Gly Phe Lys Ile Ser Leu His
    210                 215                 220

Cys Pro Cys Cys Thr Phe Val Pro Ser Asn Asn Tyr Ile Ile Pro Asn
225                 230                 235                 240

Lys Ser Glu Glu Leu Glu Ala Arg Phe Ala Gly Ile Asp Gly Thr Ser
                245                 250                 255

Thr Tyr Thr Ser Gly Asp Gln Lys Thr Ile Lys Ser Thr Arg Lys Lys
            260                 265                 270

Asn Ser Gly Lys Thr Pro His Leu Leu Leu Met Leu Leu Pro Ser Tyr
        275                 280                 285

Arg Leu Glu Ser Gln Gln Thr Asn Arg Arg Lys Lys Arg Ala Leu Asp
    290                 295                 300

Ala Ala Tyr Cys Phe Arg Asn Val Gln Asp Asn Cys Cys Leu Arg Pro
305                 310                 315                 320

Leu Tyr Ile Asp Phe Lys Arg Asp Leu Gly Trp Lys Trp Ile His Glu
                325                 330                 335
```

```
Pro Lys Gly Tyr Asn Ala Asn Phe Cys Ala Gly Ala Cys Pro Tyr Leu
            340                 345                 350

Trp Ser Ser Asp Thr Gln His Ser Arg Val Leu Ser Leu Tyr Asn Thr
            355                 360                 365

Ile Asn Pro Glu Ala Ser Ala Ser Pro Cys Cys Val Ser Gln Asp Leu
            370                 375                 380

Glu Pro Leu Thr Ile Leu Tyr Tyr Ile Gly Lys Thr Pro Lys Ile Glu
385                 390                 395                 400

Gln Leu Ser Asn Met Ile Val Lys Ser Cys Lys Cys Ser
            405                 410

<210> SEQ ID NO 79
<211> LENGTH: 412
<212> TYPE: PRT
<213> ORGANISM: Homo sapiens

<400> SEQUENCE: 79

Met Lys Met His Leu Gln Arg Ala Leu Val Val Leu Ala Leu Leu Asn
  1               5                  10                  15

Phe Ala Thr Val Ser Leu Ser Leu Ser Thr Cys Thr Thr Leu Asp Phe
             20                  25                  30

Gly His Ile Lys Lys Lys Arg Val Glu Ala Ile Arg Gly Gln Ile Leu
         35                  40                  45

Ser Lys Leu Arg Leu Thr Ser Pro Pro Glu Pro Thr Val Met Thr His
 50                  55                  60

Val Pro Tyr Gln Val Leu Ala Leu Tyr Asn Ser Thr Arg Glu Leu Leu
 65                  70                  75                  80

Glu Glu Met His Gly Glu Arg Glu Gly Cys Thr Gln Glu Asn Thr
                 85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Thr
290                 295                 300
```

-continued

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
            325                 330                 335

Lys Gly Tyr Tyr Ala Asn Phe Cys Ser Gly Pro Cys Pro Tyr Leu Arg
                340                 345                 350

Ser Ala Asp Thr Thr His Ser Thr Val Leu Gly Leu Tyr Asn Thr Leu
                355                 360                 365

Asn Pro Glu Ala Ser Ala Ser Pro Cys Cys Val Pro Gln Asp Leu Glu
370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 80
<211> LENGTH: 304
<212> TYPE: PRT
<213> ORGANISM: Homo sapiens

<400> SEQUENCE: 80

Met Asp Pro Met Ser Ile Gly Pro Lys Ser Cys Gly Gly Ser Pro Trp
1               5                   10                  15

Arg Pro Pro Gly Thr Ala Pro Trp Ser Ile Gly Ser Arg Arg Ala Thr
                20                  25                  30

Ala Ser Ser Ser Cys Ser Thr Ser Ser Arg Val Arg Ala Glu Val Gly
            35                  40                  45

Gly Arg Ala Leu Leu His Arg Ala Glu Leu Arg Met Leu Arg Gln Lys
50                  55                  60

Ala Ala Ala Asp Ser Ala Gly Thr Glu Gln Arg Leu Glu Leu Tyr Gln
65                  70                  75                  80

Gly Tyr Gly Asn Ala Ser Trp Arg Tyr Leu His Gly Arg Ser Val Arg
                85                  90                  95

Ala Thr Ala Asp Asp Glu Trp Leu Ser Phe Asp Val Thr Asp Ala Val
            100                 105                 110

His Gln Trp Leu Ser Gly Ser Glu Leu Leu Gly Val Phe Lys Leu Ser
        115                 120                 125

Val His Cys Pro Cys Glu Met Gly Pro Gly His Ala Asp Glu Met Arg
    130                 135                 140

Ile Ser Ile Glu Gly Phe Glu Gln Gln Arg Gly Asp Met Gln Ser Ile
145                 150                 155                 160

Ala Lys Lys His Arg Arg Val Pro Tyr Val Leu Ala Met Ala Leu Pro
                165                 170                 175

Ala Glu Arg Ala Asn Glu Leu His Ser Ala Arg Arg Arg Arg Asp Leu
            180                 185                 190

Asp Thr Asp Tyr Cys Phe Gly Pro Gly Thr Asp Glu Lys Asn Cys Cys
        195                 200                 205

Val Arg Pro Leu Tyr Ile Asp Phe Arg Lys Asp Leu Gln Trp Lys Trp
    210                 215                 220

Ile His Glu Pro Lys Gly Tyr Met Ala Asn Phe Cys Met Gly Pro Cys
225                 230                 235                 240

Pro Tyr Ile Trp Ser Ala Asp Thr Gln Tyr Thr Lys Val Leu Ala Leu
                245                 250                 255

Tyr Asn Gln His Asn Pro Gly Ala Ser Ala Ala Pro Cys Cys Val Pro

```
                    260                 265                 270
Gln Thr Leu Asp Pro Leu Pro Ile Ile Tyr Tyr Val Gly Arg Asn Val
            275                 280                 285

Arg Val Glu Gln Leu Ser Asn Met Val Val Arg Ala Cys Lys Cys Ser
        290                 295                 300

<210> SEQ ID NO 81
<211> LENGTH: 396
<212> TYPE: PRT
<213> ORGANISM: Homo sapiens

<400> SEQUENCE: 81

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335
```

```
Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 82
<211> LENGTH: 472
<212> TYPE: PRT
<213> ORGANISM: Homo sapiens

<400> SEQUENCE: 82

Met Ala Gly Ala Ser Arg Leu Leu Phe Leu Trp Leu Gly Cys Phe Cys
1               5                   10                  15

Val Ser Leu Ala Gln Gly Glu Arg Pro Lys Pro Pro Phe Pro Glu Leu
            20                  25                  30

Arg Lys Ala Val Pro Gly Asp Arg Thr Ala Gly Gly Gly Pro Asp Ser
        35                  40                  45

Glu Leu Gln Pro Gln Asp Lys Val Ser Glu His Met Leu Arg Leu Tyr
50                  55                  60

Asp Arg Tyr Ser Thr Val Gln Ala Ala Arg Thr Pro Gly Ser Leu Glu
65                  70                  75                  80

Gly Gly Ser Gln Pro Trp Arg Pro Arg Leu Leu Arg Glu Gly Asn Thr
            85                  90                  95

Val Arg Ser Phe Arg Ala Ala Ala Ala Glu Thr Leu Glu Arg Lys Gly
            100                 105                 110

Leu Tyr Ile Phe Asn Leu Thr Ser Leu Thr Lys Ser Glu Asn Ile Leu
        115                 120                 125

Ser Ala Thr Leu Tyr Phe Cys Ile Gly Glu Leu Gly Asn Ile Ser Leu
130                 135                 140

Ser Cys Pro Val Ser Gly Gly Cys Ser His His Ala Gln Arg Lys His
145                 150                 155                 160

Ile Gln Ile Asp Leu Ser Ala Trp Thr Leu Lys Phe Ser Arg Asn Gln
            165                 170                 175

Ser Gln Leu Leu Gly His Leu Ser Val Asp Met Ala Lys Ser His Arg
            180                 185                 190

Asp Ile Met Ser Trp Leu Ser Lys Asp Ile Thr Gln Phe Leu Arg Lys
        195                 200                 205

Ala Lys Glu Asn Glu Glu Phe Leu Ile Gly Phe Asn Ile Thr Ser Lys
210                 215                 220

Gly Arg Gln Leu Pro Lys Arg Arg Leu Pro Phe Pro Glu Pro Tyr Ile
225                 230                 235                 240

Leu Val Tyr Ala Asn Asp Ala Ala Ile Ser Glu Pro Glu Ser Val Val
            245                 250                 255

Ser Ser Leu Gln Gly His Arg Asn Phe Pro Thr Gly Thr Val Pro Lys
            260                 265                 270

Trp Asp Ser His Ile Arg Ala Ala Leu Ser Ile Glu Arg Arg Lys Lys
        275                 280                 285

Arg Ser Thr Gly Val Leu Leu Pro Leu Gln Asn Asn Glu Leu Pro Gly
290                 295                 300

Ala Glu Tyr Gln Tyr Lys Lys Asp Glu Val Trp Glu Glu Arg Lys Pro
305                 310                 315                 320
```

```
Tyr Lys Thr Leu Gln Ala Gln Ala Pro Glu Lys Ser Lys Asn Lys Lys
                325                 330                 335

Lys Gln Arg Lys Gly Pro His Arg Lys Ser Gln Thr Leu Gln Phe Asp
            340                 345                 350

Glu Gln Thr Leu Lys Lys Ala Arg Arg Lys Gln Trp Ile Glu Pro Arg
        355                 360                 365

Asn Cys Ala Arg Arg Tyr Leu Lys Val Asp Phe Ala Asp Ile Gly Trp
    370                 375                 380

Ser Glu Trp Ile Ile Ser Pro Lys Ser Phe Asp Ala Tyr Tyr Cys Ser
385                 390                 395                 400

Gly Ala Cys Gln Phe Pro Met Pro Lys Ser Leu Lys Pro Ser Asn His
                405                 410                 415

Ala Thr Ile Gln Ser Ile Val Arg Ala Val Gly Val Val Pro Gly Ile
            420                 425                 430

Pro Glu Pro Cys Cys Val Pro Glu Lys Met Ser Ser Leu Ser Ile Leu
        435                 440                 445

Phe Phe Asp Glu Asn Lys Asn Val Val Leu Lys Val Tyr Pro Asn Met
    450                 455                 460

Thr Val Glu Ser Cys Ala Cys Arg
465                 470

<210> SEQ ID NO 83
<211> LENGTH: 408
<212> TYPE: PRT
<213> ORGANISM: Homo sapiens

<400> SEQUENCE: 83

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
```

-continued

```
            210                 215                 220
Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 84
<211> LENGTH: 454
<212> TYPE: PRT
<213> ORGANISM: Homo sapiens

<400> SEQUENCE: 84

Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
            20                  25                  30

His Val His Ser Ser Phe Ile Tyr Arg Arg Leu Arg Asn His Glu Arg
        35                  40                  45

Arg Glu Ile Gln Arg Glu Ile Leu Ser Ile Leu Gly Leu Pro His Arg
    50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
                85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

Leu Ser Arg Thr Thr Pro Leu Thr Thr Gln Ser Pro Pro Leu Ala Ser
    130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175
```

```
Tyr Lys Glu Phe Arg Phe Asp Leu Thr Gln Ile Pro His Gly Glu Ala
                180                 185                 190

Val Thr Ala Ala Glu Phe Arg Ile Tyr Lys Asp Arg Ser Asn Asn Arg
            195                 200                 205

Phe Glu Asn Glu Thr Ile Lys Ile Ser Ile Tyr Gln Ile Ile Lys Glu
        210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
    290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser His Gln Asp Ser Ser
                325                 330                 335

Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln
        355                 360                 365

Asp Trp Ile Ile Ala Pro Glu Gly Tyr Ala Ala Phe Tyr Cys Asp Gly
    370                 375                 380

Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
                405                 410                 415

Pro Cys Cys Ala Pro Thr Lys Leu Asn Ala Ile Ser Val Leu Tyr Phe
            420                 425                 430

Asp Asp Ser Ser Asn Val Ile Leu Lys Lys Tyr Arg Asn Met Val Val
        435                 440                 445

Arg Ser Cys Gly Cys His
    450

<210> SEQ ID NO 85
<211> LENGTH: 513
<212> TYPE: PRT
<213> ORGANISM: Homo sapiens

<400> SEQUENCE: 85

Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
                20                  25                  30

Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
        50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95
```

-continued

```
His Gly Leu Gln Gln Pro Gln Pro Pro Ala Leu Arg Gln Gln Glu Glu
            100                 105                 110

Gln Gln Gln Gln Gln Gln Leu Pro Arg Gly Glu Pro Pro Pro Gly Arg
        115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Gln Arg Arg Gln Pro Pro Pro
                165                 170                 175

Gly Ala Ala His Pro Leu Asn Arg Lys Ser Leu Leu Ala Pro Gly Ser
                180                 185                 190

Gly Ser Gly Gly Ala Ser Pro Leu Thr Ser Ala Gln Asp Ser Ala Phe
            195                 200                 205

Leu Asn Asp Ala Asp Met Val Met Ser Phe Val Asn Leu Val Glu Tyr
            210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
                260                 265                 270

Leu Ile Ser Ile Tyr Gln Val Leu Gln Glu His Gln His Arg Asp Ser
            275                 280                 285

Asp Leu Phe Leu Leu Asp Thr Arg Val Val Trp Ala Ser Glu Glu Gly
            290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
                340                 345                 350

Tyr Asp Lys Gln Pro Phe Met Val Ala Phe Phe Lys Val Ser Glu Val
            355                 360                 365

His Val Arg Thr Thr Arg Ser Ala Ser Ser Arg Arg Gln Gln Ser
            370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
            420                 425                 430

Pro Lys Gly Tyr Ala Ala Asn Tyr Cys Asp Gly Glu Cys Ser Phe Pro
            435                 440                 445

Leu Asn Ala His Met Asn Ala Thr Asn His Ala Ile Val Gln Thr Leu
    450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
            500                 505                 510
```

-continued

His

<210> SEQ ID NO 86
<211> LENGTH: 431
<212> TYPE: PRT
<213> ORGANISM: Homo sapiens

<400> SEQUENCE: 86

Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

```
Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 87
<211> LENGTH: 402
<212> TYPE: PRT
<213> ORGANISM: Homo sapiens

<400> SEQUENCE: 87

Met Thr Ala Leu Pro Gly Pro Leu Trp Leu Leu Gly Leu Ala Leu Cys
1               5                   10                  15

Ala Leu Gly Gly Gly Pro Gly Leu Arg Pro Pro Gly Cys Pro
            20                  25                  30

Gln Arg Arg Leu Gly Ala Arg Glu Arg Arg Asp Val Gln Arg Glu Ile
        35                  40                  45

Leu Ala Val Leu Gly Leu Pro Gly Arg Pro Arg Pro Arg Ala Pro Pro
50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Asp Glu Asp Gly Ala Pro Ala Glu
                85                  90                  95

Arg Arg Leu Gly Arg Ala Asp Leu Val Met Ser Phe Val Asn Met Val
            100                 105                 110

Glu Arg Asp Arg Ala Leu Gly His Gln Glu Pro His Trp Lys Glu Phe
        115                 120                 125

Arg Phe Asp Leu Thr Gln Ile Pro Ala Gly Glu Ala Val Thr Ala Ala
130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
        195                 200                 205

Lys Arg His Lys Asp Leu Gly Leu Arg Leu Tyr Val Glu Thr Glu Asp
210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
                245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
        275                 280                 285

Phe Asp Asp Val His Gly Ser His Gly Arg Gln Val Cys Arg Arg His
290                 295                 300

Glu Leu Tyr Val Ser Phe Gln Asp Leu Gly Trp Leu Asp Trp Val Ile
305                 310                 315                 320
```

```
Ala Pro Gln Gly Tyr Ser Ala Tyr Tyr Cys Glu Gly Glu Cys Ser Phe
                325                 330                 335

Pro Leu Asp Ser Cys Met Asn Ala Thr Asn His Ala Ile Leu Gln Ser
            340                 345                 350

Leu Val His Leu Met Lys Pro Asn Ala Val Pro Lys Ala Cys Cys Ala
        355                 360                 365

Pro Thr Lys Leu Ser Ala Thr Ser Val Leu Tyr Tyr Asp Ser Ser Asn
    370                 375                 380

Asn Val Ile Leu Arg Lys His Arg Asn Met Val Val Lys Ala Cys Gly
385                 390                 395                 400

Cys His

<210> SEQ ID NO 88
<211> LENGTH: 424
<212> TYPE: PRT
<213> ORGANISM: Homo sapiens

<400> SEQUENCE: 88

Met Gly Ser Leu Val Leu Thr Leu Cys Ala Leu Phe Cys Leu Ala Ala
  1               5                  10                  15

Tyr Leu Val Ser Gly Ser Pro Ile Met Asn Leu Glu Gln Ser Pro Leu
             20                  25                  30

Glu Glu Asp Met Ser Leu Phe Gly Asp Val Phe Ser Glu Gln Asp Gly
         35                  40                  45

Val Asp Phe Asn Thr Leu Leu Gln Ser Met Lys Asp Glu Phe Leu Lys
 50                  55                  60

Thr Leu Asn Leu Ser Asp Ile Pro Thr Gln Asp Ser Ala Lys Val Asp
 65                  70                  75                  80

Pro Pro Glu Tyr Met Leu Glu Leu Tyr Asn Lys Phe Ala Thr Asp Arg
                 85                  90                  95

Thr Ser Met Pro Ser Ala Asn Ile Ile Arg Ser Phe Lys Asn Glu Asp
            100                 105                 110

Leu Phe Ser Gln Pro Val Ser Phe Asn Gly Leu Arg Lys Tyr Pro Leu
        115                 120                 125

Leu Phe Asn Val Ser Ile Pro His His Glu Glu Val Ile Met Ala Glu
    130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
        195                 200                 205

Arg Trp Gln Lys Ser Gly Ser Ser Thr His Gln Leu Glu Val His Ile
    210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Leu Asp Asn Leu Gly Leu Asp
        275                 280                 285
```

```
Ser Phe Ser Ser Gly Pro Gly Glu Glu Ala Leu Leu Gln Met Arg Ser
    290                 295                 300

Asn Ile Ile Tyr Asp Ser Thr Ala Arg Ile Arg Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
            340                 345                 350

Arg Gly Val Cys Asn Tyr Pro Leu Ala Glu His Leu Thr Pro Thr Lys
        355                 360                 365

His Ala Ile Ile Gln Ala Leu Val His Leu Lys Asn Ser Gln Lys Ala
    370                 375                 380

Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
                405                 410                 415

Ala Val Ser Glu Cys Gly Cys Arg
            420

<210> SEQ ID NO 89
<211> LENGTH: 372
<212> TYPE: PRT
<213> ORGANISM: Homo sapiens

<400> SEQUENCE: 89

Met Pro Pro Pro Gln Gln Gly Pro Cys Gly His His Leu Leu Leu Leu
1               5                   10                  15

Leu Ala Leu Leu Leu Pro Ser Leu Pro Leu Thr Arg Ala Pro Val Pro
            20                  25                  30

Pro Gly Pro Ala Ala Ala Leu Leu Gln Ala Leu Gly Leu Arg Asp Glu
        35                  40                  45

Pro Gln Gly Ala Pro Arg Leu Arg Pro Val Pro Pro Val Met Trp Arg
    50                  55                  60

Leu Phe Arg Arg Arg Asp Pro Gln Glu Thr Arg Ser Gly Ser Arg Arg
65                  70                  75                  80

Thr Ser Pro Gly Val Thr Leu Gln Pro Cys His Val Glu Glu Leu Gly
                85                  90                  95

Val Ala Gly Asn Ile Val Arg His Ile Pro Asp Arg Gly Ala Pro Thr
            100                 105                 110

Arg Ala Ser Glu Pro Ala Ser Ala Ala Gly His Cys Pro Glu Trp Thr
        115                 120                 125

Val Val Phe Asp Leu Ser Ala Val Glu Pro Ala Glu Arg Pro Ser Arg
    130                 135                 140

Ala Arg Leu Glu Leu Arg Phe Ala Ala Ala Ala Ala Ala Ala Pro Glu
145                 150                 155                 160

Gly Gly Trp Glu Leu Ser Val Ala Gln Ala Gly Gln Gly Ala Gly Ala
                165                 170                 175

Asp Pro Gly Pro Val Leu Leu Arg Gln Leu Val Pro Ala Leu Gly Pro
            180                 185                 190

Pro Val Arg Ala Glu Leu Leu Gly Ala Ala Trp Ala Arg Asn Ala Ser
        195                 200                 205

Trp Pro Arg Ser Leu Arg Leu Ala Leu Ala Leu Arg Pro Arg Ala Pro
    210                 215                 220

Ala Ala Cys Ala Arg Leu Ala Glu Ala Ser Leu Leu Leu Val Thr Leu
```

-continued

```
            225                 230                 235                 240

Asp Pro Arg Leu Cys His Pro Leu Ala Arg Pro Arg Arg Asp Ala Glu
                245                 250                 255

Pro Val Leu Gly Gly Gly Pro Gly Gly Ala Cys Arg Ala Arg Arg Leu
                260                 265                 270

Tyr Val Ser Phe Arg Glu Val Gly Trp His Arg Trp Val Ile Ala Pro
                275                 280                 285

Arg Gly Phe Leu Ala Asn Tyr Cys Gln Gly Gln Cys Ala Leu Pro Val
            290                 295                 300

Ala Leu Ser Gly Ser Gly Gly Pro Pro Ala Leu Asn His Ala Val Leu
305                 310                 315                 320

Arg Ala Leu Met His Ala Ala Ala Pro Gly Ala Ala Asp Leu Pro Cys
                325                 330                 335

Cys Val Pro Ala Arg Leu Ser Pro Ile Ser Val Leu Phe Phe Asp Asn
                340                 345                 350

Ser Asp Asn Val Val Leu Arg Gln Tyr Glu Asp Met Val Val Asp Glu
                355                 360                 365

Cys Gly Cys Arg
        370

<210> SEQ ID NO 90
<211> LENGTH: 429
<212> TYPE: PRT
<213> ORGANISM: Homo sapiens

<400> SEQUENCE: 90

Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
                20                  25                  30

Ala Gly Gly Asn Ala His Ser Pro Leu Gly Val Pro Gly Gly Gly Leu
            35                  40                  45

Pro Glu His Thr Phe Asn Leu Lys Met Phe Leu Glu Asn Val Lys Val
    50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
                100                 105                 110

Ser Met Glu Asp Ala Ile Ser Ile Thr Ala Thr Glu Asp Phe Pro Phe
            115                 120                 125

Gln Lys His Ile Leu Leu Phe Asn Ile Ser Ile Pro Arg His Glu Gln
    130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175

Asp Gly Thr Asp Ala Trp Asp Ser Ala Thr Glu Thr Lys Thr Phe Leu
                180                 185                 190

Val Ser Gln Asp Ile Gln Asp Glu Gly Trp Glu Thr Leu Glu Val Ser
            195                 200                 205

Ser Ala Val Lys Arg Trp Val Arg Ser Asp Ser Thr Lys Ser Lys Asn
    210                 215                 220
```

```
Lys Leu Glu Val Thr Val Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285

Lys Asp Gly Ser Thr Glu Ala Gly Glu Ser Ser His Glu Glu Asp Thr
    290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335

Glu Asp Ile Gly Trp Asp Ser Trp Ile Ile Ala Pro Lys Glu Tyr Glu
            340                 345                 350

Ala Tyr Glu Cys Lys Gly Gly Cys Phe Phe Pro Leu Ala Asp Asp Val
        355                 360                 365

Thr Pro Thr Lys His Ala Ile Val Gln Thr Leu Val His Leu Lys Phe
    370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
                405                 410                 415

His Tyr Glu Gly Met Ser Val Ala Glu Cys Gly Cys Arg
            420                 425

<210> SEQ ID NO 91
<211> LENGTH: 364
<212> TYPE: PRT
<213> ORGANISM: Homo sapiens

<400> SEQUENCE: 91

Met Leu Arg Phe Leu Pro Asp Leu Ala Phe Ser Phe Leu Leu Ile Leu
1               5                   10                  15

Ala Leu Gly Gln Ala Val Gln Phe Gln Glu Tyr Val Phe Leu Gln Phe
            20                  25                  30

Leu Gly Leu Asp Lys Ala Pro Ser Pro Gln Lys Phe Gln Pro Val Pro
        35                  40                  45

Tyr Ile Leu Lys Lys Ile Phe Gln Asp Arg Glu Ala Ala Ala Thr Thr
    50                  55                  60

Gly Val Ser Arg Asp Leu Cys Tyr Val Lys Glu Leu Gly Val Arg Gly
65                  70                  75                  80

Asn Val Leu Arg Phe Leu Pro Asp Gln Gly Phe Phe Leu Tyr Pro Lys
                85                  90                  95

Lys Ile Ser Gln Ala Ser Ser Cys Leu Gln Lys Leu Leu Tyr Phe Asn
            100                 105                 110

Leu Ser Ala Ile Lys Glu Arg Glu Gln Leu Thr Leu Ala Gln Leu Gly
        115                 120                 125

Leu Asp Leu Gly Pro Asn Ser Tyr Tyr Asn Leu Gly Pro Glu Leu Glu
    130                 135                 140

Leu Ala Leu Phe Leu Val Gln Glu Pro His Val Trp Gly Gln Thr Thr
145                 150                 155                 160

Pro Lys Pro Gly Lys Met Phe Val Leu Arg Ser Val Pro Trp Pro Gln
                165                 170                 175
```

```
Gly Ala Val His Phe Asn Leu Leu Asp Val Ala Lys Asp Trp Asn Asp
            180                 185                 190

Asn Pro Arg Lys Asn Phe Gly Leu Phe Leu Glu Ile Leu Val Lys Glu
            195                 200                 205

Asp Arg Asp Ser Gly Val Asn Phe Gln Pro Glu Asp Thr Cys Ala Arg
    210                 215                 220

Leu Arg Cys Ser Leu His Ala Ser Leu Leu Val Val Thr Leu Asn Pro
225                 230                 235                 240

Asp Gln Cys His Pro Ser Arg Lys Arg Ala Ala Ile Pro Val Pro
            245                 250                 255

Lys Leu Ser Cys Lys Asn Leu Cys His Arg His Gln Leu Phe Ile Asn
            260                 265                 270

Phe Arg Asp Leu Gly Trp His Lys Trp Ile Ile Ala Pro Lys Gly Phe
            275                 280                 285

Met Ala Asn Tyr Cys His Gly Glu Cys Pro Phe Ser Leu Thr Ile Ser
            290                 295                 300

Leu Asn Ser Ser Asn Tyr Ala Phe Met Gln Ala Leu Met His Ala Val
305                 310                 315                 320

Asp Pro Glu Ile Pro Gln Ala Val Cys Ile Pro Thr Lys Leu Ser Pro
            325                 330                 335

Ile Ser Met Leu Tyr Gln Asp Asn Asn Asp Asn Val Ile Leu Arg His
            340                 345                 350

Tyr Glu Asp Met Val Val Asp Glu Cys Gly Cys Gly
            355                 360

<210> SEQ ID NO 92
<211> LENGTH: 501
<212> TYPE: PRT
<213> ORGANISM: Homo sapiens

<400> SEQUENCE: 92

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Ser Arg Pro Gly Leu Ala Lys Ala Glu Ala Lys
            35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
            85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
            115                 120                 125

Pro Gly Gly Lys Ala Pro Pro Lys Ala Gly Ser Val Pro Ser Ser Phe
            130                 135                 140

Leu Leu Lys Lys Ala Arg Glu Pro Gly Pro Pro Arg Glu Pro Lys Glu
145                 150                 155                 160

Pro Phe Arg Pro Pro Pro Ile Thr Pro His Glu Tyr Met Leu Ser Leu
            165                 170                 175

Tyr Arg Thr Leu Ser Asp Ala Asp Arg Lys Gly Gly Asn Ser Ser Val
```

-continued

```
            180                 185                 190
Lys Leu Glu Ala Gly Leu Ala Asn Thr Ile Thr Ser Phe Ile Asp Lys
            195                 200                 205

Gly Gln Asp Asp Arg Gly Pro Val Val Arg Lys Gln Arg Tyr Val Phe
        210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Val Pro Arg
                245                 250                 255

Ser Arg Arg Ala Ala Gln Leu Lys Leu Ser Ser Cys Pro Ser Gly Arg
            260                 265                 270

Gln Pro Ala Ala Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Thr Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Ser
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 93
<211> LENGTH: 321
<212> TYPE: PRT
<213> ORGANISM: Homo sapiens

<400> SEQUENCE: 93

Asn Ser Asp Leu Ser His Thr Pro Leu Arg Arg Gln Lys Tyr Leu Phe
1               5                   10                  15

Asp Val Ser Met Leu Ser Asp Lys Glu Glu Leu Val Gly Ala Glu Leu
            20                  25                  30

Arg Leu Phe Arg Gln Ala Pro Ser Ala Pro Trp Gly Pro Pro Ala Gly
        35                  40                  45
```

-continued

```
Pro Leu His Val Gln Leu Phe Pro Cys Leu Ser Pro Leu Leu Leu Asp
     50                  55                  60

Ala Arg Thr Leu Asp Pro Gln Gly Ala Pro Ala Gly Trp Glu Val
 65                  70                  75                  80

Phe Asp Val Trp Gln Gly Leu Arg His Gln Pro Trp Lys Gln Leu Cys
                 85                  90                  95

Leu Glu Leu Arg Ala Ala Trp Gly Glu Leu Asp Ala Gly Glu Ala Glu
            100                 105                 110

Ala Arg Ala Arg Gly Pro Gln Gln Pro Pro Pro Asp Leu Arg Ser
        115                 120                 125

Leu Gly Phe Gly Arg Arg Val Arg Pro Gln Glu Arg Ala Leu Leu
    130                 135                 140

Val Val Phe Thr Arg Ser Gln Arg Lys Asn Leu Phe Ala Glu Met Arg
145                 150                 155                 160

Glu Gln Leu Gly Ser Ala Glu Ala Ala Gly Pro Gly Ala Gly Ala Glu
                165                 170                 175

Gly Ser Trp Pro Pro Ser Gly Ala Pro Asp Ala Arg Pro Trp Leu
            180                 185                 190

Pro Ser Pro Gly Arg Arg Arg Arg Thr Ala Phe Ala Ser Arg His
        195                 200                 205

Gly Lys Arg His Gly Lys Lys Ser Arg Leu Arg Cys Ser Lys Lys Pro
    210                 215                 220

Leu His Val Asn Phe Lys Glu Leu Gly Trp Asp Asp Trp Ile Ile Ala
225                 230                 235                 240

Pro Leu Glu Tyr Glu Ala Tyr His Cys Glu Gly Val Cys Asp Phe Pro
                245                 250                 255

Leu Arg Ser His Leu Glu Pro Thr Asn His Ala Ile Ile Gln Thr Leu
            260                 265                 270

Met Asn Ser Met Asp Pro Gly Ser Thr Pro Pro Ser Cys Cys Val Pro
        275                 280                 285

Thr Lys Leu Thr Pro Ile Ser Ile Leu Tyr Ile Asp Ala Gly Asn Asn
    290                 295                 300

Val Val Tyr Lys Gln Tyr Glu Asp Met Val Val Glu Ser Cys Gly Cys
305                 310                 315                 320

Arg
```

<210> SEQ ID NO 94
<211> LENGTH: 388
<212> TYPE: PRT
<213> ORGANISM: Homo sapiens

<400> SEQUENCE: 94

```
Pro Gly Arg Arg Arg Pro Leu Leu Trp Ala Arg Leu Ala Ala Phe Arg
 1               5                  10                  15

Leu Gly Gln Arg Arg Gly Val Gly Arg Trp Leu Gln Gln Ala Trp Leu
                20                  25                  30

Pro His Arg Arg Gln Leu Gly His Leu Leu Leu Gly Gly Pro Ala Leu
            35                  40                  45

Thr Val Cys Arg Ile Cys Ser Tyr Thr Ala Leu Ser Leu Cys Pro Cys
     50                  55                  60

Arg Ser Pro Ala Asp Glu Ser Ala Ala Glu Thr Gly Gln Ser Phe Leu
 65                  70                  75                  80

Phe Asp Val Ser Ser Leu Asn Asp Ala Asp Glu Val Val Gly Ala Glu
                 85                  90                  95
```

```
Leu Arg Val Leu Arg Gly Ser Pro Glu Gly Pro Gly Ser Trp
        100                 105                 110

Thr Ser Pro Pro Leu Leu Leu Ser Thr Cys Pro Gly Ala Ala Arg
        115                 120                 125

Ala Pro Arg Leu Leu Tyr Ser Arg Ala Ala Glu Pro Leu Val Gly Gln
        130                 135                 140

Arg Trp Glu Ala Phe Asp Val Ala Asp Ala Met Arg Arg His Arg Arg
145                 150                 155                 160

Glu Pro Arg Pro Arg Ala Phe Cys Leu Leu Arg Ala Val Ala
                165                 170                 175

Gly Pro Val Pro Ser Pro Leu Ala Leu Arg Arg Leu Gly Phe Gly Trp
                180                 185                 190

Pro Gly Gly Gly Gly Ser Ala Ala Glu Glu Arg Ala Val Leu Val Val
                195                 200                 205

Ser Ser Arg Thr Gln Arg Lys Glu Ser Leu Phe Arg Glu Ile Arg Ala
        210                 215                 220

Gln Ala Arg Ala Leu Gly Ala Ala Leu Ala Ser Glu Pro Leu Pro Asp
225                 230                 235                 240

Pro Gly Thr Gly Thr Ala Ser Pro Arg Ala Val Ile Gly Gly Arg Arg
                245                 250                 255

Arg Arg Arg Thr Ala Leu Ala Gly Thr Arg Thr Ala Gln Gly Ser Gly
                260                 265                 270

Gly Gly Ala Gly Arg Gly His Gly Arg Arg Gly Arg Ser Arg Cys Ser
        275                 280                 285

Arg Lys Pro Leu His Val Asp Phe Lys Glu Leu Gly Trp Asp Asp Trp
290                 295                 300

Ile Ile Ala Pro Leu Asp Tyr Glu Ala Tyr His Cys Glu Gly Leu Cys
305                 310                 315                 320

Asp Phe Pro Leu Arg Ser His Leu Glu Pro Thr Asn His Ala Ile Ile
                325                 330                 335

Gln Thr Leu Leu Asn Ser Met Ala Pro Asp Ala Ala Pro Ala Ser Cys
        340                 345                 350

Cys Val Pro Ala Arg Leu Ser Pro Ile Ser Ile Leu Tyr Ile Asp Ala
                355                 360                 365

Ala Asn Asn Val Val Tyr Lys Gln Tyr Glu Asp Met Val Val Glu Ala
        370                 375                 380

Cys Gly Cys Arg
385

<210> SEQ ID NO 95
<211> LENGTH: 375
<212> TYPE: PRT
<213> ORGANISM: Homo sapiens

<400> SEQUENCE: 95

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
                20                  25                  30

Val Glu Lys Glu Gly Leu Cys Asn Ala Cys Thr Trp Arg Gln Asn Thr
            35                  40                  45

Lys Ser Ser Arg Ile Glu Ala Ile Lys Ile Gln Ile Leu Ser Lys Leu
        50                  55                  60

Arg Leu Glu Thr Ala Pro Asn Ile Ser Lys Asp Val Ile Arg Gln Leu
65                  70                  75                  80
```

```
Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
    370                 375

<210> SEQ ID NO 96
<211> LENGTH: 478
<212> TYPE: PRT
<213> ORGANISM: Homo sapiens

<400> SEQUENCE: 96

Met Ala His Val Pro Ala Arg Thr Ser Pro Gly Pro Gly Pro Gln Leu
1               5                   10                  15

Leu Leu Leu Leu Leu Pro Leu Phe Leu Leu Leu Arg Asp Val Ala
            20                  25                  30

Gly Ser His Arg Ala Pro Ala Trp Ser Ala Leu Pro Ala Ala Ala Asp
            35                  40                  45

Gly Leu Gln Gly Asp Arg Asp Leu Gln Arg His Pro Gly Asp Ala Ala
    50                  55                  60

Ala Thr Leu Gly Pro Ser Ala Gln Asp Met Val Ala Val His Met His
```

-continued

```
            65                  70                  75                  80
Arg Leu Tyr Glu Lys Tyr Ser Arg Gln Gly Ala Arg Pro Gly Gly Gly
                    85                  90                  95

Asn Thr Val Arg Ser Phe Arg Ala Arg Leu Glu Val Val Asp Gln Lys
                100                 105                 110

Ala Val Tyr Phe Phe Asn Leu Thr Ser Met Gln Asp Ser Glu Met Ile
                115                 120                 125

Leu Thr Ala Thr Phe His Phe Tyr Ser Glu Pro Pro Arg Trp Pro Arg
130                 135                 140

Ala Leu Glu Val Leu Cys Lys Pro Arg Ala Lys Asn Ala Ser Gly Arg
145                 150                 155                 160

Pro Leu Pro Leu Gly Pro Pro Thr Arg Gln His Leu Leu Phe Arg Ser
                165                 170                 175

Leu Ser Gln Asn Thr Ala Thr Gln Gly Leu Leu Arg Gly Ala Met Ala
                180                 185                 190

Leu Ala Pro Pro Pro Arg Gly Leu Trp Gln Ala Lys Asp Ile Ser Pro
                195                 200                 205

Ile Val Lys Ala Ala Arg Arg Asp Gly Glu Leu Leu Leu Ser Ala Gln
                210                 215                 220

Leu Asp Ser Glu Glu Arg Asp Pro Gly Val Pro Arg Pro Ser Pro Tyr
225                 230                 235                 240

Ala Pro Tyr Ile Leu Val Tyr Ala Asn Asp Leu Ala Ile Ser Glu Pro
                245                 250                 255

Asn Ser Val Ala Val Thr Leu Gln Arg Tyr Asp Pro Phe Pro Ala Gly
                260                 265                 270

Asp Pro Glu Pro Arg Ala Ala Pro Asn Asn Ser Ala Asp Pro Arg Val
                275                 280                 285

Arg Arg Ala Ala Gln Ala Thr Gly Pro Leu Gln Asp Asn Glu Leu Pro
                290                 295                 300

Gly Leu Asp Glu Arg Pro Arg Ala His Ala Gln His Phe His Lys
305                 310                 315                 320

His Gln Leu Trp Pro Ser Pro Phe Arg Ala Leu Lys Pro Arg Pro Gly
                325                 330                 335

Arg Lys Asp Arg Arg Lys Lys Gly Gln Glu Val Phe Met Ala Ala Ser
                340                 345                 350

Gln Val Leu Asp Phe Asp Glu Lys Thr Met Gln Lys Ala Arg Arg Lys
                355                 360                 365

Gln Trp Asp Glu Pro Arg Val Cys Ser Arg Arg Tyr Leu Lys Val Asp
                370                 375                 380

Phe Ala Asp Ile Gly Trp Asn Glu Trp Ile Ile Ser Pro Lys Ser Phe
385                 390                 395                 400

Asp Ala Tyr Tyr Cys Ala Gly Ala Cys Glu Phe Pro Met Pro Lys Ile
                405                 410                 415

Val Arg Pro Ser Asn His Ala Thr Ile Gln Ser Ile Val Arg Ala Val
                420                 425                 430

Gly Ile Ile Pro Gly Ile Pro Glu Pro Cys Cys Val Pro Asp Lys Met
                435                 440                 445

Asn Ser Leu Gly Val Leu Phe Leu Asp Glu Asn Arg Asn Val Val Leu
                450                 455                 460

Lys Val Tyr Pro Asn Met Ser Val Asp Thr Cys Ala Cys Arg
465                 470                 475

<210> SEQ ID NO 97
```

-continued

```
<211> LENGTH: 407
<212> TYPE: PRT
<213> ORGANISM: Homo sapiens

<400> SEQUENCE: 97

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
        355                 360                 365

Gly Pro Cys Cys Thr Pro Thr Lys Met Ser Pro Ile Asn Met Leu Tyr
370                 375                 380

Phe Asn Asp Lys Gln Gln Ile Ile Tyr Gly Lys Ile Pro Gly Met Val
```

```
                385                 390                 395                 400

Val Asp Arg Cys Gly Cys Ser
                405

<210> SEQ ID NO 98
<211> LENGTH: 309
<212> TYPE: PRT
<213> ORGANISM: Homo sapiens

<400> SEQUENCE: 98

Met Pro Gly Gln Glu Leu Arg Thr Leu Asn Gly Ser Gln Met Leu Leu
 1               5                  10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His
        35                  40                  45

Thr Glu Asp Ser Phe Arg Arg Glu Leu Arg Lys Arg Tyr Glu Asp Leu
    50                  55                  60

Leu Thr Arg Leu Arg Ala Asn Gln Ser Trp Glu Asp Ser Asn Thr Asp
65                  70                  75                  80

Leu Val Pro Ala Pro Ala Val Arg Ile Leu Thr Pro Glu Val Arg Leu
                85                  90                  95

Gly Ser Gly Gly His Leu His Leu Arg Ile Ser Arg Ala Ala Leu Pro
            100                 105                 110

Glu Gly Leu Pro Glu Ala Ser Arg Leu His Arg Ala Leu Phe Arg Leu
        115                 120                 125

Ser Pro Thr Ala Ser Arg Ser Trp Asp Val Thr Arg Pro Leu Arg Arg
    130                 135                 140

Gln Leu Ser Leu Ala Arg Pro Gln Ala Pro Ala Leu His Leu Arg Leu
145                 150                 155                 160

Ser Pro Pro Pro Ser Gln Ser Asp Gln Leu Leu Ala Glu Ser Ser Ser
                165                 170                 175

Ala Arg Pro Gln Leu Glu Leu His Leu Arg Pro Gln Ala Ala Arg Gly
            180                 185                 190

Arg Arg Arg Ala Arg Ala Arg Asn Gly Asp His Cys Pro Leu Gly Pro
        195                 200                 205

Gly Arg Cys Cys Arg Leu His Thr Val Arg Ala Ser Leu Glu Asp Leu
    210                 215                 220

Gly Trp Ala Asp Trp Val Leu Ser Pro Arg Glu Val Gln Val Thr Met
225                 230                 235                 240

Cys Ile Gly Ala Cys Pro Ser Gln Phe Arg Ala Ala Asn Met His Ala
                245                 250                 255

Gln Ile Lys Thr Ser Leu His Arg Leu Lys Pro Asp Thr Val Pro Ala
            260                 265                 270

Pro Cys Cys Val Pro Ala Ser Tyr Asn Pro Met Val Leu Ile Gln Lys
        275                 280                 285

Thr Asp Thr Gly Val Ser Leu Gln Thr Tyr Asp Asp Leu Leu Ala Lys
    290                 295                 300

Asp Cys His Cys Ile
305

<210> SEQ ID NO 99
<211> LENGTH: 426
<212> TYPE: PRT
<213> ORGANISM: Homo sapiens
```

<400> SEQUENCE: 99

| | | | | | | | | | | | | | | |
|---|---|---|---|---|---|---|---|---|---|---|---|---|---|---|
|Met|Pro|Leu|Leu|Trp|Leu|Arg|Gly|Phe|Leu|Leu|Ala|Ser|Cys|Trp|Ile|
|1| | | |5| | | | |10| | | | |15| |

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
            35                  40                  45

Asn Ser Gln Pro Glu Met Val Glu Ala Val Lys Lys His Ile Leu Asn
50                    55                  60

Met Leu His Leu Lys Lys Arg Pro Asp Val Thr Gln Pro Val Pro Lys
65                    70                  75                  80

Ala Ala Leu Leu Asn Ala Ile Arg Lys Leu His Val Gly Lys Val Gly
            85                  90                  95

Glu Asn Gly Tyr Val Glu Ile Glu Asp Asp Ile Gly Arg Arg Ala Glu
            100                105              110

Met Asn Glu Leu Met Glu Gln Thr Ser Glu Ile Ile Thr Phe Ala Glu
            115                120              125

Ser Gly Thr Ala Arg Lys Thr Leu His Phe Glu Ile Ser Lys Glu Gly
            130                135              140

Ser Asp Leu Ser Val Val Glu Arg Ala Glu Val Trp Leu Phe Leu Lys
145                    150                  155                  160

Val Pro Lys Ala Asn Arg Thr Arg Thr Lys Val Thr Ile Arg Leu Phe
            165                170              175

Gln Gln Gln Lys His Pro Gln Gly Ser Leu Asp Thr Gly Glu Glu Ala
            180                185              190

Glu Glu Val Gly Leu Lys Gly Glu Arg Ser Glu Leu Leu Leu Ser Glu
            195                200              205

Lys Val Val Asp Ala Arg Lys Ser Thr Trp His Val Phe Pro Val Ser
210                    215                  220

Ser Ser Ile Gln Arg Leu Leu Asp Gln Gly Lys Ser Ser Leu Asp Val
225                    230                  235                  240

Arg Ile Ala Cys Glu Gln Cys Gln Glu Ser Gly Ala Ser Leu Val Leu
            245                250              255

Leu Gly Lys Lys Lys Lys Lys Glu Glu Glu Gly Glu Gly Lys Lys Lys
            260                265              270

Gly Gly Gly Glu Gly Gly Ala Gly Ala Asp Glu Glu Lys Glu Gln Ser
            275                280              285

His Arg Pro Phe Leu Met Leu Gln Ala Arg Gln Ser Glu Asp His Pro
            290                295              300

His Arg Arg Arg Arg Gly Leu Glu Cys Asp Gly Lys Val Asn Ile
305                    310                  315                  320

Cys Cys Lys Lys Gln Phe Phe Val Ser Phe Lys Asp Ile Gly Trp Asn
            325                330              335

Asp Trp Ile Ile Ala Pro Ser Gly Tyr His Ala Asn Tyr Cys Glu Gly
            340                345              350

Glu Cys Pro Ser His Ile Ala Gly Thr Ser Gly Ser Ser Leu Ser Phe
            355                360              365

His Ser Thr Val Ile Asn His Tyr Arg Met Arg Gly His Ser Pro Phe
            370                375              380

Ala Asn Leu Lys Ser Cys Cys Val Pro Thr Lys Leu Arg Pro Met Ser
385                    390                  395                  400

Met Leu Tyr Tyr Asp Asp Gly Gln Asn Ile Ile Lys Lys Asp Ile Gln
            405                410              415

```
Asn Met Ile Val Glu Glu Cys Gly Cys Ser
            420                 425
```

<210> SEQ ID NO 100
<211> LENGTH: 407
<212> TYPE: PRT
<213> ORGANISM: Homo sapiens

<400> SEQUENCE: 100

```
Met Asp Gly Leu Pro Gly Arg Ala Leu Gly Ala Ala Cys Leu Leu Leu
 1               5                  10                  15

Leu Ala Ala Gly Trp Leu Gly Pro Glu Ala Trp Gly Ser Pro Thr Pro
            20                  25                  30

Pro Pro Thr Pro Ala Ala Pro Pro Pro Pro Pro Gly Ala Pro
        35                  40                  45

Gly Gly Ser Gln Asp Thr Cys Thr Ser Cys Gly Gly Phe Arg Arg Pro
 50                  55                  60

Glu Glu Leu Gly Arg Val Asp Gly Asp Phe Leu Glu Ala Val Lys Arg
 65                  70                  75                  80

His Ile Leu Ser Arg Leu Gln Met Arg Gly Arg Pro Asn Ile Thr His
                85                  90                  95

Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly
        115                 120                 125

His Ala Ser Pro Gly Ala Asp Gly Gln Glu Arg Val Ser Glu Ile Ile
    130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Val Gln Ala
                165                 170                 175

Ser Leu Trp Leu Tyr Leu Lys Leu Leu Pro Tyr Val Leu Glu Lys Gly
            180                 185                 190

Ser Arg Arg Lys Val Arg Val Lys Val Tyr Phe Gln Glu Gln Gly His
        195                 200                 205

Gly Asp Arg Trp Asn Met Val Glu Lys Arg Val Asp Leu Lys Arg Ser
    210                 215                 220

Gly Trp His Thr Phe Pro Leu Thr Glu Ala Ile Gln Ala Leu Phe Glu
225                 230                 235                 240

Arg Gly Glu Arg Arg Leu Asn Leu Asp Val Gln Cys Asp Ser Cys Gln
                245                 250                 255

Glu Leu Ala Val Val Pro Val Phe Val Asp Pro Gly Glu Glu Ser His
            260                 265                 270

Arg Pro Phe Val Val Val Gln Ala Arg Leu Gly Asp Ser Arg His Arg
        275                 280                 285

Ile Arg Lys Arg Gly Leu Glu Cys Asp Gly Arg Thr Asn Leu Cys Cys
    290                 295                 300

Arg Gln Gln Phe Phe Ile Asp Phe Arg Leu Ile Gly Trp Asn Asp Trp
305                 310                 315                 320

Ile Ile Ala Pro Thr Gly Tyr Tyr Gly Asn Tyr Cys Glu Gly Ser Cys
                325                 330                 335

Pro Ala Tyr Leu Ala Gly Val Pro Gly Ser Ala Ser Ser Phe His Thr
            340                 345                 350

Ala Val Val Asn Gln Tyr Arg Met Arg Gly Leu Asn Pro Gly Thr Val
```

-continued

```
              355                 360                 365
Asn Ser Cys Cys Ile Pro Thr Lys Leu Ser Thr Met Ser Met Leu Tyr
    370                 375                 380

Phe Asp Asp Glu Tyr Asn Ile Val Lys Arg Asp Val Pro Asn Met Ile
385                 390                 395                 400

Val Glu Glu Cys Gly Cys Ala
                405

<210> SEQ ID NO 101
<211> LENGTH: 352
<212> TYPE: PRT
<213> ORGANISM: Homo sapiens

<400> SEQUENCE: 101

Met Thr Ser Ser Leu Leu Ala Phe Leu Leu Ala Pro Thr Thr
  1               5                  10                  15

Val Ala Thr Pro Arg Ala Gly Gly Gln Cys Pro Ala Cys Gly Gly Pro
            20                  25                  30

Thr Leu Glu Leu Glu Ser Gln Arg Glu Leu Leu Asp Leu Ala Lys
        35                  40                  45

Arg Ser Ile Leu Asp Lys Leu His Leu Thr Gln Arg Pro Thr Leu Asn
 50                  55                  60

Arg Pro Val Ser Arg Ala Ala Leu Arg Thr Ala Leu Gln His Leu His
65                  70                  75                  80

Gly Val Pro Gln Gly Ala Leu Leu Glu Asp Asn Arg Glu Gln Glu Cys
                85                  90                  95

Glu Ile Ile Ser Phe Ala Glu Thr Gly Leu Ser Thr Ile Asn Gln Thr
            100                 105                 110

Arg Leu Asp Phe His Phe Ser Ser Asp Arg Thr Ala Gly Asp Arg Glu
        115                 120                 125

Val Gln Gln Ala Ser Leu Met Phe Phe Val Gln Leu Pro Ser Asn Thr
    130                 135                 140

Thr Trp Thr Leu Lys Val Arg Val Leu Val Leu Gly Pro His Asn Thr
145                 150                 155                 160

Asn Leu Thr Leu Ala Thr Gln Tyr Leu Leu Glu Val Asp Ala Ser Gly
                165                 170                 175

Trp His Gln Leu Pro Leu Gly Pro Glu Ala Gln Ala Ala Cys Ser Gln
            180                 185                 190

Gly His Leu Thr Leu Glu Leu Val Leu Glu Gly Gln Val Ala Gln Ser
        195                 200                 205

Ser Val Ile Leu Gly Gly Ala Ala His Arg Pro Phe Val Ala Ala Arg
    210                 215                 220

Val Arg Val Gly Gly Lys His Gln Ile His Arg Arg Gly Ile Asp Cys
225                 230                 235                 240

Gln Gly Gly Ser Arg Met Cys Cys Arg Gln Glu Phe Phe Val Asp Phe
                245                 250                 255

Arg Glu Ile Gly Trp His Asp Trp Ile Ile Gln Pro Glu Gly Tyr Ala
            260                 265                 270

Met Asn Phe Cys Ile Gly Gln Cys Pro Leu His Ile Ala Gly Met Pro
        275                 280                 285

Gly Ile Ala Ala Ser Phe His Thr Ala Val Leu Asn Leu Leu Lys Ala
    290                 295                 300

Asn Thr Ala Ala Gly Thr Thr Gly Gly Gly Ser Cys Cys Val Pro Thr
305                 310                 315                 320
```

```
Ala Arg Arg Pro Leu Ser Leu Leu Tyr Tyr Asp Arg Asp Ser Asn Ile
            325                 330                 335

Val Lys Thr Asp Ile Pro Asp Met Val Val Glu Ala Cys Gly Cys Ser
            340                 345                 350

<210> SEQ ID NO 102
<211> LENGTH: 350
<212> TYPE: PRT
<213> ORGANISM: Mus musculus

<400> SEQUENCE: 102

Met Lys Leu Pro Lys Ala Gln Leu Trp Leu Ile Leu Leu Trp Ala Leu
  1               5                  10                  15

Val Trp Val Gln Ser Arg Arg Ser Ala Cys Pro Ser Cys Gly Gly Pro
             20                  25                  30

Thr Leu Ala Pro Gln Gly Glu Arg Ala Leu Val Leu Glu Leu Ala Lys
         35                  40                  45

Gln Gln Ile Leu Glu Gly Leu His Leu Thr Ser Arg Pro Arg Ile Thr
     50                  55                  60

Arg Pro Leu Pro Gln Ala Ala Leu Thr Arg Ala Leu Arg Arg Leu Gln
 65                  70                  75                  80

Pro Lys Ser Met Val Pro Gly Asn Arg Glu Lys Val Ile Ser Phe Ala
                 85                  90                  95

Thr Ile Ile Asp Lys Ser Thr Ser Tyr Arg Ser Met Leu Thr Phe
            100                 105                 110

Gln Leu Ser Pro Leu Trp Ser His His Leu Tyr His Ala Arg Leu Trp
            115                 120                 125

Leu His Val Pro Pro Ser Phe Pro Gly Thr Leu Tyr Leu Arg Ile Phe
        130                 135                 140

Arg Cys Gly Thr Thr Arg Cys Arg Gly Phe Arg Thr Phe Leu Ala Glu
145                 150                 155                 160

His Gln Thr Thr Ser Ser Gly Trp His Ala Leu Thr Leu Pro Ser Ser
                165                 170                 175

Gly Leu Arg Ser Glu Asp Ser Gly Val Val Lys Leu Gln Leu Glu Phe
            180                 185                 190

Arg Pro Leu Asp Leu Asn Ser Thr Ala Ala Gly Leu Pro Arg Leu Leu
        195                 200                 205

Leu Asp Thr Ala Gly Gln Gln Arg Pro Phe Leu Glu Leu Lys Ile Arg
    210                 215                 220

Ala Asn Glu Pro Gly Ala Gly Arg Ala Arg Arg Thr Pro Thr Cys
225                 230                 235                 240

Glu Pro Glu Thr Pro Leu Cys Cys Arg Arg Asp His Tyr Val Asp Phe
                245                 250                 255

Gln Glu Leu Gly Trp Arg Asp Trp Ile Leu Gln Pro Glu Gly Tyr Gln
            260                 265                 270

Leu Asn Tyr Cys Ser Gly Gln Cys Pro Pro His Leu Ala Gly Ser Pro
        275                 280                 285

Gly Ile Ala Ala Ser Phe His Ser Ala Val Phe Ser Leu Leu Lys Ala
    290                 295                 300

Asn Asn Pro Trp Pro Ala Gly Ser Ser Cys Cys Val Pro Thr Ala Arg
305                 310                 315                 320

Arg Pro Leu Ser Leu Leu Tyr Leu Asp His Asn Gly Asn Val Val Lys
                325                 330                 335

Thr Asp Val Pro Asp Met Val Val Glu Ala Cys Gly Cys Ser
            340                 345                 350
```

<210> SEQ ID NO 103
<211> LENGTH: 351
<212> TYPE: PRT
<213> ORGANISM: Homo sapiens

<400> SEQUENCE: 103

Gly Val Ser Ser Gln Gly Leu Glu Leu Ala Arg Glu Leu Val Leu Ala
1               5                   10                  15

Lys Val Arg Ala Leu Phe Leu Asp Ala Leu Gly Pro Pro Ala Val Thr
            20                  25                  30

Arg Glu Gly Gly Asp Pro Gly Val Arg Arg Leu Pro Arg Arg His Ala
        35                  40                  45

Leu Gly Gly Phe Thr His Arg Gly Ser Glu Pro Glu Glu Glu Glu Asp
    50                  55                  60

Val Ser Gln Ala Ile Leu Phe Pro Ala Thr Asp Ala Ser Cys Glu Asp
65                  70                  75                  80

Lys Ser Ala Ala Arg Gly Leu Ala Gln Glu Ala Glu Gly Leu Phe
            85                  90                  95

Arg Tyr Met Phe Arg Pro Ser Gln His Thr Arg Ser Arg Gln Val Thr
            100                 105                 110

Ser Ala Gln Leu Trp Phe His Thr Gly Leu Asp Arg Gln Gly Thr Ala
        115                 120                 125

Ala Ser Asn Ser Ser Glu Pro Leu Leu Gly Leu Leu Ala Leu Ser Pro
    130                 135                 140

Gly Gly Pro Val Ala Val Pro Met Ser Leu Gly His Ala Pro Pro His
145                 150                 155                 160

Trp Ala Val Leu His Leu Ala Thr Ser Ala Leu Ser Leu Leu Thr His
                165                 170                 175

Pro Val Leu Val Leu Leu Leu Arg Cys Pro Leu Cys Thr Cys Ser Ala
            180                 185                 190

Arg Pro Glu Ala Thr Pro Phe Leu Val Ala His Thr Arg Thr Arg Pro
        195                 200                 205

Pro Ser Gly Gly Glu Arg Ala Arg Arg Ser Thr Pro Leu Met Ser Trp
    210                 215                 220

Pro Trp Ser Pro Ser Ala Leu Arg Leu Leu Gln Arg Pro Pro Glu Glu
225                 230                 235                 240

Pro Ala Ala His Ala Asn Cys His Arg Val Ala Leu Asn Ile Ser Phe
                245                 250                 255

Gln Glu Leu Gly Trp Glu Arg Trp Ile Val Tyr Pro Pro Ser Phe Ile
            260                 265                 270

Phe His Tyr Cys His Gly Cys Gly Leu His Ile Pro Pro Asn Leu
        275                 280                 285

Ser Leu Pro Val Pro Gly Ala Pro Pro Thr Pro Ala Gln Pro Tyr Ser
    290                 295                 300

Leu Leu Pro Gly Ala Gln Pro Cys Cys Ala Ala Leu Pro Gly Thr Met
305                 310                 315                 320

Arg Pro Leu His Val Arg Thr Thr Ser Asp Gly Tyr Ser Phe Lys
                325                 330                 335

Tyr Glu Thr Val Pro Asn Leu Leu Thr Gln His Cys Ala Cys Ile
            340                 345                 350

<210> SEQ ID NO 104
<211> LENGTH: 5
<212> TYPE: PRT

<213> ORGANISM: Homo sapiens

<400> SEQUENCE: 104

Tyr Gly Gly Phe Leu
1               5

<210> SEQ ID NO 105
<211> LENGTH: 5
<212> TYPE: PRT
<213> ORGANISM: Homo sapiens

<400> SEQUENCE: 105

Tyr Gly Gly Phe Met
1               5

<210> SEQ ID NO 106
<211> LENGTH: 8
<212> TYPE: PRT
<213> ORGANISM: Homo sapiens

<400> SEQUENCE: 106

Tyr Gly Gly Phe Met Arg Gly Leu
1               5

<210> SEQ ID NO 107
<211> LENGTH: 7
<212> TYPE: PRT
<213> ORGANISM: Homo sapiens

<400> SEQUENCE: 107

Tyr Gly Gly Phe Met Arg Phe
1               5

<210> SEQ ID NO 108
<211> LENGTH: 22
<212> TYPE: PRT
<213> ORGANISM: Homo sapiens

<400> SEQUENCE: 108

Tyr Gly Gly Phe Met Arg Arg Val Gly Arg Pro Glu Trp Trp Met Asp
1               5                   10                  15

Tyr Gln Lys Arg Tyr Gly
            20

<210> SEQ ID NO 109
<211> LENGTH: 22
<212> TYPE: PRT
<213> ORGANISM: Necturus maculosus

<400> SEQUENCE: 109

Tyr Gly Gly Phe Met Arg Arg Val Gly Arg Pro Glu Trp Trp Leu Asp
1               5                   10                  15

Tyr Gln Lys Arg Tyr Gly
            20

<210> SEQ ID NO 110
<211> LENGTH: 22
<212> TYPE: PRT
<213> ORGANISM: Bombina orientalis

<400> SEQUENCE: 110

Tyr Gly Gly Phe Met Arg Arg Val Gly Arg Pro Glu Trp Trp Gln Asp
1               5                   10                  15

Tyr Gln Lys Arg Tyr Gly
           20

<210> SEQ ID NO 111
<211> LENGTH: 22
<212> TYPE: PRT
<213> ORGANISM: Xenopus laevis

<400> SEQUENCE: 111

Tyr Gly Gly Phe Met Arg Arg Val Gly Arg Pro Glu Trp Trp Glu Asp
1               5                   10                  15

Tyr Gln Lys Arg Tyr Gly
           20

<210> SEQ ID NO 112
<211> LENGTH: 22
<212> TYPE: PRT
<213> ORGANISM: Neoceratodus forsteri

<400> SEQUENCE: 112

Tyr Gly Gly Phe Met Arg Arg Val Gly Arg Pro Glu Trp Lys Leu Asp
1               5                   10                  15

Asn Gln Lys Arg Tyr Gly
           20

<210> SEQ ID NO 113
<211> LENGTH: 21
<212> TYPE: PRT
<213> ORGANISM: Danio rerio

<400> SEQUENCE: 113

Tyr Gly Gly Phe Met Arg Arg Val Gly Arg Pro Asp Trp Trp Gln Glu
1               5                   10                  15

Ser Lys Arg Tyr Gly
           20

<210> SEQ ID NO 114
<211> LENGTH: 4
<212> TYPE: PRT
<213> ORGANISM: Homo sapiens

<400> SEQUENCE: 114

Tyr Pro Trp Phe
 1

<210> SEQ ID NO 115
<211> LENGTH: 4
<212> TYPE: PRT
<213> ORGANISM: Homo sapiens

<400> SEQUENCE: 115

Tyr Pro Phe Phe
 1

<210> SEQ ID NO 116
<211> LENGTH: 10
<212> TYPE: PRT
<213> ORGANISM: Homo sapiens

<400> SEQUENCE: 116

Tyr Gly Gly Phe Leu Arg Lys Tyr Pro Lys
1               5                   10

```
<210> SEQ ID NO 117
<211> LENGTH: 31
<212> TYPE: PRT
<213> ORGANISM: Homo sapiens

<400> SEQUENCE: 117

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 118
<211> LENGTH: 31
<212> TYPE: PRT
<213> ORGANISM: Homo sapiens

<400> SEQUENCE: 118

Tyr Gly Gly Phe Met Ser Ser Glu Lys Ser Gln Thr Pro Leu Val Thr
1               5                   10                  15

Leu Phe Lys Asn Ala Ile Ile Lys Asn Ala His Lys Lys Gly Gln
            20                  25                  30

<210> SEQ ID NO 119
<211> LENGTH: 9
<212> TYPE: PRT
<213> ORGANISM: Homo sapiens

<400> SEQUENCE: 119

Tyr Gly Gly Phe Leu Arg Lys Tyr Pro
1               5

<210> SEQ ID NO 120
<211> LENGTH: 17
<212> TYPE: PRT
<213> ORGANISM: Homo sapiens

<400> SEQUENCE: 120

Tyr Gly Gly Phe Met Thr Ser Glu Lys Ser Gln Thr Pro Leu Val Thr
1               5                   10                  15

Leu

<210> SEQ ID NO 121
<211> LENGTH: 17
<212> TYPE: PRT
<213> ORGANISM: Homo sapiens

<400> SEQUENCE: 121

Tyr Gly Gly Phe Leu Arg Arg Ile Arg Pro Lys Leu Lys Trp Asp Asn
1               5                   10                  15

Gln

<210> SEQ ID NO 122
<211> LENGTH: 13
<212> TYPE: PRT
<213> ORGANISM: Homo sapiens

<400> SEQUENCE: 122

Tyr Gly Gly Phe Leu Arg Arg Ile Arg Pro Lys Leu Lys
1               5                   10

<210> SEQ ID NO 123
<211> LENGTH: 16
<212> TYPE: PRT
```

```
<213> ORGANISM: Homo sapiens

<400> SEQUENCE: 123

Gly Gly Phe Leu Arg Arg Ile Arg Pro Lys Leu Lys Trp Asp Asn Gln
 1               5                  10                  15

<210> SEQ ID NO 124
<211> LENGTH: 12
<212> TYPE: PRT
<213> ORGANISM: Homo sapiens

<400> SEQUENCE: 124

Gly Gly Phe Leu Arg Arg Ile Arg Pro Lys Leu Lys
 1               5                  10

<210> SEQ ID NO 125
<211> LENGTH: 17
<212> TYPE: PRT
<213> ORGANISM: Xenopus laevis

<400> SEQUENCE: 125

Tyr Gly Gly Phe Leu Arg Arg Ile Arg Pro Lys Leu Arg Trp Asp Asn
 1               5                  10                  15

Gln

<210> SEQ ID NO 126
<211> LENGTH: 17
<212> TYPE: PRT
<213> ORGANISM: Xenopus laevis

<400> SEQUENCE: 126

Tyr Gly Gly Phe Leu Arg Arg Ile Arg Pro Arg Leu Arg Trp Asp Asn
 1               5                  10                  15

Gln

<210> SEQ ID NO 127
<211> LENGTH: 17
<212> TYPE: PRT
<213> ORGANISM: Protopterus annectens

<400> SEQUENCE: 127

Tyr Gly Gly Phe Met Arg Arg Ile Arg Pro Lys Ile Arg Trp Asp Asn
 1               5                  10                  15

Gln

<210> SEQ ID NO 128
<211> LENGTH: 17
<212> TYPE: PRT
<213> ORGANISM: Danio rerio

<400> SEQUENCE: 128

Tyr Gly Gly Phe Met Arg Arg Ile Arg Pro Lys Leu Arg Trp Asp Asn
 1               5                  10                  15

Gln

<210> SEQ ID NO 129
<211> LENGTH: 17
<212> TYPE: PRT
<213> ORGANISM: Anguilla rostrata

<400> SEQUENCE: 129

Tyr Gly Gly Phe Met Arg Arg Ile Arg Pro Lys Leu Lys Trp Asp Ser
```

```
                1               5                  10                  15

Gln

<210> SEQ ID NO 130
<211> LENGTH: 29
<212> TYPE: PRT
<213> ORGANISM: Homo sapiens

<400> SEQUENCE: 130

Tyr Gly Gly Phe Leu Arg Arg Gln Phe Lys Val Val Thr Arg Ser Gln
  1               5                  10                  15

Glu Asp Pro Asn Ala Tyr Ser Gly Glu Leu Phe Asp Ala
             20                  25

<210> SEQ ID NO 131
<211> LENGTH: 28
<212> TYPE: PRT
<213> ORGANISM: Rattus norvegicus

<400> SEQUENCE: 131

Tyr Gly Gly Phe Leu Arg Arg Gln Phe Lys Val Val Thr Arg Ser Gln
  1               5                  10                  15

Glu Asn Pro Asn Thr Tyr Ser Glu Asp Leu Asp Val
             20                  25

<210> SEQ ID NO 132
<211> LENGTH: 28
<212> TYPE: PRT
<213> ORGANISM: Mus musculus

<400> SEQUENCE: 132

Tyr Gly Gly Phe Leu Arg Arg Gln Phe Lys Val Val Thr Arg Ser Gln
  1               5                  10                  15

Glu Ser Pro Asn Thr Tyr Ser Glu Asp Leu Asp Val
             20                  25

<210> SEQ ID NO 133
<211> LENGTH: 29
<212> TYPE: PRT
<213> ORGANISM: Cavia porcellus

<400> SEQUENCE: 133

Tyr Gly Gly Phe Leu Arg Arg Gln Phe Lys Val Val Thr Arg Ser Gln
  1               5                  10                  15

Glu Asp Pro Asn Ala Tyr Ser Glu Glu Phe Phe Asp Val
             20                  25

<210> SEQ ID NO 134
<211> LENGTH: 29
<212> TYPE: PRT
<213> ORGANISM: Sus scrofa

<400> SEQUENCE: 134

Tyr Gly Gly Phe Leu Arg Arg Gln Phe Lys Val Val Thr Arg Ser Gln
  1               5                  10                  15

Glu Asp Pro Asn Ala Tyr Tyr Glu Glu Leu Phe Asp Val
             20                  25

<210> SEQ ID NO 135
<211> LENGTH: 29
<212> TYPE: PRT
<213> ORGANISM: Canis familiaris
```

<400> SEQUENCE: 135

Tyr Gly Gly Phe Leu Arg Arg Gln Phe Lys Val Val Thr Arg Ser Gln
1               5                   10                  15

Glu Asp Pro Asn Ala Tyr Ser Gly Glu Leu Leu Asp Gly
            20                  25

<210> SEQ ID NO 136
<211> LENGTH: 29
<212> TYPE: PRT
<213> ORGANISM: Bos taurus

<400> SEQUENCE: 136

Tyr Gly Gly Phe Leu Arg Arg Gln Phe Lys Val Val Thr Arg Ser Gln
1               5                   10                  15

Glu Asp Pro Ser Ala Tyr Tyr Glu Glu Leu Phe Asp Val
            20                  25

<210> SEQ ID NO 137
<211> LENGTH: 29
<212> TYPE: PRT
<213> ORGANISM: Bufo marinus

<400> SEQUENCE: 137

Tyr Gly Gly Phe Leu Arg Arg Gln Phe Lys Val Thr Thr Arg Ser Glu
1               5                   10                  15

Glu Asp Pro Ser Thr Phe Ser Gly Glu Leu Ser Asn Leu
            20                  25

<210> SEQ ID NO 138
<211> LENGTH: 29
<212> TYPE: PRT
<213> ORGANISM: Bombina orientalis

<400> SEQUENCE: 138

Tyr Gly Gly Phe Leu Arg Arg Gln Phe Lys Val Thr Thr Arg Ser Glu
1               5                   10                  15

Glu Glu Pro Gly Ser Phe Ser Gly Glu Ile Ser Asn Leu
            20                  25

<210> SEQ ID NO 139
<211> LENGTH: 29
<212> TYPE: PRT
<213> ORGANISM: Xenopus laevis

<400> SEQUENCE: 139

Tyr Gly Gly Phe Leu Arg Arg Gln Phe Lys Val Asn Ala Arg Ser Glu
1               5                   10                  15

Glu Asp Pro Thr Met Phe Ser Asp Glu Leu Ser Tyr Leu
            20                  25

<210> SEQ ID NO 140
<211> LENGTH: 29
<212> TYPE: PRT
<213> ORGANISM: Xenopus laevis

<400> SEQUENCE: 140

Tyr Gly Gly Phe Leu Arg Arg Gln Phe Lys Val Asn Ala Arg Ser Glu
1               5                   10                  15

Glu Asp Pro Thr Met Phe Ser Gly Glu Leu Ser Tyr Leu
            20                  25

<210> SEQ ID NO 141
<211> LENGTH: 29
<212> TYPE: PRT
<213> ORGANISM: Polypterus senegalus

<400> SEQUENCE: 141

Tyr Gly Gly Phe Leu Arg Arg His Phe Lys Ile Ser Val Arg Ser Asp
1               5                   10                  15

Glu Glu Pro Ser Ser Tyr Ser Asp Glu Val Leu Glu Leu
            20                  25

<210> SEQ ID NO 142
<211> LENGTH: 27
<212> TYPE: PRT
<213> ORGANISM: Danio rerio

<400> SEQUENCE: 142

Tyr Gly Gly Phe Leu Arg Arg His Phe Lys Ile Ser Val Arg Ser Asp
1               5                   10                  15

Glu Glu Pro Ser Ser Tyr Glu Asp Tyr Ala Leu
            20                  25

<210> SEQ ID NO 143
<211> LENGTH: 27
<212> TYPE: PRT
<213> ORGANISM: Anguilla rostrata

<400> SEQUENCE: 143

Tyr Gly Gly Phe Leu Arg Arg His Phe Lys Ile Ser Val Arg Ser Asp
1               5                   10                  15

Glu Glu Pro Gly Ser Tyr Asp Val Ile Gly Leu
            20                  25

<210> SEQ ID NO 144
<211> LENGTH: 29
<212> TYPE: PRT
<213> ORGANISM: Neoceratodus forsteri

<400> SEQUENCE: 144

Tyr Gly Gly Phe Leu Arg Arg His Phe Lys Ile Thr Val Arg Ser Asp
1               5                   10                  15

Glu Asp Pro Ser Pro Tyr Leu Asp Glu Phe Ser Asp Leu
            20                  25

<210> SEQ ID NO 145
<211> LENGTH: 27
<212> TYPE: PRT
<213> ORGANISM: Oncorhynchus masou

<400> SEQUENCE: 145

Tyr Gly Gly Phe Leu Arg Arg His Tyr Lys Leu Ser Val Arg Ser Asp
1               5                   10                  15

Glu Glu Pro Ser Ser Tyr Asp Asp Phe Gly Leu
            20                  25

<210> SEQ ID NO 146
<211> LENGTH: 13
<212> TYPE: PRT
<213> ORGANISM: Homo sapiens

<400> SEQUENCE: 146

Tyr Gly Gly Phe Leu Arg Arg Gln Phe Lys Val Val Thr

```
                1               5                   10

<210> SEQ ID NO 147
<211> LENGTH: 13
<212> TYPE: PRT
<213> ORGANISM: Bufo marinus

<400> SEQUENCE: 147

Tyr Gly Gly Phe Leu Arg Arg Gln Phe Lys Val Thr Thr
 1               5                   10

<210> SEQ ID NO 148
<211> LENGTH: 13
<212> TYPE: PRT
<213> ORGANISM: Xenopus laevis

<400> SEQUENCE: 148

Tyr Gly Gly Phe Leu Arg Arg Gln Phe Lys Val Asn Ala
 1               5                   10

<210> SEQ ID NO 149
<211> LENGTH: 13
<212> TYPE: PRT
<213> ORGANISM: Polypterus senegalus

<400> SEQUENCE: 149

Tyr Gly Gly Phe Leu Arg Arg His Phe Lys Ile Ser Val
 1               5                   10

<210> SEQ ID NO 150
<211> LENGTH: 13
<212> TYPE: PRT
<213> ORGANISM: Neoceratodus forsteri

<400> SEQUENCE: 150

Tyr Gly Gly Phe Leu Arg Arg His Phe Lys Ile Thr Val
 1               5                   10

<210> SEQ ID NO 151
<211> LENGTH: 13
<212> TYPE: PRT
<213> ORGANISM: Oncorhynchus masou

<400> SEQUENCE: 151

Tyr Gly Gly Phe Leu Arg Arg His Tyr Lys Leu Ser Val
 1               5                   10

<210> SEQ ID NO 152
<211> LENGTH: 17
<212> TYPE: PRT
<213> ORGANISM: Homo sapiens

<400> SEQUENCE: 152

Phe Gly Gly Phe Thr Gly Ala Arg Lys Ser Ala Arg Lys Arg Lys Asn
 1               5                   10                  15

Gln

<210> SEQ ID NO 153
<211> LENGTH: 17
<212> TYPE: PRT
<213> ORGANISM: Homo sapiens

<400> SEQUENCE: 153

Phe Gly Gly Phe Thr Gly Ala Arg Lys Ser Ala Arg Lys Leu Ala Asn
```

-continued

```
                1               5                  10                  15
Gln

<210> SEQ ID NO 154
<211> LENGTH: 17
<212> TYPE: PRT
<213> ORGANISM: Homo sapiens

<400> SEQUENCE: 154

Phe Gly Gly Phe Thr Gly Ala Arg Lys Ser Ala Arg Lys Tyr Ala Asn
1               5                   10                  15
Gln

<210> SEQ ID NO 155
<211> LENGTH: 11
<212> TYPE: PRT
<213> ORGANISM: Homo sapiens

<400> SEQUENCE: 155

Phe Gly Gly Phe Thr Gly Ala Arg Lys Ser Ala
1               5                   10

<210> SEQ ID NO 156
<211> LENGTH: 11
<212> TYPE: PRT
<213> ORGANISM: Homo sapiens

<400> SEQUENCE: 156

Phe Gly Gly Phe Thr Gly Ala Arg Lys Tyr Ala
1               5                   10

<210> SEQ ID NO 157
<211> LENGTH: 11
<212> TYPE: PRT
<213> ORGANISM: Homo sapiens

<400> SEQUENCE: 157

Phe Gly Gly Phe Thr Gly Ala Arg Lys Ser Tyr
1               5                   10

<210> SEQ ID NO 158
<211> LENGTH: 13
<212> TYPE: PRT
<213> ORGANISM: Homo sapiens

<400> SEQUENCE: 158

Phe Gly Gly Phe Thr Gly Ala Arg Lys Ser Ala Arg Lys
1               5                   10

<210> SEQ ID NO 159
<211> LENGTH: 30
<212> TYPE: PRT
<213> ORGANISM: Homo sapiens

<400> SEQUENCE: 159

Met Pro Arg Val Arg Ser Leu Phe Gln Glu Gln Glu Glu Pro Glu Pro
1               5                   10                  15
Gly Met Glu Glu Ala Gly Glu Met Glu Gln Lys Gln Leu Gln
            20                  25                  30

<210> SEQ ID NO 160
<211> LENGTH: 17
<212> TYPE: PRT
```

<213> ORGANISM: Homo sapiens

<400> SEQUENCE: 160

Phe Ser Glu Phe Met Arg Gln Tyr Leu Val Leu Ser Met Gln Ser Ser
1               5                   10                  15

Gln

<210> SEQ ID NO 161
<211> LENGTH: 8
<212> TYPE: PRT
<213> ORGANISM: Homo sapiens

<400> SEQUENCE: 161

Thr Leu His Gln Asn Gly Asn Val
1               5

<210> SEQ ID NO 162
<211> LENGTH: 13
<212> TYPE: PRT
<213> ORGANISM: Homo sapiens

<400> SEQUENCE: 162

Ser Tyr Ser Met Glu His Phe Arg Trp Gly Lys Pro Val
1               5                   10

<210> SEQ ID NO 163
<211> LENGTH: 18
<212> TYPE: PRT
<213> ORGANISM: Homo sapiens

<400> SEQUENCE: 163

Asp Glu Gly Pro Tyr Arg Met Glu His Phe Arg Trp Gly Ser Pro Pro
1               5                   10                  15

Lys Asp

<210> SEQ ID NO 164
<211> LENGTH: 11
<212> TYPE: PRT
<213> ORGANISM: Homo sapiens

<400> SEQUENCE: 164

Tyr Val Met Gly His Phe Arg Trp Asp Arg Phe
1               5                   10

<210> SEQ ID NO 165
<211> LENGTH: 39
<212> TYPE: PRT
<213> ORGANISM: Homo sapiens

<400> SEQUENCE: 165

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
                20                  25                  30

Glu Ala Phe Pro Leu Glu Phe
            35

<210> SEQ ID NO 166
<211> LENGTH: 21
<212> TYPE: PRT
<213> ORGANISM: Homo sapiens

<400> SEQUENCE: 166

-continued

```
Pro Val Lys Val Tyr Pro Asn Gly Ala Glu Asp Glu Ser Ala Glu Ala
1               5                   10                  15

Phe Pro Leu Glu Phe
            20

<210> SEQ ID NO 167
<211> LENGTH: 89
<212> TYPE: PRT
<213> ORGANISM: Homo sapiens

<400> SEQUENCE: 167

Glu Leu Thr Gly Gln Arg Leu Arg Glu Gly Asp Gly Pro Asp Gly Pro
1               5                   10                  15

Ala Asp Asp Gly Ala Gly Ala Gln Ala Asp Leu Glu His Ser Leu Leu
            20                  25                  30

Val Ala Ala Glu Lys Lys Asp Glu Gly Pro Tyr Arg Met Glu His Phe
        35                  40                  45

Arg Trp Gly Ser Pro Pro Lys Asp Lys Arg Tyr Gly Gly Phe Met Thr
    50                  55                  60

Ser Glu Lys Ser Gln Thr Pro Leu Val Thr Leu Phe Lys Asn Ala Ile
65                  70                  75                  80

Ile Lys Asn Ala Tyr Lys Lys Gly Glu
                85

<210> SEQ ID NO 168
<211> LENGTH: 56
<212> TYPE: PRT
<213> ORGANISM: Homo sapiens

<400> SEQUENCE: 168

Glu Leu Thr Gly Gln Arg Leu Arg Glu Gly Asp Gly Pro Asp Gly Pro
1               5                   10                  15

Ala Asp Asp Gly Ala Gly Ala Gln Ala Asp Leu Glu His Ser Leu Leu
            20                  25                  30

Val Ala Ala Glu Lys Lys Asp Glu Gly Pro Tyr Arg Met Glu His Phe
        35                  40                  45

Arg Trp Gly Ser Pro Pro Lys Asp
    50                  55

<210> SEQ ID NO 169
<211> LENGTH: 30
<212> TYPE: PRT
<213> ORGANISM: Homo sapiens

<400> SEQUENCE: 169

Glu Asp Val Ser Ala Gly Glu Asp Cys Gly Pro Leu Pro Glu Gly Gly
1               5                   10                  15

Pro Glu Pro Arg Ser Asp Gly Ala Lys Pro Gly Pro Arg Glu
            20                  25                  30

<210> SEQ ID NO 170
<211> LENGTH: 23
<212> TYPE: PRT
<213> ORGANISM: Homo sapiens

<400> SEQUENCE: 170

Ser Ser Glu Met Ala Arg Asp Glu Asp Gly Gly Gln Asp Gly Asp Gln
1               5                   10                  15

Val Gly His Glu Asp Leu Tyr
```

-continued

<210> SEQ ID NO 171
<211> LENGTH: 76
<212> TYPE: PRT
<213> ORGANISM: Homo sapiens

<400> SEQUENCE: 171

Trp Cys Leu Glu Ser Ser Gln Cys Gln Asp Leu Thr Thr Glu Ser Asn
1               5                   10                  15

Leu Leu Glu Cys Ile Arg Ala Cys Lys Pro Asp Leu Ser Ala Glu Thr
            20                  25                  30

Pro Met Phe Pro Gly Asn Gly Asp Glu Gln Pro Leu Thr Glu Asn Pro
        35                  40                  45

Arg Lys Tyr Val Met Gly His Phe Arg Trp Asp Arg Phe Gly Arg Arg
    50                  55                  60

Asn Ser Ser Ser Ser Gly Ser Ser Gly Ala Gly Gln
65                  70                  75

<210> SEQ ID NO 172
<211> LENGTH: 30
<212> TYPE: PRT
<213> ORGANISM: Homo sapiens

<400> SEQUENCE: 172

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 173
<211> LENGTH: 59
<212> TYPE: PRT
<213> ORGANISM: Homo sapiens

<400> SEQUENCE: 173

Glu Leu Arg Pro Glu Asp Asp Met Lys Pro Gly Ser Phe Asp Arg Ser
1               5                   10                  15

Ile Pro Glu Asn Asn Ile Met Arg Thr Ile Ile Glu Phe Leu Ser Phe
            20                  25                  30

Leu His Leu Lys Glu Ala Gly Ala Leu Asp Arg Leu Leu Asp Leu Pro
        35                  40                  45

Ala Ala Ala Ser Ser Gly Asp Ile Glu Arg Ser
    50                  55

<210> SEQ ID NO 174
<211> LENGTH: 113
<212> TYPE: PRT
<213> ORGANISM: Homo sapiens

<400> SEQUENCE: 174

Leu Pro Val Asn Ser Pro Met Asn Lys Gly Asp Thr Glu Val Met Lys
1               5                   10                  15

Cys Ile Val Glu Val Ile Ser Asp Thr Leu Ser Lys Pro Ser Pro Met
            20                  25                  30

Pro Val Ser Gln Glu Cys Phe Glu Thr Leu Arg Gly Asp Glu Arg Ile
        35                  40                  45

Leu Ser Ile Leu Arg His Gln Asn Leu Leu Lys Glu Leu Gln Asp Leu
    50                  55                  60

Ala Leu Gln Gly Ala Lys Glu Arg Ala His Gln Gln Lys Lys His Ser
65                  70                  75                  80

Gly Phe Glu Asp Glu Leu Ser Glu Val Leu Glu Asn Gln Ser Ser Gln
                85                  90                  95

Ala Glu Leu Lys Glu Ala Val Glu Glu Pro Ser Ser Lys Asp Val Met
            100                 105                 110

Glu

<210> SEQ ID NO 175
<211> LENGTH: 76
<212> TYPE: PRT
<213> ORGANISM: Homo sapiens

<400> SEQUENCE: 175

Leu Pro Val Asn Ser Pro Met Asn Lys Gly Asp Thr Glu Val Met Lys
1               5                   10                  15

Cys Ile Val Glu Val Ile Ser Asp Thr Leu Ser Lys Pro Ser Pro Met
                20                  25                  30

Pro Val Ser Gln Glu Cys Phe Glu Thr Leu Arg Gly Asp Glu Arg Ile
            35                  40                  45

Leu Ser Ile Leu Arg His Gln Asn Leu Leu Lys Glu Leu Gln Asp Leu
        50                  55                  60

Ala Leu Gln Gly Ala Lys Glu Arg Ala His Gln Gln
65                  70                  75

<210> SEQ ID NO 176
<211> LENGTH: 20
<212> TYPE: PRT
<213> ORGANISM: Homo sapiens

<400> SEQUENCE: 176

Ser Gly Glu Ala Thr Asp Gly Ala Arg Pro Gln Ala Leu Pro Glu Pro
1               5                   10                  15

Met Gln Glu Ser
            20

<210> SEQ ID NO 177
<211> LENGTH: 53
<212> TYPE: PRT
<213> ORGANISM: Homo sapiens

<400> SEQUENCE: 177

Gly Glu Ser Arg Ser Glu Ala Leu Ala Val Asp Gly Ala Gly Lys Pro
1               5                   10                  15

Gly Ala Glu Glu Ala Gln Asp Pro Glu Gly Lys Gly Glu Gln Glu His
                20                  25                  30

Ser Gln Gln Lys Glu Glu Glu Glu Met Ala Val Val Pro Gln Gly
        35                  40                  45

Leu Phe Arg Gly Gly
        50

<210> SEQ ID NO 178
<211> LENGTH: 14
<212> TYPE: PRT
<213> ORGANISM: Homo sapiens

<400> SEQUENCE: 178

Trp Ser Lys Met Asp Gln Leu Ala Lys Glu Leu Thr Ala Glu
1               5                   10

```
<210> SEQ ID NO 179
<211> LENGTH: 21
<212> TYPE: PRT
<213> ORGANISM: Homo sapiens

<400> SEQUENCE: 179

Ser Ser Met Lys Leu Ser Phe Arg Ala Arg Ala Tyr Gly Phe Arg Gly
1               5                   10                  15

Pro Gly Pro Gln Leu
            20

<210> SEQ ID NO 180
<211> LENGTH: 72
<212> TYPE: PRT
<213> ORGANISM: Homo sapiens

<400> SEQUENCE: 180

Leu Ser Phe Arg Ala Arg Ala Tyr Gly Phe Arg Gly Pro Gly Pro Gln
1               5                   10                  15

Leu Arg Arg Gly Trp Arg Pro Ser Ser Arg Glu Asp Ser Leu Glu Ala
            20                  25                  30

Gly Leu Pro Leu Gln Val Arg Gly Tyr Pro Glu Glu Lys Lys Glu Glu
        35                  40                  45

Glu Gly Ser Ala Asn Arg Arg Pro Glu Asp Gln Glu Leu Glu Ser Leu
    50                  55                  60

Ser Ala Ile Glu Ala Glu Leu Glu
65                  70

<210> SEQ ID NO 181
<211> LENGTH: 25
<212> TYPE: PRT
<213> ORGANISM: Homo sapiens

<400> SEQUENCE: 181

Gly Trp Arg Pro Ser Ser Arg Glu Asp Ser Leu Glu Ala Gly Leu Pro
1               5                   10                  15

Leu Gln Val Arg Gly Tyr Pro Glu Glu
            20                  25

<210> SEQ ID NO 182
<211> LENGTH: 67
<212> TYPE: PRT
<213> ORGANISM: Homo sapiens

<400> SEQUENCE: 182

Arg Val Gln Glu Ser Gln Arg Asp Lys Ala Arg Arg Leu Pro Gly
1               5                   10                  15

Glu Leu Arg Asn Tyr Leu Asp Tyr Gly Glu Glu Lys Gly Glu Glu Ala
            20                  25                  30

Ala Arg Gly Lys Trp Gln Pro Gln Gly Asp Pro Arg Asp Ala Asp Glu
        35                  40                  45

Asn Arg Glu Glu Ala Arg Leu Arg Gly Lys Gln Tyr Ala Pro His His
    50                  55                  60

Ile Thr Glu
65

<210> SEQ ID NO 183
<211> LENGTH: 14
<212> TYPE: PRT
<213> ORGANISM: Homo sapiens
```

-continued

<400> SEQUENCE: 183

Gln Tyr Asp Arg Val Ala Gln Leu Asp Gln Leu Leu His Tyr
1               5                   10

<210> SEQ ID NO 184
<211> LENGTH: 14
<212> TYPE: PRT
<213> ORGANISM: Bos taurus

<400> SEQUENCE: 184

Gln Tyr Asp Arg Val Ala Glu Leu Asp Gln Leu Leu His Tyr
1               5                   10

<210> SEQ ID NO 185
<211> LENGTH: 11
<212> TYPE: PRT
<213> ORGANISM: Homo sapiens

<400> SEQUENCE: 185

Gln Lys Ile Ala Glu Lys Phe Ser Gln Arg Gly
1               5                   10

<210> SEQ ID NO 186
<211> LENGTH: 13
<212> TYPE: PRT
<213> ORGANISM: Homo sapiens

<400> SEQUENCE: 186

Gln Lys Ile Ala Glu Lys Phe Ser Gly Thr Arg Arg Gly
1               5                   10

<210> SEQ ID NO 187
<211> LENGTH: 33
<212> TYPE: PRT
<213> ORGANISM: Homo sapiens

<400> SEQUENCE: 187

Thr Asn Glu Ile Val Glu Glu Gln Tyr Thr Pro Gln Ser Leu Ala Thr
1               5                   10                  15

Leu Glu Ser Val Phe Gln Glu Leu Gly Lys Leu Thr Gly Pro Asn Asn
            20                  25                  30

Gln

<210> SEQ ID NO 188
<211> LENGTH: 11
<212> TYPE: PRT
<213> ORGANISM: Homo sapiens

<400> SEQUENCE: 188

Arg Pro Lys Pro Gln Gln Phe Phe Gly Leu Met
1               5                   10

<210> SEQ ID NO 189
<211> LENGTH: 12
<212> TYPE: PRT
<213> ORGANISM: Homo sapiens

<400> SEQUENCE: 189

Arg Pro Lys Pro Gln Gln Phe Phe Gly Leu Met Gly
1               5                   10

<210> SEQ ID NO 190

```
<211> LENGTH: 13
<212> TYPE: PRT
<213> ORGANISM: Homo sapiens

<400> SEQUENCE: 190

Arg Pro Lys Pro Gln Gln Phe Phe Gly Leu Met Gly Lys
1               5                   10

<210> SEQ ID NO 191
<211> LENGTH: 14
<212> TYPE: PRT
<213> ORGANISM: Homo sapiens

<400> SEQUENCE: 191

Arg Pro Lys Pro Gln Gln Phe Phe Gly Leu Met Gly Lys Arg
1               5                   10

<210> SEQ ID NO 192
<211> LENGTH: 36
<212> TYPE: PRT
<213> ORGANISM: Homo sapiens

<400> SEQUENCE: 192

Asp Ala Asp Ser Ser Ile Glu Lys Gln Val Ala Leu Leu Lys Ala Leu
1               5                   10                  15

Tyr Gly His Gly Gln Ile Ser His Lys Arg His Lys Thr Asp Ser Phe
            20                  25                  30

Val Gly Leu Met
        35

<210> SEQ ID NO 193
<211> LENGTH: 19
<212> TYPE: PRT
<213> ORGANISM: Homo sapiens

<400> SEQUENCE: 193

Gly His Gly Gln Ile Ser His Lys Arg His Lys Thr Asp Ser Phe Val
1               5                   10                  15

Gly Leu Met

<210> SEQ ID NO 194
<211> LENGTH: 10
<212> TYPE: PRT
<213> ORGANISM: Homo sapiens

<400> SEQUENCE: 194

His Lys Thr Asp Ser Phe Val Gly Leu Met
1               5                   10

<210> SEQ ID NO 195
<211> LENGTH: 10
<212> TYPE: PRT
<213> ORGANISM: Rattus norvegicus

<400> SEQUENCE: 195

Asp Met His Asp Phe Phe Val Gly Leu Met
1               5                   10

<210> SEQ ID NO 196
<211> LENGTH: 10
<212> TYPE: PRT
<213> ORGANISM: Homo sapiens

<400> SEQUENCE: 196
```

```
Ser Arg Thr Arg Gln Phe Tyr Gly Leu Met
  1               5                  10
```

<210> SEQ ID NO 197
<211> LENGTH: 10
<212> TYPE: PRT
<213> ORGANISM: Homo sapiens

<400> SEQUENCE: 197

```
Gly Lys Ala Ser Gln Phe Phe Gly Leu Met
  1               5                  10
```

<210> SEQ ID NO 198
<211> LENGTH: 14
<212> TYPE: PRT
<213> ORGANISM: Homo sapiens

<400> SEQUENCE: 198

```
Lys Lys Ala Tyr Gln Leu Glu His Thr Phe Gln Gly Leu Leu
  1               5                  10
```

<210> SEQ ID NO 199
<211> LENGTH: 14
<212> TYPE: PRT
<213> ORGANISM: Homo sapiens

<400> SEQUENCE: 199

```
Val Gly Ala Tyr Gln Leu Glu His Thr Phe Gln Gly Leu Leu
  1               5                  10
```

<210> SEQ ID NO 200
<211> LENGTH: 58
<212> TYPE: PRT
<213> ORGANISM: Homo sapiens

<400> SEQUENCE: 200

```
Val Ser Gln Arg Thr Asp Gly Glu Ser Arg Ala His Leu Gly Ala Leu
  1               5                  10                  15

Leu Ala Arg Tyr Ile Gln Gln Ala Arg Lys Ala Pro Ser Gly Arg Met
             20                  25                  30

Ser Ile Val Lys Asn Leu Gln Asn Leu Asp Pro Ser His Arg Ile Ser
         35                  40                  45

Asp Arg Asp Tyr Met Gly Trp Met Asp Phe
         50                  55
```

<210> SEQ ID NO 201
<211> LENGTH: 58
<212> TYPE: PRT
<213> ORGANISM: Pan troglodytes

<400> SEQUENCE: 201

```
Val Ser Gln Arg Thr Asp Gly Glu Ser Arg Ala His Leu Gly Ala Leu
  1               5                  10                  15

Leu Ala Arg Tyr Ile Gln Gln Ala Arg Lys Ala Pro Ser Gly Arg Met
             20                  25                  30

Ser Val Val Lys Asn Leu Gln Asn Leu Asp Pro Ser His Arg Ile Ser
         35                  40                  45

Asp Arg Asp Tyr Met Gly Trp Met Asp Phe
         50                  55
```

<210> SEQ ID NO 202

<211> LENGTH: 58
<212> TYPE: PRT
<213> ORGANISM: Macaca fascicularis

<400> SEQUENCE: 202

Ala Val Gln Arg Thr Asp Gly Glu Ser Arg Ala His Leu Gly Ala Leu
1               5                   10                  15

Leu Ala Arg Tyr Ile Gln Gln Ala Arg Lys Ala Pro Ser Gly Arg Met
            20                  25                  30

Ser Ile Ile Lys Asn Leu Gln Asn Leu Asp Pro Ser His Arg Ile Ser
        35                  40                  45

Asp Arg Asp Tyr Met Gly Trp Met Asp Phe
    50                  55

<210> SEQ ID NO 203
<211> LENGTH: 58
<212> TYPE: PRT
<213> ORGANISM: Canis familiaris

<400> SEQUENCE: 203

Ala Val Gln Lys Val Asp Gly Glu Pro Arg Ala His Leu Gly Ala Leu
1               5                   10                  15

Leu Ala Arg Tyr Ile Gln Gln Ala Arg Lys Ala Pro Ser Gly Arg Met
            20                  25                  30

Ser Val Ile Lys Asn Leu Gln Asn Leu Asp Pro Ser His Arg Ile Ser
        35                  40                  45

Asp Arg Asp Tyr Met Gly Trp Met Asp Phe
    50                  55

<210> SEQ ID NO 204
<211> LENGTH: 58
<212> TYPE: PRT
<213> ORGANISM: Sus scrofa

<400> SEQUENCE: 204

Ala Val Gln Lys Val Asp Gly Glu Ser Arg Ala His Leu Gly Ala Leu
1               5                   10                  15

Leu Ala Arg Tyr Ile Gln Gln Ala Arg Lys Ala Pro Ser Gly Arg Val
            20                  25                  30

Ser Met Ile Lys Asn Leu Gln Ser Leu Asp Pro Ser His Arg Ile Ser
        35                  40                  45

Asp Arg Asp Tyr Met Gly Trp Met Asp Phe
    50                  55

<210> SEQ ID NO 205
<211> LENGTH: 58
<212> TYPE: PRT
<213> ORGANISM: Mus musculus

<400> SEQUENCE: 205

Ala Val Leu Arg Thr Asp Gly Glu Pro Arg Ala Arg Leu Gly Ala Leu
1               5                   10                  15

Leu Ala Arg Tyr Ile Gln Gln Val Arg Lys Ala Pro Ser Gly Arg Met
            20                  25                  30

Ser Val Leu Lys Asn Leu Gln Ser Leu Asp Pro Ser His Arg Ile Ser
        35                  40                  45

Asp Arg Asp Tyr Met Gly Trp Met Asp Phe
    50                  55

-continued

<210> SEQ ID NO 206
<211> LENGTH: 58
<212> TYPE: PRT
<213> ORGANISM: Mus musculus

<400> SEQUENCE: 206

Ala Val Leu Arg Pro Asp Arg Glu Pro Arg Ala Arg Leu Gly Ala Leu
1               5                   10                  15

Leu Ala Arg Tyr Ile Gln Gln Val Arg Lys Ala Pro Ser Gly Arg Met
            20                  25                  30

Ser Val Leu Lys Asn Leu Gln Ser Leu Asp Pro Ser His Arg Ile Ser
        35                  40                  45

Asp Arg Asp Tyr Met Gly Trp Met Asp Phe
    50                  55

<210> SEQ ID NO 207
<211> LENGTH: 58
<212> TYPE: PRT
<213> ORGANISM: Bos taurus

<400> SEQUENCE: 207

Ala Val Pro Arg Val Asp Asp Glu Pro Arg Ala Gln Leu Gly Ala Leu
1               5                   10                  15

Leu Ala Arg Tyr Ile Gln Gln Ala Arg Lys Ala Pro Ser Gly Arg Met
            20                  25                  30

Ser Val Ile Lys Asn Leu Gln Ser Leu Asp Pro Ser His Arg Ile Ser
        35                  40                  45

Asp Arg Asp Tyr Met Gly Trp Met Asp Phe
    50                  55

<210> SEQ ID NO 208
<211> LENGTH: 58
<212> TYPE: PRT
<213> ORGANISM: Rattus norvegicus

<400> SEQUENCE: 208

Ala Val Leu Arg Pro Asp Ser Glu Pro Arg Ala Arg Leu Gly Ala Leu
1               5                   10                  15

Leu Ala Arg Tyr Ile Gln Gln Val Arg Lys Ala Pro Ser Gly Arg Met
            20                  25                  30

Ser Val Leu Lys Asn Leu Gln Gly Leu Asp Pro Ser His Arg Ile Ser
        35                  40                  45

Asp Arg Asp Tyr Met Gly Trp Met Asp Phe
    50                  55

<210> SEQ ID NO 209
<211> LENGTH: 59
<212> TYPE: PRT
<213> ORGANISM: Trachemys scripta

<400> SEQUENCE: 209

Gln Arg Leu Asp Gly Asn Val Asp Gln Lys Ala Asn Ile Gly Ala Leu
1               5                   10                  15

Leu Ala Lys Tyr Leu Gln Gln Ala Arg Lys Gly Pro Thr Gly Arg Ile
            20                  25                  30

Ser Met Met Gly Asn Arg Val Gln Asn Ile Asp Pro Thr His Arg Ile
        35                  40                  45

Asn Asp Arg Asp Tyr Met Gly Trp Met Asp Phe
    50                  55

```
<210> SEQ ID NO 210
<211> LENGTH: 59
<212> TYPE: PRT
<213> ORGANISM: Squalus acanthias

<400> SEQUENCE: 210

Leu Lys Pro Leu Gln Asp Ser Glu Gln Arg Ala Asn Leu Gly Ala Leu
1               5                   10                  15

Leu Thr Arg Tyr Leu Gln Gln Val Arg Lys Gly Pro Leu Gly Arg Gly
                20                  25                  30

Thr Leu Val Gly Thr Lys Leu Gln Asn Met Asp Pro Ser His Arg Ile
            35                  40                  45

Ala Asp Arg Asp Tyr Met Gly Trp Met Asp Phe
        50                  55

<210> SEQ ID NO 211
<211> LENGTH: 59
<212> TYPE: PRT
<213> ORGANISM: Struthio camelus

<400> SEQUENCE: 211

Pro Arg Leu Asp Gly Ser Ile Asp Gln Arg Ala Asn Ile Gly Ala Leu
1               5                   10                  15

Leu Ala Lys Tyr Leu Gln Gln Ala Arg Lys Gly Pro Thr Gly Arg Ile
                20                  25                  30

Ser Val Met Gly Asn Arg Val Gln Ser Ile Asp Pro Thr His Arg Ile
            35                  40                  45

Asn Asp Arg Asp Tyr Met Gly Trp Met Asp Phe
        50                  55

<210> SEQ ID NO 212
<211> LENGTH: 59
<212> TYPE: PRT
<213> ORGANISM: Gallus gallus

<400> SEQUENCE: 212

Pro Arg Leu Asp Gly Ser Phe Glu Gln Arg Ala Thr Ile Gly Ala Leu
1               5                   10                  15

Leu Ala Lys Tyr Leu Gln Gln Ala Arg Lys Gly Ser Thr Gly Arg Phe
                20                  25                  30

Ser Val Leu Gly Asn Arg Val Gln Ser Ile Asp Pro Thr His Arg Ile
            35                  40                  45

Asn Asp Arg Asp Tyr Met Gly Trp Met Asp Phe
        50                  55

<210> SEQ ID NO 213
<211> LENGTH: 57
<212> TYPE: PRT
<213> ORGANISM: Python molurus

<400> SEQUENCE: 213

Gln Leu Val Asp Gly Ser Ile Asp Gln Lys Ala Asn Leu Gly Ala Leu
1               5                   10                  15

Leu Ala Lys Tyr Leu Gln Gln Ala Arg Arg Gly Ser Thr Gly Lys Ala
                20                  25                  30

Ser Val Met Gly Leu Gln Asn Phe Asp Pro Thr His Arg Ile Lys Asp
            35                  40                  45

Arg Asp Tyr Met Gly Trp Met Asp Phe
        50                  55
```

-continued

<210> SEQ ID NO 214
<211> LENGTH: 59
<212> TYPE: PRT
<213> ORGANISM: Xenopus laevis

<400> SEQUENCE: 214

Ser Phe Gln Arg Thr Asp Gly Asp Gln Arg Ser Asn Ile Gly Asn Ala
1               5                   10                  15

Leu Val Lys Tyr Leu Gln Gln Ser Arg Lys Ala Gly Pro Ser Gly Arg
            20                  25                  30

Tyr Val Val Leu Pro Asn Arg Pro Ile Phe Asp Gln Ser His Arg Ile
        35                  40                  45

Asn Asp Arg Asp Tyr Met Gly Trp Met Asp Phe
    50                  55

<210> SEQ ID NO 215
<211> LENGTH: 59
<212> TYPE: PRT
<213> ORGANISM: Xenopus laevis

<400> SEQUENCE: 215

Ser Phe Gln Arg Thr Asp Gly Asp Gln Arg Ser Asn Ile Gly Asn Val
1               5                   10                  15

Leu Val Lys Tyr Leu Gln Gln Ser Arg Lys Ala Gly Pro Ser Gly Arg
            20                  25                  30

Tyr Val Val Leu Pro Asn Arg Pro Ile Phe Asp Gln Pro His Arg Ile
        35                  40                  45

Asn Asp Arg Asp Tyr Met Gly Trp Met Asp Phe
    50                  55

<210> SEQ ID NO 216
<211> LENGTH: 36
<212> TYPE: PRT
<213> ORGANISM: Homo sapiens

<400> SEQUENCE: 216

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 217
<211> LENGTH: 36
<212> TYPE: PRT
<213> ORGANISM: Homo sapiens

<400> SEQUENCE: 217

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 218
<211> LENGTH: 33
<212> TYPE: PRT

<213> ORGANISM: Homo sapiens

<400> SEQUENCE: 218

Glu Pro Val Tyr Pro Gly Asp Asn Ala Thr Pro Glu Gln Met Ala Gln
1               5                   10                  15

Tyr Ala Ala Asp Leu Arg Arg Tyr Ile Asn Met Leu Thr Arg Pro Arg
                20                  25                  30

Tyr

<210> SEQ ID NO 219
<211> LENGTH: 36
<212> TYPE: PRT
<213> ORGANISM: Homo sapiens

<400> SEQUENCE: 219

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
                20                  25                  30

Arg Pro Arg Tyr
            35

<210> SEQ ID NO 220
<211> LENGTH: 20
<212> TYPE: PRT
<213> ORGANISM: Homo sapiens

<400> SEQUENCE: 220

His Lys Glu Asp Thr Leu Ala Phe Ser Glu Trp Gly Ser Pro His Ala
1               5                   10                  15

Ala Val Pro Arg
            20

<210> SEQ ID NO 221
<211> LENGTH: 41
<212> TYPE: PRT
<213> ORGANISM: Homo sapiens

<400> SEQUENCE: 221

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
                20                  25                  30

Ser Asn Arg Lys Leu Met Glu Ile Ile
            35                  40

<210> SEQ ID NO 222
<211> LENGTH: 8
<212> TYPE: PRT
<213> ORGANISM: Homo sapiens

<400> SEQUENCE: 222

Lys Arg Gln His Pro Gly Lys Arg
1               5

<210> SEQ ID NO 223
<211> LENGTH: 8
<212> TYPE: PRT
<213> ORGANISM: Homo sapiens

<400> SEQUENCE: 223

-continued

```
Lys Arg Gln His Pro Gly Arg Arg
 1               5

<210> SEQ ID NO 224
<211> LENGTH: 18
<212> TYPE: PRT
<213> ORGANISM: Homo sapiens

<400> SEQUENCE: 224

Arg Glu Arg Lys Ala Gly Cys Lys Asn Phe Phe Trp Lys Thr Phe Thr
 1               5                  10                  15

Ser Cys

<210> SEQ ID NO 225
<211> LENGTH: 202
<212> TYPE: PRT
<213> ORGANISM: Homo sapiens

<400> SEQUENCE: 225

Met Lys Val Leu Ala Ala Gly Val Val Pro Leu Leu Leu Val Leu His
 1               5                  10                  15

Trp Lys His Gly Ala Gly Ser Pro Leu Pro Ile Thr Pro Val Asn Ala
                20                  25                  30

Thr Cys Ala Ile Arg His Pro Cys His Asn Asn Leu Met Asn Gln Ile
            35                  40                  45

Arg Ser Gln Leu Ala Gln Leu Asn Gly Ser Ala Asn Ala Leu Phe Ile
        50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Ile Ile Ala Val Leu Ala Gln Ala Phe
        195                 200

<210> SEQ ID NO 226
<211> LENGTH: 269
<212> TYPE: PRT
<213> ORGANISM: Homo sapiens

<400> SEQUENCE: 226

Met Ala Glu Val Pro Glu Leu Ala Ser Glu Met Met Ala Tyr Tyr Ser
 1               5                  10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45
```

```
Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
                115                 120                 125

Ser Gln Gln Lys Ser Leu Val Met Ser Gly Pro Tyr Glu Leu Lys Ala
            130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 227
<211> LENGTH: 9
<212> TYPE: PRT
<213> ORGANISM: Homo sapiens

<400> SEQUENCE: 227

Arg Pro Pro Gly Phe Ser Pro Phe Arg
1               5

<210> SEQ ID NO 228
<211> LENGTH: 10
<212> TYPE: PRT
<213> ORGANISM: Homo sapiens

<400> SEQUENCE: 228

Lys Arg Pro Pro Gly Phe Ser Pro Phe Arg
1               5                   10

<210> SEQ ID NO 229
<211> LENGTH: 8
<212> TYPE: PRT
<213> ORGANISM: Homo sapiens

<400> SEQUENCE: 229

Arg Pro Pro Gly Phe Ser Pro Phe
1               5

<210> SEQ ID NO 230
<211> LENGTH: 9
```

```
<212> TYPE: PRT
<213> ORGANISM: Homo sapiens

<400> SEQUENCE: 230

Lys Arg Pro Pro Gly Phe Ser Pro Phe
1               5

<210> SEQ ID NO 231
<211> LENGTH: 64
<212> TYPE: PRT
<213> ORGANISM: Homo sapiens

<400> SEQUENCE: 231

Met Gly Pro Arg Arg Leu Leu Val Ala Ala Cys Phe Ser Leu Cys
1               5                   10                  15

Gly Pro Leu Leu Ser Ala Arg Thr Ala Arg Arg Pro Glu Ser Lys
                20                  25                  30

Ala Thr Asn Ala Thr Leu Asp Pro Arg Ser Phe Leu Leu Arg Asn Pro
                35                  40                  45

Asn Asp Lys Tyr Glu Pro Phe Trp Glu Asp Glu Lys Asn Glu Ser
        50                  55                  60

<210> SEQ ID NO 232
<211> LENGTH: 59
<212> TYPE: PRT
<213> ORGANISM: Homo sapiens

<400> SEQUENCE: 232

Met Arg Ser Pro Ser Ala Ala Trp Leu Leu Gly Ala Ala Ile Leu Leu
1               5                   10                  15

Ala Ala Ser Leu Ser Cys Ser Gly Thr Ile Gln Gly Thr Asn Arg Ser
                20                  25                  30

Ser Lys Gly Arg Ser Leu Ile Gly Lys Val Asp Gly Thr Ser His Val
            35                  40                  45

Thr Gly Lys Gly Val Thr Val Glu Thr Val Phe
        50                  55

<210> SEQ ID NO 233
<211> LENGTH: 60
<212> TYPE: PRT
<213> ORGANISM: Homo sapiens

<400> SEQUENCE: 233

Met Lys Ala Leu Ile Phe Ala Ala Ala Gly Leu Leu Leu Leu Pro
1               5                   10                  15

Thr Phe Cys Gln Ser Gly Met Glu Asn Asp Thr Asn Asn Leu Ala Lys
                20                  25                  30

Pro Thr Leu Pro Ile Lys Thr Phe Arg Gly Ala Pro Pro Asn Ser Phe
            35                  40                  45

Glu Glu Phe Pro Phe Ser Ala Leu Glu Gly Trp Thr
        50                  55                  60

<210> SEQ ID NO 234
<211> LENGTH: 70
<212> TYPE: PRT
<213> ORGANISM: Homo sapiens

<400> SEQUENCE: 234

Met Trp Gly Arg Leu Leu Leu Trp Pro Leu Val Leu Gly Phe Ser Leu
1               5                   10                  15
```

-continued

Ser Gly Gly Thr Gln Thr Pro Ser Val Tyr Asp Glu Ser Gly Ser Thr
                20                  25                  30

Gly Gly Gly Asp Asp Ser Thr Pro Ser Ile Leu Pro Ala Pro Arg Gly
        35                  40                  45

Tyr Pro Gly Gln Val Cys Ala Asn Asp Ser Asp Thr Leu Glu Leu Pro
    50                  55                  60

Asp Ser Ser Arg Ala Leu
65                  70

<210> SEQ ID NO 235
<211> LENGTH: 13
<212> TYPE: PRT
<213> ORGANISM: Artificial Sequence
<220> FEATURE:
<223> OTHER INFORMATION: SV-40 virus large T
<220> FEATURE:
<221> NAME/KEY: PEPTIDE
<222> LOCATION: (1)...(13)
<223> OTHER INFORMATION: SV-40 virus large T

<400> SEQUENCE: 235

Cys Gly Gly Gly Pro Lys Lys Lys Arg Lys Val Gly Gly
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Human immunodeficiency virus transactivator
      protein (TAT, 47-57)
<220> FEATURE:
<221> NAME/KEY: PEPTIDE
<222> LOCATION: (1)...(11)
<223> OTHER INFORMATION: Human immunodeficiency virus transactivator
      protein (TAT, 47-57)

<400> SEQUENCE: 236

Tyr Gly Arg Lys Lys Arg Arg Gln Arg Arg Arg
1               5                   10

<210> SEQ ID NO 237
<211> LENGTH: 13
<212> TYPE: PRT
<213> ORGANISM: Artificial Sequence
<220> FEATURE:
<223> OTHER INFORMATION: Adenovirus
<220> FEATURE:
<221> NAME/KEY: PEPTIDE
<222> LOCATION: (1)...(13)
<223> OTHER INFORMATION: Adenovirus

<400> SEQUENCE: 237

Cys Gly Gly Phe Ser Thr Ser Leu Arg Ala Arg Lys Ala
1               5                   10

<210> SEQ ID NO 238
<211> LENGTH: 15
<212> TYPE: PRT
<213> ORGANISM: Artificial Sequence
<220> FEATURE:
<223> OTHER INFORMATION: Integrin binding domain
<220> FEATURE:
<221> NAME/KEY: PEPTIDE
<222> LOCATION: (1)...(15)
<223> OTHER INFORMATION: Integrin binding domain

<400> SEQUENCE: 238

```
Cys Lys Lys Lys Lys Lys Lys Gly Gly Arg Gly Glu Met Phe Gly
1               5                   10                  15
```

<210> SEQ ID NO 239
<211> LENGTH: 16
<212> TYPE: PRT
<213> ORGANISM: Artificial Sequence
<220> FEATURE:
<223> OTHER INFORMATION: Kaposi fibroblast growth factor
      membrane-translocating sequence (kFGF MTS)
<220> FEATURE:
<221> NAME/KEY: PEPTIDE
<222> LOCATION: (1)...(16)
<223> OTHER INFORMATION: Kaposi fibroblast growth factor
      membrane-translocating sequence (kFGF MTS)

<400> SEQUENCE: 239

```
Ala Ala Val Ala Leu Leu Pro Ala Val Leu Leu Ala Leu Leu Ala Pro
1               5                   10                  15
```

<210> SEQ ID NO 240
<211> LENGTH: 12
<212> TYPE: PRT
<213> ORGANISM: Artificial Sequence
<220> FEATURE:
<223> OTHER INFORMATION: Nuclear localization signal (NLS)
<220> FEATURE:
<221> NAME/KEY: PEPTIDE
<222> LOCATION: (1)...(12)
<223> OTHER INFORMATION: Nuclear localization signal (NLS)

<400> SEQUENCE: 240

```
Thr Pro Pro Lys Lys Lys Arg Lys Val Glu Asp Pro
1               5                   10
```

<210> SEQ ID NO 241
<211> LENGTH: 27
<212> TYPE: PRT
<213> ORGANISM: Artificial Sequence
<220> FEATURE:
<223> OTHER INFORMATION: Transportan
<220> FEATURE:
<221> NAME/KEY: PEPTIDE
<222> LOCATION: (1)...(27)
<223> OTHER INFORMATION: Transportan

<400> SEQUENCE: 241

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 242
<211> LENGTH: 34
<212> TYPE: PRT
<213> ORGANISM: Artificial Sequence
<220> FEATURE:
<223> OTHER INFORMATION: Herpes simplex virus type 1 protein 22 (VP22)
<220> FEATURE:
<221> NAME/KEY: PEPTIDE
<222> LOCATION: (1)...(34)
<223> OTHER INFORMATION: Herpes simplex virus type 1 protein 22 (VP22)

<400> SEQUENCE: 242

```
Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30
```

-continued

Val Glu

<210> SEQ ID NO 243
<211> LENGTH: 16
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 243

Arg Gln Ile Lys Ile Trp Phe Gln Asn Arg Arg Met Lys Trp Lys Lys
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 244

Lys Lys Trp Lys Met Arg Arg Asn Gln Phe Trp Ile Lys Ile Gln Arg
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 245

Arg Gln Ile Lys Ile Trp Phe Gln Asn Arg Arg Met Lys Trp Lys Lys
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 246

Arg Gln Ile Lys Ile Trp Phe Pro Asn Arg Arg Met Lys Trp Lys Lys
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE

```
<222> LOCATION: (1)...(16)
<223> OTHER INFORMATION: Penetratin peptide

<400> SEQUENCE: 247

Arg Gln Pro Lys Ile Trp Phe Pro Asn Arg Arg Met Pro Trp Lys Lys
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 248

Arg Gln Ile Lys Ile Trp Phe Gln Asn Met Arg Arg Lys Trp Lys Lys
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 249

Arg Gln Ile Arg Ile Trp Phe Gln Asn Arg Arg Met Arg Trp Arg Arg
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 250

Arg Arg Trp Arg Arg Trp Trp Arg Arg Trp Trp Arg Arg Trp Arg Arg
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 251

Arg Gln Ile Lys Ile Phe Phe Gln Asn Arg Arg Met Lys Phe Lys Lys
1               5                   10                  15

<210> SEQ ID NO 252
<211> LENGTH: 15
```

-continued

```
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 252

Thr Glu Arg Gln Ile Lys Ile Trp Phe Gln Asn Arg Arg Met Lys
 1               5                  10                  15

<210> SEQ ID NO 253
<211> LENGTH: 15
<212> TYPE: PRT
<213> ORGANISM: Artificial Sequence
<220> FEATURE:
<223> OTHER INFORMATION: Penetratin peptide
<220> FEATURE:
<221> NAME/KEY: PEPTIDE
<222> LOCATION: (1)...(16)
<223> OTHER INFORMATION: Penetratin peptide

<400> SEQUENCE: 253

Lys Ile Trp Phe Gln Asn Arg Arg Met Lys Trp Lys Lys Glu Asn
 1               5                  10                  15

<210> SEQ ID NO 254
<211> LENGTH: 5
<212> TYPE: PRT
<213> ORGANISM: Artificial Sequence
<220> FEATURE:
<223> OTHER INFORMATION: Bovine enterokinase cleavage site
<220> FEATURE:
<221> NAME/KEY: SITE
<222> LOCATION: (1)...(5)
<223> OTHER INFORMATION: Bovine enterokinase cleavage site

<400> SEQUENCE: 254

Asp Asp Asp Asp Lys
 1               5

<210> SEQ ID NO 255
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
<221> NAME/KEY: SITE
<222> LOCATION: (1)...(7)
<223> OTHER INFORMATION: Tobacco Etch Virus cleavage site

<400> SEQUENCE: 255

Glu Asn Leu Tyr Phe Gln Gly
 1               5

<210> SEQ ID NO 256
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
<221> NAME/KEY: SITE
<222> LOCATION: (1)...(7)
<223> OTHER INFORMATION: Tobacco Etch Virus cleavage site

<400> SEQUENCE: 256
```

-continued

```
Glu Asn Leu Tyr Phe Gln Ser
 1               5

<210> SEQ ID NO 257
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
<221> NAME/KEY: SITE
<222> LOCATION: (1)...(7)
<223> OTHER INFORMATION: Tobacco Etch Virus cleavage site

<400> SEQUENCE: 257

Glu Asn Ile Tyr Thr Gln Gly
 1               5

<210> SEQ ID NO 258
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
<221> NAME/KEY: SITE
<222> LOCATION: (1)...(7)
<223> OTHER INFORMATION: Tobacco Etch Virus cleavage site

<400> SEQUENCE: 258

Glu Asn Ile Tyr Thr Gln Ser
 1               5

<210> SEQ ID NO 259
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
<221> NAME/KEY: SITE
<222> LOCATION: (1)...(7)
<223> OTHER INFORMATION: Tobacco Etch Virus cleavage site

<400> SEQUENCE: 259

Glu Asn Ile Tyr Leu Gln Gly
 1               5

<210> SEQ ID NO 260
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
<221> NAME/KEY: SITE
<222> LOCATION: (1)...(7)
<223> OTHER INFORMATION: Tobacco Etch Virus cleavage site

<400> SEQUENCE: 260

Glu Asn Ile Tyr Leu Gln Ser
 1               5

<210> SEQ ID NO 261
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
```

```
<221> NAME/KEY: SITE
<222> LOCATION: (1)...(7)
<223> OTHER INFORMATION: Tobacco Etch Virus cleavage site

<400> SEQUENCE: 261

Glu Asn Val Tyr Phe Gln Gly
 1               5

<210> SEQ ID NO 262
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
<221> NAME/KEY: SITE
<222> LOCATION: (1)...(7)
<223> OTHER INFORMATION: Tobacco Etch Virus cleavage site

<400> SEQUENCE: 262

Glu Asn Val Tyr Ser Gln Ser
 1               5

<210> SEQ ID NO 263
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
<221> NAME/KEY: SITE
<222> LOCATION: (1)...(7)
<223> OTHER INFORMATION: Tobacco Etch Virus cleavage site

<400> SEQUENCE: 263

Glu Asn Val Tyr Ser Gln Gly
 1               5

<210> SEQ ID NO 264
<211> LENGTH: 7
<212> TYPE: PRT
<213> ORGANISM: Artificial Sequence
<220> FEATURE:
<223> OTHER INFORMATION: Tobacco Etch Virus cleavage site
<220> FEATURE:
<221> NAME/KEY: SITE
<222> LOCATION: (1)...(7)
<223> OTHER INFORMATION: Tobacco Etch Virus cleavage site

<400> SEQUENCE: 264

Glu Asn Val Tyr Ser Gln Ser
 1               5

<210> SEQ ID NO 265
<211> LENGTH: 7
<212> TYPE: PRT
<213> ORGANISM: Artificial Sequence
<220> FEATURE:
<223> OTHER INFORMATION: Human Rhinovirus 3C cleavage site
<220> FEATURE:
<221> NAME/KEY: SITE
<222> LOCATION: (1)...(7)
<223> OTHER INFORMATION: Human Rhinovirus 3C cleavage site

<400> SEQUENCE: 265

Glu Ala Leu Phe Gln Gly Pro
 1               5

<210> SEQ ID NO 266
```

```
<211> LENGTH: 7
<212> TYPE: PRT
<213> ORGANISM: Artificial Sequence
<220> FEATURE:
<223> OTHER INFORMATION: Human Rhinovirus 3C cleavage site
<220> FEATURE:
<221> NAME/KEY: SITE
<222> LOCATION: (1)...(7)
<223> OTHER INFORMATION: Human Rhinovirus 3C cleavage site

<400> SEQUENCE: 266

Glu Val Leu Phe Gln Gly Pro
 1               5

<210> SEQ ID NO 267
<211> LENGTH: 7
<212> TYPE: PRT
<213> ORGANISM: Artificial Sequence
<220> FEATURE:
<223> OTHER INFORMATION: Human Rhinovirus 3C cleavage site
<220> FEATURE:
<221> NAME/KEY: SITE
<222> LOCATION: (1)...(7)
<223> OTHER INFORMATION: Human Rhinovirus 3C cleavage site

<400> SEQUENCE: 267

Glu Leu Leu Phe Gln Gly Pro
 1               5

<210> SEQ ID NO 268
<211> LENGTH: 7
<212> TYPE: PRT
<213> ORGANISM: Artificial Sequence
<220> FEATURE:
<223> OTHER INFORMATION: Human Rhinovirus 3C cleavage site
<220> FEATURE:
<221> NAME/KEY: SITE
<222> LOCATION: (1)...(7)
<223> OTHER INFORMATION: Human Rhinovirus 3C cleavage site

<400> SEQUENCE: 268

Asp Ala Leu Phe Gln Gly Pro
 1               5

<210> SEQ ID NO 269
<211> LENGTH: 7
<212> TYPE: PRT
<213> ORGANISM: Artificial Sequence
<220> FEATURE:
<223> OTHER INFORMATION: Human Rhinovirus 3C cleavage site
<220> FEATURE:
<221> NAME/KEY: SITE
<222> LOCATION: (1)...(7)
<223> OTHER INFORMATION: Human Rhinovirus 3C cleavage site

<400> SEQUENCE: 269

Asp Val Leu Phe Gln Gly Pro
 1               5

<210> SEQ ID NO 270
<211> LENGTH: 7
<212> TYPE: PRT
<213> ORGANISM: Artificial Sequence
<220> FEATURE:
<223> OTHER INFORMATION: Human Rhinovirus 3C cleavage site
<220> FEATURE:
<221> NAME/KEY: SITE
<222> LOCATION: (1)...(7)
<223> OTHER INFORMATION: Human Rhinovirus 3C cleavage site

<400> SEQUENCE: 270
```

-continued

```
Asp Leu Leu Phe Gln Gly Pro
 1               5

<210> SEQ ID NO 271
<211> LENGTH: 98
<212> TYPE: PRT
<213> ORGANISM: Artificial Sequence
<220> FEATURE:
<223> OTHER INFORMATION: SUMO/ULP-1 cleavage site
<220> FEATURE:
<221> NAME/KEY: SITE
<222> LOCATION: (1)...(98)
<223> OTHER INFORMATION: SUMO/ULP-1 cleavage site

<400> SEQUENCE: 271

Met Ala Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
             20                  25                  30

Ser Glu Ile Phe Phe Lys Ile Lys Lys Thr Thr Pro Leu Arg Arg Leu
         35                  40                  45

Met Glu Ala Phe Ala Lys Arg Gln Gly Lys Glu Met Asp Ser Leu Arg
     50                  55                  60

Phe Leu Tyr Asp Gly Ile Arg Ile Gln Ala Asp Gln Thr Pro Glu Asp
 65                  70                  75                  80

Leu Asp Met Glu Asp Asn Asp Ile Ile Glu Ala His Arg Glu Gln Ile
                 85                  90                  95

Gly Gly

<210> SEQ ID NO 272
<211> LENGTH: 4
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(4)
<223> OTHER INFORMATION: Thrombin cleavage site

<400> SEQUENCE: 272

Gly Val Arg Gly
 1

<210> SEQ ID NO 273
<211> LENGTH: 4
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(4)
<223> OTHER INFORMATION: Thrombin cleavage site

<400> SEQUENCE: 273

Ser Ala Arg Gly
 1

<210> SEQ ID NO 274
<211> LENGTH: 4
<212> TYPE: PRT
<213> ORGANISM: Artificial Sequence
<220> FEATURE:
<223> OTHER INFORMATION: Thrombin cleavage site
```

```
<220> FEATURE:
<221> NAME/KEY: SITE
<222> LOCATION: (1)...(4)
<223> OTHER INFORMATION: Thrombin cleavage site

<400> SEQUENCE: 274

Ser Leu Arg Gly
 1

<210> SEQ ID NO 275
<211> LENGTH: 4
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(4)
<223> OTHER INFORMATION: Thrombin cleavage site

<400> SEQUENCE: 275

Asp Gly Arg Ile
 1

<210> SEQ ID NO 276
<211> LENGTH: 4
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(4)
<223> OTHER INFORMATION: Thrombin cleavage site

<400> SEQUENCE: 276

Gln Gly Lys Ile
 1

<210> SEQ ID NO 277
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site

<400> SEQUENCE: 277

Leu Val Pro Arg Gly Ser
 1               5

<210> SEQ ID NO 278
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site

<400> SEQUENCE: 278

Leu Val Pro Lys Gly Ser
 1               5
```

```
<210> SEQ ID NO 279
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site

<400> SEQUENCE: 279

Phe Ile Pro Arg Thr Phe
 1               5

<210> SEQ ID NO 280
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site

<400> SEQUENCE: 280

Val Leu Pro Arg Ser Phe
 1               5

<210> SEQ ID NO 281
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site

<400> SEQUENCE: 281

Ile Val Pro Arg Ser Phe
 1               5

<210> SEQ ID NO 282
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site

<400> SEQUENCE: 282

Ile Val Pro Arg Gly Tyr
 1               5

<210> SEQ ID NO 283
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site
```

```
<400> SEQUENCE: 283

Val Val Pro Arg Gly Val
 1               5

<210> SEQ ID NO 284
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site

<400> SEQUENCE: 284

Val Leu Pro Arg Leu Ile
 1               5

<210> SEQ ID NO 285
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site

<400> SEQUENCE: 285

Val Met Pro Arg Ser Leu
 1               5

<210> SEQ ID NO 286
<211> LENGTH: 6
<212> TYPE: PRT
<213> ORGANISM: Artificial Sequence
<220> FEATURE:
<223> OTHER INFORMATION: Thrombin cleavage site
<220> FEATURE:
<221> NAME/KEY: SITE
<222> LOCATION: (1)...(6)
<223> OTHER INFORMATION: Thrombin cleavage site

<400> SEQUENCE: 286

Met Phe Pro Arg Ser Leu
 1               5

<210> SEQ ID NO 287
<211> LENGTH: 4
<212> TYPE: PRT
<213> ORGANISM: Artificial Sequence
<220> FEATURE:
<223> OTHER INFORMATION: Coagulation Factor Xa cleavage site
<220> FEATURE:
<221> NAME/KEY: SITE
<222> LOCATION: (1)...(4)
<223> OTHER INFORMATION: Coagulation Factor Xa cleavage site

<400> SEQUENCE: 287

Ile Asp Gly Arg
 1

<210> SEQ ID NO 288
<211> LENGTH: 4
<212> TYPE: PRT
<213> ORGANISM: Artificial Sequence
<220> FEATURE:
```

```
<223> OTHER INFORMATION: Coagulation Factor Xa cleavage site
<220> FEATURE:
<221> NAME/KEY: SITE
<222> LOCATION: (1)...(4)
<223> OTHER INFORMATION: Coagulation Factor Xa cleavage site

<400> SEQUENCE: 288

Ile Glu Gly Arg
 1

<210> SEQ ID NO 289
<211> LENGTH: 5
<212> TYPE: PRT
<213> ORGANISM: Artificial Sequence
<220> FEATURE:
<223> OTHER INFORMATION: Flexible spacer
<220> FEATURE:
<221> NAME/KEY: DOMAIN
<222> LOCATION: (1)...(5)
<223> OTHER INFORMATION: Flexible spacer

<400> SEQUENCE: 289

Gly Gly Gly Gly Ser
 1               5

<210> SEQ ID NO 290
<211> LENGTH: 5
<212> TYPE: PRT
<213> ORGANISM: Artificial Sequence
<220> FEATURE:
<223> OTHER INFORMATION: Flexible spacer
<220> FEATURE:
<221> NAME/KEY: DOMAIN
<222> LOCATION: (1)...(5)
<223> OTHER INFORMATION: Flexible spacer

<400> SEQUENCE: 290

Glu Ala Ala Ala Lys
 1               5

<210> SEQ ID NO 291
<211> LENGTH: 16
<212> TYPE: PRT
<213> ORGANISM: Homo sapiens

<400> SEQUENCE: 291

Tyr Gly Gly Phe Met Thr Ser Glu Lys Ser Gln Thr Pro Leu Val Thr
 1               5                  10                  15
```